United States Patent
Bobinski et al.

(10) Patent No.: US 11,479,551 B2
(45) Date of Patent: Oct. 25, 2022

(54) MTA-COOPERATIVE PRMT5 INHIBITORS

(71) Applicant: Mirati Therapeutics, Inc., San Diego, CA (US)

(72) Inventors: Thomas P. Bobinski, San Diego, CA (US); Christopher Ronald Smith, San Diego, CA (US); Matthew Arnold Marx, San Diego, CA (US); John Michael Ketcham, San Diego, CA (US); Aaron Craig Burns, San Diego, CA (US); John David Lawson, Carlsbad, CA (US); Svitlana Kulyk, Redwood City, CA (US); Jon Kuehler, San Diego, CA (US); Anthony Ivetac, San Diego, CA (US)

(73) Assignee: Mirati Therapeutics, Inc., San Diego, CA (US)

( * ) Notice: Subject to any disclaimer, the term of this patent is extended or adjusted under 35 U.S.C. 154(b) by 9 days.

(21) Appl. No.: 16/948,312

(22) Filed: Sep. 11, 2020

(65) Prior Publication Data

US 2021/0078994 A1    Mar. 18, 2021

Related U.S. Application Data

(60) Provisional application No. 62/899,575, filed on Sep. 12, 2019, provisional application No. 62/942,833, filed on Dec. 3, 2019, provisional application No. 62/961,371, filed on Jan. 15, 2020, provisional application No. 62/994,927, filed on Mar. 26, 2020, provisional application No. 63/060,261, filed on Aug. 3, 2020.

(51) Int. Cl.
| | |
|---|---|
| C07D 471/04 | (2006.01) |
| C07D 237/32 | (2006.01) |
| C07D 401/10 | (2006.01) |
| C07D 403/10 | (2006.01) |
| C07D 403/12 | (2006.01) |
| C07D 413/10 | (2006.01) |
| C07D 413/14 | (2006.01) |
| C07D 417/10 | (2006.01) |
| C07D 487/04 | (2006.01) |
| C12N 9/10 | (2006.01) |
| C07D 401/14 | (2006.01) |

(52) U.S. Cl.
CPC ......... *C07D 471/04* (2013.01); *C07D 237/32* (2013.01); *C07D 401/10* (2013.01); *C07D 401/14* (2013.01); *C07D 403/10* (2013.01); *C07D 403/12* (2013.01); *C07D 413/10* (2013.01); *C07D 413/14* (2013.01); *C07D 417/10* (2013.01); *C07D 487/04* (2013.01); *C12N 9/1007* (2013.01)

(58) Field of Classification Search
CPC .. C07D 237/32; C07D 401/04; C07D 401/14; C07D 403/14; C07D 471/04; C07D 487/02
See application file for complete search history.

(56) References Cited

U.S. PATENT DOCUMENTS

2004/0034221 A1 *   2/2004   Anthony ............... A61K 31/54
                                                             544/184

FOREIGN PATENT DOCUMENTS

| WO | 02/06285 A1 | 1/2002 |
| WO | 03/014090 A1 | 2/2003 |
| WO | 2017-153518 A1 | 9/2017 |

OTHER PUBLICATIONS

Stopa et al. Cell. Mol. Life Sci. (2015) 72:2041-2059. (Year: 2015).*
Yuan et al. Cellular Oncology (2021) 44:33-44 (Year: 2021).*
Morishita et al. Chemical Abstract vol. 52, No. 77530. Abstract for JP 32007783 (Sep. 18, 1957). (Year: 1957).*
International Search Report and Written Opinion for PCT/US2020/050457 dated Nov. 2, 2020, 16 pages.
Puodzhyunas et al., "Phthalazine and Heterocycles Related To It XI. Derivatives of 4-(Aminomethyl)-1-Phthalazone", Pharmaceutical Chemistry Journal, 1973, vol. 7, 566-570.
Mahmoud et al., "Synthesis and spectral characterisation of some phthalazinone derivatives", Journal of Chemical Research, 2012, 36(2), 75-82.
Mackanova et al., "1-Aminoethyl-4-phthalazone", Zhurnal Obshchei Khimii, 1958, vol. 28, 2798-2801.
International Preliminary Report on Patentability dated Mar. 15, 2022, in International Application No. PCT/US2020/050457, 7 pages.

* cited by examiner

Primary Examiner — Erich A Leeser
(74) Attorney, Agent, or Firm — McDonnell Boehnen Hulbert & Berghoff LLP

(57) ABSTRACT

The present invention relates to compounds that inhibit Protein Arginine N-Methyl Transferase 5 (PRMT5) activity. In particular, the present invention relates to compounds of Formula (I)

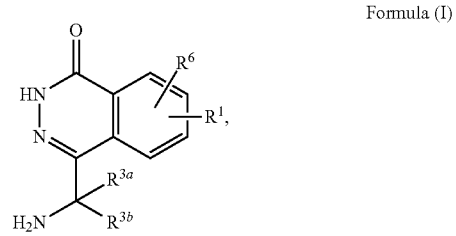

Formula (I)

to pharmaceutical compositions comprising compounds of Formula (I) and to methods of use thereof, such as methods of treating cancer using the compounds of Formula (I) and pharmaceutical compositions comprising those compounds.

30 Claims, No Drawings

MTA-COOPERATIVE PRMT5 INHIBITORS

CROSS-REFERENCE TO RELATED APPLICATIONS

This application claims the benefit of priority of U.S. Provisional Application No. 62/899,575, filed Sep. 12, 2019, U.S. Provisional Application No. 62/942,833, filed Dec. 3, 2019, U.S. Provisional Application No. 62/961,371, filed Jan. 15, 2020, U.S. Provisional Application No. 62/994,927, filed Mar. 26, 2020, and U.S. Provisional Application No. 63/060,261, filed Aug. 3, 2020, the disclosure of each of which is hereby incorporated by reference in its entirety.

FIELD OF THE INVENTION

The present invention relates to compounds that are MTA-cooperative inhibitors of Protein Arginine N-Methyl Transferase 5 (PRMT5). In particular, the present invention relates to compounds, pharmaceutical compositions comprising the compounds and methods for use therefor.

BACKGROUND OF THE INVENTION

Protein Arginine N-Methyl Transferase (PRMT5) is a type II arginine methyltransferase that catalyzes the transfer of a methyl group from S-adenosyl-L-methionine (SAM) to an omega-nitrogen of the guanidino function of protein L-arginine residues (omega-monomethylation) and the transfer of a second methyl group to the other omega-nitrogen, yielding symmetric dimethylarginine (sDMA). PRMT5 forms a complex with MEP50 (methylosome protein 50), which is required for substrate recognition and orientation and is also required for PRMT5-catalyzed histone 2A and histone 4 methyltransferase activity (e.g., see Ho et al., (2013) PLOS ONE 8(8): 10.1371/annotation/e6b5348e-9052-44ab-8f06-90d01dc88fc2).

Homozygous deletions of p16/CDKN2a are prevalent in cancer and these mutations commonly involve the co-deletion of adjacent genes, including the gene encoding methylthioadenosine phosphorylase (MTAP). It is estimated that approximately 15% of all human cancers have a homozygous deletion of the MTAP gene (e.g., see Firestone & Schramm (2017) J. Am. Chem Soc. 139(39):13754-13760. doi: 10.1021/jacs.7b05803. Epub 2017 Sep. 20).

Cells lacking MTAP activity have elevated levels of the MTAP substrate, methylthioadenosine (MTA), which is a potent inhibitor of PRMT5. Inhibition of PRMT5 activity results in reduced methylation activity and increased sensitivity of cellular proliferation to PRMT5 depletion or loss of activity. Hence, the loss of MTAP activity reduces methylation activity of PRMT5 making the cells selectively dependent on PRMT5 activity.

SUMMARY OF THE INVENTION

Thus, we realized that MTA-cooperative inhibition of PRMT5 activity in MTAP deleted cancers will provide therapeutic benefit for a wide range of cancers. The compounds of the present invention provide this therapeutic benefit as MTA-cooperative inhibitors of PRMT5 that negatively modulate the activity of MTA-bound PRMT5 in a cell, particularly an MTAP-deficient cell, or for treating various forms of MTAP-associated cancer.

There is a need to develop new MTA-cooperative PRMT5 inhibitors that are capable of inhibiting PRMT5 activity in the presence of elevated MTA concentrations, particularly in MTAP-deficient cells.

In one aspect of the invention, compounds are provided that are represented by Formula (I):

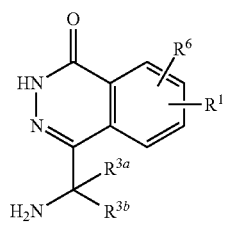

Formula (I)

and pharmaceutically acceptable salts thereof:
wherein:
$R^1$ is hydrogen, halogen, hydroxyalkyl, -L-CN, —Y—C1-C5 alkyl, —Y-cycloalkyl, —Y-heterocyclyl, —Y-aryl, —Y-arC1-C3 alkyl or —Y-heteroaryl, wherein the cycloalkyl, the heterocyclyl, the aryl, and the heteroaryl portions are each optionally substituted with one or more $R^2$;

each Y is independently a bond or —$NR^4$—;

each $R^2$ is independently hydroxy, halogen, cyano, cyanomethyl, —$(NR^4)_2$, hydroxyalkyl, alkoxy, —$SO_2$C1-C3 alkyl, —X-arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$;

each X is independently a bond, O, S, —$NR^4$— or —$NR^4$C(O)— each Z is independently a bond, —SO—, —$SO_2$—, —CH(OH)— or —C(O)—;

each L is independently a bond or C1-C3 alkylene;

$R^{3a}$ and $R^{3b}$ are each independently hydrogen or deuterium, or $R^{3a}$ and $R^{3b}$ together are oxo;

each $R^4$ is independently hydrogen or C1-C3 alkyl;

each $R^5$ is independently cyano, oxo, halogen, C1-C3 alkyl, hydroxyalkyl, alkoxy, —X-haloalkyl, —Z-cycloalkyl, —X-arC1-C3alkyl, X-arC1-C3alkyl substituted with cyano —X-L-cycloalkyl, —X-L-heteroaryl optionally substituted with one or more C1-C3alkyl or oxo, or —X-aryl; and $R^6$ is hydrogen, halogen, C1-C3 alkyl, haloalkyl or alkoxy.

In one aspect of the invention, compounds are provided that are represented by Formula (I-A):

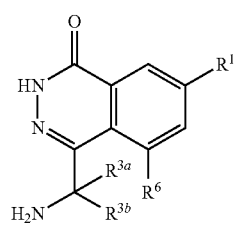

Formula (I-A)

or a pharmaceutically acceptable salt thereof, wherein $R^1$, $R^2$, $R^{3a}$, $R^{3b}$, $R^4$, $R^5$, Y, X, Z and L are as each defined for Formula I.

In one aspect of the invention, compounds are provided that are represented by Formula (I-B):

Formula (I-B)

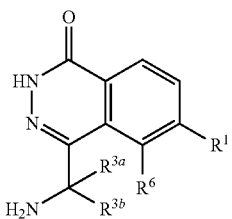

or a pharmaceutically acceptable salt thereof, wherein $R^1$, $R^2$, $R^{3a}$, $R^{3b}$, $R^4$, $R^5$, Y, X, Z and L are as each defined for Formula I.

In one aspect of the invention, compounds are provided that are represented by Formula (I-C):

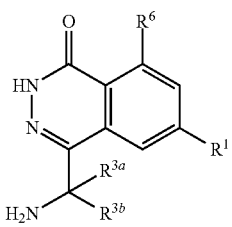

Formula (I-C)

or a pharmaceutically acceptable salt thereof, wherein $R^1$, $R^2$, $R^{3a}$, $R^{3b}$, $R^4$, $R^5$, $R^6$, Y, X, Z and L are as each defined for Formula I.

In another aspect of the invention, compounds are provided that are represented by Formula (I-D):

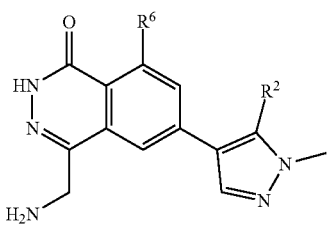

Formula (I-D)

or a pharmaceutically acceptable salt thereof:
wherein:
each Y is independently a bond or —$NR^4$—;
each $R^2$ is independently hydroxy, halogen, cyano, cyanomethyl, —$(NR^4)_2$, hydroxyalkyl, alkoxy, —$SO_2$C1-C3alkyl, —X-arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$, or;
each X is independently a bond, O, S, —$NR^4$— or —$NR^4$C(O)—;
each Z is independently a bond, —SO—, —$SO_2$—, —CH(OH)— or —C(O)—;
each L is independently a bond or C1-C3 alkylene;
each $R^4$ is independently hydrogen or C1-C3 alkyl;
each $R^5$ is independently cyano, oxo, halogen, C1-C3 alkyl, hydroxyalkyl, alkoxy, —X-haloalkyl, —Z-cycloalkyl, —X-arC1-C3 alkyl, X-arC1-C3 alkyl substituted with cyano, —X-L-cycloalkyl, —X-L-heteroaryl optionally substituted with one or more C1-C3alkyl or oxo, or —X-aryl; and
$R^6$ is hydrogen, halogen, C1-C3 alkyl, haloalkyl or alkoxy.

In another aspect of the invention, intermediates are provided that are useful for the preparation of compounds of Formula (I), Formula (I-A), Formula (I-B) and Formula (I-C).

In another aspect of the invention, pharmaceutical compositions are provided comprising a therapeutically effective amount of a compound of the present invention or a pharmaceutically acceptable salt thereof and a pharmaceutically acceptable excipient.

In yet another aspect of the invention, methods for inhibiting PRMT5 activity in a in a cell, comprising contacting the cell with a compound of Formula (I), Formula (I-A), Formula (I-B) and Formula (I-C). In one embodiment, the contacting is in vitro. In one embodiment, the contacting is in vivo.

Also provided herein is a method of inhibiting cell proliferation, in vitro or in vivo, the method comprising contacting a cell with an effective amount of a compound of Formula (I), Formula (I-A), Formula (I-B), Formula (I-C) or a pharmaceutically acceptable salt thereof, or a pharmaceutical composition thereof as defined herein. In one embodiment, the cell is an MTAP-deficient cell.

Also provided are methods for treating cancer in a patient comprising administering a therapeutically effective amount of a compound or pharmaceutical composition of the present invention or a pharmaceutically acceptable salt thereof to a patient in need thereof.

Also provided herein is a method for treating cancer in a patient in need thereof, the method comprising (a) determining that the cancer is associated with MTAP double deletion (e.g., an MTAP-associated cancer); and (b) administering to the patient a therapeutically effective amount of a compound of Formula (I), Formula (I-A), Formula (I-B), Formula (I-C) or a pharmaceutically acceptable salt thereof, or a pharmaceutical composition thereof.

DETAILED DESCRIPTION OF THE INVENTION

The present invention relates to MTA-cooperative PRMT5 inhibitors. In particular, the present invention relates to compounds that inhibit PRMT5 activity in the presence of bound MTA, pharmaceutical compositions comprising a therapeutically effective amount of the compounds, and methods of use therefor.

Definitions

Unless defined otherwise, all technical and scientific terms used herein have the same meaning as is commonly understood by one of skill in the art to which this invention belongs. All patents, patent applications, and publications referred to herein are incorporated by reference to the extent they are consistent with the present disclosure. Terms and ranges have their generally defined definition unless expressly defined otherwise.

For simplicity, chemical moieties are defined and referred to throughout primarily as univalent chemical moieties (e.g., alkyl, aryl, etc.). Nevertheless, such terms may also be used to convey corresponding multivalent moieties under the appropriate structural circumstances clear to those skilled in the art. For example, while an "alkyl" moiety generally refers to a monovalent radical (e.g. CH$_3$—CH$_2$—), in certain circumstances a bivalent linking moiety can be "alkyl," in which case those skilled in the art will understand the alkyl to be a divalent radical (e.g., —CH$_2$—CH$_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

As used herein, "PRMT5" refers to a mammalian Protein Arginine N-Methyl Transferase 5 (PRMT5) enzyme.

As used herein, a "PRMT5 inhibitor" or "MTA-cooperative PRMT5 inhibitor" refers to compounds of the present invention that are represented by Formula (I) as described herein. These compounds are capable of negatively modulating or inhibiting all or a portion of the enzymatic activity of the PRMT5 in the presence of bound MTA in vitro or in vivo, or in cells expressing elevated levels of MTA.

As used herein, "MTAP" refers to a mammalian methylthioadenosine phosphorylase (MTAP) enzyme.

An "MTAP-associated disease or disorder" as used herein refers to diseases or disorders associated with or mediated by or having a loss of MTAP activity resulting in sensitizing the disorder to selective inhibition of PRMT5 activity. A non-limiting example of an MTAP-associated disease or disorder is an MTAP-associated cancer.

The term "amino" refers to —NH$_2$.

The term "acetyl" refers to "—C(O)CH$_3$.

As herein employed, the term "acyl" refers to an alkylcarbonyl or arylcarbonyl substituent wherein the alkyl and aryl portions are as defined herein.

The term "alkyl" as employed herein refers to saturated straight and branched chain aliphatic groups having from 1 to 12 carbon atoms. As such, "alkyl" encompasses $C_1$, $C_2$, $C_3$, $C_4$, $C_5$, $C_6$, $C_7$, $C_8$, $C_9$, $C_{10}$, $C_{11}$ and $C_{12}$ groups. Examples of alkyl groups include, without limitation, methyl, ethyl, propyl, isopropyl, butyl, isobutyl, sec-butyl, tert-butyl, pentyl, and hexyl.

The term "alkenyl" as used herein means an unsaturated straight or branched chain aliphatic group with one or more carbon-carbon double bonds, having from 2 to 12 carbon atoms. As such, "alkenyl" encompasses $C_2$, $C_3$, $C_4$, $C_5$, $C_6$, $C_7$, $C_8$, $C_9$, $C_{10}$, $C_{11}$ and $C_{12}$ groups. Examples of alkenyl groups include, without limitation, ethenyl, propenyl, butenyl, pentenyl, and hexenyl.

The term "alkynyl" as used herein means an unsaturated straight or branched chain aliphatic group with one or more carbon-carbon triple bonds, having from 2 to 12 carbon atoms. As such, "alkynyl" encompasses $C_2$, $C_3$, $C_4$, $C_5$, $C_6$, $C_7$, $C_8$, $C_9$, $C_{10}$, $C_{11}$ and $C_{12}$ groups. Examples of alkynyl groups include, without limitation, ethynyl, propynyl, butynyl, pentynyl, and hexynyl.

An "alkylene," "alkenylene," or "alkynylene" group is an alkyl, alkenyl, or alkynyl group, as defined hereinabove, that is positioned between and serves to connect two other chemical groups. Examples of alkylene groups include, without limitation, methylene, ethylene, propylene, and butylene. Exemplary alkenylene groups include, without limitation, ethenylene, propenylene, and butenylene. Exemplary alkynylene groups include, without limitation, ethynylene, propynylene, and butynylene.

The term "alkoxy" refers to —OC1-C6 alkyl.

The term "cycloalkyl" as employed herein is a saturated and partially unsaturated cyclic hydrocarbon group having 3 to 12 carbons. As such, "cycloalkyl" includes $C_3$, $C_4$, $C_5$, $C_6$, $C_7$, $C_8$, $C_9$, $C_{10}$, $C_{11}$ and $C_{12}$ cyclic hydrocarbon groups. Examples of cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroalkyl" refers to an alkyl group, as defined hereinabove, wherein one or more carbon atoms in the chain are independently replaced O, S, or NR$^x$, wherein R$^x$ is hydrogen or C1-C3 alkyl. Examples of heteroalkyl groups include methoxymethyl, methoxyethyl and methoxypropyl.

An "aryl" group is a $C_6$-$C_{14}$ aromatic moiety comprising one to three aromatic rings. As such, "aryl" includes $C_6$, $C_{10}$, $C_{13}$, and $C_{14}$ cyclic hydrocarbon groups. An exemplary aryl group is a $C_6$-$C_{10}$ aryl group. Particular aryl groups include, without limitation, phenyl, naphthyl, anthracenyl, and fluorenyl. An "aryl" group also includes fused multicyclic (e.g., bicyclic) ring systems in which one or more of the fused rings is non-aromatic, provided that at least one ring is aromatic, such as indenyl.

An "aralkyl" or "arylalkyl" group comprises an aryl group covalently linked to an alkyl group wherein the moiety is linked to another group via the alkyl moiety. An exemplary aralkyl group is —(C1-C6)alkyl(C6-C10)aryl, including, without limitation, benzyl, phenethyl, and naphthylmethyl. For example, an arC1-C3alkyl is an aryl group covalently linked to a C1-C3 alkyl.

A "heterocyclyl" or "heterocyclic" group is a mono- or bicyclic (fused or spiro) ring structure having from 3 to 12 atoms, (3, 4, 5, 6, 7, 8, 9, 10, 11 or 12 atoms), for example 4 to 8 atoms, wherein one or more ring atoms are independently —C(O)—, N, NR$^4$, O, or S, and the remainder of the ring atoms are quaternary or carbonyl carbons. Examples of heterocyclic groups include, without limitation, epoxy, oxiranyl, oxetanyl, azetidinyl, aziridinyl, THFyl, tetrahydropyranyl, tetrahydrothiophenyl, pyrrolidinyl, piperidinyl, piperazinyl, imidazolidinyl, thiazolidinyl, thiatanyl, dithianyl, trithianyl, azathianyl, oxathianyl, dioxolanyl, oxazolidinyl, oxazolidinonyl, decahydroquinolinyl, piperidonyl, 4-piperidonyl, thiomorpholinyl, dimethyl-morpholinyl, and morpholinyl. Specifically excluded from the scope of this term are compounds having adjacent ring O and/or S atoms.

As used herein, "L-heterocyclyl" refers to a heterocyclyl group covalently linked to another group via an alkylene linker As used herein, the term "heteroaryl" refers to a group having 5 to 14 ring atoms, preferably 5, 6, 10, 13 or 14 ring atoms; having 6, 10, or 14 π electrons shared in a cyclic array; and having, in addition to carbon atoms, from one to three heteroatoms that are each independently N, O, or S. "Heteroaryl" also includes fused multicyclic (e.g., bicyclic) ring systems in which one or more of the fused rings is non-aromatic, provided that at least one ring is aromatic and at least one ring contains an N, O, or S ring atom.

Examples of heteroaryl groups include acridinyl, azocinyl, benzimidazolyl, benzofuranyl, benzo[d]oxazol-2(3H)-one, 2H-benzo[b][1,4]oxazin-3(4H)-one, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, furanyl, furazanyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolinyl, 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

A "L-heteroaralkyl" or "L-heteroarylalkyl" group comprises a heteroaryl group covalently linked to another group via an alkylene linker. Examples of heteroalkyl groups comprise a C1-C6 alkyl group and a heteroaryl group having 5, 6, 9, or 10 ring atoms. Examples of heteroaralkyl groups include pyridylmethyl, pyridylethyl, pyrrolylmethyl, pyrrolylethyl, imidazolylmethyl, imidazolylethyl, thiazolylmethyl, thiazolylethyl, benzimidazolylmethyl, benzimidazolylethyl quinazolinylmethyl, quinolinylmethyl, quinolinylethyl, benzofuranylmethyl, indolinylethyl isoquinolinylmethyl, isoinodylmethyl, cinnolinylmethyl, and benzothiophenylethyl. Specifically excluded from the scope of this term are compounds having adjacent ring O and/or S atoms.

An "arylene," "heteroarylene," or "heterocyclylene" group is a bivalent aryl, heteroaryl, or heterocyclyl group, respectively, as defined hereinabove, that is positioned between and serves to connect two other chemical groups.

As employed herein, when a moiety (e.g., cycloalkyl, aryl, heteroaryl, heterocyclyl, urea, etc.) is described as "optionally substituted" without expressly stating the substituents it is meant that the group optionally has from one to four, preferably from one to three, more preferably one or two, non-hydrogen substituents.

The term "halogen" or "halo" as employed herein refers to chlorine, bromine, fluorine, or iodine.

The term "haloalkyl" refers to an alkyl chain in which one or more hydrogens have been replaced by a halogen. Exemplary haloalkyls are trifluoromethyl, difluoromethyl, flurochloromethyl, chloromethyl, and fluoromethyl.

The term "hydroxyalkyl" refers to -alkylene-OH.

As used herein, "an effective amount" of a compound is an amount that is sufficient to negatively modulate or inhibit the activity of PRMT5 enzyme.

As used herein, a "therapeutically effective amount" of a compound is an amount that is sufficient to ameliorate or in some manner reduce a symptom or stop or reverse progression of a condition, or negatively modulate or inhibit the activity of PRMT5. Such amount may be administered as a single dosage or may be administered according to a regimen, whereby it is effective.

As used herein, "treatment" means any manner in which the symptoms or pathology of a condition, disorder or disease in a patient are ameliorated or otherwise beneficially altered.

As used herein, "amelioration of the symptoms of a particular disorder by administration of a particular compound or pharmaceutical composition" refers to any lessening, whether permanent or temporary, lasting or transient, that can be attributed to or associated with administration of the composition.

Compounds

In one aspect of the invention, compounds are provided that are represented by Formula (I):

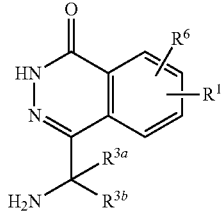

Formula (I)

or a pharmaceutically acceptable salt thereof:
wherein:
$R^1$ is hydrogen, halogen, hydroxyalkyl, -L-CN, —Y—C1-C5 alkyl, —Y-cycloalkyl, —Y-heterocyclyl, —Y-aryl, —Y-arC1-C3alkyl or —Y-heteroaryl, wherein the cycloalkyl, the heterocyclyl, the aryl, and the heteroaryl portions are each optionally substituted with one or more $R^2$;

each Y is a bond or —$NR^4$—;

each $R^2$ is independently hydroxy, halogen, cyano, cyanomethyl, —$(NR^4)_2$, hydroxyalkyl, alkoxy, —$SO_2$C1-C3alkyl, —X-arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$;

each X is independently a bond, O, S, —$NR^4$— or —$NR^4C(O)$—;

each Z is independently a bond, —SO—, —$SO_2$—, —CH(OH)— or —C(O)—;

each L is independently a bond or C1-C3 alkylene;

$R^{3a}$ and $R^{3b}$ are each independently hydrogen or deuterium, or $R^{3a}$ and $R^{3b}$ together are oxo;

each $R^4$ is independently hydrogen or C1-C3 alkyl;

each $R^5$ is independently cyano, oxo, halogen, C1-C3 alkyl, hydroxyalkyl, alkoxy, —X-haloalkyl, —Z-cycloalkyl, —X-arC1-C3alkyl, X-arC1-C3alkyl substituted with cyano, —X-L-cycloalkyl, —X-L-heteroaryl optionally substituted with one or more C1-C3alkyl or oxo, or —X-aryl; and $R^6$ is hydrogen, halogen, haloalkyl, C1-C3 alkyl or alkoxy.

In one embodiment for compounds of Formula (I), $R^1$ is hydrogen.

In another embodiment for compounds of Formula (I), $R^1$ is halogen. In certain embodiments, the halogen is bromine.

In one embodiment for compounds of Formula (I), $R^1$ is -L-CN. In one embodiment, L is C1-C3 alkylene. In certain embodiments, the C1-C3 alkylene is methylene.

In one embodiment for compounds of Formula (I), $R^1$ is —Y—C1-C5 alkyl. In one embodiment, Y is a bond and the C1-C5 alkyl is methyl. In one embodiment, Y is —$NR^4$— and the C1-C5 alkyl is methyl, ethyl or propyl.

In one embodiment for compounds of Formula (I), $R^1$ is hydroxyalkyl.

In one embodiment for compounds of Formula (I), $R^1$ is —Y-heterocyclyl. In certain embodiments, Y is a bond and the heterocyclyl is azetidinyl, THFyl or morpholinyl.

In one embodiment for compounds of Formula (I), $R^1$ is —Y-aryl wherein the aryl is optionally substituted with one or more $R^2$.

In certain embodiments, Y is a bond and the aryl is phenyl optionally substituted with one or two $R^2$. In one embodiment, the one or two $R^2$ groups are each independently C1-C3 alkyl, cyano or halogen.

In one embodiment for compounds of Formula (I), $R^1$ is —Y-cycloalkyl. In one embodiment, Y is a bond and the cycloalkyl is cyclopentyl.

In one embodiment for compounds of Formula (I), $R^1$ is —Y-heteroaryl optionally substituted with one or more $R^2$. In certain embodiment, the heteroaryl is, pyrazolyl, imidazolyl, thiazolyl, isothiazolyl, oxazolyl, triazolyl, oxidazolyl, pyridyl, pyridiazinyl, pyrimidinyl, quinolinyl, isoquinolinyl, phthalazinyl, pyrazolopyridinyl, 1H-pyrrolopyridyl, pyrazolopyrimidinyl, imidazopyridyl, tetrahydropyrazolopyrazinyl, 2H-4$\lambda^4$-imidazopyrimidinyl, 2H-4$\lambda^4$-imidazopyridazinyl, oxazolopyridyl or 5,6-dihydro-8H-imidazooxazinyl, each optionally substituted with one or more $R^2$. In one embodiment, Y is a bond.

In one embodiment, $R^1$ is —Y-heteroaryl, Y is a bond and the heteroaryl is azetidinyl and $R^2$ is —$(NR^4)_2$.

In one embodiment, $R^1$ is heteroaryl, Y is a bond and the heteroaryl is tetrahydropyrazolopyrazinyl, optionally substituted with one or more $R^2$. In one embodiment, the tetrahydropyrazolopyrazinyl is 4,5,6,7-tetrahydropyrazolo[1,5-a]pyrazin-3-yl optionally substituted with one or more $R^2$. In one embodiment, the tetrahydropyrazolopyrazinyl is substituted with one $R^2$. In one embodiment, $R^2$ is —X—C1-C5 alkyl, arC1-C3alkyl, —Z—C1-C5 alkyl, —Z-cycloalkyl or —X-aryl. In one embodiment, $R^2$ is —Z-cycloalkyl, wherein Z is a bond and the cycloalkyl is cyclopropyl. In one embodiment, $R^2$ is —Z-cycloalkyl, wherein Z is —C(O)— and the cycloalkyl is cyclopropyl, cyclobutyl, cyclopentyl, cyclohexyl or bicyclo[1.1.1]pentyl.

In one embodiment wherein $R^1$ is Y-heteroaryl, Y is a bond and the heteroaryl is pyrazolopyridinyl optionally substituted with one or more $R^2$. In one embodiment, the pyrazolylpyridinyl is substituted with one $R^2$, wherein the one $R^2$ is alkoxy or —X-aryl. In one embodiment, the alkoxy is methoxy or isopropyloxy. In certain embodiments, the —X-aryl, the X is O and the aryl is phenyl.

In one embodiment, Y is a bond and the $R^1$ heteroaryl is pyridyl, optionally substituted with one or two $R^2$. In certain embodiments, the pyridyl is substituted with one $R^2$, wherein $R^2$ is hydroxy, halogen, cyano, cyanomethyl, —$(NR^4)_2$, hydroxyalkyl, alkoxy, —$SO_2$C1-C3alkyl, arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$.

In one embodiment, $R^1$ is —Y-heteroaryl, Y is a bond and the heteroaryl is pyridyl and $R^2$ is —X—C1-C5 alkyl, X is a bond and the C1-C5 alkyl is methyl, ethyl propyl, isopropyl, butyl, isobutyl, pentyl or isopentyl.

In one embodiment, $R^1$ is —Y-heteroaryl, Y is a bond and the heteroaryl is pyridyl and $R^2$ is —X-haloalkyl, X is a bond and the haloalkyl is difluoromethyl or trifluoromethyl. In another embodiment, $R^2$ is —X-haloalkyl, wherein X is O, and wherein the haloalkyl is difluoromethyl or trifluoromethyl.

In one embodiment, $R^1$ is —Y-heteroaryl, Y is a bond and the heteroaryl is pyridyl and $R^2$ is —X-L-cycloalkyl, wherein X is a bond, L is a bond and the cycloalkyl is cyclopropyl or cyclohexyl. In another embodiment, $R^2$ is —X-L-cycloalkyl, wherein X is a bond, L is methylene and the cycloalkyl is cyclopropyl. In one embodiment, $R^2$ is —X-L-cycloalkyl, wherein X is O, L is methylene and the cycloalkyl is cyclopropyl.

In one embodiment, $R^1$ is —Y-heteroaryl, Y is a bond and the heteroaryl is pyridyl and $R^2$ is C2-C4 alkynyl, wherein the alkynyl is ethynyl or prop-2-ynyl.

In another embodiment, $R^1$ is —Y-heteroaryl, Y is a bond and the heteroaryl is pyridyl and $R^2$ is —$SO_2$C1-C3 alkyl, wherein the C1-C3 alkyl is methyl.

In one embodiment, $R^1$ is —Y-heteroaryl, Y is a bond and the heteroaryl is pyridyl and $R^2$ is heterocyclyl, wherein the heterocyclyl is morpholinyl or tertrahydropyranyl.

In other embodiments, $R^1$ is —Y-heteroaryl, Y is a bond and the heteroaryl is pyridyl and $R^2$ is —X-heteroaryl, wherein the heteroaryl is optionally substituted with one or more $R^5$. In one embodiment, X is a bond, the heteroaryl is pyrazolyl substituted with one $R^5$, wherein $R^5$ is C1-C3 alkyl. In one embodiment, X is a bond, the heteroaryl is pyridyl or pyrimidinyl, each optionally substituted with one $R^5$.

In one embodiment, $R^1$ is —Y-heteroaryl, Y is a bond and the heteroaryl is pyridyl and $R^2$ is arC1-C3alkyl, wherein the arC1-C3alkyl is benzyl.

In one embodiment wherein $R^1$ is —Y-heteroaryl, Y is a bond and the heteroaryl is pyridyl and $R^2$ is —X-heteroaryl, wherein the X is O, and the heteroaryl is quinolinyl optionally substituted with one or more $R^5$. In another embodiment, the X is —$NR^4$—, and the heteroaryl is quinolinyl optionally substituted with one or more $R^5$.

In one embodiment, $R^1$ is —Y-heteroaryl, Y is a bond and the heteroaryl is pyridyl and $R^2$ is —X-aryl, wherein X is O and the aryl is phenyl optionally substituted with one, two or three $R^5$. In one embodiment, each of the one, two or three $R^5$ groups is independently selected from the group consisting of cyano, halogen, C1-C3 alkyl and alkoxy. In one embodiment, X is S and the aryl is phenyl optionally substituted with one $R^5$, wherein $R^5$ is halogen or C1-C3 alkyl. In one embodiment, X is O and the aryl is phenyl optionally substituted with two $R^5$ groups, wherein each $R^5$ group is independently cyano. In one embodiment, X is —$NR^4$— and the aryl is phenyl optionally substituted with two $R^5$ groups, wherein each $R^5$ group is independently alkoxy. In certain embodiments, each alkoxy is methoxy.

In one embodiment, $R^1$ is —Y-heteroaryl, Y is a bond and the heteroaryl is pyridyl and $R^2$ is halogen, wherein the halogen is chlorine or fluorine. In one embodiment, $R^1$ is —Y-heteroaryl, Y is a bond and the heteroaryl is pyridyl and $R^2$ is —X-L-cycloalkyl, heterocyclyl or —X-aryl, wherein the aryl is optionally substituted with one or more $R^5$. In one embodiment, is—X-L-cycloalkyl, wherein X and L are each a bond and the cycloalkyl is cyclohexyl. In one embodiment, $R^2$ is heterocyclyl, wherein the heterocyclyl is tetrahydropyranyl. In one embodiment, $R^2$ is —X-aryl, wherein the aryl is phenyl substituted with two $R^5$, wherein each $R^5$ is cyano.

In certain embodiments, $R^1$ is —Y-heteroaryl, Y is a bond and the heteroaryl is pyridyl substituted with two $R^2$. In one embodiment, each $R^2$ is independently —X—C1-C5 alkyl or one $R^2$ is halogen or cycloalkyl and the second $R^2$ is —X—C1-C5 alkyl, wherein X is a bond.

In one embodiment for compounds of Formula (I), $R^1$ is —Y-heteroaryl, Y is a bond and the heteroaryl is pyrimidinyl, optionally substituted with one or two $R^2$. In one embodiment, the pyrimidinyl is substituted with one $R^2$, wherein $R^2$ is —X—C1-C5 alkyl or —X-haloalkyl. In one embodiment, each X is a bond.

In one embodiment for compounds of Formula (I), $R^1$ is —Y-heteroaryl, Y is a bond and the heteroaryl is quinolinyl, optionally substituted with one or two $R^2$. In certain embodiments, the one $R^2$ group is cyano. In certain embodiments, one $R^2$ group is cyano and the second $R^2$ is halogen or —X—C1-C5 alkyl.

In one embodiment for compounds of Formula (I), $R^1$ is —Y-heteroaryl, Y is a bond and the heteroaryl is isothiazolyl, optionally substituted with one or two $R^2$. In one embodiment, $R^2$ is —X-aryl optionally substituted with one $R^5$, wherein the aryl is naphthyl substituted with one $R^5$, wherein $R^5$ is cyano.

In one embodiment for compounds of Formula (I), $R^1$ is —Y-heteroaryl, Y is a bond and the heteroaryl is pyrazolyl, optionally substituted with one, two or three $R^2$ groups.

In certain embodiments, the pyrazolyl is substituted with one $R^2$, wherein $R^2$ is cyano, —X—C1-C5 alkyl, hydroxyalkyl, arC1-C3alkyl or —X-aryl, wherein the aryl is optionally substituted with one or more $R^5$. In one embodiment, $R^2$ is —X—C1-C5 alkyl, wherein X is a bond and the C1-C5 alkyl is methyl, ethyl, propyl, isopropyl, butyl, isobutyl, pentyl or isopentyl.

In other embodiments, the pyrazolyl is substituted with two $R^2$ groups, wherein the two $R^2$ groups are independently (1) —X—C1-C5 alkyl, (2) —X—C1-C5 alkyl and halogen, (3) —X—C1-C5 alkyl and alkoxy, (4) —X—C1-C5 alkyl and —N($R^4$)$_2$, -(5) X—C1-C5 alkyl and —X-haloalkyl, (6) —X—C1-C5 alkyl and arC1-C3alkyl, (7) —X—C1-C5 alkyl and —X-L-cyclolalkyl, -(8) —X—C1-C5 alkyl and -heterocyclyl, (9) —X—C1-C5 alkyl and —X-aryl optionally substituted with one or more $R^5$, (10) —X—C1-C5 alkyl and —X-heteroaryl optionally substituted with one or more $R^5$, (11) —X—C1-C5 alkyl and cyanomethyl, (12) —X—C1-C5 alkyl and cyano, (13) cyano and halogen, wherein the halogen is chlorine or fluorine, (14) cyano and —X-L-cycloalkyl, (15) independently halogen, (16) cyano and alkoxy, wherein each X is a bond, (17) cyano and —X-aryl, (18) cyano and —X-heteroaryl, (19) cyano and heterocyclyl (20) halogen and —X-arC1-C3alkyl or X-arC1-C3alkyl substituted with cyano, and (21) halogen and —X-aryl.

In one embodiment wherein $R^1$ is pyrazolyl, the pyrazolyl is substituted with two $R^2$, wherein one $R^2$ is —X—C1-C5 alkyl and the second $R^2$ is —X-aryl optionally substituted with one or more $R^5$. In one embodiment, each X is a bond and the aryl is phenyl substituted with two $R^5$, wherein (1) each $R^5$ is independently —X—C1-C5 alkyl, wherein X is a bond; (2) one $R^5$ is cyano and one $R^5$ is —X—C1-C5 alkyl, wherein X is a bond; (3) one $R^5$ is cyano and one $R^5$ is —X-L-cycloalkyl, wherein X is a bond and L is a bond, methylene or ethylene; (4) one $R^5$ is cyano and one $R^5$ is halogen; (5) one $R^5$ is cyano and one $R^5$ is alkoxy; (6) each $R^5$ is independently cyano or (7) each $R^5$ is independently halogen.

In one embodiment wherein $R^1$ is pyrazolyl, the pyrazolyl is substituted with two $R^2$, wherein one $R^2$ is —X—C1-C5 alkyl and the second $R^2$ is —X-aryl optionally substituted with one or more $R^5$. In one embodiment, the X is a bond and the aryl is naphthyl substituted with one $R^5$, wherein $R^5$ is cyano or halogen. In one embodiment, the naphthyl is substituted with two $R^5$ groups, wherein one $R^5$ is cyano and the second $R^5$ is halogen, alkoxy or cyano. In one embodiment, the naphthyl is substituted with three $R^5$ groups, wherein one $R^5$ is cyano and the second $R^5$ is X-haloalkyl and the third $R^5$ is —X-L-cycloalkyl.

In one embodiment wherein $R^1$ is pyrazolyl, the pyrazolyl is substituted with two $R^2$, wherein one $R^2$ is —X—C1-C5 alkyl and the second $R^2$ is —X-aryl optionally substituted with one or more $R^5$. In one embodiment, the X is a bond and the aryl is phenyl substituted with three $R^5$, wherein (1) each $R^5$ is independently —X—C1-C5 alkyl, wherein each X is a bond; (2) one $R^5$ is cyano and two $R^5$ are —X—C1-C5 alkyl, wherein each X is a bond; (3) one $R^5$ is cyano, one $R^5$ is halogen, and one $R^5$ is —X—C1-C5 alkyl, wherein X is a bond; (4) one $R^5$ is cyano and two $R^5$ are alkoxy, (5) one $R^5$ is cyano and two $R^5$ are halogens (6) one $R^5$ is cyano, one $R^5$ is halogen and one $R^5$ is alkoxy, (7) or one $R^5$ is cyano, one $R^5$ is halogen, and one $R^5$ is —X-L-cycloalkyl.

In one embodiment wherein $R^1$ is pyrazolyl, the pyrazolyl is substituted with two $R^2$, wherein one $R^2$ is —X—C1-C5 alkyl and the second $R^2$ is —X-heteroaryl optionally substituted with one or more $R^5$. In one embodiment, each X is a bond and the heteroaryl is quinolinyl, pyrazolyl, chromanyl, indolizinyl, dihydrobenzylfuranyl or imidzaopyridinyl, each optionally substituted with one or more $R^5$.

In one embodiment, the pyrazolyl is substituted with three $R^2$, wherein each $R^2$ is independently —X—C1-C5 alkyl and each X is a bond.

In one embodiment wherein $R^1$ is pyrazolyl, the pyrazolyl is substituted with three $R^2$, wherein (1) one $R^2$ is cyano and two $R^2$ are halogen; (2) one $R^2$ is cyano, one $R^2$ is halogen and one $R^2$ is alkoxy. In other embodiments, one $R^2$ is alkoxy, and two $R^2$ are independently halogen In one embodiment for compounds of Formula (I), $R^1$ is —Y-heteroaryl, Y is a bond and the heteroaryl is imidazolyl, 1H-pyrrolopyridyl, tetrahydropyrazolopyrazinyl, 2H-4$\lambda^4$-imidazopyrimidinyl, 2H-4$\lambda^4$-imidazopyridazinyl, or oxazolopyridyl, each substituted with one $R^2$ group, wherein $R^2$ is —X—C1-C5 alkyl, wherein X is a bond. In one embodiment, the heteroaryl is 1H-pyrrolopyridyl substituted with one $R^2$, wherein $R^2$ is cyano or —X-aryl. In certain embodiments, the X of the —X-aryl is a bond and the aryl is phenyl. In one embodiment, the heteroaryl is imidazolyl substituted with one $R^2$, wherein $R^2$ is hydroxyalkyl or —X-aryl.

In one embodiment for compounds of Formula (I), $R^1$ is —Y-heteroaryl, Y is a bond and the heteroaryl is imidazopyridyl substituted with one $R^2$ group, wherein $R^2$ is cyano, alkoxy, halogen or —X—C1-C5 alkyl. In other embodiments, the heteroaryl is imidazopyridyl substituted with two $R^2$ groups, wherein one $R^2$ is halogen and the second $R^2$ group is —X—C1-C5 alkyl or halogen.

In one embodiment for compounds of Formula (I), $R^1$ is —Y-aryl, Y is —$NR^4$— and the aryl is phenyl optionally substituted with one or more $R^5$.

In one embodiment, $R^1$ is —Y-arC1-C3alkyl. In one embodiment, Y is —$NR^4$— and the arC1-C3alkyl is benzyl.

In one embodiment, $R^{3a}$ and $R^{3b}$ are each hydrogen. In another embodiment, $R^{3a}$ and $R^{3b}$ are each deuterium. In certain embodiments, one of $R^{3a}$ and $R^{3b}$ is hydrogen and the other is deuterium. In one embodiment, $R^{3a}$ and $R^{3b}$ taken together are oxo.

In one embodiment, each $R^4$ is hydrogen. In one embodiment, each $R^4$ is independently C1-C3 alkyl. In one embodiment, one $R^4$ is hydrogen and the other $R^4$ is C1-C3 alkyl.

In one embodiment, the cycloalkyl, aryl or heteroaryl rings are optionally substituted with one or more $R^5$, wherein $R^5$ is cyano, oxo, halogen, C1-C3 alkyl, hydroxyalkyl, alkoxy, —X-haloalkyl, —Z-cycloalkyl, —X-arC1-C3alkyl, —X-L-cycloalkyl or —X-aryl.

In one embodiment, $R^6$ is hydrogen. In one embodiment, $R^6$ is halogen. In certain embodiments, the halogen is chlorine or fluorine. In one embodiment, $R^6$ is C1-C3 alkyl. In one embodiment, the C1-C3 alkyl is methyl or ethyl. In one embodiment, $R^6$ is alkoxy. In certain embodiments, the alkoxy is methoxy. In one embodiment, $R^6$ is haloalkyl. In certain embodiments, the haloalkyl is trifluoromethyl.

In one aspect of the invention, compounds are provided that are represented by Formula (I-A):

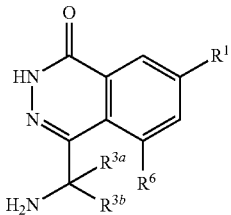

Formula (I-A)

or a pharmaceutically acceptable salt thereof, wherein $R^1$, $R^2$, $R^{3a}$, $R^{3b}$, $R^4$, $R^5$, $R^6$, Y, X, Z, and L are as each defined for Formula I.

In one aspect of the invention, compounds are provided that are represented by Formula (I-B):

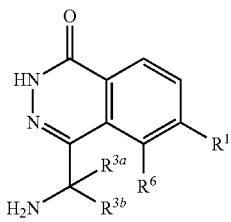

Formula (I-B)

or a pharmaceutically acceptable salt thereof, wherein $R^1$, $R^2$, $R^{3a}$, $R^{3b}$, $R^4$, $R^5$, $R^6$, Y, X, Z, and L are as each defined for Formula I.

In one aspect of the invention, compounds are provided that are represented by Formula (I-C):

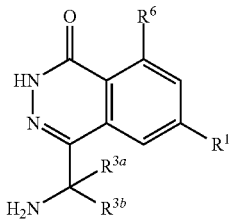

Formula (I-C)

or a pharmaceutically acceptable salt thereof, wherein $R^1$, $R^2$, $R^{3a}$, $R^{3b}$, $R^4$, $R^5$, $R^6$, Y, X, Z and L are as each defined for Formula I.

In another aspect of the invention, compounds are provided that are represented by Formula (I-D):

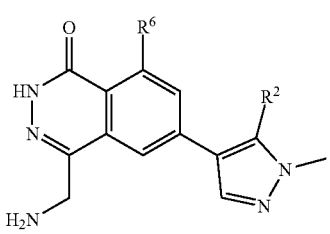

Formula (I-D)

or a pharmaceutically acceptable salt thereof:

wherein:

each Y is independently a bond or —$NR^4$—;

each $R^2$ is independently hydroxy, halogen, cyano, cyanomethyl, —$(NR^4)_2$, hydroxyalkyl, alkoxy, —$SO_2$C1-C3alkyl, —X-arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$, or;

each X is independently a bond, O, S, —$NR^4$— or —$NR^4$C(O)—;

each Z is independently a bond, —SO—, —$SO_2$—, —CH(OH)— or —C(O)—;

each L is independently a bond or C1-C3 alkylene;

each $R^4$ is independently hydrogen or C1-C3 alkyl;

each $R^5$ is independently cyano, oxo, halogen, C1-C3 alkyl, hydroxyalkyl, alkoxy, —X-haloalkyl, —Z-cycloalkyl, —X-arC1-C3alkyl, X-arC1-C3alkyl substituted with cyano, —X-L-cycloalkyl, —X-L-heteroaryl optionally substituted with one or more C1-C3alkyl or oxo, or —X-aryl; and $R^6$ is hydrogen, halogen, C1-C3 alkyl, haloalkyl or alkoxy.

In one embodiment, the compound of Formula (I), Formula (I-A), Formula (I-B), and/or Formula (I-C) is:

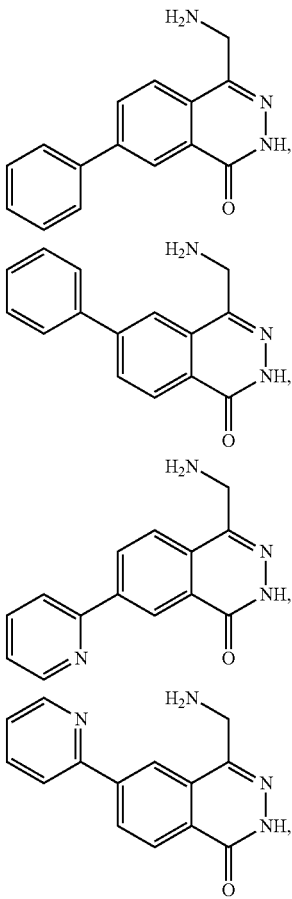

-continued
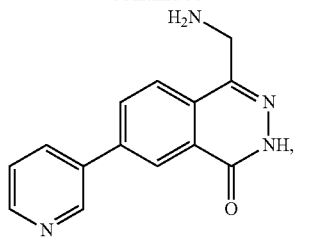
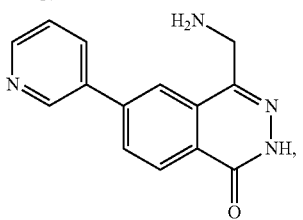
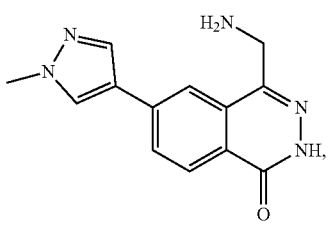
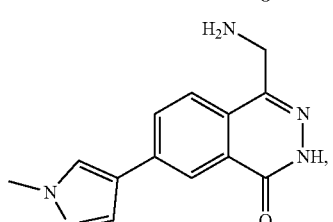
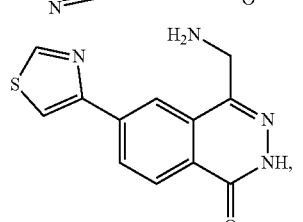
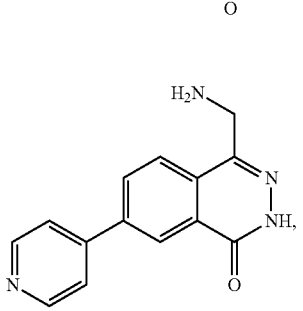
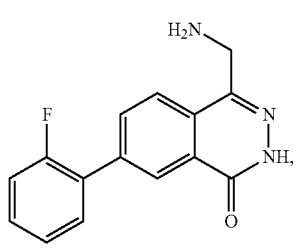
-continued
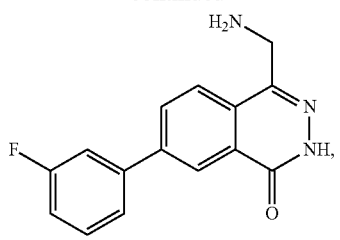
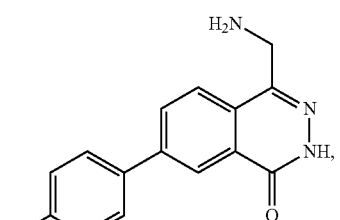
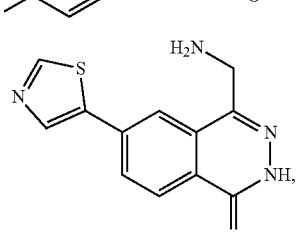
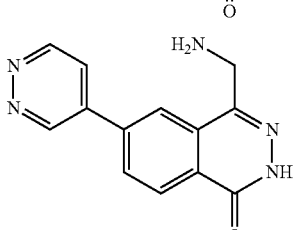
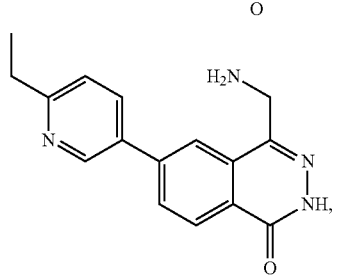
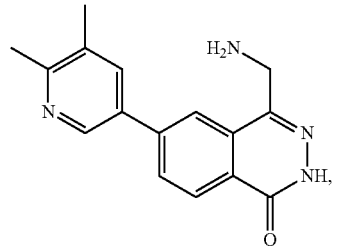
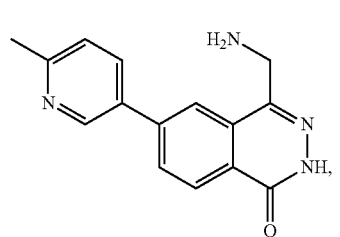

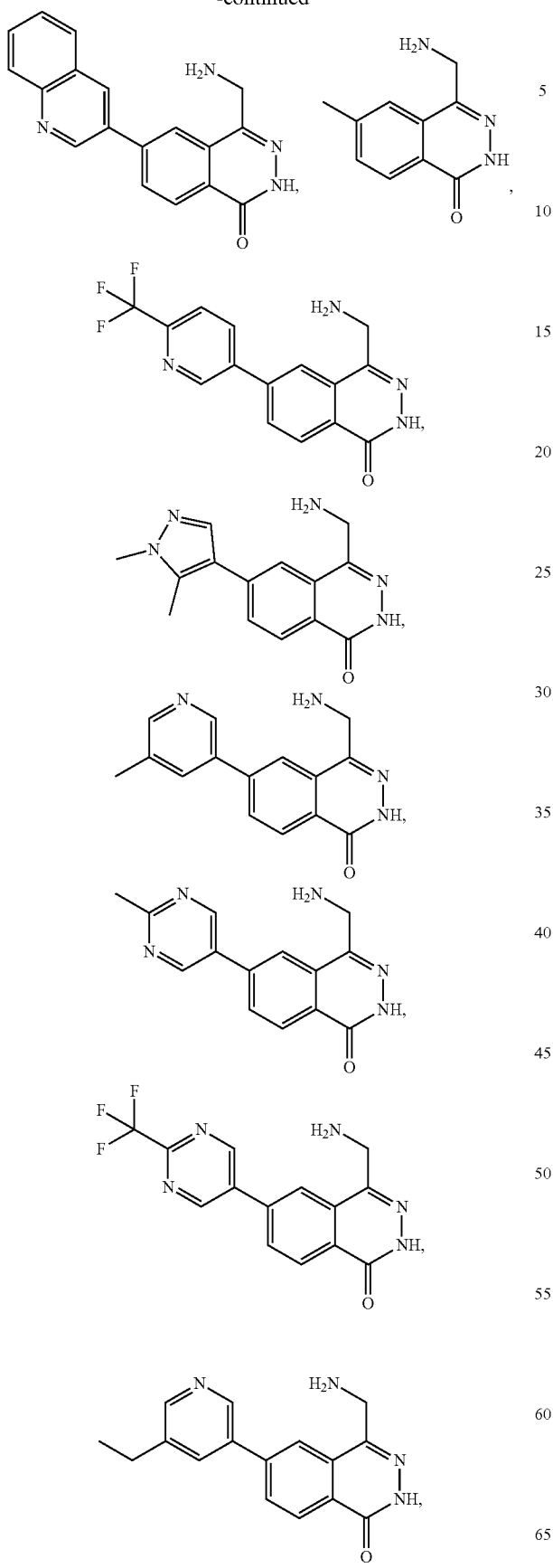
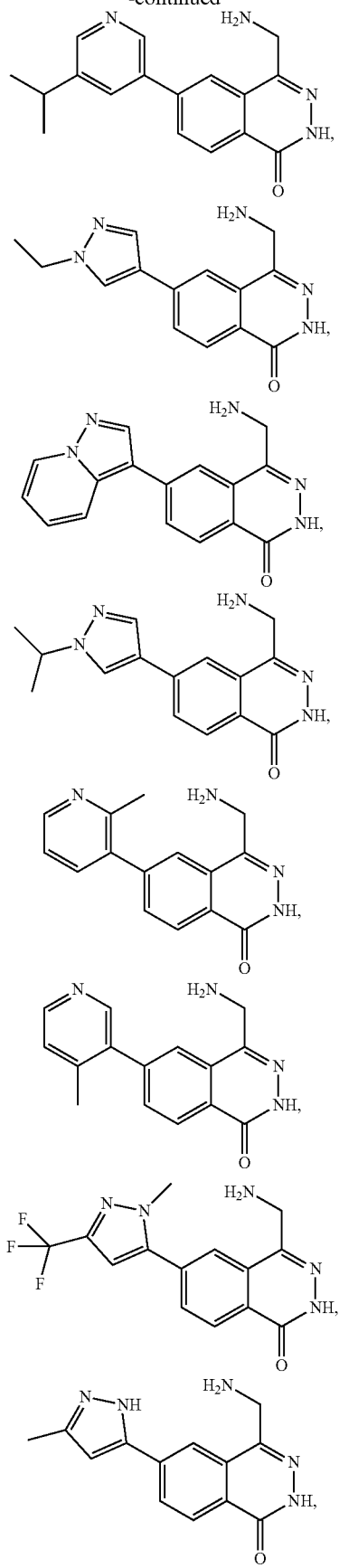

-continued
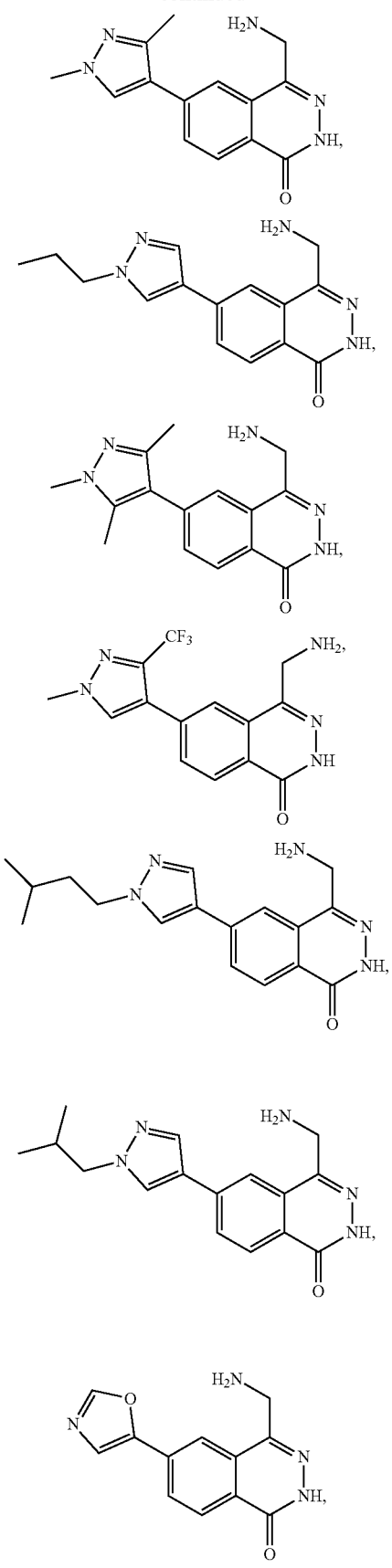
-continued
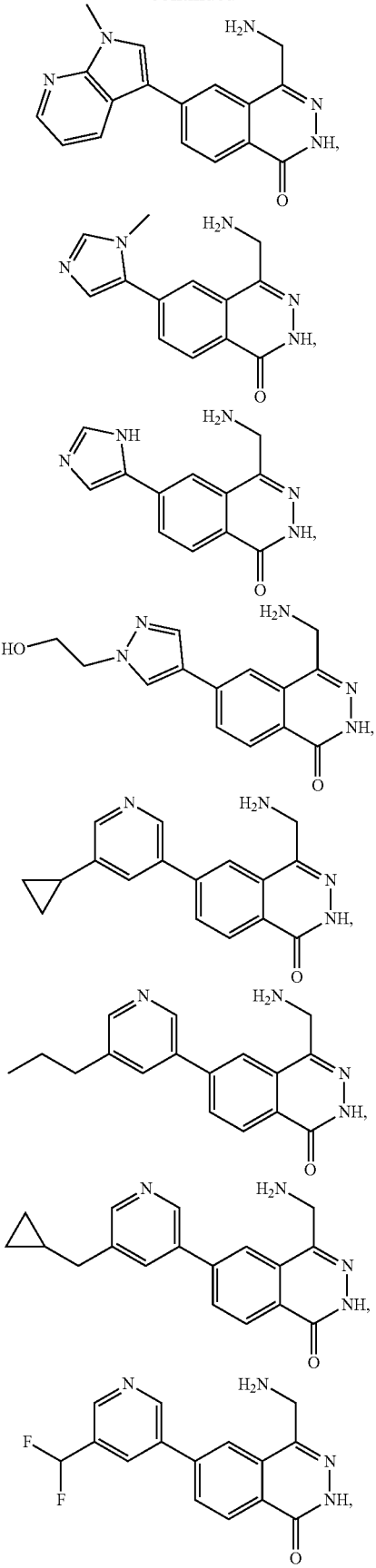

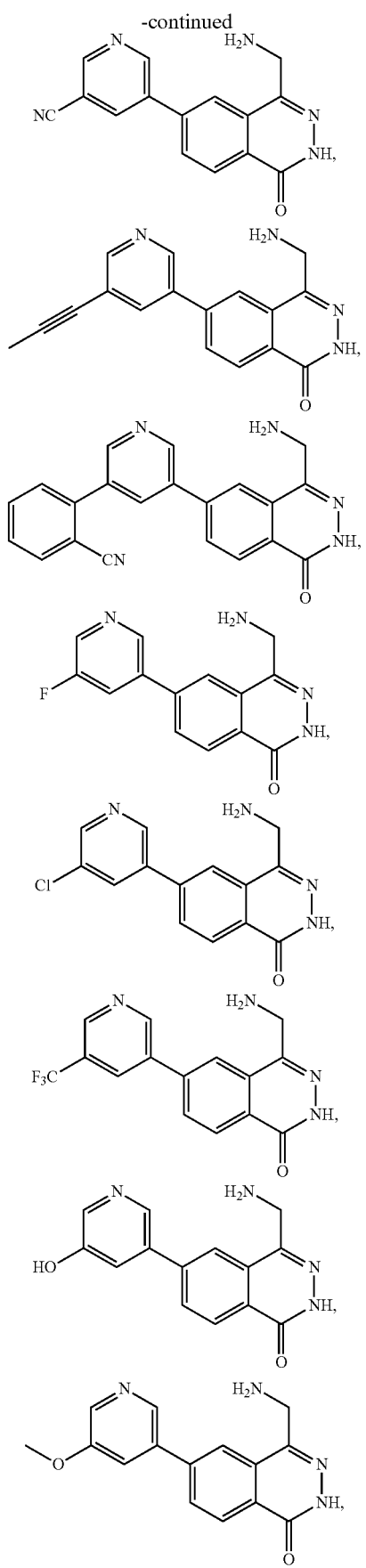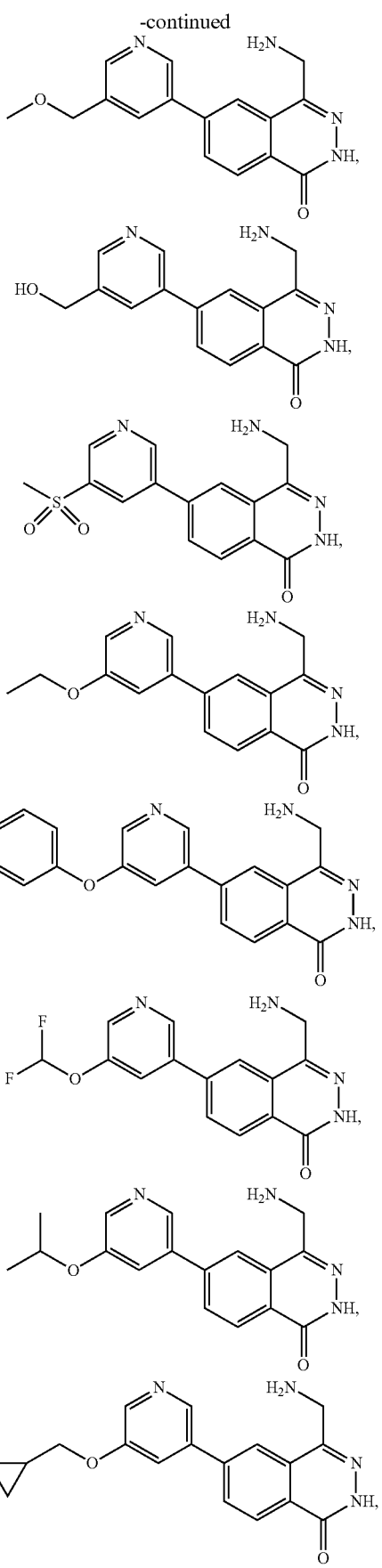

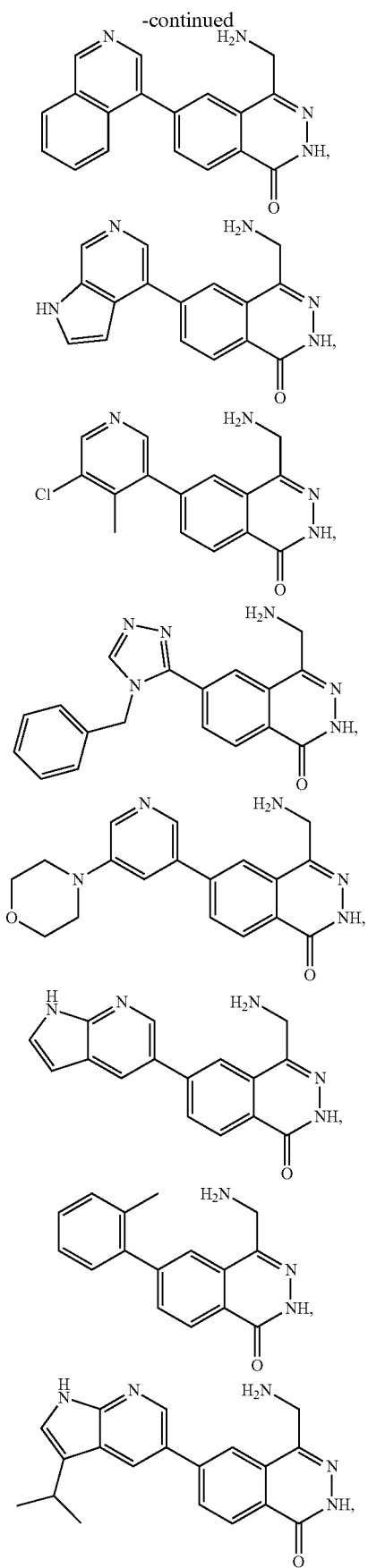
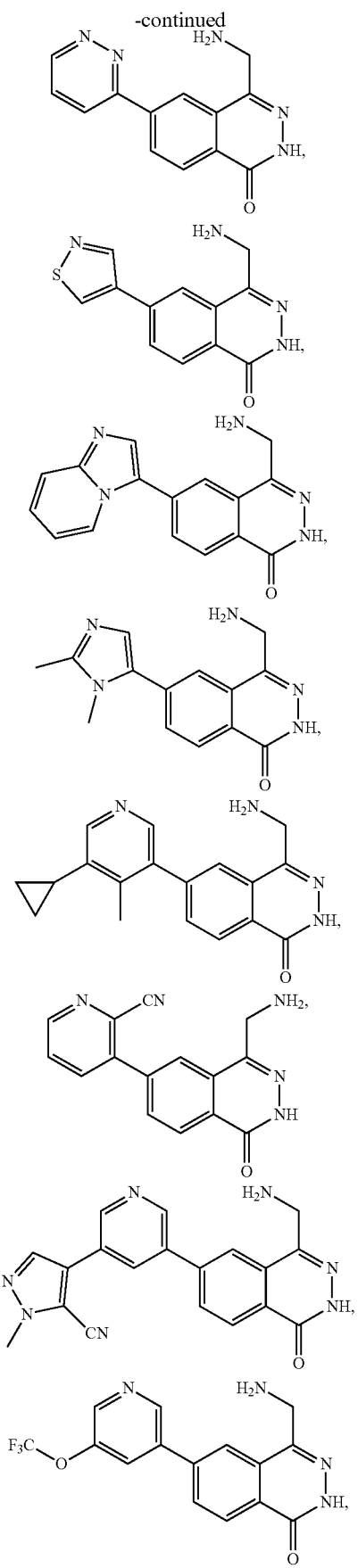

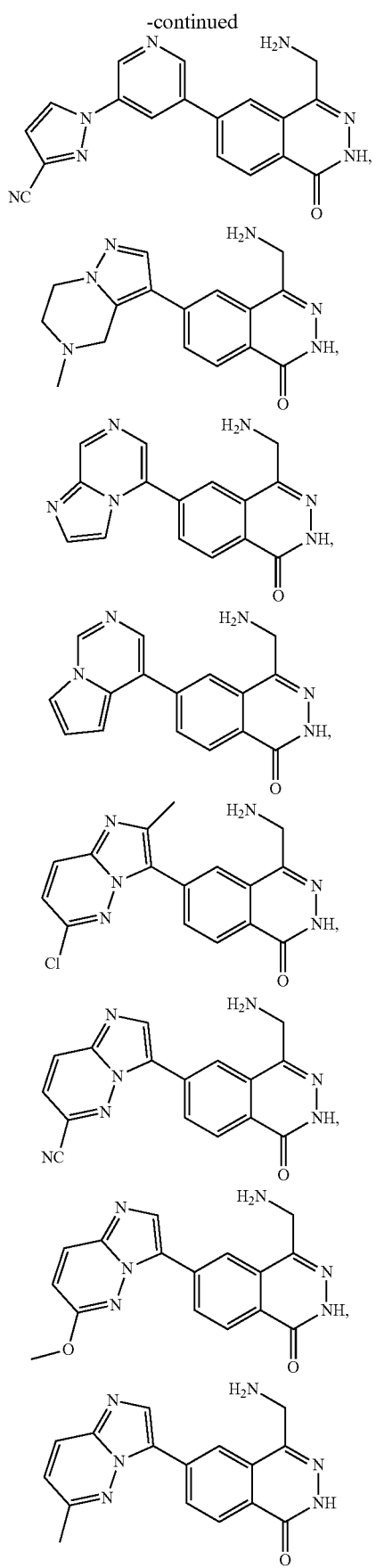
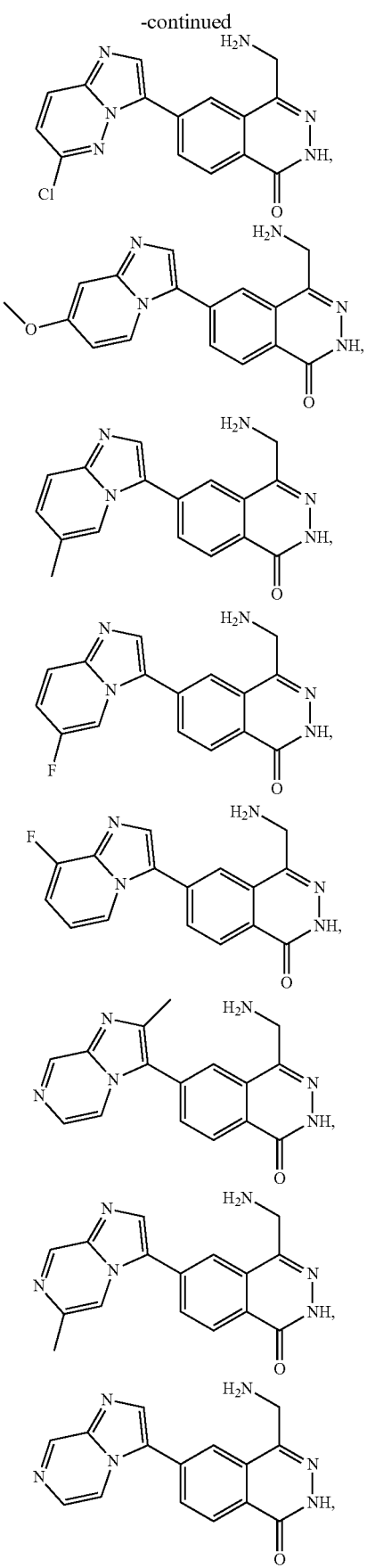

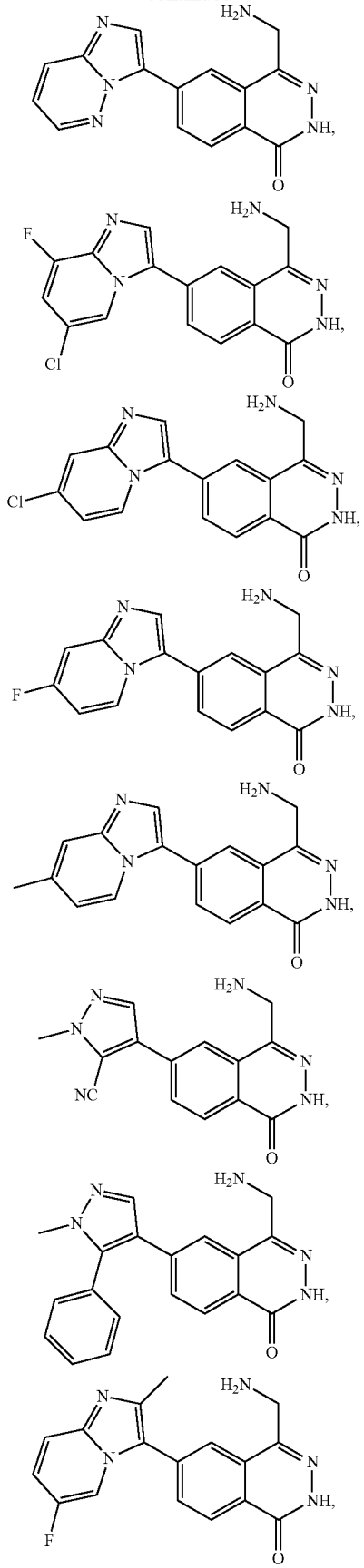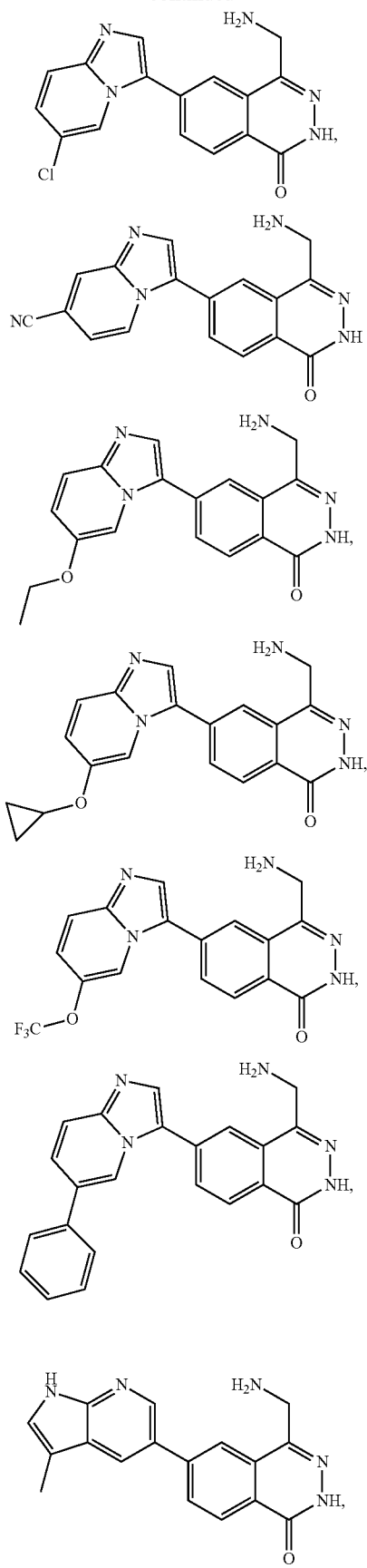

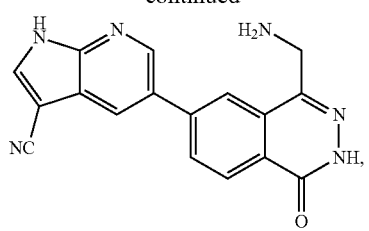

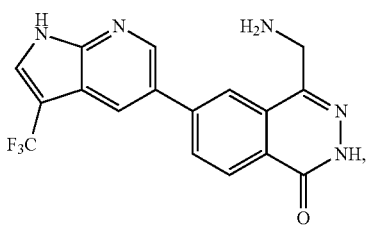
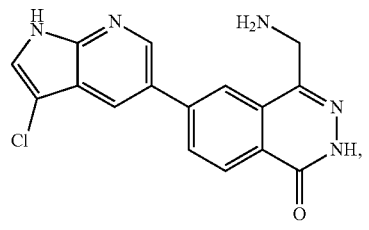
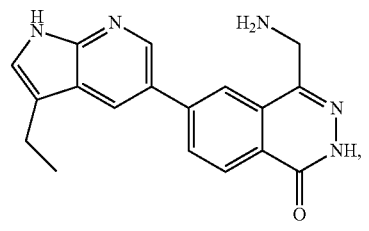
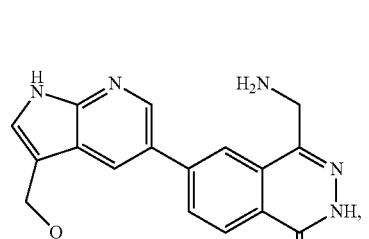
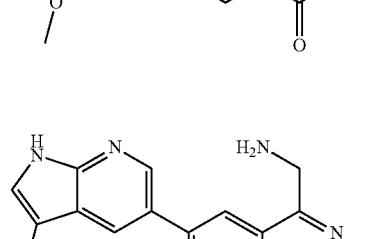
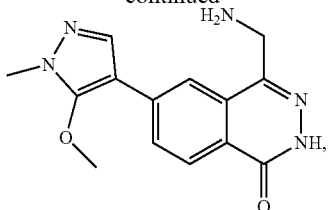
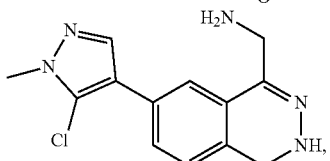
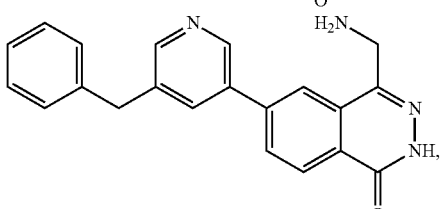
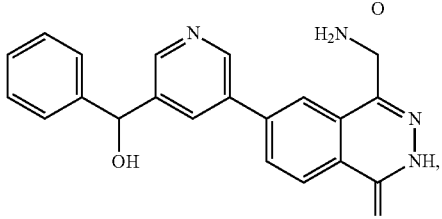
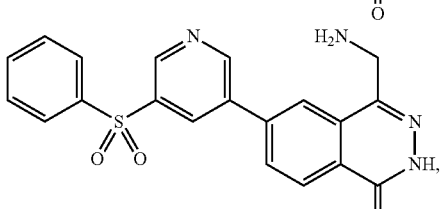
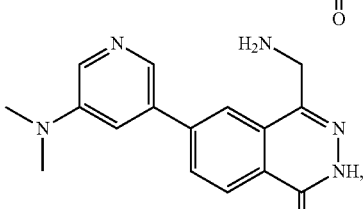
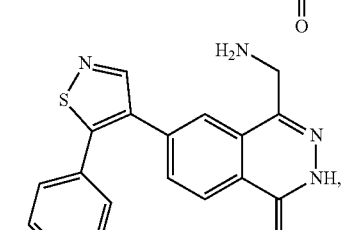
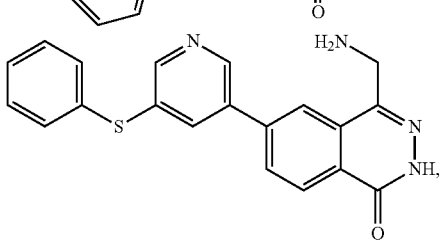

-continued
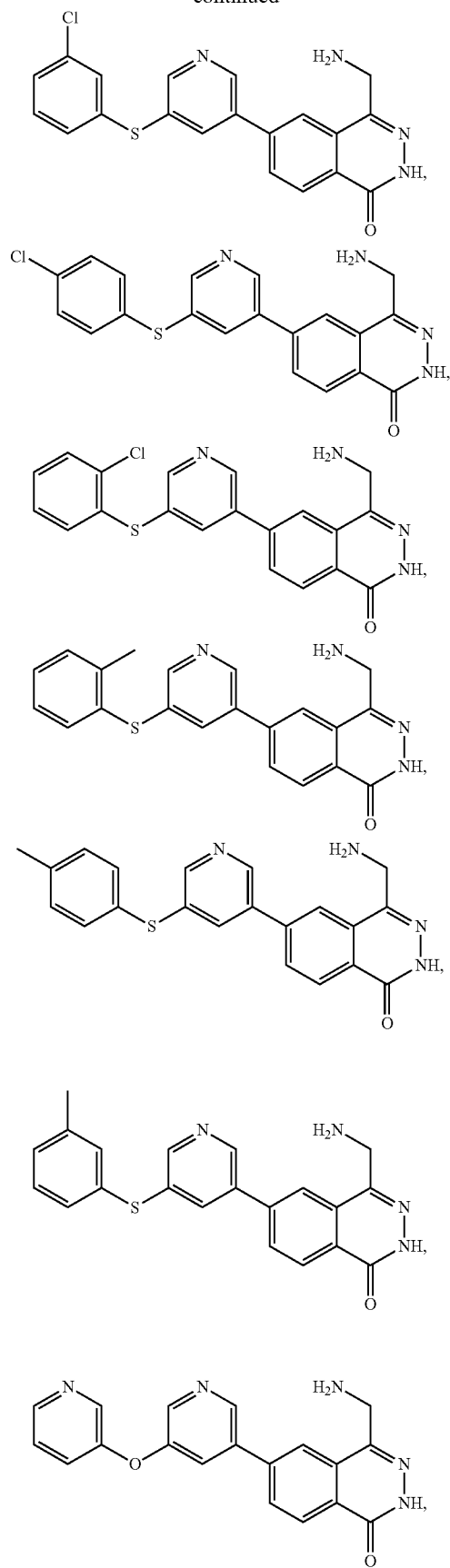
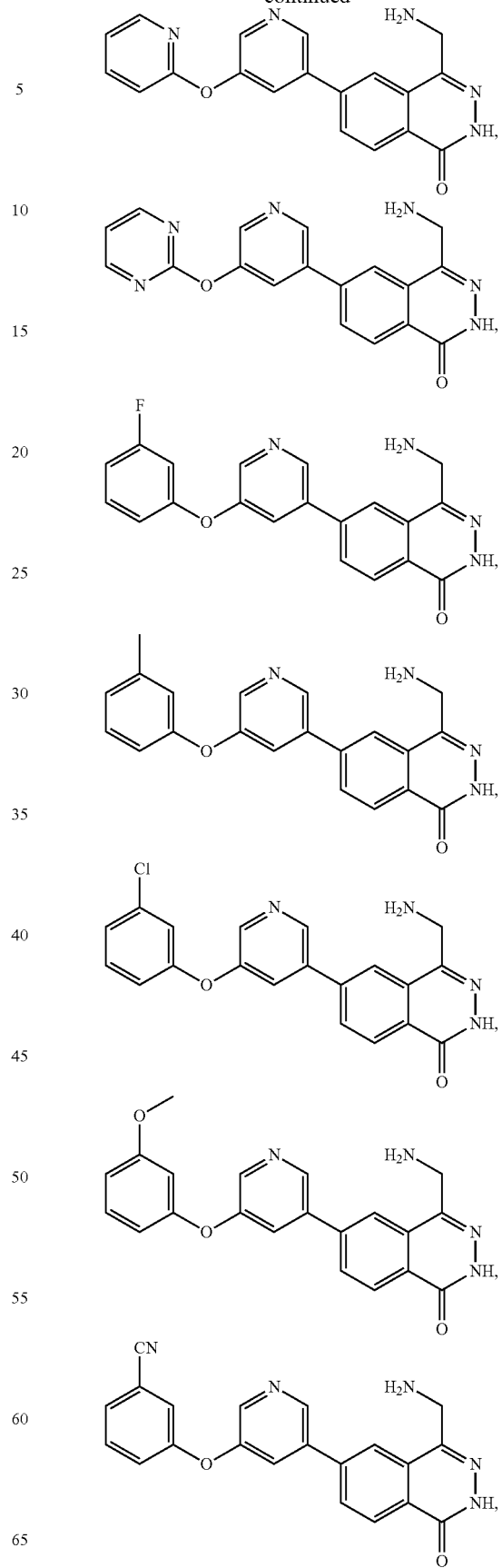

33
-continued
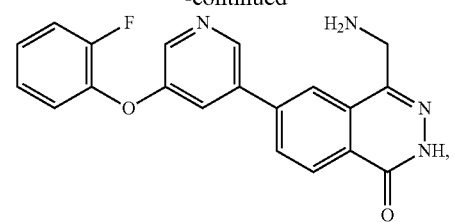
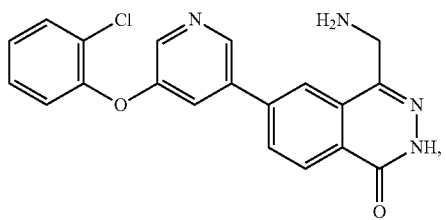
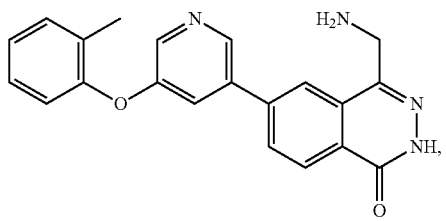
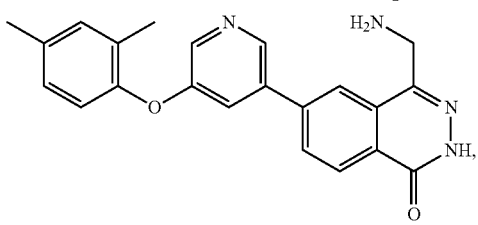
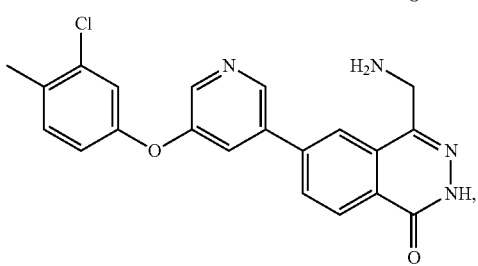
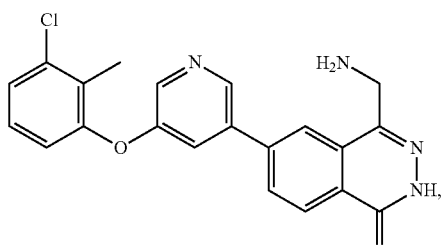
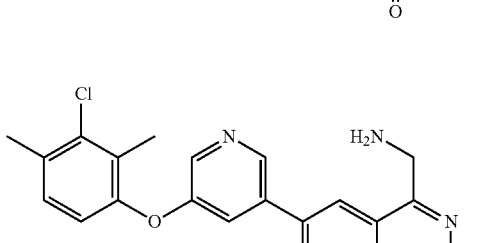
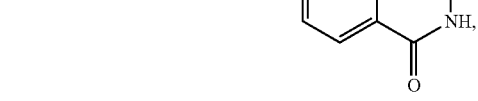
34
-continued
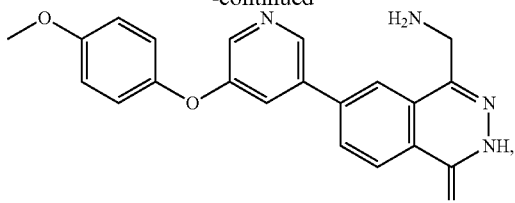
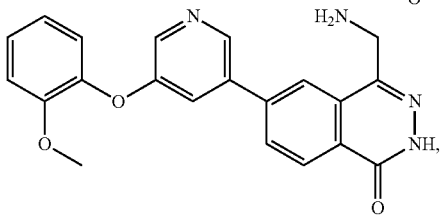
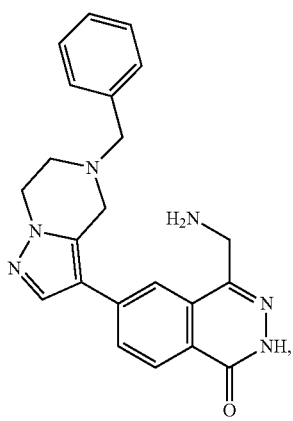
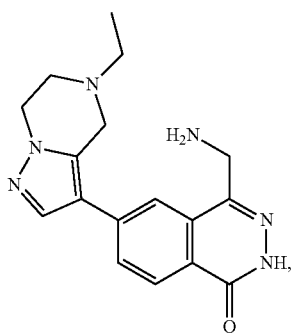
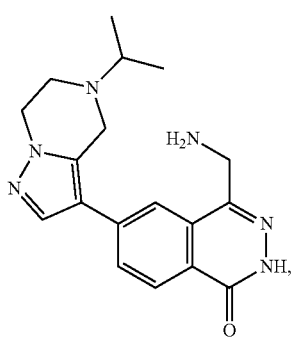

-continued
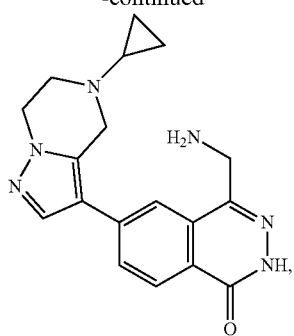
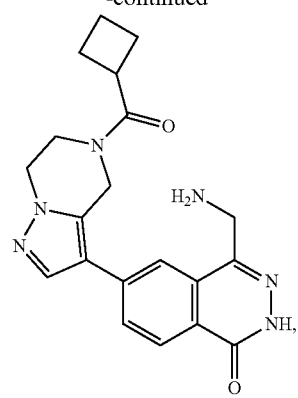
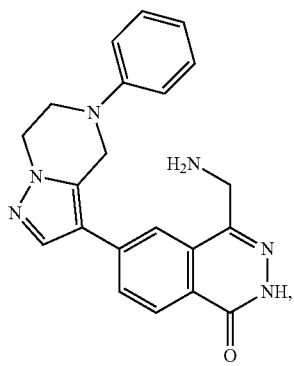
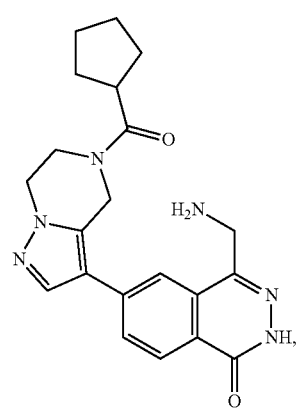
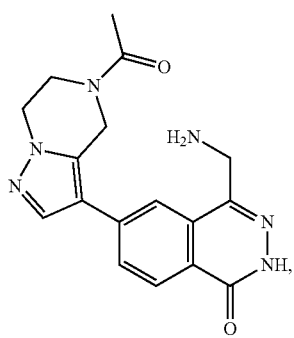
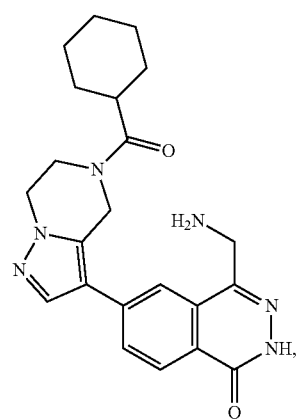
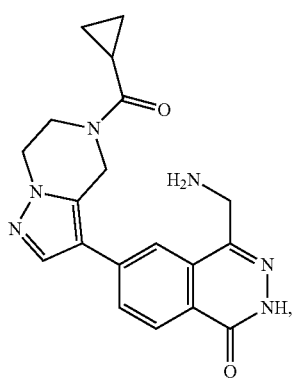
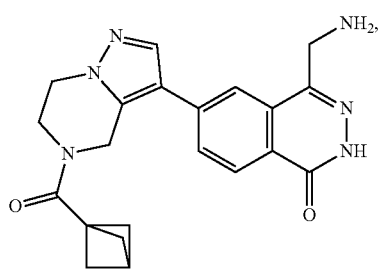

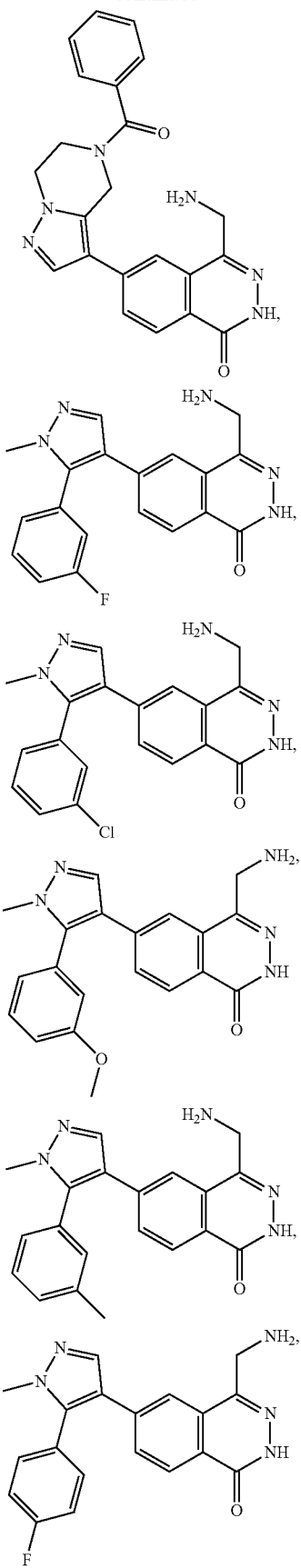
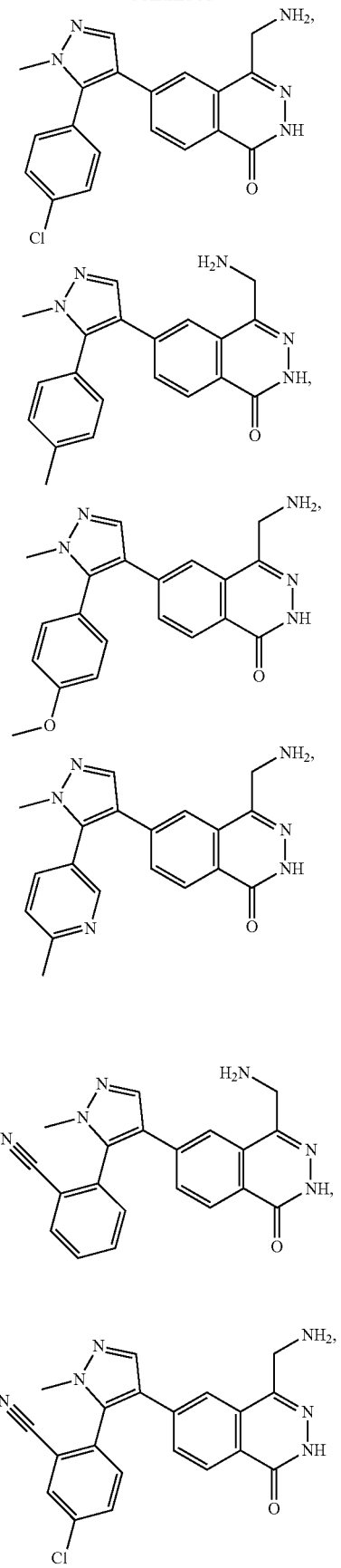

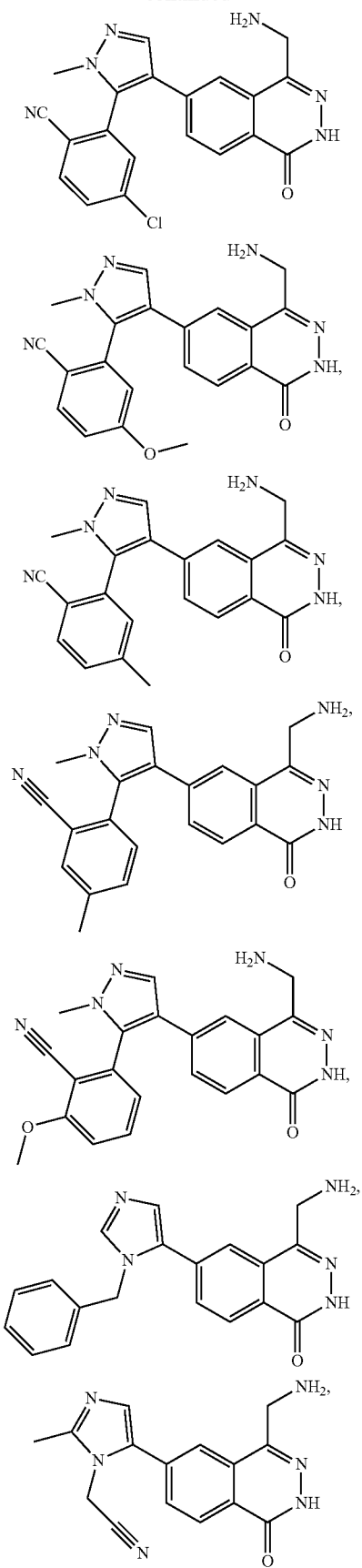
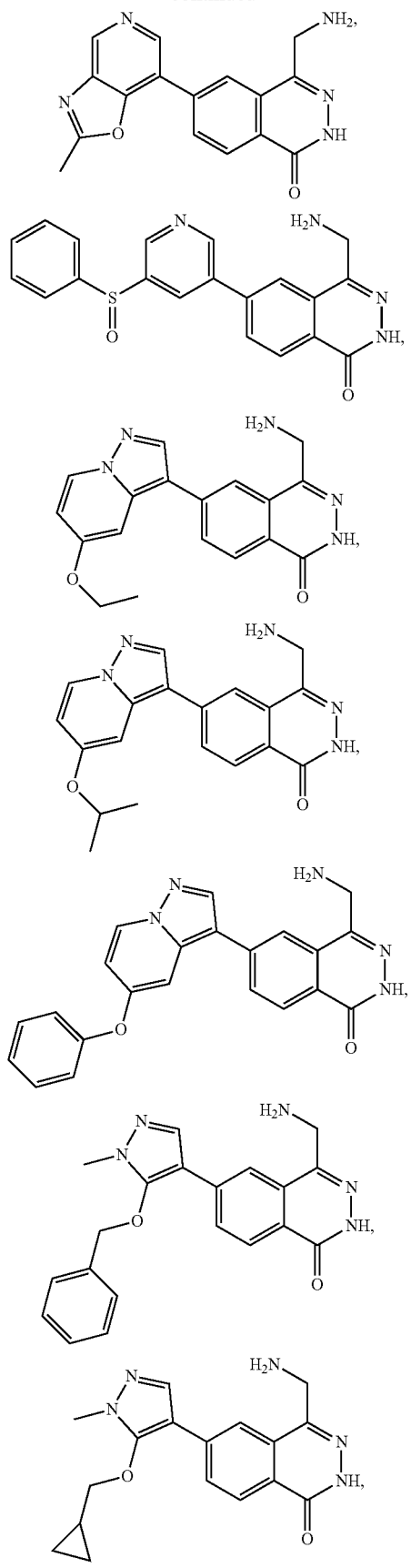

-continued
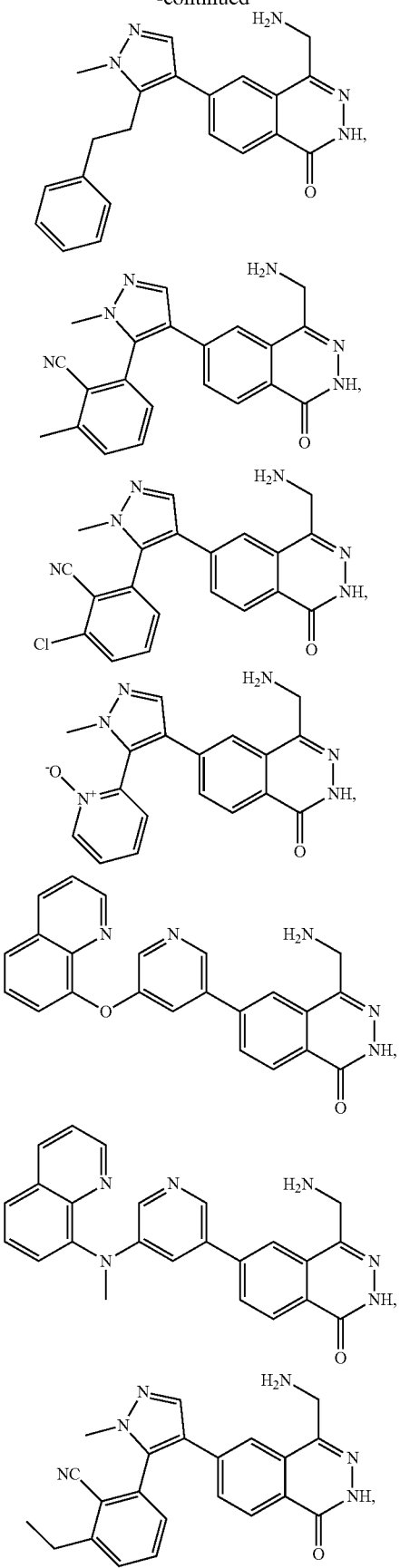
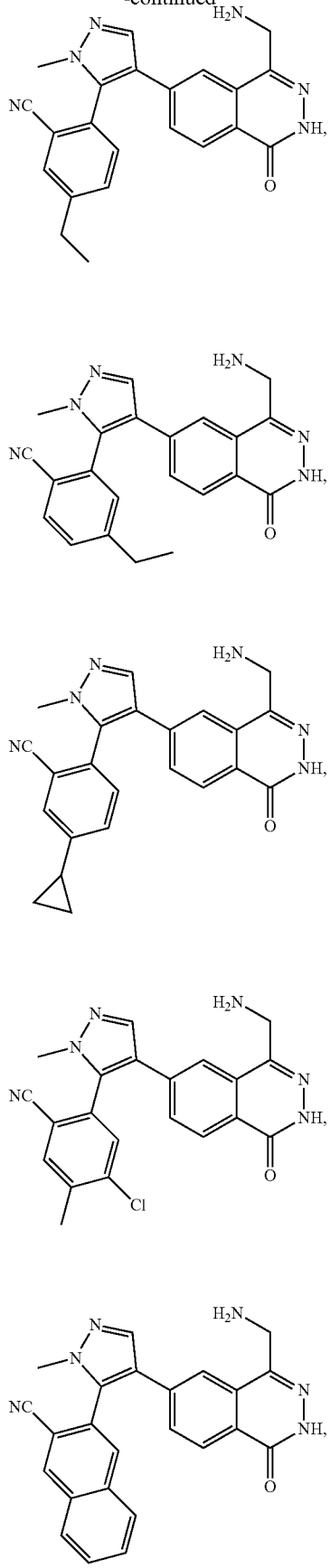

-continued
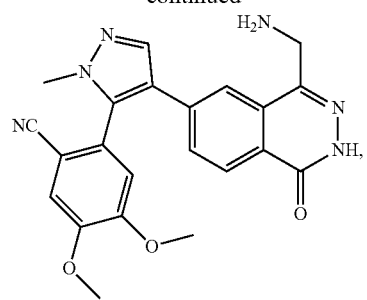
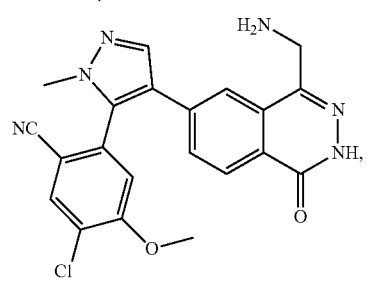
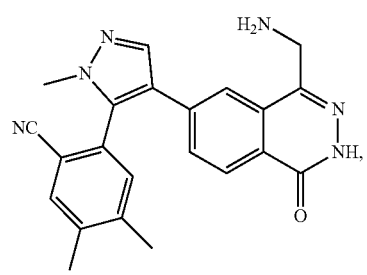
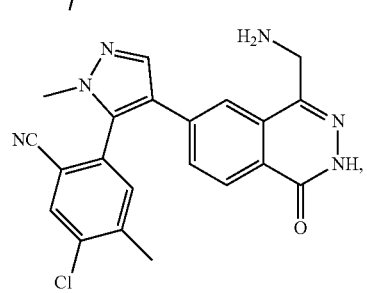
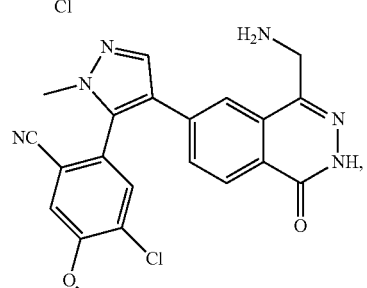
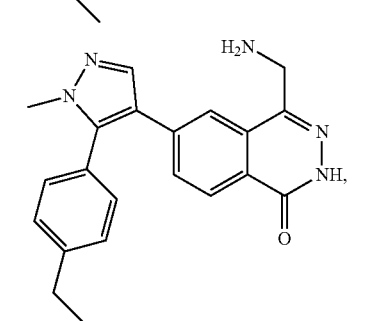
-continued
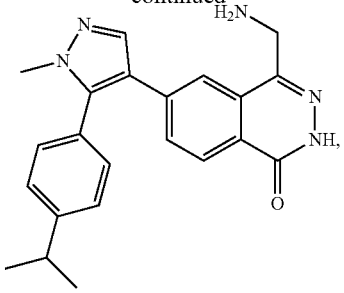
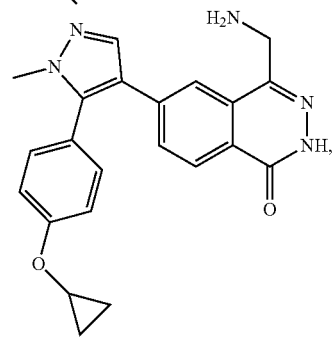
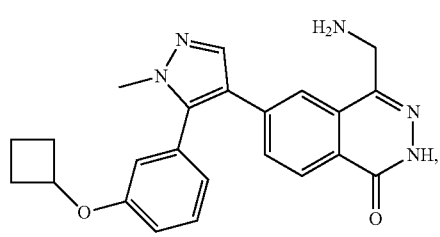
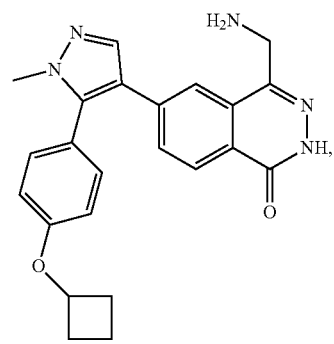
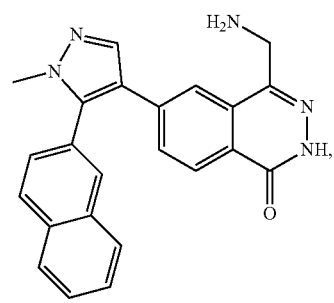

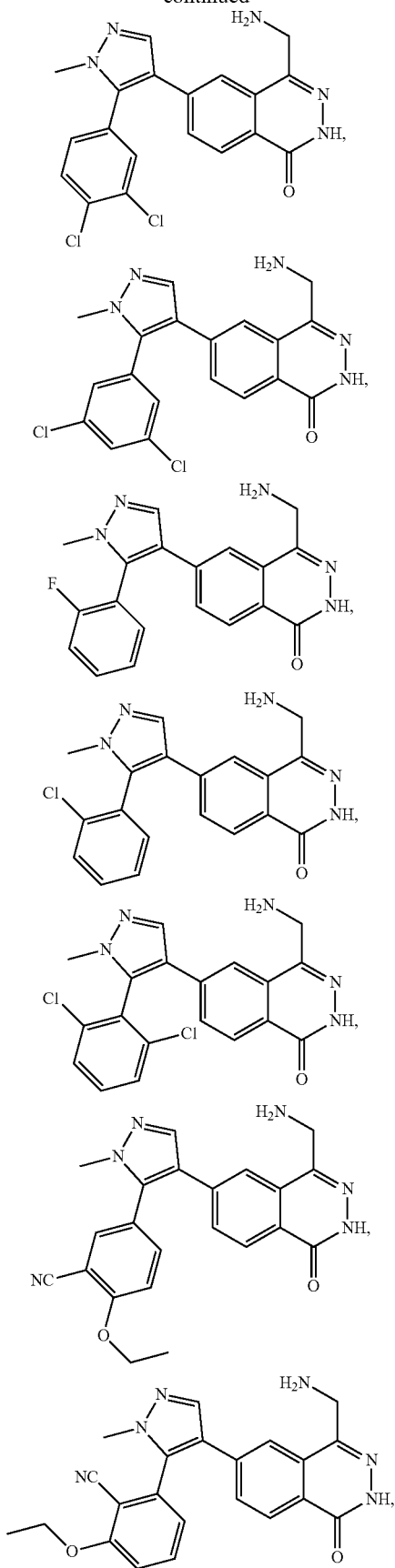
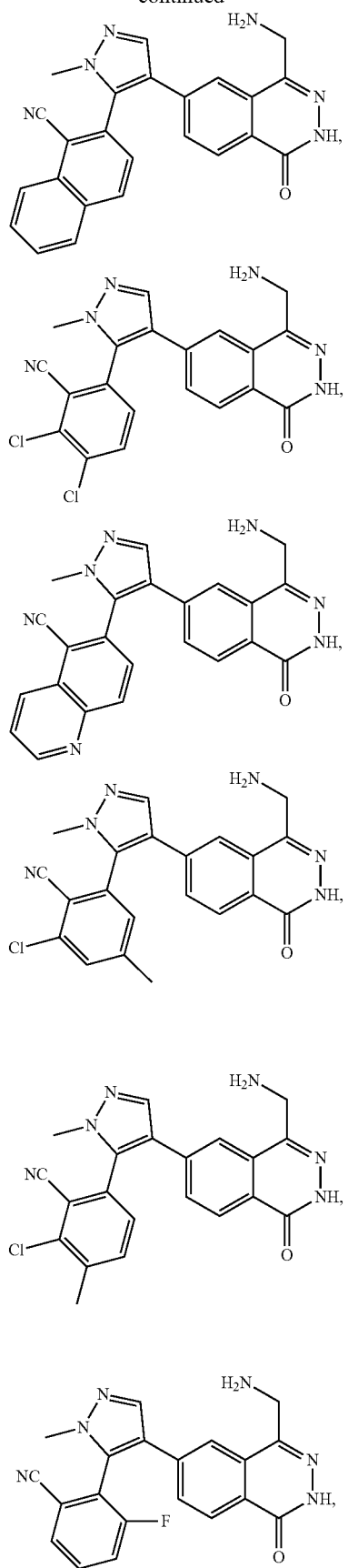

-continued
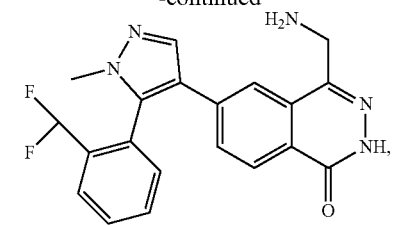
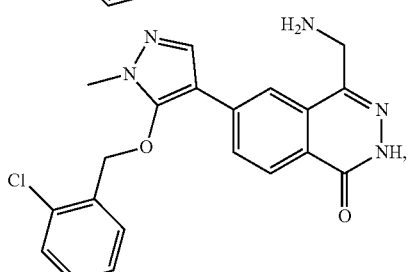
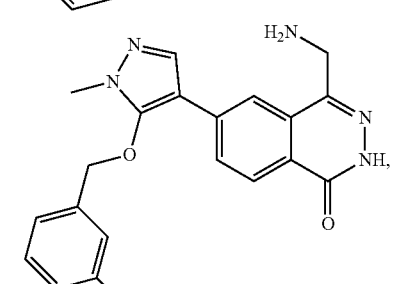
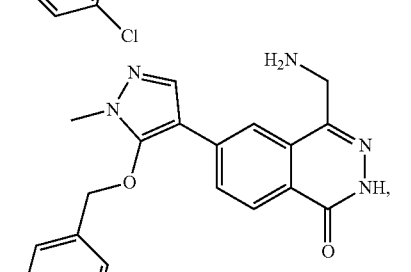
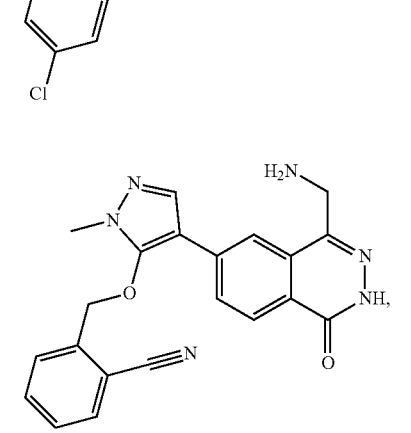
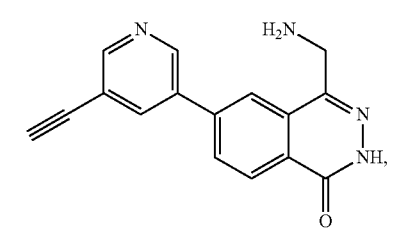
-continued
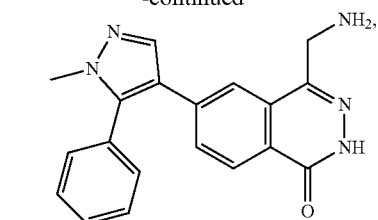
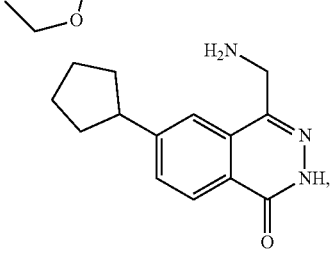
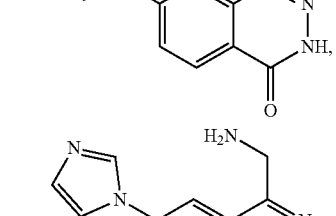
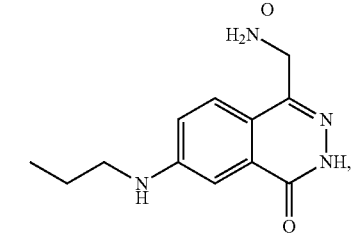
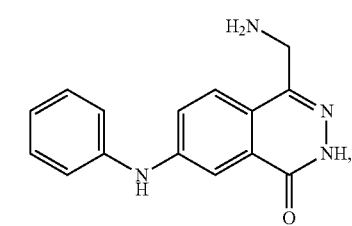
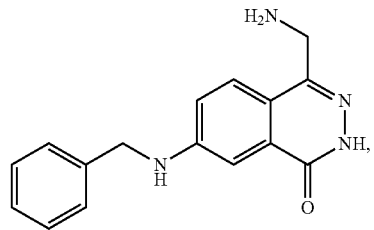

49
-continued
50
-continued
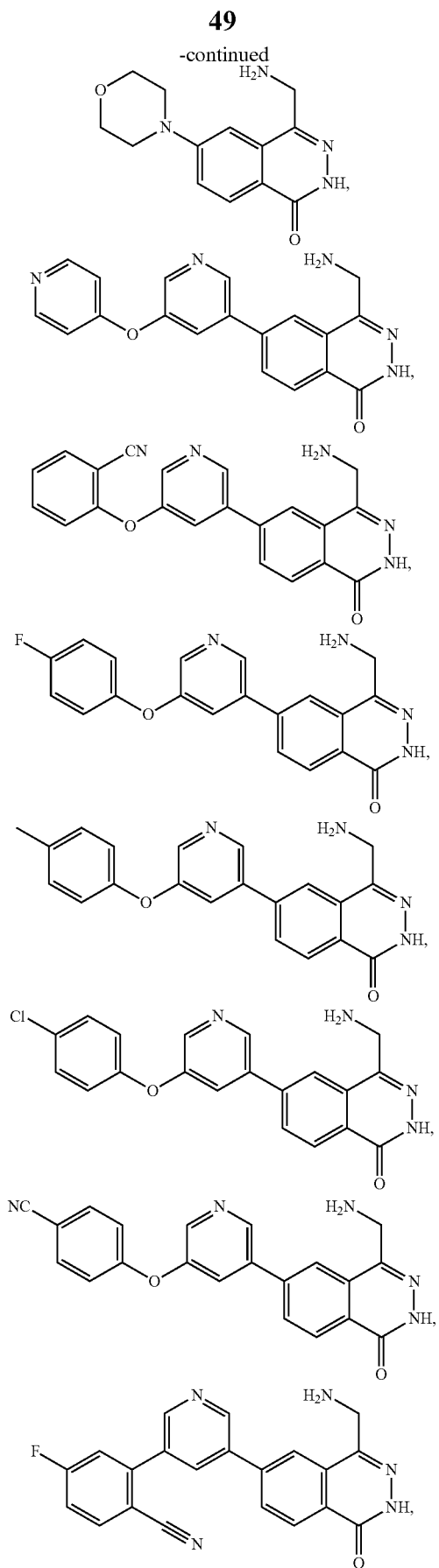
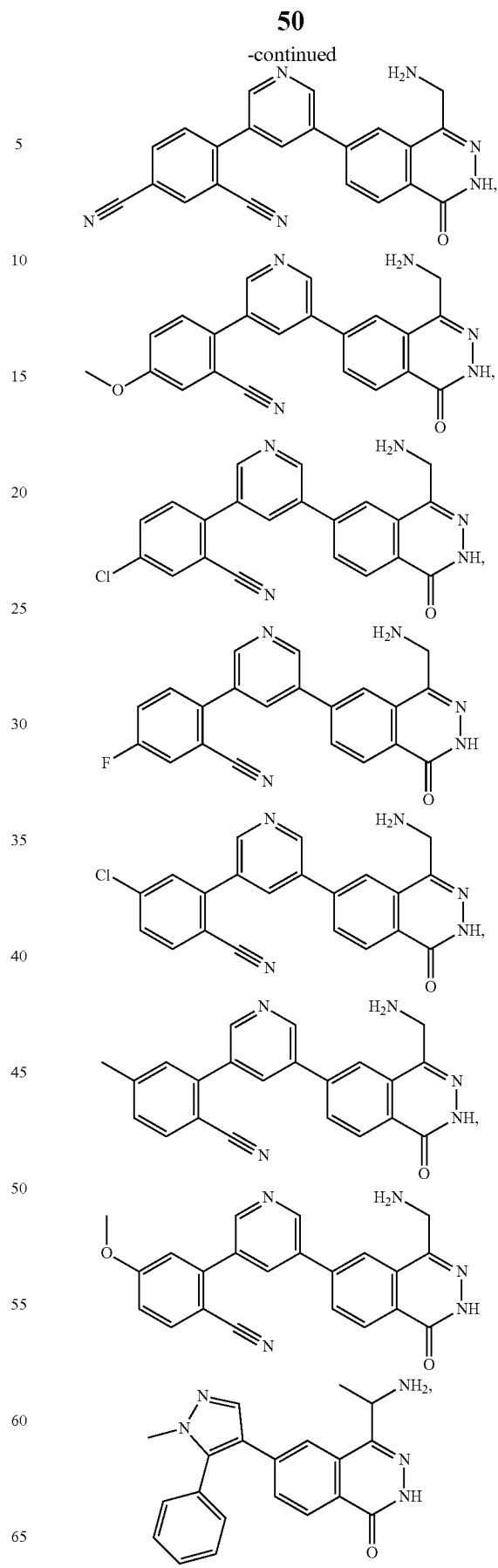

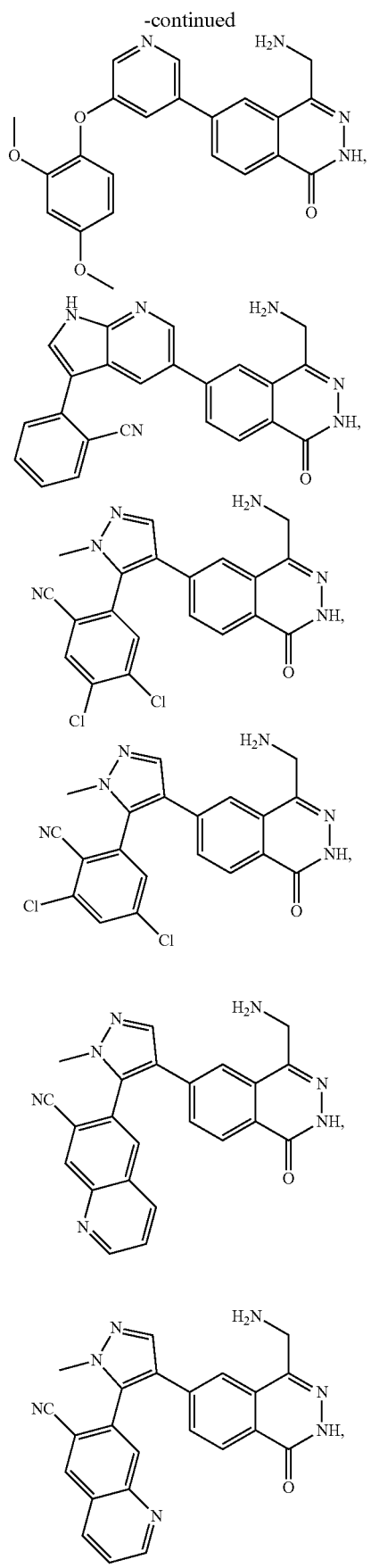
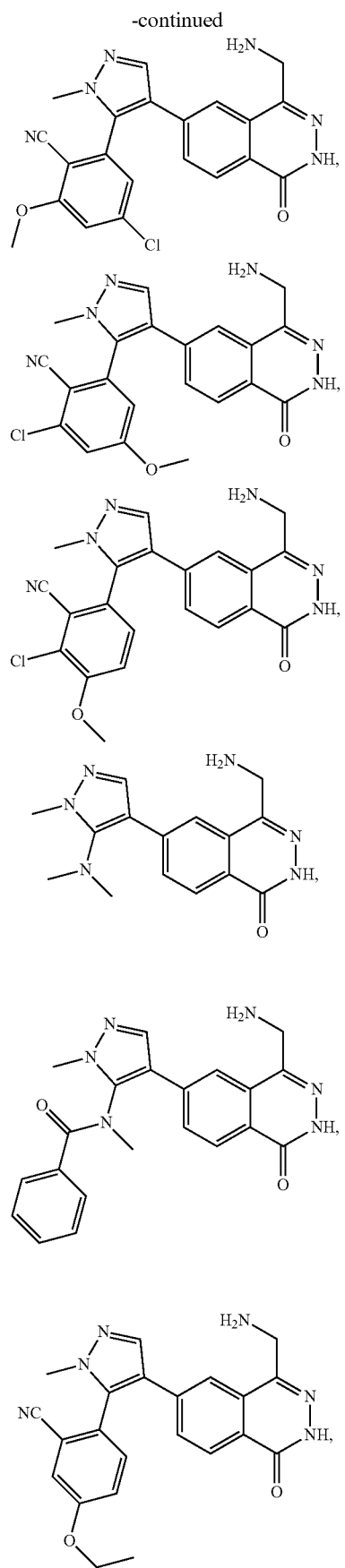

53
-continued
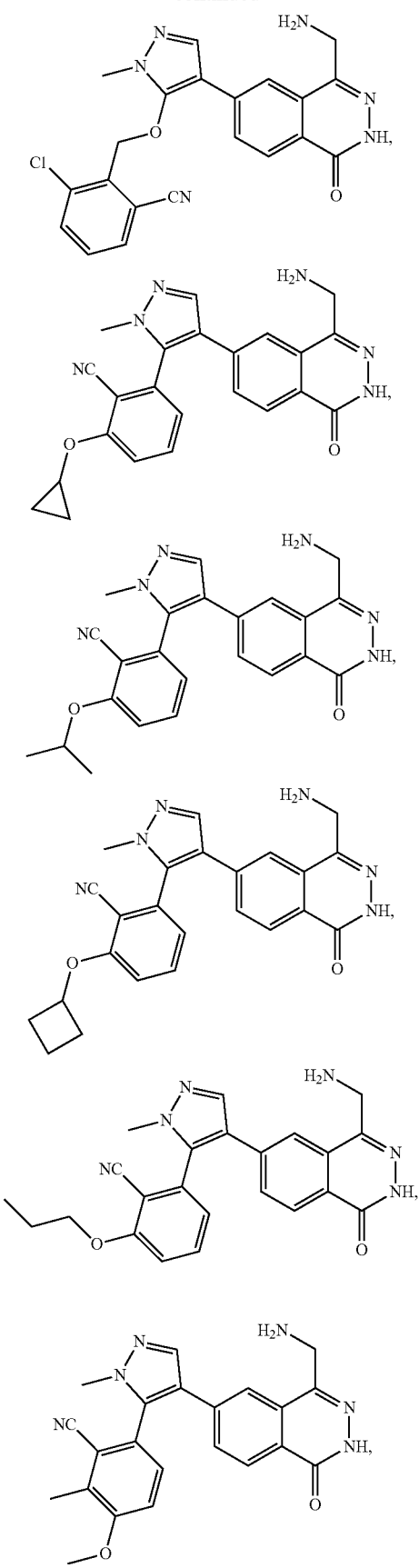
54
-continued
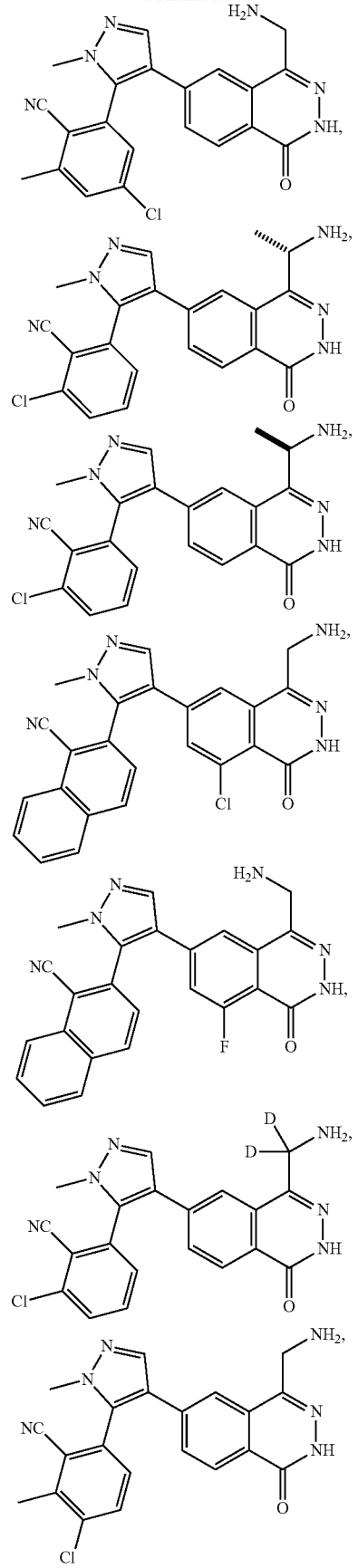

-continued
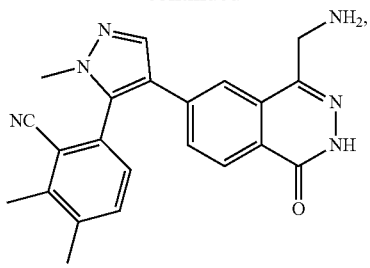
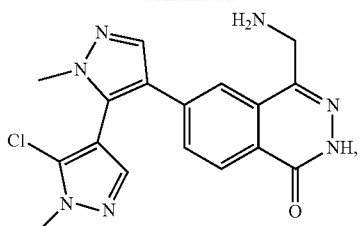
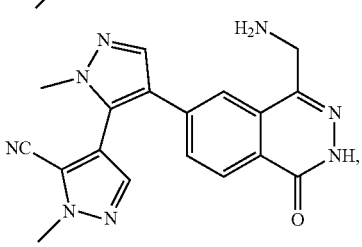
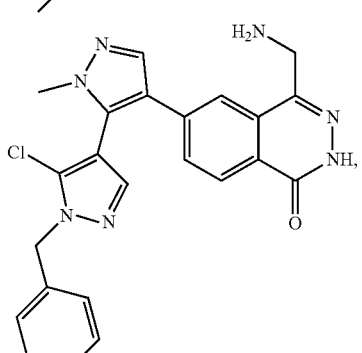
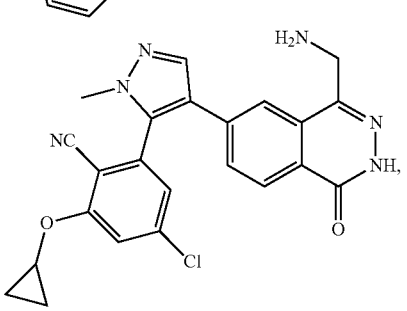
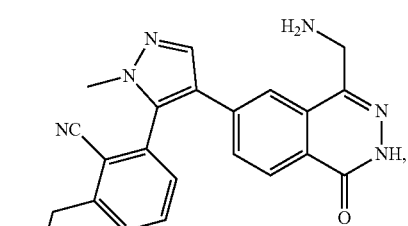
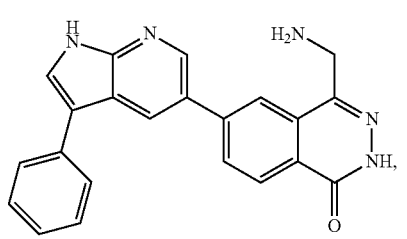

57
-continued
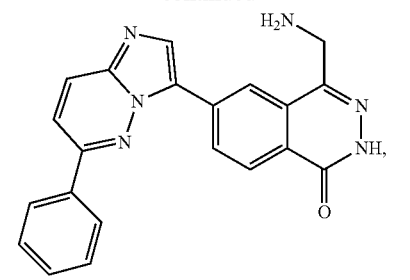
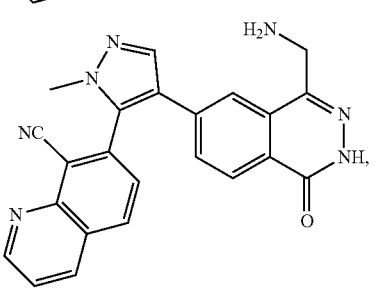
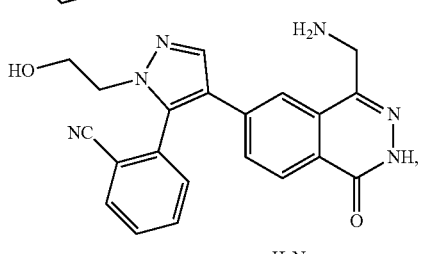
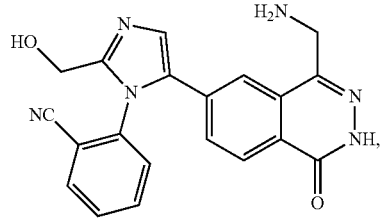
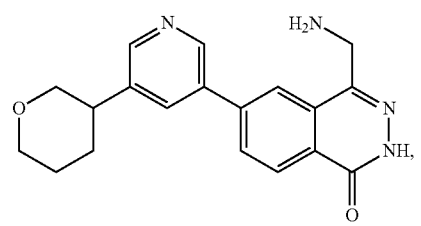
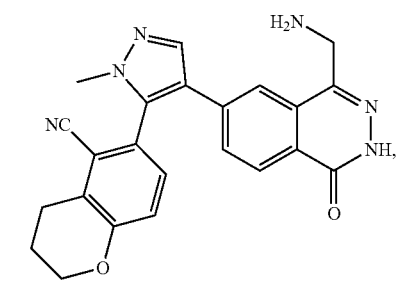
58
-continued
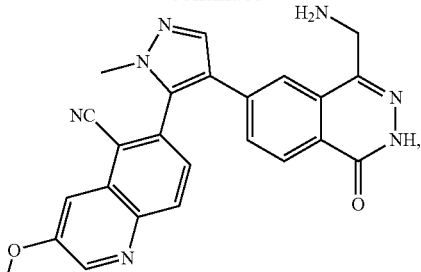
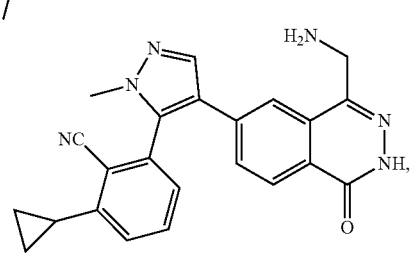
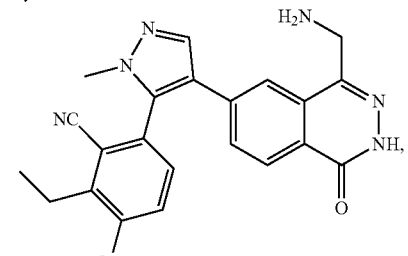
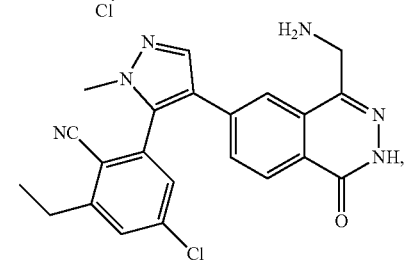
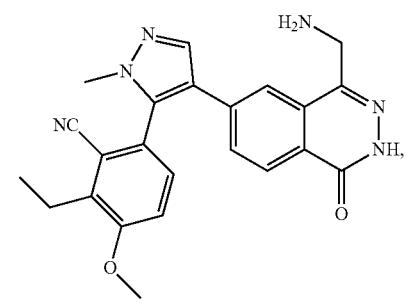
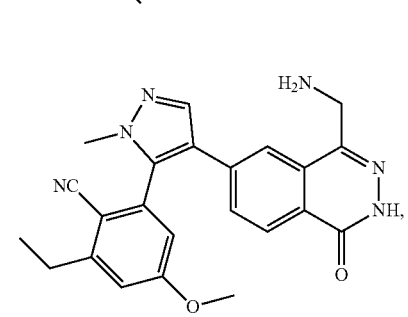

59
-continued
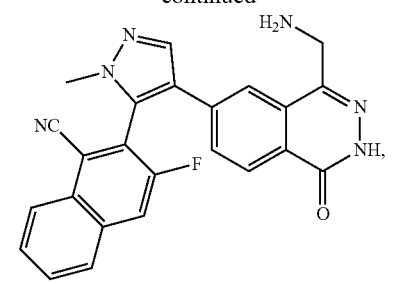
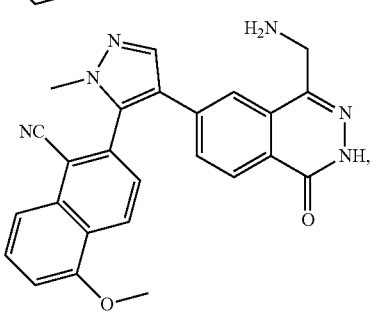
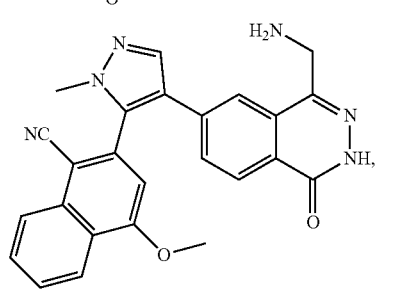
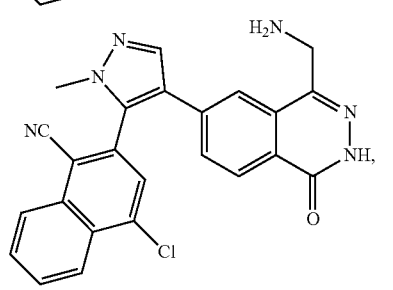
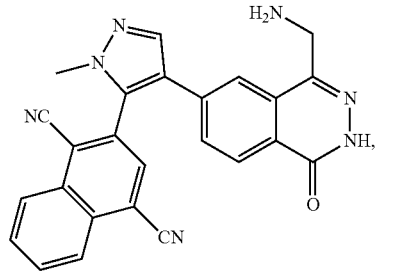
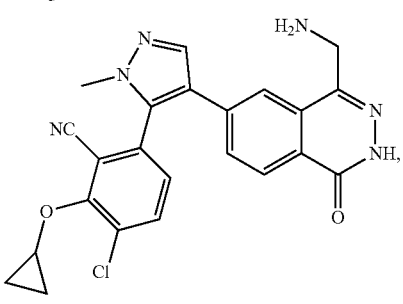
60
-continued
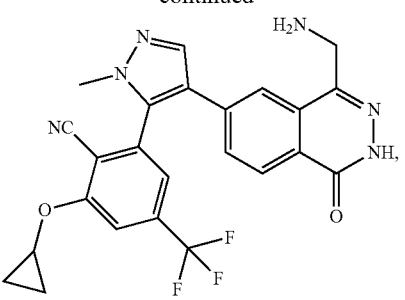
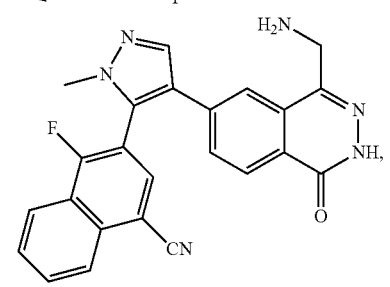
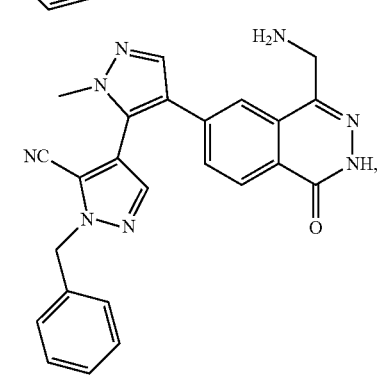
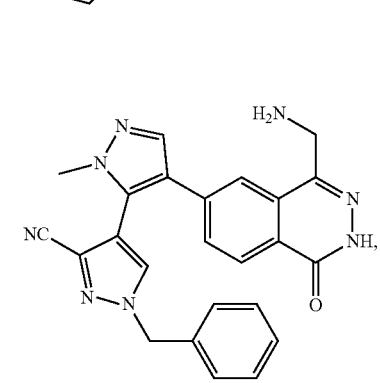
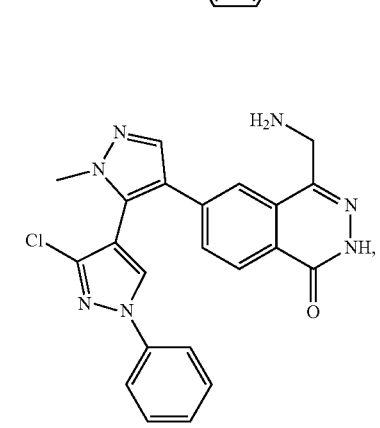

-continued
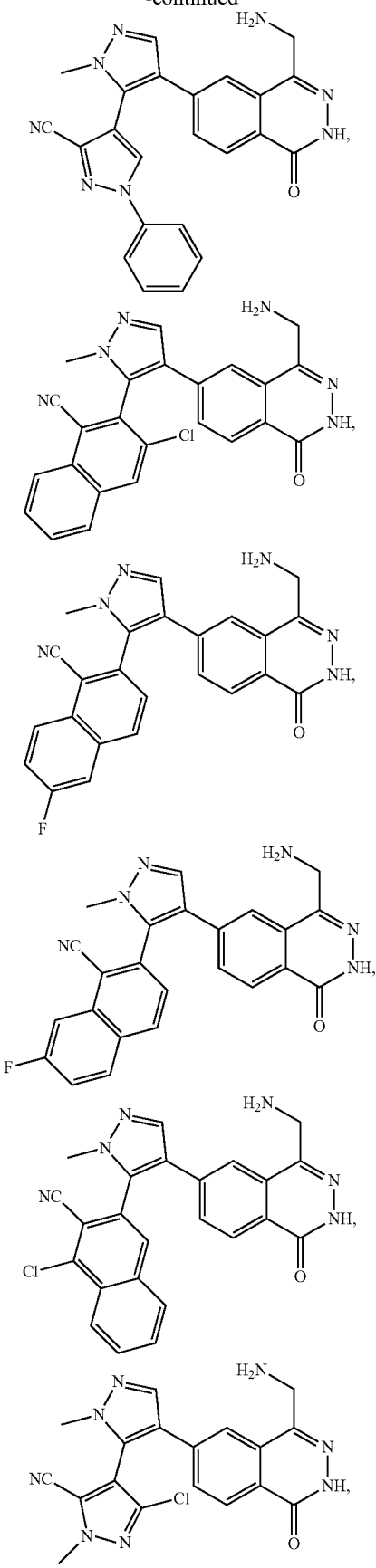
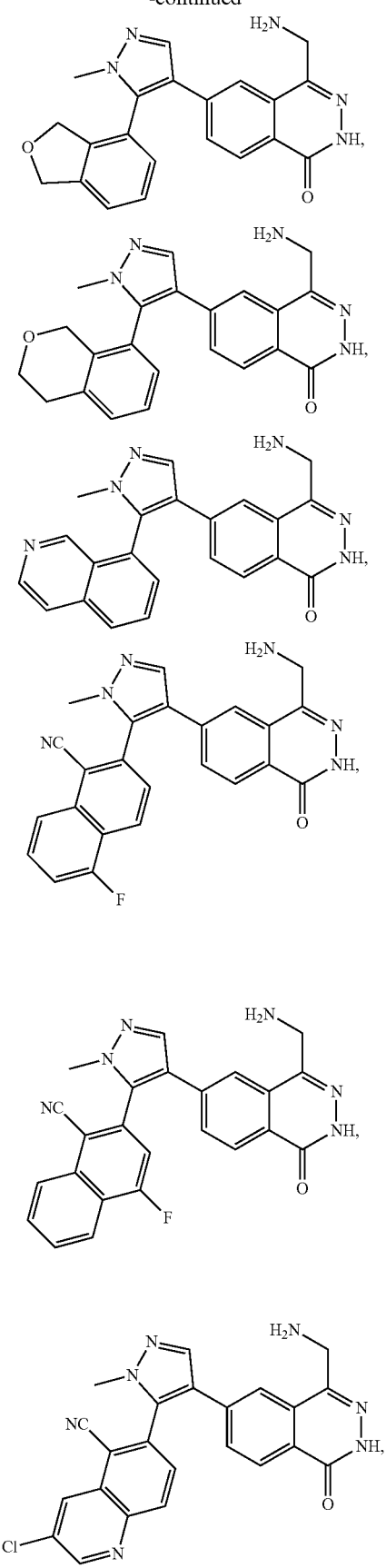

63
-continued
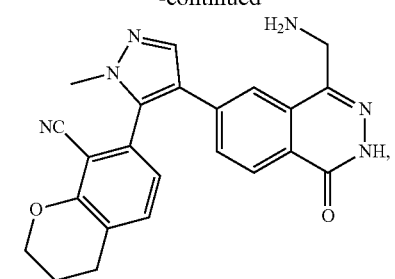
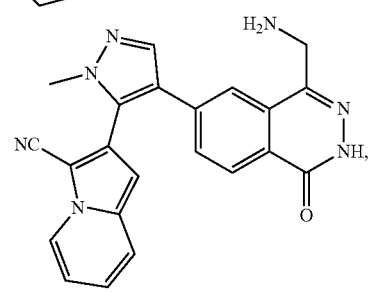
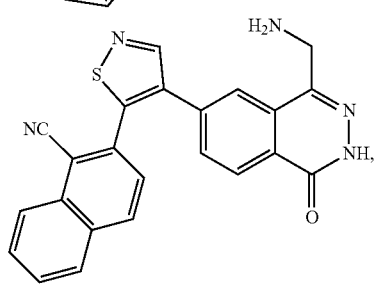
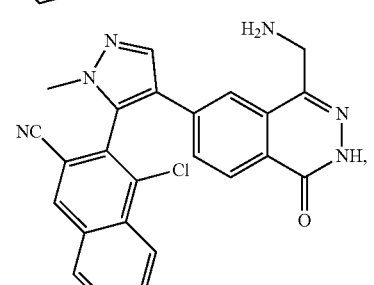
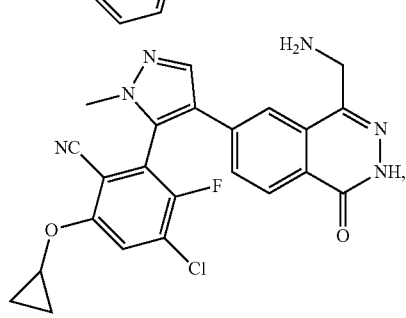
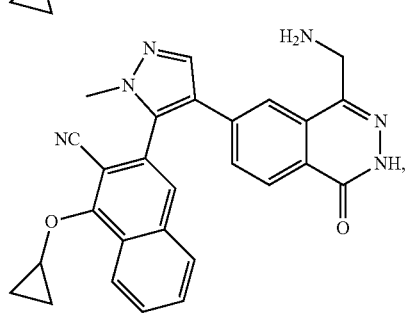
64
-continued
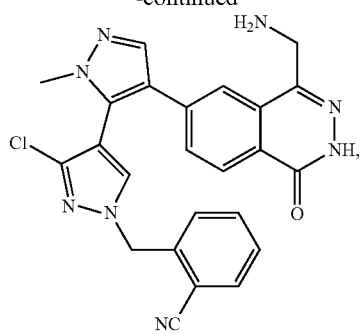
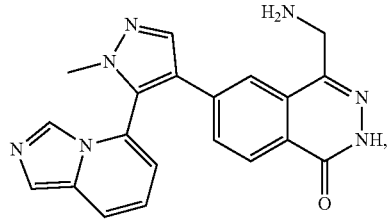
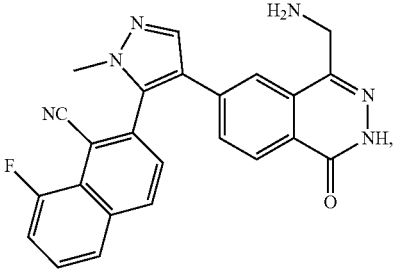
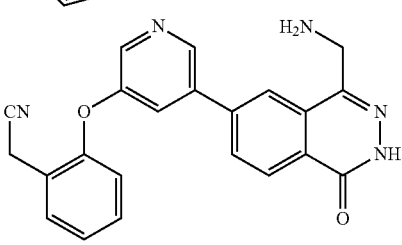
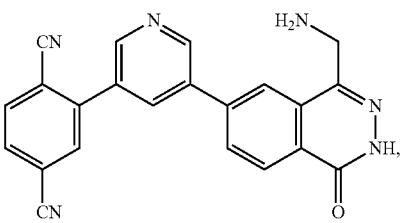
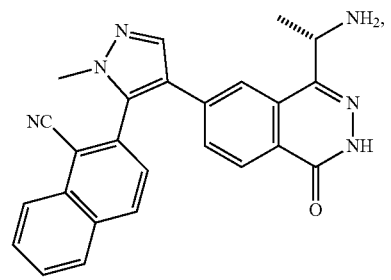

65
-continued
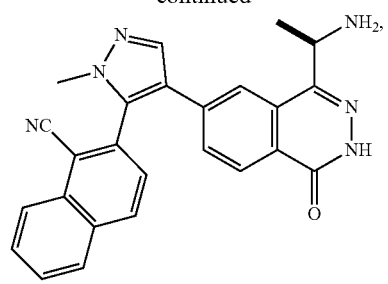
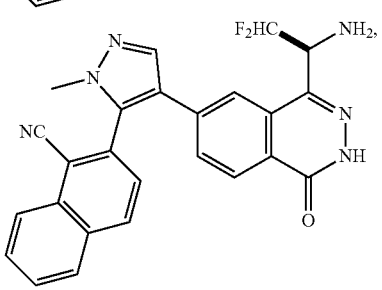
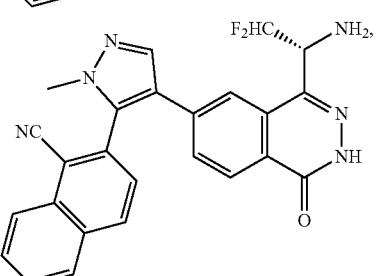
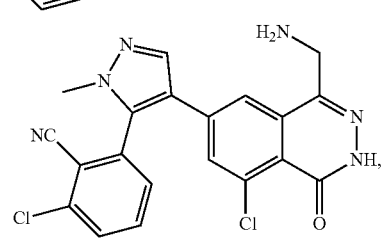
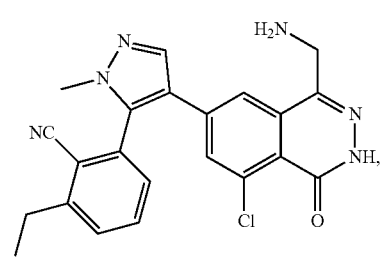
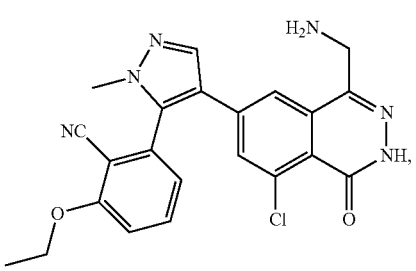
66
-continued
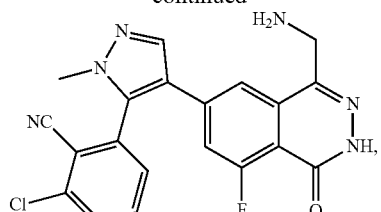
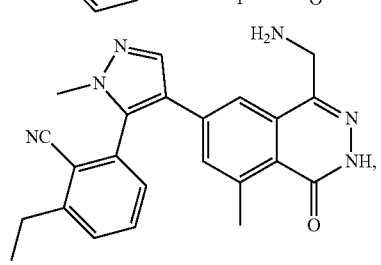
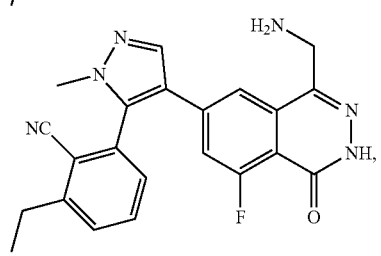
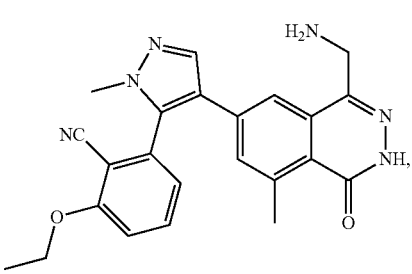
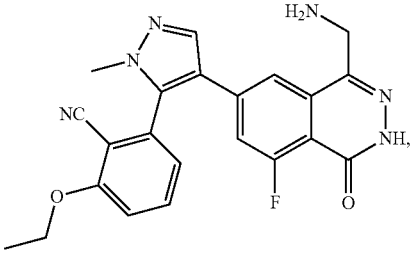
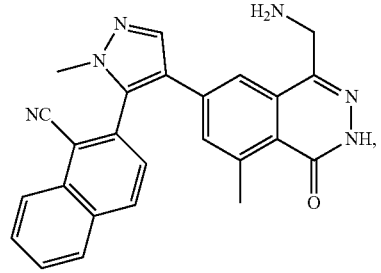

-continued
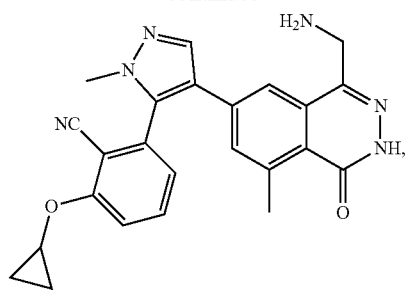
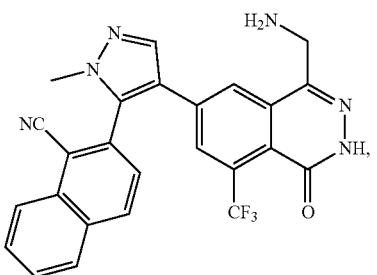
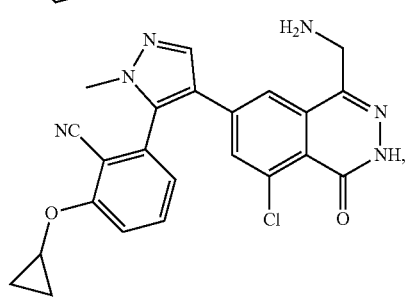
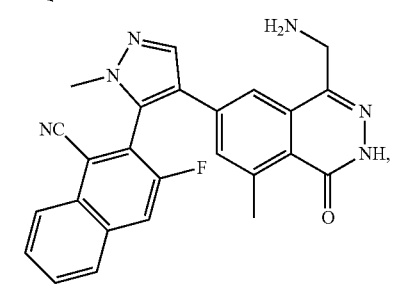
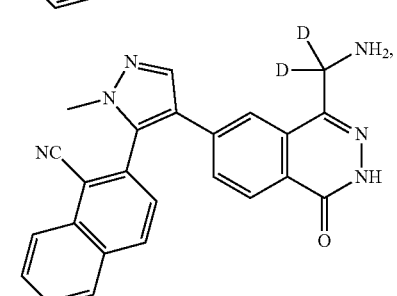
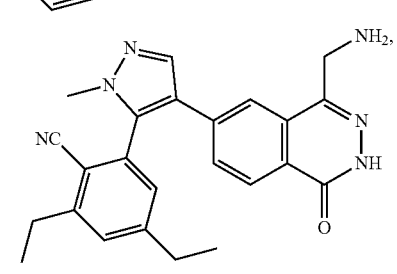
-continued
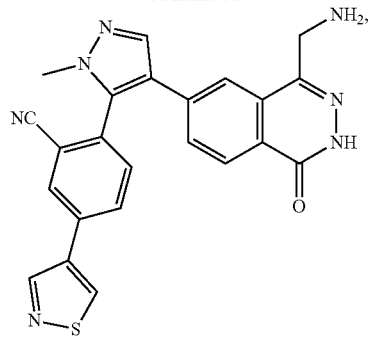
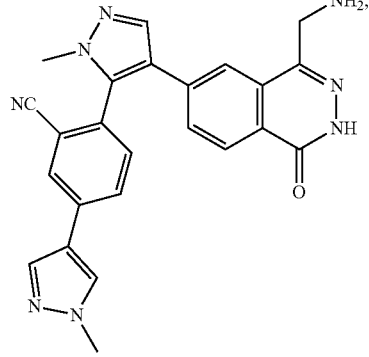
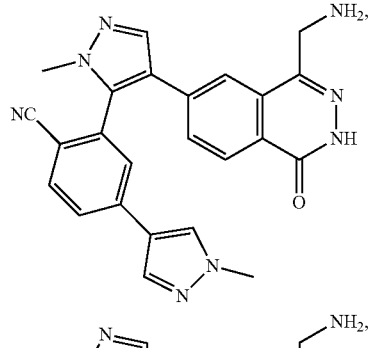
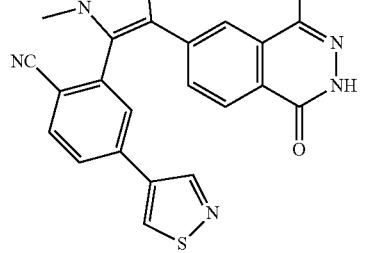
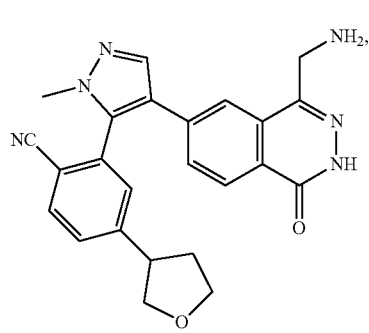

69
-continued
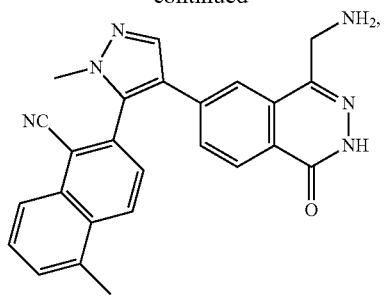
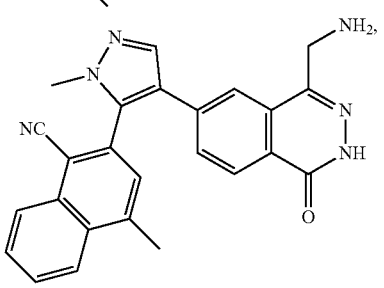
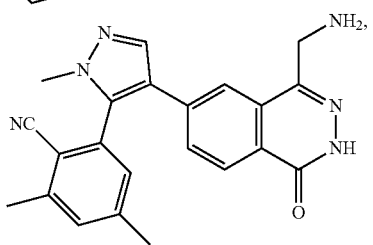
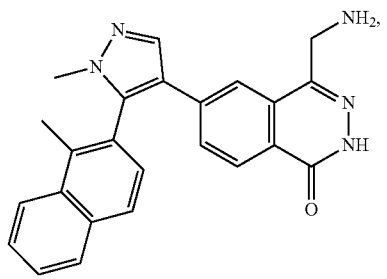
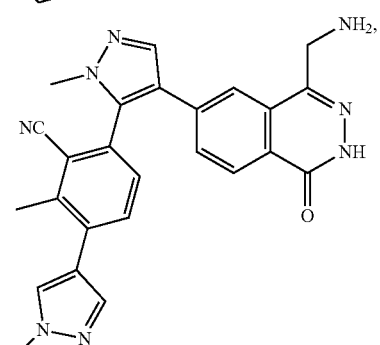
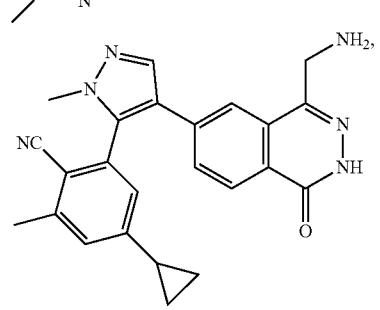
70
-continued
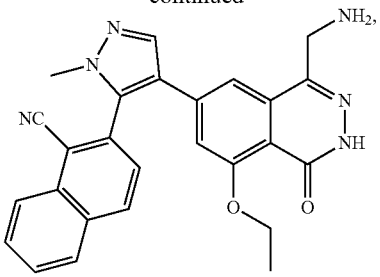
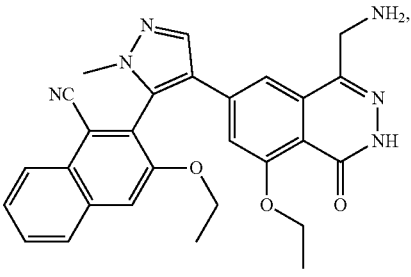
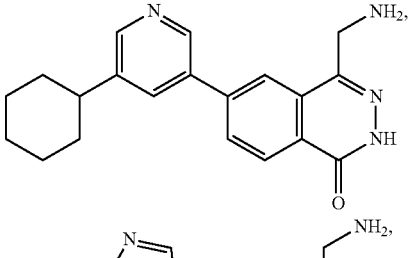
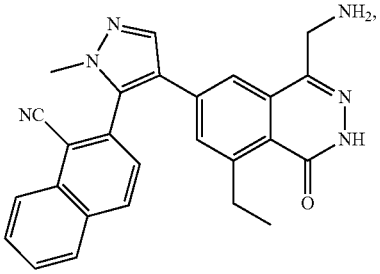
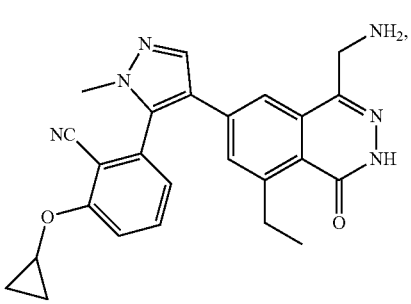
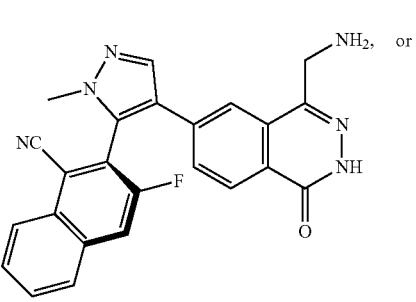

71
-continued
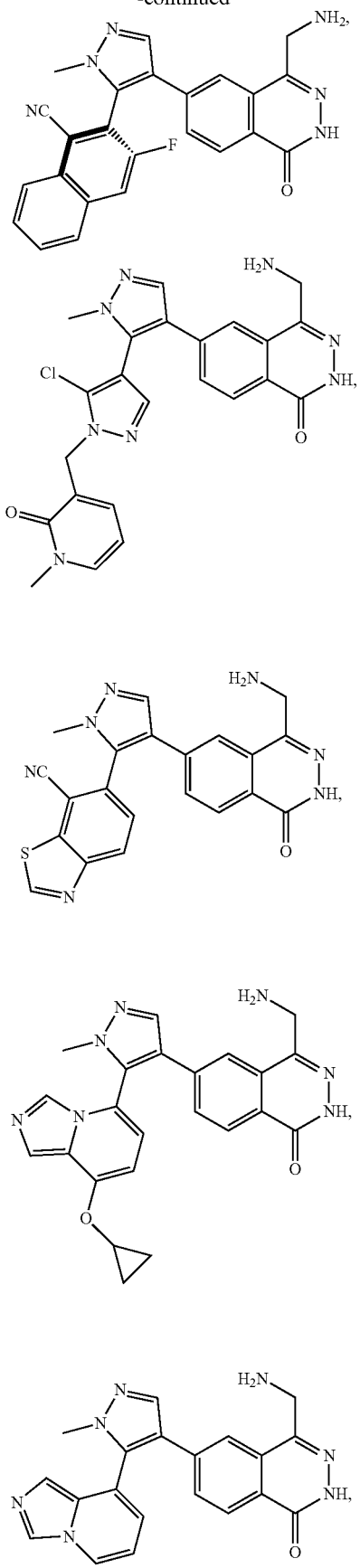
72
-continued
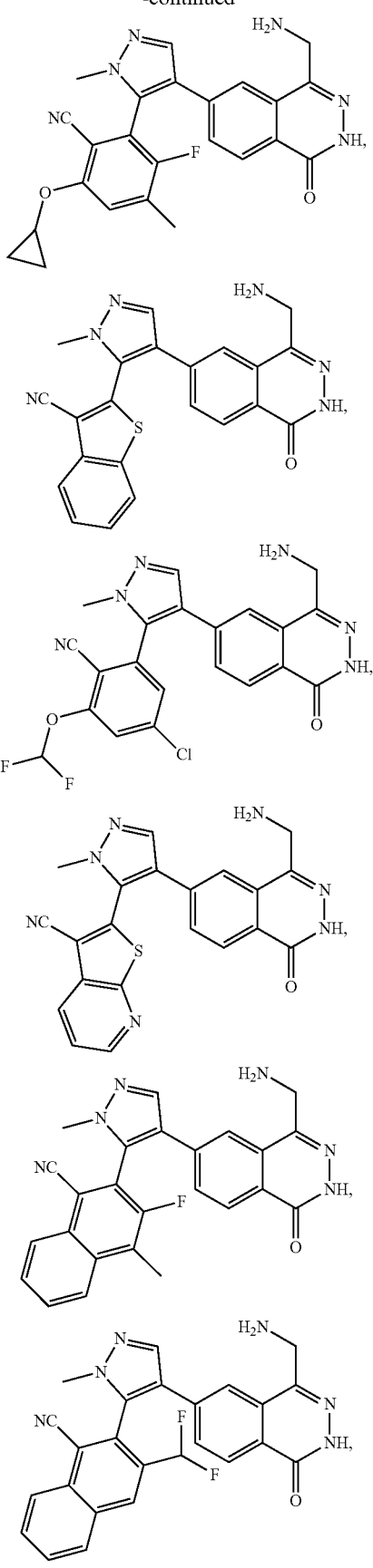

-continued
| 73 | 74 |
|---|---|
| 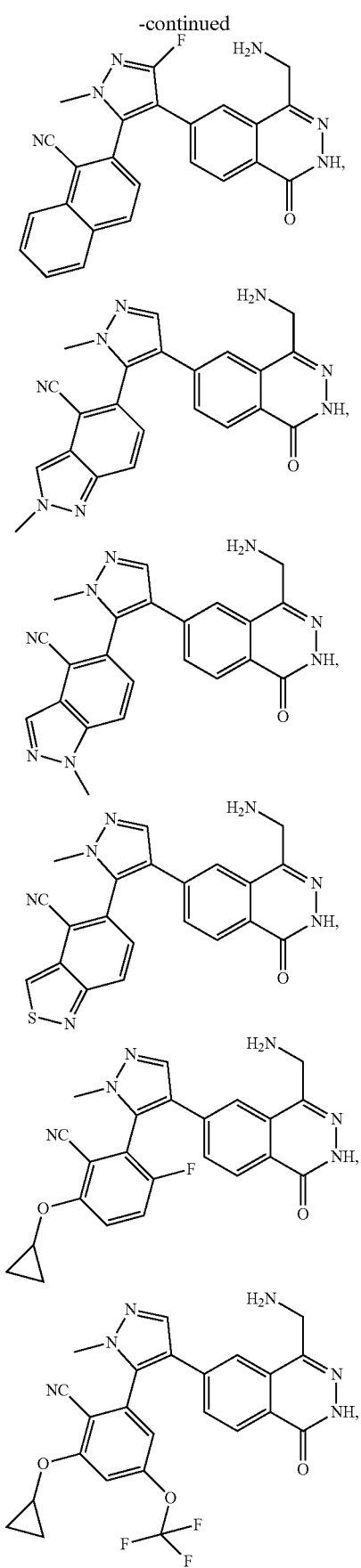 | 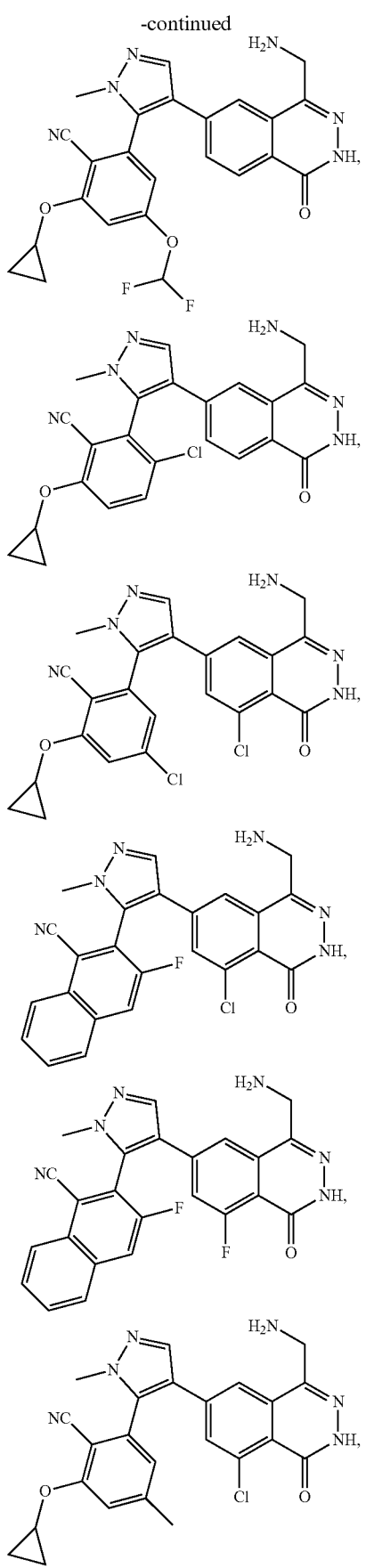 |

75
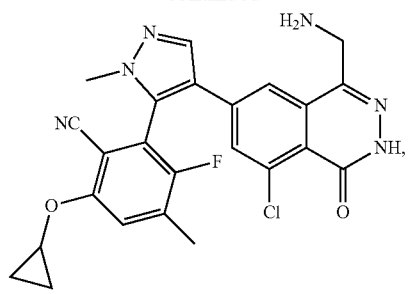
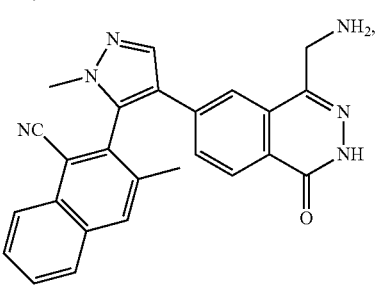
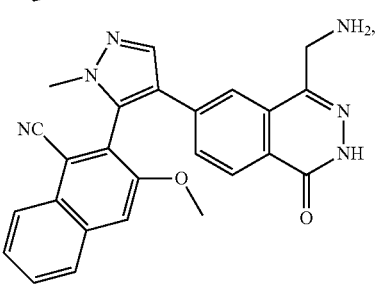
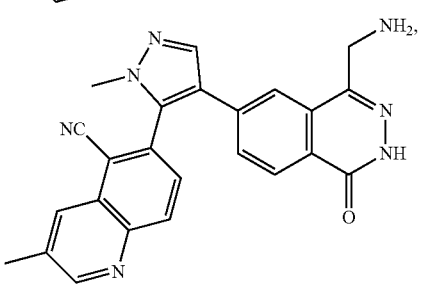
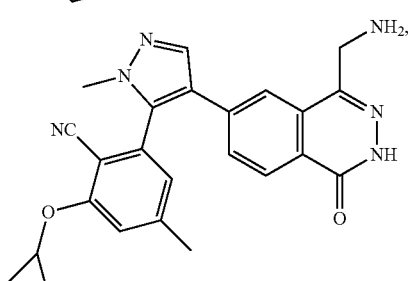
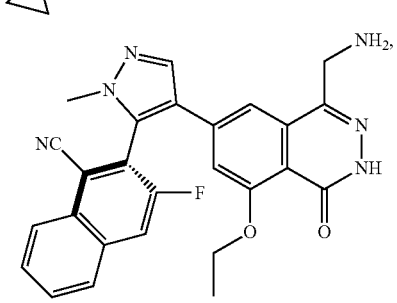
76
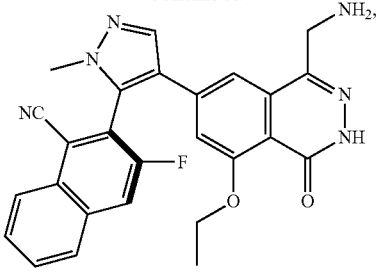
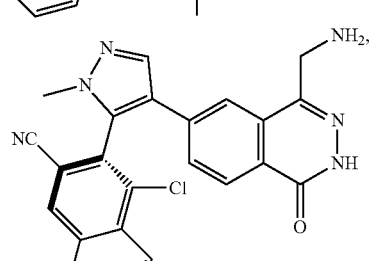
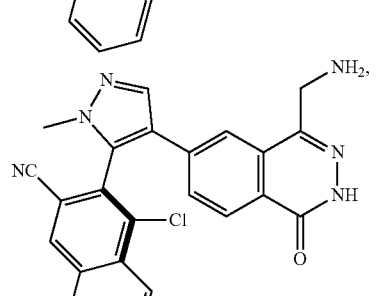
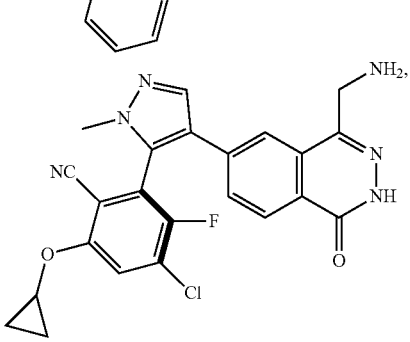
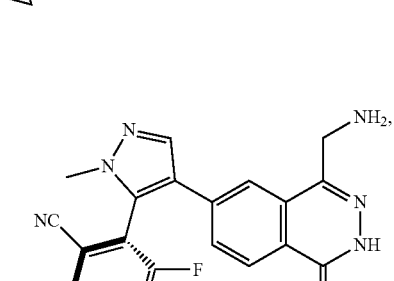
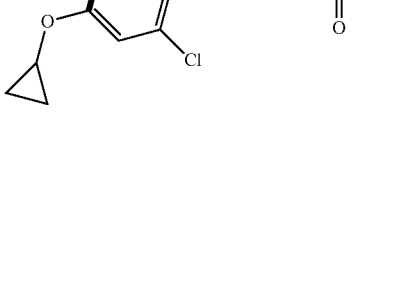
and pharmaceutically acceptable salts of the foregoing compounds.

In one embodiment, the compound of Formula (I) is:

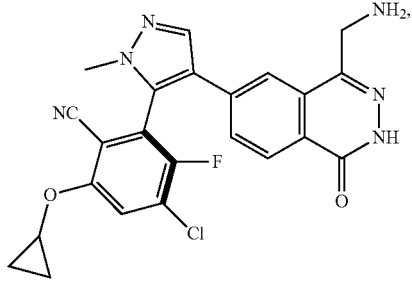
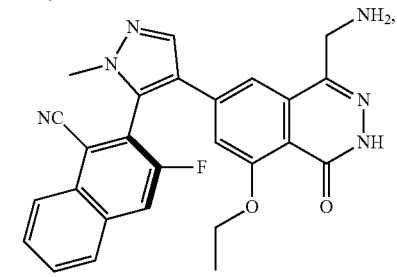
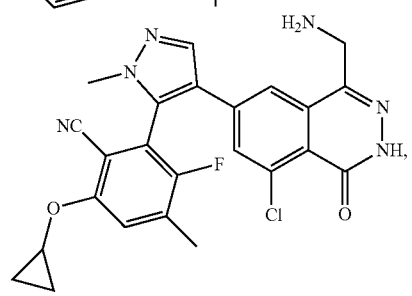
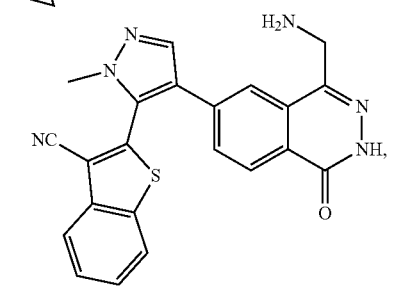
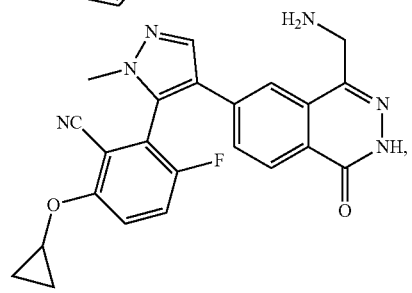
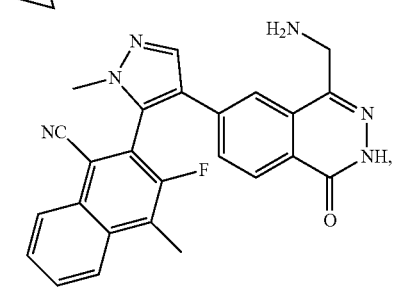

-continued

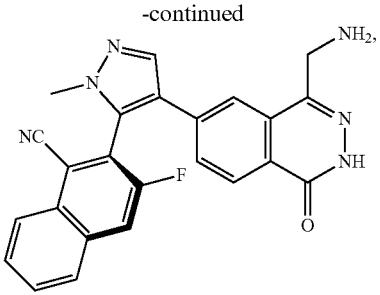
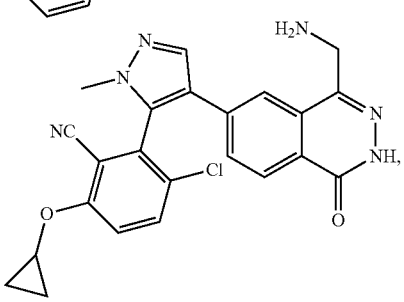
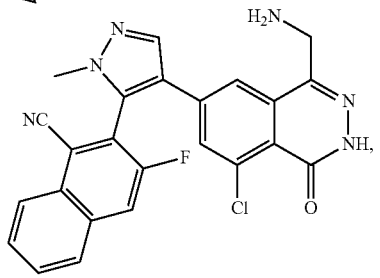
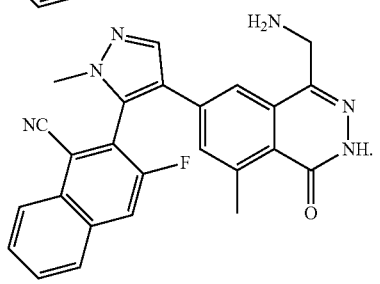

or a pharmaceutically acceptable salt of the foregoing compounds.

The compounds of Formula (I), Formula (I-A), Formula (I-B) and Formula (I-C) may be formulated into pharmaceutical compositions.

Pharmaceutical Compositions

In another aspect, the invention provides pharmaceutical compositions comprising a PRMT5 inhibitor according to the invention and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain embodiments, compounds of the invention are administered intravenously in a hospital setting. In certain other embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18$^{th}$ Edition, ed. A. Gennaro, Mack Publishing Co., Easton, Pa., 1990.

As used herein, the term "pharmaceutically acceptable salts" refers to salts that retain the desired biological activity of the above-identified compounds and exhibit minimal or no undesired toxicological effects. Examples of such salts include, but are not limited to acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid. The compounds can also be administered as pharmaceutically acceptable quaternary salts known by those skilled in the art, which specifically include the quaternary ammonium salt of the formula —NR+Z—, wherein R is hydrogen, alkyl, or benzyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

The active compound is included in the pharmaceutically acceptable carrier or diluent in an amount sufficient to deliver to a patient a therapeutically effective amount without causing serious toxic effects in the patient treated. A dose of the active compound for all of the above-mentioned conditions is in the range from about 0.01 to 300 mg/kg, preferably 0.1 to 100 mg/kg per day, more generally 0.5 to about 25 mg per kilogram body weight of the recipient per day. A typical topical dosage will range from 0.01-3% wt/wt in a suitable carrier. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

The pharmaceutical compositions comprising compounds of the present invention may be used in the methods described herein.

Methods of Use

In yet another aspect, the invention provides for methods for inhibiting PRMT5 activity in a cell, comprising contacting the cell in which inhibition of PRMT5 activity is desired in vitro with an effective amount of a compound of Formula (I), Formula (I-A), Formula (I-B) or Formula (I-C), pharmaceutically acceptable salts thereof or pharmaceutical compositions containing the compound or pharmaceutically acceptable salt thereof. In one embodiment, the cell is an MTAP-deficient cell.

The compositions and methods provided herein are particularly deemed useful for inhibiting PRMT5 activity in a cell in vivo. In one embodiment, a cell in which inhibition of PRMT5 activity is desired is contacted in vivo with a therapeutically effective amount of a compound of Formula (I), Formula (I-A), Formula (I-B), or Formula (I-C), or a pharmaceutically acceptable salt thereof, to negatively modulate the activity of PRMT5. In other embodiments, a therapeutically effective amount of pharmaceutically acceptable salt or pharmaceutical compositions containing the compound of Formula (I), Formula (I-A), Formula (I-B) or Formula (I-C) may be used. In one embodiment, the cell is an MTAP-deficient cell. In one embodiment, the negatively modulating the activity of PRMT5 occurs in the presence of bound MTA.

By negatively modulating the activity of PRMT5, particularly in cases for cells that lack MTAP activity, the methods are designed to inhibit PRMT5 activity to block cellular proliferation. The cells may be contacted in a single dose or multiple doses in accordance with a particular treatment regimen to affect the desired negative modulation of PRMT5. The degree PRMT5 inhibition may be monitored in vitro against the enzyme in the presence and absence of MTA and in the cell using well known methods, including those described in Example B below, to assess the effectiveness of treatment and dosages.

In another aspect, methods of treating cancer comprising administering to a patient having cancer a therapeutically effective amount of a compound of Formula (I), Formula (I-A), Formula (I-B) of Formula (I-C), pharmaceutically acceptable salts thereof or pharmaceutical compositions comprising the compound or pharmaceutically acceptable salts thereof are provided. In one embodiment, the cancer is an MTAP-associated cancer.

The compositions and methods provided herein may be used for the treatment of a wide variety of cancer including tumors such as prostate, breast, brain, skin, cervical carcinomas, testicular carcinomas, etc More particularly, cancers that may be treated by the compositions and methods of the invention include, but are not limited to tumor types such as astrocytic, breast, cervical, colorectal, endometrial, esophageal, gastric, head and neck, hepatocellular, laryngeal, lung, oral, ovarian, prostate and thyroid carcinomas and sarcomas. More specifically, these compounds can be used to treat: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma. In certain embodiments, the cancer is diffuse large B-cell lymphoma (DLBCL).

In one embodiment, the cancer is an MTAP-associated cancer selected from hepatocellular carcinoma, breast cancer, skin cancer, bladder cancer, liver cancer, pancreatic cancer, and head and neck cancer.

The concentration and route of administration to the patient will vary depending on the cancer to be treated. The compounds, pharmaceutically acceptable salts thereof and pharmaceutical compositions comprising such compounds and salts also may be co-administered with other antineoplastic compounds, e.g., chemotherapy, or used in combination with other treatments, such as radiation or surgical intervention, either as an adjuvant prior to surgery or postoperatively.

General Reaction Schemes, Intermediates and Examples

General Reaction Schemes

The compounds of the present invention may be prepared using commercially available reagents and intermediates in the synthetic methods and reaction schemes described herein, or may be prepared using other reagents and conventional methods well known to those skilled in the art.

For instance, intermediates for preparing compounds and compounds of Formula (I), Formula (I-A), Formula (I-B) or Formula (I-C) of the present invention may be prepared according to General Reaction Schemes I-XVI:

GENERAL REACTION SCHEME I

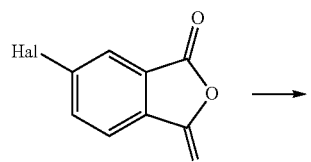

1

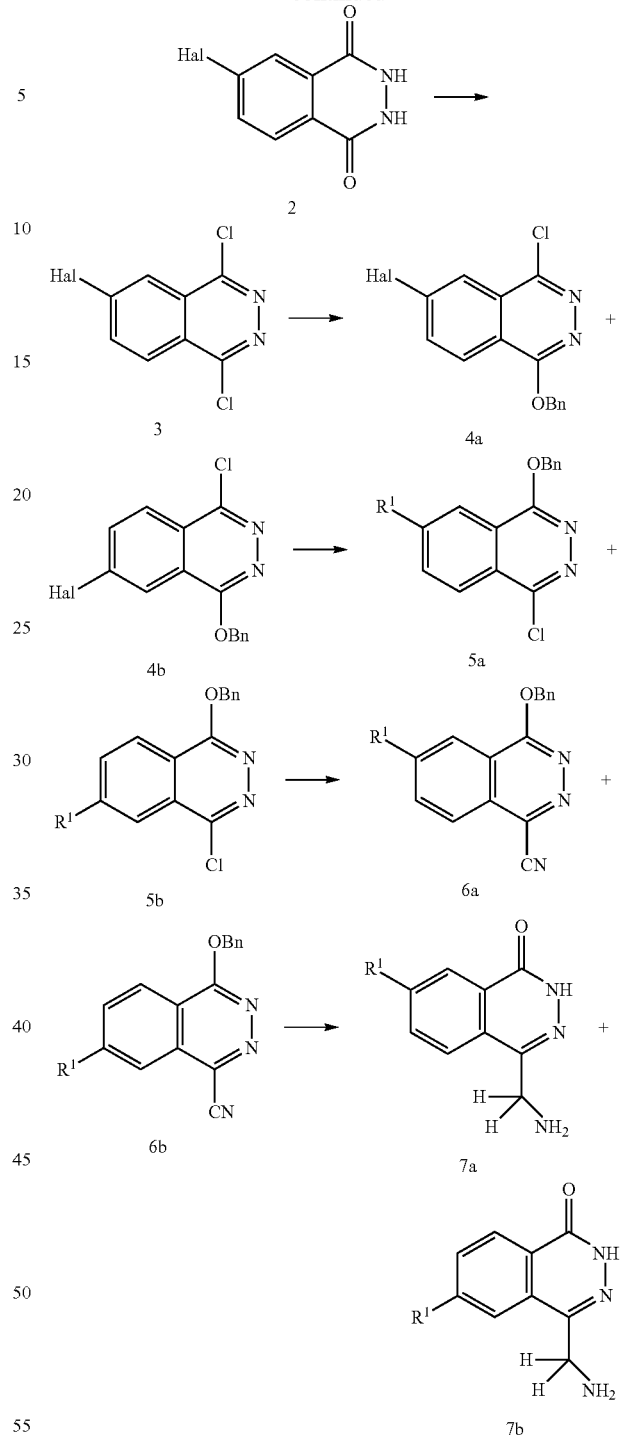

Wherein $R^1$ = Aryl/Heteroaryl, Hal = Cl, Br, or I

Compounds of Formula (I) wherein $R^1$ is aryl or heteroaryl, may be prepared according to General Reaction Scheme I. Compounds 7a and 7b are both examples of Formula (I) wherein $R^1$ is aryl or heteroaryl and $R^{3a}$ and $R^{3b}$ are H. A haloaryl cyclic anhydride 1 is treated with bis (nucleophile) such as hydrazine hydrate in acetic acid at elevated temperature, to form a phthalhydrazide 2 which is treated with a halogenating agent, for example $POCl_3$ to afford the trihalophthalazine 3. Treatment of the trihalophthalazine 3 with an alcohol, for example benzyl alcohol and NaH in THF at 0° C., furnishes dihaloalkoxyphthalazine 4a and 4b as a mixture of regioisomers. The mixture of 4a and 4b is subjected to palladium catalyzed cross coupling conditions, such as the Stille coupling or the Suzuki coupling with aryl/heteroaryl metal reactants, for example with the corresponding aryl/heteroaryl-tributyltin or aryl/heteroaryl boronic acids/esters to provide substituted haloalkoxyphthalazine 5a and 5b as a mixture of regioisomers. The substituted haloalkoxyphthalazine mixture 5a and 5b is subjected to metal-mediated cyanation conditions with for example, $Pd_2(dba)_3$, dppf, Zn and $ZnCN_2$ in DMF at elevated temperature and the resulting cyanoalkoxyphthalazine mixture 6a and 6b is subjected to hydrogenation conditions, for example with Pd/C, HCl and $H_2$ in methanol to give the phthalazinone methylamine mixture 7a and 7b. The regioisomeric mixture of 7a and 7b is separated by chromatography, such as supercritical fluid chromatography (SFC) to furnish the desired compounds 7a and 7b of Formula (I).

GENERAL REACTION SCHEME II

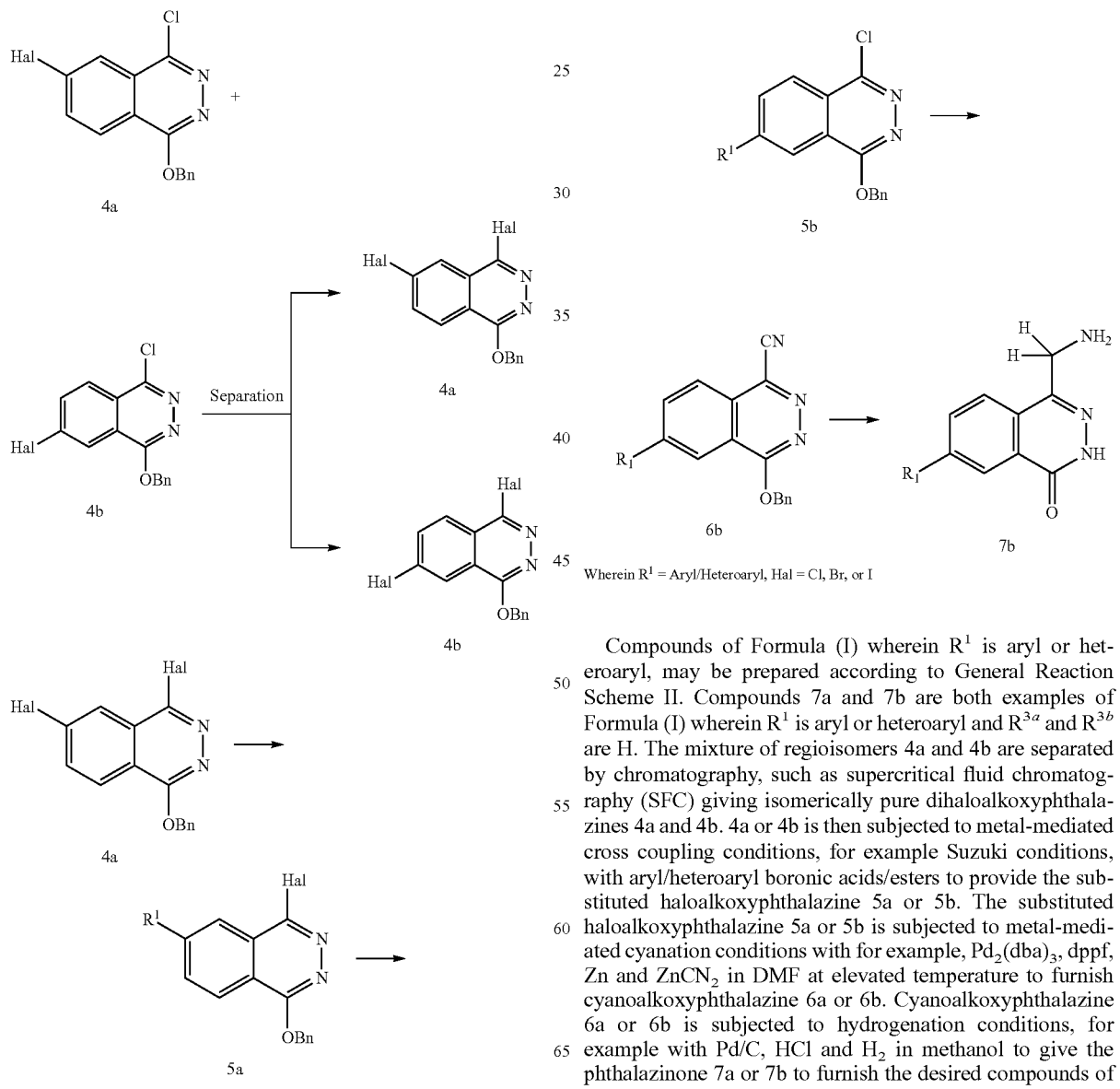

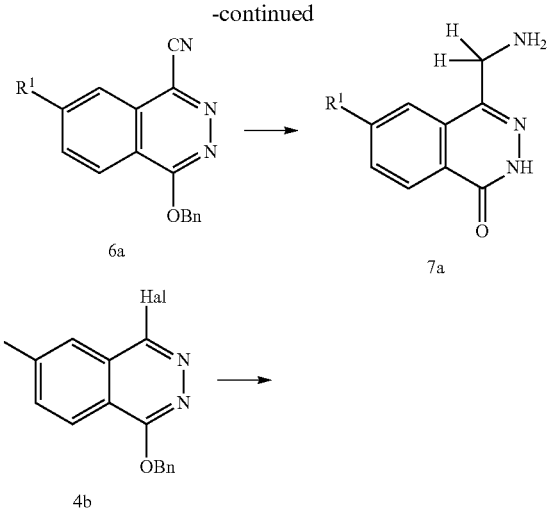

Wherein $R^1$ = Aryl/Heteroaryl, Hal = Cl, Br, or I

Compounds of Formula (I) wherein $R^1$ is aryl or heteroaryl, may be prepared according to General Reaction Scheme II. Compounds 7a and 7b are both examples of Formula (I) wherein $R^1$ is aryl or heteroaryl and $R^{3a}$ and $R^{3b}$ are H. The mixture of regioisomers 4a and 4b are separated by chromatography, such as supercritical fluid chromatography (SFC) giving isomerically pure dihaloalkoxyphthalazines 4a and 4b. 4a or 4b is then subjected to metal-mediated cross coupling conditions, for example Suzuki conditions, with aryl/heteroaryl boronic acids/esters to provide the substituted haloalkoxyphthalazine 5a or 5b. The substituted haloalkoxyphthalazine 5a or 5b is subjected to metal-mediated cyanation conditions with for example, $Pd_2(dba)_3$, dppf, Zn and $ZnCN_2$ in DMF at elevated temperature to furnish cyanoalkoxyphthalazine 6a or 6b. Cyanoalkoxyphthalazine 6a or 6b is subjected to hydrogenation conditions, for example with Pd/C, HCl and $H_2$ in methanol to give the phthalazinone 7a or 7b to furnish the desired compounds of Formula (I).

GENERAL REACTION SCHEME III-A

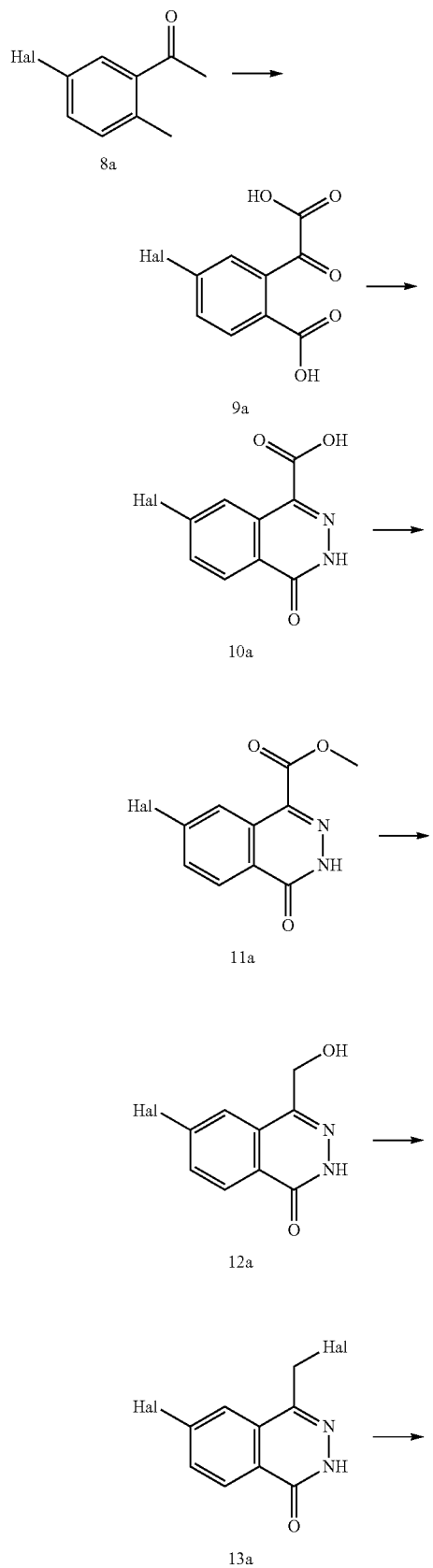

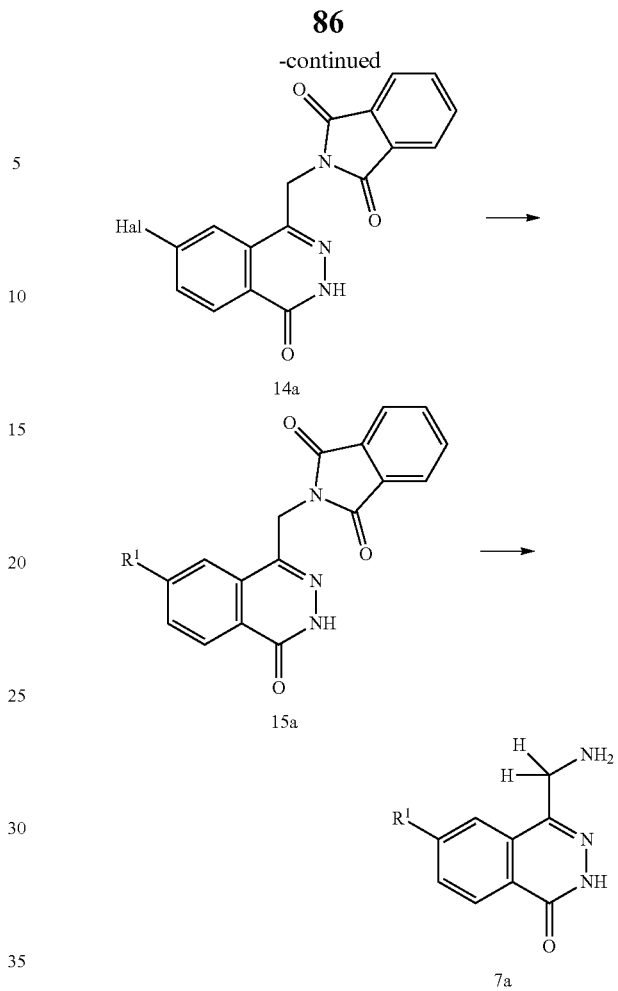

Wherein R¹ = Aryl, heteroaryl, alkyl and Hal = Cl, Br, or I

Compounds of Formula (I) wherein $R^1$ is aryl, heteroaryl, heterocyclyl or alkyl, may be prepared according to General Reaction Scheme III-A. Compound 7a is an example of Formula (I) wherein $R^1$ is aryl, heteroaryl, heterocyclyl or alkyl and $R^{3a}$ and $R^{3b}$ are H. 1-(5-halo-2-methylphenyl) ethenone 8a is treated with an oxidant, for example $KMnO_4$ in water at 50° C. to furnish 2-(carboxycarbonyl)-4-halobenzoic acid 9a. Condensation of 9a, for example with hydrazine hydrate in ethanol at elevated temperature, yields 7-halo-4-oxo-3,4-dihydrophthalazine-1-carboxylic acid 10a which is then esterified with acid and alcohol, for example sulfuric acid and methanol. Methyl 7-halo-4-oxo-3,4-dihydrophthalazine-1-carboxylate 11a is reduced via hydride reduction, for example with sodium borohydride and $CaCl_2$) in methanol, to afford the 6-halo-4-(hydroxymethyl)phthalazin-1(2H)-one 12a, which is then treated with halogenating agent, for example thionyl chloride for 12 hours to provide 6-halo-4-(halomethyl)phthalazin-1(2H)-one 13a. Nucleophilic $S_N2$ displacement of 13a with a nitrogen nucleophile for example, potassium phthalimide in DMF at elevated temperature furnishes 14a which is subjected to metal-mediated cross coupling conditions, for example Suzuki conditions, with aryl/heteroaryl/heterocyclyl/alkyl boronic acids/esters to provide phthalazinone coupling product 15a. The phthalimide protecting group of 15a is removed under solvolysis conditions, for example with hydrazine hydrate in ethanol to furnish the desired compound 7a of Formula (I).

GENERAL REACTION SCHEME III-B

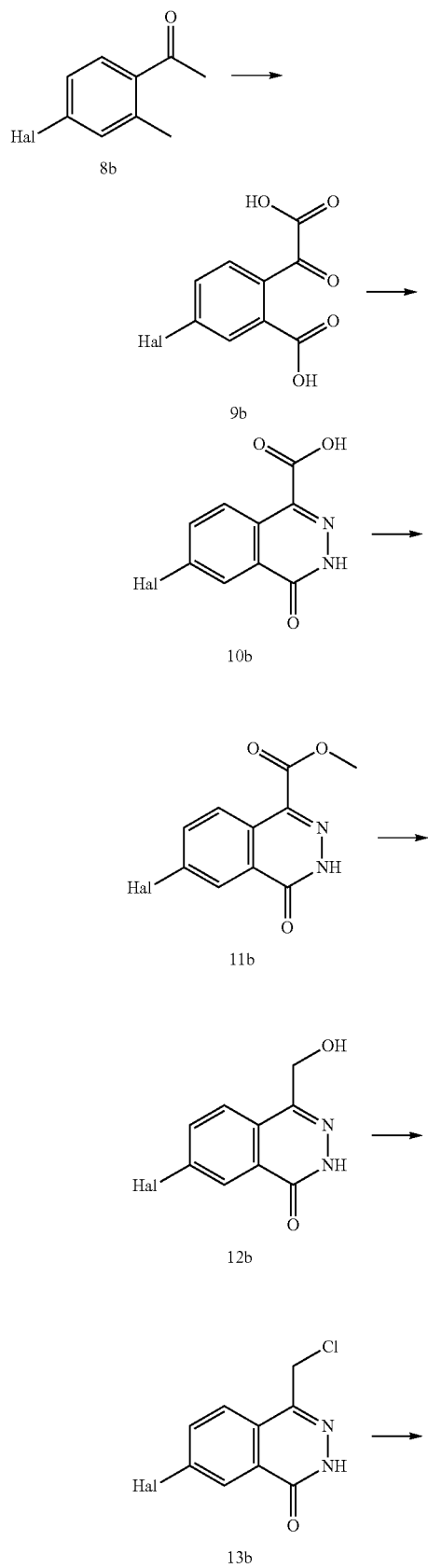

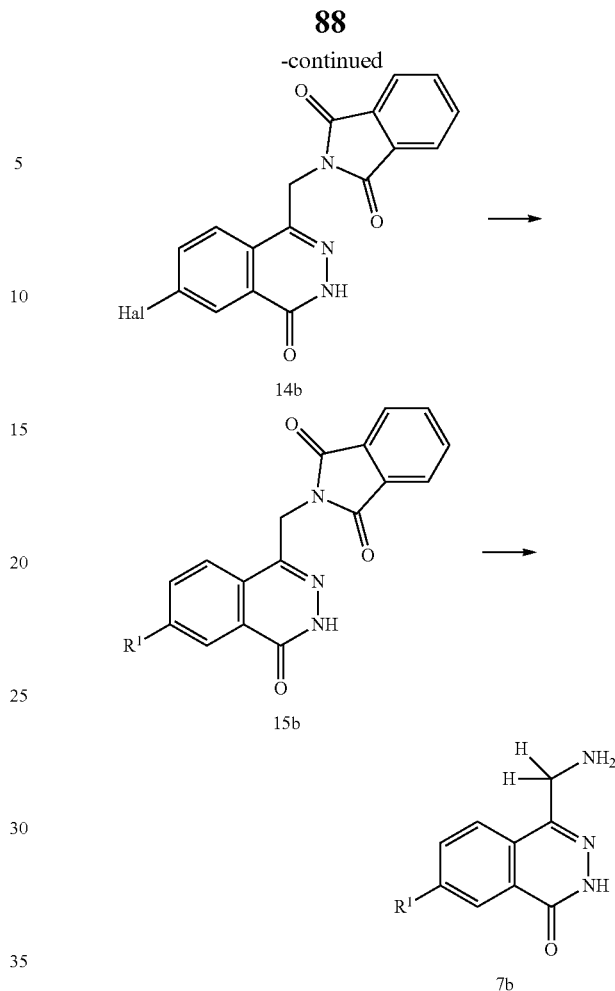

Wherein R¹ = Aryl, heteroaryl, alkyl and Hal = Cl, Br, or I

Compounds of Formula (I) wherein R¹ is aryl, heteroaryl, heterocyclyl or alkyl, may be prepared according to General Reaction Scheme III-B. Compound 7b is an example of Formula (I) wherein R¹ is aryl, heteroaryl, heterocyclyl or alkyl and $R^{3a}$ and $R^{3b}$ are H. 1-(5-halo-2-methylphenyl) ethenone 8b is treated with an oxidant, for example $KMnO_4$ in water at 50° C. to furnish 2-(carboxycarbonyl)-4-halobenzoic acid 9b. Condensation of 9b, for example with hydrazine hydrate in ethanol at elevated temperature, yields 7-halo-4-oxo-3,4-dihydrophthalazine-1-carboxylic acid 10b which is then esterified with acid and alcohol, for example sulfuric acid and methanol. Methyl 7-halo-4-oxo-3,4-dihydrophthalazine-1-carboxylate 11b is reduced via hydride reduction, for example with sodium borohydride and $CaCl_2$) in methanol, to afford the 6-halo-4-(hydroxymethyl)phthalazin-1(2H)-one 12b, which is then treated with halogenating agent, for example thionyl chloride for 12 hours to provide 6-halo-4-(halomethyl)phthalazin-1(2H)-one 13b. Nucleophilic $S_N2$ displacement of 13b with a nitrogen nucleophile for example, potassium phthalimide in DMF at elevated temperature furnishes 14b which is subjected to metal-mediated cross coupling conditions, for example Suzuki conditions, with aryl/heteroaryl/heterocyclyl/alkyl boronic acids/esters to provide phthalazinone coupling product 15b. The phthalimide protecting group of 15b is removed under solvolysis conditions, for example with hydrazine hydrate in ethanol to furnish the desired compound 7b of Formula (I).

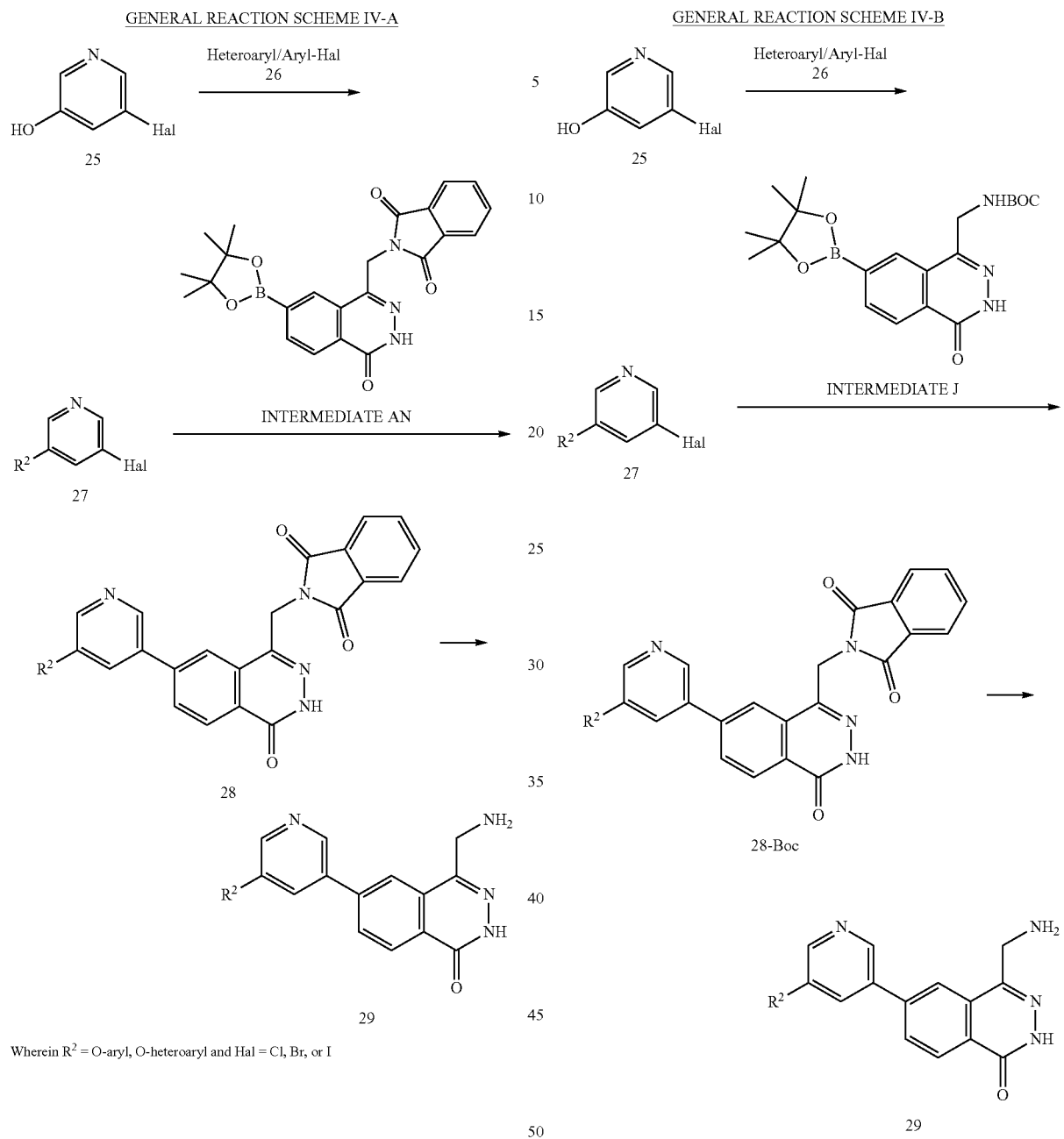

Compounds of Formula (I) wherein $R^1$ is pyridyl and $R^2$ is —O-aryl or —O-heteroaryl, may be prepared according to General Reaction Scheme IV-A. Compound 29 is an example of Formula (I) wherein $R^1$ is pyridyl, $R^2$ is —O-aryl or —O-heteroaryl, and $R^{3a}$ and $R^{3b}$ are H. 5-bromopyridin-3-ol 25 is heated with an appropriately substituted aryl/heteroaryl halide 26, for example in a mixture of DMF and NaH, to furnish 3-halo-5-$R^2$-oxypyridine 27. 3-halo-5-$R^2$-pyridine 27 is coupled to boronic acid, Intermediate AN under palladium catalyzed cross coupling conditions, for example the Suzuki coupling, to generate $R^2$-pyridyl coupling product 28. $R^2$-pyridyl coupling product 28 is subjected to solvolysis conditions, for example with hydrazine hydrate in ethanol, to furnish the free amine 29 of Formula (I).

Compounds of Formula (I) wherein $R^1$ is pyridyl and $R^2$ is —O-aryl or —O-heteroaryl, may be prepared according to General Reaction Scheme IV-B. Compound 29 is an example of Formula (I) wherein $R^1$ is pyridyl, $R^2$ is —O-aryl or —O-heteroaryl, and $R^{3a}$ and $R^{3b}$ are H. 5-bromopyridin-3-ol 25 is heated with aryl/heteroaryl halide 26, for example in a mixture of DMF and NaH, to furnish 3-bromo-5-$R^2$-pyridine 27. 3-bromo-5-$R^2$-pyridine 27 is coupled to boronic acid Intermediate J under palladium catalyzed cross coupling conditions, for example Suzuki conditions, to generate coupling product 28-Boc. Coupling product 28-Boc is subjected to acidic conditions, for example with TFA, to furnish the desired compound 29 of Formula (I).

GENERAL REACTION SCHEME IV-C

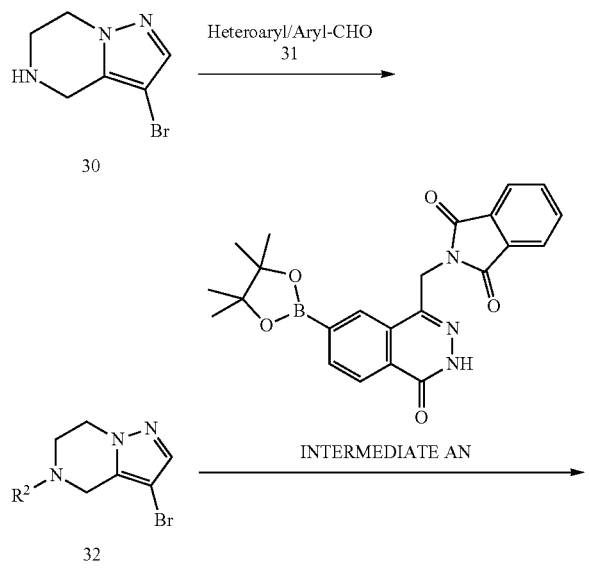

GENERAL REACTION SCHEME IV-D

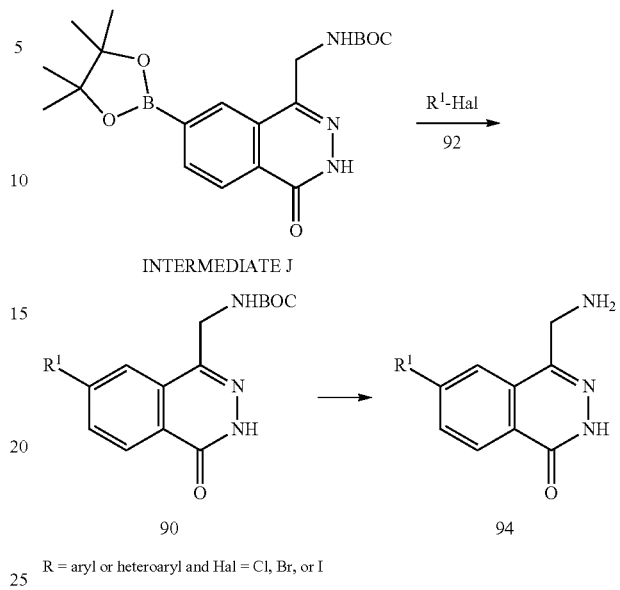

R = aryl or heteroaryl and Hal = Cl, Br, or I

Compounds of Formula (I) wherein $R^1$ is aryl or heteroaryl, may be prepared according to General Reaction Scheme IV-D. Compound 94 is an example of Formula (I) wherein $R^1$ is an appropriately substituted aryl or heteroaryl and $R^{3a}$ and $R^{3b}$ are H. N-Boc boronic ester Intermediate J is coupled to an aryl/heteroaryl-substituted halide 92 under palladium catalyzed cross coupling conditions, for example Suzuki coupling conditions, to generate N-Boc-$R^1$-substituted coupling product 90. N-Boc-$R^1$-substituted coupling product 90 is subjected to acidic conditions to remove the Boc group, for example TFA, to afford $R^1$-substituted amine 94 of Formula (I).

$R^2$ = -C1-C5 alkyl, heterocyclyl, -L-cycloalkyl, $CH_2$-aryl and $CH_2$-heteroaryl where L is a bond or C1-C3 alkylene Compounds of Formula (I) wherein $R^1$ is 5-$R^2$-6,7-dihydro-4H-pyrazolo[1,5-a]pyrazine-3-yl and $R^2$ is —C1-C5 alkyl, heterocyclyl, -L-cycloalkyl, —$CH_2$-aryl and —$CH_2$-heteroaryl where L is a bond or C1-C3 alkylene, may be prepared according to General Reaction Scheme IV-C. Compound 34 is an example of Formula (I) wherein $R^1$ is 5-$R^2$-6,7-dihydro-4H-pyrazolo[1,5-a]pyrazine-3-yl, $R^2$ is —C1-C5 alkyl, heterocyclyl, -L-cycloalkyl, —$CH_2$-aryl and —$CH_2$-heteroaryl where L is a bond or C1-C3 alkylene and $R^{3a}$ and $R^{3b}$ are H. 3-Bromo-4,5,6,7-tetrahydropyrazolo[1,5-a]pyrazine 30 is reacted with aldehyde or ketone 31 under reductive amination conditions, for example with sodium borohydride in methanol, to form $R^2$-substituted product 32. Amination product 32 is coupled to boronic ester Intermediate AN under palladium catalyzed cross-coupling, for example Suzuki conditions, furnishing coupling product 33. Coupling product 33 is then exposed to solvolysis conditions, for example with hydrazine hydrate, to deliver free amine 34 of Formula (I).

GENERAL REACTION SCHEME IV-E

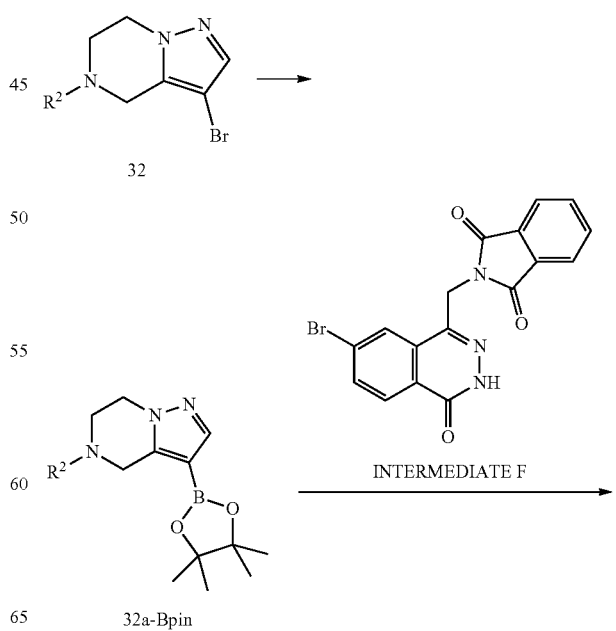

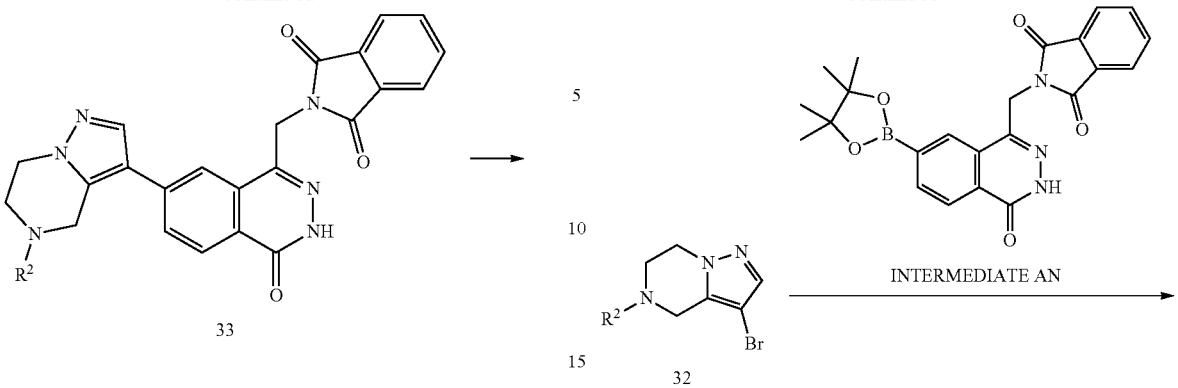

$R^2$ = -C1-C5 alkyl, heterocyclyl, -L-cycloalkyl, CH$_2$-aryl and CH$_2$-heteroaryl where L is a bond or C1-C3 alkylene Compounds of Formula (I) wherein $R^1$ is 5-$R^2$-6,7-dihydro-4H-pyrazolo[1,5-a]pyrazine-3-yl and $R^2$ is —C1-C5 alkyl, heterocyclyl, -L-cycloalkyl, —CH$_2$-aryl and —CH$_2$-heteroaryl where L is a bond or C1-C3 alkylene, may be prepared according to General Reaction Scheme IV-E. Compound 34 is an example of Formula (I) wherein $R^1$ is 5-$R^2$-6,7-dihydro-4H-pyrazolo[1,5-a]pyrazine-3-yl, $R^2$ is —C1-C5 alkyl, heterocyclyl, -L-cycloalkyl, —CH$_2$-aryl and —CH$_2$-heteroaryl where L is a bond or C1-C3 alkylene and $R^{3a}$ and $R^{3b}$ are H. 3-Bromo-5-$R^2$-6,7-dihydro-4H-pyrazolo[1,5-a]pyrazine 32 is borylated, for example with Miyaura conditions, to supply boronate ester 32a-Bpin. Borylation product 32a-Bpin is coupled to Intermediate F under palladium catalyzed cross-coupling conditions, for example Suzuki conditions, furnishing coupling product 33a. Coupling product 33a is deprotected under acidic conditions, for example TFA, to deliver amine 34a of Formula (I).

GENERAL REACTION SCHEME IV-F

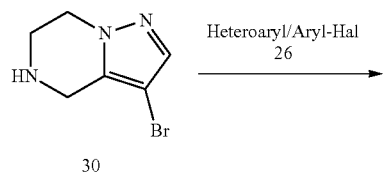

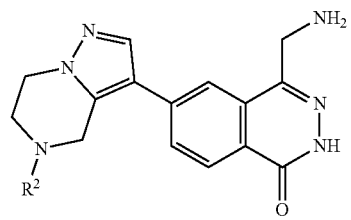

Wherein $R^2$ = aryl or heteroaryl, and Hal = Cl, Br or I

Compounds of Formula (I) wherein $R^1$ is 5-$R^2$-6,7-dihydro-4H-pyrazolo[1,5-a]pyrazine-3-yl and $R^2$ is aryl or heteroaryl, may be prepared according to General Reaction Scheme IV-F. Compound 34 is an example of Formula (I) wherein $R^1$ is 5-$R^2$-6,7-dihydro-4H-pyrazolo[1,5-a]pyrazine-3-yl, $R^2$ is aryl or heteroaryl and $R^{3a}$ and $R^{3b}$ are H. 3-Bromo-4,5,6,7-tetrahydropyrazolo[1,5-a]pyrazine 30 is reacted with aryl/heteroaryl halide 26, under copper catalyst mediated Ullman coupling conditions, for example with Cu(I)I, Cs$_2$CO$_3$, L-proline in DMF, at elevated temperature, to form amination product 32. $R^2$-substituted amination product 32 is coupled to Intermediate AN under palladium catalyzed cross-coupling conditions, for example Suzuki conditions, furnishing coupling product 33. Coupling product 33 is subjected to solvolysis conditions, for example hydrazine hydrate, to deliver amine 34 of Formula (I).

GENERAL REACTION SCHEME IV-G

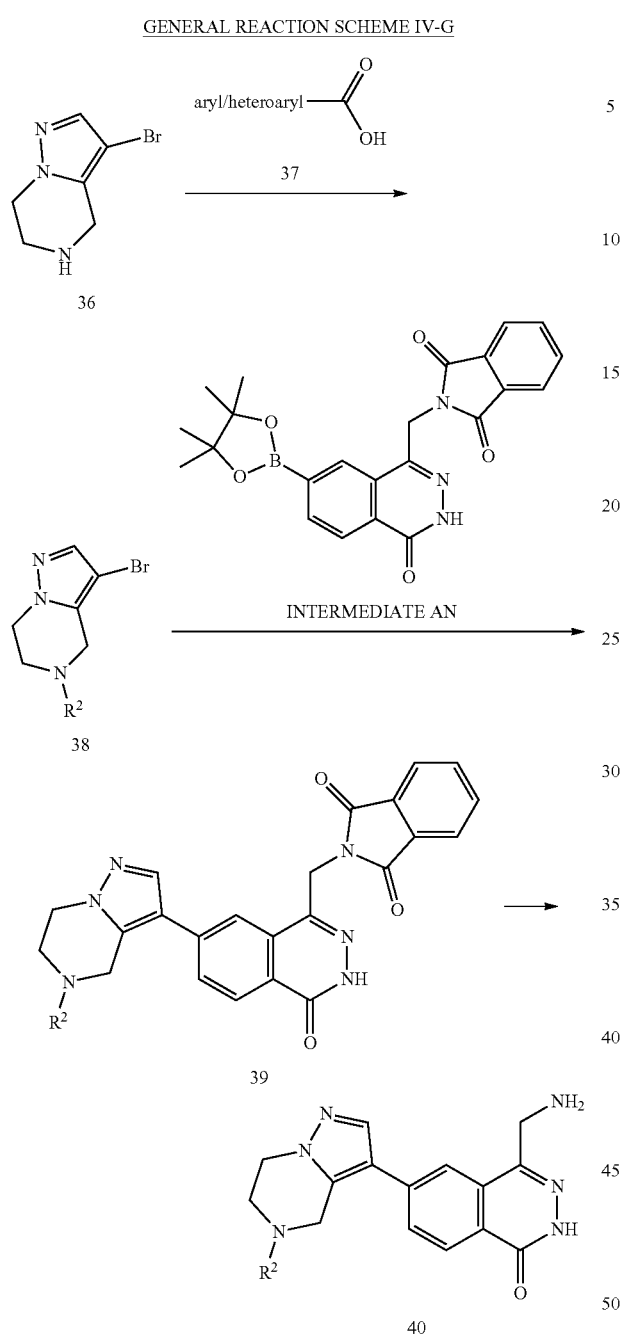

wherein R² = -C(O)-aryl or -C(O)-heteroaryl dium catalyzed cross-coupling conditions, for example the Suzuki coupling, to yield coupling product 39. R²-coupling product 39 is subjected to solvolysis conditions, for example with hydrazine monohydrate, to remove the phthalimide moiety and provide amine compound 40 of Formula (I).

GENERAL REACTION SCHEME IV-H

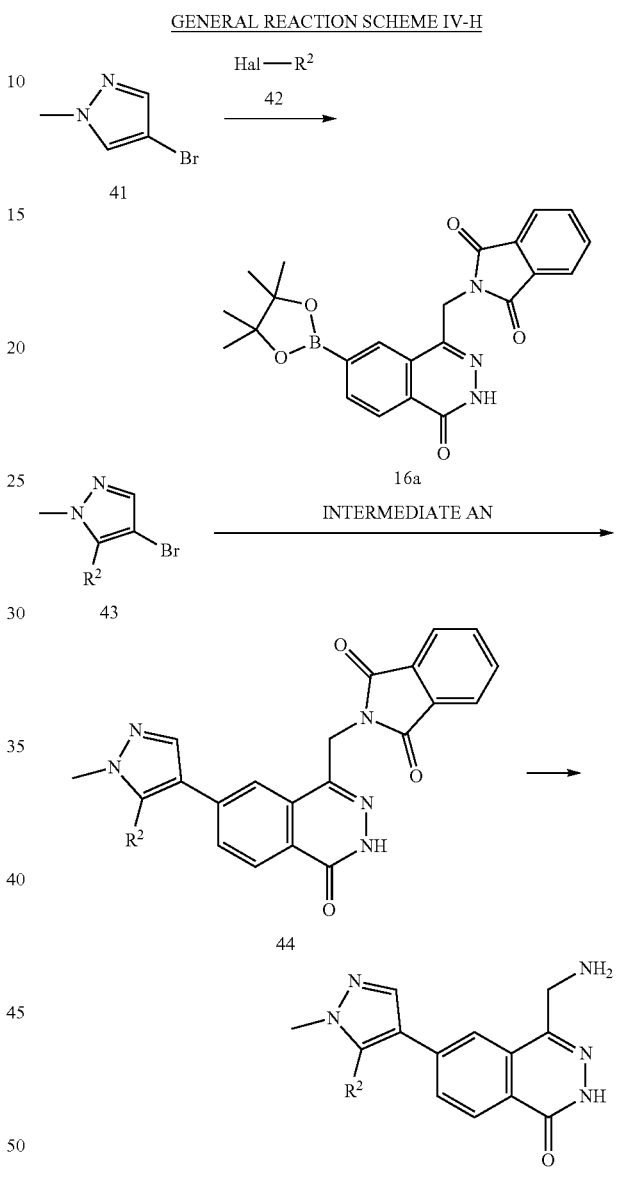

wherein R² = alkyl, aryl, heteroaryl, and Hal = Cl, Br or I

Compounds of Formula (I) wherein $R^1$ is 5-$R^2$-6,7-dihydro-4H-pyrazolo[1,5-a]pyrazine-3-yl and $R^2$ is —C(O)—aryl or —C(O)— heteroaryl, may be prepared according to General Reaction Scheme IV-G. Compound 40 is an example of Formula (I) wherein $R^1$ is 5-$R^2$-6,7-dihydro-4H-pyrazolo[1,5-a]pyrazine-3-yl, $R^2$ is —C(O)— aryl or —C(O)— heteroaryl and $R^{3a}$ and $R^{3b}$ are H. 3-Bromo-4,5,6,7-tetrahydropyrazolo[1,5-a]pyrazine 30 is coupled to carboxylic acid 37 with a coupling reagent, for example 1-[bis(dimethylamino)methylene]-1H-1,2,3-triazolo[4,5-b]pyridinium 3-oxid hexafluorophosphate (HATU) with a base such as triethylamine in DMF to form amide 38. Amide 38 is coupled to boronic ester Intermediate AN, under palla- Compounds of Formula (I) wherein $R^1$ is 1-methyl-5-$R^2$-1H-pyrazole-4-yl and $R^2$ is alkyl, aryl or heteroaryl, may be prepared according to General Reaction Scheme IV-H. Compound 45 is an example of Formula (I) wherein $R^1$ is 1-methyl-5-$R^2$-1H-pyrazole-4-yl, $R^2$ is alkyl, aryl or heteroaryl and $R^{3a}$ and $R^{3b}$ are H. 4-bromo-1-methyl-1H-pyrazole 41 is coupled to alkyl/aryl/heteroaryl-substituted halide 42, for example with palladium acetate, DavePhos, tetrabutylammoniumacetate, pivalic acid in NMP at elevated temperature to furnish $R^2$-substituted-bromopyrazole 43. $R^2$-substituted-bromopyrazole 43 is coupled to Intermediate AN under palladium-mediated cross coupling conditions, for example Suzuki conditions, to provide R²-substituted coupling product 44. The coupling product 44 is subjected to solvolysis conditions, for example with hydrazine hydrate to furnish amine 45 of Formula (I).

GENERAL REACTION SCHEME IV-I

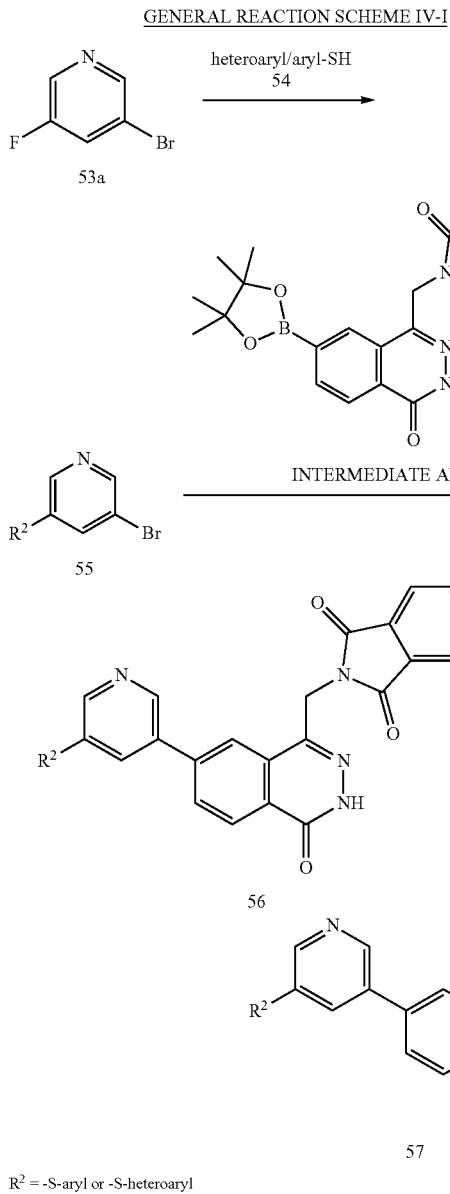

R² = -S-aryl or -S-heteroaryl

Compounds of Formula (I) wherein R¹ is pyridyl, R² is —S-aryl or —S-heteroaryl, may be prepared according to General Reaction Scheme Iv-I. Compound 57 is an example of Formula (I) wherein R¹ is pyridyl, R² is —S-aryl or —S-heteroaryl and $R^{3a}$ and $R^{3b}$ are H. 3-bromo-5-fluoropyridine 53a is subjected to $S_NAr$ substitution conditions, for example sodium aryl/heteroaryl thiolate 54, NaH in DMF at elevated temperature, to provide 3-bromo-5-(aryl/heteroarylthio)pyridine 55. 3-bromo-5-(aryl/heteroarylthio)pyridine 55 is coupled with boronic ester Intermediate AN under palladium cross coupling conditions, for example Suzuki conditions, to furnish R²-pyridyl-cross coupling product 56. R²-pyridyl-cross coupling product 56 is subjected to solvolysis conditions, with for example hydrazine hydrate, to produce amine 57 of Formula (I).

GENERAL REACTION SCHEME IV-J

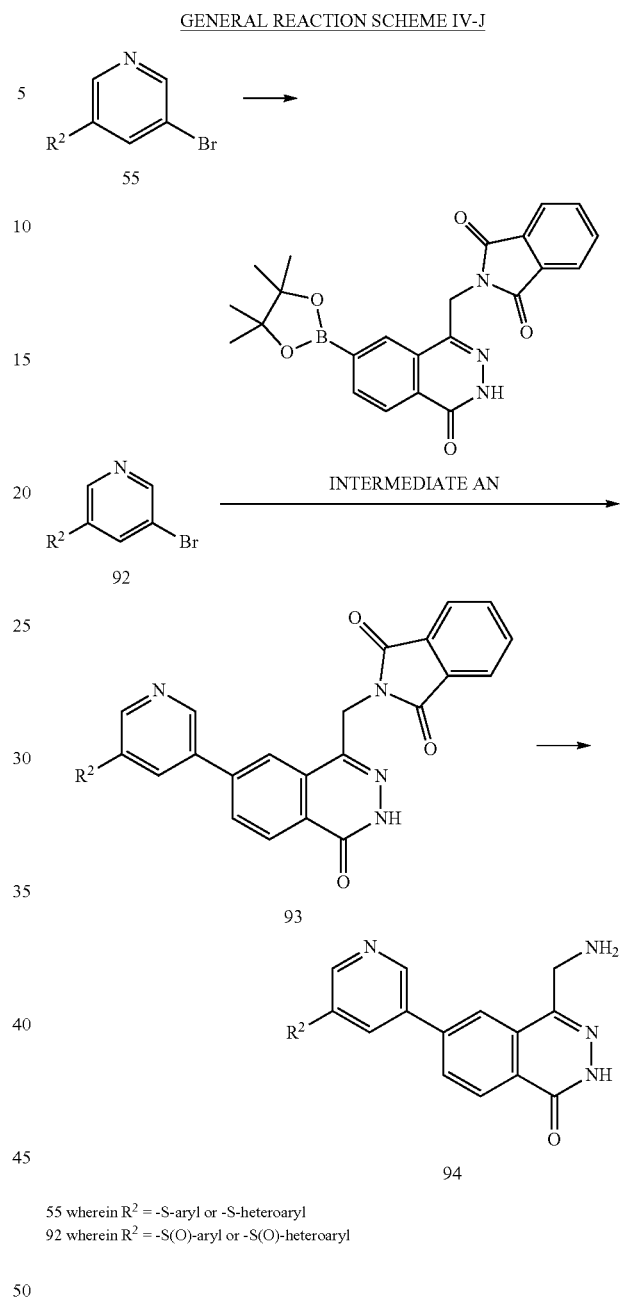

55 wherein R² = -S-aryl or -S-heteroaryl
92 wherein R² = -S(O)-aryl or -S(O)-heteroaryl Compounds of Formula (I) wherein R¹ is pyridyl, R² is —S(O)-aryl or —S(O)-heteroaryl, may be prepared according to General Reaction Scheme IV-J. Compound 94 is an example of Formula (I) wherein R¹ is pyridyl, R² is —S(O)-aryl or —S(O)-heteroaryl and $R^{3a}$ and $R^{3b}$ are H. 3-bromo-5-(R²-thio)pyridine 55 is subjected to oxidation conditions, for example mCPBA in dichloromethane at ambient temperature, to afford 3-bromo-5-(R²-sulfinyl)pyridine 92. 3-bromo-5-(R²-sulfinyl)pyridine 92 is coupled with boronic ester intermediate AN under palladium catalyzed cross-coupling conditions, for example Suzuki conditions, to provide R²-substituted sulfinylpyridyl product 93. R²-substituted sulfinylpyridyl product 93 is subjected to solvolysis conditions, for example with hydrazine hydrate, to procure the R²-substituted sulfinylpyridyl amine 94 of Formula (I).

GENERAL REACTION SCHEME IV-K

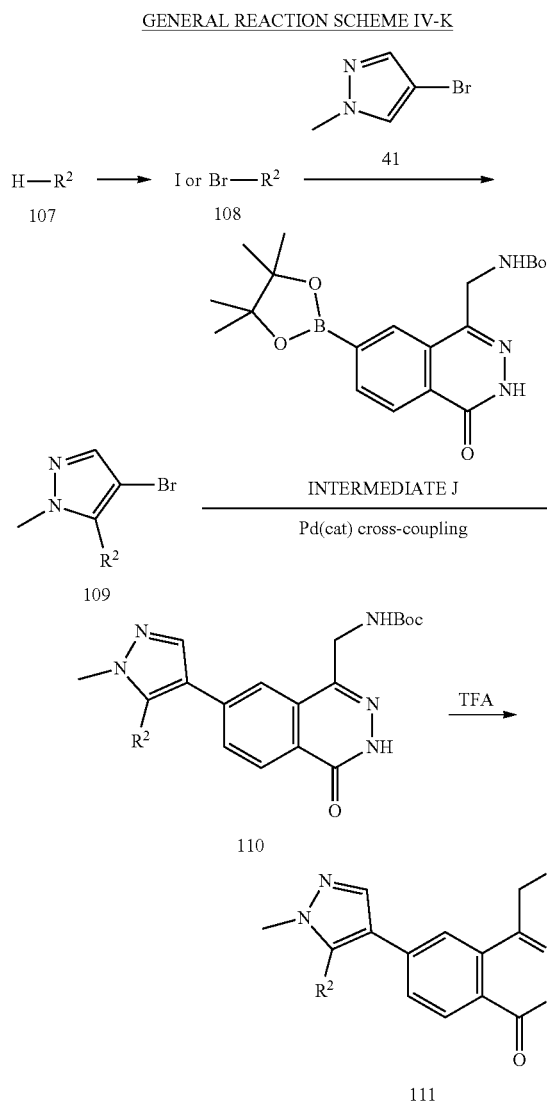

GENERAL REACTION SCHEME V

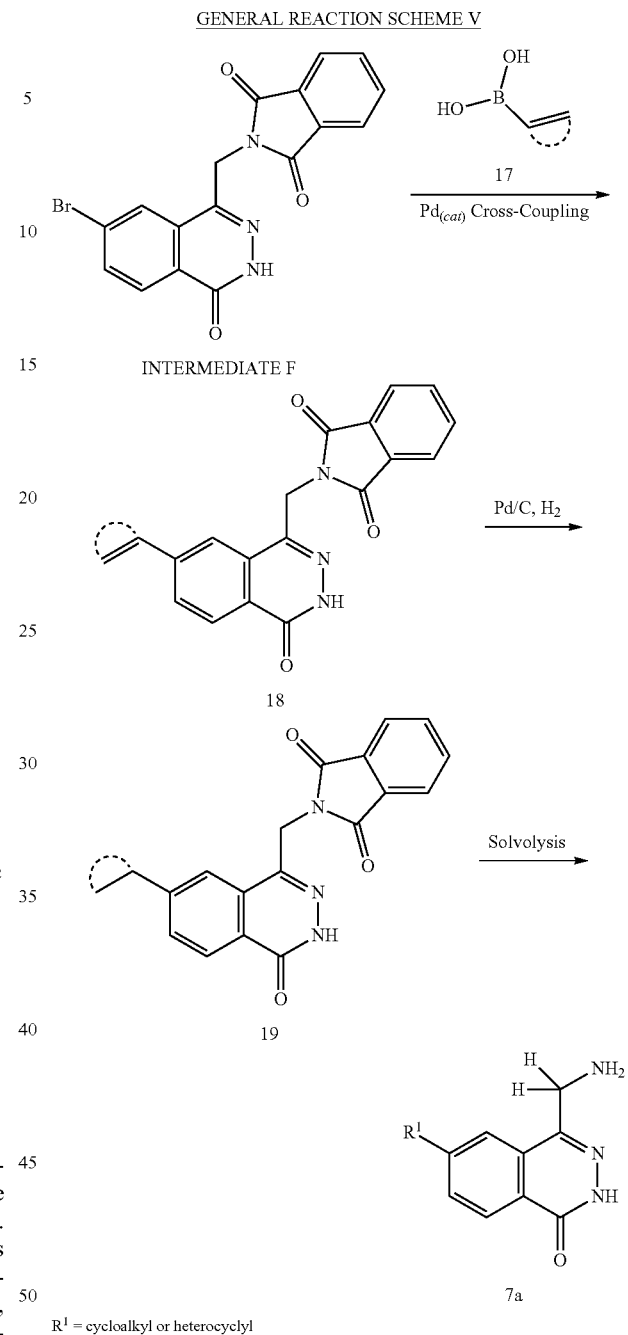

R¹ = cycloalkyl or heterocyclyl

Compounds of Formula (I) wherein R¹ is 1-methyl-5-R²-1H-pyrazole-4-yl and R² is alkyl, aryl or heteroaryl, may be prepared according to General Reaction Scheme IV-K. Compound 111 is an example of Formula (I) wherein R¹ is 1-methyl-5-R²-1H-pyrazole-4-yl, R² is alkyl, aryl or heteroaryl and $R^{3a}$ and $R^{3b}$ are H. H—R² 107 is halogenated, for example with a halogenating agent such N-bromosuccinimide or N-chlorosuccinimide under palladium catalyzed conditions such as palladium acetate in the presence of an acid such as p-toluenesulfonic acid in a solvent such as dichloroethane under elevated temperature for example 70° C. to give halide 108. 4-bromo-1-methyl-1H-pyrazole 41 is coupled to alkyl/aryl/heteroaryl-substituted halide 108, for example with palladium acetate, DavePhos, tetrabutylammoniumacetate, pivalic acid in NMP at elevated temperature to furnish R²-substituted-bromopyrazole 109. R²-substituted-bromopyrazole 109 is coupled to Intermediate J under palladium-mediated cross coupling conditions, for example Suzuki conditions, to provide N-Boc-R²-substituted coupling product 110. The coupling product 110 is subjected to acidic conditions to remove the Boc group, for example TFA, to afford R²-substituted amine 111 of Formula (I).

Compounds of Formula (I) wherein R¹ is cycloalkyl or heterocyclyl, may be prepared according to General Reaction Scheme V. Compound 7a is an example of Formula (I) wherein R¹ is cycloalkyl or heterocyclyl and $R^{3a}$ and $R^{3b}$ are H. 2-((7-bromo-4-oxo-3,4-dihydrophthalazin-1-yl)methyl) isoindoline-1,3-dione Intermediate F is coupled to a 4-6 membered ring olefin boronic acid 17 under palladium catalyzed coupling conditions, for example Suzuki coupling conditions to provide the appropriate olefinic coupling product 18. The olefin coupling product 18 is then subjected to hydrogenation conditions, for example Pd/C and H₂, to furnish the appropriate hydrogenation product 19. The hydrogenation product is then subjected to hydrazine solvolysis conditions, for example with hydrazine hydrate to provide the primary amine compound 7a of Formula (I).

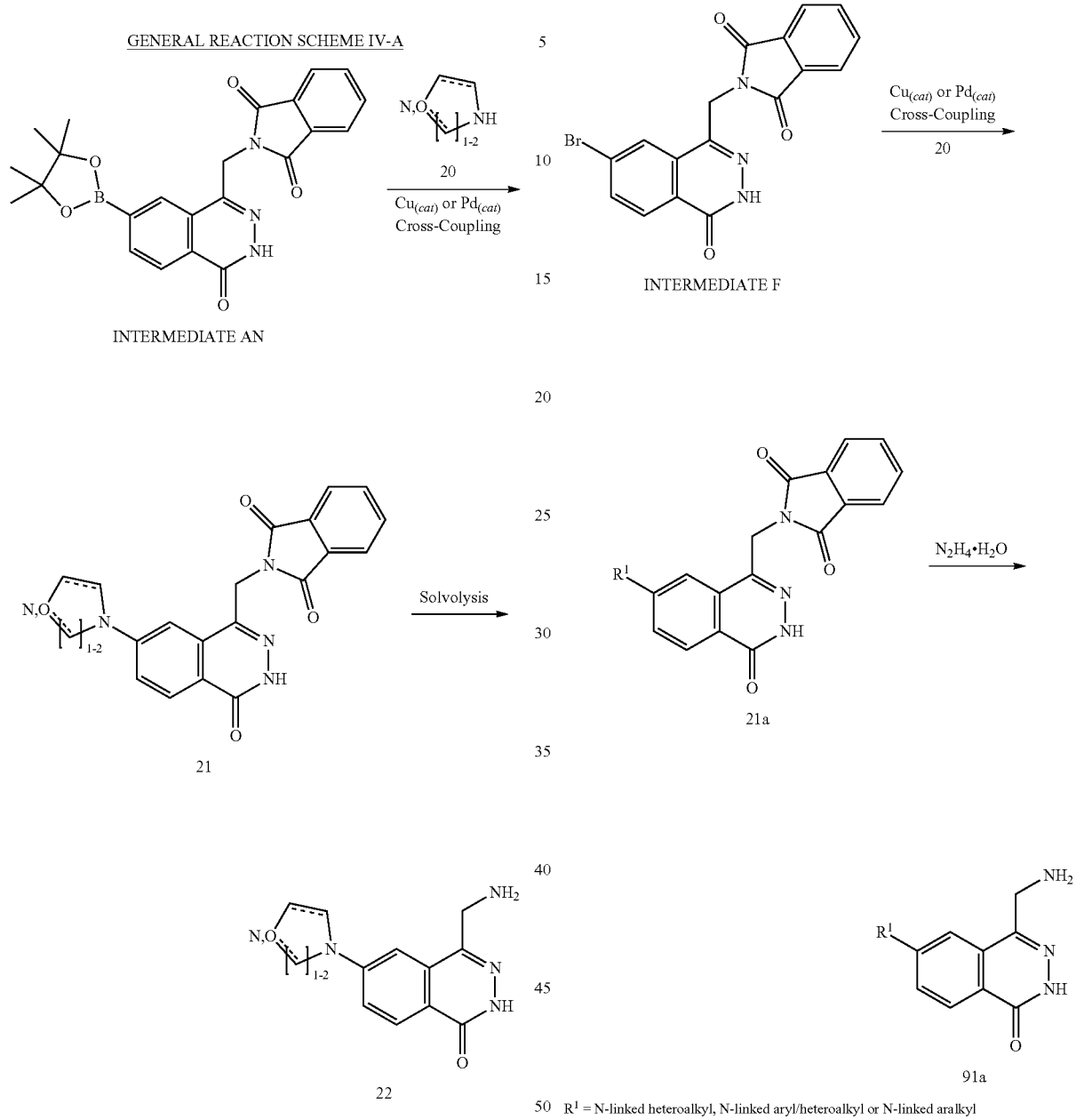

Compounds of Formula (I) wherein $R^1$ is N-linked heteroaryl or N-linked heterocyclyl, may be prepared according to General Reaction Scheme VI-A. Compound 22 is an example of Formula (I) wherein $R^1$ is N-linked heteroaryl or N-linked heterocyclyl and $R^{3a}$ and $R^{3b}$ are H. Boronic ester intermediate AN, is subjected to metal catalyzed cross-coupling conditions, for example Ullman, Buchwald-Hartwig or Chan-Lam conditions with a nitrogen containing heterocyclyl or a nitrogen containing heteroaryl 20 to provide the appropriate N-coupled product 21. This N-coupled product 21 is subjected to solvolysis conditions, for example with hydrazine hydrate to remove the phthalimide to furnish the desired primary amine 22 of Formula (I).

Compounds of Formula (I) wherein $R^1$ is N-linked heteroaryl or N-linked heterocyclyl, may be prepared according to General Reaction Scheme VI-B. Compound 23 is an example of Formula (I) wherein $R^1$ is N-linked heteroaryl or N-linked heterocyclyl and $R^{3a}$ and $R^{3b}$ are H. 2-((7-bromo-4-oxo-3,4-dihydrophthalazin-1-yl)methyl)isoindoline-1,3-dione Intermediate F, is subjected to metal catalyzed cross-coupling conditions, for example Ullman, Buchwald-Hartwig or Chan-Lam conditions with a nitrogen containing heterocyclyl or nitrogen containing heteroaryl 20 to provide the appropriate N-coupled product 21a. This N-coupled product 21a is then subjected to solvolysis conditions, for example with hydrazine hydrate to furnish the desired primary amine 91a of Formula (I).

GENERAL REACTION SCHEME VI-C

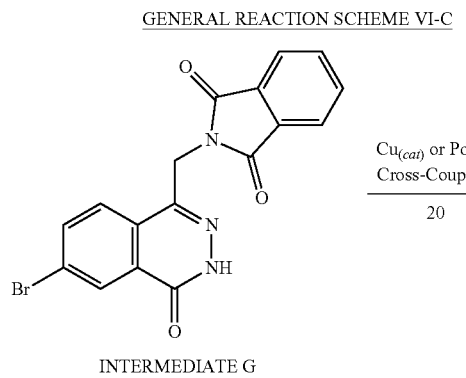

INTERMEDIATE G

21b

91b

R¹ = N-linked heteroalkyl, N-linked aryl/heteroalkyl or N-linked aralkyl

Compounds of Formula (I) wherein R¹ is N-linked heteroalkyl, N-linked arylheteroalkyl or N-linked aralkyl, may be prepared according to General Reaction Scheme VI-C. Compound 24 is an example of Formula I wherein R¹ is N-linked heteroalkyl, N-linked arylheteroalkyl or N-linked aralkyl and $R^{3a}$ and $R^{3b}$ are H. 2-((6-bromo-4-oxo-3,4-dihydrophthalazin-1-yl)methyl)isoindoline-1,3-dione intermediate F, is subject to metal catalyzed cross-coupling conditions, for example Ullman, Buchwald-Hartwig or Chan-Lam conditions with an heteroalkyl/arylheteroalkyl/aralkyl amine 20 to provide the appropriate N-coupled product 21b. This N-coupled product 21b is then subject to solvolysis conditions, for example with hydrazine hydrate to furnish the desired R¹ substituted product 91b of Formula (I).

GENERAL REACTION SCHEME VII

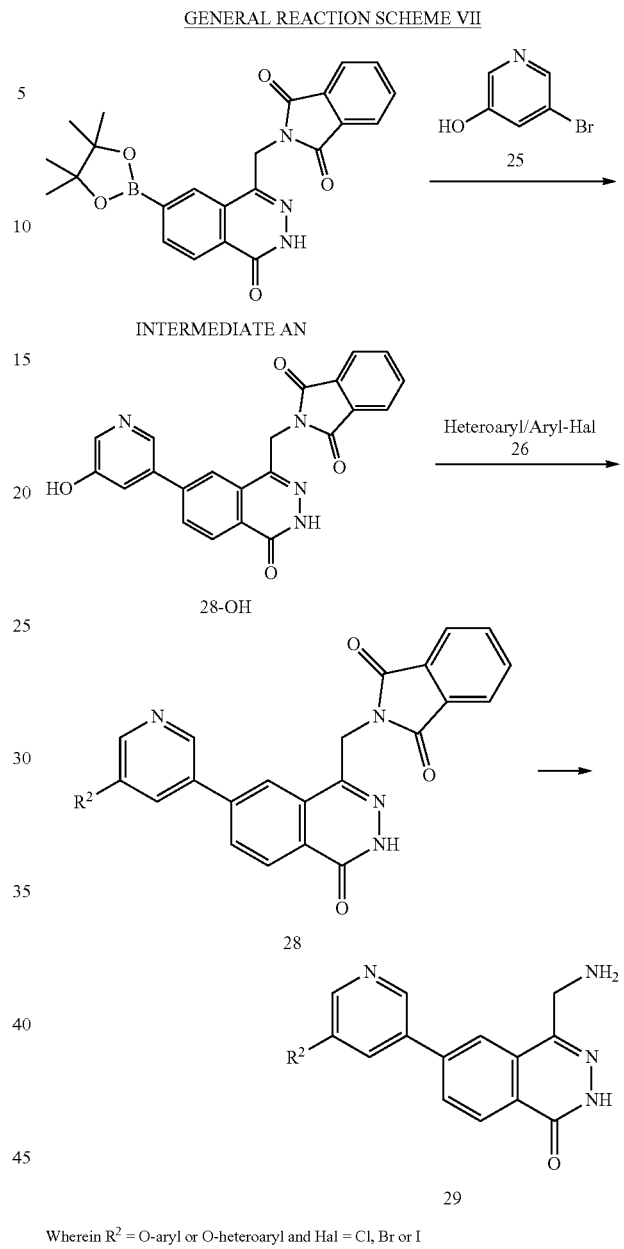

INTERMEDIATE AN

28-OH

28

29

Wherein R² = O-aryl or O-heteroaryl and Hal = Cl, Br or I

Compounds of Formula (I) wherein R¹ is pyridyl and R² is O-aryl or O-heteroaryl, may be prepared according to General Reaction Scheme VII. Compound 29 is an example of Formula (I) wherein R¹ is pyridyl, R² is O-aryl or O-heteroaryl and $R^{3a}$ and $R^{3b}$ are H. 3-bromo-5-hydroxypyridine 25 is coupled to boronic ester Intermediate AN under palladium catalyzed cross coupling conditions, for example the Suzuki coupling conditions Pd(dppf)Cl₂, NaHCO₃, dioxane/water at 80° C., to generate coupling product 28-OH. Coupling product 28-OH was subjected to $S_NAr$ reaction conditions for example K₂CO₃ in DMF at 110° C. with R²-substituted aryl/heteroaryl halide 26, to furnish R²-substituted aryl/heteroaryl pyridyl ether 28. R²-substituted aryl/heteroaryl pyridyl ether 28 was subjected to solvolysis conditions, for example hydrazine hydrate to furnish free amine 29 of Formula (I).

GENERAL REACTION SCHEME VIII-A

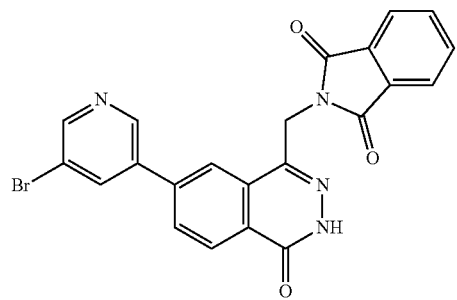

INTERMEDIATE CB

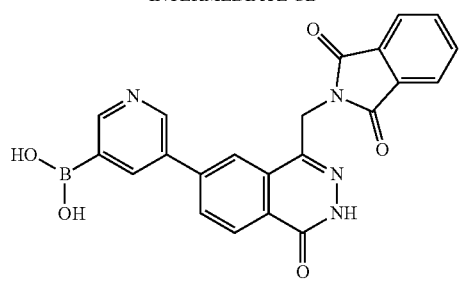

86

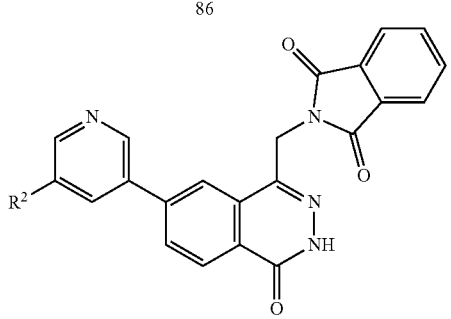

84

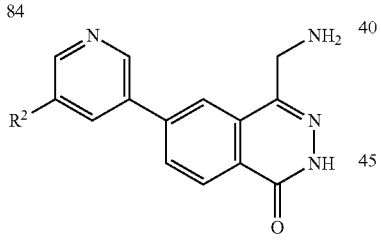

85

Wherein R² = aryl or heteroaryl

GENERAL REACTION SCHEME VIII-B

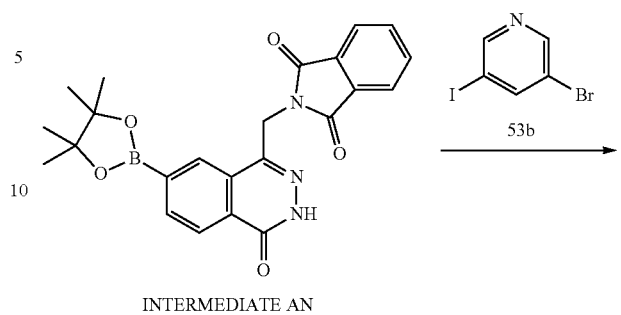

INTERMEDIATE AN

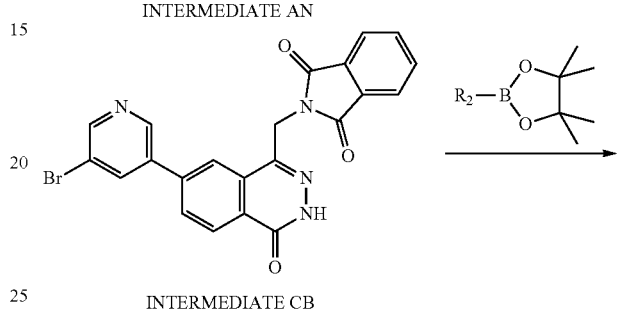

INTERMEDIATE CB

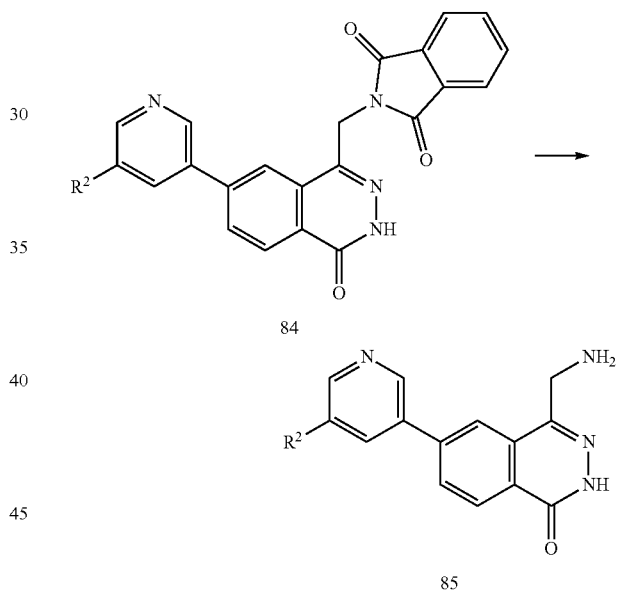

wherein R² = aryl or heteroaryl

Compounds of Formula (I) wherein R¹ is pyridyl and R² is aryl or heteroaryl, may be prepared according to General Reaction Scheme VIII-A. Compound 85 is an example of Formula (I) wherein R¹ is pyridyl, R² is aryl or heteroaryl and R³ᵃ and R³ᵇ are H. Intermediate CB is borylated under Miyaura conditions, for example with bis(pinacolato)diboron, Pd(dppf)Cl₂, KOAc in dioxane at elevated temperature to provide boronic acid 86. Boronic acid 86 is coupled with R² halide 26 under palladium catalyzed cross coupling conditions, for example Suzuki conditions, to yield R²-pyridyl coupling product 84. R²-pyridyl coupling product 84 is subjected to solvolysis conditions, for example with hydrazine hydrate, to provide primary amine 85 of Formula (I).

Compounds of Formula (I) wherein R¹ is pyridyl and R² is aryl or heteroaryl, may be prepared according to General Reaction Scheme VIII-B. Compound 85 is an example of Formula (I) wherein R¹ is pyridyl, R² is aryl or heteroaryl and R³ᵃ and R³ᵇ are H. Intermediate AN is coupled to 3-bromo-5-iodopyridine 53b under palladium catalyzed cross coupling conditions, for example Suzuki conditions, to give 3-bromo-pyridyl coupling product Intermediate CB. Intermediate CB is then coupled to aryl/heteroaryl-substituted boronic ester under palladium catalyzed cross-coupling conditions, for example Suzuki coupling conditions, to provide R²-substituted pyridyl coupling product 84. Coupling product 84 undergoes solvolysis, for example with hydrazine hydrate, to provide primary amine 85 of Formula (I).

107

GENERAL REACTION SCHEME IX-A

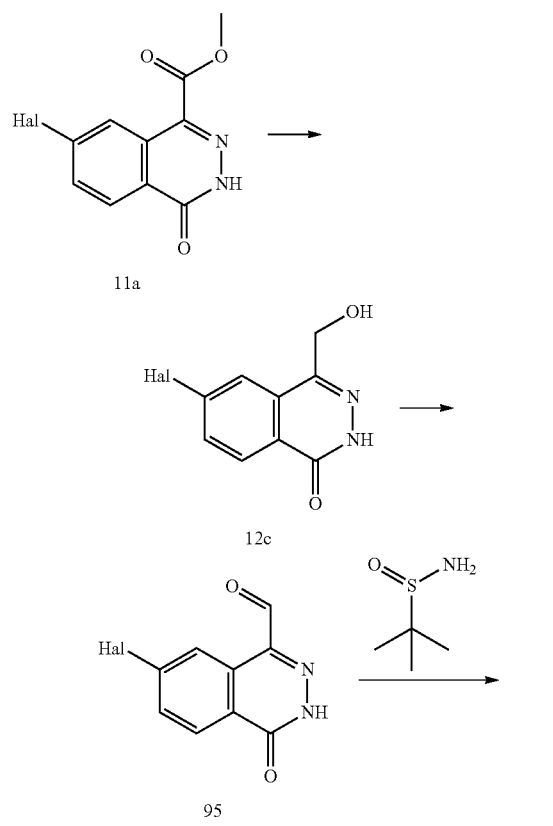

11a

12c

95

96

97

108

-continued

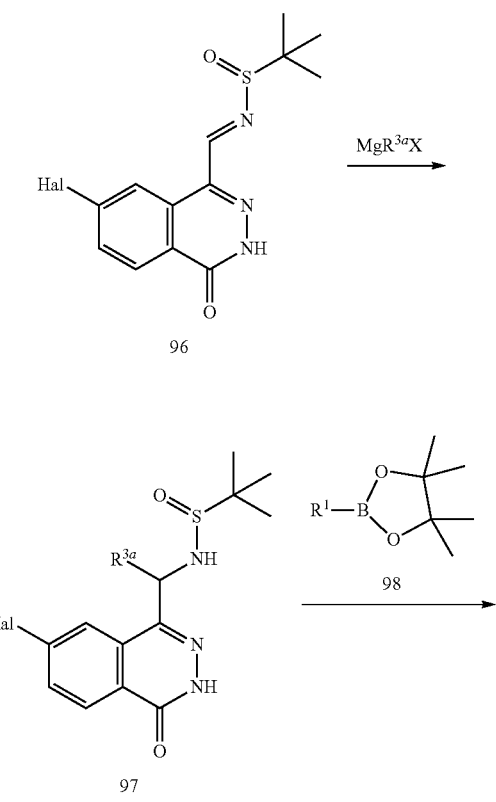

99

100

Wherein $R^1$ = aryl/heteroaryl, $R^{3a}$ = alkyl and Hal = Cl, Br or I

Compounds of Formula (I), wherein $R^1$ is aryl or heteroaryl, $R^{3a}$ is alkyl and $R^{3b}$ is H, may be prepared according to General Reaction Scheme IX-A. Compound 100 is an example of Formula (I) wherein $R^1$ is aryl or heteroaryl, $R^{3a}$ is alkyl and $R^{3b}$ is H. Methyl 7-halo-4-oxo-3,4-dihydrophthalazine-1-carboxylate 11a is reduced using a hydride reducing conditions, for example sodium borohydride, $CaCl_2$ in methanol at 0° C., to afford primary alcohol 6-halo-4-(hydroxymethyl)phthalazin-1(2H)-one 12a. 6-halo-4-(hydroxymethyl)phthalazin-1(2H)-one 12a is reacted with an oxidant, for example $MnO_2$ in dichloroethane to furnish 7-halo-4-oxo-3,4-dihydrophthalazine-1-carbaldehyde 95. 7-halo-4-oxo-3,4-dihydrophthalazine-1-carbaldehyde 95 is converted to the sulfinamide compound 96 by for example, adding t-butanesulfinamide, titanium tetra-isopropoxide in THF and heating to 60° C. for 12 hours. t-Butyl sulfonamide 96 is then reacted with alkylmagnesium halide in THF at −78° C. to generate methyl sulfonamide 97. Methyl sulfonamide 97 is coupled to an appropriate $R^1$-substituted boronic ester under palladium catalyzed cross coupling conditions, for example Suzuki conditions, to supply $R^1$-substituted coupling product 99. $R^1$-substituted coupling product 99 is desulfinylated under acidic conditions, for example HCl/dioxane to furnish $R^1$-substituted primary amine 100 of Formula (I).

GENERAL REACTION SCHEME IX-B

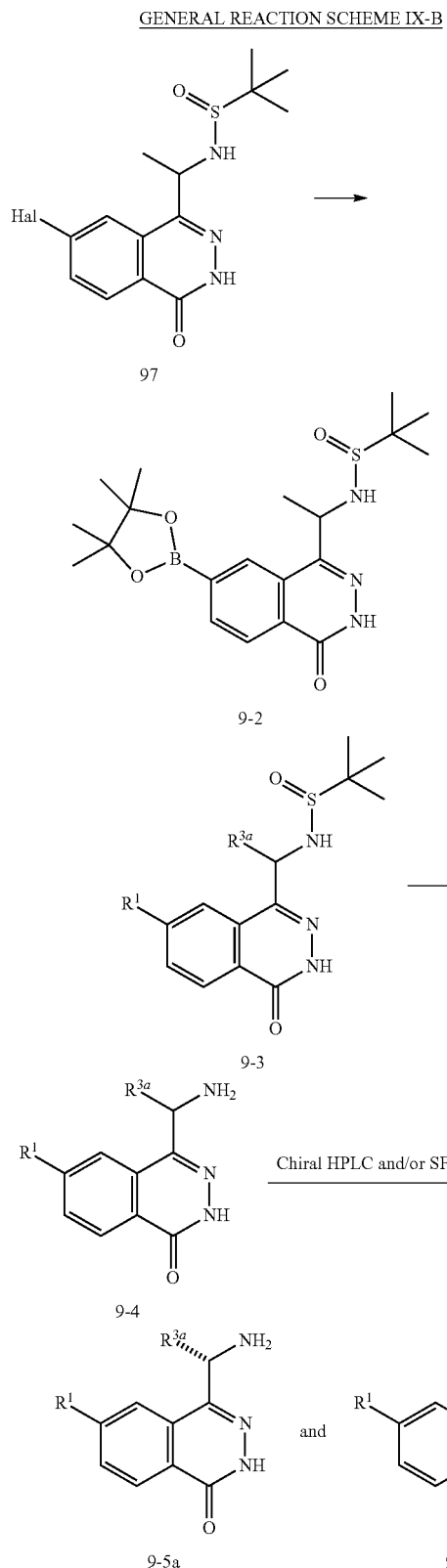

9-5a 9-5b
wherein R¹ = aryl/heteroaryl R³ᵃ = alkyl and Hal = Cl, Br or I

Compounds of Formula (I), wherein R¹ is aryl or heteroaryl, R³ᵃ is alkyl and R³ᵇ is H, may be prepared according to General Reaction Scheme IX-B. Compounds 9-5a and 9-5b are examples of Formula (I) wherein R¹ is aryl or heteroaryl, R³ᵃ is alkyl and R³ᵇ is H. t-Butyl sulfinamide intermediate 97 is borylated under Miyaura conditions, for example with bis(pinacolato)diboron, Pd(dppf)Cl₂, KOAc in dioxane at elevated temperature to provide boronic ester 9-2 which is then reacted coupled to an appropriate R¹-substituted halide under palladium catalyzed cross coupling conditions, for example Suzuki conditions, to supply R¹-substituted coupling product 9-3. R¹-substituted coupling product 9-3 is desulfinylated under acidic conditions, for example HCl/dioxane to furnish R¹-substituted primary amine 9-4 of Formula (I). The racemic mixture of 9-4 is then separated into the corresponding pure enantiomers via chiral prep HPLC and or chiral SFC to give chiral amines 9-5a and 9-5b examples of compounds of Formula (I).

GENERAL REACTION SCHEME X

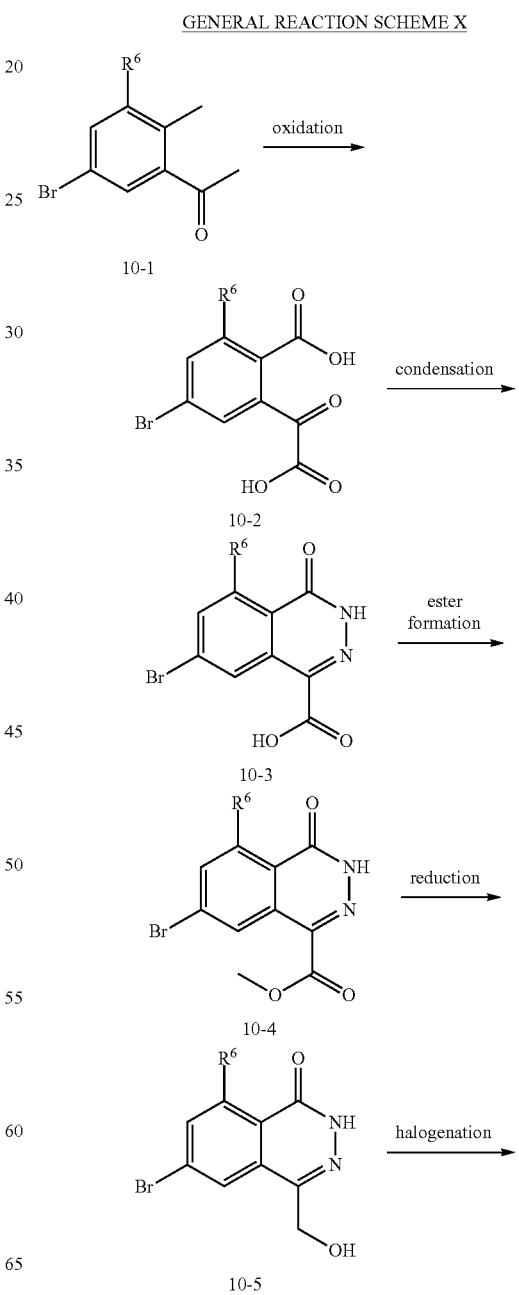

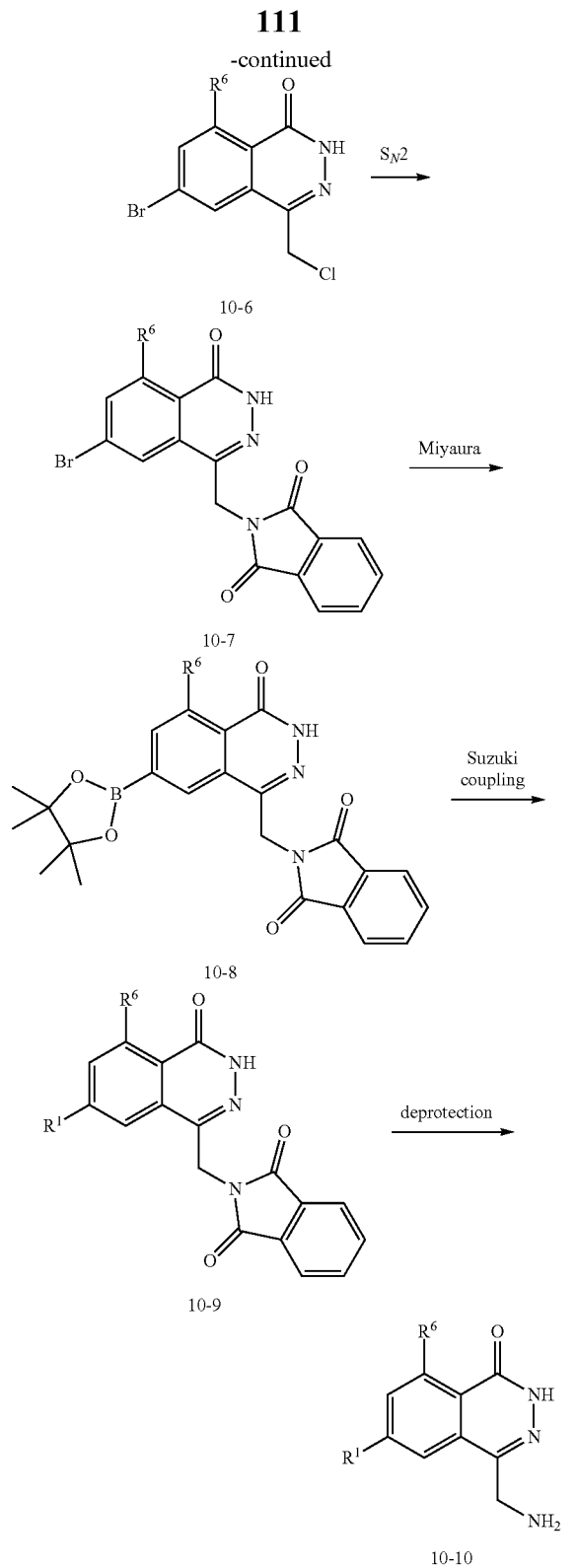

wherein R¹ = aryl/heteroaryl and R⁶ = H, halogen, C1-C3 alkyl or alkoxy

Compounds of Formula (I) wherein $R^1$ is aryl, heteroaryl, heterocyclyl or alkyl, may be prepared according to General Reaction Scheme X. Compound 10-10 is an example of Formula (I) wherein $R^1$ is aryl, heteroaryl, heterocyclyl or alkyl, $R^{3a}$ and $R^{3b}$ are H and $R^6$ is hydrogen, halogen, C1-C3 alkyl or alkoxy. 1-(5-bromo-2-methyl-3-substituted phenyl) ethanone 10-1 is treated with an oxidant, for example $KMnO_4$ in water at 50° C. to furnish 4-bromo-2-(carboxycarbonyl)-6-substituted-benzoic acid 10-2. Condensation of 10-2, for example with hydrazine hydrate in ethanol at elevated temperature, yields 7-bromo-4-oxo-3,4-dihydrophthalazine-5-substituted-1-carboxylic acid 10-3 which is then esterified with acid and alcohol, for example sulfuric acid and methanol to give ester 10-4. Methyl 7-bromo-4-oxo-3,4-dihydrophthalazine-5-substituted-1-carboxylate 10-4 is reduced via hydride reduction, for example with sodium borohydride and $CaCl_2$) in methanol, to afford the 6-bromo-4-(hydroxymethyl)-8-substituted-phthalazin-1(2H)-one 10-5, which is then treated with halogenating agent, for example thionyl chloride for 12 hours to provide 6-halo-4-(chloromethyl)-8-substituted-phthalazin-1(2H)-one 10-6. Nucleophilic $S_N2$ displacement of 10-6 with a nitrogen nucleophile for example, potassium phthalimide in DMF at elevated temperature furnishes 10-7 which is borylated, for example with Miyaura conditions, to give boronate ester 10-8. Palladium-mediated cross coupling conditions, for example Suzuki conditions, with boronic ester 10-8 and aryl/heteroaryl/heterocyclyl/alkyl halides provides phthalazinone coupling product 10-9. The phthalimide protecting group of 10-9 is removed under solvolysis conditions, for example with hydrazine hydrate in ethanol to furnish the desired compound 10-10 of Formula (I).

GENERAL REACTION SCHEME XI

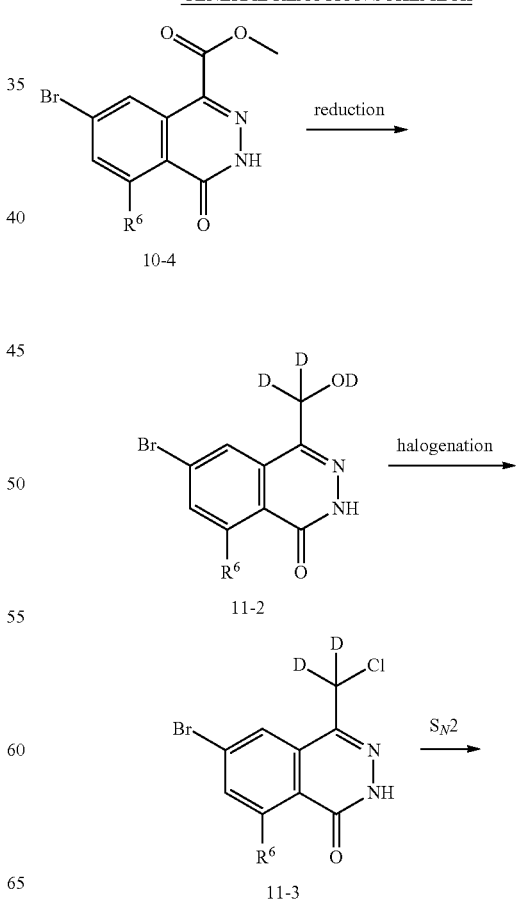

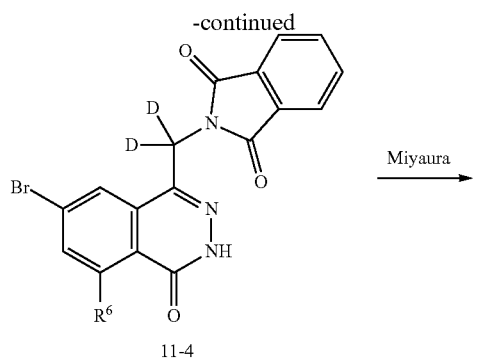
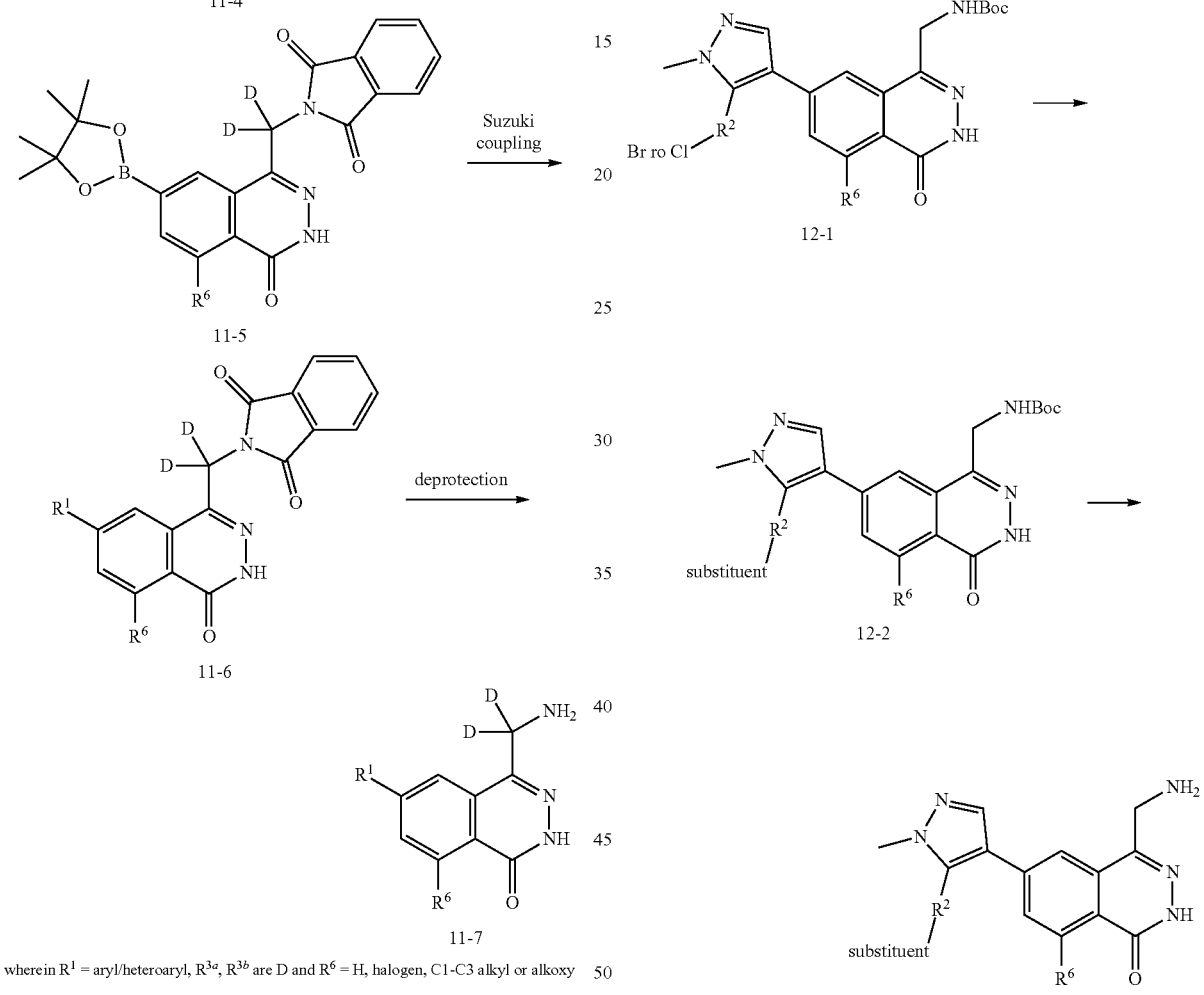

elevated temperature furnishes 11-4 which is borylated, for example with Miyaura conditions, to give boronate ester 11-5. Palladium-mediated cross coupling conditions, for example Suzuki conditions, with boronic ester 11-5 and aryl/heteroaryl/heterocyclyl/alkyl halides provides phthalazinone coupling product 11-6. The phthalimide protecting group of 11-6 is removed under solvolysis conditions, for example with hydrazine hydrate in ethanol to furnish the desired compound 11-7 of Formula (I).

Compounds of Formula (I) wherein $R^1$ is aryl, heteroaryl, heterocyclyl or alkyl, may be prepared according to General Reaction Scheme XI. Compound 11-7 is an example of Formula (I) wherein $R^1$ is aryl, heteroaryl, heterocyclyl or alkyl, $R^{3a}$ and $R^{3b}$ are D and $R^6$ is hydrogen, halogen, C1-C3 alkyl or alkoxy. Methyl 7-bromo-4-oxo-3,4-dihydrophthalazine-5-substituted-1-carboxylate 10-4 is reduced via deuteride reduction, for example with sodium borodeuteride and $CaCl_2$ in methanol-d4, to afford the 6-bromo-4-((hydroxy-d)methyl-d2)-8-substituted-phthalazin-1(2H)-one 11-2, which is then treated with halogenating agent, for example thionyl chloride for 12 hours to provide 6-bromo-4-(chloromethyl-d2)-8-substituted-phthalazin-1(2H)-one 11-3. Nucleophilic $S_N2$ displacement of 11-3 with a nitrogen nucleophile for example, potassium phthalimide in DMF at Compounds of Formula (I) wherein $R^2$ is aryl or heteroaryl, may be prepared according to General Reaction Scheme XII. Compound 12-3 is an example of Formula (I) wherein $R^2$ is aryl or heteroaryl, $R^{3a}$ and $R^{3b}$ are H, $R^6$ is hydrogen, halogen, C1-C3 alkyl or alkoxy and substituent is alkyl, aryl or heteroaryl. Bromo or chloro compound 12-1 is subjected to palladium-mediated cross coupling conditions, for example Suzuki conditions, with an alkyl/aryl/heteroaryl boronic acid/ester to give substituent coupled product 12-2. The BOC group is then removed with acidiemc conditions, for example TFA, to afford $R^2$-substituted amine 12-3 of Formula (I).

GENERAL REACTION SCHEME XIII

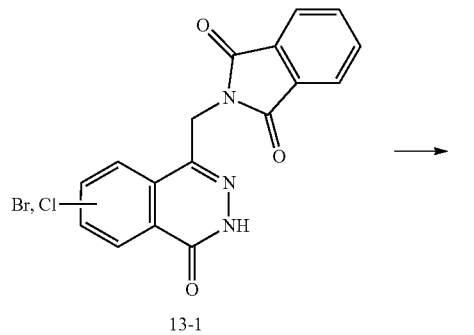

13-1

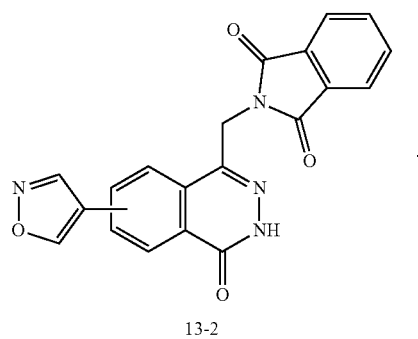

13-2

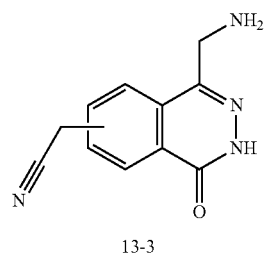

13-3

Compounds of Formula (I) wherein $R^1$ is alkyl-cyano, may be prepared according to General Reaction Scheme XIII Compound 13-3 is an example of Formula (I) wherein $R^1$ is —CH$_2$CN. Bromo or chloro compound 13-1 is subjected to palladium-mediated cross coupling conditions, for example Suzuki conditions, with an isoxazole boronic acid/ester to give substituent coupled product 13-2. The isoxazole is then subjected to hydrazine hydrate in an alcoholic solvent such as ethanol at elevated temperature followed by acidic work up, for example with HCl at pH 1 to give nitrile product 13-3 of Formula (I).

GENERAL REACTION SCHEME XIV

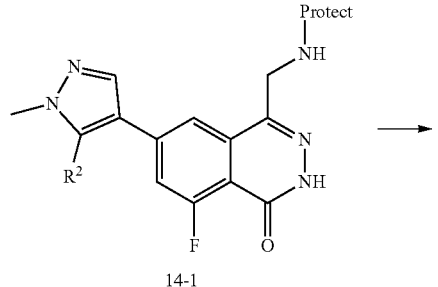

14-1

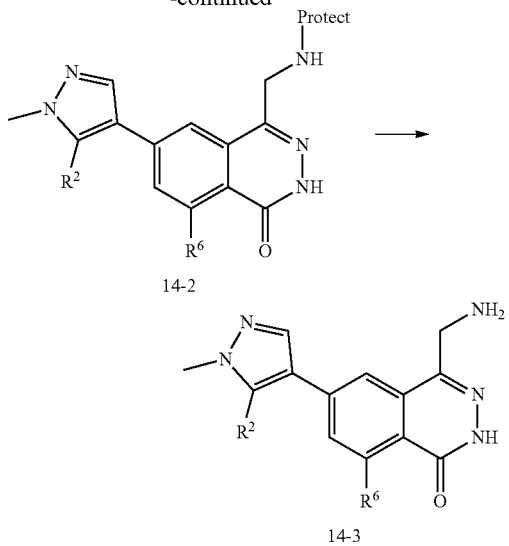

14-2

14-3 wherein $R^2$ = aryl/heteroaryl and $R^6$ = alkoxy

Compounds of Formula (I) wherein $R^2$ is aryl or heteroaryl and $R^6$ is alkoxy may be prepared according to General Reaction Scheme XIV. Compound 14-3 is an example of Formula (I) wherein $R^2$ is aryl or heteroaryl, and $R^6$ is alkoxy. Fluoro compound 14-1 with the amine suitably protected with for example, a BOC group or phthalimide group is subjected to aromatic $S_N2$ conditions with —F as the leaving group and the corresponding oxy anion as the nucleophile. For example, with a sodium alkyl oxide in a polar solvent with heat to give substituent substituted product 14-2. The protecting group is then removed under appropriate conditions. For example, the BOC is removed under acidic conditions such as HCl or TFA in dioxane or the phthalimide group is removed under basic nucleophilic conditions such as hydrazine hydrate in ethanol with heat to afford $R^6$-substituted amine 14-3 of Formula (I).

GENERAL REACTION SCHEME XV

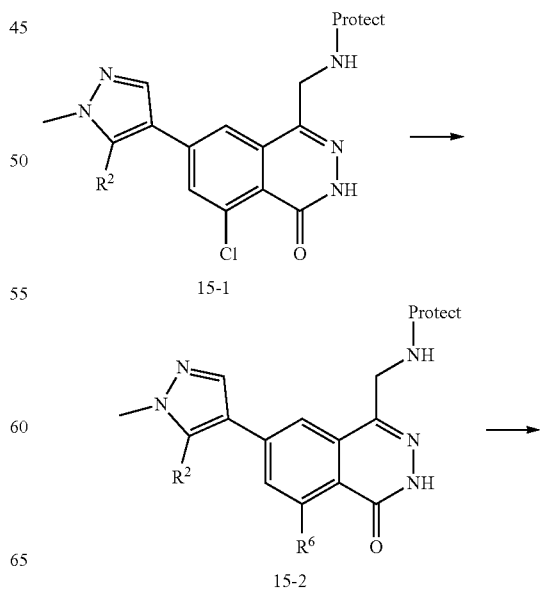

15-1

15-2

-continued

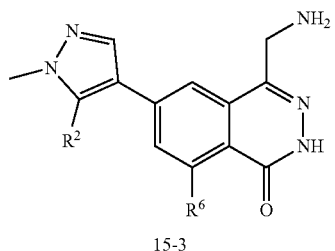

15-3 wherein R² = aryl/heteroaryl and R⁶ = C1-C3 alkyl

-continued

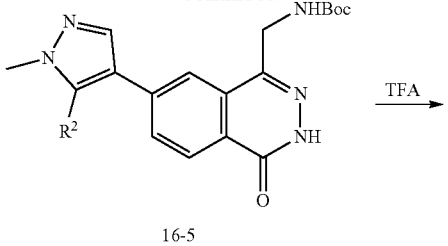

16-5

Compounds of Formula (I) wherein $R^2$ is aryl or heteroaryl and $R^6$ is C1-C3 alkyl may be prepared according to General Reaction Scheme XV. Compound 15-3 is an example of Formula (I) wherein $R^2$ is aryl or heteroaryl, and $R^6$ is C1-C3 alkyl. Chloro compound 15-1 with the amine suitably protected with for example, a BOC group or phthalimide group, is coupled to the appropriate C1-C3 trialkylborane under palladium catalyzed cross coupling conditions, for example Suzuki-Miyaura coupling conditions, to supply the corresponding $R^6$-substituted coupling product 15-2. The protecting group is then removed under appropriate conditions. For example, the BOC is removed under acidic conditions such as HCl in dioxane or TFA in dioxane and the phthalimide group is removed under basic nucleophilic conditions such as hydrazine hydrate in ethanol with heat to afford $R^6$-substituted amine 15-3 of Formula (I).

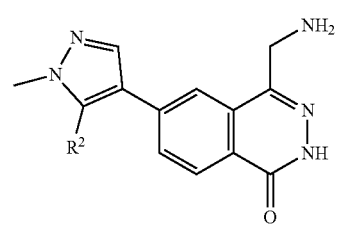

16-6

GENERAL REACTION SCHEME XVI

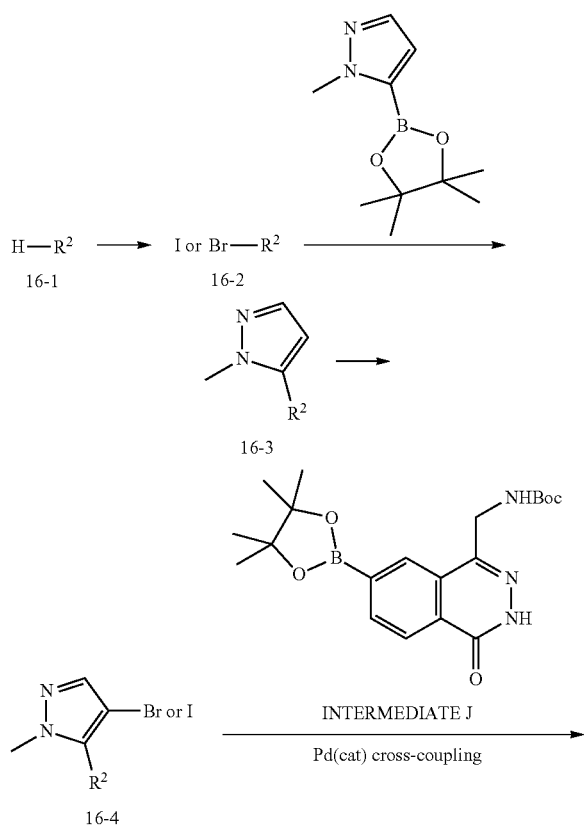

Compounds of Formula (I) wherein $R^1$ is 1-methyl-5-$R^2$-1H-pyrazole-4-yl and $R^2$ is alkyl, aryl or heteroaryl, may be prepared according to General Reaction Scheme XVI. Compound 16-6 is an example of Formula (I) wherein $R^1$ is 1-methyl-5-$R^2$-1H-pyrazole-4-yl, $R^2$ is alkyl, aryl or heteroaryl and $R^{3a}$ and $R^{3b}$ are H. H—$R^2$ 16-1 is halogenated, for example with a halogenating agent such N-bromosuccinimide or N-iodosuccinimide under palladium catalyzed conditions such as palladium acetate in the presence of an acid such as p-toluenesulfonic acid in a solvent such as dichloroethane under elevated temperature for example 70° C. to give halide 16-2. Bromo or iodo compound 16-2 is subjected to palladium-mediated cross coupling conditions, for example Suzuki conditions, with 1-methyl-5-(4,4,5,5-tetramethyl-1,3,2-dioxaborolan-2-yl)-1H-pyrazole to give coupled product 16-3. 1-methyl-5-$R^2$-1H-pyrazole 16-3 is halogenated for example with a halogenating agent such N-bromosuccinimide or N-iodosuccinimide in a polar solvent such as acetonitrile to give 4-halo-1-methyl-5-$R^2$-1H-pyrazole compound 16-4. 4-bromo-1-methyl-5-$R^2$-1H-pyrazole 16-4 is coupled to Intermediate J under palladium-mediated cross coupling conditions, for example Suzuki conditions, to provide N-Boc-$R^2$-substituted coupling product 16-5. The coupling product 16-5 is subjected to acidic conditions to remove the Boc group, for example TFA, to afford $R^2$-substituted amine 16-6 of Formula (I).

Intermediates C, D and E

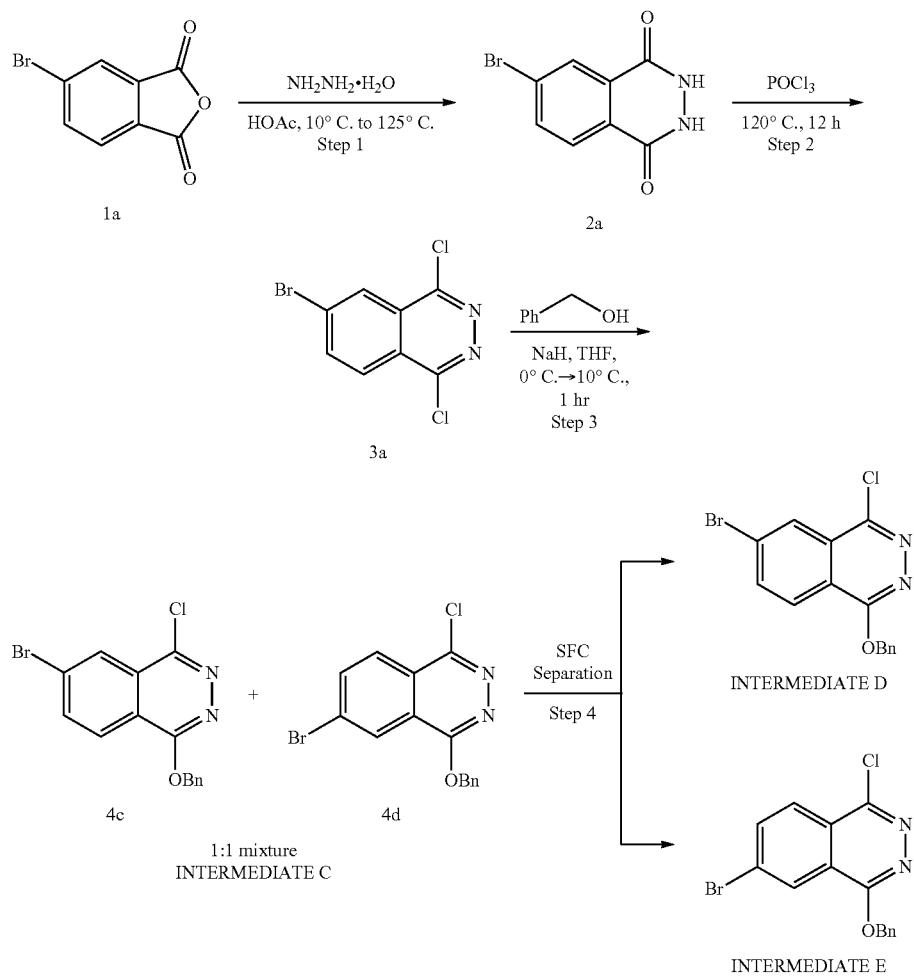

Step 1: A mixture of 5-bromoisobenzofuran-1,3-dione 1a (55.0 g, 242 mmol, 1.00 eq.) and acetic acid (165 mL) was stirred at 125° C. for 1 hour. After such time the mixture was cooled to 10° C. and hydrazine hydrate (12.7 g, 254 mmol, 12.4 mL, 1.05 eq.) was added dropwise, resulting in the formation of a thick white precipitate. Additional acetic acid (55 mL) was added and the mixture stirred at 125° C. for a further 30 mins. After such time the mixture was cooled, diluted with acetic acid (150 mL) and filtered. The filter cake was washed with acetic acid (50 mL×3), dried and then dissolved in a 5% (w/w) sodium hydroxide solution (800 mL). The solution was acidified with acetic acid (200 mL) to give a thick white precipitate which was filtered. The filter cake was washed with water (50 mL×3) followed by methanol then dried in vacuo to give 6-bromo-2,3-dihydrophthalazine-1,4-dione 2a (45.6 g, crude) as a white solid. This solid was then used in the next step without further purification. $^1$H NMR (400 MHz, DMSO-$d_6$) δ=8.17 (d, J=2.0 Hz, 1H), 8.01-7.97 (m, 1H), 7.95-7.89 (m, 1H).

Step 2: A solution of 6-bromo-2,3-dihydrophthalazine-1,4-dione 2a (20.0 g, crude) in phosphorus oxychloride (330 g, 2.15 mol, 200 mL) was stirred at 120° C. for 12 hours. After such time the reaction mixture was concentrated under reduced pressure and the residue dissolved in dichloromethane (150 mL) and added dropwise to ice-water. The mixture was then extracted with dichloromethane (300 mL×3) and the combined organic layers were washed with sodium bicarbonate aqueous solution (200 mL×5), brine (200 mL×2), dried over sodium sulfate, filtered and concentrated under reduced pressure to give 6-bromo-1,4-dichloro-phthalazine 3a (14.5 g, crude) as a yellow solid. This solid was then used in the next step without further purification. $^1$H NMR (400 MHz, CDCl$_3$) δ=8.49 (d, J=1.2 Hz, 1H), 8.23-8.15 (m, 2H).

Step 3: A solution of benzyl alcohol (4.59 g, 42.4 mmol, 4.41 mL) and sodium hydride (3.77 g, 94.3 mmol, 60% dispersion in mineral oil) in THF (30 mL) was stirred at 0° C. for 0.5 hour. The mixture was then added dropwise to a solution of 6-bromo-1,4-dichloro-phthalazine 3a (13.1 g, crude) in THF (80 mL) at 0° C. The reaction mixture was warmed to 10° C. and stirred at 10° C. for 1 hour. After such time the reaction mixture was diluted with water (100 mL) and extracted with ethyl acetate (150 mL×3). The combined organic layers were washed with brine (100 mL), dried over anhydrous sodium sulfate, filtered and concentrated under reduced pressure. The residue was purified by column chromatography (SiO$_2$, petroleumether:ethylacetate 10-25%) to give Intermediate C, a 1:1 mixture of 4-benzyloxy-7-bromo-1-chloro-phthalazine 4c and 4-benzyloxy-6-bromo-1-chloro-phthalazine 4d (9.79 g, 28.0 mmol, 66% yield) as a yellow solid. ¹H NMR (400 MHz, CDCl₃) δ=8.39 (d, J=1.2 Hz, 1H), 8.35 (d, J=1.6 Hz, 1H), 8.17-8.10 (m, 1H), 8.08-8.05 (m, 1H), 8.04 (d, J=2.0 Hz, 1H), 8.00 (dt, J=1.6, 8.4 Hz, 1H), 7.59-7.53 (m, 4H), 7.47-7.36 (m, 6H), 5.70 (s, 4H).

Step 4: The regioisomers of Intermediate C, a 1:1 mixture of 4c and 4d (9.79 g, 28.0 mmol) were separated by SFC (column: DAICEL CHIRALPAK AD (250×30 mm, 10 μm); mobile phase: [0.1% NH₃H₂O MeOH]; B %: 0%-60%; 40 min) to give Intermediate D, 4-benzyloxy-7-bromo-1-chloro-phthalazine (2.40 g, 6.86 mmol) as a white solid and Intermediate E, 4-benzyloxy-6-bromo-1-chloro-phthalazine (2.54 g, 7.27) as a white solid. Intermediate D: 4-benzyloxy-7-bromo-1-chloro-phthalazine: ¹H NMR (400 MHz, CDCl₃) δ=8.36 (d, J=2.0 Hz, 1H), 8.13 (d, J=8.8 Hz, 1H), 7.99 (dd, J=2.0, 8.8 Hz, 1H), 7.58-7.54 (m, 2H), 7.46-7.36 (m, 3H), 5.70 (s, 2H). LCMS [M+1]⁺ 351.0. Intermediate E: 4-benzyloxy-6-bromo-1-chloro-phthalazine: ¹H NMR (400 MHz, CDCl₃) δ=8.39 (d, J=1.6 Hz, 1H), 8.10-8.01 (m, 2H), 7.61-7.54 (m, 2H), 7.48-7.35 (m, 3H), 5.70 (s, 2H). LCMS [M+1]⁺ 351.0.

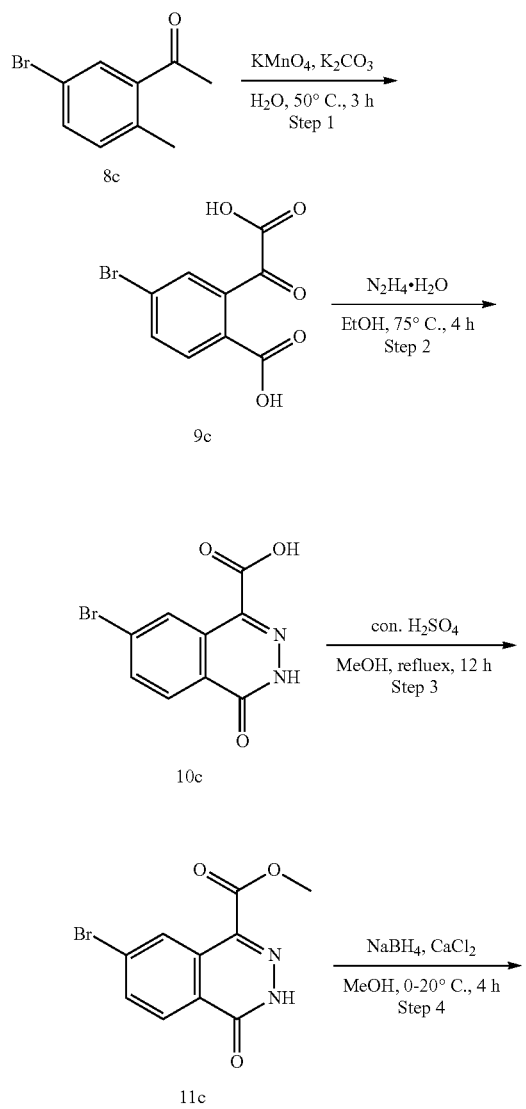

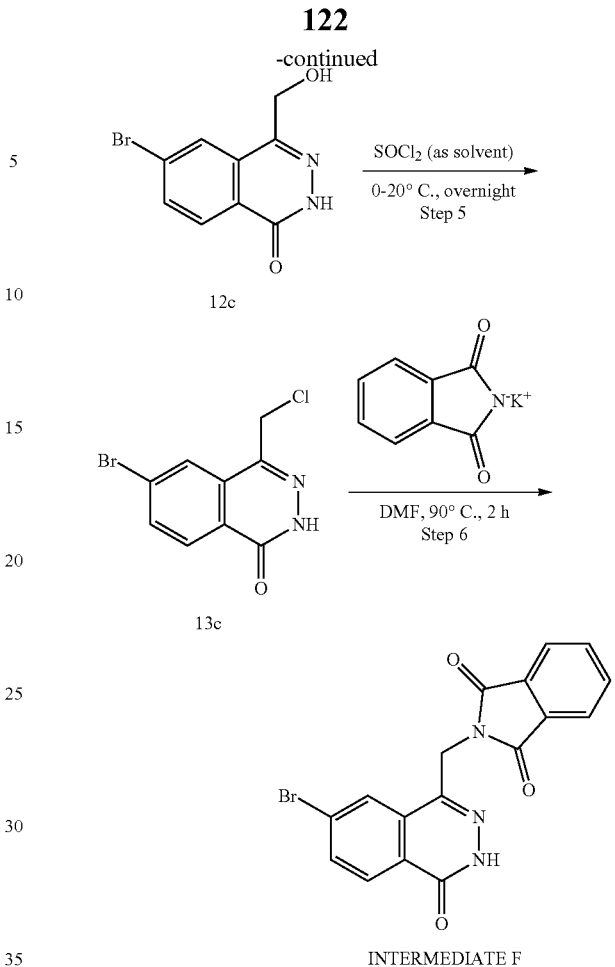

INTERMEDIATE F

Step 1: To a solution of 1-(5-bromo-2-methyl-phenyl)ethenone 8c (100 g, 445 mmol, 1.00 eq.) in water (1.00 L) was added potassium carbonate (92.4 g, 668 mmol, 1.50 eq.) and potassium permanganate (493 g, 3.12 mol, 7.00 eq.). The mixture was stirred at 50° C. for 3 hours before ethanol (1.00 L) was added and the resulting mixture stirred at 50° C. for a further 30 minutes. After such time the solid was filtered and the filtrate pH adjusted to pH 2 with conc. hydrochloric acid (500 mL). The mixture was then extracted with ethyl acetate (1.00 L), the organic layer separated then concentrated in vacuo to give 4-bromo-2-oxalo-benzoic acid 9c (278 g, 997 mmol, 75% yield) as a white solid which was used in the next step without further purification. LCMS [M+1]⁺=271.1.

Step 2: To a solution of 4-bromo-2-oxalo-benzoic acid 9c (382 g, 1.27 mol) in ethyl alcohol (3.00 L) was added hydrazine hydrate (71.2 g, 1.39 mol, 69.1 mL). The mixture was stirred at 75° C. for 4 hours and the formed precipitate was filtered, washed with ethyl alcohol (500 mL) and dried to give 7-bromo-4-oxo-3H-phthalazine-1-carboxylic acid 10c (280 g, 1.03 mol, 81% yield) as a white solid which was used in the next step without further purification. ¹H NMR (400 MHz, DMSO-d₆) δ=8.72-8.81 (m, 1H), 8.11-8.21 (m, 1H), 7.95-8.09 (m, 1H).

Step 3: To a solution of 7-bromo-4-oxo-3H-phthalazine-1-carboxylic acid 10c (200 g, 675 mmol) in methyl alcohol (2.00 L) was added sulfuric acid (131 g, 1.31 mol, 71.0 mL) and the reaction mixture stirred at 65° C. for 24 hours. After such time the cooled reaction mixture was filtered and the filter cake dried under reduced pressure to give methyl 7-bromo-4-oxo-3H-phthalazine-1-carboxylate 11b (216 g, crude) as a white solid which was used in the next step without further purification. LCMS [M+1]$^+$=283.0; $^1$H NMR (400 MHz, DMSO-d$_6$) δ=13.31 (s, 1H), 8.72 (s, 1H), 8.16-8.18 (d, J=8.4 Hz, 1H), 8.03-8.05 (d, J=8.4 Hz, 1H), 3.91 (s, 3H).

Step 4: A stirred solution of methyl 7-bromo-4-oxo-3H-phthalazine-1-carboxylate 11c (159 g, 494 mmol) in ethyl alcohol (1.50 L) was treated portion wise with sodium borohydride (48.6 g, 1.29 mol, 2.60 eq) at 0° C. To this mixture was added a solution of calcium chloride (65.8 g, 593 mmol, 1.20 eq). The mixture was then stirred for 2 hours at 0° C. and a further 1 hour at 20° C. After such time the reaction mixture was concentrated under reduced pressure, and the residue was suspended in water (800 mL), the pH was adjusted to pH 5 with 1N hydrochloric acid (300 mL) and the precipitate was filtered, washed with water (300 mL×3) and dried to give 6-bromo-4-(hydroxymethyl)-2H-phthalazin-1-one 12c (162 g, crude) as a yellow solid. LCMS [M+1]$^+$=255.0; $^1$H NMR (400 MHz, DMSO-d$_6$) δ=12.66 (s, 1H), 8.30 (d, J=1.6 Hz, 1H), 8.16 (d, J=8.8 Hz, 1H), 8.01 (dd, J=8.4, 2.0 Hz, 1H), 5.58 (t, J=5.6 Hz, 1H), 4.67 (d, J=6.0 Hz, 2H).

Step 5: 6-bromo-4-(hydroxymethyl)-2H-phthalazin-1-one 12c (162 g, crude) was dissolved in thionyl chloride (1.00 L) and the mixture was stirred at 70° C. for 2 hours then concentrated under reduced pressure (35° C.). The concentrated residue was dissolved in dichloromethane (1.00 L) and concentrated to dryness to give 6-bromo-4-(chloromethyl)-2H-phthalazin-1-one 13c (154 g, crude) as a white solid which was used in the next step without further purification. LCMS [M+1]$^+$=274.8; $^1$H NMR (400 MHz, DMSO-d$_6$) δ=12.92 (s, 1H), 8.30 (s, 1H), 8.18-8.20 (d, J=7.6 Hz, 1H), 8.06-8.08 (t, J=8.8 Hz, 1H), 5.07 (s, 2H).

Step 6: To a solution of 6-bromo-4-(chloromethyl)-2H-phthalazin-1-one 13c (148 g, crude) in DMF (1.5 L) was added (1,3-dioxoisoindolin-2-yl)potassium (121 g, 653 mmol). The reaction mixture was stirred at 90° C. for 2 hours and then cooled to 25° C. The formed precipitate was filtered and washed with DMF (200 mL×2) and the filter cake triturated with water (1.00 L), filtered and dried to give Intermediate F, 2-[(7-bromo-4-oxo-3H-phthalazin-1-yl) methyl]isoindoline-1,3-dione (162 g, 413 mmol, 76% yield) as a white solid. $^1$H NMR (400 MHz, DMSO-d$_6$) δ=12.59 (s, 1H), 8.43 (d, J=1.2 Hz, 1H), 8.18 (d, J=8.4 Hz, 1H), 8.07 (dd, J=1.6, 8.4 Hz, 1H), 7.97-7.93 (m, 2H), 7.92-7.86 (m, 2H), 5.19 (s, 2H). LCMS [M+1]: 383.9.

Intermediate F—Route 2

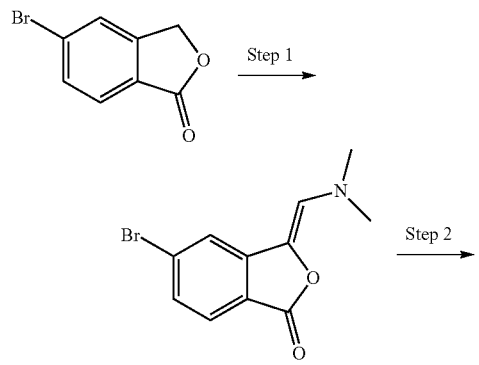

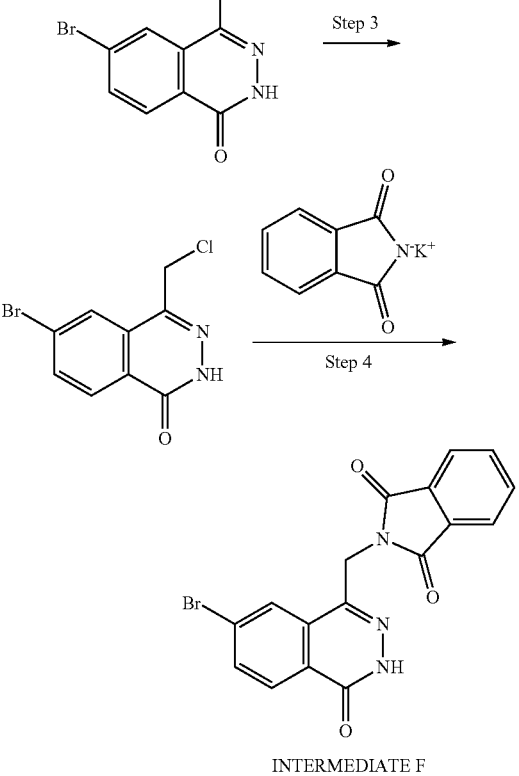

INTERMEDIATE F

Step 1: A mixture of 5-bromoisobenzofuran-1(3H)-one (50.0 g, 235 mmol, 1.00 eq), DMF-DMA (180 g, 1.51 mol, 201 mL, 6.44 eq) and t-BuOK (2.63 g, 23.5 mmol, 0.10 eq) was degassed and purged with N$_2$ 3 times and then stirred at 110° C. for 20 h under a N$_2$ atmosphere. After such time the reaction mixture concentrated under reduced pressure to remove the DMF-DMA and the formed residue was stirred in petroleum ether (100 mL) at 25° C. for 30 mins. The formed solid was filtered and the filter cake stirred in ethyl acetate (200 mL) at 80° C. for 12 h, filtered and the filter cake was dried under reduced pressure to give (Z)-5-bromo-3-((dimethylamino)methylene)isobenzofuran-1(3H)-one (39.0 g, 120 mmol, 51% yield, 82% purity) as a red solid. LCMS [M+1]$^+$=270.1; $^1$H NMR (400 MHz, DMSO-d$_6$) δ=7.97 (d, J=1.2 Hz, 1H), 7.61-7.59 (d, J=8.0, 1H), 7.30-7.27 (dd, J=8.0 &1.2 Hz, 1H), 3.10 (s, 6H).

Step 2: To a mixture of (Z)-5-bromo-3-((dimethylamino) methylene)isobenzofuran-1(3H)-one (39.0 g, 119 mmol, 82.0% purity, 1.00 eq) in EtOH (650 mL) was added NH$_2$NH$_2$.H$_2$O (12.5 g, 245 mmol, 12.1 mL, 2.05 eq) at 25° C. The mixture was degassed with N$_2$ then stirred at 25° C. for 0.5 h and then at 70° C. for 12 h. After such time the reaction mixture was filtered and the solid was dried to give 6-bromo-4-((dimethylamino)methyl)phthalazin-1(2H)-one (30.0 g, 105 mmol, 88% yield, 99% purity) as a yellow solid. LCMS [M+1]$^+$=282.1; $^1$H NMR (400 MHz, DMSO-d$_6$) δ 12.6 (s, 1H), 8.33 (s, 1H), 8.14-8.12 (d, J=8.4 Hz, 1H), 8.00-7.98 (m, 1H), 3.61 (s, 1H), 2.18 (s, 1H).

Step 3: A mixture of 6-bromo-4-((dimethylamino)methyl) phthalazin-1(2H)-one (15.0 g, 53.2 mmol, 1.00 eq) in THF (187 mL) and degassed with N$_2$ 3 times before being cooled to 0° C. Isobutyl carbonochloridate (8.71 g, 63.80 mmol, 8.38 mL, 1.20 eq) was then added dropwise and then the mixture stirred at 25° C. for 6 h under N₂. After such time the mixture was cooled to 0° C. before HCl (0.5 M, 250 mL) was added maintaining a temperature between 0° C. and 10° C. After the addition was complete the solid was filtered, washed with THF (30 mL×3) and dried to afford a 6-bromo-4-(chloromethyl)phthalazin-1(2H)-one (11.0 g, 37.56 mmol, 71% yield, 93% purity) as a yellow solid. LCMS [M+1]⁺=256.1; ¹H NMR (400 MHz, DMSO-d₆) δ 12.9 (s, 1H), 8.29 (d, J=1.6 Hz, 1H), 8.19-8.17 (d, J=8.0 Hz, 1H), 8.06-80.4 (dd, J=8.0 Hz & 1.6 Hz, 1H), 5.06 (s, 2H).

Step 4: To a mixture of 6-bromo-4-(chloromethyl)phthalazin-1(2H)-one (8.06 g, 27.5 mmol, 93% purity, 1.00 eq) in DMF (160 mL) was added (1,3-dioxoisoindolin-2-yl)potassium (5.61 g, 30.3 mmol, 1.10 eq) and stirred at 25° C. for 1 hr. After such time the mixture was washed with HCl (0.5 M, 100 mL), filtered and the solid washed with sat. NaHCO₃. (30 mL×2), pure water (30 mL×2) and then triturated with EtOH (15 mL) at 70° C. for 1 hr. The solid was then filtered and dried to give Intermediate F (8.30 g, 17.9 mmol, 65.0% yield, 83% purity) as a yellow solid. LCMS [M+1]⁺=384.1/386.1; ¹H NMR (400 MHz, DMSO-d₆) δ 12.6 (s, 1H), 8.43 (s, 1H), 8.18-8.16 (d, J=8.0 Hz, 1H), 8.08 (d, J=8.0 Hz, 1H), 7.95-7.89 (m, 4H), 5.18 (s, 2H).

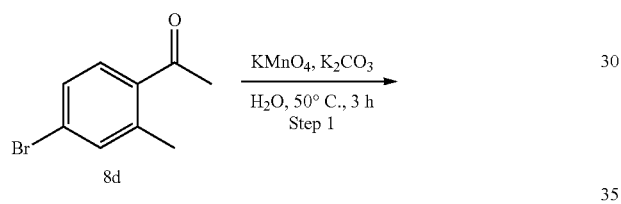

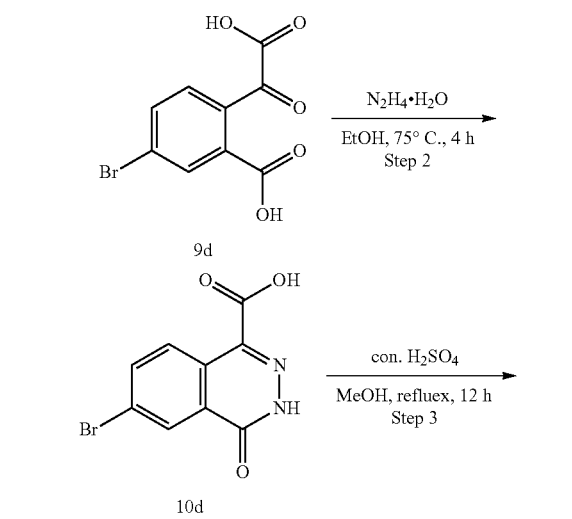

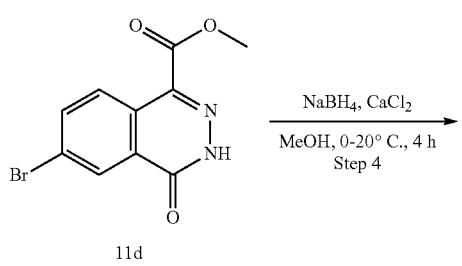

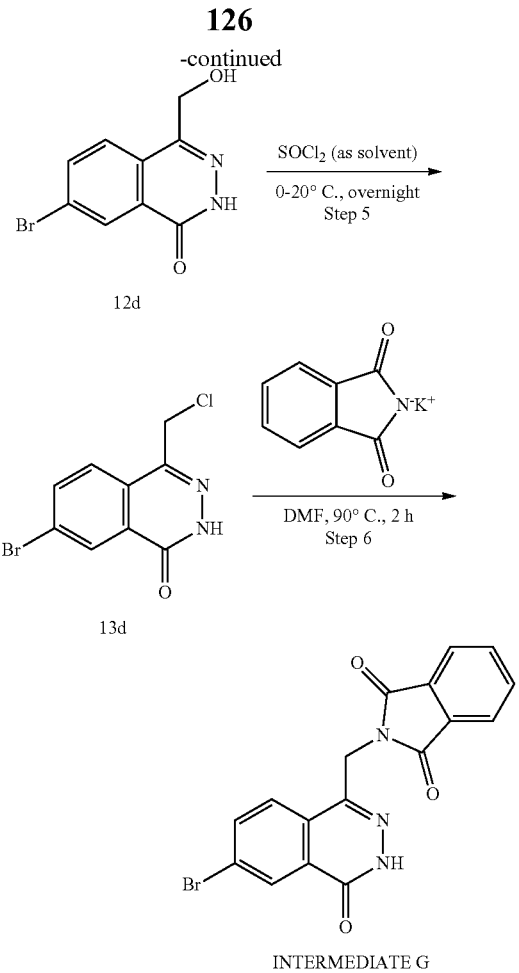

INTERMEDIATE G

Step 1: To a solution of 1-(4-bromo-2-methyl-phenyl)ethenone 8d (10.0 g, 46.9 mmol, 1.00 eq.) in water (50 mL) was added potassium carbonate (9.73 g, 70.40 mmol, 1.50 eq.) and potassium permanganate (51.9 g, 329 mmol, 7.00 eq.). The mixture was stirred at 50° C. for 3 hours before ethanol (50 mL) was added and the resulting mixture stirred at 50° C. for a further 30 minutes. After such time the solid was filtered and the filtrate pH adjusted to pH 2 with conc. hydrochloric acid (5 mL). The mixture was then extracted with ethyl acetate (50 mL), the organic layer separated and concentrated in vacuo to give 5-bromo-2-oxalo-benzoic acid 9d (10.0 g, crude) as a white solid which was used in the next step without further purification. LCMS [M+1]⁺=273.0.

Step 2: To a solution of 5-bromo-2-oxalo-benzoic acid 9d (10.0 g, crude) in ethyl alcohol (120 mL) was added hydrazine hydrate (1.87 g, 36.6 mmol, 1.82 mL) and the mixture was stirred at 75° C. for 4 hours. After such time the formed precipitate was filtered and washed with ethyl alcohol (5 mL) and dried to give 6-bromo-4-oxo-3H-phthalazine-1-carboxylic acid 10d (7.50 g, 27.9 mmol, 59% yield) as a white solid. LCMS [M+1]⁺=269.0.

Step 3: To a solution of 6-bromo-4-oxo-3H-phthalazine-1-carboxylic acid 10d (7.50 g, 27.9 mmol, 1.00 eq.) in methyl alcohol (40 mL) was added sulfuric acid (16.7 g, 167 mmol, 9.10 mL, 6.00 eq.) and the reaction mixture stirred at 65° C. for 12 hours. After such time the reaction mixture was allowed to cool and the formed precipitate was filtered and dried to give methyl 6-bromo-4-oxo-3H-phthalazine-1-carboxylate 11d (7.00 g, 24.7 mmol, 89% yield) as a white solid. LCMS [M+1]⁺=282.9.

Step 4: A stirred solution of sodium borohydride (2.43 g, 64.29 mmol, 2.60 eq.) in ethyl alcohol (250 mL) was treated portion wise with methyl 6-bromo-4-oxo-3H-phthalazine-1-carboxylate 11d (7.00 g, 24.7 mmol, 1.00 eq.) at 0° C. To this mixture was added a solution of calcium chloride (3.29 g, 29.7 mmol, 1.20 eq.) in ethyl alcohol (250 mL) in a dropwise fashion. The mixture was then stirred for 3 hours at 0° C. and an additional hour at 20° C. After such time the mixture was concentrated under reduced pressure and the concentrated residue was suspended in water (30 mL) and the pH adjusted to pH 5 with 1N hydrochloric acid (5 mL). The formed precipitate was filtered, washed with water (5 mL×3) and triturated with ethyl alcohol (50 mL), filtered and dried to give 7-bromo-4-(hydroxymethyl)-2H-phthalazin-1-one 12d (6.00 g, 23.5 mmol, 95% yield) as a white solid. LCMS $[M+1]^+$=255.0.

Step 5: 7-bromo-4-(hydroxymethyl)-2H-phthalazin-1-one 12d (6.00 g, 23.5 mmol) was dissolved in thionyl chloride (50 mL) at 0° C. The reaction mixture was stirred at 20° C. for 12 hours and then concentrated under reduced pressure (35° C.). The concentrated residue was dissolved in dichloromethane (20 mL) and concentrated to give 7-bromo-4-(chloromethyl)-2H-phthalazin-1-one 13d (5.50 g, crude) as a white solid which was used in the next step without further purification. LCMS $[M+1]^+$=275.0.

Step 6: To a solution of 7-bromo-4-(chloromethyl)-2H-phthalazin-1-one 13d (5.50 g, crude) in DMF (60.0 mL) was added (1,3-dioxoisoindolin-2-yl)potassium (5.59 g, 30.2 mmol). The reaction mixture was stirred at 90° C. for 2 hours, then cooled to 25° C. and the formed precipitate was filtered and triturated with ethyl alcohol (150 mL) to give Intermediate G, 2-[(6-bromo-4-oxo-3H-phthalazin-1-yl)methyl]isoindoline-1,3-dione (5.00 g, 13.0 mmol, 65% yield) as a white solid. $^1$H NMR (400 MHz, DMSO-d$_6$) δ=12.66 (s, 1H), 8.36 (d, J=2.0 Hz, 1H), 8.22-8.18 (m, 1H), 8.14-8.10 (m, 1H), 7.97-7.93 (m, 2H), 7.91-7.87 (m, 2H), 5.18 (s, 2H). LCMS [M+1]: 386.1.

Intermediate I

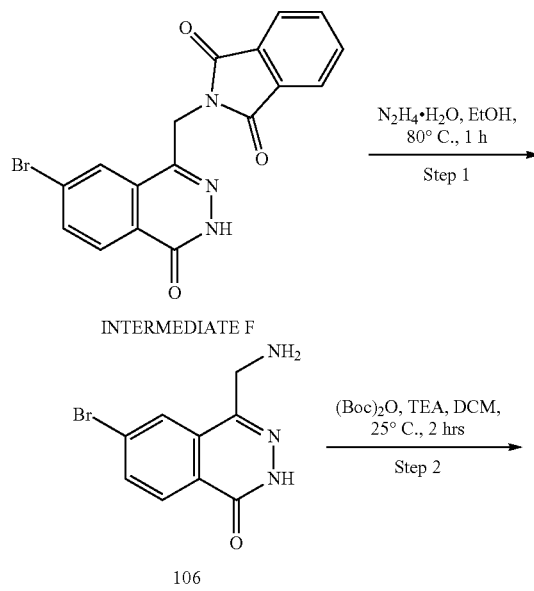

Step 1: A solution of Intermediate F (3.00 g, 7.81 mmol, 1.00 eq.) and hydrazine hydrate (1.60 g, 31.2 mmol, 1.55 mL, 4.00 eq.) was stirred at 80° C. for 2 hours, cooled and concentrated under reduced pressure. The concentrated residue was then washed with water and triturated with ethyl alcohol at 25° C. to give 4-(aminomethyl)-6-bromo-2H-phthalazin-1-one 106 (1.95 g, 7.67 mmol, 98% yield) as a white solid. LCMS $[M+1]^+$=256.1.

Step 2 To a solution of 4-(aminomethyl)-6-bromo-2H-phthalazin-1-one 106 (1.90 g, 7.48 mmol, 1.00 eq.) and triethylamine (2.27 g, 22.4 mmol, 3.12 mL, 3.00 eq) in dichloromethane (40.0 mL) was added di-tert-butyl dicarbonate (3.26 g, 15.0 mmol, 3.44 mL, 2.00 eq.). The mixture was stirred at 25° C. for 2 hours, filtered and concentrated under reduced pressure to give a residue. The concentrated residue was triturated with dichloromethane (40 mL) then filtered and dried to give t-butyl-N-[(7-bromo-4-oxo-3H-phthalazin-1-yl)methyl]carbamate, Intermediate I (1.97 g, 5.56 mmol, 74% yield) as a white solid. LCMS $[M+1]^+$=356.1. $^1$H NMR (400 MHz, DMSO-d$_6$) δ=12.71 (s, 1H), 8.26 (br s, 1H), 8.16 (br d, J=8.0 Hz, 1H), 8.02 (br d, J=8.0 Hz, 1H), 7.46 (br s, 1H), 4.41 (br d, J=4.4 Hz, 2H), 1.40 (br s, 9H).

Intermediate J

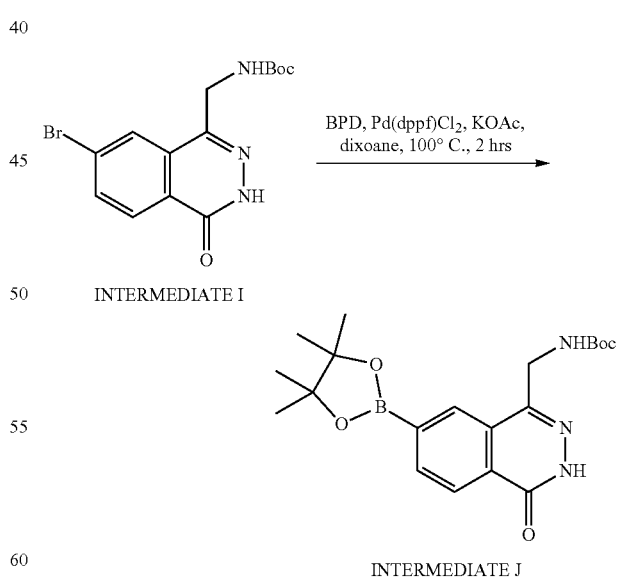

A mixture of Intermediate I (130.0, 275 mmol, 1.00 eq.), bis(pinacolato)diboron (BPD) (104.9 g, 412.9 mmol, 1.50 eq.), Pd(dppf)Cl$_2$ (20.1 g, 27.5 mmol, 0.10 eq.), KOAc (81.0 g, 825 mmol, 3.00 eq.) in dioxane (2.60 L) was degassed and purged with N$_2$. The mixture was then stirred at 100° C. for 2 hours. After such time the mixture was filtered, concentrated and the residue triturated with petroleum ether/ethyl acetate 10/1 (400 mL) at 25° C. for 1 hr. The solid was then filtered and dried to give Intermediate J as a brown solid (68.0 g, 162 mmol, 59% yield). LCMS [M+1]⁺=402.3; ¹H NMR (400 MHz, CDCl₃) δ=12.62 (s, 1H), 8.25 (s, 2H), 8.01-8.13 (m, 1H), 7.21-7.45 (m, 1H), 4.34-4.63 (m, 2H), 1.42 (s, 9H), 1.32 (s, 12H).

Intermediate K

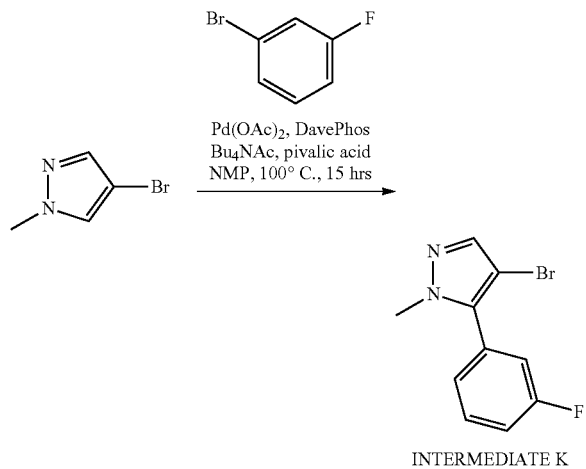

INTERMEDIATE K

A solution of 4-bromo-1-methyl-pyrazole (500 mg, 3.11 mmol, 1.00 eq.) and the 1-bromo-3-fluoro-benzene (543 mg, 3.11 mmol, 346 µL, 1.00 eq.) in N-methylpyrrolidone (10 mL) was degassed with nitrogen. Then, palladium acetate (7.0 mg, 31.1 µmol, 0.10 eq.) and 2-(2-dicyclohexylphosphanylphenyl)-N,N-dimethyl-aniline (DavePhos) (24.0 mg, 62.1 µmol, 0.02 eq.) was added. To the resulting dark brown solution, tetrabutylammonium acetate (1.87 g, 6.21 mmol, 2 mL, 2.00 eq.) and pivalic acid (317 mg, 3.11 mmol, 357 µL, 1.00 eq.) were added and the resulting solution stirred at 100° C. for 15 hours. After the reaction was completed, the mixture was cooled. Ethyl acetate (100 mL) was added and the resulting mixture was washed with brine (3×100 mL). The organic phase was dried over anhydrous sodium sulfate and concentrated in vacuo to give a crude oil. The crude oil was purified by silica gel chromatography (petroleum ether/ethyl acetate 0-10%) to give 4-bromo-5-(3-fluorophenyl)-1-methyl-1H-pyrazole, Intermediate K (600 mg, 2.35 mmol, 76% yield) as a colorless oil. LCMS [M+1]⁺=255.0. ¹H NMR (400 MHz, CDCl₃) δ=7.56 (s, 1H), 7.50 (dt, J=6.0, 8.0 Hz, 1H), 7.24-7.18 (m, 2H), 7.18-7.13 (m, 1H), 3.85 (s, 3H).

The Intermediates A-1 to A-32 shown in Table I-I were prepared following the teachings of the General Reaction Schemes and the method to prepare INTERMEDIATE K.

TABLE I-I

| Intermediate | Structure | Spectral Data |
|---|---|---|
| A-1 | 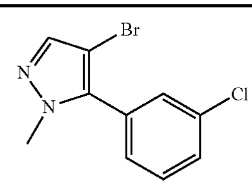 | 4-bromo-5-(3-chlorophenyl)-1-methyl-1H-pyrazole<br>LCMS [M + 1]⁺ = 353.0; ¹H NMR (400 MHz, CDCl₃) δ = 7.54 (s, 1H), 7.47-7.43 (m, 2H), 7.42-7.40 (m, 1H), 7.30 (dt, J = 1.6, 4.4 Hz, 1H), 3.83 (s, 3H) |
| A-2 | 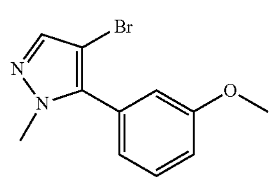 | 4-bromo-5-(3-methoxyphenyl)-1-methyl-1H-pyrazole<br>LCMS [M + 1]⁺ = 267.0; ¹H NMR (400 MHz, DMSO-d₆) δ = 7.93 (s, 1H), 7.51 (s, 1H), 7.50-7.44 (t, J = 8.4, 1H), 7.11-7.07 (m, 1H), 7.05-7.03 (m, 1H), 3.83 (s, 3H), 3.82 (s, 3H) |
| A-3 | 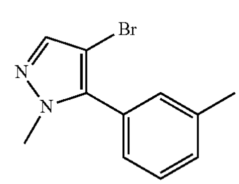 | 4-bromo-5-(3-methylphenyl)-1-methyl-1H-pyrazole<br>LCMS [M + 1]⁺ = 251.0; ¹H NMR (400 MHz, CDCl₃) δ = 7.50 (s, 1H), 7.39-7.33 (m, 1H), 7.25 (br d, J = 7.6 Hz, 1H), 7.21-7.14 (m, 2H), 3.79 (s, 3H), 2.41 (s, 3H) |
| A-4 | 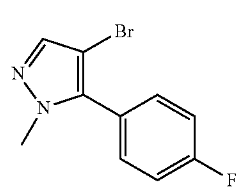 | 4-bromo-5-(4-fluorophenyl)-1-methyl-1H-pyrazole<br>¹H NMR (400 MHz, DMSO-d₆) δ = 7.65 (s, 1H), 7.58-7.54 (m, 2H), 7.42-7.38 (m, 2H), 3.35 (s, 3H) |

TABLE I-I-continued

| Intermediate | Structure | Spectral Data |
| --- | --- | --- |
| A-5 | 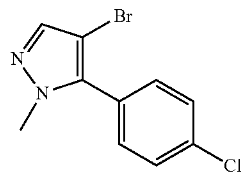 | 4-bromo-5-(4-chlorophenyl)-1-methyl-1H-pyrazole<br>LCMS [M + 1]$^+$ = 272.9; $^1$H NMR (400 MHz, CDCl$_3$) δ = 3.82 (s, 3 H) 7.34-7.38 (d, J = 8.8 Hz, 2 H) 7.48-7.52 (d, J = 8.8 Hz, 2 H) 7.55 (s, 1 H) |
| A-6 | 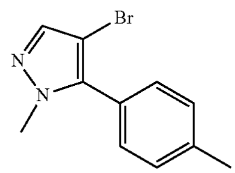 | 4-bromo-5-(4-methylphenyl)-1-methyl-1H-pyrazole<br>LCMS [M + 1]$^+$ = 251.0 |
| A-7 | 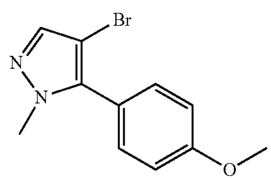 | 4-bromo-5-(4-methoxyphenyl)-1-methyl-1H-pyrazole<br>LCMS [M + 1]$^+$ = 269.0; $^1$H NMR (400 MHz, CDCl$_3$-d) δ = 7.53 (s, 1H), 7.36-7.32 (m, 2H), 7.05-7.01 (m, 2H), 3.88 (s, 3H), 3.81 (s, 3H) |
| A-8 | 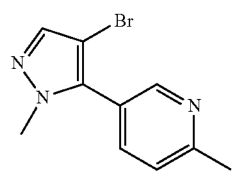 | 5-(4-bromo-1-methyl-1H-pyrazol-5-yl)-2-methylpyridine<br>LCMS [M + 1]$^+$ = 252.0; $^1$H NMR (400 MHz, CDCl$_3$) δ = 8.56 (d, J = 2.4 Hz, 1H), 7.65 (dd, J = 2.4, 8.0 Hz, 1H), 7.56 (s, 1H), 7.32 (d, J = 8.0 Hz, 1H), 3.84 (s, 3H), 2.65 (s, 3H) |
| A-9 | 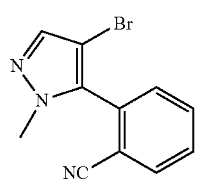 | 2-(4-bromo-1-methyl-1H-pyrazol-5-yl)-benzonitrile<br>$^1$H NMR (400 MHz, CDCl$_3$) δ = 7.86 (dd, J = 0.8, 7.6 Hz, 1H), 7.76 (dt, J = 1.2, 7.6 Hz, 1H), 7.63 (dt, J = 1.2, 7.6 Hz, 1H), 7.60 (s, 1H), 7.49 (dd, J = 0.8, 7.6 Hz, 1H), 3.81 (s, 3H) |
| A-10 | 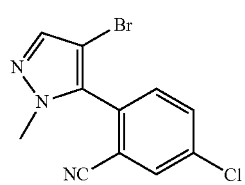 [SMILES: Cn1ncc(Br)c1-c1ccc(Cl)cc1C#N] | 2-(4-bromo-1-methyl-1H-pyrazol-5-yl)-5-chlorobenzonitrile<br>LCMS [M + 1]$^+$ = 297.9; $^1$H NMR (400 MHz, CDCl$_3$) δ = 7.84 (d, J = 2.0 Hz, 1 H) 7.73 (dd, J = 8.4, 2.0 Hz, 1 H) 7.60 (s, 1 H) 7.43 (d, J = 8.4 Hz, 1 H) 3.81 (s, 3 H) |
| A-11 | 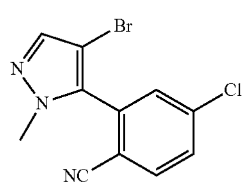 [SMILES: Cn1ncc(Br)c1-c1cc(Cl)ccc1C#N] | 2-(4-bromo-1-methyl-1H-pyrazol-5-yl)-4-chlorobenzonitrile<br>$^1$H NMR (400 MHz, DMSO-d$_6$) δ = 8.13 (d, J = 8.4 Hz, 1H), 7.93-7.90 (d, J = 2.0 Hz, 1H), 7.87 (dd, J = 2.0, 8.4 Hz, 1H), 7.76 (s, 1H), 3.75 (s, 3H) |
| A-12 | 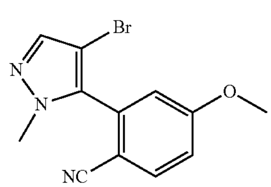 [SMILES: COc1ccc(C#N)c(-c2c(Br)cnn2C)c1] | 2-(4-bromo-1-methyl-1H-pyrazol-5-yl)-4-methoxybenzonitrile<br>LCMS [M + 1]$^+$ = 294.1; $^1$H NMR (400 MHz, CDCl$_3$) δ = 7.77 (d, J = 8.8 Hz, 1H), 7.59 (s, 1H), 7.09 (dd, J = 2.8, 8.8 Hz, 1H), 6.95 (d, J = 2.8 Hz, 1H), 3.92 (s, 3H), 3.82 (s, 3H) |

TABLE I-I-continued

| Intermediate | Structure | Spectral Data |
|---|---|---|
| A-13 | 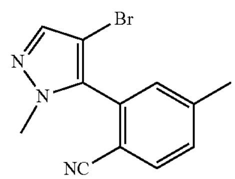 [SMILES: Cc1ccc(C#N)c(-c2c(Br)cnn2C)c1] | 2-(4-bromo-1-methyl-1H-pyrazol-5-yl)-4-methylbenzonitrile LCMS [M + 1]⁺ = 276.0; ¹H NMR (400 MHz, CDCl₃) δ = 7.73 (d, J = 8.0 Hz, 1H), 7.59 (s, 1H), 7.42 (dd, J = 0.8, 8.0 Hz, 1H), 7.28 (d, J = 2.8 Hz, 1H), 3.80 (s, 3H), 2.51 (s, 3H) |
| A-14 | 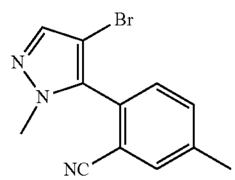 [SMILES: Cc1ccc(-c2c(Br)cnn2C)c(C#N)c1] | 2-(4-bromo-1-methyl-1H-pyrazol-5-yl)-5-methylbenzonitrile LCMS [M + 1]⁺ = 276.1; ¹H NMR (400 MHz, CDCl₃) δ = 7.58 (s, 1H), 7.50 (s, 1H), 7.48 (br d, J = 8.0 Hz, 1H), 7.28 (d, J = 8.0 Hz, 1H), 3.72 (s, 3H), 2.42 (s, 3H) |
| A-15 | 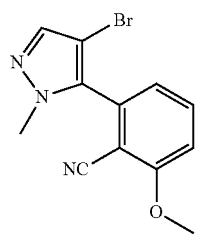 [SMILES: COc1cccc(-c2c(Br)cnn2C)c1C#N] | 2-(4-bromo-1-methyl-1H-pyrazol-5-yl)-6-methoxybenzonitrile LCMS [M + 1]⁺ = 292.1; ¹H NMR (400 MHz, DMSO-d₆) δ = 7.87-7.80 (m, 1H), 7.74 (s, 1H), 7.44 (d, J = 8.8 Hz, 1H), 7.19 (d, J = 7.6 Hz, 1H), 3.99 (s, 3H), 3.71 (s, 3H) |
| A-16 | 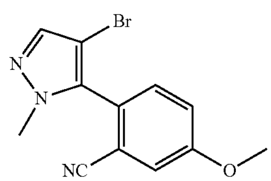 [SMILES: COc1ccc(-c2c(Br)cnn2C)c(C#N)c1] | 2-(4-bromo-1-methyl-1H-pyrazol-5-yl)-5-methoxybenzonitrile LCMS [M + 1]⁺ = 294.1; ¹H NMR (400 MHz, CDCl₃) δ = 7.50 (s, 1H),7.30 (d, J = 8.8 Hz, 1H), 7.24 (d, J = 2.8 Hz, 1H), 7.21-7.17 (m, 1H), 3.84 (s, 3H), 3.71 (s, 3H). |
| A-17 | 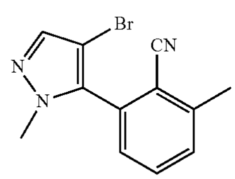 [SMILES: Cc1cccc(-c2c(Br)cnn2C)c1C#N] | 2-(4-bromo-1-methyl-1H-pyrazol-5-yl)-6-methylbenzonitrile LCMS [M + 1]⁺ = 278.0; ¹H NMR (400 MHz, DMSO-d₆) δ = 7.80 (t, J = 7.6 Hz, 1H), 7.74 (s, 1H),7.66 (d, J = 7.6 Hz, 1H), 7.48 (d, J = 7.6 Hz, 1H), 3.70 (s, 3H), 2.58 (s, 3H) |
| A-18 | 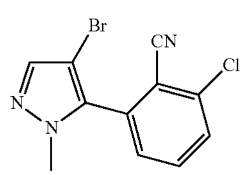 [SMILES: Cn1ncc(Br)c1-c1cccc(Cl)c1C#N] | 2-(4-bromo-1-methyl-1H-pyrazol-5-yl)-6-chlorobenzonitrile LCMS [M + 1]⁺ = 298.0; ¹H NMR (400 MHz, DMSO-d₆) δ = 7.98 (dd, J = 1.2, 6.8 Hz, 1H), 7.94 (d, J = 7.6 Hz, 1H), 7.77 (s, 1H), 7.69 (dd, J = 1.2 Hz, 1H), 3.75 (s, 3H) |
| A-19 | 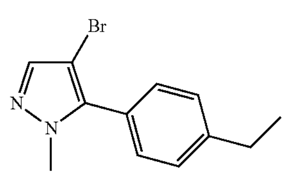 | 4-bromo-5-(4-ethylphenyl)-1-methyl-1H-pyrazole LCMS [M + 1]⁺ = 265.1; ¹H NMR (400 MHz, CDCl₃) δ = 7.54 (s, 1H), 7.33 (m, 4H), 3.82 (s, 3H), 2.81-2.71 (m, 2H), 1.31 (t, J = 7.6 Hz, 3H) |
| A-20 | 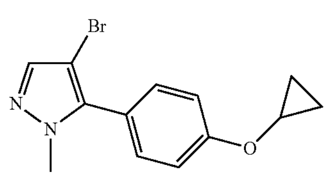 [SMILES: Cn1ncc(Br)c1-c1ccc(OC2CC2)cc1] | 4-bromo-5-(4-cyclopropoxyphenyl)-1-methyl-1H-pyrazole LCMS [M + 1]⁺ = 295.0; ¹H NMR (400 MHz, CDCl₃) δ = 7.58 (s, 1H), 7.36-7.33 (m, 2H), 7.21-7.18 (m, 2H), 3.84 (s, 3H), 3.83-3.78 (m, 1H), 0.87-0.84 (m, 2H), 0.83 (m, 2H) |

TABLE I-I-continued

| Intermediate | Structure | Spectral Data |
|---|---|---|
| A-21 | 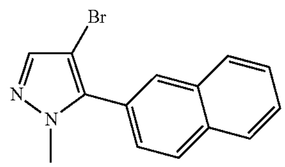 [SMILES: Cn1ncc(Br)c1-c1ccc2ccccc2c1] | 4-bromo-1-methyl-5-(naphthalen-2-yl)-1H-pyrazole<br>LCMS [M + 1]$^+$ = 289.1; $^1$H NMR (400 MHz, CDCl$_3$) δ = 7.98 (d, J = 8.4 Hz, 1H), 7.95-7.87 (m, 3H), 7.63-7.55 (m, 3H), 7.50 (dd, J = 1.6, 8.4 Hz, 1H), 3.88 (s, 3H) |
| A-22 | 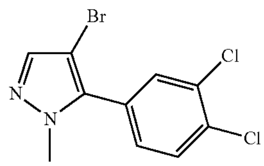 | 4-bromo-5-(3,4-dichlorophenyl)-1-methyl-1H-pyrazole<br>LCMS [M + 1]$^+$ = 306.8; $^1$H NMR (400 MHz, CDCl$_3$) δ = 7.60 (d, J = 8.4 Hz, 1H), 7.55 (s, 1H), 7.52 (d, J = 2.0 Hz, 1H), 7.27 (dd, J = 2.0 Hz, J = 8.4 Hz, 1H), 3.83 (s, 3H) |
| A-23 | 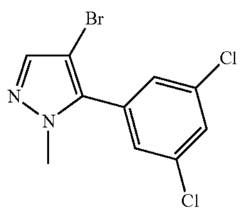 | 4-bromo-5-(3,5-dichlorophenyl)-1-methyl-1H-pyrazole<br>LCMS [M + 1]$^+$ = 306.9; $^1$H NMR (400 MHz, CDCl$_3$) δ = 7.55 (s, 1H), 7.48 (t, J = 1.8 Hz, 1H), 7.31 (d, J = 2.0 Hz, 2H), 3.84 (s, 3H) |
| A-24 | 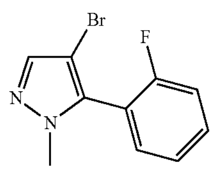 | 4-bromo-5-(2-fluorophenyl)-1-methyl-1H-pyrazole<br>LCMS [M + 1]$^+$ = 255.0; $^1$H NMR (400 MHz, CDCl$_3$) δ = 7.57 (s, 1H), 7.54-7.47 (m, 1H), 7.41-7.37 (m, 1H), 7.30 (br t, J = 8.0 Hz, 1H), 7.26-7.20 (m, 1H), 3.79 (s, 3H) |
| A-25 | 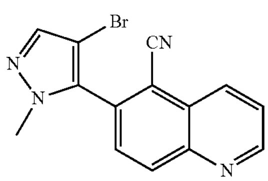 [SMILES: Cn1ncc(Br)c1-c1ccc2ncccc2c1C#N] | 6-(4-bromo-1-methyl-1H-pyrazol-5-yl)quinoline-5-carbonitrile<br>LCMS [M + 1]$^+$ = 313.0; $^1$H NMR (400 MHz, CDCl$_3$) δ = 9.15 (dd, J = 1.6, 4.0 Hz, 1H), 8.67 (dd, J = 0.8, 8.4 Hz, 1H), 8.49 (d, J = 8.8 Hz, 1H), 7.77 (d, J = 8.8 Hz, 1H), 7.73 (dd, J = 4.0, 8.4 Hz, 1H), 7.67 (s, 1H), 3.88 (s, 3H) |
| A-26 | 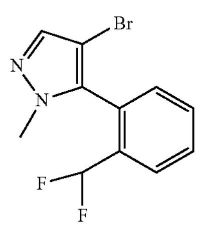 [SMILES: Cn1ncc(Br)c1-c1ccccc1C(F)F] | 4-bromo-5-(2-(difluoromethyl)phenyl)-1-methyl-1H-pyrazole<br>LCMS [M + 1]$^+$ = 287.0; $^1$H NMR (400 MHz, CDCl$_3$) δ = 7.86-7.80 (m, 1H), 7.69-7.60 (m, 2H), 7.58 (s, 1H), 7.32-7.28 (m, 1H), 6.59-6.27 (m, 1H), 3.65 (s, 3H) |
| A-27 | 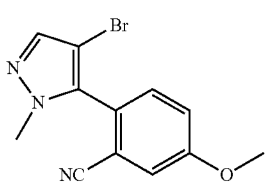 [SMILES: COc1ccc(-c2c(Br)cnn2C)c(C#N)c1] | 2-(4-bromo-1-methyl-1H-pyrazol-5-yl)-5-methoxybenzonitrile<br>LCMS [M + 1]$^+$ = 294.1; $^1$H NMR (400 MHz, CDCl$_3$) δ = 7.50 (s, 1H), 7.30 (d, J = 8.8 Hz, 1H), 7.24 (d, J = 2.8 Hz, 1H), 7.21-7.17 (m, 1H), 3.84 (s, 3H), 3.71 (s, 3H). |
| A-28 | 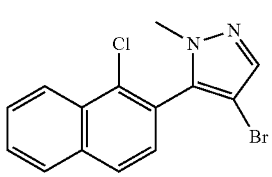 [SMILES: Cn1ncc(Br)c1-c1ccc2ccccc2c1Cl] | 4-bromo-5-(1-chloronaphthalen-2-yl)-1-methyl-1H-pyrazole<br>LCMS [M + 1]$^+$ = 323.2; $^1$H NMR (400 MHz, CDCl$_3$) δ = 8.41 (d, J = 8.4 Hz, 1H), 8.00-7.87 (m, 2H), 7.77-7.62 (m, 3H), 7.37 (d, J = 8.4 Hz, 1H), 3.77 (s, 3H) |

TABLE I-I-continued

| Intermediate | Structure | Spectral Data |
|---|---|---|
| A-29 | 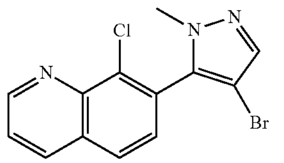 | 7-(4-bromo-1-methyl-1H-pyrazol-5-yl)quinoline-8-carbonitrile<br>LCMS [M + 1]⁺ = 313.2; ¹H NMR (400 MHz, CDCl₃) δ = 9.19 (dd, J = 1.6, 4.0 Hz, 1H), 8.34 (dd, J = 1.6, 8.4 Hz, 1H), 8.20 (d, J = 8.4 Hz, 1H), 7.72-7.60 (m, 3H), 3.89 (s, 3H) |
| A-30 | 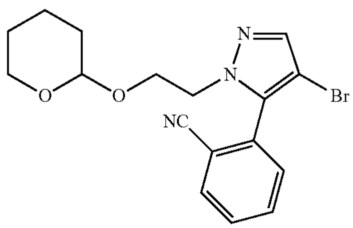 [SMILES: N#Cc1ccccc1-c1c(Br)cnn1CCOC1CCCCO1] | 2-(4-bromo-1-(2-((tetrahydro-2H-pyran-2-yl)oxy)ethyl)-1H-pyrazol-5-yl)benzonitrile<br>LCMS [M − 83]⁺ = 292.1; ¹H NMR (400 MHz, CDCl₃) δ = = 7.84 (d, J = 7.9 Hz, 1H), 7.76-7.70 (m, 1H), 7.65 (s, 1H), 7.63-7.58 (m, 1H), 7.58-7.51 (m, 1H), 4.49-4.40 (m, 1H), 4.31-4.03 (m, 3H), 4.01-3.81 (m, 1H), 3.76-3.62 (m, 1H), 3.48-3.36 (m, 1H), 1.60-1.38 (m, 6H) |
| A-31 | 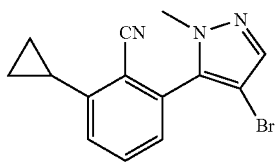 | 2-(4-bromo-1-methyl-1H-pyrazol-5-yl)-6-cyclopropylbenzonitrile<br>LCMS [M + 1]⁺ = 397.3; ¹H NMR (400 MHz, CD₃OD) δ = 8.23 (d, J = 8.4 Hz, 1H), 8.14 (s, 1H), 7.81-7.75 (m, 1H), 7.70 (d, J = 8.4 Hz, 1H), 7.57 (s, 1H), 7.50-7.45 (m, 1H), 7.30 (d, J = 8.0 Hz, 1H), 3.85 (s, 2H), 3.80 (s, 3H), 2.36-2.19 (m, 1H), 1.24-1.17 (m, 2H), 0.98-0.86 (m, 2H) |
| A-32 | 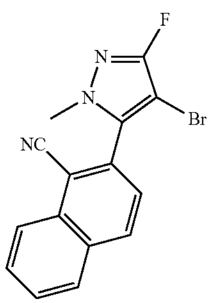 [SMILES: Cn1nc(F)c(Br)c1-c1ccc2ccccc2c1C#N] | 2-(4-bromo-3-fluoro-1-methyl-1H-pyrazol-5-yl)-1-naphthonitrile<br>LCMS [M + 1]⁺ = 330.0; ¹H NMR (400 MHz, CDCl₃) δ = 8.33 (d, J = 8.4 Hz, 1H), 8.21 (d, J = 8.4 Hz, 1H), 8.01 (d, J = 7.6 Hz, 1H), 7.80 (dt, J = 1.2, 7.6 Hz, 1H), 7.76-7.70 (m, 1H), 7.50 (d, J = 8.4 Hz, 1H), 3.72 (s, 3H) |

Intermediate AA

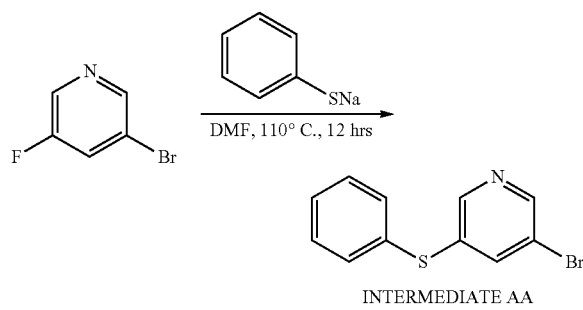

INTERMEDIATE AA

To a solution of 3-bromo-5-fluoro-pyridine (2.20 g, 12.5 mmol, 1.00 eq.) in dimethylformamide (50 mL) was added phenylsulfanylsodium (1.98 g, 15.0 mmol, 1.20 eq.) followed by stirring at 110° C. for 12 hours. After such time the reaction mixture was diluted with water (700 mL) and extracted with ethyl acetate (150 mL×3). The combined organic layers were washed with brine (300 mL), dried over anhydrous sodium sulfate, filtered and concentrated under reduced pressure. The residue was purified by column chromatography (SiO₂, petroleumether:ethylacetate 0-10%) to give 3-bromo-5-phenylsulfanyl-pyridine, Intermediate AA (1.31 g, 4.48 mmol, 35% yield) as a yellow oil. LCMS [M+1]⁺=268.0; ¹H NMR (400 MHz, MeOD) δ=8.44 (d, J=2.0 Hz, 1H), 8.31 (d, J=2.0 Hz, 1H), 7.73 (t, J=2.0 Hz, 1H), 7.50-7.46 (m, 2H), 7.45-7.41 (m, 3H).

Intermediate AB

INTERMEDIATE AB

To a solution of 2-chlorobenzenethiol (296 mg, 2.05 mmol, 233 μL, 1.20 eq.) in DMF (2 mL) was added sodium hydride (82 mg, 2.05 mmol, 60% purity, 1.20 eq.) and 3-bromo-5-fluoro-pyridine (300 mg, 1.70 mmol, 1.00 eq.)

and stirred at 25° C. for 2 hours. The reaction mixture was then quenched by addition water (10 mL) and then extracted with ethyl acetate (30 mL×3). The combined organic layers were washed with brine (50 mL×2), dried over anhydrous sodium sulfate, filtered and concentrated under reduced pressure. The residue was purified by prep-TLC (petroleumether:ethylacetate 20%) to give 3-bromo-5-(2-chlorophenyl)sulfanyl-pyridine, Intermediate AB (280 mg, 931 µmol, 54% yield) as a white solid. LCMS [M+1]$^+$=302.0; $^1$H NMR (400 MHz, CDCl$_3$-d) δ=8.56 (d, J=2.0 Hz, 1H), 8.45 (d, J=2.0 Hz, 1H), 7.73 (t, J=2.0 Hz, 1H), 7.51-7.47 (m, 1H), 7.33-7.28 (m, 2H), 7.26-7.22 (m, 1H).

The INTERMEDIATES AC to AG shown in Table I-IIa were prepared following the teachings of the General Reaction Schemes and the method to prepare INTERMEDIATE AB.

Step 1: To a solution of 2-methyl-1H-imidazole (1.00 g, 12.2 mmol, 1.00 eq.) in DMF (10 mL) was added potassium carbonate (1.68 g, 12.2 mmol, 1.00 eq.) and 2-chloroacetonitrile (920 mg, 12.2 mmol, 773 µL, 1.00 eq.) and the mixture stirred at 50° C. for 5 hours. After such time the reaction mixture was diluted with water (20 mL), extracted with ethyl acetate (20 mL×3) and the combined organic phases were washed with brine (20 mL), dried over anhydrous sodium sulfate, filtered and concentrated. The residue was purified by column chromatography (SiO$_2$, petroleumether:ethylacetate 10-100%) to give 2-(2-methylimidazol-1-yl)acetonitrile (460 mg, 3.80 mmol, 31% yield) as a yellow oil, $^1$H NMR (400 MHz, CDCl$_3$) δ=6.98 (d, J=1.2 Hz, 1H), 6.94 (d, J=1.2 Hz, 1H), 4.79 (s, 2H), 2.47 (s, 3H).

TABLE I-IIa

| Intermediate | Structure | Characterization |
|---|---|---|
| AC | 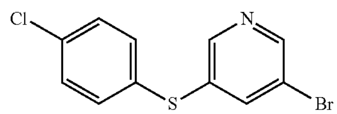 [SMILES: Clc1ccc(Sc2cncc(Br)c2)cc1] | 3-bromo-5-((4-chlorophenyl)thio)pyridine<br>LCMS [M + 1]$^+$ = 302.0 |
| AD | 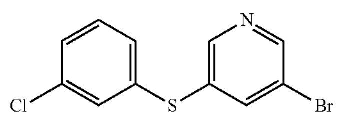 [SMILES: Clc1cccc(Sc2cncc(Br)c2)c1] | 3-bromo-5-((3-chlorophenyl)thio)pyridine<br>LCMS [M + 1]$^+$ = 302.0; $^1$H NMR (400 MHz, CDCl$_3$) δ = 8.55 (d, J = 2.0 Hz, 1H), 8.46 (d, J = 1.6 Hz, 1H), 7.74 (t, J = 2.0 Hz, 1H), 7.40-7.38 (m, 1H), 7.34-7.30 (m, 2H), 7.29-7.27 (m, 1H) |
| AE | 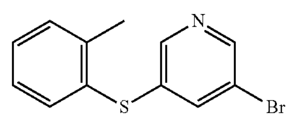 | 3-bromo-5-(o-tolylthio)pyridine<br>LCMS [M + 1]$^+$ = 280.0; $^1$H NMR (400 MHz, CDCl$_3$) δ = 8.45 (br s, 1H), 8.29 (br s, 1H), 7.48 (s, 1H), 7.44 (d, J = 7.6 Hz, 1H), 7.37-7.31 (m, 2H), 7.26-7.21 (m, 1H), 2.40 (s, 3H) |
| AF | 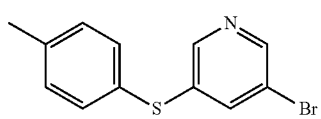 | 3-bromo-5-(p-tolylthio)pyridine<br>LCMS [M + 1]$^+$ = 281.0; $^1$H NMR (400 MHz, DMSO-d$_6$) δ = 8.53 (d, J = 1.6 Hz, 1H), 8.41 (d, J = 2.4 Hz, 1H), 7.82 (q, J = 2.4 Hz, 1H), 7.49-7.41 (m, 1H), 7.31-7.23 (m, 2H), 7.11-7.06 (m, 1H) |
| AG | 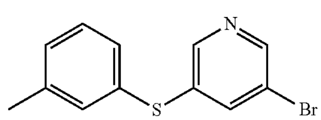 | 3-bromo-5-(m-tolylthio)pyridine<br>LCMS [M + 1]$^+$ = 279.9; $^1$H NMR (400 MHz, CDCl$_3$) δ = 8.48 (d, J = 2.0 Hz, 1H), 8.40 (d, J = 1.6 Hz, 1H), 7.67-7.61 (m, 1H), 7.34-7.28 (m, 3H), 7.21-7.19 (m, 1H), 2.38 (s, 3H) |

Intermediate AH

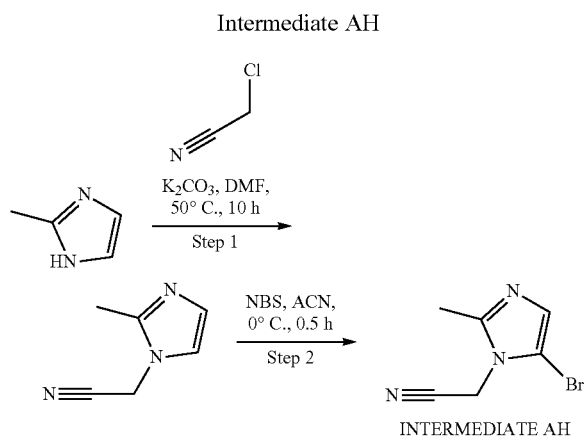

INTERMEDIATE AH

Step 2: To a solution of 2-(2-methylimidazol-1-yl)acetonitrile (410 mg, 3.38 mmol, 1.00 eq.) in acetonitrile (10 mL) was added a solution of N-bromosuccinimide (542 mg, 3.05 mmol, 0.90 eq.) in acetonitrile (10 mL) dropwise at 0° C. The reaction mixture was stirred at 0° C. for 30 minutes and after such time the reaction mixture was quenched with water (2 mL) and extracted with ethyl acetate (2 mL×3). The combined organic phases were washed with brine (2 mL), dried over anhydrous sodium sulfate, filtered and concentrated to a residue. The residue was purified by column chromatography (SiO$_2$, petroleumether:ethylacetate 10-100%) followed by a second column (SiO$_2$, petroleumether:ethylacetate:methanol 1:1:0.4) to give 2-(5-bromo-2-methyl-imidazol-1-yl)acetonitrile, Intermediate AH (460 mg, 2.30 mmol, 67% yield) as a brown solid. $^1$H NMR (400 MHz, CDCl$_3$) δ=6.97 (s, 1H), 4.82 (s, 2H), 2.53 (s, 3H).

Intermediate AI

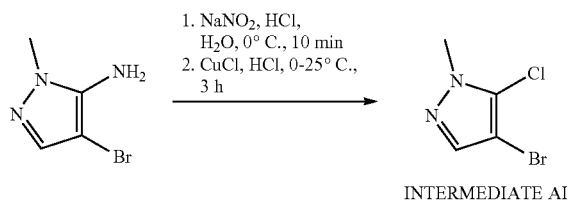

INTERMEDIATE AI

To a solution of 4-bromo-2-methyl-pyrazol-3-amine (0.20 g, 1.14 mmol, 1.00 eq.) in hydrochloric acid (12 M, 2 mL, 21.1 eq.) was slowly added a solution of sodium nitrite (86 mg, 1.25 mmol, 1.10 eq.) in water (1.8 mL) at 0° C. After stirring for 10 minutes, the mixture was added in portions to a solution of cuprous chloride (112 mg, 1.14 mmol, 27.2 µL, 1.00 eq.) in hydrochloric acid (12 M, 1.00 mL, 10.6 eq.). The reaction mixture was stirred at 25° C. for 3 hours. After such time the reaction mixture was diluted with water (5 mL) and extracted with ethyl acetate (5 mL×3). Combined organic phases were washed with aqueous sodium bicarbonate (5 mL), brine (5 mL), dried over anhydrous sodium sulfate, filtered and concentrated. The residue was purified by prep-TLC (petroleum ether:ethyl acetate 25%) to give 4-bromo-5-chloro-1-methyl-pyrazole, Intermediate AI (92 mg, 363 µmol, 31% yield) as a white solid. LCMS [M+1]$^+$=197.0; $^1$H NMR (400 MHz, CDCl$_3$-d) δ=7.48 (s, 1H), 3.88 (s, 3H).

Intermediate AJ

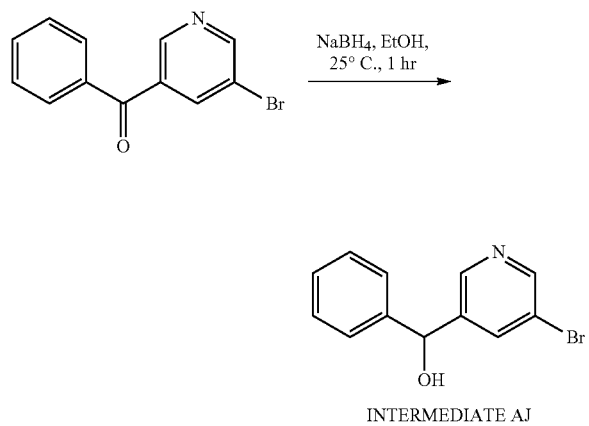

INTERMEDIATE AJ

Sodium borohydride (22 mg, 572 µmol, 1.50 eq.) was added slowly to a solution of (5-bromo-3-pyridyl)-phenyl-methanone (100 mg, 381 µmol, 1.00 eq.) in ethyl alcohol (5 mL). After stirring at 25° C. for 2 hours the reaction was quenched with water (2 mL) and concentrated under vacuum. The residue was diluted with ethyl acetate (10 mL), washed with brine (10×3 mL), dried over anhydrous sodium sulfate, filtered and concentrated to give (5-bromopyridin-3-yl)(phenyl)methanol, Intermediate AJ (97 mg, 367 µmol, 96% yield) as a colorless oil. LCMS [M+1]$^+$=263.9. $^1$H NMR (400 MHz, CDCl$_3$) δ=8.53 (d, J=2.0 Hz, 1H), 8.48 (d, J=2.0 Hz, 1H), 7.89 (t, J=2.0 Hz, 1H), 7.43-7.38 (m, 1H), 7.38-7.31 (m, 4H), 5.85 (s, 1H), 2.85 (s, 1H).

Intermediate AK

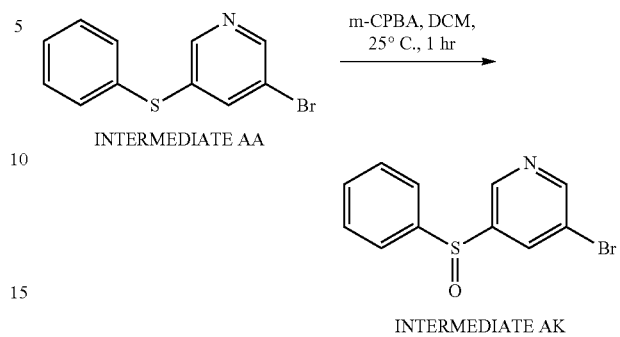

INTERMEDIATE AK

To a solution of 3-bromo-5-(phenylthio)pyridine, Intermediate AA (200 mg, 751 µmol, 1.00 eq.) in dichloromethane (4 mL) was added 3-chloroperoxybenzoic acid (153 mg, 751 µmol, 85.0% purity, 1.00 eq.). The resulting mixture was stirred at 25° C. under nitrogen for 1 hour. After such time sodium hydroxide aqueous solution (4 N, 40 mL) was added and the mixture extracted with dichloromethane (20 mL×2). The combined organic layers were washed with brine (5 mL×2), dried over sodium sulfate and concentrated. The residue was purified by column chromatography (SiO$_2$, petroleumether:ethylacetate 5-20%) to give 3-bromo-5-(phenylsulfinyl)pyridine, Intermediate AK (150 mg, 532 µmol, 70% yield) as a white solid. $^1$H NMR (400 MHz, CDCl$_3$) δ=8.72 (d, J=2.0 Hz, 1H), 8.66 (d, J=2.0 Hz, 1H), 8.16 (t, J=2.0 Hz, 1H), 7.72-7.68 (m, 2H), 7.55-7.27 (m, 3H).

Intermediate AL

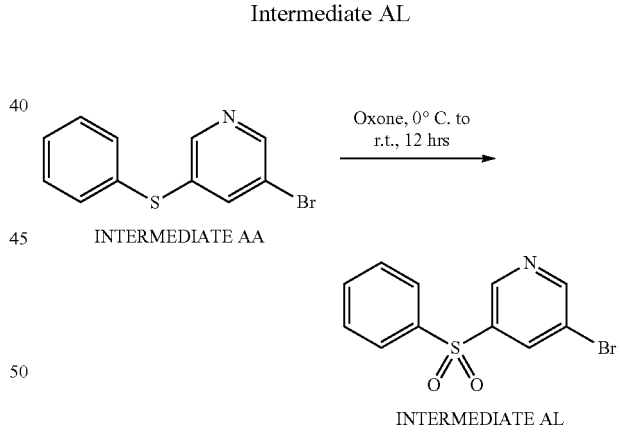

INTERMEDIATE AL

A solution of oxone (2.10 g, 3.42 mmol, 2.00 eq.) in water (10 mL) was added to a solution of 3-bromo-5-phenylsulfanyl-pyridine intermediate AA (500 mg, 1.71 mmol, 1.00 eq.) in THF (10 mL) and methyl alcohol (10 mL) at 0° C. The resulting mixture was stirred at 35° C. for 12 hours and after such time was filtered and the filtrate concentrated under reduced pressure. The formed residue was purified by reversed-phase HPLC (0.1% FA condition) to give 3-(benzenesulfonyl)-5-bromo-pyridine, Intermediate AL (300 mg, 1.01 mmol, 59% yield) as a white solid. $^1$H NMR (400 MHz, DMSO-d$_6$) δ=9.13 (d, J=2.0 Hz, 1H), 9.01 (d, J=2.0 Hz, 1H), 8.66 (t, J=2.0 Hz, 1H), 8.12-8.08 (m, 2H), 7.77-7.72 (m, 1H), 7.69-7.64 (m, 2H).

Intermediate AM

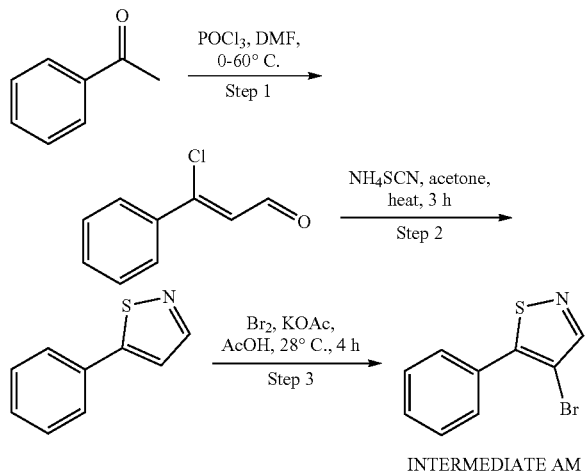

INTERMEDIATE AM

Step 1: Phosphorus oxychloride (4.71 g, 30.7 mmol, 2.9 mL, 1.23 eq.) was added dropwise to DMF (6 mL) at 0° C., and then the mixture was stirred at 0° C. for 10 minutes. After such time a solution of 1-phenylethanone (3.00 g, 25.0 mmol, 2.91 mL, 1.00 eq.) in DMF (25 mL) was added dropwise with stirring. The reaction mixture was then heated 3 hours at 60° C. After such time the solution was cooled to room temperature and poured slowly into an aqueous sodium acetate solution (10%, 100 mL). The pH was adjusted to 4 with additional sodium acetate solution (10 mL) and extracted with ethyl acetate (20 mL×3). The combined organic phases were washed with brine (20 mL), dried over anhydrous sodium sulfate, filtered and concentrated to give (Z)-3-chloro-3-phenyl-prop-2-enal (2.50 g, 14.1 mmol, 56% yield) as a yellow oil. LCMS [M+1]$^+$=167.1. $^1$H NMR (400 MHz, CDCl$_3$) δ=10.24 (d, J=6.8 Hz, 1H), 7.49 (m, 5H), 6.69 (d, J=6.8 Hz, 1H).

Step 2: Hydrogen Cyanide (HCN) is produced as a byproduct in this reaction. Appropriate safety precaution and procedures should be employed. A mixture of (Z)-3-chloro-3-phenyl-prop-2-enal (1.76 g, 10.6 mmol, 1.00 eq.), ammonium thiocyanate (1.61 g, 21.1 mmol, 1.61 mL, 2.00 eq.) in acetone (25 mL) was degassed and purged with nitrogen and stirred at 80° C. for 1 hour. After such time the cooled mixture was poured into saturated sodium bicarbonate aqueous solution (200 mL) and extracted with ethyl acetate (100 mL×3). The combined organic phases were washed with brine (100 mL), dried over anhydrous sodium sulfate, filtered and concentrated. The formed residue was purified by column chromatography (Sift, petroleum ether/ethyl acetate 0-50%) to give 5-phenylisothiazole (1.00 g, 6.20 mmol, 58% yield) as a yellow oil. LCMS [M+1]$^+$=162.2. $^1$H NMR (400 MHz, CDCl$_3$) δ=8.49 (d, J=2.0 Hz, 1H), 7.64-7.60 (m, 2H), 7.48-7.43 (m, 3H), 7.42 (d, J=2.0 Hz, 1H).

Step 3: Bromine (952 mg, 5.95 mmol, 307 µL, 3.20 eq.) was added dropwise over a period of 30 min to a stirred mixture of 5-phenylisothiazole (300 mg, 1.86 mmol, 1.00 eq), potassium acetate (365 mg, 3.72 mmol, 2.00 eq.) and acetic acid (12 mL). The reaction mixture was stirred at 25° C. 5 hours and after such time treated with aqueous sodium bisulfite (33%, 10 mL). The solution was made basic with aqueous sodium hydroxide (20%, 10 mL), extracted with dichloromethane (3×80 mL). The combined organic extracts were dried (anhydrous sodium sulfate), filtered and concentrated to give to 4-bromo-5-phenylisothiazole, Intermediate AM (300 mg, 1.25 mmol, 67% yield) as colorless oil. LCMS [M+1]$^+$=240.9. $^1$H NMR (400 MHz, CDCl$_3$) δ=8.39 (s, 1H), 7.69-7.65 (m, 2H), 7.52-7.47 (m, 3H). $^{13}$C NMR (400 MHz, CDCl$_3$) δ=161.0, 159.5, 129.9, 129.3, 129.0, 128.5, 106.0.

Intermediate AN

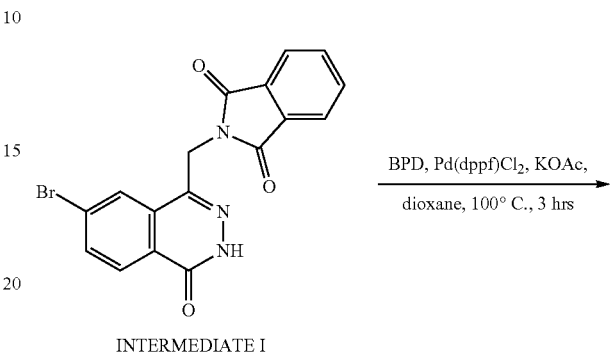

INTERMEDIATE AN

A mixture of intermediate I (160 g, 416 mmol, 1.00 eq.), 4,4,5,5-tetramethyl-2-(4,4,5,5-tetramethyl-1,3,2-dioxaborolan-2-yl)-1,3,2-dioxaborolane (BPD) (158 g, 624 mmol, 1.50 eq.), Pd(dppf)Cl$_2$ (30.4 g, 41.6 mmol, 0.10 eq.), potassium acetate (122 g, 1.25 mol, 3.00 eq.) in dioxane (2.0 L) was purged with nitrogen and stirred at 100° C. for 3 hrs. After such time the reaction mixture was filtered and concentrated under reduced pressure. The residue was triturated with MeOH (1.0 L) at 25° C. for 2 h, filtered and dried to give 2-((4-oxo-7-(4,4,5,5-tetramethyl-1,3,2-dioxaborolan-2-yl)-3,4-dihydrophthalazin-1-yl)methyl)isoindoline-1,3-dione, Intermediate AN (93.0 g, 209 mmol, 50% yield) as a gray solid. LCMS [M+1]$^+$=432.4. $^1$H NMR: (400 MHz DMSO-d$_6$) δ: 12.54 (s, 1H), 8.24-8.37 (m, 2H), 8.13 (d, J=7.6 Hz, 1H), 7.93-7.99 (m, 2H), 7.87-7.93 (m, 2H), 5.22 (s, 2H), 1.36 (s, 12H).

Intermediate AO

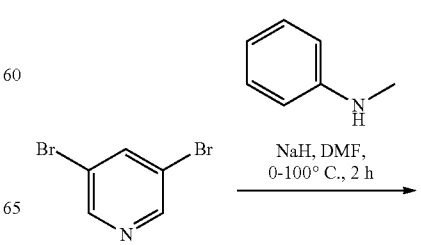

INTERMEDIATE AO

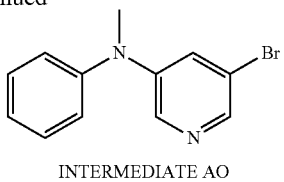

To a solution of 3,5-dibromopyridine (1.00 g, 4.22 mmol, 1.00 eq.) in DMF (10 mL) was added sodium hydride (270 mg, 6.75 mmol, 60% purity, 1.60 eq.) at 0° C. over 10 min followed by N-methylaniline (452 mg, 4.22 mmol, 458 µL, 1.00 eq.). The resulting mixture was stirred at 100° C. for 2 hours. After such time the reaction mixture was diluted with water (10 mL) and extracted with ethyl acetate (10 mL×3). The combined organic layers were washed with brine (50 mL×2), dried over anhydrous sodium sulfate, filtered and concentrated under reduced pressure. The residue was purified by flash silica gel chromatography (400 g SiO$_2$, water/acetonitrile, 0-100% 70 mL/min) to give 5-bromo-N-methyl-N-phenyl-pyridin-3-amine, Intermediate AO (50.0 mg, 190 µmol, 5% yield) as a yellow solid. LCMS [M+1]$^+$ 262.9. $^1$H NMR (400 MHz, CDCl$_3$-d) δ=8.12 (br d, J=6.4 Hz, 2H), 7.44-7.35 (m, 2H), 7.26-7.24 (m, 1H), 7.23-7.19 (m, 1H), 7.19-7.17 (m, 1H), 7.17-7.14 (m, 1H), 3.33 (s, 3H).

Intermediate AP

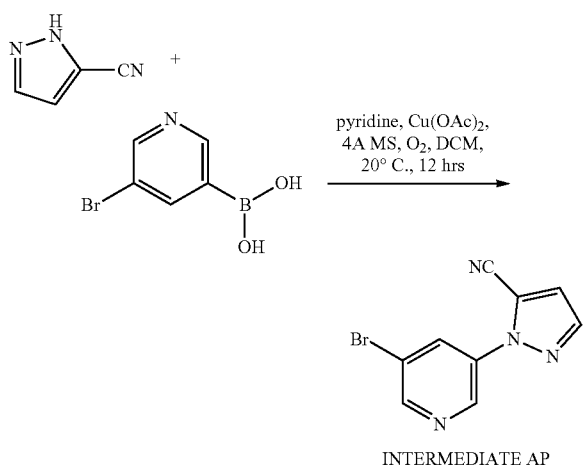

INTERMEDIATE AP

A mixture of (5-bromo-3-pyridyl)boronic acid (325 mg, 1.61 mmol, 1.50 eq.), 1H-pyrazole-5-carbonitrile (100 mg, 1.07 mmol, 1.00 eq.), pyridine (255 mg, 3.22 mmol, 260 µL, 3.00 eq.), 4 Å molecular sieves (20.0 mg, 1.07 mmol) and copper acetate (585 mg, 3.22 mmol, 3.00 eq) in dichloromethane (5 mL) was degassed with nitrogen and stirred at 20° C. for 12 hours under an oxygen atmosphere (15 psi). After such time the reaction mixture was filtered and concentrated under reduced pressure and the residue was purified by column chromatography (Sift, petroleumether:ethylacetate 5-20%) to give 2-(5-bromo-3-pyridyl)pyrazole-3-carbonitrile, Intermediate AP (150 mg, 602 µmol, 56% yield) as a white solid. LCMS [M+1]$^+$ 249.0. $^1$H NMR (400 MHz, DMSO-d$_6$) δ=9.15 (d, J=2.4 Hz, 1H), 8.91 (d, J=2.4 Hz, 1H), 8.78 (d, J=2.0 Hz, 1H), 8.63 (t, J=2.0 Hz, 1H), 7.34 (d, J=2.4 Hz, 1H).

Intermediate AS

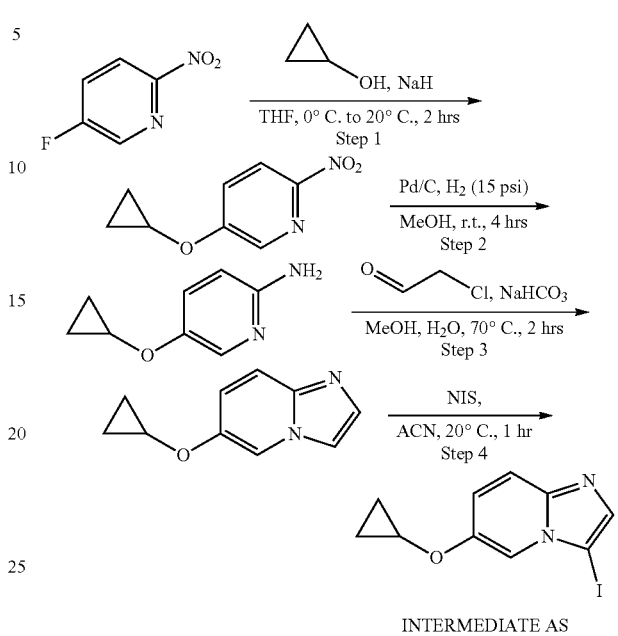

INTERMEDIATE AS

Step 1: To a solution of cyclopropanol (450 mg, 7.74 mmol, 1.10 eq.) in THF (10 mL) was added sodium hydride (310 mg, 7.74 mmol, 60.0% purity, 1.10 eq.) at 0° C., followed by 5-fluoro-2-nitro-pyridine (1.00 g, 7.04 mmol, 1.00 eq.) and the mixture was warmed to 20° C. and stirred for 2 hours. After completion, the mixture was filtered and concentrated in vacuum and the residue purified by column chromatography (SiO$_2$, petroleum ether:ethyl acetate 20-80%) to give 5-(cyclopropoxy)-2-nitro-pyridine (1.10 g, 6.11 mmol, 86% yield) as a white solid. LCMS [M+1]$^+$=181.1.

Step 2: To a solution of 5-(cyclopropoxy)-2-nitro-pyridine (200 mg, 1.11 mmol, 1.00 eq.) in methyl alcohol (4 mL) was added palladium on activated carbon (100 mg, 1.11 mmol, 10% purity, 1.00 eq.) and the mixture was stirred at 30° C. for 4 hours under a hydrogen (15 psi) atmosphere. After completion, the reaction mixture was filtered, washed with methanol (5 mL×2) and concentrated to give 5-(cyclopropoxy)pyridin-2-amine (120 mg, 799 µmol, 72% yield) as a black oil which used for the next step without further purification. LCMS [M+1]$^+$=151.1.

Step 3: To a solution of 5-(cyclopropoxy)pyridin-2-amine (120 mg, 799 µmol, 1.00 eq.) in methyl alcohol (2 mL) and water (1.0 mL) was added 2-chloroacetaldehyde (313 mg, 1.60 mmol, 257 µL, 2.00 eq.) and sodium bicarbonate (70.5 mg, 839 µmol, 1.05 eq.). The mixture was stirred at 70° C. for 2 hours. After such time the solvent was removed under reduced pressure, diluted with ethyl acetate (3 mL) and water (2 mL), and extracted with ethyl acetate (5 mL×3). The combined organic layers were washed with brine (10 mL×3), dried over anhydrous sodium sulfate, filtered and concentrated under reduced pressure to give 6-(cyclopropoxy)imidazo[1,2-a]pyridine (220 mg, crude) as a yellow solid which used for the next step without further purification. LCMS [M+1]$^+$=175.2.

Step 4: To a solution of 6-(cyclopropoxy)imidazo[1,2-a]pyridine (220 mg, crude) in acetonitrile (2 mL) was added N-iodosuccinimide (313 mg, 1.39 mmol). The mixture was stirred at 20° C. for 1 hour. Upon completion the reaction mixture was concentrated under reduced pressure and the residue purified by column chromatography (SiO₂, petroleum ether:ethyl acetate 20-80%) to give 6-(cyclopropoxy)-3-iodo-imidazo[1,2-a]pyridine, Intermediate AS (220 mg, 733 µmol, 58% yield) as a white solid. LCMS [M+1]⁺=300.9. ¹H NMR (400 MHz, DMSO-d₆) δ=8.03 (d, J=2.0 Hz, 1H), 7.76 (s, 1H), 7.60 (d, J=9.6 Hz, 1H), 7.17 (dd, J=2.4, 9.6 Hz, 1H), 4.08-4.05 (m, 1H), 0.88-0.82 (m, 2H), 0.80-0.72 (m, 2H).

Intermediate AT

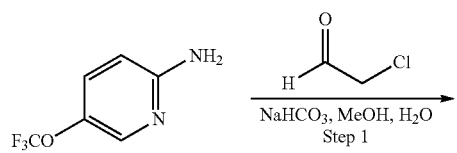

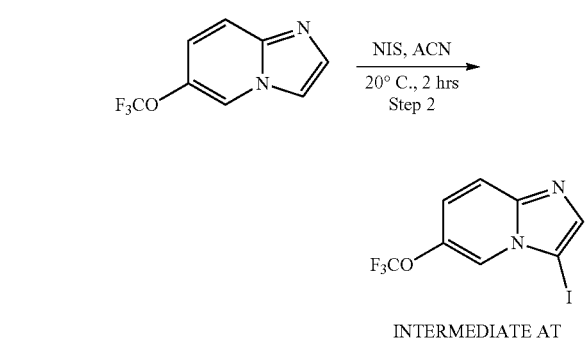

INTERMEDIATE AT

Step 1: To a solution of 5-(trifluoromethoxy)pyridin-2-amine (250 mg, 1.40 mmol, 1.00 eq.) in methanol (5 mL) and water (2.5 mL) was added 2-chloroacetaldehyde (289 mg, 1.47 mmol, 237 µL, 1.05 eq.) and sodium bicarbonate (118 mg, 1.41 mmol, 54.8 µL, 1.00 eq.). The mixture was stirred at 70° C. for 2 hours. The reaction mixture was then concentrated under reduced pressure and the residue diluted with water (20 mL) and extracted with ethyl acetate (20 mL×2). The combined organic layers were concentrated to give 6-(trifluoromethoxy)imidazo[1,2-a]pyridine (250 mg, crude) as a colorless oil which used for the next step without further purification.

Step 2: To a solution of 6-(trifluoromethoxy)imidazo[1,2-a]pyridine (238 mg, crude) in acetonitrile (10 mL) was added N-iodosuccinimide (291 mg, 1.30 mmol) in acetonitrile (5 mL) at 0° C., and the resulting yellow suspension was allowed to warm to 20° C. for 2 hours. The reaction mixture was then diluted with water (10 mL), extracted with ethyl acetate (10 mL×3) and the combined organic extracts were washed with brine (10 mL), dried, filtered and concentrated. The residue was purified by silica gel chromatography (petroleumether:ethylacetate 10-15%) to give 3-iodo-6-(trifluoromethoxy)imidazo[1,2-a]pyridine, Intermediate AT (180 mg, 548 µmol, 46% yield) as yellow solid. LCMS [M+1]⁺=329.0. ¹H NMR (400 MHz, CDCl₃) δ=8.23-8.19 (s, 1H), 7.80 (s, 1H), 7.71 (d, J=9.6 Hz, 1H), 7.27 (m, 1H).

Intermediate AU

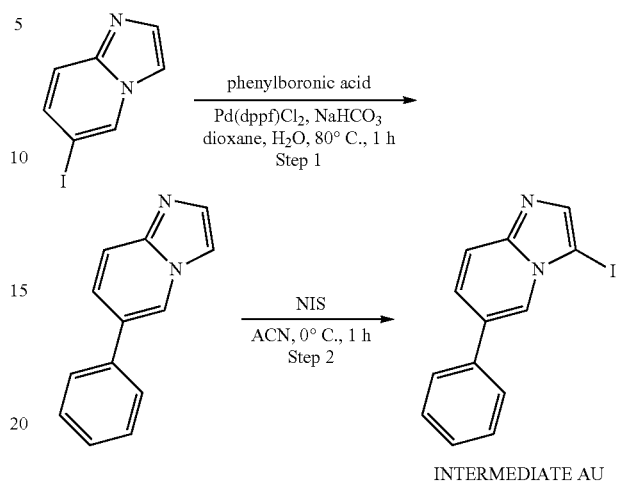

INTERMEDIATE AU

Step 1: A mixture of 6-iodoimidazo[1,2-a]pyridine (500 mg, 2.05 mmol, 1.00 eq.), phenylboronic acid (275 mg, 2.25 mmol, 1.10 eq.), Pd(dppf)Cl₂ (150 mg, 205 µmol, 0.10 eq.), sodium bicarbonate (344 mg, 4.10 mmol, 159 µL, 2.00 eq.) in dioxane (5 mL) and water (1.00 mL) was degassed with nitrogen and stirred at 80° C. for 1 hour. After such time the reaction mixture was concentrated under reduced pressure and the residue diluted with ethyl alcohol (5 mL) and the solution was then concentrated. The residue was purified by prep-TLC (dichloromethane:methyl alcohol, 10%) to give 6-phenylimidazo[1,2-a]pyridine (250 mg, 1.29 mmol, 62% yield) as a white solid. LCMS [M+1]⁺=195.1.

Step 2: To a solution of 6-phenylimidazo[1,2-a]pyridine (100 mg, 515 µmol, 1.00 eq.) in acetonitrile (2 mL) was added N-iodosuccinimide (127 mg, 566 µmol, 1.10 eq.) and the mixture was stirred at 0° C. for 1 hour. After such time the reaction mixture was concentrated under reduced pressure and the residue diluted with ethyl alcohol (2 mL) and the supernatant removed and concentrated under reduced pressure. The residue was purified by prep-TLC (petroleumether:ethylacetate 10%) to give 3-iodo-6-phenyl-imidazo[1,2-a]pyridine, Intermediate AU (120 mg, 375 µmol, 72% yield) as a yellow solid. LCMS [M+1]⁺=321.0. ¹H NMR (400 MHz, DMSO-d₆) δ=8.40 (br s, 1H), 7.77 (m, 3H), 7.73-7.62 (m, 2H), 7.58-7.49 (m, 2H), 7.45 (m, 1H).

Intermediate AV

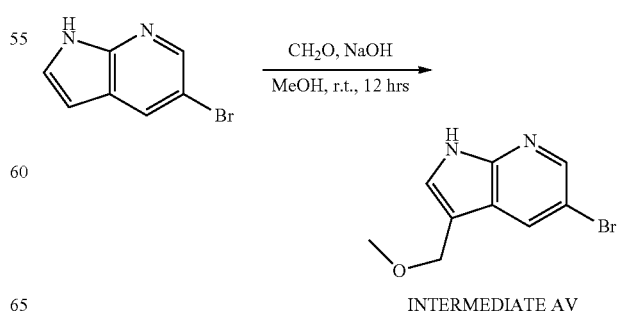

INTERMEDIATE AV

To a solution of 5-bromo-1H-pyrrolo[2,3-b]pyridine (2.00 g, 10.2 mmol, 1.00 eq.) in methyl alcohol (10 mL) was added formaldehyde (610 mg, 20.3 mmol, 559 μL, 2.00 eq.) and sodium hydroxide (812 mg, 20.3 mmol, 2.00 eq.) and the mixture was stirred at 20° C. for 2 hours. After completion the reaction mixture was then filtered and concentrated under vacuum. The residue was purified by silica gel column chromatography (petroleum ether:ethyl acetate 5-20%) then by prep-TLC (petroleumether:ethylacetate 20%) to give 5-bromo-3-(methoxymethyl)-1H-pyrrolo[2,3-b]pyridine, Intermediate AV (120 mg, 498 μmol, 5% yield) as white solid. LCMS [M+1]$^+$=243.0. $^1$H NMR (400 MHz, DMSO-d$_6$) δ=11.83 (br s, 1H), 8.28 (d, J=2.4 Hz, 1H), 8.18 (d, J=2.0 Hz, 1H), 7.56 (d, J=2.4 Hz, 1H), 4.53 (s, 2H), 3.25 (s, 3H).

Intermediate AX

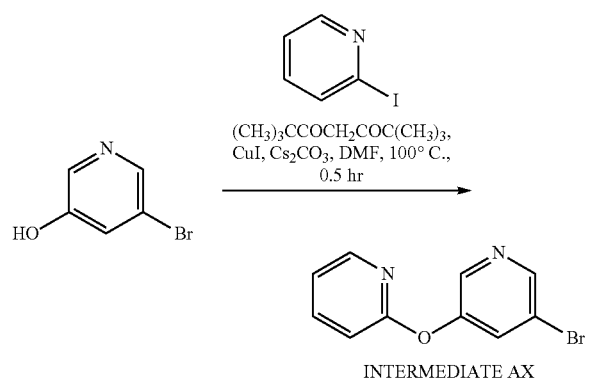

INTERMEDIATE AX

To a solution of 5-bromopyridin-3-ol (500 mg, 2.87 mmol, 1.00 eq.) in DMF (10 mL) was added cesium carbonate (1.87 g, 5.75 mmol, 2.00 eq.), 2-iodopyridine (707 mg, 3.45 mmol, 366 μL, 1.20 eq.), 2,2,6,6-tetramethylheptane-3,5-dione (212 mg, 1.15 mmol, 237 μL, 0.40 eq.) and cuprous iodide (109 mg, 575 μmol, 0.20 eq.). The mixture was stirred at 100° C. for 0.5 hour. The reaction mixture was then diluted with water (100 mL) and extracted with ethyl acetate (70.0 mL×3). The combined organic layers were washed with brine (100 mL), dried, filtered and concentrated under reduced pressure. The residue was purified by column chromatography (Sift, petroleumether:ethylacetate 0-20%) to give 3-bromo-5-(2-pyridyloxy)pyridine Intermediate AX (600 mg, 1.45 mmol, 50% yield) as a yellow oil. LCMS [M+1]$^+$=250.8. $^1$H NMR (400 MHz, DMSO-d$_6$) δ=8.57 (d, J=2.0 Hz, 1H), 8.48 (d, J=2.4 Hz, 1H), 8.16 (ddd, J=0.8, 2.0, 4.8 Hz, 1H), 8.02 (s, 1H), 7.91 (ddd, J=2.0, 7.2, 8.0 Hz, 1H), 7.21-7.15 (m, 2H).

Intermediate AY

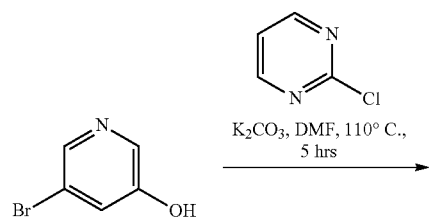

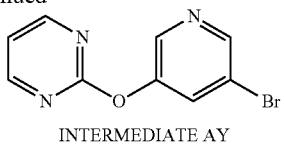

INTERMEDIATE AY

To a solution of 2-chloropyrimidine (300 mg, 2.62 mmol, 1.00 eq.) in DMF (2 mL) was added potassium carbonate (724 mg, 5.24 mmol, 2.00 eq.) and 5-bromopyridin-3-ol (479 mg, 2.75 mmol, 1.05 eq.). The mixture was stirred at 110° C. for 5 hours. The reaction mixture was diluted with water (200 mL) and extracted with ethyl acetate (80 mL×3). The combined organic layers were washed with brine (150 mL), dried over anhydrous sodium sulfate, filtered and concentrated under reduced pressure to give 2-[(5-bromo-3-pyridyl)oxy]pyrimidine, Intermediate AY (523 mg, crude) as a red solid and used into the next step directly without further purification. LCMS [M+1]$^+$=252.0; $^1$H NMR (400 MHz, DMSO-d$_6$) δ=8.70 (s, 1H), 8.69 (s, 1H), 8.63 (d, J=2.0 Hz, 1H), 8.57 (d, J=2.4 Hz, 1H), 8.17 (t, J=2.0 Hz, 1H), 7.34 (t, J=4.8 Hz, 1H).

Intermediate AY-1

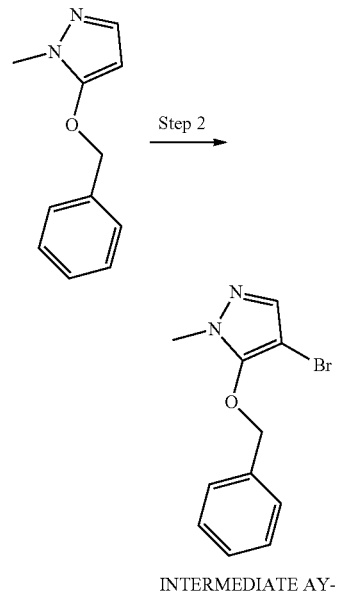

INTERMEDIATE AY-1

Step 1: To a solution of 2-methylpyrazol-3-ol (500 mg, 5.10 mmol, 1.00 eq.), (bromomethyl)benzene (1.05 g, 6.12 mmol, 726 μL, 1.20 eq.) in DMF (6.00 mL) was added potassium carbonate (1.06 g, 7.65 mmol, 1.50 eq.). The mixture was stirred at 120° C. for 4 hours. The reaction mixture was then diluted with water (10 mL) and extracted with ethyl acetate (20 mL×3). The combined organic layers were washed with brine (50 mL×2), dried over anhydrous sodium sulfate, filtered and concentrated under reduced pressure. The residue was purified by column chromatography (SiO$_2$, petroleum ether/ethyl acetate 50/1 to 6/1) to give 5-benzyloxy-1-methyl-pyrazole (450 mg, 2.39 mmol, 47% yield) as a colorless oil. LCMS [M+1]$^+$=189.2; $^1$H NMR (400 MHz, CDCl$_3$) δ=7.43-7.41 (m, 3H), 7.40-7.35 (m, 2H), 7.31 (d, J=2.0 Hz, 1H), 7.24-7.21 (d, J=2.0 Hz, 1H), 5.08 (s, 2H), 3.67 (s, 3H).

Step 2: To a solution of 5-benzyloxy-1-methyl-pyrazole (400 mg, 2.13 mmol, 1.00 eq.) in acetonitrile (6 mL) was added NBS (416 mg, 2.34 mmol, 1.10 eq.). The mixture was stirred at 0° C. for 0.5 hours. The reaction mixture was then concentrated under reduced pressure and the residue was purified by column chromatography (SiO$_2$, petroleum ether/ethyl acetate=100/1 to 20/1) to give 5-benzyloxy-4-bromo-1-methyl-pyrazole (320 mg, 1.20 mmol, 56% yield) as a yellow oil. LCMS [M+1]$^+$=266.9; $^1$H NMR (400 MHz, CDCl$_3$) δ=7.39 (s, 5H), 7.32 (s, 1H), 5.28 (s, 2H), 3.45 (s, 3H).

Intermediate AY-2 shown in Table I-IIb was prepared following the teachings of the General Reaction Schemes and the method to prepare Intermediate AY-1.

TABLE I-IIb

| Intermediate | Structure | Spectral Data |
|---|---|---|
| AY-2 | 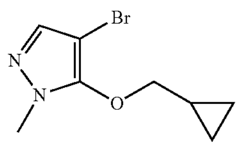 | 4-bromo-5-(cyclopropylmethoxy)-1-methyl-1H-pyrazole LCMS [M + 1]$^+$ = 233.1; $^1$H NMR (400 MHz, CDCl$_3$) δ = 7.32-7.28 (s, 1H), 4.11-4.07 (m, 2H), 3.74-3.68 (s, 3H), 1.25-1.16 (m, 1H), 0.67-0.57 (m, 2H), 0.37-0.28 (m, 2H) |

General Procedure for Intermediates B-1 to B-15

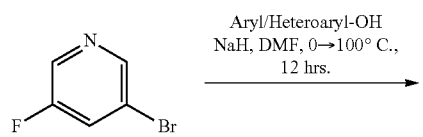

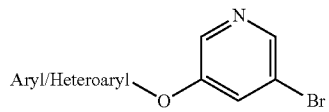

To the corresponding aryl/heteroaryl phenol (3.89 mmol, 1.00 eq.) in DMF (10 mL) was added sodium hydride (4.28 mmol, 60% purity, 1.10 eq.) at 0° C. under nitrogen. After the addition was complete the mixture was stirred at 25° C. for 0.5 hour, followed by addition with 3-bromo-5-fluoro-pyridine (3.89 mmol, 1.00 eq.) and stirred at 100° C. for a further 12 hours. After such time the reaction mixture was quenched by the addition water (10 mL) and then extracted with ethyl acetate (20 mL×3). The combined organic layers were washed with brine (50 mL×2), dried over anhydrous sodium sulfate, filtered and concentrated under reduced pressure to give a residue which was used directly in the next step without further purification.

Following the teachings of the General Reaction Schemes and the general procedure for Intermediates B-1 to B-15 the intermediates in Table I-III were prepared.

| Intermediate | Structure | Characterization |
|---|---|---|
| B-1 | 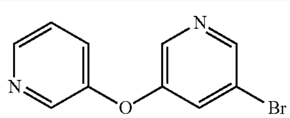 [SMILES: Brc1cncc(Oc2cccnc2)c1] | 3-Bromo-5-(pyridin-3-yloxy)pyridine LCMS [M + 1]$^+$ = 250.9; $^1$H NMR (400 MHz, CDCl$_3$) δ = 8.51-8.48 (m, 2H), 8.48-8.45 (m, 1H), 8.36 (d, J = 2.8 Hz, 1H), 7.47(t, J = 2.0 Hz 1H), 7.40-7.35 (m, 2H) |
| B-2 | 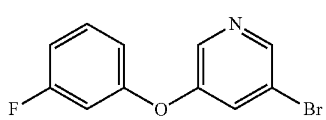 [SMILES: Fc1cccc(Oc2cncc(Br)c2)c1] | 3-Bromo-5-(3-fluorophenoxy)pyridine LCMS [M + 1]$^+$ = 268.0; $^1$H NMR (400 MHz, DMSO-d$_6$) δ = 8.53 (d, J = 1.6 Hz, 1H), 8.41 (d, J = 2.4 Hz, 1H), 7.81 (t, J = 2.0 Hz, 1H), 7.51-7.43 (m, 1H), 7.08-7.03 (m, 2H), 6.97-6.92 (m, 1H) |
| B-3 | 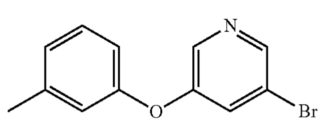 | 3-Bromo-5-(m-tolyloxy)pyridine LCMS [M + 1]$^+$ = 265.9; $^1$H NMR (400 MHz, CDCl$_3$) δ = 8.40 (d, J = 2.0 Hz, 1H), 8.33 (d, J = 2.4 Hz, 1H), 7.41 (t, J = 2.0 Hz, 1H), 7.31-7.27 (m, 1H), 7.03 (d, J = 7.6 Hz, 1H), 6.92-6.81 (m, 2H), 2.37 (s, 3H) |
| B-4 | 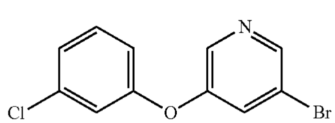 [SMILES: Clc1cccc(Oc2cncc(Br)c2)c1] | 3-Bromo-5-(3-chlorophenoxy)pyridine [M + 1]$^+$ = 286.0; $^1$H NMR (400 MHz, DMSO-d$_6$) δ = 8.53 (d, J = 1.6 Hz, 1H), 8.41 (d, J = 2.4 Hz, 1H), 7.82 (q, J = 2.4 Hz, 1H), 7.49-7.41 (m, 1H), 7.31-7.23 (m, 2H), 7.11-7.06 (m, 1H) |
| B-5 | 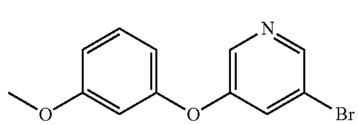 [SMILES: COc1cccc(Oc2cncc(Br)c2)c1] | 3-Bromo-5-(3-methoxyphenoxy)pyridine LCMS [M + 1]$^+$ = 279.9; $^1$H NMR (400 MHz, CDCl$_3$) δ = 8.42 (d, J = 2.0 Hz, 1H), 8.34 (d, J = 2.4 Hz, 1H), 7.44 (t, J = 2.4 Hz, 1H), 7.30 (t, J = 8.4 Hz, 1H), 6.79-6.74 (m, 1H), 6.64-6.59 (m, 2H), 3.81 (s, 3H) |

-continued

| Intermediate | Structure | Characterization |
|---|---|---|
| B-6 | 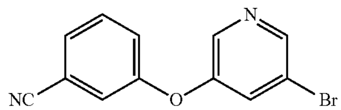 [SMILES: N#Cc1cccc(Oc2cncc(Br)c2)c1] | 3-((5-Bromopyridin-3-yl)oxy)benzonitrile<br>LCMS [M + 1]$^+$ = 277.0; $^1$H NMR (400 MHz, DMSO-d$_6$) δ = 8.55 (d, J = 1.6 Hz, 1H), 8.43 (d, J = 2.4 Hz, 1H), 7.86 (t, J = 2.4 Hz, 1H), 7.69-7.66 (m, 2H), 7.62 (t, J = 8.4 Hz, 1H), 7.47 (ddd, J = 1.2, 2.4, 8.0 Hz, 1H) |
| B-7 | 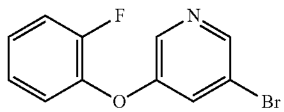 [SMILES: Fc1ccccc1Oc1cncc(Br)c1] | 3-Bromo-5-(2-fluorophenoxy)pyridine<br>LCMS [M + 1]$^+$ = 269.9; $^1$H NMR (400 MHz, DMSO-d$_6$) δ = 8.50 (d, J = 1.6 Hz, 1H), 8.38 (d, J = 2.4 Hz, 1H), 7.70 (t, J = 2.0 Hz, 1H), 7.48-7.39 (m, 1H), 7.36-7.27 (m, 3H) |
| B-8 | 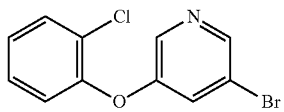 [SMILES: Clc1ccccc1Oc1cncc(Br)c1] | 3-Bromo-5-(2-chlorophenoxy)pyridine<br>LCMS [M + 1]$^+$ = 286.0; $^1$H NMR (400 MHz, DMSO-d$_6$) δ = 8.49 (d, J = 1.6 Hz, 1H), 8.33 (d, J = 2.4 Hz, 1H), 7.66-7.62 (m, 2H), 7.43 (td, J = 1.6, 8.0 Hz, 1H), 7.34-7.28 (m, 2H) |
| B-9 | 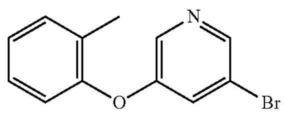 | 3-Bromo-5-(o-tolyloxy)pyridine<br>LCMS [M + 1]$^+$ = 266.0; $^1$H NMR (400 MHz, CDCl$_3$) δ = 8.37 (d, J = 2.0 Hz, 1H), 8.28 (d, J = 2.4 Hz, 1H), 7.31 (dd, J = 0.8, 7.2 Hz, 1H), 7.29 (s, 1H), 7.27-7.22 (td, J = 1.6,7.6 Hz,1H), 7.20-7.14 (td, J = 1.2, 7.6 Hz, 1H), 6.96 (dd, J = 1.2, 8.0 Hz, 1H), 2.23 (s, 3H) |
| B-10 | 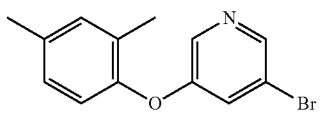 [SMILES: Cc1ccc(Oc2cncc(Br)c2)c(C)c1] | 3-Bromo-5-(2,4-dimethylphenoxy)pyridine<br>LCMS [M + 1]$^+$ = 278.0; $^1$H NMR (400 MHz, CDCl$_3$) δ = 8.35 (d, J = 2.0 Hz, 1H), 8.26 (d, J = 2.4 Hz, 1H), 7.26-7.24 (t, J = 2.4 Hz, 1H), 7.10 (s, 1H), 7.04 (dd, J = 1.2, 8.4 Hz, 1H), 6.86 (d, J = 8.4 Hz, 1H), 2.35 (s, 3H), 2.17 (s, 3H) |
| B-11 | 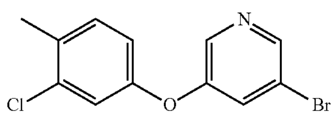 [SMILES: Cc1ccc(Oc2cncc(Br)c2)cc1Cl] | 3-Bromo-5-(3-chloro-4-methylphenoxy)pyridine<br>LCMS [M + 1]$^+$ = 299.9; $^1$H NMR (400 MHz, CDCl$_3$) δ = 8.43 (d, J = 2.0 Hz, 1H), 8.32 (d, J = 2.4 Hz, 1H), 7.44-7.41 (t, J = 2.4 Hz, 1H), 7.26 (d, J = 8.8 Hz, 1H), 7.08 (d, J = 2.4 Hz, 1H), 6.87 (dd, J = 1.6, 4.4 Hz, 1H), 2.38 (s, 3H). |
| B-12 | 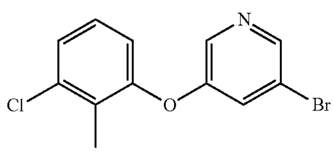 [SMILES: Cc1c(Cl)cccc1Oc1cncc(Br)c1] | 3-Bromo-5-(3-chloro-2-methylphenoxy)pyridine<br>LCMS [M + 1]$^+$ = 299.9; $^1$H NMR (400 MHz, CDCl$_3$) δ = 8.41 (d, J = 2.0 Hz, 1H), 8.28 (d, J = 2.4 Hz, 1H), 7.32-7.31 (t, J = 2.0 Hz, 1H), 7.17 (t, J = 8.0 Hz, 1H), 6.88 (dd, J = 0.8, 8.0 Hz, 1H), 6.69 (dd, J = 1.6, 7.6 Hz, 1H), 2.31 (s, 3H) |
| B-13 | 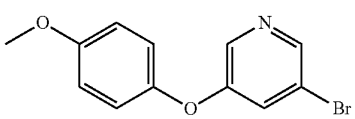 [SMILES: COc1ccc(Oc2cncc(Br)c2)cc1] | 3-Bromo-5-(4-methoxyphenoxy)pyridine<br>LCMS [M + 1]$^+$ = 280.1; $^1$H NMR (400 MHz, CDCl$_3$) δ = 8.36 (d, J = 2.0 Hz, 1H), 8.29 (d, J = 2.4 Hz, 1H), 7.35-7.33 (m, 1H), 7.04-6.99 (m, 2H), 6.96-6.91 (m, 2H), 3.84 (s, 3H) |
| B-14 | 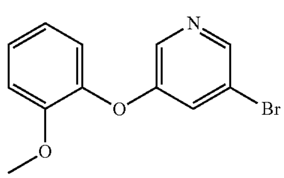 [SMILES: COc1ccccc1Oc1cncc(Br)c1] | 3-Bromo-5-(2-methoxyphenoxy)pyridine<br>LCMS [M + 1]$^+$ = 280.1; $^1$H NMR (400 MHz, CDCl3) δ = 8.35 (d, J = 1.6 Hz, 1H), 8.27 (d, J = 2.4 Hz, 1H), 7.29 (dd, J = 2.0, 2.4 Hz, 1H), 7.08-7.01 (m, 2H), 6.95-6.86 (m, 2H), 3.82 (s, 3H) |
| B-15 | 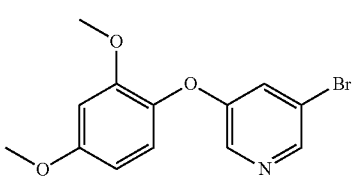 [SMILES: COc1ccc(Oc2cncc(Br)c2)c(OC)c1] | 3-bromo-5-(2,4-dimethoxyphenoxy)pyridine<br>LCMS [M + 1]$^+$ = 312.0; $^1$H NMR (400 MHz, CDCl$_3$) δ = 8.32 (d, J = 1.6 Hz, 1H), 8.25 (d, J = 2.4 Hz, 1H), 7.24 (t, J = 2.0 Hz, 1H), 7.02 (d, J = 8.8 Hz, 1H), 6.60 (d, J = 2.8 Hz, 1H), 6.49 (dd, J = 2.8, 8.8 Hz, 1H), 3.84 (s, 3H), 3.78 (s, 3H) |

Intermediate BN

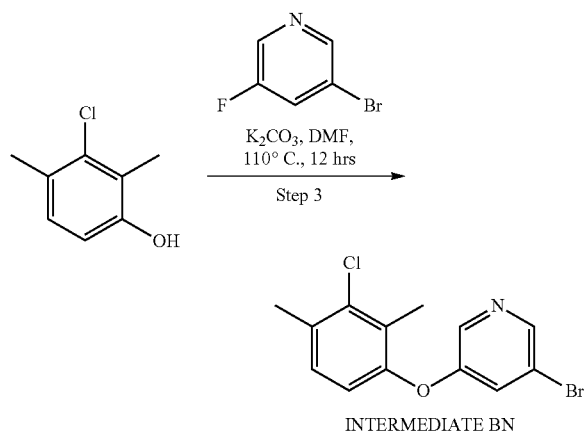

INTERMEDIATE BN

To a solution of 3-bromo-5-fluoro-pyridine (210 mg, 1.19 mmol, 0.95 eq.) in DMF (10 mL) was added potassium carbonate (347 mg, 2.51 mmol, 2.00 eq.) and 3-chloro-2,4-dimethyl-phenol (197 mg, 1.26 mmol, 1.00 eq.). The mixture was stirred at 110° C. for 12 hours. After such time the reaction mixture was diluted with water (80 mL) and extracted with ethyl acetate (50 mL×3). The combined organic layers were then washed with brine (50 mL), dried over anhydrous sodium sulfate, filtered and concentrated under reduced pressure. The residue was purified by column chromatography (SiO$_2$, Petroleum ether:ethyl acetate 0-20%) to give 3-bromo-5-(3-chloro-2,4-dimethyl-phenoxy) pyridine, Intermediate BN (178 mg, 569 μmol, 45% yield) as a colorless oil. LCMS [M+1]$^+$=314.0. $^1$H NMR (400 MHz, DMSO-d$_6$) δ=8.45 (d, J=2.0 Hz, 1H), 8.31 (d, J=2.4 Hz, 1H), 7.57 (t, J=2.0 Hz, 1H), 7.27 (d, J=8.4 Hz, 1H), 6.99 (d, J=8.4 Hz, 1H), 2.34 (s, 3H), 2.22 (s, 3H).

Intermediate BP

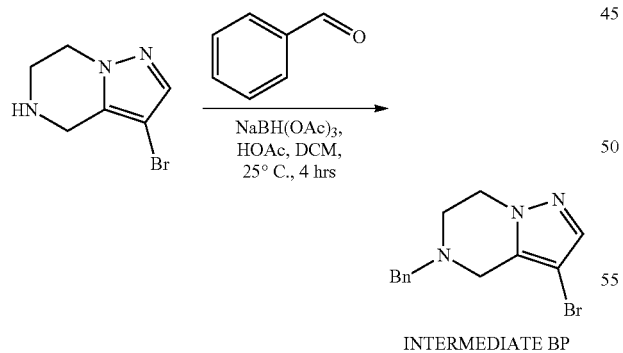

INTERMEDIATE BP

To a solution of 3-bromo-4,5,6,7-tetrahydropyrazolo[1,5-a]pyrazine (300 mg, 949 μmol, 1.00 eq., TFA) and benzaldehyde (131 mg, 1.23 mmol, 125 μL, 1.30 eq.) in dichloromethane (10 mL) was added sodium triacetoxyborohydride (402 mg, 1.90 mmol, 2.00 eq.) and acetic acid (114 mg, 1.90 mmol, 109 μL, 2.00 eq.). The mixture was then stirred at 25° C. for 4 hours. After such time the reaction mixture was diluted with water (10 mL) and extracted with ethyl acetate (15 mL×3). The combined organic layers were washed with brine (50 mL×2), dried over anhydrous sodium sulfate, filtered and concentrated. The residue was purified by prep-TLC (SiO$_2$, petroleumether:ethylacetate 25%) to give 5-benzyl-3-bromo-6,7-dihydro-4H-pyrazolo[1,5-a]pyrazine, Intermediate BP (170 mg, 582 μmol, 61% yield) as a colorless oil. LCMS [M+1]$^+$=294.0. $^1$H NMR (400 MHz, CD$_3$OD) δ=7.45 (s, 1H), 7.41-7.32 (m, 5H), 4.12 (t, J=5.6 Hz, 2H), 3.77 (s, 2H), 3.57 (s, 2H), 2.96 (t, J=5.6 Hz, 2H).

Intermediate BQ

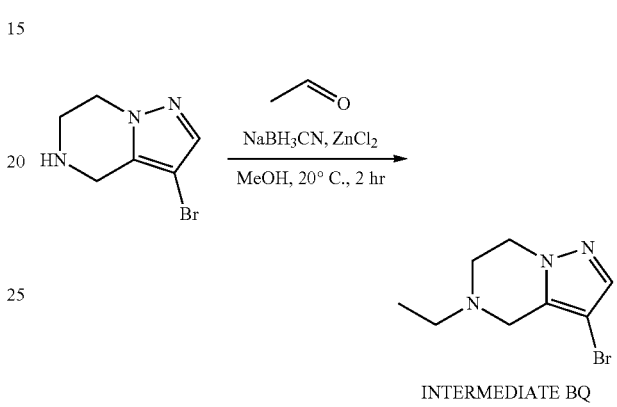

INTERMEDIATE BQ

A mixture of 3-bromo-4,5,6,7-tetrahydropyrazolo[1,5-a] pyrazine (400 mg, 1.27 mmol, 1.00 eq.), acetaldehyde (5.0 M, 508 uL, 2.01 eq.), sodium cyanoborohydride (160 mg, 2.54 mmol, 2.01 eq.), zinc chloride (1.0 M, 2.53 mL, 2.00 eq.) in methanol (8 mL) was stirred at 25° C. for 2 hours. After such time the solvent was evaporated and the residue purified by column chromatography (SiO$_2$, dichloromethane:methanol 0-10%). The product was further purified by prep-HPLC (Waters Xbridge C18 150×50 mm×10 μm; mobile phase: [water (10 mM NH$_4$HCO$_3$)-ACN]; B %: 16%-46%, 11.5 min) to give 3-bromo-5-ethyl-6,7-dihydro-4H-pyrazolo[1,5-a]pyrazine, intermediate BQ (100 mg, 434 μmol, 34% yield) as an colorless oil. $^1$H NMR (400 MHz, CD$_3$OD) δ=7.47 (s, 1H), 4.21-4.11 (t, J=6.0 Hz, 2H), 3.61 (s, 2H), 3.03-2.94 (t, J=6.0 Hz, 2H), 2.69 (q, J=7.2 Hz, 2H), 1.20 (t, J=7.2 Hz, 3H).

Intermediate BR

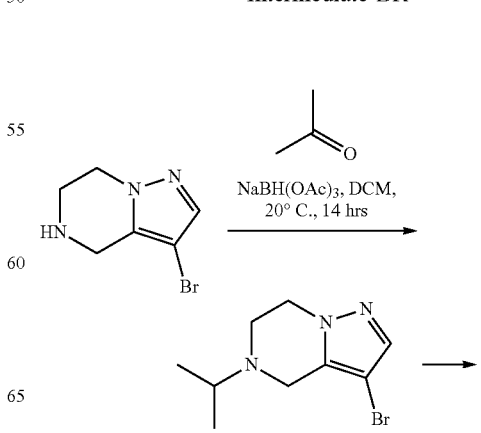

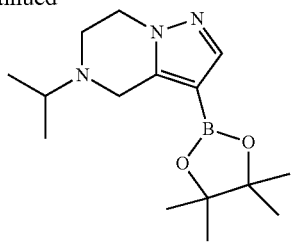

INTERMEDIATE BR

Step 1: To a mixture of 3-bromo-4,5,6,7-tetrahydropyrazolo[1,5-a]pyrazine (200 mg, 990 μmol, 1.00 eq.) and acetone (862 mg, 14.9 mmol, 1.09 mL, 15.0 eq.) in dichloromethane (1.00 mL), was added sodium triacetoxyborohydride (420 mg, 1.98 mmol, 2.00 eq.). After stirring at 25° C. for 14 hours the mixture was extracted with dichloromethane (5 mL×3), washed with brine, dried over sodium sulfate, filtered and concentrated under reduced pressure. The residue was purified by prep-TLC (SiO$_2$, dichloromethane:methyl alcohol 10%) to give 3-bromo-5-isopropyl-6,7-dihydro-4H-pyrazolo[1,5-a]pyrazine (150 mg, 531 μmol, 54% yield) as a yellow oil. LCMS [M+1]$^+$=244.0. $^1$H NMR (400 MHz, CDCl$_3$) δ=7.35 (s, 1H), 4.12-4.06 (t, J=5.2 Hz, 2H), 3.59 (s, 2H), 2.96-2.90 (m, 1H), 2.89-2.86 (t, J=5.2 Hz, 2H), 1.09 (s, 3H), 1.07 (s, 3H).

Step 2: A mixture of 3-bromo-5-isopropyl-6,7-dihydro-4H-pyrazolo[1,5-a]pyrazine (80.0 mg, 328 μmol, 1.00 eq.), 4,4,4',4',5,5,5',5'-octamethyl-2,2'-bi(1,3,2-dioxaborolane) (166 mg, 655 μmol, 2.00 eq.), potassium acetate (113 mg, 1.15 mmol, 3.50 eq.) and PdCl$_2$[P(Cy)$_3$]$_2$ (24.2 mg, 32.8 μmol, 0.10 eq.) in dimethylaminopyridine (1 mL) was purged with nitrogen then stirred at 90° C. for 20 hours. The mixture was then concentrated under reduced pressure to give 5-isopropyl-3-(4,4,5,5-tetramethyl-1,3,2-dioxaborolan-2-yl)-6,7-dihydro-4H-pyrazolo[1,5-a]pyrazine, Intermediate BR (700 mg, 303 umol, 92% yield) as a black solid. LCMS [M+1]$^+$=292.2.

Intermediate BS

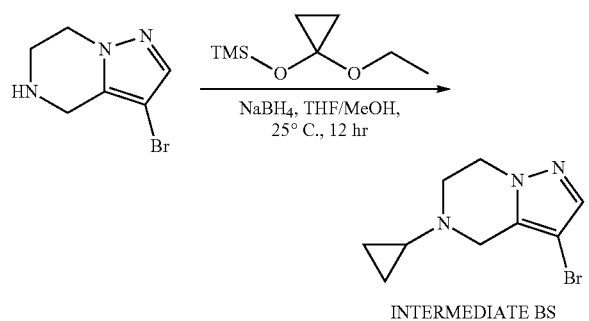

INTERMEDIATE BS

A pressure tube was charged with 3-bromo-4,5,6,7-tetrahydropyrazolo[1,5-a]pyrazine (260 mg, 1.29 mmol, 1.00 eq.), (1-ethoxycyclopropoxy)trimethylsilane (673 mg, 3.86 mmol, 776 μL, 3.00 eq.), sodium cyanoborohydride (243 mg, 3.86 mmol, 3.00 eq.) and acetic acid (773 mg, 12.9 mmol, 736 μL, 10.0 eq.) in THF (5 mL) and ethyl alcohol (5 mL). The resulting solution was stirred for 2 hours at 60° C., then the reaction mixture was concentrated to give a residue. The residue was purified by prep-TLC (SiO$_2$, petroleum ether:ethyl acetate 20%) to give 3-bromo-5-cyclopropyl-6,7-dihydro-4H-pyrazolo[1,5-a]pyrazine, Intermediate BS (150 mg, 620 μmol, 48% yield) as yellow solid. $^1$H NMR (400 MHz, CD$_3$OD) δ=7.45 (s, 1H), 4.14-4.09 (m, 2H), 3.75 (s, 2H), 3.20-3.10 (m, 2H), 2.02-1.96 (m, 1H), 0.65-0.57 (m, 2H), 0.56-0.44 (m, 2H).

Intermediate BT

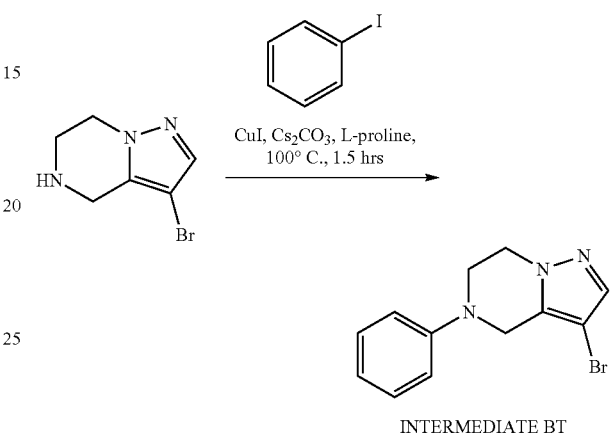

INTERMEDIATE BT

A mixture of 3-bromo-4,5,6,7-tetrahydropyrazolo[1,5-a]pyrazine (500 mg, 1.58 mmol, 1.00 eq.), iodobenzene (1.29 g, 6.33 mmol, 705 μL, 4.00 eq.), copper iodide (60.3 mg, 316 μmol, 0.20 eq.), (2S)-pyrrolidine-2-carboxylic acid (72.9 mg, 633 μmol, 0.40 eq.) and cesium carbonate (1.03 g, 3.16 mmol, 2.00 eq.) in DMF (10 mL) was degassed and purged with nitrogen then stirred at 100° C. for 1.5 hours. After such time the mixture was cooled, extracted with ethyl acetate (5 mL×3), washed with brine, dried over sodium sulfate, filtered and concentrated under reduced pressure. The formed residue was purified by column chromatography (SiO$_2$, petroleum ether/ethyl acetate 5-10%) to give 3-bromo-5-phenyl-6,7-dihydro-4H-pyrazolo[1,5-a]pyrazine, Intermediate BT (55 mg, 197 μmol, 12% yield) as yellow solid. LCMS [M+1]$^+$=278.2.

Intermediate BU

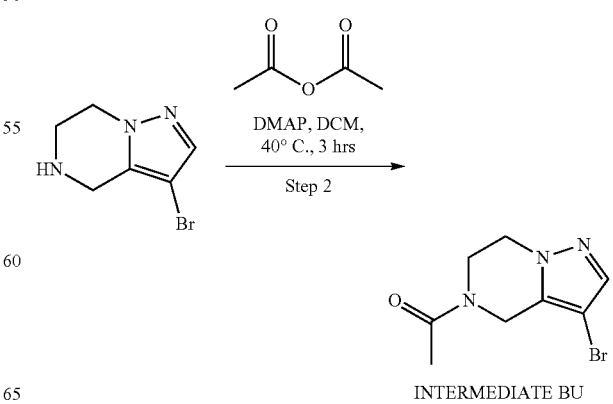

INTERMEDIATE BU

A mixture of 3-bromo-4,5,6,7-tetrahydropyrazolo[1,5-a]pyrazine (200 mg, 633 μmol, 1.00 eq.), acetyl acetate (96.9 mg, 949 μmol, 88.9 μL, 1.50 eq.) and DMAP (7.73 mg, 63.3 μmol, 0.10 eq.) in dichloromethane (10 mL) was degassed and purged with nitrogen then stirred at 40° C. for 3 hours. Upon completion the reaction mixture was concentrated under reduced pressure to give 1-(3-bromo-6,7-dihydro-4H-pyrazolo[1,5-a]pyrazin-5-yl)ethenone, Intermediate BU (100 mg, crude) as a white solid. LCMS [M+1]⁺=244.2.

Intermediate BV

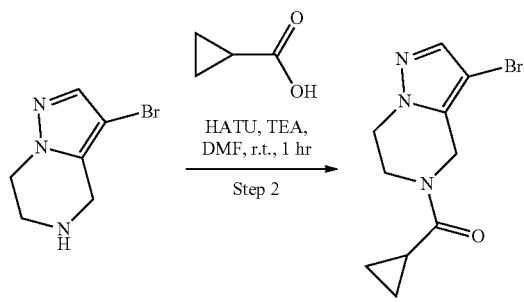 [SMILES: Brc1cnn2c1CNCC2 ; O=C(O)C1CC1 ; O=C(C1CC1)N1CCn2ncc(Br)c2C1]

To a solution of 3-bromo-4,5,6,7-tetrahydropyrazolo[1,5-a]pyrazine (250 mg, 791 μmol, 1.00 eq.) in dimethylformamide (2 mL) was added triethylamine (240 mg, 2.37 mmol, 330 μL, 3.00 eq.), HATU (601 mg, 1.58 mmol, 2.00 eq.), and cyclopropane carboxylic acid (102 mg, 1.19 mmol, 93.7 μL, 1.50 eq.). The mixture was stirred at 35° C. for 1 hour. After such time the reaction mixture was diluted with water (100 mL) and extracted with ethyl acetate (30.0 mL×3) and the combined organic layers were washed with brine (50 mL), dried over anhydrous sodium sulfate, filtered and concentrated under reduced pressure. The formed residue was purified by column chromatography (SiO$_2$, petroleum ether: ethyl acetate 0-50%) to give (3-bromo-6,7-dihydro-4H-pyrazolo[1,5-a]pyrazin-5-yl)-cyclopropyl-methanone, Intermediate BV (139 mg, 515 μmol, 65% yield) as a colorless oil. ¹H NMR (400 MHz, CDCl$_3$) δ=7.48 (s, 1H), 4.89-4.68 (m, 2H), 4.33-4.05 (m, 4H), 1.87-1.79 (m, 1H), 1.09-1.04 (m, 2H), 0.93-0.84 (m, 2H).

Following the teachings of the General Reaction Schemes, and the procedure for INTERMEDIATE BV, INTERMEDIATES C-1 to C-5 were prepared as shown in Table I-IV:

TABLE I-IV

| Intermediate | Structure | Characterization |
|---|---|---|
| C-1 | 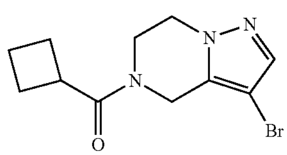 [SMILES: O=C(C1CCC1)N1CCn2ncc(Br)c2C1] | (3-Bromo-6,7-dihydropyrazolo[1,5-a]pyrazin-5(4H)-yl)(cyclobutyl)methanone<br>LCMS [M + 1]⁺ = 286.1 ¹H NMR (400 MHz, DMSO-d$_6$) δ = 7.59 (s, 1H), 4.60-4.49 (m, 2H), 4.14-4.05 (m, 2H), 3.96-3.79 (m, 2H), 3.55-3.47 (m, 1H), 2.25-2.10 (m, 4H), 1.98-1.88 (m, 1H), 1.81-1.70 (m, 1H) |
| C-2 | 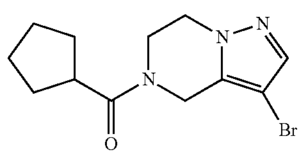 [SMILES: O=C(C1CCCC1)N1CCn2ncc(Br)c2C1] | (3-Bromo-6,7-dihydropyrazolo[1,5-a]pyrazin-5(4H)-yl)(cyclopentyl)methanone<br>LCMS [M + 1]⁺ = 297.9 |
| C-3 | 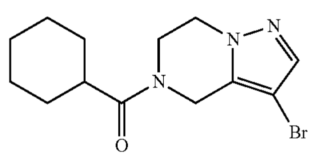 [SMILES: O=C(C1CCCCC1)N1CCn2ncc(Br)c2C1] | (3-Bromo-6,7-dihydropyrazolo[1,5-a]pyrazin-5(4H)-yl)(cyclohexyl)methanone<br>¹H NMR (400 MHz, DMSO-d$_6$) δ = 7.59 (s, 1H), 4.78-4.50 (m, 2H), 4.16 (m, 1H), 4.06-3.91 (m, 3H), 2.79-2.70 (m, 1H), 1.77-1.58 (m, 5H), 1.44-1.17 (m, 5H) |
| C-4 | 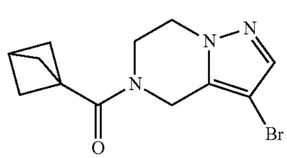 [SMILES: O=C(N1CCn2ncc(Br)c2C1)C12CC(C1)C2] | bicyclo[1.1.1]pentan-1-yl(3-bromo-6,7-dihydropyrazolo[1,5-a]pyrazin-5(4H)-yl)methanone<br>LCMS [M + 1]⁺ = 298.1 |
| C-5 | 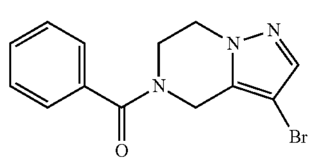 [SMILES: O=C(c1ccccc1)N1CCn2ncc(Br)c2C1] | (3-Bromo-6,7-dihydropyrazolo[1,5-a]pyrazin-5(4H)-yl)(phenyl)methanone<br>LCMS [M + 1]⁺ = 308.0 |

Intermediate CB

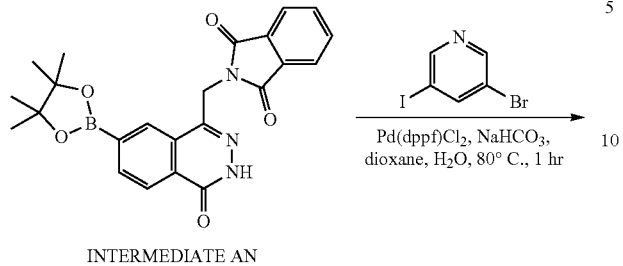

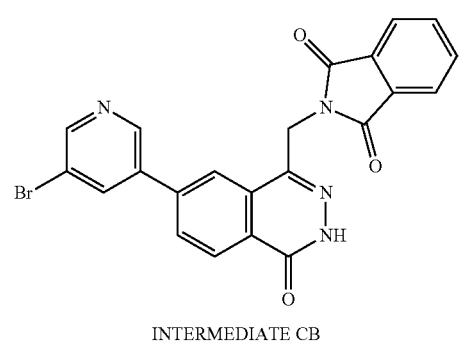

INTERMEDIATE CB

A mixture of 3-bromo-5-iodo-pyridine (3.00 g, 10.6 mmol, 1.00 eq.), intermediate AN (2.28 g, 5.28 mmol, 0.50 eq.), sodium bicarbonate (1.78 g, 21.1 mmol, 822 μL, 2.00 eq.), Pd(dppf)Cl₂ (773 mg, 1.06 mmol, 0.10 eq.) in dioxane (50 mL) and water (10 mL) was degassed with nitrogen 3 then stirred at 80° C. for 1 hour. The cooled reaction mixture was then concentrated under reduced, diluted with water (200 mL), filtered and the filter cake was triturated with dichloromethane:methyl alcohol (10%, 150 mL). The solid was filtered, dried and the solid was triturated a second time in methyl alcohol (100 mL), then filtered and dried to give 2-[[7-(5-bromo-3-pyridyl)-4-oxo-3H-phthalazin-1-yl]methyl]isoindoline-1,3-dione, Intermediate CB (775 mg, crude) as a gray solid. ¹H NMR (400 MHz, DMSO-d₆) δ=12.54 (s, 1H), 9.16 (d, J=1.2 Hz, 1H), 8.82 (d, J=1.6 Hz, 1H), 8.73 (s, 1H), 8.52 (s, 1H), 8.38-8.28 (m, 2H), 7.98-7.95 (m, 2H), 7.90 (m, 2H), 5.38 (s, 2H).

Intermediate CC

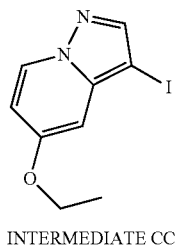

INTERMEDIATE CC

Step 1: To a solution of pyrazolo[1,5-a]pyridin-5-ol (250 mg, 1.86 mmol, 1.00 eq.) in DMF (2 mL) was added potassium carbonate (773 mg, 5.59 mmol, 3.00 eq.) and the mixture stirred at 30° C. for 0.5 hour. Iodoethane (872 mg, 5.59 mmol, 447 μL, 3.00 eq.) was then added and the resulting mixture stirred at 30° C. for 12 hours. After such time the reaction mixture was diluted with water (50 mL) extracted with ethyl acetate (20 mL×3) and the combined organic layers were washed with brine (50 mL), dried over anhydrous sodium sulfate, filtered and concentrated under reduced pressure. The residue was purified by prep-TLC (SiO₂, Petroleum ether/Ethyl acetate 20%) to give 5-ethoxy-pyrazolo[1,5-a]pyridine (272 mg, 1.68 mmol, 90% yield) as a white solid. LCMS [M+1]⁺=163.2; ¹H NMR (400 MHz, DMSO-d₆) δ=8.50 (d, J=7.6 Hz, 1H), 7.86 (d, J=2.0 Hz, 1H), 6.98 (d, J=2.8 Hz, 1H), 6.52 (dd, J=2.8, 7.6 Hz, 1H), 6.35 (d, J=2.0 Hz, 1H), 4.06 (q, J=6.8 Hz, 2H), 1.35 (t, J=6.8 Hz, 3H).

Step 2: To a solution of 5-ethoxypyrazolo[1,5-a]pyridine (260 mg, 1.60 mmol, 1.00 eq.) in acetonitrile (1.0 mL) was added NIS (397 mg, 1.76 mmol, 1.10 eq.). The mixture was stirred at 25° C. for 1 hour before the mixture was diluted with water (30 mL) and extracted with ethyl acetate (10 mL×3). The combined organic layers were washed with brine (20 mL), dried over anhydrous sodium sulfate, filtered and concentrated under reduced pressure. The residue was purified by prep-TLC (SiO₂, Petroleum ether/Ethyl acetate 20%) to give 5-ethoxy-3-iodo-pyrazolo[1,5-a]pyridine (369 mg, 1.28 mmol, 80% yield) as a pink solid. LCMS [M+1]⁺=289.1; ¹H NMR (400 MHz, DMSO-d₆) δ=8.57 (d, J=7.6 Hz, 1H), 7.96 (s, 1H), 6.67 (d, J=2.4 Hz, 1H), 6.59 (dd, J=2.4, 7.6 Hz, 1H), 4.14 (q, J=6.8 Hz, 2H), 1.37 (t, J=6.8 Hz, 3H).

Intermediate CD

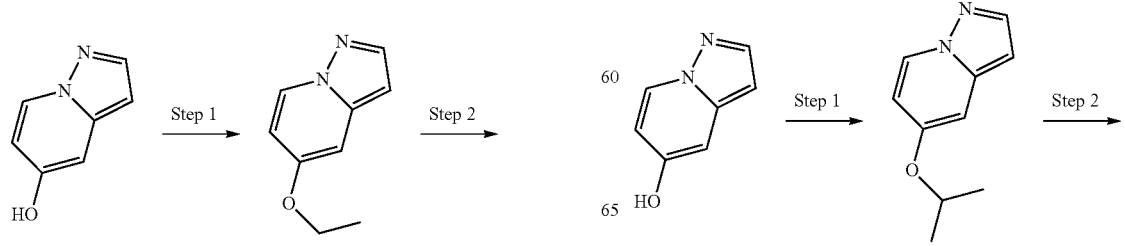

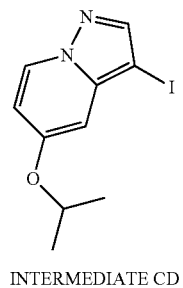

INTERMEDIATE CD

Intermediate CD, 3-iodo-5-isopropoxy-pyrazolo[1,5-a]pyridine was prepares as a yellow solid (299 mg, 0.99 mmol, 87% yield over 2 steps) using 2-iodopropane following the same procedure as used for the preparation of Intermediate CC. LCMS [M+1]$^+$=303.0; $^1$H NMR (400 MHz, DMSO-$d_6$) δ=8.56 (d, J=7.6 Hz, 1H), 7.96 (s, 1H), 6.67 (d, J=2.8 Hz, 1H), 6.57 (dd, J=2.8, 7.6 Hz, 1H), 4.77 (td, J=6.0, 12.0 Hz, 1H), 1.32 (s, 3H), 1.30 (s, 3H).

Intermediate CE

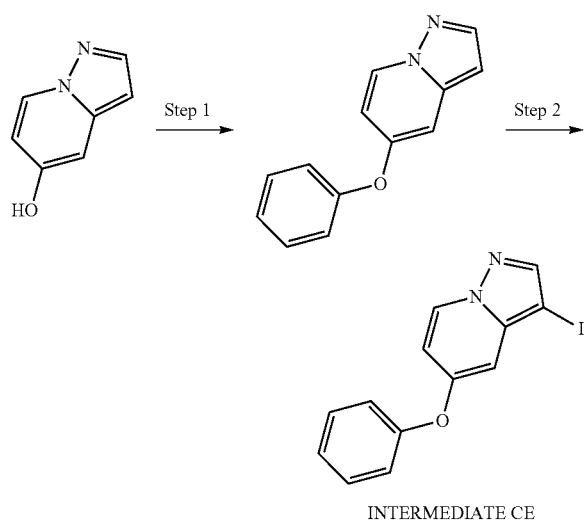

INTERMEDIATE CE

Step 1: A mixture of pyrazolo[1,5-a]pyridin-5-ol (300 mg, 2.24 mmol, 1.00 eq.), phenylboronic acid (545 mg, 4.47 mmol, 2.00 eq.), 4 Å MS (30 mg), copper acetate (812 mg, 4.47 mmol, 2.00 eq.) and triethylamine (1.13 g, 11.2 mmol, 1.56 mL, 5.00 eq.) in dichloromethane (10 mL) was degassed with oxygen and stirred at 25° C. for 10 hours under an oxygen (15 psi) atmosphere. After such time the reaction mixture was filtered, concentrated and the formed residue was purified by column chromatography (SiO$_2$, petroleum ether/ethyl acetate 0-20%) to give 5-phenoxy-pyrazolo[1,5-a]pyridine (200 mg, 0.95 mmol, 43% yield) as a yellow oil. LCMS [M+1]$^+$=211.2.

Step 2: To a solution of 5-phenoxypyrazolo[1,5-a]pyridine (180 mg, 0.86 mmol, 1.00 eq.) in acetonitrile (2 mL) was added NIS (212 mg, 0.94 mmol, 1.10 eq.). The mixture was stirred at 0° C. for 1 hour. The reaction mixture was then concentrated and the residue purified by column chromatography (SiO$_2$, petroleum ether/ethyl acetate 0-5%) to give 3-iodo-5-phenoxy-pyrazolo[1,5-a]pyridine (170 mg, 0.51 mmol, 59% yield) as a yellow oil. LCMS [M+1]$^+$=336.9.

Intermediate CF

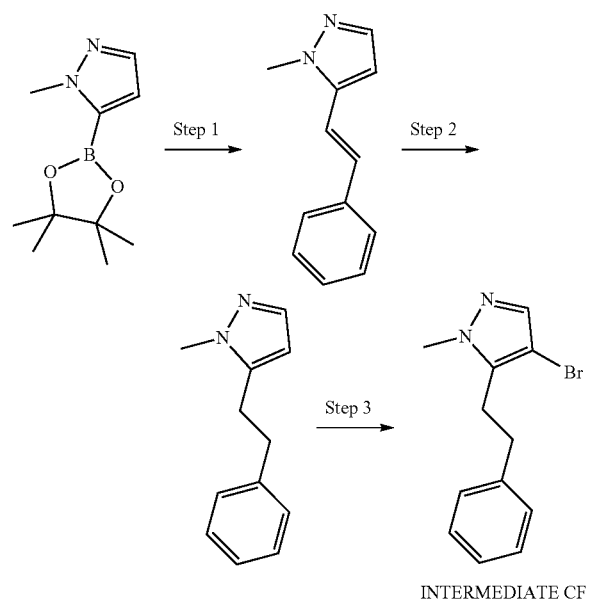

INTERMEDIATE CF

Step 1: A mixture of 1-methyl-5-(4,4,5,5-tetramethyl-1,3,2-dioxaborolan-2-yl)pyrazole (1.50 g, 7.21 mmol, 1.00 eq.), [(E)-2-bromovinyl]benzene (2.90 g, 15.8 mmol, 2.03 mL, 2.20 eq.), Pd(PPh$_3$)$_2$Cl$_2$ (506 mg, 721 umol, 0.10 eq.), potassium carbonate (1.30 g, 9.41 mmol, 1.30 eq.) in ethyl alcohol (3.8 mL) and DMF (7.5 mL) was degassed with nitrogen and then stirred at 75° C. for 2 hours. After such time the mixture was cooled to ambient temperature, diluted with water (100 mL) and extracted with ethyl acetate (80 mL×3). The combined organic layers were washed with brine (150 mL), dried over anhydrous sodium sulfate, filtered and concentrated under reduced pressure. The residue was purified by column chromatography (SiO$_2$, Petroleum ether/ethyl acetate 0-20%) to give 1-methyl-5-[(E)-styryl]pyrazole (990 mg, 5.37 mmol, 74% yield) as a yellow solid. LCMS [M+1]$^+$=185.2; $^1$H NMR (400 MHz, DMSO-$d_6$) δ=7.65 (d, J=7.2 Hz, 2H), 7.42-7.36 (m, 3H), 7.32-7.25 (m, 2H), 7.12 (d, J=16.0 Hz, 1H), 6.63 (d, J=2.0 Hz, 1H), 3.91 (s, 3H).

Step 2: To a solution of 1-methyl-5-[(E)-styryl]pyrazole (400 mg, 2.17 mmol, 1.00 eq.) in ethyl alcohol (3 mL) was added Pd/C (10.0 mg, 10% Pd) under nitrogen. The suspension was degassed under vacuum and purged with hydrogen several times and the mixture was then stirred under hydrogen (15.0 psi) at 25° C. for 12 hours. After such time the reaction mixture was filtered and concentrated under reduced pressure to give 1-methyl-5-(2-phenylethyl)pyrazole (385 mg, 1.93 mmol, 89% yield) as a yellow oil and used into the next step without further purification. LCMS [M+1]$^+$=187.2.

Step 3: To a solution of 1-methyl-5-(2-phenylethyl)pyrazole (385 mg, 1.93 mmol, 1.00 eq.) in acetonitrile (10 mL) was added N-bromosuccinimide (343 mg, 1.93 mmol, 1.00 eq.). The mixture was then stirred at 0° C. for 0.5 hour. After such time the reaction mixture was concentrated under reduced pressure and the residue purified by prep-TLC (SiO$_2$, Petroleum ether/ethyl acetate 20%) to give 4-bromo-1-methyl-5-(2-phenylethyl)pyrazole (430 mg, 1.62 mmol, 84% yield) as a yellow oil. $^1$H NMR (400 MHz, DMSO-$d_6$)

δ=7.43 (s, 1H), 7.31-7.24 (m, 2H), 7.23-7.18 (m, 1H), 7.17-7.11 (m, 2H), 3.58 (s, 3H), 2.97-2.89 (t, J=7.2 Hz, 2H), 2.84-2.77 (t, J=7.2 Hz, 2H).

Intermediate CG

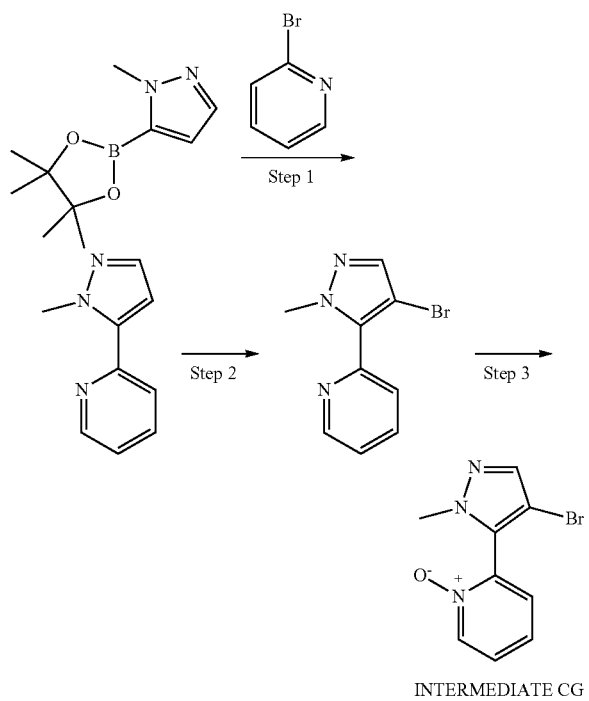

INTERMEDIATE CG

Step 1: A mixture of 1-methyl-5-(4,4,5,5-tetramethyl-1,3,2-dioxaborolan-2-yl)pyrazole (1.00 g, 4.81 mmol, 1.00 eq.), 2-bromopyridine (911 mg, 5.77 mmol, 0.55 mL, 1.20 eq.), cesium carbonate (3.13 g, 9.61 mmol, 2.00 eq.) and Pd(dppf)Cl$_2$ (352 mg, 0.48 mmol, 0.10 eq.) in dioxane (10 mL) and water (2 mL) was degassed and purged with nitrogen and then the mixture was stirred at 100° C. for 1 hour. After such time the cooled reaction mixture was concentrated under reduced pressure and purified by column chromatography (SiO$_2$, petroleum ether/ethyl acetate 0-20%) to give 2-(2-methylpyrazol-3-yl)pyridine (860 mg, crude) as a red oil which used into the next step directly without further purification. $^1$H NMR (400 MHz, DMSO-d$_6$) δ=8.69-8.66 (m, 1H), 7.89 (dt, J=1.6, 7.6 Hz, 1H), 7.78 (td, J=1.2, 8.0 Hz, 1H), 7.48 (d, J=2.0 Hz, 1H), 7.37 (ddd, J=1.2, 4.8, 7.6 Hz, 1H), 6.78 (d, J=1.6 Hz, 1H), 4.14 (s, 3H).

Step 2: To a solution of 2-(2-methylpyrazol-3-yl)pyridine (760 mg, crude) in acetonitrile (10 mL) was added N-bromosuccinimide (850 mg, 4.77 mmol). The mixture was stirred at 0° C. for 0.5 hour. The reaction mixture was then concentrated under reduced pressure and the residue purified by prep-TLC (SiO$_2$, petroleum ether/ethyl acetate 20%) to give 2-(4-bromo-2-methyl-pyrazol-3-yl)pyridine (507 mg, 2.13 mmol, 44% yield) as an off-white solid. $^1$H NMR (400 MHz, DMSO-d$_6$) δ=8.77 (td, J=0.8, 4.0 Hz, 1H), 8.01 (dt, J=2.0, 7.6 Hz, 1H), 7.76-

Step 3: To a solution of 2-(4-bromo-2-methyl-pyrazol-3-yl)pyridine (150 mg, 0.63 mmol, 1.00 eq.) in dichloroethane (3 mL) was added meta-chloroperbenzoic acid (435 mg, 2.14 mmol, 85% purity, 3.40 eq.). The mixture was stirred at 60° C. for 5 hours. The reaction mixture was then quenched by addition saturated sodium sulfite solution (20 mL) and extracted with dichloromethane (20 mL×3). The combined organic layers were washed with brine (30 mL), dried over anhydrous sodium sulfate, filtered and concentrated and the residue purified by prep-TLC (SiO$_2$, petroleum ether/ethyl acetate 50%) to give 2-(4-bromo-1-methyl-1H-pyrazol-5-yl)pyridine 1-oxide (185 mg, crude) as a yellow solid, which was used into the next step directly without further purification. LCMS [M+1]$^+$=254.1; $^1$H NMR (400 MHz, DMSO-d$_6$) δ=8.46 (d, J=6.4 Hz, 1H), 7.70 (s, 1H), 7.5 (dt, J=1.2, 7.6 Hz, 2H), 7.52-7.47 (m, 1H), 3.74 (s, 3H).

Intermediate CH

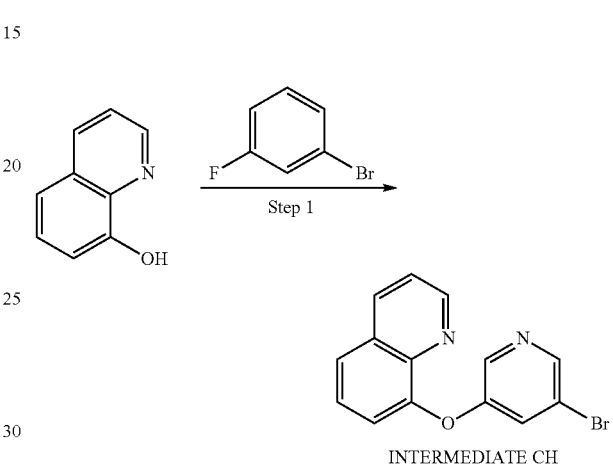

INTERMEDIATE CH

Step 1: A mixture of quinolin-8-ol (454 mg, 3.13 mmol, 0.54 mL, 1.10 eq.), 3-bromo-5-fluoro-pyridine (500 mg, 2.84 mmol, 1.00 eq.), potassium carbonate (785 mg, 5.68 mmol, 2.00 eq.) in DMF (6 mL) was degassed with nitrogen then stirred at 110° C. for 3 hours. After such time the mixture was extracted with ethyl acetate (5 mL×3) and the combined extracts were washed with brine (2 mL), dried over anhydrous sodium sulfate, filtered and concentrated to give 8-[(5-bromo-3-pyridyl)oxy]quinoline (0.30 g, 0.75 mmol, 26% yield) as a yellow oil. LCMS [M+1]$^+$=301.0; $^1$H NMR (400 MHz, CDCl$_3$) δ=8.95 (dd, J=2.0, 4.0 Hz, 1H), 8.43 (d, J=2.0 Hz, 1H), 8.39 (d, J=2.4 Hz, 1H), 8.25 (dd, J=2.0, 8.4 Hz, 1H), 7.73 (dd, J=1.6, 8.4 Hz, 1H), 7.55 (t, J=8.0 Hz, 1H), 7.50 (dd, J=4.0, 8.4 Hz, 1H), 7.47-7.43 (m, 2H).

Intermediate CI

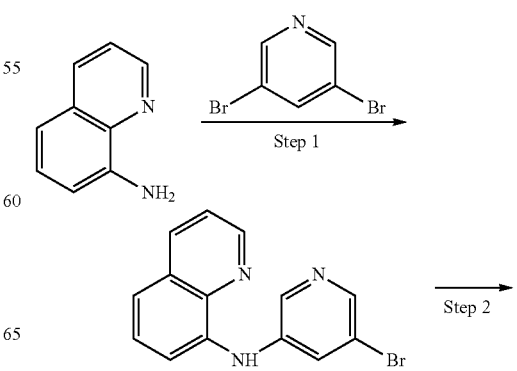

-continued

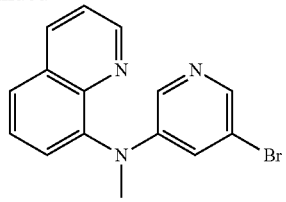

INTERMEDIATE CI

Step 1: A mixture of 3,5-dibromopyridine (1.48 g, 6.25 mmol, 1.00 eq.), quinolin-8-amine (901 mg, 6.25 mmol, 1.00 eq.), sodium tert-butoxide (901 mg, 9.37 mmol, 1.50 eq.), Pd$_2$(dba)$_3$ (57.2 mg, 62.5 µmol, 0.01 eq.) and Xantphos (72.3 mg, 125 µmol, 0.02 eq.) in dioxane (10 mL) was degassed with nitrogen then stirred at 100° C. for 2 hours. After such time the mixture was diluted with water (20 mL) and extracted with ethyl acetate (20 mL×3). The combined organic phases were washed with brine (20 mL), dried over anhydrous sodium sulfate, filtered, concentrated and the residue purified by reversed-phase HPLC (0.1% formic acid (FA) condition) to give N-(5-bromo-3-pyridyl) quinolin-8-amine (160 mg, 486 µmol, 7% yield) as a yellow solid. LCMS [M+1]$^+$=300.0; $^1$H NMR (400 MHz, CDCl$_3$) δ=8.82 (dd, J=1.6, 4.0 Hz, 1H), 8.61 (d, J=2.4 Hz, 1H), 8.40 (br s, 1H), 8.31 (d, J=1.6 Hz, 1H), 8.17 (dd, J=1.6, 8.4 Hz, 1H), 7.92 (t, J=2.0 Hz, 1H), 7.51-7.46 (m, 3H), 7.37 (dd, J=1.6, 8.0 Hz, 1H).

Step 2: N-(5-bromo-3-pyridyl)quinolin-8-amine (130 mg, 394 µmol, 1.00 eq.) was dissolved in DMF (2 mL), then sodium hydride (32 mg, 790 µmol, 60.0% purity, 2.00 eq.) was added at 0° C. and the mixture was stirred at 0° C. for 10 minutes. After such time methyl iodide (224 mg, 1.58 mmol, 98 µL, 4.00 eq.) was added and the resulting mixture was stirred at 20° C. for 1 hour. The reaction mixture was then quenched with water (10 mL), extracted with ethyl acetate (20 mL×3) and the combined organic phases were washed with brine (20 mL), dried over anhydrous sodium sulfate, filtered and concentrated to give N-(5-bromo-3-pyridyl)-N-methyl-quinolin-8-amine (150 mg, 334 µmol, 85% yield) as a yellow oil. LCMS [M+1]$^+$=314.1; $^1$H NMR (400 MHz, CDCl$_3$) δ=8.90 (dd, J=1.6, 4.4 Hz, 1H), 8.24 (dd, J=1.6, 8.4 Hz, 1H), 8.01 (d, J=2.0 Hz, 1H), 7.92 (d, J=2.8 Hz, 1H), 7.82 (dd, J=1.6, 8.0 Hz, 1H), 7.65-7.62 (m, 1H), 7.61-7.57 (m, 1H), 7.46 (dd, J=4.4, 8.4 Hz, 1H), 7.10 (t, J=2.4 Hz, 1H), 3.49 (s, 3H).

Intermediate CJ

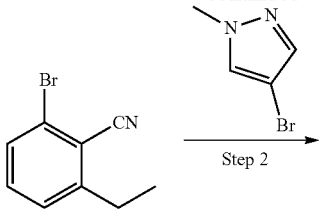

-continued

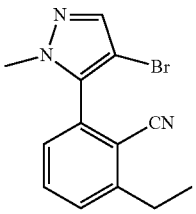

Intermediate CJ

Step 1: A mixture of 2-ethylbenzonitrile (500 mg, 3.81 mmol, 0.51 mL, 1.00 eq.), p-toluenesulfonic acid (363 mg, 1.91 mmol, 0.50 eq.), N-Bromosuccinimide (746 mg, 4.19 mmol, 1.10 eq.) and palladium acetate (85.6 mg, 0.38 mol, 0.10 eq.) in 1,2-dichloroethane (10 mL) was degassed with nitrogen then stirred at 70° C. for 12 hours. After such time the reaction mixture was concentrated under reduced pressure and the residue was purified by column chromatography (SiO$_2$, petroleum ether/ethyl acetate 0-5%) to give 2-bromo-6-ethyl-benzonitrile (446 mg, 1.15 mmol, 30% yield) as a yellow oil. $^1$H NMR (400 MHz, DMSO-d$_6$) δ=7.76 (dd, J=0.8, 7.6 Hz, 1H), 7.70 (d, J=8.0 Hz, 1H), 7.60-7.54 (m, 1H), 2.81 (m, 2H), 1.22 (m, 3H).

Step 2: A mixture of 2-bromo-6-ethyl-benzonitrile (446 mg, 1.15 mmol, 1.00 eq.), 4-bromo-1-methyl-pyrazole (203 mg, 1.26 mmol, 1.10 eq.), palladium acetate (2.57 mg, 0.12 mmol, 0.01 eq.), DavePhos (9.0 mg, 0.23 mmol, 0.02 eq.), 2-methylpropanoic acid (30.3 mg, 0.34 mmol, 31.9 uL, 0.30 eq.) and tetrabutylammonium acetate (691 mg, 2.29 mmol, 0.70 mL, 2.00 eq.) in N-methyl pyrrolidone (10 mL) was degassed with nitrogen then stirred at 100° C. for 12 hours. After such time the reaction mixture was diluted with water (100 mL), extracted with ethyl acetate (60 mL×3) and the combined organic layers were washed with brine (80 mL), dried over anhydrous sodium sulfate, filtered and concentrated under reduced pressure. The residue was purified by column chromatography (SiO$_2$, petroleum ether/ethyl acetate 10-20%) to give 2-(4-bromo-2-methyl-pyrazol-3-yl)-6-ethyl-benzonitrile (310 mg, 0.44 mmol, 39% yield) as a yellow solid. LCMS [M+1]$^+$=290.1; $^1$H NMR (400 Hz, DMSO-d6) δ=7.83-7.78 (m, 1H), 7.73 (s, 1H), 7.68 (d, J=7.6 Hz, 1H), 7.50-7.47 (m, 1H), 3.71 (s, 3H), 2.90 (q, J=7.6 Hz, 2H), 1.28 (t, J=7.6 Hz, 3H).

The INTERMEDIATES D-1 to D-20 shown in Table I-V were prepared following the teachings of the General Reaction Schemes and the method to prepare INTERMEDIATE CJ.

TABLE I-V

| Intermediate | Structure | Spectral Data |
|---|---|---|
| D-1 | ![structure] | 2-(4-bromo-1-methyl-1H-pyrazol-5-yl)-5-ethylbenzonitrile<br>LCMS [M + 1]$^+$ = 289.9; $^1$H NMR (400 MHz, CDCl$_3$) δ = 7.67 (d, J = 1.2 Hz, 1H), 7.60-7.55 (m, 2H), 7.38 (d, J = 8.0 Hz, 1H), 5.30 (s, 1H), 3.80 (s, 3H), 2.79 (q, J = 7.6 Hz, 2H), 1.33 (t, J = 7.6 Hz, 3H) |

TABLE I-V-continued

| Intermediate | Structure | Spectral Data |
| --- | --- | --- |
| D-2I | 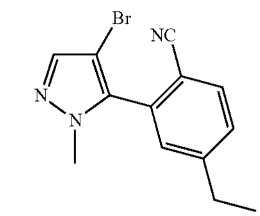 [SMILES: CCc1ccc(C#N)c(-c2c(Br)cnn2C)c1] | 2-(4-bromo-1-methyl-1H-pyrazol-5-yl)-5-ethylbenzonitrile<br>LCMS [M + 1] $^+$ = 290.0; $^1$H NMR (400 MHz, CDCl$_3$) δ = 7.67 (d, J = 8.0 Hz, 1H), 7.49 (s, 1H), 7.36 (dd, J = 2.0, 8.0 Hz, 1H), 7.22 (d, J = 1.2 Hz, 1H), 3.72 (s, 3H), 2.72 (q, J = 7.6 Hz, 2H), 1.23 (t, J = 7.6 Hz, 3H) |
| D-3 | 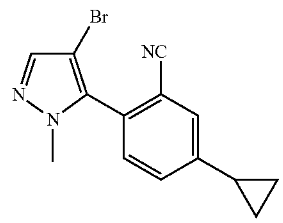 [SMILES: Cn1ncc(Br)c1-c1ccc(C2CC2)cc1C#N] | 2-(4-bromo-1-methyl-1H-pyrazol-5-yl)-5-cyclopropylbenzonitrile<br>LCMS [M + 1] $^+$ = 304.1; $^1$H NMR (400 MHz, CDCl$_3$) δ = 7.58 (s, 1H), 7.51 (d, J = 2.0 Hz, 7.43-7.39 (m, 1H), 7.36-7.31 (m, 1H), 3.79 (s, 3H), 2.01 (tt, J = 5.2, 8.4 Hz, 1H), 1.18-1.11 (m, 2H), 0.86-0.78 (m, 2H) |
| D-4 | 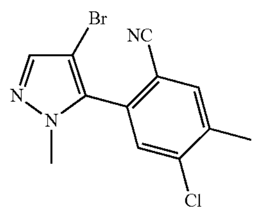 [SMILES: Cc1cc(C#N)c(-c2c(Br)cnn2C)cc1Cl] | 2-(4-bromo-1-methyl-1H-pyrazol-5-yl)-5-methylbenzonitrile<br>LCMS [M + 1] $^+$ = 312.0; $^1$H NMR (400 MHz, CDCl$_3$) δ = 7.71 (s, 1H), 7.59 (s, 1H), 7.47 (s, 1H), 3.81 (s, 3H), 2.51 (s, 3H) |
| D-5 | 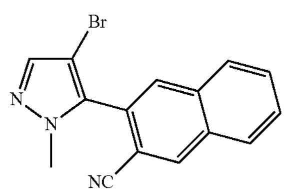 [SMILES: Cn1ncc(Br)c1-c1cc2ccccc2cc1C#N] | 3-(4-bromo-1-methyl-1H-pyrazol-5-yl)-2-naphthonitrile<br>LCMS [M + 1] $^+$ = 312.1; $^1$H NMR (400 MHz, CDCl$_3$) δ = 8.43 (s, 1H), 8.04-7.96 (m, 2H), 7.95 (s, 1H), 7.79-7.70 (m, 2H), 7.64 (s, 1H), 3.85 (s, 3H) |
| D-6 | 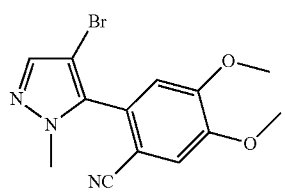 [SMILES: COc1cc(C#N)c(-c2c(Br)cnn2C)cc1OC] | 2-(4-bromo-1-methyl-1H-pyrazol-5-yl)-4,5-dimethoxybenzonitrile<br>LCMS [M + 1] $^+$ = 324.0; $^1$H NMR (400 MHz, CDCl$_3$) δ = 7.59 (s, 1H), 7.23 (s, 1H), 6.87 (s, 1H), 3.99 (s, 3H), 3.97 (s, 3H), 3.83 (s, 3H) |
| D-7 | 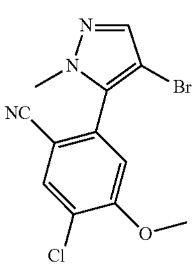 [SMILES: COc1cc(-c2c(Br)cnn2C)c(C#N)cc1Cl] | 2-(4-bromo-1-methyl-1H-pyrazol-5-yl)-5-chloro-4-methoxybenzonitrile<br>LCMS [M + 1] $^+$ = 327.9; $^1$H NMR (400 MHz, CDCl$_3$) δ = 7.83 (s, 1H), 7.61 (s, 1H), 6.96 (s, 1H), 4.01 (s, 3H), 3.84 (s, 3H) |
| D-8 | 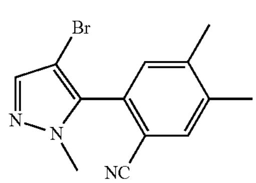 [SMILES: Cc1cc(C#N)c(-c2c(Br)cnn2C)cc1C] | 2-(4-bromo-1-methyl-1H-pyrazol-5-yl)-4,5-dimethylbenzonitrile<br>LCMS [M + 1] $^+$ = 292.0; $^1$H NMR (400 MHz, CDCl$_3$) δ = 7.60 (s, 1H), 7.58 (s, 1H), 7.22 (s, 1H), 3.79 (s, 3H), 2.40 (s, 3H), 2.39 (s, 3H) |

TABLE I-V-continued

| Intermediate | Structure | Spectral Data |
| --- | --- | --- |
| D-9 | 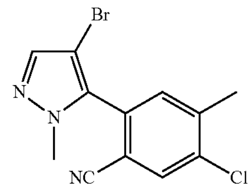 [SMILES: Cc1cc(-c2c(Br)cnn2C)c(C#N)cc1Cl] | 2-(4-bromo-1-methyl-1H-pyrazol-5-yl)-5-chloro-4-methylbenzonitrile<br>LCMS [M + 1]$^+$ = 312.0; $^1$H NMR (400 MHz, CDCl$_3$) δ = 7.82 (s, 1H), 7.59 (s, 1H), 7.34 (s, 1H), 3.81 (s, 3H), 2.53 (s, 3H) |
| D-10 | 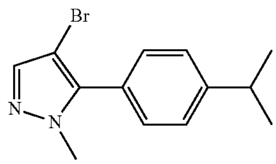 [SMILES: CC(C)c1ccc(-c2c(Br)cnn2C)cc1] | 4-bromo-5-(4-isopropylphenyl)-1-methyl-1H-pyrazole<br>LCMS [M + 1]$^+$ = 281.1; $^1$H NMR (400 MHz, CDCl$_3$) δ = 7.54 (s, 1H), 7.39-7.32 (m, 4H), 3.83 (s, 3H), 1.31 (d, J = 6.8 Hz, 6H) |
| D-11 | 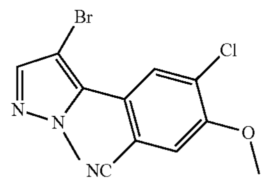 [SMILES: COc1cc(C#N)c(-c2c(Br)cnn2C)cc1Cl] | 2-(4-bromo-1-methyl-1H-pyrazol-5-yl)-4-chloro-5-methoxybenzonitrile<br>LCMS [M + 1]$^+$ = 328.0; $^1$H NMR (400 MHz, MeOD) δ = 7.67 (s, 1H), 7.64 (s, 1H), 7.62 (s, 1H), 4.03 (s, 3H), 3.77 (s, 3H) |
| D-12 | 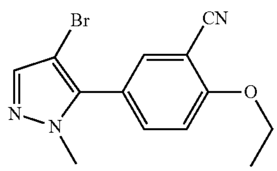 [SMILES: CCOc1ccc(-c2c(Br)cnn2C)cc1C#N] | 2-(4-bromo-1-methyl-1H-pyrazol-5-yl)-5-ethoxyterephthalonitrile<br>LCMS [M + 1]$^+$ = 306.1; $^1$H NMR (400 MHz, CDCl$_3$) δ = 7.53 (d, J = 2.0 Hz, 1H), 7.49 (dd, J = 2.4, 8.8 Hz, 1H), 7.44 (s, 1H), 7.03 (d, J = 8.8 Hz, 1H), 4.16 (q, J = 7.2 Hz, 2H), 3.73 (s, 3H), 1.45 (t, J = 7.2 Hz, 3H) |
| D-13 | 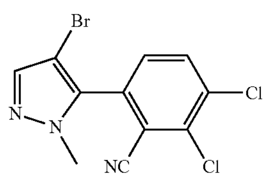 | 6-(4-bromo-1-methyl-1H-pyrazol-5-yl)-2,3-dichlorobenzonitrile<br>LCMS [M + 1]$^+$ = 392.3; $^1$H NMR (400 MHz, CDCl$_3$) δ = 7.83 (d, J = 8.4 Hz, 1H), 7.61 (s, 1H), 7.34 (d, J = 8.4 Hz, 1H), 3.82 (s, 3H) |
| D-14 | 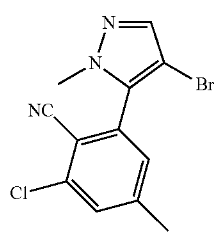 [SMILES: Cc1cc(Cl)c(C#N)c(-c2c(Br)cnn2C)c1] | 2-(4-bromo-1-methyl-1H-pyrazol-5-yl)-6-chloro-4-methylbenzonitrile<br>LCMS [M + 1]$^+$ = 311.9; $^1$H NMR (400 MHz, CDCl$_3$) δ = 7.83 (s, 1H), 7.61 (s, 1H), 6.96 (s, 1H), 4.01 (s, 3H), 3.84 (s, 3H) |
| D-15 | 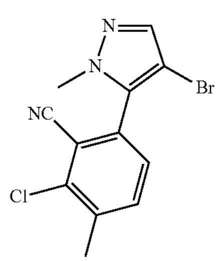 [SMILES: Cc1ccc(-c2c(Br)cnn2C)c(C#N)c1Cl] | 2-(4-bromo-1-methyl-1H-pyrazol-5-yl)-6-chloro-5-methylbenzonitrile<br>LCMS [M + 1]$^+$ = 312; $^1$H NMR (400 MHz, CDCl$_3$) δ = 7.62 (d, J = 8.0 Hz, 1H), 7.59 (d, J = 2.0 Hz, 1H), 7.31-7.26 (m, 1H), 3.81 (d, J = 1.2 Hz, 3H), 2.54 (s, 3H) |

TABLE I-V-continued

| Intermediate | Structure | Spectral Data |
|---|---|---|
| D-16 | 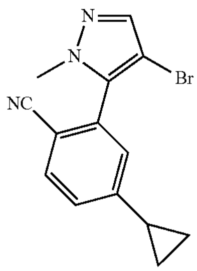 [SMILES: Cn1ncc(Br)c1-c1cc(C2CC2)ccc1C#N] | 2-(4-bromo-1-methyl-1H-pyrazol-5-yl)-4-cyclopropylbenzonitrile LCMS [M + 1]⁺ = 304.1; ¹H NMR (400 MHz, CDCl₃) δ = 7.71 (d, J = 8.4 Hz, 1H), 7.59 (s, 1H), 7.26-7.23 (dd, J = 1.6, 8.4, 1H), 7.11 (d, J = 1.6 Hz, 1H), 3.81 (s, 3H), 2.03-1.99 (m, 1H), 1.20-1.17 (m, 2H), 0.87-0.82 (m, 2H) |
| D-17 | 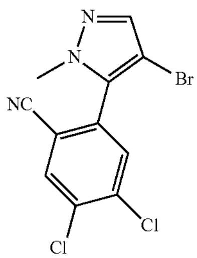 [SMILES: Cn1ncc(Br)c1-c1cc(Cl)c(Cl)cc1C#N] | 2-(4-bromo-1-methyl-1H-pyrazol-5-yl)-4,5-dichlorobenzonitrile LCMS [M + 1]⁺ = 329.9; ¹H NMR (400 MHz, CDCl₃) δ = 7.93 (s, 1H), 7.60 (m, 2H), 3.83 (s, 3H) |
| D-18 | 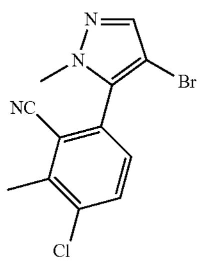 [SMILES: Cc1c(Cl)ccc(-c2c(Br)cnn2C)c1C#N] | 6-(4-bromo-1-methyl-1H-pyrazol-5-yl)-3-chloro-2-methylbenzonitrile LCMS [M + 1]⁺ = 312.0; ¹H NMR (400 MHz, CDCl₃) δ = 7.71 (d, J = 8.4 Hz, 1H), 7.59 (s, 1H), 7.24 (d, J = 8.4 Hz, 1H), 3.79 (s, 3H), 2.71 (s, 3H) |
| D-19 | 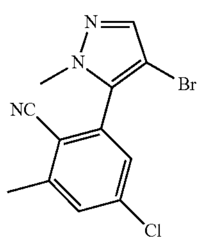 [SMILES: Cc1cc(Cl)cc(-c2c(Br)cnn2C)c1C#N] | 2-(4-bromo-1-methyl-1H-pyrazol-5-yl)-4-chloro-6-methylbenzonitrile LCMS [M + 1]⁺ = 312.0; ¹H NMR (400 MHz, CDCl₃) δ = 7.59 (s, 1H), 7.48 (d, J = 1.2 Hz, 1H), 7.29 (d, J = 1.6 Hz, 1H), 3.81 (s, 3H) |
| D-20 | 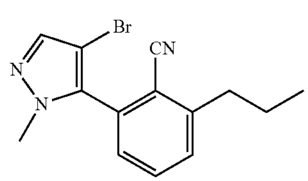 [SMILES: CCCc1cccc(-c2c(Br)cnn2C)c1C#N] | 2-(4-bromo-1-methyl-1H-pyrazol-5-yl)-6-propylbenzonitrile LCMS [M + 1]⁺ = 305.9; ¹H NMR (400 MHz, DMSO-d₆) δ = 7.84-7.77 (m, 1H), 7.74 (s, 1H), 7.66 (d, J = 7.6 Hz, 1H), 7.49 (d, J = 7.6 Hz, 1H), 3.71 (s, 3H), 2.89-2.83 (m, 2H), 1.75-1.64 (m, 2H), 0.98-0.92 (m, 3H) |

Intermediate DA

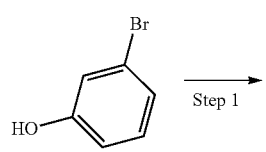

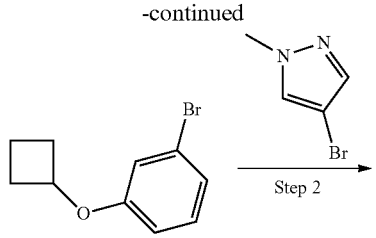

Intermediate DB

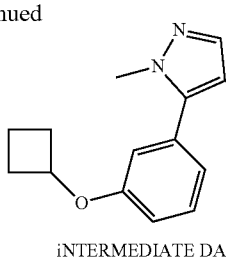

INTERMEDIATE DA

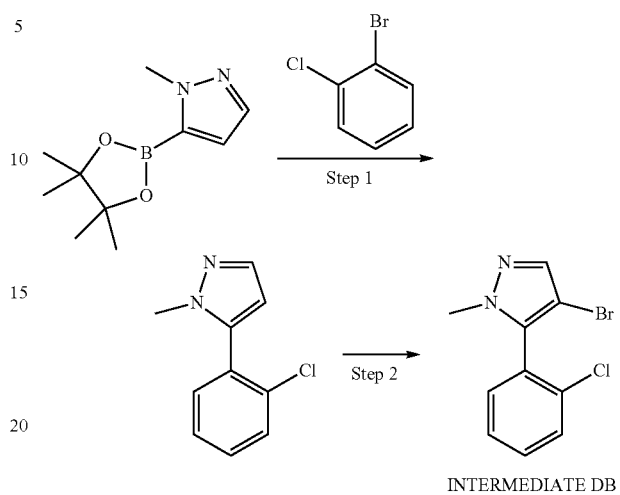

INTERMEDIATE DB

Step 1: A mixture of 3-bromophenol (1.00 g, 5.78 mmol, 1.00 eq.), bromocyclobutane (1.17 g, 8.65 mmol, 0.82 mL, 1.50 eq.) and potassium carbonate (3.20 g, 23.1 mmol, 4.00 eq.) in DMF (10 mL) and stirred at 120° C. for 6 hours. The reaction mixture was diluted with water (80 mL) and extracted with (petroleum ether/ethyl acetate 20%) (50 mL×3) and the combined extracts were washed with aqueous sodium hydroxide (1.00 M, 50 mL), brine (50 mL) and dried over sodium sulfate and concentrated to give 1-bromo-3-(cyclobutoxy)benzene (1.20 g, 5.27 mmol, 91% yield) as a colorless oil. $^1$H NMR (400 MHz, CDCl$_3$) δ=7.04-6.93 (m, 2H), 6.86 (t, J=2.4 Hz, 1H), 6.64 (ddd, J=1.2, 2.4, 8.0 Hz, 1H), 4.60-4.44 (m, 1H), 2.34 (tddd, J=2.8, 6.8, 8.0, 9.6 Hz, 2H), 2.14-1.98 (m, 2H), 1.83-1.71 (m, 1H), 1.66-1.50 (m, 1H).

Step 2: 1-bromo-3-(cyclobutoxy)benzene (300 mg, 1.32 mmol, 1.00 eq.), 4-bromo-1-methyl-pyrazole (213 mg, 1.32 mmol, 1.00 eq.), palladium acetate (2.97 mg, 13.2 µmol, 0.01 eq.), tetrabutylammonium acetate (224 mg, 2.91 mmol, 2.20 eq.), 2-methylpropanoic acid (34.9 mg, 396 µmol, 36.8 µL, 0.30 eq.) and DavePhos (10.4 mg, 26.4 µmol, 0.02 eq.) in NMP (5 mL) was degassed with nitrogen and heated to 100° C. for 12 hours. The reaction mixture was then diluted with water (20 mL), extracted with ethyl acetate (30 mL×3) and the combined organic phases were washed with brine (30 mL), dried over anhydrous sodium sulfate, filtered and concentrated under reduced pressure. The residue was purified by column chromatography (SiO$_2$, petroleum ether/ethyl acetate 1-5%) to give 4-bromo-5-[3-(cyclobutoxy)phenyl]-1-methyl-pyrazole (40.0 mg) as a yellow oil. $^1$H NMR (400 MHz, CDCl$_3$) δ=7.54 (s, 1H), 7.45 (s, 1H), 6.98-6.90 (m, 2H), 6.86-6.83 (m, 1H), 4.68 (t, J=7.2 Hz, 1H), 3.83 (s, 3H), 2.54-2.40 (m, 2H), 2.27-2.14 (m, 2H), 1.95-1.66 (m, 2H).

The INTERMEDIATES E-1 and E-2 shown in Table I-VI were prepared following the teachings of the General Reaction Schemes and the method to prepare Intermediate DA.

Step 1: A mixture of 1-methyl-5-(4,4,5,5-tetramethyl-1,3,2-dioxaborolan-2-yl)pyrazole (1.50 g, 7.21 mmol, 1.00 eq.), 1-bromo-2-chloro-benzene (1.38 g, 7.21 mmol, 0.84 mL, 1.00 eq.), sodium carbonate (2.29 g, 21.6 mmol, 3.00 eq.), Pd(dppf)Cl$_2$ (528 mg, 0.72 mmol, 0.10 eq.) in water (2.4 mL) and dioxane (12 mL) was degassed with nitrogen then stirred at 80° C. for 2 hours. After such time the mixture was concentrated under reduced pressure and purified by column chromatography (SiO$_2$, Petroleum ether/ethyl acetate 10-20%) to give 5-(2-chlorophenyl)-1-methyl-pyrazole (0.56 g, 2.88 mmol, 40% yield) as a yellow solid. LCMS [M+1]$^+$=193.1; $^1$H NMR (400 MHz, CDCl$_3$) δ=7.56 (d, J=2.0 Hz, 1H), 7.52 (dd, J=1.2, 7.6 Hz, 1H), 7.43-7.33 (m, 3H), 6.30 (d, J=2.0 Hz, 1H), 3.74 (s, 3H).

Step 2: A mixture of 5-(2-chlorophenyl)-1-methyl-pyrazole (200 mg, 1.04 mmol, 1.00 eq.), N-bromo-succinimide (203 mg, 1.14 mmol, 1.10 eq.) in acetonitrile (2 mL) was degassed with nitrogen then stirred at 0° C. for 2 hours. After such time the mixture was concentrated under reduced pressure and the residue was purified by prep-TLC (Petroleum ether/ethyl acetate 20%) to give 4-bromo-5-(2-chloro

TABLE I-VI

| Intermediate | Structure | Spectral Data |
| --- | --- | --- |
| E-1 | 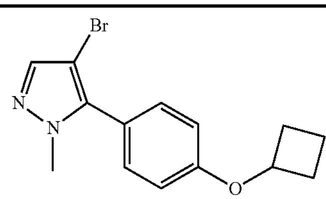 | 4-bromo-5-(4-cyclobutoxyphenyl)-1-methyl-1H-pyrazole LCMS [M + 1]$^+$ = 307.1; $^1$H NMR (400 MHz, CDCl$_3$) δ = 7.52 (s, 1H), 7.30 (d, J = 8.8 Hz, 2H), 6.93 (d, J = 8.8 Hz, 2H), 4.70 (quin, J = 7.2 Hz, 1H), 3.81 (s, 3H), 2.54-2.47 (m, 2H), 2.28-2.19 (m, 2H), 1.94-1.87 (m, 1H), 1.78-1.7(m, 1H) |
| E-2 | | 2-(4-bromo-1-methyl-1H-pyrazol-5-yl)-5-ethoxybenzonitrile LCMS [M + 1]$^+$ = 307.9; $^1$H NMR (400 MHz, CDCl$_3$) δ = 7.58 (s, 1H), 7.36 (d, J = 8.8 Hz, 1H), 7.30 (d, J = 2.8 Hz, 1H), 7.26-7.21 (dd, J = 2.8, 8.8 Hz, 1H), 4.16-4.10 (q, J = 7.2 Hz, 2H), 3.79 (s, 3H), 1.49 (t, J = 7.2 Hz, 3H) | phenyl)-1-methyl-pyrazole (220 mg, 0.77 mmol, 74% yield) as a yellow solid. LCMS [M+1]⁺=273.1; ¹H NMR (400 MHz, CDCl₃) δ=7.59-7.55 (m, 2H), 7.50-7.40 (m, 2H), 7.36-7.33 (m, 1H), 3.74 (s, 3H).

The INTERMEDIATES F-1 to F-22 shown in Table I-VII were prepared following the teachings of the General Reaction Schemes and the method to prepare INTERMEDIATE DB.

TABLE I-VII

| Intermediate | Structure | Spectral Data |
| --- | --- | --- |
| F-1 | 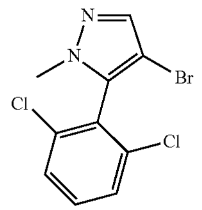 | 4-bromo-5-(2,6-dichlorophenyl)-1-methyl-1H-pyrazole<br>LCMS [M + 1] ⁺ = 306.9; ¹H NMR (400 MHz, CDCl₃) δ = 7.59 (s, 1H), 7.53-7.51 (m, 1H), 7.50-7.47 (m, 1H), 7.46-7.35 (m, 1H), 3.70 (s, 3H) |
| F-2 | 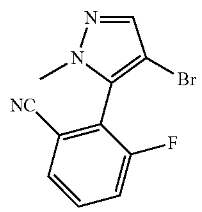 [SMILES: Cn1ncc(Br)c1-c1c(F)cccc1C#N] | 2-(4-bromo-1-methyl-1H-pyrazol-5-yl)-3-fluorobenzonitrile<br>LCMS [M + 1] ⁺ = 282.0; ¹H NMR (400 MHz, CDCl₃) δ = 7.72-7.64 (m, 2H), 7.63 (s, 1H), 7.55-7.49 (m, 1H), 3.80 (s, 3H) |
| F-3 | 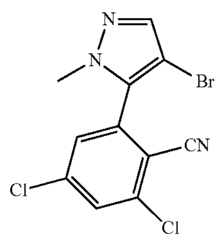 [SMILES: Cn1ncc(Br)c1-c1cc(Cl)cc(Cl)c1C#N] | 2-(4-bromo-1-methyl-1H-pyrazol-5-yl)-4,6-dichlorobenzonitrile<br>LCMS [M + 1] ⁺ = 331.9; ¹H NMR (400 MHz, CDCl₃) δ = 7.70 (d, J = 2.0 Hz, 1H), 7.61 (s, 1H), 7.39 (d, J = 2.0 Hz, 1H), 3.84 (s, 3H) |
| F-4 | 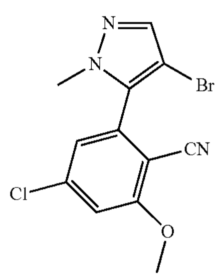 [SMILES: COc1cc(Cl)cc(-c2c(Br)cnn2C)c1C#N] | 2-(4-bromo-1-methyl-1H-pyrazol-5-yl)-4-chloro-6-methoxybenzonitrile<br>LCMS [M + 1⁺] = 327.9; ¹H NMR (400 MHz, CDCl₃) δ = 7.57 (s, 1H), 7.11 (d, J = 2.0 Hz, 1H), 7.03 (d, J = 2.0 Hz, 1H), 4.02 (s, 3H), 3.82 (s, 3H) |
| F-5 | 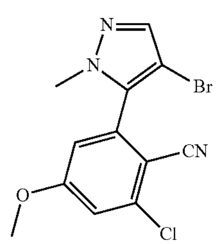 [SMILES: COc1cc(Cl)c(C#N)c(-c2c(Br)cnn2C)c1] | 2-(4-bromo-1-methyl-1H-pyrazol-5-yl)-4-methoxy-6-chlorobenzonitrile<br>LCMS [M + 1] ⁺ = 328.0; ¹H NMR (400 MHz, DMSO-d₆) δ = 7.75 (s, 1H), 7.56 (d, J = 2.4 Hz, 1H), 7.28 (d, J = 2.4 Hz, 1H), 3.93 (s, 3H), 3.75 (s, 3H) |
| F-6 | 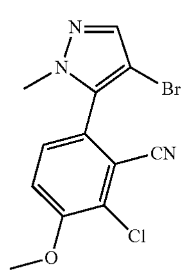 [SMILES: COc1ccc(-c2c(Br)cnn2C)c(C#N)c1Cl] | 2-(4-bromo-1-methyl-1H-pyrazol-5-yl)-5-methoxy-6-chlorobenzonitrile<br>LCMS [M + 1] ⁺ = 328.1; ¹H NMR (400 MHz, CDCl₃) δ = 7.58 (s, 1H), 7.34 (d, J = 8.4 Hz, 1H), 7.27 (d, J = 8.8 Hz, 1H), 4.03 (s, 3H), 3.80 (s, 3H) |

TABLE I-VII-continued

| Intermediate | Structure | Spectral Data |
|---|---|---|
| F-7 | 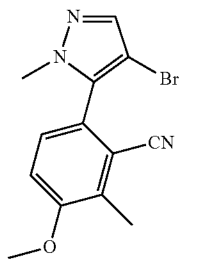 [SMILES: COc1ccc(-c2c(Br)cnn2C)c(C#N)c1C] | 2-(4-bromo-1-methyl-1H-pyrazol-5-yl)-5-methoxy-6-methylbenzonitrile<br>LCMS [M + 1]$^+$ = 308.0; $^1$H NMR (400 MHz, CDCl$_3$) δ = 7.58 (s, 1H), 7.34 (d, J = 8.8 Hz, 1H), 7.27 (d, J = 8.8 Hz, 1H), 4.03 (s, 3H), 3.80 (s, 3H), 2.50 (s, 3H) |
| F-8 | 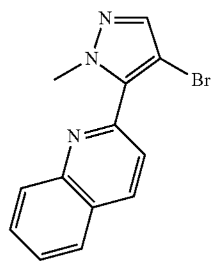 [SMILES: Cn1ncc(Br)c1-c1ccc2ccccc2n1] | 2-(4-bromo-1-methyl-1H-pyrazol-5-yl)quinoline<br>LCMS [M + 1]$^+$ = 290.0; $^1$H NMR (400 MHz, CDCl$_3$) δ = 8.21 (d, J = 8.8 Hz, 1H), 8.07 (d, J = 8.4 Hz, 1H), 7.81 (d, J = 8.8 Hz, 2H), 7.70 (dt, J = 1.2, 7.6 Hz, 1H), 7.58-7.51 (m, 1H), 7.50 (s, 1H), 4.08 (s, 3H) |
| F-9 | 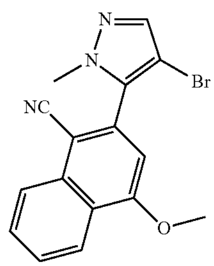 [SMILES: COc1cc(-c2c(Br)cnn2C)c(C#N)c2ccccc12] | 2-(4-bromo-1-methyl-1H-pyrazol-5-yl)-4-methoxy-1-naphthonitrile<br>LCMS [M + 1]$^+$ = 344.0; $^1$H NMR (400 MHz, CDCl$_3$) δ = 8.40 (d, J = 8.0 Hz, 1H), 8.29 (d, J = 8.0 Hz, 1H), 7.79 (ddd, J = 1.2, 7.2, 8.4 Hz, 1H), 7.70 (ddd, J = 1.2, 7.2, 8.4 Hz, 1H), 7.64 (s, 1H), 6.80 (s, 1H), 4.12 (s, 3H), 3.88 (s, 3H) |
| F-10 | 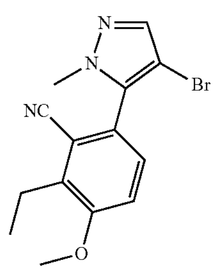 [SMILES: CCc1c(OC)ccc(-c2c(Br)cnn2C)c1C#N] | 6-(4-bromo-1-methyl-1H-pyrazol-5-yl)-2-ethyl-3-methoxybenzonitrile<br>LCMS [M + 1]$^+$ = 322.1; $^1$H NMR (400 MHz, CDCl$_3$) δ = 7.56 (s, 1H), 7.26-7.22 (m, 1H), 7.18-7.11 (m, 1H), 3.94 (s, 3H), 3.77 (s, 3H), 2.96 (q, J = 7.6 Hz, 2H), 1.28-1.24 (m, 3H) |
| F-11 | 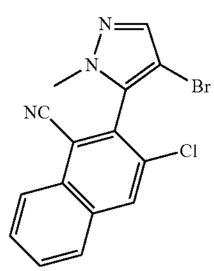 [SMILES: Cn1ncc(Br)c1-c1c(Cl)cc2ccccc2c1C#N] | 2-(4-bromo-1-methyl-1H-pyrazol-5-yl)-3-chloro-1-naphthonitrile<br>LCMS [M + 1]$^+$ = 346.0, 348.0; 1H NMR (400 MHz, DMSO-d6) δ = 8.78 (s, 1H), 8.23 (t, J = 9.2, 2H), 7.95-7.90 (m, 2H), 7.85 (s, 1H), 3.74 (s, 1H) |
| F-12 | 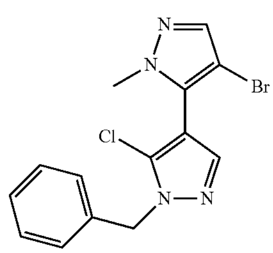 [SMILES: Cn1ncc(Br)c1-c1cnn(Cc2ccccc2)c1Cl] | 1'-benzyl-4-bromo-5'-chloro-2-methyl-1'H,2H-3,4'-bipyrazole<br>LCMS [M + 1]$^+$ = 353.0; $^1$H NMR (400 MHz, CDCl$_3$) δ = 7.67 (s, 1H), 7.54 (s, 1H), 7.41-7.33 (m, 3H), 7.31-7.27 (m, 2H), 5.43 (s, 2H), 3.79 (s, 3H) |

TABLE I-VII-continued

| Intermediate | Structure | Spectral Data |
|---|---|---|
| F-13 | 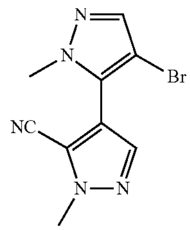 | 4-bromo-1',2-dimethyl-1'H-1,2H-[3,4'-bipyrazole]-5'-carbonitrile<br>LCMS [M + 1]$^+$ = 265.9; $^1$H NMR (400 MHz, CDCl$_3$) δ = 7.70 (s, 1H), 7.56 (s, 1H), 4.16 (s, 3H), 3.87 (s, 3H) |
| F-14 | 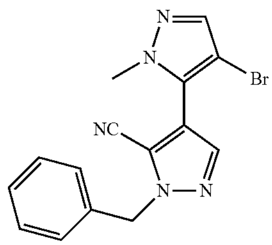 [SMILES: Cn1ncc(Br)c1-c1cnn(Cc2ccccc2)c1C#N] | 1'-benzyl-4-bromo-2-methyl-1'H,2H-[3,4'-bipyrazole]-5'-carbonitrile<br>LCMS [M + 1]$^+$ = 342.0 |
| F-15 | 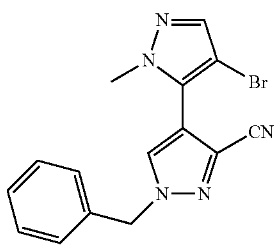 [SMILES: Cn1ncc(Br)c1-c1cn(Cc2ccccc2)nc1C#N] | 1'-benzyl-4-bromo-2-methyl-1'H-1,2H-[3,4'-bipyrazole]-3'-carbonitrile<br>LCMS [M + 1]$^+$ = 342.0; $^1$H NMR (400 MHz, CDCl$_3$-d) δ = 7.61 (s, 1H), 7.54 (s, 1H), 7.47-7.39 (m, 1H), 7.36-7.30 (m, 2H), 5.43 (s, 2H), 3.87 (s, 3H) |
| F-16 | 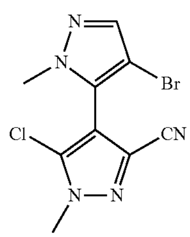 [SMILES: Cn1nc(C#N)c(-c2c(Br)cnn2C)c1Cl] | 4-bromo-5'-chloro-1',2-dimethyl-1'H,2H-[3,4'-bipyrazole]-3'-carbonitrile<br>LCMS [M + 1]$^+$ = 302.0; $^1$H NMR (400 MHz, CDCl$_3$) δ = 7.59 (s, 1H), 4.04 (s, 3H), 3.84 (s, 3H) |
| F-17 | 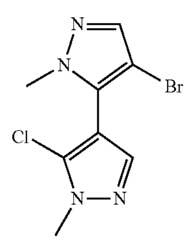 | 4-bromo-5'-chloro-1',2-dimethyl-1'H,2H-3,4'-bipyrazole<br>LCMS [M + 1]$^+$ = 277.0; $^1$H NMR (400 MHz, CDCl$_3$) δ = 7.60 (s, 1H), 7.53 (s, 1H), 3.94 (s, 3H), 3.79 (s, 3H) |
| F-18 | 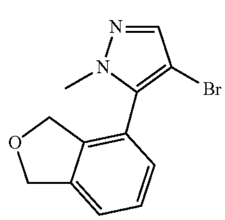 [SMILES: Cn1ncc(Br)c1-c1cccc2c1COC2] | 4-bromo-5-(1,3-dihydroisobenzofuran-4-yl)-1-methyl-1H-pyrazole<br>LCMS [M + 1]$^+$ = 280.9; $^1$H NMR (400 MHz, CDCl$_3$) δ = 7.54 (s, 1H), 7.45-7.35 (m, 2H), 7.18 (d, J = 7.2 Hz, 1H), 5.26-5.11 (m, 3H), 4.88-4.83 (m, 1H), 3.72 (s, 3H) |

TABLE I-VII-continued

| Intermediate | Structure | Spectral Data |
|---|---|---|
| F-19 | 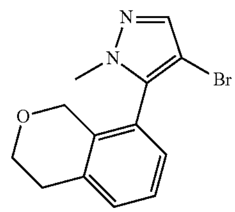 [SMILES: Cn1ncc(Br)c1-c1cccc2c1COCC2] | 4-bromo-5-(isochroman-8-yl)-1-methyl-1H-pyrazole<br>LCMS [M + 1]$^+$ = 293.0; $^1$H NMR (400 MHz, CDCl$_3$) δ = 7.54 (s, 1H), 7.34-7.26 (m, 2H), 7.04 (d, J = 6.8 Hz, 1H), 4.65-4.57 (m, 1H), 4.34-4.28 (m, 1H), 4.07-3.92 (m, 2H), 3.65 (s, 3H), 3.05-2.88 (m, 2H) |
| F-20 | 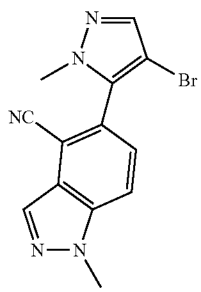 [SMILES: Cn1ncc(Br)c1-c1ccc2c(cnn2C)c1C#N] | 5-(4-bromo-1-methyl-1H-pyrazol-5-yl)-1-methyl-1H-indazole-4-carbonitrile<br>LCMS [M + 1]$^+$ = 318.0 |
| F-21 | 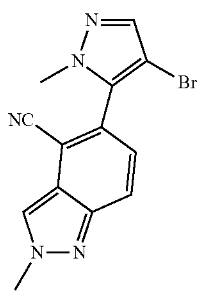 [SMILES: Cn1cc2c(C#N)c(-c3c(Br)cnn3C)ccc2n1] | 5-(4-bromo-1-methyl-1H-pyrazol-5-yl)-2-methyl-2H-indazole-4-carbonitrile<br>LCMS [M + 1]$^+$ = 318.0 |
| F-22 | 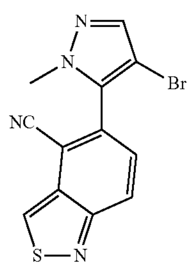 [SMILES: Cn1ncc(Br)c1-c1ccc2nscc2c1C#N] | 5-(4-bromo-1-methyl-1H-pyrazol-5-yl)benzo[c]isothiazole-4-carbonitrile<br>LCMS [M + 1]$^+$ = 318.9; $^1$H NMR (400 MHz, CDCl3,) δ = 9.62 (d, J = 0.8 Hz, 1H), 8.22 (dd, J = 1.2, 9.2 Hz, 1H), 7.65 (s, 1H), 7.50 (d, J = 9.2 Hz, 1H), 3.88 (s, 3H) |

Intermediate DC

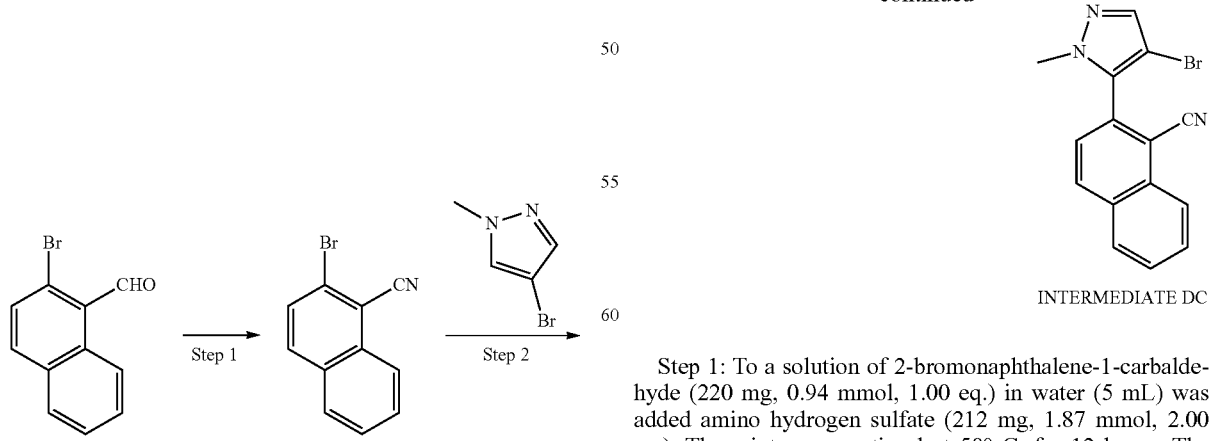

INTERMEDIATE DC

Step 1: To a solution of 2-bromonaphthalene-1-carbaldehyde (220 mg, 0.94 mmol, 1.00 eq.) in water (5 mL) was added amino hydrogen sulfate (212 mg, 1.87 mmol, 2.00 eq.). The mixture was stirred at 50° C. for 12 hours. The suspension was then filtered and the filter cake dried under reduced pressure to give (1E)-2-bromonaphthalene-1-carbaldehyde oxime (220 mg, 0.88 mmol, 94% yield) as a white solid which used without further purification. $^1$H NMR (400 MHz, DMSO-d$_6$) δ=11.79 (s, 1H), 8.58 (s, 1H), 8.55 (dd, J=1.6, 8.0 Hz, 1H), 8.03-7.98 (m, 1H), 7.92 (d, J=8.8 Hz, 1H), 7.77 (d, J=8.8 Hz, 1H), 7.67-7.57 (m, 2H). To a solution of (1E)-2-bromonaphthalene-1-carbaldehyde oxime (220 mg, crude) in THF (5 mL) was added triethylamine (890 mg, 8.80 mmol, 1.22 mL) and trifluoroacetic anhydride (924 mg, 4.40 mmol, 0.61 mL) and the mixture stirred at 20° C. for 1 hour. After such time the reaction mixture was concentrated under reduced pressure and the residue was purified by prep-TLC (SiO$_2$, petroleum ether/ethyl acetate 10%) to give 2-bromonaphthalene-1-carbonitrile (190 mg, 0.82 mmol, 93% yield) as a white solid. GCMS [M+1]$^+$=230.9; $^1$H NMR (400 MHz, DMSO-d$_6$) δ=8.26 (d, J=8.8 Hz, 1H), 8.16 (d, J=8.0 Hz, 1H), 8.09 (d, J=8.0 Hz, 1H), 7.93 (d, J=8.8 Hz, 1H), 7.85 (dt, J=1.2, 8.4 Hz, 1H), 7.79-7.71 (m, 1H).

Step 2: A mixture of 2-bromonaphthalene-1-carbonitrile (190 mg, 0.82 mmol, 1.00 eq.), 4-bromo-1-methyl-pyrazole (132 mg, 0.82 mmol, 1.00 eq.), tetrabutylammonium acetate (494 mg, 1.64 mmol, 0.50 mL, 2.00 eq.), DavePhos (6.4 mg, 16 μmol, 0.02 eq.), 2-methylpropanoic acid (22 mg, 246 μmol, 23 μL, 0.30 eq.) and palladium acetate (1.8 mg, 8.2 μmol, 0.01 eq.) in N-methyl pyrrolidone (NMP) (6 mL) was degassed with nitrogen then the mixture was stirred at 100° C. for 12 hours. After such time the reaction mixture was diluted with water (30 mL) and extracted with ethyl acetate (50 mL×3). The combined organic layers were washed with brine (100 mL×2), dried over anhydrous sodium sulfate, filtered and concentrated under reduced pressure. The residue was purified by reversed-phase HPLC (0.1% formic acid condition) to give 2-(4-bromo-2-methyl-pyrazol-3-yl)naphthalene-1-carbonitrile (190 mg, 0.61 mmol, 74% yield) as a yellow oil. LCMS [M+1]$^+$=314.1; $^1$H NMR (400 MHz, DMSO-d$_6$) δ=8.49 (d, J=8.4 Hz, 1H), 8.24 (t, J=8.4 Hz, 2H), 7.92 (dt, J=1.2, 8.4 Hz, 1H), 7.87-7.82 (m, 1H), 7.81 (s, 1H), 7.76 (d, J=8.4 Hz, 1H), 3.79 (s, 3H).

Intermediate DD

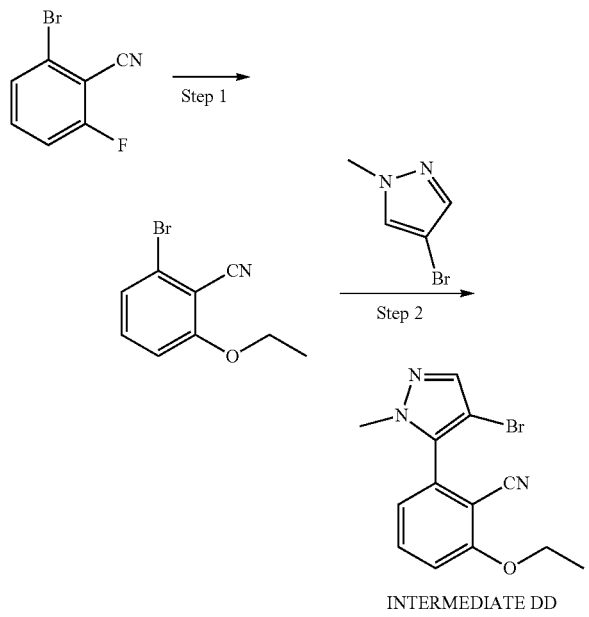

INTERMEDIATE DD

Step 1: To a solution of ethyl alcohol (207 mg, 4.50 mmol, 0.26 mL, 3.00 eq.) in THF (3 mL) was added sodium hydride (180 mg, 4.50 mmol, 60.0% purity, 3.00 eq.), followed by a solution of 2-bromo-6-fluoro-benzonitrile (300 mg, 1.50 mmol, 1.00 eq.) in THF (1 mL) in a dropwise fashion. After the addition was complete the mixture was stirred at 25° C. for 3 hours. After such time the reaction was quenched with water (0.2 mL) and concentrated in vacuum and the residue was purified by column chromatography (SiO$_2$, petroleum ether/ethyl acetate 10%) to give 2-bromo-6-ethoxy-benzonitrile (200 mg, 0.89 mmol, 59% yield) as a white solid. $^1$H NMR (400 MHz, CDCl$_3$) δ=7.38-7.32 (t, J=8.4 Hz, 1H), 7.20 (d, J=8.0 Hz, 1H), 6.90 (d, J=8.4 Hz, 1H), 4.15 (q, J=7.2 Hz, 2H), 1.47 (t, J=7.2 Hz, 3H).

Step 2: A mixture of 2-bromo-6-ethoxy-benzonitrile (200 mg, 0.89 mmol, 1.00 eq.), 4-bromo-1-methyl-pyrazole (185 mg, 1.15 mmol, 1.30 eq.), palladium acetate (2.0 mg, 8.9 μmol, 0.01 eq.), DavePhos (7.0 mg, 17.7 μmol, 0.02 eq.), 2-methylpropanoic acid (23.4 mg, 265 μmol, 25 μL, 0.30 eq.) and tetrabutylammonium acetate (533 mg, 1.77 mmol, 2.00 eq.) was degassed with nitrogen then the mixture was stirred at 100° C. for 15 hours. After such time the mixture was diluted with ethyl acetate (20 mL), washed with water (20 mL×3) and the combined organic phases were dried over anhydrous sodium sulfate, filtered and concentrated in vacuum. The residue was then purified by prep-TLC (SiO$_2$, petroleum ether/ethyl acetate 20%) to give 2-(4-bromo-1-methyl-1H-pyrazol-5-yl)-6-ethoxybenzonitrile (60.0 mg, 0.20 mmol, 22% yield) as a white solid. LCMS [M+1]$^+$=306.1; $^1$H NMR (400 MHz, CDCl$_3$) δ=7.56 (dd, J=7.6, 8.4 Hz, 1H), 7.49 (s, 1H), 7.02 (d, J=8.4 Hz, 1H), 6.91 (d, J=7.6 Hz, 1H), 4.15 (q, J=7.2 Hz, 2H), 3.73 (s, 3H), 1.46 (t, J=7.2 Hz, 3H).

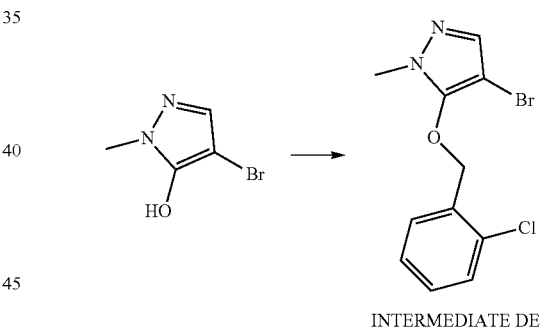

INTERMEDIATE DE

A mixture of 4-bromo-2-methyl-pyrazol-3-ol (300 mg, 1.69 mmol, 1.00 eq.), 1-(bromomethyl)-2-chloro-benzene (348 mg, 1.69 mmol, 0.22 mL, 1.00 eq.), and potassium carbonate (469 mg, 3.39 mmol, 2.00 eq.) in DMF (8 mL) was stirred at 18° C. for 2 hours. After such time the reaction mixture was diluted with water (20 mL) and extracted with ethyl acetate (20 mL×3). The combined organic extracts were washed with brine (20 mL), dried over anhydrous sodium sulfate, filtered, concentrated under reduced pressure and the residue purified by reversed-phase HPLC (0.1% FA condition) to give 4-bromo-5-[(2-chlorophenyl)methoxy]-1-methyl-pyrazole (220 mg, 0.72 mmol, 42% yield) as a yellow solid. LCMS [M+1]$^+$=303.0; $^1$H NMR (400 MHz, CDCl$_3$) δ=7.48-7.43 (m, 2H), 7.37-7.27 (m, 3H), 5.40 (s, 2H), 3.55 (s, 3H).

The INTERMEDIATES to G-1 to G-4 shown in Table I-VIII were prepared following the teachings of the General Reaction Schemes and the method to prepare INTERMEDIATE DE.

TABLE I-VIII

| Intermediate | Structure | Spectral Data |
|---|---|---|
| G-1 | 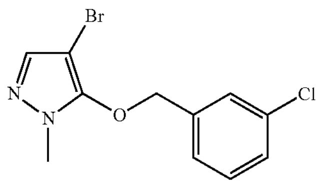 [SMILES: Cn1ncc(Br)c1OCc1cccc(Cl)c1] | 4-bromo-5-((3-chlorobenzyl)oxy)-1-methyl-1H-pyrazole LCMS [M + 1]$^+$ = 303.0; $^1$H NMR (400 MHz, CDCl$_3$) δ = 7.43 (d, J = 1.6 Hz, 1H), 7.37-7.35 (m, 1H), 7.34-7.30 (m, 2H), 7.28 (t, J = 1.6 Hz, 1H), 5.26 (s, 2H), 3.54 (s, 3H) |
| G-2 | 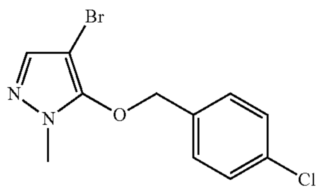 [SMILES: Cn1ncc(Br)c1OCc1ccc(Cl)cc1] | 4-bromo-5-((4-chlorobenzyl)oxy)-1-methyl-1H-pyrazole LCMS [M + 1]$^+$ = 303.0; $^1$H NMR (400 MHz, CDCl$_3$) δ = 7.43-7.35 (m, 2H), 7.35-7.29 (m, 3H), 5.25 (s, 2H), 3.49 (s, 3H) |
| G-3 | 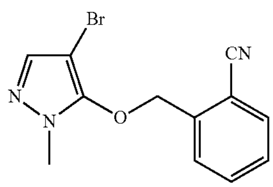 [SMILES: Cn1ncc(Br)c1OCc1ccccc1C#N] | 4-bromo-5-((2-cyanobenzyl)oxy)-1-methyl-1H-pyrazole LCMS [M + 1]$^+$ = 294.1; $^1$H NMR (400 MHz, CDCl$_3$) δ = 7.75 (d, J = 7.6 Hz, 1H), 7.69-7.59 (m, 2H), 7.55-7.49 (m, 1H), 7.32 (s, 1H), 5.46 (s, 2H), 3.64 (s, 3H) |
| G-4 | 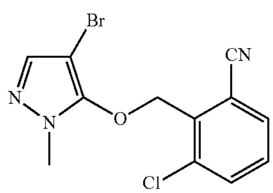 [SMILES: Cn1ncc(Br)c1OCc1c(Cl)cccc1C#N] | 2-(((4-bromo-1-methyl-1H-pyrazol-5-yl)oxy)methyl)-3-chlorobenzonitrile LCMS [M + 1]$^+$ = 327.9; $^1$H NMR (400 MHz, CDCl$_3$) δ = 7.63-7.58 (m, 1H), 7.58-7.54 (m, 2H), 7.34-7.30 (m, 1H), 5.46 (s, 2H), 3.68 (s, 3H) |

Intermediate H-1

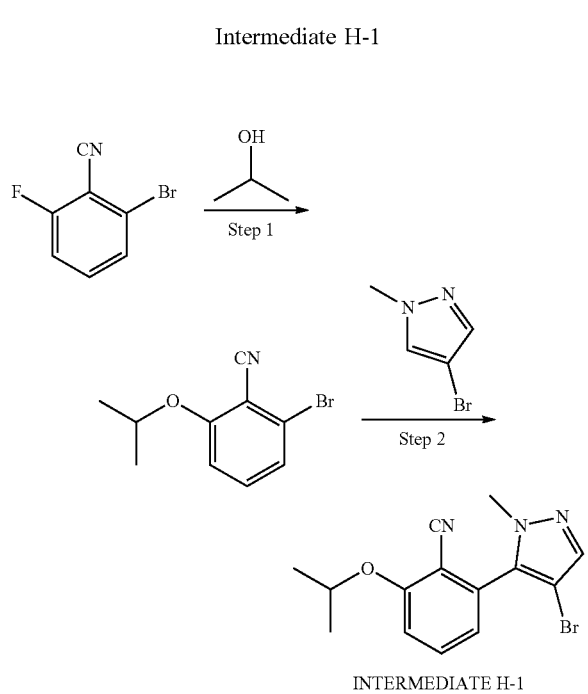

INTERMEDIATE H-1

Step 1: A mixture of 2-bromo-6-fluoro-benzonitrile (600 mg, 3.00 mmol, 1.00 eq.), propan-2-ol (225 mg, 3.75 mmol, 0.29 mL, 1.25 eq.), cesium carbonate (1.47 g, 4.50 mmol, 1.50 eq.) in DMF (6 mL) was stirred at 75° C. for 1 hour. After such time the reaction mixture was diluted with water (30 mL) and extracted with ethyl acetate (50 mL×3). The combined organic layers were washed with brine (100 mL×2), dried over anhydrous sodium sulfate, filtered and concentrated under reduced pressure. The residue was purified by reversed-phase HPLC (0.1% formic acid condition) to give 2-bromo-6-isopropoxy-benzonitrile (540 mg, 2.25 mmol, 75% yield) as a white solid. LCMS [M+1]$^+$=241.9; $^1$H NMR (400 MHz, DMSO-d$_6$) δ=7.56 (t, J=8.4 Hz, 1H), 7.37 (d, J=7.6 Hz, 1H), 7.31 (d, J=8.4 Hz, 1H), 4.90-4.75 (m, 1H), 1.32 (d, J=6.0 Hz, 6H).

Step 2: A mixture of 2-bromo-6-isopropoxy-benzonitrile (500 mg, 2.08 mmol, 1.00 eq.), 4-bromo-1-methyl-pyrazole (335 mg, 2.08 mmol, 1.00 eq.), diacetoxypalladium (4.7 mg, 0.021 mmol, 0.01 eq.), DavePhos (16 mg, 0.042 mmol, 0.02 eq.), tetrabutylammonium; acetate (1.26 g, 4.16 mmol, 2.00 eq.) and 2-methylpropanoic acid (55 mg, 0.63 mmol, 0.06 mL, 0.30 eq.) in 1-methyl-2-pyrrolidinone (7 mL) was degassed with nitrogen then stirred at 100° C. for 12 hours. After such time the reaction mixture was diluted with water (30 mL) and extracted with ethyl acetate (40 mL×3). The combined organic layers were washed with brine (100 mL×2), dried over anhydrous sodium sulfate, filtered and concentrated under reduced pressure. The residue was purified by reversed-phase HPLC (0.1% formic acid condition) to give 2-(4-bromo-2-methyl-pyrazol-3-yl)-6-isopropoxy-benzonitrile (160 mg, 0.50 mmol, 24 yield) as a white solid. LCMS [M+1]$^+$=319.9; $^1$H NMR (400 MHz, DMSO-d$_6$) δ=7.81-7.76 (m, 1H), 7.72 (s, 1H), 7.46 (d, J=8.8 Hz, 1H), 7.14 (d, J=7.2 Hz, 1H), 4.88 (td, J=6.0, 12.0 Hz, 1H), 3.71 (s, 3H), 1.36 (d, J=6.0 Hz, 6H).

The INTERMEDIATES to H-2 to H-8 shown in Table I-IX were prepared following the teachings of the General Reaction Schemes and the method to prepare INTERMEDIATE H-1.

TABLE I-IX

| Intermediate | Structure | Spectral Data |
|---|---|---|
| H-2 | 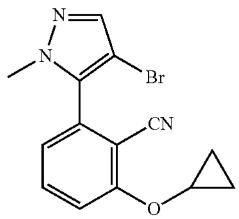 [SMILES: Cn1ncc(Br)c1-c1cccc(OC2CC2)c1C#N] | 2-(4-bromo-1-methyl-1H-pyrazol-5-yl)-6-cyclopropoxybenzonitrile<br>LCMS [M + 1]$^+$ = 318.0; $^1$H NMR (400 MHz, CDCl$_3$) δ = 7.71-7.64 (m, 1H), 7.58 (s, 1H), 7.49 (d, J = 8.8 Hz, 1H), 7.05-7.01 (m, 1H), 3.92 (td, J = 2.8, 5.6 Hz, 1H), 0.96-0.91 (m, 4H) |
| H-3 | 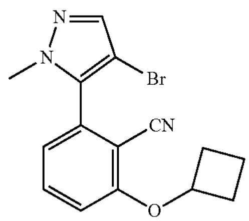 [SMILES: Cn1ncc(Br)c1-c1cccc(OC2CCC2)c1C#N] | 2-(4-bromo-1-methyl-1H-pyrazol-5-yl)-6-cyclobutoxybenzonitrile<br>LCMS [M + 1]$^+$ = 334.0; $^1$H NMR (400 MHz, CDCl$_3$) δ = 7.65-7.59 (m, 1H), 7.59 (s, 1H), 7.00-6.93 (m, 2H), 4.80 (q, J = 7.2 Hz, 1H), 3.82-3.79 (s, 3H), 2.61-2.48 (m, 2H), 2.39-2.27 (m, 2H), 2.03-1.91 (m, 1H), 1.84-1.70 (m, 1H) |
| H-4 | 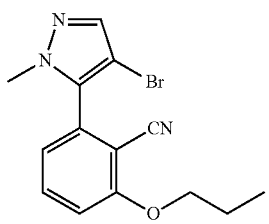 [SMILES: CCCOc1cccc(-c2c(Br)cnn2C)c1C#N] | 2-(4-bromo-1-methyl-1H-pyrazol-5-yl)-6-propoxybenzonitrile<br>LCMS [M + 1]$^+$ = 320.0; $^1$H NMR (400 MHz, DMSO-d$_6$) δ = 7.80 (dd, J = 8.0, 8.4 Hz, 1H), 7.73 (s, 1H), 7.43 (d, J = 8.4 Hz, 1H), 7.17 (d, J = 7.6 Hz, 1H), 4.18 (dt, J = 2.0, 6.4 Hz, 2H), 1.81 (q, J = 7.6 Hz, 2H), 1.02 (t, J = 7.6 Hz, 3H) |
| H-5 | 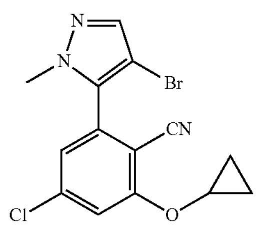 [SMILES: Cn1ncc(Br)c1-c1cc(Cl)cc(OC2CC2)c1C#N] | 2-(4-bromo-1-methyl-1H-pyrazol-5-yl)-4-chloro-6-cyclopropoxybenzonitrile<br>LCMS [M + 1]$^+$ = 353.9; $^1$H NMR (400 MHz, CDCl$_3$) δ = 7.57 (s, 1H), 7.48 (d, J = 2.0 Hz, 1H), 7.04 (d, J = 2.0 Hz, 1H), 3.95-3.90 (m, 1H), 3.81 (s, 3H), 0.99-0.94 (m, 4H) |
| H-6 | 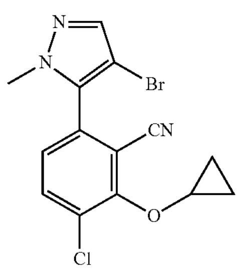 [SMILES: Cn1ncc(Br)c1-c1ccc(Cl)c(OC2CC2)c1C#N] | 6-(4-bromo-1-methyl-1H-pyrazol-5-yl)-3-chloro-2-cyclopropoxybenzonitrile<br>LCMS [M + 1]$^+$ = 354.0; $^1$H NMR (400 MHz, CDCl$_3$) δ = 7.73 (d, J = 8.4 Hz, 1H), 7.60 (s, 1H), 7.13 (d, J = 8.4 Hz, 1H), 4.61 (m, 1H), 3.82 (s, 3H), 1.11-1.04 (m, 2H), 0.80-0.72 (m, 2H) |
| H-7 | 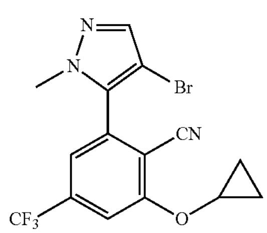 [SMILES: Cn1ncc(Br)c1-c1cc(C(F)(F)F)cc(OC2CC2)c1C#N] | 2-(4-bromo-1-methyl-1H-pyrazol-5-yl)-6-cyclopropoxy-4-(trifluoromethyl)benzonitrile<br>$^1$H NMR (500 MHz, CDCl$_3$) δ = 7.69 (d, J = 1.2 Hz, 1 H), 7.59 (s, 1 H), 7.29 (d, J = 1.2 Hz, 1 H), 4.01-3.97 (m, 1 H), 3.81 (s, 3 H), 1.01-0.97 (m, 4 H) |

TABLE I-IX-continued

| Intermediate | Structure | Spectral Data |
|---|---|---|
| H-8 | 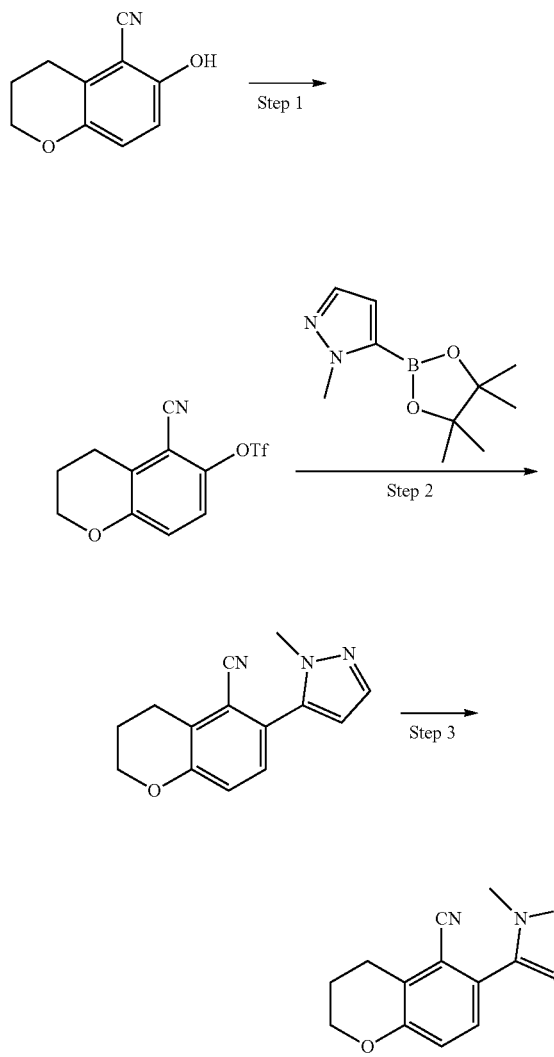 | 3-(4-bromo-1-methyl-1H-pyrazol-5-yl)-1-cyclopropoxy-2-naphthonitrile<br>$^1$H NMR (400 MHz, CDCl$_3$) δ = 8.26 (d, J = 8.4 Hz, 1H), 7.90 (d, J = 8.4 Hz, 1H), 7.76-7.70 (m, 1H), 7.70-7.65 (m, 1H), 7.63 (s, 1H), 7.57 (s, 1H), 4.74 (tt, J = 2.8, 6.0 Hz, 1H), 3.86 (s, 3H), 1.13-1.07 (m, 2H), 0.95-0.87 (m, 2H) |

Intermediate I-1

Step 1: To a solution of 6-hydroxychromane-5-carbonitrile (150 mg, 0.86 mmol, 1.00 eq.) and triethylamine (2.57 mmol, 0.36 mL, 3.00 eq.) in dichloromethane (2 mL) was added a solution of trifluoromethanesulfonic anhydride (0.86 mmol, 0.141 mL, 1.00 eq.) in dichloromethane (1 mL) dropwise at 0° C., The mixture was then stirred at 0° C. for 0.5 hour. After such time the mixture was diluted with ethyl acetate (50 mL), washed with brine (50 mL×3) and dried over anhydrous sodium sulfate, filtered and concentrated. The residue was purified by prep-TLC (SiO$_2$, petroleum ether/ethyl acetate 10%) to give (5-cyanochroman-6-yl) trifluoromethanesulfonate (80 mg, 0.26 mmol, 30% yield) as a colorless liquid. $^1$H NMR (400 MHz, CDCl$_3$) δ=7.21-7.15 (m, 1H), 7.09-7.04 (m, 1H), 4.31-4.20 (m, 2H), 3.00 (t, J=6.4 Hz, 2H), 2.18-2.02 (m, 2H).

Step 2: A mixture of (5-cyanochroman-6-yl) trifluoromethanesulfonate (70 mg, 0.23 mmol, 1.00 eq.), 1-methyl-5-(4,4,5,5-tetramethyl-1,3,2-dioxaborolan-2-yl)pyrazole (71.mg, 0.34 mmol, 1.50 eq.), Pd(dtbpf)Cl$_2$ (15 mg, 0.23 mmol, 0.10 eq.), sodium bicarbonate (38 mg, 0.46 mmol, 2.00 eq.) in DMF (2 mL) was degassed with nitrogen. The mixture was then stirred at 80° C. for 1 hour, cooled to 25° C., diluted with ethyl acetate (30 mL) and washed with brine (30 mL×3), dried over anhydrous sodium sulfate, filtered and concentrated under reduced pressure. The residue was purified by prep-TLC (SiO$_2$, petroleum ether/ethyl acetate 30%) to give 6-(2-methylpyrazol-3-yl)chromane-5-carbonitrile (40 mg, 0.17 mmol, 73% yield) as a white solid. LCMS [M+1]$^+$=240.0; $^1$H NMR (400 MHz, CDCl$_3$)=7.57 (d, J=1.6 Hz, 1H), 7.19-7.14 (m, 1H), 7.12-7.06 (m, 1H), 6.40 (d, J=2.0 Hz, 1H), 4.30-4.24 (m, 2H), 3.82 (s, 3H), 3.03 (t, J=6.4 Hz, 2H), 2.17-2.09 (m, 2H).

Step 3: To a solution of 6-(2-methylpyrazol-3-yl)chromane-5-carbonitrile (30 mg, 0.125 mmol, 1.00 eq.) in acetonitrile (1.5 mL) was added NBS (34 mg, 0.19 mmol, 1.50 eq.). The mixture was stirred at 25° C. for 1 hour then concentrated. The residue was purified by prep-TLC (SiO$_2$, petroleum ether/ethyl acetate 30%) to give 6-(4-bromo-2-methyl-pyrazol-3-yl)chromane-5-carbonitrile (25 mg, 0.79 mmol, 63% yield) as a yellow solid. LCMS [M+1]$^+$=320.1; $^1$H NMR (400 MHz, CDCl$_3$) δ=7.57 (s, 1H), 7.18-7.11 (m, 2H), 4.29 (dd, J=4.4, 6.0 Hz, 2H), 3.79 (s, 3H), 3.05 (dt, J=2.0, 6.4 Hz, 2H), 2.15 (dq, J=4.4, 6.4 Hz, 2H).

The INTERMEDIATES to 1-2 to 1-4 shown in Table I-X were prepared following the teachings of the General Reaction Schemes and the method to prepare INTERMEDIATE I-1

TABLE I-X

| Intermediate | Structure | Spectral Data |
|---|---|---|
| I-2 | 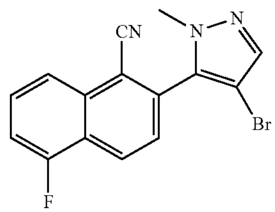 [SMILES: Cn1ncc(Br)c1-c1ccc2c(F)cccc2c1C#N] | 2-(4-bromo-1-methyl-1H-pyrazol-5-yl)-5-fluoro-1-naphthonitrile LCMS [M + 1] = 329.9; $^1$H NMR (400 MHz, CDCl$_3$) δ = 8.49 (d, J = 8.8 Hz, 1H), 8.16 (d, J = 8.4 Hz, 1H), 7.75 (dt, J = 5.2, 8.0 Hz, 1H), 7.66 (s, 1H), 7.59 (d, J = 8.8 Hz, 1H), 7.41 (dd, J = 7.2, 9.2 Hz, 1H), 3.86 (s, 3H) |
| I-3 | 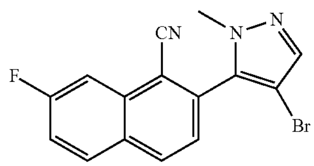 [SMILES: Cn1ncc(Br)c1-c1ccc2ccc(F)cc2c1C#N] | 2-(4-bromo-1-methyl-1H-pyrazol-5-yl)-7-fluoro-1-naphthonitrile LCMS [M + 1] = 329.9; $^1$H NMR (400 MHz, CDCl$_3$) δ = 8.21 (d, J = 8.4 Hz, 1H), 8.04 (dd, J = 5.4, 9.1 Hz, 1H), 8.00 (dd, J = 2.4, 9.5 Hz, 1H), 7.65 (s, 1H), 7.56-7.47 (m, 2H), 3.86 (s, 3H) |
| I-4 | 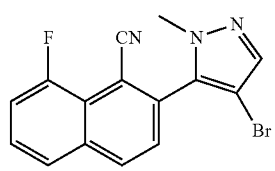 [SMILES: Cn1ncc(Br)c1-c1ccc2cccc(F)c2c1C#N] | 2-(4-bromo-1-methyl-1H-pyrazol-5-yl)-8-fluoro-1-naphthonitrile $^1$H NMR (400 MHz, CDCl$_3$) δ = 8.22 (dd, J = 1.6, 8.4 Hz, 1H), 7.82 (d, J = 8.4 Hz, 1H), 7.71-7.66 (m, 1H), 7.65 (s, 1H), 7.55 (d, J = 8.4 Hz, 1H), 7.49-7.42 (m, 1H), 3.87 (s, 3H) |

Intermediate DF

Intermediate DG

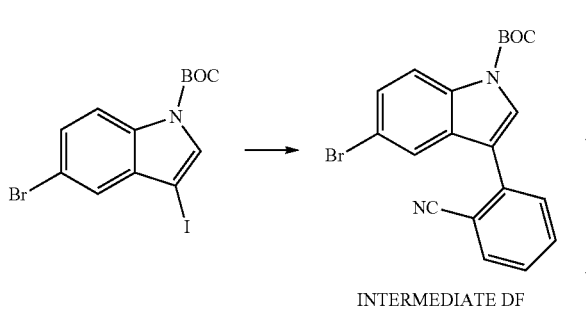

INTERMEDIATE DF

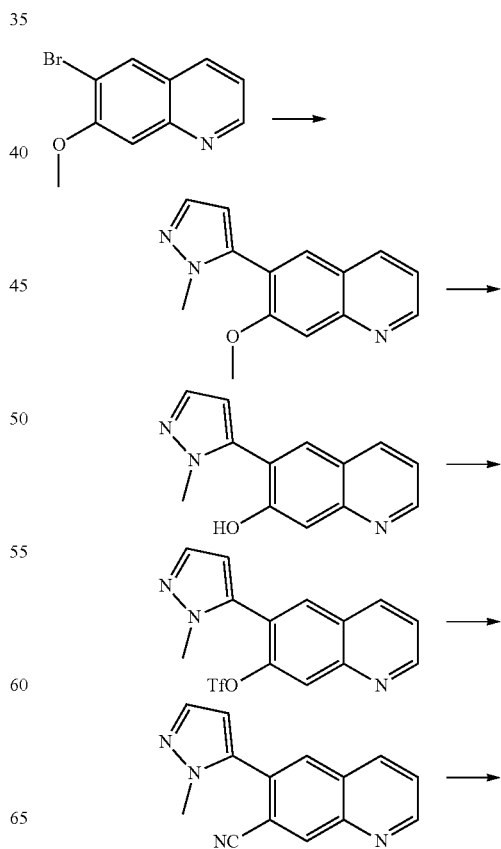

A mixture of tert-butyl 5-bromo-3-iodo-pyrrolo[2,3-b]pyridine-1-carboxylate (120 mg, 0.28 mmol, 1 eq), (2-cyanophenyl)boronic acid (83 mg, 0.57 mmol, 2 eq), Pd(dppf)Cl$_2$ (21 mg, 0.03 mmol, 0.1 eq), NaHCO$_3$ (71 mg, 0.85 mmol) in DMF (2 mL) was degassed with nitrogen then stirred at 80° C. for 3 hr. After such time mixture was diluted with ethyl acetate (20 mL) and washed by water (20 mL×3). The organic phase was concentrated and the residue purified by prep-TLC (SiO$_2$, petroleum ether/ethyl acetate 15%) to give intermediate E-1, tert-butyl 5-bromo-3-(2-cyanophenyl)pyrrolo[2,3-b]pyridine-1-carboxylate (50 mg, 0.13 mmol, 44% yield) as a white solid. LCMS [M−55]$^+$=342.1; $^1$H NMR (400 MHz, CDCl$_3$) δ=8.62 (d, J=2.0 Hz, 1H), 8.06 (d, J=2.4 Hz, 1H), 8.03 (s, 1H), 7.84 (dd, J=1.2, 8.0 Hz, 1H), 7.76-7.70 (m, 1H), 7.63 (d, J=7.2 Hz, 1H), 7.52 (dt, J=1.2, 7.6 Hz, 1H), 1.70 (s, 9H).

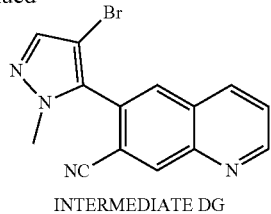

INTERMEDIATE DG

Step 1: A mixture of 6-bromo-7-methoxy-quinoline (100 mg, 0.420 mmol, 1.00 eq.), 1-methyl-5-(4,4,5,5-tetramethyl-1,3,2-dioxaborolan-2-yl)pyrazole (105 mg, 0.504 mmol, 1.20 eq.), Pd(dtbpf)Cl$_2$ (27 mg, 0.042 mmol, 0.10 eq.) and sodium carbonate (89 mg, 0.840 mmol, 2.00 eq.) in dioxane (1.0 mL) and water (0.2 mL) was degassed with nitrogen. The mixture was then stirred at 80° C. for 2 hours, concentrated under reduced pressure and the residue purified by prep-TLC (SiO$_2$, ethyl acetate) to give 7-methoxy-6-(2-methylpyrazol-3-yl)quinoline (80 mg, 0.334 mmol, 80% yield) as a yellow solid. LCMS [M+1]$^+$=240.2; $^1$H NMR (400 MHz, CDCl$_3$) δ=8.82 (dd, J=1.6, 4.4 Hz, 1H), 8.04 (d, J=8.0 Hz, 1H), 7.65 (s, 1H), 7.51 (d, J=1.6 Hz, 1H), 7.48 (s, 1H), 7.27 (dd, J=4.4, 8.0 Hz, 1H), 6.28 (d, J=1.6 Hz, 1H), 3.91 (s, 3H), 3.70 (s, 3H).

Step 2: A mixture of 7-methoxy-6-(2-methylpyrazol-3-yl)quinoline (500 mg, 2.09 mmol, 1.00 eq.) and pyridine hydrochloride (2.41 g, 20.9 mmol, 10.0 eq.) was stirred at 160° C. for 0.5 hour. After such time the residue was purified by reverse prep-HPLC (0.1% formic acid) to give 6-(2-methylpyrazol-3-yl) quinolin-7-ol (260 mg, 1.07 mmol, 51% yield, 92% purity) as a yellow solid. LCMS [M+1]$^+$=226.1.

Step 3: To a solution of 6-(2-methylpyrazol-3-yl)quinolin-7-ol (260 mg, 1.15 mmol, 1.00 eq.) and triethylamine (0.32 mL, 2.31 mmol, 2.00 eq.) in dichloromethane (5 mL) was added trifluoromethanesulfonic anhydride (0.29 mL, 1.73 mmol, 1.50 eq.) in a dropwise fashion at 0° C. The mixture was stirred at 20° C. for 1 hour, quenched with water (12 mL) and extracted with dichloromethane (15 mL×3). The combined organic extracts were washed with brine (12 mL), dried over anhydrous sodium sulfate, filtered and concentrated and the residue purified by column chromatography (SiO$_2$, petroleum ether/ethyl acetate 10-100%) to give [6-(2-methylpyrazol-3-yl)-7-quinolyl] trifluoromethanesulfonate (0.97 g, 0.706 mmol, 61%) as a yellow oil. LCMS [M+1]$^+$=358.1.

Step 4: A mixture of [6-(2-methylpyrazol-3-yl)-7-quinolyl] trifluoromethanesulfonate (970 mg, 0.668 mmol, 1.00 eq.), zinc cyanide (157 mg, 1.34 mmol, 2.00 eq.), Pd$_2$(dba)$_3$ (61 mg, 0.67 mmol, 0.1 eq.), DPPF (74 mg, 0.134 mmol, 0.20 eq.) and zinc powder (4.3 mg, 0.67 mmol, 0.10 eq.) in DMF (10 mL) was degassed with nitrogen then stirred at 100° C. for 2 hours. After such time the reaction mixture was diluted with water (20 mL) and extracted with ethyl acetate (20 mL×3). The combined organic phases were washed with brine (20 mL), dried over anhydrous sodium sulfate, filtered, concentrated and the residue purified by HPLC (0.1% formic acid condition) to give 6-(2-methylpyrazol-3-yl)quinoline-7-carbonitrile (100 mg, 0.249 mmol, 37% yield) as a brown solid. LCMS [M+1]$^+$=235.2.

Step 5: To a solution of 6-(2-methylpyrazol-3-yl)quinoline-7-carbonitrile (90 mg, 0.384 mmol, 1.00 eq.) in acetonitrile (5 mL) was added N-bromosuccinimide (103 mg, 0.576 mmol, 1.50 eq.). The mixture was stirred at 20° C. for 0.5 hours then concentrated under reduced pressure and the residue was purified by prep-TLC (dichloromethane/methyl alcohol 10%) to give 6-(4-bromo-2-methyl-pyrazol-3-yl) quinoline-7-carbonitrile (50 mg, 0.160 mmol, 41% yield) as a yellow solid. LCMS [M+1]$^+$=315.1; $^1$H NMR (400 MHz, CDCl$_3$) δ=9.14 (dd, J=1.6, 4.4 Hz, 1H), 8.68 (s, 1H), 8.31 (d, J=8.4 Hz, 1H), 7.96 (s, 1H), 7.69-7.65 (m, 1H), 7.65 (s, 1H), 3.86 (s, 3H).

Intermediate DH

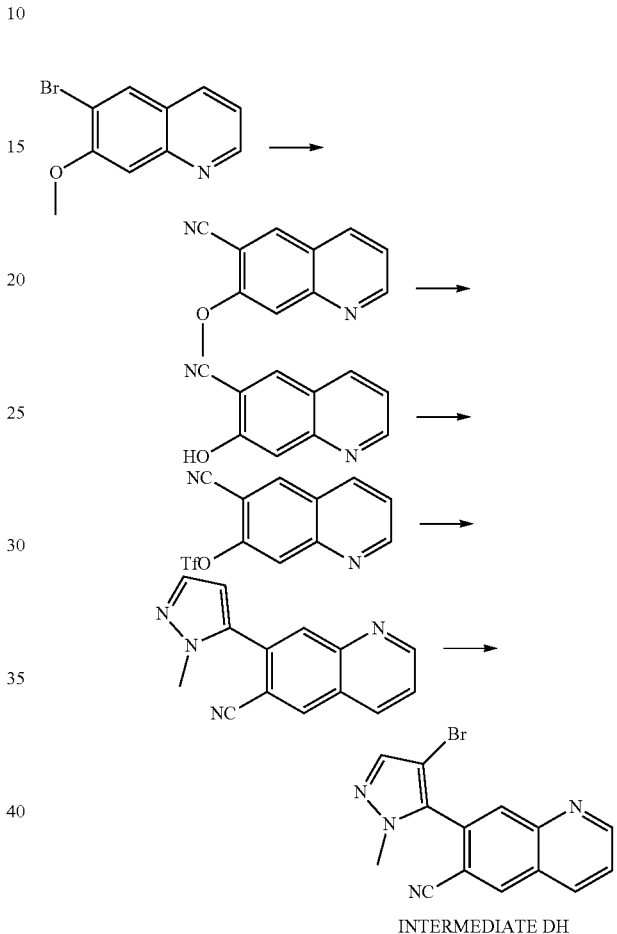

INTERMEDIATE DH

Step 1: A mixture of 6-bromo-7-methoxy-quinoline (100 mg, 0.420 mmol, 1.00 eq.), zinc cyanide (98 mg, 0.840 mmol, 2.00 eq.), Pd$_2$(dba)$_3$ (38 mg, 0.042 mmol, 0.10 eq.), DPPF (47 mg, 0.084 mmol, 0.20 eq.) and zinc powder (2.8 mg, 0.042 mmol, 0.10 eq.) in DMF (2 mL) was degassed and purged with nitrogen. The mixture was then stirred at 100° C. for 2 hours then diluted with water (2 mL) and extracted with ethyl acetate (2 mL×3). The combined organic extracts were washed with brine (2 mL), dried over anhydrous sodium sulfate, filtered and concentrated. The residue was purified by HPLC (0.1% formic acid) to give 7-methoxyquinoline-6-carbonitrile (56 mg, 0.304 mmol, 72% yield) as a white solid. LCMS [M+1]$^+$=185.2; $^1$H NMR (400 MHz, CDCl$_3$) δ=8.97 (dd, J=1.6, 4.0 Hz, 1H), 8.17 (s, 1H), 8.15 (dd, J=1.2, 8.4 Hz, 1H), 7.53 (s, 1H), 7.40 (dd, J=4.0, 8.4 Hz, 1H), 4.09 (s, 3H).

Step 2: To a solution of 7-methoxyquinoline-6-carbonitrile (1.40 g, 7.60 mmol, 1.00 eq) in toluene (20 mL) was added aluminum trichloride (3.04 g, 22.8 mmol, 1.25 mL, 3.00 eq). The mixture was stirred at 100° C. for 1 hour and then the reaction mixture was diluted with water (3 mL) and pH adjusted to 4-5 with sodium hydroxide (2N, 0.1 mL). The formed solid was filtered and dried under reduced pressure to give 7-hydroxyquinoline-6-carbonitrile (1.20 g, crude) as a black solid which used into next step directly without further purification. LCMS [M+1]$^+$=171.1.

Step 3: To a solution of 7-hydroxyquinoline-6-carbonitrile (500 mg, 2.94 mmol, 1 eq.) and triethylamine (0.82 mL, 5.88 mmol, 2.00 eq.) in dichloromethane (10 mL) was added trifluoromethanesulfonic anhydride (0.73 mL, 4.41 mmol, 1.50 eq.) in a dropwise fashion at 0° C. The mixture was stirred at 20° C. for 1 hour and after such time the reaction mixture was quenched with water (20 mL) and extracted with dichloromethane (50 mL×3). The combined organic extracts were washed with brine (20 mL), dried over anhydrous sodium sulfate, filtered and concentrated. The residue was purified by column chromatography (SiO$_2$, petroleum ether/ethyl acetate 10-50%) to give (6-cyano-7-quinolyl) trifluoromethanesulfonate (250 mg, 0.570 mmol, 19% yield) as a yellow oil. LCMS [M+1]$^+$=303.0; $^1$H NMR (400 MHz, CDCl$_3$) δ=9.15 (dd, J=1.6, 4.0 Hz, 1H), 8.37 (s, 1H), 8.32-8.30 (d, J=8.4 Hz 1H), 8.23 (s, 1H), 7.65 (dd, J=4.0, 8.4 Hz, 1H).

Step 4: A mixture of (6-cyano-7-quinolyl) trifluoromethanesulfonate (237 mg, 0.541 mmol, 1.00 eq.), 1-methyl-5-(4,4,5,5-tetramethyl-1,3,2-dioxaborolan-2-yl)pyrazole (135 mg, 0.649 mmol, 1.20 eq.), sodium bicarbonate (91 mg, 1.08 mmol, 2.00 eq.) and Pd(dtbpf)Cl$_2$ (35 mg, 0.054 mmol, 0.10 eq.) in dioxane (10 mL) and water (2 mL) was degassed with nitrogen and stirred at 80° C. for 1 hour. After such time the mixture was concentrated and the residue was purified by column chromatography (SiO$_2$, petroleum ether/ethyl acetate 10-100%) to give 7-(2-methylpyrazol-3-yl)quinoline-6-carbonitrile (120 mg, 0.498 mmol, 92% yield) as a yellow solid. LCMS [M+1]$^+$=235.2.

Step 5: A mixture of 7-(2-methylpyrazol-3-yl)quinoline-6-carbonitrile (120 mg, 0.512 mmol, 1.00 eq.) and N-bromosuccinimide (164 mg, 0.922 mmol, 1.80 eq.) in acetonitrile (4 mL) was degassed with nitrogen and stirred at 20° C. for 2 hours. After such time the mixture was concentrated and the residue was purified by prep-TLC (SiO$_2$, dichloromethane/methyl alcohol 10%) to give 7-(4-bromo-2-methyl-pyrazol-3-yl)quinoline-6-carbonitrile (121 mg, 0.385 mmol, 75% yield) as a yellow solid. LCMS [M+1]$^+$=314.9; $^1$H NMR (400 MHz, CDCl$_3$) δ=9.15 (dd, J=2.0, 4.4 Hz, 1H), 8.43 (s, 1H), 8.33 (dd, J=0.8, 8.4 Hz, 1H), 8.23 (s, 1H), 7.68-7.63 (m, 2H), 3.87 (s, 3H).

Intermediate DI

To a solution of N-(4-bromo-2-methyl-pyrazol-3-yl)benzamide (500 mg, 1.78 mmol, 1.00 eq.) in DMF (5 mL) at 0° C. was added sodium hydride (143 mg, 3.57 mmol, 60.0% purity, 2.00 eq.) and the mixture stirred at 0° C. for 30 minutes. After such time iodomethane (0.133 mL, 2.14 mmol, 1.20 eq.) in DMF (1 mL) was added and the mixture was stirred at 0° C. for a further 10 minutes. The reaction mixture was then diluted with water (50 mL) and extracted with ethyl acetate (40 mL×3) and the combined organic extracts were washed with brine (70 mL), dried over anhydrous sodium sulfate, filtered and concentrated under reduced pressure. The residue was purified by column chromatography (SiO$_2$, petroleum ether/ethyl acetate 0-30%) to give N-(4-bromo-2-methyl-pyrazol-3-yl)-N-methyl-benzamide (400 mg, 1.36 mmol, 76% yield) as a white solid. $^1$H NMR (400 MHz, DMSO-d$_6$) δ=7.44 (s, 1H), 7.36-7.41 (m, 1H), 7.26-7.33 (m, 4H), 3.72 (s, 3H), 3.23 (s, 3H).

Intermediate DJ

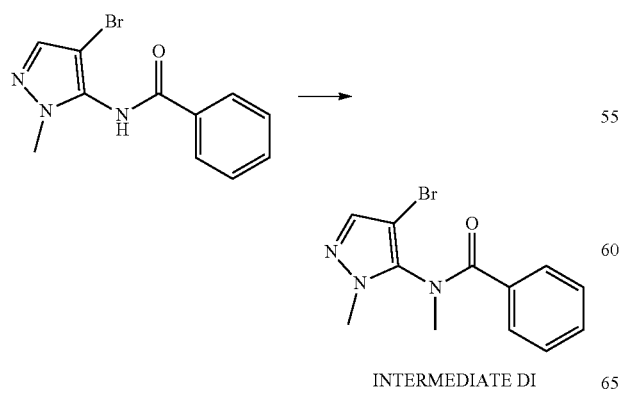

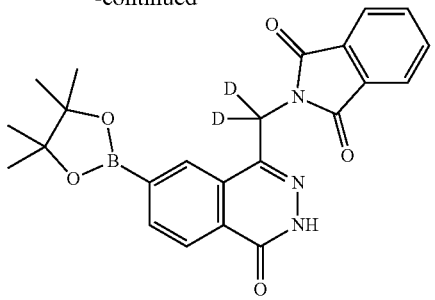

INTERMEDIATE DJ

Intermediate DK

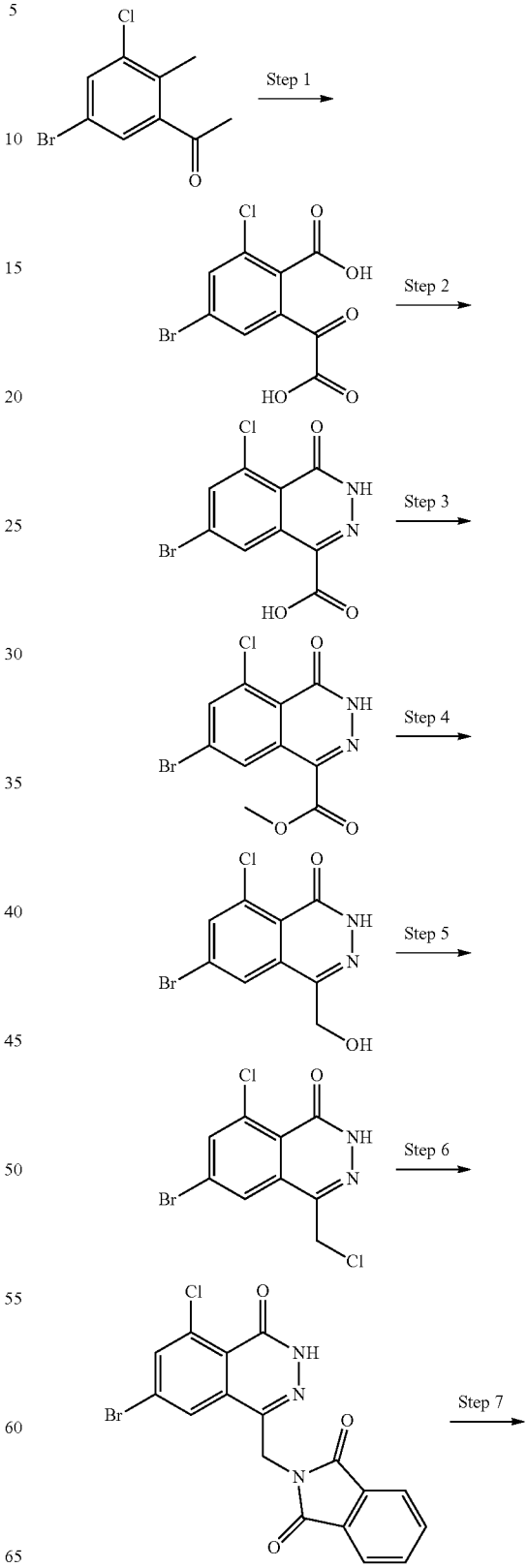

Step 1: To a stirred solution of methyl 7-bromo-4-oxo-3H-phthalazine-1-carboxylate (1.00 g, 3.53 mmol, 1.00 eq.), sodium borodeuteride (347 mg, 9.18 mmol, 2.60 eq.) in methanol-d4 (30 mL) at 0° C. was added calcium chloride (470 mg, 4.24 mmol, 1.20 eq.). The mixture then stirred at 0° C. for 3 hours then at 20° C. for 1 hour. After such time the reaction mixture was concentrated. The residue was diluted with water (30 mL), the pH adjusted to 5 with hydrochloric acid (1N, 5 mL) and the mixture filtered and the filter cake washed with water (5 mL×3) then triturated with ethyl alcohol (20 mL) to give 6-bromo-4-((hydroxy-d)methyl-d2)phthalazin-1(2H)-one (463 mg, 1.61 mmol, 46% yield) as a white solid. LCMS [M+1]$^+$=259.0; $^1$H NMR (400 MHz, DMSO-d$_6$) δ=12.66 (s, 1H), 8.31 (d, J=2.0 Hz, 1H), 8.17 (d, J=8.4 Hz, 1H), 8.02 (dd, J=2.0, 8.4 Hz, 1H), 5.53 (s, 1H).

Step 2: A mixture of 6-bromo-4-((hydroxy-d)methyl-d2)phthalazin-1(2H)-one (463 mg, 1.61 mmol, 1.00 eq.) and thionyl chloride (10 mL) was stirred at 30° C. for 12 hours. After such time the mixture was concentrated and the residue dissolved in dichloromethane and concentrated 3 times (2 mL×3) to give 6-bromo-4-(chloromethyl-d2)phthalazin-1(2H)-one (450 mg, 1.43 mmol, 88% yield) as a yellow solid. LCMS [M+1]$^+$=277.0.

Step 3: To a solution of 6-bromo-4-(chloromethyl-d2)phthalazin-1(2H)-one (450 mg, 1.63 mmol, 1.00 eq.) in DMF (3 mL) was added (1,3-dioxoisoindolin-2-yl)potassium (454 mg, 2.45 mmol, 1.50 eq.) and the mixture stirred at 90° C. for 2 hours. After such time the cooled reaction mixture was filtered and the collected solid was triturated with ethyl alcohol (5 mL), filtered and dried to give 2-((7-bromo-4-oxo-3,4-dihydrophthalazin-1-yl)methyl-d2)isoindoline-1,3-dione (300 mg, crude) as a white solid. LCMS [M+1]$^+$=386.0; $^1$H NMR (400 MHz, DMSO-d$_6$) δ=12.60 (s, 1H), 8.43 (d, J=1.6 Hz, 1H), 8.17 (d, J=8.4 Hz, 1H), 8.09-8.05 (m, 1H), 7.97-7.92 (m, 2H), 7.92-7.87 (m, 2H).

Step 4: A mixture of 2-((7-bromo-4-oxo-3,4-dihydrophthalazin-1-yl)methyl-d2)isoindoline-1,3-dione (200 mg, crude), 4,4,5,5-tetramethyl-2-(4,4,5,5-tetramethyl-1,3,2-dioxaborolan-2-yl)-1,3,2-dioxaborolane (197 mg, 0.78 mmol), Pd(dppf)Cl$_2$ (38 mg, 0.052 mmol) and potassium acetate (152 mg, 1.55 mmol) in dioxane (10 mL) was degassed with nitrogen. The mixture was stirred at 100° C. for 2 hours and after such time the mixture was concentrated and the residue triturated with methyl alcohol (3 mL), filtered and dried to give 2-((4-oxo-7-(4,4,5,5-tetramethyl-1,3,2-dioxaborolan-2-yl)-3,4-dihydrophthalazin-1-yl)methyl-d2)isoindoline-1,3-dione (200 mg, 0.303 mmol, 59% yield over 2 steps) as a white solid. LCMS [M+1]$^+$=352.1; $^1$H NMR (400 MHz, DMSO-d$_6$) δ=12.70-12.28 (m, 1H), 8.35-8.25 (m, 2H), 8.13 (br s, 1H), 7.93 (br d, J=17.0 Hz, 4H), 1.34 (br s, 12H).

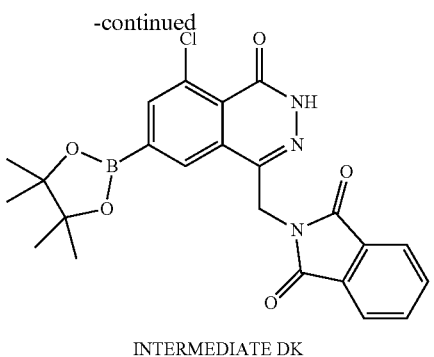

INTERMEDIATE DK

Step 1: To a solution of $K_2CO_3$ (44.7 g, 323 mmol) in water (500 mL) was added 1-(5-bromo-3-chloro-2-methylphenyl)ethan-1-one (40.0 g, 162 mmol) and warmed to 50° C. $KMnO_4$ was then added carefully in 10 batches (165 g, 1.04 mol) and the temperature maintained below 80° C. to avoid an uncontrolled exotherm. After completion of the addition the mixture was stirred at 60° C. for 6 hrs. After such time the mixture was cooled to 0° C. and quenched by the dropwise addition of saturated sodium sulfite solution (200 mL) while maintaining the temperature below 10° C. The mixture was then stirred for 30 min at 0° C. After such time the clear colorless mixture was filtrated with celatom and the filter cake was washed with water (100 mL) and the aqueous phase washed with MTBE (200 mL). The aqueous phase was then acidified to pH 2 by the addition of 3M HCl followed by extraction with ethyl acetate (300 mL×3). The combined organic phases were washed with brine (300 mL), dried with anhydrous $Na_2SO_4$, filtered and concentrated in vacuum to give compound 4-bromo-2-(carboxycarbonyl)-6-chlorobenzoic acid (20.0 g, 65.0 mmol, 36% yield) as white solid. LCMS [M−1]⁻=306.8; ¹H NMR (400 MHz, DMSO-$d_6$) δ 12.7 (s, 1H), 8.10 (s, 1H), 8.00 (s, 1H).

Step 2: To a solution of compound 4-bromo-2-(carboxycarbonyl)-6-chlorobenzoic acid (20.0 g, 65.0 mmol) in EtOH (200 mL) was added $NH_2NH_2.H_2O$ (4.30 g, 85.9 mmol) in one portion under $N_2$. The mixture was then stirred at 70° C. for 1 hr. After such time the cooled reaction mixture was filtered, washed and the solid dried in vacuum to give 7-bromo-5-chloro-4-oxo-3,4-dihydrophthalazine-1-carboxylic acid (14.0 g, 46.1 mmol, 71% yield) as white solid. LCMS [M+1]⁺=305.2; ¹H NMR (400 MHz, DMSO-$d_6$) δ 7.77 (d, J=2.0 Hz, 1H), 7.59 (d, J=2.0 Hz, 1H).

Step 3: To a mixture of 7-bromo-5-chloro-4-oxo-3,4-dihydrophthalazine-1-carboxylic acid (14.0 g, 46.1 mmol) in MeOH (250 mL) was added conc. $H_2SO_4$ (9.23 g, 92.2 mmol) in one portion under nitrogen. The mixture was then heated to 70° C. for 16 hrs then allowed to cool to ambient temperature, filtered and dried gave methyl 7-bromo-5-chloro-4-oxo-3,4-dihydrophalazine-1-carboxylate (7.50 g, 23.6 mmol, 51% yield) as a white solid. ¹H NMR (400 MHz, DMSO-$d_6$) δ 13.2 (s, 1H), 6.68 (d, J=1.6 Hz, 1H), 8.18 (d, J=1.6 Hz, 1H).

Step 4: A solution of methyl 7-bromo-5-chloro-4-oxo-3,4-dihydrophthalazine-1-carboxylate (7.50 g, 23.6 mmol) in EtOH (70 mL) was added $NaBH_4$ (2.32 g, 61.4 mmol) at 0° C. followed by the careful, slow addition of $CaCl_2$ (3.15 g, 28.3 mmol) at 0° C. over 2 hours. The mixture was then allowed to warm to 15° C. and stirred for a further 2 hours. After such time the reaction was poured onto sat. $NH_4Cl$ (100 mL) and the solid filtered, washed with water (10 mL) then EtOH (10 mL) and dried to give 6-bromo-8-chloro-4-(hydroxymethyl)phthalazin-1(2H)-one (4.00 g, 13.8 mmol, 54% yield) as white solid. LCMS [M+1]⁺=291.0; ¹H NMR (400 MHz, DMSO-$d_6$) δ 12.6 (s, 1H), 8.24 (d, J=1.6 Hz, 1H), 8.14 (d, J=1.6 Hz, 1H), 5.61-5.58 (t, J=2 Hz, 1H), 4.65-4.63 (d, J=8 Hz, 2H).

Step 5: A mixture of 6-bromo-8-chloro-4-(hydroxymethyl)phthalazin-1(2H)-one (4.00 g, 13.8 mmol) and $SOCl_2$ (36.4 g, 306 mmol) was stirred at 65° C. for 1 hr. After such time the mixture was concentrated, and the crude residue triturated with MTBE (30 mL) at 25° C. for 30 min. The solid was then filtered and dried to give 6-bromo-8-chloro-4-(chloromethyl)phthalazin-1(2H)-one (3.50 g, 11.4 mmol, 82% yield) as light yellow solid. LCMS [M+1]⁺=309.1; ¹H NMR (400 MHz, DMSO-$d_6$) δ 12.9 (s, 1H), 8.24 (s, 1H), 8.19 (s, 1H), 5.06 (s, 1H).

Step 6: To a mixture of potassium phthalimide (2.53 g, 13.6 mmol) in DMF (5 mL) was added a solution of 6-bromo-8-chloro-4-(chloromethyl)phthalazin-1(2H)-one (3.50 g, 11.3 mmol) in DMF (35 mL) at 0° C. and the mixture stirred at 0° C. for 2 hrs. After such time the mixture was poured onto ice-water (200 mL), stirred for 30 min., filtered then the solid was dried and then triturated with MeOH (30 mL) at 15° C. for 30 min. The solid was filtered and dried to give 2-((7-bromo-5-chloro-4-oxo-3,4-dihydrophthalazin-1-yl)methyl)isoindoline-1,3-dione (1.30 g, 3.10 mmol, 27% yield) as light yellow solid. LCMS [M+1]⁺=420.0; ¹H NMR (400 MHz, DMSO-$d_6$) δ 12.5 (s, 1H), 8.36 (s, 1H), 8.19 (s, 1H), 7.97-7.94 (m, 2H), 7.92-7.89 (m, 2H), 5.14 (s, 2H).

Step 7: A mixture of 2-((7-bromo-5-chloro-4-oxo-3,4-dihydrophthalazin-1-yl)methyl)isoindoline-1,3-dione (1.30 g, 3.10 mmol), bis(pinacolato)diboron (1.20 g, 4.66 mmol) and potassium acetate (762 mg, 7.76 mmol) in dioxane (20 mL) was degassed with nitrogen. Then $Pd(dppf)Cl_2$ (114 mg, 0.16 mmol) was added and the mixture stirred at 70° C. for 2.5 hrs. After such time the mixture was cooled to room temperature, filtered and the concentrated residue triturated with MeOH (30.0 mL) at 15° C. for 30 min. The solid was then filtered, washed with MTB and dried to give 2-((5-chloro-4-oxo-7-(4,4,5,5-tetramethyl-1,3,2-dioxaborolan-2-yl)-3,4-dihydrophthalazin-1-yl)methyl)isoindoline-1,3-dione (910 mg, 1.95 mmol, 63% yield) as light yellow solid. LCMS [M+1]⁺=383.9; ¹H NMR (400 MHz, DMSO-$d_6$) δ 12.5 (s, 1H), 8.20 (s, 1H), 7.79 (s, 1H), 7.96-7.94 (m, 2H), 7.91-7.89 (m, 2H), 5.17 (s, 2H), 1.35 (s, 12H).

Intermediate DL

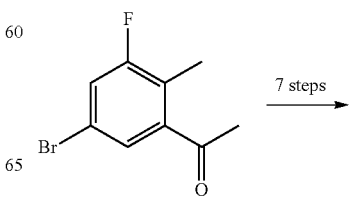

203

-continued

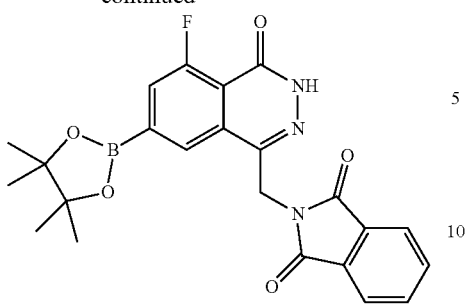

INTERMEDIATE DL

Following the same procedure for the synthesis of Intermediate DK, 2-((5-fluoro-4-oxo-7-(4,4,5,5-tetramethyl-1,3,2-dioxaborolan-2-yl)-3,4-dihydrophthalazin-1-yl)methyl)isoindoline-1,3-dione, Intermediate DL, was prepared as a white solid (200 mg, 0.42 mmol, 2.1% yield) in 7 steps from 1-(5-bromo-3-fluoro-2-methylphenyl)ethan-1-one. LCMS [M+1]$^+$=368.1; $^1$H NMR (400 MHz, DMSO-d$_6$) δ=12.51 (s, 1H), 8.09 (s, 1H), 7.96-7.89 (m, 4H), 7.40 (d, 1H), 5.17 (s, 2H), 1.36 (s, 12H).

Intermediate DM

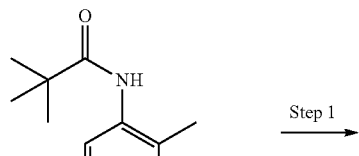

Step 1

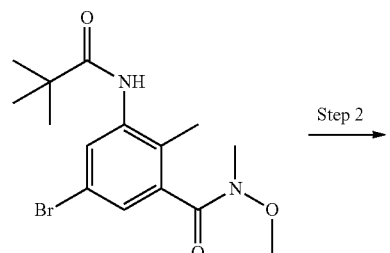

Step 2

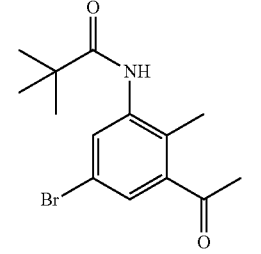

Step 3

204

-continued

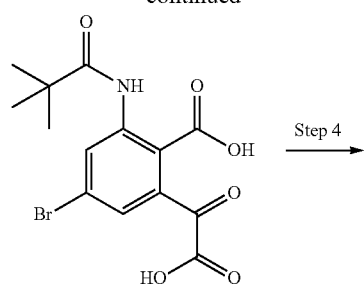

Step 4

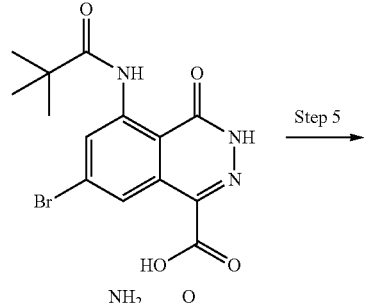

Step 5

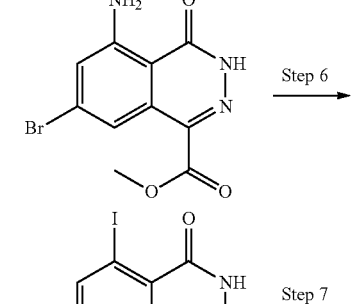

Step 6

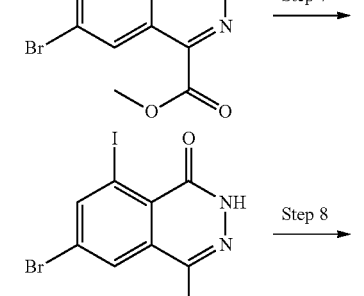

Step 7

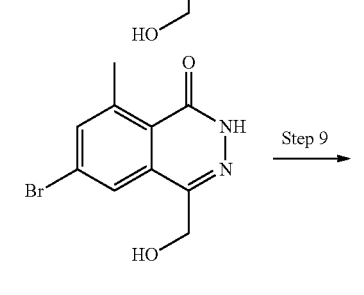

Step 8

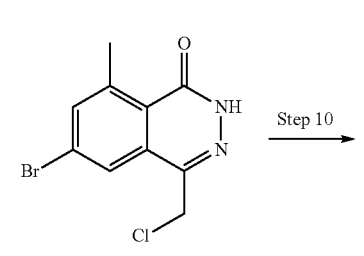

Step 9

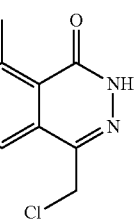

Step 10

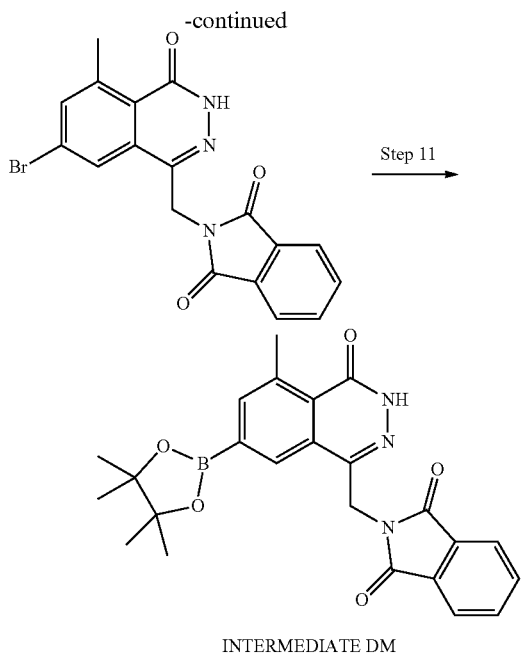

INTERMEDIATE DM

Step 1: To a solution of 5-bromo-2-methyl-3-pivalamidobenzoic acid (120 g, 382 mmol) in DMF (1.20 L) was added DIEA (98.7 g, 764 mmol, 133 mL), HATU (189 g, 497 mmol), followed by N,O-dimethylhydroxylamine (55.9 g, 573 mmol, HCl) at 20° C. The resulting solution was stirred at 20° C. for 2 hrs and after such time the reaction mixture was poured into ice water (5.0 L). The mixture was extracted with ethyl acetate (2.0 L×3) and the combined organic phase was washed with brine (1.0 L), dried with anhydrous $Na_2SO_4$, filtered and the filtrate was concentrated under reduced pressure to dry to afford 5-bromo-N-methoxy-N,2-dimethyl-3-pivalamidobenzamide (135 g, 378 mmol, 99% yield) as brown oil. $^1$H NMR: 400 MHz, DMSO-d6 δ 9.06 (s, 1H), 7.45 (d, J=2.0 Hz, 1H), 7.35 (d, J=2.0 Hz, 1H), 3.43 (s, 3H), 3.27 (s, 3H), 2.01 (s, 3H), 1.23 (s, 9H).

Step 2: To a solution of 5-bromo-N-methoxy-N,2-dimethyl-3-pivalamidobenzamide (135 g, 378 mmol) in THF (1.5 L) was added MeMgBr (3.0 M, 315 mL) at 0° C. The resulting solution was allowed to warm to 20° C. and stirred for 12 hrs. After such time an additional aliquot of MeMgBr (3 M, 63.0 mL) was added and the mixture stirred for a further 4 hrs. The mixture was then diluted with $NH_4Cl$ (1.5 L), extracted with ethyl acetate (1.0 L×3) and the combined organic phases were washed with brine (1.0 L), dried with anhydrous $Na_2SO_4$ and filtered. The filtrate was concentrated to afford N-(3-acetyl-5-bromo-2-methylphenyl)pivalamide (115 g, 368 mmol, 98% yield) as yellow solid. $^1$H NMR 400 MHz, DMSO-d6 δ 9.10 (s, 1H), 7.75 (d, J=2.0 Hz, 1H), 7.51 (d, J=2.0 Hz, 1H), 2.55 (s, 3H), 2.10 (s, 3H), 1.23 (s, 9H).

Step 3: To a solution of N-(3-acetyl-5-bromo-2-methylphenyl)pivalamide (57.5 g, 184 mmol) in $H_2O$ (600 mL) was added $K_2CO_3$ (50.9 g, 368 mmol) and $KMnO_4$ (204 g, 1.29 mol) at 50° C. The result solution was stirred at 50° C. for 17 hrs. After such time the reaction mixture was quenched by saturated sodium thiosulfate solution and filtered through diatomite. The pH was adjusted to 2 with 2N HCl and the mixture extracted with an ethyl acetate:THF 10:1 mixture (1.00 L×3), washed with brine (500 mL), dried over $Na_2SO_4$, filtered and concentrated under reduced pressure to give 4-bromo-2-(carboxycarbonyl)-6-pivalamidobenzoic acid (58.0 g, crude) as light yellow oil. $^1$H NMR 400 MHz, DMSO-d6 δ 9.87 (s, 1H), 8.63 (d, J=2.0 Hz, 1H), 7.54 (d, J=2.0 Hz, 1H), 1.27 (s, 9H).

Step 4: To a solution of 4-bromo-2-(carboxycarbonyl)-6-pivalamidobenzoic acid (110 g, 296 mmol) in EtOH (1.10 L) was added $NH_2NH_2.H_2O$ (18.1 g, 355 mmol, 17.6 mL) and the solution was stirred at 75° C. for 3 hrs. After such time the reaction mixture was filtered and the filter cake dried to give 7-bromo-4-oxo-5-pivalamido-3,4-dihydrophthalazine-1-carboxylic acid (30.0 g, 81.5 mmol, 28% yield) as white solid. $^1$H NMR 400 MHz, DMSO-d6 δ 13.0 (s, 1H), 9.06 (d, J=2.0 Hz, 1H), 8.18 (d, J=2.0 Hz, 1H), 1.27 (s, 9H).

Step 5: To a solution of 7-bromo-4-oxo-5-pivalamido-3,4-dihydrophthalazine-1-carboxylic acid (30.0 g, 81.5 mmol) in MeOH (400 mL) was added a solution of HCl/MeOH (4 M, 400 mL). The reaction mixture was warmed to 70° C. and stirred for 36 hrs to form a yellow solid. The reaction was concentrated, diluted with water (100 mL) and the pH adjusted to pH 8 with 1 N NaOH, stirred for 0.5 hr then filtered. The filter cake was washed with water (50 mL) then EtOH (100 mL) and dried to give the crude product methyl 5-amino-7-bromo-4-oxo-3,4-dihydrophthalazine-1-carboxylate (20.0 g, crude) as a yellow solid.

Step 6: To a solution of methyl 5-amino-7-bromo-4-oxo-3,4-dihydrophthalazine-1-carboxylate (15.0 g, 50.3 mmol) in MeCN (500 mL) was added TosOH (34.6 g, 200 mmol) at 0° C. under $N_2$. To this solution was added a solution of $NaNO_2$ (8.68 g, 125 mmol) in $H_2O$ (20 mL) and the mixture was stirred at 0° C. for 10 minutes then a solution of KI (25.0 g, 150 mmol) in $H_2O$ (20.0 mL) was added dropwise. The mixture was stirred at 20° C. for 1 hr and the reaction was quenched by $Na_2S_2O_3$. The mixture was concentrated to remove the MeCN then diluted with water (200 mL) and filtered. The filter cake was washed with water (50 mL) then EtOH (100 mL) and dried to give the methyl 7-bromo-5-iodo-4-oxo-3,4-dihydrophthalazine-1-carboxylate (15.0 g, crude) as a yellow solid.

Step 7: In 8 batches a solution of methyl 7-bromo-5-iodo-4-oxo-3,4-dihydrophthalazine-1-carboxylate (4.00 g, 9.78 mmol) in EtOH (60 mL) was added $NaBH_4$ (740 mg, 19.6 mmol) in batches at 0° C. followed by the addition of $CaCl_2$ (1.30 g, 11.7 mmol) in batches at 0° C. The reaction was stirred at 20° C. for 1 hr. The 8 batches were then combined and quenched with $NH_4Cl$ (200 mL). The mixture was concentrated to remove EtOH, diluted with water (200 mL) and then filtered and the filter cake was washed with water (100 mL) and dried. The residue was triturated in MeOH (200 mL) for 10 hrs, filtered and dried to give the 6-bromo-4-(hydroxymethyl)-8-iodophthalazin-1(2H)-one (19.0 g, 38.9 mmol, 50% yield) as a yellow solid. $^1$H NMR 400 MHz, DMSO-d6 δ 12.64 (s, 1H), 8.56 (d, J=1.88 Hz, 1H), 8.29 (d, J=1.88 Hz, 1H), 5.62-5.54 (m, 1H), 4.62 (d, J=5.70 Hz, 2H).

Step 8: In three batches, to a mixture of 6-bromo-4-(hydroxymethyl)-8-iodophthalazin-1(2H)-one (2.00 g, 5.25 mmol) in dioxane (40 mL) was added a solution of 2,4,6-trimethyl-1,3,5,2,4,6-trioxatriborinane in THF (3.67 mL, 13.1 mmol, 50% purity), $Cs_2CO_3$ (4.28 g, 13.1 mmol) and Pd(dppf)$Cl_2$ (384 mg, 524 μmol). The reaction was stirred at 100° C. for 10 hrs. The three batches were combined and filtered through diatomite. The filtrate was concentrated and the residue purified by Prep-HPLC (Phenomenex luna C18 250×150 mm×15 μm; mobile phase: [water (0.1% TFA)-MeOH]; B %: 30%-60%, 20 min) to give the 6-bromo-4-(hydroxymethyl)-8-methylphthalazin-1(2H)-one (1.1 g, 4.06 mmol, 26% yield) as a light yellow solid. LCMS

[M+1]⁺=271; ¹H NMR 400 MHz, DMSO-d6 δ 12.44 (s, 1H), 8.10 (s, 1H), 7.82 (s, 1H), 4.63 (s, 3H), 2.81 (s, 3H).

Step 9: A solution of 6-bromo-4-(hydroxymethyl)-8-methylphthalazin-1(2H)-one (1.20 g, 4.46 mmol) in SOCl₂ (13 mL) was stirred at 70° C. for 2 hr. After such time the mixture was concentrated and the residue triturated in petroleum ether for 0.5 hr, filtered and dried to give 6-bromo-4-(chloromethyl)-8-methylphthalazin-1(2H)-one (1.20 g, 4.17 mmol, 94% yield) as a light yellow solid. LCMS [M+1]⁺=289; ¹H NMR 400 MHz, DMSO-d₆ δ 12.70 (s, 1H), 8.08 (s, 1H), 7.88 (s, 1H), 5.03 (s, 2H), 2.81 (s, 3H).

Step 10: To a mixture of give 6-bromo-4-(chloromethyl)-8-methylphthalazin-1(2H)-one (1.10 g, 3.83 mmol) in DMF (30 mL) was added potassium isoindoline-1,3-dione (850 mg, 4.59 mmol) in one portion at 0° C. under N₂. The mixture was stirred at 25° C. for 1 hr and after such time the mixture was slowly poured into ice water (100 mL) and the formed white solid was filtrated, washed with water and dried to give the crude product 2-((7-bromo-5-methyl-4-oxo-3,4-dihydrophthalazin-1-yl)methyl)isoindoline-1,3-dione (1.10 g, 2.32 mmol, 61% yield) as a white solid. LCMS [M+1]⁺=400; ¹H NMR 400 MHz, DMSO-d6 δ 12.37 (s, 1H), 8.20 (d, J=1.32 Hz, 1H), 7.97-7.87 (m, 5H), 5.12 (s, 2H), 2.81 (s, 3H).

Step 11: 2-((7-bromo-5-methyl-4-oxo-3,4-dihydrophthalazin-1-yl)methyl)isoindoline-1,3-dione (1.10 g, 2.76 mmol), Pd(dppf)Cl₂ (202 mg, 276 μmol), KOAc (542 mg, 5.52 mmol) and bis(pinacolato)diboron (1.05 g, 4.14 mmol) in dioxane (20 mL) was de-gassed with nitrogen then heated at 80° C. for 10 hours. After such time the reaction was filtered through diatomite and the cake washed with MeOH (10 mL) and the filtrate concentrated. The residue was then triturated with MeOH (10 mL) for 1 hr, filtered and the filter cake washed with MeOH and dried to give 2-((5-methyl-4-oxo-7-(4,4,5,5-tetramethyl-1,3,2-dioxaborolan-2-yl)-3,4-dihydrophthalazin-1-yl)methyl)isoindoline-1,3-dione, Intermediate DM (510 mg, 1.15 mmol, 42% yield) as a gray solid. LCMS:Boronic acid [M+1]⁺=364; boronate ester [M+1]⁺=446). ¹H NMR 400 MHz, DMSO-d6 δ 12.27 (s, 1H), 8.06 (s, 1H), 7.92-7.82 (m, 5H), 5.11 (s, 2H), 2.80 (s, 3H), 1.31 (s, 12H).

trated under reduced pressure. The residue was purified by column chromatography (SiO₂, petroleum ether/ethyl acetate 10-50%) to give 3-(2-methylpyrazol-3-yl)-2-phenyl-propanenitrile (300 mg, 1.42 mmol, 41% yield) as a brown oil. LCMS [M+1]⁺=212.0; ¹H NMR (400 MHz, CDCl₃) δ=7.35-7.22 (m, 4H), 7.18-7.10 (m, 2H), 6.11 (d, J=1.6 Hz, 1H), 3.98 (t, J=6.8 Hz, 1H), 3.41 (s, 3H), 3.26-3.18 (m, 1H), 3.16-3.05 (m, 1H).

Step 2: To a mixture of 3-(2-methylpyrazol-3-yl)-2-phenyl-propanenitrile (160 mg, 0.76 mmol, 1.00 eq.) in dry acetonitrile (2.0 mL) was added NBS (121 mg, 0.68 mmol, 0.90 eq.) in several portions. The mixture was stirred at 15° C. for 2 hours. After such time ethyl acetate (40 mL) and water (40 mL) were added and the layers separated. The aqueous phase was extracted with ethyl acetate (30 mL×2) and the combined organic extracts were washed with brine (50 mL), dried over anhydrous sodium sulfate, filtered, and concentrated in vacuum. The residue was purified by prep-HPLC (Phenomenex Gemini-NX C18 75×30 mm×3 μm; mobile phase: [water (10 mM NH₄HCO₃)-ACN]; B %: 30%-60%, 8 min) to give 3-(4-bromo-2-methyl-pyrazol-3-yl)-2-phenyl-propanenitrile (90.0 mg, 0.31 mmol, 41% yield) as a yellow oil. LCMS [M+1]⁺=289.8; ¹H NMR (400 MHz, CDCl₃) δ=7.37 (s, 1H), 7.35-7.26 (m, 3H), 7.20-7.14 (m, 2H), 4.04 (t, J=7.6 Hz, 1H), 3.40 (s, 3H), 3.30 (dd, J=7.2, 14.8 Hz, 1H), 3.07 (dd, J=8.0, 14.8 Hz, 1H).

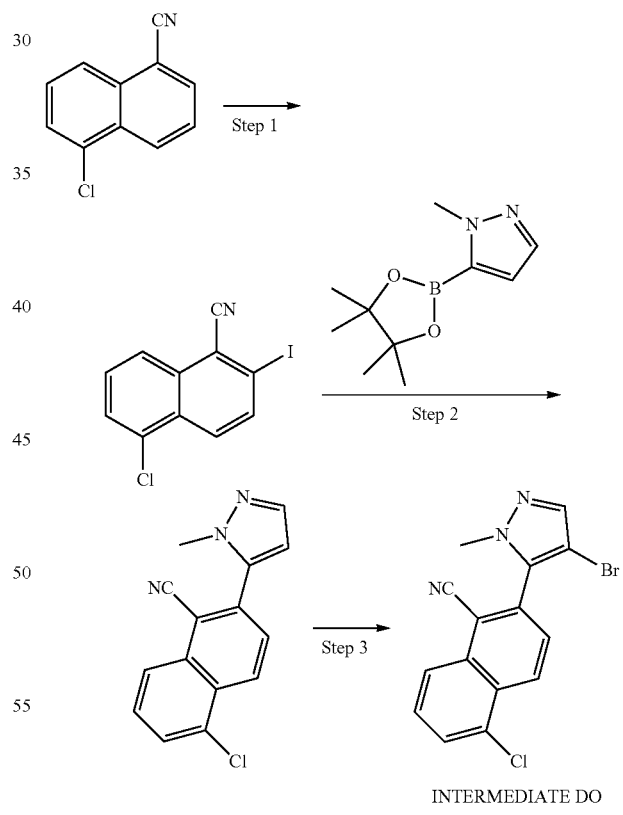

INTERMEDIATE DO

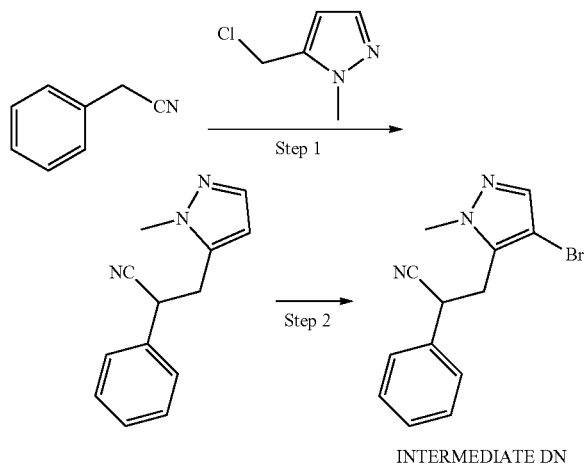

INTERMEDIATE DN

Step 1: To a solution of 5-(chloromethyl)-1-methyl-pyrazole (584 mg, 3.50 mmol, 1.00 eq) and 2-phenylacetonitrile (819 mg, 6.99 mmol, 2.00 eq.) in DMF (10 mL) was added potassium carbonate (966 mg, 6.99 mmol, 2.00 eq.). The mixture was stirred at 120° C. for 4 hours then and concen- Step 1: n-Butyllithium (2.5 M in hexane, 959 μL, 1.50 eq.) was added dropwise over 5 minutes to a solution of 2,2,6,6-tetramethylpiperidine (2.40 mmol, 407 μL, 1.50 eq.) in THF (3 mL) maintained at 0° C. After 30 minutes, the reaction mixture was cooled to −78° C. and a solution of 5-chloronaphthalene-1-carbonitrile (300 mg, 1.60 mmol, 1.00 eq.) in THF (1.00 mL) was added dropwise over 10 minutes. The resulting dark solution was maintained at −78° C. for 2 hours. A solution of iodine (609 mg, 2.40 mmol, 1.50 eq.) in THF (3 mL) was then added dropwise over 10 minutes. The reaction mixture was maintained at −78° C. for 2 hours then allowed to warm to 20° C. for 3 hours. The reaction mixture was quenched with water (1 mL) and the resulting mixture diluted with ethyl acetate (150 mL). The mixture was washed successively with saturated aqueous sodium thiosulfate (3×150 mL), 1 M HCl (2×150 mL), and brine (1×150 mL). The organic layer was dried over anhydrous sodium sulfate, filtered, and concentrated. The residue was purified by column chromatography (SiO$_2$, petroleumether:ethylacetate 5%) to give 5-chloro-2-iodo-1-naphthonitrile (180 mg, 574 μmol, 36% yield) as a yellow solid. GCMS [M+H]$^+$=312.9; $^1$H NMR (400 MHz, CDCl$_3$) δ=8.55 (d, J=8.8 Hz, 1H), 8.01-7.97 (m, 1H), 7.73-7.69 (m, 1H), 7.67-7.64 (m, 1H), 7.63-7.58 (m, 1H).

Step 2: A mixture of 1-methyl-5-(4,4,5,5-tetramethyl-1,3,2-dioxaborolan-2-yl)-1H-pyrazole (104 mg, 498 μmol, 1.30 eq.), 5-chloro-2-iodo-1-naphthonitrile (120 mg, 383 μmol, 1.00 eq.), Pd(dtbpf)Cl$_2$(25 mg, 38 μmol, 0.10 eq.) and sodium carbonate (81 mg, 766 μmol, 2.00 eq.) in the dioxane (3 mL) and water (0.6 mL) was degassed with nitrogen then stirred at 80° C. for 1 hour. The mixture was then concentrated and the residue purified by prep-TLC (SiO$_2$, petroleum ether:ethyl acetate 30%) to give 5-chloro-2-(2-methylpyrazol-3-yl)naphthalene-1-carbonitrile (90 mg, 336 μmol, 87% yield) as a yellow solid. LCMS [M+1]$^+$=268.2; $^1$H NMR (400 MHz, CDCl$_3$) δ=8.62 (d, J=8.8 Hz, 1H), 8.30 (d, J=8.4 Hz, 1H), 7.81-7.77 (m, 1H), 7.73-7.67 (m, 1H), 7.67-7.63 (m, 2H), 6.61 (d, J=2.0 Hz, 1H), 3.91 (s, 3H).

Step 3: To a solution of 5-chloro-2-(2-methylpyrazol-3-yl)naphthalene-1-carbonitrile (170 mg, 635 μmol, 1.00 eq.) in acetonitrile (3 mL) was added NBS (124 mg, 699 μmol, 1.10 eq.). The mixture was stirred at 35° C. for 2 hours then concentrated to give a residue. The residue was purified by prep-TLC (SiO$_2$, petroleum ether/ethyl acetate 30%) to give 2-(4-bromo-1-methyl-1H-pyrazol-5-yl)-5-chloro-1-naphthonitrile, Intermediate DO (130 mg, 375 μmol, 59% yield) as a white solid. LCMS [M+1]$^+$=347.8; $^1$H NMR (400 MHz, CDCl$_3$) δ=8.67 (dd, J=0.8, 8.8 Hz, 1H), 8.31 (d, J=8.4 Hz, 1H), 7.83 (dd, J=1.2, 7.6 Hz, 1H), 7.75-7.69 (m, 1H), 7.66 (s, 1H), 7.64 (d, J=8.8 Hz, 1H), 3.86 (s, 3H).

Step 1: To a solution of 2,2,6,6-tetramethylpiperidine (553 mg, 3.92 mmol, 0.67 mL, 1.20 eq.) in THF (7 mL) was added n-butyl lithium (2.50 M, 1.57 mL, 1.20 eq.) at −10° C. under a nitrogen atmosphere. The mixture was stirred for 10 minutes, cooled to −65° C. and triisopropyl borate (859 mg, 4.57 mmol, 1.05 mL, 1.40 eq.) was added. After 5 minutes, a solution of 1-naphthonitrile (500 mg, 3.26 mmol, 1.00 eq.) in THF (3 mL) was added in a dropwise fashion and the reaction was then allowed to warm slowly to 25° C. and then stirred for 16 hours. After such time acetic acid (392 mg, 6.53 mmol, 0.37 mL, 2.00 eq.) was added followed by the addition of propane-1,3-diol (994 mg, 13.1 mmol, 0.95 mL, 4.00 eq.) then the mixture was stirred at 25° C. for 1 hour. The reaction was then quenched by the addition of saturated ammonium chloride solution (20 mL) and then diluted with water (10 mL) and extracted with ethyl acetate (30 mL×2). The combined organic layers were dried over anhydrous sodium sulfate, filtered and concentrated under reduced pressure to give 2-(1,3,2-dioxaborinan-2-yl)-1-naphthonitrile (600 mg, 2.53 mmol, 78% yield) as a light-yellow solid. $^1$H NMR (400 MHz, CDCl$_3$) δ=8.40 (d, J=8.0 Hz, 1H), 8.04-8.00 (m, 1H), 7.90 (d, J=8.0 Hz, 2H), 7.71-7.60 (m, 2H), 4.30 (t, J=5.6 Hz, 4H), 2.17 (quin, J=5.6 Hz, 2H).

Step 2: To a solution of 5-bromoisothiazole (150 mg, 0.915 mmol, 1.00 eq.) and 2-(1,3,2-dioxaborinan-2-yl)-1-naphthonitrile (217 mg, 0.915 mmol, 1.00 eq.) in toluene (8 mL) and ethyl alcohol (0.8 mL) were added aqueous potassium carbonate (2.00 M, 0.915 mL, 2.00 eq.) and Pd(PPh$_3$)$_4$ (106 mg, 0.091 mmol, 0.10 eq.) at 20° C. under a nitrogen atmosphere. The mixture was stirred at 100° C. for 16 hours, concentrated to dryness and the residue was purified by column chromatography (SiO$_2$, petroleumether:ethylacetate 10-15%) to give 2-(isothiazol-5-yl)-1-naphthonitrile (200 mg, 0.85 mmol, 93% yield) as a light yellow solid. $^1$H NMR (400 MHz, CDCl$_3$) δ=8.62 (d, J=1.6 Hz, 1H), 8.37 (d, J=8.8 Hz, 1H), 8.15 (d, J=8.8 Hz, 1H), 7.97 (d, J=8.0 Hz, 1H), 7.89 (d, J=2.0 Hz, 1H), 7.79 (dt, J=1.2, 7.6 Hz, 1H), 7.74-7.66 (m, 2H).

Step 3: To a solution of 2-(isothiazol-5-yl)-1-naphthonitrile (100 mg, 0.42 mmol, 1.00 eq.) in acetonitrile (2 mL) was added N-bromo-succinimide (753 mg, 4.23 mmol, 10.0 eq.) at 20° C. and the mixture was stirred at 100° C. for 48 hours in a sealed tube. The mixture was then concentrated under reduced pressure and the residue diluted with ethyl acetate (30 mL) and washed with water (30 mL×2), dried over anhydrous sodium sulfate, filtered and concentrated. The residue was then purified by prep-HPLC (Waters Xbridge BEH C18 100×30 mm×10 μm; mobile phase: [water (10 mM NH$_4$HCO$_3$)-ACN]; B %: 45%-75%, 8 min) to give 2-(4-bromoisothiazol-5-yl)-1-naphthonitrile (50 mg, 0.16 mmol, 38% yield) as a white solid. $^1$H NMR (400 MHz, CDCl$_3$) δ=8.51 (s, 1H), 8.37 (d, J=8.8 Hz, 1H), 8.19 (d, J=8.8 Hz, 1H), 8.02 (d, J=8.0 Hz, 1H), 7.81 (dt, J=1.2, 7.6 Hz, 1H), 7.77-7.69 (m, 1H), 7.59 (d, J=8.4 Hz, 1H).

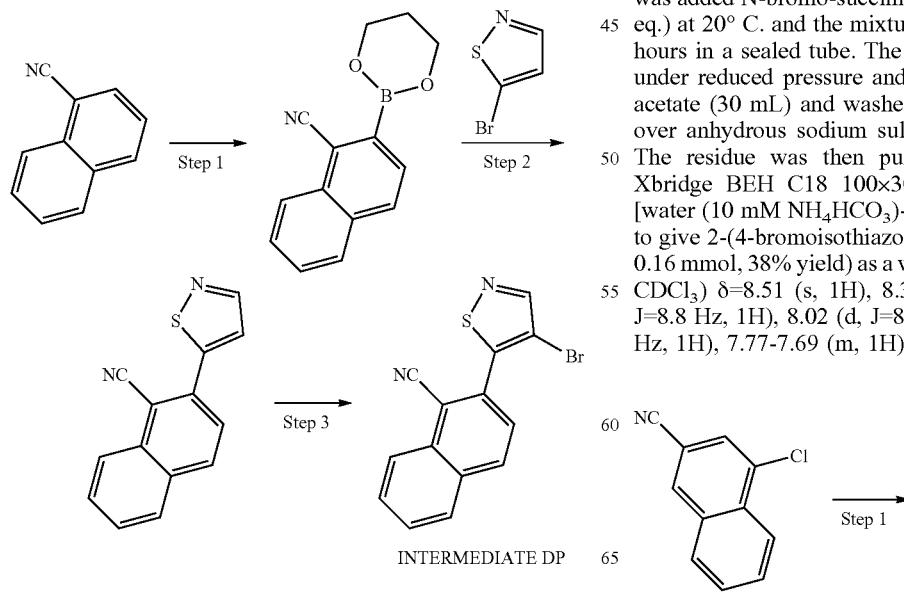

INTERMEDIATE DP

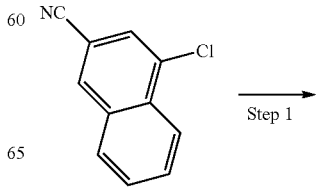

-continued

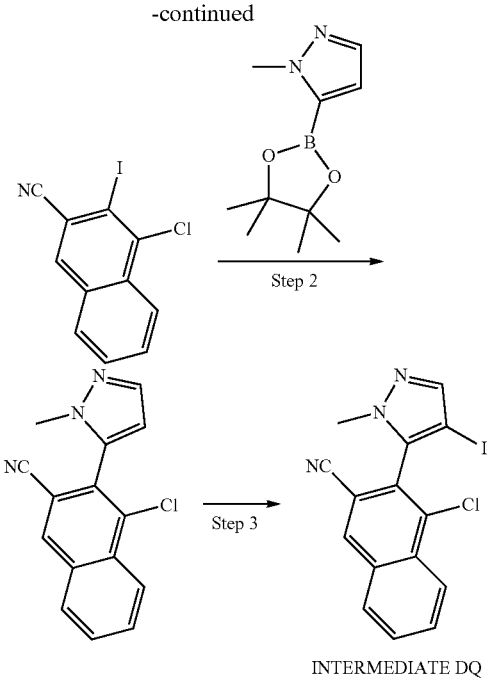

INTERMEDIATE DQ

Step 1: To a solution of LDA (2.00 M, 0.587 mL, 1.10 eq.) in THF (10 mL) was added in a dropwise fashion a solution of 4-chloro-2-naphthonitrile (200 mg, 1.07 mmol, 1.00 eq) in THF (5 mL) at −78° C. Then the mixture was stirred at −78° C. for 1 hour. After such time a solution of iodine (285 mg, 1.12 mmol, 1.05 eq.) in THF (2 mL) was added dropwise at −78° C. The mixture was then allowed to warm to room temperature and stirred at 20° C. for 2 hours. After such time the reaction mixture was quenched by adding saturated ammonium chloride solution (15 mL) and saturated sodium hyposulfite solution (10 mL×3). The mixture was then extracted with ethyl acetate (20 mL×2) and the combined organic layers were dried over anhydrous sodium sulfate, filtered, concentrated and the residue purified by flash chromatography (SiO$_2$, petroleumether:ethylacetate 0-5%) to give 4-chloro-3-iodo-2-naphthonitrile (200 mg, 0.606 mmol, 30% yield) as a white solid. $^1$H NMR (400 MHz, CDCl$_3$) δ=8.35 (d, J=8.4 Hz, 1H), 8.13 (s, 1H), 7.93-7.87 (m, 1H), 7.77 (ddd, J=1.2, 7.2, 8.4 Hz, 1H), 7.72-7.65 (m, 1H).

Step 2: To a solution of 4-chloro-3-iodo-2-naphthonitrile (320 mg, 1.02 mmol, 1.00 eq.) and 1-methyl-5-(4,4,5,5-tetramethyl-1,3,2-dioxaborolan-2-yl)pyrazole (319 mg, 1.53 mmol, 1.50 eq.) in dioxane (30 mL) and water (6 mL) was added potassium carbonate (283 mg, 2.04 mmol, 2.00 eq.) and Pd(dppf)Cl$_2$ (75 mg, 0.102 mmol, 0.10 eq.) at 25° C. The mixture was degassed with nitrogen then stirred at 100° C. for 16 hours. The reaction mixture was then quenched with water (20 mL) and extracted with ethyl acetate (30 mL×4). The combined organic layers were washed with brine (25 mL×2), dried over anhydrous sodium sulfate, filtered, concentrated and the residue purified by flash chromatography (SiO$_2$, petroleumether:ethylacetate 0-5%) to give 4-chloro-3-(1-methyl-1H-pyrazol-5-yl)-2-naphthonitrile (50 mg, 0.178 mmol, 30% yield) as a yellow solid. LCMS [M+1]$^+$=268.0/270.0; $^1$H NMR (400 MHz, CDCl$_3$) δ=8.48-8.39 (m, 1H), 8.34-8.27 (m, 1H), 8.04-7.95 (m, 1H), 7.90-7.81 (m, 1H), 7.78 (br t, J=7.6 Hz, 1H), 7.70-7.63 (m, 1H), 6.52-6.43 (m, 1H), 3.80-3.72 (m, 3H).

Step 3: To a solution of 4-chloro-3-(1-methyl-1H-pyrazol-5-yl)-2-naphthonitrile (100 mg, 0.374 mmol, 1.00 eq.) in acetonitrile (10 mL) was added N-iodosuccinimide (504 mg, 2.24 mmol, 6.00 eq.) at 25° C. and the mixture was stirred at 80° C. for 16 hours. After such time the reaction mixture was quenched with water (2 mL) at 0° C., and then extracted with ethyl acetate (3 mL×3). The combined organic layers were washed with brine (5 mL×2), dried over anhydrous sodium sulfate, filtered and concentrated. The formed residue was purified by prep-TLC (SiO$_2$, petroleumether:ethylacetate 30%) to give 4-chloro-3-(4-iodo-1-methyl-1H-pyrazol-5-yl)-2-naphthonitrile (50 mg, 0.121 mmol, 32% yield) as a white solid. LCMS [M+1]$^+$=393.9/395.9; $^1$H NMR (400 MHz, CDCl$_3$) δ=8.46 (d, J=8.4 Hz, 1H), 8.35 (s, 1H), 8.04 (d, J=8.0 Hz, 1H), 7.92-7.86 (m, 1H), 7.84-7.79 (m, 1H), 7.71 (s, 1H), 3.81 (s, 3H).

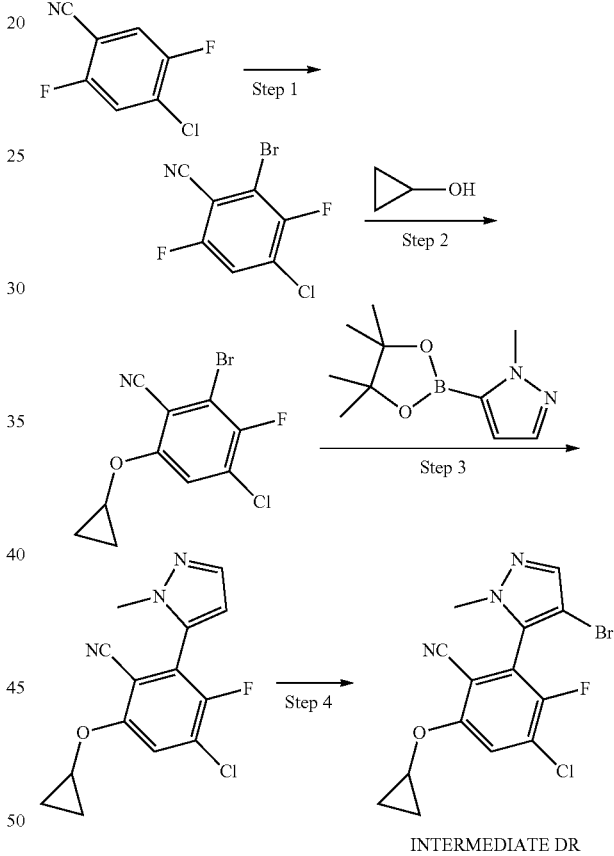

INTERMEDIATE DR

Step 1: A mixture of 4-chloro-2,5-difluoro-benzonitrile (2.00 g, 11.5 mmol, 1.00 eq.), N-bromosuccinimide (4.10 g, 23.1 mmol, 2.00 eq.), palladium acetate (259 mg, 1.15 mmol, 0.10 eq.) and p-toluene sulphonic acid (992 mg, 5.76 mmol, 0.50 eq.) in dichloroethane (50 mL) was degassed with nitrogen then stirred at 75° C. for 12 hours. After such time the cooled mixture was extracted with dichloromethane (50 mL×3), washed with brine (50 mL), dried over anhydrous sodium sulfate, filtered, concentrated under reduced pressure and the residue purified by column chromatography (SiO$_2$, petroleum ether:ethyl acetate 0-3%) to give 2-bromo-4-chloro-3,6-difluoro-benzonitrile (1.10 g, 4.36 mmol, 38% yield) as a white solid. $^1$H NMR (400 MHz, CDCl$_3$) δ=7.38-7.31 (m, 1H).

Step 2: A mixture of 2-bromo-4-chloro-3,6-difluoro-benzonitrile (1.10 g, 4.36 mmol, 1.00 eq.), cyclopropanol (380 mg, 6.54 mmol, 1.50 eq.) and potassium carbonate (1.51 g, 10.9 mmol, 2.50 eq.) in DMF (10 mL) was degassed with nitrogen then stirred at 75° C. for 2 hours. After such time the mixture was concentrated and the residue was purified by prep-TLC (SiO$_2$, petroleumether:ethylacetate 7%) to give 2-bromo-4-chloro-6-(cyclopropoxy)-3-fluoro-benzonitrile (600 mg, 2.07 mmol, 47% yield) as a white solid. $^1$H NMR (400 MHz, CDCl$_3$) δ=7.36 (d, J=5.6 Hz, 1H), 3.88-3.79 (m, 1H), 0.91 (d, J=4.8 Hz, 4H).

Step 3: A mixture of 1-methyl-5-(4,4,5,5-tetramethyl-1,3,2-dioxaborolan-2-yl)pyrazole (1.29 g, 6.20 mmol, 3.00 eq.), 2-bromo-4-chloro-6-(cyclopropoxy)-3-fluoro-benzonitrile (600 mg, 2.07 mmol, 1.00 eq.), aqueous sodium bicarbonate (694 mg, 8.26 mmol, 0.321 mL, 4.00 eq.), ditert-butyl (cyclopentyl)phosphane; dichloropalladium-iron (135 mg, 0.207 mmol, 0.10 eq.) in dioxane (20 mL) and water (4 mL) was degassed with nitrogen and the mixture was stirred at 80° C. for 16 hours. After such time the mixture was concentrated and the residue purified by column chromatography (SiO$_2$, petroleum ether: ethyl acetate 5-20%) to give 4-chloro-6-(cyclopropoxy)-3-fluoro-2-(2-methylpyrazol-3-yl)benzonitrile (180 mg, 0.524 mmol, 25% yield) as a yellow solid. LCMS [M+1]$^+$=292.1; $^1$H NMR (400 MHz, CDCl$_3$) δ=7.62 (d, J=2.0 Hz, 1H), 7.49 (d, J=6.0 Hz, 1H), 6.50 (d, J=2.0 Hz, 1H), 3.92-3.85 (m, 1H), 3.81 (d, J=1.2 Hz, 3H), 0.96-0.92 (m, 4H).

Step 4: A mixture of 4-chloro-6-(cyclopropoxy)-3-fluoro-2-(2-methylpyrazol-3-yl)benzonitrile (180 mg, 0.617 mmol, 1.00 eq) and N-bromosuccinimide (220 mg, 1.23 mmol, 2.00 eq.) in acetonitrile (10 mL) was stirred at 40° C. for 2 hours under a nitrogen atmosphere. After such time the mixture was concentrated and the residue was purified by prep-TLC (SiO$_2$, petroleumether:ethylacetate 20%) to give 2-(4-bromo-2-methyl-pyrazol-3-yl)-4-chloro-6-(cyclopropoxy)-3-fluoro-benzonitrile (170 mg, 0.455 mmol, 74% yield) as a white solid. LCMS [M+1]$^+$=371.8; $^1$H NMR (400 MHz, CDCl$_3$) δ=7.61 (s, 1H), 7.55 (d, J=6.0 Hz, 1H), 3.93-3.85 (m, 1H), 3.80 (s, 4H), 0.97-0.94 (m, 4H).

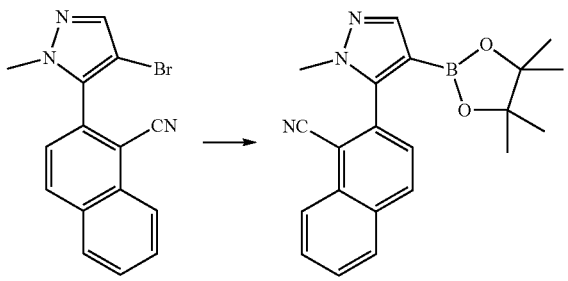

INTERMEDIATE DC

A mixture of 2-(4-bromo-2-methyl-pyrazol-3-yl)naphthalene-1-carbonitrile (150 mg, 0.48 mmol, 1.00 eq.), 4,4,5,5-tetramethyl-2-(4,4,5,5-tetramethyl-1,3,2-dioxaborolan-2-yl)-1,3,2-dioxaborolane (134 mg, 0.528 mmol, 1.10 eq.), potassium acetate (141 mg, 1.44 mmol, 3.00 eq.) and ditert-butyl(cyclopentyl)phosphane; dichloropalladium-iron (31.3 mg, 0.048 mmol, 0.10 eq.) in dioxane (3 mL) was degassed with nitrogen and then stirred at 80° C. for 2 hours. After such time the reaction mixture was concentrated under reduced pressure to give 2-[2-methyl-4-(4,4,5,5-tetramethyl-1,3,2-dioxaborolan-2-yl)pyrazol-3-yl]naphthalene-1-carbonitrile (160 mg, crude) as brown liquid which used into the next step without further purification. LCMS [M+1]$^+$=360.2.

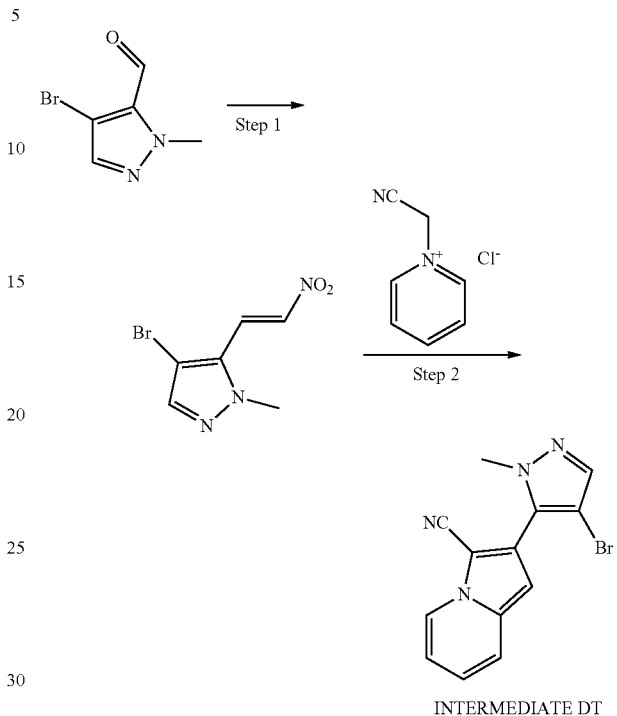

INTERMEDIATE DT

Step 1: To a solution of 4-bromo-2-methyl-pyrazole-3-carbaldehyde (1.00 g, 5.29 mmol, 1.00 eq.) and nitromethane (420 mg, 6.88 mmol, 0.37 mL, 1.30 eq.) in methanol (10 mL) was added in a dropwise fashion a solution of sodium hydroxide (466 mg, 11.6 mmol, 2.20 eq.) in water (1 mL) at 0° C. The reaction mixture was then stirred at 0° C. for 0.5 hour. After such time the reaction mixture was quenched by addition of HCl (1.00 M, 5 mL), filtered and the filtrate concentrated under reduced pressure to give 4-bromo-1-methyl-5-[(E)-2-nitrovinyl]pyrazole (627 mg, crude) as a yellow solid which used into the next step without further purification. $^1$H NMR (400 MHz, CDCl$_3$) δ=8.10 (d, J=13.6 Hz, 1H), 7.93 (d, J=13.6 Hz, 1H), 7.57 (s, 1H), 4.03 (s, 3H).

Step 2: A suspension of 2-pyridin-1-ium-1-ylacetonitrile chloride (627 mg) and 4 Å MS (1.00 g, o.215 mmol) in dichloroethane (30 mL) was cooled to 0° C. then 2,6-lutidine (1.45 g, 13.5 mmol, 1.57 mL, 5.00 eq.) was added. After stirring for 15 minutes, 4-bromo-1-methyl-5-[(E)-2-nitrovinyl]pyrazole (627 mg, 2.70 mmol, 1.00 eq.) was added, followed by the addition of cupric acetate (736 mg, 4.05 mmol, 1.50 eq.). This mixture was then stirred at 0° C. for 15 minutes then warmed to 25° C. and stirred at 25° C. for 5 hours. After such time the reaction mixture was diluted with water (300 mL) and extracted with EtOAc (100 mL×3). The combined organic layers were dried over anhydrous sodium sulfate, filtered, concentrated and the residue was purified by column chromatography (SiO$_2$, petroleum ether: ethyl acetate 10-20%) to give 2-(4-bromo-2-methyl-pyrazol-3-yl)indolizine-3-carbonitrile (380 mg, 1.26 mmol, 47% yield) as a yellow solid. LCMS [M+1]$^+$=301.0; $^1$H NMR (400 MHz, CDCl$_3$) δ=8.34 (d, J=6.0 Hz, 1H), 7.62-7.53 (m, 2H), 7.18-7.11 (m, 1H), 6.96 (dt, J=1.2, 6.8 Hz, 1H), 6.62 (s, 1H), 3.91 (s, 3H).

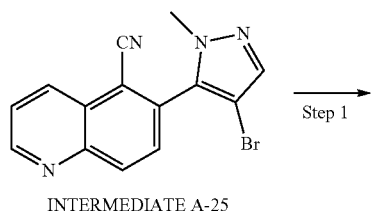

INTERMEDIATE A-25

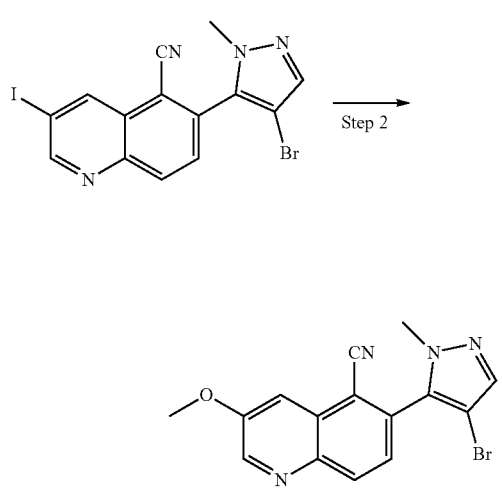

Step 1: A mixture of 6-(4-bromo-1-methyl-1H-pyrazol-5-yl)quinoline-5-carbonitrile, Intermediate A-25 (120 mg, 0.38 mmol, 1.00 eq.), N-iodosuccinimide (517 mg, 2.30 mmol, 6.00 eq.) in acetic acid (5 mL) was stirred at 80° C. for 48 hours under a nitrogen atmosphere. The mixture was then concentrated and to the residue was added saturated sodium sulfite solution (10 mL). The mixture was then extracted with ethyl acetate (5 mL) and the organic phase was washed with brine (10 mL), dried over anhydrous sodium sulfate and concentrated. The residue was purified by prep-TLC (SiO$_2$, petroleumether:ethylacetate 50%) to give 6-(4-bromo-1-methyl-1H-pyrazol-5-yl)-3-iodoquinoline-5-carbonitrile (38 mg, 0.086 mmol, 22% yield) as a white solid. LCMS [M+1]$^+$=441.1; $^1$H NMR (400 MHz, CDCl$_3$) δ=9.26 (d, J=2.0 Hz, 1H), 9.03 (dd, J=0.8, 2.0 Hz, 1H), 8.43 (dd, J=0.8, 8.8 Hz, 1H), 7.77 (d, J=8.8 Hz, 1H), 7.67 (s, 1H), 3.87 (s, 3H).

Step 2: A mixture of 6-(4-bromo-1-methyl-1H-pyrazol-5-yl)-3-iodoquinoline-5-carbonitrile (35 mg, 0.080 mmol, 1.00 eq.), sodium methoxide (13 mg, 0.24 mmol, 3.00 eq.), cuprous iodide (1.5 mg, 0.008 mmol, 0.10 eq.) in methanol (1 mL) was degassed with nitrogen then stirred at 105° C. for 16 hours. After such time the mixture was filtered and the filtrate concentrated and the residue was purified by prep-TLC (SiO$_2$, petroleum ether: ethyl acetate 50%) to give 6-(4-bromo-1-methyl-1H-pyrazol-5-yl)-3-methoxyquinoline-5-carbonitrile (12 mg, 0.035 mmol, 44% yield) as a white solid. LCMS [M+1]$^+$=345.1; $^1$H NMR (400 MHz, CDCl$_3$) δ=8.86 (d, J=2.8 Hz, 1H), 8.40 (d, J=8.4 Hz, 1H), 7.76 (d, J=2.8 Hz, 1H), 7.66 (s, 1H), 7.58 (d, J=8.4 Hz, 1H), 4.07 (s, 3H), 3.87 (s, 3H).

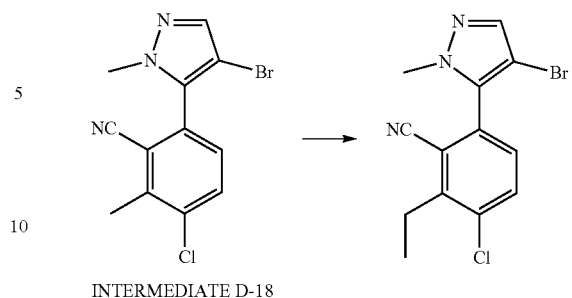

INTERMEDIATE D-18

A mixture of 6-(4-bromo-2-methyl-pyrazol-3-yl)-3-chloro-2-methyl-benzonitrile, Intermediate D-18 (400 mg, 1.29 mmol, 1.00 eq.) in THF (5 mL) was added lithium diisopropyl amine (2.00 M, 1.29 mL, 2.00 eq.) at −78° C. and stirred at −78° C. for 30 minutes. Then methyl iodide (5.15 mmol, 0.32 mL, 4.00 eq.) was added at −78° C. and the mixture stirred for 2 hours. The reaction mixture was then quenched with ammonium chloride solution (10 mL) and extracted with dichloromethane (20 mL×3) and the combined organic extracts were washed with brine (50 mL), dried over anhydrous sodium sulfate, filtered and concentrated. The residue was purified by prep-TLC (SiO$_2$, petroleumether:ethylacetate 20%) to give 6-(4-bromo-2-methyl-pyrazol-3-yl)-3-chloro-2-ethyl-benzonitrile (280 mg, 0.86 mmol, 67% yield) as a yellow oil. LCMS [M+1]$^+$=326.0; $^1$H NMR (400 MHz, CDCl$_3$) δ=7.71 (d, J=8.4 Hz, 1H), 7.59 (s, 1H), 7.24 (d, J=8.4 Hz, 1H), 3.80 (s, 3H), 3.14-3.11 (m, 2H), 1.35-1.32 (m, 3H).

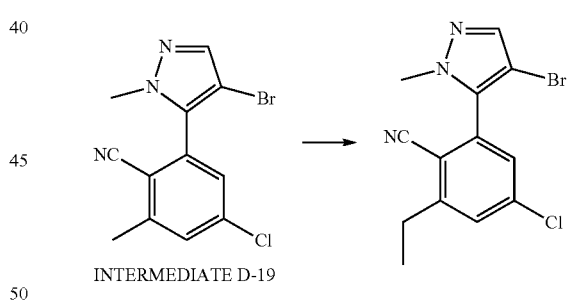

INTERMEDIATE D-19

2-(4-bromo-1-methyl-1H-pyrazol-5-yl)-4-chloro-6-ethyl-benzonitrile was prepared using the same method as for the preparation of Intermediate DV using Intermediate D-19 in place of Intermediate D-18 as a white solid (30 mg, 0.074 mmol, 23%). LCMS [M+1]$^+$=419.2; $^1$H NMR (400 MHz, DMSO-d$_6$) δ=12.88 (s, 1H), 8.38 (br s, 3H), 8.28 (s, 1H), 8.11 (d, J=8.4 Hz, 1H), 7.85 (d, J=2.0 Hz, 1H), 7.82 (d, J=2.0 Hz, 1H), 7.75 (d, J=1.2 Hz, 1H), 7.42 (dd, J=1.6, 8.4 Hz, 1H), 4.39-4.22 (m, 2H), 3.75 (s, 3H), 2.83 (q, J=7.6 Hz, 2H), 1.21 (t, J=7.6 Hz, 3H).

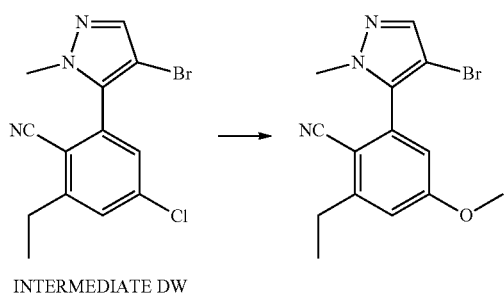

INTERMEDIATE DW

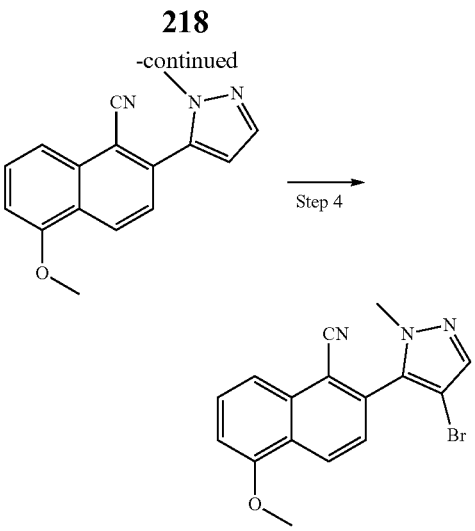

Step 4

To a mixture of 2-(4-bromo-2-methyl-pyrazol-3-yl)-4-chloro-6-ethyl-benzonitrile, Intermediate DW (270 mg, 0.83 mmol, 1.00 eq.) in methanol (2 mL) was added sodium methoxide (449 mg, 8.32 mmol, 10.0 eq.) in one portion at 20° C. under nitrogen atmosphere. The mixture was stirred at 100° C. for 2 hours in a sealed tube and a light-yellow solution was formed. The mixture was then concentrated and the residue taken up in ethyl acetate (10 mL) and water (5 mL). The layers were separated, and the aqueous phase extracted with ethyl acetate (5 mL×2). The combined organic layers were washed with brine (20 mL), dried over anhydrous sodium sulfate, filtered and concentrated under reduced pressure to give a residue. The residue was purified by prep-TLC (SiO$_2$, Petroleum ether:Ethyl acetate 25%) to give 2-(4-bromo-2-methyl-pyrazol-3-yl)-6-ethyl-4-methoxy-benzonitrile (220 mg, ~70% purity) as a white solid. LCMS [M+1]$^+$=321.9; $^1$H NMR (400 MHz, CDCl$_3$) δ=7.58 (s, 1H), 6.97 (d, J=2.4 Hz, 1H), 6.77 (d, J=2.4 Hz, 1H), 3.91 (s, 3H), 3.81 (s, 3H), 2.97-2.92 (m, 2H), 1.37-1.34 (t, J=6.8 Hz 3H).

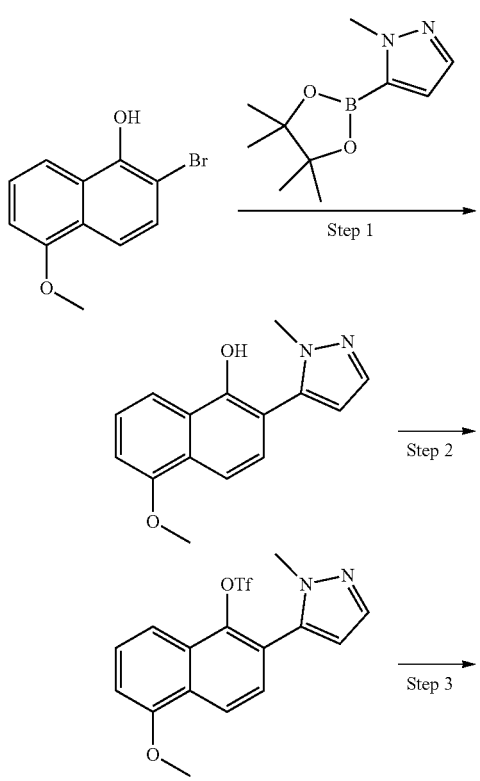

Step 1: A mixture of 2-bromo-5-methoxy-naphthalen-1-ol (2.60 g, 10.3 mmol, 1.00 eq.), 1-methyl-5-(4,4,5,5-tetramethyl-1,3,2-dioxaborolan-2-yl)pyrazole (3.21 g, 15.4 mmol, 1.50 eq.), ditert-butyl(cyclopentyl)phosphane; dichloropalladium; iron (670 mg, 1.03 mmol, 0.10 eq.) and sodium carbonate (2.18 g, 20.6 mmol, 2.00 eq.) in dioxane (30 mL) and water (6 mL) was degassed with nitrogen then stirred at 100° C. for 0.5 hour. After such time the reaction mixture was concentrated under reduced pressure and the residue was purified by column chromatography (SiO$_2$, petroleumether:ethylacetate 10-100%) to give 5-methoxy-2-(2-methylpyrazol-3-yl)naphthalen-1-ol (720 mg, 2.83 mmol, 28% yield) as a yellow solid. $^1$H NMR (400 MHz, DMSO-d$_6$) δ=9.57 (s, 1H), 7.86 (d, J=8.6 Hz, 1H), 7.72 (d, J=8.6 Hz, 1H), 7.50 (d, J=1.6 Hz, 1H), 7.48-7.42 (m, 1H), 7.26 (d, J=8.6 Hz, 1H), 7.03 (d, J=7.6 Hz, 1H), 6.33 (d, J=1.6 Hz, 1H), 3.97 (s, 3H), 3.69 (s, 3H).

Step 2: To a solution of 5-methoxy-2-(2-methylpyrazol-3-yl)naphthalen-1-ol (650 mg, 2.56 mmol, 1.00 eq.), 4 Å molecular sieves (1.00 g) and triethylamine (7.67 mmol, 1.07 mL, 3.00 eq.) in dichloromethane (20 mL) was added Tf$_2$O (3.83 mmol, 0.63 mL, 1.50 eq.) in a dropwise fashion at −40° C. under nitrogen. The reaction mixture was stirred at −40° C. for 0.5 hour then concentrated under reduced pressure and the residue purified by column chromatography (SiO$_2$, petroleumether:ethylacetate 0-15%) to give [5-methoxy-2-(2-methylpyrazol-3-yl)-1-naphthyl] trifluoromethanesulfonate (341 mg, 0.79 mmol, 30% yield) as a yellow oil. LCMS [M+1]$^+$=387.1; $^1$H NMR (400 MHz, CDCl$_3$) δ=8.40 (dd, J=0.8, 8.8 Hz, 1H), 7.76 (d, J=8.8 Hz, 1H), 7.64 (d, J=8.0 Hz, 1H), 7.61 (d, J=2.0 Hz, 1H), 7.43 (d, J=8.8 Hz, 1H), 7.00 (d, J=7.6 Hz, 1H), 6.45 (d, J=2.0 Hz, 1H), 4.07 (s, 3H), 3.82 (s, 3H).

Step 3: A mixture of [5-methoxy-2-(2-methylpyrazol-3-yl)-1-naphthyl] trifluoromethanesulfonate (290 mg, 0.67 mmol, 1.00 eq.), zinc cyanide (0.81 mmol, 51.1 μL, 1.20 eq.), Pd$_2$(dba)$_3$ (612 mg, 0.067 mmol, 0.10 eq.), DPPF (74 mg, 0.134 mmol, 0.20 eq.) and zinc powder (4.4 mg, 0.067 mmol, 0.10 eq.) in DMF (10 mL) was degassed with nitrogen then stirred at 120° C. for 1 hour. The reaction mixture was then diluted with water (100 mL) and extracted with ethyl acetate (100 mL×3). The combined organic layers were washed with brine (200 mL), dried over anhydrous sodium sulfate, filtered and concentrated under reduced pressure and the residue purified by column chromatography (SiO$_2$, petroleum ether: ethyl acetate 10-50%) to give 5-methoxy-2-(2-methylpyrazol-3-yl)naphthalene-1-carbonitrile (156 mg, 0.59 mmol, 88% yield) as an off-white solid. LCMS [M+1]+=264.1; $^1$H NMR (400 MHz, CDCl$_3$) δ=8.59 (dd, J=0.8, 8.8 Hz, 1H), 7.90 (d, J=8.4 Hz, 1H), 7.68 (t, J=8.4 Hz, 1H), 7.64 (d, J=2.0 Hz, 1H), 7.49 (d, J=8.4 Hz, 1H), 7.01 (d, J=7.6 Hz, 1H), 6.58 (d, J=2.0 Hz, 1H), 4.07 (s, 3H), 3.89 (s, 3H).

Step 4: To a solution of 5-methoxy-2-(2-methylpyrazol-3-yl)naphthalene-1-carbonitrile (180 mg, 0.68 mmol, 1.00 eq.) in acetonitrile (2 mL) was added N-bromosuccinimide (146 mg, 0.82 mmol, 1.20 eq.). The mixture was stirred at 35° C. for 0.5 hour then concentrated under reduced pressure and the residue purified by prep-TLC (SiO$_2$, petroleumether:ethylacetate 30%) to give 2-(4-bromo-2-methyl-pyrazol-3-yl)-5-methoxy-naphthalene-1-carbonitrile (174 mg, 0.51 mmol, 74% yield) as an off-white solid. LCMS [M+1]+=342.0; $^1$H NMR (400 MHz, CDCl$_3$) δ=8.64 (dd, J=0.8, 8.8 Hz, 1H), 7.92 (d, J=8.4 Hz, 1H), 7.70 (t, J=8.4 Hz, 1H), 7.64 (s, 1H), 7.47 (d, J=8.8 Hz, 1H), 7.04 (d, J=7.6 Hz, 1H), 4.08 (s, 3H), 3.84 (s, 3H).

Intermediate DZ, 2-(4-bromo-1-methyl-1H-pyrazol-5-yl)-4-chloro-1-naphthonitrile was prepared as a yellow solid (25 mg, 0.072 mmol, 2% yield over 4 steps) starting from 2-bromo-4-chloro-naphthalen-1-ol according to the method described for the preparation of Intermediate DX. LCMS [M+1]+=347.8; $^1$H NMR (400 MHz, CDCl$_3$-d) δ=8.48-8.43 (m, 1H), 8.42-8.38 (m, 1H), 7.91-7.82 (m, 2H), 7.65 (d, J=4.4 Hz, 2H), 3.88 (s, 3H).

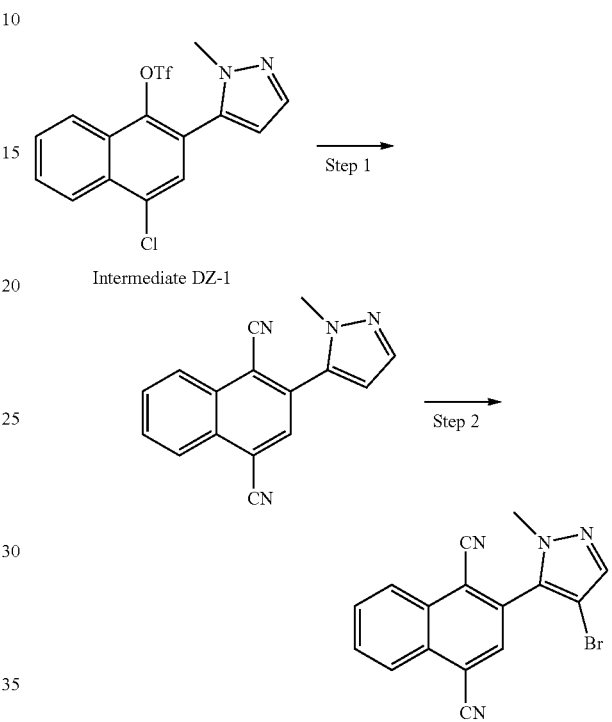

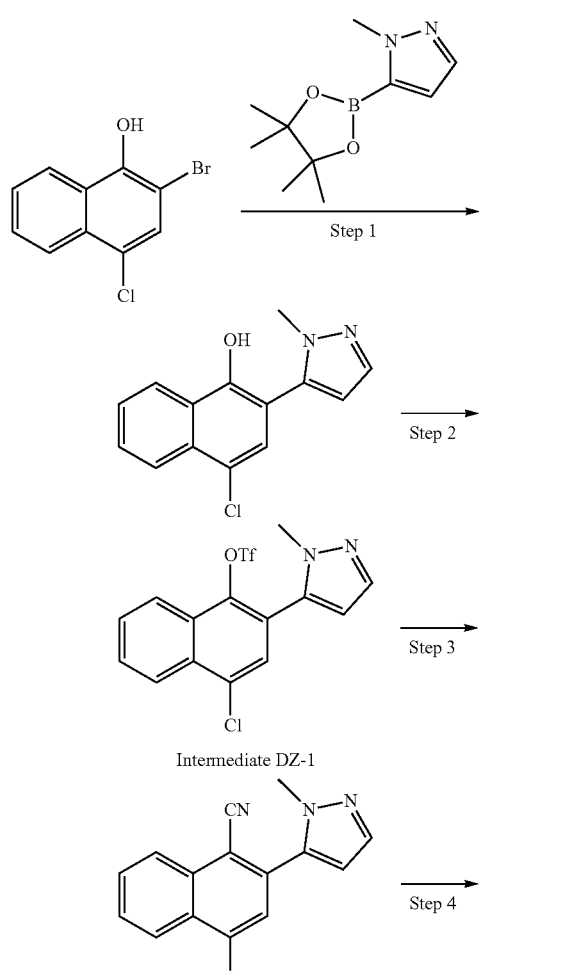

Step 1: A mixture of [4-chloro-2-(2-methylpyrazol-3-yl)-1-naphthyl] trifluoromethanesulfonate (38 mg, 0.097 mmol, 1.00 eq.), zinc cyanide (22 mg, 190 μmol, 12.4 μL, 2.00 eq.), DPPF (5.4 mg, 9.7 μmol, 0.10 eq.), zinc powder (640 μg, 9.7 μmol, 0.10 eq.) and Pd$_2$(dba)$_3$ (4.5 mg, 4.86 μmol, 0.05 eq.) in DMF (1.0 mL) was degassed with nitrogen then stirred at 100° C. for 4 hours. The mixture was then concentrated and the residue was purified by prep-TLC (SiO$_2$, petroleumether:ethylacetate 20%) to give 2-(2-methylpyrazol-3-yl)naphthalene-1,4-dicarbonitrile (30 mg, 93.4 μmol, 96% yield) as a yellow solid. LCMS [M+1]+=259.0; $^1$H NMR (400 MHz, CDCl$_3$) δ=8.48-8.44 (m, 1H), 8.44-8.39 (m, 1H), 7.96 (s, 1H), 7.96-7.94 (m, 1H), 7.94-7.92 (m, 1H), 7.67 (d, J=2.0 Hz, 1H), 6.62 (d, J=2.0 Hz, 1H), 3.92 (s, 3H).

Step 2: A mixture of 2-(2-methylpyrazol-3-yl)naphthalene-1,4-dicarbonitrile (30 mg, 0.093 mmol, 1.00 eq.), N-bromosuccinimide (41 mg, 0.23 mmol, 2.00 eq.) in acetonitrile (2.0 mL) was degassed nitrogen then stirred at 35° C. for 2 hours. The mixture was then concentrated and the residue purified by prep-TLC (SiO$_2$, petroleumether:ethylacetate 25%) to give 2-(4-bromo-2-methyl-pyrazol-3-yl)naphthalene-1,4-dicarbonitrile (25 mg, 0.067 mmol, 58% yield) as a yellow solid. LCMS [M+1]+=339.0; $^1$H NMR (400 MHz, CDCl$_3$-d) δ=8.52-8.41 (m, 2H), 8.01-7.96 (m, 2H), 7.95 (s, 1H), 7.68 (s, 1H), 3.88 (s, 3H).

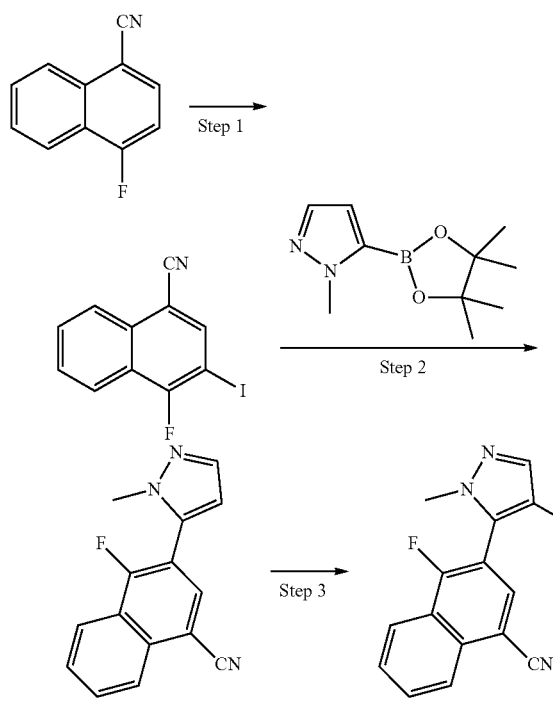

Step 1: A solution of n-butyl lithium (2.50 M, 1.87 mL, 1.00 eq.) was added dropwise over 30 min to a solution of 2,2,6,6-tetramethylpiperidine (660 mg, 4.67 mmol, 0.79 mL, 1.00 eq.) in THF (10 mL) at 0° C. and the mixture was then was cooled to −78° C. and a solution of 4-fluoronaphthalene-1-carbonitrile (0.80 g, 4.67 mmol, 1.00 eq.) in THF (3 mL) was added over 15 min. The mixture was then stirred at −78° C. for 2 hours. After such time a solution of iodine (1.19 g, 4.67 mmol, 1.00 eq.) in THF (3 mL) was added over 30 min and the reaction mixture was stirred at −78° C. for 2 hours, then allowed to warm-up to 25° C. and stirred for a further 12 hours. The reaction mixture was then quenched with water (50 mL) and extracted with ethyl acetate (30 mL×2). The combine organic layers were washed with saturated sodium thiosulfate (30 mL×3), 1 M hydrochloride (30 mL×3) and brine (50 mL) and dried over anhydrous sodium sulfate and filtered. The filtrate was concentrated, and the residue was purified by flash silica gel chromatography (ethyl acetate:petroleum ether 0-5%) to give 4-fluoro-3-iodo-naphthalene-1-carbonitrile (1.00 g, 3.37 mmol, 72% yield) as a white solid. $^1$H NMR (400 MHz, CDCl$_3$) δ=8.15 (d, J=8.4 Hz, 1H), 8.13-8.07 (m, 2H), 7.72 (dt, J=1.2, 7.7 Hz, 1H), 7.68-7.61 (m, 1H).

Step 2: To a solution of 4-fluoro-3-iodo-naphthalene-1-carbonitrile (900 mg, 3.03 mmol, 1.00 eq.), 1-methyl-5-(4,4,5,5-tetramethyl-1,3,2-dioxaborolan-2-yl)pyrazole (1.58 g, 7.57 mmol, 2.50 eq.) and potassium phosphate (1.29 g, 6.06 mmol, 2.00 eq.) in dioxane (10 mL) and water (2 mL) was added ditert-butyl(cyclopentyl)phosphane; dichloropalladium-iron (197 mg, 0.30 mmol, 0.10 eq.). The reaction was stirred at 80° C. for 18 hours under nitrogen atmosphere. The reaction mixture was then partitioned between water (20 mL) and ethyl acetate (10 mL), extracted with ethyl acetate (10 mL×2) and the combined the organic layers dried over anhydrous magnesium sulfate, filtered and concentrated. The residue was then purified by flash silica gel chromatography (0-25% ethyl acetate:petroleum ether gradient) to give 4-fluoro-3-(2-methylpyrazol-3-yl)naphthalene-1-carbonitrile (0.80 g, 2.87 mmol, 95% yield) as a white solid. $^1$H NMR (400 MHz, CDCl$_3$) δ=8.33-8.25 (m, 2H), 7.91 (s, 1H), 7.88-7.82 (m, 1H), 7.82-7.75 (m, 1H), 7.63 (d, J=2.0 Hz, 1H), 6.46 (d, J=2.0 Hz, 1H), 3.89 (d, J=1.6 Hz, 3H).

Step 3: To a solution of 4-fluoro-3-(2-methylpyrazol-3-yl)naphthalene-1-carbonitrile (200 mg, 0.80 mmol, 1.00 eq.) in acetonitrile (5 mL) was added 1-bromopyrrolidine-2,5-dione (212 mg, 1.19 mmol, 1.50 eq.) and the reaction was stirred at 25° C. for 12 hours. The reaction was then concentrated and the residue purified by flash silica gel chromatography (0-15% ethyl acetate:petroleum ether) to give 3-(4-bromo-2-methyl-pyrazol-3-yl)-4-fluoro-naphthalene-1-carbonitrile (0.20 g, 0.61 mmol, 76% yield) as a gray solid. LCMS [M+1]$^+$=332.1/300.1; $^1$H NMR (400 MHz, CDCl$_3$) δ=8.32 (dd, J=8.4, 13.1 Hz, 2H), 7.95-7.86 (m, 2H), 7.84-7.76 (m, 1H), 7.64 (s, 1H), 3.85 (d, J=1.2 Hz, 3H).

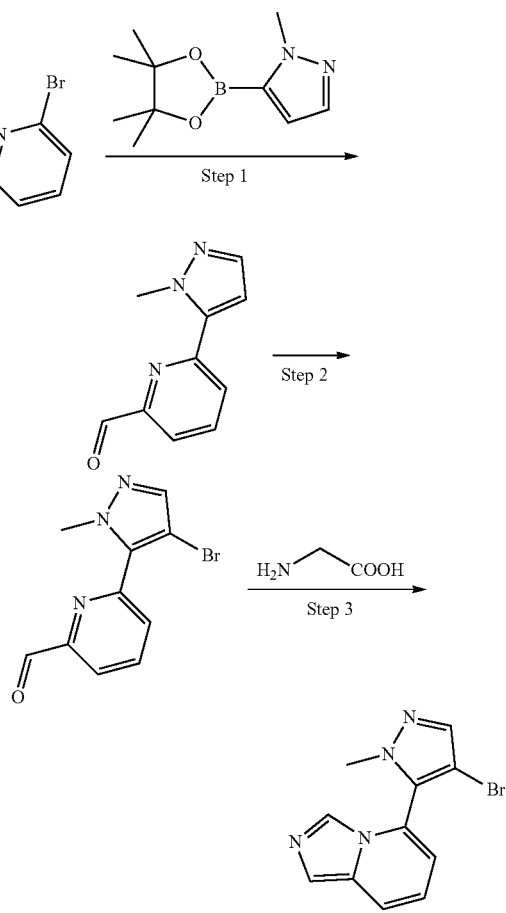

INTERMEDIATE EC

Step 1: To a solution of 6-bromopicolinaldehyde (1.00 g, 5.38 mmol, 1.00 eq.) and 1-methyl-5-(4,4,5,5-tetramethyl-1,3,2-dioxaborolan-2-yl)-1H-pyrazole (1.12 g, 5.38 mmol, 1.00 eq.) in dioxane (15 mL) and water (3 mL) was added potassium carbonate (1.49 g, 10.8 mmol, 2.00 eq.) and Pd(dppf)Cl$_2$ (393 mg, 0.538 mmol, 0.10 eq.) at 20° C. under a nitrogen atmosphere. The mixture was then stirred at 80° C. for 6 hours. After such time the reaction mixture was diluted with water (50 mL) and extracted with dichloromethane (50 mL×2). The combined organic layers were washed with brine (15 mL×2), dried over anhydrous sodium sulfate, filtered and concentrated under reduced pressure and the residue was purified by column chromatography (SiO$_2$, petroleumether:ethylacetate 25-50%) to give 6-(1-methyl-1H-pyrazol-5-yl)picolinaldehyde (800 mg, 4.27 mmol, 80% yield) as a yellow solid. $^1$H NMR (400 MHz, CDCl$_3$) δ=10.13 (d, J=0.8 Hz, 1H), 7.99-7.89 (m, 2H), 7.83 (dd, J=1.6, 7.2 Hz, 1H), 7.55 (d, J=2.0 Hz, 1H), 6.69 (d, J=2.0 Hz, 1H), 4.35 (s, 3H).

Step 2: To a solution of 6-(1-methyl-1H-pyrazol-5-yl)picolinaldehyde (800 mg, 4.27 mmol, 1.00 eq.) in acetonitrile (12 mL) was added N-bromo-succinimide (1.14 g, 6.41 mmol, 1.50 eq.) at 20° C. and the mixture was stirred for 16 hours. After such time the mixture was concentrated and the residue was purified by prep-TLC (SiO$_2$, petroleumether: ethylacetate 25%) to give 6-(4-bromo-1-methyl-1H-pyrazol-5-yl)picolinaldehyde (750 mg, 2.82 mmol, 66% yield) as a white solid. $^1$H NMR (400 MHz, CDCl$_3$) δ=10.13 (s, 1H), 8.08-7.98 (m, 3H), 7.58 (s, 1H), 4.15 (s, 3H).

Step 3: To a solution of 6-(4-bromo-1-methyl-1H-pyrazol-5-yl)picolinaldehyde (250 mg, 0.94 mmol, 1.00 eq.) in DMF (3 mL) was added 2-aminoacetic acid (78 mg, 1.03 mmol, 1.10 eq.), iodine (238 mg, 0.940 mmol, 0.19 mL, 1.00 eq), sodium bicarbonate (158 mg, 1.88 mmol, 2.00 eq.) at 20° C. The mixture was then stirred at 60° C. for 6 hours then diluted with water (20 mL) and extracted with ethyl acetate (20 mL×2). The combined organic layers were washed with brine (10 mL×2), dried over anhydrous sodium sulfate, filtered, concentrated and the residue purified by prep-TLC (SiO$_2$, ethyl acetate) to give 5-(4-bromo-1-methyl-1H-pyrazol-5-yl)imidazo[1,5-a]pyridine (35 mg, 0.126 mmol, 13% yield) as a yellow solid. $^1$H NMR (400 MHz, CDCl$_3$) δ=7.77 (s, 1H), 7.68 (s, 1H), 7.64-7.59 (m, 2H), 6.87 (dd, J=6.4, 9.2 Hz, 1H), 6.66 (d, J=6.4 Hz, 1H), 3.79 (s, 3H).

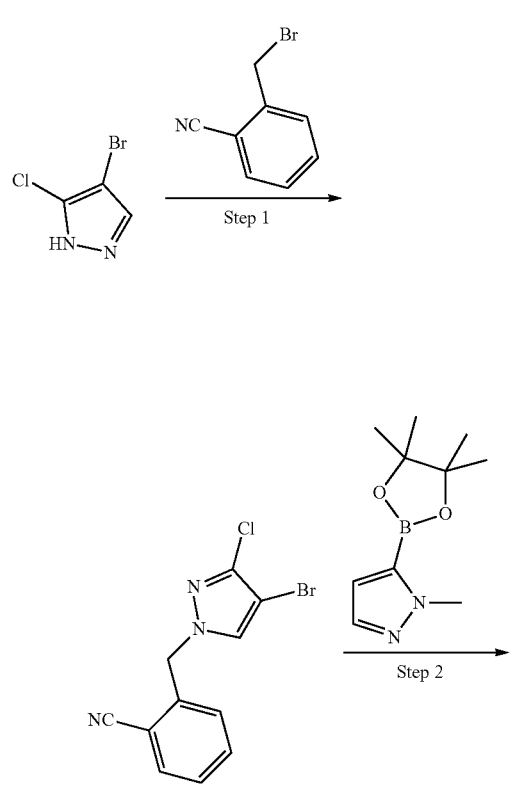

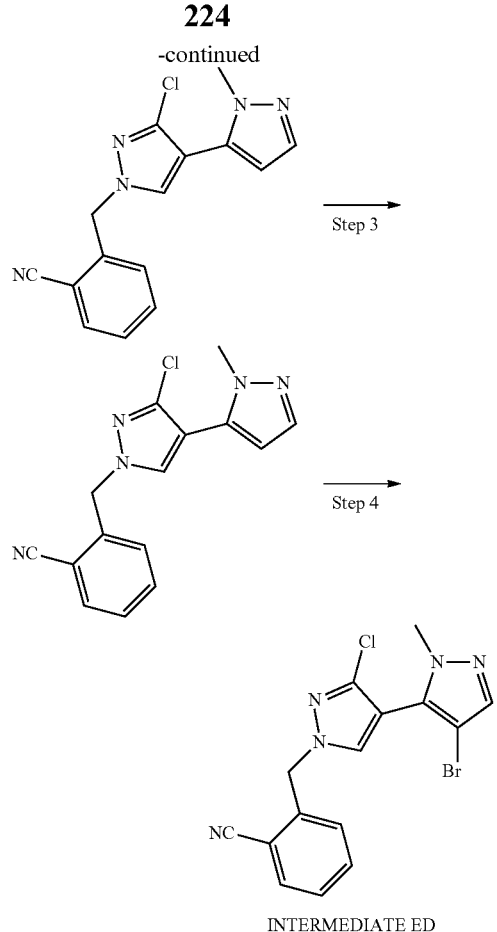

INTERMEDIATE ED

Step 1: To a solution of 4-bromo-5-chloro-1H-pyrazole (1.00 g, 5.51 mmol, 1.00 eq.) 2-(bromomethyl)benzonitrile (1.08 g, 5.51 mmol, 1.00 eq.) in acetonitrile (20 mL) was added potassium carbonate (914 mg, 6.61 mmol, 1.20 eq.) and the mixture was stirred at 80° C. for 10 hours under a nitrogen atmosphere. After such time the reaction was quenched by water (200 mL) and then extracted with ethyl acetate (150 mL×3). The combined organic extracts were washed with brine (200.mL), dried over anhydrous sodium sulfate, filtered, concentrated and the formed residue was purified by column chromatography (SiO$_2$, petroleumether: ethylacetate=10:1) to give 2-((4-bromo-3-chloro-1H-pyrazol-1-yl)methyl)benzonitrile (1.00 g, 3.37 mmol, 61% yield) as a white solid. LCMS [M+1]$^+$=297.9; $^1$H NMR (400 MHz, DMSO-d$_6$) δ=8.27 (s, 1H), 7.89 (dd, J=0.8, 7.6 Hz, 1H), 7.77-7.68 (m, 1H), 7.61-7.49 (m, 1H), 7.37 (d, J=7.6 Hz, 1H), 5.52 (s, 2H).

Step 2: To a solution of 2-((4-bromo-3-chloro-1H-pyrazol-1-yl)methyl)benzonitrile (400 mg, 1.35 mmol, 1.00 eq.), 1-methyl-5-(4,4,5,5-tetramethyl-1,3,2-dioxaborolan-2-yl)-1H-pyrazole (561 mg, 2.70 mmol, 2.00 eq.) and sodium bicarbonate (227 mg, 2.70 mmol, 2.00 eq.) in dioxane (10 mL) and water (1 mL) was added Pd(dppf)Cl$_2$ (99 mg, 0.135 mmol, 0.10 eq.) under a nitrogen atmosphere. The mixture was stirred at 110° C. for 10 hours and then the reaction was quenched by adding water (200 mL) then extracted with ethyl acetate (150 mL×3). The combined organic phases were washed with brine (200 mL), dried over anhydrous sodium sulfate, filtered, concentrated and the residue was purified by column chromatography (SiO$_2$, petroleumether: ethylacetate 30%) to give 2-((3'-chloro-2-methyl-1'H,2H-[3, 4'-bipyrazol]-1'-yl)methyl)benzonitrile (200 mg, 0.672 mmol, 50% yield) as a white solid. LCMS [M+1]$^+$=298.0; $^1$H NMR (400 MHz, DMSO-d$_6$) δ=8.41 (s, 1H), 7.91 (d, J=7.6 Hz, 1H), 7.79-7.70 (m, 1H), 7.62-7.52 (m, 1H), 7.50-7.42 (m, 2H), 6.42 (d, J=2.0 Hz, 1H), 5.58 (s, 2H), 3.81 (s, 3H).

Step 3: To a solution of 2-((3'-chloro-2-methyl-1'H,2H-[3,4'-bipyrazol]-1'-yl)methyl)benzonitrile (200 mg, 0.672 mmol, 1.00 eq.) in acetonitrile (10 mL) was added N-bromosuccinimide (132 mg, 0.739 mmol, 1.10 eq.) and the mixture was stirred at 25° C. for 10 hours under nitrogen atmosphere. After such time the reaction was quenched with water (50 mL) and extracted with ethyl acetate (40 mL×3). The combined organic phases was washed with brine (50 mL), dried over anhydrous sodium sulfate, filtered, concentrated and the residue was purified by column chromatography (SiO$_2$, petroleumether:ethylacetate 5%) to give 2-((4-bromo-3'-chloro-2-methyl-1'H,2H-[3,4'-bipyrazol]-1'-yl)methyl)benzonitrile (130 mg, 0.345 mmol, 51% yield) as a yellow solid. LCMS [M+1]$^+$=377.9; $^1$H NMR (400 MHz, DMSO-d$_6$) δ=8.37 (s, 1H), 7.92 (d, J=7.6 Hz, 1H), 7.83-7.71 (m, 1H), 7.67 (s, 1H), 7.62-7.55 (m, 1H), 7.45 (d, J=8.0 Hz, 1H), 5.61 (s, 2H), 3.73 (s, 3H).

Step 4: To a solution of tert-butyl ((4-oxo-7-(4,4,5-trimethyl-1,3,2-dioxaborolan-2-yl)-3,4-dihydrophthalazin-1-yl)methyl)carbamate (256 mg, 0.637 mmol, 2.00 eq.), 2-((4-bromo-3'-chloro-2-methyl-1'H,2H-[3,4'-bipyrazol]-1'-yl)methyl)benzonitrile (120 mg, 0.319 mmol, 1.00 eq.), sodium bicarbonate (54 mg, 0.637 mmol, 25 µL, 2.00 eq.) in water (0.5 mL) and dioxane (5.0 mL) was added Pd(dtbpf)Cl$_2$ (21 mg, 32 µmol, 0.10 eq.) under a nitrogen atmosphere and then the mixture was stirred at 110° C. for 10 hours. The reaction was then quenched with water (50 mL), extracted with ethyl acetate (40 mL×3) and the combined organic phases were washed with brine (50 mL), dried over anhydrous sodium sulfate, filtered and concentrated in vacuo. The residue was purified by column chromatography (SiO$_2$, petroleumether:ethylacetate 15%) to give tert-butyl((7-(3'-chloro-1'-(2-cyanobenzyl)-2-methyl-1'H,2H-[3,4'-bipyrazol]-4-yl)-4-oxo-3,4-dihydrophthalazin-1-yl)methyl)carbamate (115 mg, 0.201 mmol, 63% yield) as a black brown oil. LCMS [M+1]$^+$=571.1; $^1$H NMR (400 MHz, DMSO-d$_6$) δ=12.48 (s, 1H), 11.94 (s, 1H), 8.42 (s, 1H), 8.13-8.05 (m, 2H), 7.92 (d, J=7.6 Hz, 1H), 7.80-7.72 (m, 1H), 7.62-7.55 (m, 2H), 7.47 (d, J=8.0 Hz, 1H), 7.40-7.31 (m, 1H), 5.64 (s, 2H), 4.36 (br d, J=5.6 Hz, 2H), 3.74 (s, 3H), 1.38 (s, 9H).

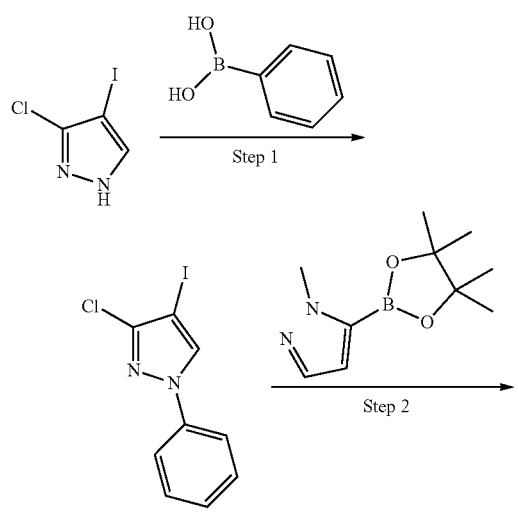

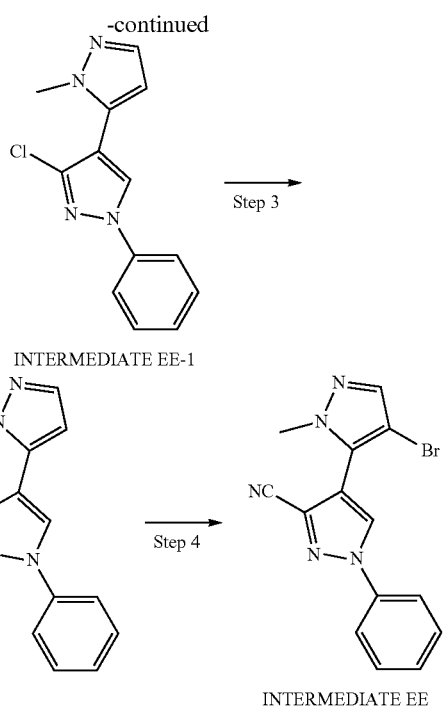

Step 1: To a mixture of phenylboronic acid (1.92 g, 15.8 mmol, 2.00 eq.) and 3-chloro-4-iodo-1H-pyrazole (1.80 g, 7.88 mmol, 1.00 eq.) in dichloromethane (30 mL) was added pyridine (1.86 g, 23.5 mmol, 1.90 mL, 2.99 eq.) and copper acetate (1.72 g, 9.46 mmol, 1.20 eq.) in one portion. The mixture was stirred at 20° C. for 16 hours, then filtered and concentrated and the residue purified by flash silica gel chromatography (0-5% ethyl acetate:petroleum ether) to give 3-chloro-4-iodo-1-phenyl-pyrazole (1.50 g, 4.93 mmol, 63% yield) as a yellow liquid. LCMS [M+1]$^+$=305.0; $^1$H NMR (400 MHz, CDCl$_3$) δ 7.91 (s, 1H), 7.63-7.59 (m, 2H), 7.49-7.43 (m, 2H), 7.36-7.30 (m, 1H).

Step 2: 1-methyl-5-(4,4,5,5-tetramethyl-1,3,2-dioxaborolan-2-yl)pyrazole (1.23 g, 5.91 mmol, 1.50 eq.), 3-chloro-4-iodo-1-phenyl-pyrazole (1.20 g, 3.94 mmol, 1.00 eq.), potassium phosphate (1.67 g, 7.88 mmol, 2.00 eq.) and ditert-butyl(cyclopentyl)phosphane; dichloropalladium-iron (256 mg, 0.39 mmol, 0.10 eq.) in dioxane (20 mL) and water (4 mL) was de-gassed and then heated to 80° C. for 16 hours under a nitrogen atmosphere. The reaction mixture was then concentrated, and the residue diluted with water (10 mL) and extracted with ethyl acetate (10 mL×3), dried over sodium sulfate, concentrated under reduced pressure and the residue purified by column chromatography (SiO$_2$, petroleumether:ethylacetate 10-15%) to give 3-chloro-4-(2-methylpyrazol-3-yl)-1-phenyl-pyrazole, Intermediate EE-1 (0.80 g, 3.09 mmol, 79% yield) as a yellow oil. LCMS [M+1]$^+$=258.9; $^1$H NMR (400 MHz, CDCl$_3$) δ 7.97 (s, 1H), 7.71-7.67 (m, 2H), 7.55 (d, J=2.0 Hz, 1H), 7.49 (t, J=8.0 Hz, 2H), 7.39-7.34 (m, 1H), 6.43 (d, J=2.0 Hz, 1H), 3.91 (s, 3H).

Step 3: A mixture of 3-chloro-4-(2-methylpyrazol-3-yl)-1-phenyl-pyrazole (210 mg, 0.811 mmol, 1.00 eq.), tetrapotassium-hexacyanoiron(4-) trihydrate (1.03 g, 2.44 mmol, 3.00 eq.) and [2-(2-aminophenyl)phenyl]-methylsulfonyloxy-palladium-dicyclohexyl-[3,6-dimethoxy-2-(2,4,6-triisopropylphenyl)phenyl]phosphane (73.6 mg, 0.081 mmol, 0.10 eq.) in dimethylacetamide (6 mL) and water (3 mL) was heated to 100° C. for 16 hours under nitrogen atmosphere.

The reaction mixture was then diluted with water (10 mL) and extracted with ethyl acetate (10 mL×3). The combined organic layers were washed with brine (15 mL), dried over sodium sulfate, filtered, concentrated under reduced pressure and the residue purified by column chromatography (SiO$_2$, petroleumether:ethylacetate 10-15%) to give 4-(2-methylpyrazol-3-yl)-1-phenyl-pyrazole-3-carbonitrile (200 mg, 0.80 mmol, 99% yield) as a yellow solid. LCMS [M+1]$^+$=249.9; $^1$H NMR (400 MHz, CDCl$_3$) δ=8.09 (s, 1H), 7.76-7.72 (m, 2H), 7.56 (d, J=2.0 Hz, 1H), 7.51-7.56 (m, 2H), 7.43-7.48 (m, 1H), 6.59 (d, J=2.0 Hz, 1H), 3.98 (s, 3H).

Step 4: To a mixture of 4-(2-methylpyrazol-3-yl)-1-phenyl-pyrazole-3-carbonitrile (180 mg, 0.722 mmol, 1.00 eq.) in acetonitrile (5 mL) was added N-bromosuccinimide (192 mg, 1.08 mmol, 1.50 eq.). The mixture was stirred at 20° C. for 16 hours. The reaction mixture was then quenched with saturated sodium sulfite (15 mL), extracted with ethyl acetate (15 mL×3), dried over anhydrous sodium sulfate, concentrated and the residue purified by column chromatography (SiO$_2$, petroleumether:ethylacetate 10-20%) to give 4-(4-bromo-2-methyl-pyrazol-3-yl)-1-phenyl-pyrazole-3-carbonitrile (220 mg, 0.67 mmol, 93% yield) as a yellow solid. LCMS [M+1]$^+$=327.9; $^1$H NMR (500 MHz, CDCl$_3$) δ=8.17 (s, 1H), 7.78-7.74 (m, 2H), 7.59 (s, 1H), 7.58-7.54 (m, 2H), 7.49-7.45 (m, 1H), 3.95 (s, 3H).

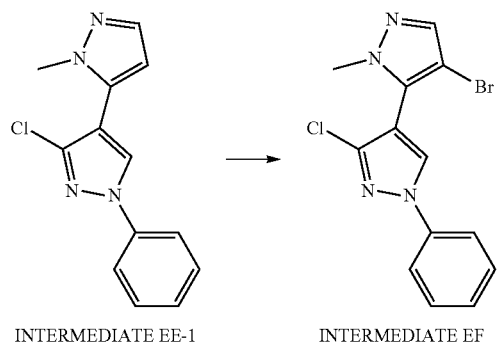 [SMILES: Cn1nccc1-c1cn(-c2ccccc2)nc1Cl ; Cn1ncc(Br)c1-c1cn(-c2ccccc2)nc1Cl]

INTERMEDIATE EE-1    INTERMEDIATE EF

To a mixture of 3-chloro-4-(2-methylpyrazol-3-yl)-1-phenyl-pyrazole, Intermediate EE-1 (200 mg, 0.773 mmol, 1.00 eq.) in acetonitrile (1 mL) was added 1-bromopyrrolidine-2,5-dione (165 mg, 0.927 mmol, 1.20 eq.) in one portion at 20° C. The mixture was stirred at 20° C. for 16 hours. The reaction mixture was then concentrated and the residue purified by flash silica gel chromatography (0-17% ethyl acetate:petroleum ether) to give 4-bromo-5-(3-chloro-1-phenyl-pyrazol-4-yl)-1-methyl-pyrazole (200 mg, 0.592 mmol, 77% yield) as a yellow oil. $^1$H NMR (500 MHz, CDCl$_3$) δ=8.07-8.04 (m, 1H), 7.72 (dd, J=1.2, 8.4 Hz, 2H), 7.58 (s, 1H), 7.54-7.49 (m, 2H), 7.42-7.35 (m, 1H), 3.88 (s, 3H).

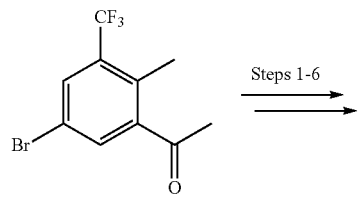

Steps 1-6:

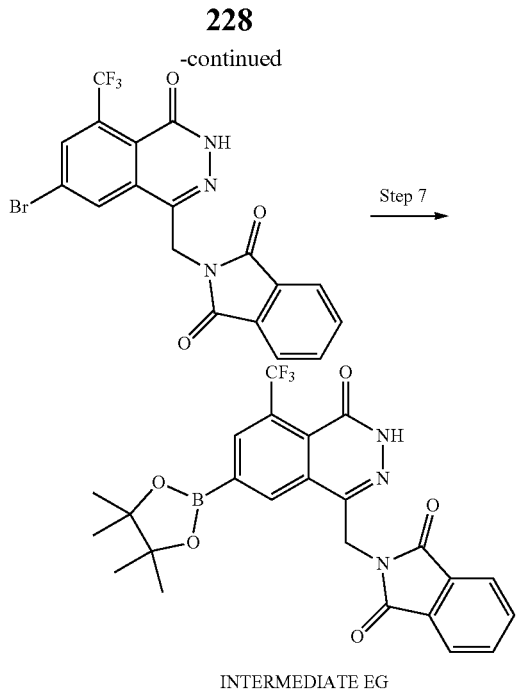

INTERMEDIATE EG

Steps 1-6: 2-((7-bromo-4-oxo-5-(trifluoromethyl)-3,4-dihydrophthalazin-1-yl)methyl)isoindoline-1,3-dione was prepared as a white solid (0.50 g, 1.11 mmol, 6% yield over 6 steps) starting from 1-(5-bromo-2-methyl-3-(trifluoromethyl)phenyl)ethan-1-one following the same procedure described for the first 6 steps of Intermediate DK. LCMS [M+1]$^+$=454.0; $^1$H NMR (400 MHz, DMSO-d$_6$) δ=12.75 (s, 1H), 8.74 (d, J=1.6 Hz, 1H), 8.41 (s, 1H), 7.97-7.92 (m, 2H), 7.91-7.86 (m, 2H), 5.22 (s, 2H).

Step 7: A mixture of 2-((7-bromo-4-oxo-5-(trifluoromethyl)-3,4-dihydrophthalazin-1-yl)methyl)isoindoline-1,3-dione (50 mg, 0.111 mmol, 1.00 eq.), bis(pinacolato)diboron (34 mg, 0.133 mmol, 1.20 eq.), Pd(dppf)Cl$_2$ (8 mg, 0.011 mmol, 0.10 eq.) and potassium acetate (22 mg, 0.221 mmol, 2.00 eq.) in dioxane (2 mL) was degassed with nitrogen and stirred at 100° C. for 1 hour. The reaction mixture was then concentrated under reduced pressure to give [4-[(1,3-dioxoisoindolin-2-yl)methyl]-1-oxo-8-(trifluoromethyl)-2H-phthalazin-6-yl]boronic acid (46.0 mg, crude) as a brown solid. LCMS [M−81]$^+$=418.1.

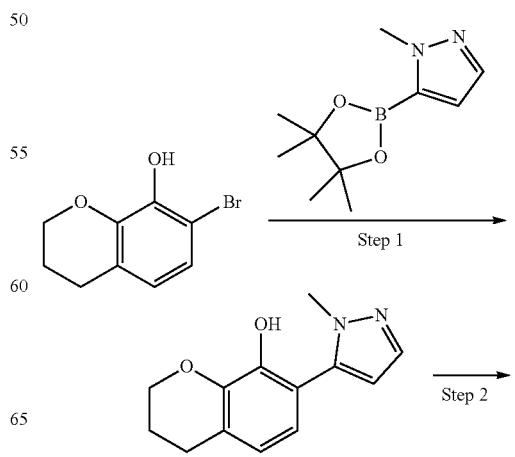

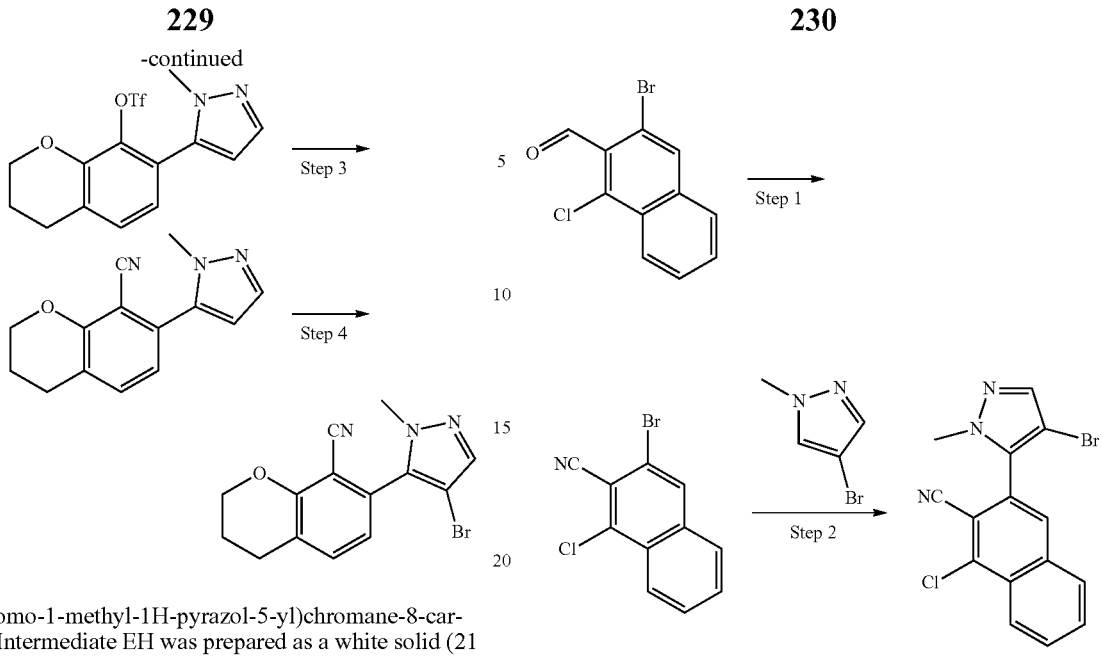

7-(4-bromo-1-methyl-1H-pyrazol-5-yl)chromane-8-carbonitrile, Intermediate EH was prepared as a white solid (21 mg, 0.049 mmol, 84% yield) using the same 4 step procedure as used for the preparation of Intermediate DY but starting with 7-bromochroman-8-ol. LCMS [M+1]$^+$=413.2; $^1$H NMR (400 MHz, DMSO-d$_6$) δ=12.40 (br s, 1H), 8.17 (s, 1H), 8.12 (d, J=8.4 Hz, 1H), 7.70 (dd, J=1.6, 8.0 Hz, 1H), 7.60 (d, J=8.0 Hz, 1H), 7.58 (d, J=1.6 Hz, 1H), 7.14 (d, J=7.6 Hz, 1H), 4.35 (br t, J=4.8 Hz, 2H), 3.72 (s, 3H), 3.68 (d, J=2.0 Hz, 2H), 2.89 (br t, J=6.0 Hz, 2H), 2.05-2.00 (m, 2H).

3-(4-bromo-1-methyl-1H-pyrazol-5-yl)-1-chloro-2-naphthonitrile, Intermediate EJ was prepared as a light yellow solid (35 mg, 0.101 mmol, 18% yield over 2 steps) following the same procedure as described for the preparation of Intermediate DC starting from 3-bromo-1-chloro-2-naphthaldehyde. $^1$H NMR (400 MHz, CCDCl$_3$-d) δ=10.60 (s, 1H), 8.47-8.41 (m, 1H), 8.11 (s, 1H), 7.89-7.77 (m, 1H), 7.74-7.66 (m, 2H).

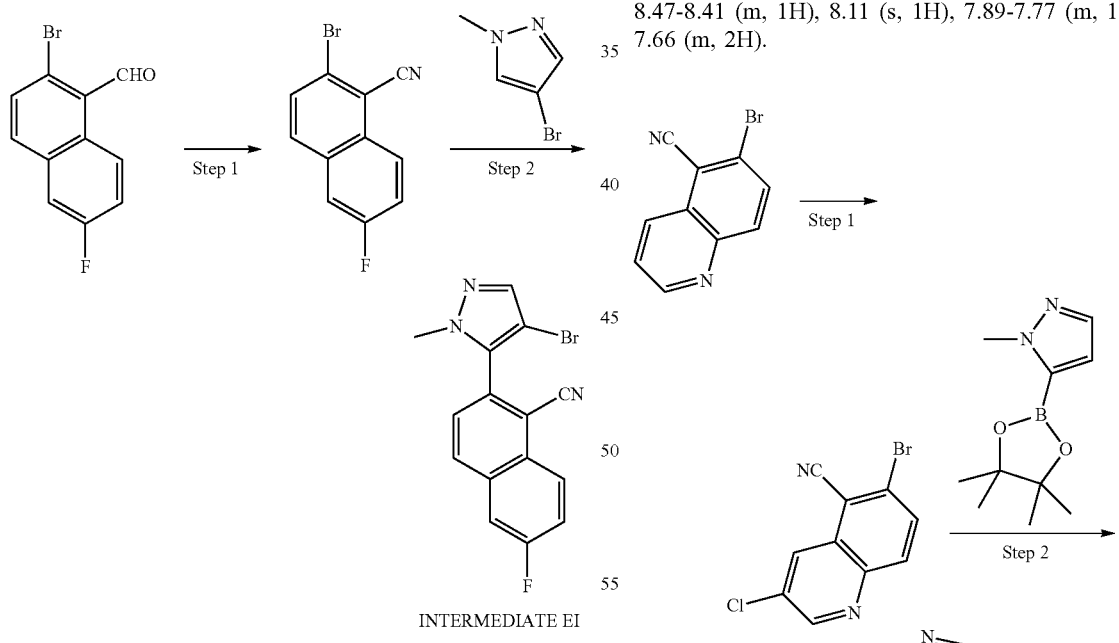

2-(4-bromo-1-methyl-1H-pyrazol-5-yl)-6-fluoro-1-naphthonitrile, Intermediate EI was prepared as a white solid (60 mg, 0.182 mmol, 31% yield over 2 steps) following the same procedure as described for the preparation of Intermediate DC starting from 2-bromo-6-fluoro-1-naphthaldehyde. LCMS [M+1]$^+$=329.8/331.8; $^1$H NMR (400 MHz, CCDCl$_3$-d) δ=8.39 (dd, J=5.2, 9.2 Hz, 1H), 8.15 (d, J=8.6 Hz, 1H), 7.68-7.63 (m, 2H), 7.62-7.56 (m, 1H), 7.54 (d, J=8.6 Hz, 1H), 3.86 (s, 3H).

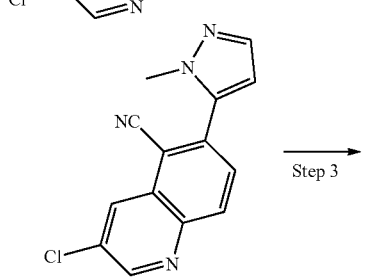

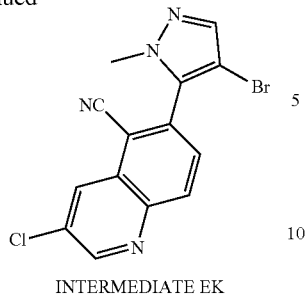

INTERMEDIATE EK

Step 1: To a solution of 6-bromoquinoline-5-carbonitrile (1.00 g, 4.29 mmol, 1.00 eq.) in acetic acid (20 mL) was added N-chlorosuccinimide (5.73 g, 42.9 mmol, 10.0 eq.). The mixture was stirred at 135° C. for 24 hours. The pH of the reaction mixture was then adjusted to pH 7 with 2 N sodium hydroxide aqueous solution (5 mL), diluted with water (50 mL) and extracted with dichloromethane (30 mL×3). The combined organic layers were washed with brine (100 mL), dried over anhydrous sodium sulfate, filtered, concentrated and the residue was purified by column chromatography (SiO$_2$, petroleumether:ethylacetate 10-15%) to give 6-bromo-3-chloro-quinoline-5-carbonitrile (512 mg, 1.91 mmol, 45% yield) as an off-white solid. LCMS [M+1]$^+$=269.0; $^1$H NMR (400 MHz, CDCl$_3$) δ=8.94 (s, 1H), 8.49 (dd, J=0.8, 2.4 Hz, 1H), 8.18 (s, 1H), 7.93 (d, J=9.2 Hz, 1H).

Step 2: A mixture of 6-bromo-3-chloro-quinoline-5-carbonitrile (512 mg, 1.91 mmol, 1.00 eq.), 1-methyl-5-(4,4,5,5-tetramethyl-1,3,2-dioxaborolan-2-yl)pyrazole (398 mg, 1.91 mmol, 1.00 eq.), ditert-butyl(cyclopentyl)phosphane; dichloropalladium-iron (125 mg, 0.19 mmol, 0.10 eq.), sodium bicarbonate (322 mg, 3.83 mmol, 0.15 mL, 2.00 eq.) in dioxane (10 mL) and water (2 mL) was degassed with nitrogen and stirred at 80° C. for 0.5 hour. After such time the reaction mixture was concentrated under reduced pressure and the residue was purified by prep-TLC (SiO$_2$, petroleumether:ethylacetate 30%) to give 3-chloro-6-(2-methylpyrazol-3-yl)quinoline-5-carbonitrile (250 mg, 0.930 mmol, 49% yield) as a yellow solid. LCMS [M+1]$^+$=269.1; $^1$H NMR (400 MHz, CDCl$_3$) δ=9.00 (d, J=2.4 Hz, 1H), 8.61 (d, J=2.0 Hz, 1H), 8.42 (d, J=8.8 Hz, 1H), 7.78 (d, J=8.8 Hz, 1H), 7.66 (d, J=1.6 Hz, 1H), 6.63 (d, J=1.6 Hz, 1H), 3.92 (s, 3H).

Step 3: To a solution of 3-chloro-6-(2-methylpyrazol-3-yl)quinoline-5-carbonitrile (249 mg, 0.927 mmol, 1.00 eq.) in acetonitrile (5 mL) was added N-bromosuccinimide (214 mg, 1.20 mmol, 1.30 eq.). The mixture was stirred at 35° C. for 0.5 hour. The reaction mixture was concentrated under reduced pressure and the residue was purified by column chromatography (SiO$_2$, petroleumether:ethylacetate 10-15%) to give 6-(4-bromo-2-methyl-pyrazol-3-yl)-3-chloro-quinoline-5-carbonitrile (289 mg, 0.831 mmol, 90% yield) as a yellow solid. LCMS [M+1]$^+$=349.0; $^1$H NMR (400 MHz, CDCl$_3$) δ=9.04 (d, J=2.4 Hz, 1H), 8.64 (dd, J=0.8, 2.4 Hz, 1H), 8.49-8.46 (m, 1H), 7.76 (d, J=8.8 Hz, 1H), 7.67 (s, 1H), 3.87 (s, 3H).

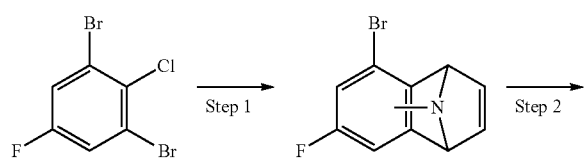

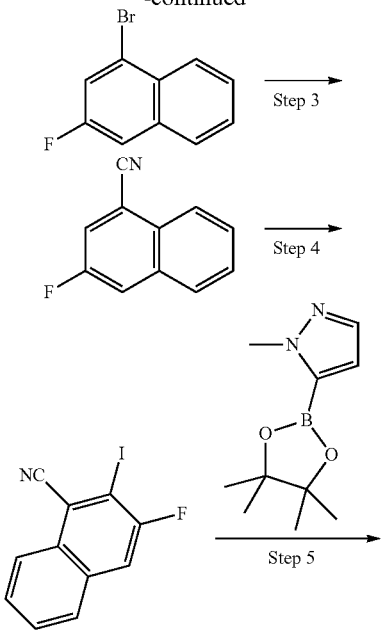

INTERMEDIATE EL-A

INTERMEDIATE EL-B

Step 1: To a solution of 1,3-dibromo-2-chloro-5-fluorobenzene (61.0 g, 212 mmol, 1.00 eq.) and 1-methylpyrrole (34.3 g, 423 mmol, 37.7 mL, 2.00 eq.) in toluene (1500 mL) was added n-butyl lithium (2.50 M in THF, 88.9 mL, 1.05 eq.) dropwise at −30° C. under nitrogen. The mixture was then stirred at −30° C. for 0.5 hour then allowed to warm to 25° C. and stirred for 12 hours. After such time the reaction mixture was quenched with water (20 mL) and concentrated under reduced pressure to give a residue. The residue was diluted with ethyl acetate (1000 mL), washed with brine (1000 mL), dried over anhydrous sodium sulfate, filtered, concentrated and the residue was purified by column chromatography (SiO$_2$, petroleumether:ethylacetate 10-50%) to give 3-bromo-5-fluoro-11-methyl-11-azatricyclo[6.2.1.02,7]undeca-2(7),3,5,9-tetraene (30.0 g, 118 mmol, 56% yield) as a brown liquid. $^1$H NMR (400 MHz, CDCl$_3$) δ=7.10-6.65 (m, 4H), 4.83-4.44 (m, 2H), 2.31-2.09 (m, 3H).

Step 2: To a solution of 3-bromo-5-fluoro-11-methyl-11-azatricyclo[6.2.1.02,7]undeca-2(7),3,5,9-tetraene (61.5 g, 242 mmol, 1.00 eq.) in chloroform (1300 mL) was carefully added m-CPBA (98.2 g, 484 mmol, 85% purity, 2.00 eq.) in portions maintaining the inner temperature below 40° C. After 2 hours, the brown solution turned yellow and the mixture was stirred at 25° C. for a further 24 hours. After such time the mixture was diluted with dichloromethane (1000 mL) and washed with saturated sodium sulfite (1500 mL×2) followed by brine (1500 mL), then dried over anhydrous sodium sulfate, filtered, concentrated and the residue was purified by column chromatography (SiO$_2$, petroleum ether: ethyl acetate 0-10%) to give 1-bromo-3-fluoro-naphthalene (37.8 g, 168 mmol, 70% yield) as a colorless liquid. $^1$H NMR (400 MHz, CDCl$_3$) δ=8.25-8.18 (m, 1H), 7.75 (br d, J=3.2 Hz, 1H), 7.63 (dd, J=2.4, 8.0 Hz, 1H), 7.58-7.52 (m, 2H), 7.47-7.40 (m, 1H).

Step 3: A mixture of 1-bromo-3-fluoro-naphthalene (34.8 g, 155 mmol, 1.00 eq.), Pd$_2$(dba)$_3$ (14.2 g, 15.5 mmol, 0.10 eq.), zinc cyanide (45.4 g, 387 mmol, 24.5 mL, 2.50 eq.), DPPF (17.1 g, 30.9 mmol, 0.20 eq.) and Zn power (1.01 g, 15.5 mmol, 0.10 eq.) in DMF (400 mL) was degassed with nitrogen and then the mixture was stirred at 115° C. for 4 hours. After such time the mixture was filtered, diluted with ethyl acetate (1000 mL), washed with brine (1000 mL×2), dried over anhydrous sodium sulfate, filtered, concentrated and the residue was purified by column chromatography (SiO$_2$, petroleumether:ethylacetate 0-10%) to give 3-fluoronaphthalene-1-carbonitrile (21.5 g, 126 mmol, 81% yield) as a yellow solid. $^1$H NMR (400 MHz, CDCl$_3$) δ=8.26-8.21 (m, 1H), 7.92-7.85 (m, 1H), 7.76-7.65 (m, 4H).

Step 4: n-butyl lithium (2.50 M in hexane, 2.83 mL, 1.10 eq.) was added to a solution of N-isopropylpropan-2-amine (845 mg, 8.35 mmol, 1.18 mL, 1.30 eq.) in THF (15 mL) at −70° C. and the reaction mixture was stirred at −70° C. for 15 minutes and then 3-fluoronaphthalene-1-carbonitrile (1.10 g, 6.43 mmol, 1.00 eq.) in THF (2 mL) was added to the mixture and the reaction mixture was stirred for 30 minutes at −70° C. A solution of iodine (2.12 g, 8.35 mmol, 1.30 eq.) in THF (2.00 mL) was then added to the reaction mixture at −70° C. and the solution was stirred at −70° C. for a further 30 minutes and then the mixture was warmed to 25° C. and stirred at 25° C. for 10 hours. After such time the reaction was quenched with water (100 mL), and diluted with ethyl acetate (250 mL), washed with saturated sodium thiosulfate (100 mL×2) and brine (250 mL). The organic phase was dried over anhydrous sodium sulfate filtered, concentrated and the formed residue was purified by column chromatography (SiO$_2$, petroleumether:ethylacetate 0-15%) to give 3-fluoro-2-iodo-naphthalene-1-carbonitrile (1.70 g, 5.72 mmol, 89% yield) as a white solid. $^1$H NMR (400 MHz, CDCl$_3$) δ=8.36-8.24 (m, 1H), 7.83-7.71 (m, 1H), 7.59-7.48 (m, 3H).

Step 5: A mixture of 3-fluoro-2-iodo-naphthalene-1-carbonitrile (800 mg, 2.69 mmol, 1.00 eq.), 1-methyl-5-(4,4,5,5-tetramethyl-1,3,2-dioxaborolan-2-yl)pyrazole (1.23 g, 5.92 mmol, 2.20 eq.), Pd(dtbpf)Cl$_2$ (176 mg, 0.269 mmol, 0.10 eq.), sodium bicarbonate (679 mg, 8.08 mmol, 3.00 eq.) in dioxane (10 mL) and water (2 mL) was degassed with nitrogen and stirred at 80° C. for 12 hours. After such time the mixture was concentrated and the residue purified by column chromatography (SiO$_2$, petroleumether:ethylacetate 5-50%) to give 3-fluoro-2-(2-methylpyrazol-3-yl)naphthalene-1-carbonitrile (500 mg, 1.99 mmol, 74% yield) as a yellow solid. LCMS [M+1]$^+$=252.1; $^1$H NMR (400 MHz, CDCl$_3$) δ=8.35-8.27 (m, 1H), 8.00-7.92 (m, 1H), 7.87 (d, J=9.6 Hz, 1H), 7.79-7.70 (m, 2H), 7.68 (d, J=2.0 Hz, 1H), 6.62 (d, J=2.0 Hz, 1H), 3.85 (d, J=1.2 Hz, 3H).

Step 6: To a solution of 3-fluoro-2-(2-methylpyrazol-3-yl)naphthalene-1-carbonitrile (500 mg, 1.99 mmol, 1.00 eq.) in acetonitrile (8 mL) was added N-bromosuccinimide (638 mg, 3.58 mmol, 1.80 eq.). The mixture was stirred at 25° C. for 3 hours. After such time the mixture was concentrated and the residue was purified by column chromatography (SiO$_2$, petroleumether:ethylacetate 10-50%) to give 2-(4-bromo-2-methyl-pyrazol-3-yl)-3-fluoro-naphthalene-1-carbonitrile (550 mg, 1.56 mmol, 78% yield) as a yellow solid. LCMS [M+1]$^+$=331.9; $^1$H NMR (400 MHz, CDCl$_3$) δ=8.40-8.31 (m, 1H), 8.01-7.95 (m, 1H), 7.91 (d, J=9.6 Hz, 1H), 7.79-7.73 (m, 2H), 7.68 (s, 1H), 3.84 (s, 3H).

Step 7: To a solution of 3-fluoro-2-(2-methylpyrazol-3-yl)naphthalene-1-carbonitrile (20.0 g, 79.6 mmol, 1.00 eq.) in acetonitrile (300 mL) was added N-iodosuccinimide (89.5 g, 398 mmol, 5.00 eq.). The mixture was stirred at 80° C. for 12 hours. After such time the mixture was concentrated and the residue was triturated with methyl alcohol (100 mL) at 25° C. for 30 min and the mixture filtered and dried to give 3-fluoro-2-(4-iodo-2-methyl-pyrazol-3-yl)naphthalene-1-carbonitrile (25.2 g, 66.8 mmol, 84% yield) as a yellow solid. LCMS [M+1]$^+$=378.0; $^1$H NMR (400 MHz, CDCl$_3$) δ=8.35 (br d, J=8.4 Hz, 1H), 7.98 (br d, J=8.4 Hz, 1H), 7.92 (d, J=9.2 Hz, 1H), 7.82-7.74 (m, 2H), 7.74-7.67 (m, 1H), 3.92-3.82 (m, 3H).

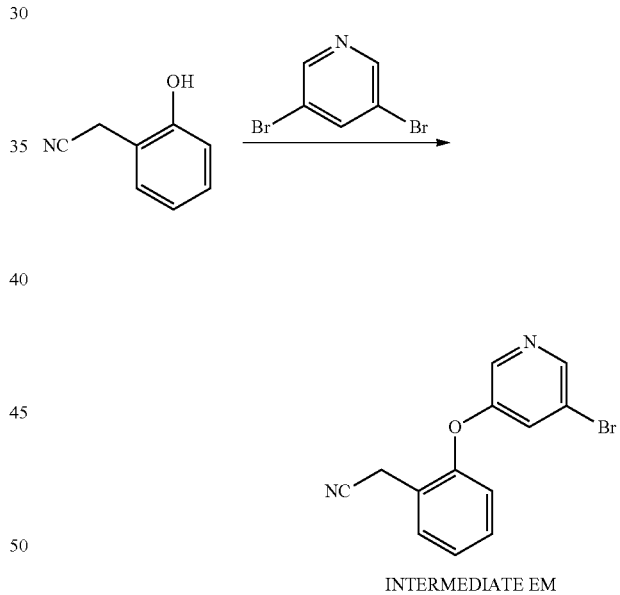

INTERMEDIATE EM

A mixture of 2-(2-hydroxyphenyl)acetonitrile (182 mg, 1.36 mmol, 1.20 eq.), 3-bromo-5-fluoro-pyridine (200 mg, 1.14 mmol, 1.00 eq.), potassium carbonate (393 mg, 2.84 mmol, 2.50 eq.) in DMF (10 mL) was stirred at 75° C. for 3 hours under a nitrogen atmosphere. The mixture was concentrated and the residue was purified by prep-TLC (SiO$_2$, petroleumether:ethylacetate 15%) to give 2-[2-[(5-bromo-3-pyridyl)oxy]phenyl]acetonitrile (200 mg, 0.43 mmol, 38% yield) as a yellow oil. LCMS [M+1]$^+$=289.0.

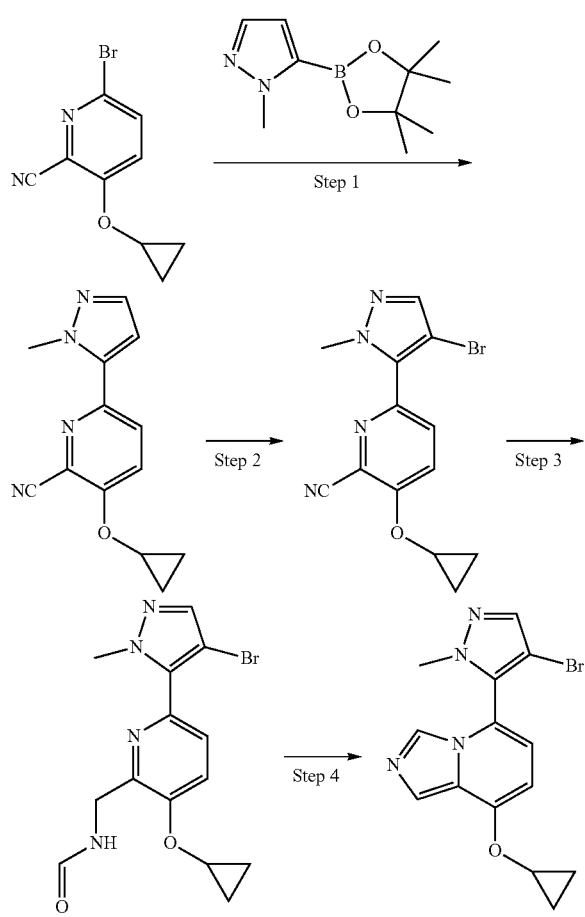

Step 1: To a solution of 6-bromo-3-cyclopropoxypicolinonitrile (800 mg, 3.35 mmol, 1.00 eq.) and 1-methyl-5-(4,4,5,5-tetramethyl-1,3,2-dioxaborolan-2-yl)-1H-pyrazole (732 mg, 3.51 mmol, 1.05 eq.) in dioxane (20 mL) and water (0.4 mL) was added ditert-butyl(cyclopentyl)phosphane-dichloropalladium-iron (218 mg, 0.335 mmol, 0.10 eq.) and sodium carbonate (709 mg, 6.69 mmol, 2.00 eq.) at 25° C. The mixture was degassed and purged with nitrogen for 3 times, and then stirred at 80° C. for 2 hours. After such time the reaction mixture was quenched with water (20 mL) and then extracted with ethyl acetate (30 mL×3). The combined organic layers were washed with brine (20 mL), dried over anhydrous sodium sulfate, filtered, concentrated and the residue was purified by flash silica gel chromatography (SiO$_2$, petroleumether:ethylacetate 0-10%) to give 3-cyclopropoxy-6-(1-methyl-1H-pyrazol-5-yl)picolinonitrile (750 mg, 2.97 mmol, 89% yield) as a white solid. $^1$H NMR (400 MHz, CD$_3$OD) δ=7.77 (s, 2H), 7.51 (d, J=2.0 Hz, 1H), 6.57 (d, J=2.0 Hz, 1H), 4.22 (s, 3H), 3.96-3.91 (m, 1H), 0.98-0.92 (m, 4H).

Step 2: To a solution of 3-cyclopropoxy-6-(1-methyl-1H-pyrazol-5-yl)picolinonitrile (650 mg, 2.71 mmol, 1.00 eq.) in acetonitrile (20 mL) was added N-bromosuccinimide (723 mg, 4.06 mmol, 1.50 eq.) at 0° C. and the mixture was stirred at 25° C. for 16 hours. The reaction mixture was quenched with water (2 mL) and extracted with ethyl acetate (3 mL×3). The combined organic layers were washed with brine (10 mL), dried over anhydrous sodium sulfate, filtered, concentrated and the residue purified by prep-TLC (SiO$_2$, petroleumether:ethylacetate=1:1) to give 6-(4-bromo-1-methyl-1H-pyrazol-5-yl)-3-cyclopropoxypicolinonitrile (1.1 g, crude) as a yellow solid. LCMS [M+1]$^+$=318.9/320.9; $^1$H NMR (400 MHz, CDCl$_3$) δ=8.00 (d, J=8.8 Hz, 1H), 7.84 (d, J=9.2 Hz, 1H), 7.52 (s, 1H), 4.05 (s, 3H), 3.99-3.92 (m, 1H), 0.99-0.92 (m, 4H).

Step 3: To a solution of 6-(4-bromo-1-methyl-1H-pyrazol-5-yl)-3-cyclopropoxypicolinonitrile (300 mg, 0.94 mmol, 1.00 eq.) in THF (20 mL) was added DIBAL-H (1.00 M, 5.64 mL, 6.00 eq.) at 25° C. and the mixture was stirred at 25° C. for 3 hours. After such time the reaction was quenched by the addition of sodium thiosulfate solution (20 mL). The mixture was extracted with ethyl acetate (30 mL×3) and the combined organic layers were washed with brine (20 mL), dried over anhydrous sodium sulfate, filtered, concentrated and the residue was purified by prep-TLC (SiO$_2$, petroleum ether:ethyl acetate 1:1) to give (6-(4-bromo-1-methyl-1H-pyrazol-5-yl)-3-cyclopropoxypyridin-2-yl) methanamine (160 mg, 0.495 mmol) as a yellow solid. A mixture of (6-(4-bromo-1-methyl-1H-pyrazol-5-yl)-3-cyclopropoxypyridin-2-yl) methanamine (160 mg, 0.495 mmol, 1.00 eq.) in ethyl formate (3 mL) was stirred at 25° C. for 2 hours followed by the addition of water (2 mL). The mixture was then extracted with ethyl acetate (3 mL×3) and the combined organic layers were washed with brine (10 mL), dried over anhydrous sodium sulfate, filtered, concentrated and the residue was purified by prep-TLC (SiO$_2$, petroleumether:ethylacetate 0-10%) to give N-((6-(4-bromo-1-methyl-1H-pyrazol-5-yl)-3-cyclopropoxypyridin-2-yl) methyl) formamide (140 mg, 0.359 mmol, 73% yield) as a yellow solid. LCMS [M+1]$^+$=351.0/353.0; $^1$H NMR (400 MHz, CDCl$_3$) δ=8.36 (s, 1H), 7.68-7.61 (m, 2H), 7.55-7.52 (m, 1H), 7.03 (br s, 1H), 4.62 (d, J=4.4 Hz, 2H), 3.99 (s, 3H), 3.85 (tt, J=3.2, 5.6 Hz, 1H), 0.92-0.85 (m, 4H).

Step 4: To a solution of N-((6-(4-bromo-1-methyl-1H-pyrazol-5-yl)-3-cyclopropoxypyridin-2-yl) methyl) formamide (140 mg, 0.359 mmol, 1.00 eq) and diisopropylethylamine (104 mg, 0.80 mmol, 0.14 mL, 2.00 eq.) in dichloromethane (8 mL) was added Tf$_2$O (225 mg, 0.078 mmol, 0.13 mL, 2.00 eq.) at −40° C. then allowed to warm to ambient temperature and stirred at 25° C. for 6 hours. After such time water (2 mL) was added and the mixture extracted with ethyl acetate (3 mL×3). The combined organic layers were washed with brine (10 mL), dried over anhydrous sodium sulfate, filtered, concentrated and the residue was purified by prep-TLC (SiO$_2$, petroleumether:ethylacetate 0-10%) to give 5-(4-bromo-1-methyl-1H-pyrazol-5-yl)-8-cyclopropoxyimidazo[1,5-a]pyridine (110 mg, 0.314 mmol, 79% yield) as a yellow solid. LCMS [M+1]$^+$=332.9/334.9; $^1$H NMR (400 MHz, CDCl$_3$) δ=7.72-7.60 (m, 3H), 6.61 (d, J=7.6 Hz, 1H), 6.49 (d, J=7.4 Hz, 1H), 3.98-3.92 (m, 1H), 3.77 (s, 3H), 0.98-0.87 (m, 4H).

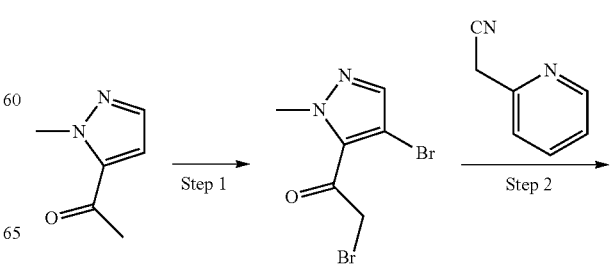

-continued

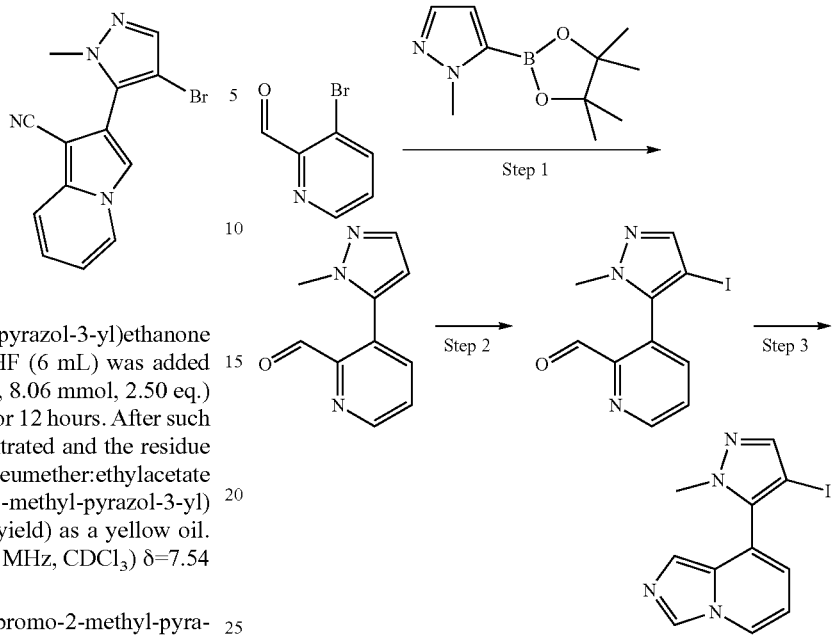

Step 1: To a solution of 1-(2-methylpyrazol-3-yl)ethanone (400 mg, 3.22 mmol, 1.00 eq.) in THF (6 mL) was added 1-bromopyrrolidine-2,5-dione (1.43 g, 8.06 mmol, 2.50 eq.) and the mixture was stirred at 25° C. for 12 hours. After such time the reaction mixture was concentrated and the residue purified by prep-TLC (SiO$_2$, petroleumether:ethylacetate 20%) to give 2-bromo-1-(4-bromo-2-methyl-pyrazol-3-yl) ethanone (800 mg, 2.84 mmol, 88% yield) as a yellow oil. LCMS [M+1]$^+$=282.9; $^1$H NMR (400 MHz, CDCl$_3$) δ=7.54 (s, 1H), 4.62 (s, 2H), 4.16 (s, 3H).

Step 2: A solution of 2-bromo-1-(4-bromo-2-methyl-pyrazol-3-yl)ethanone (400 mg, 1.42 mmol, 1.00 eq.) and 2-(2-pyridyl)acetonitrile (335 mg, 2.84 mmol, 0.31 mL, 2.00 eq.) in acetonitrile (6 mL) was stirred at 70° C. for 11 hours followed by the addition of triethylamine (431 mg, 4.26 mmol, 0.59 mL, 3.00 eq.) and stirred at 70° C. for a further 1 hour. The reaction mixture was then concentrated and the residue purified by prep-TLC (SiO$_2$, petroleumether:ethylacetate 30%) to give 2-(4-bromo-2-methyl-pyrazol-3-yl)indolizine-1-carbonitrile (100 mg, 0.332 mmol, 23% yield) as a yellow solid. LCMS [M+1]$^+$=301.0; $^1$H NMR (400 MHz, CDCl$_3$) δ=8.10 (d, J=6.8 Hz, 1H), 7.72 (d, J=9.2 Hz, 1H), 7.59 (s, 1H), 7.44 (s, 1H), 7.22-7.15 (m, 1H), 6.89 (t, J=6.4 Hz, 1H), 3.96 (s, 3H).

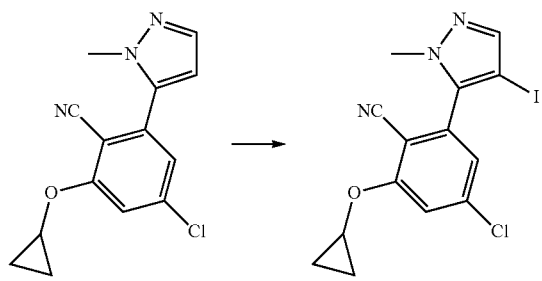 [SMILES: Cn1nccc1-c1cc(Cl)cc(OC2CC2)c1C#N ; Cn1ncc(I)c1-c1cc(Cl)cc(OC2CC2)c1C#N]

To a solution of 4-chloro-2-(cyclopropoxy)-6-(2-methylpyrazol-3-yl)benzonitrile (150 mg, 0.55 mmol, 1.00 eq.) in acetic acid (1.0 mL) was added N-iodosuccinimide (247 mg, 1.10 mmol, 2.00 eq.) and the mixture was stirred at 25° C. for 1 hour. The reaction mixture was then diluted with ethyl acetate (30 mL) and washed with brine (30 mL×3), dried over anhydrous sodium sulfate, filtered, concentrated and the residue purified by prep-TLC (SiO$_2$, petroleumether: ethylacetate 20%) to give 4-chloro-2-(cyclopropoxy)-6-(4-iodo-2-methyl-pyrazol-3-yl)benzonitrile (135 mg, 0.33 mmol, 61% yield) as a yellow solid. LCMS [M+H]$^+$=399.9; $^1$H NMR (400 MHz, CDCl$_3$) δ=7.53 (s, 1H), 7.41 (d, J=2.0 Hz, 1H), 6.94 (d, J=2.0 Hz, 1H), 3.90-3.79 (m, 1H), 3.75 (s, 3H), 0.99-0.76 (m, 4H).

Step 1: A mixture of 3-bromopyridine-2-carbaldehyde (1.00 g, 5.38 mmol, 1.00 eq.), 1-methyl-5-(4,4,5,5-tetramethyl-1,3,2-dioxaborolan-2-yl)pyrazole (1.12 g, 5.38 mmol, 1.00 eq.), sodium bicarbonate (1.13 g, 13.4 mmol, 0.52 mL, 2.50 eq.) and triphenyl phosphine (141 mg, 0.54 mmol, 0.10 eq.) in DMF (10 mL) and water (2 mL) was degassed and purged with nitrogen 3 times, then palladium acetate (60 mg, 0.27 mmol, 0.05 eq.) was added to the mixture and stirred at 80° C. for 16 hours. After such time the reaction solution was filtered, poured into water (2 mL) and extracted with ethyl acetate (10 mL×3). The combined organic layers were washed with brine (5 mL), dried over anhydrous sodium sulfate, filtered, concentrated and the residue was purified by column chromatography (SiO$_2$, petroleum ether: ethyl acetate 20-100%) to give 3-(2-methylpyrazol-3-yl)pyridine-2-carbaldehyde (637 mg, 3.40 mmol, 63% yield) as a brown solid. LCMS [M+1]$^+$=188.0; $^1$H NMR (400 MHz, CDCl$_3$) δ=10.14-10.06 (m, 1H), 8.93 (dd, J=1.6, 4.8 Hz, 1H), 7.79 (dd, J=1.2, 7.6 Hz, 1H), 7.64-7.58 (m, 2H), 6.30 (d, J=2.0 Hz, 1H), 3.67 (s, 3H).

Step 2: To a solution of 3-(2-methylpyrazol-3-yl)pyridine-2-carbaldehyde (200 mg, 1.07 mmol, 1.00 eq.) in acetonitrile (5 mL) was added N-iodosuccinimide (480 mg, 2.14 mmol, 2.00 eq.) and the mixture was stirred at 20° C. for 16 hours. The reaction was diluted by ethyl acetate (35 mL), washed with saturated sodium thiosulfate (5 mL×2), dried over anhydrous sodium sulfate, filtered, concentrated and the residue was purified by column chromatography (SiO$_2$, petroleumether:ethylacetate 20-100%) to give 3-(4-iodo-2-methyl-pyrazol-3-yl)pyridine-2-carbaldehyde (290 mg, 0.93 mmol, 87% yield) as a white solid. LCMS [M+1]$^+$=313.8; $^1$H NMR (400 MHz, CDCl$_3$) δ=10.07 (s, 1H), 8.97 (dd, J=1.6, 4.8 Hz, 1H), 7.79-7.73 (m, 1H), 7.68 (dd, J=4.8, 7.6 Hz, 1H), 7.63 (s, 1H), 3.69 (s, 3H).

Step 3: To a solution of 3-(4-iodo-2-methyl-pyrazol-3-yl)pyridine-2-carbaldehyde (290 mg, 0.93 mmol, 1.00 eq.) in DMF (5 mL) was added 2-aminoacetic acid (77 mg, 1.02 mmol, 1.10 eq.), iodine (235 mg, 0.93 mmol, 0.18 mL, 1.00 eq.) and sodium bicarbonate (155 mg, 1.85 mmol, 2.00 eq.). Then the mixture was then stirred at 60° C. for 6 hours. The reaction mixture was diluted with ethyl acetate (35 mL), washed with saturated sodium thiosulfate solution (2 mL×3), dried over anhydrous sodium sulfate, filtered, concentrated and the residue was purified by column chromatography (SiO$_2$, petroleumether:ethylacetate 20-100%) to give 8-(4-iodo-2-methyl-pyrazol-3-yl)imidazo[1,5-a]pyridine (100 mg, 0.31 mmol, 33% yield) as a yellow gum. LCMS [M−1]=324.9; $^1$H NMR (400 MHz, CDCl$_3$) δ=8.24 (s, 1H), 8.05 (d, J=6.4 Hz, 1H), 7.65 (s, 1H), 7.19 (s, 1H), 6.78-6.69 (m, 2H), 3.82 (s, 3H).

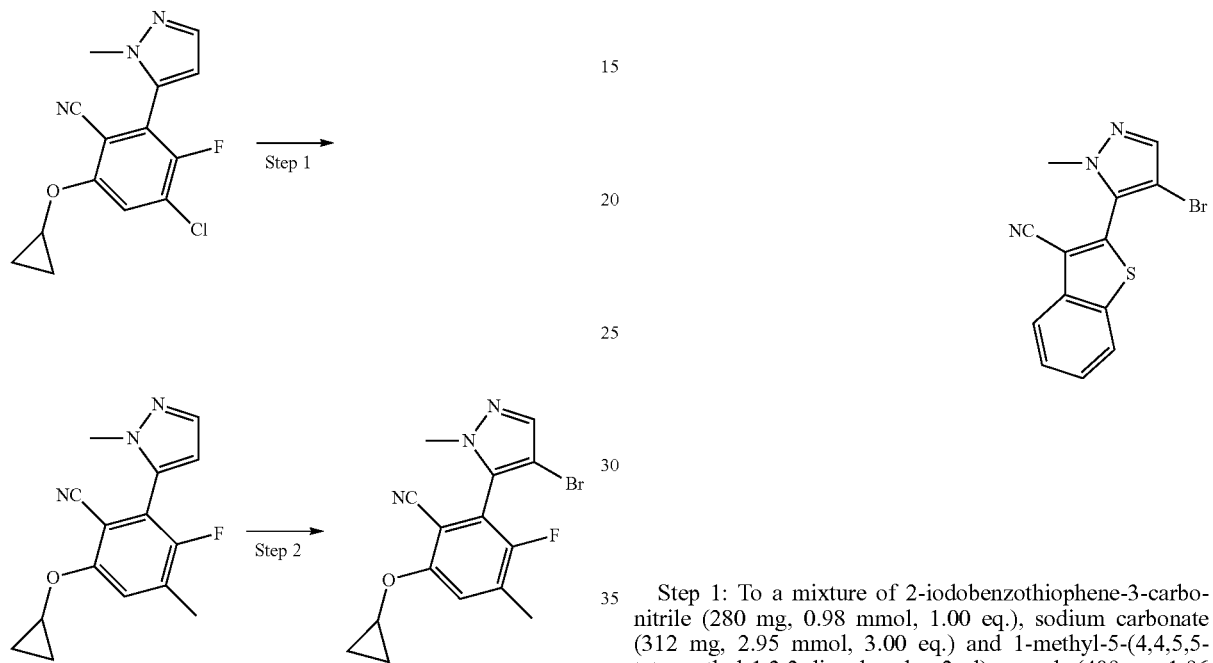

Step 1: A mixture of 4-chloro-6-(cyclopropoxy)-3-fluoro-2-(2-methylpyrazol-3-yl)benzonitrile (200 mg, 0.69 mmol, 1.00 eq.), methylboronic acid (205 mg, 3.43 mmol, 5.00 eq.), ditert-butyl(cyclopentyl)phosphane-dichloropalladium-iron (45 mg, 0.069 mmol, 0.10 eq.) and potassium carbonate (284 mg, 2.06 mmol, 3.00 eq.) in dioxane (2 mL) was degassed, purged with nitrogen 3 times and stirred at 100° C. for 2 hours. The mixture was then concentrated and purified by prep-TLC (SiO$_2$, petroleumether:ethylacetate 25%) to give 6-(cyclopropoxy)-3-fluoro-4-methyl-2-(2-methylpyrazol-3-yl)benzonitrile (35 mg, 0.10 mmol, 15% yield) as a yellow oil. LCMS [M+1]$^+$=274.3; $^1$H NMR (400 MHz, CDCl$_3$) δ=7.60 (d, J=2.0 Hz, 1H), 7.24 (d, J=6.0 Hz, 1H), 6.46 (d, J=2.0 Hz, 1H), 3.86 (td, J=2.8, 5.6 Hz, 1H), 3.80 (s, 3H), 2.43 (d, J=2.0 Hz, 3H), 0.93-0.88 (m, 4H).

Step 2: A mixture of 6-(cyclopropoxy)-3-fluoro-4-methyl-2-(2-methylpyrazol-3-yl)benzonitrile (35 mg, 0.13 mmol, 1.00 eq.), N-bromosuccinimide (46 mg, 0.26 mmol, 2.00 eq.) in acetonitrile (3 mL) was stirred at 40° C. for 2 hours under a nitrogen atmosphere. The mixture was then concentrated and the residue was purified by prep-TLC (SiO$_2$, petroleum ether: ethyl acetate 25%) to give 2-(4-bromo-2-methyl-pyrazol-3-yl)-6-(cyclopropoxy)-3-fluoro-4-methyl-benzonitrile (25 mg, 0.040 mmol, 31% yield) as a white solid. LCMS [M+1]$^+$=352.0; $^1$H NMR (400 MHz, CDCl$_3$) δ=7.59 (d, J=2.8 Hz, 1H), 7.31 (br d, J=2.8 Hz, 1H), 3.90-3.83 (m, 1H), 3.78 (d, J=2.8 Hz, 3H), 2.44 (br s, 3H), 0.92 (br dd, J=3.2, 6.4 Hz, 4H).

Step 1: To a mixture of 2-iodobenzothiophene-3-carbonitrile (280 mg, 0.98 mmol, 1.00 eq.), sodium carbonate (312 mg, 2.95 mmol, 3.00 eq.) and 1-methyl-5-(4,4,5,5-tetramethyl-1,3,2-dioxaborolan-2-yl)pyrazole (409 mg, 1.96 mmol, 2.00 eq.) in dioxane (4 mL) and water (1 mL) was added ditert-butyl(cyclopentyl)phosphane-dichloropalladium-iron (64 mg, 0.098 mmol, 0.10 eq.) and sodium carbonate (312 mg, 2.95 mmol, 3.00 eq.) and the mixture was stirred at 80° C. for 2 hours. After such time water (5 mL) was added and the mixture extracted with ethyl acetate (10 mL×3). The combined organic phase were washed with brine (10 mL), dried over anhydrous sodium sulfate, filtered, concentrated and the residue was purified by prep-TLC (SiO$_2$, petroleumether:ethylacetate 10%) to give 2-(2-methylpyrazol-3-yl)benzothiophene-3-carbonitrile (150 mg, 64% yield) as a yellow solid. $^1$H NMR (400 MHz, CDCl$_3$) δ (ppm)=8.06-8.01 (m, 1H), 7.94-7.89 (m, 1H), 7.64-7.61 (m, 1H), 7.61-7.51 (m, 2H), 6.79 (d, J=1.6 Hz, 1H), 4.09 (s, 3H).

Step 2: To a mixture of 2-(2-methylpyrazol-3-yl)benzothiophene-3-carbonitrile (150 mg, 0.63 mmol, 1.00 eq.) in acetonitrile (2 mL) was added N-bromosuccinimide (112 mg, 0.63 mmol, 1.00 eq.) and the mixture was stirred at 25° C. for 12 hours. After such time the reaction mixture was added to a saturated sodium bicarbonate solution (5 mL) and extracted with ethyl acetate (10 mL×3). The combined organic phases were washed with brine (15 mL), dried over anhydrous sodium sulfate, filtered, concentrated and the residue was purified by column chromatography (SiO$_2$, petroleumether:ethylacetate 0-100%) to give 2-(4-bromo-2-methyl-pyrazol-3-yl)benzothiophene-3-carbonitrile (160 mg, 75% yield) as a yellow solid. LCMS [M+1]$^+$=319.9; $^1$H NMR (400 MHz, CDCl$_3$) δ (ppm)=8.10-8.05 (m, 1H), 7.98-7.93 (m, 1H), 7.65 (s, 1H), 7.63-7.56 (m, 2H), 3.98 (s, 3H).

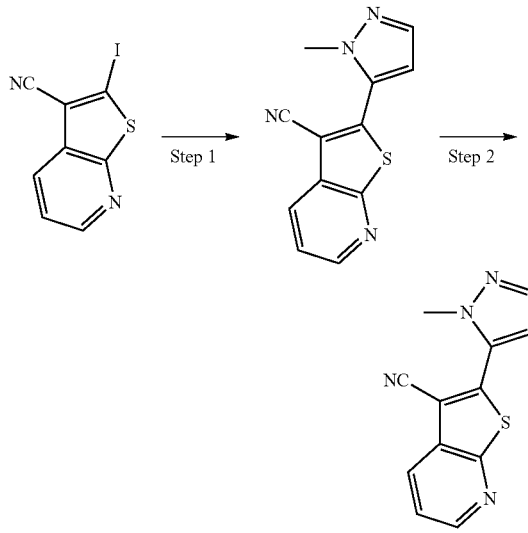

Intermediate ES, 2-(4-bromo-2-methyl-pyrazol-3-yl)thieno[2,3-b]pyridine-3-carbonitrile, was prepared as a yellow solid (80.0 mg, 0.25 mmol, 22% yield over 2 steps) from thieno[2,3-b]pyridine-3-carbonitrile in steps following the procedure described for Intermediate ER. LCMS [M+1]⁺=320.9; ¹H NMR (400 MHz, CDCl₃) δ (ppm)=8.78 (dd, J=1.6, 4.4 Hz, 1H), 8.34 (dd, J=1.6, 8.0 Hz, 1H), 7.66 (s, 1H), 7.58 (dd, J=4.4, 8.0 Hz, 1H), 3.99 (s, 3H).

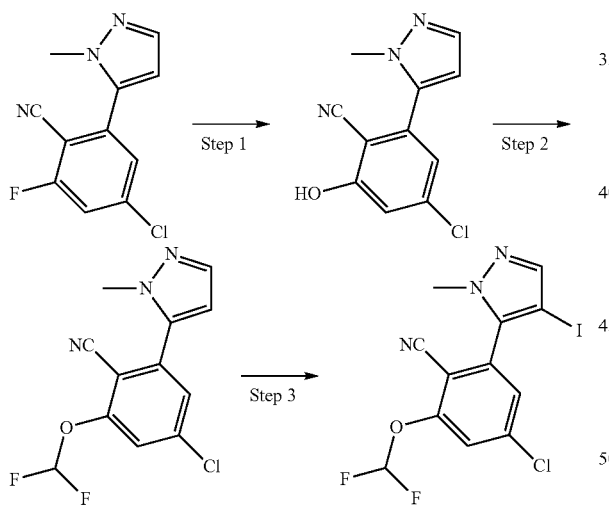

Step 1: To a solution of 2-methylsulfonylethanol (569 mg, 4.58 mmol, 1.20 eq.) in DMF (30 mL) was added sodium hydride (183 mg, 4.58 mmol, 60.0% purity, 1.20 eq.) at 0° C. After stirring for 0.5 hour 4-chloro-2-fluoro-6-(2-methylpyrazol-3-yl)benzonitrile (900 mg, 3.82 mmol, 1.00 eq.) in DMF (5 mL) was added in a dropwise fashion at 0° C. The reaction mixture was stirred at 25° C. for 1 hour. After such time the mixture was diluted with water (100 mL), extracted with ethyl acetate (100 mL×3), the aqueous phase adjusted to pH 1 with HCl (10 mL) and further extracted with ethyl acetate (100 mL×3). The combined organic layers were dried over anhydrous sodium sulfate, filtered and concentrated to give 4-chloro-2-hydroxy-6-(2-methylpyrazol-3-yl)benzonitrile (455 mg, crude) as a yellow solid which used into the next step without further purification. LCMS [M]⁺=234.1; ¹H NMR (400 MHz, DMSO-d₆) δ=11.96 (br s, 1H), 7.54 (d, J=2.0 Hz, 1H), 7.16 (d, J=2.0 Hz, 1H), 7.12 (d, J=2.0 Hz, 1H), 6.50 (d, J=2.0 Hz, 1H), 3.76 (s, 3H).

Step 2: To a solution of 4-chloro-2-hydroxy-6-(2-methylpyrazol-3-yl)benzonitrile (150 mg, 0.642 mmol, 1.00 eq.) and sodium 2-chloro-2,2-difluoro-acetate (392 mg, 2.57 mmol, 4.00 eq.) in DMF (2 mL) and water (0.2 mL) was added cesium carbonate (314 mg, 0.96 mmol, 1.50 eq.). The mixture was stirred at 100° C. for 1 hour. The reaction mixture was then quenched by addition water (40 mL) and extracted with ethyl acetate (20 mL×3). The combined organic layers were washed with brine (20 mL), dried over anhydrous sodium sulfate, filtered, concentrated and the residue was purified by prep-TLC (SiO₂, petroleum ether:ethyl acetate 25%) to give 4-chloro-2-(difluoromethoxy)-6-(2-methylpyrazol-3-yl) benzonitrile (85 mg, 0.30 mmol, 47% yield) as a yellow solid. LCMS [M]⁺=284.0; ¹H NMR (400 MHz, DMSO-d₆) δ (ppm)=7.76 (s, 1H), 7.74 (d, J=2.0 Hz, 1H), 7.72-7.71 (m, 1H), 7.58 (d, J=2.0 Hz, 1H), 7.54 (s, 1H), 7.36 (s, 1H), 6.60 (d, J=2.0 Hz, 1H), 3.80 (s, 3H).

Step 3: To a solution of 4-chloro-2-(difluoromethoxy)-6-(2-methylpyrazol-3-yl) benzonitrile (85 mg, 0.30 mmol, 1.00 eq.) in acetic acid (2 mL) was added N-iodide succinimide (135 mg, 0.60 mmol, 2.00 eq.). The mixture was stirred at 25° C. for 1 hour then the reaction mixture was quenched by addition of water (40 mL) and extracted with ethyl acetate (20 mL×3). The combined organic layers were washed with brine (40 mL), dried over anhydrous sodium sulfate, filtered, concentrated and the residue was purified by prep-TLC (SiO₂, petroleumether:ethylacetate 20%) to give 4-chloro-2-(difluoromethoxy)-6-(4-iodo-2-methyl-pyrazol-3-yl) benzonitrile (90 mg, 0.22 mmol, 73% yield) as a yellow solid. LCMS [M+H]=409.9; ¹H NMR (400 MHz, CD₃OD-d₄) δ (ppm)=7.72-7.68 (m, 1H), 7.67 (s, 1H), 7.52 (d, J=2.0 Hz, 1H), 7.42-7.02 (m, 1H), 3.83 (s, 3H).

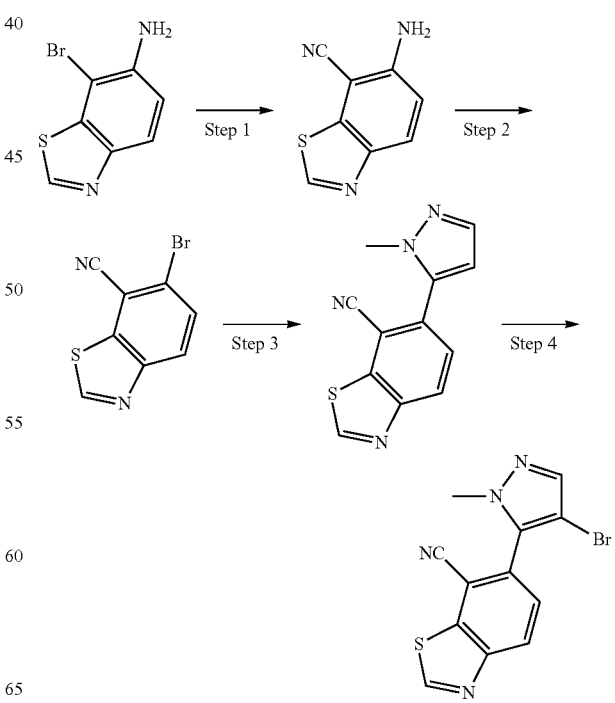

Step 1: A mixture of 7-bromo-1,3-benzothiazol-6-amine (2.00 g, 8.73 mmol, 1.00 eq.), zinc cyanide (1.54 g, 13.1 mmol, 1.50 eq.), Pd$_2$(dba)$_3$ (80 mg, 0.87 mmol, 0.01 eq.), DPPF (97 mg, 0.175 mmol, 0.02 eq.) and zinc powder (5.7 mg, 0.087 mmol, 0.01 eq.) in DMF (20 mL) was degassed, purged with nitrogen 3 times, and then stirred at 140° C. for 16 hours. After such time the reaction mixture was extracted with ethyl acetate 150 mL (50 mL×3) and the combined organic layers were washed with brine (50 mL), dried over anhydrous sodium sulfate, filtered, concentrated and the formed residue purified by column chromatography (SiO$_2$, petroleumether:ethylacetate 10-25%) to give 6-amino-1,3-benzothiazole-7-carbonitrile (1.05 g, 4.66 mmol, 53% yield) as a yellow solid. LCMS [M+1]$^+$=176.1; $^1$H NMR (400 MHz, CDCl$_3$-d) δ=8.79 (s, 1H), 8.05 (d, J=8.8 Hz, 1H), 6.90 (d, J=8.8 Hz, 1H), 4.69 (br s, 2H).

Step 2: A mixture of 6-amino-1,3-benzothiazole-7-carbonitrile (500 mg, 2.85 mmol, 1.00 eq.), para-toluenesulfonic acid (590 mg, 3.42 mmol, 1.20 eq.), tert-butyl nitrite (353 mg, 3.42 mmol, 407 uL, 1.20 eq.), tetrabutylammonium bromide (1.84 g, 5.71 mmol, 2.00 eq.) and copper bromide (64 mg, 0.286 mmol, 0.10 eq.) in acetonitrile (15 mL) was degassed with nitrogen and stirred at 25° C. for 6 hours. The mixture was then concentrated under reduced pressure and the residue was purified by column chromatography (SiO$_2$, petroleum ether: ethyl acetate 10-25%) to give 6-bromo-1,3-benzothiazole-7-carbonitrile (300 mg, 1.25 mmol, 44% yield) as a yellow solid. LCMS [M+1]$^+$=240.9; $^1$H NMR (400 MHz, CDCl$_3$) δ=9.11 (s, 1H), 8.20 (d, J=8.8 Hz, 1H), 7.81 (d, J=8.8 Hz, 1H).

Step 3: A mixture of 1-methyl-5-(4,4,5,5-tetramethyl-1,3,2-dioxaborolan-2-yl)pyrazole (261 mg, 1.25 mmol, 1.00 eq.), 6-bromo-1,3-benzothiazole-7-carbonitrile (300 mg, 1.25 mmol, 1.00 eq.), ditert-butyl(cyclopentyl)phosphane; dichloropalladium iron (82 mg, 0.125 mmol, 0.10 eq.) and sodium bicarbonate (316 mg, 3.76 mmol, 3.00 eq.) in dioxane (10 mL) and water (2 mL) was degassed with nitrogen and then stirred at 80° C. for 3 hours under a nitrogen atmosphere. The mixture was then concentrated and the residue purified by column chromatography (SiO$_2$, petroleumether:ethylacetate 5-25%) to give 6-(2-methylpyrazol-3-yl)-1,3-benzothiazole-7-carbonitrile (280 mg, 0.89 mmol, 71% yield) as a yellow solid. LCMS [M+1]$^+$=241.0; $^1$H NMR (400 MHz, CDCl$_3$-d) δ=9.21 (s, 1H), 8.43 (d, J=8.4 Hz, 1H), 7.66-7.58 (m, 2H), 6.58 (d, J=2.0 Hz, 1H), 3.91 (s, 3H).

Step 4: A mixture of 6-(2-methylpyrazol-3-yl)-1,3-benzothiazole-7-carbonitrile (140 mg, 0.58 mmol, 1.00 eq.), N-bromosuccinimide (207 mg, 1.17 mmol, 2.00 eq.) in acetonitrile (3 mL) was stirred at 40° C. for 2 hours under a nitrogen atmosphere. The mixture was then concentrated and the residue purified by column chromatography (SiO$_2$, petroleum ether: ethyl 5-20%) to give 6-(4-bromo-2-methylpyrazol-3-yl)-1,3-benzothiazole-7-carbonitrile (300 mg, 0.47 mmol, 81% yield) as a white solid. LCMS [M+1]$^+$=321.0; $^1$H NMR (400 MHz, CDCl$_3$-d) δ=9.25 (s, 1H), 8.48 (d, J=8.4 Hz, 1H), 7.65 (s, 1H), 7.61 (d, J=8.4 Hz, 1H), 3.85 (s, 3H).

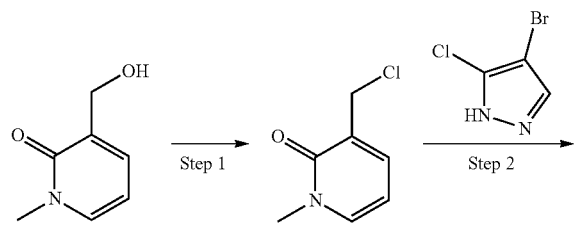

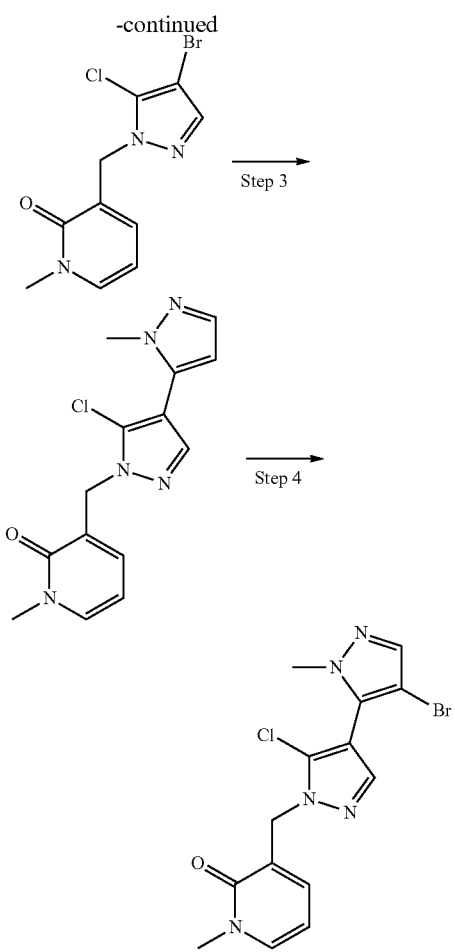

Step 1: To a solution of 3-(hydroxymethyl)-1-methylpyridin-2(1H)-one (650 mg, 4.67 mmol, 1.00 eq.) in dichloromethane (15 mL) was added thionyl chloride (667 mg, 5.61 mmol, 407 uL, 1.20 eq.) and the mixture was stirred at 25° C. for 2 hrs. The mixture was concentrated in vacuum to give 3-(chloromethyl)-1-methyl-pyridin-2-one (650 mg, crude) as a white solid.

Step 2: To a solution of 3-(chloromethyl)-1-methyl-pyridin-2-one (650 mg, 4.12 mmol, 1.00 eq.), 4-bromo-5-chloro-1H-pyrazole (747 mg, 4.12 mmol, 1.00 eq.) in acetonitrile (20 mL) was added potassium carbonate (683 mg, 4.94 mmol, 1.20 eq.) and the mixture was stirred at 80° C. for 12 hours. The reaction was then quenched with water (100 mL) and extracted with ethyl acetate (50 mL×3). The combined organic phases were washed with brine (50 mL), dried over anhydrous sodium sulfate, filtered and concentrated in vacuo to give a residue. The residue was purified by column chromatography (SiO$_2$, petroleum ether: ethyl acetate 5%) to give 3-[(4-bromo-5-chloro-pyrazol-1-yl)methyl]-1-methyl-pyridin-2-one (270 mg, 0.89 mmol, 51% yield) as a yellow solid. LCMS [M+1]$^+$=304.0.

Step 3: To a solution of 3-[(4-bromo-5-chloro-pyrazol-1-yl)methyl]-1-methyl-pyridin-2-one (270 mg, 0.89 mmol, 1.00 eq.), 4-bromo-1-methyl-5-(4,4,5,5-tetramethyl-1,3,2-dioxaborolan-2-yl)pyrazole (512 mg, 1.78 mmol, 2.00 eq.) in dioxane (10 mL) and water (1 mL) was added Pd(dppf)Cl$_2$ (65 mg, 0.089 mmol, 0.10 eq.) and sodium bicarbonate (150 mg, 1.78 mmol, 69 μL, 2.00 eq.). The mixture was stirred at 110° C. for 10 hours. The reaction mixture was then quenched by addition water (50 mL) and extracted with ethyl acetate (30 mL×3). The combined organic layers were washed with brine (30 mL), dried over anhydrous sodium sulfate, filtered and concentrated under reduced pressure to give a residue. The residue was purified by prep-HPLC (Phenomenex Gemini-NX 80 mm×40 mm×3 μm; mobile phase: [water (10 mM NH$_4$HCO$_3$)-ACN]; B %: 5%-35%, 8 min) to give 3-[[5-chloro-4-(2-methylpyrazol-3-yl)pyrazol-1-yl]methyl]-1-methyl-pyridin-2-one (60.0 mg, 0.198 mmol, 22% yield) as a grey solid. LCMS [M+1]$^+$=304.1; $^1$H NMR (400 MHz, DMSO-d$_6$) δ=8.24 (s, 1H), 7.73 (d, J=2.0, 6.8 Hz, 1H), 7.46 (d, J=2.0 Hz, 1H), 7.32 (d, J=5.2 Hz, 1H), 6.39 (d, J=2.0 Hz, 1H), 6.25 (t, J=6.8 Hz, 1H), 5.14 (s, 2H), 3.79 (s, 3H), 3.45 (s, 3H)

Step 4: To a solution of 3-((5'-chloro-2-methyl-1'H,2H-[3,4'-bipyrazol]-1'-yl)methyl)-1-methylpyridin-2(1H)-one (47.0 mg, 0.155 mmol, 1.00 eq.) in acetonitrile (1 mL) was added N-bromosuccinimide (26 mg, 0.147 mmol, 0.95 eq.). The mixture was stirred at 25° C. for 10 hours. The reaction mixture was then quenched by addition of water (5 mL) and extracted with ethyl acetate (5 mL×3). The combined organic layers were washed with brine (5 mL), dried over anhydrous sodium sulfate, filtered, concentrated and the residue was purified by prep-TLC (SiO$_2$, dichloromethane:methanol 10%) to give 3-((4-bromo-5'-chloro-2-methyl-1'H,2H-[3,4'-bipyrazol]-1'-yl)methyl)-1-methylpyridin-2(1H)-one (45 mg, 0.118 mmol, 76% yield) as a white solid. LCMS [M+1]$^+$=383.9; $^1$H NMR (400 MHz, DMSO-d$_6$) δ=7.89 (s, 1H), 7.71 (d, J=6.8, 1.2 Hz, 1H), 7.67 (s, 1H), 6.93-6.96 (m, 1H), 6.23 (t, J=6.8 Hz, 1H), 5.22 (s, 2H), 3.74 (s, 3H), 3.47 (s, 3H).

Steps 1-6: 2-((7-bromo-4-oxo-5-(methoxy)-3,4-dihydrophthalazin-1-yl)methyl)isoindoline-1,3-dione was prepared as a white solid (4.22 g, 10.2 mmol, 8% yield over 6 steps) starting from 1-(5-bromo-2-methyl-3-(methoxy)phenyl)ethan-1-one following the same procedure described for the first 6 steps of Intermediate DK. LCMS [M+1]$^+$=414.0.

Step 7: A mixture of 2-((7-bromo-4-oxo-5-(methoxy)-3,4-dihydrophthalazin-1-yl)methyl)isoindoline-1,3-dione (4.22 g, 10.2 mmol, 1.0 eq.), bis(pinacolato)diboron (3.88 g, 15.3 mmol, 1.5 eq.), Pd(dppf)Cl$_2$.CH$_2$Cl$_2$ (745 mg, 1.02 mmol, 0.1 eq.) and potassium acetate (3.00 g, 30.6 mmol, 3.0 eq.) in dioxane (60 mL) was degassed and purged with nitrogen 3 times, and stirred at 100° C. for 1 hour. The mixture was then concentrated, and the residue triturated with methanol, filtered and dried to give Intermediate EX as a grey solid (2.01 g, 43% yield). LCMS [M+1]$^+$=380.1 (boronic acid from loss of pinicol).

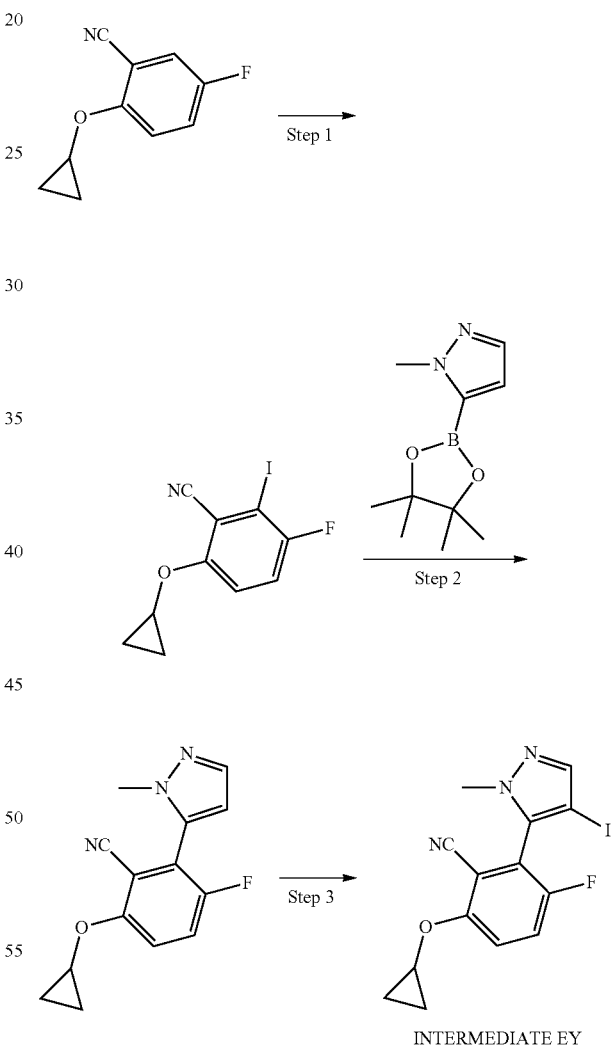

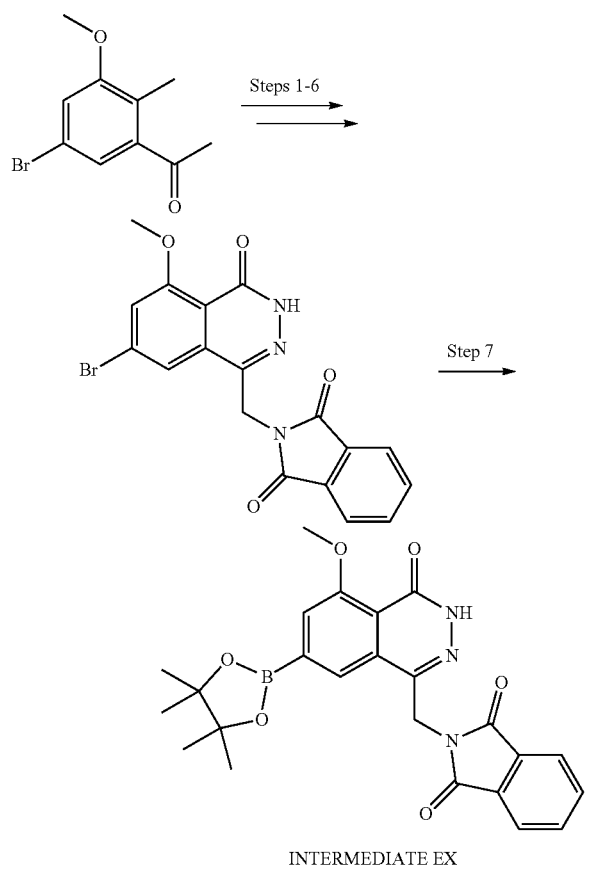

INTERMEDIATE EX

INTERMEDIATE EY 6-cyclopropoxy-3-fluoro-2-(4-iodo-1-methyl-1H-pyrazol-5-yl)benzonitrile, intermediate EY, was prepared as a white solid (120 mg, 0.30 mmol, 20% over 3 steps) following the procedure described for the preparation of Intermediate DQ. LCMS [M+1]$^+$=383.8; $^1$H NMR (400 MHz, CDCl$_3$) δ=7.65 (s, 1H), 7.51-7.40 (m, 2H), 3.93-3.87 (m, 1H), 3.83 (s, 3H), 1.00-0.89 (m, 4H).

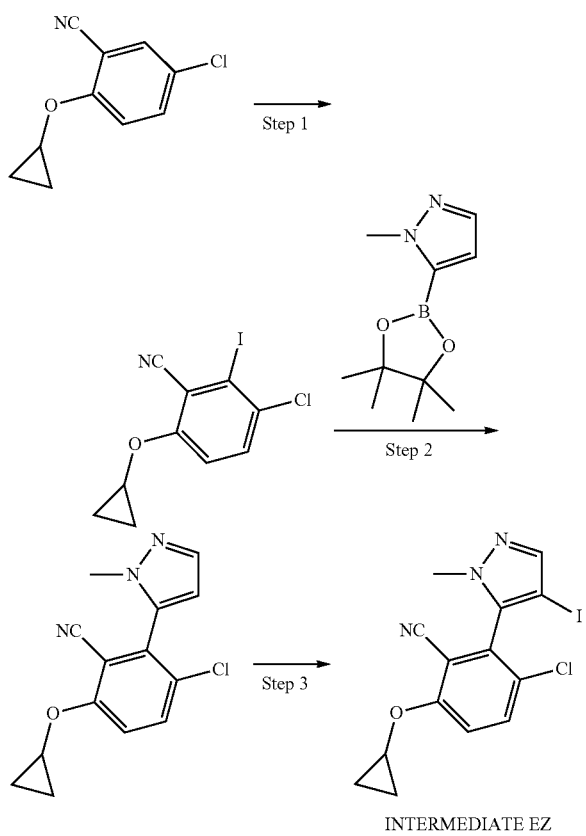

INTERMEDIATE EZ 6-cyclopropoxy-3-chloro-2-(4-iodo-1-methyl-1H-pyrazol-5-yl)benzonitrile, intermediate EZ, was prepared as a yellow solid (160 mg, 0.40 mmol, 22% over 3 steps) following the procedure described for the preparation of Intermediate DQ. LCMS [M+1]$^+$399.9; $^1$H NMR (400 MHz, CDCl$_3$) δ=7.70 (d, J=9.2 Hz, 1H), 7.64 (s, 1H), 7.47 (d, J=9.2 Hz, 1H), 3.92 (td, J=2.8, 5.6 Hz, 1H), 3.78 (s, 3H), 0.99-0.90 (m, 4H).

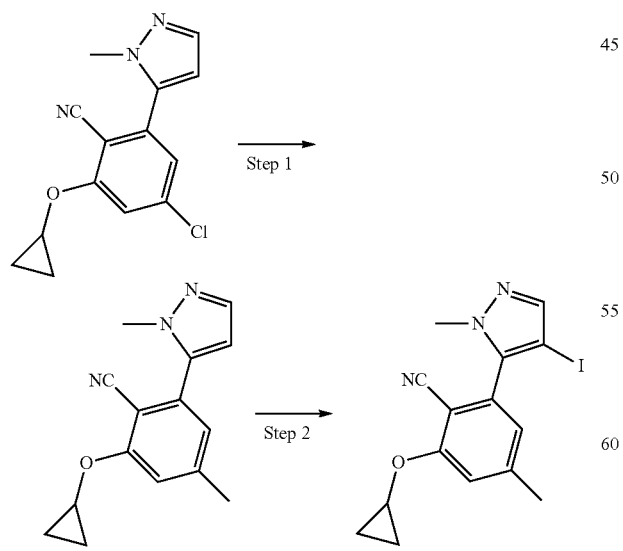

Step 1: To a solution of 4-chloro-2-cyclopropoxy-6-(1-methyl-1H-pyrazol-5-yl)benzonitrile (177 mg, 0.65 mmol, 1.00 eq.) in dioxane (10 mL) was added potassium carbonate (268 mg, 1.94 mmol, 3.00 eq.), ditert-butyl(cyclopentyl)phosphane; dichloropalladium-iron (42 mg, 0.064 mmol, 0.10 eq.) and methylboronic acid (194 mg, 3.23 mmol, 5.00 eq.). The mixture was stirred at 100° C. for 2 hours then diluted with water (50 mL) and extracted with ethyl acetate (50 mL×3). The combined organic layers were washed with brine (20 mL), dried over anhydrous sodium sulfate, filtered, concentrated and the residue was purified by prep-TLC (SiO$_2$, petroleum ether: ethyl acetate 25%) to give 2-(cyclopropoxy)-4-methyl-6-(2-methylpyrazol-3-yl)benzonitrile (111 mg, 0.44 mmol, 68% yield) as a white solid. LCMS [M+1]$^+$=254.1; $^1$H NMR (400 MHz, CDCl$_3$) δ=7.98 (d, J=2.0 Hz, 1H), 7.65 (d, J=0.8 Hz, 1H), 7.27 (s, 1H), 6.85 (d, J=2.0 Hz, 1H), 4.35-4.29 (m, 1H), 4.27 (s, 3H), 2.91 (s, 3H), 1.36-1.31 (m, 4H).

Step 2: To a solution of 2-(cyclopropoxy)-4-methyl-6-(2-methylpyrazol-3-yl)benzonitrile (100 mg, 0.40 mmol, 1.00 eq.) in acetic acid (2 mL) was added N-iodosuccinimide (178 mg, 0.79 mmol, 2.00 eq.). The mixture was stirred at 25° C. for 1 hour then diluted with water (20 mL) and extracted with ethyl acetate (20 mL×3). The combined organic layers were washed with brine (20 mL), dried over anhydrous sodium sulfate, filtered, concentrated and the residue purified by prep-TLC (SiO$_2$, petroleumether:ethylacetate 25%) to give 2-(cyclopropoxy)-6-(4-iodo-2-methylpyrazol-3-yl)-4-methyl-benzonitrile (94 mg, 0.25 mmol, 63% yield) as a yellow solid. LCMS [M+1]$^+$=380.0; $^1$H NMR (400 MHz, CDCl$_3$) δ=7.66-7.55 (m, 1H), 7.27 (s, 1H), 6.80 (s, 1H), 3.89 (tt, J=3.2, 6.0 Hz, 1H), 3.85-3.79 (m, 3H), 2.50 (s, 3H), 1.04-0.80 (m, 4H).

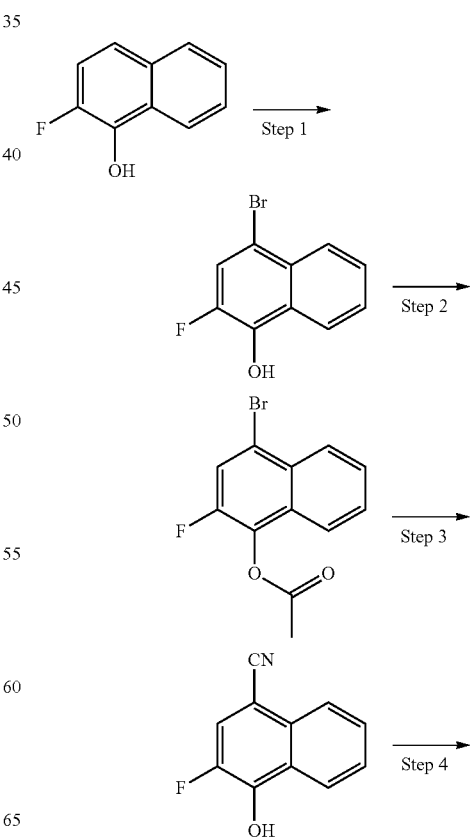

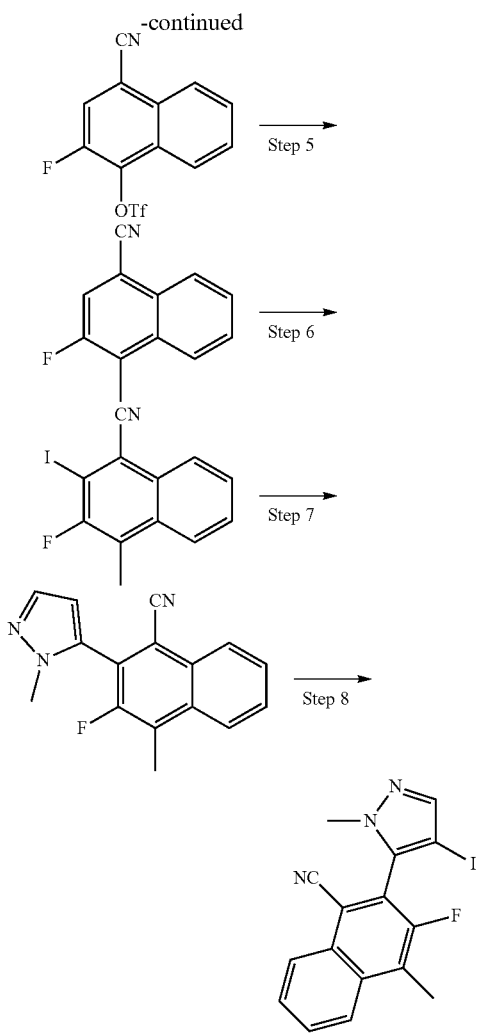

Step 1: To a solution of 2-fluoronaphthalen-1-ol (0.50 g, 3.08 mmol, 1.00 eq.) in dichloromethane (8 mL) was added NBS (521 mg, 2.93 mmol, 0.95 eq.) and the mixture was stirred at −50° C. for 0.25 hr. Water (10 mL) was then added and the separated organic phase was dried, concentrated and the residue purified by column chromatography (SiO$_2$, petroleum ether/ethyl acetate 1%) to give 4-bromo-2-fluoro-naphthalen-1-ol (500 mg, 2.07 mmol, 67% yield) as a light yellow solid. $^1$H NMR (400 MHz, CDCl$_3$) δ=8.27-8.21 (m, 1H), 8.19-8.11 (m, 1H), 7.63 (d, J=10.2 Hz, 1H), 7.61-7.54 (m, 2H), 5.68 (br d, J=4.0 Hz, 1H).

Step 2: To a solution of 4-bromo-2-fluoro-naphthalen-1-ol (2.30 g, 9.54 mmol, 1.00 eq.), DIEA (21.0 mmol, 3.66 mL, 2.20 eq.) and DMAP (58 mg, 0.48 mmol, 0.05 eq.) in dichloromethane (40 mL) at 0° C. was added acetyl chloride (19.1 mmol, 1.36 mL, 2.00 eq.) in a dropwise fashion. The mixture was stirred at 28° C. for 1 hr before the mixture was concentrated and the formed residue purified by column chromatography (SiO$_2$, pether/ethyl acetate 1%) to give (4-bromo-2-fluoro-1-naphthyl) acetate (2.50 g, 8.83 mmol, 93% yield) as a white solid. $^1$H NMR (400 MHz, CDCl$_3$) δ=8.26-8.18 (m, 1H), 7.94-7.86 (m, 1H), 7.72 (d, J=9.2 Hz, 1H), 7.66-7.56 (m, 2H), 2.51 (s, 3H).

Step 3: A mixture of (4-bromo-2-fluoro-1-naphthyl) acetate (2.50 g, 8.83 mmol, 1.00 eq.), Pd$_2$(dba)$_3$ (809 mg, 0.88 mmol, 0.10 eq.), Zn(CN)$_2$ (9.71 mmol, 0.62 mL, 1.10 eq.), Zn (29 mg, 0.442 mmol, 0.05 eq.) and DPPF (979 mg, 1.77 mmol, 0.20 eq.) in DMA (40 mL) was degassed with nitrogen 3 times then stirred at 120° C. for 3 hr. The reaction mixture was then diluted with ethyl acetate (100 mL), filtered and the filtrate was washed with brine (50 mL×3), dried, concentrated and the residue was purified by column chromatography (SiO$_2$, petroleum ether/ethyl acetate 2-10%) to give 3-fluoro-4-hydroxy-naphthalene-1-carbonitrile (980 mg, 5.24 mmol, 59% yield) as a yellow solid. $^1$H NMR (400 MHz, CDCl$_3$) δ=8.36-8.27 (m, 1H), 8.18 (d, J=8.0 Hz, 1H), 7.76 (d, J=9.6 Hz, 1H), 7.72-7.62 (m, 2H).

Step 4: To a solution of 3-fluoro-4-hydroxy-naphthalene-1-carbonitrile (880 mg, 4.70 mmol, 1.00 eq.) in dichloromethane (20 mL) was added triethylamine (9.40 mmol, 1.31 mL, 2.00 eq.) and Tf$_2$O (8.46 mmol, 1.40 mL, 1.80 eq.) at 0° C. The mixture was then stirred at 28° C. for 0.5 hr. The reaction mixture was then concentrated, and the residue purified by column chromatography (SiO$_2$, petroleum ether/ethyl acetate 2%) to give (4-cyano-2-fluoro-1-naphthyl) trifluoromethanesulfonate (1.15 g, 3.60 mmol, 77% yield) as a yellow solid.

Step 5: A mixture of (4-cyano-2-fluoro-1-naphthyl) trifluoromethanesulfonate (0.38 g, 1.19 mmol, 1.00 eq.), Pd(PPh$_3$)$_4$ (138 mg, 0.12 mmol, 0.10 eq.), AlMe$_3$ (2 M in PhMe, 1.79 mL, 3.00 eq.) in toluene (3.5 mL) was degassed with nitrogen 3 times and stirred at 120° C. for 2 hr. After such time the reaction was quenched by the addition of water (5 mL) then diluted with ethyl acetate (40 ml) and filtered. The filtrate was washed with water (20 mL×3), dried, concentrated and the residue purified by prep-TLC (SiO$_2$, Petroleum ether/Ethyl acetate 5%) to give compound 3-fluoro-4-methyl-naphthalene-1-carbonitrile (90 mg, 0.49 umol, 41% yield) as a white solid. $^1$H NMR (400 MHz, CDCl$_3$) δ=8.29-8.22 (m, 1H), 8.11-8.03 (m, 1H), 7.75-7.63 (m, 3H), 2.66 (d, J=2.4 Hz, 3H).

Step 6: To a solution of N-isopropylpropan-2-amine (0.86 mmol, 0.12 mL, 2.00 eq.) in THF (2 mL) was added n-BuLi (2.5 M in THF, 0.31 mL, 1.80 eq.) in a dropwise fashion at −70° C. The mixture was then stirred at −70° C. for 0.5 hr, then 3-fluoro-4-methyl-naphthalene-1-carbonitrile (80 mg, 0.43 mmol, 1 eq.) was added and stirred for a further 0.5 hr before iodine (0.87 mmol, 0.17 mL, 2.00 eq.) was added. After completion of the addition the mixture was stirred at 30° C. for 1 hr. The reaction mixture was then quenched by the addition of water (2 mL) and extracted with ethyl acetate (10 mL×2). The combined organic phases were dried and concentrated to give 3-fluoro-2-iodo-4-methyl-naphthalene-1-carbonitrile (110 mg, 0.35 mmol) as a brown solid.

Step 7: A mixture of 3-fluoro-2-iodo-4-methyl-naphthalene-1-carbonitrile (110 mg, 0.35 mmol, 1.00 eq.), 1-methyl-5-(4,4,5,5-tetramethyl-1,3,2-dioxaborolan-2-yl)pyrazole (96 mg, 0.46 mmol, 1.30 eq.), [2-(2-aminophenyl)phenyl]palladium(1+)-bis(1-adamantyl)-butyl-phosphane-methanesulfonate (26 mg, 0.035 mmol, 0.10 eq.), K$_3$PO$_4$ (1.50 M, 0.71 mL, 3.00 eq.) in n-butyl alcohol (2.8 mL) was degassed with nitrogen 3 times then stirred at 60° C. for 6 hr. The reaction mixture was then filtered, concentrated and the residue was purified by prep-TLC (SiO$_2$, petroleum ether/ethyl acetate 20%) to give 3-fluoro-4-methyl-2-(2-methylpyrazol-3-yl)naphthalene-1-carbonitrile (50 mg, 0.19 mmol, 53% yield) as a brown solid. LCMS [M+1]$^+$ 266.1.

Step 8: To a solution of 3-fluoro-4-methyl-2-(2-methylpyrazol-3-yl)naphthalene-1-carbonitrile (50 mg, 0.19 mmol, 1.00 eq.) in acetic acid (2 mL) was added NIS (127 mg, 0.57 mmol, 3.00 eq.). The mixture was stirred at 30° C. for 12 hrs. The pH was then adjusted to pH 7 with saturated sodium bicarbonate aqueous solution and then extracted with ethyl acetate (10 mL×3) and the combined organic phases were dried and concentrated. The residue was purified by prep-TLC (SiO$_2$, petroleum ether/ethyl acetate 20%) to give compound 3-fluoro-2-(4-iodo-2-methyl-pyrazol-3-yl)-4-methyl-naphthalene-1-carbonitrile (30 mg, 0.076 mmol, 41% yield) as a brown solid. LCMS [M+1]$^+$ 392.0.

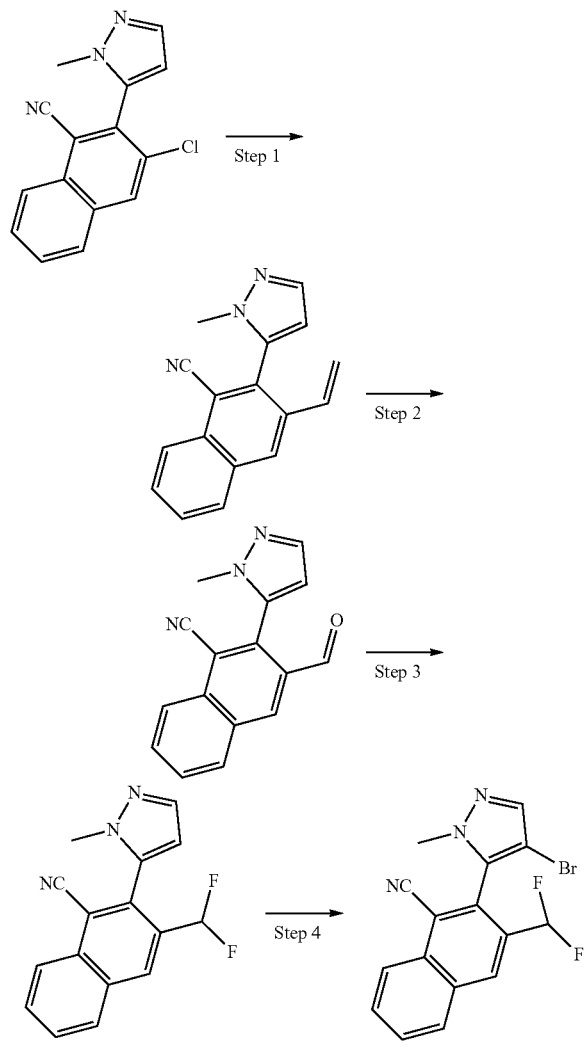

Step 1: To a solution of 3-chloro-2-(1-methyl-1H-pyrazol-5-yl)-1-naphthonitrile (200 mg, 0.747 mmol, 1.00 eq), potassium trifluoro(vinyl)borate (120 mg, 0.896 mmol, 1.20 eq), cesium carbonate (730 mg, 2.24 mmol, 3.00 eq) and dicyclohexyl(2',6'-diisopropoxy-[1,1'-biphenyl]-2-yl)phosphine (34.9 mg, 0.074 mmol, 0.10 eq) in THF (2 mL) and water (0.2 mL) was added palladium(II) chloride (13.3 mg, 0.074 mmol, 0.10 eq) under a nitrogen atmosphere. The resulting mixture was stirred at 90° C. for 16 hours. The mixture was then diluted with water (3 mL) and extracted with ethyl acetate (5 mL×3). The combined organic layers were washed with brine (5 mL×2), dried over anhydrous sodium sulfate, filtered and concentrated under reduced pressure. The residue was purified by column chromatography (SiO$_2$, Petroleum ether/Ethyl acetate 5-20%) to give 2-(1-methyl-1H-pyrazol-5-yl)-3-vinyl-1-naphthonitrile (130 mg, 0.049 mmol, 66% yield) as a light yellow solid. LCMS [M+1]$^+$=260.2.

Step 2: 2-(1-methyl-1H-pyrazol-5-yl)-3-vinyl-1-naphthonitrile (130 mg, 491 µmol, 1.00 eq) were dissolved in dichloromethane (20 mL) and cooled to −70° C. Ozone was bubbled into the reaction solution with stirring for 15 min. Dimethylsulfane (8.46 g, 136 mmol, 10 mL, 277 eq) was then added and the mixture stirred at −70° C. for 15 min. After such time the mixture was concentrated and then purified by column chromatography (SiO$_2$, Petroleum ether/Ethyl acetate 5-20%) to give 3-formyl-2-(1-methyl-1H-pyrazol-5-yl)-1-naphthonitrile (60 mg, 222 µmol, 45.3% yield) as a white solid. LCMS [M+1]$^+$=262.2.

Step 3: A solution of 3-formyl-2-(1-methyl-1H-pyrazol-5-yl)-1-naphthonitrile (20 mg, 74.2 µmol, 1.00 eq) and (bis-(2-methoxyethyl)amino)sulfur trifluoride (41 mg, 185 µmol, 41 µL, 2.50 eq) in dichloromethane (1.0 mL) was stirred at 25° C. for 6 hours. The reaction was then quenched with saturated sodium bicarbonate aqueous (2 mL) and extracted with ethyl acetate (5 mL×3). The combined organic layers were washed by brine (3 mL×3), dried over anhydrous sodium sulfate, filtered, concentrated and the residue purified by Prep-TLC (Petroleum ether/Ethyl acetate 20%) to give 3-(difluoromethyl)-2-(2-methylpyrazol-3-yl)naphthalene-1-carbonitrile (11.0 mg, 38.4 µmol, 52% yield) as a white solid. LCMS [M+1]$^+$=284.2.

Step 4: To a solution of 3-(difluoromethyl)-2-(1-methyl-1H-pyrazol-5-yl)-1-naphthonitrile (11 mg, 38 µmol, 1.00 eq) in dichloromethane (1.0 mL) was added 1-bromopyrrolidine-2,5-dione (10 mg, 58 µmol, 1.50 eq). The mixture was stirred at 25° C. for 10 hours. The reaction mixture was the concentrated and purified by Prep-TLC (SiO$_2$, Petroleum ether/Ethyl acetate 20%) to give 2-(4-bromo-1-methyl-1H-pyrazol-5-yl)-3-(difluoromethyl)-1-naphthonitrile (12 mg, 33 µmol, 86% yield) as a colorless oil. LCMS [M+1]$^+$=362.1.

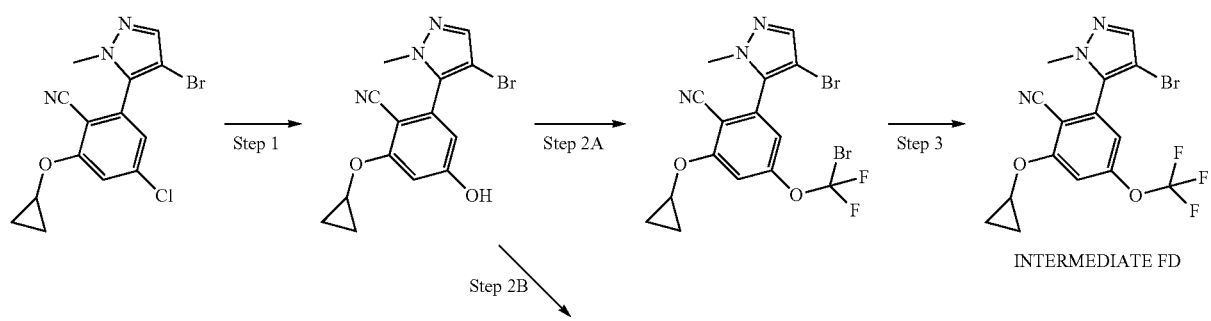

-continued

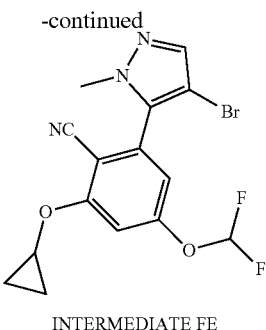

INTERMEDIATE FE

Step 1: A mixture of sodium hidride (51 mg, 1.28 mmol, 60% purity, 1.20 eq.) and 2-methylsulfonylethanol (158 mg, 1.28 mmol, 1.20 eq.) in DMF (3 mL) at 0° C. under nitrogen was stirred at 0° C. for 30 minutes. Then, a solution of 2-(4-bromo-2-methyl-pyrazol-3-yl)-4-chloro-6-(cyclopropoxy)benzonitrile (375 mg, 1.06 mmol, 1 eq.) in DMF (2 mL) was added dropwise and the reaction mixture was stirred at 25° C. for 2 hours. The mixture was then quenched with water (5 mL) and extracted with ethyl acetate (3×10 mL). The combined organic layers were dried over sodium sulfate, filtered, concentrated and purified by column chromatography (SiO$_2$, Petroleum ether/Ethyl acetate 10-30%) to give 2-(4-bromo-2-methyl-pyrazol-3-yl)-6-(cyclopropoxy)-4-hydroxy-benzonitrile (120 mg, 33% yield) as colorless oil. LCMS [M+1]$^+$=334.0; $^1$H NMR (400 MHz, CDCl$_3$) δ=9.77-9.37 (m, 1H), 7.54 (s, 1H), 6.98 (d, J=2.0 Hz, 1H), 6.51 (d, J=2.0 Hz, 1H), 3.85-3.82 (m, 1H), 3.80 (s, 3H), 0.94-0.84 (m, 5H).

Step 2A: To a mixture of 2-(4-bromo-2-methyl-pyrazol-3-yl)-6-(cyclopropoxy)-4-hydroxy-benzonitrile (20 mg, 59 μmol, 1.00 eq.) in DMF (0.5 mL) was added sodium hydride (4.8 mg, 119 μmol, 60% purity, 2.00 eq.) at 0° C. under nitrogen and the mixture was stirred at 0° C. for 30 minutes. Then dibromo(difluoro)methane (38 mg, 180 μmol, 17 uL, 3.00 eq.) was added to the mixture at 0° C. and the mixture was stirred at 25° C. for 1 hour. Water (3.00 mL) was then added and the mixture extracted with ethyl acetate (3×5 mL). The combined organic layers were dried over sodium sulfate, filtered, concentrated under vacuum and the residue was purified by prep-TLC (SiO$_2$, petroleum ether:ether acetate 20%) to give 4-[bromo(difluoro)methoxy]-2-(4-bromo-2-methyl-pyrazol-3-yl)-6-(cyclopropoxy)benzonitrile (10.0 mg, 36% yield) as a white solid. LCMS [M+1]$^+$=463.9

Step 2B: To a mixture of 2-(4-bromo-2-methyl-pyrazol-3-yl)-6-(cyclopropoxy)-4-hydroxy-benzonitrile (100 mg, 299 μmol, 1.00 eq.) and sodium 2-chloro-2,2-difluoro-acetate (114 mg, 748 μmol, 2.50 eq.) in DMF (1.0 mL) and water (0.1 mL) was added cesium carbonate (146 mg, 449 μmol, 1.50 eq.). The mixture was stirred at 100° C. for 3 hours. The reaction mixture was then quenched with water (5 mL) and extracted with ethyl acetate (3×10 mL). The combined organic phases were washed with brine (15 mL), dried with anhydrous sodium sulfate, filtered, concentrated in vacuum and the residue purified by column chromatography (SiO$_2$, Petroleum ether/Ethyl acetate 0-30%) to give 2-(4-bromo-2-methyl-pyrazol-3-yl)-6-(cyclopropoxy)-4-(difluoromethoxy)benzonitrile (70 mg, 61% yield) as colorless oil. LCMS [M+1]$^+$=386.0; $^1$H NMR (400 MHz, CDCl$_3$) δ=7.57 (s, 1H), 7.23 (d, J=2.4 Hz, 1H), 6.87-6.43 (m, 2H), 3.95-3.87 (m, 1H), 3.82 (s, 3H), 0.99-0.90 (m, 4H)

Step 3: A mixture of 4-[bromo(difluoro)methoxy]-2-(4-bromo-2-methyl-pyrazol-3-yl)-6-(cyclopropoxy)benzonitrile (100 mg, 216 μmol, 1.00 eq.) and silver tetrafluoroborate (273 mg, 1.40 mmol, 6.50 eq.) in DCE (2. mL) was stirred at 65° C. for 3 hours. Then, the reaction mixture was quenched with water (5 mL) and extracted with ethyl acetate (3×10 mL). The combined organic phases were washed with brine (15 mL), dried with anhydrous sodium sulfate, filtered, concentrated in vacuum and the residue purified by reversed phase flash (0.1% FA condition) to give 2-(4-bromo-2-methyl-pyrazol-3-yl)-6-(cyclopropoxy)-4-(trifluoromethoxy)benzonitrile (55 mg, 63% yield) as a yellow solid. LCMS [M+1]$^+$=402.1.

In one aspect of the invention, provided herein are Intermediates that may be used in the preparation of compounds of Formula (I), Formula (I-A), Formula (I-B), Formula (I-C) and Formulate (1-D). In one embodiment, the intermediates include Intermediates A-1 through FE.

The following Examples are intended to illustrate further certain embodiments of the invention and are not intended to limit the scope of the invention.

General Reaction Methods for the Preparation of Examples 1-1 to 1-8

Examples 1-1 and 1-2

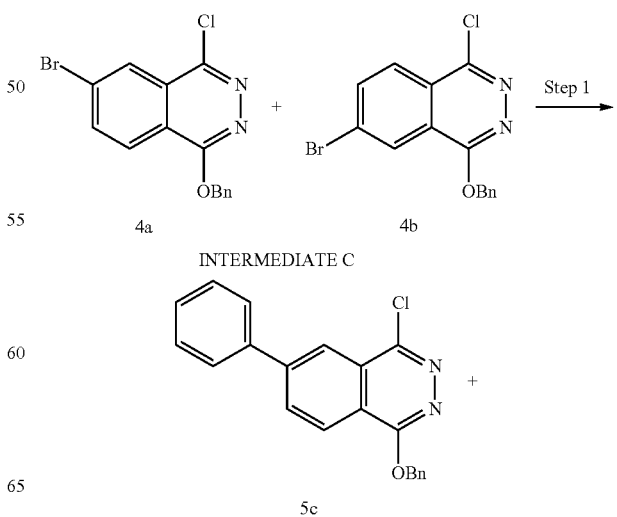

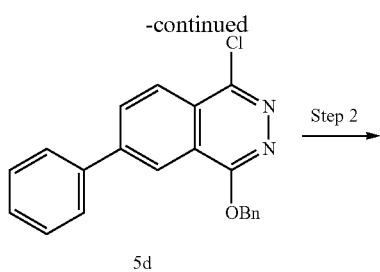

5d

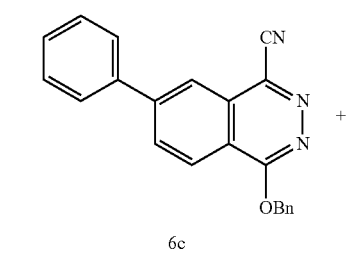

6c

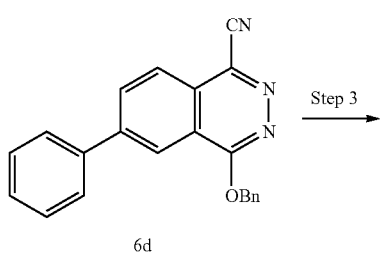

6d

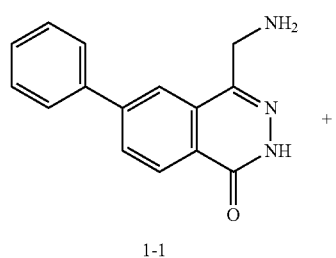

1-1

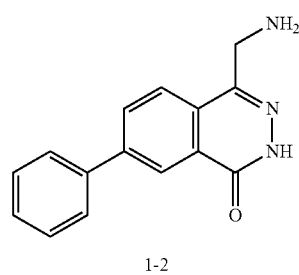 [SMILES: NCc1n[nH]c(=O)c2cc(-c3ccccc3)ccc12]

1-2

Step 1: A mixture of Intermediate C, a 1:1 mixture of 4c and 4d (587 mg, 1.68 mmol, 1.00 eq.), phenylboronic acid pinacol ester, Pd(dppf)Cl$_2$ (168 μmol, 0.10 eq.) and sodium carbonate (3.36 mmol, 2.00 eq.) in DMF (10 mL) was purged with nitrogen 3 times and stirred at 100° C. for 2 hours. After such time the reaction mixture was diluted with water (50 mL) and extracted with ethyl acetate (50 mL×3). The combined organic layers were washed with brine (50 mL), dried over anhydrous sodium sulfate, filtered and concentrated under reduced pressure. The residue was purified by prep-TLC (SiO$_2$, petroleum ether:ethyl acetate 5:1) to give a 1:1 mixture of 4-(benzyloxy)-1-chloro-7-phenylphthalazine 5c and 5d 4-benzyloxy-1-chloro-6-phenylphthalazine (355 mg, 818 μmol, 48% yield) as a yellow solid.

Step 2: To a 1:1 mixture of 4-(benzyloxy)-1-chloro-6-phenylphthalazine 5c and 4-(benzyloxy)-1-chloro-7-phenylphthalazine 5d (350 mg, 806 μmol, 1.00 eq.) in DMF (10 mL) was added zinc cyanide (1.21 mmol, 1.50 eq.), 1,1'-bis(diphenylphosphino)ferrocene (80.6 μmol, 0.10 eq.), Pd$_2$(dba)$_3$ (40.3 μmol, 0.05 eq.) and zinc powder (80.6 μmol, 0.10 eq.). The mixture was purged with nitrogen 3 times and stirred at 100° C. for 3 hours. After such time the reaction mixture was diluted with water (50 mL) and extracted with ethyl acetate (50 mL×3). The combined organic layers were washed with brine (50 mL), dried over anhydrous sodium sulfate, filtered and concentrated under reduced pressure to a residue. The residue was purified by column chromatography (SiO$_2$, petroleumether:ethylacetate 10:1 to 3:1) to give a 1:1 mixture of 4-(benzyloxy)-7-phenylphthalazine-1-carbonitrile 6c and 4-benzyloxy-6-phenyl-phthalazine-1-carbonitrile 6d (158 mg, 468 μmol, 58% yield) as a yellow solid.

Step 3: To a 1:1 mixture of 4-(benzyloxy)-7-phenylphthalazine-1-carbonitrile 6c and 4-(benzyloxy)-6,6-phenylphthalazine-1-carbonitrile 6d (100 mg, 296 μmol, 1.00 eq.) was added hydrochloric acid (6.00 M, 10.1 eq.) and methyl alcohol (3.00 mL) followed by palladium on activated carbon (29.6 μmol, 10% by mass) under nitrogen. The suspension was degassed under vacuum and purged with hydrogen several times. The mixture was then stirred under a hydrogen atmosphere (50 psi) at 40° C. for 2 hours. After such time the reaction mixture was filtered, concentrated under reduced pressure and the residue purified by prep-HPLC (Phenomenex Luna C18 150×25 mm×10 μm; mobile phase: [water (0.1% TFA)-ACN]; B %: 2%-25%, 10 min) followed by separation of the regioisomers by SFC (column: DAICEL CHIRALPAK AD (250 mm×30 mm, 10 μm); mobile phase: [0.1% NH$_3$H$_2$O MeOH]; B %: 60%-60%, 40 min] to give the desired compounds 4-(aminomethyl)-6-phenyl-phthalazin-1-ol, Example 1-1 (13.7 mg, 53.6 μmol, 26% yield) LCMS [M+1]$^+$=252.2; $^1$H NMR (400 MHz, MeOD) δ=8.37 (d, J=8.0 Hz, 1H), 8.09-8.02 (m, 2H), 7.76 (d, J=7.2 Hz, 2H), 7.54-7.48 (m, 2H), 7.47-7.41 (m, 1H), 4.22 (s, 2H). LCMS [M+1]: 252.2 and 4-(aminomethyl)-7-phenyl-phthalazin-1-ol, Example 1-2 (23.6 mg, 91.8 μmol, 46% yield) LCMS [M+1]: 252.3; $^1$H NMR (400 MHz, MeOD) δ=8.64 (d, J=2.0 Hz, 1H), 8.28 (dd, J=2.0, 8.4 Hz, 1H), 8.01 (d, J=8.4 Hz, 1H), 7.83-7.74 (d, J=7.2 Hz, 2H), 7.58-7.51 (m, 2H), 7.50-7.44 (m, 1H), 4.61 (s, 2H).

Following the teachings of the General Reaction Schemes, the synthesis procedure for Examples 1-1 & 1-2 and using the Intermediates disclosed herein, the Examples 1-3 to 1-8 were prepared as shown in Table 1:

TABLE 1

| Example | Structure | Compound Name and Characterization |
|---|---|---|
| 1-3 | 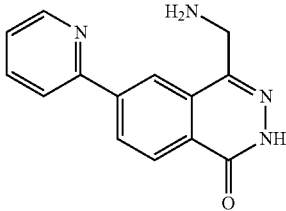 [SMILES: NCc1n[nH]c(=O)c2ccc(-c3ccccn3)cc12] | 4-(aminomethyl)-6-(pyridin-2-yl)phthalazin-1(2H)-one<br>LCMS [M + 1]$^+$ = 253.2; $^1$H NMR (400 MHz, MeOD) δ = 8.76-8.72 (m, 1H), 8.55 (s, 1H), 8.50-8.43 (m, 2H), 8.14-8.09 (m, 1H), 8.00 (dt, J = 2.0, 7.6 Hz, 1H), 7.49 (ddd, J = 0.8, 5.2, 7.6 Hz, 1H), 4.29 (br s, 2H) |
| 1-4 | 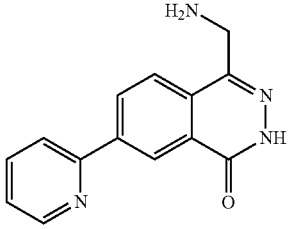 [SMILES: NCc1n[nH]c(=O)c2cc(-c3ccccn3)ccc12] | 4-(aminomethyl)-7-(pyridin-2-yl)phthalazin-1(2H)-one<br>LCMS [M + 1]$^+$ = 253.2; $^1$H NMR (400 MHz, MeOD) δ = 8.96 (d, J = 1.6 Hz, 1H), 8.74-8.70 (m, 1H), 8.60 (dd, J = 2.0, 8.4 Hz, 1H), 8.12-8.05 (m, 2H), 8.02-7.95 (m, 1H), 7.46 (ddd, J = 1.2, 4.8, 7.6 Hz, 1H), 4.28 (s, 2H). |
| 1-5 | 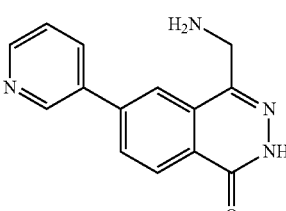 | 4-(aminomethyl)-6-(pyridin-3-yl)phthalazin-1(2H)-one<br>LCMS [M + 1]$^+$ = 253.2; $^1$H NMR (400 MHz, MeOD) δ = 8.91 (dd, J = 0.8, 2.4 Hz, 1H), 8.54 (dd, J = 1.6, 4.8 Hz, 1H), 8.39 (d, J = 8.4 Hz, 1H), 8.24-8.18 (m, 1H), 8.13 (d, J = 1.2 Hz, 1H), 8.09 (dd, J = 1.6, 8.4 Hz, 1H), 7.52 (ddd, J = 0.8, 4.8, 8.0 Hz, 1H), 4.24 (s, 2H). |
| 1-6 | 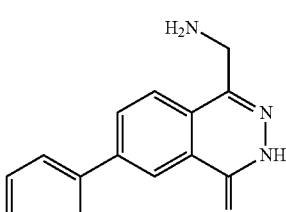 | 4-(aminomethyl)-7-(pyridin-3-yl)phthalazin-1(2H)-one<br>LCMS [M + 1]$^+$ = 253.2; $^1$H NMR (400 MHz, MeOD) δ = 8.95 (d, J = 1.6 Hz, 1H), 8.66-8.60 (m, 2H), 8.32-8.22 (m, 2H), 8.11 (d, J = 8.4 Hz, 1H), 7.60 (ddd, J = 0.8, 4.8, 8.0 Hz, 1H), 4.23 (s, 2H). |
| 1-7 | 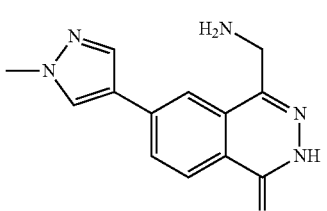 | 4-(aminomethyl)-6-(1-methyl-1H-pyrazol-4-yl)phthalazin-1(2H)-one<br>LCMS [M + 1]$^+$ = 256.2; $^1$H NMR (400 MHz, MeOD) δ = 8.38 (d, J = 8.4 Hz, 1H), 8.28 (s, 1H), 8.16-8.10 (m, 2H), 8.05 (s, 1H), 4.64 (s, 2H), 3.99 (s, 3H) |
| 1-8 | 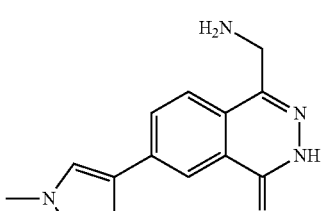 | 4-(aminomethyl)-7-(1-methyl-1H-pyrazol-4-yl)phthalazin-1(2H)-one<br>LCMS [M + 1]$^+$ = 256.2; $^1$H NMR (400 MHz, MeOD) δ = 8.50 (d, J = 2.0 Hz, 1H), 8.23 (s, 1H), 8.18 (dd, J = 2.0, 8.4 Hz, 1H), 8.02 (s, 1H), 7.91 (d, J = 8.4 Hz, 1H), 4.57 (s, 2H), 3.98 (s, 3H). |

Example 2-1

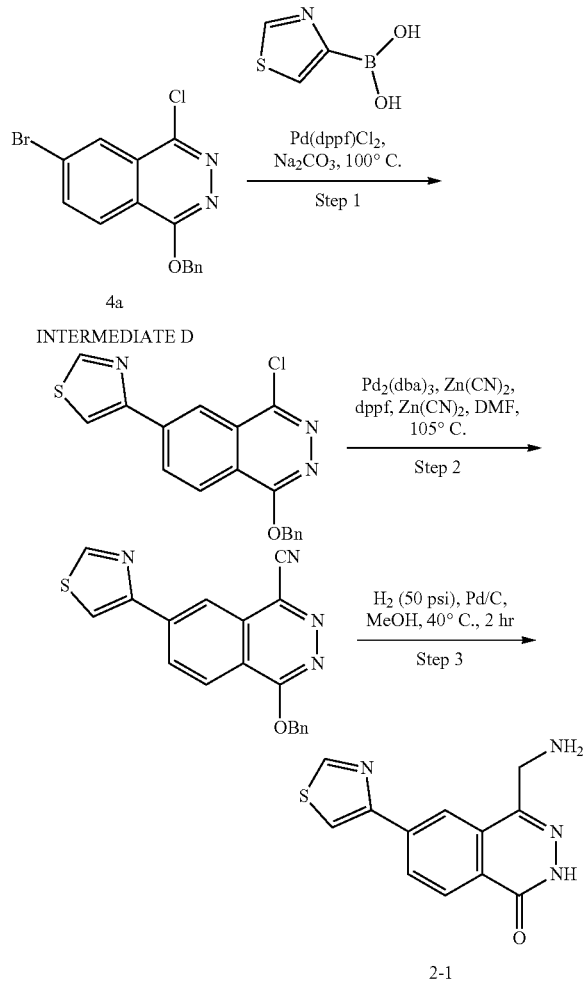

Step 1: A mixture of Intermediate D (150 mg, 429 µmol, 1.00 eq.), thiazol-4-ylboronic acid (66 mg, 515 µmol, 1.20 eq.), sodium carbonate (91 mg, 858 µmol, 2.00 eq.) and Pd(dppf)Cl₂ (31 mg, 42.9 µmol, 0.10 eq.) in DMF (1.00 mL) was purged with nitrogen 3 times and stirred at 100° C. for 12 hours under nitrogen. After such time the reaction mixture was diluted with water (20 mL) and extracted with ethyl acetate (20 mL×3). The combined organic layers were washed with brine (30 mL), dried over sodium sulfate, filtered and concentrated under reduced pressure to a residue. The residue was then purified by column chromatography (Sift, petroleumether:ethylacetate 5:1 to 1:1) to give 4-(1-(benzyloxy)-4-chlorophthalazin-6-yl)thiazole (76 mg, 214 µmol, 50% yield).

Step 2: A mixture of 4-(1-(benzyloxy)-4-chlorophthalazin-6-yl)thiazole (76 mg, 214 µmol, 1.00 eq.), zinc cyanide (38 mg, 321 µmol, 20 µL, 1.50 eq.), DPPF (12 mg, 21 µmol, 0.10 eq.), Pd₂(dba)₃ (10 mg, 10 µmol, 0.05 eq.) and zinc powder (1 mg, 21 µmol, 0.10 eq.) in DMF (1.00 mL) was degassed and purged with nitrogen 3 times. The mixture was then stirred at 105° C. for 2 hours under a nitrogen atmosphere. After such time the reaction mixture was diluted with water (20 mL), extracted with ethyl acetate (20 mL×3) and the combined organic layers washed with brine (30 mL), dried (Na₂SO₄ anhydrous), filtered and concentrated under reduced pressure. The residue was purified by column chromatography (SiO₂, petroleumether:ethylacetate=5:1 to 1:1) to give 4-(benzyloxy)-7-(thiazol-4-yl)phthalazine-1-carbonitrile (51 mg, 148 µmol, 69% yield).

Step 3: To a solution of 4-(benzyloxy)-7-(thiazol-4-yl)phthalazine-1-carbonitrile (103 mg, 299 µmol, 1.00 eq), HCl (6.0 M, 1.00 eq.) in MeOH (10 mL) was added palladium on activated carbon (296 µmol, 10.0% purity) under nitrogen. The suspension was degassed under vacuum and purged with hydrogen several times. The mixture was then stirred vigorously in a hydrogen atmosphere (50.0 psi) at 40° C. for 2 hours. After such time the reaction mixture was filtered, concentrated under reduced pressure and purified by prep-HPLC (Waters Xbridge 150×25 mm×5 µm; mobile phase: [water (0.05% ammonia hydroxide v/v)-ACN]; B %: 12%-42%, 10 min) to furnish 4-(aminomethyl)-6-(thiazol-4-yl)phthalazin-1(2H)-one, Example 2-1 (3 mg, 12 µmol, 4% yield, 97% purity) as a white solid. LCMS [M+1]: 259.2; ¹H NMR (400 MHz, MeOD) δ=9.17 (d, J=2.0 Hz, 1H), 8.56 (s, 1H), 8.47-8.43 (m, 2H), 8.33 (d, J=2.0 Hz, 1H), 4.29 (s, 2H).

General Reaction Method 2 for the Preparation of Examples 2-2 to 2-5

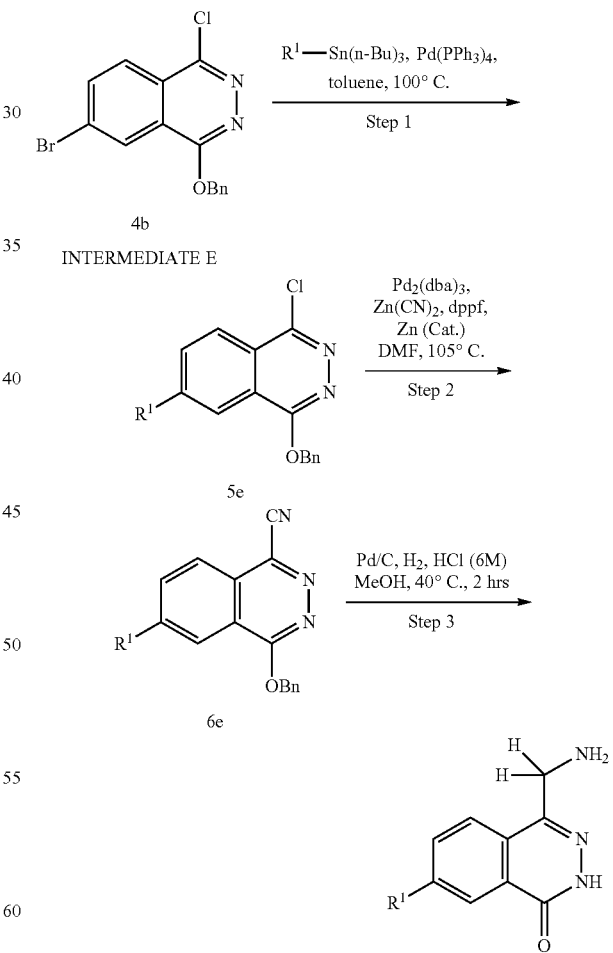

wherein R¹ = Aryl or Heteroaryl

Step 1: A mixture of Intermediate E (429 μmol, 1.00 eq.), the appropriate aryl/heteroaryl-tributyltin reagent (644 μmol, 1.50 eq) and Pd(PPh$_3$)$_4$ (43 μmol, 0.10 eq.) in toluene (2 mL) was purged with nitrogen 3 times and stirred at 100° C. for 12 hours. After such time the mixture was diluted with water (20 mL) and extracted with ethyl acetate (20 mL×3). The combined organic layers were washed with brine (30.0 mL), dried over anhydrous sodium sulfate, filtered and concentrated under reduced pressure to a residue. The residue was then purified by column chromatography (SiO$_2$, petroleumether:ethylacetate 5:1 to 1:1) to give appropriate R$^1$-coupled product 5e.

Step 2: A mixture of the R$^1$-coupled product 5e (214 μmol, 1.00 eq.), zinc cyanide (321 μmol, 20 μL, 1.50 eq.), DPPF (21 μmol, 0.10 eq.), Pd$_2$(dba)$_3$ (10 μmol, 0.05 eq.) and zinc powder (21 μmol, 0.10 eq.) in DMF (1.00 mL) was purged with nitrogen 3 times. The mixture was then stirred at 105° C. for 2 hours. After such time the mixture was diluted with water (20 mL) and extracted with ethyl acetate (20 mL×3). The combined organic layers were washed with brine (30.0 mL), dried over anhydrous sodium sulfate, filtered and concentrated under reduced pressure to a residue. The concentrated residue was then purified by column chromatography (SiO$_2$, petroleumether:ethylacetate 5:1 to 1:1) to give the appropriate R$^1$-cyanide 6e which were used in the next step without further purification.

Step 3: To a solution of the appropriate R$^1$-cyanide 6e (287 μmol, 1.00 eq), HCl (6.0 M, 1.00 eq.) in MeOH (10 mL) was added palladium on activated carbon (296 μmol, 10% Pd) under nitrogen. The suspension was degassed under vacuum and purged with hydrogen several times. The mixture was then vigorously stirred under a hydrogen atmosphere (50 psi) at 40° C. for 2 hours before being filtered and concentrated under reduced pressure. The residue was purified by prep-HPLC (Waters Xbridge 150×25 mm×5 μm; mobile phase: [water (0.05% ammonia hydroxide v/v)-ACN]; B %: 12%-42%, 10 min) to return the desired compounds shown in Table 2.

Following the teachings of the General Reaction Schemes, the general reaction method 2 and the Intermediates disclosed herein, the Examples 2-2 to 2-5 are prepared as shown in Table 2.

TABLE 2

| Example | Structure | Compound Name and Characterization |
|---|---|---|
| 2-2 | 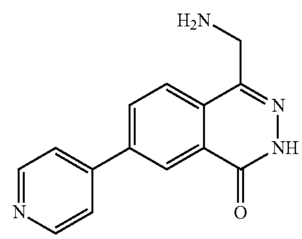 [SMILES: NCc1n[nH]c(=O)c2cc(-c3ccncc3)ccc12] | 4-(aminomethyl)-7-(pyridin-4-yl)phthalazin-1(2H)-one<br>LCMS [M + 1]$^+$ = 253.2; $^1$H NMR (400 MHz, MeOD) δ = 8.73 (d, J = 2.0 Hz, 1H), 8.71-8.68 (m, 2H), 8.34 (dd, J = 2.0, 8.4 Hz, 1H), 8.15 (d, J = 8.6 Hz, 1H), 7.89-7.86 (m, 2H), 4.21 (s, 2H). |
| 2-3 | 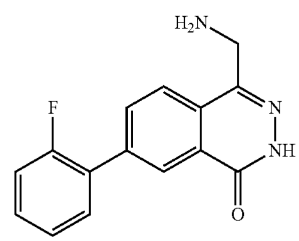 [SMILES: NCc1n[nH]c(=O)c2cc(-c3ccccc3F)ccc12] | 4-(aminomethyl)-7-(2-fluorophenyl)phthalazin-1(2H)-one<br>LCMS [M + 1]$^+$ = 270.2; $^1$H NMR (400 MHz, MeOD) δ = 8.55 (s, 1H), 8.19-8.14 (m, 1H), 8.11-8.06 (m, 1H), 7.63 (dt, J = 1.6, 8.0 Hz, 1H), 7.52-7.45 (m, 1H), 7.35 (dt, J = 1.2, 7.6 Hz, 1H), 7.28 (ddd, J = 1.2, 8.4, 11.2 Hz, 1H), 4.25 (s, 2H). |
| 2-4 | 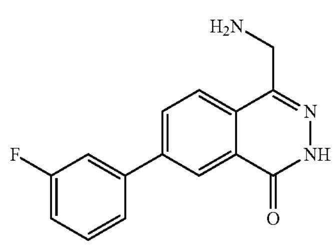 [SMILES: NCc1n[nH]c(=O)c2cc(-c3cccc(F)c3)ccc12] | 4-(aminomethyl)-7-(3-fluorophenyl)phthalazin-1(2H)-one<br>LCMS [M + 1]$^+$ = 270.2; $^1$H NMR (400 MHz, MeOD) δ = 8.62 (d, J = 2.0 Hz, 1H), 8.25 (dd, J = 2.0, 8.6 Hz, 1H), 8.10 (d, J = 8.6 Hz, 1H), 7.65-7.61 (m, 1H), 7.60-7.53 (m, 2H), 7.26-7.18 (m, 1H), 4.22 (s, 2H). |
| 2-5 | 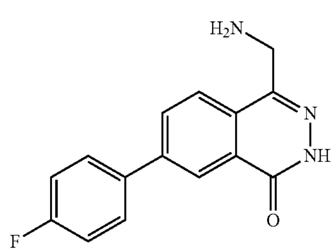 [SMILES: NCc1n[nH]c(=O)c2cc(-c3ccc(F)cc3)ccc12] | 4-(aminomethyl)-7-(4-fluorophenyl)phthalazin-1(2H)-one<br>LCMS [M + 1]$^+$ = 270.2; $^1$H NMR (400 MHz, MeOD) δ = 8.58 (d, J = 2.0 Hz, 1H), 8.22 (dd, J = 2.0, 8.6 Hz, 1H), 8.08 (d, J = 8.4 Hz, 1H), 7.86-7.78 (m, 2H), 7.33-7.25 (m, 2H), 4.24 (s, 2H). |

General Coupling Methods (CM) and Purification Methods (PM) for the Preparation of Examples 3-1 to 3-61

CM 3A

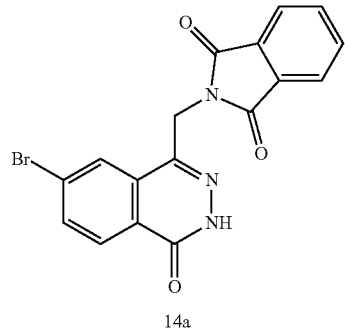

INTERMEDIATE F

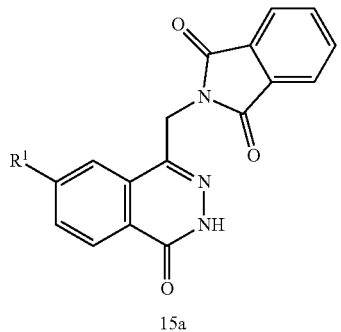

15a

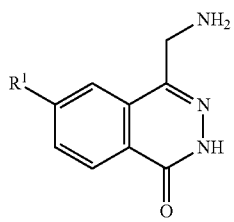

7a

R¹ = aryl, heteroaryl, alkyl

CM 3B:

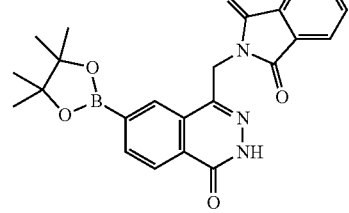

INTERMEDIATE AN

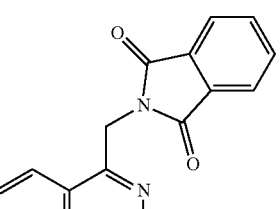

15a

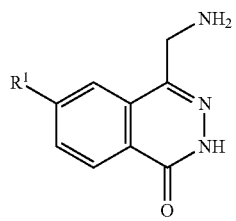

7a

Wherein R¹ = alkyl, aryl or heteroaryl

Step 1: A mixture of the appropriate aryl/heteroaryl/alkyl-boronic ester (390 µmol, 1.5 eq.), intermediate F (260 µmol, 1.00 eq.), Pd(dppf)Cl₂ (26 µmol, 0.10 eq.), sodium bicarbonate (43 mg, 521 µmol, 20.3 µL, 2.00 eq.) in dioxane (1.00 mL) and water (0.20 mL) was purged with nitrogen 3 times. The mixture was then stirred at 80° C. for 2 hours. After such time the mixture was filtered, washed with a dichloromethane:methyl alcohol 10:1 mixture and the filtrate concentrated under reduced pressure. The concentrated residue was then triturated with methyl alcohol (3.00 mL) to give the corresponding Suzuki coupling product 15a as a black solid.

Step 2: To a solution of corresponding Suzuki coupling product 15a in ethyl alcohol (1.00 mL) was added hydrazine hydrate (242 µmol, 14 µL). The mixture was stirred at 80° C. for 1 hour, cooled and concentrated under reduced pressure. The concentrated residue was then purified by prep-HPLC according to one of the purification methods 3-1,3-2, 3-3 or 3-4 described herein to furnish 7a.

Step 1: Intermediate AN, the appropriate alkyl/aryl/heteroaryl bromide (464 µmol), sodium bicarbonate (464 µmol, 18.0 µL, 2.00 eq.) and Pd(dppf)Cl₂ (17 mg, 23 µmol, 0.10 eq.) in dioxane (2 mL) and water (0.40 mL) was purged with nitrogen 3 times. The mixture was then stirred at 80° C. for 1 hour. After such time the reaction mixture was diluted with water (2 mL), filtered under reduced pressure and the filter cake triturated with ethyl alcohol (3 mL) to give the corresponding R¹-Suzuki coupling product 15a as a black solid which was directly in the next step without further purification.

Step 2: To a solution of corresponding R¹-Suzuki coupling product 15a in ethyl alcohol (1.00 mL) was added hydrazine hydrate (242 µmol, 14 µL). The mixture was stirred at 80° C. for 1 hour. After such time the mixture was concentrated under reduced pressure and the residue purified by prep-HPLC according to one of the purification methods 3-1 to 3-4.

CM 3C

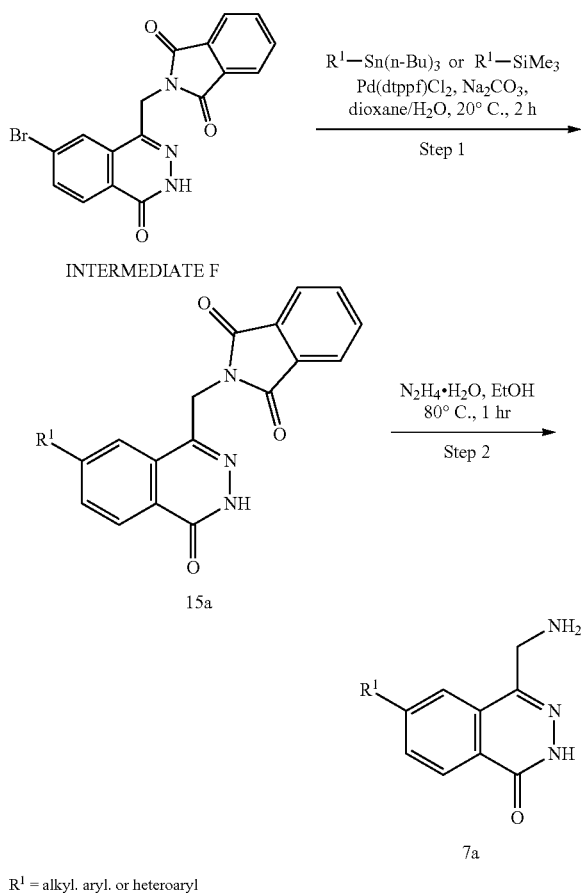

INTERMEDIATE F

R¹ = alkyl, aryl, or heteroaryl

Step 1: A mixture of Intermediate F (312 μmol, 1.00 eq.), the appropriate alkyl/aryl/heteroaryl tributyltin or alkyl/aryl/heteroaryl trimethyl silicon reagent (625 μmol, 2.00 eq.), Pd(PPh$_3$)$_4$ (72 mg, 62 μmol, 0.20 eq.) in dioxane (3.00 mL) was purged with nitrogen 3 times. The mixture was then stirred at 100° C. for 1 hour. After such time the reaction mixture was diluted with a potassium fluoride solution (3.0 mL) to form a suspension. The suspension was filtered, and the filtrate extracted with ethyl acetate (8 mL×3). The combined organic layers were washed with brine (10 mL), dried over anhydrous sodium sulfate, filtered and concentrated under reduced pressure. The residue was purified by prep-TLC (SiO$_2$, dichloromethane:methyl alcohol 10:1) to give the corresponding C—C bond formation compound 15a as a black solid.

Step 2: To a solution of 15a in ethyl alcohol (1.0 mL) was added hydrazine hydrate (242 μmol, 14 μL). The mixture was stirred at 80° C. for 1 hour. After such time the mixture was concentrated under reduced pressure and the residue was purified by prep-HPLC according to one of the purification methods 3-1 to 3-4.

Purification Methods (PM)

PM 3-1: column: Phenomenex Synergi C18 150×25×10 μm; mobile phase: [water (0.05% HCl)-ACN]; B %: 5%-25%, 11 min.

PM 3-2: column: Waters Xbridge 150×25 mm×5 μm; mobile phase: [water (0.05% ammonia hydroxide v/v)-ACN]; B %: 12%-42%, 10 min.

PM 3-3: column: Waters Xbridge 150×25 mm×5 μm; mobile phase: [water (10 mM NH$_4$HCO$_3$)-ACN]; B %: 2%-32%, 10 min.

PM 3-4: column: Phenomenex Luna C18 75×10 mm×3 μm; mobile phase: [water (0.05% HCl)-ACN]; B %: 11%-31%, 6.5 min.

Following the teachings of the General Reaction Schemes, the coupling methods 3A, 3B and 3C and using purification methods 3-1,3-2, 3-3 and 3-4 and the Intermediates disclosed herein, the Examples 3-1 to 3-61 are prepared as shown in Table 3.

TABLE 3

| Example | Structure | CM | PM | Compound Name and Characterization |
|---|---|---|---|---|
| 3-1 | 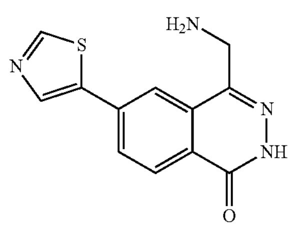 | 3C | 3-1 | 4-(aminomethyl)-6-(thiazol-5-yl)phthalazin-1(2H)-one LCMS [M + 1]$^+$ = 259.2; $^1$H NMR (400 MHz, DMSO-d6) δ = 12.97 (s, 1H), 9.27 (s, 1H), 8.71 (s, 1H), 8.59 (br s, 3H), 8.33 (d, J = 8.4 Hz, 1H), 8.27-8.24 (d, J = 1.6 Hz, 1H), 8.19 (dd, J = 1.6, 8.4 Hz, 1H), 4.59-4.50 (d, J = 5.6 Hz, 2H) |
| 3-2 | 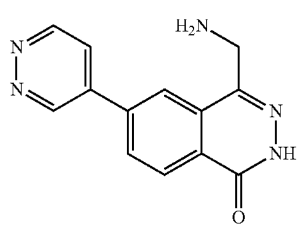 [SMILES: NCc1n[nH]c(=O)c2ccc(-c3ccnnc3)cc12] | 3B | 3-1 | 4-(aminomethyl)-6-(pyridazin-4-yl)phthalazin-1(2H)-one LCMS [M + 1]$^+$ = 253.26; $^1$H NMR (400 MHz, DMSO-d6) δ = 13.06 (s, 1H), 9.97 (d, J = 1.2 Hz, 1H), 9.48 (d, J = 4.4 Hz, 1H), 8.68 (br s, 3H), 8.54 (s, 1H), 8.44 (m, 2H), 8.42 (dd, J = 2.4, 5.2 Hz, 1H), 4.59 (br d, J = 5.6 Hz, 2H) |

TABLE 3-continued

| Example | Structure | CM | PM | Compound Name and Characterization |
|---|---|---|---|---|
| 3-3 | 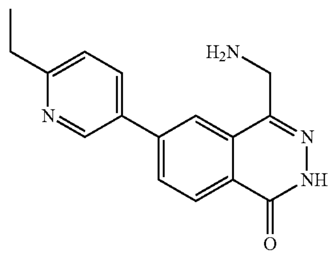 [SMILES: CCc1ccc(-c2ccc3c(=O)[nH]nc(CN)c3c2)cn1] | 3A | 3-1 | 4-(aminomethyl)-6-(6-ethylpyridin-3-yl)phthalazin-1(2H)-one<br>LCMS [M + 1]$^+$ = 281.3; $^1$H NMR (400 MHz, DMSO-d6) δ = 13.01 (s, 1H), 9.33 (d, J = 2.0 Hz, 1H), 8.85 (br d, J = 7.6 Hz, 1H), 8.66 (br s, 3H), 8.43 (d, J = 1.2 Hz, 1H), 8.42-8.39 (m, 1H), 8.37-8.32 (m, 1H), 7.95 (br d, J = 8.4 Hz, 1H), 4.70-4.48 (m, 2H), 3.07 (q, J = 7.6 Hz, 2H), 1.34 (t, J = 7.6 Hz, 3H) |
| 3-4 | 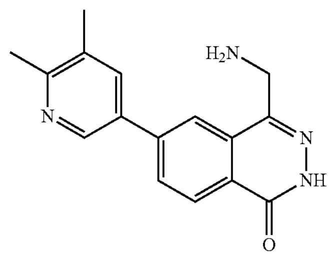 [SMILES: Cc1cc(-c2ccc3c(=O)[nH]nc(CN)c3c2)cnc1C] | 3A | 3-3 | 4-(aminomethyl)-6-(5,6-dimethylpyridin-3-yl)phthalazin-1(2H)-one<br>LCMS [M + 1]$^+$ = 281.3; $^1$H NMR (400 MHz, DMSO-d6) δ = 8.72 (s, 1H), 8.35 (d, J = 8.4 Hz, 1H), 8.28 (s, 1H), 8.11 (d, J = 8.8 Hz, 1H), 7.96 (s, 1H), 4.12 (s, 2H), 2.52 (s, 3H), 2.39 (s, 3H) |
| 3-5 | 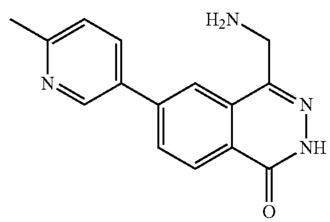 [SMILES: Cc1ccc(-c2ccc3c(=O)[nH]nc(CN)c3c2)cn1] | 3A | 3-3 | 4-(aminomethyl)-6-(6-methylpyridin-3-yl)phthalazin-1(2H)-one<br>LCMS [M + 1]$^+$ = 267.3; $^1$H NMR (400 MHz, DMSO-d6) δ = 8.91 (d, J = 2.0 Hz, 1H), 8.36 (d, J = 8.0 Hz, 1H), 8.30 (d, J = 1.6 Hz, 1H), 8.11 (dd, J = 2.0, 8.0 Hz, 2H), 7.40 (d, J = 8.0 Hz, 1H), 4.12 (s, 2H), 2.57 (s, 3H) |
| 3-6 | 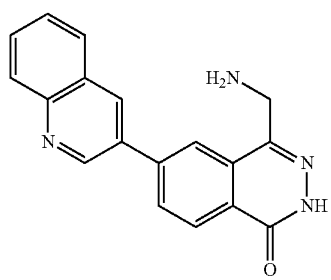 [SMILES: NCc1n[nH]c(=O)c2ccc(-c3cnc4ccccc4c3)cc12] | 3A | 3-2 | 4-(aminomethyl)-6-(quinolin-3-yl)phthalazin-1(2H)-one<br>LCMS [M + 1]$^+$ = 303.2; $^1$H NMR (400 MHz, DMSO-d6) δ = 12.55 (br s, 1H), 9.43 (d, J = 2.4 Hz, 1H), 8.90 (d, J = 2.4 Hz, 1H), 8.52 (d, J = 1.2 Hz, 1H), 8.43-8.38 (m, 1H), 8.38-8.33 (m, 1H), 8.12 (dd, J = 4.8, 7.6 Hz, 2H), 7.84 (dt, J = 1.2, 7.6 Hz, 1H), 7.75-7.67 (m, 1H), 4.14 (s, 2H) |
| 3-7 | 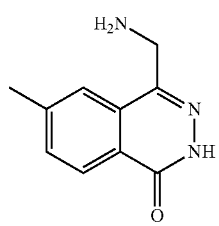 | 3A | 3-1 | 4-(aminomethyl)-6-methylphthalazin-1(2H)-one<br>LCMS [M + 1]$^+$ = 189.21; $^1$H NMR (400 MHz, DMSO-d6) δ = 12.39 (br s, 1H), 8.14 (d, J = 8.0 Hz, 1H), 7.88 (s, 1H), 7.66 (dd, J = 0.8, 8.0 Hz, 1H), 3.98 (s, 2H), 2.52 (br s, 3H) |
| 3-8 | 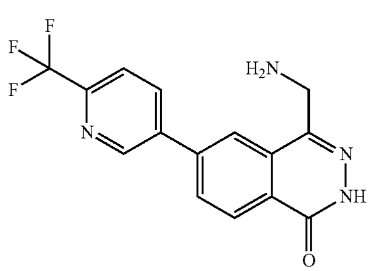 [SMILES: NCc1n[nH]c(=O)c2ccc(-c3ccc(C(F)(F)F)nc3)cc12] | 3A | 3-1 | 4-(aminomethyl)-6-(6-(trifluoromethyl)pyridin-3-yl)phthalazin-1(2H)-one<br>LCMS [M + 1]$^+$ = 320.9; $^1$H NMR (400 MHz, DMSO-d6) δ = 13.04 (s, 1H), 9.35 (d, J = 2.0 Hz, 1H), 8.64 (dd, J = 2.0, 8.4 Hz, 1H), 8.50 (br s, 3H), 8.46-8.41 (m, 1H), 8.40 (s, 1H), 8.38-8.34 (m, 1H), 8.13 (d, J = 8.0 Hz, 1H), 4.60 (br s, 2H) |

TABLE 3-continued

| Example | Structure | CM | PM | Compound Name and Characterization |
|---|---|---|---|---|
| 3-9 | 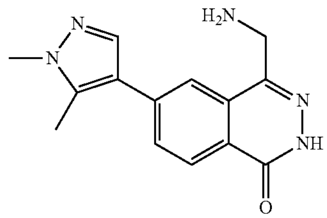 [SMILES: Cc1c(-c2ccc3c(=O)[nH]nc(CN)c3c2)cnn1C] | 3A | 3-1 | 4-(aminomethyl)-6-(1,5-dimethyl-1H-pyrazol-4-yl)phthalazin-1(2H)-one<br>LCMS [M + 1]⁺ = 270.1; ¹H NMR (400 MHz, DMSO-d6) δ = 12.9 (s, 1H), 8.48 (br s, 3H), 8.29 (d, J = 8.4 Hz, 1H), 7.97 (dd, J = 1.6, 8.4 Hz, 1H), 7.90 (s, 2H), 4.52 (br d, J = 5.6 Hz, 2H), 3.83 (s, 3H), 2.52 (br s, 3H) |
| 3-10 | 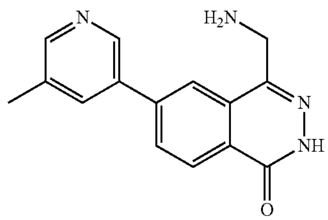 [SMILES: Cc1cncc(-c2ccc3c(=O)[nH]nc(CN)c3c2)c1] | 3A | 3-1 | 4-(aminomethyl)-6-(5-methylpyridin-3-yl)phthalazin-1(2H)-one<br>LCMS [M + 1]⁺ = 267.0; ¹H NMR (400 MHz, DMSO-d6) δ = 13.0 (s, 1H), 9.18 (s, 1H), 8.71 (s, 1H), 8.59 (br s, 1H), 8.56 (br s, 3H), 8.45-8.39 (m, 1H), 8.38 (s, 1H), 8.36-8.32 (m, 1H), 4.59 (br d, J = 5.6 Hz, 2H), 2.54-2.52 (s, 3H) |
| 3-11 | 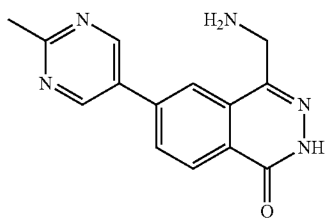 [SMILES: Cc1ncc(-c2ccc3c(=O)[nH]nc(CN)c3c2)cn1] | 3A | 3-1 | 4-(aminomethyl)-6-(2-methylpyrimidin-5-yl)phthalazin-1(2H)-one<br>LCMS [M + 1]⁺ = 268.3; ¹H NMR (400 MHz, DMSO-d6) δ = 12.99 (s, 1H), 9.34 (s, 2H), 8.71 (br s, 3H), 8.43-8.30 (m, 3H), 4.56 (br d, J = 5.6 Hz, 2H), 2.73 (s, 3H) |
| 3-12 | 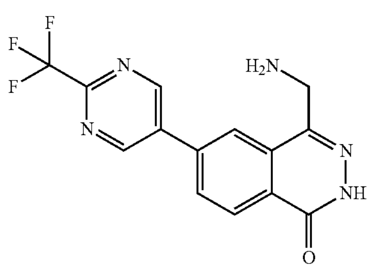 [SMILES: NCc1n[nH]c(=O)c2ccc(-c3cnc(C(F)(F)F)nc3)cc12] | 3A | 3-2 | 4-(aminomethyl)-6-(2-(trifluoromethyl)pyrimidin-5-yl)phthalazin-1(2H)-one<br>LCMS [M + 1]⁺ = 322.2; ¹H NMR (400 MHz, DMSO-d6) δ = 9.53 (s, 2H), 8.51 (s, 1H), 8.43 (d, J = 8.4 Hz, 1H), 8.29 (dd, J = 1.6, 8.4 Hz, 1H), 4.13 (s, 2H) |
| 3-13 | 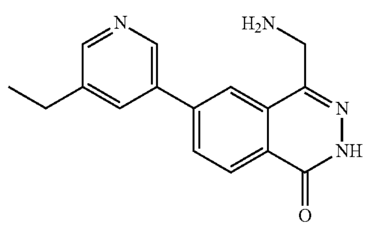 [SMILES: CCc1cncc(-c2ccc3c(=O)[nH]nc(CN)c3c2)c1] | 3A | 3-2 | 4-(aminomethyl)-6-(5-ethylpyridin-3-yl)phthalazin-1(2H)-one<br>LCMS [M + 1]⁺ = 281.3; ¹H NMR (400 MHz, DMSO-d6) δ = 8.86 (d, J = 2.0 Hz, 1H), 8.54 (d, J = 2.0 Hz, 1H), 8.36 (d, J = 8.4 Hz, 1H), 8.33 (d, J = 1.6 Hz, 1H), 8.15 (dd, J = 2.0, 8.4 Hz, 1H), 8.06 (s, 1H), 4.13 (s, 2H), 2.77 (q, J = 7.6 Hz, 2H), 1.31 (t, J = 7.6 Hz, 3H) |
| 3-14 | 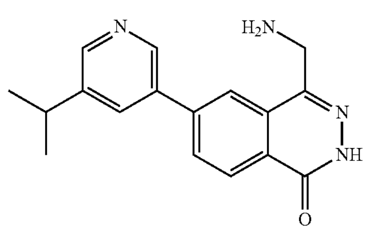 [SMILES: CC(C)c1cncc(-c2ccc3c(=O)[nH]nc(CN)c3c2)c1] | 3B | 3-1 | 4-(aminomethyl)-6-(5-isopropylpyridin-3-yl)phthalazin-1(2H)-one<br>LCMS [M + 1]⁺ = 295.1; ¹H NMR (400 MHz, DMSO-d6) δ = 13.03 (s, 1H), 9.28 (br s, 1H), 8.82 (s, 1H), 8.79-8.74 (m, 1H), 8.65 (br s, 3H), 8.44-8.37 (m, 3H), 4.60 (q, J = 5.6 Hz, 2H), 3.25-3.17 (m, 1H), 1.37 (d, J = 7.2 Hz, 6H) |
| 3-15 | 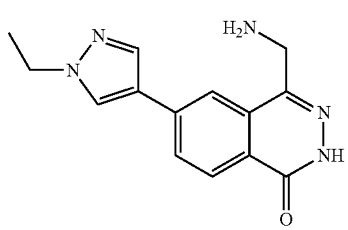 [SMILES: CCn1cc(-c2ccc3c(=O)[nH]nc(CN)c3c2)cn1] | 3A | 3-1 | 4-(aminomethyl)-6-(1-ethyl-1H-pyrazol-4-yl)phthalazin-1(2H)-one<br>LCMS [M + 1]⁺ = 270.0; ¹H NMR (400 MHz, DMSO-d6) δ = 12.81 (s, 1H), 8.56 (m, 4H), 8.24 (d, J = 8.8 Hz, 1H), 8.20 (s, 1H), 8.14-8.09 (m, 2H), 4.48 (br d, J = 5.6 Hz, 2H), 4.19 (d, J = 7.2 Hz, 2H), 1.43 (t, J = 7.2 Hz, 3H). |

TABLE 3-continued

| Example | Structure | CM | PM | Compound Name and Characterization |
|---|---|---|---|---|
| 3-16 | 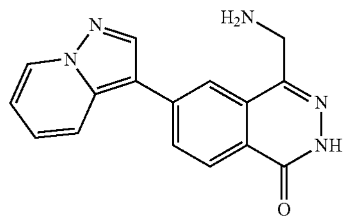 [SMILES: NCc1n[nH]c(=O)c2ccc(-c3cnn4ccccc34)cc12] | 3A | 3-1 | 4-(aminomethyl)-6-(pyrazolo[1,5-a]pyridin-3-yl)phthalazin-1(2H)-one<br>LCMS [M + 1]$^+$ = 292.0; $^1$H NMR (400 MHz, DMSO-d6) δ = 12.88 (s, 1H), 8.84 (d, J = 6.8 Hz, 1H), 8.74 (s, 1H), 8.59 (br s, 3H), 8.37-8.31 (m, 1H), 8.30-8.24 (m, 2H), 8.16 (d, J = 1.2 Hz, 1H), 7.48 (ddd, J = 1.2, 6.8, 9.2 Hz, 1H), 7.08 (dt, J = 1.2, 6.8 Hz, 1H), 4.61 (br s, 2H) |
| 3-17 | 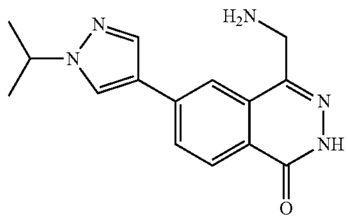 [SMILES: CC(C)n1cc(-c2ccc3c(=O)[nH]nc(CN)c3c2)cn1] | 3A | 3-2 | 4-(aminomethyl)-6-(1-isopropyl-1H-pyrazol-4-yl)phthalazin-1(2H)-one<br>LCMS [M + 1]$^+$ = 284.3; $^1$H NMR (400 MHz, DMSO-d6) δ = 8.54 (s, 1H), 8.20 (d, J = 8.4 Hz, 1H), 8.15 (d, J = 1.2 Hz, 1H), 8.13 (s, 1H), 8.06 (dd, J = 1.6, 8.4 Hz, 1H), 4.59-4.47 (m, 1H), 4.05 (s, 2H), 1.48 (d, J = 6.8 Hz, 6H) |
| 3-18 | 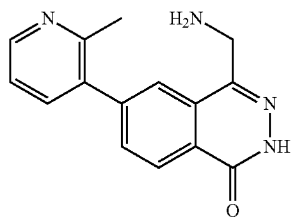 [SMILES: Cc1ncccc1-c1ccc2c(=O)[nH]nc(CN)c2c1] | 3A | 3-2 | 4-(aminomethyl)-6-(2-methylpyridin-3-yl)phthalazin-1(2H)-one<br>LCMS [M + 1]$^+$ = 267.3; $^1$H NMR (400 MHz, DMSO-d6) δ = 12.53 (br s, 1H), 8.54 (dd, J = 1.6, 4.8 Hz, 1H), 8.32 (d, J = 8.4 Hz, 1H), 8.11 (d, J = 1.6 Hz, 1H), 7.88 (dd, J = 1.6, 8.0 Hz, 1H), 7.76 (dd, J = 1.6, 7.6 Hz, 1H), 7.38 (dd, J = 4.8, 7.6 Hz, 1H), 4.02 (s, 2H), 2.47 (s, 3H) |
| 3-19 | 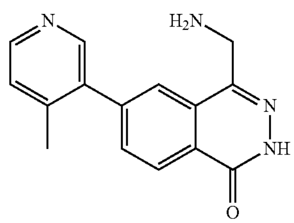 [SMILES: Cc1ccncc1-c1ccc2c(=O)[nH]nc(CN)c2c1] | 3A | 3-3 | 4-(aminomethyl)-6-(4-methylpyridin-3-yl)phthalazin-1(2H)-one<br>LCMS [M + 1]$^+$ = 267.3; $^1$H NMR (400 MHz, DMSO-d6) δ = 8.52-8.49 (m, 2H), 8.36 (d, J = 8.0 Hz, 1H), 8.08 (d, J = 1.2 Hz, 1H), 7.84 (dd, J = 1.6, 8.0 Hz, 1H), 7.38 (d, J = 5.2 Hz, 1H), 4.07 (s, 2H), 2.32 (s, 3H) |
| 3-20 | 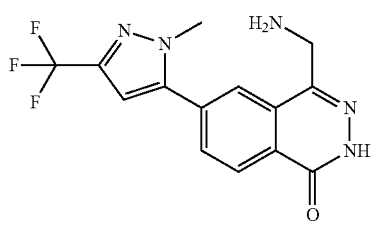 [SMILES: Cn1nc(C(F)(F)F)cc1-c1ccc2c(=O)[nH]nc(CN)c2c1] | 3A | 3-2 | 4-(aminomethyl)-6-(1-methyl-3-(trifluoromethyl)-1H-pyrazol-5-yl)phthalazin-1(2H)-one<br>LCMS [M + 1]$^+$ 323.9; $^1$H NMR (400 MHz, DMSO-d6) δ = 12.71 (br s, 1H), 8.37 (d, J = 8.0 Hz, 1H), 8.26 (d, J = 1.2 Hz, 1H), 8.08 (dd, J = 1.6, 8.4 Hz, 1H), 7.18 (s, 1H), 4.17 (s, 2H), 4.02 (s, 3H), 2.52 (br s, 2H) |
| 3-21 | 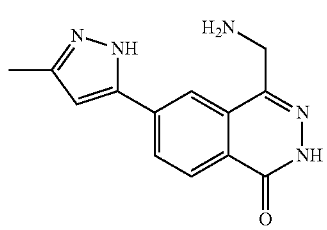 [SMILES: Cc1cc(-c2ccc3c(=O)[nH]nc(CN)c3c2)[nH]n1] | 3A | 3-1 | 4-(aminomethyl)-6-(5-methyl-1H-pyrazol-3-yl)phthalazin-1(2H)-one<br>LCMS [M + 1]$^+$ = 256.0; $^1$H NMR (400 MHz, DMSO-d6) δ = 12.86 (s, 1H), 8.55 (br s, 3H), 8.32-8.26 (m, 2H), 8.24 (s, 1H), 6.82 (d, J = 0.8 Hz, 1H), 4.60-4.43 (m, 2H), 2.37-2.22 (m, 3H) |
| 3-22 | 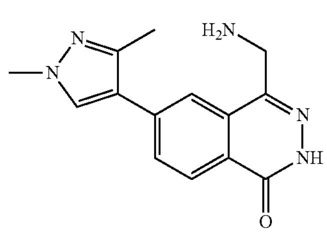 [SMILES: Cc1nn(C)cc1-c1ccc2c(=O)[nH]nc(CN)c2c1] | 3A | 3-2 | 4-(aminomethyl)-6-(1,3-dimethyl-1H-pyrazol-4-yl)phthalazin-1(2H)-one<br>LCMS [M + 1]$^+$ = 270.3; $^1$H NMR (400 MHz, DMSO-d6) δ = 12.43 (br s, 1H), 8.23 (d, J = 8.4 Hz, 1H), 8.19 (s, 1H), 8.04 (d, J = 1.2 Hz, 1H), 7.91 (dd, J = 1.6, 8.4 Hz, 1H), 4.06 (s, 2H), 3.83 (s, 3H), 2.40 (s, 3H) |

TABLE 3-continued

| Example | Structure | CM | PM | Compound Name and Characterization |
|---|---|---|---|---|
| 3-23 | 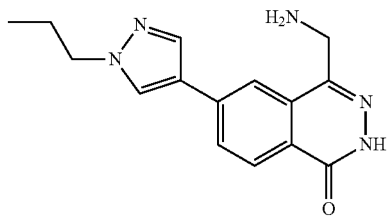 [SMILES: CCCn1cc(-c2ccc3c(=O)[nH]nc(CN)c3c2)cn1] | 3A | 3-2 | 4-(aminomethyl)-6-(1-propyl-1H-pyrazol-4-yl)phthalazin-1(2H)-one<br>LCMS [M + 1] $^+$ = 284.3; $^1$H NMR (400 MHz, DMSO-d6) δ = 12.49-12.35 (s, 1H), 8.49 (s, 1H), 8.20 (d, J = 8.4 Hz, 1H), 8.15 (s, 2H), 8.05 (dd, J = 1.6, 8.4 Hz, 1H), 4.12 (t, J = 6.8 Hz, 2H), 4.08 (s, 2H), 1.89-1.81 (m, 2H), 0.87 (t, J = 7.2 Hz, 3H) |
| 3-24 | 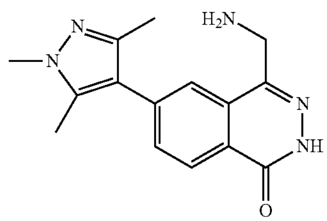 [SMILES: Cc1nn(C)c(C)c1-c1ccc2c(=O)[nH]nc(CN)c2c1] | 3A | 3-1 | 4-(aminomethyl)-6-(1,3,5-trimethyl-1H-pyrazol-4-yl)phthalazin-1(2H)-one<br>LCMS [M + 1] $^+$ = 284.0; $^1$H NMR (400 MHz, DMSO-d6) δ = 12.9 (s, 1H), 8.63 (br s, 3H), 8.31 (d, J = 8.4 Hz, 1H), 7.81 (dd, J = 1.2, 8.4 Hz, 1H), 7.76 (s, 1H), 4.46 (br d, J = 5.6 Hz, 2H), 3.76 (s, 3H), 2.32 (s, 3H), 2.22 (s, 3H) |
| 3-25 | 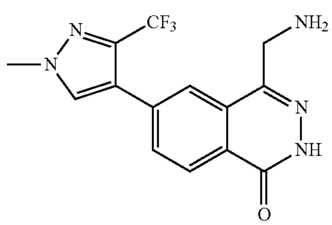 [SMILES: Cn1cc(-c2ccc3c(=O)[nH]nc(CN)c3c2)c(C(F)(F)F)n1] | 3A | 3-2 | 4-(aminomethyl)-6-(1-methyl-3-(trifluoromethyl)-1H-pyrazol-4-yl)phthalazin-1(2H)-one<br>LCMS [M + 1] $^+$ = 324.2 $^1$H NMR (400 MHz, DMSO-d6) δ = 12.52 (br s, 1H), 8.40 (s, 1H), 8.30 (d, J = 8.0 Hz, 1H), 8.07 (s, 1H), 7.83 (br d, J = 8.8 Hz, 1H), 4.00 (s, 5H) |
| 3-26 | 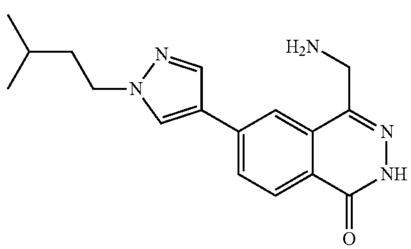 [SMILES: CC(C)CCn1cc(-c2ccc3c(=O)[nH]nc(CN)c3c2)cn1] | 3A | 3-1 | 4-(aminomethyl)-6-(1-isopentyl-1H-pyrazol-4-yl)phthalazin-1(2H)-one<br>LCMS [M + 1] $^+$ = 312.1 $^1$H NMR (400 MHz, DMSO-d6) δ = 12.84 (s, 1H), 8.59 (s, 4H), 8.26-8.20 (m, 2H), 8.14 (d, J = 1.6 Hz, 1H), 8.12 (s, 1H), 4.57-4.43 (m, 2H), 4.19 (t, J = 7.2 Hz, 2H), 1.81-1.69 (m, 2H), 1.52 (td, J = 6.8, 13.2 Hz, 1H), 0.93 (d, J = 6.4 Hz, 6H) |
| 3-27 | 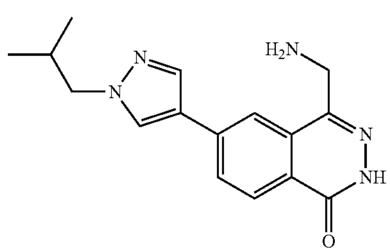 [SMILES: CC(C)Cn1cc(-c2ccc3c(=O)[nH]nc(CN)c3c2)cn1] | 3A | 3-1 | 4-(aminomethyl)-6-(1-isobutyl-1H-pyrazol-4-yl)phthalazin-1(2H)-one<br>LCMS [M + 1] $^+$ = 296.0 $^1$H NMR (400 MHz, DMSO-d6) δ = 12.9-12.8 (s, 1H), 8.49 (s, 1H), 8.44-8.36 (s, 3H), 8.25 (d, J = 8.4 Hz, 1H), 8.20 (s, 1H), 8.13 (dd, J = 1.6, 8.4 Hz, 1H), 8.08 (s, 1H), 4.51 (q, J = 5.6 Hz, 2H), 3.98 (d, J = 7.2 Hz, 2H), 2.22-2.14 (m, 1H), 0.89 (d, J = 6.8 Hz, 6H). |
| 3-28 | 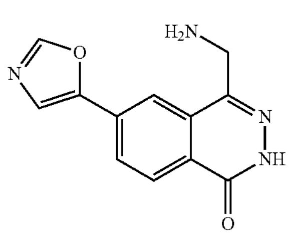 [SMILES: NCc1n[nH]c(=O)c2ccc(-c3cnco3)cc12] | 3A | 3-3 | 4-(aminomethyl)-6-(oxazol-5-yl)phthalazin-1(2H)-one<br>LCMS [M + 1] $^+$ = 243.2; $^1$H NMR (400 MHz, DMSO-d6) δ = 8.51 (s, 1H), 8.35 (br s, 2H), 8.15 (br d, J = 8.4 Hz, 1H), 7.96 (s, 1H), 4.09 (s, 2H). |

TABLE 3-continued

| Example | Structure | CM | PM | Compound Name and Characterization |
|---|---|---|---|---|
| 3-29 | 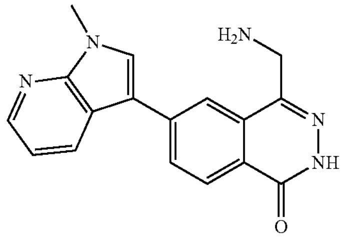 [SMILES: Cn1cc(-c2ccc3c(=O)[nH]nc(CN)c3c2)c2cccnc21] | 3A | 3-1 | 4-(aminomethyl)-6-(1-methyl-1H-pyrrolo[2,3-b]pyridin-3-yl)phthalazin-1(2H)-one<br>LCMS [M + 1]⁺ = 306.1 ¹H NMR (400 MHz, DMSO-d6) δ = 12.86 (s, 1H), 8.57 (dd, J = 1.6, 8.0 Hz, 1H), 8.51 (br s, 3H), 8.40 (dd, J = 1.2, 4.4 Hz, 1H), 8.37 (s, 1H), 8.35-8.31 (m, 1H), 8.30-8.26 (m, 1H), 8.14 (d, J = 1.2 Hz, 1H), 7.29 (dd, J = 4.8, 8.0 Hz, 1H), 4.61 (br d, J = 5.6 Hz, 2H), 3.94 (s, 3H) |
| 3-30 | 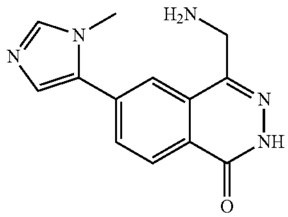 [SMILES: Cn1cncc1-c1ccc2c(=O)[nH]nc(CN)c2c1] | 3A | 3-1 | 4-(aminomethyl)-6-(1-methyl-1H-imidazol-5-yl)phthalazin-1(2H)-one<br>LCMS [M + 1]⁺ = 256.1 ¹H NMR (400 MHz, DMSO-d6) δ = 13.08 (s, 1H), 9.15 (s, 1H), 8.62-8.53 (br s, 3H), 8.43 (d, J = 8.4 Hz, 1H), 8.22 (d, J = 1.2 Hz, 1H), 8.14 (dd, J = 1.6, 8.4 Hz, 1H), 8.07 (s, 1H), 4.54-4.47 (m, 2H), 3.95 (s, 3H) |
| 3-31 | 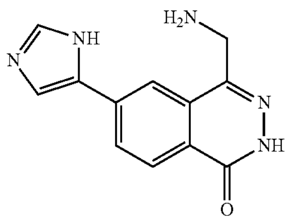 [SMILES: NCc1n[nH]c(=O)c2ccc(-c3cnc[nH]3)cc12] | 3A | 3-1 | 4-(aminomethyl)-6-(1H-imidazol-5-yl)phthalazin-1(2H)-one<br>LCMS [M + 1]⁺ = 242.0 ¹H NMR (400 MHz, DMSO-d6) δ = 12.99 (s, 1H), 9.11 (br s, 1H), 8.62 (s, 1H), 8.58 (br s, 3H), 8.46 (s, 1H), 8.38 (m, 2H), 4.53 (br s, 2H) |
| 3-32 | 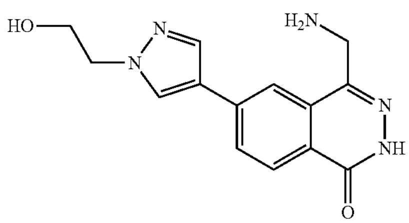 [SMILES: NCc1n[nH]c(=O)c2ccc(-c3cnn(CCO)c3)cc12] | 3A | 3-1 | 4-(aminomethyl)-6-(1-(2-hydroxyethyl)-1H-pyrazol-4-yl)phthalazin-1(2H)-one<br>LCMS [M + 1]⁺ = 286.1 ¹H NMR (400 MHz, DMSO-d6) δ = 12.84 (s, 1H), 8.53-8.49 (s, 1H), 8.46 (br s, 3H), 8.27-8.19 (m, 2H), 8.16-8.11 (m, 1H), 8.09 (s, 1H), 4.55-4.47 (m, 2H), 4.20 (br t, J = 5.6 Hz, 2H), 3.79 (br t, J = 5.6 Hz, 2H) |
| 3-33 | 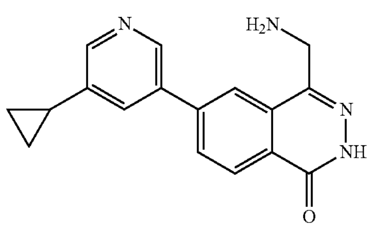 [SMILES: NCc1n[nH]c(=O)c2ccc(-c3cncc(C4CC4)c3)cc12] | 3C | 3-1 | 4-(aminomethyl)-6-(5-cyclopropylpyridin-3-yl)phthalazin-1(2H)-one<br>LCMS [M + 1]⁺ = 293.1 ¹H NMR (400 MHz, DMSO-d6) δ = 13.04 (s, 1H), 9.32 (d, J = 2.0 Hz, 1H), 8.86-8.69 (m, 4H), 8.65 (s, 1H), 8.48 (s, 1H), 8.40 (s, 2H), 4.59 (br d, J = 5.6 Hz, 2H), 2.36-2.25 (m, 1H), 1.29-1.03 (m, 4H) |
| 3-34 | 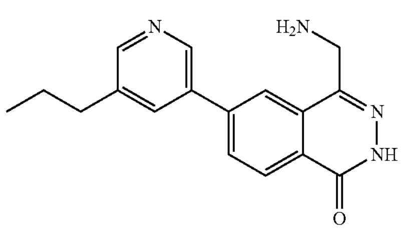 [SMILES: CCCc1cncc(-c2ccc3c(=O)[nH]nc(CN)c3c2)c1] | 3A | 3-1 | 4-(aminomethyl)-6-(5-propylpyridin-3-yl)phthalazin-1(2H)-one<br>¹H NMR (400 MHz, MeOD) δ = 8.82 (s, 1H), 8.51-8.47 (m, 2H), 8.24 (s, 1H), 8.20-8.13 (m, 2H), 4.27 (s, 2H), 2.78 (t, J = 7.6 Hz, 2H), 1.02 (t, J = 7.6 Hz, 3H) |
| 3-35 | 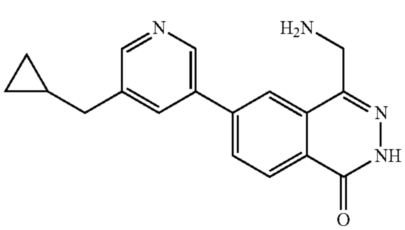 [SMILES: NCc1n[nH]c(=O)c2ccc(-c3cncc(CC4CC4)c3)cc12] | 3A | 3-2 | 4-(aminomethyl)-6-(5-(cyclopropylmethyl)pyridin-3-yl)phthalazin-1(2H)-one<br>LCMS [M + 1]⁺ 307.2 ¹H NMR (400 MHz, DMSO-d6) δ = 12.76-12.38 (m, 1H), 8.93 (d, J = 2.0 Hz, 1H), 8.59 (d, J = 1.6 Hz, 1H), 8.39-8.32 (m, 2H), 8.23-8.19 (m, 1H), 8.17 (t, J = 2.0 Hz, 1H), 4.17 (s, 2H), 2.64 (d, J = 6.8 Hz, 2H), 1.14-1.04 (m, 1H), 0.55-0.48 (m, 2H), 0.33-0.26 (m, 2H) |

TABLE 3-continued

| Example | Structure | CM | PM | Compound Name and Characterization |
|---------|-----------|----|----|------------------------------------|
| 3-36 | 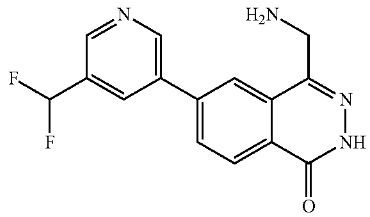 [SMILES: NCc1n[nH]c(=O)c2ccc(-c3cncc(C(F)F)c3)cc12] | 3B | 3-2 | 4-(aminomethyl)-6-(5-(difluoromethyl)pyridin-3-yl)phthalazin-1(2H)-one<br>LCMS [M + 1]$^+$ = 303.2 $^1$H NMR (400 MHz, DMSO-d6) δ = 9.26-9.18 (m, 1H), 8.87 (d, J = 1.6 Hz, 1H), 8.44-8.36 (m, 3H), 8.22-8.18 (m, 1H), 7.36-7.07 (m, 1H), 4.14 (s, 2H) |
| 3-37 | 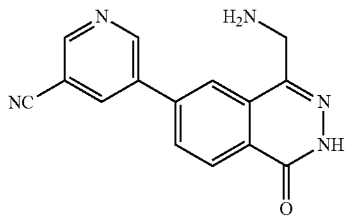 [SMILES: N#Cc1cncc(-c2ccc3c(=O)[nH]nc(CN)c3c2)c1] | 3B | 3-3 | 5-(4-(aminomethyl)-1-oxo-1,2-dihydrophthalazin-6-yl)nicotinonitrile<br>LCMS [M + 1]$^+$ = 278.0 $^1$H NMR (400 MHz, DMSO-d6) δ = 13.02 (s, 1H), 9.46 (d, J = 2.4 Hz, 1H), 9.14 (d, J = 2.0 Hz, 1H), 8.97 (t, J = 2.0 Hz, 1H), 8.62 (br s, 3H), 8.42-8.39 (m, 2H), 8.38-8.34 (m, 1H), 4.57 (q, J = 5.6 Hz, 2H) |
| 3-39 | 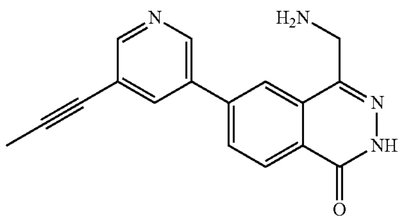 [SMILES: CC#Cc1cncc(-c2ccc3c(=O)[nH]nc(CN)c3c2)c1] | 3A | 3-1 | 4-(aminomethyl)-6-(5-(prop-1-yn-1-yl)pyridin-3-yl)phthalazin-1(2H)-one<br>LCMS [M + 1]$^+$ = 291.0 $^1$H NMR (400 MHz, DMSO-d6) δ = 12.55 (s, 1H), 9.02 (d, J = 2.4 Hz, 1H), 8.67 (d, J = 1.6 Hz, 1H), 8.38 (d, J = 1.2 Hz, 1H), 8.36-8.32 (m, 2H), 8.22 (dd, J = 1.6, 8.4 Hz, 1H), 4.12 (s, 2H), 2.13 (s, 3H) |
| 3-40 | 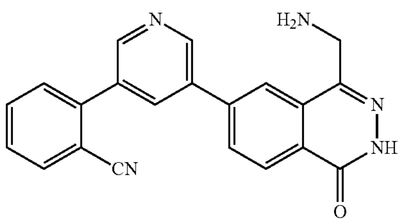 [SMILES: N#Cc1ccccc1-c1cncc(-c2ccc3c(=O)[nH]nc(CN)c3c2)c1] | 3A | 4-3 | 2-(5-(4-(aminomethyl)-1-oxo-1,2-dihydrophthalazin-6-yl)pyridin-3-yl)benzonitrile<br>LCMS [M + 1]$^+$ = 354.0 $^1$H NMR (400 MHz, DMSO-d6) δ = 13.02 (s, 1H), 9.35 (d, J = 2.0 Hz, 1H), 8.98 (d, J = 2.0 Hz, 1H), 8.74 (t, J = 2.0 Hz, 1H), 8.63 (br s, 3H), 8.46-8.40 (m, 3H), 8.08 (d, J = 7.6 Hz, 1H), 7.93-7.87 (m, 2H), 7.75-7.68 (m, 1H), 4.63-4.53 (m, 2H) |
| 3-41 | 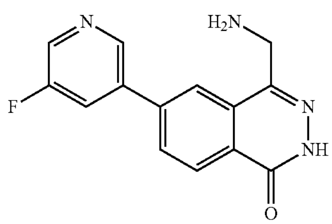 [SMILES: NCc1n[nH]c(=O)c2ccc(-c3cncc(F)c3)cc12] | 3A | 3-1 | 4-(aminomethyl)-6-(5-fluoropyridin-3-yl)phthalazin-1(2H)-one<br>LCMS [M + 1]$^+$ = 271.1 $^1$H NMR (400 MHz, DMSO-d6) δ = 13.0 (s, 1H), 9.08 (t, J = 1.6 Hz, 1H), 8.73 (d, J = 2.4 Hz, 1H), 8.51 (br s, 3H), 8.42 (m, 2H), 8.37-8.34 (m, 2H), 4.63-4.57 (m, 2H) |
| 3-42 | 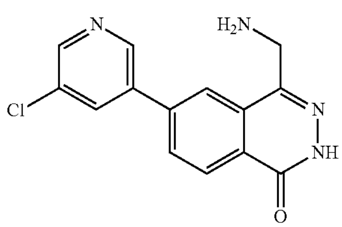 [SMILES: NCc1n[nH]c(=O)c2ccc(-c3cncc(Cl)c3)cc12] | 3A | 3-1 | 4-(aminomethyl)-6-(5-chloropyridin-3-yl)phthalazin-1(2H)-one<br>LCMS [M + 1]$^+$ 287.0 $^1$H NMR (400 MHz, DMSO-d6) δ = 12.6 (br s, 1H), 9.06 (d, J = 2.0 Hz, 1H), 8.73 (d, J = 2.4 Hz, 1H), 8.51 (t, J = 2.0 Hz, 1H), 8.40 (d, J = 1.6 Hz, 1H), 8.34 (d, J = 8.4 Hz, 1H), 8.24 (dd, J = 1.6, 8.4 Hz, 1H), 4.10 (s, 2H), 2.31-1.93 (br s, 2H) |
| 3-43 | 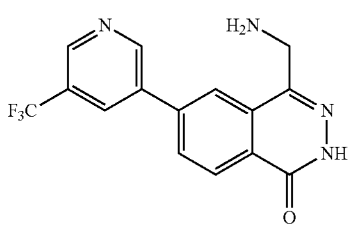 | 3A | 4-3 | 4-(aminomethyl)-6-(5-(trifluoromethyl)pyridin-3-yl)phthalazin-1(2H)-one<br>LCMS [M + 1]$^+$ = 321.0 $^1$H NMR (400 MHz, DMSO-d6) δ = 13.03 (s, 1H), 9.47 (d, J = 2.4 Hz, 1H), 9.12-9.10 (s, 1H), 8.79 (s, 1H), 8.50 (br s, 3H), 8.42-8.39 (m, 3H), 4.64-4.58 (m, 2H) |

TABLE 3-continued

| Example | Structure | CM | PM | Compound Name and Characterization |
|---|---|---|---|---|
| 3-44 | 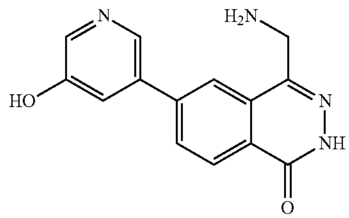 [SMILES: NCc1n[nH]c(=O)c2ccc(-c3cncc(O)c3)cc12] | 3A | 3-1 | 4-(aminomethyl)-6-(5-hydroxypyridin-3-yl)phthalazin-1(2H)-one<br>LCMS [M + 1] $^+$ = 269.1 $^1$H NMR (400 MHz, DMSO-d6) δ = 13.02 (s, 1H), 11.61 (s, 1H), 8.91 (d, J = 1.2 Hz, 1H), 8.61 (br s, 3H), 8.47 (d, J = 2.4 Hz, 1H), 8.42-8.36 (m, 2H), 8.29 (dd, J = 1.6, 8.0 Hz, 1H), 8.24 (br s, 1H), 4.58 (br d, J = 5.6 Hz, 2H) |
| 3-45 | 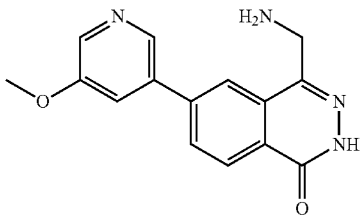 | 3A | 3-1 | 4-(aminomethyl)-6-(5-methoxypyridin-3-yl)phthalazin-1(2H)-one<br>LCMS [M + 1] $^+$ = 282.9 $^1$H NMR (400 MHz, DMSO-d6) δ = 13.01 (s, 1H), 8.95 (d, J = 1.6 Hz, 1H), 8.67 (br s, 3H), 8.57 (d, J = 2.8 Hz, 1H), 8.42-8.34 (m, 3H), 8.28 (s, 1H), 4.69-4.44 (m, 2H), 4.03 (s, 3H) |
| 3-46 | 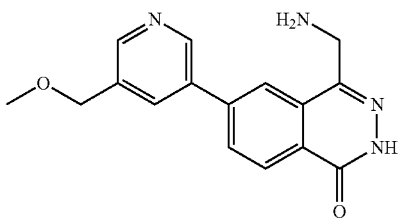 [SMILES: COCc1cncc(-c2ccc3c(=O)[nH]nc(CN)c3c2)c1] | 3A | 3-1 | 4-(aminomethyl)-6-(5-(methoxymethyl)pyridin-3-yl)phthalazin-1(2H)-one<br>LCMS [M + 1] $^+$ = 297.2 $^1$H NMR (400 MHz, DMSO-d6) δ = 12.54 (br s, 1H), 9.02 (d, J = 2.0 Hz, 1H), 8.63 (d, J = 2.0 Hz, 1H), 8.38-8.34 (m, 2H), 8.23-8.18 (m, 2H), 4.57 (s, 2H), 4.11 (s, 2H), 3.37 (s, 3H), 2.30-1.93 (m, 2H) |
| 3-47 | 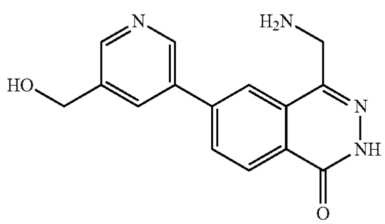 [SMILES: NCc1n[nH]c(=O)c2ccc(-c3cncc(CO)c3)cc12] | 3A | 3-2 | 4-(aminomethyl)-6-(5-(hydroxymethyl)pyridin-3-yl)phthalazin-1(2H)-one<br>LCMS [M + 1] $^+$ = 283.2 $^1$H NMR (400 MHz, DMSO-d6) δ = 12.48-12.06 (m, 1H), 8.92 (d, J = 2.0 Hz, 1H), 8.63 (d, J = 2.0 Hz, 1H), 8.38 (d, J = 8.4 Hz, 1H), 8.33 (d, J = 1.2 Hz, 1H), 8.16-8.12 (m, 2H), 5.15 (br s, 1H), 4.68 (s, 2H), 4.13 (s, 2H) |
| 3-48 | 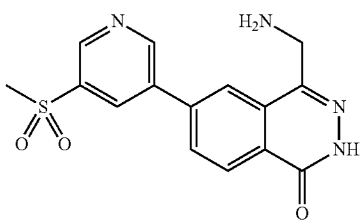 [SMILES: CS(=O)(=O)c1cncc(-c2ccc3c(=O)[nH]nc(CN)c3c2)c1] | 3A | 3-2 | 4-(aminomethyl)-6-(5-(methylsulfonyl)pyridin-3-yl)phthalazin-1(2H)-one<br>LCMS [M + 1] $^+$ = 331.0 $^1$H NMR (400 MHz, DMSO-d6) δ = 13.03 (s, 1H), 9.49 (d, J = 2.0 Hz, 1H), 9.17 (d, J = 2.0 Hz, 1H), 8.84 (t, J = 2.0 Hz, 1H), 8.61 (br s, 3H), 8.46-8.37 (m, 3H), 4.60 (s, 2H), 3.46 (s, 3H) |
| 349 | 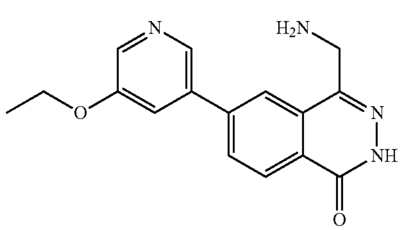 [SMILES: CCOc1cncc(-c2ccc3c(=O)[nH]nc(CN)c3c2)c1] | 3A | 3-1 | 4-(aminomethyl)-6-(5-ethoxypyridin-3-yl)phthalazin-1(2H)-one<br>LCMS [M + 1] $^+$ = 297.0 $^1$H NMR (400 MHz, DMSO-d6) δ = 13.02 (s, 1H), 8.97 (d, J = 1.6 Hz, 1H), 8.68 (br s, 3H), 8.58 (d, J = 2.8 Hz, 1H), 8.43-8.35 (m, 3H), 8.33 (s, 1H), 4.71-4.53 (m, 2H), 4.35 (q, J = 7.2 Hz, 2H), 1.43 (t, J = 7.2 Hz, 3H) |
| 3-50 | 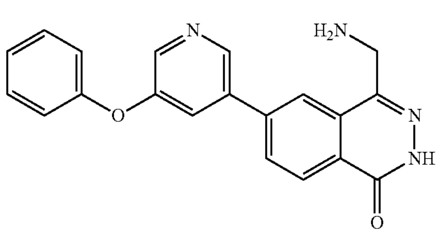 [SMILES: NCc1n[nH]c(=O)c2ccc(-c3cncc(Oc4ccccc4)c3)cc12] | 3A | 3-1 | 4-(aminomethyl)-6-(5-phenoxypyridin-3-yl)phthalazin-1(2H)-one<br>LCMS [M + 1] $^+$ = 345.1 $^1$H NMR (400 MHz, MeOH-d4) δ = 8.91 (s, 1H), 8.54 (d, J = 9.2 Hz, 1H), 8.46 (d, J = 2.4 Hz, 1H), 8.26-8.22 (m, 2H), 8.19 (t, J = 2.0 Hz, 1H), 7.52-7.47 (m, 2H), 7.31-7.26 (m, 1H), 7.23-7.19 (m, 2H), 4.69 (s, 2H) |

TABLE 3-continued

| Example | Structure | CM | PM | Compound Name and Characterization |
|---|---|---|---|---|
| 3-51 | 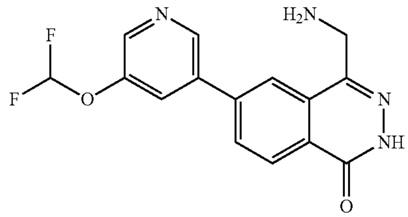 [SMILES: NCc1n[nH]c(=O)c2ccc(-c3cncc(OC(F)F)c3)cc12] | 3B | 3-1 | 4-(aminomethyl)-6-(5-(difluoromethoxy)pyridin-3-yl)phthalazin-1(2H)-one<br>LCMS [M + 1]⁺ = 318.9 ¹H NMR (400 MHz, DMSO-d6) δ = 13.00 (s, 1H), 9.08 (d, J = 2.0 Hz, 1H), 8.63 (br d, J = 2.8 Hz, 4H), 8.42-8.36 (m, 2H), 8.35-8.30 (m, 2H), 7.77-7.31 (d, J = 73.2 Hz, 1H), 4.67-4.47 (m, 2H) |
| 3-52 | 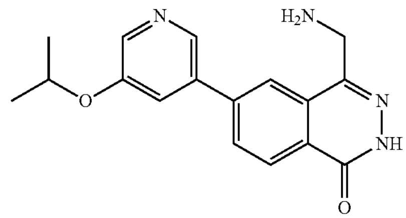 [SMILES: CC(C)Oc1cncc(-c2ccc3c(=O)[nH]nc(CN)c3c2)c1] | 3A | 3-2 | 4-(aminomethyl)-6-(5-isopropoxypyridin-3-yl)phthalazin-1(2H)-one<br>LCMS [M + 1]⁺ = 311.2 ¹H NMR (400 MHz, DMSO-d6) δ = 12.54 (br s, 1H), 8.63 (d, J = 1.6 Hz, 1H), 8.38-8.27 (m, 3H), 8.19 (dd, J = 1.6, 8.4 Hz, 1H), 7.81 (t, J = 2.4 Hz, 1H), 4.90 (spt, J = 6.0 Hz, 1H), 4.10 (s, 2H), 1.33 (d, J = 6.0 Hz, 6H). |
| 3-53 | 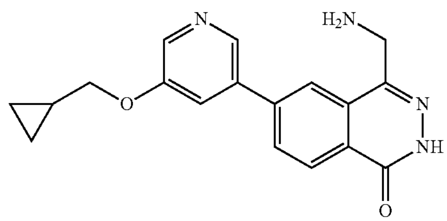 [SMILES: NCc1n[nH]c(=O)c2ccc(-c3cncc(OCC4CC4)c3)cc12] | 3A | 3-1 | 4-(aminomethyl)-6-(5-(cyclopropylmethoxy)pyridin-3-yl)phthalazin-1(2H)-one<br>LCMS [M + 1]⁺ = 323.1 ¹H NMR (400 MHz, DMSO-d6) δ = 13.02 (s, 1H), 9.00 (d, J = 1.6 Hz, 1H), 8.72 (br s, 3H), 8.59 (d, J = 2.4 Hz, 1H), 8.46-8.29 (m, 4H), 4.62-4.56 (m, 2H), 4.15 (d, J = 7.2 Hz, 2H), 1.40-1.16 (m, 1H), 0.76-0.56 (m, 2H), 0.45-0.29 (m, 2H) |
| 3-54 | 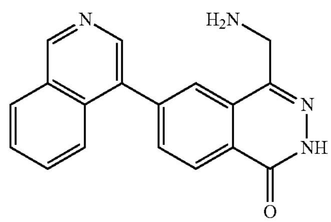 [SMILES: NCc1n[nH]c(=O)c2ccc(-c3cncc4ccccc34)cc12] | 3A | 3-1 | 4-(aminomethyl)-6-(isoquinolin-4-yl)phthalazin-1(2H)-one<br>LCMS [M + 1]⁺ = 303.0 ¹H NMR (400 MHz, DMSO-d6) δ = 13.08 (s, 1H), 9.85 (s, 1H), 8.82 (s, 1H), 8.66 (br s, 3H), 8.57 (d, J = 8.4 Hz, 1H), 8.49 (d, J = 8.4 Hz, 1H), 8.29 (d, J = 1.0 Hz, 1H), 8.19-7.93 (m, 4H), 4.51 (br d, J = 5.6 Hz, 2H) |
| 3-55 | 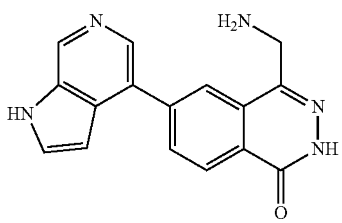 [SMILES: NCc1n[nH]c(=O)c2ccc(-c3cncc4[nH]ccc34)cc12] | 3A | 3-1 | 4-(aminomethyl)-6-(1H-pyrrolo[2,3-c]pyridin-4-yl)phthalazin-1(2H)-one<br>LCMS [M + 1]⁺ = 292.0; ¹H NMR (400 MHz, DMSO-d6) δ = 13.46 (br s, 1H), 13.05 (s, 1H), 9.27 (s, 1H), 8.77 (s, 1H), 8.67 (br s, 3H), 8.53-8.42 (m, 2H), 8.40-8.31 (m, 2H), 7.21 (br s, 1H), 4.60 (br d, J = 4.4 Hz, 2H) |
| 3-56 | 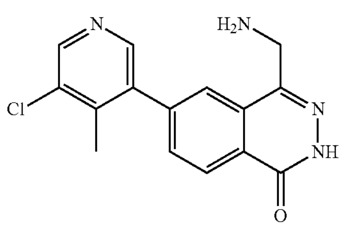 [SMILES: Cc1c(Cl)cncc1-c1ccc2c(=O)[nH]nc(CN)c2c1] | 3A | 3-1 | 4-(aminomethyl)-6-(5-chloro-4-methylpyridin-3-yl)phthalazin-1(2H)-one<br>LCMS [M + 1]⁺ = 301.0; ¹H NMR (400 MHz, DMSO-d6) δ = 13.04-13.00 (s, 1H), 8.71 (s, 1H), 8.59-8.44 (m, 4H), 8.39 (d, J = 8.4 Hz, 1H), 8.07 (d, J = 1.2 Hz, 1H), 7.99 (dd, J = 1.6, 8.4 Hz, 1H), 4.54-4.45 (m, 2H), 2.33 (s, 3H). |
| 3-57 | 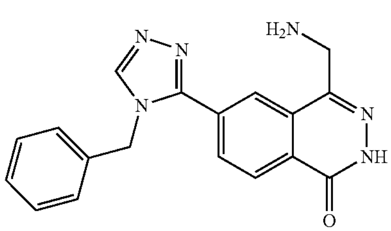 [SMILES: NCc1n[nH]c(=O)c2ccc(-c3nncn3Cc3ccccc3)cc12] | 3A | 3-1 | 4-(aminomethyl)-6-(4-benzyl-4H-1,2,4-triazol-3-yl)phthalazin-1(2H)-one<br>LCMS [M + 1]⁺ 333.1; ¹H NMR (400 MHz, DMSO-d6) δ = 13.08 (s, 1H), 9.05 (s, 1H), 8.59 (br s, 3H), 8.37 (d, J = 8.4 Hz, 1H), 8.17 (s, 1H), 8.14 (dd, J = 1.6, 8.4 Hz, 1H), 7.35-7.23 (m, 3H), 7.10-7.05 (m, 2H), 5.56 (s, 2H), 4.47-4.35 (m, 2H). |

TABLE 3-continued

| Example | Structure | CM | PM | Compound Name and Characterization |
|---|---|---|---|---|
| 3-58 | 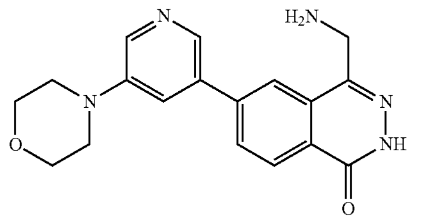 [SMILES: NCc1n[nH]c(=O)c2ccc(-c3cncc(N4CCOCC4)c3)cc12] | 3A | 3-1 | 4-(aminomethyl)-6-(5-morpholinopyridin-3-yl)phthalazin-1(2H)-one<br>LCMS [M + 1]$^+$ = 338.1; $^1$H NMR (400 MHz, DMSO-d6) δ = 13.03 (s, 1H), 8.71 (s, 1H), 8.53 (br s, 3H), 8.49 (d, J = 2.8 Hz, 1H), 8.43-8.39 (d, J = 8.4 Hz, 1H), 8.38-8.34 (dd, J = 1.6, 8.4 Hz, 1H), 8.34 (s, 1H), 8.17-8.07 (s, 1H), 4.61 (q, J = 6.0 Hz, 2H), 3.83-3.79 (t, J = 4.8 Hz, 4H), 3.47-3.45 (m, 4H) |
| 3-59 | 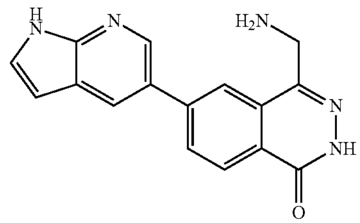 [SMILES: NCc1n[nH]c(=O)c2ccc(-c3cnc4[nH]ccc4c3)cc12] | 3A | 3-2 | 4-(aminomethyl)-6-(1H-pyrrolo[2,3-b]pyridin-5-yl)phthalazin-1(2H)-one<br>LCMS [M + 1]$^+$ = 292.0; $^1$H NMR (400 MHz, DMSO-d6) δ = 12.6 (br s, 1H), 11.85 (br s, 1H), 8.73 (d, J = 2.0 Hz, 1H), 8.46 (d, J = 2.0 Hz, 1H), 8.37-8.31 (m, 2H), 8.27-8.17 (m, 1H), 7.57 (dd, J = 2.0, 3.2 Hz, 1H), 6.60-6.54 (m, 1H), 4.20 (s, 2H), 3.88-3.54 (s, 2H) |
| 3-60 | 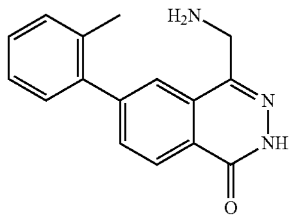 [SMILES: Cc1ccccc1-c1ccc2c(=O)[nH]nc(CN)c2c1] | 3A | 3-1 | 4-(aminomethyl)-6-(o-tolyl)phthalazin-1(2H)-one<br>LCMS [M + 1]$^+$ = 266.1; $^1$H NMR (400 MHz, DMSO-d6) δ = 13.0 (s, 1H), 8.39-8.33 (m, 4H), 7.94-7.90 (m, 2H), 7.40-7.34 (m, 4H), 4.51 (s, 2H), 2.28 (s, 3H) |
| 3-61 | 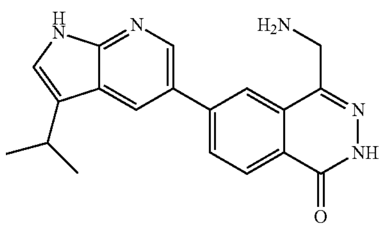 [SMILES: CC(C)c1c[nH]c2ncc(-c3ccc4c(=O)[nH]nc(CN)c4c3)cc12] | 3A | 3-4 | 4-(aminomethyl)-6-(3-isopropyl-1H-pyrrolo[2,3-b]pyridin-5-yl)phthalazin-1(2H)-one<br>LCMS [M + 1]$^+$ = 334.1; $^1$H NMR (400 MHz, DMSO-d6) δ = 12.94 (s, 1H), 11.80 (br s, 1H), 8.83 (d, J = 2.0 Hz, 1H), 8.64 (d, J = 2.0 Hz, 1H), 8.60 (br s, 3H), 8.41-8.36 (m, 1H), 8.36-8.31 (m, 1H), 8.29 (s, 1H), 7.36 (d, J = 2.0 Hz, 1H), 4.63 (br d, J = 5.6 Hz, 2H), 3.36-3.19 (m, 1H), 1.37 (d, J = 6.8 Hz, 6H) |

Examples 4-1 to 4-180 Coupling Methods (CM) and Purification Methods (PM) for the Preparation of Examples in Table 4

CM 4A:

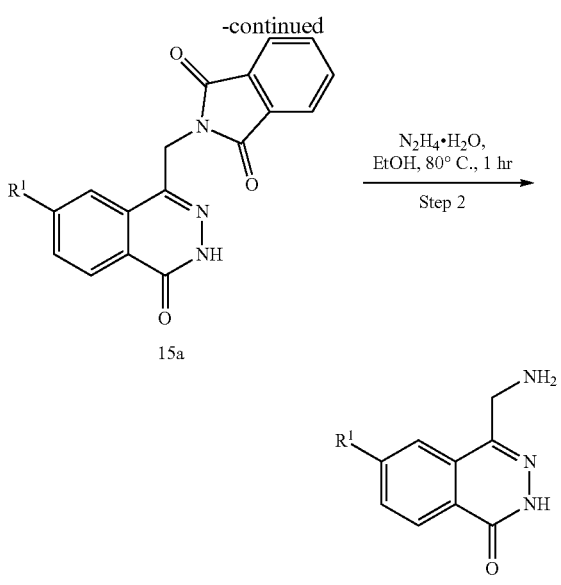

Wherein R$^1$ = aryl or heteroaryl and Hal = Cl, Br, I

Step 1: A mixture of the appropriate aryl/heteroaryl-halide 26 (390 μmol, 1.5 eq.), intermediate AN (260 μmol, 1.00 eq.), Pd(dppf)Cl₂ (26 μmol, 0.10 eq.), sodium bicarbonate (43.7 mg, 521 μmol, 20.3 μL, 2.00 eq.) in dioxane (1.0 mL) and water (0.2 mL) was purged with nitrogen 3 times. The mixture was then stirred at 80° C. for 2 hours. After such time the mixture was filtered, washed with a dichloromethane:methyl alcohol 10:1 mixture and the filtrate concentrated under reduced pressure to give a residue. This concentrated residue was triturated with methyl alcohol (3.0 mL), filtered and dried to give the corresponding coupling product 15a as a black solid.

Step 2: To a solution of corresponding coupling product 15a in ethyl alcohol (1.00 mL) was added hydrazine hydrate (242 μmol, 14 The mixture was stirred at 80° C. for 1 hour. After such time the mixture was concentrated in vacuo and the residue purified by prep-HPLC according to one of the purification methods 4-1 to 4-13.
CM 4B:

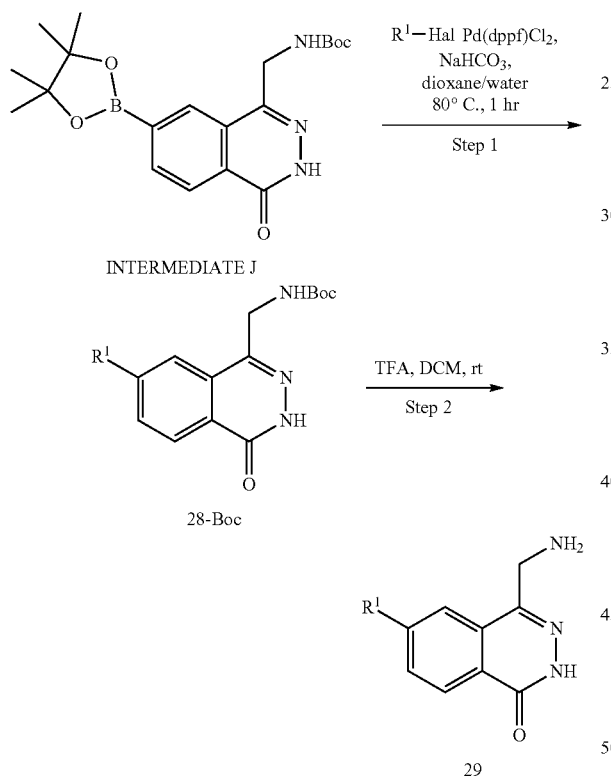

$R^1$ = Aryl or Heteroaryl and Hal = Cl, Br, I

Step 1: Intermediate J (189 mg, 470 μmol, 1.00 eq.), aryl/heteroaryl-halide 26 (564 μmol, 1.20 eq.), Pd(dppf)Cl₂ (34 mg, 47 μmol, 0.10 eq.), sodium bicarbonate (79 mg, 940 μmol, 37 μL, 2.00 eq.) in dioxane (1 mL) and water (0.20 mL) was purged with nitrogen 3 times, and stirred at 80° C. for 2 hours. Upon completion, the reaction mixture was poured into water (40 mL), filtered and the filter cake was dried under reduced pressure to give $R^2$-Pyridyl-Suzuki coupling product 28-Boc (71 mg, crude) as a gray solid and used into the next step directly without further purification.

Step 2: To a solution of tert-butyl N-[[4-oxo-7-(5-pyrimidin-2-yloxy-3-pyridyl)-3H-phthalazin-1-yl]methyl]carbamate $R^2$-Pyridyl-Suzuki coupling product 28-Boc (60 mg, crude) in dichloromethane (1 mL) was added trifluoroacetic acid (462 mg, 4.05 mmol, 0.30 mL). The mixture was stirred at 30° C. for 0.5 hour and upon completion concentrated to a residue under reduced pressure. The concentrated residue 29 was purified by prep-HPLC according to one of the purification methods 4-1 through 4-13.
CM 4C

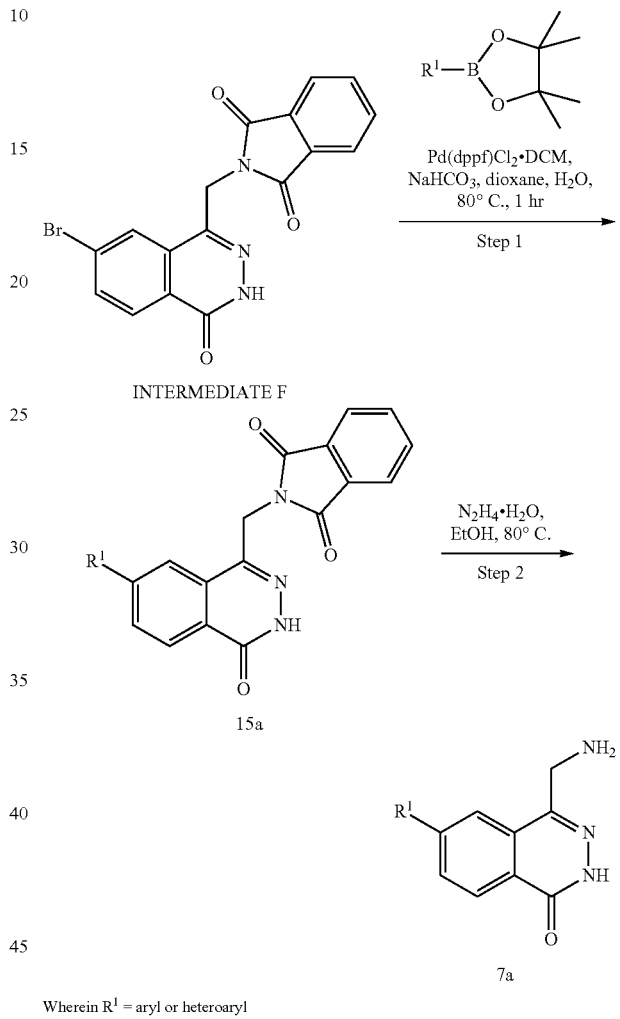

Wherein $R^1$ = aryl or heteroaryl

Step 1: A mixture of the appropriate aryl/heteroaryl boronic ester (303 μmol, 1.16 eq.), intermediate F (100 mg, 260 μmol, 1.00 eq.), Pd(dppf)Cl₂ (19 mg, 26 μmol, 0.10 eq.), sodium bicarbonate (66 mg, 781 μmol, 30 μL, 3.00 eq.) in dioxane (1 mL) and water (0.20 mL) was degassed and purged with nitrogen 3 times and stirred at 80° C. for 1 hour under a nitrogen atmosphere. After such time the mixture was filtered and concentrated under reduced pressure to give a residue. The concentrated residue was purified by column chromatography (SiO₂, petroleumether:ethylacetate 10:1 to 0:1) to give the corresponding Suzuki coupling product 15a (12.0 mg, crude) as a yellow solid.

Step 2: To a solution of corresponding Suzuki coupling product 15a (10 mg, crude), in ethyl alcohol (1.0 mL) was added hydrazine hydrate (10 mg, 207 μmol, 10 μL). The mixture was stirred at 80° C. for 1 hour, cooled and concentrated under reduced pressure. The concentrated residue 7a was then purified by prep-HPLC according to one of the purification methods 4-1 to 4-13 described herein.

CM 4D

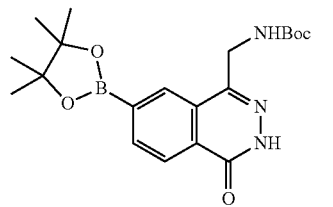

INTERMEDIATE J

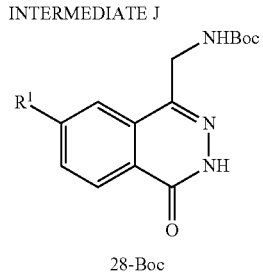

28-Boc

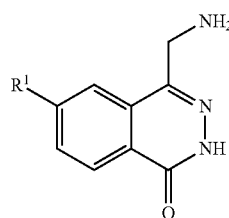

29

$R^1$ = Aryl or Heteroaryl and Hal = Cl, Br, I

Step 1: Intermediate J (69 mg, 17 μmol, 1.30 eq.), aryl/heteroaryl-halide 26 (132 μmol, 1.0 eq.), Pd(dtbpf)Cl$_2$ (9 mg, 13 μmol, 0.10 eq.), sodium carbonate (28 mg, 263 μmol, 2.00 eq.) in dioxane (1.5 mL) and water (0.30 mL) was purged with nitrogen 3 times, and stirred at 80° C. for 2 hours. After such time the mixture was concentrated and the residue purified by prep-TLC (SiO$_2$, CH$_2$Cl$_2$:MeOH 20:1) to give $R^1$-Suzuki coupling product 28-Boc and used into the next step directly without further purification.

Step 2: To a solution of tert-butyl N-[[4-oxo-7-($R^1$)-3H-phthalazin-1-yl]methyl]carbamate Suzuki coupling product 28-Boc (40 mg) in dichloromethane (1.5 mL) was added trifluoroacetic acid (5.4 mmol, 0.4 mL). The mixture was stirred at 25° C. for 0.5 hour and upon completion concentrated to a residue under reduced pressure. The concentrated residue 29 was purified by prep-HPLC according to one of the purification methods 4-1 through 4-13.

CM 4E

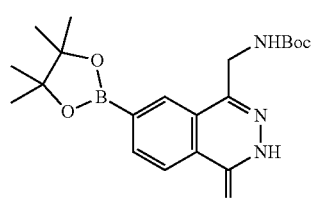

INTERMEDIATE J

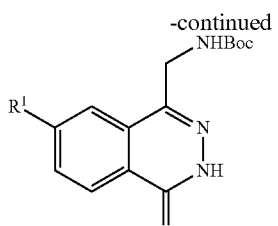

28-Boc

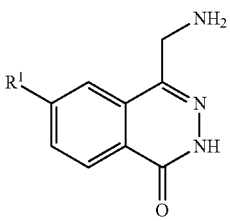

29

$R^1$ = Aryl or Heteroaryl and Hal = Cl, Br, I

Step 1: Intermediate J (80 mg, 0.20 mmol, 1.00 eq.), aryl/heteroaryl-halide 26 (239 μmol, 1.2 eq.), [2-(2-aminophenyl)phenyl]-chloro-palladium; dicyclohexyl-[2-(2,6-dimethoxyphenyl)phenyl]phosphane (14.4 mg, 19.9 μmol, 0.10 eq.), sodium bicarbonate (34 mg, 398 μmol, 2.00 eq.) in 2-methyl-2-butanol (2.00 mL) and water (0.4 mL) was purged with nitrogen 3 times, and stirred at 80° C. for 3 hours. After such time the mixture was diluted with water (5 mL) and extracted with ethyl acetate (10 mL×3) and the combined organic extracts were dried over anhydrous sodium sulfate, filtered and concentrated under reduced pressure. The residue was then purified by prep-TLC (SiO$_2$, petroleum ether:ethyl acetate=1:1.5) to give $R^1$-Suzuki coupling product 28-Boc which was used in the next.

Step 2: A solution of tert-butyl N-[[4-oxo-7-($R^1$)-3H-phthalazin-1-yl]methyl]carbamate Suzuki coupling product 28-Boc (0.08 mmol, 1.00 eq) in HCl.dioxane (2.00 mL, 101 eq.) was stirred at 25° C. for 12 hours. The reaction was concentrated in vacuo and the residue purified by prep-HPLC according to one of the purification methods 4-1 through 4-13.

CM 4F:

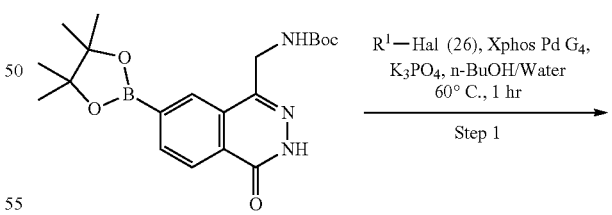

INTERMEDIATE J

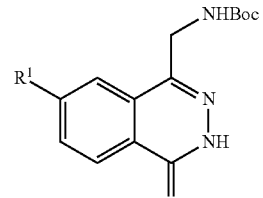

28-Boc

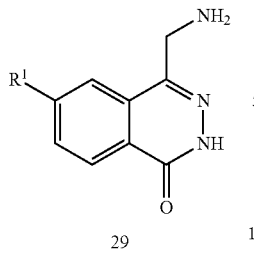

29

$R^1$ = Aryl or Heteroaryl and Hal = Cl, Br, I

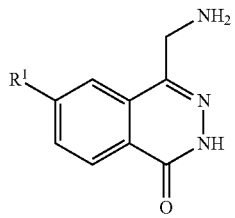

29

$R^1$ = Aryl or Heteroaryl and Hal = Cl, Br, I

Step 1: Intermediate J (80 mg, 0.20 mmol, 1.00 eq.), aryl/heteroaryl-halide 26 (0.24 mmol, 1.2 eq.), methanesulfonato(2-dicyclohexylphosphino-2',4',6'-tri-i-propyl-1,1'-biphenyl)(2'-methylamino-1,1'-biphenyl-2-yl)palladium(II) (20 μmol, 0.10 eq.), potassium phosphate, 0.40 mmol, 2.00 eq.) in n-butanol (2.0 mL) and water (0.4 mL) was purged with nitrogen 3 times, and stirred at 60° C. for 1 hour. After such time the mixture was diluted with water (5 mL) and extracted with ethyl acetate (10 mL×3) and the combined organic extracts were dried over anhydrous sodium sulfate, filtered and concentrated under reduced pressure. The residue was then purified by prep-TLC (SiO$_2$, petroleumether:ethylacetate 20%) to give $R^1$-Suzuki coupling product 28-Boc which was used in the next step.

Step 2: To a solution of tert-butyl N-[[4-oxo-7-($R^1$)-3H-phthalazin-1-yl]methyl]carbamate Suzuki coupling product 28-Boc (40.0 mg) in dichloromethane (1.5 mL) was added trifluoroacetic acid (5.4 mmol, 0.40 mL). The mixture was stirred at 25° C. for 0.5 hour and upon completion concentrated to a residue under reduced pressure. The concentrated residue 29 was purified by prep-HPLC according to one of the purification methods 4-1 through 4-13.

CM 4G:

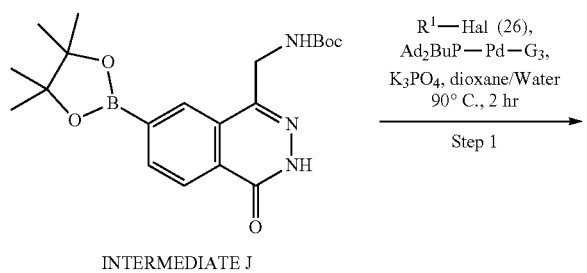

INTERMEDIATE J

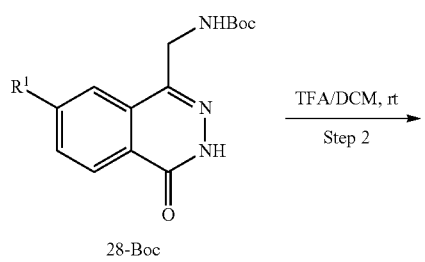

28-Boc

Step 1: Intermediate J (40 mg, 0.10 mmol, 1.25 eq.), aryl/heteroaryl-halide 26 (0.076 mmol, 1.0 eq), [2-(2-aminophenyl)phenyl]palladium(1+); bis(1-adamantyl)-butylphosphane methanesulfonate (8 μmol, 0.10 eq.), potassium phosphate, (0.23 mmol, 3.00 eq.) in dioxane (1.5 mL) and water (0.3 mL) was purged with nitrogen 3 times, and stirred at 90° C. for 2 hours. After such time the mixture was filtered, concentrated and the residue was then purified by prep-TLC (SiO$_2$, petroleumether:ethylacetate 60%) to give $R^1$-Suzuki coupling product 28-Boc which was used in the next step.

Step 2: To a solution of tert-butyl N-[[4-oxo-7-($R^1$)-3H-phthalazin-1-yl]methyl]carbamate Suzuki coupling product 28-Boc (30.0 mg) in dichloromethane (2.0 mL) was added trifluoroacetic acid (0.2 mL). The mixture was stirred at 25° C. for 0.5 hour and upon completion concentrated to a residue under reduced pressure. The concentrated residue 29 was purified by prep-HPLC according to one of the purification methods 4-1 through 4-13.

Purification Methods (PM)

PM 4-1: column: Phenomenex Synergi C18 150×25 mm×10 μm; mobile phase: [water (0.05% HCl)-ACN]; B %: 5%-30%, 10 min.

PM 4-2: column: Waters Xbridge 150×25 mm×5 μm; mobile phase: [water (0.05% ammonia hydroxide v/v)-ACN]; B %: 5%-40%, 10 min.

PM 4-3: column: Waters Atlantis T3 150×30 mm×5 μm; mobile phase: [water (0.225% FA)-ACN]; B %: 1%-20%, 10 min.

PM 4-4: column: Phenomenex luna C18 150×25 mm×10 μm; mobile phase: [water (0.1% TFA)-ACN]; B %: 1%-30%, 10 min.

PM 4-5: column: Phenomenex Gemini NX-C18 75×30 mm×3 μm; mobile phase: [water (0.05% ammonia hydroxide v/v)-ACN]; B %: 5%-40%, 7 min.

PM 4-6: column: Phenomenex Luna C18 75×30 mm×3 μm; mobile phase: [water (0.05% HCl)-ACN]; B %: 10%-35%, 6.5 min.

PM 4-7: column: Xtimate C18 150×40 mm×10 μm; mobile phase: [water (0.05% ammonia hydroxide v/v)-ACN]; B %: 5%-35%, 10 min.

PM 4-8: column: Waters Xbridge BEH C18 150×25 mm×5 μm; mobile phase: [water (0.05% NH$_4$HCO$_3$ v/v)-ACN]; B %: 5%-40%, 10 min.

PM 4-9: column: Nano-micro Kromasil C18 100 mm×40 mm×10 μm; mobile phase: [water (0.1% TFA)-ACN]; B %: 1%-40%, 8 min.

PM 4-10: SFC (column: Daicel ChiralPak IG (250 mm×30 mm, 10 μm); mobile phase: [0.1% NH$_3$H$_2$O/MeOH]; B %: 40% isocratic, 7.8 min; 109 min).

PM 4-11: SFC (column: Phenomenex-Cellulose-2 (250 mm×30 mm, 10 μm); mobile phase: [0.1% NH$_3$H$_2$O/ MeOH]; B %: 50% isocratic, 11.0 min; 95 min).

PM-4-12: The residue was diluted with 50% sodium bicarbonate (20 mL) and extracted with dichloromethane (15 mL×3). The combined organic layers were dried over anhydrous sodium sulfate, filtered and concentrated under reduced pressure to give title compound.

PM 4-13: column: Welch Xtimate C18 150 mm×25 mm×5 μm; mobile phase: [water (0.05% HCl)-ACN]; B %: 10%-40%, 8 min.

Following the teachings of the General Reaction Schemes, the coupling methods 4A-G, and using purification methods 4-1 to 4-13 and the Intermediates disclosed herein, the Examples 4-1 to 4-252 are prepared as shown in Table 4:

TABLE 4

| Example | Structure | CM | PM | Compound Name and Characterization |
|---|---|---|---|---|
| 4-1 | 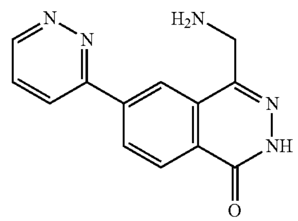 [SMILES: NCc1n[nH]c(=O)c2ccc(-c3cccnn3)cc12] | 4A | 4-1 | 4-(aminomethyl)-6-(pyridazin-3-yl)phthalazin-1(2H)-one<br>LCMS [M + 1] $^+$ = 254.2; $^1$H NMR (400 MHz, DMSO-d6) δ = 13.04 (s, 1H), 9.35 (dd, J = 1.6, 5.2 Hz, 1H), 8.71 (dd, J = 1.6, 8.4 Hz, 1H), 8.65 (d, J = 1.2 Hz, 1H), 8.62 (br dd, J = 1.6, 8.8 Hz, 4H), 8.46 (d, J = 8.4 Hz, 1H), 7.95 (dd, J = 4.8, 8.8 Hz, 1H), 4.61 (q, J = 5.2 Hz, 2H) |
| 4-2 | 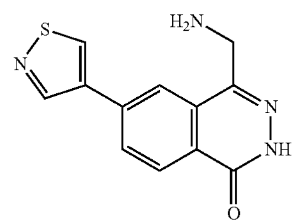 [SMILES: NCc1n[nH]c(=O)c2ccc(-c3cnsc3)cc12] | 4A | 4-1 | 4-(aminomethyl)-6-(isothiazol-4-yl)phthalazin-1(2H)-one<br>LCMS [M + 1] $^+$ = 258.8; $^1$H NMR (400 MHz, DMSO-d6) δ = 12.96 (s, 1H), 9.76 (s, 1H), 9.35 (s, 1H), 8.52 (br s, 3H), 8.39-8.34 (m, 3H), 4.56 (br d, J = 5.6 Hz, 2H) |
| 4-3 | 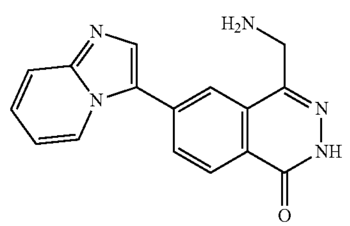 [SMILES: NCc1n[nH]c(=O)c2ccc(-c3cnc4ccccn34)cc12] | 4A | 4-1 | 4-(aminomethyl)-6-(imidazo[1,2-a]pyridin-3-yl)phthalazin-1(2H)-one<br>LCMS [M + 1] $^+$ = 292.0; $^1$H NMR (400 MHz, DMSO-d6) δ = 13.08 (s, 1H), 9.14 (d, J = 6.8 Hz, 1H), 8.80-8.60 (m, 4H), 8.51-8.39 (m, 2H), 8.24 (dd, J = 1.2, 8.4 Hz, 1H), 8.10 (d, J = 9.2 Hz, 1H), 8.03-7.92 (m, 1H), 7.50 (t, J = 6.4 Hz, 1H), 4.53 (br d, J = 5.6 Hz, 2H) |
| 4-4 | 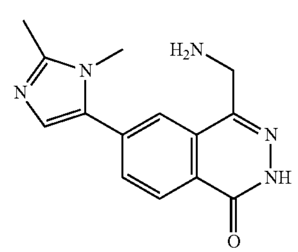 [SMILES: Cc1ncc(-c2ccc3c(=O)[nH]nc(CN)c3c2)n1C] | 4A | 4-1 | 4-(aminomethyl)-6-(1,2-dimethyl-1H-imidazol-5-yl)phthalazin-1(2H)-one<br>LCMS [M + 1] $^+$ = 270.1; $^1$H NMR (400 MHz, DMSO-d6) δ = 13.07 (s, 1H), 8.69 (br s, 3H), 8.43 (d, J = 8.4 Hz, 1H), 8.20 (d, J = 1.2 Hz, 1H), 8.08 (dd, J = 1.6, 8.4 Hz, 1H), 8.03 (s, 1H), 4.49 (br d, J = 4.8 Hz, 2H), 3.79 (s, 3H), 2.72 (s, 3H) |
| 4-5 | 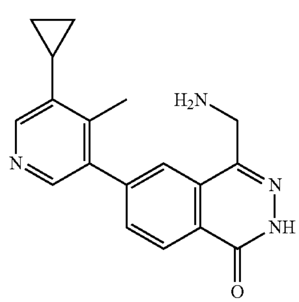 [SMILES: Cc1c(-c2ccc3c(=O)[nH]nc(CN)c3c2)cncc1C1CC1] | 4A | 4-2 | 4-(aminomethyl)-6-(5-cyclopropyl-4-methylpyridin-3-yl)phthalazin-1(2H)-one<br>LCMS [M + 1] $^+$ = 307.3; $^1$H NMR (400 MHz, DMSO-d6) δ = 8.37-8.28 (m, 3H), 8.05 (d, J = 1.2 Hz, 1H), 7.80 (dd, J = 1.6, 8.0 Hz, 1H), 4.05 (s, 2H), 2.35 (s, 3H), 2.02-1.94 (m, 1H), 1.08-1.00 (m, 2H), 0.81-0.72 (m, 2H) |

TABLE 4-continued

| Example | Structure | CM | PM | Compound Name and Characterization |
|---|---|---|---|---|
| 4-6 | 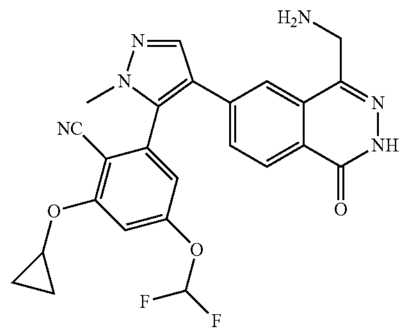 [SMILES: Cn1ncc(-c2ccc3c(=O)[nH]nc(CN)c3c2)c1-c1cc(OC(F)F)cc(OC2CC2)c1C#N] | 4D | 4-6 | 2-(4-(4-(aminomethyl)-1-oxo-1,2-dihydrophthalazin-6-yl)-1-methyl-1H-pyrazol-5-yl)-6-cyclopropoxy-4-(difluoromethoxy)benzonitrile<br>LCMS [M + 1]⁺ = 479.1; ¹H NMR (400 MHz, DMSO-d₆) δ = 12.88 (s, 1H), 8.48 (br s, 3H), 8.29 (s, 1H), 8.13 (d, J = 8.4 Hz, 1H), 7.81-7.39 (m, 4H), 7.21 (d, J = 2.0 Hz, 1H), 4.39-4.13 (m, 3H), 3.75 (s, 3H), 0.98-0.70 (m, 4H). |
| 4-7 | 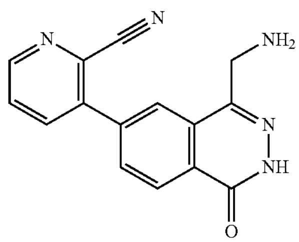 [SMILES: N#Cc1ncccc1-c1ccc2c(=O)[nH]nc(CN)c2c1] | 4A | 4-1 | 3-(4-(aminomethyl)-1-oxo-1,2-dihydrophthalazin-6-yl)picolinonitrile<br>LCMS [M + 1]⁺ = 278.0; ¹H NMR (400 MHz, DMSO-d6) δ = 13.08 (s, 1H), 8.88 (dd, J = 1.2, 4.4 Hz, 1H), 8.57 (br s, 3H), 8.45 (d, J = 8.4 Hz, 1H), 8.37-8.31 (m, 2H), 8.23 (dd, J = 1.6, 8.0 Hz, 1H), 7.95 (dd, J = 4.8, 8.0 Hz, 1H), 4.52-4.45 (m, 2H) |
| 4-8 | 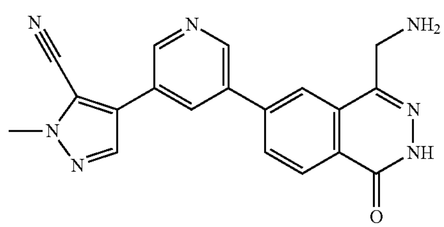 [SMILES: Cn1ncc(-c2cncc(-c3ccc4c(=O)[nH]nc(CN)c4c3)c2)c1C#N] | 4A | 4-1 | 4-(5-(4-(aminomethyl)-1-oxo-1,2-dihydrophthalazin-6-yl)pyridin-3-yl)-1-methyl-1H-pyrazole-5-carbonitrile<br>LCMS [M + 1]⁺ = 358.1; ¹H NMR (400 MHz, DMSO-d6) δ = 13.03 (s, 1H), 9.19 (d, J = 2.0 Hz, 1H), 9.02 (d, J = 2.0 Hz, 1H), 8.58 (t, J = 2.0 Hz, 1H), 8.50-8.42 (m, 4H), 8.39-8.33 (m, 3H), 4.67-4.55 (s, 2H), 4.13 (s, 3H) |
| 4-9 | 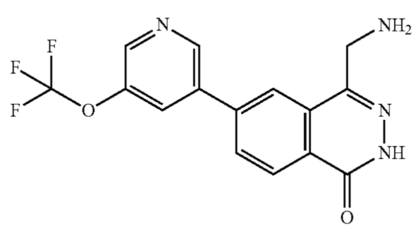 [SMILES: NCc1n[nH]c(=O)c2ccc(-c3cncc(OC(F)(F)F)c3)cc12] | 4A | 4-1 | 4-(aminomethyl)-6-(5-(trifluoromethoxy)pyridin-3-yl)phthalazin-1(2H)-one<br>LCMS [M + 1]⁺ = 337.0; ¹H NMR (400 MHz, DMSO-d6) δ = 13.02 (s, 1H), 9.25 (d, J = 2.0 Hz, 1H), 8.82 (d, J = 1.6 Hz, 1H), 8.65-8.49 (m, 4H), 8.42-8.38 (m, 1H), 8.38-8.33 (m, 2H), 4.65-4.54 (m, 2H) |
| 4-10 | 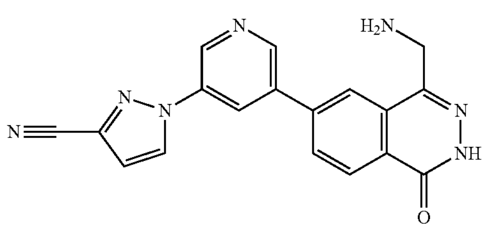 [SMILES: N#Cc1ccn(-c2cncc(-c3ccc4c(=O)[nH]nc(CN)c4c3)c2)n1] | 4A | 4-2 | 1-(5-(4-(aminomethyl)-1-oxo-1,2-dihydrophthalazin-6-yl)pyridin-3-yl)-1H-pyrazole-3-carbonitrile<br>LCMS [M + 1]⁺ = 344.2; ¹H NMR (400 MHz, DMSO-d6) δ = 12.65-12.51 (m, 1H), 9.23 (d, J = 2.4 Hz, 1H), 9.18 (d, J = 2.0 Hz, 1H), 9.02 (d, J = 2.8 Hz, 1H), 8.76 (t, J = 2.0 Hz, 1H), 8.48 (s, 1H), 8.41-8.37 (m, 1H), 8.35-8.30 (m, 1H), 7.40 (d, J = 2.4 Hz, 1H), 4.13 (s, 2H) |
| 4-11 | 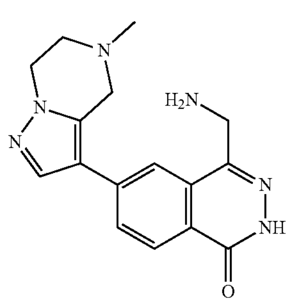 [SMILES: CN1CCn2ncc(-c3ccc4c(=O)[nH]nc(CN)c4c3)c2C1] | 4A | 4-1 | 4-(aminomethyl)-6-(5-methyl-4,5,6,7-tetrahydropyrazolo[1,5-a]pyrazin-3-yl)phthalazin-1(2H)-one<br>LCMS [M + 1]⁺ = 311.2; ¹H NMR (400 MHz, DMSO-d6) δ = 12.91 (s, 1H), 12.28 (br s, 1H), 8.57 (br s, 3H), 8.36-8.23 (m, 2H), 7.98-7.84 (m, 2H), 4.84 (br s, 2H), 4.54 (br d, J = 4.0 Hz, 4H), 3.74 (br s, 2H), 2.99 (br s, 3H) |

TABLE 4-continued

| Example | Structure | CM | PM | Compound Name and Characterization |
|---|---|---|---|---|
| 4-12 | 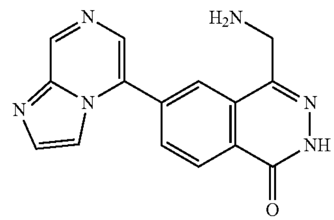 [SMILES: NCc1n[nH]c(=O)c2ccc(-c3cncc4nccn34)cc12] | 4A | 4-1 | 4-(aminomethyl)-6-(imidazo[1,2-a]pyrazin-5-yl)phthalazin-1(2H)-one<br>LCMS [M + 1]$^+$ = 293.1; $^1$H NMR (400 MHz, DMSO-d6) δ = 13.12 (s, 1H), 9.29-9.23 (s, 1H), 8.52 (br s, 3H), 8.49 (s, 1H), 8.46 (d, J = 1.2 Hz, 1H), 8.39 (s, 1H), 8.33 (dd, J = 1.6, 8.4 Hz, 1H), 8.23 (s, 1H), 8.04-8.01 (m, 1H), 4.59-4.51 (d, J = 5.6 Hz, 2H) |
| 4-13 | 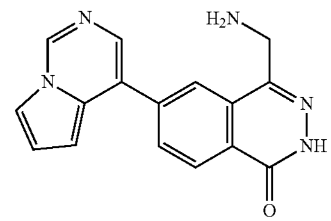 [SMILES: NCc1n[nH]c(=O)c2ccc(-c3cncn4cccc34)cc12] | 4A | 4-1 | 4-(aminomethyl)-6-(pyrrolo[1,2-c]pyrimidin-4-yl)phthalazin-1(2H)-one<br>LCMS [M + 1]$^+$ = 292.1; $^1$H NMR (400 MHz, DMSO-d6) δ = 13.00 (s, 1H), 9.41 (s, 1H), 8.62 (br s, 3H), 8.42 (d, J = 8.4 Hz, 1H), 8.30-8.25 (m, 2H), 7.90 (dd, J = 1.2, 2.8 Hz, 1H), 7.78 (s, 1H), 7.06 (dd, J = 2.8, 3.6 Hz, 1H), 6.83 (d, J = 3.6 Hz, 1H), 4.57 (q, J = 5.4 Hz, 2H) |
| 4-14 | 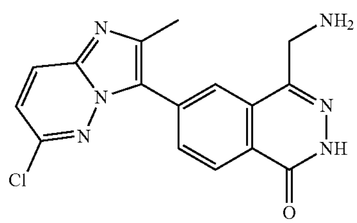 [SMILES: Cc1nc2ccc(Cl)nn2c1-c1ccc2c(=O)[nH]nc(CN)c2c1] | 4A | 4-1 | 4-(aminomethyl)-6-(6-chloro-2-methylimidazo[1,2-b]pyridazin-3-yl)phthalazin-1(2H)-one<br>LCMS [M + 1]$^+$ = 341.1<br>$^1$H NMR (400 MHz, DMSO-d6) δ = 13.02 (s, 1H), 8.62 (br s, 3H), 8.45 (d, J = 8.4 Hz, 1H), 8.31 (d, J = 9.6 Hz, 1H), 8.29-8.22 (m, 2H), 7.56 (d, J = 9.2 Hz, 1H), 4.47 (br d, J = 5.6 Hz, 2H), 2.61 (s, 3H) |
| 4-15 | 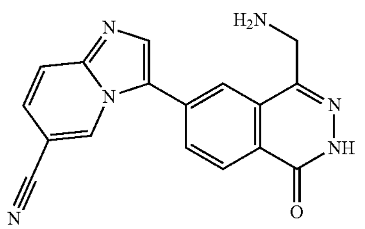 [SMILES: N#Cc1ccc2ncc(-c3ccc4c(=O)[nH]nc(CN)c4c3)n2c1] | 4A | 4-2 | 3-(4-(aminomethyl)-1-oxo-1,2-dihydrophthalazin-6-yl)imidazo[1,2-a]pyridine-6-carbonitrile<br>LCMS [M + 1]$^+$ = 317.2; $^1$H NMR (400 MHz, DMSO-d6) δ = 12.56 (s, 1H), 9.53-9.43 (m, 1H), 8.42-8.36 (m, 2H), 8.23-8.12 (m, 2H), 7.88 (dd, J = 0.8, 9.2 Hz, 1H), 7.63 (dd, J = 1.2, 9.2 Hz, 1H), 4.10 (s, 2H) |
| 4-16 | 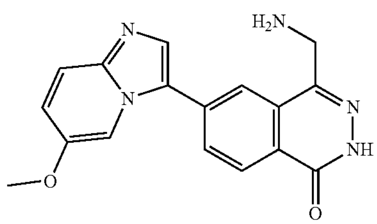 [SMILES: COc1ccc2ncc(-c3ccc4c(=O)[nH]nc(CN)c4c3)n2c1] | 4A | 4-2 | 4-(aminomethyl)-6-(6-methoxyimidazo[1,2-a]pyridin-3-yl)phthalazin-1(2H)-one<br>LCMS [M + 1]$^+$ = 322.1; $^1$H NMR (400 MHz, DMSO-d6) δ = 12.51 (br s, 1H), 8.47 (s, 1H), 8.36 (d, J = 8.0 Hz, 1H), 8.26 (s, 1H), 8.13 (d, J = 8.4 Hz, 1H), 7.97 (s, 1H), 7.65 (d, J = 10.0 Hz, 1H), 7.17 (dd, J = 2.0, 9.6 Hz, 1H), 4.07 (s, 2H), 3.83 (s, 3H) |
| 4-17 | 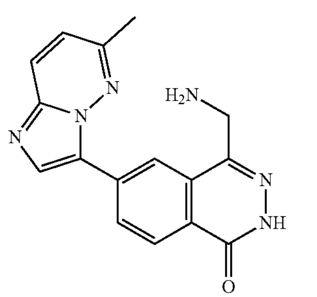 [SMILES: Cc1ccc2ncc(-c3ccc4c(=O)[nH]nc(CN)c4c3)n2n1] | 4A | 4-1 | 4-(aminomethyl)-6-(6-methylimidazo[1,2-b]pyridazin-3-yl)phthalazin-1(2H)-one<br>LCMS [M + 1]$^+$ = 307.0; $^1$H NMR (400 MHz, DMSO-d6) δ = 12.98 (s, 1H), 8.87 (s, 1H), 8.75 (dd, J = 1.2, 8.4 Hz, 1H), 8.71 (d, J = 1.2 Hz, 1H), 8.69 (br s, 3H), 8.42 (d, J = 8.4 Hz, 1H), 8.36 (d, J = 9.6 Hz, 1H), 7.58 (d, J = 9.6 Hz, 1H), 4.58-4.51 (m, 2H), 2.71 (s, 3H). |

TABLE 4-continued

| Example | CM | PM | Compound Name and Characterization |
|---|---|---|---|
| 4-18 | 4A | 4-1 | 4-(aminomethyl)-6-(6-chloroimidazo[1,2-b]pyridazin-3-yl)phthalazin-1(2H)-one LCMS [M + 1]$^+$ = 327.0; $^1$H NMR (400 MHz, DMSO-d6) δ = 12.97 (s, 1H), 8.74 (s, 1H), 8.71-8.61 (m, 4H), 8.59 (d, J = 1.2 Hz, 1H), 8.42 (m, 2H), 7.58 (d, J = 9.6 Hz, 1H), 4.59-4.47 (s, 2H). |
| 4-19 | 4A | 4-2 | 4-(aminomethyl)-6-(7-methoxyimidazo[1,2-a]pyridin-3-yl)phthalazin-1(2H)-one LCMS [M + 1]$^+$ = 322.0; $^1$H NMR (400 MHz, DMSO-d6) δ = 12.57 (br s, 1H), 8.72 (d, J = 7.6 Hz, 1H), 8.39 (d, J = 8.4 Hz, 1H), 8.34 (d, J = 1.2 Hz, 1H), 8.14 (dd, J = 1.6, 8.4 Hz, 1H), 7.95 (s, 1H), 7.16 (d, J = 2.4 Hz, 1H), 6.81 (dd, J = 2.8, 7.6 Hz, 1H), 4.14 (s, 2H), 3.95 (s, 3H) |
| 4-20 | 4A | 4-2 | 4-(aminomethyl)-6-(6-methylimidazo[1,2-a]pyridin-3-yl)phthalazin-1(2H)-one LCMS [M + 1]$^+$ = 306.2; $^1$H NMR (400 MHz, DMSO-d6) δ = 12.52 (br s, 1H), 8.60 (s, 1H), 8.43-8.31 (m, 2H), 8.21-8.06 (m, 1H), 8.03-7.89 (m, 1H), 7.64 (d, J = 9.2 Hz, 1H), 7.26 (dd, J = 1.2, 9.2 Hz, 1H), 4.09 (s, 2H), 2.36-2.33 (s, 3H) |
| 4-21 | 4A | 4-1 | 4-(aminomethyl)-6-(6-fluoroimidazo[1,2-a]pyridin-3-yl)phthalazin-1(2H)-one LCMS [M + 1]$^+$ = 310.0; $^1$H NMR (400 MHz, DMSO-d6) δ = 13.04-13.01 (s, 1H), 9.20-9.16 (m, 1H), 8.45 (br d, J = 0.8 Hz, 3H), 8.43 (d, J = 8.4 Hz, 1H), 8.29 (m, 2H), 8.22 (dd, J = 1.6, 8.4 Hz, 1H), 7.96-7.89 (m, 1H), 7.74-7.64 (m, 1H), 4.61-4.55 (m, 2H) |
| 4-22 | 4A | 4-1 | 4-(aminomethyl)-6-(8-fluoroimidazo[1,2-a]pyridin-3-yl)phthalazin-1(2H)-one LCMS [M + 1]$^+$ = 310.0; $^1$H NMR (400 MHz, DMSO-d6) δ = 13.03 (s, 1H), 8.81 (d, J = 6.8 Hz, 1H), 8.58 (br s, 3H), 8.44 (d, J = 8.4 Hz, 1H), 8.30 (s, 1H), 8.27-8.19 (m, 2H), 7.44 (dd, J = 7.6, 10.8 Hz, 1H), 7.11 (dt, J = 5.2, 7.2 Hz, 1H), 4.76-4.34 (m, 2H) |
| 4-23 | 4A | 4-1 | 4-(aminomethyl)-6-(2-methylimidazo[1,2-a]pyrazin-3-yl)phthalazin-1(2H)-one LCMS [M + 1]$^+$ = 307.0; $^1$H NMR (400 MHz, DMSO-d6) δ = 13.08 (s, 1H), 9.41-9.25 (m, 1H), 8.71 (s, 3H), 8.48 (d, J = 8.4 Hz, 1H), 8.33 (br s, 1H), 8.14 (dd, J = 1.2, 8.2 Hz, 1H), 8.12-8.04 (m, 1H), 4.52 (br d, J = 5.6 Hz, 2H), 2.59 (s, 3H) |

TABLE 4-continued

| Example | Structure | CM | PM | Compound Name and Characterization |
|---|---|---|---|---|
| 4-24 | 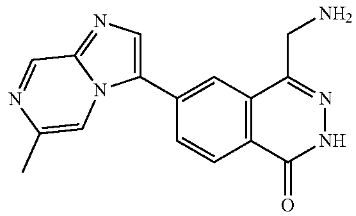 [SMILES: Cc1cn2c(-c3ccc4c(=O)[nH]nc(CN)c4c3)cnc2cn1] | 4A | 4-1 | 4-(aminomethyl)-6-(6-methylimidazo[1,2-a]pyrazin-3-yl)phthalazin-1(2H)-one<br>LCMS [M + 1]$^+$ = 307.1 $^1$H NMR (400 MHz, DMSO-d6) δ = 13.05 (s, 1H), 9.25 (d, J = 0.8 Hz, 1H), 8.89 (s, 1H), 8.61 (br s, 3H), 8.45 (d, J = 8.4 Hz, 1H), 8.40 (s, 1H), 8.36 (s, 1H), 8.27 (dd, J = 1.2, 8.4 Hz, 1H), 4.65-4.52 (d, J = 5.6 Hz, 2H), 2.54 (s, 3H) |
| 4-25 | 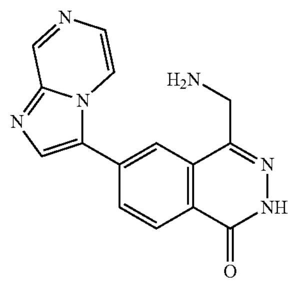 [SMILES: NCc1n[nH]c(=O)c2ccc(-c3cnc4cnccn34)cc12] | 4A | 4-2 | 4-(aminomethyl)-6-(imidazo[1,2-a]pyrazin-3-yl)phthalazin-1(2H)-one<br>LCMS [M + 1]$^+$ = 293.2; $^1$H NMR (400 MHz, DMSO-d6) δ = 9.17 (d, J = 1.6 Hz, 1H), 8.71 (dd, J = 1.6, 4.8 Hz, 1H), 8.45-8.39 (m, 2H), 8.24 (s, 1H), 8.16 (dd, J = 1.6, 8.4 Hz, 1H), 8.00 (d, J = 4.8 Hz, 1H), 4.12 (s, 2H) |
| 4-26 | 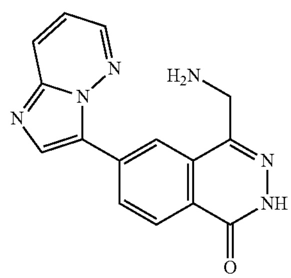 [SMILES: NCc1n[nH]c(=O)c2ccc(-c3cnc4cccnn34)cc12] | 4A | 4-1 | 4-(aminomethyl)-6-(imidazo[1,2-b]pyridazin-3-yl)phthalazin-1(2H)-one<br>LCMS [M + 1]$^+$ = 293.2; $^1$H NMR (400 MHz, DMSO-d6) δ = 12.98 (s, 1H), 8.87 (dd, J = 1.6, 4.4 Hz, 1H), 8.93 (s, 1H), 8.79 (dd, J = 1.6, 8.4 Hz, 1H), 8.64 (br d, J = 1.2 Hz, 4H), 8.47-8.39 (m, 2H), 7.57 (dd, J = 4.4, 9.2 Hz, 1H), 4.56 (br d, J = 5.6 Hz, 2H) |
| 4-27 | 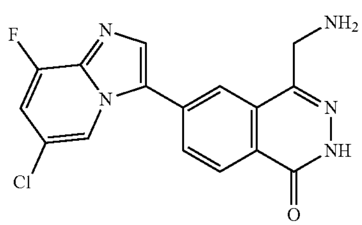 [SMILES: NCc1n[nH]c(=O)c2ccc(-c3cnc4c(F)cc(Cl)cn34)cc12] | 4A | 4-1 | 4-(aminomethyl)-6-(6-chloro-8-fluoroimidazo[1,2-a]pyridin-3-yl)phthalazin-1(2H)-one<br>LCMS [M + 1]$^+$ = 344.0; $^1$H NMR (400 MHz, DMSO-d6) δ = 13.03 (s, 1H), 8.93 (d, J = 1.6 Hz, 1H), 8.55 (br s, 3H), 8.43 (d, J = 8.4 Hz, 1H), 8.31 (d, J = 1.2 Hz, 1H), 8.22 (dd, J = 1.6, 8.4 Hz, 1H), 8.17 (s, 1H), 7.65 (dd, J = 1.6, 10.8 Hz, 1H), 4.63-4.42 (d, J = 5.6 Hz, 2H) |
| 4-28 | 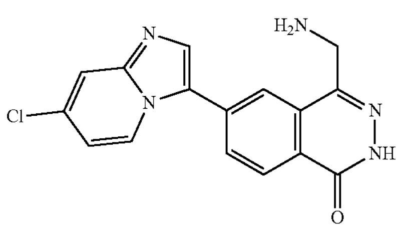 [SMILES: NCc1n[nH]c(=O)c2ccc(-c3cnc4cc(Cl)ccn34)cc12] | 4A | 4-1 | 4-(aminomethyl)-6-(7-chloroimidazo[1,2-a]pyridin-3-yl)phthalazin-1(2H)-one<br>LCMS [M + 1]$^+$ = 326.0<br>$^1$H NMR (400 MHz, DMSO-d6) δ = 13.02 (s, 1H), 8.92 (d, J = 7.2 Hz, 1H), 8.43-8.41 (d, J = 8.4 Hz,1H), 8.40 (s, 3H), 8.23 (s, 1H), 8.23-8.20 (dd, J = 1.2, 8.4 Hz, 1H), 8.11 (s, 1H), 7.94 (d, J = 1.6 Hz, 1H), 7.10 (dd, J = 2.0, 7.2 Hz, 1H), 4.58 (br d, J = 2.0 Hz, 2H) |
| 4-29 | 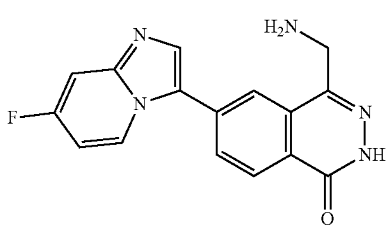 [SMILES: NCc1n[nH]c(=O)c2ccc(-c3cnc4cc(F)ccn34)cc12] | 4A | 4-1 | 4-(aminomethyl)-6-(7-fluoroimidazo[1,2-a]pyridin-3-yl)phthalazin-1(2H)-one<br>LCMS [M + 1]$^+$ = 310.0<br>$^1$H NMR (400 MHz, DMSO-d6) δ = 12.80 (br s, 1H), 8.92 (br t, J = 6.4 Hz, 1H), 8.53 (m, 1H), 8.50-8.43 (brs, 3H), 8.25 (s, 1H), 8.22-8.17 (m, 1H), 8.15 (s, 1H), 7.65-7.60 (m, 1H), 7.15 (br t, J = 7.3 Hz, 1H), 4.53 (br s, 2H) |

TABLE 4-continued

| Example | Structure | CM | PM | Compound Name and Characterization |
|---|---|---|---|---|
| 4-30 | 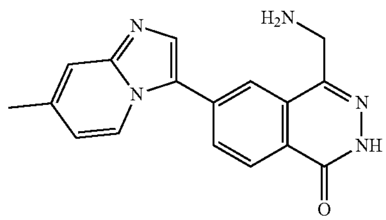 [SMILES: Cc1ccn2c(-c3ccc4c(=O)[nH]nc(CN)c4c3)cnc2c1] | 4A | 4-1 | 4-(aminomethyl)-6-(7-methylimidazo[1,2-a]pyridin-3-yl)phthalazin-1(2H)-one<br>LCMS [M + 1]$^+$ = 306.1; $^1$H NMR (400 MHz, DMSO-d6) δ = 12.59-12.48 (s, 1H), 8.71 (d, J = 7.2 Hz, 1H), 8.34 (d, J = 8.4 Hz, 1H), 8.31 (d, J = 1.2 Hz, 1H), 8.11 (dd, J = 1.6, 8.4 Hz, 1H), 7.97 (s, 1H), 7.50 (s, 1H), 6.90 (dd, J = 1.6, 7.2 Hz, 1H), 4.11-4.05 (s, 2H), 2.41 (s, 3H) |
| 4-31 | 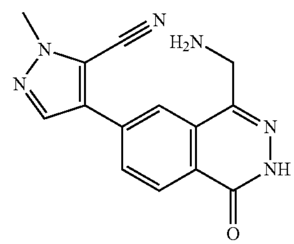 [SMILES: Cn1ncc(-c2ccc3c(=O)[nH]nc(CN)c3c2)c1C#N] | 4A | 4-1 | 4-(4-(aminomethyl)-1-oxo-1,2-dihydrophthalazin-6-yl)-1-methyl-1H-pyrazole-5-carbonitrile<br>LCMS [M + 1]$^+$ = 281.1; $^1$H NMR (400 MHz, DMSO-d6) δ = 13.00 (s, 1H), 8.50 (br s, 3H), 8.45 (s, 1H), 8.43-8.40 (d, J = 8.8 Hz, 1H), 8.23 (s, 1H), 8.22-8.20 (dd, J = 1.6, 8.8 Hz 1H), 4.51 (br d, J = 5.6 Hz, 2H), 4.12 (s, 3H) |
| 4-32 | 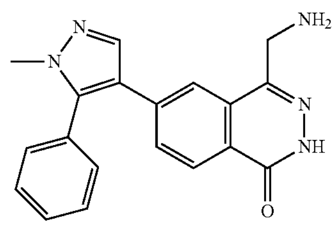 [SMILES: Cn1ncc(-c2ccc3c(=O)[nH]nc(CN)c3c2)c1-c1ccccc1] | 4A | 4-1 | 4-(aminomethyl)-6-(1-methyl-5-phenyl-1H-pyrazol-4-yl)phthalazin-1(2H)-one<br>LCMS [M + 1]$^+$ = 332.0; $^1$H NMR (400 MHz, DMSO-d6) δ = 12.82 (s, 1H), 8.45 (br s, 3H), 8.386 (s, 1H), 8.12 (d, J = 8.8 Hz, 1H), 7.7 (s, 1H), 7.6 (m, 3H), 7.501 (s, 1H), 7.437 (m, 2H), 4.23 (bs, 2H), 3.74 (s, 3H) |
| 4-33 | 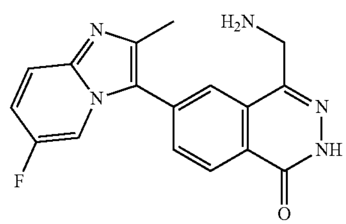 [SMILES: Cc1nc2ccc(F)cn2c1-c1ccc2c(=O)[nH]nc(CN)c2c1] | 4A | 4-2 | 4-(aminomethyl)-6-(6-fluoro-2-methylimidazo[1,2-a]pyridin-3-yl)phthalazin-1(2H)-one<br>LCMS [M + 1]$^+$ = 324.0; $^1$H NMR (400 MHz, DMSO-d6) δ = 11.70-11.56 (s, 1H), 7.70 (dd, J = 2.0, 4.8 Hz, 1H), 7.46 (d, J = 8.4 Hz, 1H), 7.35 (d, J = 1.2 Hz, 1H), 7.08 (dd, J = 1.6, 8.4 Hz, 1H), 6.73 (dd, J = 5.2, 9.8 Hz, 1H), 6.51-6.43 (m, 1H), 3.12 (s, 2H), 1.52 (s, 3H) |
| 4-34 | 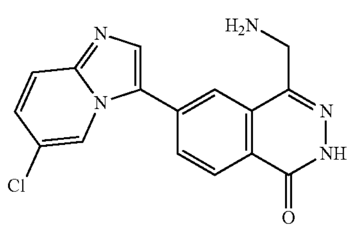 [SMILES: NCc1n[nH]c(=O)c2ccc(-c3cnc4ccc(Cl)cn34)cc12] | 4A | 4-4 | 4-(aminomethyl)-6-(6-chloroimidazo[1,2-a]pyridin-3-yl)phthalazin-1(2H)-one<br>LCMS [M + 1]$^+$ = 326.1; $^1$H NMR (400 MHz, DMSO-d6) δ = 13.01 (s, 1H), 9.04 (d, J = 1.2 Hz, 1H), 8.45-8.42 (m, 1H), 8.42-8.35 (s, 3H), 8.30-8.21 (m, 2H), 8.16-8.13 (m, 1H), 7.82 (d, J = 9.2 Hz, 1H), 7.50 (dd, J = 2.0, 9.6 Hz, 1H), 4.59 (q, J = 5.2 Hz, 2H) |
| 4-35 | 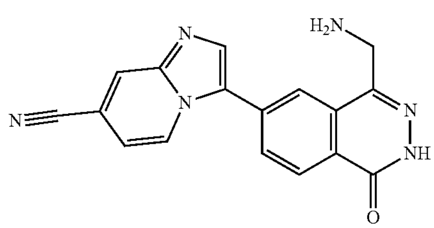 [SMILES: N#Cc1ccn2c(-c3ccc4c(=O)[nH]nc(CN)c4c3)cnc2c1] | 4B | 4-1 | 3-(4-(aminomethyl)-1-oxo-1,2-dihydrophthalazin-6-yl)imidazo[1,2-a]pyridine-7-carbonitrile<br>LCMS [M + 1]$^+$ = 317.0; $^1$H NMR (400 MHz, DMSO-d6) δ = 13.05 (s, 1H), 9.13 (d, J = 6.8 Hz, 1H), 8.68 (br s, 3H), 8.59 (s, 1H), 8.49 (s, 1H), 8.43 (d, J = 8.4 Hz, 1H), 8.35 (d, J = 1.2 Hz, 1H), 8.23 (dd, J = 1.2, 8.4 Hz, 1H), 7.45 (dd, J = 1.6, 7.2 Hz, 1H), 4.55 (br d, J = 5.6 Hz, 2H), 2.54 (s, 1H) |

TABLE 4-continued

| Example | Structure | CM | PM | Compound Name and Characterization |
|---|---|---|---|---|
| 4-36 | 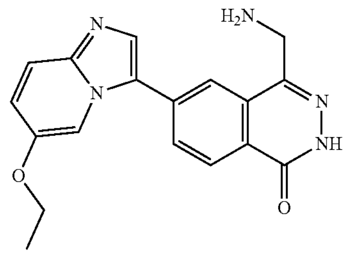 [SMILES: CCOc1ccc2ncc(-c3ccc4c(=O)[nH]nc(CN)c4c3)n2c1] | 4A | 4-2 | 4-(aminomethyl)-6-(6-ethoxyimidazo[1,2-a]pyridin-3-yl)phthalazin-1(2H)-one<br>LCMS [M + 1]$^+$ = 336.1; $^1$H NMR (400 MHz, DMSO-d6) δ = 12.84 (s, 1H), 8.40 (d, J = 8.4 Hz, 1H), 8.32 (s, 1H), 8.28 (d, J = 2.4 Hz, 1H), 8.21 (d, J = 8.2 Hz, 1H), 7.99 (s, 1H), 7.67 (d, J = 9.6 Hz, 1H), 7.20 (dd, J = 2.4, 9.6 Hz, 1H), 4.42 (br s, 2H), 4.09 (q, J = 7.2 Hz, 2H), 1.37 (t, J = 7.2 Hz, 3H) |
| 4-37 | 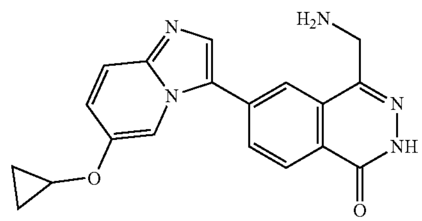 [SMILES: NCc1n[nH]c(=O)c2ccc(-c3cnc4ccc(OC5CC5)cn34)cc12] | 4A | 4-5 | 4-(aminomethyl)-6-(6-cyclopropoxyimidazo[1,2-a]pyridin-3-yl)phthalazin-1(2H)-one<br>LCMS [M + 1]$^+$ = 348.1; $^1$H NMR (400 MHz, DMSO-d6) δ = 12.81 (s, 1H), 8.51 (d, J = 2.0 Hz, 1H), 8.41 (d, J = 8.4 Hz, 1H), 8.35 (d, J = 1.2 Hz, 1H), 8.22 (dd, J = 1.6, 8.4 Hz, 1H), 8.03 (s, 1H), 7.68 (d, J = 9.6 Hz, 1H), 7.20 (dd, J = 2.0, 9.6 Hz, 1H), 6.87-6.32 (br s, 2H), 4.37 (d, J = 5.6 Hz, 1H), 4.00 (tt, J = 3.2, 5.6 Hz, 1H), 0.83-0.74 (m, 4H). |
| 4-38 | 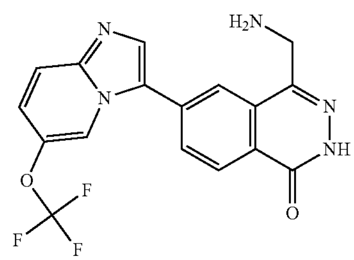 [SMILES: NCc1n[nH]c(=O)c2ccc(-c3cnc4ccc(OC(F)(F)F)cn34)cc12] | 4A | 4-1 | 4-(aminomethyl)-6-(6-(trifluoromethoxy)imidazo[1,2-a]pyridin-3-yl)phthalazin-1(2H)-one<br>LCMS [M + 1]$^+$ = 376.0; $^1$H NMR (400 MHz, DMSO-d6) δ = 13.05 (s, 1H), 9.34 (s, 1H), 8.66 (br s, 3H), 8.52 (s, 1H), 8.49-8.43 (dd, J = 2.0, 8.4 Hz 1H), 8.38 (s, 1H), 8.21 (d, J = 8.4 Hz, 1H), 8.09 (d, J = 9.6 Hz, 1H), 7.89 (d, J = 9.6 Hz, 1H), 4.52 (br d, J = 5.2 Hz, 2H). |
| 4-39 | 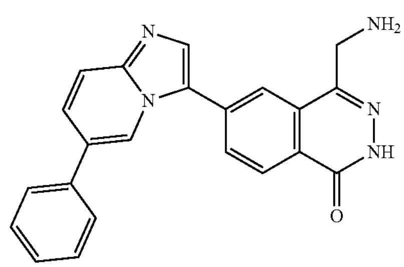 [SMILES: NCc1n[nH]c(=O)c2ccc(-c3cnc4ccc(-c5ccccc5)cn34)cc12] | 4A | 4-5 | 4-(aminomethyl)-6-(6-phenylimidazo[1,2-a]pyridin-3-yl)phthalazin-1(2H)-one<br>LCMS [M + 1]$^+$ = 368.1; $^1$H NMR (400 MHz, DMSO-d6) δ = 13.05 (s, 1H), 9.01 (s, 1H), 8.61-8.38 (m, 5H), 8.36-8.29 (m, 2H), 8.02 (m, 2H), 7.84-7.77 (m, 2H), 7.57-7.49 (m, 2H), 7.48-7.42 (m, 1H), 4.62-4.55 (s, 2H) |
| 4-40 | 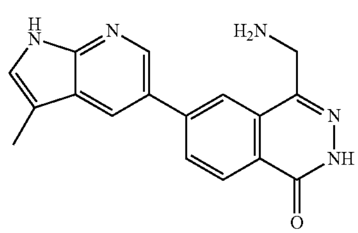 [SMILES: Cc1c[nH]c2ncc(-c3ccc4c(=O)[nH]nc(CN)c4c3)cc12] | 4A | 4-1 | 4-(aminomethyl)-6-(3-methyl-1H-pyrrolo[2,3-b]pyridin-5-yl)phthalazin-1(2H)-one<br>LCMS [M + 1]$^+$ = 306.1; $^1$H NMR (400 MHz, DMSO-d6) δ = 12.93 (s, 1H), 11.69 (br s, 1H), 8.82 (d, J = 2.0 Hz, 1H), 8.57 (br s, 4H), 8.39-8.37 (m, 1H), 8.36-8.34 (s, 1H), 8.29 (s, 1H), 7.37 (s, 1H), 4.65-4.59 (d, J = 5.6 Hz, 2H), 2.36 (s, 3H) |
| 4-41 | 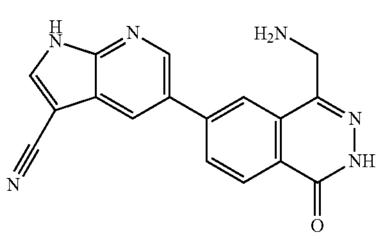 [SMILES: N#Cc1c[nH]c2ncc(-c3ccc4c(=O)[nH]nc(CN)c4c3)cc12] | 4A | 4-1 | 5-(4-(aminomethyl)-1-oxo-1,2-dihydrophthalazin-6-yl)-1H-pyrrolo[2,3-b]pyridine-3-carbonitrile<br>LCMS [M + 1]$^+$ = 317.1<br>$^1$H NMR (400 MHz, DMSO-d6) δ = 13.12-13.06 (s, 1H), 12.97 (s, 1H), 8.97 (d, J = 2.0 Hz, 1H), 8.71 (d, J = 2.0 Hz, 1H), 8.57 (d, J = 2.8 Hz, 1H), 8.49 (br s, 3H), 8.39 (m, 2H), 8.34 (s, 1H), 4.71-4.59 (d, J = 5.6 Hz, 2H) |

TABLE 4-continued

| Example | Structure | CM | PM | Compound Name and Characterization |
|---|---|---|---|---|
| 4-42 | 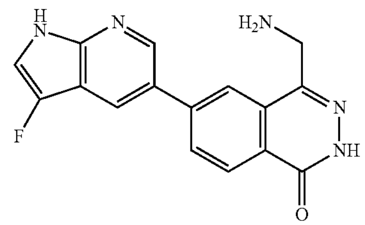 [SMILES: NCc1n[nH]c(=O)c2ccc(-c3cnc4[nH]cc(F)c4c3)cc12] | 4A | 4-4 | 4-(aminomethyl)-6-(3-fluoro-1H-pyrrolo[2,3-b]pyridin-5-yl)phthalazin-1(2H)-one<br>LCMS [M + 1]$^+$ = 310.0; $^1$H NMR (400 MHz, DMSO-d6) δ = 12.95 (s, 1H), 11.75-11.72 (s, 1H), 8.85 (d, J = 2.0 Hz, 1H), 8.59 (d, J = 2.0 Hz, 1H), 8.39 (br s, 3H), 8.37 (m, 1H), 8.36 (m, 1H), 8.29 (s, 1H), 7.59 (t, J = 2.4 Hz, 1H), 4.63 (br d, J = 5.6 Hz, 2H) |
| 4-43 | 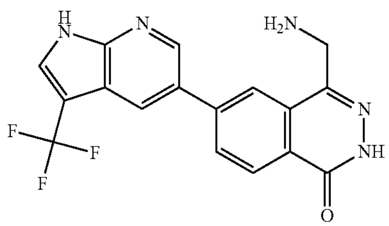 [SMILES: NCc1n[nH]c(=O)c2ccc(-c3cnc4[nH]cc(C(F)(F)F)c4c3)cc12] | 4A | 4-1 | 4-(aminomethyl)-6-(3-(trifluoromethyl)-1H-pyrrolo[2,3-b]pyridin-5-yl)phthalazin-1(2H)-one<br>LCMS [M + 1]$^+$ = 360.0; $^1$H NMR (400 MHz, DMSO-d6) δ = 12.97 (s, 1H), 12.77 (s, 1H), 8.94 (d, J = 2.0 Hz, 1H), 8.52 (s, 1H), 8.47 (s, 3H), 8.40-8.36 (m, 1H), 8.36-8.31 (m, 1H), 8.28 (m, 2H), 4.65 (d, J = 5.6 Hz, 2H) |
| 4-44 | 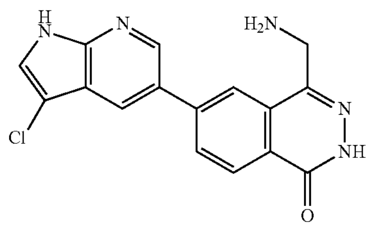 [SMILES: NCc1n[nH]c(=O)c2ccc(-c3cnc4[nH]cc(Cl)c4c3)cc12] | 4A | 4-2 | 4-(aminomethyl)-6-(3-chloro-1H-pyrrolo[2,3-b]pyridin-5-yl)phthalazin-1(2H)-one<br>LCMS [M + 1]$^+$ = 326.0; $^1$H NMR (400 MHz, DMSO-d6) δ = 12.95 (s, 1H), 12.23 (s, 1H), 8.88 (d, J = 2.4 Hz, 1H), 8.47 (d, J = 1.6 Hz, 1H), 8.46-8.38 (s, 3H), 8.38-8.34 (m, 2H), 8.30 (s, 1H), 7.81 (d, J = 2.8 Hz, 1H), 4.65 (br d, J = 4.0 Hz, 2H). |
| 4-45 | 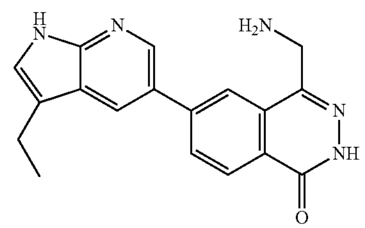 [SMILES: CCc1c[nH]c2ncc(-c3ccc4c(=O)[nH]nc(CN)c4c3)cc12] | 4A | 4-5 | 4-(aminomethyl)-6-(3-ethyl-1H-pyrrolo[2,3-b]pyridin-5-yl)phthalazin-1(2H)-one<br>LCMS [M + 1]$^+$ = 320.1; $^1$H NMR (400 MHz, DMSO-d6) δ = 12.95-12.88 (s, 1H), 11.59-11.49 (s, 1H), 8.76 (d, J = 2.0 Hz, 1H), 8.46 (d, J = 2.0 Hz, 1H), 8.43-8.36 (br s, 3H), 8.35-8.30 (m, 2H), 8.23 (s, 1H), 7.33 (s, 1H), 4.71-4.57 (m, 2H), 2.79 (q, J = 7.2 Hz, 2H), 1.34-1.27 (q, J = 7.6 Hz, 3H) |
| 4-46 | 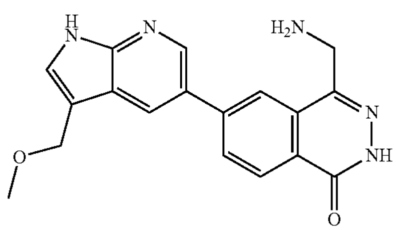 | 4A | 4-2 | 4-(aminomethyl)-6-(3-(methoxymethyl)-1H-pyrrolo[2,3-b]pyridin-5-yl)phthalazin-1(2H)-one<br>LCMS [M + 1]$^+$ = 366.1; $^1$H NMR (400 MHz, DMSO-d6) δ = 12.75-12.60 (s, 1H), 11.86-11.78 (s, 1H), 8.77 (d, J = 2.4 Hz, 1H), 8.46 (d, J = 2.4 Hz, 1H), 8.38-8.34 (m, 1H), 8.31 (d, J = 1.2 Hz, 1H), 8.27-8.23 (m, 1H), 7.59 (d, J = 2.0 Hz, 1H), 4.65 (s, 2H), 4.34 (s, 2H), 3.28 (s, 3H) |
| 4-47 | 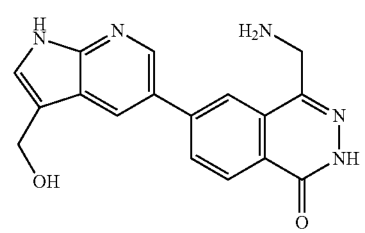 [SMILES: NCc1n[nH]c(=O)c2ccc(-c3cnc4[nH]cc(CO)c4c3)cc12] | 4A | 4-5 | 4-(aminomethyl)-6-(3-(hydroxymethyl)-1H-pyrrolo[2,3-b]pyridin-5-yl)phthalazin-1(2H)-one<br>LCMS [M + 1]$^+$ = 322.3; $^1$H NMR (400 MHz, DMSO-d6) δ = 8.68 (d, J = 2.0 Hz, 1H), 8.44 (d, J = 2.4 Hz, 1H), 8.36 (d, J = 8.4 Hz, 1H), 8.32 (d, J = 1.6 Hz, 1H), 8.17 (dd, J = 1.6, 8.4 Hz, 1H), 7.41 (s, 1H), 4.75 (s, 2H), 4.14 (s, 2H) |
| 4-48 | 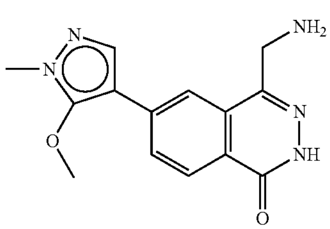 | 4A | 4-2 | 4-(aminomethyl)-6-(5-methoxy-1-methyl-1H-pyrazol-4-yl)phthalazin-1(2H)-one<br>LCMS [M + 1]$^+$ = 286.1; NMR (400 MHz, DMSO-d6) δ = 12.41 (br s, 1H), 8.23 (d, J = 8.4 Hz, 1H), 8.18 (d, J = 1.2 Hz, 1H), 8.03 (dd, J = 1.6, 8.4 Hz, 1H), 8.00 (s, 1H), 4.09-3.97 (s, 2H), 3.90 (s, 3H), 3.73 (s, 3H). |

TABLE 4-continued

| Example | Structure | CM | PM | Compound Name and Characterization |
|---|---|---|---|---|
| 4-49 | 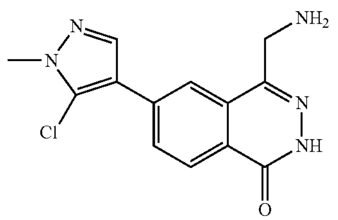 [SMILES: Cn1ncc(-c2ccc3c(=O)[nH]nc(CN)c3c2)c1Cl] | 4A | 4-1 | 4-(aminomethyl)-6-(5-chloro-1-methyl-1H-pyrazol-4-yl)phthalazin-1(2H)-one<br>LCMS [M + 1]$^+$ = 290.0; $^1$H NMR (400 MHz, DMSO-d6) δ = 12.92 (s, 1H), 8.53 (br s, 3H), 8.34 (d, J = 8.4 Hz, 1H), 8.26 (s, 1H), 8.20 (dd, J = 1.6, 8.4 Hz, 1H), 8.10 (d, J = 1.2 Hz, 1H), 4.52 (br d, J = 5.6 Hz, 2H), 3.91 (s, 3H) |
| 4-50 | 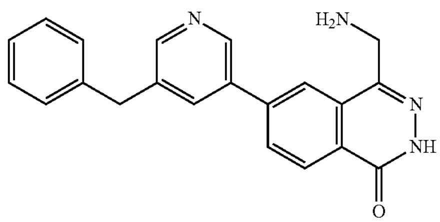 | 4A | 4-1 | 4-(aminomethyl)-6-(5-benzylpyridin-3-yl)phthalazin-1(2H)-one<br>LCMS [M + 1]$^+$ = 343.1; $^1$H NMR (400 MHz, DMSO-d6) δ = 13.01 (s, 1H), 9.05 (d, J = 2.0 Hz, 1H), 8.67 (d, J = 1.6 Hz, 1H), 8.48 (br s, 3H), 8.41-8.37 (m, 1H), 8.35 (t, J = 2.0 Hz, 1H), 8.29-8.20 (m, 2H), 7.37-7.27 (m, 4H), 7.23-7.18 (m, 1H), 4.60 (br d, J = 5.6 Hz, 2H), 4.12 (s, 2H) |
| 4-51 | 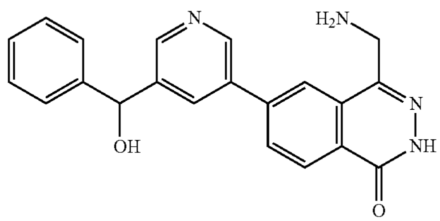 [SMILES: NCc1n[nH]c(=O)c2ccc(-c3cncc(C(O)c4ccccc4)c3)cc12] | 4A | 4-5 | 4-(aminomethyl)-6-(5-(hydroxy(phenyl)methyl)pyridin-3-yl)phthalazin-1(2H)-one<br>LCMS [M + 1]$^+$ = 359.1; $^1$H NMR (400 MHz, DMSO-d6) δ = 12.7 (br s, 1H), 8.96 (d, J = 2.4 Hz, 1H), 8.67 (d, J = 2.0 Hz, 1H), 8.36 (d, J = 8.4 Hz, 1H), 8.29 (d, J = 1.2 Hz, 1H), 8.24 (s, 1H), 8.17 (dd, J = 1.6, 8.4 Hz, 1H), 7.48 (d, J = 7.2 Hz, 2H), 7.38-7.30 (m, 2H), 7.27-7.16 (m, 1H), 6.22 (br d, J = 3.6 Hz, 1H), 5.91 (br s, 1H), 4.27 (br s, 2H) |
| 4-52 | 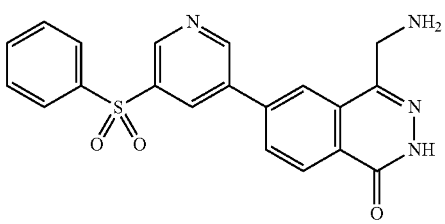 [SMILES: NCc1n[nH]c(=O)c2ccc(-c3cncc(S(=O)(=O)c4ccccc4)c3)cc12] | 4A | 4-6 | 4-(aminomethyl)-6-(5-(phenylsulfonyl)pyridin-3-yl)phthalazin-1(2H)-one<br>LCMS [M + 1]$^+$ = 393.1; $^1$H NMR (400 MHz, DMSO-d6) δ = 13.02 (s, 1H), 9.43 (d, J = 1.2 Hz, 1H), 9.24 (d, J = 1.2 Hz, 1H), 8.87 (s, 1H), 8.63 (br s, 3H), 8.42-8.32 (m, 3H), 8.15 (br d, J = 7.6 Hz, 2H), 7.74 (br d, J = 7.2 Hz, 1H), 7.70-7.64 (m, 2H), 4.60 (br d, J = 5.2 Hz, 2H). |
| 4-53 | 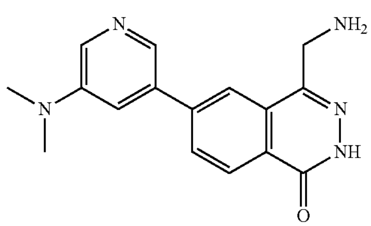 [SMILES: CN(C)c1cncc(-c2ccc3c(=O)[nH]nc(CN)c3c2)c1] | 4A | 4-1 | 4-(aminomethyl)-6-(5-(dimethylamino)pyridin-3-yl)phthalazin-1(2H)-one<br>LCMS [M + 1]$^+$ = 296.0; $^1$H NMR (400 MHz, DMSO-d6) δ = 13.06 (s, 1H), 8.70 (s, 1H), 8.68 (s, 1H), 8.46-8.35 (m, 3H), 8.26 (d, J = 2.4 Hz, 1H), 8.09 (s, 1H), 4.60 (br d, J = 5.6 Hz, 2H), 3.17 (s, 6H). |
| 4-54 | 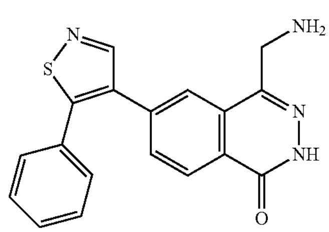 [SMILES: NCc1n[nH]c(=O)c2ccc(-c3cnsc3-c3ccccc3)cc12] | 4A | 4-6 | 4-(aminomethyl)-6-(5-phenylisothiazol-4-yl)phthalazin-1(2H)-one<br>LCMS [M + 1]$^+$ = 335.0; $^1$H NMR (400 MHz, DMSO-d6) δ = 12.96 (s, 1H), 8.96 (s, 1H), 8.45 (br s, 3H), 8.18 (d, J = 8.2 Hz, 1H), 8.10 (d, J = 1.2 Hz, 1H), 7.65 (dd, J = 1.6, 8.2 Hz, 1H), 7.49-7.41 (m, 3H), 7.37 (m, 1H), 7.35 (m, 1H), 4.38 (s, 2H) |
| 4-55 | 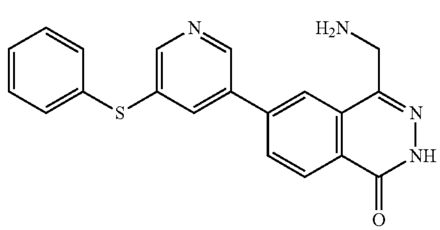 [SMILES: NCc1n[nH]c(=O)c2ccc(-c3cncc(Sc4ccccc4)c3)cc12] | 4A | 4-1 | 4-(aminomethyl)-6-(5-(phenylthio)pyridin-3-yl)phthalazin-1(2H)-one<br>LCMS [M + 1]$^+$ = 361.1; $^1$H NMR (400 MHz, DMSO-d6) δ = 13.01 (s, 1H), 9.12 (d, J = 2.0 Hz, 1H), 8.61 (br s, 3H), 8.55 (d, J = 2.0 Hz, 1H), 8.46 (t, J = 2.0 Hz, 1H), 8.39-8.35 (m, 1H), 8.32 (d, J = 1.2 Hz, 1H), 8.30-8.26 (m, 1H), 7.49-7.36 (m, 5H), 4.58 (br d, J = 5.6 Hz, 2H). |

TABLE 4-continued

| Example | Structure | CM | PM | Compound Name and Characterization |
|---|---|---|---|---|
| 4-56 | 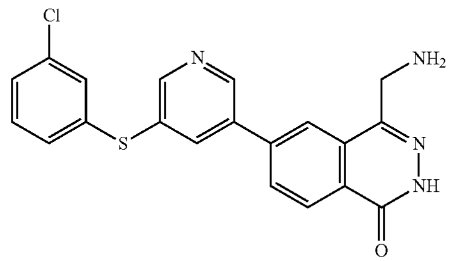 [SMILES: NCc1n[nH]c(=O)c2ccc(-c3cncc(Sc4cccc(Cl)c4)c3)cc12] | 4A | 4-4 | 4-(aminomethyl)-6-(5-((3-chlorophenyl)thio)pyridin-3-yl)phthalazin-1(2H)-one<br>LCMS [M + 1]$^+$ = 395.0; $^1$H NMR (400 MHz, DMSO-d6) δ = 13.01 (s, 1H), 9.15 (d, J = 2.0 Hz, 1H), 8.69 (d, J = 2.4 Hz, 1H), 8.50 (t, J = 2.0 Hz, 1H), 8.49-8.41 (m, 3H), 8.40-8.37 (m, 1H), 8.33-8.30 (m, 2H), 7.45-7.43 (m, 1H), 7.43-7.36 (m, 2H), 7.36-7.32 (m, 1H), 4.60 (br d, J = 5.6 Hz, 2H). |
| 4-57 | 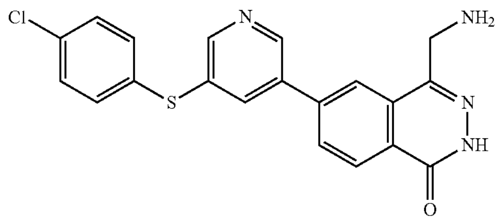 [SMILES: NCc1n[nH]c(=O)c2ccc(-c3cncc(Sc4ccc(Cl)cc4)c3)cc12] | 4A | 4-4 | 4-(aminomethyl)-6-(5-((4-chlorophenyl)thio)pyridin-3-yl)phthalazin-1(2H)-one<br>LCMS [M + 1]$^+$ = 395.0; $^1$H NMR (400 MHz, DMSO-d6) δ = 13.01 (s, 1H), 9.11 (d, J = 2.0 Hz, 1H), 8.62 (d, J = 2.4 Hz, 1H), 8.44 (t, J = 2.0 Hz, 1H), 8.43-8.33 (m, 4H), 8.31-8.28 (m, 2H), 7.50-7.46 (m, 2H), 7.45-7.42 (m, 2H), 4.60 (d, J = 5.2 Hz, 2H). |
| 4-58 | 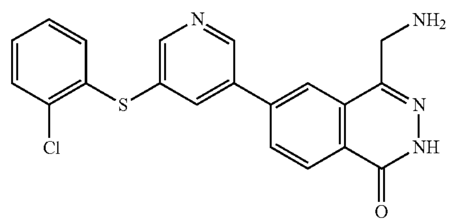 [SMILES: NCc1n[nH]c(=O)c2ccc(-c3cncc(Sc4ccccc4Cl)c3)cc12] | 4A | 4-5 | 4-(aminomethyl)-6-(5-((2-chlorophenyl)thio)pyridin-3-yl)phthalazin-1(2H)-one<br>LCMS [M + 1]$^+$ = 395.1; $^1$H NMR (400 MHz, DMSO-d6) δ = 13.06-12.98 (s, 1H), 9.19 (d, J = 2.4 Hz, 1H), 8.64 (d, J = 2.0 Hz, 1H), 8.52 (t, J = 2.0 Hz, 1H), 8.49-8.38 (s, 3H), 8.38-8.35 (m, 1H), 8.34-8.30 (m, 2H), 7.65-7.57 (m, 1H), 7.40-7.30 (m, 2H), 7.20-7.12 (m, 1H), 4.61 (d, J = 5.2 Hz, 2H) |
| 4-59 | 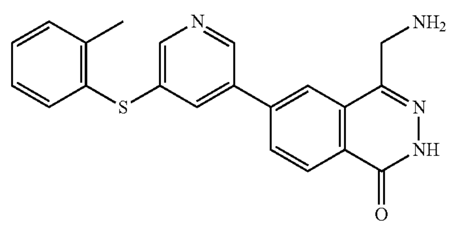 [SMILES: Cc1ccccc1Sc1cncc(-c2ccc3c(=O)[nH]nc(CN)c3c2)c1] | 4A | 4-4 | 4-(aminomethyl)-6-(5-(o-tolylthio)pyridin-3-yl)phthalazin-1(2H)-one<br>LCMS [M + 1]$^+$ = 375.1; $^1$H NMR (400 MHz, DMSO-d6) δ = 13.00 (s, 1H), 9.03 (d, J = 2.0 Hz, 1H), 8.51-8.38 (m, 3H), 8.38-8.31 (m, 2H), 8.27 (br s, 1H), 8.27-8.26 (m, 1H), 8.24 (br d, J = 1.6 Hz, 1H), 7.42-7.37 (m, 1H), 7.36-7.31 (m, 2H), 7.29-7.24 (m, 1H), 4.59 (br d, J = 5.2 Hz, 2H), 2.40 (s, 3H) |
| 4-60 | 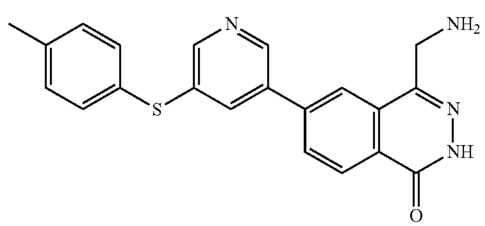 [SMILES: Cc1ccc(Sc2cncc(-c3ccc4c(=O)[nH]nc(CN)c4c3)c2)cc1] | 4A | 4-5 | 4-(aminomethyl)-6-(5-(p-tolylthio)pyridin-3-yl)phthalazin-1(2H)-one<br>LCMS [M + 1]$^+$ = 375.1; $^1$H NMR (400 MHz, DMSO-d6) δ = 8.91 (d, J = 2.0 Hz, 1H), 8.50 (d, J = 2.0 Hz, 1H), 8.35 (d, J = 8.8 Hz, 1H), 8.31 (s, 1H), 8.13-8.09 (m, 2H), 7.43 (d, J = 8.0 Hz, 2H), 7.27 (d, J = 8.0 Hz, 2H), 4.15-4.09 (m, 2H), 2.35 (s, 3H) |
| 4-61 | 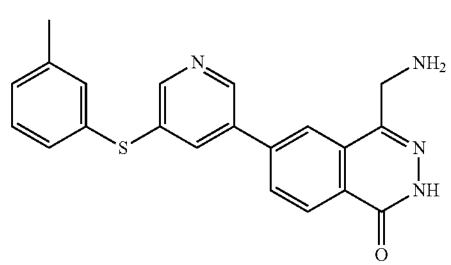 [SMILES: Cc1cccc(Sc2cncc(-c3ccc4c(=O)[nH]nc(CN)c4c3)c2)c1] | 4A | 4-2 | 4-(aminomethyl)-6-(5-(m-tolylthio)pyridin-3-yl)phthalazin-1(2H)-one<br>LCMS [M + 1]$^+$ = 375.1; $^1$H NMR (400 MHz, DMSO-d6) δ = 8.95 (s, 1H), 8.55 (d, J = 1.6 Hz, 1H), 8.36 (d, J = 8.4 Hz, 1H), 8.33 (s, 1H), 8.19 (s, 1H), 8.13 (br d, J = 8.4 Hz, 1H), 7.35 (s, 1H), 7.32 (d, J = 7.2 Hz, 1H), 7.30-7.26 (m, 1H), 7.21 (br d, J = 7.2 Hz, 1H), 4.19-4.05 (m, 2H), 2.33 (s, 3H) |

TABLE 4-continued

| Example | Structure | CM | PM | Compound Name and Characterization |
|---|---|---|---|---|
| 4-62 | 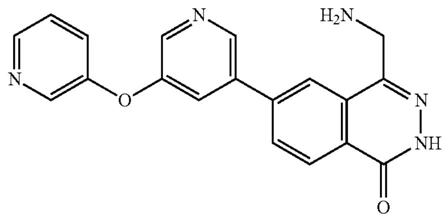 [SMILES: NCc1n[nH]c(=O)c2ccc(-c3cncc(Oc4cccnc4)c3)cc12] | 4A | 4-2 | 4-(aminomethyl)-6-(5-(pyridin-3-yloxy)pyridin-3-yl)phthalazin-1(2H)-one<br>LCMS [M + 1]$^+$ = 346.1; $^1$H NMR (400 MHz, DMSO-d6) δ = 8.91 (d, J = 1.6 Hz, 1H), 8.51 (d, J = 2.8 Hz, 1H), 8.49 (d, J = 2.4 Hz, 1H), 8.43 (dd, J = 1.2, 4.8 Hz, 1H), 8.38-8.33 (m, 2H), 8.16 (dd, J = 1.6, 8.4 Hz, 1H), 8.02 (t, J = 2.4 Hz, 1H), 7.59 (ddd, J = 1.2, 2.8, 8.4 Hz, 1H), 7.46 (dd, J = 4.4, 8.4 Hz, 1H), 4.12 (s, 2H) |
| 4-63 | 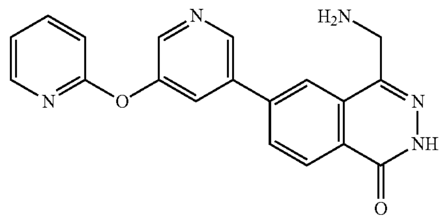 [SMILES: NCc1n[nH]c(=O)c2ccc(-c3cncc(Oc4ccccn4)c3)cc12] | 4A | 4-5 | 4-(aminomethyl)-6-(5-(pyridin-2-yloxy)pyridin-3-yl)phthalazin-1(2H)-one<br>LCMS [M + 1]$^+$ = 346.1; $^1$H NMR (400 MHz, DMSO-d6) δ = 13.00 (s, 1H), 9.03 (d, J = 1.6 Hz, 1H), 8.59 (d, J = 2.4 Hz, 1H), 8.38 (br d, J = 8.0 Hz, 4H), 8.35-8.29 (m, 2H), 8.26 (t, J = 2.0 Hz, 1H), 8.16 (dd, J = 1.2, 4.9 Hz, 1H), 7.94 (td, J = 2.0, 7.2, 8.4 Hz, 1H), 7.24-7.16 (m, 2H), 4.64-4.56 (d, J = 5.6 Hz, 2H). |
| 4-64 | 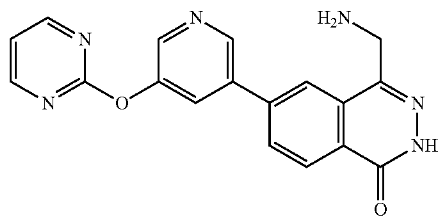 [SMILES: NCc1n[nH]c(=O)c2ccc(-c3cncc(Oc4ncccn4)c3)cc12] | 4B | 4-2 | 4-(aminomethyl)-6-(5-(pyrimidin-2-yloxy)pyridin-3-yl)phthalazin-1(2H)-one<br>LCMS [M + 1]$^+$ = 347.2; $^1$H NMR (400 MHz, DMSO-d6) δ = 12.55 (br s, 1H), 9.02 (d, J = 2.0 Hz, 1H), 8.70 (d, J = 4.8 Hz, 2H), 8.64 (d, J = 2.4 Hz, 1H), 8.40 (d, J = 1.6 Hz, 1H), 8.36-8.32 (m, 2H), 8.26-8.22 (m, 1H), 7.37-7.32 (m, 1H), 4.09 (s, 2H). |
| 4-65 | 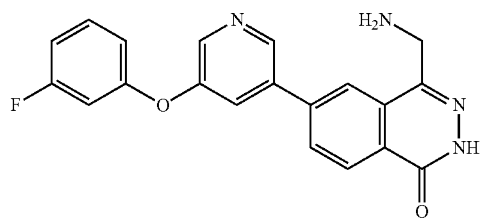 [SMILES: NCc1n[nH]c(=O)c2ccc(-c3cncc(Oc4cccc(F)c4)c3)cc12] | 4A | 4-1 | 4-(aminomethyl)-6-(5-(3-fluorophenoxy)pyridin-3-yl)phthalazin-1(2H)-one<br>LCMS [M + 1]$^+$ = 363.1; $^1$H NMR (400 MHz, DMSO-d6) δ = 13.00 (s, 1H), 9.09 (d, J = 2.0 Hz, 1H), 8.65 (br s, 3H), 8.55 (d, J = 2.8 Hz, 1H), 8.39-8.34 (m, 2H), 8.33-8.27 (m, 2H), 7.51-7.43 (m, 1H), 7.10-7.02 (m, 2H), 7.00-6.96 (d, J = 7.2 Hz, 1H), 4.61-4.54 (d, J = 6.0 Hz, 2H). |
| 4-66 | 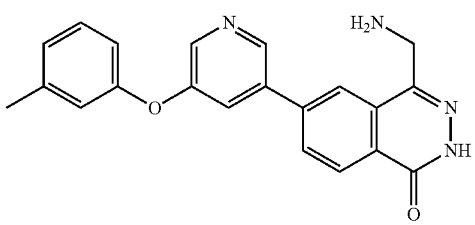 [SMILES: Cc1cccc(Oc2cncc(-c3ccc4c(=O)[nH]nc(CN)c4c3)c2)c1] | 4A | 4-1 | 4-(aminomethyl)-6-(5-(m-tolyloxy)pyridin-3-yl)phthalazin-1(2H)-one<br>LCMS [M + 1]$^+$ 359.1; $^1$H NMR (400 MHz, DMSO-d6) δ = 12.76 (s, 1H), 8.93 (d, J = 2.0 Hz, 1H), 8.54-8.31 (m, 5H), 8.31-8.26 (m, 1H), 8.24 (d, J = 8.4 Hz, 1H), 8.01 (t, J = 2.0 Hz, 1H), 7.32 (t, J = 8.0 Hz, 1H), 7.03 (d, J = 7.6 Hz, 1H), 6.97 (s, 1H), 6.93 (dd, J = 2.8, 8.0 Hz, 1H), 4.55 (s, 2H), 2.34 (s, 3H) |
| 4-67 | 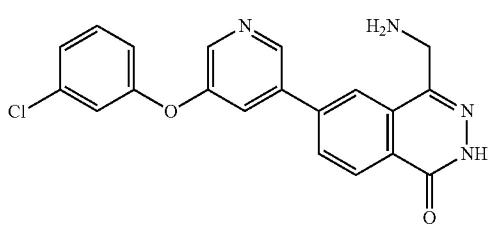 [SMILES: NCc1n[nH]c(=O)c2ccc(-c3cncc(Oc4cccc(Cl)c4)c3)cc12] | 4A | 4-1 | 4-(aminomethyl)-6-(5-(3-chlorophenoxy)pyridin-3-yl)phthalazin-1(2H)-one<br>LCMS [M + 1]$^+$ = 379.1; $^1$H NMR (400 MHz, DMSO-d6) δ = 13.00 (s, 1H), 9.03 (d, J = 2.0 Hz, 1H), 8.52 (d, J = 2.8 Hz, 1H), 8.44 (br s, 3H), 8.40-8.36 (d, J = 8.8 Hz, 1H), 8.33-8.28 (m, 2H), 8.18 (t, J = 2.4 Hz, 1H), 7.48-7.43 (t, J = 8.0 Hz, 1H), 7.28-7.24 (m, 1H), 7.22 (t, J = 2.0 Hz, 1H), 7.10 (td, J = 0.8, 8.4 Hz, 1H), 4.60 (br d, J = 5.6 Hz, 2H) |
| 4-68 | 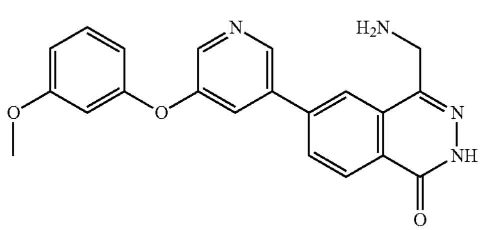 [SMILES: COc1cccc(Oc2cncc(-c3ccc4c(=O)[nH]nc(CN)c4c3)c2)c1] | 4A | 4-1 | 4-(aminomethyl)-6-(5-(3-methoxyphenoxy)pyridin-3-yl)phthalazin-1(2H)-one<br>LCMS [M + 1]$^+$ 375.1; $^1$H NMR (400 MHz, DMSO-d6) δ = 12.76 (s, 1H), 8.94 (d, J = 2.0 Hz, 1H), 8.48 (br s, 3H), 8.45 (d, J = 2.4 Hz, 1H), 8.40 (d, J = 8.0 Hz, 1H), 8.29 (d, J = 1.6 Hz, 1H), 8.24 (dd, J = 1.6, 8.4 Hz, 1H), 8.04 (t, J = 2.4 Hz, 1H), 7.34 (t, J = 8.0 Hz, 1H), 6.80 (dd, J = 2.0, 8.0 Hz, 1H), 6.72 (t, J = 2.4 Hz, 1H), 6.71-6.67 (dd, J = 2.0, 6.8 Hz, 1H), 4.55 (s, 2H), 3.79 (s, 3H) |

TABLE 4-continued

| Example | Structure | CM | PM | Compound Name and Characterization |
|---|---|---|---|---|
| 4-69 | 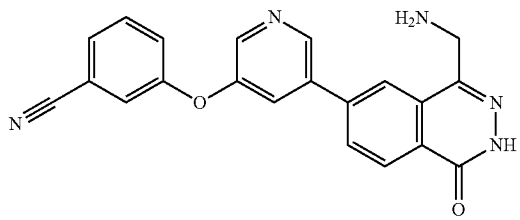 [SMILES: N#Cc1cccc(Oc2cncc(-c3ccc4c(=O)[nH]nc(CN)c4c3)c2)c1] | 4A | 4-1 | 3-((5-(4-(aminomethyl)-1-oxo-1,2-dihydrophthalazin-6-yl)pyridin-3-yl)oxy)benzonitrile<br>LCMS [M + 1]$^+$ = 370.1; $^1$H NMR (400 MHz, DMSO-d6) δ = 13.00 (s, 1H), 9.12 (d, J = 2.0 Hz, 1H), 8.65 (br s, 3H), 8.60 (d, J = 2.8 Hz, 1H), 8.39-8.30 (m, 4H), 7.70-7.62 (m, 3H), 7.54-7.49 (m, 1H), 4.57 (br d, J = 5.6 Hz, 2H). |
| 4-70 | 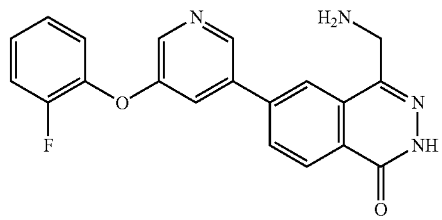 [SMILES: NCc1n[nH]c(=O)c2ccc(-c3cncc(Oc4ccccc4F)c3)cc12] | 4A | 4-5 | 4-(aminomethyl)-6-(5-(2-fluorophenoxy)pyridin-3-yl)phthalazin-1(2H)-one<br>LCMS [M + 1]$^+$ = 363.0; $^1$H NMR (400 MHz, DMSO-d6) δ = 13.01 (s, 1H), 8.97 (d, J = 1.6 Hz, 1H), 8.43 (br d, J = 2.4 Hz, 3H), 8.42-8.35 (m, 2H), 8.32-8.26 (m, 2H), 8.11-8.05 (m, 1H), 7.50-7.42 (m, 1H), 7.35-7.24 (m, 3H), 4.61 (br d, J = 5.6 Hz, 2H) |
| 4-71 | 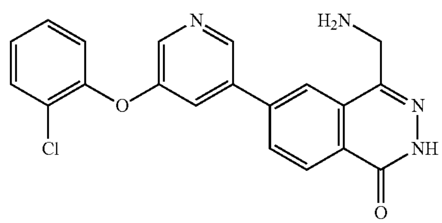 [SMILES: NCc1n[nH]c(=O)c2ccc(-c3cncc(Oc4ccccc4Cl)c3)cc12] | 4A | 4-1 | 4-(aminomethyl)-6-(5-(2-chlorophenoxy)pyridin-3-yl)phthalazin-1(2H)-one<br>LCMS [M + 1]$^+$ = 379.1; $^1$H NMR (400 MHz, DMSO-d6) δ = 13.00 (s, 1H), 9.07 (d, J = 2.0 Hz, 1H), 8.67 (br s, 3H), 8.42 (d, J = 2.8 Hz, 1H), 8.39-8.35 (m, 2H), 8.31-8.27 (m, 1H), 8.25 (t, J = 2.0 Hz, 1H), 7.67 (dd, J = 1.2, 8.0 Hz, 1H), 7.42 (dd, J = 1.6, 7.8 Hz, 1H), 7.34-7.26 (m, 2H), 4.58 (br d, J = 5.6 Hz, 2H). |
| 4-72 | 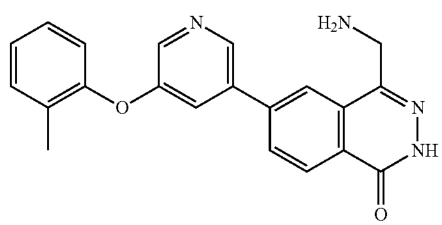 [SMILES: Cc1ccccc1Oc1cncc(-c2ccc3c(=O)[nH]nc(CN)c3c2)c1] | 4A | 4-1 | 4-(aminomethyl)-6-(5-(o-tolyloxy)pyridin-3-yl)phthalazin-1(2H)-one<br>LCMS [M + 1]$^+$ = 359.1; $^1$H NMR (400 MHz, DMSO-d6) δ = 13.00 (s, 1H), 8.96 (d, J = 2.0 Hz, 1H), 8.54 (br s, 3H), 8.37 (d, J = 8.4 Hz, 1H), 8.33-8.30 (m, 2H), 8.26 (dd, J = 1.6, 8.4 Hz, 1H), 8.05 (t, J = 2.4 Hz, 1H), 7.39 (d, J = 7.6 Hz, 1H), 7.31-7.23 (td, J = 0.8, 7.2 Hz, 1H), 7.20-7.14 (td, J = 0.8, 7.2 Hz, 1H), 7.02 (d, J = 7.6 Hz, 1H), 4.59 (br d, J = 5.6 Hz, 2H), 2.27 (s, 3H) |
| 4-73 | 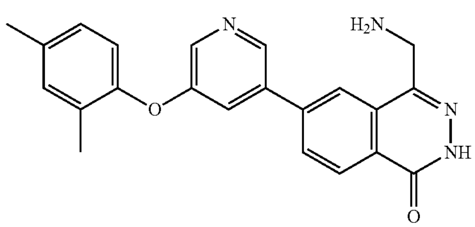 [SMILES: Cc1ccc(Oc2cncc(-c3ccc4c(=O)[nH]nc(CN)c4c3)c2)c(C)c1] | 4A | 4-6 | 4-(aminomethyl)-6-(5-(2,4-dimethylphenoxy)pyridin-3-yl)phthalazin-1(2H)-one<br>LCMS [M + 1]$^+$ = 373.1; $^1$H NMR (400 MHz, DMSO-d6) δ = 13.00 (s, 1H), 8.94 (d, J = 1.8 Hz, 1H), 8.56 (br s, 3H), 8.38 (d, J = 8.4 Hz, 1H), 8.32 (d, J = 1.2 Hz, 1H), 8.29 (d, J = 2.4 Hz, 1H), 8.25 (dd, J = 1.6, 8.4 Hz, 1H), 8.01 (t, J = 2.2 Hz, 1H), 7.20 (s, 1H), 7.08 (dd, J = 2.0, 8.0 Hz, 1H), 6.95 (d, J = 8.0 Hz, 1H), 4.59 (br d, J = 5.6 Hz, 2H), 2.31 (s, 3H), 2.21 (s, 3H) |
| 4-74 | 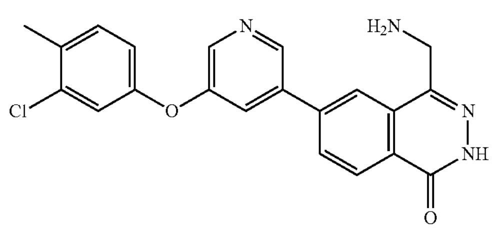 [SMILES: Cc1ccc(Oc2cncc(-c3ccc4c(=O)[nH]nc(CN)c4c3)c2)cc1Cl] | 4A | 4-2 | 4-(aminomethyl)-6-(5-(3-chloro-4-methylphenoxy)pyridin-3-yl)phthalazin-1(2H)-one<br>LCMS [M + 1]$^+$ = 393.0; $^1$H NMR (400 MHz, DMSO-d6) δ = 12.60-12.48 (s, 1H), 8.93 (d, J = 2.0 Hz, 1H), 8.46 (d, J = 2.4 Hz, 1H), 8.38 (d, J = 1.6 Hz, 1H), 8.34 (d, J = 8.4 Hz, 1H), 8.20 (dd, J = 1.6, 8.4 Hz, 1H), 8.07 (t, J = 2.4 Hz, 1H), 7.41 (d, J = 8.4 Hz, 1H), 7.26 (d, J = 2.4 Hz, 1H), 7.06 (dd, J = 2.4, 8.4 Hz, 1H), 4.09 (s, 2H), 2.33 (s, 3H) |

TABLE 4-continued

| Example | Structure | CM | PM | Compound Name and Characterization |
|---|---|---|---|---|
| 4-75 | 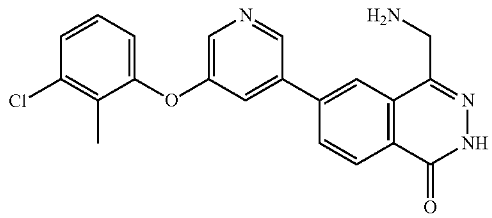 [SMILES: Cc1c(Cl)cccc1Oc1cncc(-c2ccc3c(=O)[nH]nc(CN)c3c2)c1] | 4A | 4-2 | 4-(aminomethyl)-6-(5-(3-chloro-2-methylphenoxy)pyridin-3-yl)phthalazin-1(2H)-one<br>LCMS [M + 1]$^+$ = 393.0; $^1$H NMR (400 MHz, DMSO-d6) δ = 12.55 (br s, 1H), 8.91 (d, J = 2.0 Hz, 1H), 8.38 (d, J = 2.4 Hz, 2H), 8.34 (d, J = 8.4 Hz, 1H), 8.18 (dd, J = 1.6, 8.4 Hz, 1H), 7.99 (t, J = 2.4 Hz, 1H), 7.36-7.32 (dd, J = 1.6, 8.4 Hz,1H), 7.31-7.25 (t, J = 8.0 Hz,1H), 7.01 (d, J = 7.6 Hz, 1H), 4.09 (s, 2H), 2.34 (s, 3H) |
| 4-76 | 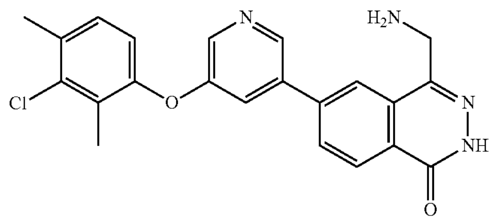 [SMILES: Cc1ccc(Oc2cncc(-c3ccc4c(=O)[nH]nc(CN)c4c3)c2)c(C)c1Cl] | 4A | 4-2 | 4-(aminomethyl)-6-(5-(3-chloro-2,4-dimethylphenoxy)pyridin-3-yl)phthalazin-1(2H)-one<br>LCMS [M + 1]$^+$ = 407.0; $^1$H NMR (400 MHz, DMSO-d6) δ = 12.54 (br s, 1H), 8.85 (d, J = 1.6 Hz, 1H), 8.34 (s, 1H), 8.31 (m, 2H), 8.14 (br d, J = 8.4 Hz, 1H), 7.90 (s, 1H), 7.25 (br d, J = 8.4 Hz, 1H), 6.96 (d, J = 8.4 Hz, 1H), 4.08 (s, 2H), 2.33 (s, 3H), 2.30 (s, 3H) |
| 4-77 | 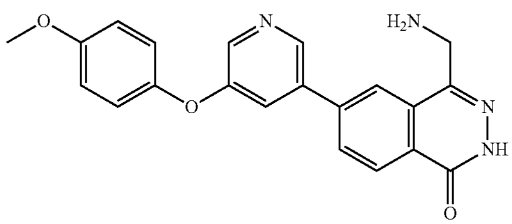 [SMILES: COc1ccc(Oc2cncc(-c3ccc4c(=O)[nH]nc(CN)c4c3)c2)cc1] | 4A | 4-1 | 4-(aminomethyl)-6-(5-(4-methoxyphenoxy)pyridin-3-yl)phthalazin-1(2H)-one<br>LCMS [M + 1]$^+$ = 375.1; $^1$H NMR (400 MHz, DMSO-d6) δ = 13.00 (s, 1H), 8.95 (d, J = 2.0 Hz, 1H), 8.55 (br s, 3H), 8.39-8.36 (m, 2H), 8.31 (d, J = 1.2 Hz, 1H), 8.26 (dd, J = 1.6, 8.4 Hz, 1H), 8.05 (t, J = 2.2 Hz, 1H), 7.17-7.14 (m, 2H), 7.04-7.00 (m, 2H), 4.58 (br d, J = 5.6 Hz, 2H), 3.77 (s, 3H) |
| 4-78 | 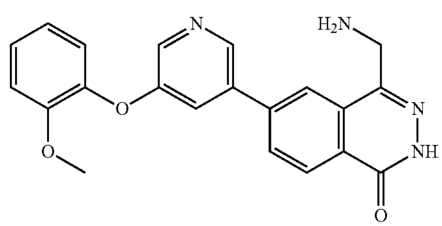 [SMILES: COc1ccccc1Oc1cncc(-c2ccc3c(=O)[nH]nc(CN)c3c2)c1] | 4A | 4-1 | 4-(aminomethyl)-6-(5-(2-methoxyphenoxy)pyridin-3-yl)phthalazin-1(2H)-one<br>LCMS [M + 1]$^+$ = 375.1; $^1$H NMR (400 MHz, DMSO-d6) δ = 12.99 (s, 1H), 8.89 (d, J = 1.6 Hz, 1H), 8.53 (br s, 3H), 8.37 (d, J = 8.4 Hz, 1H), 8.29 (d, J = 1.2 Hz, 1H), 8.25-8.21 (m, 2H), 7.96-7.93 (t, J = 2.0 Hz,1H), 7.32-7.27 (dt, J = 1.6, 7.6 Hz, 1H), 7.26-7.22 (dd, J = 1.6, 8.4,1H), 7.21 (dd, J = 1.6, 7.6 Hz, 1H), 7.04 (dt, J = 1.6, 7.6 Hz, 1H), 4.59 (br d, J = 5.6 Hz, 2H), 3.78 (s, 3H) |
| 4-79 | 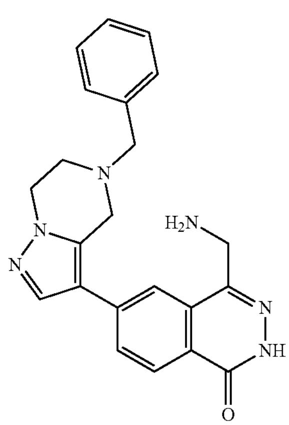 [SMILES: NCc1n[nH]c(=O)c2ccc(-c3cnn4c3CN(Cc3ccccc3)CC4)cc12] | 4B | 4-2 | 4-(aminomethyl)-6-(5-benzyl-4,5,6,7-tetrahydropyrazolo[1,5-a]pyrazin-3-yl)phthalazin-1(2H)-one<br>LCMS [M + 1]$^+$ 387.1; $^1$H NMR (400 MHz, DMSO-d6) δ = 12.40 (br s, 1H), 8.20 (d, J = 8.0 Hz, 1H), 8.05 (s, 1H), 7.88 (s, 1H), 7.85 (dd, J = 1.6, 8.4 Hz, 1H), 7.42-7.31 (m, 4H), 7.30-7.23 (m, 1H), 4.18 (br t, J = 5.4 Hz, 2H), 3.99 (s, 2H), 3.95 (s, 2H), 3.81 (s, 2H), 2.98 (br t, J = 5.4 Hz, 2H) |

TABLE 4-continued

| Example | Structure | CM | PM | Compound Name and Characterization |
|---|---|---|---|---|
| 4-80 | 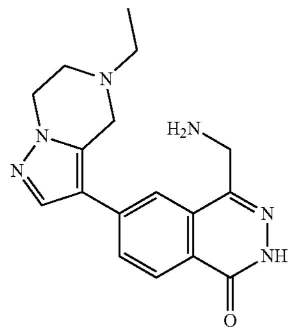 [SMILES: CCN1CCn2ncc(-c3ccc4c(=O)[nH]nc(CN)c4c3)c2C1] | 4B | 4-4 | 4-(aminomethyl)-6-(5-ethyl-4,5,6,7-tetrahydropyrazolo[1,5-a]pyrazin-3-yl)phthalazin-1(2H)-one<br>LCMS [M + 1]⁺: 325.3; ¹H NMR (400 MHz, MeOD) δ = 8.44 (d, J = 8.4 Hz, 1H), 8.14 (s, 1H), 7.97 (dd, J = 1.6, 8.4 Hz, 1H), 7.90 (s, 1H), 5.02 (s, 2H), 4.71 (s, 2H), 4.64 (br t, J = 5.6 Hz, 2H), 4.01 (br s, 2H), 3.58 (q, J = 7.2 Hz, 2H), 1.51 (t, J = 7.2 Hz, 3H). |
| 4-81 | 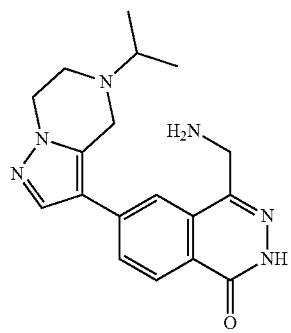 [SMILES: CC(C)N1CCn2ncc(-c3ccc4c(=O)[nH]nc(CN)c4c3)c2C1] | 4C | 4-2 | 4-(aminomethyl)-6-(5-isopropyl-4,5,6,7-tetrahydropyrazolo[1,5-a]pyrazin-3-yl)phthalazin-1(2H)-one<br>LCMS [M + 1]⁺ = 339.1; ¹H NMR (400 MHz, DMSO-d6) δ = 8.25 (d, J = 8.2 Hz, 1H), 7.98 (d, J = 1.6 Hz, 1H), 7.95 (s, 1H), 7.87 (dd, J = 1.6, 8.4 Hz, 1H), 4.16 (t, J = 5.6 Hz, 2H), 4.08 (s, 2H), 4.02 (s, 2H), 3.03 (t, J = 5.6 Hz, 2H), 2.55 (td, J = 2.0, 4.0 Hz, 1H), 1.13 (d, J = 6.8 Hz, 6 H) |
| 4-82 | 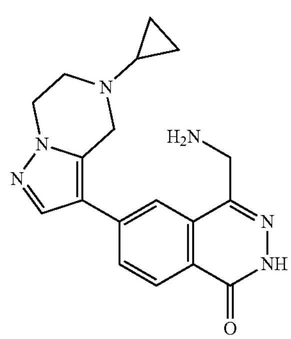 [SMILES: NCc1n[nH]c(=O)c2ccc(-c3cnn4c3CN(C3CC3)CC4)cc12] | 4B | 4-2 | 4-(aminomethyl)-6-(5-cyclopropyl-4,5,6,7 tetrahydropyrazolo[1,5-a]pyrazin-3-yl)phthalazin-1(2H)-one<br>LCMS [M + 1]⁺ 337.3; ¹H NMR (400 MHz, MeOD) δ = 8.36 (d, J = 8.4 Hz, 1H), 7.99 (s, 1H), 7.87 (m, 2H), 4.23 (br s, 2H), 4.19 (s, 2H), 4.14 (s, 2H), 3.24 (br s, 2H), 2.07 (br s, 1H), 0.62 (br d, J = 5.2 Hz, 2H), 0.54 (br s, 2H). |
| 4-83 | 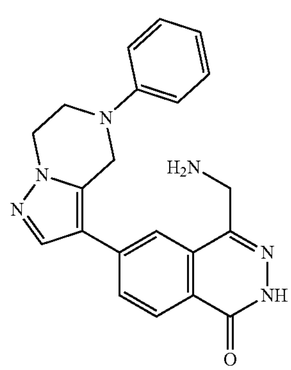 [SMILES: NCc1n[nH]c(=O)c2ccc(-c3cnn4c3CN(c3ccccc3)CC4)cc12] | 4A | 4-1 | 4-(aminomethyl)-6-(5-phenyl-4,5,6,7-tetrahydropyrazolo[1,5-a]pyrazin-3-yl)phthalazin-1(2H)-one<br>LCMS [M + 1]⁺ = 373.1; ¹H NMR (400 MHz, DMSO-d6) δ = 12.88 (s, 1H), 8.56 (br s, 3H), 8.31 (d, J = 8.4 Hz, 1H), 8.19 (s, 1H), 8.05 (dd, J = 1.2, 8.4 Hz, 1H), 7.93 (d, J = 1.2,1H), 7.31-7.23 (m, 2H), 7.15 (d, J = 8.0 Hz, 2H), 6.86 (t, J = 7.2 Hz, 1H), 4.82 (s, 2H), 4.58 (br d, J = 5.6 Hz, 2H), 4.29 (br t, J = 5.2 Hz, 2H), 3.85 (br t, J = 5.2 Hz, 2H) |

TABLE 4-continued

| Example | Structure | CM | PM | Compound Name and Characterization |
|---|---|---|---|---|
| 4-84 | 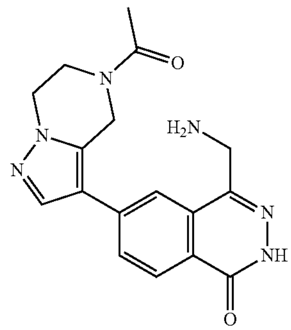 [SMILES: CC(=O)N1CCn2ncc(-c3ccc4c(=O)[nH]nc(CN)c4c3)c2C1] | 4B | 4-1 | 6-(5-acetyl-4,5,6,7-tetrahydropyrazolo[1,5-a]pyrazin-3-yl)-4-(aminomethyl)phthalazin-1(2H)-one<br>LCMS [M + 1]$^+$ 339.1; $^1$H NMR (400 MHz, DMSO-d6) δ = 12.64 (br s, 1H), 8.55 (br s, 3H), 8.33 (d, J = 8.0 Hz, 1H), 8.11 (s, 1H), 7.94 (br d, J = 8.4 Hz, 1H), 7.91 (d, J = 1.2 Hz, 1H), 5.05 (br s, 2H), 4.48 (br s, 2H), 4.26 (br s, 2H), 4.01 (t, J = 5.6 Hz, 2H), 2.18 (s, 3H) |
| 4-85 | 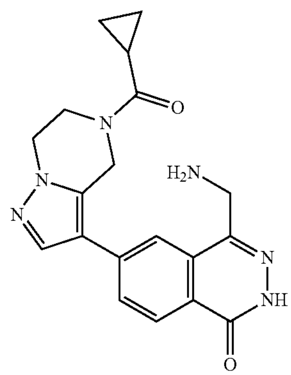 [SMILES: NCc1n[nH]c(=O)c2ccc(-c3cnn4c3CN(C(=O)C3CC3)CC4)cc12] | 4A | 4-5 | 4-(aminomethyl)-6-(5-(cyclopropanecarbonyl)-4,5,6,7-tetrahydropyrazolo[1,5-a]pyrazin-3-yl)phthalazin-1(2H)-one<br>LCMS [M + 1]$^+$ = 365.2; $^1$H NMR (400 MHz, DMSO-d6) δ = 8.41 (br s, 3H), 8.33 (d, J = 8.4 Hz, 1H), 8.09 (s, 1H), 7.96 (dd, J = 1.2, 8.4 Hz, 1H), 7.87 (d, J = 1.2 Hz, 1H), 5.14 (s, 2H), 4.51 (s, 2H), 4.33-4.24 (m, 2H), 4.17 (br s, 2H), 2.18-2.11 (m, 1H), 0.84-0.79 (m, 4H). |
| 4-86 | 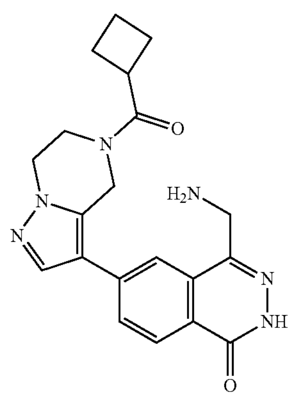 [SMILES: NCc1n[nH]c(=O)c2ccc(-c3cnn4c3CN(C(=O)C3CCC3)CC4)cc12] | 4A | 4-5 | 4-(aminomethyl)-6-(5-(cyclobutanecarbonyl)-4,5,6,7-tetrahydropyrazolo[1,5-a]pyrazin-3-yl)phthalazin-1(2H)-one<br>LCMS [M + 1]$^+$ = 379.1; $^1$H NMR (400 MHz, DMSO-d6) δ = 12.2 (s, 1H), 8.29 (d, J = 8.4 Hz, 1H), 8.01 (s, 1H), 8.01 (d, J = 1.6 Hz, 1H), 7.89 (dd, J = 1.6, 8.4 Hz, 1H), 4.97 (s, 2H), 4.21 (t, J = 5.6 Hz, 2H), 4.09 (s, 2H), 3.95 (br s, 2H), 3.53 (t, J = 8.4 Hz, 1H), 2.30-2.18 (m, 4H), 2.00-1.89 (m, 1H), 1.87-1.75 (m, 1H) |
| 4-87 | 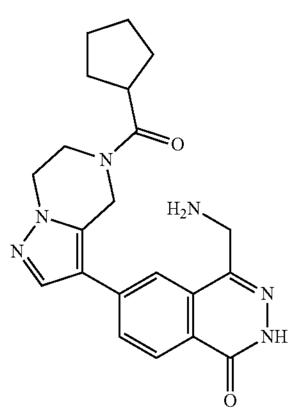 [SMILES: NCc1n[nH]c(=O)c2ccc(-c3cnn4c3CN(C(=O)C3CCCC3)CC4)cc12] | 4A | 4-6 | 4-(aminomethyl)-6-(5-(cyclopentanecarbonyl)-4,5,6,7-tetrahydropyrazolo[1,5-a]pyrazin-3-yl)phthalazin-1(2H)-one<br>LCMS [M + 1]$^+$ = 393.1; $^1$H NMR (400 MHz, DMSO-d6) δ = 12.64 (br s, 1H), 8.53 (br s, 3H), 8.33 (d, J = 8.4 Hz, 1H), 8.11 (s, 1H), 7.94 (br d, J = 9.2 Hz, 1H), 7.91 (s, 1H), 5.07 (br s, 2H), 4.48 (s, 2H), 4.24 (br t, J = 5.2 Hz, 2H), 4.07 (br t, J = 5.2 Hz, 2H), 3.23-3.16 (m, 1H), 1.82 (m, 2H), 1.77-1.68 (m, 2H), 1.63-1.62 (m, 2H), 1.60-1.51 (m, 2H) |

TABLE 4-continued

| Example | Structure | CM | PM | Compound Name and Characterization |
|---|---|---|---|---|
| 4-88 | 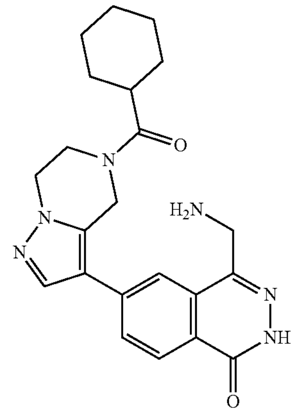 [SMILES: NCc1n[nH]c(=O)c2ccc(-c3cnn4c3CN(C(=O)C3CCCCC3)CC4)cc12] | 4A | 4-4 | 4-(aminomethyl)-6-(5-(cyclohexanecarbonyl)-4,5,6,7-tetrahydropyrazolo[1,5-a]pyrazin-3-yl)phthalazin-1(2H)-one<br>LCMS [M + 1]⁺ = 407.3; ¹H NMR (400 MHz, DMSO-d6) δ = 12.65 (br s, 1H), 8.52 (br s, 3H), 8.34 (d, J = 8.0 Hz, 1H), 8.12 (s, 1H), 7.95 (d, J = 8.0 Hz, 1H), 7.92 (s, 1H), 5.06 (s, 2H), 4.49 (br s, 2H), 4.28-4.22 (m, 2H), 4.09-4.04 (m, 2H), 2.84-2.75 (m, 1H), 1.73-1.70 (m, 5H), 1.45-1.23 (m, 5H) |
| 4-89 | 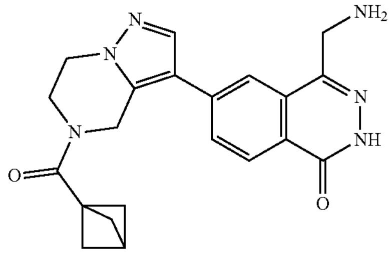 [SMILES: NCc1n[nH]c(=O)c2ccc(-c3cnn4c3CN(C(=O)C35CC(C3)C5)CC4)cc12] | 4A | 4-5 | 4-(aminomethyl)-6-(5-(bicyclo[1.1.1]pentane-1-carbonyl)-4,5,6,7-tetrahydropyrazolo[1,5-a]pyrazin-3-yl)phthalazin-1(2H)-one<br>LCMS [M + 1]⁺ = 391.3; ¹H NMR (400 MHz, DMSO-d6) δ = 12.88 (s, 1H), 8.45 (br s, 3H), 8.32 (br d, J = 8.4 Hz, 1H), 8.16 (s, 1H), 8.00-7.88 (m, 2H), 5.24-4.95 (m, 2H), 4.52 (br s, 2H), 4.32-4.09 (m, 4H), 2.22-2.06 (m, 7H). |
| 4-90 | 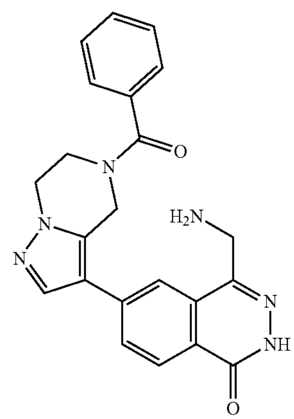 [SMILES: NCc1n[nH]c(=O)c2ccc(-c3cnn4c3CN(C(=O)c3ccccc3)CC4)cc12] | 4A | 4-5 | 4-(aminomethyl)-6-(5-benzoyl-4,5,6,7-tetrahydropyrazolo[1,5-a]pyrazin-3-yl)phthalazin-1(2H)-one<br>LCMS [M + 1]⁺ = 401.0<br>¹H NMR (400 MHz, DMSO-d6) δ = 12.90 (br s, 1H), 8.59-8.37 (s, 3H), 8.36-8.25 (m, 1H), 8.18 (s, 1H), 8.04-7.79 (m, 2H), 7.52 (br d, J = 4.0 Hz, 5H), 5.15 (br s, 2H), 4.52 (br s, 2H), 4.29 (br d, J = 4.8 Hz, 2H), 4.08-3.70 (m, 2H) |
| 4-91 | 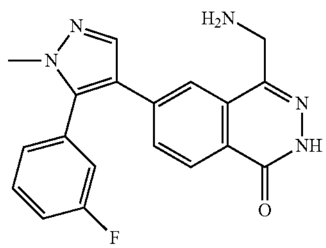 [SMILES: Cn1ncc(-c2ccc3c(=O)[nH]nc(CN)c3c2)c1-c1cccc(F)c1] | 4A | 4-5 | 4-(aminomethyl)-6-(5-(3-fluorophenyl)-1-methyl-1H-pyrazol-4-yl)phthalazin-1(2H)-one<br>LCMS [M + 1]⁺ = 350.0<br>¹H NMR (400 MHz, DMSO-d6) δ = 12.84 (s, 1H), 8.40 (br s, 3H), 8.14 (s, 1H), 8.09 (d, J = 8.4 Hz, 1H), 7.74 (d, J = 1.2 Hz, 1H), 7.64-7.54 (m, 1H), 7.51 (dd, J = 1.6, 8.4 Hz, 1H), 7.44-7.32 (m, 2H), 7.24 (d, J = 7.6 Hz, 1H), 4.27 (s, 2H), 3.76 (s, 3H) |
| 4-92 | 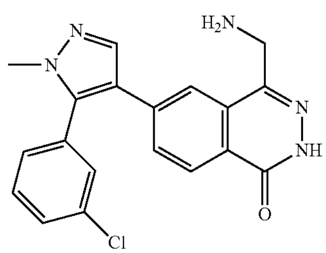 [SMILES: Cn1ncc(-c2ccc3c(=O)[nH]nc(CN)c3c2)c1-c1cccc(Cl)c1] | 4A | 4-5 | 4-(aminomethyl)-6-(5-(3-chlorophenyl)-1-methyl-1H-pyrazol-4-yl)phthalazin-1(2H)-one<br>LCMS [M + 1]⁺ = 366.1; ¹H NMR (400 MHz, DMSO-d6) δ = 12.84 (s, 1H), 8.46 (br s, 3H), 8.16 (s, 1H), 8.09 (d, J = 8.4 Hz, 1H), 7.79 (d, J = 1.2 Hz, 1H), 7.65-7.61 (m, 1H), 7.60-7.55 (m, 2H), 7.47 (dd, J = 1.6, 8.4 Hz, 1H), 7.40 (td, J = 1.2, 7.6 Hz, 1H), 4.32-4.27 (d, J = 5.6 Hz, 2H), 3.76 (s, 3H) |

TABLE 4-continued

| Example | Structure | CM | PM | Compound Name and Characterization |
|---|---|---|---|---|
| 4-93 | 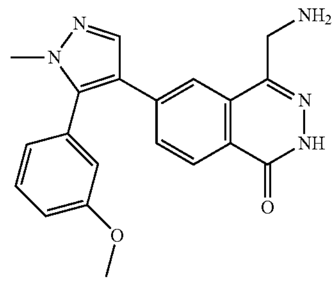 [SMILES: COc1cccc(-c2c(-c3ccc4c(=O)[nH]nc(CN)c4c3)cnn2C)c1] | 4A | 4-4 | 4-(aminomethyl)-6-(5-(3-methoxyphenyl)-1-methyl-1H-pyrazol-4-yl)phthalazin-1(2H)-one<br>LCMS [M + 1]$^+$ = 362.1; $^1$H NMR (400 MHz, DMSO-d6) δ = 12.83 (s, 1H), 8.39-8.29 (s,3H), 8.14 (s, 1H), 8.08 (d, J = 8.4 Hz, 1H), 7.75 (d, J = 1.2 Hz, 1H), 7.54 (dd, J = 1.6, 8.4 Hz, 1H), 7.47 (t, J = 8.0 Hz, 1H), 7.15-7.10 (dd, J = 2.8, 8.4 Hz, 1H), 7.01-6.99 (t, J = 1.2 Hz, 1H), 6.98-6.94 (dt, J = 7.6 Hz, 1H), 4.27 (br d, J = 4.8 Hz, 2H), 3.77 (s, 3H), 3.75 (s, 3H). |
| 4-94 | 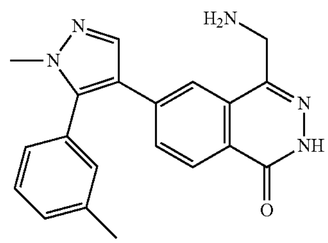 [SMILES: Cc1cccc(-c2c(-c3ccc4c(=O)[nH]nc(CN)c4c3)cnn2C)c1] | 4A | 4-4 | 4-(aminomethyl)-6-(1-methyl-5-(m-tolyl)-1H-pyrazol-4-yl)phthalazin-1(2H)-one<br>LCMS [M + 1]$^+$ = 346.1; $^1$H NMR (400 MHz, DMSO-d6) δ = 12.83 (s, 1H), 8.35 (br s, 3H), 8.15 (s, 1H), 8.06 (d, J = 8.4 Hz, 1H), 7.72 (d, J = 1.2 Hz, 1H), 7.53 (dd, J = 1.2, 8.4 Hz, 1H), 7.44 (t, J = 7.6 Hz,, 1H), 7.38 (d, J = 7.6 Hz, 1H), 7.26 (s, 1H), 7.21 (d, J = 7.2 Hz, 1H), 4.24 (br s, 2H), 3.73 (s, 3H), 2.36 (s, 3H) |
| 4-95 | 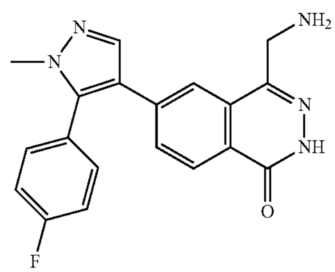 [SMILES: Cn1ncc(-c2ccc3c(=O)[nH]nc(CN)c3c2)c1-c1ccc(F)cc1] | 4A | 4-1 | 4-(aminomethyl)-6-(5-(4-fluorophenyl)-1-methyl-1H-pyrazol-4-yl)phthalazin-1(2H)-one<br>LCMS [M + 1]$^+$ = 350.1; $^1$H NMR (400 MHz, DMSO-d6) δ = 12.84 (s, 1H), 8.49 (br s, 3H), 8.16 (s, 1H), 8.08 (d, J = 8.4 Hz, 1H), 7.78 (d, J = 1.2 Hz, 1H), 7.53-7.46 (m, 3H), 7.43-7.37 (m, 2H), 4.28 (br d, J = 5.6 Hz, 2H), 3.74 (s, 3H) |
| 4-96 | 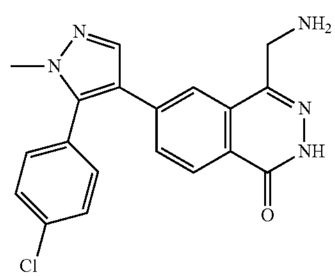 [SMILES: Cn1ncc(-c2ccc3c(=O)[nH]nc(CN)c3c2)c1-c1ccc(Cl)cc1] | 4A | 4-1 | 4-(aminomethyl)-6-(5-(4-chlorophenyl)-1-methyl-1H-pyrazol-4-yl)phthalazin-1(2H)-one<br>LCMS [M + 1]$^+$ = 366.0; $^1$H NMR (400 MHz, DMSO-d6) δ = 12.84 (s, 1H), 8.54 (br s, 3H), 8.16 (s, 1H), 8.08 (d, J = 8.4 Hz, 1H), 7.85 (d, J = 1.2 Hz, 1H), 7.63-7.58 (m, 2H), 7.48-7.45 (dd, J = 1.2, 8.4 Hz, 2H), 7.43 (dd, J = 1.2, 8.4 Hz, 1H), 4.33 (br d, J = 5.6 Hz, 2H), 3.75 (s, 3H) |
| 4-97 | 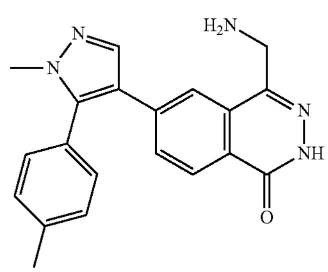 [SMILES: Cc1ccc(-c2c(-c3ccc4c(=O)[nH]nc(CN)c4c3)cnn2C)cc1] | 4A | 4-4 | 4-(aminomethyl)-6-(1-methyl-5-(p-tolyl)-1H-pyrazol-4-yl)phthalazin-1(2H)-one<br>LCMS [M + 1]$^+$ = 346.1; $^1$H NMR (400 MHz, DMSO-d6) δ = 12.83 (s, 1H), 8.34 (br s, 3H), 8.13 (s, 1H), 8.07 (d, J = 8.4 Hz, 1H), 7.74 (d, J = 1.2 Hz, 1H), 7.52 (dd, J = 1.6, 8.4 Hz, 1H), 7.40-7.34 (m, 2H), 7.33-7.28 (m, 2H), 4.27 (br s, 2H), 3.73 (s, 3H), 2.42 (s, 3H) |
| 4-98 | 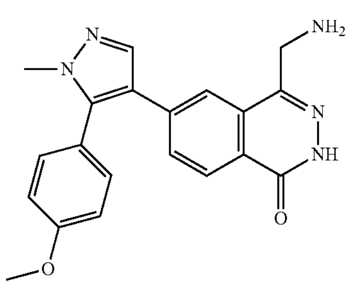 [SMILES: COc1ccc(-c2c(-c3ccc4c(=O)[nH]nc(CN)c4c3)cnn2C)cc1] | 4A | 4-5 | 4-(aminomethyl)-6-(5-(4-methoxyphenyl)-1-methyl-1H-pyrazol-4-yl)phthalazin-1(2H)-one<br>LCMS [M + 1]$^+$ = 362.1; $^1$H NMR (400 MHz, DMSO-d6) δ = 12.83 (s, 1H), 8.36 (br s, 3H), 8.12 (s, 1H), 8.07 (d, J = 8.4 Hz, 1H), 7.77 (d, J = 1.2 Hz, 1H), 7.52 (dd, J = 1.6, 8.4 Hz, 1H), 7.38-7.31 (m, 2H), 7.15-7.06 (m, 2H), 4.30 (br d, J = 4.0 Hz, 2H), 3.84 (s, 3H), 3.72 (s, 3H). |

TABLE 4-continued

| Example | Structure | CM | PM | Compound Name and Characterization |
|---------|-----------|----|----|-----------------------------------|
| 4-99 | 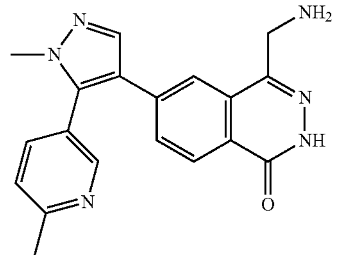 [SMILES: Cc1ccc(-c2c(-c3ccc4c(=O)[nH]nc(CN)c4c3)cnn2C)cn1] | 4A | 4-1 | 4-(aminomethyl)-6-(1-methyl-5-(6-methylpyridin-3-yl)-1H-pyrazol-4-yl)phthalazin-1(2H)-one<br>LCMS [M + 1]$^+$ = 347.1; $^1$H NMR (400 MHz, DMSO-d6) δ = 12.86 (s, 1H), 8.73 (s, 1H), 8.58 (br s, 3H), 8.22 (s, 1H), 8.17 (br d, J = 7.2 Hz, 1H), 8.10 (d, J = 8.4 Hz, 1H), 7.83 (d, J = 1.2 Hz, 1H), 7.77 (br d, J = 8.4 Hz, 1H), 7.52 (dd, J = 1.2, 8.4 Hz, 1H), 4.31 (br d, J = 5.6 Hz, 2H), 3.81 (s, 3H), 2.73 (s, 3H) |
| 4-100 | 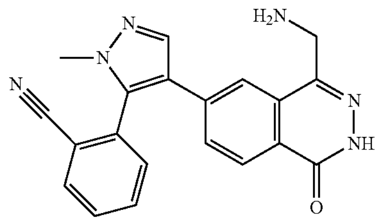 [SMILES: Cn1ncc(-c2ccc3c(=O)[nH]nc(CN)c3c2)c1-c1ccccc1C#N] | 4A | 4-4 | 2-(4-(4-(aminomethyl)-1-oxo-1,2-dihydrophthalazin-6-yl)-1-methyl-1H-pyrazol-5-yl)benzonitrile<br>LCMS [M + 1]$^+$ = 357.1; $^1$H NMR (400 MHz, DMSO-d6) δ = 12.86 (s, 1H), 8.36 (br s, 3H), 8.28 (s, 1H), 8.09(m, 2H), 7.99-7.89 (td, J = 1.2 Hz, 7.6 Hz, 1H), 7.80 (t, J = 7.6 Hz, 2H), 7.68 (d, J = 1.2 Hz, 1H), 7.45 (dd, J = 1.6, 8.4 Hz, 1H), 4.24 (br d, J = 12.4 Hz, 2H), 3.74 (s, 3H). |
| 4-101 | 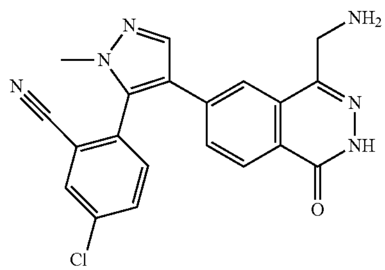 [SMILES: Cn1ncc(-c2ccc3c(=O)[nH]nc(CN)c3c2)c1-c1ccc(Cl)cc1C#N] | 4A | 4-6 | 2-(4-(4-(aminomethyl)-1-oxo-1,2-dihydrophthalazin-6-yl)-1-methyl-1H-pyrazol-5-yl)-5-chlorobenzonitrile<br>LCMS [M + 1]$^+$ = 391.0; $^1$H NMR (400 MHz, DMSO-d6) δ = 12.86 (s, 1H), 8.59-8.44 (br s, 3H), 8.31 (s, 1H), 8.29 (d, J = 2.4 Hz, 1H), 8.11 (d, J = 8.4 Hz, 1H), 8.03 (dd, J = 2.4, 8.4 Hz, 1H), 7.84 (d, J = 1.2 Hz, 1H), 7.82 (d, J = 8.4 Hz, 1H), 7.38 (dd, J = 1.2, 8.4 Hz, 1H), 4.34 (d, J = 5.6 Hz, 2H), 3.74 (s, 3H) |
| 4-102 | 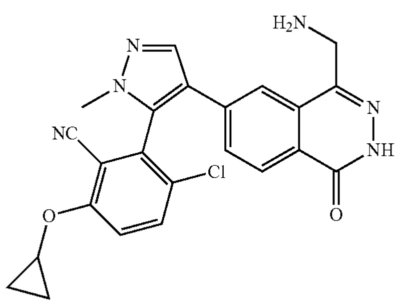 [SMILES: Cn1ncc(-c2ccc3c(=O)[nH]nc(CN)c3c2)c1-c1c(Cl)ccc(OC2CC2)c1C#N] | 4G | 4-6 | 2-(4-(4-(aminomethyl)-1-oxo-1,2-dihydrophthalazin-6-yl)-1-methyl-1H-pyrazol-5-yl)-3-chloro-6-cyclopropoxybenzonitrile<br>LCMS [M + 1]$^+$ = 447.1; $^1$H NMR (400 MHz, DMSO-d$_6$) δ = 12.86 (s, 1H), 8.52 (br s, 3H), 8.39 (s, 1H), 8.13 (d, J = 8.4 Hz, 1H), 8.10 (d, J = 9.2 Hz, 1H), 7.81 (d, J = 9.2 Hz, 1H), 7.75 (d, J = 1.2 Hz, 1H), 7.42 (dd, J = 1.6, 8.4 Hz, 1H), 4.29 (br s, 2H), 4.24-4.17 (m, 1H), 3.69 (s, 3H), 0.90 (br dd, J = 3.4, 5.9 Hz, 2H), 0.87-0.74 (m, 2H) |
| 4-103 | 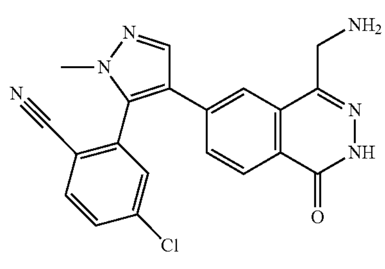 [SMILES: Cn1ncc(-c2ccc3c(=O)[nH]nc(CN)c3c2)c1-c1cc(Cl)ccc1C#N] | 4A | 4-6 | 2-(4-(4-(aminomethyl)-1-oxo-1,2-dihydrophthalazin-6-yl)-1-methyl-1H-pyrazol-5-yl)-4-chlorobenzonitrile<br>LCMS [M + 1]$^+$ = 391.2; $^1$H NMR (400 MHz, DMSO-d6) δ = 12.86 (s, 1H), 8.50 (br s, 3H), 8.31 (s, 1H), 8.11 (m, 2H), 8.01 (d, J = 2.0 Hz, 1H), 7.91 (dd, J = 2.0, 8.6 Hz, 1H), 7.78 (d, J = 1.6 Hz, 1H), 7.42 (dd, J = 1.6, 8.4 Hz, 1H), 4.29 (d, J = 6.4 Hz, 2H), 3.77 (s, 3H) |
| 4-104 | 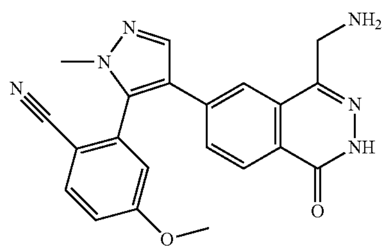 [SMILES: COc1ccc(C#N)c(-c2c(-c3ccc4c(=O)[nH]nc(CN)c4c3)cnn2C)c1] | 4A | 4-6 | 2-(4-(4-(aminomethyl)-1-oxo-1,2-dihydrophthalazin-6-yl)-1-methyl-1H-pyrazol-5-yl)-4-methoxybenzonitrile<br>LCMS [M + 1]$^+$ = 387.1; $^1$H NMR (400 MHz, DMSO-d6) δ = 12.86 (s, 1H), 8.58-8.45 (s, 3H), 8.30 (s, 1H), 8.10 (d, J = 8.4 Hz, 1H), 7.99 (d, J = 8.8 Hz, 1H), 7.74 (d, J = 1.6 Hz, 1H), 7.47 (dd, J = 1.6, 8.4 Hz, 1H), 7.37-7.36 (m, 1H), 7.35-7.32 (m, 1H), 4.34-4.19 (m, 2H), 3.92 (s, 3H), 3.74 (s, 3H) |

TABLE 4-continued

| Example | Structure | CM | PM | Compound Name and Characterization |
|---|---|---|---|---|
| 4-105 | 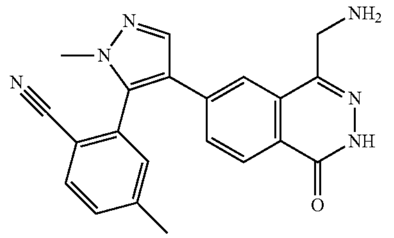 [SMILES: Cc1ccc(C#N)c(-c2c(-c3ccc4c(=O)[nH]nc(CN)c4c3)cnn2C)c1] | 4A | 4-4 | 2-(4-(4-(aminomethyl)-1-oxo-1,2-dihydrophthalazin-6-yl)-1-methyl-1H-pyrazol-5-yl)-4-methylbenzonitrile LCMS [M + 1]$^+$ = 371.1; $^1$H NMR (400 MHz, MeOD) δ = 8.20 (d, J = 8.4 Hz, 1H), 8.14 (s, 1H), 7.83 (d, J = 8.0 Hz, 1H), 7.70 (d, J = 1.6 Hz, 1H), 7.63-7.59 (m, 1H), 7.59 (s, 1H), 7.54 (dd, J = 1.6, 8.4 Hz, 1H), 4.45-4.29 (m, 2H), 3.81 (s, 3H), 2.54 (s, 3H) |
| 4-106 | 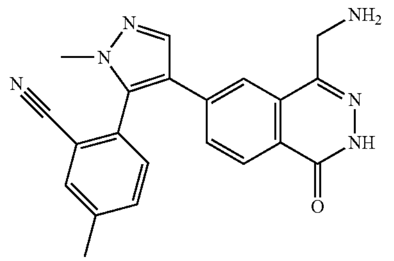 [SMILES: Cc1ccc(-c2c(-c3ccc4c(=O)[nH]nc(CN)c4c3)cnn2C)c(C#N)c1] | 4A | 4-4 | 2-(4-(4-(aminomethyl)-1-oxo-1,2-dihydrophthalazin-6-yl)-1-methyl-1H-pyrazol-5-yl)-5-methylbenzonitrile LCMS [M + 1]$^+$ = 371.2; $^1$H NMR (400 MHz, DMSO-d6) δ = 12.85 (s, 1H), 8.44 (br s, 3H), 8.26 (s, 1H), 8.09 (d, J = 8.4 Hz, 1H), 7.90 (s, 1H), 7.79-7.72 (m, 1H), 7.71-7.59 (m, 2H), 7.45 (br d, J = 8.4 Hz, 1H), 4.31 (d, J = 11.2 Hz, 2H), 3.72 (s, 3H), 2.47 (s, 3H) |
| 4-107 | 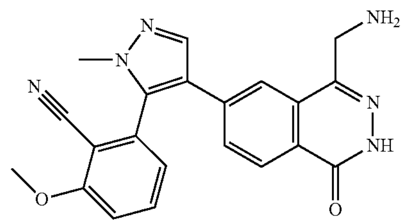 [SMILES: COc1cccc(-c2c(-c3ccc4c(=O)[nH]nc(CN)c4c3)cnn2C)c1C#N] | 4A | 4-4 | 2-(4-(4-(aminomethyl)-1-oxo-1,2-dihydrophthalazin-6-yl)-1-methyl-1H-pyrazol-5-yl)-6-methoxybenzonitrile LCMS [M + 1]$^+$ = 387.2; $^1$H NMR (400 MHz, DMSO-d6) δ = 12.86 (s, 1H), 8.59 (br s, 3H), 8.31 (s, 1H), 8.09 (d, J = 8.4 Hz, 1H), 7.89 (d, 8.4 Hz, 1H), 7.71 (d, J = 1.2 Hz, 1H), 7.52-7.46 (m, 2H), 7.28 (d, J = 7.6 Hz, 1H), 4.24 (br d, J = 5.6 Hz, 2H), 4.00 (s, 3H), 3.72 (s, 3H) |
| 4-108 | 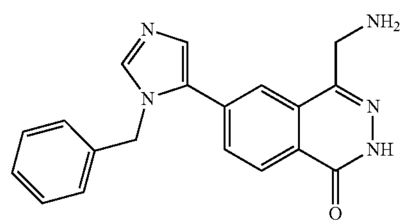 [SMILES: NCc1n[nH]c(=O)c2ccc(-c3cncn3Cc3ccccc3)cc12] | 4B | 4-7 | 4-(aminomethyl)-6-(1-benzyl-1H-imidazol-5-yl)phthalazin-1(2H)-one LCMS [M + 1]$^+$ = 332.1; $^1$H NMR (400 MHz, MeOD) δ = 8.35 (d, J = 8.4 Hz, 1H), 7.99 (s, 1H), 7.88 (dd, J = 1.6, 8.4 Hz, 1H), 7.76 (d, J = 1.6 Hz, 1H), 7.37 (d, J = 0.8 Hz, 1H), 7.34-7.24 (m, 3H), 7.02 (d, J = 6.8 Hz, 2H), 5.45 (s, 2H), 3.92 (s, 2H) |
| 4-109 | 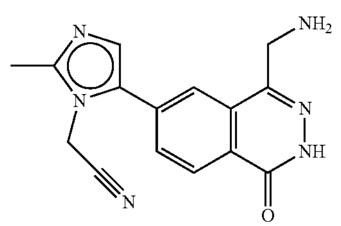 | 4A | 4-3 | 2-(5-(4-(aminomethyl)-1-oxo-1,2-dihydrophthalazin-6-yl)-2-methyl-1H-imidazol-1-yl)acetonitrile $^1$H NMR (400 MHz, MeOD) δ = 8.59 (d, J = 8.4 Hz, 1H), 8.13 (d, J = 1.2 Hz, 1H), 8.07 (dd, J = 1.6, 8.4 Hz, 1H), 7.75 (s, 1H), 5.45 (s, 2H), 4.65 (s, 2H), 2.83 (s, 3H) |
| 4-110 | 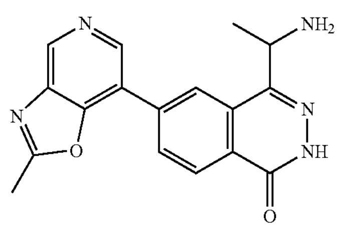 | 4B | 4-2 | 4-(aminomethyl)-6-(2-methyloxazolo[4,5-c]pyridin-7-yl)phthalazin-1(2H)-one LCMS [M + 1]$^+$ = 308.3; $^1$H NMR (400 MHz, DMSO-d6) δ = 12.59 (br s, 1H), 9.05 (br s, 1H), 9.01 (br s, 1H), 8.58 (br s, 1H), 8.41 (br s, 1H), 8.38 (br s, 1H), 4.10 (d, J = 5.6 Hz, 2H), 2.73 (s, 3H) |

TABLE 4-continued

| Example | Structure | CM | PM | Compound Name and Characterization |
|---|---|---|---|---|
| 4-111 | 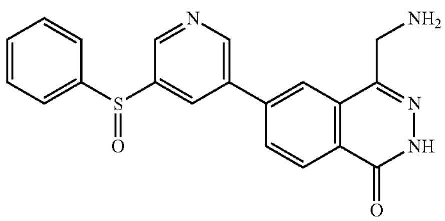 [SMILES: NCc1n[nH]c(=O)c2ccc(-c3cncc(S(=O)c4ccccc4)c3)cc12] | 4A | 4-6 | 4-(aminomethyl)-6-(5-(phenylsulfinyl)pyridin-3-yl)phthalazin-1(2H)-one<br>LCMS [M + 1]⁺ = 377.0; ¹H NMR (400 MHz, DMSO-d6) δ = 13.0 (s, 1H), 9.27 (d, J = 2.0 Hz, 1H), 8.97 (d, J = 2.0 Hz, 1H), 8.72-8.66 (m, 1H), 8.65-8.45 (br s,3H), 8.44-8.37 (m, 1H), 8.36-8.32 (m, 1H), 8.30 (dd, J = 1.6, 8.4 Hz, 1H), 7.90 (d, J = 1.6 Hz, 1H), 7.89-7.84 (m, 1H), 7.62-7.52(m,3H), 4.59 (br d, J = 5.6 Hz, 2H) |
| 4-112 | 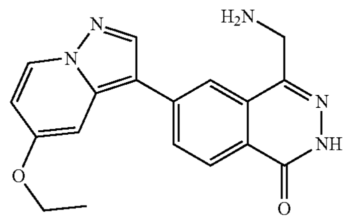 [SMILES: CCOc1ccn2ncc(-c3ccc4c(=O)[nH]nc(CN)c4c3)c2c1] | 4B | 4-4 | 4-(aminomethyl)-6-(5-ethoxypyrazolo[1,5-a]pyridin-3-yl)phthalazin-1(2H)-one<br>LCMS [M + 1]⁺ = 336.2; ¹H NMR (400 MHz, DMSO-d6) δ = 12.86 (s, 1H), 8.68 (d, J = 7.6 Hz, 1H), 8.62 (m, 4H), 8.32-8.29 (m, 1H), 8.25-8.21 (m, 1H), 8.09 (s, 1H), 7.41 (d, J = 2.4 Hz, 1H), 6.73 (dd, J = 2.4, 7.6 Hz, 1H), 4.58 (br d, J = 5.6 Hz, 2H), 4.24 (q, J = 6.8 Hz, 2H), 1.41 (t, J = 6.8 Hz, 3H) |
| 4-113 | 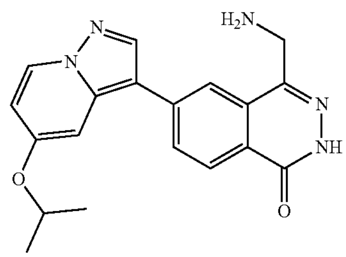 [SMILES: CC(C)Oc1ccn2ncc(-c3ccc4c(=O)[nH]nc(CN)c4c3)c2c1] | 4B | 4-4 | 4-(aminomethyl)-6-(5-isopropoxypyrazolo[1,5-a]pyridin-3-yl)phthalazin-1(2H)-one<br>LCMS [M + 1]⁺ = 350.2; ¹H NMR (400 MHz, DMSO-d6) δ = 12.84 (s, 1H), 8.68 (d, J = 7.6 Hz, 1H), 8.60 (s, 4H), 8.33-8.28 (m, 1H), 8.21 (dd, J = 1.2, 8.4 Hz, 1H), 8.08 (s, 1H), 7.42 (d, J = 2.4 Hz, 1H), 6.71 (dd, J = 2.4, 7.6 Hz, 1H), 4.94 (td, J = 6.0, 12.0 Hz, 1H), 4.58 (br d, J = 5.2 Hz, 2H), 1.37 (s, 3H), 1.36 (s, 3H) |
| 4-114 | 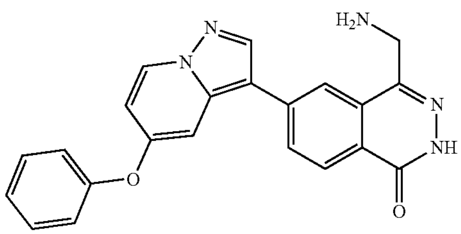 [SMILES: NCc1n[nH]c(=O)c2ccc(-c3cnn4ccc(Oc5ccccc5)cc34)cc12] | 4B | 4-4 | 4-(aminomethyl)-6-(5-phenoxypyrazolo[1,5-a]pyridin-3-yl)phthalazin-1(2H)-one<br>LCMS [M + 1]⁺ = 384.1; ¹H NMR (400 MHz, DMSO-d6) δ = 12.86 (s, 1H), 8.84 (d, J = 7.6 Hz, 1H), 8.66 (s, 1H), 8.43 (br s, 3H), 8.28 (d, J = 8.4 Hz, 1H), 8.16 (br d, J = 7.6 Hz, 1H), 8.01 (d, J = 1.2 Hz, 1H), 7.63 (br s, 1H), 7.53-7.46 (m, 2H), 7.29-7.25 (m, 1H), 7.24-7.21 (m, 2H), 6.81 (dd, J = 2.4, 7.6 Hz, 1H), 4.53 (br s, 2H). |
| 4-115 | 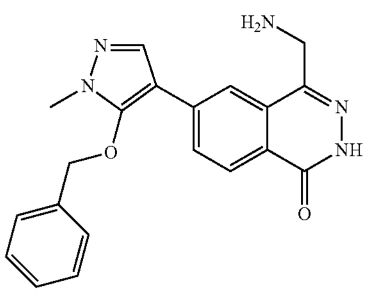 [SMILES: Cn1ncc(-c2ccc3c(=O)[nH]nc(CN)c3c2)c1OCc1ccccc1] | 4B | 4-4 | 4-(aminomethyl)-6-(5-(benzyloxy)-1-methyl-1H-pyrazol-4-yl)phthalazin-1(2H)-one<br>LCMS [M + 1]⁺ = 362.1; ¹H NMR (400 MHz, DMSO-d6) δ = 12.87 (s, 1H), 8.41 (br s, 3H), 8.27 (d, J = 8.4 Hz, 1H), 8.12 (d, J = 8.4 Hz, 1H), 8.05 (s, 1H), 7.97 (d, J = 0.8 Hz, 1H), 7.43-7.36 (m, 5H), 5.07 (s, 2H), 4.45 (br s, 2H), 3.61 (s, 3H) |
| 4-116 | 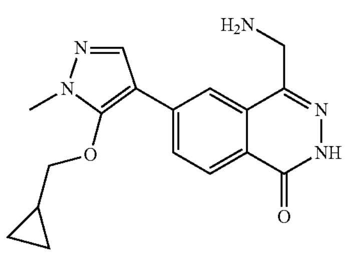 [SMILES: Cn1ncc(-c2ccc3c(=O)[nH]nc(CN)c3c2)c1OCC1CC1] | A4 | 4-2 | 4-(aminomethyl)-6-(5-(cyclopropylmethoxy)-1-methyl-1H-pyrazol-4-yl)phthalazin-1(2H)-one<br>LCMS [M + 1]⁺ = 326.2;¹H NMR (400 MHz, DMSO-d6) δ = 12.78 (br s, 1H), 8.28 (d, J = 8.4 Hz, 1H), 8.14 (dd, J = 1.6, 8.4 Hz, 1H), 8.06 (s, 1H), 8.03 (d, J = 1.2 Hz, 1H), 8.00-7.43 (br s, 2H), 4.43 (s, 2H), 3.90 (d, J = 7.6 Hz, 2H), 3.75 (s, 3H), 1.26-1.21 (m, 1H), 0.53 (m, 2H), 0.27-0.20 (m, 2H) |

TABLE 4-continued

| Example | Structure | CM | PM | Compound Name and Characterization |
|---|---|---|---|---|
| 4-117 | 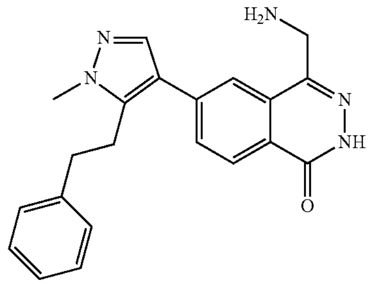 [SMILES: Cn1ncc(-c2ccc3c(=O)[nH]nc(CN)c3c2)c1CCc1ccccc1] | 4B | 4-4 | 4-(aminomethyl)-6-(1-methyl-5-phenethyl-1H-pyrazol-4-yl)phthalazin-1(2H)-one<br>LCMS [M + 1]$^+$ = 360.3; $^1$H NMR (400 MHz, DMSO-d6) δ = 12.88 (s, 1H), 8.63 (br s, 3H), 8.26 (d, J = 8.4 Hz, 1H), 7.89 (s, 1H), 7.87 (dd, J = 1.2, 8.4 Hz, 1H), 7.82 (s, 1H), 7.23 (d, J = 7.6 Hz, 2H), 7.19-7.13 (m, 3H), 4.50 (br d, J = 5.6 Hz, 2H), 3.76 (s, 3H), 3.19 (br t, J = 7.6 Hz, 2H), 2.86 (br t, J = 7.6 Hz, 2H) |
| 4-118 | 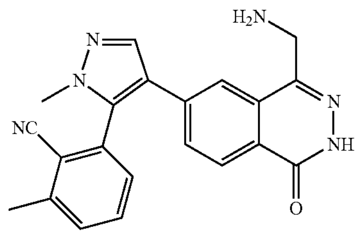 [SMILES: Cc1cccc(-c2c(-c3ccc4c(=O)[nH]nc(CN)c4c3)cnn2C)c1C#N] | 4A | 4-5 | 2-(4-(4-(aminomethyl)-1-oxo-1,2-dihydrophthalazin-6-yl)-1-methyl-1H-pyrazol-5-yl)-6-methylbenzonitrile<br>LCMS [M + 1]$^+$ = 371.1; $^1$H NMR (400 MHz, DMSO-d6) δ = 12.85 (s, 1H), 8.43-8.29 (br S, 3H), 8.27 (s, 1H), 8.08 (d, J = 8.4 Hz, 1H), 7.83-7.77 (m, 1H), 7.72-7.66 (m, 2H), 7.55 (d, J = 7.2 Hz, 1H), 7.46 (dd, J = 1.6, 8.4 Hz, 1H), 4.24 (br s, 2H), 3.70 (s, 3H), 2.55 (s, 3H) |
| 4-119 | 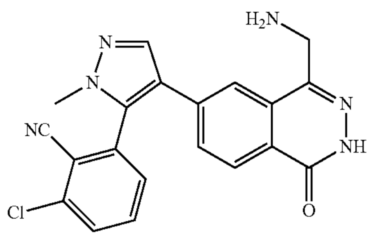 | 4A | 4-5 | 2-(4-(4-(aminomethyl)-1-oxo-1,2-dihydrophthalazin-6-yl)-1-methyl-1H-pyrazol-5-yl)-6-chlorobenzonitrile<br>LCMS [M + 1]$^+$ = 298.0; $^1$H NMR (400 MHz, DMSO-d6) δ = 7.98 (dd, J = 1.2, 6.8 Hz, 1H), 7.94 (d, J = 7.6 Hz, 1H), 7.77 (s, 1H), 7.69 (dd, J = 1.2, 8.4 Hz, 1H), 3.75 (s, 3H) |
| 4-120 | 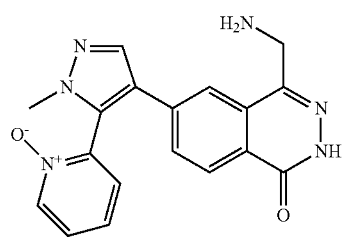 [SMILES: Cn1ncc(-c2ccc3c(=O)[nH]nc(CN)c3c2)c1-c1cccc[n+]1[O-]] | 4B | 4-2 | 2-(4-(4-(aminomethyl)-1-oxo-1,2-dihydrophthalazin-6-yl)-1-methyl-1H-pyrazol-5-yl)pyridine 1-oxide<br>LCMS [M + 1]$^+$ = 349.3; $^1$H NMR (400 MHz, DMSO-d6) δ = 12.72 (br s, 1H), 8.54 (d, J = 6.4 Hz, 1H), 8.19 (s, 1H), 8.13 (d, J = 8.4 Hz, 1H), 7.78 (d, J = 1.2 Hz, 1H), 7.69-7.61 (m, 1H), 7.59-7.52 (m, 2H), 7.48-7.41 (td, J = 0.8, 7.6 Hz, 1H), 6.97 (br s, 2H), 4.14 (br d, J = 4.8 Hz, 2H), 3.74 (s, 3H) |
| 4-121 | 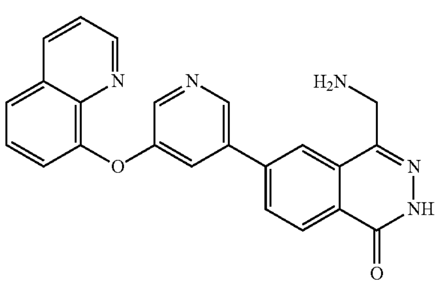 [SMILES: NCc1n[nH]c(=O)c2ccc(-c3cncc(Oc4cccc5cccnc45)c3)cc12] | 4B | 4-4 | 4-(aminomethyl)-6-(5-(quinolin-8-yloxy)pyridin-3-yl)phthalazin-1(2H)-one<br>LCMS [M + 1]$^+$ = 396.1; $^1$H NMR (400 MHz, DMSO-d6) δ = 12.98 (s, 1H), 8.88 (d, J = 2.0 Hz, 1H), 8.87 (dd, J = 1.6, 4.4 Hz, 1H), 8.49 (dd, J = 1.2, 8.4 Hz, 1H), 8.43-8.33 (m, 4H), 8.28 (d, J = 2.8 Hz, 1H), 8.24 (d, J = 8.4 Hz, 1H), 8.05-8.01 (t, J = 2.0 Hz, 1H), 7.94-7.90 (dd, J = 1.2, 8.0 Hz, 1H), 7.67 (t, J = 8.0 Hz, 1H), 7.62 (dd, J = 4.0, 8.4 Hz, 1H), 7.55 (dd, J = 1.2, 7.6 Hz, 1H), 4.61-4.57 (m, 2H) |
| 4-122 | 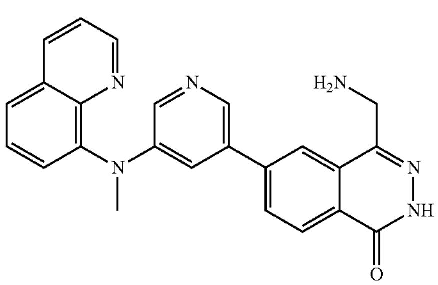 [SMILES: CN(c1cncc(-c2ccc3c(=O)[nH]nc(CN)c3c2)c1)c1cccc2cccnc12] | 4B | 4-4 | 4-(aminomethyl)-6-(5-(methyl(quinolin-8-yl)amino)pyridin-3-yl)phthalazin-1(2H)-one<br>LCMS [M + 1]$^+$ = 409.1; $^1$H NMR (400 MHz, DMSO-d6) δ = 13.04 (s, 1H), 8.90 (dd, J = 1.6, 4.4 Hz, 1H), 8.76 (s, 1H), 8.73-8.60 (m, 4H), 8.41-8.37 (m, 2H), 8.29-8.25 (m, 1H), 8.17 (dd, J = 0.8, 8.4 Hz, 1H), 8.11 (s, 1H), 7.98 (dd, J = 1.2, 7.2 Hz, 1H), 7.84 (d, J = 8.0 Hz, 1H), 7.82 (d, J = 2.4 Hz, 1H), 7.72 (dd, J = 4.4, 8.4 Hz, 1H), 4.57 (br d, J = 5.6 Hz, 2H), 3.65 (s, 3H) |

TABLE 4-continued

| Example | Structure | CM | PM | Compound Name and Characterization |
|---|---|---|---|---|
| 4-123 | 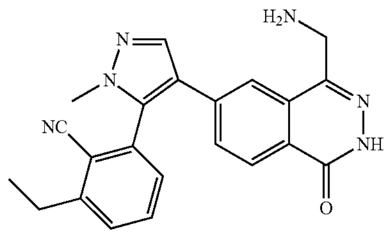 [SMILES: CCc1cccc(-c2c(-c3ccc4c(=O)[nH]nc(CN)c4c3)cnn2C)c1C#N] | 4B | 4-6 | 2-(4-(4-(aminomethyl)-1-oxo-1,2-dihydrophthalazin-6-yl)-1-methyl-1H-pyrazol-5-yl)-6-ethylbenzonitrile<br>LCMS [M + 1]$^+$ = 385.2; $^1$H NMR (400 MHz, DMSO-d6) δ = 12.84 (s, 1H), 8.54 (br s, 3H), 8.32 (s, 1H), 8.07 (d, J = 8.4 Hz, 1H), 7.87 (t, J = 8.0 Hz, 1H), 7.73 (d, J = 7.6 Hz, 1H), 7.68 (s, 1H), 7.60 (d, J = 7.2 Hz, 1H), 7.48-7.42 (m, 1H), 4.20 (br d, J = 11.6 Hz, 2H), 3.72 (s, 3H), 2.86 (q, J = 7.6 Hz, 2H), 1.23 (t, J = 7.6 Hz, 3H) |
| 4-124 | 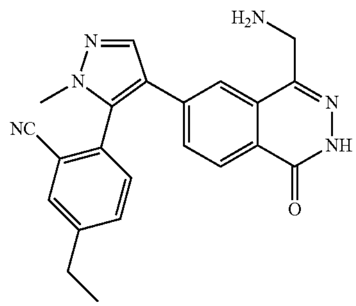 [SMILES: CCc1ccc(-c2c(-c3ccc4c(=O)[nH]nc(CN)c4c3)cnn2C)c(C#N)c1] | 4B | 4-5 | 2-(4-(4-(aminomethyl)-1-oxo-1,2-dihydrophthalazin-6-yl)-1-methyl-1H-pyrazol-5-yl)-5-ethylbenzonitrile<br>LCMS [M + 1]$^+$ = 385.2; $^1$H NMR (400 MHz, DMSO-d6) δ = 12.86 (s, 1H), 8.36 (m, 3H), 8.25 (s, 1H), 8.09 (d, J = 8.4 Hz, 1H), 7.93 (s, 1H), 7.78 (dd, J = 1.6, 8.0 Hz, 1H), 7.70 (br s, 1H), 7.69-7.66 (m, 1H), 7.43 (br d, J = 8.4 Hz, 1H), 4.36 (d, J = 14.4 Hz, 2H), 3.73 (s, 3H), 2.78 (q, J = 7.6 Hz, 2H), 1.27 (t, J = 7.6 Hz, 3H) |
| 4-125 | 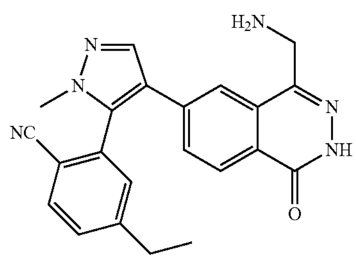 [SMILES: CCc1ccc(C#N)c(-c2c(-c3ccc4c(=O)[nH]nc(CN)c4c3)cnn2C)c1] | 4B | 4-5 | 2-(4-(4-(aminomethyl)-1-oxo-1,2-dihydrophthalazin-6-yl)-1-methyl-1H-pyrazol-5-yl)-4-ethylbenzonitrile<br>LCMS [M + 1]$^+$ = 385.2; $^1$H NMR (400 MHz, DMSO-d6) δ = 12.85 (s, 1H), 8.50-8.29 (m, 3H), 8.27 (s, 1H), 8.10 (d, J = 8.4 Hz, 1H), 7.97 (d, J = 8.4 Hz, 1H), 7.71-7.63 (m, 2H), 7.63 (s, 1H), 7.47 (br d, J = 8.4 Hz, 1H), 4.35-4.10 (d, J = 9.6 Hz, 2H), 3.73 (s, 3H), 2.78 (q, J = 7.6 Hz, 2H), 1.22 (t, J = 7.6 Hz, 3H) |
| 4-126 | 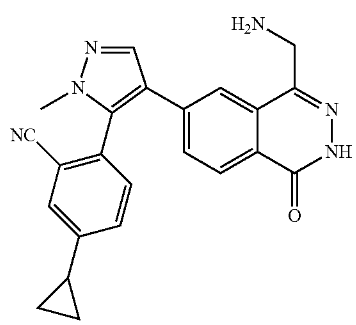 [SMILES: Cn1ncc(-c2ccc3c(=O)[nH]nc(CN)c3c2)c1-c1ccc(C2CC2)cc1C#N] | 4B | 4-5 | 2-(4-(4-(aminomethyl)-1-oxo-1,2-dihydrophthalazin-6-yl)-1-methyl-1H-pyrazol-5-yl)-5-cyclopropylbenzonitrile<br>LCMS [M + 1]$^+$ = 397.2; $^1$H NMR (400 MHz, MeOD) δ = 8.20 (d, J = 8.4 Hz, 1H), 8.11 (s, 1H), 7.74 (s, 1H), 7.64 (d, J = 1.2 Hz, 1H), 7.62-7.56 (m, 2H), 7.50 (br d, J = 8.4 Hz, 1H), 4.49-4.29 (m, 2H), 3.79 (s, 3H), 2.10 (s, 1H), 1.23-1.09 (m, 2H), 0.95-0.79 (m, 2H) |
| 4-127 | 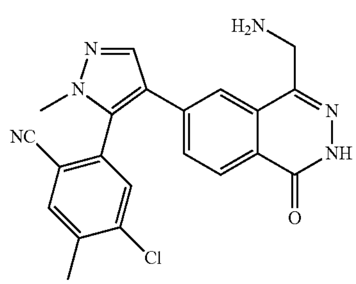 [SMILES: Cc1cc(C#N)c(-c2c(-c3ccc4c(=O)[nH]nc(CN)c4c3)cnn2C)cc1Cl] | 4B | 4-4 | 2-(4-(4-(aminomethyl)-1-oxo-1,2-dihydrophthalazin-6-yl)-1-methyl-1H-pyrazol-5-yl)-4-chloro-5-methylbenzonitrile<br>LCMS [M + 1]$^+$ = 405.2; $^1$H NMR (400 MHz, DMSO-d6) δ = 12.87 (s, 1H), 8.36 (br s, 3H), 8.26 (s, 1H), 8.15-8.07 (m, 2H), 7.97 (s, 1H), 7.78 (s, 1H), 7.42 (dd, J = 1.6, 8.4 Hz, 1H), 4.34 (d, J = 10.8 Hz, 1H), 3.75 (s, 3H), 2.48 (s, 3H) |

TABLE 4-continued

| Example | Structure | CM | PM | Compound Name and Characterization |
|---|---|---|---|---|
| 4-128 | 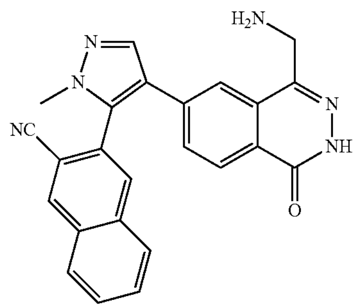 [SMILES: Cn1ncc(-c2ccc3c(=O)[nH]nc(CN)c3c2)c1-c1cc2ccccc2cc1C#N] | 4B | 4-4 | 3-(4-(4-(aminomethyl)-1-oxo-1,2-dihydrophthalazin-6-yl)-1-methyl-1H-pyrazol-5-yl)-2-naphthonitrile<br>LCMS [M + 1]$^+$ = 407.1; $^1$H NMR (400 MHz, DMSO-d6) δ = 12.83 (s, 1H), 8.82 (s, 1H), 8.37 (s, 1H), 8.32 (s, 4H), 8.22-8.18 (m, 1H), 8.15-8.11 (m, 1H), 8.02 (d, J = 8.4 Hz, 1H), 7.90 (d, J = 1.6 Hz, 1H), 7.87-7.79 (m, 2H), 7.36 (dd, J = 1.2, 8.0 Hz, 1H), 4.31 (br d, J = 0.8 Hz, 2H), 3.77 (s, 3H) |
| 4-129 | 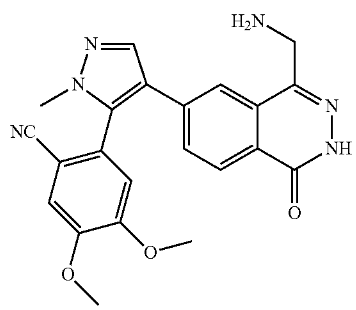 [SMILES: COc1cc(C#N)c(-c2c(-c3ccc4c(=O)[nH]nc(CN)c4c3)cnn2C)cc1OC] | 4B | 4-4 | 2-(4-(4-(aminomethyl)-1-oxo-1,2-dihydrophthalazin-6-yl)-1-methyl-1H-pyrazol-5-yl)-4,5-dimethoxybenzonitrile<br>LCMS [M + 1]$^+$ = 417.1; $^1$H NMR (400 MHz, DMSO-d6) δ = 12.85 (s, 1H), 8.37 (br s, 3H), 8.26 (s, 1H), 8.11 (d, J = 8.4 Hz, 1H), 7.80 (d, J = 1.2 Hz, 1H), 7.57 (s, 1H), 7.47 (dd, J = 1.6, 8.4 Hz, 1H), 7.35 (s, 1H), 4.40-4.26 (br d, J = 5.6 Hz, 2H), 3.90 (s, 3H), 3.88 (s, 3H), 3.74 (s, 3H) |
| 4-130 | 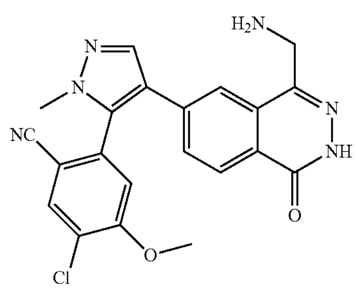 [SMILES: COc1cc(-c2c(-c3ccc4c(=O)[nH]nc(CN)c4c3)cnn2C)c(C#N)cc1Cl] | 4B | 4-4 | 2-(4-(4-(aminomethyl)-1-oxo-1,2-dihydrophthalazin-6-yl)-1-methyl-1H-pyrazol-5-yl)-5-chloro-4-methoxybenzonitrile<br>LCMS [M + 1]$^+$ = 421.1; $^1$H NMR (400 MHz, DMSO-d6) δ = 12.87 (s, 1H), 8.37 (br s, 3H), 8.28 (s, 1H), 8.22 (s, 1H), 8.13 (d, J = 8.4 Hz, 1H), 7.85 (d, J = 1.2 Hz, 1H), 7.60 (s, 1H), 7.45 (dd, J = 1.6, 8.4 Hz, 1H), 4.45-4.29 (m, 2H), 4.01 (s, 3H), 3.77 (s, 3H) |
| 4-131 | 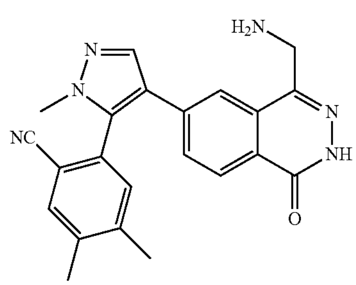 [SMILES: Cc1cc(C#N)c(-c2c(-c3ccc4c(=O)[nH]nc(CN)c4c3)cnn2C)cc1C] | 4B | 4-4 | 2-(4-(4-(aminomethyl)-1-oxo-1,2-dihydrophthalazin-6-yl)-1-methyl-1H-pyrazol-5-yl)-4-5-dimethylbenzonitrile<br>LCMS [M + 1]$^+$ = 385.1; $^1$H NMR (400 MHz, DMSO-d6) δ = 12.87 (s, 1H), 8.34 (br s, 3H), 8.27 (s, 1H), 8.09 (d, J = 8.4 Hz, 1H), 7.85 (s, 1H), 7.72 (d, J = 1.2 Hz, 1H), 7.58 (s, 1H), 7.44 (dd, J = 1.6, 8.4 Hz, 1H), 4.32 (d, J = 22.0 Hz, 2H), 3.71 (s, 3H), 2.39 (s, 3H), 2.38 (s, 3H) |
| 4-132 | 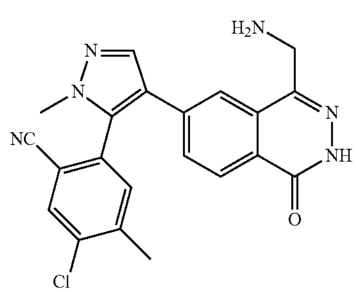 [SMILES: Cc1cc(-c2c(-c3ccc4c(=O)[nH]nc(CN)c4c3)cnn2C)c(C#N)cc1Cl] | 4B | 4-5 | 2-(4-(4-(aminomethyl)-1-oxo-1,2-dihydrophthalazin-6-yl)-1-methyl-1H-pyrazol-5-yl)-5-chloro-4-methylbenzonitrile<br>LCMS [M + 1]$^+$ = 405.2; $^1$H NMR (400 MHz, MeOD) δ = 8.22 (d, J = 8.4 Hz, 1H), 8.12 (s, 1H), 7.99 (s, 1H), 7.77 (s, 1H), 7.71 (s, 1H), 7.51 (d, J = 8.4 Hz, 1H), 4.45 (d, J = 9.2 Hz, 2H), 3.81 (s, 3H), 2.55 (s, 3H) |

TABLE 4-continued

| Example | Structure | CM | PM | Compound Name and Characterization |
|---|---|---|---|---|
| 4-133 | 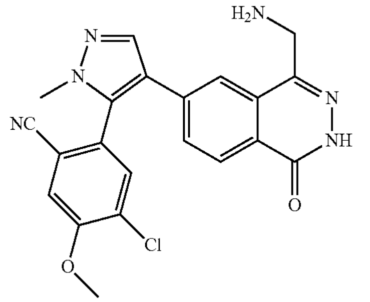 [SMILES: COc1cc(C#N)c(-c2c(-c3ccc4c(=O)[nH]nc(CN)c4c3)cnn2C)cc1Cl] | 4B | 4-6 | 2-(4-(4-(aminomethyl)-1-oxo-1,2-dihydrophthalazin-6-yl)-1-methyl-1H-pyrazol-5-yl)-4-chloro-5-methoxybenzonitrile<br>LCMS [M + 1]$^+$ = 421.1; $^1$H NMR (400 MHz, DMSO-d6) δ = 12.86 (s, 1H), 8.43 (br s, 3H), 8.27 (s, 1H), 8.12 (d, J = 8.4 Hz, 1H), 7.97 (s, 1H), 7.86 (s, 1H), 7.84-7.82 (d, J = 1.6 Hz,, 1H), 7.41 (dd, J = 1.6, 8.4 Hz, 1H), 4.40-4.30 (m, 2H), 4.01 (s, 3H), 3.74 (s, 3H) |
| 4-134 | 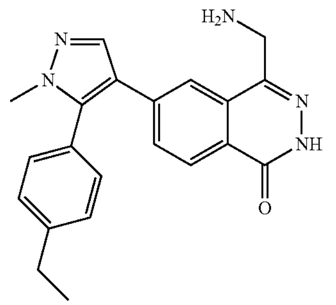 [SMILES: CCc1ccc(-c2c(-c3ccc4c(=O)[nH]nc(CN)c4c3)cnn2C)cc1] | 4B | 4-4 | 4-(aminomethyl)-6-(5-(4-ethylphenyl)-1-methyl-1H-pyrazol-4-yl)phthalazin-1(2H)-one<br>LCMS [M + 1]$^+$ = 360.2; $^1$H NMR (400 MHz, DMSO-d6) δ = 12.83 (s, 1H), 8.51-8.28 (br s, 3H), 8.12 (d, J = 8.4 Hz, 1H), 8.07 (d, J = 8.4 Hz, 1H), 7.73 (d, J = 1.2 Hz, 1H), 7.52 (dd, J = 1.2, 8.4 Hz, 1H), 7.42-7.37 (m, 2H), 7.36-7.30 (m, 2H), 4.26 (d, J = 5.6 Hz, 2H), 3.74 (s, 3H), 2.72 (q, J = 7.6 Hz, 2H), 1.25 (t, J = 7.6 Hz, 3H) |
| 4-135 | 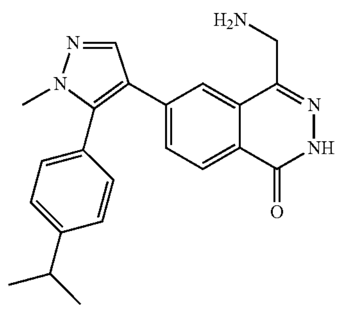 [SMILES: CC(C)c1ccc(-c2c(-c3ccc4c(=O)[nH]nc(CN)c4c3)cnn2C)cc1] | 4B | 4-5 | 4-(aminomethyl)-6-(5-(4-isopropylphenyl)-1-methyl-1H-pyrazol-4-yl)phthalazin-1(2H)-one<br>LCMS [M + 1]$^+$ = 374.2; $^1$H NMR (400 MHz, MeOD) δ = 8.13 (d, J = 8.4 Hz, 1H), 8.02 (s, 1H), 7.66-7.60 (m, 2H), 7.44 (d, J = 8.4 Hz, 2H), 7.31 (d, J = 8.4 Hz, 2H), 4.27 (s, 2H), 3.77 (s, 3H), 3.07-2.98 (m, 1H), 1.33 (s, 3H), 1.31 (s, 3H) |
| 4-136 | 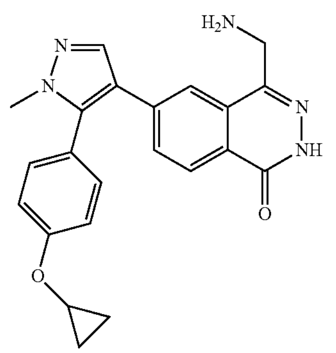 [SMILES: Cn1ncc(-c2ccc3c(=O)[nH]nc(CN)c3c2)c1-c1ccc(OC2CC2)cc1] | 4B | 44 | 4-(aminomethyl)-6-(5-(4-cyclopropoxyphenyl)-1-methyl-1H-pyrazol-4-yl)phthalazin-1(2H)-one<br>LCMS [M + 1]$^+$ = 388.2; $^1$H NMR (400 MHz, DMSO-d6) δ = 12.83 (s, 1H), 8.40 (br s, 3H), 8.11 (s, 1H), 8.08 (d, J = 8.4 Hz, 1H), 7.76 (d, J = 1.2 Hz, 1H), 7.53 (dd, J = 1.6, 8.4 Hz, 1H), 7.35 (d, J = 8.8 Hz, 2H), 7.21 (d, J = 8.8 Hz, 2H), 4.29 (br s, 2H), 3.93 (td, J = 3.2, 6.0 Hz, 1H), 3.73 (s, 3H), 0.88-0.79 (m, 2H), 0.75-0.67 (m, 2H) |
| 4-137 | 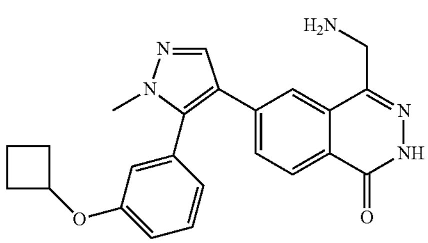 [SMILES: Cn1ncc(-c2ccc3c(=O)[nH]nc(CN)c3c2)c1-c1cccc(OC2CCC2)c1] | 4B | 4-4 | 4-(aminomethyl)-6-(5-(3-cyclobutoxyphenyl)-1-methyl-1H-pyrazol-4-yl)phthalazin-1(2H)-one<br>LCMS [M + 1]$^+$ = 402.2; $^1$H NMR (400 MHz, DMSO-d6) δ = 12.84 (s, 1H), 8.36 (br s, 3H), 8.13 (s, 1H), 8.08 (d, J = 8.4 Hz, 1H), 7.73 (d, J = 1.2 Hz, 1H), 7.52 (dd, J = 1.6, 8.4 Hz, 1H), 7.44 (t, J = 8.0 Hz, 1H), 7.02 (dd, J = 2.0, 8.4 Hz, 1H), 6.96 (d, J = 7.6 Hz, 1H), 6.85-6.82 (m, 1H), 4.69 (t, J = 7.2 Hz, 1H), 4.27 (s, 2H), 3.75 (s, 3H), 2.37-2.25 (m, 2H), 2.03-1.87 (m, 2H), 1.73 (q, J = 10.4 Hz, 1H), 1.64-1.50 (m, 1H) |

TABLE 4-continued

| Example | Structure | CM | PM | Compound Name and Characterization |
|---|---|---|---|---|
| 4-138 | 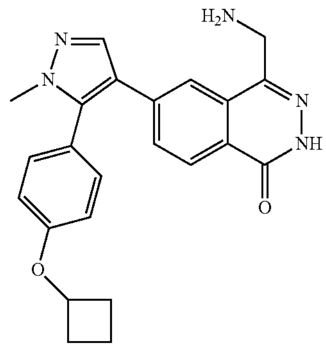 [SMILES: Cn1ncc(-c2ccc3c(=O)[nH]nc(CN)c3c2)c1-c1ccc(OC2CCC2)cc1] | 4B | 4-6 | 4-(aminomethyl)-6-(5-(4-cyclobutoxyphenyl)-1-methyl-1H-pyrazol-4-yl)phthalazin-1(2H)-one<br>LCMS [M + 1]$^+$ = 402.2; $^1$H NMR (400 MHz, DMSO-d6) δ = 12.82 (s, 1H), 8.60-8.36 (br s, 3H), 8.12 (s, 1H), 8.06 (dd, J = 1.2, 8.4 Hz, 1H), 7.79 (s, 1H), 7.52-7.46 (m, 1H), 7.31 (d, J = 8.8 Hz, 2H), 7.04-6.94 (m, 2H) 4.77 (quin, J = 7.2 Hz, 1H), 4.29 (br d, J = 5.6 Hz, 2H), 3.72 (s, 3H), 2.47-2.41 (m, 2H), 2.17-2.03 (m, 2H), 1.81 (q, J = 10.0 Hz, 1H), 1.72-1.60 (m, 1H) |
| 4-139 | 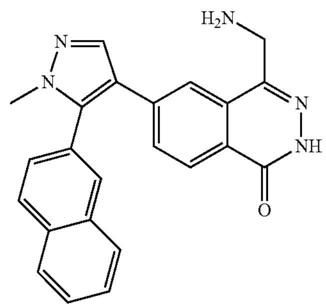 [SMILES: Cn1ncc(-c2ccc3c(=O)[nH]nc(CN)c3c2)c1-c1ccc2ccccc2c1] | 4B | 4-4 | 4-(aminomethyl)-6-(1-methyl-5-(naphthalen-2-yl)-1H-pyrazol-4-yl)phthalazin-1(2H)-one<br>LCMS [M + 1]$^+$ = 382.1; $^1$H NMR (400 MHz, DMSO-d6) δ = 12.82 (s, 1H), 8.35 (s, 3H), 8.19 (s, 1H), 8.10-7.95 (m, 5H), 7.89 (s, 1H), 7.68-7.57 (m, 2H), 7.48 (dd, J = 1.6, 8.8 Hz, 1H), 7.43 (d, J = 8.4 Hz, 1H), 4.31 (br s, 2H), 3.80 (s, 3H) |
| 4-140 | 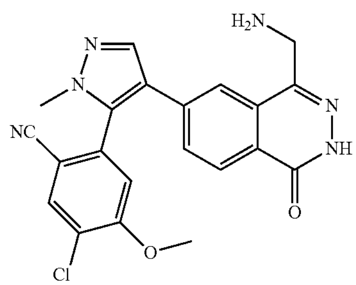 | 4B | 4-4 | 4-(aminomethyl)-6-(5-(3,4-dichlorophenyl)-1-methyl-1H-pyrazol-4-yl)phthalazin-1(2H)-one<br>LCMS [M + 1]$^+$ = 400.1; $^1$H NMR (400 MHz, DMSO-d6) δ = 12.86 (s, 1H), 8.36 (br s, 3H), 8.14-8.10 (d, J = 8.4 Hz, 2H), 7.85 (d, J = 1.2 Hz, 1H), 7.79 (m, 2H), 7.47 (dd, J = 1.6, 8.4 Hz, 1H), 7.40 (dd, J = 2.0, 8.4 Hz, 1H), 4.37 (s, 2H), 3.78 (s, 3H) |
| 4-141 | 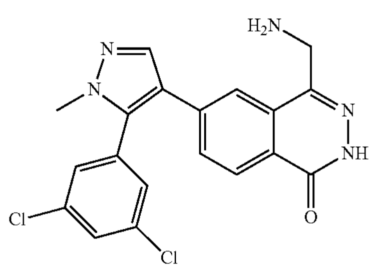 [SMILES: Cn1ncc(-c2ccc3c(=O)[nH]nc(CN)c3c2)c1-c1cc(Cl)cc(Cl)c1] | 4B | 4-4 | 4-(aminomethyl)-6-(5-(3,5-dichlorophenyl)-1-methyl-1H-pyrazol-4-yl)phthalazin-1(2H)-one<br>LCMS [M + 1]$^+$ = 400.0; $^1$H NMR (400 MHz, MeOD) δ = 8.26 (br d, J = 8.4 Hz, 1H), 8.04 (s, 1H), 7.71 (d, J = 1.2 Hz, 1H), 7.70-7.62 (m, 2H), 7.46 (d, J = 1.2 Hz, 2H), 4.39 (s, 2H), 3.83 (s, 3H) |
| 4-142 | 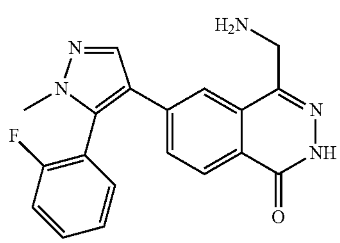 [SMILES: Cn1ncc(-c2ccc3c(=O)[nH]nc(CN)c3c2)c1-c1ccccc1F] | 4B | 4-4 | 4-(aminomethyl)-6-(5-(2-fluorophenyl)-1-methyl-1H-pyrazol-4-yl)phthalazin-1(2H)-one<br>LCMS [M + 1]$^+$ = 350.2; $^1$H NMR (400 MHz, DMSO-d6) δ = 12.85 (s, 1H), 8.40-8.28 (br s, 3H), 8.23 (s, 1H), 8.10 (d, J = 8.4 Hz, 1H), 7.75 (d, J = 1.2 Hz, 1H), 7.71-7.64 (m, 1H), 7.56-7.50 (m, 2H), 7.49-7.40 (m, 2H), 4.28 (br d, J = 5.6 Hz, 2H), 3.73 (s, 3H) |

TABLE 4-continued

| Example | Structure | CM | PM | Compound Name and Characterization |
|---|---|---|---|---|
| 4-143 | 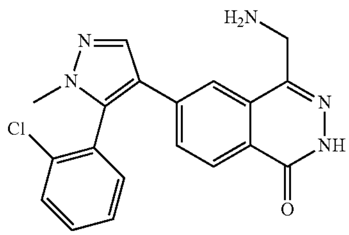 [SMILES: Cn1ncc(-c2ccc3c(=O)[nH]nc(CN)c3c2)c1-c1ccccc1Cl] | 4B | 4-4 | 4-(aminomethyl)-6-(5-(2-chlorophenyl)-1-methyl-1H-pyrazol-4-yl)phthalazin-1(2H)-one<br>LCMS [M + 1]$^+$ = 366.1; $^1$H NMR (400 MHz, DMSO-d6) δ = 12.83 (s, 1H), 8.42 (br s, 3H), 8.26 (s, 1H), 8.08 (d, J = 8.4 Hz, 1H), 7.76-7.72 (m, 1H), 7.68 (d, J = 1.6 Hz, 1H), 7.67-7.61 (m, 1H), 7.57-7.56 (m, 1H), 7.55 (d, J = 0.8 Hz, 1H), 7.49 (dd, J = 1.6, 8.4 Hz, 1H), 4.28-4.18 (m, 2H), 3.65 (s, 3H) |
| 4-144 | 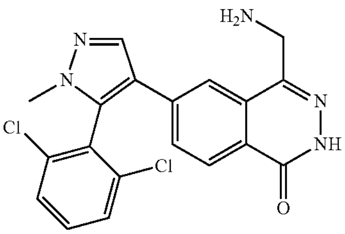 [SMILES: Cn1ncc(-c2ccc3c(=O)[nH]nc(CN)c3c2)c1-c1c(Cl)cccc1Cl] | 4B | 4-5 | 4-(aminomethyl)-6-(5-(2,6-dichlorophenyl)-1-methyl-1H-pyrazol-4-yl)phthalazin-1(2H)-one<br>LCMS [M + 1]$^+$ = 400.0; $^1$H NMR (400 MHz, DMSO-d6) δ = 12.85 (s, 1H), 8.46-8.30 (m, 4H), 8.11 (d, J = 8.4 Hz, 1H), 7.79-7.75 (m, 2H), 7.74 (d, J = 1.2 Hz, 1H), 7.72-7.65 (m, 1H), 7.43 (dd, J = 1.6, 8.4 Hz, 1H), 4.30 (br d, J = 5.2 Hz, 2H), 3.64 (s, 3H) |
| 4-145 | 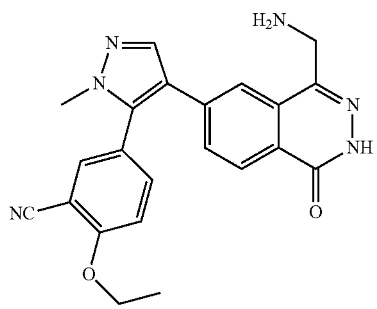 [SMILES: CCOc1ccc(-c2c(-c3ccc4c(=O)[nH]nc(CN)c4c3)cnn2C)cc1C#N] | 4B | 4-5 | 5-(4-(4-(aminomethyl)-1-oxo-1,2-dihydrophthalazin-6-yl)-1-methyl-1H-pyrazol-5-yl)-2-ethoxybenzonitrile<br>LCMS [M + 1]$^+$ = 401.2; $^1$H NMR (400 MHz, DMSO-d6) δ = 12.85 (s, 1H), 8.40 (br s, 3H), 8.13 (s, 1H), 8.10 (d, J = 8.4 Hz, 1H), 7.88 (d, J = 2.0 Hz, 1H), 7.80 (s, 1H), 7.64 (dd, J = 2.0, 8.8 Hz, 1H), 7.48 (dd, J = 1.2, 8.4 Hz, 1H), 7.36 (d, J = 8.8 Hz, 1H), 4.34 (br s, 2H), 4.28 (q, J = 6.8 Hz, 2H), 3.75 (s, 3H), 1.41 (t, J = 6.8 Hz, 3H) |
| 4-146 | 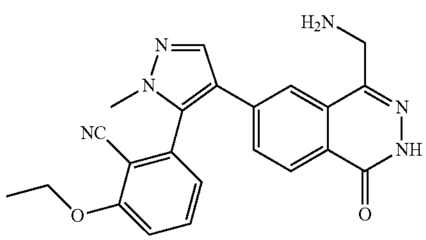 [SMILES: CCOc1cccc(-c2c(-c3ccc4c(=O)[nH]nc(CN)c4c3)cnn2C)c1C#N] | 4B | 4-4 | 2-(4-(4-(aminomethyl)-1-oxo-1,2-dihydrophthalazin-6-yl)-1-methyl-1H-pyrazol-5-yl)-6-ethoxybenzonitrile<br>LCMS [M + 1]$^+$ = 401.2; $^1$H NMR (400 MHz, DMSO-d6) δ = 12.87 (s, 1H), 8.38 (br s, 3H), 8.27 (s, 1H), 8.09 (d, J = 8.4 Hz, 1H), 7.85 (dd, J = 7.6, 8.4 Hz, 1H), 7.76 (s, 1H), 7.46 (d, J = 8.8 Hz, 1H), 7.45-7.40 (m, 1H), 7.26 (d, J = 7.6 Hz, 1H), 4.38-4.28 (m, 2H), 4.28-4.21 (m, 2H), 3.72 (s, 3H), 1.38 (t, J = 7.2 Hz, 3H) |
| 4-147 | 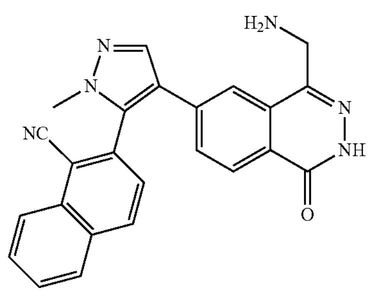 [SMILES: Cn1ncc(-c2ccc3c(=O)[nH]nc(CN)c3c2)c1-c1ccc2ccccc2c1C#N] | 4B | 4-4 | 2-(4-(4-(aminomethyl)-1-oxo-1,2-dihydrophthalazin-6-yl)-1-methyl-1H-pyrazol-5-yl)-1-naphthonitrile<br>LCMS [M + 1]$^+$ = 407.2; $^1$H NMR (400 MHz, DMSO-d6) δ = 12.85 (s, 1H), 8.52 (d, J = 8.4 Hz, 1H), 8.41-8.30 (m, 4H), 8.28 (d, J = 7.6 Hz, 1H), 8.14 (d, J = 8.0 Hz, 1H), 8.01 (d, J = 8.0 Hz, 1H), 7.93-7.84 (m, 3H), 7.83 (d, J = 8.8 Hz, 1H), 7.33 (dd, J = 1.2, 8.4 Hz, 1H), 4.42-4.20 (m, 2H), 3.78 (s, 3H) |
| 4-148 | 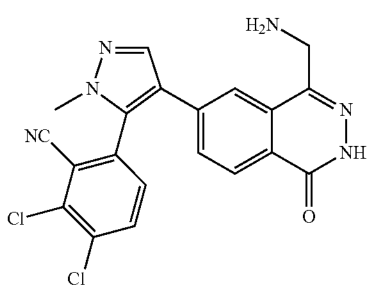 [SMILES: Cn1ncc(-c2ccc3c(=O)[nH]nc(CN)c3c2)c1-c1ccc(Cl)c(Cl)c1C#N] | 4B | 4-4 | 6-(4-(4-(aminomethyl)-1-oxo-1,2-dihydrophthalazin-6-yl)-1-methyl-1H-pyrazol-5-yl)-2,3-dichlorobenzonitrile<br>LCMS [M + 1]$^+$ = 425.0; $^1$H NMR (400 MHz, DMSO-d6) δ = 12.89 (s, 1H), 8.36 (br s, 3H), 8.29 (s, 1H), 8.21 (d, J = 8.4 Hz, 1H), 8.14 (d, J = 8.4 Hz, 1H), 7.87 (d, J = 1.2 Hz, 1H), 7.79 (d, J = 8.4 Hz, 1H), 7.44 (dd, J = 1.6, 8.4 Hz, 1H), 4.40 (br s, 2H), 3.78 (s, 3H) |

TABLE 4-continued

| Example | Structure | CM | PM | Compound Name and Characterization |
|---|---|---|---|---|
| 4-149 | 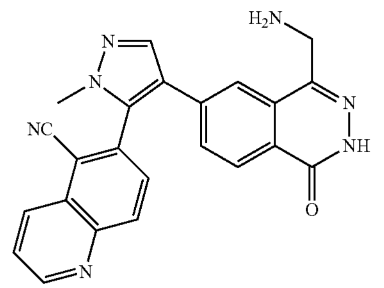 | 4B | 4-4 | 6-(4-(4-(aminomethyl)-1-oxo-1,2-dihydrophthalazin-6-yl)-1-methyl-1H-pyrazol-5-yl)quinoline-5-carbonitrile LCMS [M + 1]⁺ = 408.1; ¹H NMR (400 MHz, DMSO-d6) δ = 12.84 (s, 1H), 9.20 (dd, J = 1.6, 4.0 Hz, 1H), 8.58-8.52 (m, 2H), 8.33 (s, 1H), 8.30 (br s, 3H), 8.06 (d, J = 8.8 Hz, 1H), 8.03 (d, J = 8.4 Hz, 1H), 7.88 (dd, J = 4.0, 8.4 Hz, 1H), 7.85 (d, J = 1.2 Hz, 1H), 7.39 (dd, J = 1.2, 8.4 Hz, 1H), 4.39-4.19 (m, 2H), 3.80 (s, 3H) |
| 4-150 | 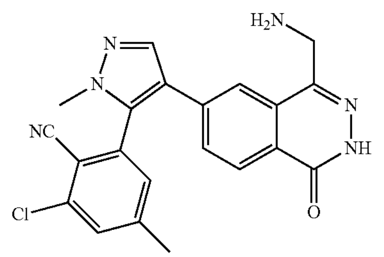 [SMILES: Cc1cc(Cl)c(C#N)c(-c2c(-c3ccc4c(=O)[nH]nc(CN)c4c3)cnn2C)c1] | 4B | 4-4 | 2-(4-(4-(aminomethyl)-1-oxo-1,2-dihydrophthalazin-6-yl)-1-methyl-1H-pyrazol-5-yl)-6-chloro-4-methylbenzonitrile LCMS [M + 1]⁺ = 405.1; ¹H NMR (400 MHz, DMSO-d6) δ = 8.23 (d, J = 8.0 Hz, 1H), 8.12 (s, 1H), 7.77 (d, J = 1.2 Hz, 1H), 7.73 (s, 1H), 7.55 (s, 1H), 7.52 (dd, J = 1.2, 8.0 Hz, 1H), 4.51-4.37 (m, 2H), 3.82 (s, 3H), 2.53 (s, 3H) |
| 4-151 | 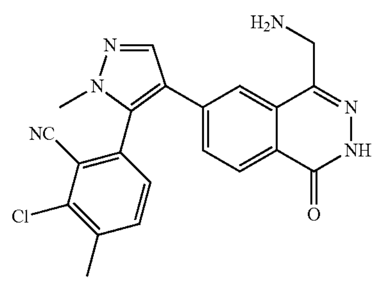 [SMILES: Cc1ccc(-c2c(-c3ccc4c(=O)[nH]nc(CN)c4c3)cnn2C)c(C#N)c1Cl] | 4B | 4-4 | 2-(4-(4-(aminomethyl)-1-oxo-1,2-dihydrophthalazin-6-yl)-1-methyl-1H-pyrazol-5-yl)-6-chloro-5-methylbenzonitrile LCMS [M + 1]⁺ = 405.1; ¹H NMR (400 MHz, DMSO-d6) δ = 12.87 (s, 1H), 8.53-8.33 (m, 3H), 8.28 (s, 1H), 8.12 (d, J = 8.4 Hz, 1H), 7.92 (d, J = 8.0 Hz, 1H), 7.78 (s, 1H), 7.68 (d, J = 8.0 Hz, 1H), 7.45 (br d, J = 8.4 Hz, 1H), 4.23 (d, J = 12 Hz, 2H), 3.75 (s, 3H), 3.33 (br s, 3H) |
| 4-152 | 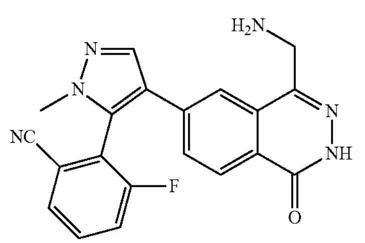 [SMILES: Cn1ncc(-c2ccc3c(=O)[nH]nc(CN)c3c2)c1-c1c(F)cccc1C#N] | 4B | 4-5 | 2-(4-(4-(aminomethyl)-1-oxo-1,2-dihydrophthalazin-6-yl)-1-methyl-1H-pyrazol-5-yl)-3-fluorobenzonitrile LCMS [M + 1]⁺ = 375.2; ¹H NMR (400 MHz, DMSO-d6) δ = 12.88 (s, 1H), 8.39 (br s, 3H), 8.35 (s, 1H), 8.13 (d, J = 8.4 Hz, 1H), 8.01-7.95 (m,1H), 7.94-7.87 (m, 2H), 7.74 (s, 1H), 7.45 (br d, J = 8.4 Hz, 1H), 4.30 (br d, J = 7.2 Hz, 2H), 3.77 (s, 3H) |
| 4-153 | 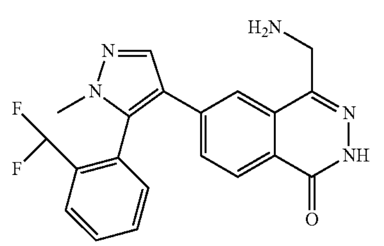 [SMILES: Cn1ncc(-c2ccc3c(=O)[nH]nc(CN)c3c2)c1-c1ccccc1C(F)F] | 4B | 4-4 | 4-(aminomethyl)-6-(5-(2-(difluoromethyl)phenyl)-1-methyl-1H-pyrazol-4-yl)phthalazin-1(2H)-one LCMS [M + 1]⁺ = 382.1; ¹H NMR (400 MHz, DMSO-d6) δ = 12.82 (s, 1H), 8.34 (br s, 3H), 8.28 (s, 1H), 8.04 (d, J = 8.4 Hz, 1H), 7.87-7.83 (m, 1H), 7.82-7.78 (m, 2H), 7.63-7.58 (m, 2H), 7.46 (d, J = 8.4 Hz, 1H), 6.77-6.46 (t, J = 54.4 Hz, 1H), 4.21-4.13 (m, 2H), 3.60 (s, 3H) |
| 4-154 | 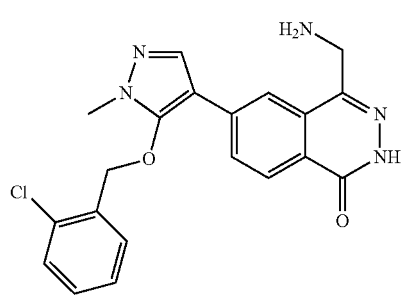 [SMILES: Cn1ncc(-c2ccc3c(=O)[nH]nc(CN)c3c2)c1OCc1ccccc1Cl] | 4B | 4-4 | 4-(aminomethyl)-6-(5-((2-chlorobenzyl)oxy)-1-methyl-1H-pyrazol-4-yl)phthalazin-1(2H)-one LCMS [M + 1]⁺ = 396.1; ¹H NMR (400 MHz, DMSO-d6) δ = 12.87 (s, 1H), 8.47-8.29 (br s, 3H), 8.24 (d, J = 8.4 Hz, 1H), 8.07 (dd, J = 1.6, 8.4 Hz, 1H), 8.03 (s, 1H), 7.93 (d, J = 1.6 Hz, 1H), 7.50-7.45 (m, 2H), 7.38 (dt, J = 2.0, 7.6 Hz, 1H), 7.36-7.30 (dt, J = 2.0, 7.6 Hz, 1H), 5.16 (s, 2H), 4.45 (s, 2H), 3.63 (s, 3H) |

TABLE 4-continued

| Example | Structure | CM | PM | Compound Name and Characterization |
|---|---|---|---|---|
| 4-155 | 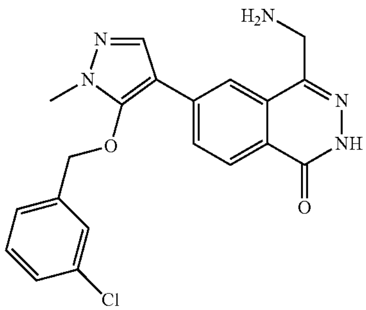 [SMILES: Cn1ncc(-c2ccc3c(=O)[nH]nc(CN)c3c2)c1OCc1cccc(Cl)c1] | 4B | 4-4 | 4-(aminomethyl)-6-(5-((3-chlorobenzyl)oxy)-1-methyl-1H-pyrazol-4-yl)phthalazin-1(2H)-one<br>LCMS [M + 1] $^+$ = 396.1; $^1$H NMR (400 MHz, DMSO-d6) δ = 12.86 (s, 1H), 8.43-8.30 (br s, 3H), 8.25 (d, J = 8.4 Hz, 1H), 8.05 (dd, J = 1.6, 8.4 Hz, 1H), 8.02 (s, 1H), 7.92 (d, J = 1.6 Hz, 1H), 7.46 (d, J = 1.2 Hz, 1H), 7.40-7.35 (m, 3H), 5.08 (s, 2H), 4.45 (s, 2H), 3.67 (s, 3H) |
| 4-156 | 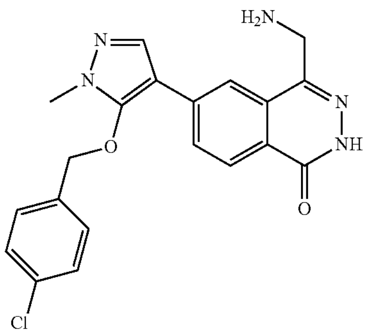 [SMILES: Cn1ncc(-c2ccc3c(=O)[nH]nc(CN)c3c2)c1OCc1ccc(Cl)cc1] | 4B | 4-4 | 4-(aminomethyl)-6-(5-((4-chlorobenzyl)oxy)-1-methyl-1H-pyrazol-4-yl)phthalazin-1(2H)-one<br>LCMS [M + 1] $^+$ = 396.1; $^1$H NMR (400 MHz, DMSO-d6) δ = 12.86 (s, 1H), 8.53-8.32 (br s, 3H), 8.26 (d, J = 8.4 Hz, 1H), 8.06 (dd, J = 1.6, 8.4 Hz, 1H), 8.03 (s, 1H), 7.92 (d, J = 1.6 Hz, 1H), 7.44-7.39 (m, 4H), 5.07 (s, 2H), 4.47 (br s, 2H), 3.65 (s, 3H) |
| 4-157 | 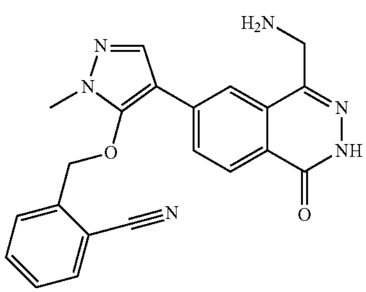 [SMILES: Cn1ncc(-c2ccc3c(=O)[nH]nc(CN)c3c2)c1OCc1ccccc1C#N] | 4B | 4-5 | 2-(((4-(4-(aminomethyl)-1-oxo-1,2-dihydrophthalazin-6-yl)-1-methyl-1H-pyrazol-5-yl)oxy)methyl)benzonitrile<br>LCMS [M + 1] $^+$ = 387.2; $^1$H NMR (400 MHz, DMSO-d6) δ = 12.88 (s, 1H), 8.57-8.34 (m, 3H), 8.23 (d, J = 8.4 Hz, 1H), 8.07-8.00 (m, 2H), 7.91 (s,1H), 7.84 (br d, J = 7.6 Hz, 1H), 7.74-7.66 (m, 1H), 7.66-7.61 (m, 1H), 7.54 (br t, J = 7.6 Hz, 1H), 5.22 (s, 2H), 4.46 (br s,2H), 3.69 (s, 3H) |
| 4-158 | 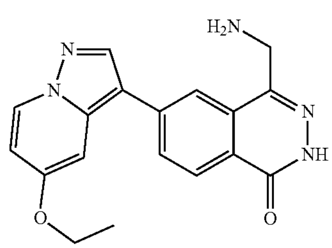 | 4B | 4-6 | 4-(aminomethyl)-6-(5-ethoxypyrazolo[1,5-a]pyridin-3-yl)phthalazin-1(2H)-one<br>LCMS [M + 1] $^+$ = 322.2; 1H NMR (400 MHz, DMSO-d6) δ = 12.84 (s, 1H), 8.68 (d, J = 7.6 Hz, 1H), 8.62 (s, 1H), 8.59 (br s, 3H), 8.34-8.29 (d, J = 8.4 Hz, 1H), 8.27-8.23 (d, J = 8.4 Hz, 1H),8.11 (s, 1H), 7.42 (d, J = 2.0 Hz, 1H), 6.74 (dd, J = 2.4, 7.6 Hz, 1H), 4.58 (br d, J = 5.6 Hz, 2H), 3.96 (s, 3H) |
| 4-159 | 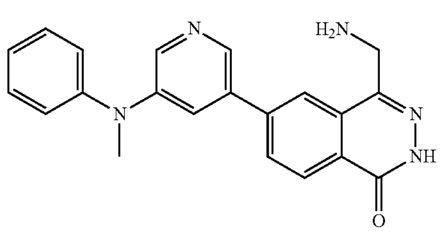 [SMILES: CN(c1ccccc1)c1cncc(-c2ccc3c(=O)[nH]nc(CN)c3c2)c1] | 4A | 4-7 | 4-(aminomethyl)-6-(5-(methyl(phenyl)amino)pyridin-3-yl)phthalazin-1(2H)-one<br>LCMS [M + 1] $^+$ 358.1; 1H NMR (400 MHz, DMSO-d6) δ = 13.00 (s, 1H), 8.63 (d, J = 1.6 Hz, 1H), 8.43 (br s, 3H), 8.38 (d, J = 8.8 Hz, 1H), 8.27 (d, J = 2.8 Hz, 1H), 8.26-8.19 (m, 2H), 7.84 (t, J = 2.4 Hz, 1H), 7.47-7.38 (m, 2H), 7.24 (dd, J = 0.8, 8.4 Hz, 2H), 7.15 (t, J = 7.2 Hz, 1H), 4.60 (br d, J = 5.6 Hz, 2H), 3.42 (s, 3H) |

TABLE 4-continued

| Example | Structure | CM | PM | Compound Name and Characterization |
|---|---|---|---|---|
| 4-160 | 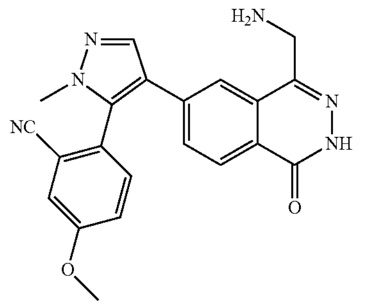 [SMILES: COc1ccc(-c2c(-c3ccc4c(=O)[nH]nc(CN)c4c3)cnn2C)c(C#N)c1] | 4A | 4-1 | 2-(4-(4-(aminomethyl)-1-oxo-1,2-dihydrophthalazin-6-yl)-1-methyl-1H-pyrazol-5-yl)-5-methoxybenzonitrile LCMS [M + 1]⁺ = 387.2; 1H NMR (400 MHz, DMSO-d6) δ = 12.86 (s, 1H), 8.50-8.35 (br s, 3H), 8.26 (s, 1H), 8.11 (d, J = 8.4 Hz, 1H), 7.76 (s, 1H),7.70-7.66 (m, 2H), 7.49 (dd, J = 2.8, 8.8 Hz, 1H), 7.44 (d, J = 8.4 Hz, 1H), 4.40-4.22 (m, 2H), 3.92 (s, 3H), 3.72 (s, 3H) |
| 4-161 | 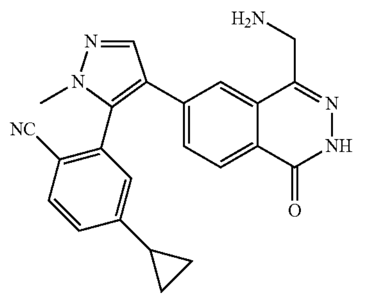 [SMILES: Cn1ncc(-c2ccc3c(=O)[nH]nc(CN)c3c2)c1-c1cc(C2CC2)ccc1C#N] | 4B | 4-1 | 2-(4-(4-(aminomethyl)-1-oxo-1,2-dihydrophthalazin-6-yl)-1-methyl-1H-pyrazol-5-yl)-4-cyclopropylbenzonitrile LCMS [M + 1]⁺ = 397.2; 1H NMR (400 MHz, DMSO-d6) δ = 12.86 (s, 1H), 8.36 (br s, 3H),'8.27 (s, 1H), 8.10 (d, J = 8.4 Hz, 1H), 7.91 (d, J = 8.0 Hz, 1H), 7.72 (d, J = 1.6 Hz, 1H), 7.48 (s, 1H), 7.47-7.44 (dd, J = 8.4, 2.0 Hz, 1H), 7.43 (dd, J = 1.6, 8.4 Hz, 1H), 4.27 (br s, 2H), 3.72 (s, 3H), 2.15-2.07 (m, 1H), 1.12 (dd, J = 2.8, 8.4 Hz, 2H), 0.95-0.81 (m, 2H) |
| 4-162 | 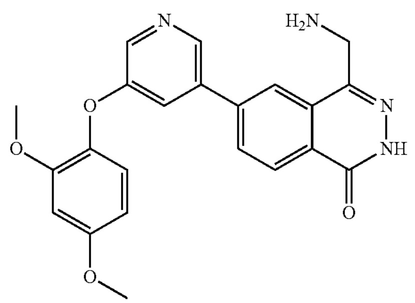 [SMILES: COc1ccc(Oc2cncc(-c3ccc4c(=O)[nH]nc(CN)c4c3)c2)c(OC)c1] | 4A | 4-1 | 4-(aminomethyl)-6-(5-(2,4-dimethoxyphenoxy)pyridin-3-yl)phthalazin-1(2H)-one LCMS [M + 1]⁺ = 405.1; 1H NMR (400 MHz, DMSO-d6) δ = 12.99 (s, 1H), 8.84 (d, J = 1.6 Hz, 1H), 8.51 (br s, 3H), 8.37 (d, J = 8.4 Hz, 1H), 8.28 (d, J = 1.2 Hz, 1H), 8.21 (dd, J = 1.6, 8.4 Hz, 1H), 8.19 (d, J = 2.8 Hz, 1H), 7.87 (t, J = 2.0 Hz, 1H), 7.17 (d, J = 8.8 Hz, 1H), 6.79 (d, J = 2.8 Hz, 1H), 6.59 (dd, J = 2.8, 8.8 Hz, 1H), 4.59 (br d, J = 5.6 Hz, 2H), 3.80-3.79 (s, 3H), 3.76 (s, 3H) |
| 4-163 | 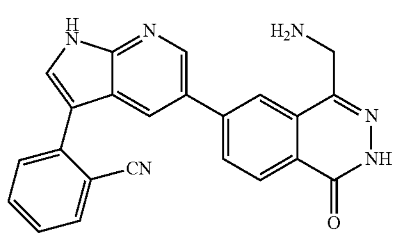 [SMILES: N#Cc1ccccc1-c1c[nH]c2ncc(-c3ccc4c(=O)[nH]nc(CN)c4c3)cc12] | 4B | 4-5 | 2-(5-(4-(aminomethyl)-1-oxo-1,2-dihydrophthalazin-6-yl)-1H-pyrrolo[2,3-b]pyridin-3-yl)benzonitrile LCMS [M + 1]⁺ = 393.2; 1H NMR (400 MHz, DMSO-d6) δ = 12.95 (s, 1H), 12.46 (d, J = 2.4 Hz, 1H), 8.90 (d, J = 2.0 Hz, 1H), 8.53 (d, J = 2.0 Hz, 1H), 8.48-8.38 (m, 3H), 8.37-8.30 (m, 2H), 8.28 (s, 1H), 8.03 (d, J = 2.8 Hz, 1H), 7.97 (d, J = 6.8 Hz, 1H), 7.91-7.85 (m, 1H), 7.84-7.78 (m, 1H), 7.54 (dt, J = 1.2, 7.6 Hz, 1H), 4.62 (br s, 2H) |
| 4-164 | 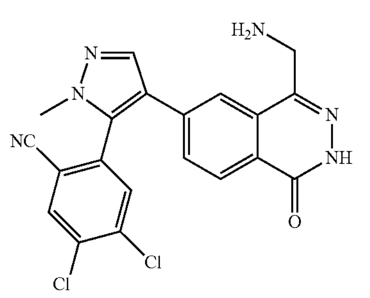 [SMILES: Cn1ncc(-c2ccc3c(=O)[nH]nc(CN)c3c2)c1-c1cc(Cl)c(Cl)cc1C#N] | 4B | 4-5 | 2-(4-(4-(aminomethyl)-1-oxo-1,2-dihydrophthalazin-6-yl)-1-methyl-1H-pyrazol-5-yl)-4,5-dichlorobenzonitrile LCMS [M + 1]⁺ = 424.9; 1H NMR (400 MHz, DMSO-d6) δ = 12.87 (s, 1H), 8.52 (br s, 3H), 8.49 (s, 1H), 8.31 (s, 1H), 8.24 (s, 1H), 8.13 (d, J = 8.4 Hz, 1H), 7.91 (d,4 = 1.2 Hz, 1H), 7.40 (dd, J = 1.6, 8.4 Hz, 1H), 4.39 (br t, J = 5.2 Hz, 2H), 3.78 (s, 3H) |

TABLE 4-continued

| Example | Structure | CM | PM | Compound Name and Characterization |
|---|---|---|---|---|
| 4-165 | 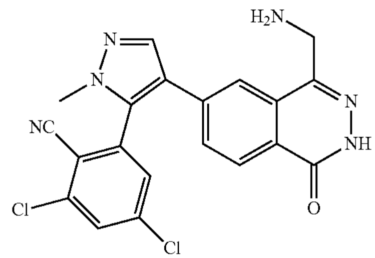 [SMILES: Cn1ncc(-c2ccc3c(=O)[nH]nc(CN)c3c2)c1-c1cc(Cl)cc(Cl)c1C#N] | 4B | 4-4 | 2-(4-(4-(aminomethyl)-1-oxo-1,2-dihydrophthalazin-6-yl)-1-methyl-1H-pyrazol-5-yl)-4,6-dichlorobenzonitrile<br>LCMS [M + 1]⁺ = 425.1; 1H NMR (400 MHz, DMSO-d6) δ = 12.90 (s, 1H), 8.46-8.31 (br s, 3H), 8.28 (s, 1H), 8.28-8.26 (m, 1H), 8.14 (d, J = 8.4 Hz, 1H), 8.03 (d, J = 2.0 Hz, 1H), 7.84 (d, J = 1.6 Hz, 1H), 7.45 (dd, J = 1.6, 8.4 Hz, 1H), 4.46-4.30 (m, 2H), 3.79 (s, 3H) |
| 4-166 | 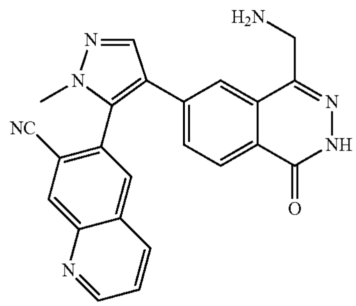 [SMILES: Cn1ncc(-c2ccc3c(=O)[nH]nc(CN)c3c2)c1-c1cc2cccnc2cc1C#N] | 4B | 4-4 | 6-(4-(4-(aminomethyl)-1-oxo-1,2-dihydrophthalazin-6-yl)-1-methyl-1H-pyrazol-5-yl)quinoline-7-carbonitrile<br>LCMS [M + 1]⁺ = 408.2; 1H NMR (400 MHz, DMSO-d6) δ = 12.84 (s, 1H), 9.18 (dd, J = 1.6, 4.4 Hz, 1H), 8.82 (s, 1H), 8.56 (d, J = 8.8 Hz, 1H), 8.47 (s, 1H), 8.34 (s, 1H), 8.33-8.23 (m, 3H), 8.03 (d, J = 8.4 Hz, 1H), 7.86 (d, J = 1.2 Hz, 1H), 7.83 (dd, J = 4.4, 8.4 Hz, 1H), 7.40 (dd, J = 1.6, 8.4 Hz, 1H), 4.33-4.23 (m, 2H), 3.78 (s, 3H) |
| 4-167 | 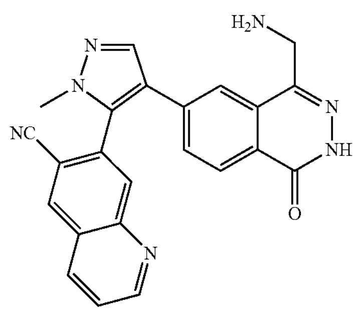 [SMILES: Cn1ncc(-c2ccc3c(=O)[nH]nc(CN)c3c2)c1-c1cc2ncccc2cc1C#N] | 4B | 4-4 | 7-(4-(4-(aminomethyl)-1-oxo-1,2-dihydrophthalazin-6-yl)-1-methyl-1H-pyrazol-5-yl)quinoline-6-carbonitrile<br>LCMS [M + 1]⁺ = 408.2; 1H NMR (400 MHz, DMSO-d6) δ = 12.84 (s, 1H), 9.17 (dd, J = 1.6, 4.4 Hz, 1H), 8.90 (s, 1H), 8.62 (d, J = 7.6 Hz, 1H), 8.40 (s, 1H), 8.36-8.25 (m, 4H), 8.02 (d, J = 8.4 Hz, 1H), 7.89 (d, J = 1.2 Hz, 1H), 7.83 (dd, J = 4.4, 8.4 Hz, 1H), 7.37 (dd, J = 1.6, 8.4 Hz, 1H), 4.30 (br t, J = 5.6 Hz, 2H), 3.80 (s, 3H) |
| 4-168 | 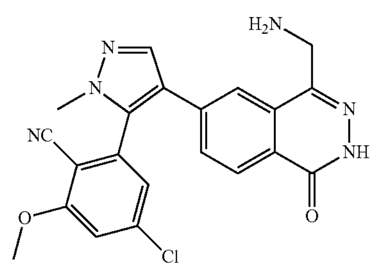 [SMILES: COc1cc(Cl)cc(-c2c(-c3ccc4c(=O)[nH]nc(CN)c4c3)cnn2C)c1C#N] | 4B | 4-5 | 2-(4-(4-(aminomethyl)-1-oxo-1,2-dihydrophthalazin-6-yl)-1-methyl-1H-pyrazol-5-yl)-4-chloro-6-methoxybenzonitrile<br>LCMS [M + 1]⁺ = 421.2; 1H NMR (400 MHz, DMSO-d6) δ = 12.88 (s, 1H), 8.39 (br s, 3H), 8.26 (s, 1H), 8.13 (d, J = 8.4 Hz, 1H), 7.81 (s, 1H), 7.64 (d, J = 1.6 Hz, 1H), 7.48 (d, J = 1.6 Hz, 1H), 7.44 (d, J = 8.4 Hz, 1H), 4.48-4.25 (m, 2H), 4.01 (s, 3H), 3.75 (s, 3H) |
| 4-169 | 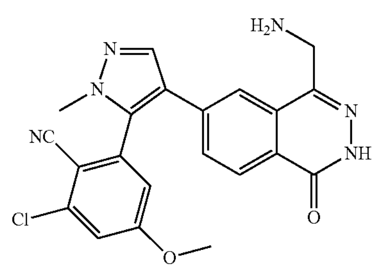 [SMILES: COc1cc(Cl)c(C#N)c(-c2c(-c3ccc4c(=O)[nH]nc(CN)c4c3)cnn2C)c1] | 4B | 4-6 | 2-(4-(4-(aminomethyl)-1-oxo-1,2-dihydrophthalazin-6-yl)-1-methyl-1H-pyrazol-5-yl)-6-chloro-4-methoxybenzonitrile<br>LCMS [M + 1]⁺ = 421.1; ¹H NMR (400 MHz, DMSO-d₆) δ = 12.86 (s, 1H), 8.60 (br s, 3H), 8.32 (s, 1H), 8.12 (d, J = 8.4 Hz, 1H), 7.81 (d, J = 1.2 Hz, 1H), 7.59 (d, J = 2.4 Hz, 1H), 7.47 (dd, J = 1.6, 8.4 Hz, 1H), 7.40 (d, J = 2.4 Hz, 1H), 4.40-4.22 (m, 2H), 3.96 (s, 3H), 3.76 (s, 3H) |

TABLE 4-continued

| Example | Structure | CM | PM | Compound Name and Characterization |
|---|---|---|---|---|
| 4-170 | 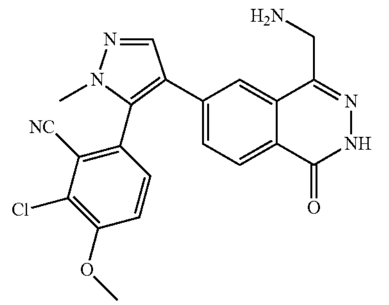 [SMILES: COc1ccc(-c2c(-c3ccc4c(=O)[nH]nc(CN)c4c3)cnn2C)c(C#N)c1Cl] | 4B | 4-4 | 6-(4-(4-(aminomethyl)-1-oxo-1,2-dihydrophthalazin-6-yl)-1-methyl-1H-pyrazol-5-yl)-2-chloro-3-methoxybenzonitrile<br>LCMS [M + 1]⁺ = 421.1; 1H NMR (400 MHz, DMSO-d6) δ = 12.87 (s, 1H), 8.37 (br s, 3H), 8.27 (s, 1H), 8.11 (d, J = 8.4 Hz, 1H), 7.83 (d, J = 1.2 Hz, 1H), 7.73 (d, J = 8.8 Hz, 1H), 7.70 (d, J = 8.8 Hz, 1H), 7.43 (dd, J = 1.2, 8.4 Hz, 1H), 4.43-4.29 (m, 2H), 4.04 (s, 3H), 3.73 (s, 3H) |
| 4-171 | 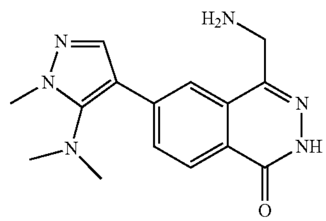 [SMILES: CN(C)c1c(-c2ccc3c(=O)[nH]nc(CN)c3c2)cnn1C] | 4B | 4-8 | 4-(aminomethyl)-6-(5-(dimethylamino)-1-methyl-1H-pyrazol-4-yl)phthalazin-1(2H)-one<br>LCMS [M + 1]⁺ = 299.1; 1H NMR (400 MHz, DMSO-d6) δ = 12.43 (s, 1H), 8.22 (d, J = 8.4 Hz, 1H), 8.07 (s, 1H), 7.86-8.92 (m, 1H), 7.77 (s, 1H), 4.03 (s, 2H), 3.74 (s, 3H), 2.80 (s, 6H), 2.12-2.31 (m, 2H) |
| 4-172 | 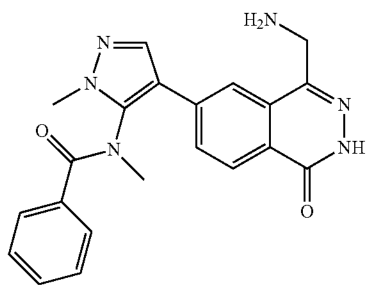 [SMILES: CN(C(=O)c1ccccc1)c1c(-c2ccc3c(=O)[nH]nc(CN)c3c2)cnn1C] | 4B | 4-8 | N-(4-(4-(aminomethyl)-1-oxo-1,2-dihydrophthalazin-6-yl)-1-methyl-1H-pyrazol-5-yl)-N-methylbenzamide<br>LCMS [M + 1]⁺ = 389.2; 1H NMR (400 MHz, DMSO-d6) δ = 12.47 (s, 1H), 8.17 (d, J = 8.0 Hz, 1H), 7.92 (s, 1H), 7.80 (d, J = 1.2 Hz, 1H), 7.63-7.72 (m, 1H), 7.19-7.31 (m, 1H), 7.02-7.12 (m, 2H), 6.83-6.93 (m, 2H), 3.99 (s, 2H), 3.83 (s, 3H), 3.45 (s, 3H), 1.80-2.24 (m, 2H). |
| 4-173 | 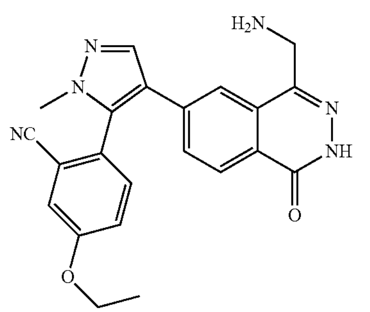 [SMILES: CCOc1ccc(-c2c(-c3ccc4c(=O)[nH]nc(CN)c4c3)cnn2C)c(C#N)c1] | 4B | 4-4 | 2-(4-(4-(aminomethyl)-1-oxo-1,2-dihydrophthalazin-6-yl)-1-methyl-1H-pyrazol-5-yl)-5-ethoxybenzonitrile<br>LCMS [M + 1]⁺ = 401.1; 1H NMR (400 MHz, DMSO-d6) δ = 12.85 (s, 1H), 8.37 (br s, 3H), 8.25 (s, 1H), 8.10 (d, J = 8.4 Hz, 1H), 7.78 (d, J = 1.2 Hz, 1H), 7.66 (d, J = 8.8 Hz, 1H), 7.64 (d, J = 2.8 Hz, 1H), 7.46 (dd, J = 2.8, 8.8 Hz, 1H), 7.42 (dd, J = 1.6, 8.4 Hz, 1H), 4.39-4.27 (m, 2H), 4.19 (q, J = 6.8 Hz, 2H), 3.71 (s, 3H), 1.38 (t, J = 7.2 Hz, 3H) |
| 4-174 | 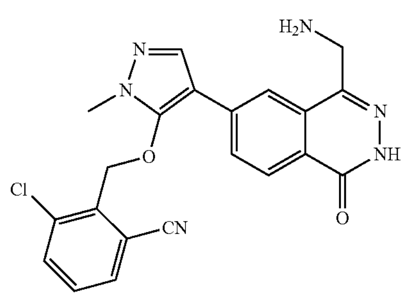 [SMILES: Cn1ncc(-c2ccc3c(=O)[nH]nc(CN)c3c2)c1OCc1c(Cl)cccc1C#N] | 4B | 4-5 | 2-(((4-(4-(aminomethyl)-1-oxo-1,2-dihydrophthalazin-6-yl)-1-methyl-1H-pyrazol-5-yl)oxy)methyl)-3-chlorobenzonitrile<br>LCMS [M + 1]⁺ = 421.2; 1H NMR (400 MHz, DMSO-d6) δ = 12.87 (s, 1H), 8.44 (br s, 3H), 8.18 (d, J = 8.4 Hz, 1H), 7.94 (s, 1H), 7.89 (dd, J = 1.6, 8.4 Hz, 1H), 7.82 (d, J = 1.2 Hz, 1H), 7.68-7.63 (m, 1H), 7.63-7.59 (m, 1H), 7.55 (dd, J = 1.6, 7.2 Hz, 1H), 5.23 (s, 2H), 4.46 (s, 2H), 3.75 (s, 3H) |

TABLE 4-continued

| Example | Structure | CM | PM | Compound Name and Characterization |
|---|---|---|---|---|
| 4-175 | 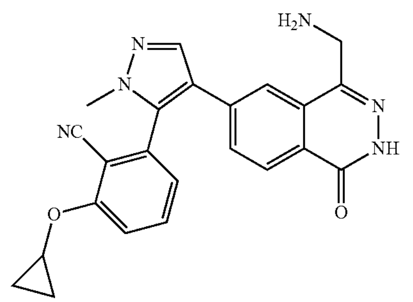 [SMILES: Cn1ncc(-c2ccc3c(=O)[nH]nc(CN)c3c2)c1-c1cccc(OC2CC2)c1C#N] | 4B | 4-4 | 2-(4-(4-(aminomethyl)-1-oxo-1,2-dihydrophthalazin-6-yl)-1-methyl-1H-pyrazol-5-yl)-6-cyclopropoxybenzonitrile LCMS [M + 1]$^+$ = 413.0; 1H NMR (400 MHz, DMSO-d6) δ = 12.87 (s, 1H), 8.41-8.29 (br s, 3H), 8.26 (s, 1H), 8.10 (d, J = 8.4 Hz, 1H), 7.93-7.88 (m, 1H), 7.75-7.71 (m, 2H), 7.44 (dd, J = 1.6, 8.4 Hz, 1H), 7.32 (d, J = 7.2 Hz, 1H), 4.29 (m, 2H), 4.13 (tt, J = 2.8, 6.4 Hz, 1H), 3.72 (s, 3H), 0.91-0.78 (m, 4H) |
| 4-176 | 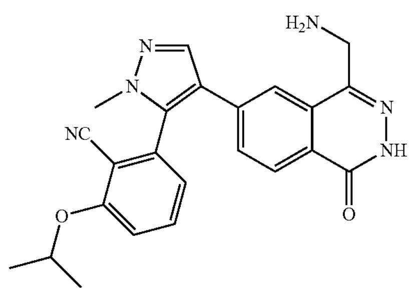 [SMILES: CC(C)Oc1cccc(-c2c(-c3ccc4c(=O)[nH]nc(CN)c4c3)cnn2C)c1C#N] | 4B | 4-4 | 2-(4-(4-(aminomethyl)-1-oxo-1,2-dihydrophthalazin-6-yl)-1-methyl-1H-pyrazol-5-yl)-6-isopropoxybenzonitrile LCMS [M + 1]$^+$ = 415.1; 1H NMR (400 MHz, DMSO-d6) = 12.87 (br s, 3H), 8.27 (s, 1H), 8.09 (d, J = 8.4 Hz, 1H), 7.84 (dd, J = 7.6, 8.8 Hz, 1H), 7.79 (d, J = 0.8 Hz, 1H), 7.50 (d, J = 8.8 Hz, 1H), 7.42 (dd, J = 1.2, 8.0 Hz, 1H), 7.26 (d, J = 7.2 Hz, 1H), 4.89 (td, J = 6.0, 12.0 Hz, 1H), 4.39-4.23 (m, 2H), 3.72 (s, 3H), 1.34 (dd, J = 1.2, 6.0 Hz, 6H) |
| 4-177 | 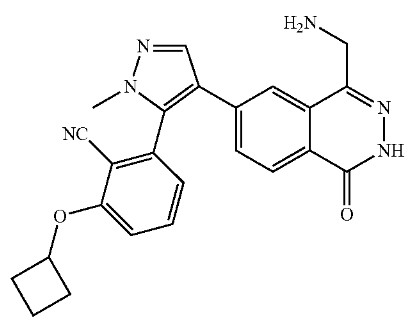 [SMILES: Cn1ncc(-c2ccc3c(=O)[nH]nc(CN)c3c2)c1-c1cccc(OC2CCC2)c1C#N] | 4B | 4-4 | 2-(4-(4-(aminomethyl)-1-oxo-1,2-dihydrophthalazin-6-yl)-1-methyl-1H-pyrazol-5-yl)-6-cyclobutoxybenzonitrile LCMS [M + 1]$^+$ = 427.3; 1H NMR (400 MHz, DMSO-d6) δ = 12.87 (s, 1H), 8.38 (br s, 3H), 8.26 (s, 1H), 8.10 (d, J = 8.4 Hz, 1H), 7.82 (dd, J = 7.6, 8.4 Hz, 1H), 7.75 (s, 1H), 7.43 (d, J = 8.4 Hz, 1H), 7.29 (d, J = 8.8 Hz, 1H), 7.26 (d, J = 7.6 Hz, 1H), 4.93 (t, J = 7.2 Hz, 1H), 4.38-4.21 (m, 2H), 3.72 (s, 3H), 2.55-2.51 (m, 2H), 2.21-2.05 (m, 2H), 1.83 (q, J = 10.2 Hz, 1H), 1.75-1.59 (m, 1H) |
| 4-178 | 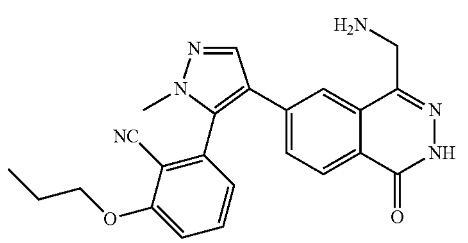 [SMILES: CCCOc1cccc(-c2c(-c3ccc4c(=O)[nH]nc(CN)c4c3)cnn2C)c1C#N] | 4B | 4-4 | 2-(4-(4-(aminomethyl)-1-oxo-1,2-dihydrophthalazin-6-yl)-1-methyl-1H-pyrazol-5-yl)-6-propoxybenzonitrile LCMS [M + 1]$^+$ = 415.3; 1H NMR (400 MHz, DMSO-d6) δ = 12.86 (s, 1H), 8.59 (br s, 3H), 8.31 (s, 1H), 8.09 (d, J = 8.4 Hz, 1H), 7.86 (dd, J = 8.0, 8.4 Hz, 1H), 7.76 (d, J = 1.2 Hz, 1H), 7.48 (d, J = 8.8 Hz, 1H), 7.45 (dd, J = 1.6, 8.4 Hz, 1H), 7.27 (d, J = 7.6 Hz, 1H), 4.30-4.13 (m, 4H), 3.72 (s, 3H), 1.77 (q, J = 7.6 Hz, 2H), 0.99 (t, J = 7.6 Hz, 3H) |
| 4-179 | 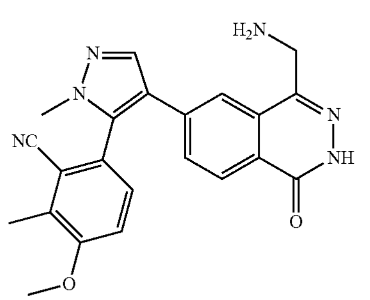 [SMILES: COc1ccc(-c2c(-c3ccc4c(=O)[nH]nc(CN)c4c3)cnn2C)c(C#N)c1C] | 4B | 4-4 | 6-(4-(4-(aminomethyl)-1-oxo-1,2-dihydrophthalazin-6-yl)-1-methyl-1H-pyrazol-5-yl)-3-methoxy-2-methylbenzonitrile LCMS [M + 1]$^+$ = 401.2; 1H NMR (400 MHz, DMSO-d6) δ = 12.85 (s, 1H), 8.35 (br s, 3H), 8.26 (s, 1H), 8.09 (d, J = 8.4 Hz, 1H), 7.78 (s, 1H), 7.54 (d, J = 8.4 Hz, 1H), 7.48 (d, J = 8.4 Hz, 1H), 7.44 (d, J = 9.6 Hz, 1H), 4.37-4.26 (m, 2H), 3.96 (s, 3H), 3.69 (s, 3H), 2.39 (s, 3H) |

TABLE 4-continued

| Example | Structure | CM | PM | Compound Name and Characterization |
|---|---|---|---|---|
| 4-180 | 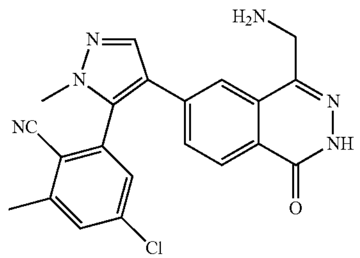 [SMILES: Cc1cc(Cl)cc(-c2c(-c3ccc4c(=O)[nH]nc(CN)c4c3)cnn2C)c1C#N] | 4B | 4-4 | 2-(4-(4-(aminomethyl)-1-oxo-1,2-dihydrophthalazin-6-yl)-1-methyl-1H-pyrazol-5-yl)-4-chloro-6-methylbenzonitrile LCMS [M + 1]$^+$ = 405.1; 1H NMR (400 MHz, DMSO-d6) δ = 12.87 (s, 1H), 8.37 (br s, 3H), 8.28 (s, 1H), 8.12 (d, J = 8.4 Hz, 1H), 7.86 (d, J = 1.6 Hz, 1H), 7.77 (dd, J = 1.6, 7.2 Hz, 2H), 7.46 (dd, J = 1.6, 8.4 Hz, 1H), 4.36-4.26 (m, 2H), 3.74 (s, 3H), 2.54 (s, 3H) |
| 4-181 | 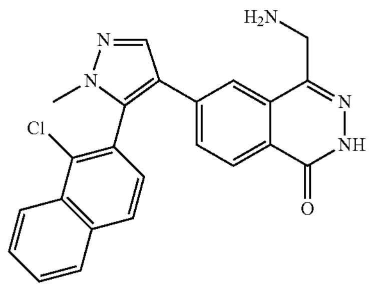 | 4D | 4-4 | 4-(aminomethyl)-6-(5-(1-chloronaphthalen-2-yl)-1-methyl-1H-pyrazol-4-yl)phthalazin-1(2H)-one LCMS [M + 1]$^+$ = 416.3; $^1$H NMR (400 MHz, DMSO-d$_6$) δ = 12.82 (s, 1H), 8.38-8.26 (m, 5H), 8.21-8.11 (m, 2H), 7.99 (d, J = 8.5 Hz, 1H), 7.89 (d, J = 1.5 Hz, 1H), 7.83-7.77 (m, 2H), 7.60 (d, J = 8.5 Hz, 1H), 7.35 (dd, J = 1.5, 8.0 Hz, 1H), 4.44-4.23 (m, 2H), 3.67 (s, 3H) |
| 4-182 | 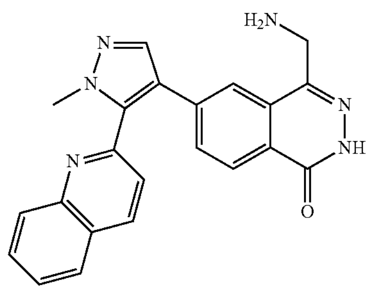 [SMILES: Cn1ncc(-c2ccc3c(=O)[nH]nc(CN)c3c2)c1-c1ccc2ccccc2n1] | 4D | 4-4 | 4-(aminomethyl)-6-(1-methyl-5-(quinolin-2-yl)-1H-pyrazol-4-yl)phthalazin-1(2H)-one LCMS [M + 1]$^+$ = 383.2; $^1$H NMR (400 MHz, DMSO-d$_6$) δ = 12.86 (s, 1H), 8.45 (s, 1H), 8.40 (br s, 3H), 8.16-8.11 (m, 2H), 8.10-8.04 (m, 2H), 7.98 (d, J = 1.2 Hz, 1H), 7.87 (dt, J = 1.2, 7.6 Hz, 1H), 7.76-7.69 (m, 1H), 7.53 (dd, J = 1.2, 8.4 Hz, 1H), 7.47 (d, J = 8.4 Hz, 1H), 4.36 (br d, J = 4.8 Hz, 2H), 3.99 (s, 3H) |
| 4-183 | 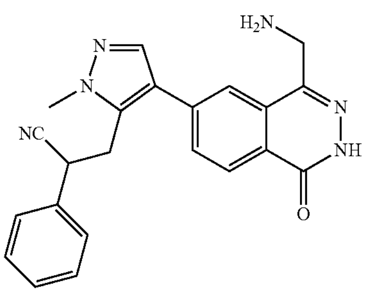 [SMILES: Cn1ncc(-c2ccc3c(=O)[nH]nc(CN)c3c2)c1CC(C#N)c1ccccc1] | 4D | 4-4 | 3-(4-(4-(aminomethyl)-1-oxo-1,2-dihydrophthalazin-6-yl)-1-methyl-1H-pyrazol-5-yl)-2-phenylpropanenitrile LCMS [M + 1]$^+$ = 385.1; $^1$H NMR (400 MHz, DMSO-d$_6$) δ = 12.90 (s, 1H), 8.47 (br d, J = 14.0 Hz, 3H), 8.23 (d, J = 8.4 Hz, 1H), 7.85 (d, J = 8.4 Hz,1H), 7.81 (s, 1H), 7.75 (d, J = 1.2 Hz, 1H), 7.27-7.21 (m, 3H), 7.21-7.14 (m, 2H), 4.65-4.45 (m, 2H),4.42 (t, J = 7.6 Hz, 1H), 3.82 (s, 3H), 3.76-3.67 (m, 1H), 3.66-3.57 (m, 1H) |
| 4-184 | 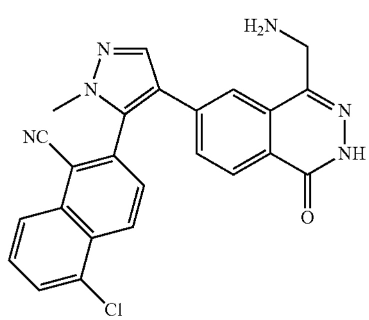 | 4D | 4-6 | 2-(4-(4-(aminomethyl)-1-oxo-1,2-dihydrophthalazin-6-yl)-1-methyl-1H-pyrazol-5-yl)-5-chloro-1-naphthonitrile LCMS [M + 1]$^+$ = 441.1; $^1$H NMR (400 MHz, DMSO-d$_6$) δ = 12.84 (s, 1H), 8.70 (d, J = 8.8 Hz, 1H), 8.54-8.39 (m, 3H), 8.38-8.34 (m, 1H), 8.16 (d, J = 8.4 Hz, 1H), 8.04 (d, J = 7.6 Hz, 1H), 8.02-7.93 (m, 3H), 7.90-7.85 (m, 1H), 7.36-7.24 (m, 1H), 4.34 (br s, 2H), 3.78 (s, 3H) |

TABLE 4-continued

| Example | Structure | CM | PM | Compound Name and Characterization |
|---|---|---|---|---|
| 4-185 | 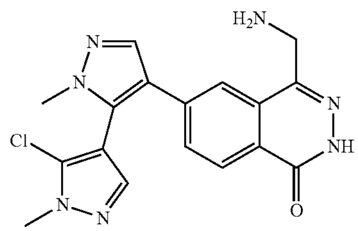 [SMILES: Cn1ncc(-c2c(-c3ccc4c(=O)[nH]nc(CN)c4c3)cnn2C)c1Cl] | | 4D | 4-(aminomethyl)-6-(5'-chloro-1',2-dimethyl-1'H,2H-[3,4'-bipyrazol]-4-yl)phthalazin-1(2H)-one<br>LCMS [M + 1]$^+$ = 370.0; $^1$H NMR (400 MHz, DMSO-d$_6$) δ = 12.86 (s, 1H), 8.43-8.30 (br s, 3H), 8.19 (s, 1H), 8.16 (d, J = 8.4 Hz, 1H), 7.92 (s, 1H), 7.81 (d, J = 1.2 Hz, 1H), 7.68 (dd, J = 1.6, 8.4 Hz, 1H), 4.40-4.32 (m, 2H), 3.90 (s, 3H), 3.74 (s, 3H) |
| 4-186 | 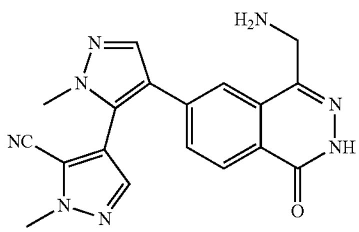 [SMILES: Cn1ncc(-c2c(-c3ccc4c(=O)[nH]nc(CN)c4c3)cnn2C)c1C#N] | | 4D | 4-(4-(aminomethyl)-1-oxo-1,2-dihydrophthalazin-6-yl)-1',2-dimethyl-1'H,2H-[3,4'-bipyrazole]-5'-carbonitrile<br>LCMS [M + 1] = 361.1; $^1$H NMR (400 MHz, DMSO-d$_6$) δ = 12.89 (s, 1H), 8.40-8.31 (br s, 3H), 8.19-8.17 (m, 2H), 8.10 (s, 1H), 7.83 (d, J = 1.2 Hz, 1H), 7.67 (dd, J = 1.6, 8.4 Hz, 1H), 4.42-4.34 (m, 2H), 4.09 (s, 3H), 3.83 (s, 3H) |
| 4-187 | 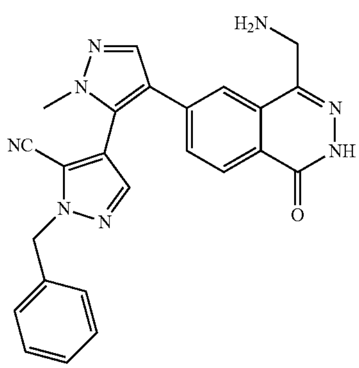 | | 4D | 4-(aminomethyl)-6-(1'-benzyl-5'-chloro-2-methyl-1'H,2H-[3,4'-bipyrazol]-4-yl)phthalazin-1(2H)-one<br>LCMS [M + 1]$^+$ = 446.1; $^1$H NMR (400 MHz, DMSO-d$_6$) δ = 12.86 (s, 1H), 8.50 (br s, 3H), 8.21 (s, 1H), 8.07 (d, J = 8.4 Hz, 1H), 8.05 (s, 1H), 7.89 (d, J = 1.2 Hz, 1H), 7.53 (dd, J = 1.6, 8.4 Hz, 1H), 7.42-7.27 (m, 3H), 7.19-7.11 (m, 2H), 5.48 (s, 2H), 4.44-4.31 (m, 2H), 3.75 (s, 3H). |
| 4-188 | 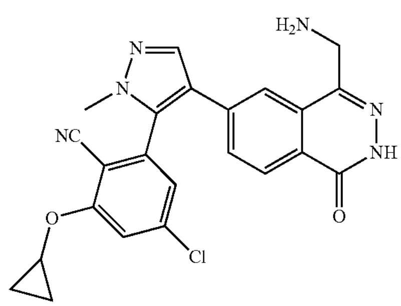 [SMILES: Cn1ncc(-c2ccc3c(=O)[nH]nc(CN)c3c2)c1-c1cc(Cl)cc(OC2CC2)c1C#N] | | 4D | 2-(4-(4-(aminomethyl)-1-oxo-1,2-dihydrophthalazin-6-yl)-1-methyl-1H-pyrazol-5-yl)-4-chloro-6-cyclopropoxybenzonitrile<br>LCMS [M + 1]$^+$ = 447.1; $^1$H NMR (400 MHz, DMSO-d$_6$) δ = 12.87 (s, 1H), 8.53 (br s, 3H), 8.28 (s, 1H), 8.12 (d, J = 8.4 Hz, 1H), 7.80 (d, J = 1.8 Hz, 2H), 7.51 (d, J = 1.8 Hz, 1H), 7.44 (dd, J = 1.6, 8.4 Hz, 1H), 4.48-4.26 (m, 2H), 4.21 (td, J = 3.2, 6.0 Hz, 1H), 3.74 (s, 3H), 0.98-0.87 (m, 2H), 0.86-0.73 (m, 2H) |
| 4-189* | | | 4D | 4-4 | 2-(4-(4-(aminomethyl)-1-oxo-1,2-dihydrophthalazin-6-yl)-1-methyl-1H-pyrazol-5-yl)-6-propylbenzonitrile<br>LCMS [M + 1]$^+$ = 399.2; $^1$H NMR (400 MHz, CD$_3$OD-d$_4$) δ = 8.19-8.13 (m, 2H), 7.87-7.81 (m, 1H), 7.74 (s, 1H), 7.67 (d, J = 8.0 Hz, 1H), 7.58 (d, J = 7.6 Hz, 1H), 7.51-7.45 (m, 1H), 4.48-4.32 (m, 2H), 3.80 (s, 3H), 2.90-2.83 (m, 2H), 1.74-1.63 (m, 2H) 0.97-0.91 (m, 3H) |

TABLE 4-continued

| Example | Structure | CM | PM | Compound Name and Characterization |
|---|---|---|---|---|
| 4-190 | 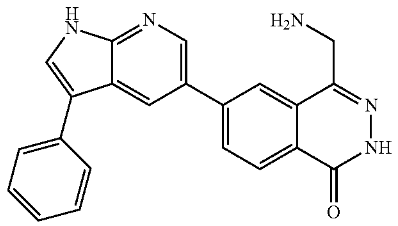 [SMILES: NCc1n[nH]c(=O)c2ccc(-c3cnc4[nH]cc(-c5ccccc5)c4c3)cc12] | 4B | 4-6 | 4-(aminomethyl)-6-(3-phenyl-1H-pyrrolo[2,3-b]pyridin-5-yl)phthalazin-1(2H)-one<br>LCMS [M + 1]$^+$ = 368.2; $^1$H NMR (400 MHz, DMSO-d$_6$) δ = 12.94 (s, 1H), 12.19 (br d, J = 7.2 Hz, 1H), 8.85 (s, 1H), 8.71 (s, 1H), 8.57 (br d, J = 1.2 Hz, 3H), 8.38 (s, 2H), 8.31 (br s, 1H), 7.99 (d, J = 2.4 Hz, 1H), 7.84 (d, J = 7.6 Hz, 2H), 7.47 (t, J = 7.6 Hz, 2H), 7.29 (t, J = 7.2 Hz, 1H), 4.63 (br s, 2H) |
| 4-191 | 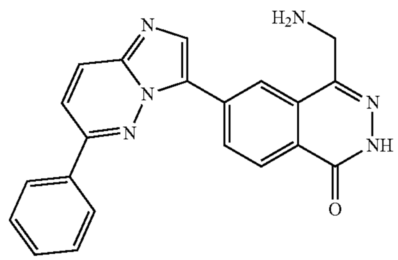 [SMILES: NCc1n[nH]c(=O)c2ccc(-c3cnc4ccc(-c5ccccc5)nn34)cc12] | 4B | 4-4 | 4-(aminomethyl)-6-(6-phenylimidazo[1,2-b]pyridazin-3-yl)phthalazin-1(2H)-one<br>LCMS [M + 1]$^+$ = 369.1; $^1$H NMR (400 MHz, DMSO-d$_6$) δ = 12.98 (s, 1H), 8.88 (d, J = 1.2 Hz, 1H), 8.78 (dd, J = 1.6, 8.4 Hz, 1H), 8.67 (s, 1H), 8.50 (br s, 3H), 8.44 (d, J = 8.4 Hz, 1H), 8.41 (d, J = 9.6 Hz, 1H), 8.22 (d, J = 7.2 Hz, 2H), 8.02 (d, J = 9.6 Hz, 1H), 7.71-7.57 (m, 3H), 4.63 (br s, 2H) |
| 4-192 | 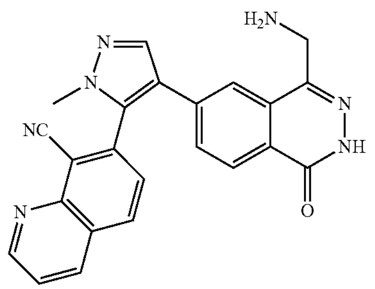 [SMILES: Cn1ncc(-c2ccc3c(=O)[nH]nc(CN)c3c2)c1-c1ccc2cccnc2c1C#N] | 4D | 4-9 | 7-(4-(4-(aminomethyl)-1-oxo-1,2-dihydrophthalazin-6-yl)-1-methyl-1H-pyrazol-5-yl)quinoline-8-carbonitrile<br>LCMS [M + 1]$^+$ = 408.2; $^1$H NMR (400 MHz, CD$_3$OD) δ = 9.09 (dd, J = 1.6, 4.0 Hz, 1H), 8.59 (dd, J = 1.6, 8.4 Hz, 1H), 8.47 (d, J = 8.4 Hz, 1H), 8.17 (s, 1H), 8.12 (d, J = 8.4 Hz, 1H), 7.87 (d, J = 8.4 Hz, 1H), 7.84 (s, 1H), 7.79 (dd, J = 4.4, 8.4 Hz, 1H), 7.46 (dd, J = 1.6, 8.4 Hz, 1H), 4.46-4.30 (m, 2H), 3.88 (s, 3H) |
| 4-193 | 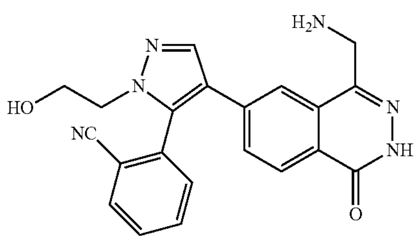 [SMILES: N#Cc1ccccc1-c1c(-c2ccc3c(=O)[nH]nc(CN)c3c2)cnn1CCO] | 4D | 4-2 | 2-(4-(4-(aminomethyl)-1-oxo-1,2-dihydrophthalazin-6-yl)-1-(2-hydroxyethyl)-1H-pyrazol-5-yl)benzonitrile<br>LCMS [M + 1]$^+$ = 387.3; $^1$H NMR (400 MHz, DMSO-d$_6$) δ = 12.50-12.33 (br s, 1H), 8.24 (s, 1H), 8.11 (d, J = 8.4 Hz, 1H), 8.04 (d, J = 7.2 Hz, 1H), 7.98-7.92 (m, 1H), 7.85-7.76 (m, 2H), 7.65 (dd, J = 1.6, 8.4 Hz, 1H), 7.54 (s, 1H), 4.98-4.76 (m, 1H), 4.08-4.01 (br s, 1H), 3.99-3.92 (m, 1H), 3.79-3.73 (m, 1H), 3.70-3.65 (m, 1H), 3.63 (br s, 2H) |
| 4-194 | 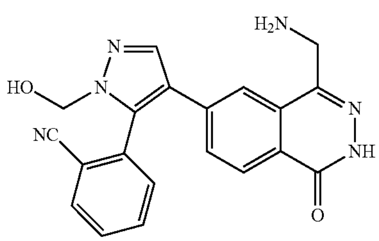 [SMILES: N#Cc1ccccc1-c1c(-c2ccc3c(=O)[nH]nc(CN)c3c2)cnn1CO] | 4D | 4-2 | 2-(5-(4-(aminomethyl)-1-oxo-1,2-dihydrophthalazin-6-yl)-2-(hydroxymethyl)-1H-imidazol-1-yl)benzonitrile<br>LCMS [M + 1]$^+$ = 373.3; $^1$H NMR (400 MHz, DMSO-d$_6$) δ = 12.91 (s, 1H), 8.50-8.33 (br s, 3H), 8.13 (d, J = 8.8 Hz, 1H), 8.00-7.93 (m, 3H), 7.75 (ddd, J = 2.8, 6.4, 7.6 Hz, 1H), 7.69 (s, 1H), 7.58-7.50 (m, 2H), 5.37 (t, J = 5.6 Hz, 1H), 4.46 (br d, J = 5.6 Hz, 1H), 4.34 (dd, J = 5.6, 13.2 Hz, 1H), 4.26-4.18 (m, 1H), 4.04 (br d, J = 16.0 Hz, 1H) |
| 4-195 | 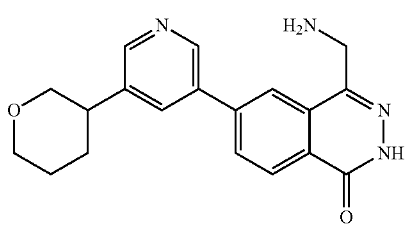 [SMILES: NCc1n[nH]c(=O)c2ccc(-c3cncc(C4CCCOC4)c3)cc12] | 4D | 4-4 | 4-(aminomethyl)-6-(5-(tetrahydro-2H-pyran-3-yl)pyridin-3-yl)phthalazin-1(2H)-one<br>LCMS [M + 1]$^+$ = 337.1; $^1$H NMR (400 MHz, DMSO-d$_6$) δ = 13.01 (s, 1H), 9.07 (d, J = 2.0 Hz, 1H), 8.69 (d, J = 2.0 Hz, 1H), 8.49 (br s, 3H), 8.40 (d, J = 2.0 Hz, 1H), 8.34 (t, J = 1.6 Hz, 1H), 8.32 (d, J = 1.6, 8.0 Hz, 1H), 8.28 (s, 1H), 4.62 (br d, J = 5.6 Hz, 2H), 3.98-3.85 (m, 2H), 3.56-3.40 (m, 2H), 3.09-2.90 (m, 1H), 2.07-1.86 (m, 2H), 1.74-1.63 (m, 2H) |

| Example | Structure | CM | PM | Compound Name and Characterization |
| --- | --- | --- | --- | --- |
| 4-196 | 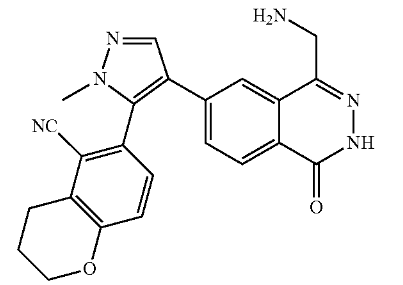 [SMILES: Cn1ncc(-c2ccc3c(=O)[nH]nc(CN)c3c2)c1-c1ccc2c(c1C#N)CCCO2] | 4D | 4-4 | 6-(4-(4-(aminomethyl)-1-oxo-1,2-dihydrophthalazin-6-yl)-1-methyl-1H-pyrazol-5-yl)chromane-5-carbonitrile<br>LCMS [M + 1]$^+$ = 435.2; $^1$H NMR (400 MHz, DMSO-d$_6$) δ = 12.85 (s, 1H), 8.39 (br s, 3H), 8.25 (s, 1H), 8.11 (d, J = 8.4 Hz, 1H), 7.72 (d, J = 1.2 Hz, 1H), 7.50 (dd, J = 1.6, 8.4 Hz, 1H), 7.42 (d, J = 8.4 Hz, 1H), 7.28 (d, J = 8.4 Hz, 1H), 4.33-4.22 (m, 4H), 3.70 (s, 3H), 2.90 (br t, J = 6.4 Hz, 2H), 2.07-1.98 (m, 2H) |
| 4-197 | 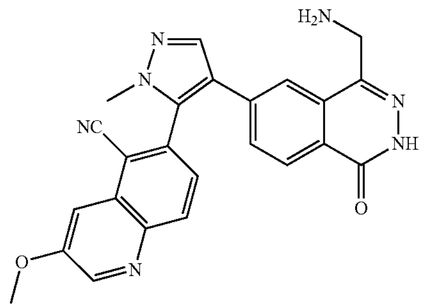 [SMILES: COc1cnc2ccc(-c3c(-c4ccc5c(=O)[nH]nc(CN)c5c4)cnn3C)c(C#N)c2c1] | 4D | 4-4 | 6-(4-(4-(aminomethyl)-1-oxo-1,2-dihydrophthalazin-6-yl)-1-methyl-1H-pyrazol-5-yl)-3-methoxyquinoline-5-carbonitrile<br>LCMS [M + 1]$^+$ = 438.2; $^1$H NMR (500 MHz, CD$_3$OD) δ = 8.86 (d, J = 3.0 Hz, 1H), 8.48 (d, J = 8.5 Hz, 1H), 8.19 (s, 1H), 8.15 (d, J = 8.5 Hz, 1H), 7.85 (d, J = 8.5 Hz, 1H), 7.77 (s, 1H), 7.73 (d, J = 2.5 Hz, 1H), 7.55-7.49 (m, 1H), 4.50-4.20 (m, 2H), 4.05 (s, 3H), 3.87 (s, 3H) |
| 4-198 | 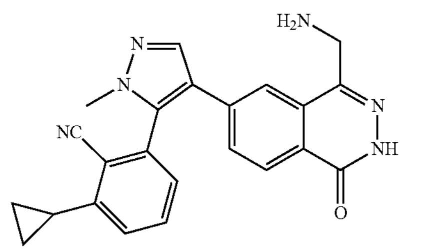 [SMILES: Cn1ncc(-c2ccc3c(=O)[nH]nc(CN)c3c2)c1-c1cccc(C2CC2)c1C#N] | 4E | 4-2 | 2-(4-(4-(aminomethyl)-1-oxo-1,2-dihydrophthalazin-6-yl)-1-methyl-1H-pyrazol-5-yl)-6-cyclopropylbenzonitrile<br>LCMS [M + 1]$^+$ = 397.3; $^1$H NMR (400 MHz, CD$_3$OD) δ = 8.23 (d, J = 8.4 Hz, 1H), 8.14 (s, 1H), 7.81-7.75 (m, 1H), 7.70 (d, J = 8.4 Hz, 1H), 7.57 (s, 1H), 7.50-7.45 (m, 1H), 7.30 (d, J = 8.0 Hz, 1H), 3.85 (s, 2H), 3.80 (s, 3H), 2.36-2.19 (m, 1H), 1.24-1.17 (m, 2H), 0.98-0.86 (m, 2H) |
| 4-199 | 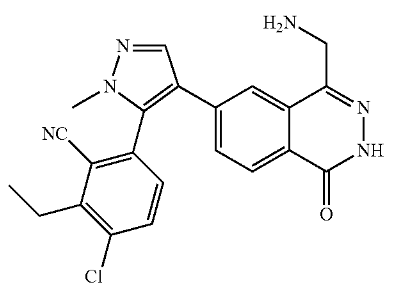 [SMILES: CCc1c(Cl)ccc(-c2c(-c3ccc4c(=O)[nH]nc(CN)c4c3)cnn2C)c1C#N] | 4D | 4-4<br>4-11 | 6-(4-(4-(aminomethyl)-1-oxo-1,2-dihydrophthalazin-6-yl)-1-methyl-1H-pyrazol-5-yl)-3-chloro-2-ethylbenzonitrile<br>LCMS [M + 1]$^+$ = 419.1; $^1$H NMR (400 MHz, DMSO-d$_6$) δ = 12.83 (br s, 1H), 8.28 (s, 1H), 8.10 (d, J = 8.4 Hz, 1H), 8.01 (d, J = 8.0 Hz, 1H), 7.79 (d, J = 1.2 Hz, 1H), 7.66 (d, J = 8.4 Hz, 1H), 7.41 (dd, J = 1.2, 8.4 Hz, 1H), 4.36-4.20 (m, 2H), 3.74 (s, 3H), 2.95 (q, J = 7.6 Hz, 2H), 1.17 (t, J = 7.6 Hz, 3H) |
| 4-200 | 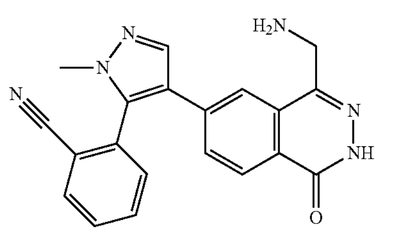 | 4D | 4-4 | 2-(4-(4-(aminomethyl)-1-oxo-1,2-dihydrophthalazin-6-yl)-1-methyl-1H-pyrazol-5-yl)-4-chloro-6-ethylbenzonitrile<br>LCMS [M + 1]$^+$ = 419.2; $^1$H NMR (400 MHz, DMSO-d6) δ = 12.88 (s, 1H), 8.38 (br s, 3H), 8.28 (s, 1H), 8.11 (d, J = 8.4 Hz, 1H), 7.85 (d, J = 2.0 Hz, 1H), 7.82 (d, J = 2.0 Hz, 1H), 7.75 (d, J = 1.2 Hz, 1H), 7.42 (dd, J = 1.6, 8.4 Hz, 1H), 4.39-4.22 (m, 2H), 3.75 (s, 3H), 2.83 (q, J = 7.6 Hz, 2H), 1.21 (t, J = 7.6 Hz, 3H) |

TABLE 4-continued

| Example | Structure | CM | PM | Compound Name and Characterization |
|---------|-----------|----|----|-----------------------------------|
| 4-201 | 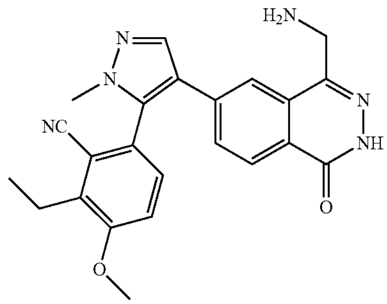 [SMILES: CCc1c(OC)ccc(-c2c(-c3ccc4c(=O)[nH]nc(CN)c4c3)cnn2C)c1C#N] | 4D | 4-4 | 2-(4-(4-(aminomethyl)-1-oxo-1,2-dihydrophthalazin-6-yl)-1-methyl-1H-pyrazol-5-yl)-6-ethyl-5-methoxybenzonitrile LCMS [M + 1]$^+$ = 415.3; $^1$H NMR (400 MHz, DMSO-d$_6$) δ = 12.85 (s, 1H), 8.40 (br d, J = 9.6 Hz, 3H), 8.26 (s, 1H), 8.08 (d, J = 8.4 Hz, 1H), 7.77 (s,1H), 7.62-7.55 (m, 1H), 7.53-7.47 (m, 1H), 7.41 (d, J = 8.4 Hz, 1H), 4.40-4.19 (m, 2H), 3.97 (s, 3H), 3.71 (s, 3H), 2.80(q, J = 7.6 Hz, 2H), 1.12 (t, J = 7.6 Hz, 3H) |
| 4-202 | 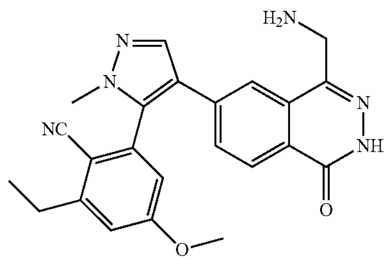 [SMILES: CCc1cc(OC)cc(-c2c(-c3ccc4c(=O)[nH]nc(CN)c4c3)cnn2C)c1C#N] | 4D | 4-1 4-10 | 2-(4-(4-(aminomethyl)-1-oxo-1,2-dihydrophthalazin-6-yl)-1-methyl-1H-pyrazol-5-yl)-6-ethyl-4-methoxybenzonitrile LCMS [M + 1]$^+$ = 415.1; $^1$H NMR (400 MHz, DMSO-d$_6$) δ = 12.85 (br s, 1H), 8.47-8.15 (m, 4H), 8.11 (d, J = 8.4 Hz, 1H), 7.73 (d, J = 0.8 Hz, 1H), 7.50 (dd, J = 1.2, 8.4 Hz, 1H), 7.26 (d, J = 2.4 Hz, 1H), 7.20 (d, J = 2.4 Hz, 1H), 4.36-4.16 (m, 2H), 3.92 (s, 3H), 3.74 (s, 3H), 2.80 (q, J = 7.6 Hz, 2H), 1.22 (t, J = 7.6 Hz, 3H) |
| 4-203 | 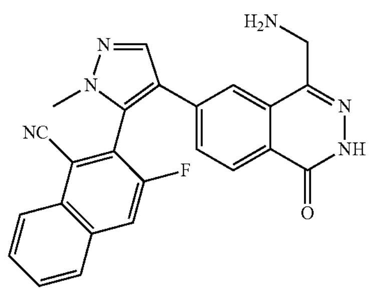 [SMILES: Cn1ncc(-c2ccc3c(=O)[nH]nc(CN)c3c2)c1-c1c(F)cc2ccccc2c1C#N] | 4E | 4-1 | 2-(4-(4-(aminomethyl)-1-oxo-1,2-dihydrophthalazin-6-yl)-1-methyl-1H-pyrazol-5-yl)-3-fluoro-1-naphthonitrile LCMS [M + 1]$^+$ = 425.2; $^1$H NMR (400 MHz, CD$_3$OD) δ = 8.28 (d, J = 10.0 Hz, 1H), 8.23 (s, 1H), 8.18 (br dd, J = 3.6, 5.2 Hz, 2H), 8.14 (d, J = 8.4 Hz, 1H), 7.86-7.79 (m, 3H), 7.46 (dd, J = 1.6, 8.0 Hz, 1H), 4.47-4.31 (m, 2H), 3.86 (s, 3H). $^{19}$F NMR (471 MHz, CD$_3$OD) δ = 116.45 (s, 1F) |
| 4-204 | 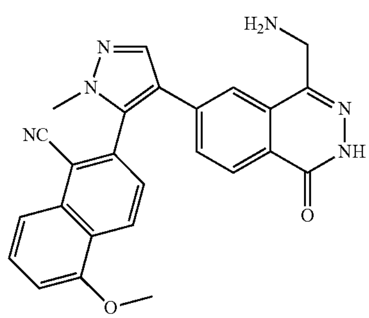 [SMILES: COc1cccc2c(C#N)c(-c3c(-c4ccc5c(=O)[nH]nc(CN)c5c4)cnn3C)ccc12] | 4D | 4-6 | 2-(4-(4-(aminomethyl)-1-oxo-1,2-dihydrophthalazin-6-yl)-1-methyl-1H-pyrazol-5-yl)-5-methoxy-1-naphthonitrile LCMS [M + 1]$^+$ = 437.2; $^1$H NMR (400 MHz, DMSO-d$_6$) δ = 12.83 (s, 1H), 8.64 (d, J = 8.8 Hz, 1H), 8.51 (br s, 3H), 8.37 (s, 1H), 7.99 (d, J = 8.4 Hz, 1H), 7.96 (d, J = 1.2 Hz, 1H), 7.84-7.78 (m, 1H), 7.76 (d, J = 8.8 Hz, 1H), 7.69 (d, J = 8.4 Hz, 1H), 7.30 (d, J = 8.0 Hz, 1H), 7.27 (dd, J = 1.2, 8.4 Hz, 1H), 4.34 (br dd, J = 5.6, 10.0 Hz, 2H), 4.07 (s, 3H), 3.76 (s, 3H) |
| 4-205 | 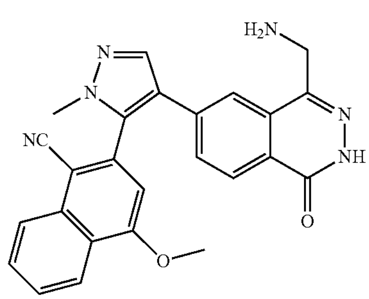 [SMILES: COc1cc(-c2c(-c3ccc4c(=O)[nH]nc(CN)c4c3)cnn2C)c(C#N)c2ccccc12] | 4D | 4-1 | 2-(4-(4-(aminomethyl)-1-oxo-1,2-dihydrophthalazin-6-yl)-1-methyl-1H-pyrazol-5-yl)-4-methoxy-1-naphthonitrile LCMS [M + 1]$^+$ = 437.2; $^1$H NMR (400 MHz, DMSO-d$_6$) δ = 12.83 (s, 1H), 8.39 (d, J = 8.4 Hz, 1H), 8.33 (s, 4H), 8.07-8.01 (m, 2H), 7.92 (d, J = 1.2 Hz, 1H), 7.88 (ddd, J = 1.2, 7.2, 8.4 Hz, 1H), 7.80 (dt, J = 1.2, 7.6 Hz, 1H), 7.41 (dd, J = 1.6, 8.4 Hz, 1H), 7.35 (s, 1H), 4.43-4.23 (m, 2H), 4.12 (s, 3H), 3.80 (s, 3H) |

TABLE 4-continued

| Example | Structure | CM | PM | Compound Name and Characterization |
|---|---|---|---|---|
| 4-206 | 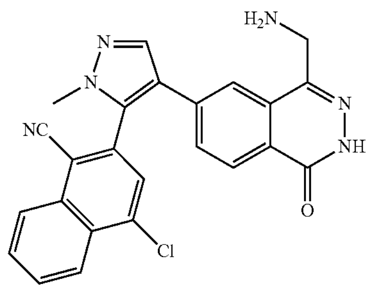 | 4D | 4-6 | 2-(4-(4-(aminomethyl)-1-oxo-1,2-dihydrophthalazin-6-yl)-1-methyl-1H-pyrazol-5-yl)-4-chloro-1-naphthonitrile LCMS [M + 1]$^+$ = 444.1; $^1$H NMR (400 MHz, DMSO-d$_6$) δ = 12.84 (s, 1H), 8.57 (br s, 3H), 8.49-8.44 (m, 1H), 8.38 (s, 1H), 8.23-8.19 (m, 1H), 8.16 (s, 1H), 8.04-8.00 (m, 2H), 7.99 (s, 2H), 7.32 (dd, J = 1.6, 8.4 Hz, 1H), 4.45-4.20 (m, 2H), 3.81 (s, 3H) |
| 4-207 | 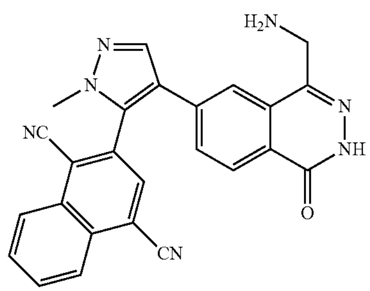 [SMILES: Cn1ncc(-c2ccc3c(=O)[nH]nc(CN)c3c2)c1-c1cc(C#N)c2ccccc2c1C#N] | 4D | 4-4 | 2-(4-(4-(aminomethyl)-1-oxo-1,2-dihydrophthalazin-6-yl)-1-methyl-1H-pyrazol-5-yl)naphthalene-1,4-dicarbonitrile LCMS [M + 1]$^+$ = 432.2; $^1$H NMR (400 MHz, DMSO-d$_6$) δ = 12.84 (s, 1H), 8.64 (s, 1H), 8.53 (br s, 3H), 8.42-8.37 (m, 2H), 8.27 (d, J = 7.6 Hz, 1H), 8.13-8.07 (m, 1H), 8.07-8.02 (m, 1H), 8.00 (d, J = 8.4 Hz, 1H), 7.95 (d, J = 1.6 Hz, 1H), 7.35 (dd, J = 1.6, 8.4 Hz, 1H), 4.42-4.21 (m, 2H), 3.82 (s, 3H) |
| 4-208 | 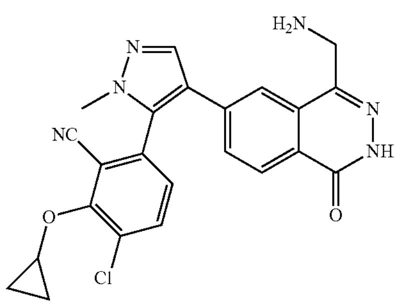 [SMILES: Cn1ncc(-c2ccc3c(=O)[nH]nc(CN)c3c2)c1-c1ccc(Cl)c(OC2CC2)c1C#N] | 4D | 4-1 | 6-(4-(4-(aminomethyl)-1-oxo-1,2-dihydrophthalazin-6-yl)-1-methyl-1H-pyrazol-5-yl)-3-chloro-2-cyclopropoxybenzonitrile LCMS [M + 1]$^+$ = 447.0; $^1$H NMR (400 MHz, DMSO-d$_6$) δ = 12.90 (s, 1H), 8.37 (br s, 3H), 8.27 (s, 1H), 8.12 (dd, J = 8.4, 17.6 Hz, 2H), 7.83 (d, J = 0.8 Hz, 1H), 7.59 (d, J = 8.4 Hz, 1H), 7.40 (dd, J = 1.2, 8.0 Hz, 1H), 4.47 (tt, J = 2.8, 6.0 Hz, 1H), 4.43-4.27 (m, 2H), 3.78 (s, 3H), 0.88-0.80 (m, 1H), 0.79-0.70 (m, 1H), 0.65 (td, J = 2.8, 6.0 Hz, 2H) |
| 4-209 | 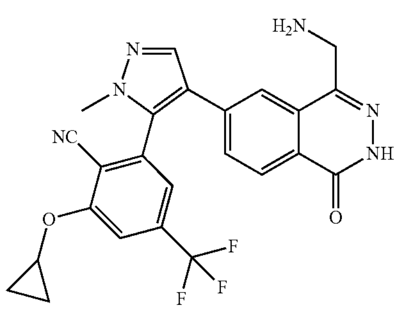 [SMILES: Cn1ncc(-c2ccc3c(=O)[nH]nc(CN)c3c2)c1-c1cc(C(F)(F)F)cc(OC2CC2)c1C#N] | 4D | 4-1 | 2-(4-(4-(aminomethyl)-1-oxo-1,2-dihydrophthalazin-6-yl)-1-methyl-1H-pyrazol-5-yl)-6-cyclopropoxy-4-(trifluoromethyl)benzonitrile LCMS [M + 1]$^+$ = 481.2; $^1$H NMR (500 MHz, DMSO-d$_6$) δ = 12.88 (s, 1 H), 8.55 (br s, 3 H), 8.33 (s, 1 H), 8.11 (d, J = 8.4 Hz, 1 H), 7.98 (s, 1 H), 7.84-7.77 (m, 2 H), 7.41 (dd, J = 8.5, 1.5 Hz, 1 H), 4.38-4.29 (m, 3 H), 3.76 (s, 3 H), 0.98-0.91 (m, 2 H), 0.89-0.79 (m, 2 H) |
| 4-210 | 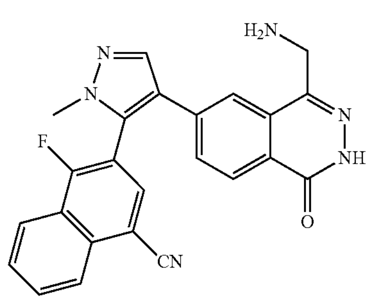 [SMILES: Cn1ncc(-c2ccc3c(=O)[nH]nc(CN)c3c2)c1-c1cc(C#N)c2ccccc2c1F] | 4E | 4-1 | 3-(4-(4-(aminomethyl)-1-oxo-1,2-dihydrophthalazin-6-yl)-1-methyl-1H-pyrazol-5-yl)-4-fluoro-1-naphthonitrile LCMS [M + 1]$^+$ = 425.2; $^1$H NMR (500 MHz, DMSO-d$_6$) δ = 12.85 (s, 1H), 8.53 (d, J = 18.5 Hz, 3H), 8.44 (d, J = 6.5 Hz, 1H), 8.35-8.31 (m, 1H), 8.29-8.23 (m, 2H), 8.06-7.97 (m, 3H), 7.90 (t, J = 7.5 Hz, 1H), 7.44 (d, J = 8.0 Hz, 1H), 4.37 (s, 2H), 3.82 (s, 3H) |

TABLE 4-continued

| Example | Structure | CM | PM | Compound Name and Characterization |
|---|---|---|---|---|
| 4-211 | 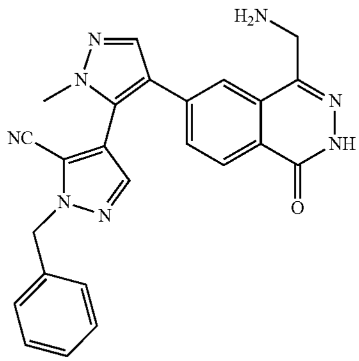 [SMILES: Cn1ncc(-c2ccc3c(=O)[nH]nc(CN)c3c2)c1-c1cnn(Cc2ccccc2)c1C#N] | 4D | 4-6 | 4-(4-(aminomethyl)-1-oxo-1,2-dihydrophthalazin-6-yl)-1'-benzyl-2-methyl-1'H,2H-[3,4'-bipyrazole]-5'-carbonitrile LCMS [M + 1]$^+$ = 437.1; $^1$H NMR (400 MHz, DMSO-d$_6$) δ = 12.89 (s, 1H), 8.48 (br s, 3H), 8.25 (s, 1H), 8.19 (s, 1H), 8.09 (d, J = 8.4 Hz, 1H), 7.89 (d, J = 1.6 Hz, 1H), 7.49 (dd, J = 1.6, 8.4 Hz, 1H), 7.43-7.33 (m, 3H), 7.24-7.20 (m, 2H), 5.62 (s, 2H), 4.41-4.32 (m, 2H), 3.84 (s, 3H) |
| 4-212 | 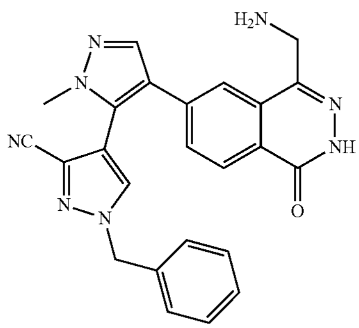 [SMILES: Cn1ncc(-c2ccc3c(=O)[nH]nc(CN)c3c2)c1-c1cn(Cc2ccccc2)nc1C#N] | 4D | 4-6 | 4-(4-(aminomethyl)-1-oxo-1,2-dihydrophthalazin-6-yl)-1'-benzyl-2-methyl-1'H,2H-[3,4'-bipyrazole]-3'-carbonitrile LCMS [M + 1]$^+$ = 437.3; $^1$H NMR (400 MHz, DMSO-d$_6$) δ = 12.89 (s, 1H), 8.63 (s, 1H), 8.48 (br s, 3H), 8.20 (s, 1H), 8.14 (d, J = 8.4 Hz, 1H), 7.89 (d, J = 1.2 Hz, 1H), 7.56 (dd, J = 1.5, 8.4 Hz, 1H), 7.45-7.36 (m, 3H), 7.36-7.30 (m, 2H), 5.58 (s, 2H), 4.38 (br s, 2H), 3.81 (s, 3H) |
| 4-213 | 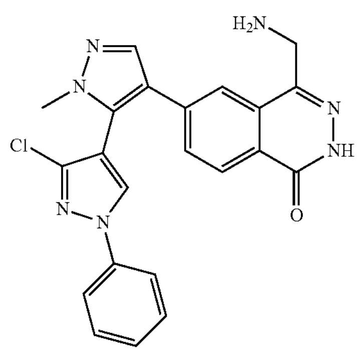 [SMILES: Cn1ncc(-c2ccc3c(=O)[nH]nc(CN)c3c2)c1-c1cn(-c2ccccc2)nc1Cl] | 4D | 4-1 | 4-(aminomethyl)-6-(3'-chloro-2-methyl-1'-phenyl-1'H,2H-[3,4'-bipyrazol]-4-yl)phthalazin-1(2H)-one LCMS [M + 1]$^+$ = 432.2; $^1$H NMR (400 MHz, DMSO-d$_6$) δ = 12.84 (s, 1H), 8.44-8.26 (m, 4H), 7.89 (t, J = 8.0 Hz, 1H), 7.61 (br d, J = 4.8 Hz, 1H), 7.50 (d, J = 8.8 Hz, 1H), 7.40 (br d, J = 2.8 Hz, 1H), 7.32 (d, J = 7.6 Hz, 1H), 4.37-4.27 (m, 2H), 4.25-4.06 (m, 2H), 3.72 (s, 3H), 1.38 (t, J = 7.2 Hz, 3H) |
| 4-214 | 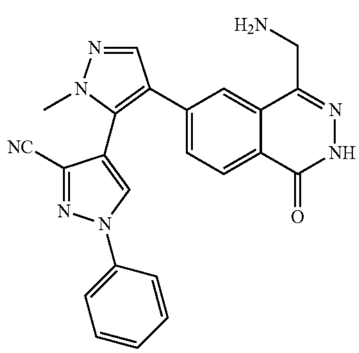 [SMILES: Cn1ncc(-c2ccc3c(=O)[nH]nc(CN)c3c2)c1-c1cn(-c2ccccc2)nc1C#N] | 4D | 4-1 | 4-(4-(aminomethyl)-1-oxo-1,2-dihydrophthalazin-6-yl)-2-methyl-11-phenyl-1'H,2H-[3,4'-bipyrazole]-3'-carbonitrile LCMS [M + 1]$^+$ = 423.2; $^1$H NMR (500 MHz, DMSO-d$_6$) δ 12.90 (s, 1H), 9.36 (s, 1H), 8.56 (br s, 3H), 8.28 (s, 1H), 8.20-8.17 (m, 1H), 8.03-7.98 (m, 3H), 7.70 (dd, J = 1.6, 8.0 Hz, 1H), 7.64 (t, J = 8.0 Hz, 2H), 7.55-7.50 (m, 1H), 4.41 (q, J = 5.6 Hz, 2H), 3.92 (s, 3H) |

TABLE 4-continued

| Example | Structure | CM | PM | Compound Name and Characterization |
|---|---|---|---|---|
| 4-215 | 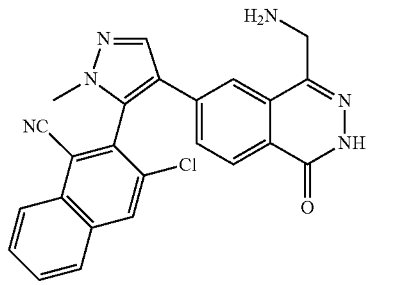 [SMILES: Cn1ncc(-c2ccc3c(=O)[nH]nc(CN)c3c2)c1-c1c(Cl)cc2ccccc2c1C#N] | 4E | 4-6 | 2-(4-(4-(aminomethyl)-1-oxo-1,2-dihydrophthalazin-6-yl)-1-methyl-1H-pyrazol-5-yl)-3-chloro-1-naphthonitrile<br>LCMS [M + 1] $^+$ = 441.3; $^1$H NMR (400 MHz, CD$_3$OD) δ = 8.67 (s, 1H), 8.27 (s, 1H), 8.23-8.18 (m, 2H), 8.15 (d, J = 8.4 Hz, 1H), 7.91-7.85 (m, 2H), 7.84 (s, 1H), 7.47 (dd, J = 1.6, 8.4 Hz, 1H), 4.55-4.30 (m, 2H), 3.82 (s, 3H) |
| 4-216 | 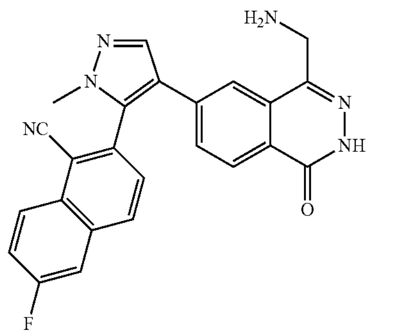 [SMILES: Cn1ncc(-c2ccc3c(=O)[nH]nc(CN)c3c2)c1-c1ccc2cc(F)ccc2c1C#N] | 4D | 4-12 | 2-(4-(4-(aminomethyl)-1-oxo-1,2-dihydrophthalazin-6-yl)-1-methyl-1H-pyrazol-5-yl)-6-fluoro-1-naphthonitrile<br>LCMS [M + 1] $^+$ = 425.1; $^1$H NMR (400 MHz, DMSO-d$_6$) δ = 12.37 (br s, 1H), 8.51 (d, J = 8.4 Hz, 1H), 8.26 (s, 1H), 8.20 (dd, J = 5.2, 9.2 Hz, 1H), 8.12 (dd, J = 2.4, 9.2 Hz, 1H), 8.06 (d, J = 8.4 Hz, 1H), 7.89 (d, J = 8.4 Hz, 1H), 7.80 (dt, J = 2.4, 8.8 Hz, 1H), 7.65 (d, J = 1.2 Hz, 1H), 7.60 (dd, J = 1.6, 8.4 Hz, 1H), 3.78 (s, 3H), 3.54 (s, 2H) |
| 4-217 | 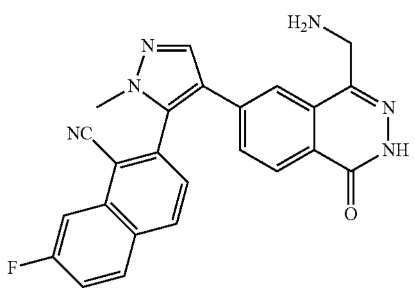 [SMILES: Cn1ncc(-c2ccc3c(=O)[nH]nc(CN)c3c2)c1-c1ccc2ccc(F)cc2c1C#N] | 4D | 4-1 | 2-(4-(4-(aminomethyl)-1-oxo-1,2-dihydrophthalazin-6-yl)-1-methyl-1H-pyrazol-5-yl)-7-fluoro-1-naphthonitrile<br>LCMS [M + 1] $^+$ = 425.0; $^1$H NMR (400 MHz, DMSO-d$_6$) δ = 12.83 (s, 1H), 8.58 (d, J = 8.4 Hz, 1H), 8.52-8.38 (m, 4H), 8.36 (s, 1H), 8.01 (d, J = 8.4 Hz, 1H), 7.87 (d, J = 1.2 Hz, 1H), 7.81 (dd, J = 8.8, 17.2 Hz, 3H), 7.35 (dd, J = 1.6, 8.4 Hz, 1H), 4.37-4.17 (m, 2H), 3.78 (s, 3H) |
| 4-218 | 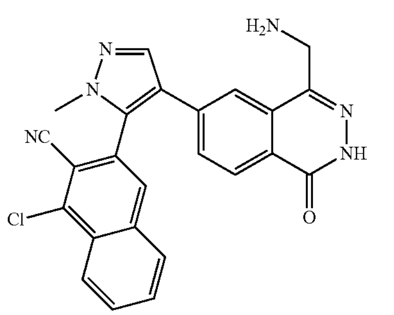 [SMILES: Cn1ncc(-c2ccc3c(=O)[nH]nc(CN)c3c2)c1-c1cc2ccccc2c(Cl)c1C#N] | 4D | 4-1 | 3-(4-(4-(aminomethyl)-1-oxo-1,2-dihydrophthalazin-6-yl)-1-methyl-1H-pyrazol-5-yl)-1-chloro-2-naphthonitrile<br>LCMS [M + 1] $^+$ = 441.2; $^1$H NMR (400 MHz, DMSO-d$_6$) δ = 12.85 (s, 1H), 8.47-8.39 (m, 5H), 8.37 (s, 1H), 8.26-8.20 (m, 1H), 8.03 (d, J = 8.4 Hz, 1H), 8.01-7.92 (m, 3H), 7.38 (dd, J = 1.2, 8.4 Hz, 1H), 4.43-4.28 (m, 2H), 3.79 (s, 3H) |
| 4-219 | 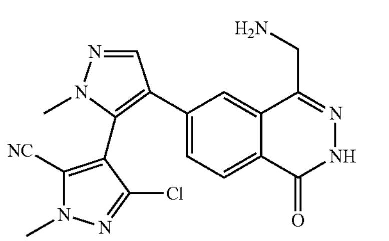 [SMILES: Cn1nc(Cl)c(-c2c(-c3ccc4c(=O)[nH]nc(CN)c4c3)cnn2C)c1C#N] | 4D | 4-6 | 4-(4-(aminomethyl)-1-oxo-1,2-dihydrophthalazin-6-yl)-3'-chloro-1',2-dimethyl-1'H,2H-[3,4'-bipyrazole]-5'-carbonitrile<br>LCMS [M + 1] $^+$ = 395.2; $^1$H NMR (400 MHz, DMSO-d$_6$) δ = 12.89 (s, 1H), 8.55 (br d, J = 1.6 Hz, 3H), 8.34 (s, 1H), 8.17 (d, J = 8.4 Hz, 1H), 7.87 (d, J = 1.2 Hz, 1H), 7.61 (dd, J = 1.6, 8.0 Hz, 1H), 4.39 (br d, J = 5.2 Hz, 2H), 4.05 (s, 3H), 3.80 (s, 3H) |

TABLE 4-continued

| Example | Structure | CM | PM | Compound Name and Characterization |
|---|---|---|---|---|
| 4-220 | 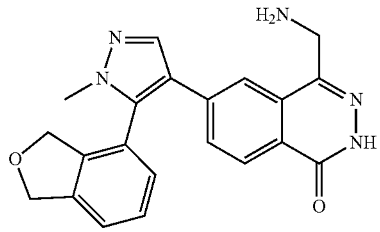 [SMILES: Cn1ncc(-c2ccc3c(=O)[nH]nc(CN)c3c2)c1-c1cccc2c1COC2] | 4D | 4-6 | 4-(aminomethyl)-6-(5-(1,3-dihydroisobenzofuran-4-yl)-1-methyl-1H-pyrazol-4-yl)phthalazin-1(2H)-one<br>LCMS [M + 1]$^+$ = 374.1; $^1$H NMR (400 MHz, MeOD) δ = $^1$H NMR (400 MHz, CDCl$_3$) δ = 8.21 (m, J = 8.4 Hz,1H), 8.15 (s, 1H), 7.71 (dd, J = 8.4, 1.2 Hz, 1H), 7.63-7.53 (m, 3H), 7.44 (d, J = 7.2 Hz, 1H), 5.09-5.18 (m, 2H), 4.80 (m, J = 12.4 Hz, 1H), 4.31-4.21 (m, 1H), 4.21-4.14 (m, 1H), 3.76 (s, 3 H); (400 MHz, T = 353K, DMSO-d$_6$) δ = 12.65 (s, 1H), 8.51 (s, 3H), 8.19 (s, 1H), 8.08 (d, J = 8.4 Hz, 1H), 7.60-7.51 (m, 4H), 7.41-7.40 (m, 1H), 5.11-5.09 (m, 2H), 4.77-4.74 (m, 1H), 4.40-4.34 (m, 1H), 4.11 (s, 2H), 3.73 (s, 3H) |
| 4-221 | 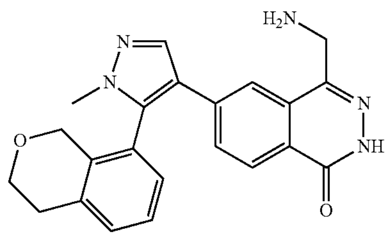 [SMILES: Cn1ncc(-c2ccc3c(=O)[nH]nc(CN)c3c2)c1-c1cccc2c1COCC2] | 4D | 4-6 | 4-(aminomethyl)-6-(5-(isochroman-8-yl)-1-methyl-1H-pyrazol-4-yl)phthalazin-1(2H)-one<br>LCMS [M + 1]$^+$ = 388.1; $^1$H NMR (400 MHz, MeOD) δ = 8.24-8.19 (m, 2H), 7.77 (dd, J = 1.2, 8.4 Hz, 1H), 7.52 (s, 1H), 7.51-7.43 (m, 2H), 7.28 (d, J = 6.8 Hz, 1H), 4.39-4.33 (m, 1H), 4.23-4.12 (m, 3H), 3.94-3.80 (m, 2H), 3.69 (s, 3H), 3.04-2.89 (m, 2H); (400 MHz, T = 352K, DMSO-d$_6$) δ = 12.64 (s, 1H), 8.48 (s, 3H), 8.24 (s, 1H), 8.08 (d, J = 8.0 Hz, 1H), 7.61 (d, J = 8.4 Hz, 1H), 7.56 (s, 1H), 7.47-7.39 (m, 2H), 7.27-7.22 (m, 1H), 4.33-4.27 (m, 1H), 4.12-4.05 (m, 3H), 3.91-3.73 (m, 2H), 3.78 (s, 3H), 3.03-2.84 (m, 2H) |
| 4-222 | 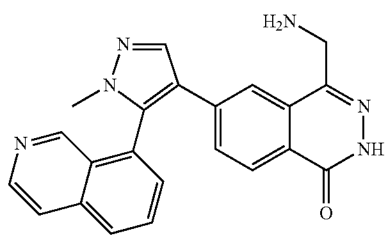 [SMILES: Cn1ncc(-c2ccc3c(=O)[nH]nc(CN)c3c2)c1-c1cccc2ccncc12] | 4D | 4-6 | 4-(aminomethyl)-6-(5-(isoquinolin-8-yl)-1-methyl-1H-pyrazol-4-yl)phthalazin-1(2H)-one<br>LCMS [M + 1]$^+$ = 383.1; $^1$H NMR (400 MHz, MeOD) δ = 9.20 (s, 1H), 8.68-8.60 (m, 2H), 8.57 (d, J = 8.4 Hz, 1H), 8.44 (t, J = 8.0 Hz, 1H), 8.31 (s, 1H), 8.27 (d, J = 7.2 Hz, 1H), 8.03 (d, J = 8.4 Hz, 1H), 7.77 (s, 1H), 7.39 (d, J = 8.4 Hz, 1H), 4.49-4.39 (m, 1H), 4.31-4.22 (m, 1H), 3.80 (s, 3H) |
| 4-223 | 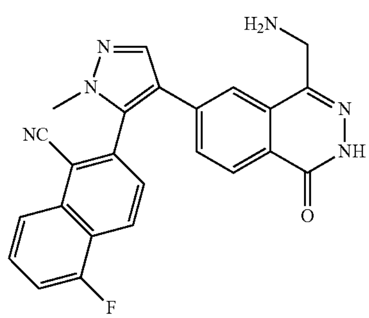 [SMILES: Cn1ncc(-c2ccc3c(=O)[nH]nc(CN)c3c2)c1-c1ccc2c(F)cccc2c1C#N] | 4D | 4-6 | 2-(4-(4-(aminomethyl)-1-oxo-1,2-dihydrophthalazin-6-yl)-1-methyl-1H-pyrazol-5-yl)-5-fluoro-1-naphthonitrile<br>LCMS [M + 1]$^+$ = 425.1; $^1$H NMR (400 MHz, DMSO-d$_6$) δ = 12.85 (s, 1H), 8.61 (d, J = 8.4 Hz, 1H), 8.41-8.25 (m, 4H), 8.07-7.96 (m, 2H), 7.96-7.84 (m, 3H), 7.71 (dd, J = 8.0, 10.0 Hz, 1H), 7.36 (dd, J = 1.6, 8.4 Hz, 1H), 4.39-4.20 (m, 2H), 3.80 (s, 3H) |
| 4-224 | 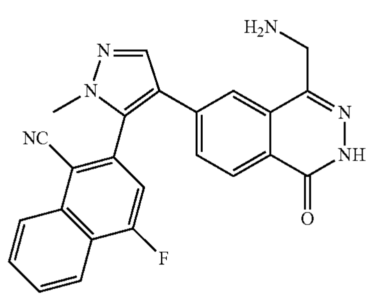 [SMILES: Cn1ncc(-c2ccc3c(=O)[nH]nc(CN)c3c2)c1-c1cc(F)c2ccccc2c1C#N] | 4D | 4-13 | 2-(4-(4-(aminomethyl)-1-oxo-1,2-dihydrophthalazin-6-yl)-1-methyl-1H-pyrazol-5-yl)-4-fluoro-1-naphthonitrile<br>LCMS [M + 1]$^+$ = 425.1; $^1$H NMR (400 MHz, DMSO-d$_6$) δ = 12.84 (s, 1H), 8.44 (br s, 3H), 8.37-8.33 (m, 2H), 8.18 (d, J = 8.0 Hz, 1H), 8.04-7.98 (m, 2H), 7.98-7.95 (m, 1H), 7.95-7.91 (m, 2H), 7.89 (d, J = 10.0 Hz, 1H), 7.73-7.65 (m, 1H), 7.36 (dd, J = 1.6, 8.4 Hz, 1H), 4.42-4.27 (m, 2H), 3.80 (s, 3H) |

TABLE 4-continued

| Example | CM | PM | Compound Name and Characterization |
|---|---|---|---|
| 4-225 | 4D | 4-6 | 6-(4-(4-(aminomethyl)-1-oxo-1,2-dihydrophthalazin-6-yl)-1-methyl-1H-pyrazol-5-yl)-3-chloroquinoline-5-carbonitrile<br>LCMS [M + 1]⁺ = 442.1; ¹H NMR (400 MHz, DMSO-d₆) δ = 12.84 (s, 1H), 9.21 (d, J = 2.4 Hz, 1H), 8.57 (d, J = 8.8 Hz, 1H), 8.54-8.52 (m, 1H), 8.44 (br s, 3H), 8.37 (s, 1H), 8.08 (d, J = 8.8 Hz, 1H), 8.02 (d, J = 8.4 Hz, 1H), 7.85 (d, J = 1.2 Hz, 1H), 7.40 (dd, J = 1.6, 8.4 Hz, 1H), 4.34-4.19 (m, 2H), 3.80 (s, 3H) |
| 4-226 | 4D | 4-2 | 7-(4-(4-(aminomethyl)-1-oxo-1,2-dihydrophthalazin-6-yl)-1-methyl-1H-pyrazol-5-yl)chromane-8-carbonitrile<br>LCMS [M + 1]⁺ = 413.2; ¹H NMR (400 MHz, DMSO-d₆) δ = 12.40 (br s, 1H), 8.17 (s, 1H), 8.12 (d, J = 8.4 Hz, 1H), 7.70 (dd, J = 1.6, 8.0 Hz, 1H), 7.60 (d, J = 8.0 Hz, 1H), 7.58 (d, J = 1.6 Hz, 1H), 7.14 (d, J = 7.6 Hz, 1H), 4.35 (br t, J = 4.8 Hz, 2H), 3.72 (s, 3H), 3.68 (d, J = 2.0 Hz, 2H), 2.89 (br t, J = 6.0 Hz, 2H), 2.05-2.00 (m, 2H) |
| 4-227 | 4D | 4-6 | 2-(4-(4-(aminomethyl)-1-oxo-1,2-dihydrophthalazin-6-yl)-1-methyl-1H-pyrazol-5-yl)indolizine-3-carbonitrile<br>LCMS [M + 1]⁺ = 396.2; ¹H NMR (400 MHz, DMSO-d6) δ = 12.84 (s, 1H), 8.48-8.45 (m, 1H), 8.41 (br s, 3H), 8.24 (s, 1H), 8.08 (d, J = 8.0 Hz, 1H), 7.94 (d, J = 1.2 Hz, 1H), 7.80 (d, J = 9.2 Hz, 1H), 7.50 (dd, J = 1.6, 8.3 Hz, 1H), 7.30-7.25 (m, 1H), 7.08 (dt, J = 1.2, 6.8 Hz, 1H), 6.93 (s, 1H), 4.37 (br d, J = 5.2 Hz, 2H), 3.84 (s, 3H) |
| 4-228 | 4D | 4-6 | 2-(4-(4-(aminomethyl)-1-oxo-1,2-dihydrophthalazin-6-yl)isothiazol-5-yl)-1-naphthonitrile<br>LCMS [M + 1]⁺ = 409.9; ¹H NMR (400 MHz, DMSO-d₆) δ = 12.96 (s, 1H), 9.21 (s, 1H), 8.49-8.36 (m, 4H), 8.21 (d, J = 7.6 Hz, 1H), 8.17 (s, 1H), 8.10 (d, J = 8.4 Hz, 2H), 7.90-7.77 (m, 2H), 7.69 (d, J = 8.4 Hz, 1H), 7.52 (dd, J = 1.6, 8.4 Hz, 1H), 4.36 (s, 2H) |
| 4-229 | 4D | 4-6 | 3-(4-(4-(aminomethyl)-1-oxo-1,2-dihydrophthalazin-6-yl)-1-methyl-1H-pyrazol-5-yl)-4-chloro-2-naphthonitrile<br>LCMS [M + 1]⁺ = 441.0/443.0; ¹H NMR (400 MHz, DMSO-d₆) δ = 12.82 (s, 1H), 8.94 (s, 1H), 8.49-8.39 (m, 5H), 8.32 (d, J = 8.0 Hz, 1H), 8.06-8.00 (m, 2H), 7.99-7.93 (m, 2H), 7.27 (d, J = 8.4 Hz, 1H), 4.41-4.32 (m, 2H), 3.71 (s, 3H) |

TABLE 4-continued

| Example | Structure | CM | PM | Compound Name and Characterization |
|---|---|---|---|---|
| 4-230 | 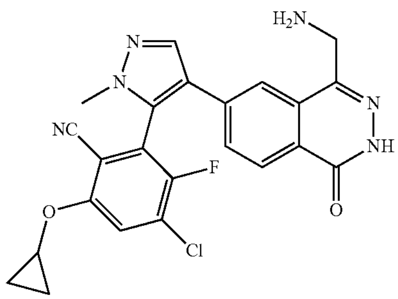 [SMILES: Cn1ncc(-c2ccc3c(=O)[nH]nc(CN)c3c2)c1-c1c(F)c(Cl)cc(OC2CC2)c1C#N] | 4D | 4-6 | 2-(4-(4-(aminomethyl)-1-oxo-1,2-dihydrophthalazin-6-yl)-1-methyl-1H-pyrazol-5-yl)-4-chloro-6-cyclopropoxy-3-fluorobenzonitrile<br>LCMS [M + 1]⁺ = 465.1; ¹H NMR (400 MHz, DMSO-d6) δ = 12.88 (s, 1H), 8.50 (br s, 3H), 8.37 (s, 1H), 8.14 (d, J = 8.4 Hz, 1H), 8.01 (d, J = 6.0 Hz, 1H), 7.85 (s, 1H), 7.47 (d, J = 8.4 Hz, 1H), 4.42-4.30 (m, 2H), 4.22 (br d, J = 3.2 Hz, 1H), 3.78 (s, 3H), 0.96-0.87 (m, 2H), 0.87-0.76 (m, 2H) |
| 4-231 | 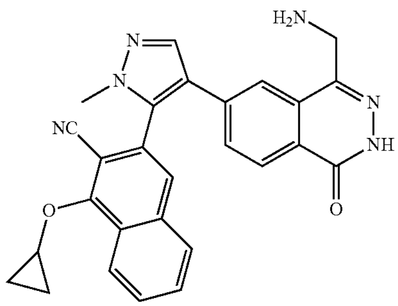 | 4D | 4-6 | 3-(4-(4-(aminomethyl)-1-oxo-1,2-dihydrophthalazin-6-yl)-1-methyl-1H-pyrazol-5-yl)-1-cyclopropoxy-2-naphthonitrile<br>LCMS [M + 1]⁺ = 215.0; ¹H NMR (400 MHz, DMSO-d₆) δ = 12.84 (s, 1H), 8.39 (br s, 3H), 8.35 (s, 1H), 8.29 (d, J = 8.0 Hz, 1H), 8.11 (d, J = 7.6 Hz, 1H), 8.08-8.02 (m, 2H), 7.96 (d, J = 1.2 Hz, 1H), 7.89-7.78 (m, 2H), 7.38 (dd, J = 1.2, 8.4 Hz, 1H), 4.61 (tt, J = 2.8, 6.0 Hz, 1H), 4.42-4.28 (m, 2H), 3.80 (s, 3H), 1.00-0.90 (m, 2H), 0.80-0.64 (m, 2H) |
| 4-232 | 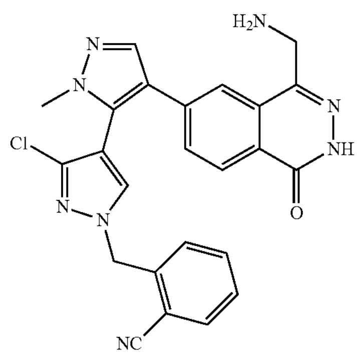 [SMILES: Cn1ncc(-c2ccc3c(=O)[nH]nc(CN)c3c2)c1-c1cn(Cc2ccccc2C#N)nc1Cl] | 4D | 4-6 | 2-((4-(4-(aminomethyl)-1-oxo-1,2-dihydrophthalazin-6-yl)-3'-chloro-2-methyl-1'H,2H-[3,4'-bipyrazol]-1'-yl)methyl)benzonitrile<br>LCMS [M + 1]⁺ = 471.0; ¹H NMR (400 MHz, DMSO-d₆) δ = 12.86 (s, 1H), 8.43 (s, 4H), 8.21 (s, 1H), 8.12 (d, J = 8.4 Hz, 1H), 7.96-7.87 (m, 2H), 7.77 (dt, J = 1.2, 7.6 Hz, 1H), 7.67-7.55 (m, 2H), 7.49 (d, J = 7.6 Hz, 1H), 5.65 (s, 2H), 4.41 (br s, 2H), 3.74 (s, 3H) |
| 4-233 | 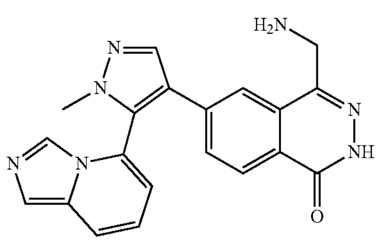 [SMILES: Cn1ncc(-c2ccc3c(=O)[nH]nc(CN)c3c2)c1-c1cccc2cncn12] | 4D | 4-6 | 4-(aminomethyl)-6-(5-(imidazo[1,5-a]pyridin-5-yl)-1-methyl-1H-pyrazol-4-yl)phthalazin-1(2H)-one<br>LCMS [M + 1]⁺ = 372.0; ¹H NMR (400 MHz, DMSO-d₆) δ = 8.72 (s, 1H), 8.39 (s, 1H), 8.07-7.97 (m, 3H), 7.76 (s, 1H), 7.52-7.38 (m, 2H), 7.35-7.26 (m, 1H), 4.34-4.11 (m, 2H), 3.82 (s, 3H) |
| 4-234 | 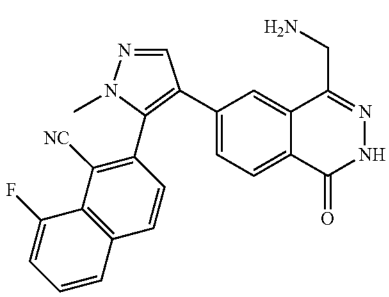 [SMILES: Cn1ncc(-c2ccc3c(=O)[nH]nc(CN)c3c2)c1-c1ccc2cccc(F)c2c1C#N] | 4D | 4-6 | 2-(4-(4-(aminomethyl)-1-oxo-1,2-dihydrophthalazin-6-yl)-1-methyl-1H-pyrazol-5-yl)-8-fluoro-1-naphthonitrile<br>LCMS [M + 1]⁺ = 425.1; ¹H NMR (400 MHz, DMSO-d₆) δ = 12.84 (s, 1H), 8.57 (dd, J = 1.6, 8.4 Hz, 1H), 8.47 (br s, 3H), 8.37 (s, 1H), 8.11 (d, J = 8.0 Hz, 1H), 8.01 (d, J = 8.4 Hz, 1H), 7.90 (d, J = 1.2 Hz, 1H), 7.87-7.78 (m, 2H), 7.67 (dd, J = 7.6, 12.2 Hz, 1H), 7.34 (dd, J = 1.6, 8.4 Hz, 1H), 4.43-4.21 (m, 2H), 3.76 (s, 3H) |

TABLE 4-continued

| Example | Structure | CM | PM | Compound Name and Characterization |
|---|---|---|---|---|
| 4-235 | 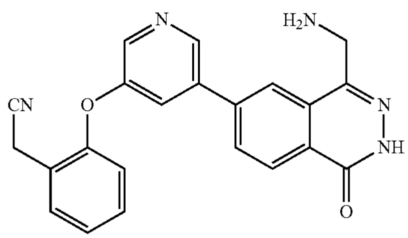 [SMILES: N#CCc1ccccc1Oc1cncc(-c2ccc3c(=O)[nH]nc(CN)c3c2)c1] | 4D | 4-6 | 2-(2-((5-(4-(aminomethyl)-1-oxo-1,2-dihydrophthalazin-6-yl)pyridin-3-yl)oxy)phenyl)acetonitrile<br>LCMS [M + 1] $^+$ = 384.0; $^1$H NMR (400 MHz, DMSO-d6) δ = 13.00 (s, 1H), 9.05 (d, J = 1.7 Hz, 1H), 8.60 (br s, 3H), 8.48-8.43 (m, 1H), 8.40-8.36 (m, 1H), 8.35-8.31 (m, 1H), 8.30-8.22 (m, 1H), 8.19 (t, J = 2.1 Hz, 1H), 7.57 (dd, J = 1.2, 7.6 Hz, 1H), 7.41 (dt, J = 1.5, 7.9 Hz, 1H), 7.34-7.18 (m, 1H), 7.09-7.01 (m, 1H), 4.58 (br d, J = 5.6 Hz, 2H), 4.11 (s, 2H) |
| 4-236 | 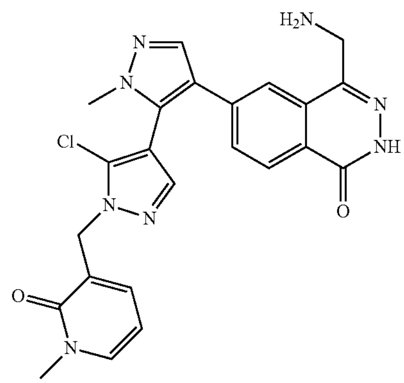 [SMILES: Cn1ncc(-c2ccc3c(=O)[nH]nc(CN)c3c2)c1-c1cnn(Cc2cccn(C)c2=O)c1Cl] | 4D | 4-6 | 4-(aminomethyl)-6-(5'-chloro-2-methyl-1'-((1-methyl-2-oxo-1,2-dihydropyridin-3-yl)methyl)-1'H,2H-[3,4'-bipyrazol]-4-yl)phthalazin-1(2H)-one<br>LCMS [M + 1] $^+$ = 477.1; $^1$H NMR (400 MHz, DMSO-d$_6$) δ = 12.85 (s, 1H), 8.43 (s, 3H), 8.28 (s, 1H), 8.20 (s, 1H), 8.14 (d, J = 8.4 Hz, 1 H), 7.85 (d, J = 1.2 Hz, 1 H), 7.75 (d, J = 6.8, 2.0 Hz, 1 H), 7.67 (d, J = 8.4, 1.2 Hz, 1 H), 7.36 (d, J = 6.8, 2.0 Hz, 1 H), 6.28 (t, J = 6.8 Hz, 1 H), 5.20 (s, 2H), 4.41 (d, J = 5.6 Hz, 2 H), 3.73 (s, 3H), 3.45 (s, 3H) |
| 4-237 | 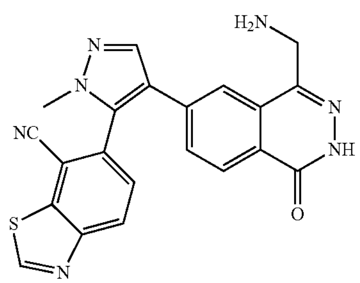 [SMILES: Cn1ncc(-c2ccc3c(=O)[nH]nc(CN)c3c2)c1-c1ccc2ncsc2c1C#N] | 4D | 4-6 | 6-(4-(4-(aminomethyl)-1-oxo-1,2-dihydrophthalazin-6-yl)-1-methyl-1H-pyrazol-5-yl)benzo[d]thiazole-7-carbonitrile<br>LCMS [M + 1] $^+$ = 414.1; $^1$H NMR (400 MHz, DMSO-d$_6$) δ = 12.84 (s, 1H), 9.73 (s, 1H), 8.63 (d, J = 8.4 Hz, 1H), 8.45 (br s, 3H), 8.35 (s, 1H), 8.04 (d, J = 8.4 Hz, 1H), 7.92 (d, J = 8.4 Hz, 1H), 7.87 (s, 1H), 7.36 (dd, J = 1.2, 8.4 Hz, 1H), 4.39-4.19 (m, 2H), 3.78 (s, 3H) |
| 4-238 | 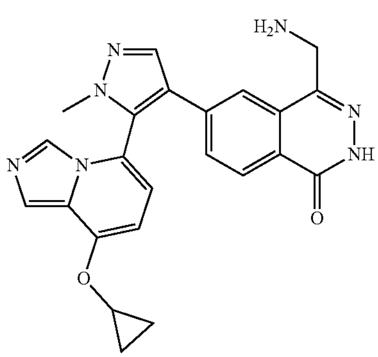 [SMILES: Cn1ncc(-c2ccc3c(=O)[nH]nc(CN)c3c2)c1-c1ccc(OC2CC2)c2cncn12] | 4B | 4-13 | 4-(aminomethyl)-6-(5-(8-cyclopropoxyimidazo[1,5-a]pyridin-5-yl)-1-methyl-1H-pyrazol-4-yl)phthalazin-1(2H)-one<br>LCMS [M + 1] $^+$ = 428.0; $^1$H NMR (400 MHz, DMSO-d$_6$) δ = 12.85 (s, 1H), 8.48 (br s, 3H), 8.42-8.37 (m, 1H), 8.15 (br s, 1H), 8.05-7.99 (m, 1H), 7.87 (br s, 1H), 7.72 (br s, 1H), 7.40 (br d, J = 8.4 Hz, 1H), 7.26-7.19 (m, 1H), 6.85-6.78 (m, 1H), 4.42-4.31 (m, 1H), 4.29-4.17 (m, 2H), 3.81-3.79 (m, 2H), 3.81-3.79 (m, 1H), 2.15-2.07 (m, 1H), 0.99-0.79 (m, 4H) |
| 4-239 | 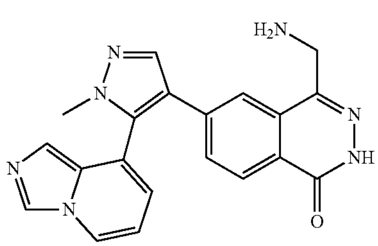 [SMILES: Cn1ncc(-c2ccc3c(=O)[nH]nc(CN)c3c2)c1-c1cccn2cncc12] | 4D | 4-13 | 4-(aminomethyl)-6-(5-(imidazo[1,5-a]pyridin-8-yl)-1-methyl-1H-pyrazol-4-yl)phthalazin-1(2H)-one<br>LCMS [M + 1] $^+$ = 372.1; $^1$H NMR (400 MHz, DMSO-d$_6$) δ = 12.83 (s, 1H), 9.31 (s, 1H), 8.68 (d, J = 7.2 Hz, 1H), 8.50 (br s, 3H), 8.31 (s, 1H), 8.00 (d, J = 8.4 Hz, 1H), 7.89 (d, J = 1.2 Hz, 1H), 7.48 (dd, J = 1.2, 8.4 Hz, 1H), 7.42 (s, 1H), 7.30 (d, J = 6.8 Hz, 1H), 7.15 (t, J = 6.8 Hz, 1H), 4.40-4.23 (m, 2H), 3.77 (s, 3H) |

TABLE 4-continued

| Example | Structure | CM | PM | Compound Name and Characterization |
|---|---|---|---|---|
| 4-240 | 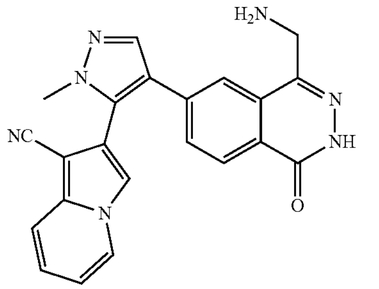 [SMILES: Cn1ncc(-c2ccc3c(=O)[nH]nc(CN)c3c2)c1-c1cn2ccccc2c1C#N] | 4F | 4-6 | 2-(4-(4-(aminomethyl)-1-oxo-1,2-dihydrophthalazin-6-yl)-1-methyl-1H-pyrazol-5-yl)indolizine-1-cathonitrile<br>LCMS [M + 1] $^+$ = 396.1; $^1$H NMR (400 MHz, DMSO-d$_6$) δ = 12.84 (s, 1H), 8.64-8.58 (m, 1H), 8.49 (br s, 3H), 8.27 (s, 1H), 8.11-8.05 (m, 2H), 7.97 (d, J = 1.2 Hz, 1H), 7.70 (d, J = 8.8 Hz, 1H), 7.54 (dd, J = 1.6, 8.0 Hz, 1H), 7.32 (ddd, J = 1.2, 6.8, 9.2 Hz, 1H), 7.04 (dt, J = 1.2,7.2 Hz, 1H), 4.37 (br d, J = 5.6 Hz, 2H), 3.83 (s, 3H) |
| 4-241 | 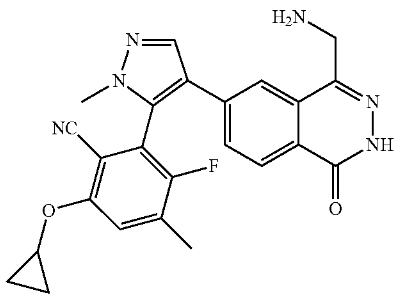 [SMILES: Cc1cc(OC2CC2)c(C#N)c(-c2c(-c3ccc4c(=O)[nH]nc(CN)c4c3)cnn2C)c1F] | 4D | 4-6 | 2-(4-(4-(aminomethyl)-1-oxo-1,2-dihydrophthalazin-6-yl)-1-methyl-1H-pyrazol-5-yl)-6-cyclopropoxy-3-fluoro-4-methylbenzonitrile<br>LCMS [M + 1]$^+$ = 445.2; $^1$H NMR (400 MHz, DMSO-d$_6$) δ = 12.87 (s, 1H), 8.77-8.36 (m, 3H), 8.34 (s, 1H), 8.14 (d, J = 8.4 Hz, 1H), 7.76 (s, 1H), 7.74 (d, J = 6.4 Hz, 1H), 7.49 (d, J = 8.4 Hz, 1H), 4.37-4.24 (m, 2H), 4.11 (td, J = 2.8, 5.6 Hz, 1H), 3.73 (s, 3H), 2.45 (s, 3H), 0.92-0.86 (m, 2H), 0.82-0.74 (m, 2H) |
| 4-242 | 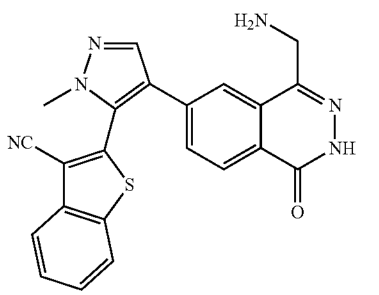 [SMILES: Cn1ncc(-c2ccc3c(=O)[nH]nc(CN)c3c2)c1-c1sc2ccccc2c1C#N] | 4D | 4-8 | 2-(4-(4-(aminomethyl)-1-oxo-1,2-dihydrophthalazin-6-yl)-1-methyl-1H-pyrazol-5-yl)benzo[b]thiophene-3-carbonitrile<br>LCMS [M + 1]$^+$ = 413.1; $^1$H NMR (400 MHz, CD$_3$OD) δ (ppm) = 8.24 (d, J = 8.4 Hz, 1H), 8.15 (s, 1H), 8.13-8.09 (m, 1H), 8.02-7.98 (m, 1H), 7.78-7.75 (m, 1H), 7.72 (dd, J = 1.6, 8.4 Hz, 1H), 7.70-7.61 (m, 2H), 3.98 (s, 3H), 3.83 (s, 2H) |
| 4-243 | 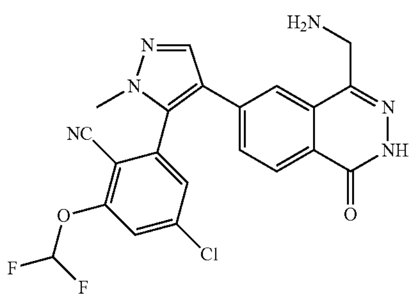 [SMILES: Cn1ncc(-c2ccc3c(=O)[nH]nc(CN)c3c2)c1-c1cc(Cl)cc(OC(F)F)c1C#N] | 4D | 4-6 | 2-(4-(4-(aminomethyl)-1-oxo-1,2-dihydrophthalazin-6-yl)-1-methyl-1H-pyrazol-5-yl)-4-chloro-6-(difluoromethoxy)benzonitrile<br>LCMS [M] $^+$ = 457.1; $^1$H NMR (400 MHz, DMSO-d$_6$) δ (ppm) = 12.89 (s, 1H), 8.55 (br s, 3H), 8.32 (s, 1H), 8.11 (d, J = 8.4 Hz, 1H), 7.90-7.88 (m, 1H), 7.88-7.85 (m, 1H), 7.83-7.79 (m, 1H), 7.79-7.52 (m, 1H), 7.47-7.42 (m, 1H), 4.39-4.27 (m, 2H), 3.81-3.74 (m, 3H) |
| 4-244 | 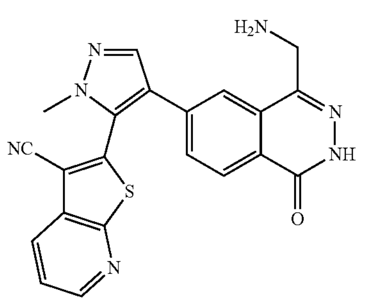 [SMILES: Cn1ncc(-c2ccc3c(=O)[nH]nc(CN)c3c2)c1-c1sc2ncccc2c1C#N] | 4D | 4-8 | 2-(4-(4-(aminomethyl)-1-oxo-1,2-dihydrophthalazin-6-yl)-1-methyl-1H-pyrazol-5-yl)thieno[2,3-b]pyridine-3-carbonitrile<br>LCMS [M + 1]$^+$ = 414.1; $^1$H NMR (400 MHz, CD$_3$OD) δ (ppm) = 8.79 (dd, J = 1.6, 4.8 Hz, 1H), 8.40 (dd, J = 1.6, 8.0 Hz, 1H), 8.26 (d, J = 8.4 Hz, 1H), 8.16 (s, 1H), 7.85 (d, J = 1.2 Hz, 1H), 7.74-7.67 (m, 2H), 4.01 (s, 3H), 3.92 (s, 2H) |

TABLE 4-continued

| Example | Structure | CM | PM | Compound Name and Characterization |
|---|---|---|---|---|
| 4-245 | 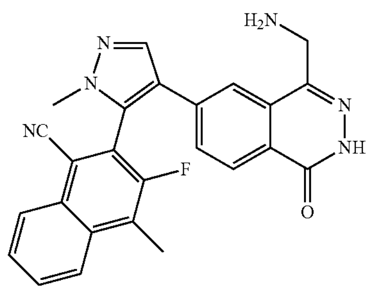 [SMILES: Cc1c(F)c(-c2c(-c3ccc4c(=O)[nH]nc(CN)c4c3)cnn2C)c(C#N)c2ccccc12] | 4G | 4-6 | 2-(4-(4-(aminomethyl)-1-oxo-1,2-dihydrophthalazin-6-yl)-1-methyl-1H-pyrazol-5-yl)-3-fluoro-4-methyl-1-naphthonitrile<br>LCMS [M + 1]⁺ = 439.2; ¹H NMR (400 MHz, CD₃OD) δ = 8.34 (d, J = 8.0 Hz, 1H), 8.23 (s, 1H), 8.18 (d, J = 8.4 Hz, 1H), 8.12 (d, J = 8.4 Hz, 1H), 7.90-7.83 (m, 2H), 7.83-7.76 (m, 1H), 7.49-7.37 (m, 1H), 4.52-4.29 (m, 2H), 3.85 (s, 3H), 2.79 (d, J = 2.4 Hz, 3H) |
| 4-246 | 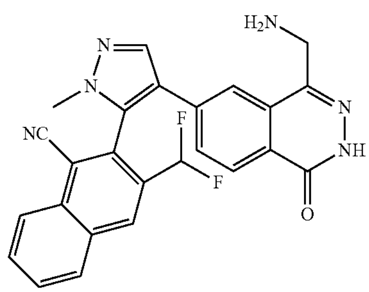 [SMILES: Cn1ncc(-c2ccc3c(=O)[nH]nc(CN)c3c2)c1-c1c(C(F)F)cc2ccccc2c1C#N] | 4D | 4-6 | 2-(4-(4-(aminomethyl)-1-oxo-1,2-dihydrophthalazin-6-yl)-1-methyl-1H-pyrazol-5-yl)-3-(difluoromethyl)-1-naphthonitrile<br>LCMS [M + 1]⁺ = 457.3; ¹H NMR (400 MHz, DMSO-d₆) δ = 12.70 (br s, 1H), 8.89 (s, 1H), 8.49-8.41 (m, 2H), 8.25 (d, J = 8.1 Hz, 1H), 8.08-7.92 (m, 3H), 7.82 (s, 1H), 7.34 (d, J = 8.4 Hz, 1H), 7.09-6.77 (m, 1H), 4.15-4.04 (m, 2H), 3.66 (s, 3H) |
| 4-247 | 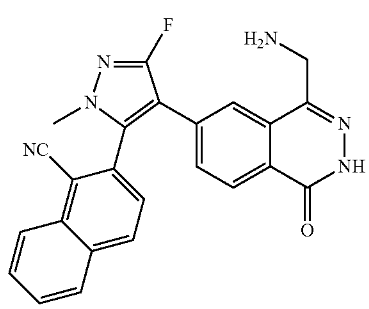 [SMILES: Cn1nc(F)c(-c2ccc3c(=O)[nH]nc(CN)c3c2)c1-c1ccc2ccccc2c1C#N] | 4D | 4-6 | 2-(4-(4-(aminomethyl)-1-oxo-1,2-dihydrophthalazin-6-yl)-3-fluoro-1-methyl-1H-pyrazol-5-yl)-1-naphthonitrile<br>LCMS [M + 1]⁺ = 425.1; ¹H NMR (400 MHz, DMSO-d₆) δ = 12.88 (s, 1H), 8.54 (d, J = 8.4 Hz, 1H), 8.46 (br s, 3H), 8.30-8.24 (m, 1H), 8.13 (d, J = 8.4 Hz, 1H), 8.11 (d, J = 8.4 Hz, 1H), 7.91-7.82 (m, 3H), 7.70 (s, 1H), 7.45 (dd, J = 1.2, 8.4 Hz, 1H), 4.25 (br d, J = 16.0 Hz, 1H), 4.06 (br d, J = 16.0 Hz, 1H), 3.71 (s, 3H) |
| 4-248 | 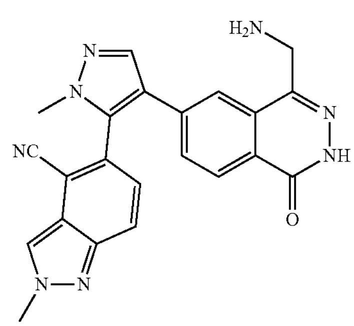 [SMILES: Cn1cc2c(C#N)c(-c3c(-c4ccc5c(=O)[nH]nc(CN)c5c4)cnn3C)ccc2n1] | 4D | 4-6 | 5-(4-(4-(aminomethyl)-1-oxo-1,2-dihydrophthalazin-6-yl)-1-methyl-1H-pyrazol-5-yl)-2-methyl-2H-indazole-4-carbonitrile<br>LCMS [M + 1]⁺ = 411.2; ¹H NMR (400 MHz, DMSO-d₆) δ = 12.83 (s, 1H), 8.80 (s, 1H), 8.49 (br s, 3H), 8.33 (s, 1H), 8.19 (dd, J = 0.8, 8.8 Hz, 1H), 8.02 (d, J = 8.4 Hz, 1H), 7.86 (d, J = 1.2 Hz, 1H), 7.49 (d, J = 8.8 Hz, 1H), 7.36 (dd, J = 2.4, 8.4 Hz, 1H), 4.33-4.19 (m, 5H), 3.75 (s, 3H) |
| 4-249 | 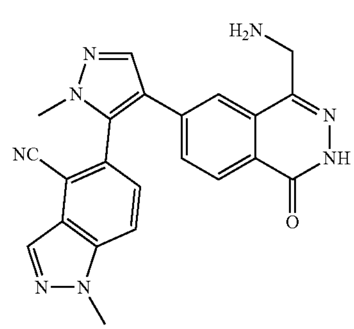 [SMILES: Cn1ncc(-c2ccc3c(=O)[nH]nc(CN)c3c2)c1-c1ccc2c(cnn2C)c1C#N] | 4D | 4-6 | 5-(4-(4-(aminomethyl)-1-oxo-1,2-dihydrophthalazin-6-yl)-1-methyl-1H-pyrazol-5-yl)-1-methyl-1H-indazole-4-carbonitrile<br>LCMS [M + 1]⁺ = 411.2; ¹H NMR (400 MHz, DMSO-d₆) δ = 12.83 (s, 1H), 8.48-8.37 (m, 3H), 8.36-8.26 (m, 3H), 8.02 (d, J = 8.4 Hz, 1H), 7.83 (s, 1H), 7.72 (d, J = 8.8 Hz, 1H), 7.34 (br d, J = 8.4 Hz, 1H), 4.22 (m, 5H), 3.74 (s, 3H) |

TABLE 4-continued

| Example | Structure | CM | PM | Compound Name and Characterization |
|---|---|---|---|---|
| 4-250 | 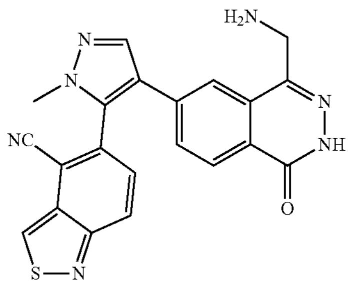 [SMILES: Cn1ncc(-c2ccc3c(=O)[nH]nc(CN)c3c2)c1-c1ccc2nscc2c1C#N] | 4D | 4-6 | 5-(4-(4-(aminomethyl)-1-oxo-1,2-dihydrophthalazin-6-yl)-1-methyl-1H-pyrazol-5-yl)benzo[c]isothiazole-4-carbonitrile<br>LCMS [M + 1]$^+$ = 414.2; $^1$H NMR (400 MHz, DMSO-d$_6$) δ = 12.87 (s, 1H), 10.07 (d, J = 1.2 Hz, 1H), 8.39-8.25 (m, 5H), 8.07 (d, J = 8.4 Hz, 1H), 7.88 (s, 1H), 7.77 (d, J = 9.2 Hz, 1H), 7.45 (dd, J = 1.6, 8.4 Hz, 1H), 4.37-4.23 (m, 2H), 3.84-3.80 (m, 3H) |
| 4-251 | 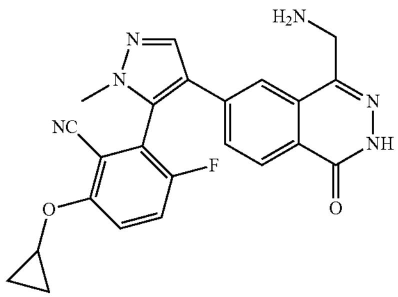 [SMILES: Cn1ncc(-c2ccc3c(=O)[nH]nc(CN)c3c2)c1-c1c(F)ccc(OC2CC2)c1C#N] | 4D | 4-6 | 2-(4-(4-(aminomethyl)-1-oxo-1,2-dihydrophthalazin-6-yl)-1-methyl-1H-pyrazol-5-yl)-6-cyclopropoxy-3-fluorobenzonitrile<br>LCMS [M + 1]$^+$ = 431.1; $^1$H NMR (400 MHz, DMSO-d$_6$) δ = 12.88 (s, 1 H), 8.45 (s, 3 H), 8.35 (s, 1 H), 8.14 (d, J = 8.4 Hz, 1 H), 7.86-7.93 (m, 1 H), 7.77-7.83 (m, 2 H), 7.47 (d, J = 8.4, 1.10 Hz, 1 H), 4.25-4.39 (m, 2 H), 4.12-4.20 (m, 1 H), 3.75 (s, 3 H), 0.85-0.93 (m, 2 H), 0.75-0.84 (m, 2 H) |
| 4-252 | 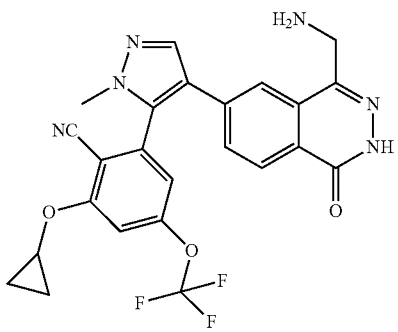 [SMILES: Cn1ncc(-c2ccc3c(=O)[nH]nc(CN)c3c2)c1-c1cc(OC(F)(F)F)cc(OC2CC2)c1C#N] | 4D | 4-6 | 2-(4-(4-(aminomethyl)-1-oxo-1,2-dihydrophthalazin-6-yl)-1-methyl-1H-pyrazol-5-yl)-6-cyclopropoxy-4-(trifluoromethoxy)benzonitrile<br>LCMS [M + 1]$^+$ = 497.1; $^1$H NMR (400 MHz, DMSO-d$_6$) δ = 8.51 (br s, 3H), 8.30 (s, 1H), 8.11 (d, J = 8.4 Hz, 1H), 7.80 (s, 1H), 7.68 (d, J = 1.2 Hz, 1H), 7.46-7.39 (m, 2H), 4.32 (br d, J = 5.6 Hz, 2H), 4.28-4.21 (m, 1H), 3.76 (s, 3H), 0.96-0.77 (m, 4H) |

Example 4-253

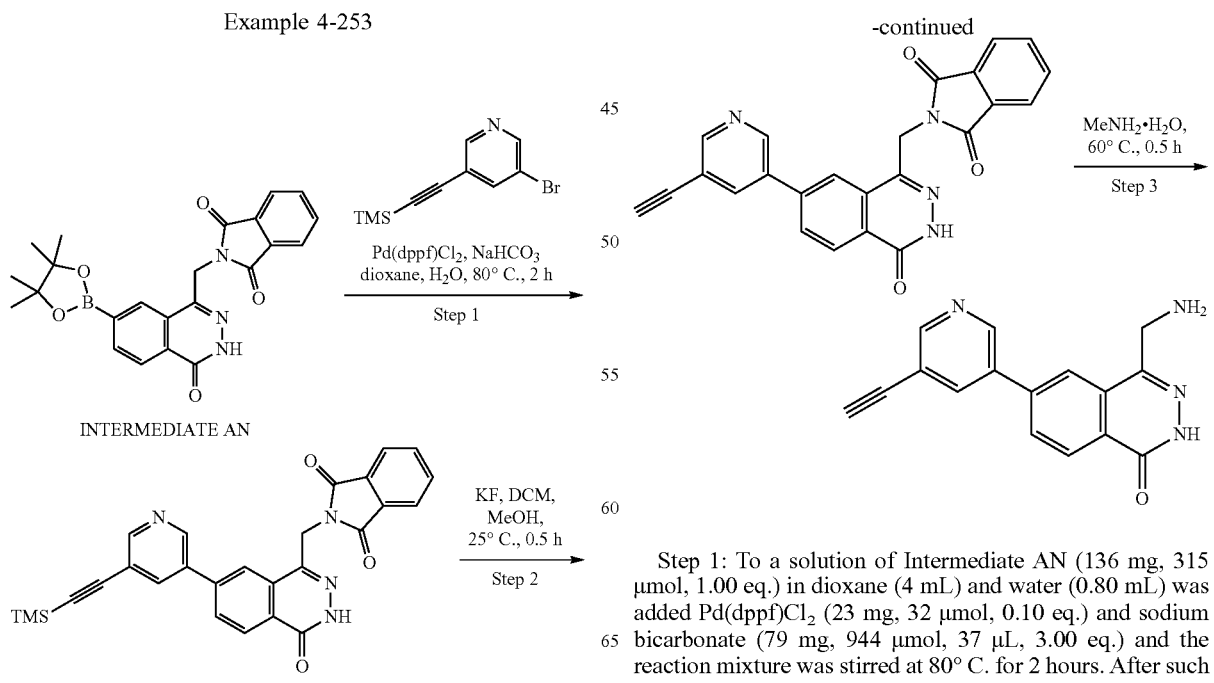

Step 1: To a solution of Intermediate AN (136 mg, 315 μmol, 1.00 eq.) in dioxane (4 mL) and water (0.80 mL) was added Pd(dppf)Cl$_2$ (23 mg, 32 μmol, 0.10 eq.) and sodium bicarbonate (79 mg, 944 μmol, 37 μL, 3.00 eq.) and the reaction mixture was stirred at 80° C. for 2 hours. After such time the reaction was filtered, the filtrate was concentrated in vacuum to a residue, the residue was purified by prep-TLC (petroleum ether:ethyl acetate 10-100%) to give 2-[[4-oxo-7-[5-(2-trimethylsilylethynyl)-3-pyridyl]-3H-phthalazin-1-yl]methyl] isoindoline-1,3-dione (100 mg, 209 µmol, 66% yield) as a brown solid. $^1$H NMR (400 MHz, DMSO-$d_6$) δ=12.32 (s, 1H), 8.96 (d, J=2.4 Hz, 1H), 8.55 (d, J=2.0 Hz, 1H), 8.36-8.31 (m, 2H), 8.14 (s, 2H), 7.79-7.74 (m, 2H), 7.73-7.69 (m, 2H), 5.19 (s, 2H), 0.09 (s, 9H).

Step 2: To a solution of 2-[[4-oxo-7-[5-(2-trimethylsilylethynyl)-3-pyridyl]-3H-phthalazin-1-yl]methyl]isoindoline-1,3-dione (100 mg, 209 µmol, 1.00 eq.) in methanol (2 mL) and dichloromethane (2 mL) was added potassium fluoride (36 mg, 627 µmol, 14.7 µL, 3.00 eq.), and the reaction was stirred at 25° C. for 0.5 hour. The reaction was concentrated under vacuum and the residue was triturated with water (5 mL), filtered and the filter cake was dried in vacuum to give 2-[[7-(5-ethynyl-3-pyridyl)-4-oxo-3H-phthalazin-1-yl]methyl]isoindoline-1,3-dione (80 mg, 197 µmol, 94% yield) as a brown solid. LCMS [M+1]$^+$=407.0.

Step 3: A mixture of 2-[[7-(5-ethynyl-3-pyridyl)-4-oxo-3H-phthalazin-1-yl] methyl]isoindoline-1,3-dione (80 mg, 197 µmol, 1.00 eq.) in methylamine aqueous solution (4 mL) was stirred at 60° C. for 0.5 hour. After such time the reaction was concentrated under vacuum and the residue was purified by prep-HPLC (column: Phenomenex Synergi C18 150×25×10 µm; mobile phase: [water (0.05% HCl)-ACN]; B %: 0%-25%, 10 min) and lyophilization to give 4-(aminomethyl)-6-(5-ethynyl-3-pyridyl)-2H-phthalazin-1-one, example 4-253 (10 mg, 32.1 µmol, 16% yield) as a yellow solid. LCMS [M+1$^+$]=277.2. $^1$H NMR (400 MHz, DMSO-$d_6$) δ=13.01 (s, 1H), 9.17 (d, J=2.4 Hz, 1H), 8.81 (d, J=1.6 Hz, 1H), 8.60-8.49 (m, 4H), 8.41-8.37 (m, 1H), 8.36-8.30 (m, 2H), 4.65-4.55 (m, 3H).

Example 4-254

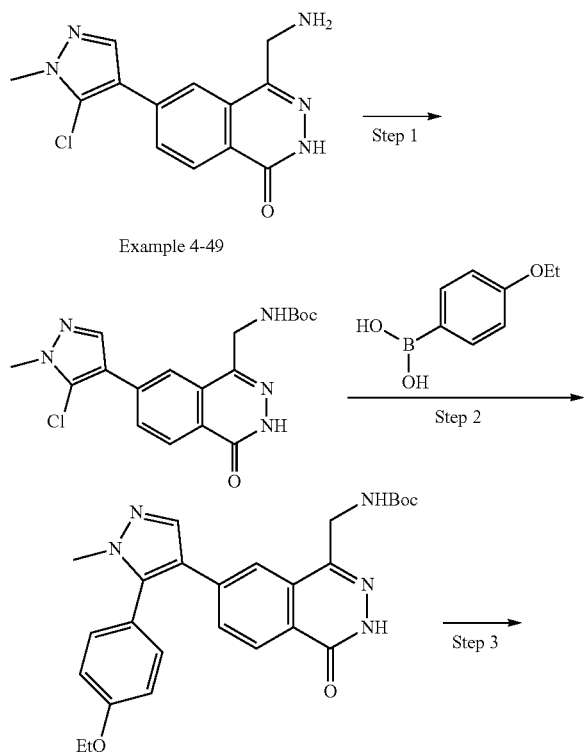

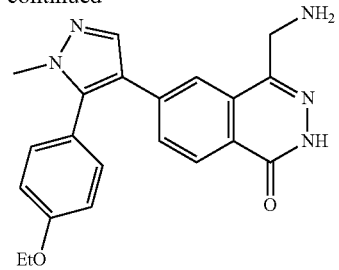

Step 1: A mixture of 4-(aminomethyl)-6-(5-chloro-1-methyl-pyrazol-4-yl)-2H-phthalazin-1-one, Example 4-49 (45 mg, 155 µmol, 1.00 eq.), di-tert-butyl dicarbonate (68 mg, 311 µmol, 71 µL, 2.00 eq.) and triethylamine (47 mg, 466 µmol, 65 µL, 3.00 eq.) in dichloromethane (1.00 mL) was purged with nitrogen 3 times and stirred at 25° C. for 3 hours. After such time the mixture was concentrated under reduced pressure to a residue. The mixture was triturated with petroleum ether (3 mL) and filtered to give tert-butyl N-[[7-(5-chloro-1-methyl-pyrazol-4-yl)-4-oxo-3H-phthalazin-1-yl]methyl]carbamate (40 mg, 96 µmol, 62% yield) as a yellow solid. LCMS [M+1]$^+$=390.2. $^1$H NMR (400 MHz, MeOD) δ=8.41 (d, J=8.4 Hz, 1H), 8.33 (s, 1H), 8.19 (br d, J=8.4 Hz, 1H), 8.05 (s, 1H), 4.62 (s, 2H), 3.96-3.92 (s, 3H), 1.48-1.40 (s, 9H).

Step 2: A mixture of (4-ethoxyphenyl)boronic acid (16 mg, 98.5 µmol, 1.20 eq.), tert-butyl N-[[7-(5-chloro-1-methyl-pyrazol-4-yl)-4-oxo-3H-phthalazin-1-yl]methyl] carbamate (32 mg, 82 µmol, 1.00 eq.), sodium carbonate (26 mg, 246 µmol, 3.00 eq.) and Pd(dppf)Cl$_2$ (6 mg, 8 µmol, 0.10 eq.) in dioxane (3 mL) and water (0.6 mL) was purged with nitrogen 3 times and stirred at 110° C. for 12 hours. The mixture was concentrated under reduced pressure and the residue was purified by column chromatography (SiO$_2$, petroleum ether/ethyl acetate 10-100%) to give tert-butyl-N-[[7-[5-(4-ethoxyphenyl)-1-methyl-pyrazol-4-yl]-4-oxo-3H-phthalazin-1-yl]methyl]carbamate (28 mg, 45 µmol, 54% yield) as a white solid. LCMS [M+1]$^+$=476.2.

Step 3: A mixture of tert-butyl-N-[[7-[5-(4-ethoxyphenyl)-1-methyl-pyrazol-4-yl]-4-oxo-3H-phthalazin-1-yl] methyl]carbamate (28 mg, 59 µmol, 1.00 eq.) and trifluoroacetic acid (1.08 g, 9.45 mmol, 700 µL, 161 eq.), in dichloromethane (3 mL) was purged with nitrogen 3 times and stirred at 25° C. for 1 hour. After such time the mixture was concentrated under reduced pressure and the residue was purified by prep-HPLC (Phenomenex Gemini-NX C18 75×30 mm×3 µm; mobile phase: [water (0.1% TFA)-ACN]; B %: 20%-30%, 7 min) to give 4-(aminomethyl)-6-[5-(4-ethoxyphenyl)-1-methyl-pyrazol-4-yl]-2H-phthalazin-1-one, Example 4-254 (25 mg, 49 µmol, 83% yield, TFA salt) as an off-white solid. LCMS [M+1]$^+$=376.1. $^1$H NMR (400 MHz, DMSO-$d_6$) δ=12.84 (s, 1H), 8.34 (br s, 3H), 8.12 (s, 1H), 8.07 (d, J=8.4 Hz, 1H), 7.79 (d, J=1.2 Hz, 1H), 7.51 (dd, J=1.6, 8.4 Hz, 1H), 7.33 (d, J=8.8 Hz, 2H), 7.08 (d, J=8.8 Hz, 2H), 4.31 (br d, J=4.4 Hz, 2H), 4.11 (q, J=6.8 Hz, 2H), 3.72 (s, 3H), 1.37 (t, J=6.8 Hz, 3H).

Examples 5-1 and 5-2

General Coupling Method for the Preparation of Examples 5-1 AND 5-2

Coupling Method 5:

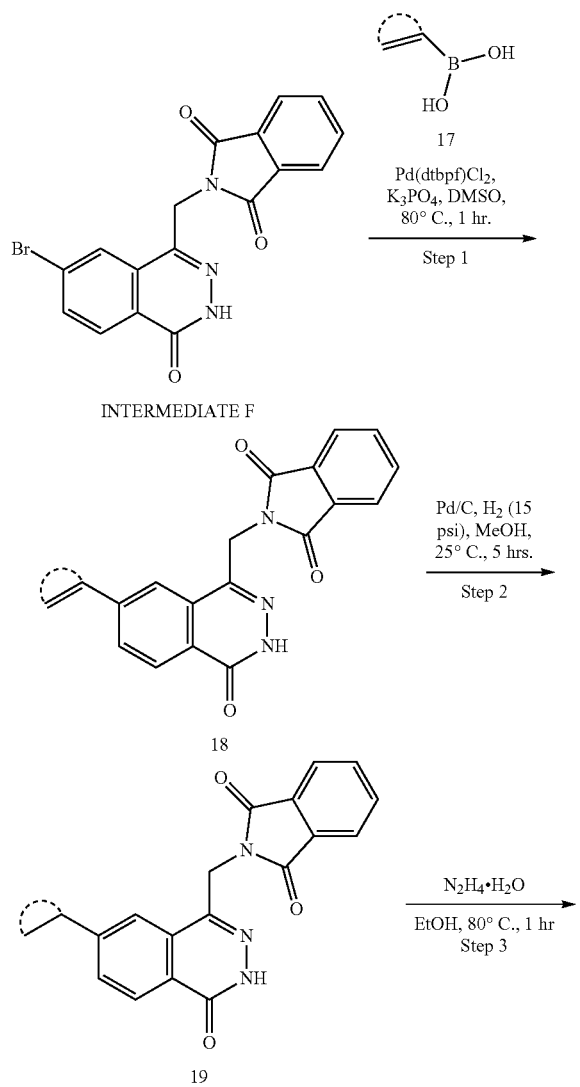

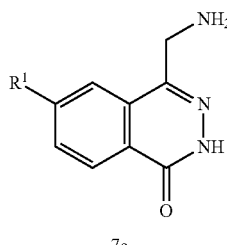

Wherein R¹ = cycloalkyl or heterocycloalkyl

Step 1: A mixture of Intermediate F (200 mg, 521 μmol, 1.00 eq.), $R^{1a}$-boronic acid 17 where $R^{1a}$ is cycloalkenyl or heterocycloalkenyl (781 μmol, 1.50 eq.), di-tert-butyl(cyclopentyl)phosphane; dichloropalladium; iron (34 mg, 52 μmol, 0.10 eq.), potassium phosphate (221 mg, 1.04 mmol, 2.00 eq.) in dimethylsulfoxide (2.5 mL) was purged with nitrogen 3 times and the mixture stirred at 80° C. for 1 hour and cooled to room temperature. Water (50 mL) was then added and the mixture extracted with ethyl acetate (40 mL×3). The combined organic extracts were washed with brine (50 mL), dried over anhydrous sodium sulfate, filtered, and concentrated in vacuo and the residue purified by column chromatography (SiO₂, dichloromethane/methanol 0 to 10% methanol) to give the corresponding coupled product 18 as a light-yellow solid.

Step 2: To a solution of the corresponding coupled product 18 (296 μmol, 1.00 eq.) in methanol (6 mL) was added 10% palladium on activated carbon (10 mg). The mixture was purged with hydrogen several times and stirred under a hydrogen atmosphere (15 psi) at 25° C. for 5 hours. After such time the reaction mixture was filtered and concentrated to give the corresponding reduced product 19 as a white solid which was used in the next step without further purification.

Step 3: A mixture of the corresponding reduced product 19 and hydrazine hydrate (27 mg, 536 μmol, 26 μL) in ethanol (5 mL) was stirred at 80° C. for 1 hour. The reaction mixture was evaporated and the residue was purified by prep-HPLC (Phenomenex Synergi C18 150×25×10 μm; mobile phase: [water (0.05% HCl)-ACN]; B %: 16%-36%, 9 min) to give the desired R¹ amino compounds where R¹ is cycloalkyl or heterocycloalkyl.

Following the teachings of the General Reaction Schemes, the coupling method 5 and the Intermediates disclosed herein, the Examples 5-1 to 5-2 are prepared as shown in Table 5:

TABLE 5

| Example | Structure | Compound Name and Characterization |
|---|---|---|
| 5-1 | 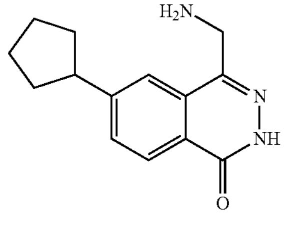 [SMILES: NCc1n[nH]c(=O)c2ccc(C3CCCC3)cc12] | 4-(aminomethyl)-6-cyclopentylphthalazin-1(2H)-one; LCMS [M + 1]⁺ 244.2; ¹H NMR (400 Hz, DMSO-d₆) δ = 12.83 (s, 1H), 8.43 (br s, 3H), 8.22 (d, J = 8.4 Hz, 1H), 7.83 (d, J = 8.4 Hz, 1H), 7.78 (s, 1H), 4.47 (br d, J = 4.8 Hz, 2H), 3.27-3.16 (m, 1H), 2.18-2.05 (m, 2H), 1.84 (m, 2H), 1.77-1.61 (m, 4H). |

TABLE 5-continued

| Example | Structure | Compound Name and Characterization |
|---|---|---|
| 5-2 | 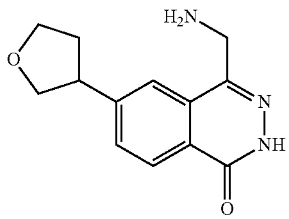 [SMILES: NCc1n[nH]c(=O)c2ccc(C3CCOC3)cc12] | (R,S)-4-(aminomethyl)-6-(THF-3-yl)phthalazin-1(2H)-one; LCMS [M + 1]⁺ 246.1; $^1$H NMR (400 Hz, DMSO-$d_6$) δ = 12.86 (s, 1H), 8.53 (s, 3H), 8.24 (d, J = 8.8 Hz, 1H), 7.89-7.81 (m, 2H), 4.46 (br d, J = 5.2 Hz, 2H), 4.14-3.98 (m, 2H), 3.85 (q, J = 7.6 Hz, 1H), 3.75-3.58 (m, 2H), 3.44-3.36 (m, 1H), 2.11-2.02 (m, 1H). |

Preparation of Examples 6-1 to 6-5

Example 6-1

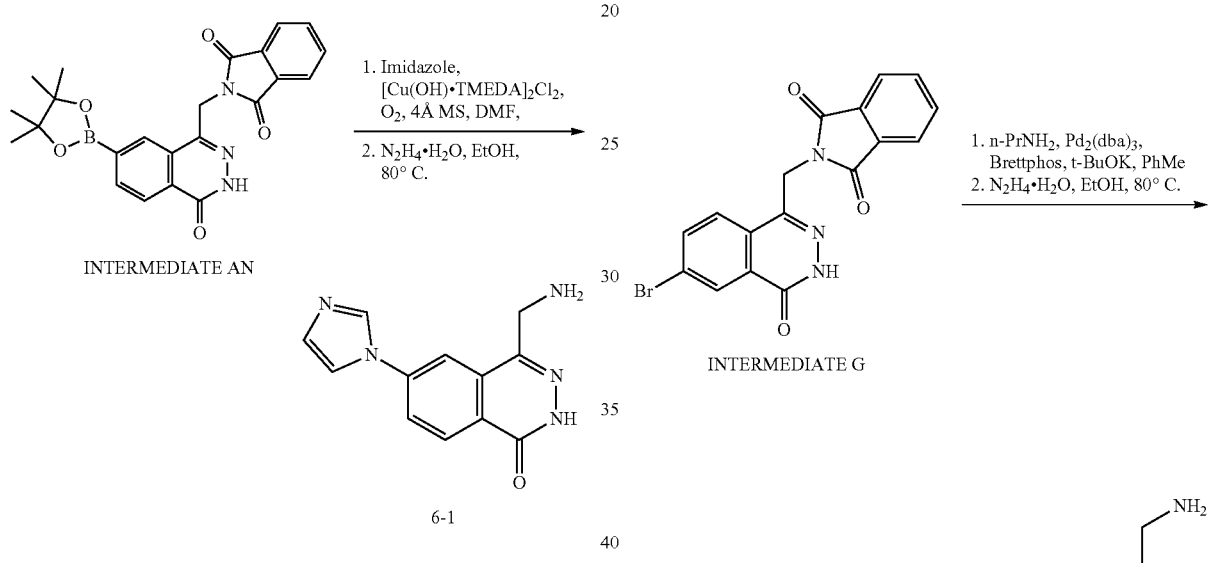

Step 1: A mixture of Intermediate AN (86 mg, 200 μmol, 1.00 eq.), imidazole (68 mg, 1.00 mmol, 5.00 eq.), chloro(hydroxy)copper-N,N,N',N'-tetramethylethane-1,2-diamine (9 mg, 20 μmol, 0.10 eq.) and 4 Å molecular sieve (10 mg) in DMF (5 mL) was degassed and purged with oxygen 3 times. The mixture was then stirred at 25° C. for 12 hours under an oxygen atmosphere (15 psi). After such time the mixture was filtered and concentrated under reduced pressure and the residue purified by prep-HPLC (Phenomenex Synergi C18 150×25×10 μm; mobile phase: [water (0.225% FA)-ACN]; B %: 3%-33%, 10 min) to give 2-[(7-imidazol-1-yl-4-oxo-3H-phthalazin-1-yl)methyl]isoindoline-1,3-dione (4 mg, 10.8 μmol, 5% yield) as a white solid LCMS [M+1]⁺=372.1.

Step 2: To a solution of 2-[(7-imidazol-1-yl-4-oxo-3H-phthalazin-1-yl)methyl]isoindoline-1,3-dione (3 mg, 8 μmol, 1.00 eq.) in ethyl alcohol (1.00 mL) was added hydrazine hydrate (4 mg, 81 μmol, 3 μL, 10.0 eq.). The mixture was stirred at 80° C. for 1 hour and then the mixture was concentrated under reduced pressure. The concentrated residue was then purified by prep-HPLC (Phenomenex Synergi C18 150×25×10 μm; mobile phase: [water (0.05% HCl)-ACN]; B %: 0%-20%, 9 min) to give 4-(aminomethyl)-6-imidazol-1-yl-2H-phthalazin-1-one, example 6-1 (1.4 mg, 5 μmol, 61% yield) as an off-white solid. LCMS [M+1]⁺=242.1. $^1$H NMR (400 MHz, DMSO-$d_6$) δ=13.12 (s, 1H), 9.71-9.57 (s, 1H), 8.70-8.61 (brs, 3H), 8.49 (d, J=8.8 Hz 1H), 8.47 (s, 1H), 8.44 (s, 1H), 8.33 (dd, J=2.0, 8.8 Hz, 1H), 7.77 (br s, 1H), 4.53 (br d, J=5.6 Hz, 2H).

Example 6-2

Step 1: To a solution of Intermediate G (50 mg, 130 μmol, 1.00 eq.) and propan-1-amine (9 mg, 156 μmol, 13 μL, 1.20 eq.) in toluene (2 mL) was added Pd₂(dba)₃ (24 mg, 26 μmol, 0.20 eq.), potassium tert-butoxide (29 mg, 260 μmol, 2.00 eq.) and BrettPhos (140 mg, 260 μmol, 2.00 eq.) under a nitrogen atmosphere. The mixture was stirred at 100° C. for 12 hours. After such time the mixture was concentrated in vacuo and the residue dissolved in a water:methyl alcohol 2:1 mixture (3 mL) and filtered. The filtrate was concentrated in vacuo to give 2-[[4-oxo-6-(propylamino)-3H-phthalazin-1-yl]methylcarbamoyl]benzoic acid (35 mg, crude) as a yellow solid, which was used in the next step without further purification. LCMS [M+1]⁺=381.1.

Example 6-3

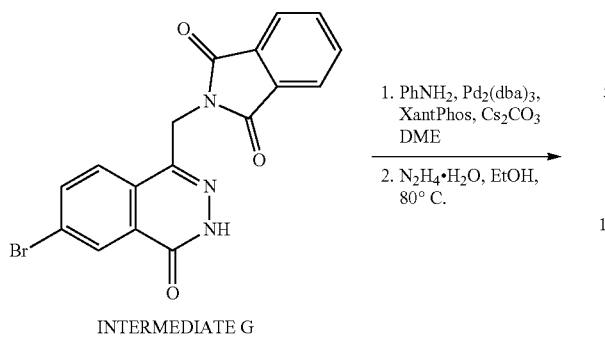

INTERMEDIATE G

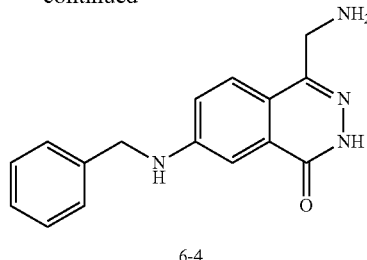

6-3

Step 1 To a solution of Intermediate G (200 mg, 521 μmol, 1.00 eq.) and aniline (58 mg, 624 μmol, 57.0 μL, 1.20 eq.) in DME (3 mL) was added cesium carbonate (678 mg, 2.08 mmol, 4.00 eq.), Pd$_2$(dba)$_3$ (48 mg, 52 μmol, 0.10 eq.) and Xantphos (331 mg, 572 μmol, 1.10 eq.). The mixture was stirred at 95° C. for 12 hours under nitrogen atmosphere. After such time the mixture was concentrated in vacuo and the residue taken up in water (5 mL) and methyl alcohol (5 mL) then filtered. The filtrate was concentrated in vacuum to give 2-[(6-anilino-4-oxo-3H-phthalazin-1-yl)methylcarbamoyl]benzoic acid (200 mg, crude) as a yellow solid, which was used in the next step without further purification.

Step 2: To a solution of 2-[(6-anilino-4-oxo-3H-phthalazin-1-yl)methylcarbamoyl]benzoic acid (50 mg, crude) in ethyl alcohol (1 mL) was added hydrazine hydrate (12.9 mg, 252 μmol, 12.5 The mixture was stirred at 80° C. for 12 hours. After such time the mixture was concentrated in vacuo and the residue purified by prep-HPLC (Phenomenex Synergi C18 150×25×10 μm; mobile phase: [water (0.05% HCl)-ACN]; B %: 2%-32%, 10 min) to give 4-(aminomethyl)-7-anilino-2H-phthalazin-1-one, example 6-3 (10 mg, 33 μmol, 24% yield) as a yellow solid. LCMS [M+1]$^+$=267.0. $^1$H NMR (400 MHz, DMSO-d$_6$) δ=12.63 (s, 1H), 9.17 (s, 1H), 8.43 (br s, 3H), 7.82 (d, J=8.8 Hz, 1H), 7.77 (d, J=2.4 Hz, 1H), 7.52 (dd, J=2.4, 8.8 Hz, 1H), 7.42-7.36 (m, 2H), 7.28-7.23 (m, 2H), 7.07 (t, J=7.2 Hz, 1H), 4.37 (br s, 2H).

Example 6-4

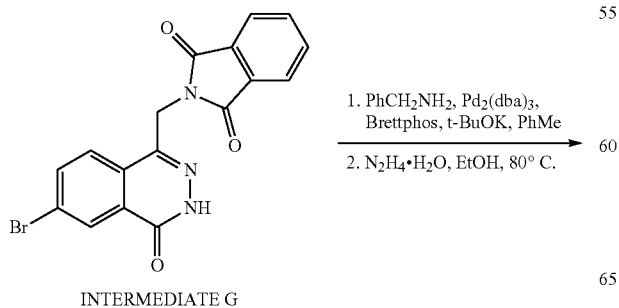

INTERMEDIATE G

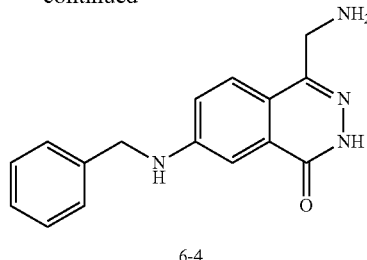

6-4

Step 1: To a solution of Intermediate G (50 mg, 130 μmol, 1.00 eq.) and phenylmethanamine (17 mg, 156 μmol, 17.0 μL, 1.20 eq.) in toluene (2 mL) was added Pd$_2$(dba)$_3$ (24 mg, 26 μmol, 0.20 eq.), potassium tert-butoxide (29 mg, 260 μmol, 2.00 eq.) and BrettPhos (140 mg, 260 μmol, 2.00 eq.) under a nitrogen atmosphere. The mixture was stirred at 100° C. for 12 hours. After such time the mixture was concentrated in vacuo and the residue dissolved in a water:methyl alcohol 2:1 mixture (3 mL) and filtered. The filtrate was concentrated in vacuo to give 2-[[6-(benzylamino)-4-oxo-3H-phthalazin-1-yl]methylcarbamoyl]benzoic acid (35 mg, crude) as a yellow solid, which was used directly in the next step without further purification. LCMS [M+1]$^+$=429.1. To a solution of 2-[[6-(benzylamino)-4-oxo-3H-phthalazin-1-yl]methylcarbamoyl] benzoic acid (35 mg, crude) in ethyl alcohol (1 mL) was added hydrazine hydrate (9 mg, 171 μmol, 8 The mixture was stirred at 80° C. for 12 hours. After such time the mixture was concentrated in vacuo and the residue purified by prep-HPLC (Phenomenex Synergi C18 150×25×10 μm; mobile phase: [water (0.05% HCl)-ACN]; B %: 2%-32%, 10 min) to give 4-(aminomethyl)-7-(benzylamino)-2H-phthalazin-1-one, example 6-4 (7 mg, 22 μmol, 17% yield) as a yellow solid. LCMS [M+1]$^+$=281.2. $^1$H NMR (400 MHz, DMSO-d$_6$) δ=12.49 (s, 1H), 8.32 (br s, 3H), 7.67 (d, J=8.8 Hz, 1H), 7.58-7.50 (m, 1H), 7.37-7.32 (m, 4H), 7.27-7.19 (m, 3H), 4.45 (br s, 2H), 4.31 (br d, J=6.0 Hz, 2H).

Example 6-5

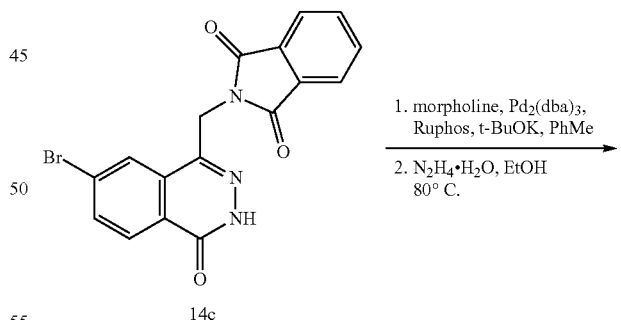

14c
INTERMEDIATE F

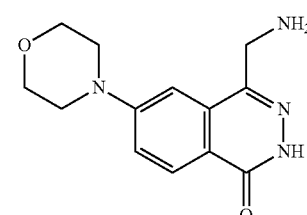

6-5

Step 1: To a solution of Intermediate F (50 mg, 130 µmol, 1.00 eq.) and morpholine (17 mg, 195 µmol, 17 µL, 1.50 eq.) in toluene (2 mL) was added Pd$_2$(dba)$_3$ (12 mg, 13 µmol, 0.10 eq.), potassium tert-butoxide (44 mg, 390 µmol, 3.00 eq.) and RuPhos (121 mg, 260 µmol, 2.00 eq.) under a nitrogen atmosphere. The mixture was stirred at 100° C. for 2 hours. After such time the mixture was concentrated in vacuo and the residue dissolved in a water:methyl alcohol 2:1 mixture (3 mL) and filtered. The filtrate was concentrated in vacuo to give 2-(morpholine-4-carbonyl)-N-[(7-morpholino-4-oxo-3H-phthalazin-1-yl)methyl]benzamide (35.0 mg, crude) as a yellow solid which was used directly in the next step without further purification. LCMS [M+1]$^+$=478.2. To a solution of 2-(morpholine-4-carbonyl)-N-[(7-morpholino-4-oxo-3H-phthalazin-1-yl)methyl]benzamide (35 mg, crude) in ethyl alcohol (1 mL) was added hydrazine hydrate (9 mg, 176 µmol, 9 The mixture was stirred at 80° C. for 12 hours. After such time the mixture was concentrated in vacuo and the residue purified by prep-HPLC (Phenomenex Synergi C18 150×25×10 µm; mobile phase: [water (0.05% HCl)-ACN]; B %: 3%-23%, 9 min) to give 4-(aminomethyl)-6-morpholino-2H-phthalazin-1-one, example 6-5 (9 mg, 28 µmol, 32% yield) as a white solid. LCMS [M+1]$^+$=261.0. $^1$H NMR (400 MHz, DMSO-d$_6$) δ=12.56 (s, 1H), 8.50 (br s, 3H), 8.08 (d, J=9.2 Hz, 1H), 7.51 (dd, J=2.4, 9.2 Hz, 1H), 7.09 (d, J=2.4 Hz, 1H), 4.38 (q, J=5.6 Hz, 2H), 3.79-3.76 (m, 4H), 3.47-3.41 (m, 4H).

General Coupling Method and Purification Methods for the Preparation of Examples 7-1 to 7-6

General Method 7

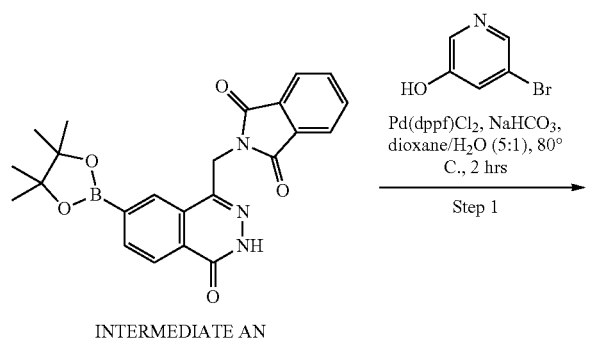

INTERMEDIATE AN

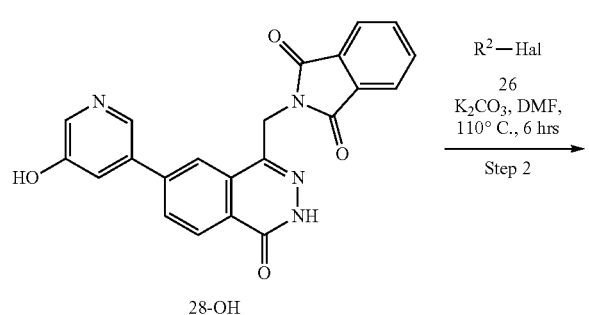

28-OH

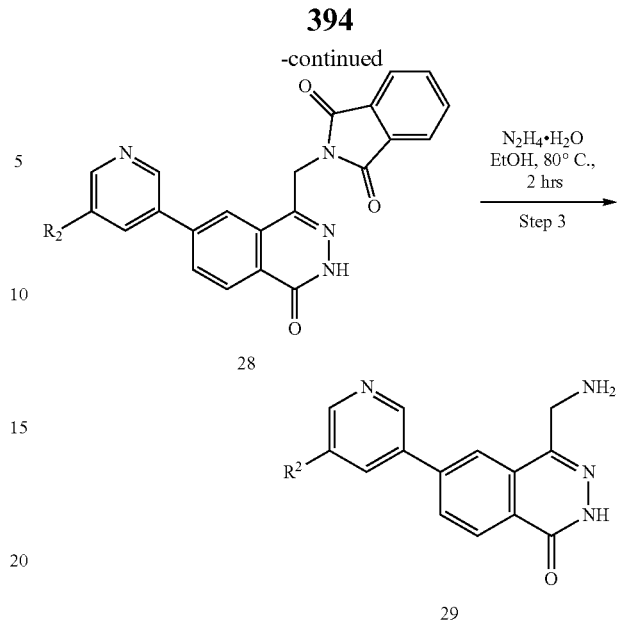

28

29

R$^2$ = O-Aryl or O-Heteroaryl and Hal = F, Br or I

Step 1: A mixture of Intermediate AN (150 mg, 348 µmol, 1.00 eq.), 5-bromopyridin-3-ol (522 µmol, 1.5 eq), Pd(dppf)Cl$_2$ (26 mg, 35 µmol, 0.10 eq.), sodium bicarbonate (58 mg, 696 µmol, 27 µL, 2.00 eq.) in dioxane (1 mL) and water (0.2 mL) was degassed and purged with nitrogen 3 times. The mixture was stirred at 80° C. for 3 hours under a nitrogen atmosphere. Upon completion the reaction mixture was diluted with water (30 mL) and extracted with ethyl acetate (30 mL×3). The aqueous phase was filtered, and the filter cake dried to give the corresponding R$^2$-Pyridyl-Suzuki coupling product 28-OH which was used directly in the next step without further purification.

Step 2: To a solution of Pyridyl-Suzuki coupling product 28-OH (80 mg, crude) in DMF (1 mL) was added potassium carbonate (83 mg, 602 µmol) and aryl/heteroaryl-substituted fluoride/bromide 26 (54 mg, 402 µmol). The mixture was stirred at 120° C. for 6 hours to furnish R$^2$-Pyridyl-S$_N$Ar coupling product 28. The reaction mixture was used in the next step directly without further purification.

Step 3: To a solution of corresponding R$^2$-Pyridyl-S$_N$Ar coupling product 28 (50 mg, crude) in ethyl alcohol (10 mL) was added hydrazine hydrate (11.0 mg, 210 µmol, 10 µL). The mixture was stirred at 80° C. for 2 hours and the cooled mixture was concentrated in vacuo. The concentrated residue 29 was purified by prep-HPLC according to one of the purification methods 7-1 through 7-3 to return desired compounds shown in table 7.

Purification Methods (PM)

PM 7-1: column: Phenomenex Synergi C18 150×25 mm×10 µm; mobile phase: [water (0.05% HCl)-ACN]; B %: 5%-25%, 11 min.

PM 7-2: column: Waters Xbridge 150×25 mm×5 µm; mobile phase: [water (10 mM NH$_4$HCO$_3$)-ACN]; B %: 2%-32%, 10 min, PM 7-3: column: Shim-pack C18 150×25 mm×10 µm; mobile phase: [water (0.1% TFA)-ACN]; B %: 1%-20%, 10 min.

Following the teachings of the General Reaction Schemes, coupling method 7 and using purification methods 7-1 through 7-3 and the Intermediates disclosed herein, the Examples 7-1 to 7-6 are prepared as shown in Table 7.

TABLE 7

| Examples | Structure | PM | Compound Name and Characterization |
|---|---|---|---|
| 7-1 | 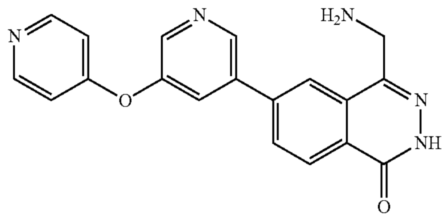 [SMILES: NCc1n[nH]c(=O)c2ccc(-c3cncc(Oc4ccncc4)c3)cc12] | 7-3 | 4-(aminomethyl)-6-(5-(pyridin-4-yloxy)pyridin-3-yl)phthalazin-1(2H)-one<br>LCMS [M + 1]$^+$ = 346.0; $^1$H NMR (400 MHz, DMSO-d$_6$) δ = 13.02 (s, 1H), 9.17 (s, 1H), 8.69 (s, 1H), 8.63 (br d, J = 5.2 Hz, 2H), 8.46-8.37 (m, 5H), 8.36 (s, 1H), 8.33 (s, 1H), 7.25 (br s, 2H), 4.59 (br d, J = 5.6 Hz, 2H). |
| 7-2 | 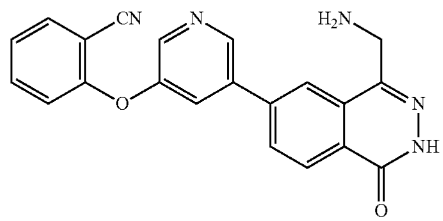 [SMILES: N#Cc1ccccc1Oc1cncc(-c2ccc3c(=O)[nH]nc(CN)c3c2)c1] | 7-2 | 2-((5-(4-(aminomethyl)-1-oxo-1,2-dihydrophthalazin-6-yl)pyridin-3-yl)oxy)benzonitrile<br>LCMS [M + 1]$^+$ = 370.0; $^1$H NMR (400 MHz, DMSO-d$_6$) δ = 8.99 (s, 1H), 8.55 (d, J = 2.8 Hz, 1H), 8.41-8.36 (m, 2H), 8.20 (d, J = 8.4 Hz, 1H), 8.15 (s, 1H), 7.92 (d, J = 7.6 Hz, 1H), 7.73 (t, J = 8.0 Hz, 1H), 7.37 (t, J = 7.6 Hz, 1H), 7.20 (d, J = 8.4 Hz, 1H), 4.13 (s, 2H). |
| 7-3 | 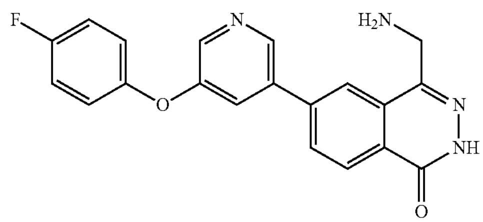 [SMILES: NCc1n[nH]c(=O)c2ccc(-c3cncc(Oc4ccc(F)cc4)c3)cc12] | 7-1 | 4-(aminomethyl)-6-(5-(4-fluorophenoxy)pyridin-3-yl)phthalazin-1(2H)-one<br>LCMS [M + 1]$^+$ = 363.1; $^1$H NMR (400 MHz, DMSO-d$_6$) δ = 13.00 (s, 1H), 9.02 (d, J = 1.6 Hz, 1H), 8.66-8.51 (brs, 3H), 8.47 (d, J = 2.8 Hz, 1H), 8.40-8.25 (m, 3H), 8.17 (s, 1H), 7.33-7.21 (m, 4H), 4.57 (br d, J = 5.6 Hz, 2H). |
| 7-4 | 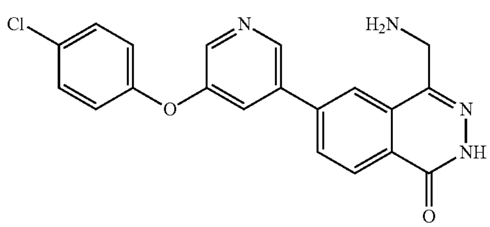 [SMILES: NCc1n[nH]c(=O)c2ccc(-c3cncc(Oc4ccc(Cl)cc4)c3)cc12] | 7-1 | 4-(aminomethyl)-6-(5-(4-chlorophenoxy)pyridin-3-yl)phthalazin-1(2H)-one<br>LCMS [M + 1]$^+$ = 379.0; $^1$H NMR (400 MHz, DMSO-d$_6$) δ = 13.00 (s, 1H), 9.05 (d, J = 2.0 Hz, 1H), 8.60 (br s, 3H), 8.53 (d, J = 2.4 Hz, 1H), 8.40-8.35 (d, J = 8.0 Hz, 1H), 8.34-8.27 (m, 2H), 8.22 (t, J = 2.4 Hz, 1H), 7.54-7.45 (d, J = 8.8 Hz, 2H), 7.22-7.15 (d, J = 8.8 Hz, 2H), 4.63-4.53 (d, J = 5.6 Hz, 2H). |
| 7-5 | 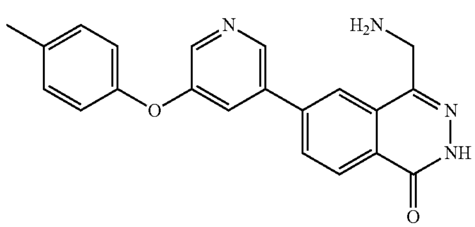 [SMILES: Cc1ccc(Oc2cncc(-c3ccc4c(=O)[nH]nc(CN)c4c3)c2)cc1] | 7-2 | 4-(aminomethyl)-6-(5-(p-tolyloxy)pyridin-3-yl)phthalazin-1(2H)-one<br>LCMS [M + 1]$^+$ = 359.3; $^1$H NMR (400 MHz, DMSO-d$_6$) δ = 8.82 (d, J = 1.6 Hz, 1H), 8.38 (d, J = 2.4 Hz, 1H), 8.37-8.32 (m, 2H), 8.14-8.09 (m, 1H), 7.87 (s, 1H), 7.25 (d, J = 8.0 Hz, 2H), 7.05 (d, J = 8.0 Hz, 2H), 4.11 (s, 2H), 2.33 (s, 3H). |
| 7-6 | 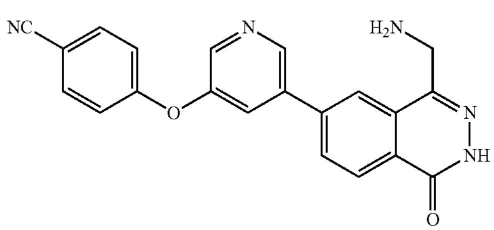 [SMILES: N#Cc1ccc(Oc2cncc(-c3ccc4c(=O)[nH]nc(CN)c4c3)c2)cc1] | 7-2 | 4-((5-(4-(aminomethyl)-1-oxo-1,2-dihydrophthalazin-6-yl)pyridin-3-yl)oxy)benzonitrile<br>LCMS [M + 1]$^+$ = 370.0; $^1$H NMR (400 MHz, DMSO-d$_6$) δ = 8.98 (d, J = 2.0 Hz, 1H), 8.53 (d, J = 2.8 Hz, 1H), 8.39-8.34 (m, 2H), 8.18 (dd, J = 2.0, 8.4 Hz, 1H), 8.11 (t, J = 2.4 Hz, 1H), 7.90-7.83 (dd, J = 2.0, 7.2 Hz, 2H), 7.31-7.25 (dd, J = 2.4, 6.8 Hz, 2H), 4.12 (s, 2H). |

Coupling Methods (CM) and Purification Methods
for the Preparation of Examples 8-1 to 8-9

CM 8A

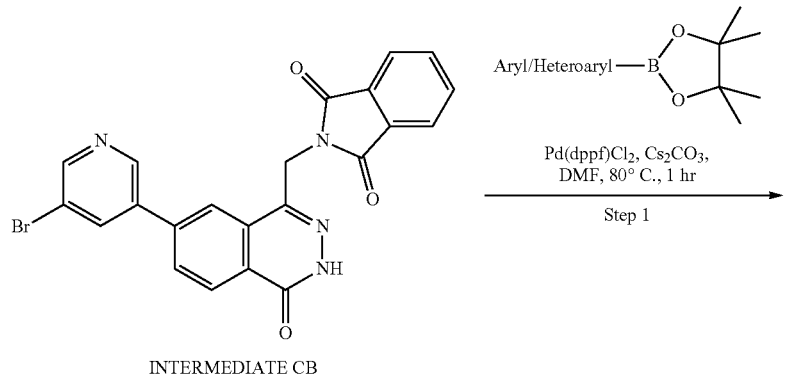

INTERMEDIATE CB

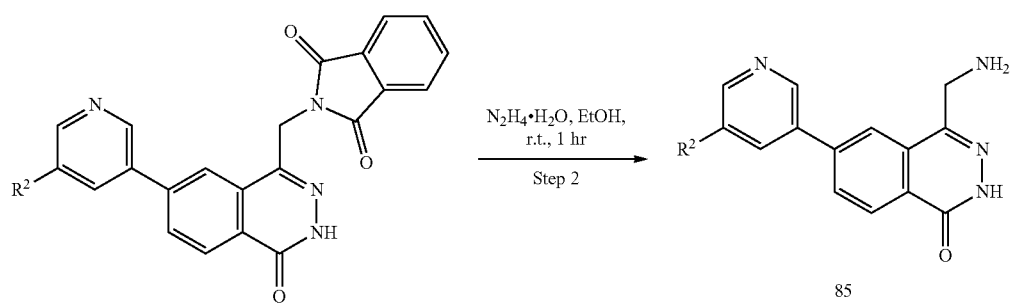

84

$R^2$ = Aryl or Heteroaryl

Step 1: A mixture of Intermediate CB (100 mg, 217 µmol, 1.00 eq.), an appropriate aryl/heteroaryl boronic ester (260 µmol, 1.20 eq.), cesium carbonate (141 mg, 434 µmol, 2.00 eq.) and Pd(dppf)Cl$_2$ (16.0 mg, 22 µmol, 0.10 eq.) in dimethylformamide (2 mL) was purged with nitrogen 3 times and stirred at 80° C. for 1 hour. Upon completion, the reaction mixture was poured into water (50 mL), filtered and filter cake dried under reduced pressure to give the appropriate $R^2$-pyridyl coupled product 84 (113 mg, crude) as a yellow solid that was used in the next step without further purification.

Step 2: To a solution of 84 (63 mg, crude) in ethyl alcohol (10 mL) was added hydrazine hydrate (13 mg, 251 µmol, 12 The mixture was stirred at 35° C. for 1 hour and upon completion the mixture was adjusted pH to 1 with hydrochloric acid (1 M, 1 mL) and concentrated under reduced pressure. The residue was diluted with hydrochloric acid (1 M, 40.0 mL) and washed with ethyl acetate (30 mL×3) and the aqueous phase was concentrated under reduced pressure. The residue was purified by prep-HPLC according to one of the purification methods 8-1 or 8-2 to give desired compounds 85.

CM 8B

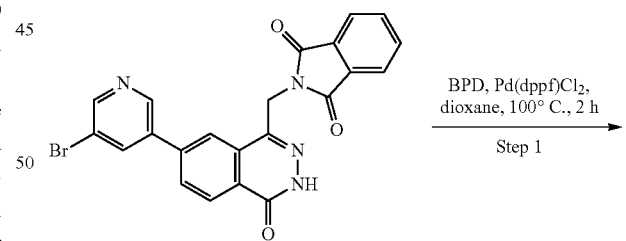

82
INTERMEDIATE CB

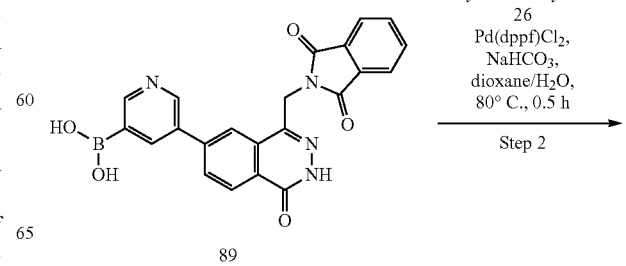

89

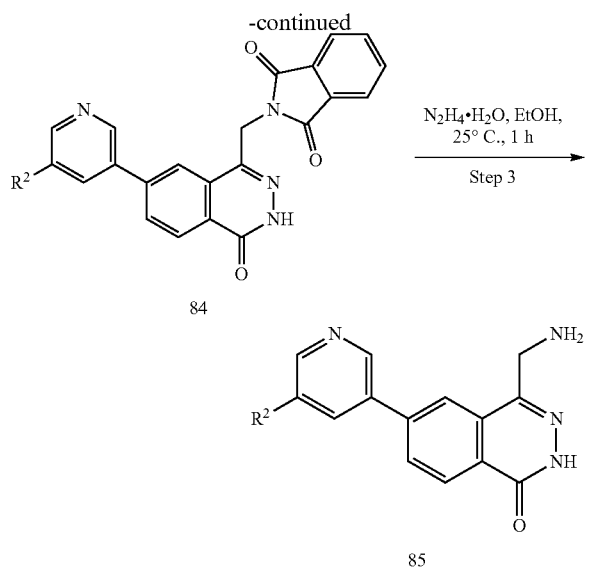

84

85

R² = Aryl or Heteroaryl and Hal = Cl, Br or I

Step 1: A mixture of Intermediate CB (300 mg, 650 μmol, 1.00 eq), 4,4,5,5-tetramethyl-2-(4,4,5,5-tetramethyl-1,3,2-dioxaborolan-2-yl)-1,3,2-dioxaborolane (BPD) (198 mg, 780 μmol, 1.20 eq), Pd(dppf)Cl₂ (47 mg, 65 μmol, 0.10 eq) and potassium acetate (128 mg, 1.30 mmol, 2.00 eq) in dioxane (5 mL) was degassed and purged with nitrogen 3 times, and stirred at 100° C. for 2 hours under a nitrogen atmosphere to furnish [5-[4-[(1,3-dioxoisoindolin-2-yl)methyl]-1-oxo-2H-phthalazin-6-yl]-3-pyridyl]boronic acid 89. The reaction mixture was used directly in next step. LCMS [M+1]⁺=427.2.

Step 2: A mixture of [5-[4-[(1,3-dioxoisoindolin-2-yl)methyl]-1-oxo-2H-phthalazin-6-yl]-3-pyridyl]boronic acid 89 (130 mg, 305 μmol, 1.00 eq), an appropriate R² bromide 42 (610 μmol, 2.00 eq), Pd(dppf)Cl₂ (22 mg, 31 μmol, 0.10 eq), sodium bicarbonate (51 mg, 610 μmol, 24 μL, 2.00 eq) in dioxane (4 mL) and water (0.8 mL) was degassed and purged with nitrogen 3 times, stirred at 80° C. for 0.5 hour under a nitrogen atmosphere. Upon completion the reaction mixture was concentrated under reduced pressure to give a residue that was purified by column chromatography (SiO₂, petroleum ether/ethyl acetate 10:1 to 0:1, then dichloromethane/methanol 10/1) to give R²-pyridyl coupled product 84 (150 mg, crude) as a black solid.

Step 3: To a solution of R²-pyridyl coupled product 84 (109 mg, 215 μmol, 1.00 eq) in ethyl alcohol (3.0 mL) was added hydrazine hydrate (110 mg, 2.15 mmol, 106 μL, 10.0 eq). The reaction mixture was stirred at 25° C. for 1 hour. Upon completion the reaction mixture was concentrated under reduced pressure to give a residue. The residue was acidified to pH 3 with hydrochloric acid (1M, 2 mL) and extracted with ethyl acetate (2 mL×3). The aqueous phase was concentrated under reduced pressure to give a residue. The residue was purified by prep-HPLC according to one of the purification methods 8-1 or 8-2 to give desired compounds 85 as off-white solids.

Purification Methods

PM 8-1: column: Phenomenex Luna C18 75×30 mm×3 μm; mobile phase: [water (0.05% HCl)-ACN]; B %: 10%-35%, 6.5 min.

PM 8-2: column: Phenomenex Luna C18 150×25 mm×10 μm; mobile phase: [water (0.1% TFA)-ACN]; B %: 10%-40%, 10 min.

Following the teachings of the General Reaction Schemes, the coupling methods 8A and 8B and using purification methods 8-1 and 8-2 and the Intermediates disclosed herein, the Examples 8-1 to 8-9 are prepared as shown in Table 8.

TABLE 8

| Example # | Structure | CM | PM | Compound Name and Characterization |
|---|---|---|---|---|
| 8-1 | 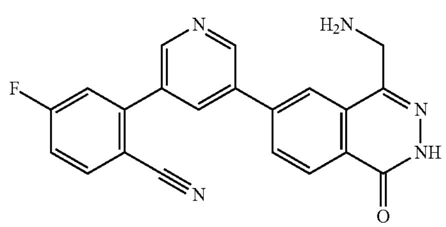 [SMILES: N#Cc1ccc(F)cc1-c1cncc(-c2ccc3c(=O)[nH]nc(CN)c3c2)c1] | 8A | 8-1 | 2-(5-(4-(aminomethyl)-1-oxo-1,2-dihydrophthalazin-6-yl)pyridin-3-yl)-4-fluorobenzonitrile; LCMS [M + 1]⁺ = 372.2; ¹H NMR (400 MHz, DMSO-d₆) δ = 13.01 (s, 1H), 9.33 (d, J = 2.0 Hz, 1H), 8.97 (d, J = 2.0 Hz, 1H), 8.68 (t, J = 2.0 Hz, 1H), 8.59 (br s, 3H), 8.42 (m, 3H), 8.18 (dd, J = 5.6, 8.8 Hz, 1H), 7.88 (dd, J = 2.8, 9.6 Hz, 1H), 7.60 (dt, J = 2.8, 8.4 Hz, 1H), 4.59 (br d, J = 5.6 Hz, 2H). |
| 8-2 | 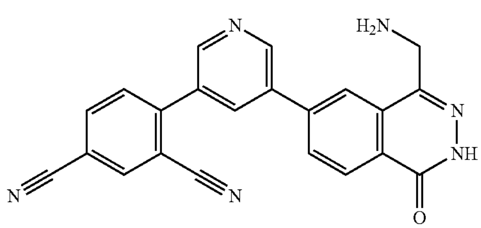 [SMILES: N#Cc1ccc(-c2cncc(-c3ccc4c(=O)[nH]nc(CN)c4c3)c2)c(C#N)c1] | 8B | 8-1 | 4-(5-(4-(aminomethyl)-1-oxo-1,2-dihydrophthalazin-6-yl)pyridin-3-yl)isophthalonitrile LCMS [M + 1]⁺ = 379.0; ¹H NMR (400 MHz, DMSO-d₆) δ = 13.02 (s, 1H), 9.33 (d, J = 2.0 Hz, 1H), 8.97 (d, J = 2.0 Hz, 1H), 8.72 (d, J = 1.6 Hz, 1H), 8.67 (t, J = 2.0 Hz, 1H), 8.52 (br s, 3H), 8.45-8.41 (d, J = 8.4 Hz, 1H), 8.40 (s, 2H), 8.37 (d, J = 1.6 Hz, 1H), 8.10 (d, J = 8.0 Hz, 1H), 4.59 (s, 2H) |

TABLE 8-continued

| Example # | Structure | CM | PM | Compound Name and Characterization |
|---|---|---|---|---|
| 8-3 | 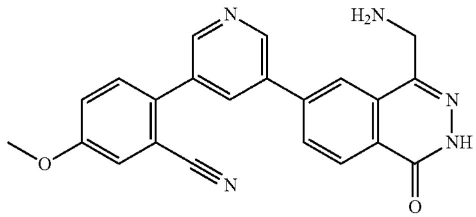 [SMILES: COc1ccc(-c2cncc(-c3ccc4c(=O)[nH]nc(CN)c4c3)c2)c(C#N)c1] | 8A | 8-3 | 2-(5-(4-(aminomethyl)-1-oxo-1,2-dihydrophthalazin-6-yl)pyridin-3-yl)-5-methoxybenzonitrile; LCMS [M + 1]$^+$ = 384.1; $^1$H NMR (400 MHz, DMSO-d$_6$) δ = 13.01 (s, 1H), 9.22 (d, J = 2.0 Hz, 1H), 8.88 (d, J = 2.0 Hz, 1H), 8.53 (t, J = 2.0 Hz, 1H), 8.47-8.41 (m, 2H), 8.41-8.36 (s, 3H), 8.36-8.34 (m, 1H), 7.78 (d, J = 8.8 Hz, 1H), 7.66 (d, J = 2.8 Hz, 1H), 7.47 (dd, J = 2.8, 8.8 Hz, 1H), 4.61 (br d, J = 2.8 Hz, 2H), 3.90 (s, 3H) |
| 8-4 | 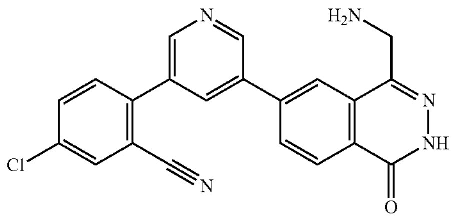 [SMILES: N#Cc1cc(Cl)ccc1-c1cncc(-c2ccc3c(=O)[nH]nc(CN)c3c2)c1] | 8B | 8-1 | 2-(5-(4-(aminomethyl)-1-oxo-1,2-dihydrophthalazin-6-yl)pyridin-3-yl)-5-chlorobenzonitrile; LCMS [M + 1]$^+$ = 388.0; $^1$H NMR (400 MHz, DMSO-d$_6$) δ = 13.01 (s, 1H), 9.33 (d, J = 2.0 Hz, 1H), 8.95 (d, J = 2.0 Hz, 1H), 8.68 (t, J = 2.0 Hz, 1H), 8.60 (br s, 3H), 8.44-8.37 (m, 3H), 8.29 (d, J = 2.0 Hz, 1H), 8.03-7.98 (dd, J = 8.4, 2.4 Hz,1H), 7.94-7.89 (d, J = 8.4 Hz,1H), 4.66-4.49 (d, J = 5.6 Hz, 2H) |
| 8-5 | 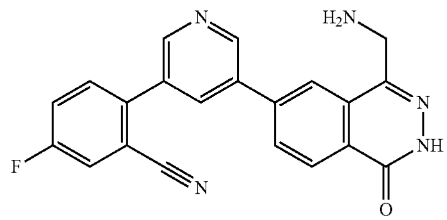 [SMILES: N#Cc1cc(F)ccc1-c1cncc(-c2ccc3c(=O)[nH]nc(CN)c3c2)c1] | 8A | 8-1 | 2-(5-(4-(aminomethyl)-1-oxo-1,2-dihydrophthalazin-6-yl)pyridin-3-yl)-5-fluorobenzonitrile; LCMS [M + 1]$^+$ = 372.2; $^1$H NMR (400 MHz, DMSO-d$_6$) δ = 13.01 (s, 1H), 9.32 (d, J = 2.0 Hz, 1H), 8.94 (d, J = 2.0 Hz, 1H), 8.68 (t, J = 2.0 Hz, 1H), 8.61 (br s, 3H), 8.44-8.37 (m, 3H), 8.11 (dd, J = 2.8, 8.8 Hz, 1H), 7.95 (dd, J = 5.6, 8.8 Hz, 1H), 7.82 (dt, J = 2.8, 8.8 Hz, 1H), 4.58 (br d, J = 5.6 Hz, 2H). |
| 8-6 | 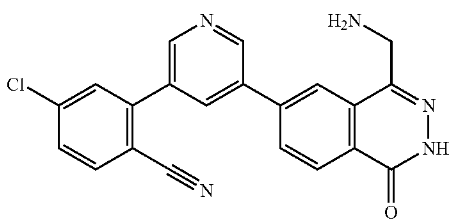 [SMILES: N#Cc1ccc(Cl)cc1-c1cncc(-c2ccc3c(=O)[nH]nc(CN)c3c2)c1] | 8B | 8-3 | 2-(5-(4-(aminomethyl)-1-oxo-1,2-dihydrophthalazin-6-yl)pyridin-3-yl)-4-chlorobenzonitrile; LCMS [M + 1]$^+$ = 388.2; $^1$H NMR (400 MHz, DMSO-d$_6$) δ = 13.01 (s, 1H) 9.33 (d, J = 2.0 Hz, 1H) 8.97 (d, J = 2.0 Hz, 1H), 8.67 (t, J = 2.0 Hz, 1H), 8.58 (br s, 3H), 8.42 (m, 3H), 8.12 (d, J = 8.4 Hz, 1H), 8.06 (d, J = 2.0 Hz, 1H), 7.81 (dd, J = 2.0, 8.4 Hz, 1H), 4.59 (br d, J = 5.6 Hz, 2H) |
| 8-7 | 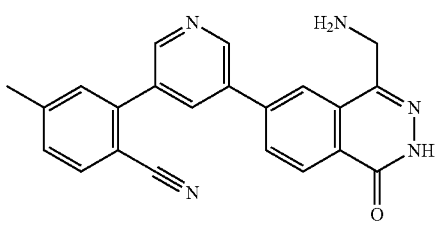 [SMILES: Cc1ccc(C#N)c(-c2cncc(-c3ccc4c(=O)[nH]nc(CN)c4c3)c2)c1] | 8A | 8-3 | 2-(5-(4-(aminomethyl)-1-oxo-1,2-dihydrophthalazin-6-yl)pyridin-3-yl)-4-methylbenzonitrile; LCMS [M + 1]$^+$ = 368.1; $^1$H NMR (400 MHz, MeOD) δ = 9.11 (d, J = 2.0 Hz, 1H), 8.87 (d, J = 2.0 Hz, 1H), 8.62-8.52 (m, 2H), 8.34 (dd, J = 1.2, 8.4 Hz, 1H), 8.26 (d, J = 1.2 Hz, 1H), 7.83 (d, J = 8.0 Hz, 1H), 7.64 (s, 1H), 7.50 (d, J = 7.6 Hz, 1H), 4.69 (s, 2H), 2.54 (s, 3H) |
| 8-8 | 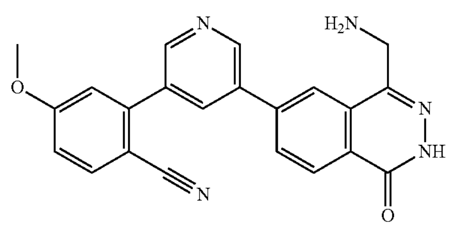 [SMILES: COc1ccc(C#N)c(-c2cncc(-c3ccc4c(=O)[nH]nc(CN)c4c3)c2)c1] | 8A | 8-1 | 2-(5-(4-(aminomethyl)-1-oxo-1,2-dihydrophthalazin-6-yl)pyridin-3-yl)-4-methoxybenzonitrile; LCMS [M + 1]$^+$ = 384.1; $^1$H NMR (400 MHz, DMSO-d$_6$) δ = 13.01 (s, 1H), 9.29 (d, J = 2.0 Hz, 1H), 8.93 (d, J = 2.0 Hz, 1H), 8.63 (t, J = 2.0 Hz, 1H), 8.59 (br s, 3H), 8.45-8.36 (m, 3H), 7.98 (d, J = 8.8 Hz, 1H), 7.41 (d, J = 2.4 Hz, 1H), 7.24 (dd, J = 2.4, 8.8 Hz, 1H), 4.64 (d, J = 5.6 Hz, 2H), 3.94 (s, 3H) |
| 8-9 | 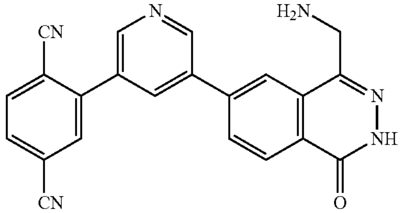 [SMILES: N#Cc1ccc(C#N)c(-c2cncc(-c3ccc4c(=O)[nH]nc(CN)c4c3)c2)c1] | 8B | 8-2 | 2-(5-(4-(aminomethyl)-1-oxo-1,2-dihydrophthalazin-6-yl)pyridin-3-yl)terephthalonitrile LCMS [M + 1]$^+$ = 379.1; $^1$H NMR (400 MHz, DMSO-d$_6$) δ = 13.02 (s, 1H), 9.32 (d, J = 2.0 Hz, 1H), 8.99 (d, J = 2.0 Hz, 1H), 8.65 (t, J = 2.0 Hz, 1H), 8.45 (m, 2H), 8.44-8.40 (m, 4H), 8.38 (s, 1H), 8.31 (d, J = 8.0 Hz, 1H), 8.20 (dd, J = 1.6, 8.0 Hz, 1H), 4.60 (br d, J = 5.2 Hz, 2H) |

Preparation of Examples 9-1 to 9-3

Example 9-1

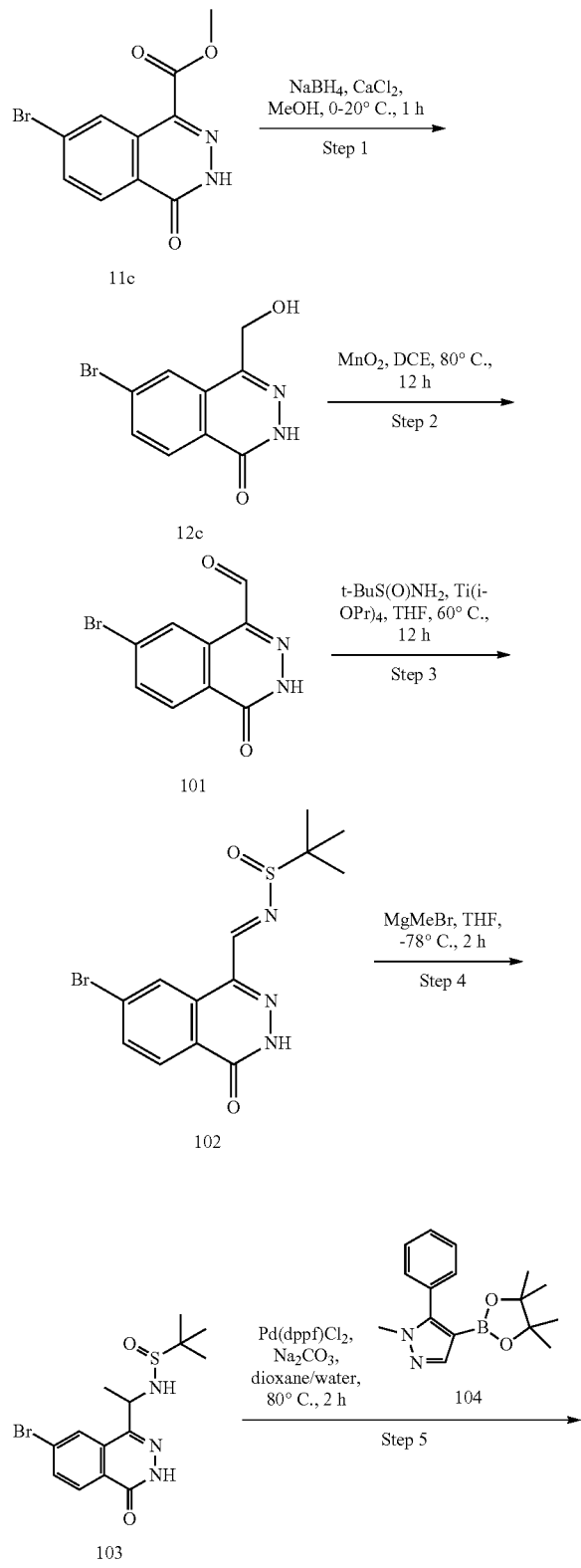

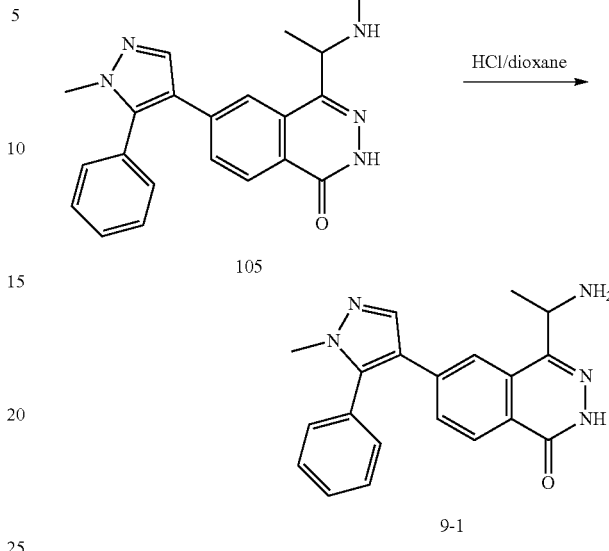

Step 1: A stirred solution of sodium borohydride (382 mg, 10.1 mmol, 2.60 eq.) in ethyl alcohol (150 mL) was treated portion-wise with methyl 7-bromo-4-oxo-3H-phthalazine-1-carboxylate 11c (1.10 g, 3.89 mmol, 1.00 eq.) at 0° C. followed by a dropwise addition of a solution of calcium chloride (518 mg, 4.66 mmol, 1.20 eq.) in ethyl alcohol (150 mL). Stirring was continued for additional 3 hours at the 0° C., and then 1 hour at 20° C. After such time the reaction mixture was concentrated under reduced pressure and the residue was diluted with water (30 mL) and adjusted to pH 5 with 1N hydrochloric acid (5 mL). The resulting solid was filtered and washed with water (5 mL×3) and then triturated with ethyl alcohol (20 mL) to afford 6-bromo-4-(hydroxymethyl)-2H-phthalazin-1-one 12c (990 mg, 3.88 mmol, 100% yield) as a white solid.

Step 2: To a solution of 6-bromo-4-(hydroxymethyl)-2H-phthalazin-1-one 12c (300 mg, 1.18 mmol, 1.00 eq.) in DCE (10 mL) was added manganese dioxide (1.02 g, 11.8 mmol, 10.0 eq.) and the mixture was stirred at 80° C. for 12 hours. After such time the reaction mixture was filtered, and the filtrate concentrated under reduced pressure to give a residue. The residue was purified by column chromatography (SiO$_2$, petroleumether:ethylacetate 10:1 to 1:1) to give 7-bromo-4-oxo-3H-phthalazine-1-carbaldehyde 101 (73 mg, 288 µmol, 25% yield) as a white solid. $^1$H NMR (400 MHz, DMSO-d$_6$) δ=13.66 (br s, 1H), 9.82 (s, 1H), 9.05 (d, J=2.0 Hz, 1H), 8.22-8.18 (d, J=8.4 Hz, 1H), 8.10 (dd, J=2.0, 8.4 Hz, 1H).

Step 3: To a solution of 7-bromo-4-oxo-3H-phthalazine-1-carbaldehyde 101 (300 mg, 1.19 mmol, 1.00 eq.) in THF (50 mL) was added titanium iso-propoxide (674 mg, 2.37 mmol, 700 µL, 2.00 eq.) and 2-methylpropane-2-sulfinamide (216 mg, 1.78 mmol, 1.50 eq.) and the mixture was stirred at 60° C. for 12 hours. After such time the reaction mixture was quenched with water (1 mL) and the resulting solid was filtered. The filtrate was dried over sodium sulfate, filtered and concentrated to give a residue. The residue was purified by column chromatography (SiO$_2$, petroleum ether/ ethyl acetate=5/1 to 1/1) to give N-[(7-bromo-4-oxo-3H-phthalazin-1-yl)methylene]-2-methyl-propane-2-sulfinamide 102 (100 mg, 171 µmol, 14% yield) as a white solid.

LCMS [M+1]⁺=358.1. ¹H NMR (400 MHz, DMSO-d6) δ=13.58 (br s, 1H), 9.32 (d, J=2.0 Hz, 1H), 8.37 (s, 1H), 8.23 (d, J=8.4 Hz, 1H), 8.12-8.10 (dd, J=2.0, 8.4 Hz, 1H), 1.26 (s, 9H).

Step 4: To a solution of N-[(7-bromo-4-oxo-3H-phthalazin-1-yl)methylene]-2-methyl-propane-2-sulfinamide 102 (100 mg, 281 μmol, 1.00 eq.) in THF (5 mL) was added methylmagnesium bromide (3M, 281 μL, 3.00 eq.) dropwise at −78° C. The reaction mixture was then stirred at −78° C. for 2 hours. After such time the reaction mixture was diluted with water (2 mL) and extracted with ethyl acetate (2 mL×3). The combined organic portions were washed with brine (2 mL), dried over anhydrous sodium sulfate, filtered and concentrated to give a residue. The residue was purified by prep-TLC (petroleum ether/ethyl acetate=10/1) to give N-[1-(7-bromo-4-oxo-3H-phthalazin-1-yl)ethyl]-2-methyl-propane-2-sulfinamide 103 (40 mg, 98.2 μmol, 35% yield) as a yellow solid. LCMS [M+1]⁺=374.2.

Step 5: A mixture of N-[1-(7-bromo-4-oxo-3H-phthalazin-1-yl)ethyl]-2-methyl-propane-2-sulfinamide 103 (35 mg, 94 μmol, 1.00 eq.), 1-methyl-5-phenyl-4-(4,4,5,5-tetramethyl-1,3,2-dioxaborolan-2-yl)pyrazole 104 (35 mg, 122 μmol, 1.30 eq.), Pd(dppf)Cl₂ (7 mg, 9 μmol, 0.10 eq.), sodium carbonate (20 mg, 188 μmol, 2.00 eq.) in water (0.2 mL) and dioxane (1 mL) was degassed and purged with nitrogen 3 times, and then stirred at 80° C. for 2 hours. After such time the reaction mixture was diluted with water (2 mL) and extracted with ethyl acetate (2 mL×3) and the combined organic phases were washed with brine (2 mL), dried over anhydrous sodium sulfate, filtered and concentrated to give a residue. The residue was purified by prep-TLC (petroleum ether:ethyl acetate 1:1) to give 2-methyl-N-[1-[7-(1-methyl-5-phenyl-pyrazol-4-yl)-4-oxo-3H-phthalazin-1-yl]ethyl]propane-2-sulfinamide 105 (40 mg, 60 μmol, 63% yield) as a brown oil. LCMS [M+1]⁺=450.4.

Step 6: A mixture of 2-methyl-N-[1-[7-(1-methyl-5-phenyl-pyrazol-4-yl)-4-oxo-3H-phthalazin-1-yl]ethyl]propane-2-sulfinamide 105 (36 mg, 80 μmol, 1.00 eq.) and hydrochloric acid/dioxane (4M, 9 mL) was stirred at 25° C. for 1 hour. The reaction mixture was concentrated under reduced pressure to give a residue. The residue was purified by prep-HPLC (Phenomenex Luna C18 75×30 mm×3 μm; mobile phase: [water (0.05% hydrochloric acid)-ACN]; B %: 12%-32%, 6.5 min) to give 4-(1-aminoethyl)-6-(1-methyl-5-phenyl-pyrazol-4-yl)-2H-phthalazin-1-one, Example 9-1 (7 mg, 19 μmol, 23% yield, HCl) as a white solid. LCMS [M+1]⁺=346.1. ¹H NMR (400 MHz, MeOD) δ=8.30 (d, J=8.4 Hz, 1H), 8.13 (s, 1H), 7.91 (dd, J=1.6, 8.4 Hz, 1H), 7.66-7.60 (m, 3H), 7.55 (d, J=1.6 Hz, 1H), 7.50-7.45 (m, 2H), 4.66-4.53 (m, 1H), 3.81 (s, 3H), 1.32 (d, J=6.8 Hz, 3H).

Examples 9-2 & 9-3

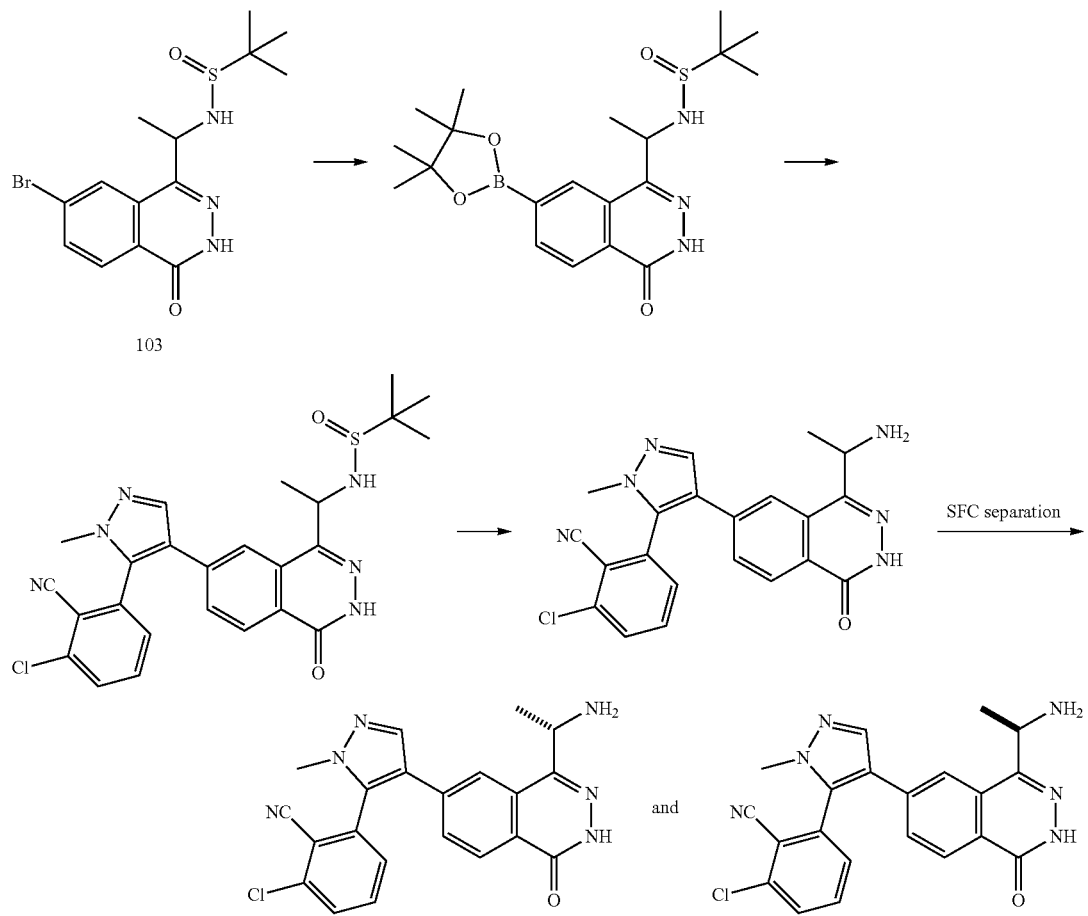

EXAMPLE 9-2 (peak 1) and EXAMPLE 9-3 (peak 2)

Step 1: A mixture of (R)—N-(1-(7-bromo-4-oxo-3,4-dihydrophthalazin-1-yl)ethyl)-2-methylpropane-2-sulfinamide 103 (410 mg, 1.10 mmol, 1.00 eq.), 4,4,5,5-tetramethyl-2-(4,4,5,5-tetramethyl-1,3,2-dioxaborolan-2-yl)-1,3,2-dioxaborolane (839 mg, 3.30 mmol, 3.00 eq.), Pd(dppf)Cl$_2$ (81 mg, 0.11 mmol, 0.10 eq.) and potassium acetate (324 mg, 3.30 mmol, 3.00 eq.) in dioxane (10 mL) was degassed and purged with nitrogen for 3 times, and then the mixture was stirred at 100° C. for 0.5 hour under nitrogen atmosphere. The reaction mixture was concentrated under reduced pressure to give a residue. The residue was triturated with petroleum ether (40 mL) to give (R)-2-methyl-N-(1-(4-oxo-7-(4,4,5,5-tetramethyl-1,3,2-dioxaborolan-2-yl)-3,4-dihydrophthalazin-1-yl)ethyl)propane-2-sulfinamide (724 mg, crude) as a gray solid which used into the next step without further purification. LCMS [M−81]$^-$=338.2.

Step 2: A mixture of (R)-2-methyl-N-(1-(4-oxo-7-(4,4,5,5-tetramethyl-1,3,2-dioxaborolan-2-yl)-3,4-dihydrophthalazin-1-yl)ethyl)propane-2-sulfinamide (670 mg, 1.60 mmol, 1.00 eq.), 2-(4-bromo-2-methyl-pyrazol-3-yl)-6-chloro-benzonitrile (308. mg, 1.04 mmol, 0.65 eq.), ditert-butyl(cyclopentyl)phosphane; dichloropalladium; iron (104 mg, 0.160 mmol, 0.10 eq.), sodium carbonate (339 mg, 3.20 mmol, 2.00 eq.) in dioxane (10 mL) and water (2 mL) was degassed and purged with nitrogen for 3 times, and then the mixture was stirred at 80° C. for 0.5 hour under nitrogen atmosphere. The reaction mixture was diluted with water (200 mL) and extracted with ethyl acetate (150 mL×3). The combined organic layers were washed with brine (100 mL), dried over anhydrous sodium sulfate, filtered and concentrated under reduced pressure to give a residue. The residue was purified by column chromatography (SiO$_2$, petroleumether:ethylacetate=1:1 to 0:1, dichloromethane:methyl alcohol=10:1) to give (R)—N-(1-(7-(5-(3-chloro-2-cyanophenyl)-1-methyl-1H-pyrazol-4-yl)-4-oxo-3,4-dihydrophthalazin-1-yl)ethyl)-2-methylpropane-2-sulfinamide (281 mg, 0.552 mmol, 34% yield) as a brown solid. LCMS [M+1]$^+$=509.2.

Step 3: To a solution of (R)—N-(1-(7-(5-(3-chloro-2-cyanophenyl)-1-methyl-1H-pyrazol-4-yl)-4-oxo-3,4-dihydrophthalazin-1-yl)ethyl)-2-methylpropane-2-sulfinamide (140 mg, 0.275 mmol, 1.00 eq.) in hydrochloride/dioxane (4.00 M, 5.4 mL) and the mixture was stirred at 15° C. for 0.5 hour. The reaction mixture was concentrated under reduced pressure to give a residue. The residue was purified by prep-HPLC (Phenomenex Luna C18 75×30 mm×3 μm; mobile phase: [water (0.05% HCl)-ACN]; B %: 12%-32%, 7 min) to give 2-[4-[4-(1-aminoethyl)-1-oxo-2H-phthalazin-6-yl]-2-methyl-pyrazol-3-yl]-6-chloro-benzonitrile (40 mg, 0.097 mmol, 36% yield) as a yellow solid. LCMS [M+1]$^+$=405.1; $^1$H NMR (400 MHz, CD$_3$OD) δ=8.33-8.23 (m, 1H), 8.13 (d, J=4.4 Hz, 1H), 8.02-7.84 (m, 2H), 7.82-7.66 (m, 2H), 7.64-7.57 (m, 1H), 4.87 (br s, 1H), 3.83 (d, J=2.8 Hz, 3H), 1.54-1.41 (m, 3H).

Step 4: Enantiomers were separated by chiral SFC (DAICEL CHIRALPAK IC (250 mm×30 mm, 10 μm); mobile phase: [0.1% NH$_4$OH/EtOH]; B %: 50%-50%, 4.2 min; 46 min) followed by chiral SFC Chiralpak IC-3 (50×4.6 mm I.D., 3 μm); Mobile phase: Phase A for CO$_2$, and Phase B for EtOH (0.05% DEA); Gradient elution: 50% EtOH (0.05% DEA) in CO$_2$ Flow rate: 3 mL/min; Detector: PDA; Column Temp: 35° C.; Back Pressure: 100 Bar to give peak 1, Example 9-2, (11 mg, 0.025 mmol, 30% yield) as a yellow solid and peak 2, Example 9-3 (18 mg, 0.444 mmol, 50% yield) as an off-white solid. Each example was converted to the HCl salt. Example 9-2, Peak 1, single enantiomer, stereochemistry unassigned: LCMS [M+1]=405.1; $^1$H NMR (400 MHz, CD$_3$OD) δ=8.31 (t, J=8.4 Hz, 1H), 8.12 (d, J=6.4 Hz, 1H), 7.92-7.87 (m, 2H), 7.80-7.67 (m, 3H), 4.88-4.84 (m, 1H), 3.83 (d, J=1.2 Hz, 3H), 1.51-1.43 (m, 3H). Example 9-3, Peak 2, single enantiomer, stereochemistry unassigned: LCMS [M+1]=405.1; $^1$H NMR (400 MHz, CD$_3$OD) δ=8.29 (dd, J=8.2, 10.4 Hz, 1H), 8.13 (d, J=7.6 Hz, 1H), 7.90-7.85 (m, 2H), 7.79-7.60 (m, 3H), 4.91-4.85 (m, 1H), 3.82 (d, J=2.8 Hz, 3H), 1.52-1.41 (m, 3H).

Examples 9-4 & 9-5

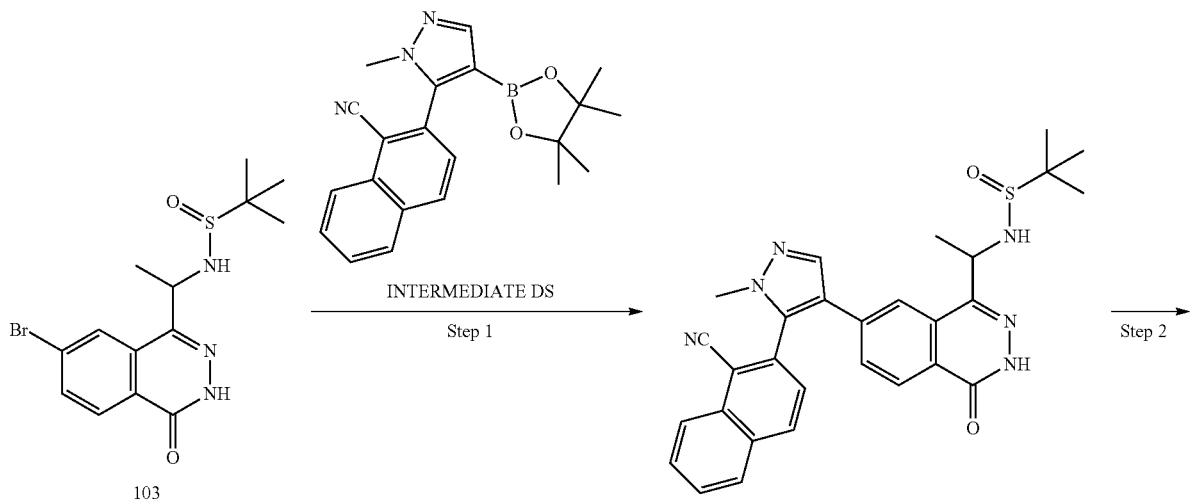

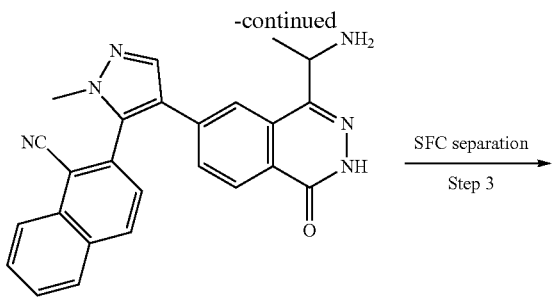

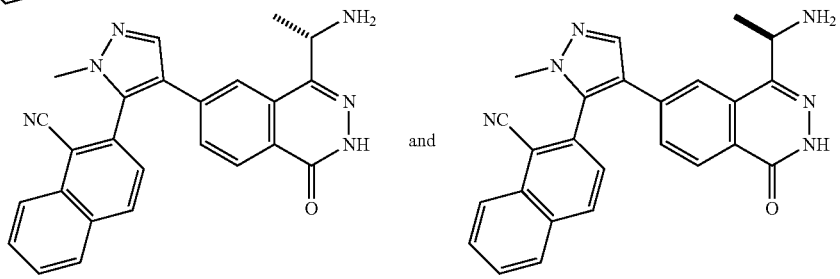

EXAMPLE 9-4 (peak 1)     EXAMPLE 9-5 (peak 2)

Step 1: A mixture of 2-[2-methyl-4-(4,4,5,5-tetramethyl-1,3,2-dioxaborolan-2-yl)pyrazol-3-yl]naphthalene-1-carbonitrile (80 mg, 0.222 mmol, 1.00 eq.), N-[1-(7-bromo-4-oxo-3H-phthalazin-1-yl)ethyl]-2-methyl-propane-2-sulfinamide (100 mg, 0.267 mmol, 1.20 eq.), ditert-butyl (cyclopentyl)phosphane-dichloropalladium-iron (29 mg, 0.044 mmol, 0.20 eq.), potassium phosphate (142 mg, 0.668 mmol, 3.00 eq.) in dioxane (4 mL) and water (0.8 mL) and was degassed and purged with nitrogen and then stirred at 100° C. for 1 hour. After such time the reaction mixture was concentrated under reduced pressure and the residue was purified by prep-HPLC (Phenomenex Synergi C18 150×30 mm×4 µm; mobile phase: [water (0.1% TFA)-ACN]; B %: 35%-64%, 11 min) to give N-[1-[7-[5-(1-cyano-2-naphthyl)-1-methyl-pyrazol-4-yl]-4-oxo-3H-phthalazin-1-yl]ethyl]-2-methyl-propane-2-sulfinamide (48 mg, 0.091 mmol, 41% yield) was obtained as a white solid. LCMS [M+1]$^+$=525.2.

Step 2: A mixture of N-[1-[7-[5-(1-cyano-2-naphthyl)-1-methyl-pyrazol-4-yl]-4-oxo-3H-phthalazin-1-yl]ethyl]-2-methyl-propane-2-sulfinamide (40.mg, 0.076 mmol, 1.00 eq.) in HCl/dioxane (1 mL, 4 M) and methanol (1 mL) was stirred at 20° C. for 1 hour. The reaction mixture was the concentrated to give 2-[4-[4-(1-aminoethyl)-1-oxo-2H-phthalazin-6-yl]-2-methyl-pyrazol-3-yl]naphthalene-1-carbonitrile (30 mg, crude) as a white solid which used into the next step without further purification. LCMS [M+1]$^+$=421.2.

Step 3: SFC purification, Chiralpak IG-3 50 Å 4.6 mm, 3 µm Mobile phase: A: CO$_2$ B: ethanol (0.05% DEA) Isocratic: 40% B. Flow rate: 4 mL/min. Column temp. 35° C. ABPR 1500 psi gave peak 1, Example 9-4 2-[4-[4-(1-aminoethyl)-1-oxo-2H-phthalazin-6-yl]-2-methyl-pyrazol-3-yl]naphthalene-1-carbonitrile (12 mg, 29 µmol, 33% yield) as a white solid $^1$H NMR (400 MHz, DMSO-d$_6$) δ=12.42 (br s, 1H), 8.59-8.50 (m, 1H), 8.30-8.22 (m, 2H), 8.20-8.09 (m, 2H), 7.78-7.54 (m, 5H), 3.95-3.70 (m, 4H), 0.50-0.80 (m, 3H). And peak 2, Example 9-5 and 2-[4-[4-(1-aminoethyl)-1-oxo-2H-phthalazin-6-yl]-2-methyl-pyrazol-3-yl]naphthalene-1-carbonitrile (12 mg, 29 µmol, 33% yield) as a white solid $^1$H NMR (400 MHz, DMSO-d$_6$) δ=12.41 (br s, 1H), 8.60-8.50 (m, 1H), 8.30-8.23 (m, 2H), 8.19-8.09 (m, 2H), 7.92-7.54 (m, 6H), 3.90-3.70 (m, 4H), 0.83-0.55 (m, 3H).

Examples 9-6 & 9-7

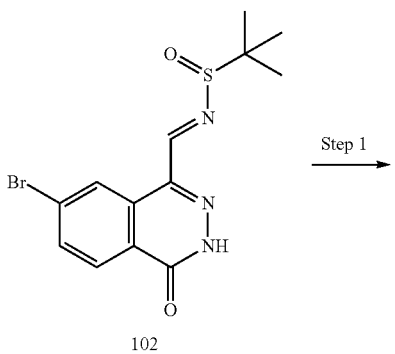

102

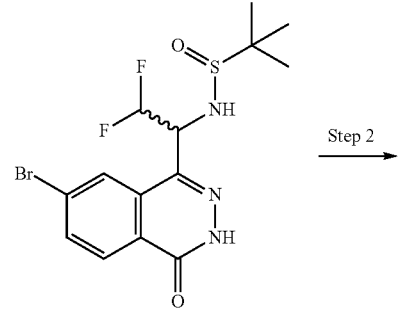

-continued

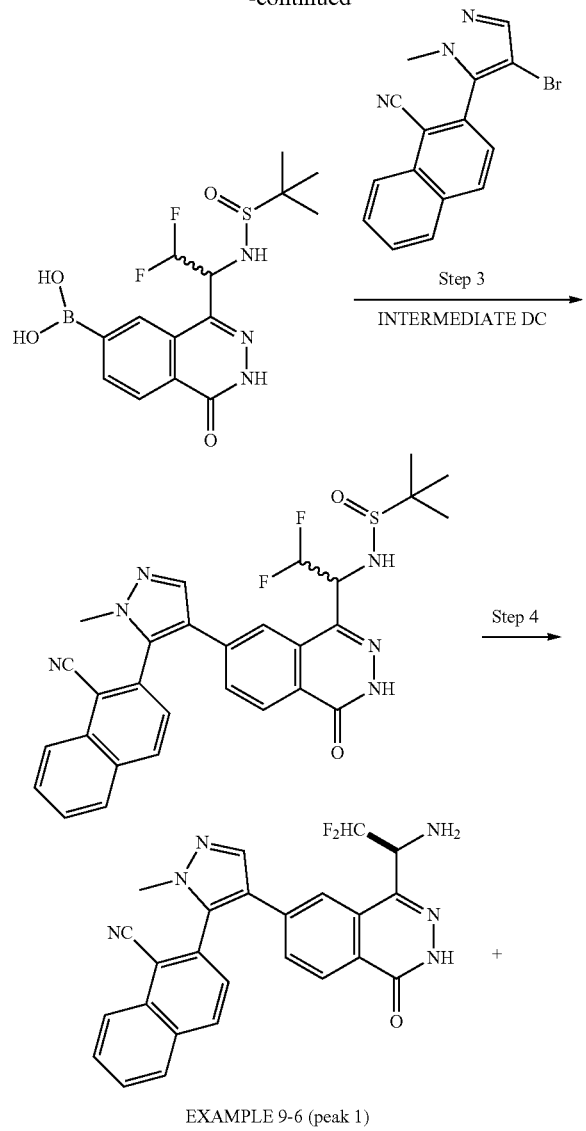

EXAMPLE 9-6 (peak 1)

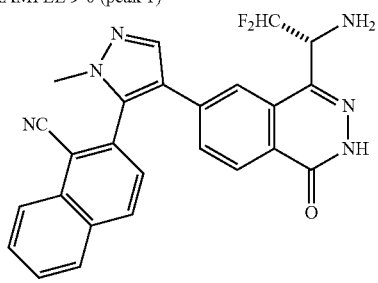

EXAMPLE 9-7 (peak 2)

Step 1: To a solution of N-[(7-bromo-4-oxo-3H-phthalazin-1-yl)methylene]-2-methyl-propane-2-sulfinamide (276 mg, 0.775 mmol, 1.00 eq.) and difluoromethyl(trimethyl)silane (289 mg, 2.32 mmol, 3.00 eq.) in THF (2.0 mL) was added potassium tert-butoxide (1 M, 2.3 mL, 3.00 eq.) and the mixture was stirred at −78° C. for 12 hours. The reaction mixture was then quenched with water (2 mL) and extracted with ethyl acetate (2 mL×3). The combined organic phase were then washed with brine (2 mL), dried over anhydrous sodium sulfate, filtered, concentrated and the residue was purified by prep-TLC (SiO$_2$, dichloromethane:methyl alcohol 10:1) to give N-[1-(7-bromo-4-oxo-3H-phthalazin-1-yl)-2,2-difluoro-ethyl]-2-methyl-propane-2-sulfinamide (107 mg, 0.182 mmol, 24% yield) as a black solid. LCMS [M+1]$^+$=410.1; $^1$H NMR (400 MHz, CDCl$_3$-d) δ=10.58-10.26 (m, 1H), 8.29-8.22 (m, 1H), 8.06 (s, 1H), 7.93-7.86 (m, 1H), 6.22-5.86 (m, 1H), 4.72 (d, J=7.2 Hz, 1H), 1.30 (s, 9H).

Step 2: A mixture of N-[1-(7-bromo-4-oxo-3H-phthalazin-1-yl)-2,2-difluoro-ethyl]-2-methyl-propane-2-sulfinamide (97 mg, 0.238 mmol, 1.00 eq.), bis(pinacolato)diboron (78 mg, 0.309 mmol, 1.30 eq.), Pd(dppf)Cl$_2$ (17 mg, 0.024 mmol, 0.10 eq.), potassium acetate (67 mg, 0.713 mmol, 3.00 eq.) in dioxane (1.0 mL) was degassed and purged with nitrogen 3 times, and then stirred at 100° C. for 1 hour. The mixture was then concentrated under reduced pressure to give [4-[1-(tert-butylsulfinylamino)-2,2-difluoro-ethyl]-1-oxo-2H-phthalazin-6-yl]boronic acid (100 mg, crude) as a black solid. LCMS [M+1]$^+$=374.1.

Step 3: A mixture of [4-[1-(tert-butylsulfinylamino)-2,2-difluoro-ethyl]-1-oxo-2H-phthalazin-6-yl]boronic acid (100 mg, crude), 2-(4-bromo-2-methyl-pyrazol-3-yl)naphthalene-1-carbonitrile (77 mg, 0.247 mmol), sodium bicarbonate (62 mg, 0.740 mmol), ditert-butyl(cyclopentyl)phosphane; dichloropalladium; iron (16 mg, 0.024 mmol, 0.10 eq.) in dioxane (3.0 mL) and water (0.6 mL) was degassed and purged with nitrogen 3 times, and then stirred at 100° C. for 2 hours under nitrogen atmosphere. The mixture was then concentrated under reduced pressure and the residue was purified by prep-TLC (dichloromethane:methyl alcohol 10:1) to give N-[1-[7-[5-(1-cyano-2-naphthyl)-1-methyl-pyrazol-4-yl]-4-oxo-3H-phthalazin-1-yl]-2,2-difluoro-ethyl]-2-methyl-propane-2-sulfinamide (36 mg, 0.037 mmol, 15% yield) as a yellow solid. LCMS [M+1]$^+$=561.2.

Step 4: A mixture of N-[1-[7-[5-(1-cyano-2-naphthyl)-1-methyl-pyrazol-4-yl]-4-oxo-3H-phthalazin-1-yl]-2,2-difluoro-ethyl]-2-methyl-propane-2-sulfinamide (30 mg, 0.053 mmol, 1.00 eq.) in hydrochloric acid/dioxane (1.0 mL) was degassed and purged with nitrogen 3 times, and the mixture stirred at 0° C. for 2 hours. The mixture was then concentrated and the residue purified by prep-HPLC (Phenomenex Luna C18 75×30 mm×3 μm; mobile phase: [water (0.05% hydrochloric acid)-ACN]; B %: 18%-38%, 7 min) then further separated by SFC (Daicel ChiralPak IG (250×30 mm, 10 μm); mobile phase: [Mobile phase: A: CO$_2$ B: ACN/EtOH (0.1% NH$_3$.water)] isocratic 60%, 50 min) to give Example 9-6, 2-[4-[4-[(1S)-1-amino-2,2-difluoro-ethyl]-1-oxo-2H-phthalazin-6-yl]-2-methyl-pyrazol-3-yl]naphthalene-1-carbonitrile (5.2 mg, 0.011 mmol, 21% yield) as a brown solid and Example 9-7, 2-[4-[4-[(1R)-1-amino-2,2-difluoro-ethyl]-1-oxo-2H-phthalazin-6-yl]-2-methyl-pyrazol-3-yl]naphthalene-1-carbonitrile (4.3 mg, 0.009 mmol, 17% yield) as a brown solid. Example 9-6: LCMS [M+1]$^+$=457.1; $^1$H NMR (400 MHz, DMSO-d$_6$) δ=12.61 (br d, J=3.6 Hz, 1H), 8.53 (dd, J=8.8, 10.4 Hz, 1H), 8.29 (s, 1H), 8.27 (d, J=7.6 Hz, 1H), 8.14 (dd, J=8.2, 14.4 Hz, 1H), 8.07 (dd, J=6.8, 8.4 Hz, 1H), 7.92-7.74 (m, 4H), 7.63 (ddd, J=1.6, 8.4, 17.2 Hz, 1H), 6.14-5.59 (m, 1H), 4.17-3.95 (m, 1H), 3.78 (d, J=1.6 Hz, 3H), 3.31 (br s, 2H). $^1$H NMR (400 MHz, MeOD) δ=8.43 (dd, J=8.4, 18.0 Hz, 1H), 8.30-8.11 (m, 4H), 7.89-7.61 (m, 5H), 5.95-5.29 (m, 1H), 4.13-3.98 (m, 1H), 3.84 (d, J=2.4 Hz, 3H). Example 9-7: LCMS [M+1]$^+$=457.0; $^1$H NMR (400 MHz, DMSO-d$_6$) δ=12.71-12.36 (m, 1H), 8.58-8.48 (m, 1H), 8.29 (s, 1H), 8.27 (d, J=7.6 Hz, 1H), 8.14 (dd, J=8.0, 14.4 Hz, 1H), 8.07 (dd, J=6.8, 8.4 Hz, 1H), 7.93-7.74 (m, 4H), 7.63 (ddd, J=1.6, 8.4, 17.2 Hz, 1H), 6.10-5.59 (m, 1H), 4.10 (q, J=5.6 Hz, 1H), 3.78 (d, J=1.6 Hz, 3H), 3.31 (br s, 2H). $^1$H NMR (400 MHz, MeOD) δ=8.44 (dd, J=8.4, 17.6 Hz, 1H), 8.29-8.12 (m, 4H), 7.90-7.62 (m, 5H), 5.94-5.36 (m, 1H), 4.12-4.06 (m, 1H), 3.85 (d, J=2.4 Hz, 3H).

Coupling Method (CM) and Purification Methods (PM) for the Preparation of Examples in Table 10

General Coupling Method 10A

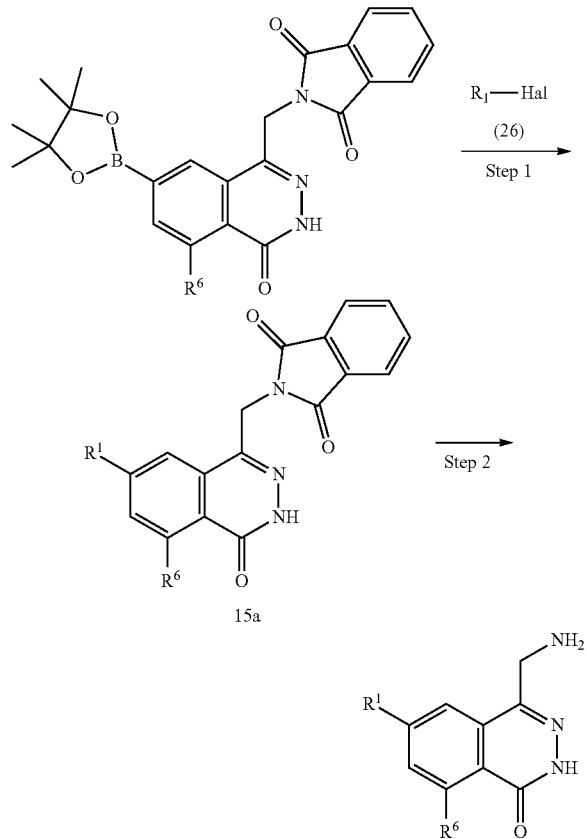

R$^6$ = Cl INTERMEDIATE DK
R$^6$ = F INTERMEDIATE DL
R$^6$ = CH$_3$ INTERMEDIATE DM
R$^6$ = CF$_3$ INTERMEDIATE EG
R$^6$ = OCH$_3$ INTERMEDIATE EX
wherein R$^1$ = aryl or heteroaryl and Hal = Cl, Br, I Step 1: A mixture of the appropriate aryl/heteroaryl-halide 26 (390 μmol, 1.5 eq.), intermediate AN (260 μmol, 1.00 eq.), palladium catalyst such as Pd(dppf)Cl$_2$, Pd(dtbpf)Cl$_2$ or Ad$_2$n-BuP)-Pd (26.0 μmol, 0.10 eq.), sodium bicarbonate (0.521 μmol, 2.0-3.0 eq.) in dioxane (1.0 mL) and water (0.2 mL) was purged with nitrogen 3 times. The mixture was then stirred at 80° C. for 2 hours. After such time the mixture was purified using the methods described for CM 10A-1 or CM 10A-2 to give coupling product 15a.

Step 2: To a solution of corresponding coupling product 15a in ethyl alcohol (1.0 mL) was added hydrazine hydrate (20 eq.). The mixture was stirred at 80° C. for 1 hour. After such time the mixture was concentrated in vacuo and the residue purified by prep-HPLC according to one of the purification methods (PM) 4-1 through 4-13.

CM 10A-1

Example 10-1

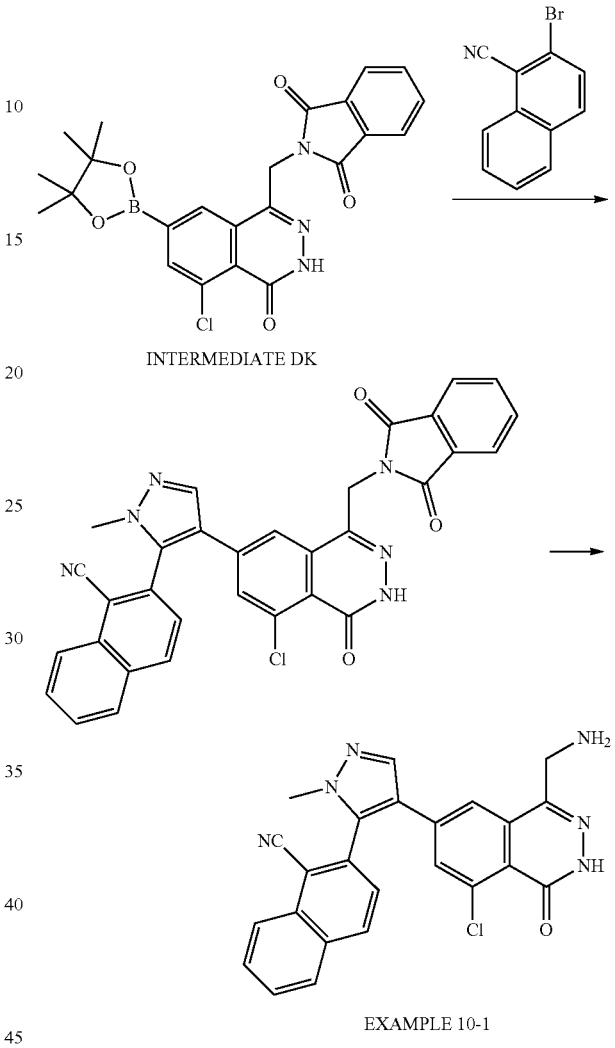

Step 1: A mixture of 2-((5-chloro-4-oxo-7-(4,4,5,5-tetramethyl-1,3,2-dioxaborolan-2-yl)-3,4-dihydrophthalazin-1-yl)methyl)isoindoline-1,3-dione, Intermediate DK (35 mg, 0.75 mmol, 1.00 eq.), 2-(4-bromo-2-methyl-pyrazol-3-yl)naphthalene-1-carbonitrile (24 mg, 0.75 mmol, 1.00 eq.), Pd(dtbpf)Cl$_2$ (4.9 mg, 0.08 mmol, 0.10 eq.), sodium bicarbonate (19 mg, 0.23 mmol, 3.00 eq.) in dioxane (2.0 mL) and water (0.4 mL) was degassed and purged with nitrogen for 3 times, and then the mixture was stirred at 80° C. for 2 hours. The mixture was then concentrated under reduced pressure and the residue purified by prep-TLC (SiO$_2$, dichloromethane/methyl alcohol 10:1) to give 2-[4-[8-chloro-4-[(1,3-dioxoisoindolin-2-yl)methyl]-1-oxo-2H-phthalazin-6-yl]-2-methyl-pyrazol-3-yl]naphthalene-1-carbonitrile (20 mg, 0.035 mmol, 47% yield) as a yellow solid. LCMS [M+1]$^+$=571.2.

Step 2: A mixture of 2-[4-[8-chloro-4-[(1,3-dioxoisoindolin-2-yl)methyl]-1-oxo-2H-phthalazin-6-yl]-2-methyl-pyrazol-3-yl]naphthalene-1-carbonitrile (15 mg, 0.026 mmol, 1.00 eq.) and hydrazine hydrate (0.525 mmol, 25 μL, 20.0 eq.) in ethyl alcohol (0.8 mL) was degassed and purged with nitrogen for 3 times, and then the mixture was stirred at 80°

C. for 1 hour. The mixture was then concentrated and the residue purified by prep-HPLC methods PM 4-6 to give to give 2-[4-[4-(aminomethyl)-8-chloro-1-oxo-2H-phthalazin-6-yl]-2-methyl-pyrazol-3-yl]naphthalene-1-carbonitrile, Example 10-1 (10 mg, 0.018 mmol, 69% yield) as an off-white solid.

CM 10A-2

Example 10-16

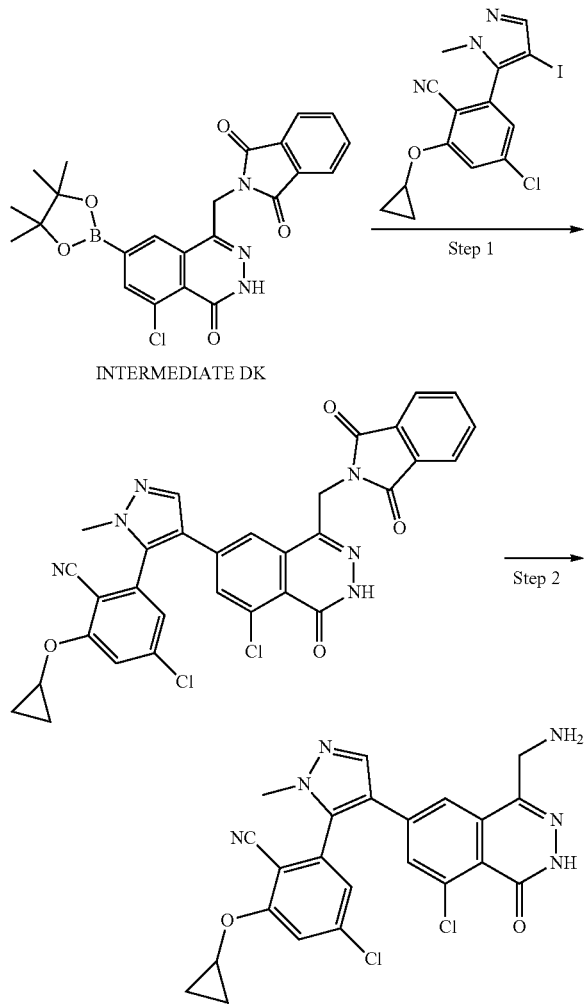

Step 1: A mixture of 4-chloro-2-(cyclopropoxy)-6-(4-iodo-2-methyl-pyrazol-3-yl)benzonitrile, Intermediate DK (18 mg, 0.45 mmol, 1.00 eq.), 2-[[5-chloro-4-oxo-7-(4,4,5,5-tetramethyl-1,3,2-dioxaborolan-2-yl)-3H-phthalazin-1-yl]methyl]isoindoline-1,3-dione (25 mg, 0.54 mmol, 1.20 eq.), sodium bicarbonate (11 mg, 0.13 mmol, 3.00 eq.), [2-(2-aminophenyl)phenyl]palladium(1+); bis(1-adamantyl)-butyl-phosphane; methanesulfonate $(Ad_2n\text{-}BuP)\text{-}Pd$ (3.3 mg, 0.005 mmol, 0.10 eq.) in water (0.2 mL) and dioxane (1.0 mL) was degassed and purged with nitrogen 3 times, and then the mixture was stirred at 80° C. for 2 hours. After such time the reaction mixture was concentrated and the residue was diluted with ethyl acetate (30 mL) and washed with brine (40 mL×3), dried over sodium sulfate, filtered, concentrated and the residue was purified by prep-TLC (SiO$_2$, petroleumether:ethylacetate=3:1) to give 4-chloro-2-[4-[8-chloro-4-[(1,3-dioxoisoindolin-2-yl)methyl]-1-oxo-2H-phthalazin-6-yl]-2-methyl-pyrazol-3-yl]-6-(cyclopropoxy)benzonitrile (20 mg, 0.032 mmol, 73% yield) as a yellow solid. LCMS [M+H]=611.1.

Step 2: To a solution of 4-chloro-2-[4-[8-chloro-4-[(1,3-dioxoisoindolin-2-yl)methyl]-1-oxo-2H-phthalazin-6-yl]-2-methyl-pyrazol-3-yl]-6-(cyclopropoxy)benzonitrile (15 mg, 0.025 mmol, 1.00 eq.) in ethyl alcohol (2 mL) was added hydrazine hydrate (2.5 mg, 0.049 mmol, 2.00 eq.). The mixture was stirred at 25° C. for 2 hours. The pH of the reaction mixture was then adjusted to pH 7 with hydrochloric acid (6.0 M, 0.5 mL), then concentrated and the residue was purified by prep-HPLC methods PM 4-6 to give 2-[4-[4-(aminomethyl)-8-chloro-1-oxo-2H-phthalazin-6-yl]-2-methyl-pyrazol-3-yl]-4-chloro-6-(cyclopropoxy)benzonitrile (3 mg, 0.005 mmol, 21% yield, HCl) as a yellow gum.

Following the teachings of the General Reaction Schemes, the general coupling method CM 10A-1 and CM 10A-2 and using purification methods 4-4 to 4-6, the synthesis of Example 10-1, Example 10-16 and the Intermediates disclosed herein, the Examples 10-1 to 10-20 are prepared as shown in Table 10.

TABLE 10

| Example | Structure | CM | PM | Compound Name and Characterization |
|---|---|---|---|---|
| 10-1 | (structure) | 8 10A-1 | 4-4 | 2-(4-(4-(aminomethyl)-8-chloro-1-oxo-1,2-dihydrophthalazin-6-yl)-1-methyl-1H-pyrazol-5-yl)-1-naphthonitrile<br>LCMS [M + 1]$^+$ = 441.1; $^1$H NMR (400 MHz, DMSO-d$_6$) δ = 12.81 (s, 1H), 8.57 (br d, J = 8.4 Hz, 1H), 8.42 (s, 1H), 8.40-8.24 (m, 4H), 8.16 (br d, J = 8.0 Hz, 1H), 7.95-7.81 (m, 3H), 7.72 (s, 1H), 7.30 (s, 1H), 4.33-4.02 (m, 2H), 3.78 (s, 3H) |

TABLE 10-continued

| Example | Structure | CM | PM | Compound Name and Characterization |
|---|---|---|---|---|
| 10-2 | 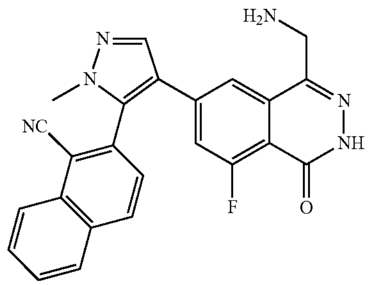 | 10A-1 | 4-4 | 2-(4-(4-(aminomethyl)-8-fluoro-1-oxo-1,2-dihydrophthalazin-6-yl)-1-methyl-1H-pyrazol-5-yl)-1-naphthonitrile<br>LCMS [M + 1]$^+$ = 425.1; $^1$H NMR (400 MHz, DMSO-d$_6$) δ = 12.81 (s, 1H), 8.57 (d, 1H), 8.39 (s, 1H), 8.30-8.25 (m, 4H), 8.15 (d, J = 8.0 Hz, 1H), 7.93-7.80 (m, 3H), 7.60 (s, 1H), 7.05 (d, 1H), 4.27-4.08 (m, 2H), 3.78 (s, 3H) |
| 10-3 | 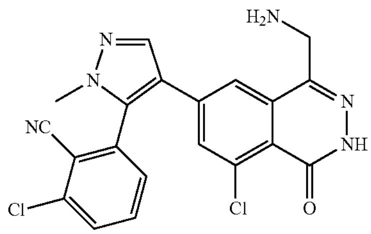 [SMILES: Cn1ncc(-c2cc(Cl)c3c(=O)[nH]nc(CN)c3c2)c1-c1cccc(Cl)c1C#N] | 10A-1 | 4-5 | 2-(4-(4-(aminomethyl)-8-chloro-1-oxo-1,2-dihydrophthalazin-6-yl)-1-methyl-1H-pyrazol-5-yl)-6-chlorobenzonitrile<br>LCMS [M + 1]$^+$ = 425.2; $^1$H NMR (400 MHz, DMSO-d$_6$) δ = 12.86 (s, 1H), 8.39-8.31 (m, 4H), 8.04-7.96 (m, 2H), 7.84 (dd, J = 1.2, 7.2 Hz, 1H), 7.59 (d, J = 1.6 Hz, 1H), 7.42 (d, J = 1.6 Hz, 1H), 4.27-4.12 (m, 2H), 3.77 (s, 3H) |
| 10-4 | 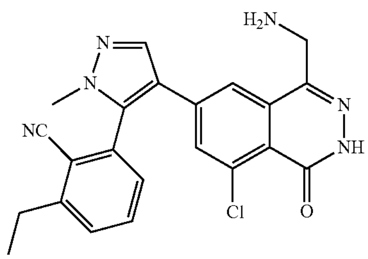 | 10A-1 | 4-5 | 2-(4-(4-(aminomethyl)-8-chloro-1-oxo-1,2-dihydrophthalazin-6-yl)-1-methyl-1H-pyrazol-5-yl)-6-ethylbenzonitrile<br>LCMS [M + 1]$^+$ = 419.2; $^1$H NMR (400 MHz, DMSO-d$_6$) δ = 12.82 (s, 1H), 8.48 (br s, 3H), 8.42 (s, 1H), 7.91 (t, J = 8.0 Hz, 1H), 7.77 (d, J = 7.6 Hz, 1H), 7.65 (d, J = 7.6 Hz, 1H), 7.58 (d, J = 1.6 Hz, 1H), 7.34 (s, 1H), 4.23-4.06 (m, 2H), 3.73 (s, 3H), 2.87 (q, J = 7.6 Hz, 2H), 1.24 (t, J = 7.6 Hz, 3H) |
| 10-5 | 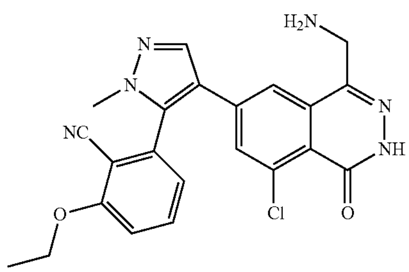 [SMILES: CCOc1cccc(-c2c(-c3cc(Cl)c4c(=O)[nH]nc(CN)c4c3)cnn2C)c1C#N] | 10A-1 | 4-5 | 2-(4-(4-(aminomethyl)-8-chloro-1-oxo-1,2-dihydrophthalazin-6-yl)-1-methyl-1H-pyrazol-5-yl)-6-ethoxybenzonitrile<br>LCMS [M + 1]$^+$ = 435.2; $^1$H NMR (400 MHz, DMSO-d$_6$) δ = 12.84 (s, 1H), 8.44-8.26 (m, 4H), 7.89 (t, J = 8.0 Hz, 1H), 7.61 (br d, J = 4.8 Hz, 1H), 7.50 (d, J = 8.8 Hz, 1H), 7.40 (br d, J = 2.8 Hz, 1H), 7.32 (d, J = 7.6 Hz, 1H), 4.37-4.27 (m, 2H), 4.25-4.06 (m, 2H), 3.72 (s, 3H), 1.38 (t, J = 7.2 Hz, 3H) |
| 10-6 | 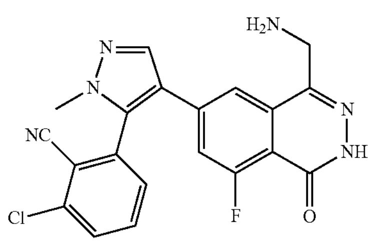 [SMILES: Cn1ncc(-c2cc(F)c3c(=O)[nH]nc(CN)c3c2)c1-c1cccc(Cl)c1C#N] | 10A-1 | 4-5 | 2-(4-(4-(aminomethyl)-8-fluoro-1-oxo-1,2-dihydrophthalazin-6-yl)-1-methyl-1H-pyrazol-5-yl)-6-chlorobenzonitrile<br>LCMS [M + 1]$^+$ = 409.2; $^1$H NMR (400 MHz, DMSO-d$_6$) δ = 12.86 (s, 1H), 8.39-8.28 (m, 4H), 8.04-7.93 (m, 2H), 7.81 (dd, J = 1.2, 7.2 Hz, 1H), 7.44 (s, 1H), 7.24 (d, J = 12.4 Hz, 1H), 4.25-4.12 (m, 2H), 3.76 (s, 3H) |
| 10-7 | 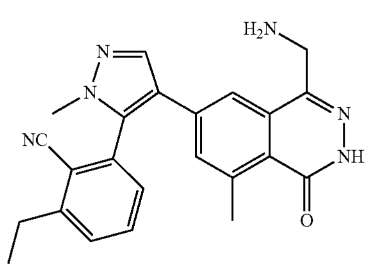 [SMILES: CCc1cccc(-c2c(-c3cc(C)c4c(=O)[nH]nc(CN)c4c3)cnn2C)c1C#N] | 10A-1 | 4-4 | 2-(4-(4-(aminomethyl)-8-methyl-1-oxo-1,2-dihydrophthalazin-6-yl)-1-methyl-1H-pyrazol-5-yl)-6-ethylbenzonitrile<br>LCMS [M + 1]$^+$ = 399.2; $^1$H NMR (400 MHz, DMSO-d$_6$) δ = 12.64 (s, 1H), 8.31 (s, 4H), 7.92-7.85 (m, 1H), 7.75 (d, J = 7.2 Hz, 1H), 7.62 (dd, J = 0.8, 7.6 Hz, 1H), 7.39 (s, 1H), 7.23 (s, 1H), 4.18-4.01 (m, 2H), 3.74 (s, 3H), 2.87 (q, J = 7.6 Hz, 2H), 2.64 (s, 3H), 1.24 (t, J = 7.6 Hz, 3H) |

TABLE 10-continued

| Example | Structure | CM | PM | Compound Name and Characterization |
|---|---|---|---|---|
| 10-8 | 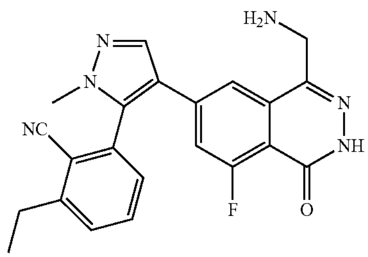 [SMILES: CCc1cccc(-c2c(-c3cc(F)c4c(=O)[nH]nc(CN)c4c3)cnn2C)c1C#N] | 10A-1 | 4-4 | 2-(4-(4-(aminomethyl)-8-fluoro-1-oxo-1,2-dihydrophthalazin-6-yl)-1-methyl-1H-pyrazol-5-yl)-6-ethylbenzonitrile<br>LCMS [M + 1]$^+$ = 403.2; $^1$H NMR (400 MHz, DMSO-d$_6$) δ = 12.82 (s, 1H), 8.48 (br s, 3H), 8.39 (s, 1H), 7.90 (t, J = 7.6 Hz, 1H), 7.76 (d, J = 7.6 Hz, 1H), 7.64 (d, J = 7.6 Hz, 1H), 7.40 (d, J = 0.8 Hz, 1H), 7.18 (d, J = 12.4 Hz, 1H), 4.20-3.99 (m, 2H), 3.73 (s, 3H), 2.88 (q, J = 7.6 Hz, 2H), 1.24 (t, J = 7.6 Hz, 3H) |
| 10-9 | 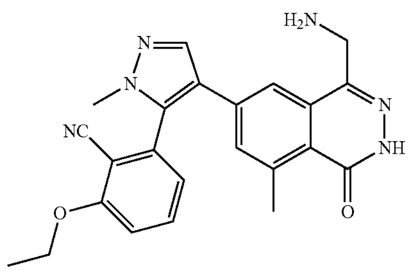 | 10A-1 | 4-4 | 2-(4-(4-(aminomethyl)-8-methyl-1-oxo-1,2-dihydrophthalazin-6-yl)-1-methyl-1H-pyrazol-5-yl)-6-ethoxybenzonitrile<br>LCMS [M + 1]$^+$ = 415.2; $^1$H NMR (400 MHz, DMSO-d$_6$) δ = 12.64 (s, 1H), 8.37-8.26 (m, 3H), 7.87 (dd, J = 7.6, 8.8 Hz, 1H), 7.48 (d, J = 8.8 Hz, 1H), 7.41 (s, 1H), 7.35-7.26 (m, 2H), 4.30 (dq, J = 2.8, 6.8 Hz, 2H), 4.21-4.01 (m, 2H), 3.72 (s, 3H), 2.67 (s, 3H), 1.39 (t, J = 7.2 Hz, 3H) |
| 10-10 | 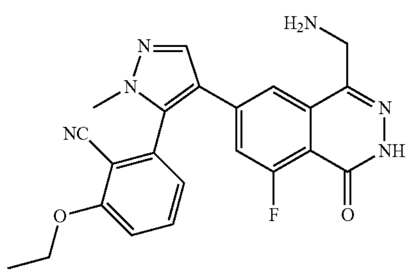 | 10A-1 | 4-4 | 2-(4-(4-(aminomethyl)-8-fluoro-1-oxo-1,2-dihydrophthalazin-6-yl)-1-methyl-1H-pyrazol-5-yl)-6-ethoxybenzonitrile<br>LCMS [M + 1]$^+$ = 419.2; $^1$H NMR (400 MHz, DMSO-d$_6$) δ = 12.84 (s, 1H), 8.45-8.25 (m, 4H), 7.89 (dd, J = 7.6, 8.4 Hz, 1H), 7.49 (d, J = 8.0 Hz, 1H), 7.31 (d, J = 7.6 Hz, 1H), 7.17 (d, J = 12.4 Hz, 1H), 4.35-4.26 (m, 2H), 4.25-4.07 (m, 2H), 3.72 (s, 3H), 1.39 (t, J = 6.8 Hz, 3H) |
| 10-11 | 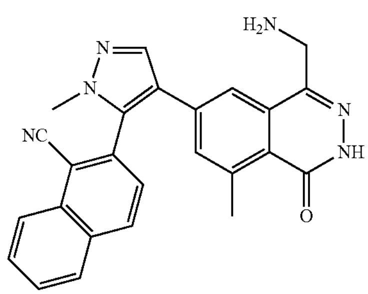 [SMILES: Cc1cc(-c2cnn(C)c2-c2ccc3ccccc3c2C#N)cc2c(CN)n[nH]c(=O)c12] | 10A-1 | 4-6 | 2-(4-(4-(aminomethyl)-8-methyl-1-oxo-1,2-dihydrophthalazin-6-yl)-1-methyl-1H-pyrazol-5-yl)-1-naphthonitrile<br>LCMS [M + 1]$^+$ = 421.1; $^1$H NMR (400 MHz, DMSO-d$_6$) δ = 12.60 (s, 1H), 8.56 (d, J = 8.4 Hz, 1H), 8.42 (br s, 3H), 8.34 (s, 1H), 8.29 (d, J = 7.6 Hz, 1H), 8.15 (d, J = 8.4 Hz, 1H), 7.93-7.82 (m, 3H), 7.54 (s, 1H), 7.19 (s, 1H), 4.25-4.12 (m, 1H), 4.07-3.94 (m, 1H), 3.77 (s, 3H), 2.52 (s, 3H) |
| 10-12 | 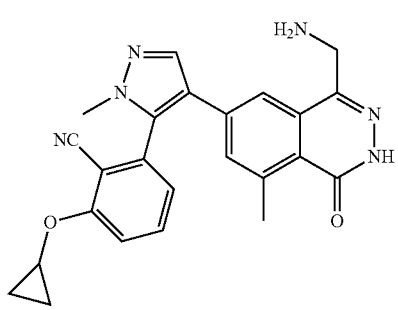 | 10A-1 | 4-6 | 2-(4-(4-(aminomethyl)-8-methyl-1-oxo-1,2-dihydrophthalazin-6-yl)-1-methyl-1H-pyrazol-5-yl)-6-cyclopropoxybenzonitrile<br>LCMS [M + 1]$^+$ = 427.2; $^1$H NMR (400 MHz, DMSO-d$_6$) δ = 12.63 (s, 1H), 8.44 (br s, 3H), 8.28 (s, 1H), 7.93 (dd, J = 7.6, 8.8 Hz, 1H), 7.75 (dd, J = 0.8, 8.8 Hz, 1H), 7.37 (d, J = 1.2 Hz, 1H), 7.35 (dd, J = 0.8, 7.6 Hz, 1H), 7.31 (s, 1H), 4.22-4.09 (m, 2H), 4.08-3.95 (m, 1H), 3.72 (s, 3H), 2.67 (s, 3H), 0.94-0.86 (m, 2H), 0.83-0.74 (m, 2H) |

TABLE 10-continued

| Example | Structure | CM | PM | Compound Name and Characterization |
|---|---|---|---|---|
| 10-13 | 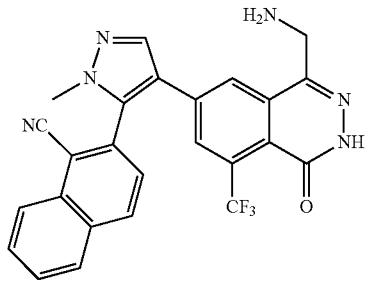 [SMILES: Cn1ncc(-c2cc(C(F)(F)F)c3c(=O)[nH]nc(CN)c3c2)c1-c1ccc2ccccc2c1C#N] | 10A-1 | 4-6 | 2-(4-(4-(aminomethyl)-1-oxo-8-(trifluoromethyl)-1,2-dihydrophthalazin-6-yl)-1-methyl-1H-pyrazol-5-yl)-1-naphthonitrile<br>LCMS [M + 1]$^+$ = 475.2; $^1$H NMR (400 MHz, DMSO-d$_6$) δ = 12.98 (s, 1H), 8.58 (d, J = 8.4 Hz, 1H), 8.52 (s, 1H), 8.39 (br d, J = 1.2 Hz, 3H), 8.30 (d, J = 7.6 Hz, 1H), 8.19 (s, 1H), 8.14 (d, J = 8.0 Hz, 1H), 7.93-7.84 (m, 3H), 7.53 (s, 1H), 4.48-4.24 (m, 2H), 3.80 (s, 3H) |
| 10-14 | 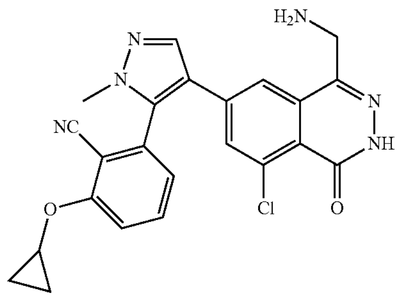 | 10A-1 | 4-6 | 2-(4-(4-(aminomethyl)-8-chloro-1-oxo-1,2-dihydrophthalazin-6-yl)-1-methyl-1H-pyrazol-5-yl)-6-cyclopropoxybenzonitrile<br>LCMS [M + 1]$^+$ = 447.2; $^1$H NMR (400 MHz, DMSO-d$_6$) δ = 12.83 (s, 1H), 8.47 (br s, 3H), 8.38 (s, 1H), 7.96 (dd, J = 7.7, 8.6 Hz, 1H), 7.81-7.75 (m, 1H), 7.57 (d, J = 1.6 Hz, 1H), 7.42 (d, J = 1.6 Hz, 1H), 7.39 (dd, J = 0.6, 7.6 Hz, 1H), 4.26-4.16 (m, 2H), 4.15-4.06 (m, 1H), 3.73 (s, 3H), 0.94-0.76 (m, 4H) |
| 10-15 | 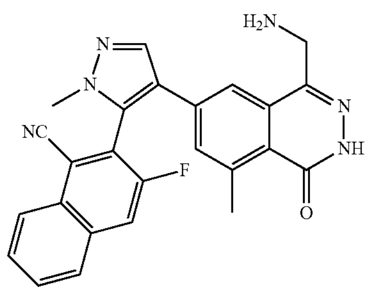 [SMILES: Cc1cc(-c2cnn(C)c2-c2c(F)cc3ccccc3c2C#N)cc2c(CN)n[nH]c(=O)c12] | 10A-1 | 4-6 | 2-(4-(4-(aminomethyl)-8-methyl-1-oxo-1,2-dihydrophthalazin-6-yl)-1-methyl-1H-pyrazol-5-yl)-3-fluoro-1-naphthonitrile<br>LCMS [M + 1]$^+$ = 439.2; $^1$H NMR (400 MHz, DMSO-d6) δ = 12.15 (s, 1H), 8.53 (d, J = 10.0 Hz, 1H), 8.31 (s, 1H), 8.27-8.23 (m, 1H), 8.19-8.13 (m, 1H), 7.92-7.83 (m, 2H), 7.53 (d, J = 0.8 Hz, 1H), 7.38 (d, J = 1.6 Hz, 1H), 3.81 (s, 3H), 3.35 (br s, 2H), 2.69 (s, 3H) |
| 10-16 | 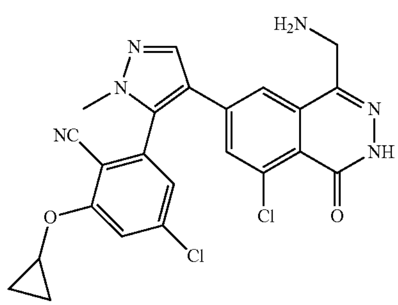 [SMILES: Cn1ncc(-c2cc(Cl)c3c(=O)[nH]nc(CN)c3c2)c1-c1cc(Cl)cc(OC2CC2)c1C#N] | 10A-2 | 4-6 | 2-(4-(4-(aminomethyl)-8-chloro-1-oxo-1,2-dihydrophthalazin-6-yl)-1-methyl-1H-pyrazol-5-yl)-4-chloro-6-cyclopropoxybenzonitrile<br>LCMS [M + 1]$^+$ = 481.1; $^1$H NMR (400 MHz, DMSO-d6) δ = 12.86 (s, 1H), 8.45 (br s, 3H), 8.36 (s, 1H), 7.85 (d, J = 1.6 Hz, 1H), 7.61 (d, J = 1.2 Hz, 2H), 7.43 (d, J = 1.2 Hz, 1H), 4.30-4.23 (m, 2H), 4.19 (br d, J = 4.4 Hz, 1H), 3.76 (s, 3H), 0.96-0.88 (m, 2H), 0.75-0.85 (m, 2H) |
| 10-17 | 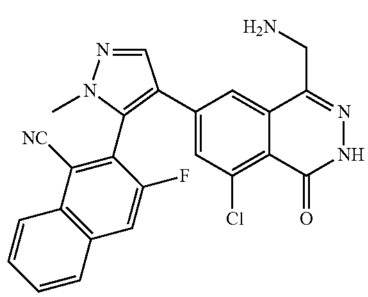 [SMILES: Cn1ncc(-c2cc(Cl)c3c(=O)[nH]nc(CN)c3c2)c1-c1c(F)cc2ccccc2c1C#N] | 10A-2 | 4-6 | 2-(4-(4-(aminomethyl)-8-chloro-1-oxo-1,2-dihydrophthalazin-6-yl)-1-methyl-1H-pyrazol-5-yl)-3-fluoro-1-naphthonitrile<br>LCMS [M + 1]$^+$ = 459.1; $^1$H NMR (400 MHz, DMSO-d6) δ = 12.82 (s, 1H), 8.58 (d, J = 10.0 Hz, 1H), 8.52 (s, 1H), 8.49 (br s, 3H), 8.31-8.26 (m, 1H), 8.20-8.14 (m, 1H), 7.92-7.85 (m, 2H), 7.76 (d, J = 1.6 Hz, 1H), 7.30 (d, J = 1.6 Hz, 1H), 4.35-4.06 (m, 2H), 3.82 (s, 3H) |

TABLE 10-continued

| Example | Structure | CM | PM | Compound Name and Characterization |
|---|---|---|---|---|
| 10-18 | 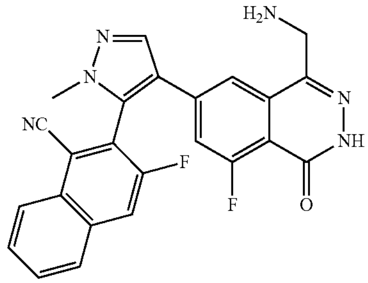 [SMILES: Cn1ncc(-c2cc(F)c3c(=O)[nH]nc(CN)c3c2)c1-c1c(F)cc2ccccc2c1C#N] | 10A-2 | 4-6 | 2-(4-(4-(aminomethyl)-8-fluoro-1-oxo-1,2-dihydrophthalazin-6-yl)-1-methyl-1H-pyrazol-5-yl)-3-fluoro-1-naphthonitrile<br>LCMS [M + 1]⁺ = 443.1 |
| 10-19 | 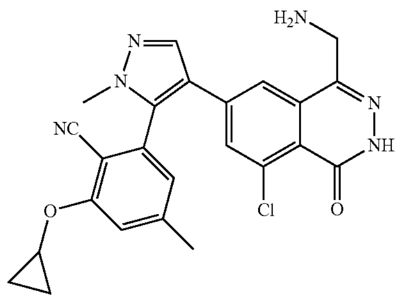 [SMILES: Cc1cc(OC2CC2)c(C#N)c(-c2c(-c3cc(Cl)c4c(=O)[nH]nc(CN)c4c3)cnn2C)c1] | 10A-2 | 4-6 | 2-(4-(4-(aminomethyl)-8-chloro-1-oxo-1,2-dihydrophthalazin-6-yl)-1-methyl-1H-pyrazol-5-yl)-6-cyclopropoxy-4-methylbenzonitrile<br>LCMS [M + 1]⁺ = 461.1; ¹H NMR (400 MHz, DMSO-d₆) δ = 12.83 (s, 1H), 8.50 (br s, 3H), 8.38 (s, 1H), 7.61 (s, 1H), 7.53 (d, J = 1.6 Hz, 1H), 7.49 (s, 1H), 7.23 (s, 1H), 4.23-4.12 (m, 2H), 4.11-4.01 (m, 1H), 3.72 (s, 3H), 2.53 (s, 3H), 0.94-0.86 (m, 2H), 0.80-0.74 (m, 2H) |
| 10-20 | 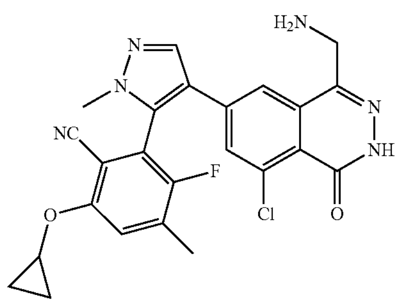 [SMILES: Cc1cc(OC2CC2)c(C#N)c(-c2c(-c3cc(Cl)c4c(=O)[nH]nc(CN)c4c3)cnn2C)c1F] | 10A-1 | 4-6 | 2-(4-(4-(aminomethyl)-8-chloro-1-oxo-1,2-dihydrophthalazin-6-yl)-1-methyl-1H-pyrazol-5-yl)-6-cyclopropoxy-3-fluoro-4-methylbenzonitrile<br>LCMS [M + 1]⁺ = 479.1; ¹H NMR (400 MHz, DMSO-d₆) δ = 12.85 (s, 1H), 8.52 (br s, 3H), 8.46 (s, 1H), 7.80 (d, J = 6.0 Hz, 1H), 7.54 (d, J = 1.6 Hz, 1H), 7.50 (d, J = 1.6 Hz, 1H), 4.27-4.05 (m, 3H), 3.76 (s, 3H), 2.48 (d, J = 1.6 Hz, 3H), 0.94-0.85 (m, 2H), 0.83-0.68 (m, 2H) |

Example 11-1

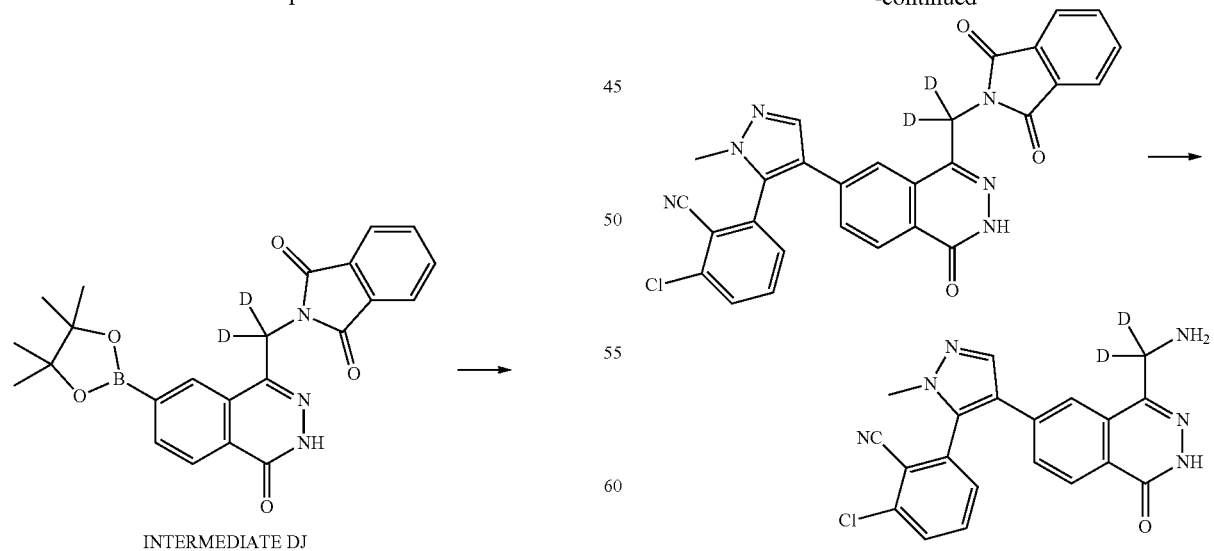

Step 1: A mixture of 2-((4-oxo-7-(4,4,5,5-tetramethyl-1,3,2-dioxaborolan-2-yl)-3,4-dihydrophthalazin-1-yl)methyl-d2)isoindoline-1,3-dione, Intermediate DJ (100 mg, 0.152 mmol, 1.00 eq.), 2-(4-bromo-2-methyl-pyrazol-3-yl)-6-chloro-benzonitrile (58 mg, 0.197 mmol, 1.30 eq.), Pd(dtbpf)Cl$_2$ (10 mg, 0.015 mmol, 0.10 eq) and sodium bicarbonate (38 mg, 0.455 mmol, 3.00 eq.) in dioxane (3.0 mL) and water (0.6 mL) was degassed and purged with nitrogen 3 times and stirred at 80° C. for 2 hours. After such time the mixture was concentrated and the residue was purified by column chromatography (SiO$_2$, petroleum ether/ethyl acetate 10/1 to 0/1) to give 2-chloro-6-(4-(4-((1,3-dioxoisoindolin-2-yl)methyl-d2)-1-oxo-1,2-dihydrophthalazin-6-yl)-1-methyl-1H-pyrazol-5-yl)benzonitrile (50 mg, 0.089 mmol, 59% yield) as a yellow solid. LCMS [M+1]$^+$=523.1.

Step 2: A mixture of 2-chloro-6-(4-(4-((1,3-dioxoisoindolin-2-yl)methyl-d2)-1-oxo-1,2-dihydrophthalazin-6-yl)-1-methyl-1H-pyrazol-5-yl)benzonitrile (50 mg, 0.089 mmol, 1.00 eq.) and hydrazine hydrate (0.044 mL, 0.89 mmol, 10.0 eq.) in ethyl alcohol (2 mL) was stirred at 80° C. for 1 hour under nitrogen atmosphere. After such time the mixture was concentrated under reduced pressure and the residue purified by prep-HPLC (Phenomenex luna C18 150×25 mm×10 μm; mobile phase: [water (0.1% trifluoroacetic acid)-ACN]; B %: 7%-37%, 10 min). to give 2-(4-(4-(aminomethyl-d2)-1-oxo-1,2-dihydrophthalazin-6-yl)-1-methyl-1H-pyrazol-5-yl)-6-chlorobenzonitrile (31 mg, 0.059 mmol, 66% yield) as a white solid. LCMS [M+1]$^+$=393.1; $^1$H NMR (400 MHz, DMSO-d$_6$) δ=12.88 (s, 1H), 8.34 (br s, 3H), 8.28 (s, 1H), 8.12 (d, J=8.4 Hz, 1H), 8.00-7.97 (dd, J=1.6, 8.4 Hz, 1H), 7.97-7.92 (t, J=7.2 Hz, 1H), 7.79-7.76 (m, 2H), 7.43 (dd, J=1.6, 8.4 Hz, 1H), 3.76 (s, 3H).

Example 11-2

2-(4-(4-(aminomethyl-d2)-1-oxo-1,2-dihydrophthalazin-6-yl)-1-methyl-1H-pyrazol-5-yl)-1-naphthonitrile, Example 11-2 was prepared as a white solid (19 mg, 0.046 mmol, 35% yield) following the same procedure as example 11-1 using intermediate DJ (60 mg, 0.138 mol, 1.00 eq.) and Intermediate DC 2-(4-bromo-2-methyl-pyrazol-3-yl)naphthalene-1-carbonitrile (56 mg, 0.18 mmol, 1.30 eq.). LCMS [M+1]$^+$=409.3; $^1$H NMR (400 MHz, DMSO-d$_6$) δ=12.85 (s, 1H), 8.53 (d, J=8.4 Hz, 1H), 8.33-8.27 (m, 4H), 8.14 (d, J=8.0 Hz, 1H), 8.00 (d, J=8.0 Hz, 1H), 7.92-7.82 (m, 4H), 7.32 (dd, J=1.6, 8.0 Hz, 1H), 3.78 (s, 3H).

Example 12-1

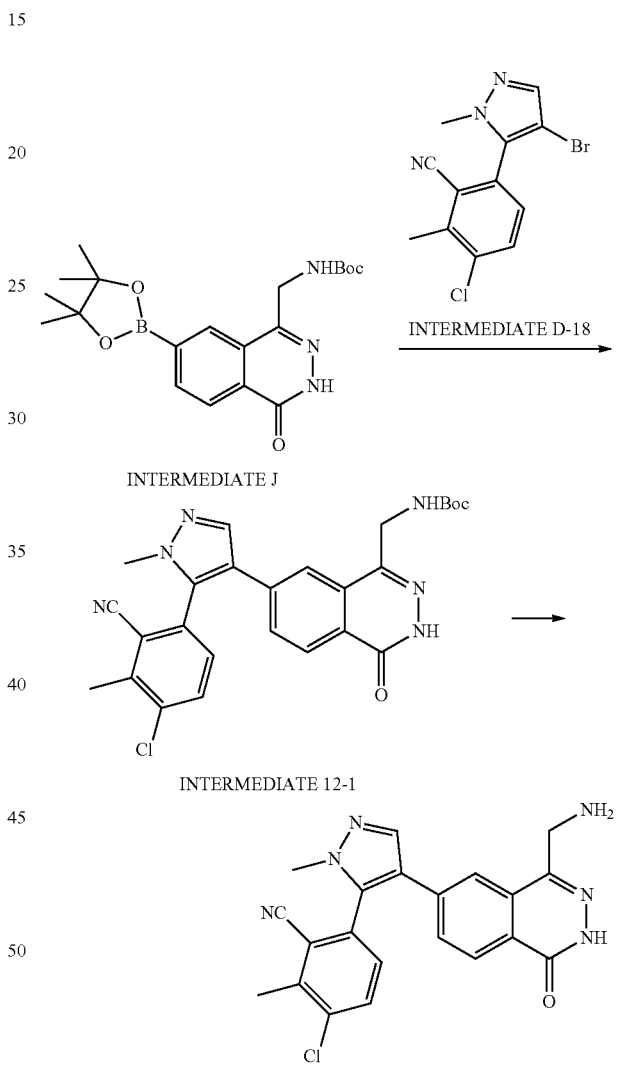

EXAMPLE 12-1

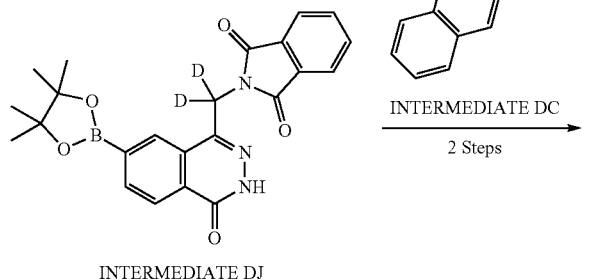

INTERMEDIATE DC
2 Steps

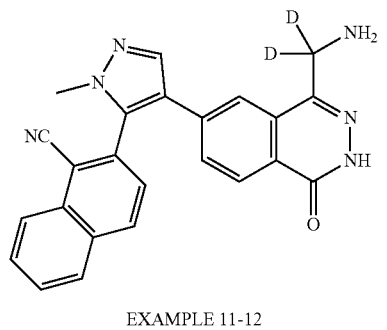

EXAMPLE 11-12

Step 1: A mixture of 6-(4-bromo-2-methyl-pyrazol-3-yl)-3-chloro-2-methyl-benzonitrile, Intermediate D-18 (200 mg, 0.64 mmol, 1.00 eq.), intermediate J, (310 mg, 0.77 mmol, 1.20 eq.), sodium bicarbonate (108 mg, 1.29 mmol, 2.00 eq.) and Pd(dtbpf)Cl$_2$ (42 mg, 0.064 mmol, 0.10 eq.) in dioxane (3 mL) and water (0.6 mL) was degassed with nitrogen and stirred at 80° C. for 1 hour. After such time the mixture was concentrated and the residue purified by prep-TLC (SiO$_2$, dichloromethane/methyl alcohol 20/1) to give tert-butyl N-[[7-[5-(4-chloro-2-cyano-3-methyl-phenyl)-1-methylpyrazol-4-yl]-4-oxo-3H-phthalazin-1-yl]methyl]carbamate, Intermediate 12-1 (150 mg, 0.30 mmol, 46% yield) as a yellow solid. LCMS [M+1]$^+$=505.2.

Step 2: To a solution of tert-butyl ((7-(5-(4-chloro-2-cyano-3-methylphenyl)-1-methyl-1H-pyrazol-4-yl)-4-oxo-3,4-dihydrophthalazin-1-yl)methyl)carbamate (50 mg, 0.10 mmol, 1.00 eq.) in dichloromethane (1.5 mL) was added trifluoroacetic acid (0.4 mL). The mixture was stirred at 25° C. for 0.5 hour, concentrated in vacuum to give a residue. The residue was purified by prep-HPLC (Phenomenex Gemini-NX C18 75×30 mm×3 μm; mobile phase: [water (0.1% TFA)-ACN]; B %: 22%-32%, 7 min) to give 6-(4-(4-(aminomethyl)-1-oxo-1,2-dihydrophthalazin-6-yl)-1-methyl-1H-pyrazol-5-yl)-3-chloro-2-methylbenzonitrile, Example 12-1 (14 mg, 0.026,mol, 27% yield) as a white solid. LCMS [M+1]$^+$=405.2; $^1$H NMR (400 MHz, DMSO-d$_6$) δ=12.87 (s, 1H), 8.55-8.34 (br s, 3H), 8.28 (s, 1H), 8.10 (d, J=8.4 Hz, 1H), 7.99 (d, J=8.4 Hz, 1H), 7.81 (s, 1H), 7.61 (d, J=8.4 Hz, 1H), 7.43 (d, J=8.4 Hz, 1H), 4.35 (br s, 2H), 3.73 (s, 3H), 2.58 (s, 3H).

Example 12-2

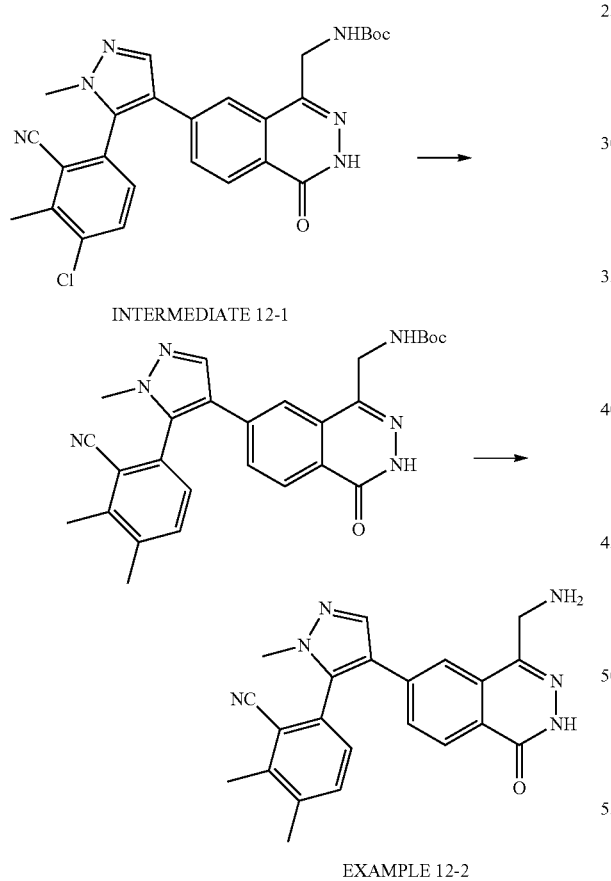

EXAMPLE 12-2

Step 1: A mixture of Intermediate 12-1 (50 mg, 0.10 mmol, 1.00 eq.), methylboronic acid (18 mg, 0.30 mmol, 3.00 eq.), Pd(dtbpf)Cl$_2$ (6.5 mg, 0.010 mmol, 0.10 eq.) and potassium carbonate (41 mg, 0.30 mmol, 3.00 eq.) in dioxane (2 mL) was degassed with nitrogen and stirred at 100° C. for 1 hour. After such time the mixture was concentrated and the residue purified by prep-TLC (SiO$_2$, dichloromethane/methyl alcohol 20/1) to give tert-butyl N-[[7-[5-(2-cyano-3,4-dimethyl-phenyl)-1-methyl-pyrazol-4-yl]-4-oxo-3H-phthalazin-1-yl]methyl]carbamate (30 mg, 0.062 mmol, 63% yield) as a yellow solid. LCMS [M+1]$^+$=485.3; $^1$H NMR (400 MHz, DMSO-d$_6$) δ=10.22 (s, 1H), 8.25 (d, J=8.4 Hz, 1H), 7.99 (s, 1H), 7.60 (s, 1H), 7.57-7.46 (m, 2H), 7.20 (d, J=7.6 Hz, 1H), 5.42-5.33 (m, 1H), 3.81 (s, 3H), 3.50 (s, 2H), 2.59 (s, 3H), 2.46 (s, 3H), 1.49 (s, 9H).

Step 2: To a solution of tert-butyl N-[[7-[5-(2-cyano-3,4-dimethyl-phenyl)-1-methyl-pyrazol-4-yl]-4-oxo-3H-phthalazin-1-yl]methyl]carbamate (30 mg, 0.062 mmol, 1.00 eq.) in dichloromethane (1.5 mL) was added trifluoroacetic acid (0.5 mL). The mixture was stirred at 25° C. for 0.5 hour then concentrated in vacuum. The formed residue was purified by prep-HPLC (Column: Phenomenex luna C18 150×25 mm×10 μm; mobile phase: [water (0.1% TFA)-ACN]; B %: 6%-36%, 10 min) to give 6-(4-(4-(aminomethyl)-1-oxo-1,2-dihydrophthalazin-6-yl)-1-methyl-1H-pyrazol-5-yl)-2,3-dimethylbenzonitrile, Example 12-2 (7.8 mg, 0.016 mmol, 25% yield) as a white solid. LCMS [M+1]$^+$=385.2; $^1$H NMR (400 MHz, DMSO-d$_6$) δ=12.84 (s, 1H), 8.32 (br s, 3H), 8.26 (s, 1H), 8.08 (d, J=8.4 Hz, 1H), 7.74-7.65 (m, 2H), 7.46 (d, J=8.0 Hz, 2H), 4.26 (br d, J=1.2 Hz, 2H), 3.70 (s, 3H), 2.48 (br s, 3H), 2.42 (s, 3H).

Example 12-3

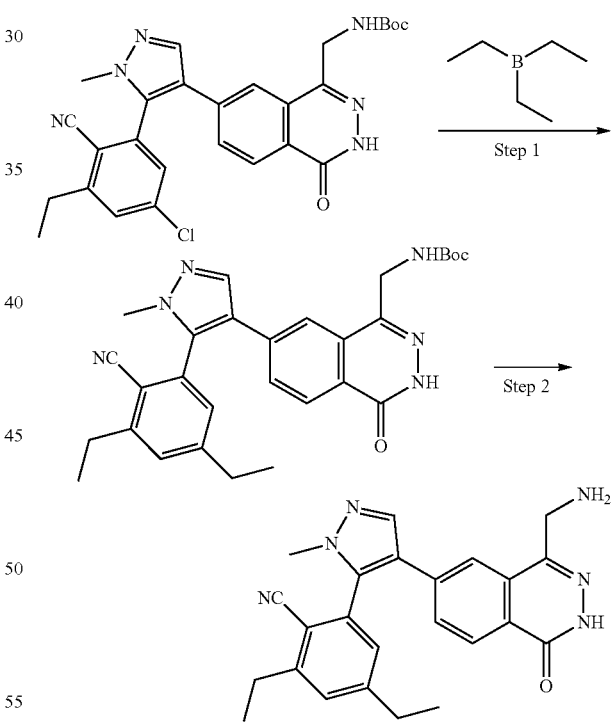

Step 1: To a solution of tert-butyl N-[[7-[5-(5-chloro-2-cyano-3-ethyl-phenyl)-1-methyl-pyrazol-4-yl]-4-oxo-3H-phthalazin-1-yl]methyl]carbamate (80 mg, 0.154 mmol, 1.00 eq.) and triethylborane (1.00 M, 0.450 mmol, 3.00 eq.) in THF (5 mL) and water (0.5 mL) was added potassium carbonate (64 mg, 0.462 mmol, 3.00 eq.) and XPhos Pd G3 (13 mg, 15 μmol, 0.10 eq.). The mixture was stirred at 85° C. for 8 hours then concentrated and the residue was diluted with water (10 mL) and extracted with ethyl acetate (20 mL×2). The combined organic extracts were washed with brine (20 mL), dried over anhydrous sodium sulfate, filtered and concentrated and the residue purified by prep-TLC (SiO$_2$, dichloromethane:methanol 20:1) to give tert-butyl N-[[7-[5-(2-cyano-3,5-diethyl-phenyl)-1-methyl-pyrazol-4-yl]-4-oxo-3H-phthalazin-1-yl]methyl]carbamate (40 mg crude) as a white solid. LCMS [M+1]$^+$=513.5.

Step 2: To a mixture of tert-butyl N-[[7-[5-(2-cyano-3,5-diethyl-phenyl)-1-methyl-pyrazol-4-yl]-4-oxo-3H-phthalazin-1-yl]methyl]carbamate (40 mg, 78 µmol, 1.00 eq.) in dichloromethane (2 mL) was added trifluoroacetic acid (0.8 mL) in one portion at 0° C. under a nitrogen atmosphere. The mixture was stirred at 20° C. for 1 hour then concentrated under reduced pressure and the formed residue was purified by Prep-HPLC (Phenomenex luna C18 150×25 mm×10 µm; mobile phase: [water (0.1% TFA)-ACN]; B %: 17%-47%, 10 min) and further purified by SFC (DAICEL CHIRALCEL OD-H (250 mm×30 mm, 5 µm); mobile phase: [0.1% NH$_3$H$_2$O EtOH]; B %: 40%) to give 2-[4-[4-(aminomethyl)-1-oxo-2H-phthalazin-6-yl]-2-methyl-pyrazol-3-yl]-4,6-diethyl-benzonitrile, Example 12-3 (14 mg, 34 µmol, 70% yield) as a light yellow solid. LCMS [M+1]$^+$=413.3; $^1$H NMR (400 MHz, CDCl$_3$) δ=8.27 (br d, J=8.0 Hz, 1H), 7.93 (s, 1H), 7.54 (br d, J=8.4 Hz, 1H), 7.45 (s, 1H), 7.36 (s, 1H), 7.13 (s, 1H), 3.88 (br s, 2H), 3.82 (s, 3H), 2.91 (q, J=8.0 Hz, 2H), 2.74 (q, J=7.6 Hz, 2H), 2.12-1.99 (m, 2H), 1.32 (br t, J=7.6 Hz, 3H), 1.28-1.23 (m, 3H).

Example 12-4

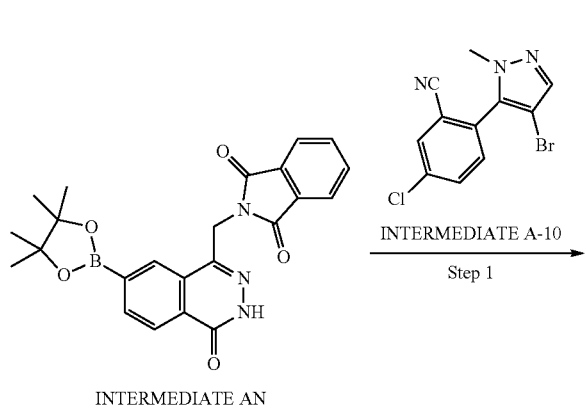

INTERMEDIATE AN

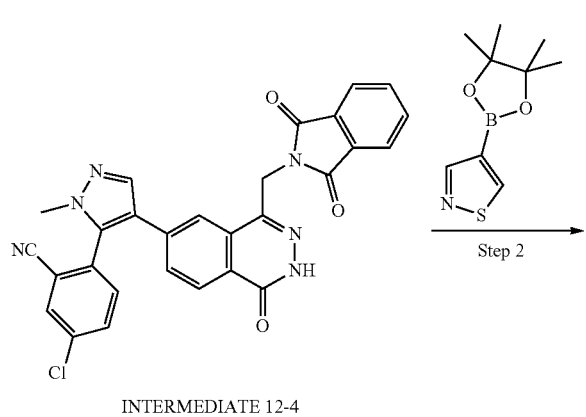

INTERMEDIATE 12-4

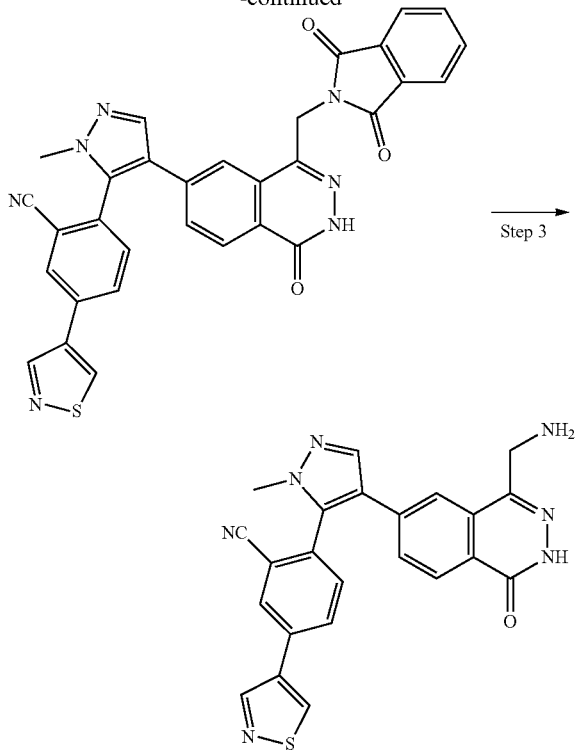

EXAMPLE 12-4

Step 1: A mixture of 2-(4-bromo-2-methyl-pyrazol-3-yl)-5-chloro-benzonitrile, Intermediate A-10 (300 mg, 1.01 mmol, 1.00 eq.), 2-[[4-oxo-7-(4,4,5,5-tetramethyl-1,3,2-dioxaborolan-2-yl)-3H-phthalazin-1-yl]methyl]isoindoline-1,3-dione, Intermediate J (523 mg, 1.21 mmol, 1.20 eq.), ditert-butyl(cyclopentyl)phosphane-dichloropalladium iron (66 mg, 0.101 mmol, 0.10 eq.), sodium bicarbonate (170 mg, 2.02 mmol, 79 µL, 2.00 eq.) in 1,4-dioxane (10 mL) and water (2 mL) was degassed and purged with nitrogen 3 times then stirred at 80° C. for 2 hours. After such time the reaction mixture was quenched by the addition of water (30 mL) at 20° C. then extracted with dichloromethane (30 mL×2). The combined organic layers were washed with brine (30 mL), dried over anhydrous sodium sulfate, filtered and concentrated under reduced pressure to give 5-chloro-2-[4-[4-[(1,3-dioxoisoindolin-2-yl)methyl]-1-oxo-2H-phthalazin-6-yl]-2-methyl-pyrazol-3-yl]benzonitrile, Intermediate 12-4 (300 mg, crude) as brown liquid which used into the next step without further purification. LCMS [M+1]$^+$=521.1

Step 2: A mixture of 4-(4,4,5,5-tetramethyl-1,3,2-dioxaborolan-2-yl)isothiazole (39 mg, 0.184 mmol, 1.20 eq.), 5-chloro-2-[4-[4-[(1,3-dioxoisoindolin-2-yl)methyl]-1-oxo-2H-phthalazin-6-yl]-2-methyl-pyrazol-3-yl]benzonitrile (80 mg, 0.153 mmol, 1.00 eq.), Xphos precatalyst G2 (36 mg, 0.046 mmol, 0.30 eq.) and potassium phosphate (65 mg, 0.307 mmol, 2.00 eq.) in 1,4-dioxane (4 mL) and water (0.4 mL) was degassed and purged with nitrogen 3 times then stirred at 110° C. for 1 hour. After such time the reaction was cooled to room temperature, diluted with dichloromethane (20 mL), washed with water (5 mL×2) and the organic layer was dried over anhydrous sodium sulfate, filtered and concentrated to give 2-[4-[4-[(1,3-dioxoisoindolin-2-yl)methyl]-1-oxo-2H-phthalazin-6-yl]-2-methyl-pyrazol-3-yl]-5-isothiazol-4-yl-benzonitrile (66 mg, crude) as a brown oil which used into the next step without further purification. LCMS [M+1]$^+$=570.1.

Step 3: To a solution of 2-[4-[4-[(1,3-dioxoisoindolin-2-yl)methyl]-1-oxo-2H-phthalazin-6-yl]-2-methyl-pyrazol-3-yl]-5-isothiazol-4-yl-benzonitrile (60 mg, 0.105 mmol, 1.00 eq.) in 1,4-dioxane (5 mL) was added hydrazine hydrate (53 mg, 1.05 mmol, 51 µL, 10 eq.). The mixture was stirred at 20° C. for 15 hours then concentrated under reduced pressure. The residue was purified by prep-HPLC (YMC-Actus Triart C18 150×30 mm×5 µm; mobile phase: [water (0.1% TFA)-ACN]; B %: 17%-43%, 11 min) to give 2-[4-[4-(aminomethyl)-1-oxo-2H-phthalazin-6-yl]-2-methyl-pyrazol-3-yl]-5-isothiazol-4-yl-benzonitrile, Example 12-4 (6 mg, 14% yield) as a white solid. LCMS [M+1]$^+$=440.0; $^1$H NMR (400 MHz, DMSO-d$_6$) δ=12.87 (s, 1H), 9.69 (s, 1H), 9.27 (s, 1H), 8.59 (d, J=1.6 Hz, 1H), 8.37 (br d, J=2.0 Hz, 2H), 8.40-8.24 (m, 4H), 8.11 (d, J=8.4 Hz, 1H), 7.89 (d, J=8.0 Hz, 1H), 7.85-7.78 (m, 1H), 7.45 (dd, J=1.6, 8.0 Hz, 1H), 4.39-4.26 (m, 2H), 3.78 (s, 3H).

Example 12-5

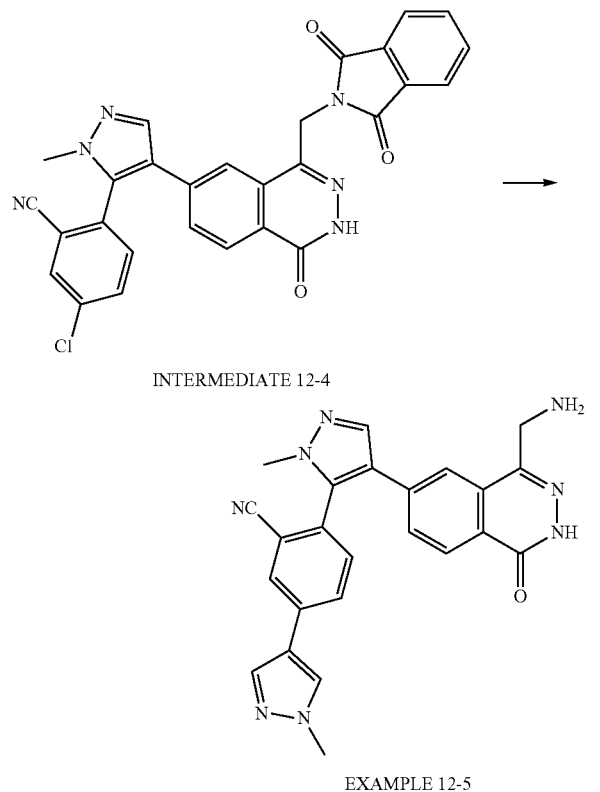

INTERMEDIATE 12-4

EXAMPLE 12-5

Example 12-5, 2-(4-(4-(aminomethyl)-1-oxo-1,2-dihydrophthalazin-6-yl)-1-methyl-1H-pyrazol-5-yl)-5-(1-methyl-1H-pyrazol-4-yl)benzonitrile was prepared from 5-chloro-2-[4-[4-[(1,3-dioxoisoindolin-2-yl)methyl]-1-oxo-2H-phthalazin-6-yl]-2-methyl-pyrazol-3-yl]benzonitrile, Intermediate 12-4 and 1-methyl-4-(4,4,5,5-tetramethyl-1,3,2-dioxaborolan-2-yl)pyrazole following the procedure described for the preparation of Example 12-4, steps 2 and 3 as a white solid (6 mg, 13 µmol, 25% yield). LCMS [M+1]$^+$=437.2. $^1$H NMR (400 MHz, CD$_3$OD) δ=8.24 (s, 1H), 8.19 (s, 1H), 8.16 (d, J=1.6 Hz, 1H), 8.12 (s, 1H), 8.09-8.04 (m, 1H), 8.01 (s, 1H), 7.72-7.64 (m, 3H), 3.96 (s, 3H), 3.88 (s, 2H), 3.83 (s, 3H).

Example 12-6

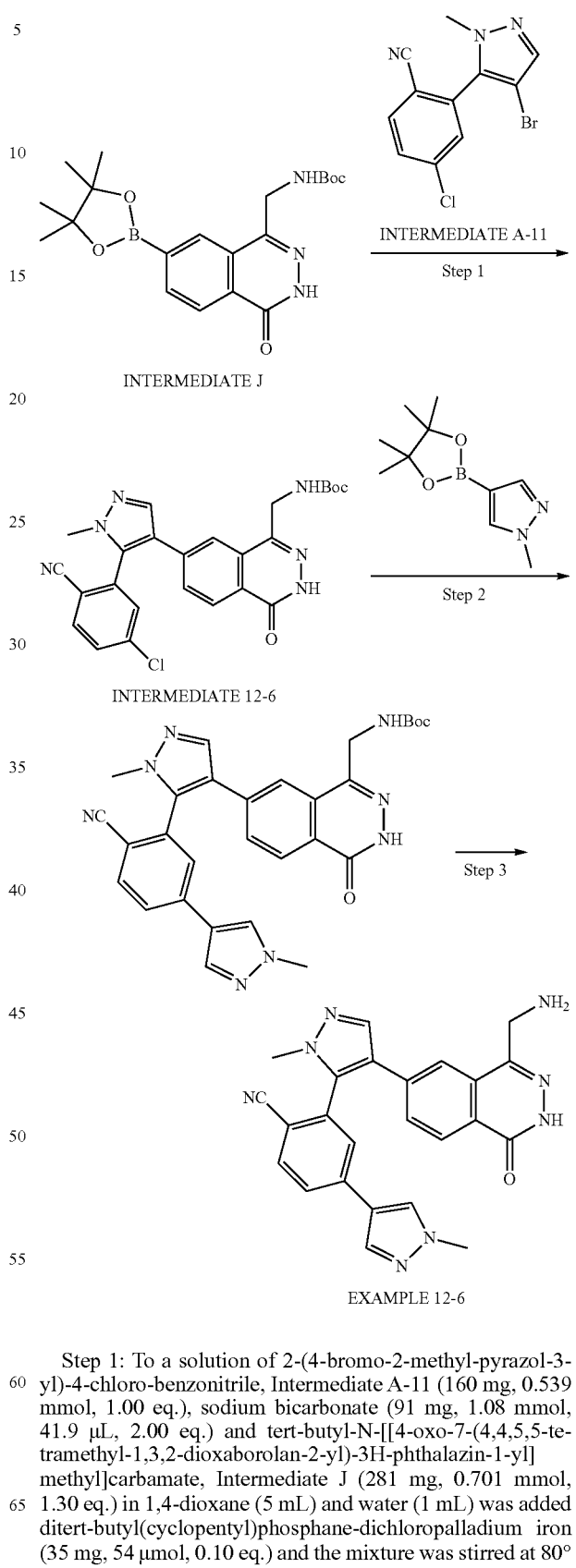

EXAMPLE 12-6

Step 1: To a solution of 2-(4-bromo-2-methyl-pyrazol-3-yl)-4-chloro-benzonitrile, Intermediate A-11 (160 mg, 0.539 mmol, 1.00 eq.), sodium bicarbonate (91 mg, 1.08 mmol, 41.9 µL, 2.00 eq.) and tert-butyl-N-[[4-oxo-7-(4,4,5,5-tetramethyl-1,3,2-dioxaborolan-2-yl)-3H-phthalazin-1-yl]methyl]carbamate, Intermediate J (281 mg, 0.701 mmol, 1.30 eq.) in 1,4-dioxane (5 mL) and water (1 mL) was added ditert-butyl(cyclopentyl)phosphane-dichloropalladium iron (35 mg, 54 µmol, 0.10 eq.) and the mixture was stirred at 80°

C. for 2 hours under nitrogen. After such time the reaction mixture was partitioned between ethyl acetate (10 mL) and water (10 mL). The organic phase was separated, washed with brine (10 mL), dried over anhydrous sodium sulfate, filtered and concentrated. The residue was purified by flash silica gel chromatography (50 to 100% petroleumether:ethylacetate gradient) to give tert-butyl N-[[7-[5-(5-chloro-2-cyano-phenyl)-1-methyl-pyrazol-4-yl]-4-oxo-3H-phthalazin-1-yl]methyl]carbamate, Intermediate 12-6 (160 mg, 0.313 mmol, 58% yield) as a gray solid. LCMS [M+1]$^+$=491.2.

Step 2: To a solution of tert-butyl N-[[7-[5-(5-chloro-2-cyano-phenyl)-1-methyl-pyrazol-4-yl]-4-oxo-3H-phthalazin-1-yl]methyl]carbamate (50 mg, 0.102 mmol, 1.00 eq.), potassium carbonate (42 mg, 0.305 mmol, 3.00 eq.) and 1-methyl-4-(4,4,5,5-tetramethyl-1,3,2-dioxaborolan-2-yl)pyrazole (42 mg, 0.204 mmol, 2.00 eq.) in 1,4-dioxane (1.0 mL) and water (0.1 mL) was added ditert-butyl(cyclopentyl)phosphane dichloropalladium iron (13 mg, 20.4 μmol, 0.20 eq.) and the mixture was stirred at 80° C. for 3 hours under nitrogen. After such time the reaction was cooled to 10° C. and the salt was removed by filtration and the filtrate concentrated. The residue was purified by prep-TLC (SiO$_2$, petroleum ether:ethyl acetate 1:1.5) to give tert-butyl N-[[7-[5-[2-cyano-5-(1-methylpyrazol-4-yl)phenyl]-1-methyl-pyrazol-4-yl]-4-oxo-3H-phthalazin-1-yl]methyl]carbamate (40 mg, 64 μmol, 63% yield) as a white solid. LCMS [M+1]$^+$=537.3.

Step 3: To a solution of tert-butyl N-[[7-[5-[2-cyano-5-(1-methylpyrazol-4-yl)phenyl]-1-methyl-pyrazol-4-yl]-4-oxo-3H-phthalazin-1-yl]methyl]carbamate (37 mg, 63 μmol, 1.00 eq.) in methanol (2 mL) was added a solution of hydrogen chloride in 1,4-dioxane (4 M, 2 mL) and the mixture was stirred at 25° C. for 2 hours. After such time the reaction mixture was concentrated and the residue was purified by prep-HPLC (Phenomenex Synergi C18 150×30 mm×4 μm; mobile phase: [water (0.05% HCl)-ACN]; B %: 15%-35%, 9 min) to give 2-[4-[4-(aminomethyl)-1-oxo-2H-phthalazin-6-yl]-2-methyl-pyrazol-3-yl]-4-(1-methylpyrazol-4-yl)benzonitrile, Example 12-6 (7 mg, 16 μmol, 23% yield) as a white solid. LCMS [M+1]$^+$=437.2; $^1$H NMR (400 MHz, CD$_3$OD) δ=8.26 (s, 1H), 8.21-8.13 (m, 2H), 8.09-8.04 (m, 1H), 8.01-7.94 (m, 2H), 7.92-7.87 (m, 1H), 7.74 (d, J=1.2 Hz, 1H), 7.58-7.55 (m, 1H), 4.38 (s, 2H), 3.96 (s, 3H), 3.85 (s, 3H).

Example 12-7

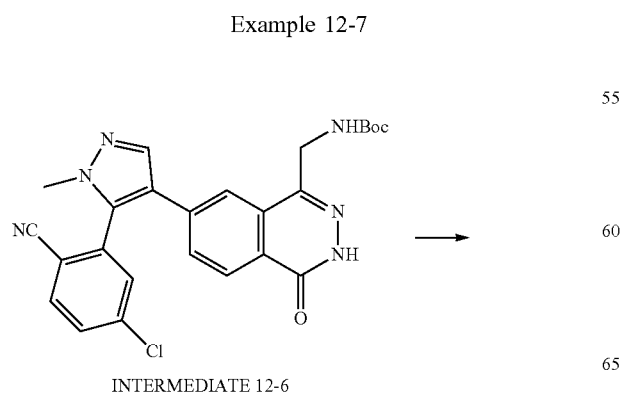

INTERMEDIATE 12-6

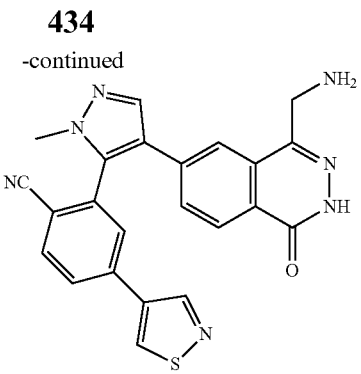

EXAMPLE 12-7

Example 12-7, 2-(4-(4-(aminomethyl)-1-oxo-1,2-dihydrophthalazin-6-yl)-1-methyl-1H-pyrazol-5-yl)-4-(isothiazol-4-yl)benzonitrile was prepared from tert-butyl N-[[7-[5-(5-chloro-2-cyano-phenyl)-1-methyl-pyrazol-4-yl]-4-oxo-3H-phthalazin-1-yl]methyl]carbamate, Intermediate 12-6 and 4-(4,4,5,5-tetramethyl-1,3,2-dioxaborolan-2-yl)isothiazole following the procedure described for the preparation of Example 12-6, steps 2 and 3 as a white solid (10 mg, 23 μmol, 21% yield). LCMS [M+1]$^+$=440.2. $^1$H NMR (400 MHz, CD$_3$OD) δ=9.43 (s, 1H), 9.05 (s, 1H), 8.21-8.14 (m, 4H), 8.00 (d, J=8.0 Hz, 1H), 7.77 (d, J=1.2 Hz, 1H), 7.58-7.56 (m, 1H), 4.46-4.33 (m, 2H), 3.87 (s, 3H).

Example 12-8

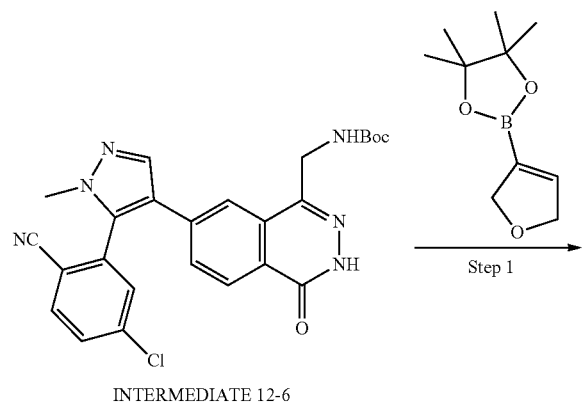

INTERMEDIATE 12-6

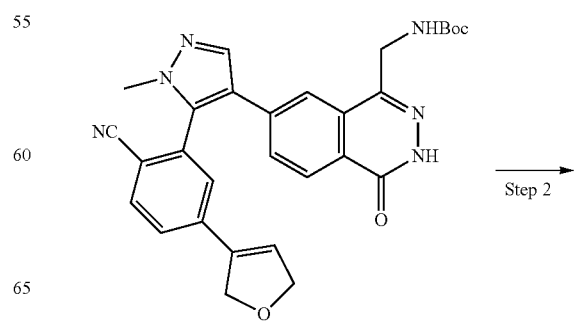

Step 2

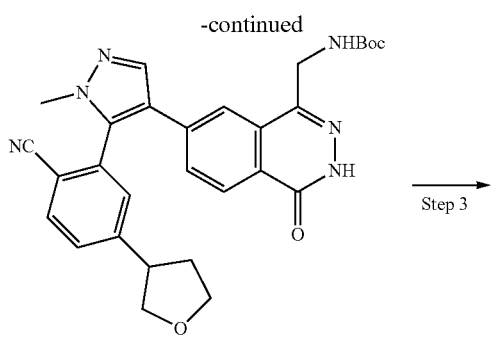

EXAMPLE 12-8

Step 1: To a solution of tert-butyl N-[[7-[5-(5-chloro-2-cyano-phenyl)-1-methyl-pyrazol-4-yl]-4-oxo-3H-phthalazin-1-yl]methyl]carbamate, Intermediate 12-6 (100 mg, 0.204 mmol, 1.00 eq.), potassium carbonate (56 mg, 0.407 mmol, 2.00 eq.) and 2-(2,5-dihydrofuran-3-yl)-4,4,5,5-tetramethyl-1,3,2-dioxaborolane (80 mg, 0.407 mmol, 2.00 eq.) in 1,4-dioxane (5 mL) and water (1 mL) was added ditert-butyl(cyclopentyl)phosphanedichloropalladium iron (26.6 mg, 40.7 µmol, 0.20 eq.). The mixture was stirred at 90° C. for 16 hours then cooled to 10° C. and the salts was removed by filtration. The filtrate was diluted with water (10 mL) and extracted with ethyl acetate (10 mL×2) and the combined organic layers were washed with brine (20 mL), dried over anhydrous magnesium sulfate, filtered and concentrated. The residue was purified by prep-TLC (SiO$_2$, dichloromethane:methanol 20:1) to give tert-butyl N-[[7-[5-[2-cyano-5-(2,5-dihydrofuran-3-yl)phenyl]-1-methyl-pyrazol-4-yl]-4-oxo-3H-phthalazin-1-yl]methyl]carbamate (0.08 g, 0.114 mmol, 56% yield) as a gray solid. LCMS [M+1]$^+$=525.3.

Step 2: To a solution of tert-butyl N-[[7-[5-[2-cyano-5-(2,5-dihydrofuran-3-yl)phenyl]-1-methyl-pyrazol-4-yl]-4-oxo-3H-phthalazin-1-yl]methyl]carbamate (80 mg, 0.114 mmol, 1.00 eq.) in methanol (20 mL) was added palladium on activated carbon (6.6 mg, 11 µmol, 10% Pd, 0.10 eq.) and the mixture was vigorously stirred at 25° C. for 2 hours. After such time the mixture was filtered and the filtrated was concentrated to give tert-butyl N-[[7-[5-(2-cyano-5-THF-3-yl-phenyl)-1-methyl-pyrazol-4-yl]-4-oxo-3H-phthalazin-1-yl]methyl]carbamate (75 mg, 105 µmol, 92% yield) as a white solid which used directly for the next step without further purification. LCMS [M+1]$^+$=527.3

Step 3: To a solution of tert-butyl N-[[7-[5-(2-cyano-5-THF-3-yl-phenyl)-1-methyl-pyrazol-4-yl]-4-oxo-3H-phthalazin-1-yl]methyl]carbamate (74.0 mg, 105 µmol, 1.00 eq.) in dichloromethane (2 mL) was added a solution of hydrogen chloride in 1,4-dioxane (4.00 M, 0.26 mL, 10.0 eq.). The mixture was stirred at 25° C. for 1 hr then concentrated under reduced pressure and the residue purified by prep-HPLC (Welch Xtimate C18 150×25 mm×5 µm; mobile phase: [water (10 mM NH$_4$HCO$_3$)-ACN]; B %: 12%-42%, 10 min) to give 2-[4-[4-(aminomethyl)-1-oxo-2H-phthalazin-6-yl]-2-methyl-pyrazol-3-yl]-4-THF-3-yl-benzonitrile, Example 12-8 (6 mg, 13 µmol, 12% yield) as a white solid. LCMS [M+1]$^+$=427.3; $^1$H NMR (400 MHz, DMSO) δ=12.37 (s, 1H), 8.17 (d, J=0.8 Hz, 1H), 8.09 (d, J=8.4 Hz, 1H), 7.97 (d, J=8.0 Hz, 1H), 7.70-7.64 (m, 3H), 7.47 (d, J=1.2 Hz, 1H), 4.05-3.84 (m, 3H), 3.79-3.72 (m, 1H), 3.70 (s, 3H), 3.65-3.48 (m, 5H), 2.39-2.26 (m, 1H), 2.01-1.87 (m, 1H).

Example 12-9

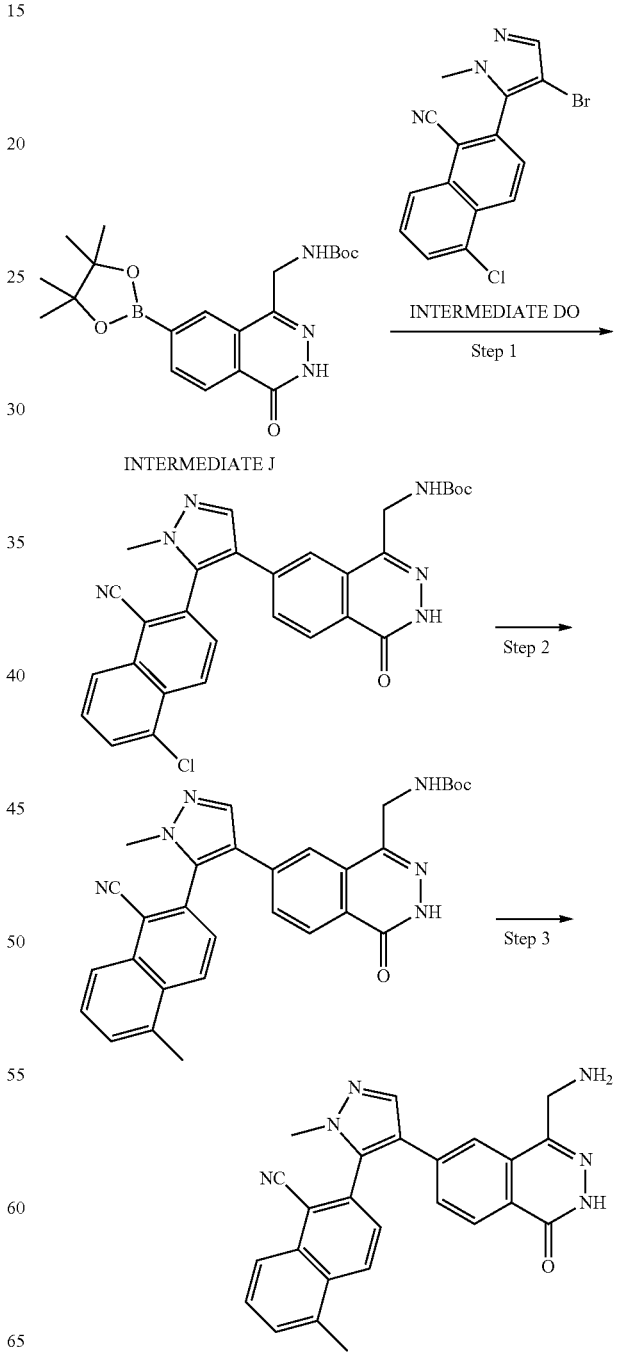

437

Step 1: A mixture of 2-(4-bromo-1-methyl-1H-pyrazol-5-yl)-5-chloro-1-naphthonitrile, Intermediate DO, (130 mg, 0.375 mmol, 1.00 eq.), tert-butyl N-[[4-oxo-7-(4,4,5,5-tetramethyl-1,3,2-dioxaborolan-2-yl)-3H-phthalazin-1-yl]methyl]carbamate, Intermediate J (181 mg, 0.45 mmol, 1.20 eq.), Pd(dtbpf)Cl$_2$ (24 mg, 38 µmol, 0.10 eq.), sodium carbonate (80 mg, 0.75 mmol, 2.00 eq.) in the mixed solvents dioxane (5 mL) and water (1 mL) was degassed with nitrogen and stirred at 80° C. for 1 hour under nitrogen atmosphere. After such time the mixture was concentrated and the residue was purified by prep-TLC (SiO$_2$, dichloromethane:methyl alcohol 20:1) to give tert-butyl N-[[7-[5-(5-chloro-1-cyano-2-naphthyl)-1-methyl-pyrazol-4-yl]-4-oxo-3H-phthalazin-1-yl]methyl]carbamate (120 mg, 0.222 mmol, 59% yield) as a white solid. LCMS [M+1]$^+$=541.1.

Step 2: A mixture of tert-butyl N-[[7-[5-(5-chloro-1-cyano-2-naphthyl)-1-methyl-pyrazol-4-yl]-4-oxo-3H-phthalazin-1-yl]methyl]carbamate (70 mg, 129 µmol, 1.00 eq.), methylboronic acid (23 mg, 0.388 mmol, 3.00 eq.), Pd(dtbpf)Cl$_2$ (8.4 mg, 12 µmol, 0.10 eq.), potassium carbonate (36 mg, 259 µmol, 2.00 eq.) in dioxane (2 mL) was degassed and purged with nitrogen and stirred at 100° C. for 1 hour under nitrogen atmosphere. The mixture was concentrated and purified by prep-TLC (SiO$_2$, dichloromethane:methyl alcohol 20:1) to give tert-butyl N-[[7-[5-(1-cyano-5-methyl-2-naphthyl)-1-methyl-pyrazol-4-yl]-4-oxo-3H-phthalazin-1-yl]methyl]carbamate (50 mg, 96 µmol, 74% yield) as a white solid. LCMS [M+1]$^+$=521.5.

Step 3: To a solution of tert-butyl N-[[7-[5-(1-cyano-5-methyl-2-naphthyl)-1-methyl-pyrazol-4-yl]-4-oxo-3H-phthalazin-1-yl]methyl]carbamate (50 mg, 96 µmol, 1.00 eq.) in dichloromethane (1.5 mL) was added trifluoroacetic acid (417 µL) and the mixture stirred at 25° C. for 0.5 hour. After such time the mixture was concentrated and the residue was purified by prep-HPLC (Phenomenex Luna C18 75×30 mm×3 µm; mobile phase: [water (0.05% HCl)-ACN]; B %: 17%-37%, 7 min) to give 2-(4-(4-(aminomethyl)-1-oxo-1,2-dihydrophthalazin-6-yl)-1-methyl-1H-pyrazol-5-yl)-5-methyl-1-naphthonitrile, Example 12-9 (21 mg, 45 µmol, 47% yield, HCl) as a white solid. LCMS [M+1]$^+$=421.1; $^1$H NMR (400 MHz, DMSO-d$_6$) δ=12.83 (s, 1H), 8.59 (dd, J=0.8, 8.8 Hz, 1H), 8.45 (br s, 3H), 8.35 (s, 1H), 8.05-7.96 (m, 2H), 7.92 (d, J=1.6 Hz, 1H), 7.85 (d, J=8.8 Hz, 1H), 7.81-7.74 (m, 1H), 7.68 (d, J=7.2 Hz, 1H), 7.31 (dd, J=1.6, 8.4 Hz, 1H), 4.44-4.17 (m, 2H), 3.77 (s, 3H), 2.79 (s, 3H).

Example 12-10

438

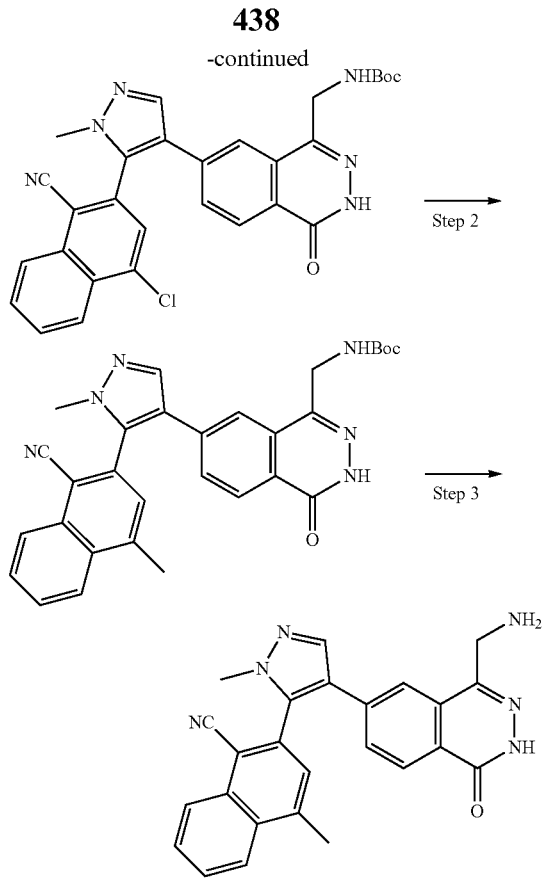

Example 12-10, 2-(4-(4-(aminomethyl)-1-oxo-1,2-dihydrophthalazin-6-yl)-1-methyl-1H-pyrazol-5-yl)-4-methyl-1-naphthonitrile was prepared from Intermediate J (346 mg, 0.863 mmol, 1.30 eq.), and Intermediate DZ (230 mg, 0.664 umol, 1.00 eq.), according to the procedure described for the synthesis of Example 12-9 as a yellow solid (20 mg, 0.042 mmol, final step 55% yield). LCMS [M+1]$^+$=421.1; $^1$H NMR (400 MHz, DMSO-d$_6$) δ=12.83 (s, 1H), 8.55-8.43 (m, 3H), 8.36 (s, 1H), 8.36-8.32 (m, 1H), 8.18-8.12 (m, 1H), 8.01 (d, J=8.4 Hz, 1H), 7.93-7.86 (m, 3H), 7.75 (d, J=0.8 Hz, 1H), 7.37 (dd, J=1.6, 8.4 Hz, 1H), 4.45-4.11 (m, 2H), 3.78 (s, 3H), 2.86 (s, 3H).

Example 12-11

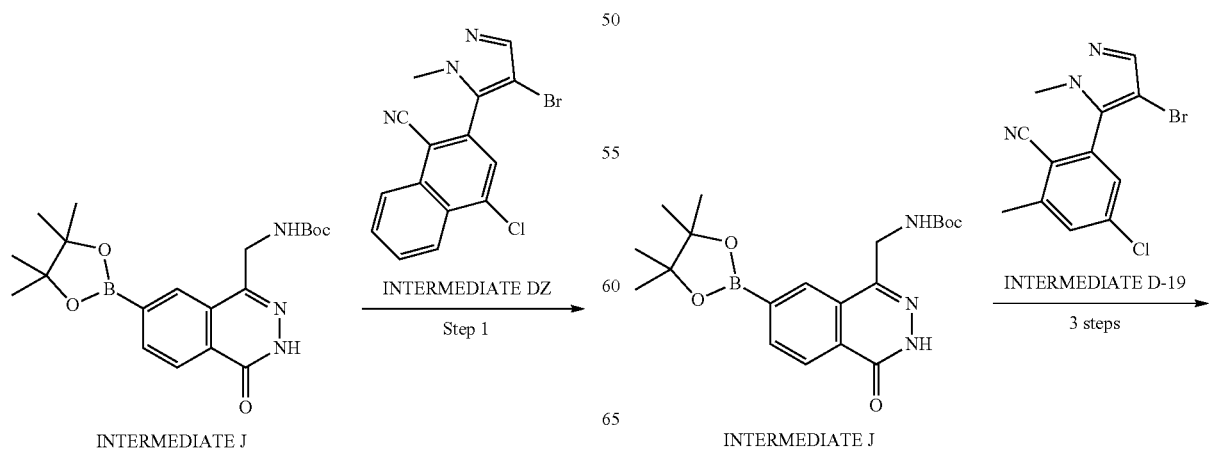

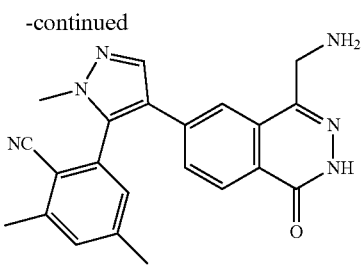

2-(4-(4-(aminomethyl)-1-oxo-1,2-dihydrophthalazin-6-yl)-1-methyl-1H-pyrazol-5-yl)-4,6-dimethylbenzonitrile, Example 12-11 was prepared using the same method as Example 12-9 starting from Intermediate DO for Intermediate D-19, as a white solid (7.6 mg, 0.015 mmol, 37% yield). LCMS [M+1]$^+$=385.2; $^1$H NMR (400 MHz, DMSO-d$_6$) δ=12.89-12.85 (m, 1H), 8.36 (br s, 3H), 8.28 (s, 1H), 8.10 (d, J=8.4 Hz, 1H), 7.69 (d, J=1.6 Hz, 1H), 7.52 (s, 1H), 7.49 (dd, J=1.6, 8.4 Hz, 1H), 7.41 (s, 1H), 4.35-4.11 (m, 2H), 3.71 (s, 3H), 2.52-2.51 (m, 3H), 2.44 (s, 3H).

Example 12-12

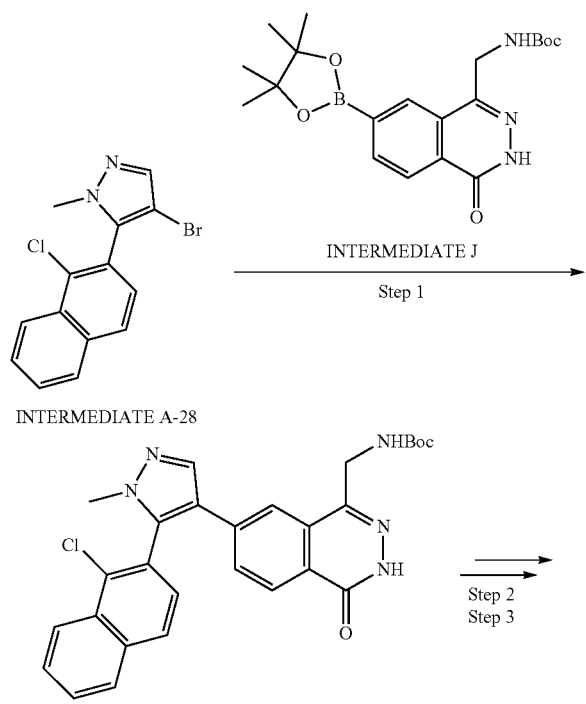

3H-phthalazin-1-yl]methyl]carbamate (1.50 g, 3.73 mmol, 1.00 eq.), sodium bicarbonate (627 mg, 7.46 mmol, 2.00 eq.) and ditert-butyl(cyclopentyl)phosphane-dichloropalladium; iron (243 mg, 0.373 mmol, 0.10 eq.) in dioxane (10 mL) and water (2 mL) was degassed and purged with nitrogen 3 times, and stirred at 80° C. for 0.5 hour. The reaction mixture was then filtered and concentrated and the residue was diluted with water (30 mL) and extracted with ethyl acetate (30 mL×2), dried over anhydrous sodium sulfate, filtered and concentrated and the residue was purified by column chromatography (SiO$_2$, petroleumether:ethylacetate=10:1 to 0:1) to give tert-butyl N-[[7-[5-(1-chloro-2-naphthyl)-1-methyl-pyrazol-4-yl]-4-oxo-3H-phthalazin-1-yl]methyl]carbamate (1.20 g, 2.33 mmol, 62% yield) as a white solid. LCMS [M+1]$^+$=516.1; $^1$H NMR (400 MHz, CDCl$_3$) δ=10.08 (s, 1H), 8.41 (d, J=8.0 Hz, 1H), 8.18-8.10 (m, 1H), 8.04 (s, 1H), 7.96 (dd, J=8.4, 16.0 Hz, 2H), 7.84-7.77 (m, 1H), 7.76-7.66 (m, 2H), 7.47-7.39 (m, 1H), 7.36 (d, J=8.8 Hz, 1H), 5.27-5.15 (m, 1H), 4.46-4.38 (m, 1H), 4.33-4.26 (m, 1H), 3.77 (s, 3H), 1.49 (s, 9H).

Step 2: To a solution of tert-butyl N-[[7-[5-(1-chloro-2-naphthyl)-1-methyl-pyrazol-4-yl]-4-oxo-3H-phthalazin-1-yl]methyl]carbamate (100 mg, 0.194 mmol, 1.00 eq.) in toluene (2 mL) was added potassium phosphate (123 mg, 0.581 mmol, 3.00 eq.), 2,4,6-trimethyl-1,3,5,2,4,6-trioxatriborinane (292 mg, 1.16 mmol, 50% purity, 6.00 eq.) and SPhos Pd G2 (15 mg, 0.194 mmol, 0.10 eq.) and the mixture was stirred at 100° C. for 10 hours under nitrogen atmosphere. After such time the mixture was filtered, diluted with water (5 mL) and extracted with ethyl acetate (5 mL) and the organic layer dried over anhydrous sodium sulfate, filtered and concentrated under reduced pressure to give tert-butyl N-[[7-[1-methyl-5-(1-methyl-2-naphthyl)pyrazol-4-yl]-4-oxo-3H-phthalazin-1-yl]methyl]carbamate (150 mg, crude) as a yellow solid. LCMS [M+1]$^+$=496.5.

Step 3: To a solution of tert-butyl N-[[7-[1-methyl-5-(1-methyl-2-naphthyl)pyrazol-4-yl]-4-oxo-3H-phthalazin-1-yl]methyl]carbamate (150 mg, 0.303 mmol, 1.00 eq.) in the dichloromethane (1 mL) was added trifluoroacetic acid (462 mg, 4.05 mmol, 0.30 mL, 13.4 eq.). The mixture was then stirred at 25° C. for 0.5 hour then concentrated and the residue purified by prep-HPLC (Phenomenex Synergi C18 150×30 mm×4 µm; mobile phase: [water (0.1% TFA)-ACN]; B %: 23%-43%, 10 min) to give 4-(aminomethyl)-6-[1-methyl-5-(1-methyl-2-naphthyl)pyrazol-4-yl]-2H-phthalazin-1-one (16 mg, 0.038. mmol, 13% yield) as an off-white solid. LCMS [M+1]$^+$=396.1; $^1$H NMR (500 MHz, MeOD) δ=8.23-8.21 (m, 1H), 8.19-8.13 (m, 2H), 8.03-7.96 (m, 2H), 7.73-7.69 (m, 1H), 7.68-7.64 (m, 2H), 7.60-7.58 (m, 1H), 7.41 (d, J=8.5 Hz, 1H), 4.14 (d, J=13.5 Hz, 1H), 3.98 (d, J=13.0 Hz, 1H), 3.70 (s, 3H), 2.43 (s, 3H).

Example 12-13

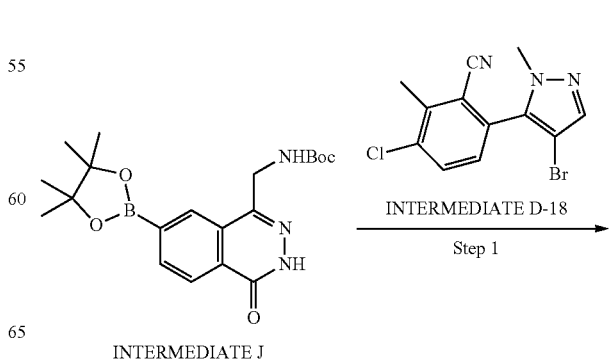

Step 1: A mixture of 4-bromo-5-(1-chloro-2-naphthyl)-1-methyl-pyrazole (1.20 g, 3.73 mmol, 1.00 eq.), tert-butyl N-[[4-oxo-7-(4,4,5,5-tetramethyl-1,3,2-dioxaborolan-2-yl)-

441
-continued

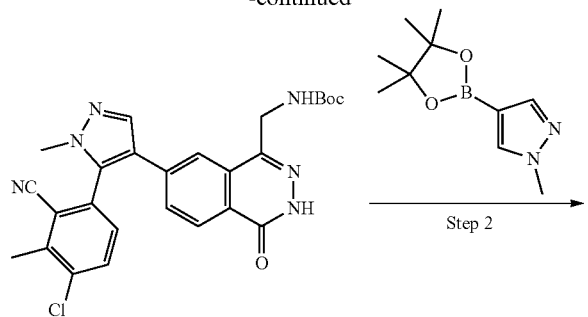

Step 2 →

442
Example 12-14

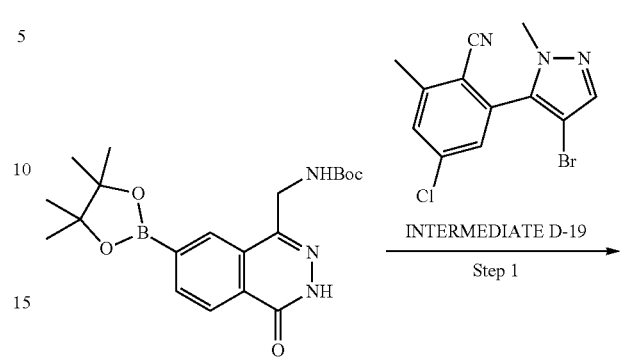

INTERMEDIATE J

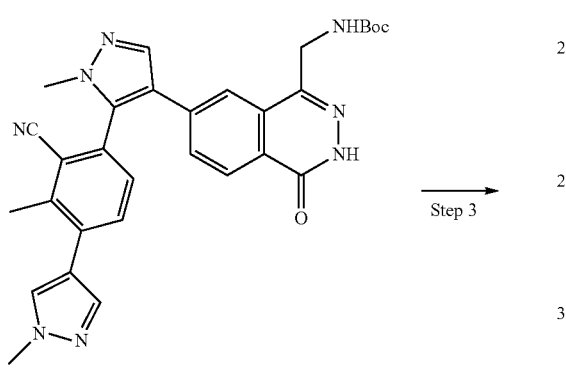

Step 3 →

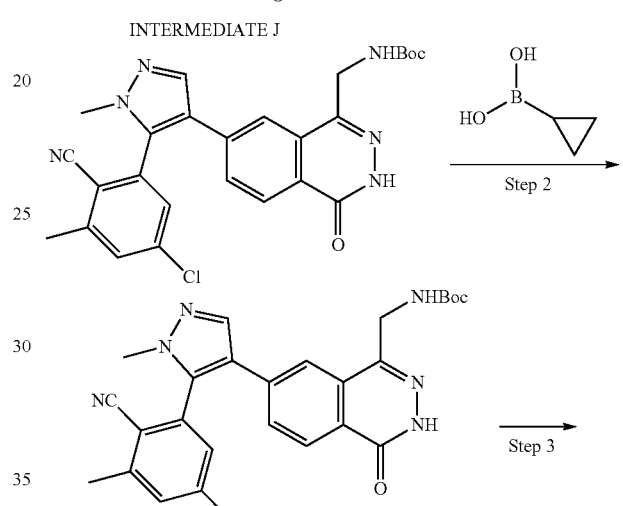

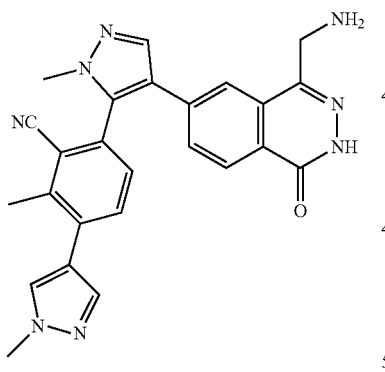

EXAMPLE 12-13

Example 12-13, 6-(4-(4-(aminomethyl)-1-oxo-1,2-dihydrophthalazin-6-yl)-1-methyl-1H-pyrazol-5-yl)-2-methyl-3-(1-methyl-1H-pyrazol-4-yl)benzonitrile was prepared as a white solid (10 mg, 0.018 mmol, 33% yield), starting with Intermediate J and Intermediate D-18 following the same procedure as described for Example 12-6. LCMS [M+1]$^+$=451.2; $^1$H NMR (500 MHz, DMSO-d$_6$) δ=12.86 (s, 1H), 8.33 (br s, 3H), 8.27 (s, 1H), 8.16 (s, 1H), 8.10 (d, J=8.5 Hz, 1H), 7.88 (d, J=8.5 Hz, 1H), 7.86 (d, J=0.5 Hz, 1H), 7.78 (d, J=1.5 Hz, 1H), 7.58 (d, J=8.5 Hz, 1H), 7.48 (dd, J=1.5, 8.5 Hz, 1H), 4.31 (br t, J=6.0 Hz, 2H), 3.93 (s, 3H), 3.74 (s, 3H), 2.62 (s, 3H).

Step 1: A mixture of Intermediate J (350 mg, 0.872 mmol, 1.00 eq.), 2-(4-bromo-2-methyl-pyrazol-3-yl)-4-chloro-6-methyl-benzonitrile, intermediate D-19 (271 mg, 0.872 mmol, 1.00 eq.), sodium bicarbonate (220 mg, 2.62 mmol, 3.00 eq.) and ditert-butyl(cyclopentyl)phosphane; dichloropalladium; iron (57 mg, 0.087 mmol, 0.10 eq.) in dioxane (3 mL) and water (0.6 mL) was degassed and purged with nitrogen 3 times and stirred at 80° C. for 1 hour. The mixture was then concentrated and the residue purified by prep-TLC (SiO$_2$, dichloromethane:methyl alcohol=10:1) to give tert-butyl N-[[7-[5-(5-chloro-2-cyano-3-methyl-phenyl)-1-methyl-pyrazol-4-yl]-4-oxo-3H-phthalazin-1-yl]methyl] carbamate (135 mg, 0.174 mmol, 20% yield) as a yellow solid. LCMS [M+1]$^+$=505.2.

Step 2: A mixture of tert-butyl N-[[7-[5-(5-chloro-2-cyano-3-methyl-phenyl)-1-methyl-pyrazol-4-yl]-4-oxo-3H- phthalazin-1-yl]methyl]carbamate (35 mg, 0.069 mmol, 1.00 eq.), cyclopropylboronic acid (24 mg, 0.277 mmol, 4.00 eq.), tricyclohexyl-phosphine (2 mg, 0.007 mmol, 2.3 µL, 0.10 eq.), Pd₂(dba)₃ (6.4 mg, 0.007 mmol, 0.10 eq.) and potassium phosphate (44 mg, 0.208 mmol, 3.00 eq.) in dioxane (2 mL) was degassed and purged with nitrogen 3 times, and stirred at 100° C. for 12 hours. The mixture was then concentrated and the residue purified by prep-TLC (SiO₂, dichloromethane:methyl alcohol=10:1) to give tert-butyl N-[[7-[5-(2-cyano-5-cyclopropyl-3-methyl-phenyl)-1-methyl-pyrazol-4-yl]-4-oxo-3H-phthalazin-1-yl]methyl]carbamate (23 mg, 0.038 mmol, 54% yield) as a yellow solid. LCMS [M+1]⁺=511.3.

Step 3: A mixture of tert-butyl N-[[7-[5-(2-cyano-5-cyclopropyl-3-methyl-phenyl)-1-methyl-pyrazol-4-yl]-4-oxo-3H-phthalazin-1-yl]methyl]carbamate (18 mg, 0.035 mmol, 1.00 eq.) in trifluoroacetic acid (0.5 mL) and dichloromethane (1.5 mL) was purged with nitrogen 3 times, and stirred at 15° C. for 1 hour. The mixture was then concentrated and the residue purified by prep-HPLC (Phenomenex luna C18 150×25 mm×10 µm; mobile phase: [water (0.1% trifluoroacetic acid)-ACN]; B %: 15%-45%, 10 min) to give 2-[4-[4-(aminomethyl)-1-oxo-2H-phthalazin-6-yl]-2-methyl-pyrazol-3-yl]-4-cyclopropyl-6-methyl-benzonitrile (11 mg, 0.021 mmol, 61% yield) as a white solid. LCMS [M+1]⁺=411.2; ¹H NMR (400 MHz, DMSO-d₆) δ=12.88 (s, 1H), 8.37 (br s, 3H), 8.28 (s, 1H), 8.10 (d, J=8.4 Hz, 1H), 7.73 (d, J=1.6 Hz, 1H), 7.46 (dd, J=1.6, 8.4 Hz, 1H), 7.37 (s, 1H), 7.28 (d, J=1.6 Hz, 1H), 4.29 (br s, 2H), 3.71 (s, 3H), 3.34-3.34 (m, 3H), 2.10-1.98 (m, 1H), 1.10 (dd, J=2.8, 8.4 Hz, 2H), 0.95-0.80 (m, 2H); ¹H NMR (400 MHz, CD₃OD) δ=8.20 (d, J=8.4 Hz, 1H), 8.13 (s, 1H), 7.75 (d, J=1.6 Hz, 1H), 7.54-7.47 (m, 1H), 7.33 (s, 1H), 7.22 (d, J=1.6 Hz, 1H), 4.41 (s, 2H), 3.79 (s, 3H), 2.53 (s, 3H), 2.09-2.01 (m, 1H), 1.18-1.11 (m, 2H), 0.92-0.79 (m, 2H).

Example 12-15

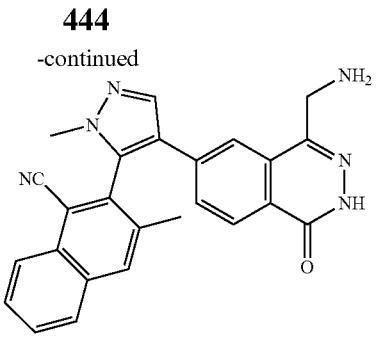

EXAMPLE 12-15

Example 12-15, 2-[4-[4-(aminomethyl)-1-oxo-2H-phthalazin-6-yl]-2-methyl-pyrazol-3-yl]-3-methyl-naphthalene-1-carbonitrile was prepared as a yellow gum starting from Intermediate F-11 and Intermediate J according to the same method as described for Example 12-9 (2.6 mg, 0.006 mmol, 3% yield over 3 steps). LCMS [M+H]⁺=421.2; ¹H NMR (400 MHz, DMSO-d₆) δ=12.80 (s, 1H), 8.43 (d, J=8.0 Hz, 2H), 8.19-8.15 (m, 1H), 8.13-8.10 (m, 1H), 8.00 (d, J=8.4 Hz, 1H), 7.86 (s, 1H), 7.85-7.79 (m, 2H), 7.26 (d, J=8.4 Hz, 1H), 4.36-4.18 (m, 2H), 4.09 (s, 2H), 3.66 (s, 3H), 2.21 (s, 3H).

Example 12-16

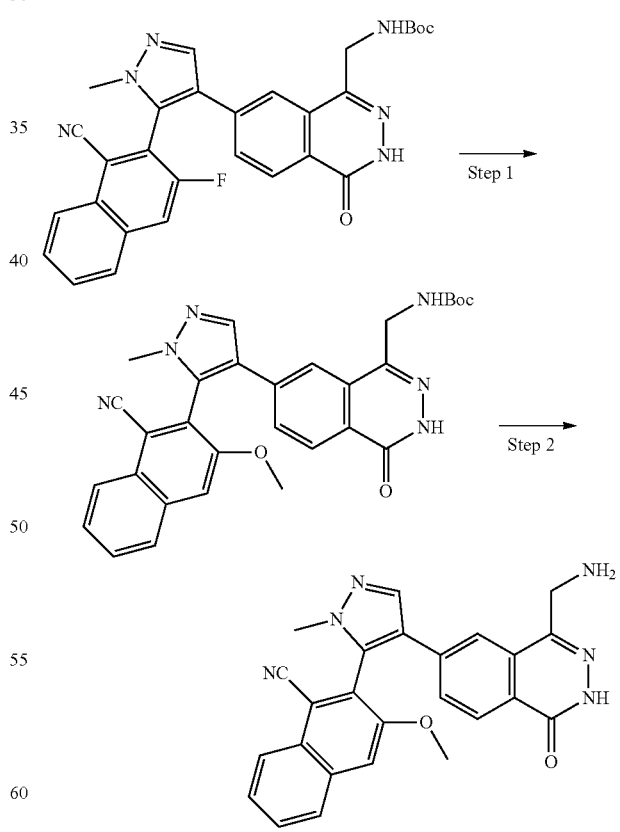

EXAMPLE 12-16

Step 1: To a solution of tert-butyl N-[[7-[5-(1-cyano-3-fluoro-2-naphthyl)-1-methyl-pyrazol-4-yl]-4-oxo-3H-phthalazin-1-yl]methyl]carbamate (100 mg, 0.19 mmol, 1.00 eq.) in methyl alcohol (3 mL) was added sodium methoxide (309 mg, 5.72 mmol, 30.0 eq.) and the mixture was stirred at 110° C. for 5 hours. After such time the mixture was diluted with ethyl acetate (20 mL) and washed with brine (20 mL×3), dried over anhydrous sodium sulfate, filtered, concentrated and the residue was purified by prep-TLC (SiO$_2$, dichloromethane:methyl alcohol=5%) to give tert-butyl N-[[7-[5-(1-cyano-3-methoxy-2-naphthyl)-1-methyl-pyrazol-4-yl]-4-oxo-3H-phthalazin-1-yl]methyl]carbamate (30 mg, 0.056 mmol, 29% yield) as a yellow solid. LCMS [M+1]$^+$=537.2.

Step 2: To a solution of tert-butyl N-[[7-[5-(1-cyano-3-methoxy-2-naphthyl)-1-methyl-pyrazol-4-yl]-4-oxo-3H-phthalazin-1-yl]methyl]carbamate (30 mg, 0.056 mmol, 1.00 eq.) in dichloromethane (1.5 mL) was added trifluoroacetic acid (0.5 mL) and the mixture was stirred at 25° C. for 0.5 hour. The mixture was then concentrated and the residue was purified by prep-HPLC, purification method 4-6 to give 2-[4-[4-(aminomethyl)-1-oxo-2H-phthalazin-6-yl]-2-methyl-pyrazol-3-yl]-3-methoxy-naphthalene-1-carbonitrile (8.33 mg, 0.017 mmol, 31% yield, HCl) as a yellow solid. LCMS [M+1]$^+$=437.2; $^1$H NMR (400 MHz, DMSO-d$_6$) δ=12.81 (s, 1H), 8.51 (br s, 3H), 8.36 (s, 1H), 8.23-8.10 (m, 2H), 8.00 (br t, J=8.0 Hz, 2H), 7.85 (s, 1H), 7.81-7.61 (m, 2H), 7.33 (br d, J=8.4 Hz, 1H), 4.41-4.14 (m, 2H), 3.97 (s, 3H), 3.68 (s, 3H).

Example 12-17

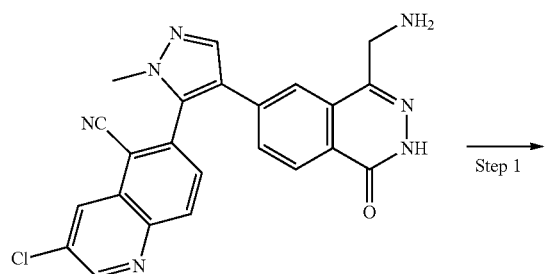

Example 4-225

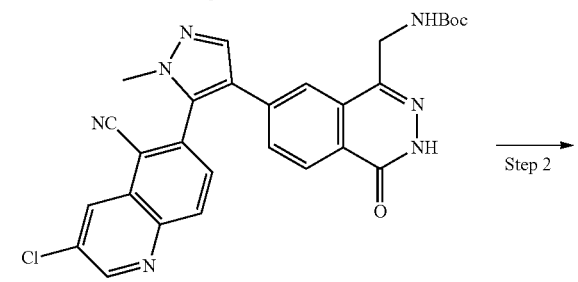

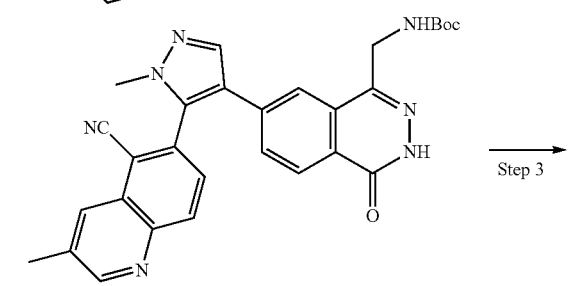

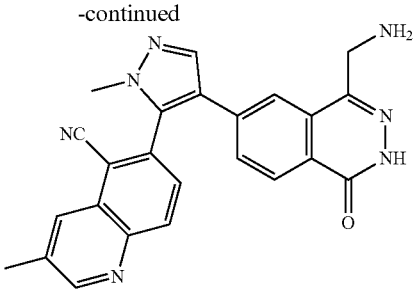

Example 12-17

Step 1: To a solution of Example 4-225, 6-[4-[4-(aminomethyl)-1-oxo-2H-phthalazin-6-yl]-2-methyl-pyrazol-3-yl]-3-chloro-quinoline-5-carbonitrile (150 mg, 0.34 mmol, 1.00 eq.) in dichloromethane (10 mL) was added diisopropylethylamine (1.02 mmol, 0.18 mL, 3.00 eq.) and di-tert-butyl dicarbonate (111 mg, 0.51 mmol, 1.50 eq.) and the mixture was stirred at 25° C. for 2 hours. The reaction mixture was then diluted with water (50 mL), extracted with ethyl acetate (50 mL×3) and the combined organic layers were washed with brine (30 mL), dried over sodium sulfate, filtered, concentrated and the residue was purified by prep-TLC (SiO$_2$, petroleumether:ethylacetate 50%) to give tert-butyl N-[[7-[5-(3-chloro-5-cyano-6-quinolyl)-1-methyl-pyrazol-4-yl]-4-oxo-3H-phthalazin-1-yl] methyl]carbamate (130 mg, 0.24 mmol, 71% yield) as a yellow solid. LCMS [M+1]$^+$=542.1.

Step 2: To a solution of tert-butyl N-[[7-[5-(3-chloro-5-cyano-6-quinolyl)-1-methyl-pyrazol-4-yl]-4-oxo-3H-phthalazin-1-yl]methyl]carbamate (120 mg, 0.22 mmol, 1.00 eq.) in dioxane (5 mL) was added potassium carbonate (92 mg, 0.66 mmol, 3.00 eq.), ditert-butyl(cyclopentyl)phosphane; dichloropalladium-iron (14 mg, 0.022 mmol, 0.10 eq.) and methylboronic acid (66 mg, 1.11 mmol, 5.00 eq.). The mixture was stirred at 100° C. for 2 hours and then the reaction mixture was diluted with water (50 mL) and extracted with ethyl acetate (50 mL×3). The combined organic layers were washed with brine (30 mL), dried over sodium sulfate, filtered, concentrated and the residue purified by prep-TLC (SiO$_2$, ethyl acetate) to give tert-butyl N-[[7-[5-(5-cyano-3-methyl-6-quinolyl)-1-methyl-pyrazol-4-yl]-4-oxo-3H-phthalazin-1-yl]methyl]carbamate (56 mg, 0.107 mmol, 49% yield) as a yellow solid. LCMS [M+1]$^+$=522.3.

Step 3: To a solution of tert-butyl N-[[7-[5-(5-cyano-3-methyl-6-quinolyl)-1-methyl-pyrazol-4-yl]-4-oxo-3H-phthalazin-1-yl]methyl]carbamate (66 mg, 0.127 mmol, 1.00 eq.) in dichloromethane (1 mL) was added trifluoroacetic acid (0.3 mL) and the mixture was stirred at 25° C. for 0.5 hour. The reaction mixture was then concentrated and the residue purified by prep-HPLC (purification method 4-6) to give 6-[4-[4-(aminomethyl)-1-oxo-2H-phthalazin-6-yl]-2-methyl-pyrazol-3-yl]-3-methyl-quinoline-5-carbonitrile (14 mg, 0.030 mmol, 24% yield, HCl) as a yellow solid. LCMS [M+1]$^+$=422.1; $^1$H NMR (400 MHz, DMSO-d$_6$) δ=12.83 (s, 1H), 9.08 (d, J=2.0 Hz, 1H), 8.52 (br d, J=8.0 Hz, 4H), 8.37 (s, 1H), 8.33-8.30 (m, 1H), 8.01 (d, J=5.2 Hz, 1H), 7.99 (d, J=5.2 Hz, 1H), 7.90 (d, J=1.2 Hz, 1H), 7.34 (dd, J=1.6, 8.4 Hz, 1H), 4.33-4.23 (m, 2H), 3.79 (s, 3H), 2.61 (s, 3H).

Example 12-18

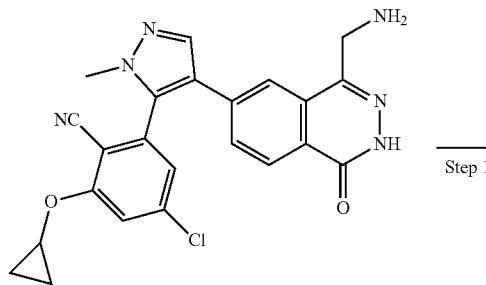

Example 4-118

Step 1 →

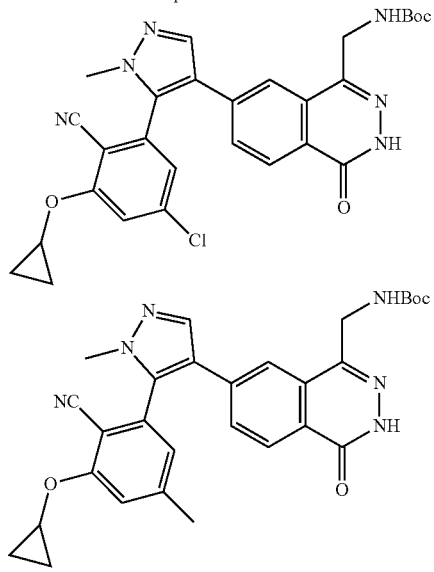

Step 2 →

(structure with NHBoc)

Step 3 →

Example 12-18

Example 12-18, 2-(4-(4-(aminomethyl)-1-oxo-1,2-dihydrophthalazin-6-yl)-1-methyl-1H-pyrazol-5-yl)-6-cyclopropoxy-4-methylbenzonitrile, was prepared as a white solid starting from Example 4-118 according to the same method as described for Example 12-17 (11 mg, 0.022 mmol, 65% yield, 3% yield over 3 steps). LCMS [M+1]$^+$=427.2; $^1$H NMR (400 MHz, DMSO-d$_6$) δ=12.85 (s, 1H), 8.54 (br s, 3H), 8.28 (s, 1H), 8.11 (d, J=8.4 Hz, 1H), 7.70 (d, J=1.2 Hz, 1H), 7.58 (s, 1H), 7.51 (dd, J=1.6, 8.4 Hz, 1H), 7.17 (s, 1H), 4.34-4.10 (m, 3H), 3.71 (s, 3H), 2.50 (br s, 3H), 0.94-0.85 (m, 2H), 0.84-0.71 (m, 2H); $^1$H NMR (400 MHz, MeOD) δ=8.20 (d, J=8.4 Hz, 1H), 8.12 (s, 1H), 7.78 (s, 1H), 7.56 (s, 1H), 7.52 (dd, J=1.6, 8.4 Hz, 1H), 7.13 (s, 1H), 4.54-4.35 (m, 2H), 4.05 (tt, J=2.8, 6.0 Hz, 1H), 3.79 (s, 3H), 2.55 (s, 3H), 0.92 (m, 2H), 0.86-0.73 (m, 2H).

Example 13-1

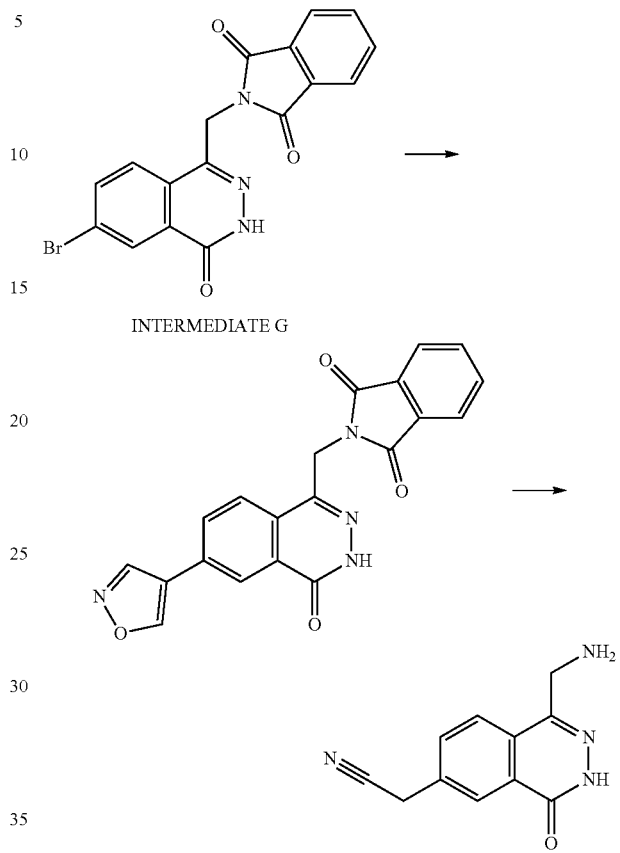

INTERMEDIATE G

EXAMPLE 13-1

Step 1: A mixture of Intermediate G (1.00 g, 2.60 mmol, 1.00 eq.), 4-(4,4,5,5-tetramethyl-1,3,2-dioxaborolan-2-yl)isoxazole (609 mg, 3.12 mmol, 1.20 eq.), potassium fluoride (1.00 M, 7.81 mL, 3.00 eq.) and Pd(dppf)Cl$_2$ (170 mg, 0.26 mmol, 0.10 eq.) in DMSO (30 mL) was degassed and purged with nitrogen 3 times then stirred at 130° C. for 16 hours. After such time the reaction mixture was diluted with water (100 mL) and extracted with ethyl acetate (30 mL×3). The combined organic extracts were washed with brine (80 mL), dried over anhydrous sodium sulfate, filtered and concentrated under reduced pressure. The residue was purified by column chromatography (SiO$_2$, petroleum ether/ethyl acetate 1/1 to I/O, then methyl alcohol/ethyl acetate 1/10 followed by dichloromethane/methyl alcohol 10/1) to give 2-[(6-isoxazol-4-yl-4-oxo-3H-phthalazin-1-yl)methyl]isoindoline-1,3-dione (239 mg, 0.642 mmol, 25% yield) as a red solid. LCMS [M+1$^+$]=373.1.

Step 2: To a solution of 2-[(6-isoxazol-4-yl-4-oxo-3H-phthalazin-1-yl)methyl]isoindoline-1,3-dione (200 mg, 0.537 mmol, 1.00 eq.) in ethyl alcohol (10 mL) was added hydrazine hydrate (0.053 mL, 1.07 mmol, 2.00 eq.) and the mixture stirred at 80° C. for 1 hour. After such time the pH of the cooled reaction mixture was adjusted to pH 1 with hydrochloric acid (1.00 M, 2.00 mL) and concentrated under reduced pressure. The residue diluted with hydrochloric acid (1.00 M, 40 mL) and extracted with ethyl acetate (30 mL×3) and the aqueous phase was concentrated under reduced pressure. The residue was purified by prep-HPLC (Waters Xbridge 150×25 mm×5 μm; mobile phase: [water (0.05% ammonia hydroxide v/v)-ACN]; B %: 0%-20%, 10 min) to give 2-[1-(aminomethyl)-4-oxo-3H-phthalazin-6-yl]acetonitrile, example 13-1 (32 mg, 0.145 mmol, 27% yield) as a white solid. LCMS [M+1]⁺=215.2; ¹H NMR (400 MHz, DMSO-d₆) δ=8.27 (d, J=1.2 Hz, 1H), 8.12 (d, J=8.4 Hz, 1H), 7.87 (dd, J=2.0, 8.4 Hz, 1H), 4.26 (s, 2H), 4.03 (s, 2H).

Example 13-2

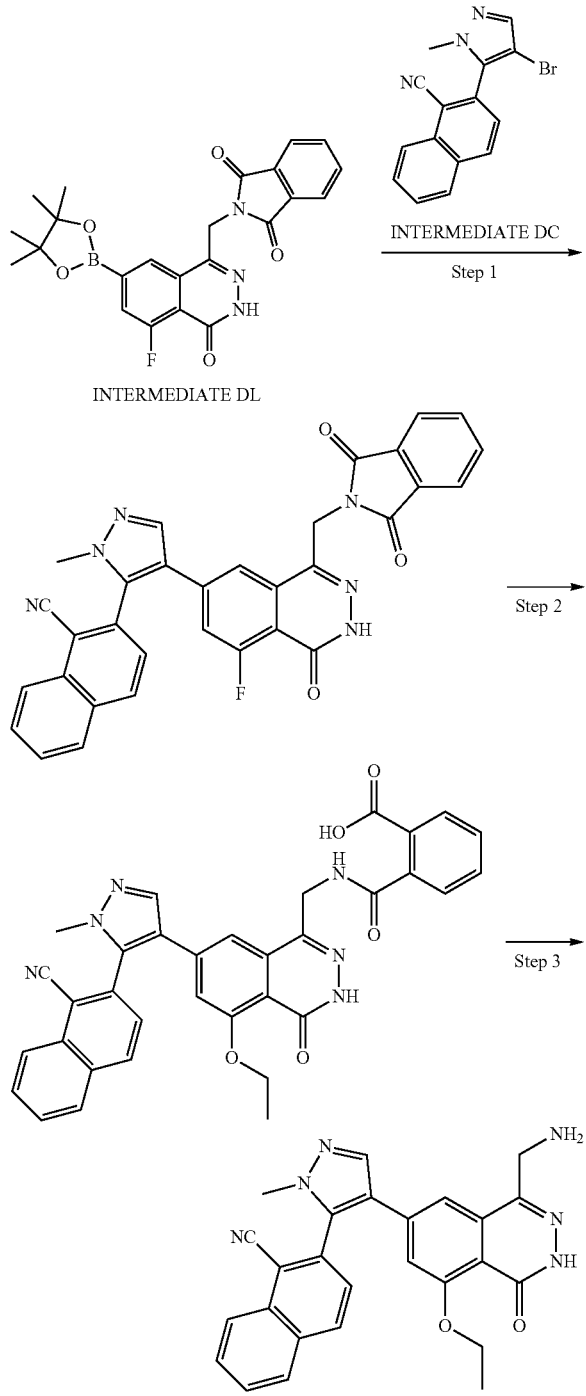

Step 1: To a mixture of 2-[[5-fluoro-4-oxo-7-(4,4,5,5-tetramethyl-1,3,2-dioxaborolan-2-yl)-3H-phthalazin-1-yl]methyl]isoindoline-1,3-dione, Intermediate DL (100 mg, 0.223 mmol, 1.00 eq.), 2-(4-bromo-2-methyl-pyrazol-3-yl) naphthalene-1-carbonitrile, Intermediate DC (70 mg, 0.223 mmol, 1.00 eq.) and sodium bicarbonate (56 mg, 0.668 mmol, 26.0 μL, 3.00 eq) in dioxane (4 mL) and water (0.8 mL) was added ditert-butyl(cyclopentyl)phosphane; dichloropalladium-iron (14.5 mg, 0.022 mmol, 0.10 eq.) and the reaction mixture was degassed and purged with nitrogen and stirred at 80° C. for 1 hour. After such time the reaction mixture was concentrated under reduced pressure and the residue was purified by prep-TLC (SiO₂, dichloromethane: methanol=10:1) to give 2-[4-[4-[(1,3-dioxoisoindolin-2-yl)methyl]-8-fluoro-1-oxo-2H-phthalazin-6-yl]-2-methyl-pyrazol-3-yl]naphthalene-1-carbonitrile (50 mg, 0.074 mmol, 34% yield) as a white solid. LCMS [M+1]⁺=555.2.

Step 2: To a mixture of 2-[4-[4-[(1,3-dioxoisoindolin-2-yl)methyl]-8-fluoro-1-oxo-2H-phthalazin-6-yl]-2-methyl-pyrazol-3-yl]naphthalene-1-carbonitrile (30 mg, 0.054 mmol, 1.00 eq.) in ethyl alcohol (2 mL) was added sodium ethoxide (74 mg, 3.20 mmol, 76 μL, 59 eq.) in one portion at 20° C. under nitrogen atmosphere. The mixture was stirred at 110° C. for 2 hours in a sealed tube then quenched with concentrated HCl (0.1 mL) to pH=5. The mixture was then concentrated under reduce pressure to give 2[[7-[5-(1-cyano-2-naphthyl)-1-methyl-pyrazol-4-yl]-5-ethoxy-4-oxo-3H-phthalazin-1-yl]methylcarbamoyl]benzoic acid (20.0 mg, crude) as a white solid which used for the next step without further purification. LCMS [M+1]⁺=599.1.

Step 3: To a mixture of 2-[[7-[5-(1-cyano-2-naphthyl)-1-methyl-pyrazol-4-yl]-5-ethoxy-4-oxo-3H-phthalazin-1-yl]methylcarbamoyl]benzoic acid (20 mg, crude) in ethyl alcohol (4 mL) was added hydrazine hydrate (334 μmol, 16 μL, 10.0 eq.) in one portion at 20° C. under nitrogen. Then the mixture was stirred at 70° C. for 12 hours and after such time the solvent was removed under reduce pressure and the residue dissolved in dimethylsulfoxide (2 mL) to which concentrated HCl (0.2 mL) was added to the reaction mixture to pH 6, and the resulting mixture was purified by Prep-HPLC (Phenomenex Luna C18 75×30 mm×3 μm; mobile phase: [water (0.05% HCl)-ACN]; B %: 17%-37%, 7 min) to give 2-[4-[4-(aminomethyl)-8-ethoxy-1-oxo-2H-phthalazin-6-yl]-2-methyl-pyrazol-3-yl]naphthalene-1-carbonitrile (6 mg, 12 μmol, 36% yield) as a yellow solid. LCMS [M+1]⁺=451.4; 1H NMR (400 MHz, CD₃OD) δ=8.49 (d, J=8.4 Hz, 1H), 8.25-8.19 (m, 3H), 7.91-7.82 (m, 2H), 7.80 (d, J=8.4 Hz, 1H), 7.33 (s, 1H), 6.78 (d, J=1.2 Hz, 1H), 4.46-4.19 (m, 2H), 3.86 (s, 3H), 3.68-3.38 (m, 2H), 0.94 (t, J=7.2 Hz, 3H).

Example 13-3

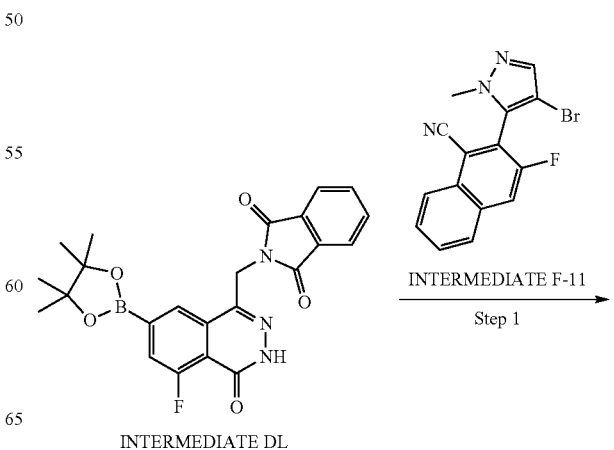

-continued

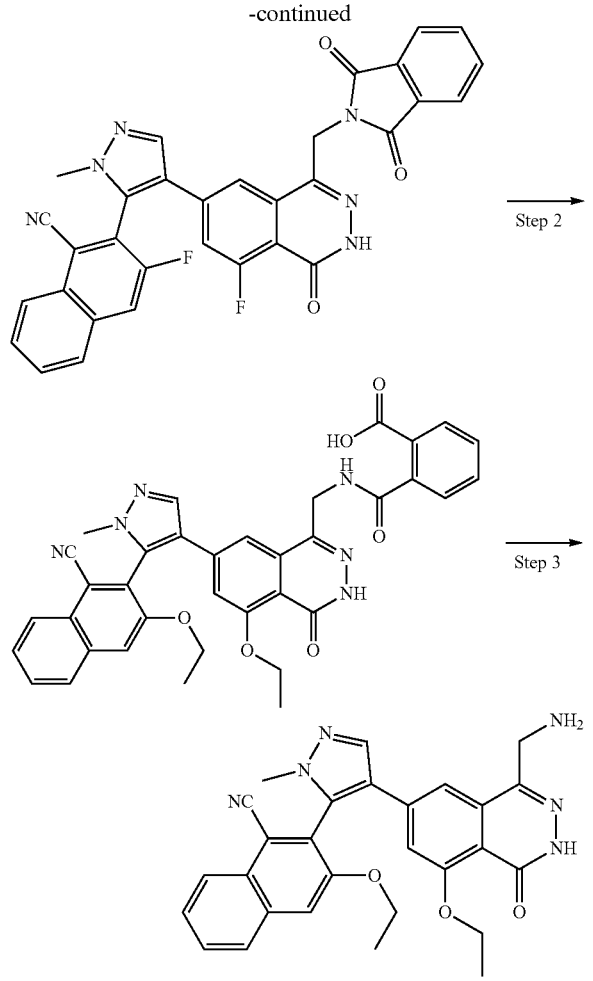

Step 1: To a mixture of 2-[[5-fluoro-4-oxo-7-(4,4,5,5-tetramethyl-1,3,2-dioxaborolan-2-yl)-3H-phthalazin-1-yl]methyl]isoindoline-1,3-dione (61 mg, 0.136 mmol, 1.50 eq), 2-(4-bromo-2-methyl-pyrazol-3-yl)-3-fluoro-naphthalene-1-carbonitrile (30 mg, 0.090 mmol, 1.00 eq) and sodium bicarbonate (23 mg, 0.273 mmol, 3.00 eq) in dioxane (3.0 mL) and H₂O (0.6 mL) was added SPhos Pd G3 (7 mg, 0.009 mmol, 0.1 eq) then stirred at 80° C. for 1 hour under nitrogen atmosphere. The reaction mixture was then concentrated under reduced pressure and purified by prep-TLC (SiO₂, dichloromethane:methanol=10:1) to give 2-[4-[4-[(1,3-dioxoisoindolin-2-yl)methyl]-8-fluoro-1-oxo-2H-phthalazin-6-yl]-2-methyl-pyrazol-3-yl]-3-fluoro-naphthalene-1-carbonitrile (10 mg, 0.005 mmol, 6% yield) as a white solid. LCMS [M+1]⁺=573.3.

Step 2: To a mixture of 2-[4-[4-[(1,3-dioxoisoindolin-2-yl)methyl]-8-fluoro-1-oxo-2H-phthalazin-6-yl]-2-methyl-pyrazol-3-yl]-3-fluoro-naphthalene-1-carbonitrile (10 mg, 0.016 mmol) in ethanol (2.0 mL) was added freshly prepared sodium ethoxide (50 mg in 0.5 mL EtOH) in one portion at 20° C. under N₂ atmosphere. The mixture was stirred at 110° C. for 2 hours in a sealed tube. The reaction was then quenched with concentrated HCl then concentrated under reduce pressure to give 2-[[7-[5-(1-cyano-3-ethoxy-2-naphthyl)-1-methyl-pyrazol-4-yl]-5-ethoxy-4-oxo-3H-phthalazin-1-yl]methylcarbamoyl]benzoic acid (10 mg, crude) as a white solid which used for the next step without further purification. LCMS [M+1]⁺=643.6.

Step 3: To a mixture of 2-[[7-[5-(1-cyano-3-ethoxy-2-naphthyl)-1-methyl-pyrazol-4-yl]-5-ethoxy-4-oxo-3H-phthalazin-1-yl]methylcarbamoyl]benzoic acid (10 mg, 0.016 mmol, 1.00 eq) in ethanol (2.0 mL) was added hydrazine hydrate (0.155 mmol, 8 uL, 10 eq.) in one portion at 20° C. under N₂ atmosphere. The mixture was then stirred at 70° C. for 12 hours, concentrated and the residue dissolved in DMSO (2.0 mL) and the pH adjusted to pH 6 via the addition of concentrated HCl. The resulting mixture was then purified by prep-HPLC (Shim-pack C18 150×25 mm×10 μm; mobile phase: [water (0.1% TFA)-ACN]; B %: 10%-40%, 10 min) to give 2-[4-[4-(aminomethyl)-8-ethoxy-1-oxo-2H-phthalazin-6-yl]-2-methyl-pyrazol-3-yl]-3-ethoxy-naphthalene-1-carbonitrile (3 mg, 0.005 mmol, 31% yield) as a yellow solid. LCMS [M+1]⁺=495.4; ¹H NMR (400 MHz, MeOD) δ=8.25 (s, 1H), 8.10 (t, J=8.0 Hz, 2H), 8.00 (s, 1H), 7.79-7.73 (m, 1H), 7.70-7.63 (m, 1H), 7.37 (d, J=1.2 Hz, 1H), 6.77 (d, J=0.8 Hz, 1H), 4.45-4.27 (m, 4H), 3.82 (s, 3H), 3.68-3.60 (m, 1H), 3.48-3.41 (m, 1H), 1.37 (s, 4H), 0.99 (t, J=6.8 Hz, 3H).

Example 14-1

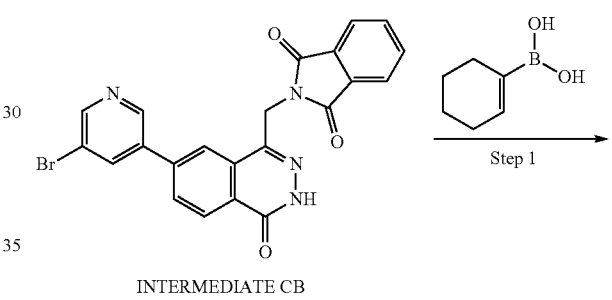

INTERMEDIATE CB

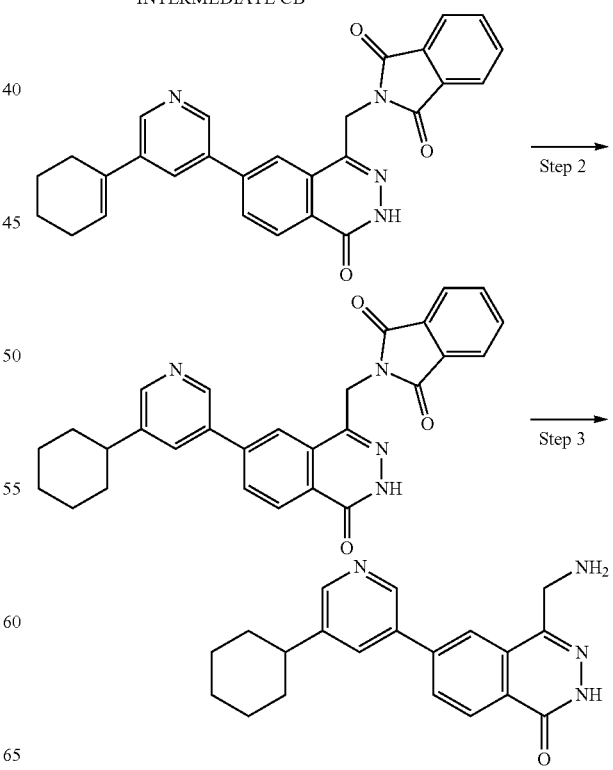

Step 1: A mixture of 2-[[7-(5-bromo-3-pyridyl)-4-oxo-3H-phthalazin-1-yl]methyl]isoindoline-1,3-dione, Intermediate CB (300 mg, 0.650 mmol, 1.00 eq.), cyclohexen-1-ylboronic acid (164 mg, 1.30 mmol, 2.00 eq.), Pd(dppf)Cl$_2$ (48 mg, 65 μmol, 0.10 eq.), sodium bicarbonate (109 mg, 1.30 mmol, 51 μL, 2.00 eq.) in dioxane (4 mL) and water (0.8 mL) was degassed and purged with nitrogen 3 times and stirred at 80° C. for 2 hours under nitrogen atmosphere. After such time the reaction mixture was concentrated and the residue was purified by column chromatography (SiO$_2$, petroleumether:ethylacetate 5:1 to 0:1) then by prep-HPLC (Phenomenex luna C18 150×25 mm×10 μm; mobile phase: [water (0.1% TFA)-ACN]; B %: 34%-54%, 10 min) to give 2-[[7-[5-(cyclohexen-1-yl)-3-pyridyl]-4-oxo-3H-phthalazin-1-yl]methyl]isoindoline-1,3-dione (20 mg, 43 μmol, 7% yield) as a yellow solid. LCMS [M+1]$^+$=463.2.

Step 2: To a solution of 2-[[7-[5-(cyclohexen-1-yl)-3-pyridyl]-4-oxo-3H-phthalazin-1-yl]methyl]isoindoline-1,3-dione (10 mg, 22 μmol, 1.00 eq.) in methyl alcohol (2 mL) was added 10% palladium on activated carbon (5 mg, 0.1 eq) and the suspension was degassed and purged with hydrogen 3 times. The mixture was then stirred under hydrogen (15 Psi) at 25° C. for 2 hours. After such time the reaction mixture was filtered and concentrated under reduced pressure to give 2-[[7-(5-cyclohexyl-3-pyridyl)-4-oxo-3H-phthalazin-1-yl]methyl]isoindoline-1,3-dione (10 mg, crude) as a yellow solid which was used into next step directly without further purification. LCMS [M+1]$^+$=465.3.

Step 3: To a solution of 2-[[7-(5-cyclohexyl-3-pyridyl)-4-oxo-3H-phthalazin-1-yl]methyl]isoindoline-1,3-dione (10 mg, 22 μmol, 1.00 eq.) in ethyl alcohol (1 mL) was added hydrazine hydrate (11 mg, 0.215 mmol, 11 μL, 10.0 eq.) and the reaction mixture stirred at 80° C. for 0.5 hour. After such time the reaction mixture was concentrated under reduced and purified by prep-HPLC (Phenomenex Gemini-NX C18 75×30 mm×3 μm; mobile phase: [water (0.1% TFA)-ACN]; B %: 15%-25%, 7 min) to give 4-(aminomethyl)-6-(5-cyclohexyl-3-pyridyl)-2H-phthalazin-1-one (3.6 mg, 8 μmol, 36% yield, TFA) as a yellow solid. LCMS [M+1]$^+$=335.2; $^1$H NMR (400 MHz, DMSO-d$_6$) δ=12.99 (s, 1H), 8.98 (d, J=2.0 Hz, 1H), 8.60 (d, J=2.0 Hz, 1H), 8.45 (br s, 3H), 8.41-8.37 (m, 1H), 8.33-8.29 (m, 1H), 8.25 (d, J=1.2 Hz, 1H), 8.18 (t, J=2.0 Hz, 1H), 4.63 (br d, J=5.6 Hz, 2H), 2.71-2.65 (m, 1H), 1.92-1.81 (m, 4H), 1.79-1.71 (m, 1H), 1.66-1.51 (m, 2H), 1.48-1.36 (m, 2H), 1.34-1.23 (m, 1H).

Example 15-1

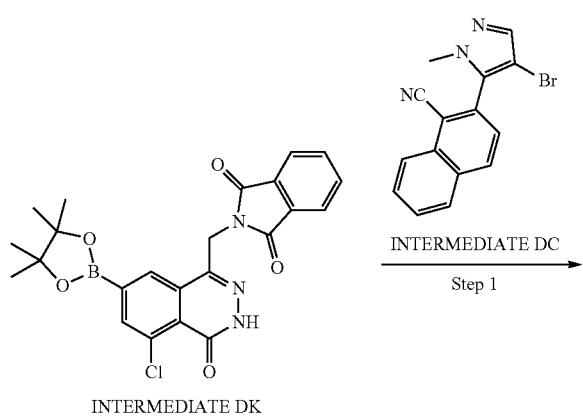

-continued

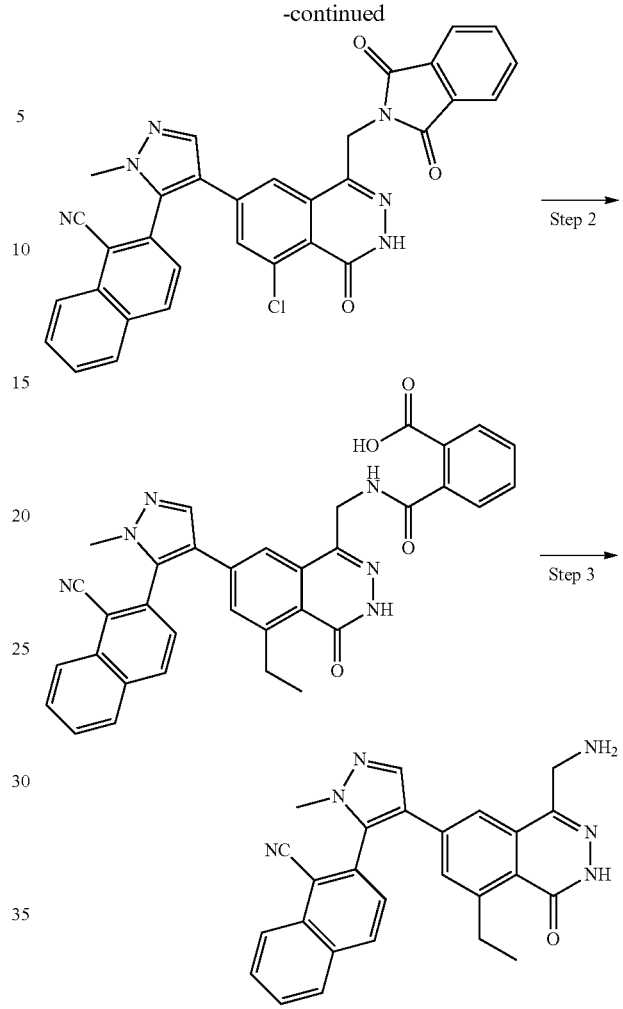

Step 1: A mixture of Intermediate DK (60 mg, 0.129 mmol, 1.00 eq.), 2-(4-bromo-2-methyl-pyrazol-3-yl)naphthalene-1-carbonitrile (40 mg, 0.129 mmol, 1.00 eq.), ditertbutyl(cyclopentyl)phosphane; dichloropalladium; iron (8.4 mg, 0.012 mmol, 0.10 eq.), sodium bicarbonate (33 mg, 0.39 mmol, 3.00 eq.) in dioxane (3.0 mL) and water (0.5 mL) was degassed and purged with nitrogen 3 times, and then stirred at 80° C. for 1 hour under nitrogen atmosphere. The mixture was then concentrated and the residue purified by prep-TLC (SiO$_2$, dichloromethane:methyl alcohol 10:1) to give 2-[4-[8-chloro-4-[(1,3-dioxoisoindolin-2-yl)methyl]-1-oxo-2H-phthalazin-6-yl]-2-methyl-pyrazol-3-yl]naphthalene-1-carbonitrile (40 mg, 0.064 mmol, 50% yield) as a yellow solid. LCMS [M+1]$^+$=571.2.

Step 2: A mixture of 2-[4-[8-chloro-4-[(1,3-dioxoisoindolin-2-yl)methyl]-1-oxo-2H-phthalazin-6-yl]-2-methyl-pyrazol-3-yl]naphthalene-1-carbonitrile (40 mg, 0.070 mmol, 1.00 eq.), triethylborane (69 mg, 0.701 mmol, 0.101 mL, 10.0 eq.), Xantphos (4 mg, 0.007 mmol, 0.10 eq.), potassium carbonate (29 mg, 0.210 mmol, 3.00 eq.) in water (0.6 mL) and THF (3.0 mL) was degassed and purged with nitrogen 3 times, and then the mixture was stirred at 80° C. in a sealed tube for 5 hours. The mixture was then concentrated under reduced pressure and the pH of the residue was adjusted to pH 7 by the addition of hydrochloric acid (1 M) aqueous solution then further concentrated to give 2-[[7-[5-(1-cyano-2-naphthyl)-1-methyl-pyrazol-4-yl]-5-ethyl-4-oxo-3H- phthalazin-1-yl]methylcarbamoyl]benzoic acid (100 mg, crude) as a black solid, which was used into next step directly without further purification. LCMS [M+1]⁺=583.0.

Step 3: A mixture of 2-[[7-[5-(1-cyano-2-naphthyl)-1-methyl-pyrazol-4-yl]-5-ethyl-4-oxo-3H-phthalazin-1-yl]methylcarbamoyl]benzoic acid (100 mg, 0.172 mmol, 1.00 eq.), hydrazine hydrate (3.43 mmol, 0.17 mL, 20.0 eq.) in ethyl alcohol (5.0 mL) was degassed and purged with nitrogen 3 times, and then the mixture was stirred at 80° C. for 18 hours. The mixture was then concentrated, and the residue acidified with hydrochloric acid (1 M) to pH 6, diluted with ethyl acetate (8 mL) and extracted with water (5 mL×3). The aqueous layers were concentrated under reduced pressure and the residue was purified by prep-HPLC (Phenomenex Luna C18 75×30 mm×3 μm; mobile phase: [water (0.05% hydrochloric acid)-ACN]; B %: 18%-38%, 7 min) to give 2-[4-[4-(aminomethyl)-8-ethyl-1-oxo-2H-phthalazin-6-yl]-2-methyl-pyrazol-3-yl]naphthalene-1-carbonitrile (13 mg, 0.027 mmol, 16% yield, HCl salt) as a yellow solid. LCMS [M+1]⁺435.3; ¹H NMR (400 MHz, DMSO-$d_6$) δ=12.61 (s, 1H), 8.56 (d, J=8.4 Hz, 1H), 8.48 (br s, 3H), 8.39 (s, 1H), 8.29 (d, J=7.6 Hz, 1H), 8.14 (d, J=8.4 Hz, 1H), 7.93-7.81 (m, 3H), 7.72 (d, J=1.6 Hz, 1H), 7.01 (d, J=1.2 Hz, 1H), 4.38-4.09 (m, 2H), 3.80 (s, 3H), 3.09-2.81 (m, 2H), 0.65 (t, J=7.6 Hz, 3H).

Example 15-2

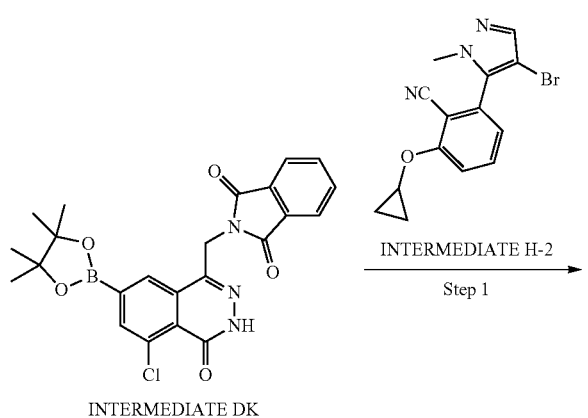

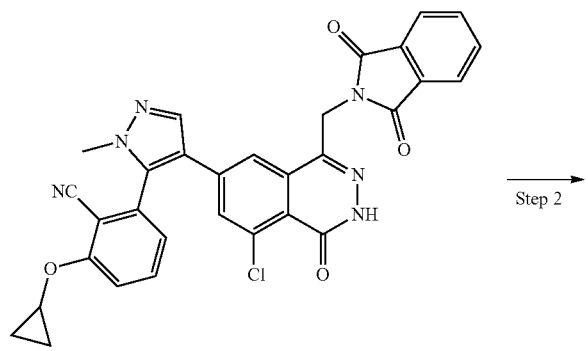

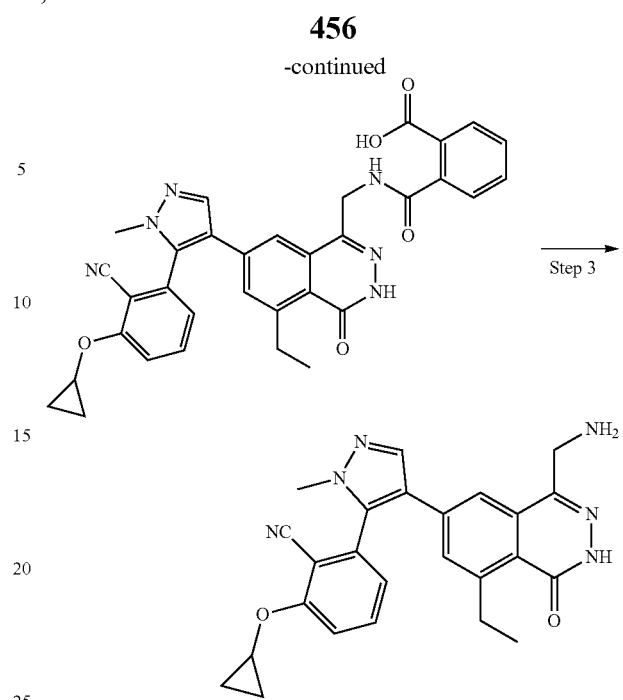

2-(4-(4-(aminomethyl)-8-ethyl-1-oxo-1,2-dihydrophthalazin-6-yl)-1-methyl-1H-pyrazol-5-yl)-6-cyclopropoxybenzonitrile, Example 15-2 was prepared as a white solid (9 mg, 0.019 mmol, 12% yield, HCl salt) following the same 3 step procedure as for example 15-1 starting with Intermediate H-2. LCMS [M+1]⁺441.3; ¹H NMR (400 MHz, DMSO-$d_6$) δ=12.63 (s, 1H), 8.51 (br s, 3H), 8.32 (s, 1H), 7.98-7.88 (m, 1H), 7.75 (d, J=8.4 Hz, 1H), 7.56 (d, J=1.6 Hz, 1H), 7.35 (d, J=7.2 Hz, 1H), 7.17 (d, J=1.2 Hz, 1H), 4.30-4.12 (m, 3H), 3.73 (s, 3H), 3.25-3.01 (m, 2H), 0.94 (t, J=7.2 Hz, 3H), 0.92-0.85 (m, 2H), 0.82-0.67 (m, 2H).

Example 16-1 & 16-2

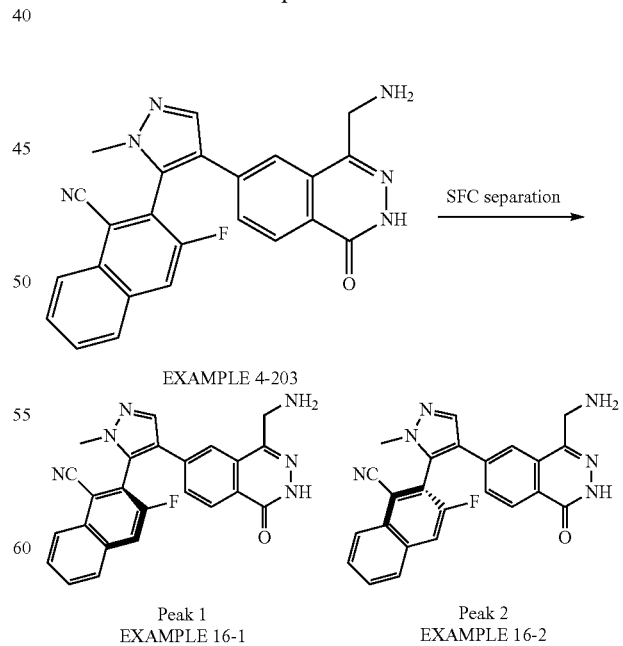

Example 4-203 (30 mg, 0.071 mmol) was separated by SFC (Daicel Chiralpak AD (250 mm×30 mm, 10 μm);

mobile phase: [0.1% NH₃H₂O EtOH]; B %: 40%-40%, 4.9 min; 40 min) to provide Example 16-1 (6 mg, 0.014 mmol, 19% yield) as a white solid LCMS [M+1]⁺=425.2; ¹H NMR (400 MHz, CD₃OD) δ=8.20-8.15 (m, 1H), 8.13-8.03 (m, 4H), 7.76-7.67 (m, 2H), 7.59 (d, J=1.2 Hz, 1H), 7.49 (dd, J=1.6, 8.4 Hz, 1H), 3.85-3.79 (m, 1H), 3.76 (s, 3H), 3.75-3.70 (m, 1H) and Example 16-2 (6 mg, 0.014 mmol, 19% yield) as a white solid LCMS [M+1]⁺=425.2; ¹H NMR (400 MHz, CD₃OD) δ=8.18 (d, J=10.0 Hz, 1H), 8.13 (s, 1H), 8.12-8.02 (m, 3H), 7.79-7.67 (m, 3H), 7.36 (dd, J=1.2, 8.4 Hz, 1H), 4.44-4.08 (m, 2H), 3.77 (s, 3H).

Example 16-3 and 16-4

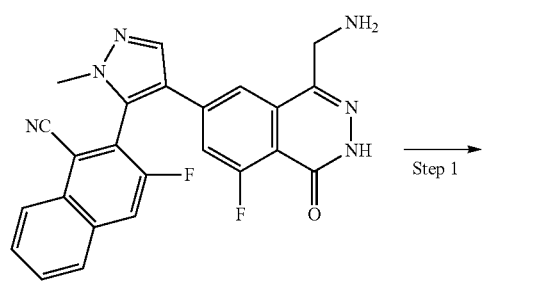

Example 10-18

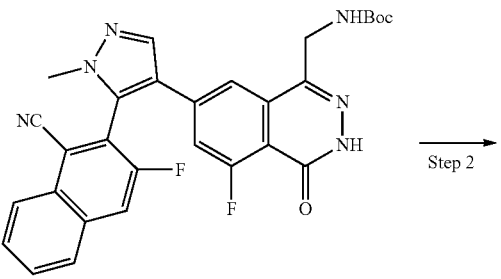

Step 1

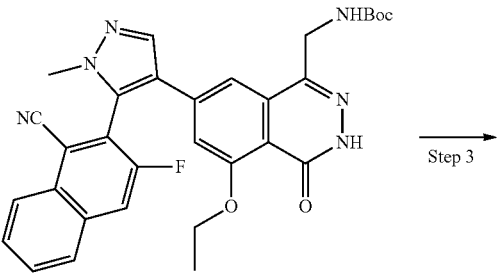

Step 2

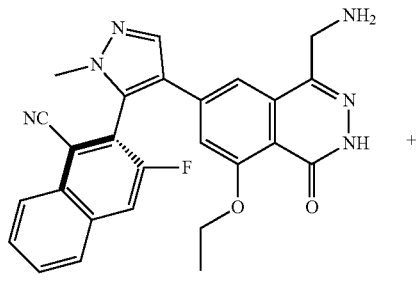

Example 16-3

Step 3

+

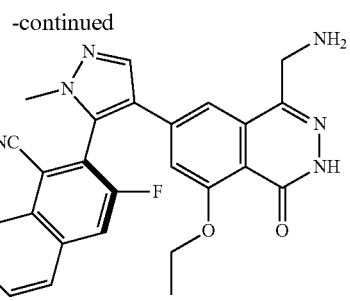

Example 16-4

Step 1: To a solution of 2-[4-[4-(aminomethyl)-8-fluoro-1-oxo-2H-phthalazin-6-yl]-2-methyl-pyrazol-3-yl]-3-fluoro-naphthalene-1-carbonitrile (35.0 mg, 0.079 mmol, 1.00 eq.) in THF (4 mL) was added Boc₂O (17 mg, 0.079 mmol, 1.00 eq.) and the mixture was stirred at rt for 12 hrs. The reaction mixture was then concentrated and the residue purified by prep-TLC (SiO₂, dichloromethane:methanol 10%) to give tert-butyl N-[[7-[5-(1-cyano-3-fluoro-2-naphthyl)-1-methyl-pyrazol-4-yl]-5-fluoro-4-oxo-3H-phthalazin-1-yl]methyl]carbamate (30 mg, 0.055 mmol, 70% yield) as a yellow solid. LCMS [M+1]⁺=543.2.

Step 2: To a solution of tert-butyl N-[[7-[5-(1-cyano-3-fluoro-2-naphthyl)-1-methyl-pyrazol-4-yl]-5-fluoro-4-oxo-3H-phthalazin-1-yl]methyl]carbamate (30 mg, 0.055 mmol, 1.00 eq.) in alcohol (2 mL) was added sodium ethoxide (19 mg, 0.276 mmol, 5.00 eq.) and the mixture was stirred at 110° C. for 0.75 hr in a sealed tube. The cooled reaction mixture was then filtered, concentrated and the residue triturated with MTBE (1 mL), filtered and dried to give compound tert-butyl N-[[7-[5-(1-cyano-3-fluoro-2-naphthyl)-1-methyl-pyrazol-4-yl]-5-ethoxy-4-oxo-3H-phthalazin-1-yl]methyl]carbamate (30 mg, 0.052 mmol, 96% yield) as a yellow solid. LCMS [M+1]⁺=569.3.

Step 3: To a solution of tert-butyl N-[[7-[5-(1-cyano-3-fluoro-2-naphthyl)-1-methyl-pyrazol-4-yl]-5-ethoxy-4-oxo-3H-phthalazin-1-yl]methyl]carbamate (30 mg, 0.052 mmol, 1.00 eq.) in dichloromethane (0.2 mL) was added TFA (0.75 mL) and the mixture was stirred at 30° C. for 0.25 hr. The reaction mixture was then concentrated and the residue purified by prep-HPLC (purification method 4-6) then stereoisomers were separated by SFC (DAICEL CHIRALPAK IG (250 mm×30 mm, 10 μm); mobile phase: [Heptane-alcohol (0.1% NH₃H₂O)]; B %: 80% isocratic; 7 min cycle, 150 min total) then each stereoisomer was further purified by prep-HPLC (Unisil 3-100 C18 Ultra 150 mm×50 mm×3 μm; mobile phase: [water (0.225% formic acid)-ACN]; B %: 15%-35%, 10 min) to give example 16-3, 2-[4-[4-(aminomethyl)-8-ethoxy-1-oxo-2H-phthalazin-6-yl]-2-methyl-pyrazol-3-yl]-3-fluoro-naphthalene-1-carbonitrile (1.4 mg, 0.002 mmol, 20% yield) as a white solid and example 16-4 2-[4-[4-(aminomethyl)-8-ethoxy-1-oxo-2H-phthalazin-6-yl]-2-methyl-pyrazol-3-yl]-3-fluoro-naphthalene-1-carbonitrile (1.7 mg, 0.003 mmol, 25% yield) as a white solid. Spectra data for Example 16-3: LCMS [M+1]⁺=569.3; ¹H NMR (400 MHz, MeOD) δ=8.53 (br s, 2H), 8.33 (d, J=10.0 Hz, 1H), 8.27 (s, 1H), 8.25-8.18 (m, 2H), 7.90-7.84 (m, 2H), 7.35 (s, 1H), 6.83 (s, 1H), 4.38-4.19 (m, 2H), 3.90 (s, 3H), 3.77-3.66 (m, 1H), 3.60-3.48 (m, 1H), 1.03 (t, J=6.8 Hz, 3H). Spectra data for Example 16-4: LCMS [M+1]⁺=569.3; ¹H NMR (400 MHz, CD₃OD) δ=8.59-8.47 (m, 1H), 8.31 (d, J=10.0 Hz, 1H), 8.25 (s, 1H), 8.24-8.16 (m, 2H), 7.88-7.81

(m, 2H), 7.32 (s, 1H), 6.82 (s, 1H), 4.33-4.13 (m, 2H), 3.88 (s, 3H), 3.76-3.64 (m, 1H), 3.59-3.46 (m, 1H), 1.01 (t, J=6.8 Hz, 3H).

Example 16-5 and 16-6

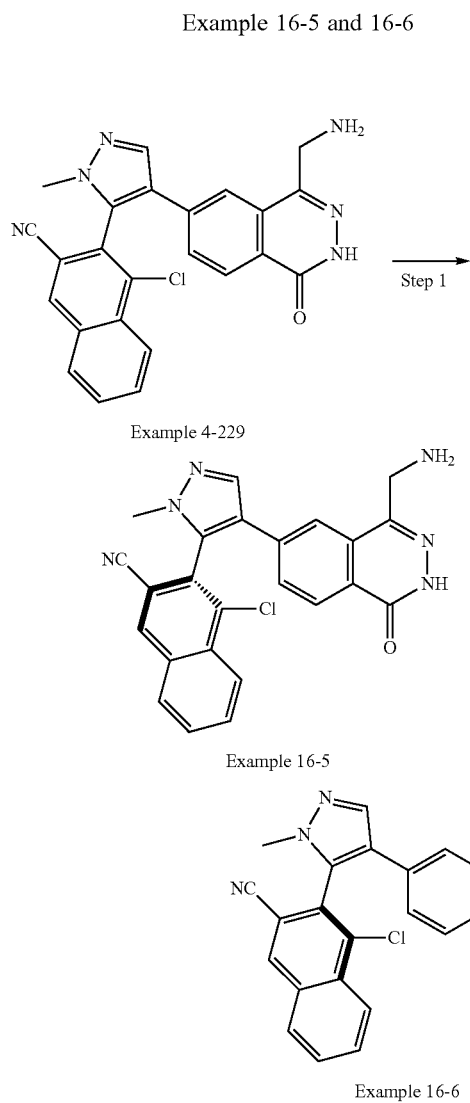

Example 4-229

Example 16-5

Example 16-6

Example 16-5 (49 mg, 0.112 mmol, 31% yield) and Example 16-6 (48 mg, 0.109 mmol, 30% yield) was separated from Example 4-229 (160 mg, 0.324 mmol) by SFC. MeOH (20 ml) was added to the sample. Waters 80Q instrument, Supercritical $CO_2$ Flow Rate: 80 g/min Cycle Time: 7 min, total time: 50 min. Single injection volume: 3.0 ml. Back Pressure: 100 bar to keep the $CO_2$ in Supercritical flow. Phenomenex-Cellulose-2 (250 mm×30 mm, 10 μm); mobile phase: [0.1% $NH_3H_2O$ MeOH]; B %: 60% isocratic). Spectra data for Example 16-5: LCMS [M+1]$^+$=441.2; $^1$H NMR (400 MHz, DMSO-d$_6$) δ=12.82 (s, 1H), 8.94 (s, 1H), 8.48 (s, 1H), 8.44-8.39 (m, 1H), 8.32 (br d, J=8.0 Hz, 1H), 8.05-7.99 (m, 2H), 7.98-7.89 (m, 2H), 7.26 (br d, J=8.4 Hz, 1H), 4.35 (br s, 2H), 3.71 (s, 3H). Spectra data for Example 16-5: LCMS [M+1]$^+$=441.2; $^1$H NMR (400 MHz, DMSO-d$_6$) δ=12.39 (br s, 1H), 8.92 (s, 1H), 8.42 (d, J=8.4 Hz, 1H), 8.34 (s, 1H), 8.30 (d, J=8.0 Hz, 1H), 8.07 (d, J=8.4 Hz, 1H), 8.06-8.00 (m, 1H), 7.98-7.92 (m, 1H), 7.67 (d, J=1.6 Hz, 1H), 7.64 (dd, J=1.6, 8.4 Hz, 1H), 3.73 (s, 3H), 3.54 (s, 2H).

Example 16-7 and 16-8

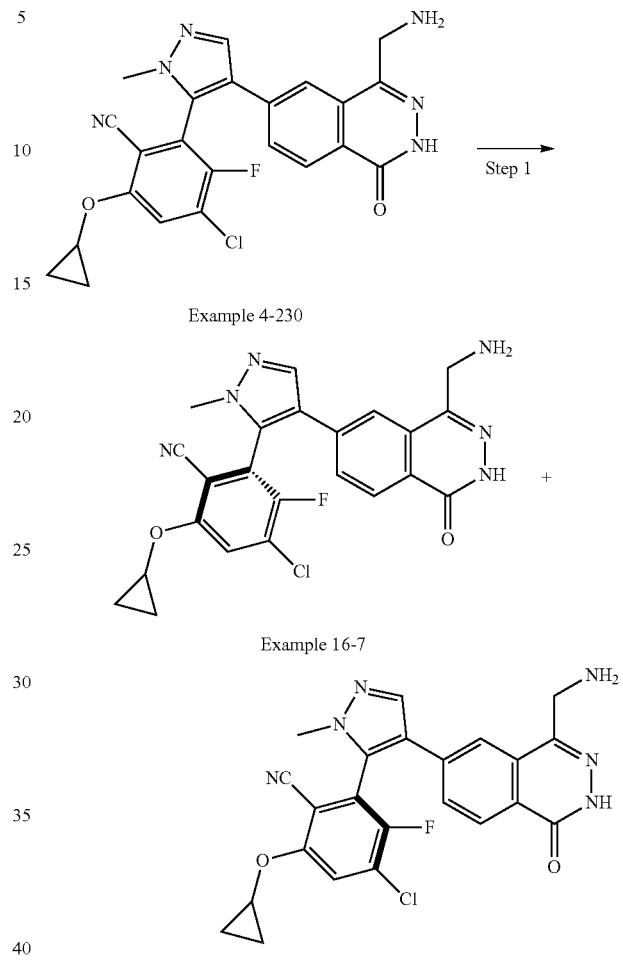

Example 4-230

Example 16-7

Example 16-8

Example 4-230, 2-(4-(4-(aminomethyl)-1-oxo-1,2-dihydrophthalazin-6-yl)-1-methyl-1H-pyrazol-5-yl)-4-chloro-6-cyclopropoxy-3-fluorobenzonitrile (30 mg, 0.065 mmol) separated by SFC (DAICEL CHIRALPAK IC (250 mm×30 mm×10 μm); mobile phase: [0.1% $NH_3H_2O$ isopropanol]; B %: 40% isocratic, 4.1 min cycle; 120 min total) to give example 16-7 (ee >99%, 13 mg, 0.026 mmol, 25% yield) as a yellow solid and example 16-8 (8 mg, ee=84%). Example 16-8 was then then further separated by SFC (DAICEL CHIRALPAK IC (250 mm×30 mm, 10 μm); mobile phase: [0.1% $NH_3H_2O$ EtOH]; B %: 60% isocratic, 3.1 min cycle; total 50 min) to give Example 16-8 (ee >99%, 4 mg, 0.007 mmol, 7% yield) as a yellow gum. Spectra data for Example 16-7: LCMS [M+1]$^+$=465.1; $^1$H NMR (400 MHz, DMSO-d$_6$) δ=12.59-12.44 (s, 1H), 8.29 (s, 1H), 8.15 (d, J=8.4 Hz, 1H), 8.01 (d, J=6.0 Hz, 1H), 7.75 (s, 1H), 7.67 (br d, J=7.6 Hz, 1H), 4.23-4.17 (m, 1H), 3.86 (br s, 2H), 3.78 (s, 3H), 0.94-0.88 (m, 2H), 0.84-0.79 (m, 2H). Spectra data for Example 16-8: LCMS [M+1]$^+$=465.1; $^1$H NMR (400 MHz, DMSO-d$_6$) δ=12.49-12.37 (s, 1H), 8.26 (s, 1H), 8.15 (d, J=8.4 Hz, 1H), 8.00 (d, J=6.0 Hz, 1H), 7.73 (d, J=1.6 Hz, 1H), 7.72-7.68 (m, 1H), 4.19 (m, 1H), 3.80 (s, 2H), 3.77 (s, 3H), 0.93-0.87 (m, 2H), 0.83-0.78 (m, 2H).

Example A

This Example illustrates that exemplary compounds of the present invention cooperatively inhibit PRMT5 enzymatic activity in the presence of MTA.

The PRMT5 inhibitory activity of compounds of the present invention was determined using either a PRMT5:MEP50 FlashPlate Assay (Reaction Biology Corporation) or a PRMT5:MEP50 HotSpot Assay (Reaction Biology Corporation).

1. PRMT5:MEP50 FlashPlate Assay

The assay uses purified human, PRMT5 enzyme to convert S-adenosyl-L-[methyl-$^3$H]methionine plus histone H4 L-arginine to S-adenosyl-L-homocysteine plus histone H4 [methyl-$^3$H]-L-arginine. The assay was carried out using Streptavidin-coated FlashPlates (Perkin Elmer), which contained a scintillant embedded in the plastic of the plate. The histone H4 peptide substrate was conjugated with biotin, which binds to the streptavidin-coated well of the plate, placing the H4 peptide in close proximity to the side well and the scintillant. The transfer of the tritiated methyl group from S-adenosyl-L-[methyl-$^3$H]methionine to the bound histone H4 peptide generated a radiolabeled histone H4, which was quantitated by measuring in a scintillation counter to determine the activity of PRMT5 enzyme in the presence and absence of compound. The assay reactions also were conducted in the presence and absence of MTA to determine whether the compounds exhibit MTA-cooperative activity. Briefly, compounds of the present invention were solubilized in 100% DMSO at a highest concentration of 10 mM. For IC$_{50}$ determinations, the initial starting concentration for the serial dilutions of each compound was 50 µM. Control samples lacking compound, PRMT5/MEP50 complex or various reaction components also were prepared and processed in parallel with compound test samples. SAH was used as a positive control for assay validation. To measure PRMT5 inhibitory activity, 3 nM PRMT5/MEP50 complex (Reaction Biology Corporation) was preincubated with test compound in assay buffer containing 40 nM histone H4 peptide (amino acids 1-15)-Biotin conjugate for 20 min at room temperature. The enzymatic reaction was initiated by adding 1 µM tritiated S-adenosyl methionine (final concentration) and the reaction is allowed to proceed for 20 min. The reaction was stopped and the amount of bound, tritiated H4 peptide in each sample was determined using a scintillation counter. The IC$_{50}$ value for each compound was calculated from each 10-point dose-response curve for samples plus and minus MTA using GraphPad Prism software and the results for exemplary compounds of Formula (I) is shown in Table 9a.

TABLE 9a

IC$_{50}$ Values for PRMT5-mediated Enzymatic Activity by Exemplary Compounds of Formula (I) in the Presence and Absence of MTA in the FlashPlate Assay

| Example | IC$_{50}$ + 2 µM MTA (nM) | IC$_{50}$ (nM) |
|---|---|---|
| 1-4 | 39000 | >100000 |
| 1-5 | 1400 | 34800 |
| 1-7 | 1200 | 31500 |
| 1-8 | 10000 | >100000 |
| 3-1 | 3700 | 89600 |
| 3-10 | 100 | 3910 |
| 3-11 | 5000 | 131000 |
| 3-12 | 210000 | >1000000 |
| 3-13 | 110 | 1420 |
| 3-14 | 17 | 413 |
| 3-15 | 650 | 18700 |
| 3-16 | 13 | 186 |
| 3-17 | 770 | 15100 |
| 3-18 | 33000 | >1000000 |
| 3-19 | 180 | 6360 |
| 3-2 | 42000 | 10000 |
| 3-20 | 53000 | 0 |
| 3-21 | 1800 | 39400 |
| 3-22 | 35000 | >100000 |
| 3-23 | 230 | 6430 |
| 3-24 | 20000 | >100000 |
| 3-25 | 71000 | >100000 |
| 3-26 | 1600 | 20600 |
| 3-27 | 4200 | 59000 |
| 3-28 | >100000 | >100000 |
| 3-29 | 10000 | 0 |
| 3-3 | 25000 | 10000 |
| 3-30 | 7700 | 85200 |
| 3-31 | 80000 | >100000 |
| 3-32 | 710 | 11600 |
| 3-33 | 61 | 1570 |
| 3-34 | 73 | 2040 |
| 3-35 | 59 | 1530 |
| 3-36 | 450 | 9130 |
| 3-37 | 3200 | 72100 |
| 3-38 | 370 | 4940 |
| 3-39 | 920 | 24300 |
| 3-4 | 1400 | 38300 |
| 3-40 | 6 | 193 |
| 3-41 | 1600 | 27500 |
| 3-42 | 200 | 3580 |
| 3-43 | 340 | 6500 |
| 3-44 | 1200 | 19400 |
| 3-45 | 370 | 6810 |
| 3-48 | 280 | 7980 |
| 3-49 | 110 | 3850 |
| 3-5 | 7400 | 87900 |
| 3-50 | 10 | 277 |
| 3-51 | 500 | 11100 |
| 3-52 | 370 | 3000 |
| 3-53 | 28 | 1350 |
| 3-54 | 64 | 1290 |
| 3-55 | 83 | 1870 |
| 3-56 | 550 | 11500 |
| 3-57 | 30000 | 0 |
| 3-58 | 510 | 8070 |
| 3-59 | 7.7 | 399 |
| 3-6 | 5100 | 47100 |
| 3-60 | 8100 | >100000 |
| 3-61 | 3.4 | 80 |
| 3-8 | >1000000 | >1000000 |
| 3-9 | 33 | 1230 |
| 4-1 | 45000 | >100000 |
| 4-10 | 1000 | >100000 |
| 4-100 | 0.5 | 80 |
| 4-101 | 0.5 | 17 |
| 4-103 | 0.5 | 115 |
| 4-104 | 0.5 | 28 |
| 4-105 | 1.8 | 71 |
| 4-106 | 0.5 | 56 |
| 4-107 | 0.5 | 37 |
| 4-108 | 900 | 8650 |
| 4-109 | 120 | 4870 |
| 4-11 | 110 | 2400 |
| 4-110 | 1000 | >100000 |
| 4-111 | 12 | 472 |
| 4-12 | 7400 | >100000 |
| 4-13 | 210 | 2560 |
| 4-14 | 7900 | >100000 |
| 4-15 | 260 | 3870 |
| 4-16 | 9.4 | 602 |
| 4-17 | 150 | 2050 |
| 4-18 | 280 | 4420 |
| 4-19 | 380 | >100000 |
| 4-2 | 490 | 13800 |
| 4-20 | 47 | 1020 |
| 4-21 | 70 | 1970 |
| 4-22 | 370 | 8680 |
| 4-23 | >100000 | >100000 |
| 4-24 | 840 | 13400 |
| 4-25 | 1700 | >100000 |
| 4-26 | 130 | 1730 |
| 4-27 | 1300 | >100000 |
| 4-28 | 140 | 6790 |
| 4-29 | 190 | 4030 |
| 4-3 | 37 | 926 |
| 4-30 | 400 | 4750 |
| 4-31 | 410 | 7630 |
| 4-32 | 1.6 | 45 |
| 4-33 | >100000 | >100000 |
| 4-34 | 110 | 2800 |
| 4-35 | 1100 | >100000 |
| 4-36 | 13 | 541 |
| 4-37 | 1.1 | 213 |
| 4-38 | 25 | 850 |
| 4-39 | 1.7 | 109 |
| 4-4 | 230 | 5910 |
| 4-40 | 10 | 276 |
| 4-41 | 56 | 4810 |
| 4-42 | 45 | 1380 |
| 4-43 | 32 | 1520 |
| 4-44 | 5.4 | 691 |
| 4-45 | 16 | 291 |
| 4-46 | 0.6 | 329 |
| 4-47 | 19 | 667 |
| 4-48 | 22.0 | 750 |
| 4-49 | 300 | 5930 |
| 4-5 | 150 | 1730 |
| 4-50 | 22 | 456 |
| 4-51 | 5.8 | 530 |
| 4-52 | 18 | 669 |
| 4-61 | 3 | 149 |
| 4-62 | 120 | 2230 |
| 4-63 | 58 | 1380 |
| 4-64 | 230 | 4110 |
| 4-65 | 16 | 517 |
| 4-67 | 4 | 204 |
| 4-68 | 10 | 243 |
| 4-69 | 10 | 624 |
| 4-7 | 8400 | >100000 |
| 4-70 | 10 | 221 |
| 4-71 | 4.9 | 116 |
| 4-72 | 3.0 | 73 |
| 4-73 | 0.6 | 24 |
| 4-74 | 1.1 | 76 |
| 4-75 | 0.7 | 33 |
| 4-76 | 1.3 | 31 |
| 4-77 | 1.1 | 96 |
| 4-78 | 0.5 | 66 |
| 4-79 | 27 | 930 |
| 4-8 | 440 | >100000 |
| 4-80 | 58 | 1570 |
| 4-81 | 18 | 826 |
| 4-82 | 28 | 1340 |
| 4-83 | 14 | 344 |
| 4-84 | 93 | 4040 |
| 4-85 | 29 | 1910 |
| 4-86 | 11 | 731 |
| 4-87 | 22 | 1590 |
| 4-88 | 45 | 1710 |
| 4-89 | 64 | 1220 |
| 4-9 | 590 | 16000 |
| 4-90 | 82 | 2730 |
| 4-91 | 16 | 249 |
| 4-92 | 3.5 | 137 |
| 4-93 | 3.3 | 85 |
| 4-94 | 2.2 | 83 |
| 4-95 | 4.9 | 228 |
| 4-96 | 3.9 | 116 |
| 4-97 | 1.6 | 49 |

TABLE 9a-continued

IC$_{50}$ Values for PRMT5-mediated Enzymatic Activity by Exemplary Compounds of Formula (I) in the Presence and Absence of MTA in the FlashPlate Assay

| Example | IC$_{50}$ + 2 μM MTA (nM) | IC$_{50}$ (nM) | Example | IC$_{50}$ + 2 μM MTA (nM) | IC$_{50}$ (nM) |
|---|---|---|---|---|---|
| 4-53 | 55 | 1140 | 4-98 | 2.1 | 90 |
| 4-54 | 77 | 1550 | 4-99 | 15 | 547 |
| 4-55 | 1.2 | 30 | 4-158 | 2.8 | 113 |
| 4-56 | 3.8 | 107 | 4-159 | 4.0 | 68.4 |
| 4-57 | 11 | 85 | 5-1 | 72000 | >100000 |
| 4-58 | 1.8 | 36 | 5-2 | 57000 | >100000 |
| 4-59 | 2.1 | 68 | 6-1 | 5800 | >100000 |
| 4-60 | 2.3 | 117 | 7-6 | 18 | 577 |
| 6-2 | >100000 | >100000 | 8-1 | 47 | 1650 |
| 6-3 | 9400 | >100000 | 8-2 | 36 | 3150 |
| 6-4 | 19000 | 0 | 8-3 | 2.3 | 237 |
| 6-5 | >100000 | >100000 | 8-4 | 3.1 | 313 |
| 7-1 | 490 | 11200 | 8-5 | 23 | 691 |
| 7-2 | 16 | 246 | 8-6 | 52 | 2140 |
| 7-3 | 15 | 388 | 8-7 | 33 | 931 |
| 7-4 | 5.6 | 151 | 8-8 | 20 | 795 |
| 7-5 | 2.0 | 64 | 9-2 | >10,000 | N.D. |
| 3-46 | 570 | 7880 | 13-1 | 25,000 | 89,600 |
| 3-47 | 56 | 2950 | | | |

The assay uses recombinant full-length histone H2A as the PRMT5 substrate. Enzymatic transfer of the tritiated methyl group from S-adenosyl-L-[methyl-3H]methionine to the histone H2A protein generated a radiolabeled histone H2A4 by measuring in a scintillation counter to determine the activity of PRMT5 enzyme in the presence and absence of compound. The assay reactions also were conducted in the presence and absence of MTA to determine whether the compounds exhibit MTA-cooperative activity. Briefly, compounds of the present invention were solubilized in 100% DMSO at a highest concentration of 10 mM. For IC$_{50}$ determinations, the initial starting concentration for the serial dilutions of each compound was 50 μM. Control samples lacking compound, PRMT5/MEP50 complex or various reaction components also were prepared and processed in parallel with compound test samples. SAH was used as a positive control for assay validation. To measure PRMT5 inhibitory activity, 1 nM PRMT5/MEP50 complex (Reaction Biology Corporation) was preincubated with test compound in assay buffer containing 5 μM full-length histone H2A for 20 min at room temperature. The enzymatic reaction was initiated by adding 1 μM tritiated S-adenosyl methionine (final concentration) and the reaction was allowed to proceed for 60 min. The reaction was stopped and transferred to filter paper for detection. The amount of tritiated H2A in each sample was determined using a scintillation counter. The IC$_{50}$ value for each compound was calculated from each 10-point dose-response curve for samples plus and minus MTA using GraphPad Prism software and the results for exemplary compounds of Formula (I) is shown in Table 9b.

TABLE 9b

IC$_{50}$ Values for PRMT5-mediated Enzymatic Activity by Exemplary Compounds of Formula (I) in the Presence and Absence of MTA in the FlashPlate Assay

| Example | IC$_{50}$ + 2 μM MTA (nM) | IC$_{50}$ (nM) | Example | IC$_{50}$ + 2 μM MTA (nM) | IC$_{50}$ (nM) |
|---|---|---|---|---|---|
| 4-112 | 1020 | — | 4-178 | 4880 | — |
| 4-113 | 561 | — | 4-179 | 1240 | — |
| 4-114 | 486 | — | 4-180 | 597 | — |
| 4-115 | 377 | — | 4-181 | 401 | — |
| 4-116 | 1080 | — | 4-182 | 1420 | — |
| 4-117 | 536 | — | 4-183 | 2770 | — |
| 4-118 | 724 | 9924 | 4-184 | 127 | — |
| 4-119 | 441 | 5260 | 4-185 | 1160 | — |
| 4-120 | >10,000 | — | 4-186 | 2310 | — |
| 4-121 | 177 | — | 4-187 | 239 | — |
| 4-122 | 3820 | — | 4-188 | 99 | — |
| 4-123 | 549 | — | 4-189 | 656 | — |
| 4-124 | 826 | — | 4-190 | 278 | — |
| 4-125 | 1000 | — | 4-191 | 612 | — |
| 4-126 | 361 | — | 4-192 | 890 | — |
| 4-127 | 2540 | — | 4-193 | >10,000 | — |
| 4-128 | 1310 | — | 4-194 | 3820 | — |
| 4-129 | 1650 | — | 4-195 | >10,000 | — |
| 4-130 | 1950 | — | 4-196 | 653 | — |
| 4-131 | 1890 | — | 4-197 | 719 | — |
| 4-132 | 2560 | — | 4-198 | 111 | — |
| 4-133 | 1570 | — | 4-199 | 276 | — |
| 4-134 | 2730 | — | 4-200 | 156 | — |
| 4-107 | 760 | — | 4-201 | 948 | — |
| 4-104 | 794 | — | 4-202 | 255 | — |
| 3-40 | 9690 | — | 4-203 | 15 | — |
| 3-59 | 1140 | >10,000 | 4-205 | 23 | — |
| 4-32 | 2040 | >10,000 | 4-206 | 35 | — |
| 4-40 | 3170 | — | 4-220 | 567 | — |
| 4-45 | 2790 | — | 4-221 | 501 | — |
| 4-36 | 2800 | — | 4-222 | 255 | — |
| 4-238 | 2310 | — | 4-242 | 102 | — |
| 4-93 | 845 | — | 4-106 | 816 | — |
| 4-96 | 868 | >10,000 | 4-105 | 1000 | — |
| 4-51 | 1510 | >10,000 | 3-50 | 3780 | >10,000 |
| 4-100 | 1510 | >10,000 | 4-16 | 8850 | — |
| 4-135 | 641 | — | 4-71 | 1050 | >10,000 |
| 4-136 | 872 | — | 4-44 | 6830 | >10,000 |
| 4-137 | 810 | — | 4-73 | 933 | — |
| 4-138 | 354 | — | 4-83 | 2710 | — |
| 4-139 | 1230 | — | 4-94 | 737 | — |
| 4-140 | 1100 | — | 4-98 | 635 | — |
| 4-141 | 794 | — | 4-101 | 892 | — |
| 4-142 | 881 | — | 8-9 | >10,000 | — |
| 4-143 | 1170 | — | 9-2 | >10,000 | — |
| 4-144 | 454 | — | 9-3 | 1273 | — |
| 4-145 | 873 | — | 9-6 | >10,000 | — |
| 4-146 | 569 | — | 9-7 | 2559 | — |
| 4-147 | 43 | 280 | 10-1 | 41.7 | — |
| 4-148 | 229 | — | 10-2 | 67.2 | — |
| 4-149 | 282 | — | 10-3 | 845 | — |
| 4-150 | 673 | — | 10-4 | 417 | — |
| 4-151 | 606 | — | 10-5 | 1150 | — |
| 4-152 | 978 | — | 10-6 | 6630 | — |
| 4-152 | 1910 | — | 10-7 | 107 | — |
| 4-153 | 1650 | — | 10-8 | 660 | — |
| 4-154 | 3280 | — | 10-9 | 1930 | — |
| 4-155 | 3460 | — | 10-10 | 2730 | — |
| 4-156 | 9130 | — | 10-11 | 34 | — |
| 4-158 | 1460 | — | 10-12 | 155 | — |
| 4-159 | 393 | — | 11-1 | 1970 | — |
| 4-160 | 1110 | — | 11-2 | 138 | — |
| 4-161 | 707 | — | 12-1 | 316 | — |
| 4-162 | 842 | — | 12-2 | 315 | — |
| 4-163 | 3820 | — | 12-3 | 212 | — |
| 4-164 | 464 | — | 12-4 | 176 | — |
| 4-165 | 2410 | — | 12-5 | 112 | — |
| 4-166 | 4510 | — | 12-6 | 730 | — |
| 4-167 | 6620 | — | 12-7 | 603 | — |
| 4-168 | 1370 | — | 12-8 | 3860 | — |
| 4-169 | 1350 | — | 12-9 | 178 | — |
| 4-170 | 728 | — | 12-11 | 234 | — |
| 4-171 | 4440 | — | 12-13 | 218 | — |

TABLE 9b-continued

IC$_{50}$ Values for PRMT5-mediated Enzymatic Activity by
Exemplary Compounds of Formula (I) in the Presence
and Absence of MTA in the FlashPlate Assay

| Example | IC$_{50}$ + 2 μM MTA (nM) | IC$_{50}$ (nM) | Example | IC$_{50}$ + 2 μM MTA (nM) | IC$_{50}$ (nM) |
|---|---|---|---|---|---|
| 4-173 | 1600 | — | 12-14 | 182 | — |
| 4-174 | >10,000 | — | 14-1 | >10,000 | — |
| 4-175 | 1120 | — | 16-1 | 38 | — |
| 4-176 | 8710 | — | 16-2 | 111 | — |
| 4-177 | 5970 | — | 16-5 | 994 | — |
|  |  |  | 16-6 | 28 | — |
|  |  |  | 16-7 | 7070 | — |
|  |  |  | 16-8 | 77 | — |

Example B

Cell-Based Assays

This Example illustrates that exemplary compounds of the present invention are capable of inhibiting proliferation of MTAP-deficient cells.

1. HCT116 MTAP Knockout Model

HCT116 cells were genetically engineered to knock out the function of both MTAP alleles using a CRISPR/Cas9 system and an sgRNA targeting the MTAP gene. Following Cas9/MTAP sgRNA transduction, clones were screened to confirm that each allele of the MTAP gene had been inactivated (i.e., homozygous MTAP knock out) creating an MTAP-deficient cell. Clones confirmed to have a homozygous MTAP knockout were used in cell-based assays to assess the inhibition of PRMT5 and anti-proliferative activity and demonstrate MTA-cooperativity of compounds of the present invention.

2. Proliferation Assays

Proliferation assays were performed using HCT116 parental and HCT116 homozygous MTAP knockout cell lines to demonstrate increased potency of compounds of the present invention in the MTAP-deficient cells. Control samples were analyzed in parallel.

Briefly, on Day 0, 250 HCT116 parental or HCT116 homozygous MTAP knockout cell were seeded in 96 well plates in McCoy's 5A supplemented with 10% fetal bovine serum and pen/strep and the cells were incubated overnight at 37° C. plus 5% $CO_2$.

The following day, cells were treated with DMSO vehicle control or a dose response of PRMT5 inhibitors and incubated at 37 C plus 5% $CO_2$ for five days. On Day 6, the cells were trypsinized and split 1:10 into new 96-well plates with fresh medium containing the same concentration of PRMT5 inhibitor and incubated for an additional 5 days at 37° C. plus 5% $CO^2$.

On Day 11, the viability of the cells was measured using a CTG assay kit (CellTiter-Glo; Promega cat.no G7573) in accordance with the manufacturer's instructions. The IC$_{50}$ values for each compound after 10 days of treatment were calculated using GraphPad PRISM software.

3. SYM11 In-Cell Western

In-Cell Western assays were performed in HCT116 parental and HCT116 homozygous MTAP Knockout cell lines to demonstrate increased PRMT5 inhibition in the MTAP-deficient cells by measuring the PRMT5-dependent Symmetric Di-methyl Arginine signal. Control samples were analyzed in parallel.

Briefly, on Day 0, 2,000 HCT116 parental or HCT116 homozygous MTAP knockout cells were seeded in 96 well plates in McCoy's 5A supplemented with 10% fetal bovine serum and pen/strep and the cells were incubated overnight at 37° C. plus 5% $CO_2$. The following day, cells were treated with DMSO vehicle control or a dose response of PRMT5 inhibitors, and incubated at 37° C. plus 5% $CO^2$ for four days.

After 4 days of treatment, the cells were fixed by adding 50 μl of 4% paraformaldehyde solution to each well and the cells were incubated for 20 min at room temperature. The paraformaldehyde solution was removed, 150 μl of ice-cold methanol was added and the plate was placed −20° C. for 10 minutes. The methanol was removed, 150 μl of Odyssey Blocking buffer+0.05% Tween20 was added and the plate was incubated at room temperature with shaking for one hour.

To each test well, 50 μl of SYM11 antibody (Millipore 07-413) diluted 1:500 in Odyssey Blocking buffer+0.05% Tween20 was added and the plate was placed at 4° C. overnight. The primary SYM11 antibody solution was removed by aspiration and the wells were washed three consecutive times with phosphate buffered saline containing 0.1% Tween-20 (PBST).

A 50 μl aliquot of a Goat anti-Rabbit IRDye 800CW secondary antibody (Li-Cor 926-32211) diluted 1:800 and nuclear stain DRAQ5 (Biostatus Limited) diluted 1:10000 in Odyssey Blocking Buffer+DRAQ5+0.05% Tween20 was added and the plate was stored for 2 hours in dark at room temperature. The secondary antibody solution was removed by aspiration and the wells were washed three consecutive times with PB ST.

The SYM11 signal and the DRAQ5 signal were quantified using a Li-Cor Odyssey machine reading at 800 nM and 700 nM, respectively. The SYM11/DRAQ5 ratio was used to calculate the inhibition of Symmetric Dimethyl Arginine as percent of DMSO control.

TABLE 11

Inhibition of PRMT5-dependent Symmetric Di-methyl Arginine (SYM11) signal and proliferation in HCT116 parental and HCT116 homozygous MTAP Knockout cell lines

| | In-cell-Western (SYM11) | | Proliferation | |
|---|---|---|---|---|
| Example | HCT116 parental IC$_{50}$ (nM) | HCT116 MTAP_KO IC$_{50}$ (nM) | HCT116 parental IC$_{50}$ (nM) | HCT116MTAP_KO IC$_{50}$ (nM) |
| 4-67 | 10000 | 945 | 7700 | 2026 |
| 4-94 | 10000 | 1176 | 4877 | 1836 |
| 4-100 | 10000 | 505 | 10000 | 5230 |
| 4-101 | 6667 | 376 | — | 2309 |
| 4-103 | 6667 | 255 | — | 4391 |
| 4-104 | 3333 | 391 | — | 5324 |
| 4-105 | 10000 | 469 | — | 1395 |

TABLE 11-continued

Inhibition of PRMT5-dependent Symmetric Di-methyl Arginine (SYM11) signal and proliferation in HCT116 parental and HCT116 homozygous MTAP Knockout cell lines

| | In-cell-Western (SYM11) | | Proliferation | |
|---|---|---|---|---|
| Example | HCT116 parental IC$_{50}$ (nM) | HCT116 MTAP_KO IC$_{50}$ (nM) | HCT116 parental IC$_{50}$ (nM) | HCT116MTAP_KO IC$_{50}$ (nM) |
| 4-106 | 3333 | 261 | — | 1596 |
| 4-107 | 10000 | 31 | — | 1057 |
| 4-127 | 5920 | 25 | >10,000 | 615 |
| 4-128 | 4024 | 39 | 9633 | 427 |
| 4-129 | >10,000 | 380 | >10,000 | 1347 |
| 4-130 | >10,000 | 24 | >10,000 | 756 |
| 4-131 | 3246 | 43 | >10,000 | 847 |
| 4-132 | >10,000 | 24 | >10,000 | 595 |
| 4-135 | 3214 | 31 | 6612 | 3764 |
| 4-137 | 5178 | 88 | >10,000 | 3236 |
| 4-139 | 5532 | 254 | 5067 | 1488 |
| 4-140 | >10,000 | 47 | 6812 | 3872 |
| 4-141 | 4958 | 88 | 5498 | 2094 |
| 4-142 | 6273 | 49 | 5737 | 1781 |
| 4-145 | 5487 | 190 | 3768 | 2161 |
| 4-146 | 6693 | 40 | >10,000 | 261 |
| 4-147 | 1260 | 11 | 1906 | 50 |
| 4-148 | 8552 | 30 | 7747 | 307 |
| 4-149 | 6351 | 135 | >10,000 | 359 |
| 4-150 | 8392 | 18 | >10,000 | 661 |
| 4-151 | 5812 | 51 | >10,000 | 504 |
| 4-158 | >10,000 | >10,000 | 1742 | 2200 |
| 4-159 | >10,000 | >10,000 | >10,000 | 8250 |
| 4-160 | >10,000 | 944 | 7700 | 2026 |
| 4-161 | 6564 | 87.5 | 6715 | 617 |
| 4-163 | >3333 | >3333 | >10,000 | >10,000 |
| 4-164 | >10,000 | 93.3 | >10,000 | 583 |
| 4-169 | 4516 | 35.5 | >10,000 | 294 |
| 4-180 | 1411 | 31.9 | 121 | 7111 |
| 4-181 | — | 25 | — | 450 |
| 4-182 | >1000 | 58 | 7252 | 572 |
| 4-183 | — | 324 | — | 897 |
| 4-184 | >10,000 | 4 | 9401 | 107 |
| 4-185 | — | 167 | — | 3022 |
| 4-186 | — | 5114 | — | 5775 |
| 4-187 | 1000 | 7 | 1363 | 1903 |
| 4-188 | >10,000 | 4 | 904 | 39 |
| 4-189 | 1833 | 31 | >10,000 | 234 |
| 4-190 | >3333 | >3333 | — | 1977 |
| 4-191 | — | 911 | — | 1519 |
| 4-192 | >10,000 | 256 | >10,000 | 2139- |
| 4-196 | 1316 | 11 | 9289 | 154 |
| 4-197 | >1000 | 25 | 8572 | 256 |
| 4-198 | 1266 | 21 | 7341 | 136 |
| 4-199 | — | 2 | 8846 | 120 |
| 4-200 | 1752 | 32 | 4297 | 71 |
| 4-201 | — | 16 | >10,000 | 155 |
| 4-202 | >1000 | 8 | 2371 | 232 |
| 4-203 | 903 | 2 | 1210 | 19 |
| 4-204 | >1000 | 12 | 1830 | 52 |
| 4-205 | >1000 | 6 | 683 | 59 |
| 4-206 | >1000 | 3 | 1003 | 34 |
| 4-207 | >10,000 | 3 | — | 98 |
| 4-208 | — | 11 | — | 124 |
| 4-209 | >1000 | 10 | 4672 | 59 |
| 4-210 | >1000 | 8 | 1365 | 416 |
| 4-211 | — | 197 | — | 2154 |
| 4-212 | — | >10,000 | — | >10,000 |
| 4-213 | — | 88 | — | 1679 |
| 4-214 | — | >10,000 | — | 4400 |
| 4-215 | >1000 | 34 | 3542 | 81 |
| 4-216 | — | 83 | — | 134 |
| 4-217 | >1000 | 87 | 2151 | 96 |
| 4-218 | — | 140 | — | 134 |
| 4-219 | — | >1000 | — | 3612 |
| 4-220 | | 212 | | 5158 |
| 4-221 | — | 196 | | 2379 |
| 4-222 | — | 296 | — | 5337 |
| 4-223 | 756 | 12 | 7808 | 75 |
| 4-224 | >1000 | 10 | 7808 | 416 |
| 4-225 | >1000 | 17 | −5169 | 84 |
| 4-226 | — | 10 | — | 191 |

TABLE 11-continued

Inhibition of PRMT5-dependent Symmetric Di-methyl Arginine (SYM11) signal and proliferation in HCT116 parental and HCT116 homozygous MTAP Knockout cell lines

| | In-cell-Western (SYM11) | | Proliferation | |
|---|---|---|---|---|
| Example | HCT116 parental IC$_{50}$ (nM) | HCT116 MTAP_KO IC$_{50}$ (nM) | HCT116 parental IC$_{50}$ (nM) | HCT116MTAP_KO IC$_{50}$ (nM) |
| 4-227 | — | >1000 | — | 2367 |
| 4-228 | — | >1000 | — | >10,000 |
| 4-229 | >1000 | 11 | 2862 | 59 |
| 4-230 | >1000 | 6 | 1886 | 41 |
| 4-231 | >1000 | 37 | 3116 | 50 |
| 4-232 | — | 148 | — | 4768 |
| 4-233 | — | >1000 | — | 4726 |
| 4-234 | — | 129 | — | 206 |
| 4-235 | — | >1000 | — | >10,000 |
| 4-236 | — | >1000 | — | >1000 |
| 4-237 | — | 136 | — | 1044 |
| 4-238 | — | 843 | — | 1942 |
| 4-239 | — | >1000 | — | >10,000 |
| 4-240 | — | >1000 | — | 3563 |
| 4-241 | >1000 | 14 | 2400 | 51 |
| 4-242 | >1000 | 2 | 4991 | 44 |
| 4-243 | — | 51 | — | 285 |
| 4-244 | — | 42 | — | 327 |
| 4-245 | — | 7 | — | 8 |
| 4-246 | — | 50 | — | 72 |
| 4-247 | — | >1000 | — | 1806 |
| 4-248 | — | >1000 | — | 1161 |
| 4-249 | — | >1000 | — | 3508 |
| 4-250 | — | 51 | — | 757 |
| 4-251 | — | 8 | — | 49 |
| 4-252 | — | 4 | — | 87 |
| 4-254 | 3333 | 377 | — | 2174 |
| 9-2 | — | >1000 | — | >10,000 |
| 9-3 | — | 141 | — | 4822 |
| 9-4 | — | >1000 | — | 4175 |
| 9-5 | >1000 | 42 | 6437 | 125 |
| 9-6 | — | >1000 | — | >10,000 |
| 9-7 | — | >1000 | — | >10,000 |
| 10-1 | 1123 | 15 | 2299 | 36 |
| 10-2 | 2484 | 6 | 3378 | 112 |
| 10-3 | 3820 | 5 | 8482 | 240 |
| 10-4 | 9215 | 7 | >10,000 | 128 |
| 10-5 | >10,000 | 30 | >10,000 | 250 |
| 10-6 | >10,000 | 219 | >10,000 | 4089 |
| 10-7 | >1000 | 31 | 8386 | 103 |
| 10-8 | 4721 | 27 | >10,000 | 276 |
| 10-9 | — | 8 | 9819 | 489 |
| 10-10 | >10,000 | 89 | >10,000 | 1254 |
| 10-11 | 4256 | 5 | 763 | 29 |
| 10-12 | >1000 | 6 | 6196 | 91 |
| 10-13 | — | 16 | — | 85 |
| 10-14 | — | 75 | — | 88 |
| 10-15 | — | 4 | — | 13 |
| 10-16 | 86 | 48 | 1762 | 86 |
| 10-17 | — | 21 | — | 21 |
| 10-19 | — | 185 | — | 312 |
| 10-20 | | 29 | | 35 |
| 11-1 | >1000 | 57 | >10,000 | 807 |
| 11-2 | >10,000 | 1 | 1952 | 94 |
| 12-1 | >1000 | 28 | >10,000 | 158 |
| 12-2 | 2196 | 16 | 208 | >10,000 |
| 12-3 | >1000 | 8 | 1686 | 137 |
| 12-4 | — | 436 | — | 4366 |
| 12-5 | — | 456 | — | 3172 |
| 12-6 | — | 380 | — | 7468 |
| 12-7 | — | 427 | — | 4985 |
| 12-8 | — | 2856 | — | 7796 |
| 12-9 | >10,000 | 9 | 3348 | 148 |
| 12-10 | >1,000 | 3 | 1332 | 38 |
| 12-11 | 1229 | 18 | 8705 | 125 |
| 12-12 | — | 26 | — | 240 |
| 12-13 | >1000 | 95 | 1998 | 1414 |
| 12-14 | 1806 | 15 | >10,000 | 226 |
| 12-15 | — | 189 | — | 261 |
| 12-16 | | 0.5 | | 75 |
| 12-15 | | 189 | | 261 |
| 12-16 | | 0.4 | | 73 |

TABLE 11-continued

Inhibition of PRMT5-dependent Symmetric Di-methyl Arginine (SYM11) signal and proliferation in HCT116 parental and HCT116 homozygous MTAP Knockout cell lines

| Example | In-cell-Western (SYM11) | | Proliferation | |
|---|---|---|---|---|
| | HCT116 parental $IC_{50}$ (nM) | HCT116 MTAP_KO $IC_{50}$ (nM) | HCT116 parental $IC_{50}$ (nM) | HCT116MTAP_KO $IC_{50}$ (nM) |
| 12-17 | — | 10 | — | 85 |
| 12-18 | — | 10 | — | 104 |
| 13-2 | — | 64 | — | 149 |
| 13-3 | — | 298 | — | 565 |
| 15-1 | >1000 | 22 | 1557 | 51 |
| 15-2 | — | 96 | — | 211 |
| 16-1 | 316 | 2 | 757 | 15 |
| 16-2 | >1,000 | 73 | 5925 | 224 |
| 16-3 | — | 15 | — | 84 |
| 16-4 | — | 12 | — | 15 |
| 16-5 | — | 272 | — | 2850 |
| 16-6 | — | 20 | — | 64 |
| 16-7 | — | 1000 | — | 4002 |
| 16-8 | — | 0.8 | — | 24 |

Clause 1. A compound of Formula (I):

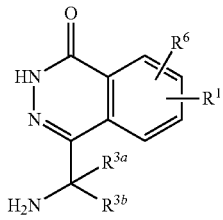

Formula (I)

or a pharmaceutically acceptable salt thereof:
wherein:
$R^1$ is hydrogen, halogen, hydroxyalkyl, -L-CN, —Y—C1-C5 alkyl, —Y-cycloalkyl, —Y-heterocyclyl, —Y-aryl, —Y-arC1-C3alkyl or —Y-heteroaryl, wherein the cycloalkyl, the heterocyclyl, the aryl, and the heteroaryl portions are each optionally substituted with one or more $R^2$;
each Y is independently a bond or —NR$^4$—;
each $R^2$ is independently hydroxy, halogen, cyano, cyanomethyl, —(NR$^4$)$_2$, hydroxyalkyl, alkoxy, —SO$_2$C1-C3alkyl, —X-arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$, or;
each X is independently a bond, O, S, —NR$^4$— or —NR$^4$C(O)—;
each Z is independently a bond, —SO—, —SO$_2$—, —CH(OH)— or —C(O)—;
each L is independently a bond or C1-C3 alkylene;
$R^{3a}$ and $R^{3b}$ are each independently hydrogen or deuterium, or $R^{3a}$ and $R^{3b}$ together are oxo;
each $R^4$ is independently hydrogen or C1-C3 alkyl;
each $R^5$ is independently cyano, oxo, halogen, C1-C3 alkyl, hydroxyalkyl, alkoxy, —X-haloalkyl, —Z-cycloalkyl, —X-arC1-C3 alkyl, X-arC1-C3 alkyl substituted with cyano, —X-L-cycloalkyl, —X-L-heteroaryl optionally substituted with one or more C1-C3alkyl or oxo, or —X-aryl; and $R^6$ is hydrogen, halogen, C1-C3 alkyl, haloalkyl or alkoxy.

Clause 2. The compound according to clause 1, wherein $R^1$ is hydrogen.

Clause 3. The compound according to clause 1, wherein $R^1$ is halogen.

Clause 4. The compound according to clause 3, wherein the halogen is bromine.

Clause 5. The compound according to clause 1, wherein $R^1$ is —Y—C1-C5 alkyl.

Clause 6. The compound of clause 5, wherein Y is a bond and the C1-C5 alkyl is methyl.

Clause 7. The compound according to clause 1, wherein $R^1$ is hydroxyalkyl.

Clause 8. The compound according to clause 1, wherein $R^1$ is -L-CN.

Clause 9. The compound according to clause 8, wherein L is C1-C3 alkylene.

Clause 10. The compound according to clause 1, wherein $R^1$ is —Y-heterocyclyl.

Clause 11. The compound according to clause 10, wherein Y is a bond and the heterocyclyl is azetidinyl, THFyl or morpholinyl.

Clause 12. The compound according to clause 1, wherein $R^1$ is —Y-aryl, wherein the aryl is optionally substituted with one or more $R^2$.

Clause 13. The compound according to clause 12, wherein Y is a bond and the aryl is phenyl optionally substituted with one or two $R^2$.

Clause 14. The compound according to clause 13, wherein the one or two $R^2$ groups are each independently cyano, halogen or —Y—C1-C5 alkyl, wherein Y is a bond.

Clause 15. The compound according to clause 1, wherein $R^1$ is —Y-cycloalkyl.

Clause 16. The compound according to clause 15, wherein Y is a bond and the cycloalkyl is cyclopentyl.

Clause 17. The compound according to clause 1, wherein $R^1$ is —Y-heteroaryl optionally substituted with one or more $R^2$.

Clause 18. The compound according to clause 17, wherein Y is a bond and the heteroaryl is pyrazolyl, imidazolyl, thiazolyl, isothiazolyl, oxazolyl, triazolyl, oxidazolyl, pyridyl, pyridiazinyl, pyrimidinyl, quinolinyl, isoquinolinyl, phthalazinyl, pyrazolopyridinyl, 1H-pyrrolopyridyl, pyrazolopyrimidinyl, imidazopyridyl, tetrahydropyrazolopyrazinyl, 2H-4λ⁴-imidazopyrimidinyl, 2H-4λ⁴-imidazopyridazinyl, oxazolopyridyl or 5,6-dihydro-8H-imidazooxazinyl, each optionally substituted with one or more $R^2$.

Clause 19. The compound according to clause 18, wherein the heteroaryl is tetrahydropyrazolopyrazinyl, optionally substituted with one or more $R^2$.

Clause 20. The compound according to clause 19, wherein the tetrahydropyrazolopyrazinyl is substituted with one $R^2$ selected from the group consisting of —X—C1-C5 alkyl, arC1-C3alkyl, —Z—C1-C5 alkyl, —Z-cycloalkyl and —X-aryl.

Clause 21. The compound according to clause 20, wherein $R^2$ is —Z-cycloalkyl.

Clause 22. The compound according to clause 21, wherein Z is a bond and the cycloalkyl is cyclopropyl.

Clause 23. The compound according to clause 21, wherein Z is —C(O)— and the cycloalkyl is cyclopropyl, cyclobutyl, cyclopentyl, cyclohexyl or bicyclo[1.1.1]pentyl.

Clause 24. The compound according to clause 17, wherein the heteroaryl is pyridyl, optionally substituted with one or two $R^2$.

Clause 25. The compound according to clause 24, wherein the pyridyl is substituted with one $R^2$.

Clause 26. The compound according to clause 25, wherein $R^2$ is hydroxy, halogen, cyano, —(NR⁴)₂, hydroxyalkyl, alkoxy, —SO₂C1-C3alkyl, arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$.

Clause 27. The compound according to clause 26, wherein $R^2$ is —X—C1-C5 alkyl, and X is a bond and the C1-C5 alkyl is methyl, ethyl, propyl, or isopropyl.

Clause 28. The compound according to clause 26, wherein $R^2$ is —X-haloalkyl, and X is a bond and the haloalkyl is difluoromethyl or trifluoromethyl.

Clause 29. The compound according to clause 26, wherein $R^2$ is —X-haloalkyl, X is O and the haloalkyl is difluoromethyl or trifluoromethyl.

Clause 30. The compound according to clause 26, wherein $R^2$ is —X-L-cycloalkyl, wherein X is a bond, L is a bond and the cycloalkyl is cyclopropyl.

Clause 31. The compound according to clause 26, wherein $R^2$ is —X-L-cycloalkyl, wherein X is a bond, L is a methylene and the cycloalkyl is cyclopropyl or cyclohexyl.

Clause 32. The compound according to clause 26, wherein $R^2$ is —X-L-cycloalkyl, wherein X is O, L is methylene and the cycloalkyl is cyclopropyl.

Clause 33. The compound according to clause 26, wherein $R^2$ is C2-C4 alkynyl, wherein the C2-C4 alkynyl is ethynyl or prop-2-ynyl.

Clause 34. The compound according to clause 26, wherein $R^2$ is —SO₂C1-C3 alkyl, wherein the C1-C3 alkyl is methyl.

Clause 35. The compound according to clause 26, wherein $R^2$ is heterocyclyl, wherein the heterocyclyl is morpholinyl or tetrahydropryanyl.

Clause 36. The compound according to clause 26, wherein $R^2$ is —X-heteroaryl, wherein the heteroaryl is optionally substituted with one or more $R^5$.

Clause 37. The compound according to clause 36, wherein X is a bond, and the heteroaryl is pyrazolyl substituted with one $R^5$, wherein $R^5$ is C1-C3 alkyl.

Clause 38. The compound according to clause 36, wherein the X is a bond, and the heteroaryl is pyridyl or pyrimidinyl, each optionally substituted with one or more $R^5$.

Clause 39. The compound according to clause 36, wherein the X is a bond or O, and the heteroaryl is quinolinyl optionally substituted with one or more $R^5$.

Clause 40. The compound according to clause 36, wherein the X is —NR⁴—, and the heteroaryl is quinolinyl optionally substituted with one or more $R^5$.

Clause 41. The compound according to clause 36, wherein $R^2$ is —X-aryl, wherein the aryl is optionally substituted with one or more $R^5$.

Clause 42. The compound according to clause 41, wherein X is a bond and the aryl is phenyl or naphthyl substituted with one, two or three $R^5$.

Clause 43. The compound according to clause 42, wherein each $R^5$ is selected from the group consisting of cyano, halogen, —X-L-cycloalkyl, —X-haloalkyl, heterocyclyl, X-heteroaryl, C1-C3 alkyl and alkoxy.

Clause 44. The compound according to clause 41, wherein X is O and the aryl is phenyl substituted with one or two $R^5$.

Clause 45. The compound according to clause 44, wherein each $R^5$ is cyano, halogen, C1-C3 alkyl or alkoxy.

Clause 46. The compound according to clause 41, wherein X is S, the aryl is phenyl substituted with one $R^5$, wherein $R^5$ is halogen or C1-C3 alkyl.

Clause 47. The compound according to clause 41, wherein the X is —NR⁴—, and the aryl is phenyl optionally substituted with one or more $R^5$.

Clause 48. The compound according to clause 26, wherein $R^2$ is halogen, wherein the halogen is chlorine or fluorine.

Clause 49. The compound according to clause 18, wherein the heteroaryl is pyrazolopyridinyl, optionally substituted with one or more $R^2$.

Clause 50. The compound of clause 49, wherein the pyrazolylpyridinyl is substituted with one $R^2$, wherein the one $R^2$ is alkoxy or —X-aryl.

Clause 51. The compound of clause 45, wherein the alkoxy is methoxy or isopropyloxy.

Clause 52. The compound of clause 45, wherein the —X-aryl, the X is O and the aryl is phenyl.

Clause 53. The compound according to clause 1, wherein $R^1$ is —Y-aryl, wherein Y is —NR⁴— and the aryl is phenyl optionally substituted with one or more $R^5$.

Clause 54. The compound according to clause 1, wherein $R^1$ is —Y—C1-C5 alkyl, wherein Y is —NR⁴— and the C1-C5 alkyl is methyl, ethyl or propyl.

Clause 55. The compound according to clause 1, wherein $R^1$ is —Y-arC1-C3alkyl, wherein Y is —NR⁴— and the arC1-C3alkyl is benzyl.

Clause 56. The compound according to clause 24, wherein the pyridyl is substituted with two $R^2$.

Clause 57. The compound according to clause 56, wherein each $R^2$ is —X—C1-C5 alkyl or one $R^2$ is halogen or —X-L-cycloalkyl and the second $R^2$ is —X—C1-C5 alkyl, wherein each X is a bond.

Clause 58. The compound according to clause 18, wherein the heteroaryl is pyrimidinyl, optionally substituted with one or more $R^2$.

Clause 59. The compound according to clause 58, wherein the pyrimidinyl is substituted with one $R^2$.

Clause 60. The compound according to clause 59, wherein $R^2$ is —X—C1-C5 alkyl or —X-haloalkyl.

Clause 61. The compound according to clause 18, wherein the heteroaryl is pyrazolyl, optionally substituted with one, two or three $R^2$ groups.

Clause 62. The compound according to clause 61, wherein the pyrazolyl is substituted with one $R^2$.

Clause 63. The compound according to clause 62, wherein $R^2$ is —X—C1-C5 alkyl, hydroxyalkyl, arC1-C3alkyl, or —X-aryl optionally substituted with one or more $R^5$.

Clause 64. The compound according to clause 63, wherein $R^2$ is —X—C1-C5 alkyl, wherein the X is a bond, and the C1-C5 alkyl is methyl, ethyl, propyl, isopropyl, butyl, isobutyl, pentyl or isopentyl.

Clause 65. The compound according to clause 61, wherein the pyrazolyl is substituted with two independently selected $R^2$.

Clause 66. The compound according to clause 65, wherein the two $R^2$ groups are (1) independently -t —X—C1-C5 alkyl, (2) —X—C1-C5 alkyl and halogen, (3) —X—C1-C5 alkyl and alkoxy, (4) —X—C1-C5 alkyl and —N($R^4$)$_2$, -(5) X-C1-C5 alkyl and —X-haloalkyl, (6) —X—C1-C5 alkyl and arC1-C3alkyl, (7) —X—C1-C5 alkyl and —X-L-cyclolalkyl, -(8) —X—C1-C5 alkyl and -heterocyclyl, (9) —X—C1-C5 alkyl and —X-aryl optionally substituted with one or more $R^5$, (10) —X—C1-C5 alkyl and —X-heteroaryl optionally substituted with one or more $R^5$, (11) —X—C1-C5 alkyl and cyanomethyl, (12) —X—C1-C5 alkyl and cyano, (13) cyano and halogen, wherein the halogen is chlorine or fluorine, (14) cyano and —X-L-cycloalkyl, (15) independently halogen, (16) cyano and alkoxy, wherein each X is a bond, (17) cyano and —X-aryl, (18) cyano and —X-heteroaryl, (19) cyano and heterocyclyl (20) halogen and —X-arC1-C3alkyl or X-arC1-C3alkyl substituted with cyano, and (21) halogen and —X-aryl.

Clause 67. The compound according to clause 66, wherein the pyrazolyl is substituted with —X—C1-C5 alkyl and —X-aryl optionally substituted with one or more $R^5$, wherein the X is a bond and the aryl is phenyl substituted with two $R^5$, wherein each $R^5$ is independently —X—C1-C5 alkyl, wherein each X is a bond; one $R^5$ is cyano and one $R^5$ is —X—C1-C5 alkyl, wherein each X is a bond; one $R^5$ is cyano and one $R^5$ is —X-L-cycloalkyl, wherein X is a bond and L is a bond, methylene or ethylene; one $R^5$ is cyano and one $R^5$ is halogen; one $R^5$ is cyano and one $R^5$ is alkoxy; or each $R^5$ is independently halogen.

Clause 68. The compound according to clause 66, wherein the pyrazolyl is substituted with —X—C1-C5 alkyl and —X-aryl optionally substituted with one or more $R^5$, wherein the X is a bond and the aryl is phenyl substituted with three $R^5$, wherein each $R^5$ is —X—C1-C5 alkyl, wherein each X is a bond; one $R^5$ is cyano and two $R^5$ are —X—C1-C5 alkyl, wherein each X is a bond; one $R^5$ is cyano, one $R^5$ is halogen, and one $R^5$ is —X—C1-C5 alkyl, wherein X is a bond; one $R^5$ is cyano and two $R^5$ are alkoxy, one $R^5$ is cyano and two $R^5$ are halogens, one $R^2$ is cyano and two $R^2$ are halogen; one $R^2$ is cyano, one $R^2$ is halogen and one $R^2$ is alkoxy, or one $R^2$ is alkoxy, and two $R^2$ are independently halogen.

Clause 69. The compound according to clause 18, wherein the heteroaryl is imidazolyl, 1H-pyrrolopyridyl, tetrahydropyrazolopyrazinyl, 2H-4$\lambda^4$-imidazopyrimidinyl, 2H-4$\lambda^4$-imidazopyridazinyl, or oxazolopyridyl, each substituted with one $R^2$ group, wherein each $R^2$ is —X—C1-C5 alkyl, wherein X is a bond.

Clause 70. The compound according to clause 18, wherein the heteroaryl is imidazopyridyl substituted with one $R^2$ group, wherein $R^2$ is cyano, alkoxy, halogen or —X—C1 C5 alkyl and X is a bond.

Clause 71. The compound according to clause 18, wherein the heteroaryl is imidazopyridyl substituted with two $R^2$ groups, wherein one $R^2$ group is halogen and the second $R^2$ group is —X—C1-C5 alkyl, wherein X is a bond, or halogen.

Clause 72. The compound according to any of clauses 2-71, wherein $R^{3a}$ and $R^{3b}$ are each hydrogen.

Clause 73. The compound according to any of clauses 2-71, wherein $R^{3a}$ and $R^{3b}$ are each deuterium.

Clause 74. The compound according to any of clauses 2-71, wherein one of $R^{3a}$ and $R^{3b}$ is hydrogen and the other is deuterium.

Clause 75. The compound according to any of clauses 2-71, wherein $R^{3a}$ and $R^{3b}$ together are oxo.

Clause 76. The compound according to any of clauses 2-75, wherein $R^4$ is hydrogen.

Clause 77. The compound according to any of clauses 2-75, wherein $R^4$ is methyl.

Clause 78. The compound according to any of clauses 2-77, wherein $R^6$ is hydrogen.

Clause 79. The compound according to any of clauses 2-77, wherein $R^6$ is halogen.

Clause 80. The compound of clause 79, wherein the halogen is chlorine or fluorine.

Clause 81. The compound according to any of clauses 2-77, wherein $R^6$ is C1-C3 alkyl.

Clause 82. The compound according to clause 81, wherein the C1-C3 alkyl is methyl or ethyl.

Clause 83. The compound according to any of clauses 2-77, wherein $R^6$ is alkoxy.

Clause 84. The compound according to clause 83, wherein the alkoxy is methoxy.

Clause 85. The compound according to any of clauses 2-77, wherein $R^6$ is haloalkyl.

Clause 86. The compound according to clause 85, wherein the haloalkyl is trifluoromethyl.

Clause 87. A compound of Formula (I-D):

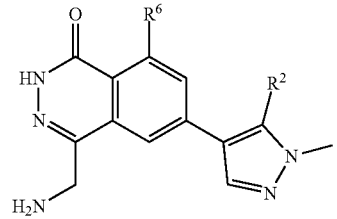

Formula (I-D)

or a pharmaceutically acceptable salt thereof:
wherein:
each Y is independently a bond or —NR$^4$—;
each $R^2$ is independently hydroxy, halogen, cyano, cyanomethyl, —(NR$^4$)$_2$, hydroxyalkyl, alkoxy, —SO$_2$C1-C3alkyl, —X-arC1-C3alkyl, heteroalkyl, C2-C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$, or;

each X is independently a bond, O, S, —NR$^4$— or —NR$^4$C(O)—;

each Z is independently a bond, —SO—, —SO$_2$—, —CH(OH)— or —C(O)—;

each L is independently a bond or C1-C3 alkylene;

each R$^4$ is independently hydrogen or C1-C3 alkyl;

each R$^5$ is independently cyano, oxo, halogen, C1-C3 alkyl, hydroxyalkyl, alkoxy, —X-haloalkyl, —Z-cycloalkyl, —X-arC1-C3 alkyl, X-arC1-C3 alkyl substituted with cyano, —X-L-cycloalkyl, —X-L-heteroaryl optionally substituted with one or more C1-C3alkyl or oxo, or —X-aryl; and R$^6$ is hydrogen, halogen, C1-C3 alkyl, haloalkyl or alkoxy.

Clause 88. The compound of clause 1, wherein the compound is:

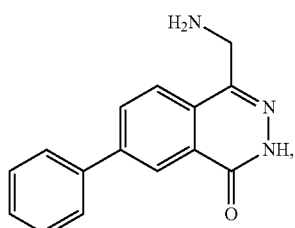

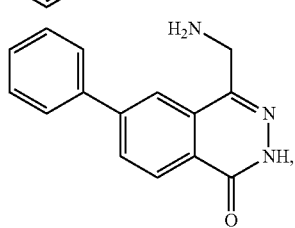

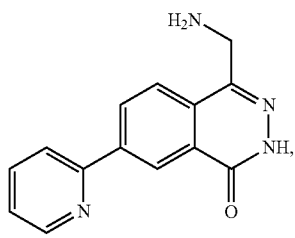

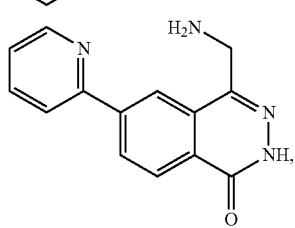

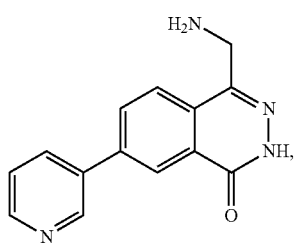

479
-continued
480
-continued
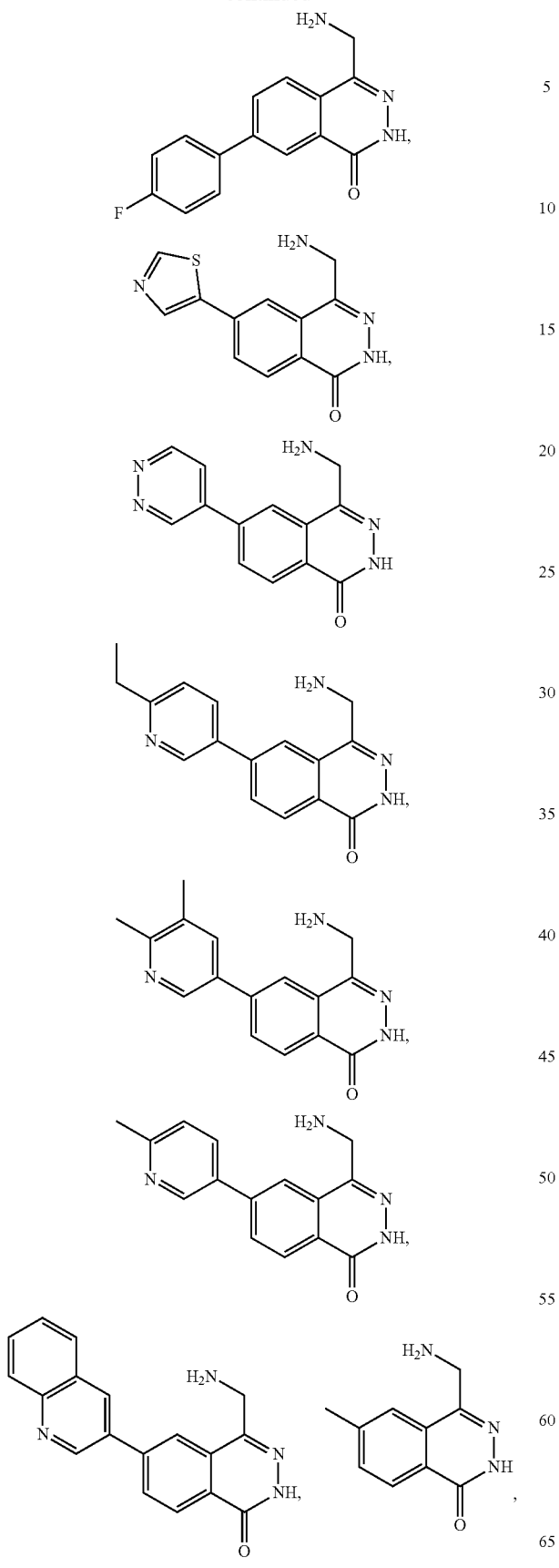
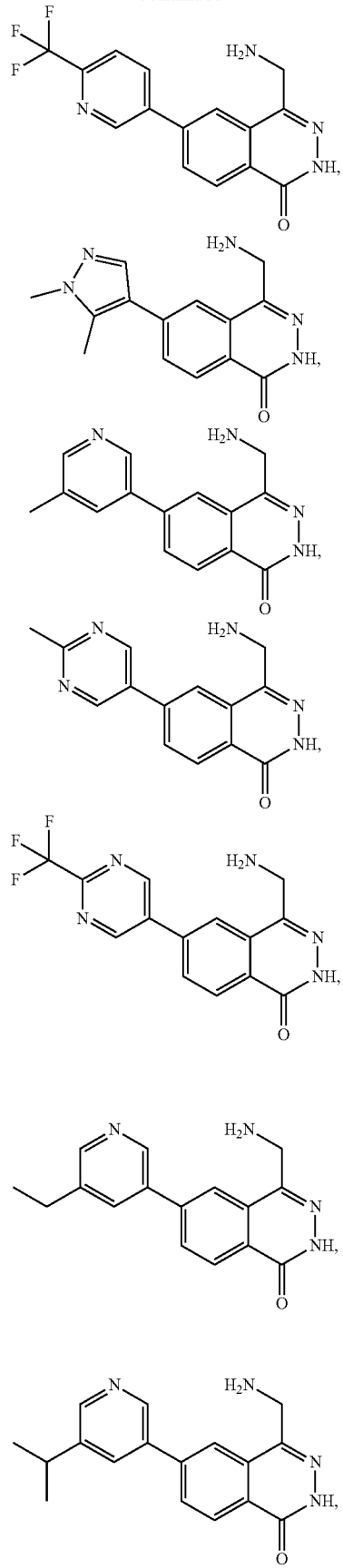

481
-continued
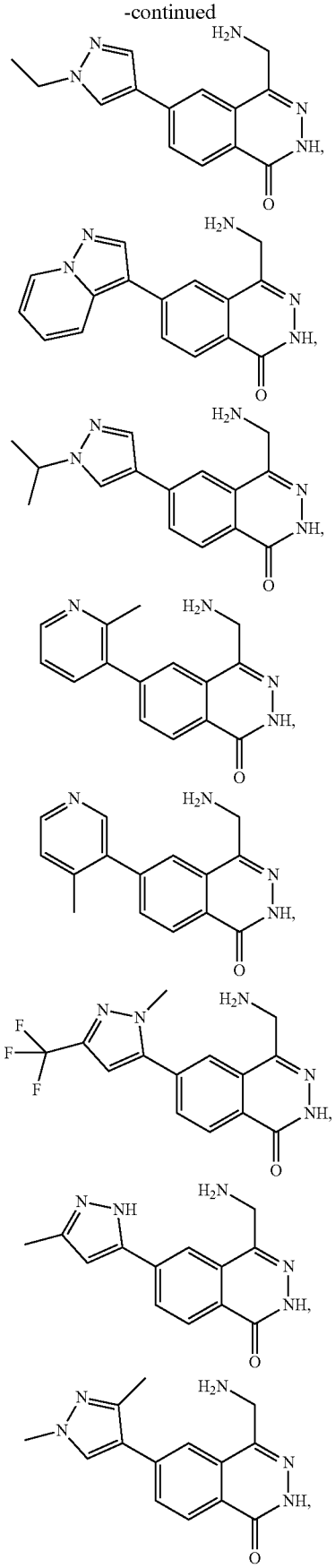
482
-continued
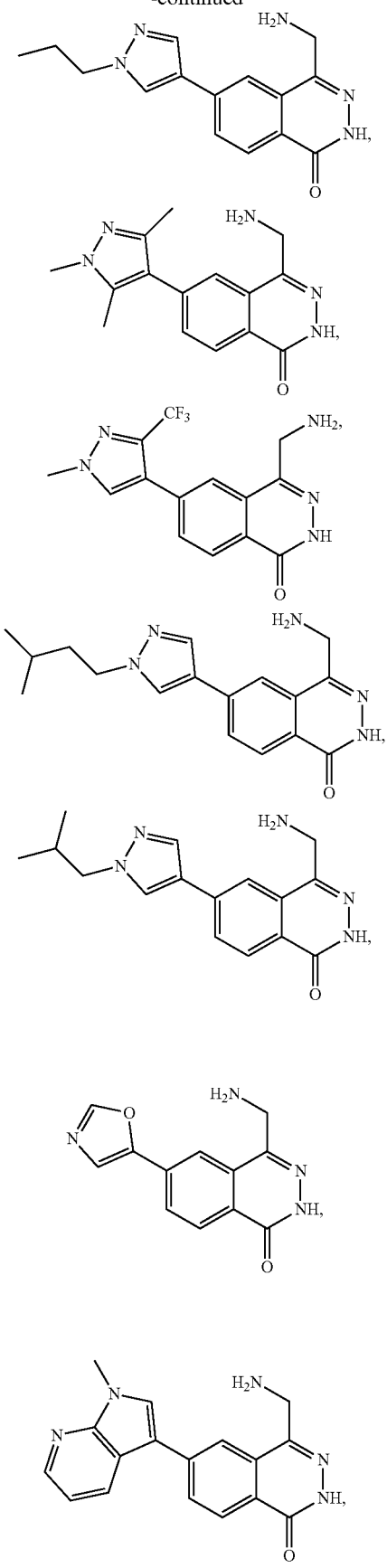

483
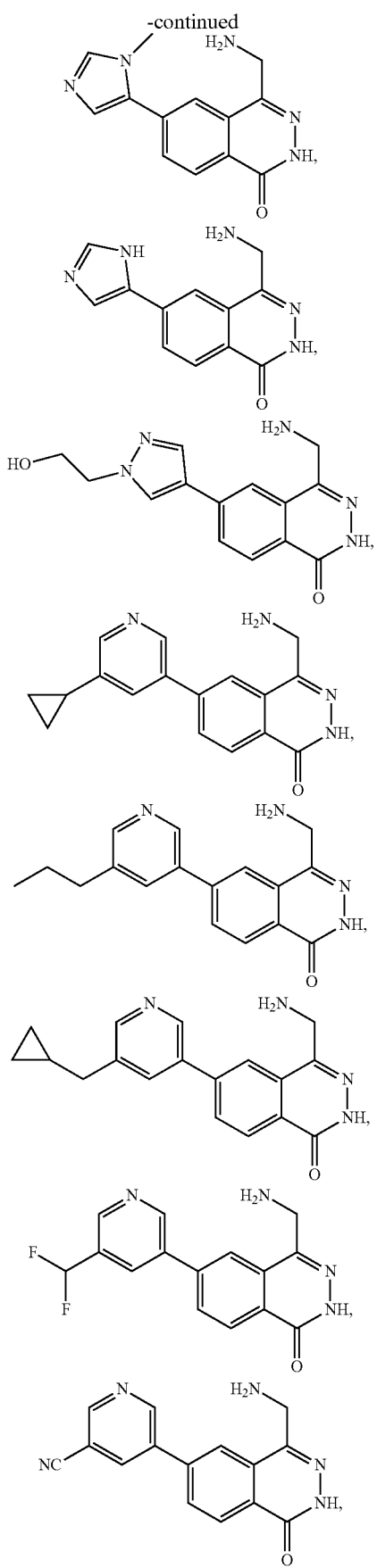
484
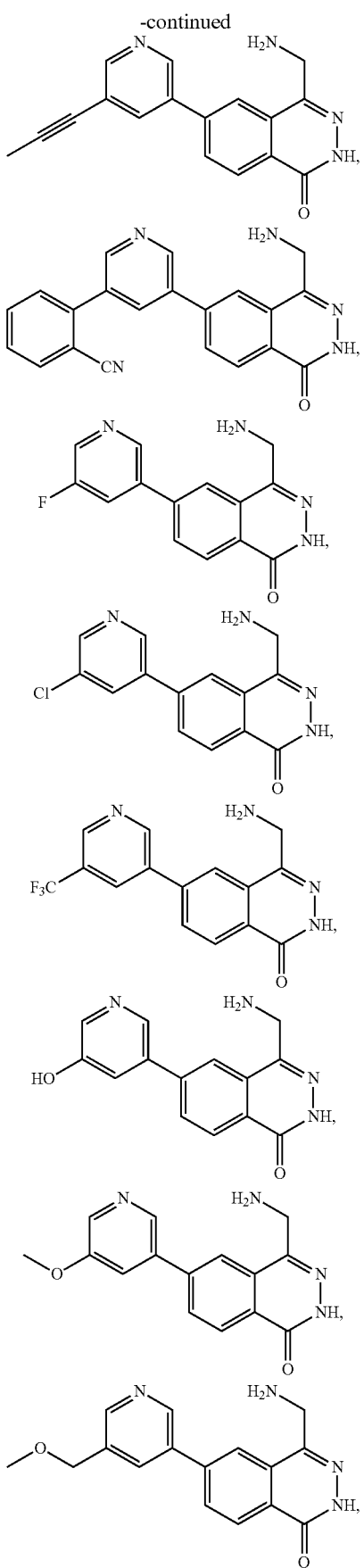

485
-continued
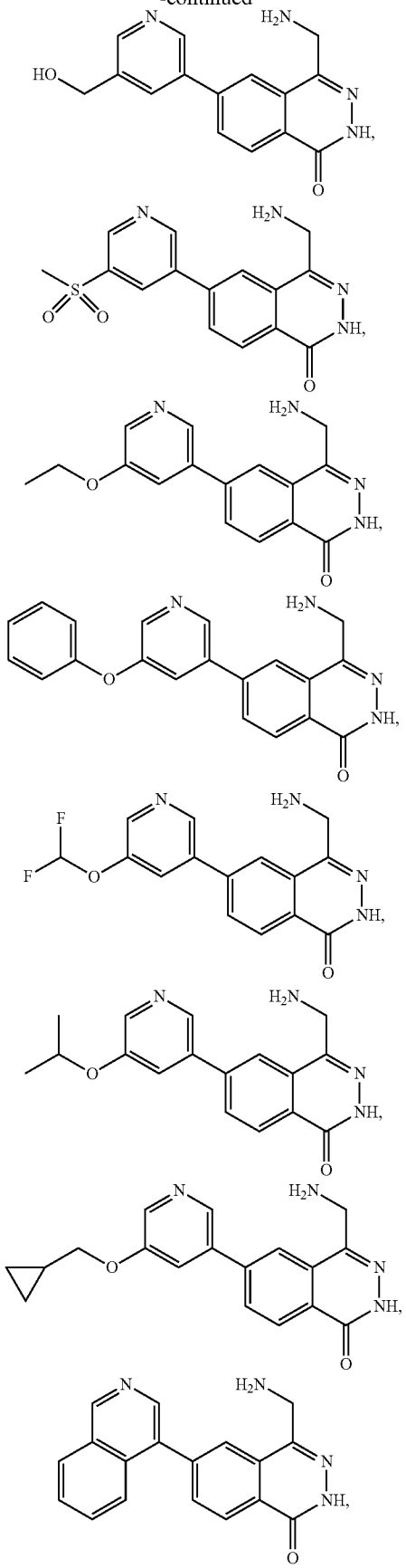
486
-continued
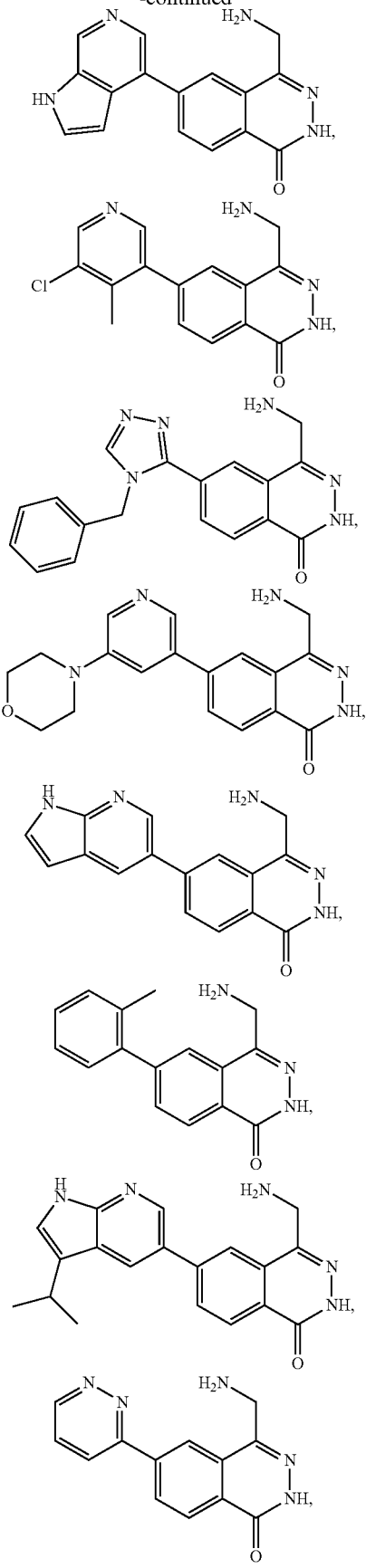

487
-continued
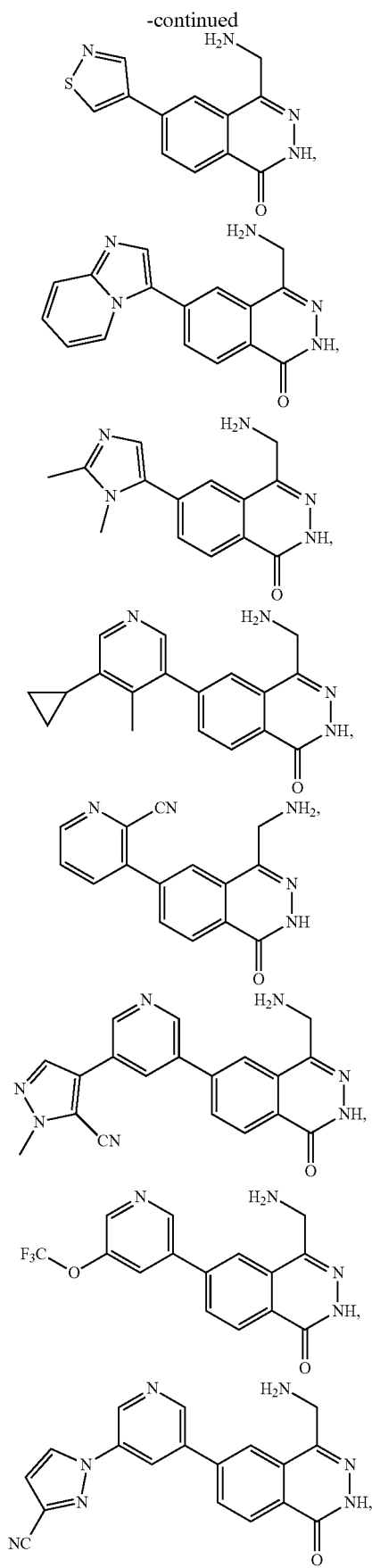
488
-continued
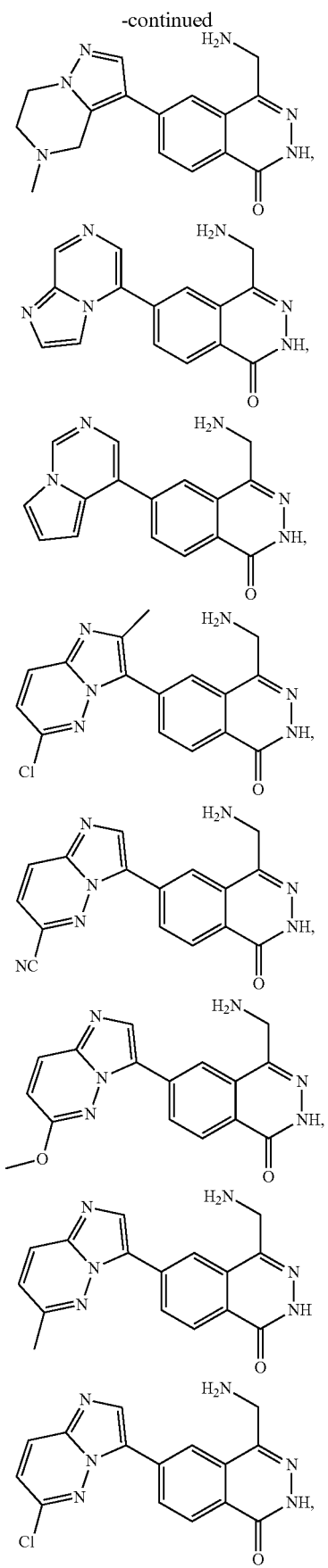

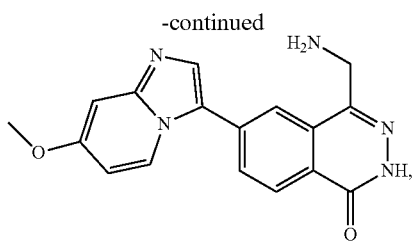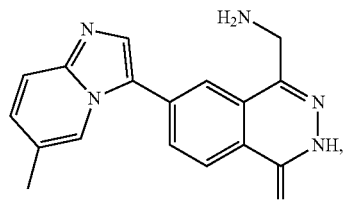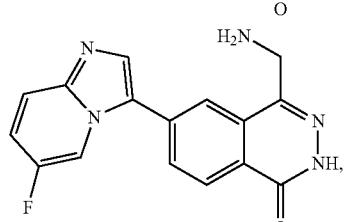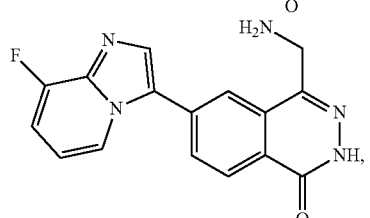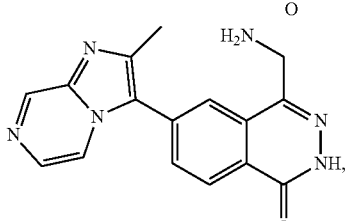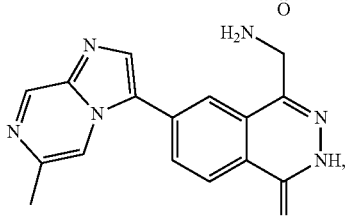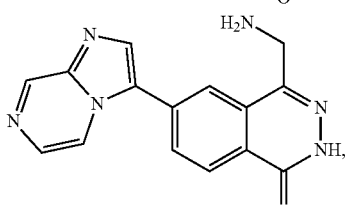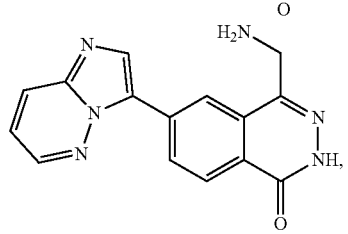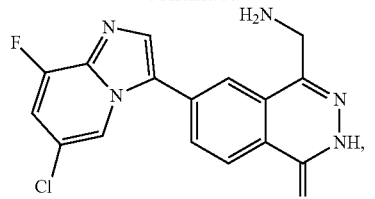

-continued
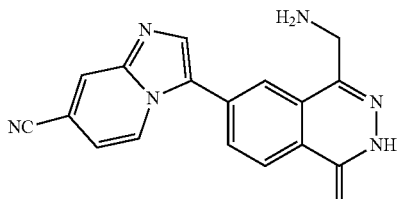
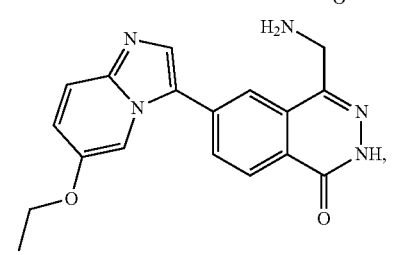
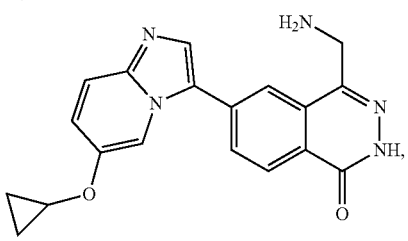
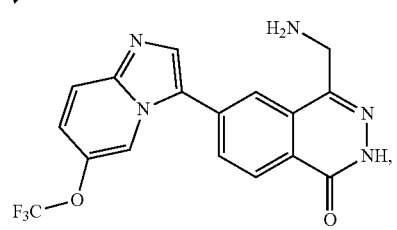
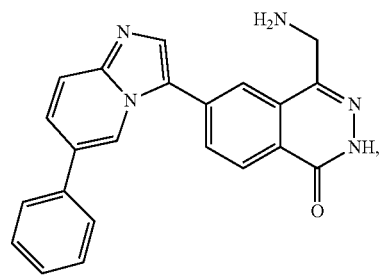
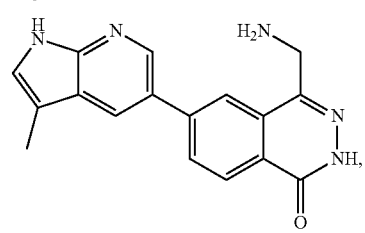
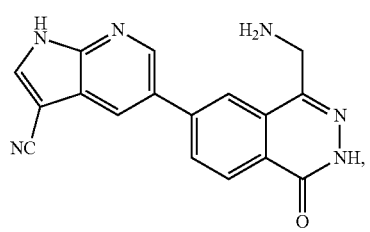
-continued
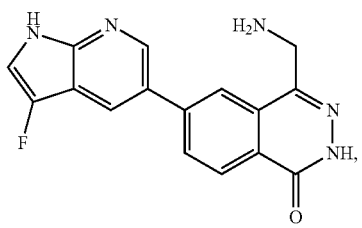
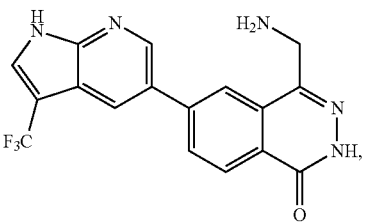
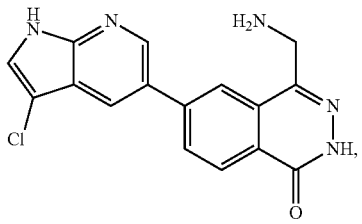
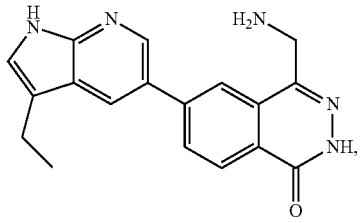
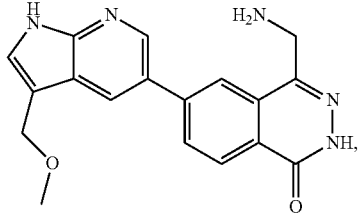
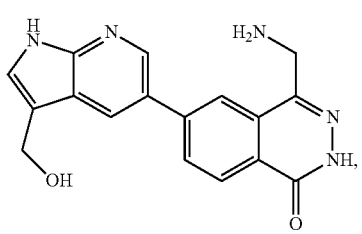
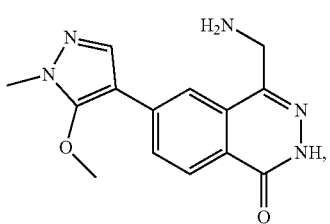

493
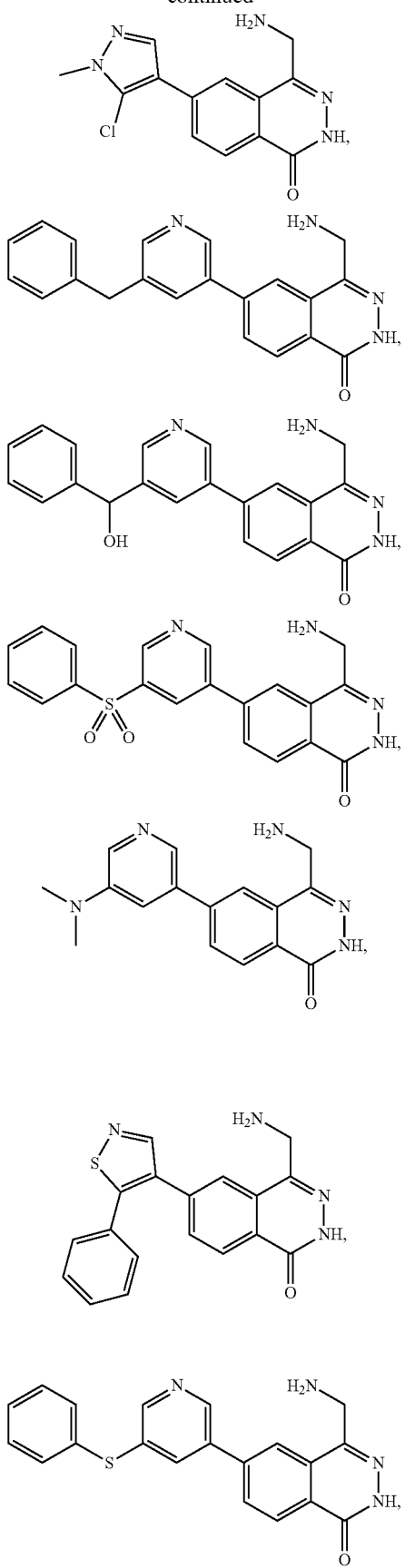
494
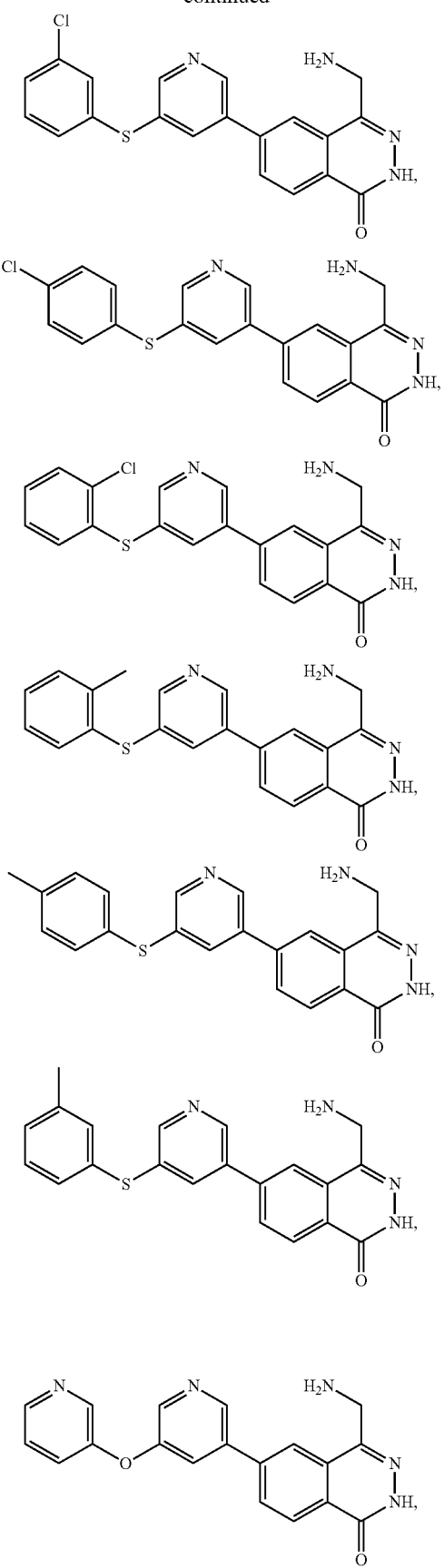

495
-continued
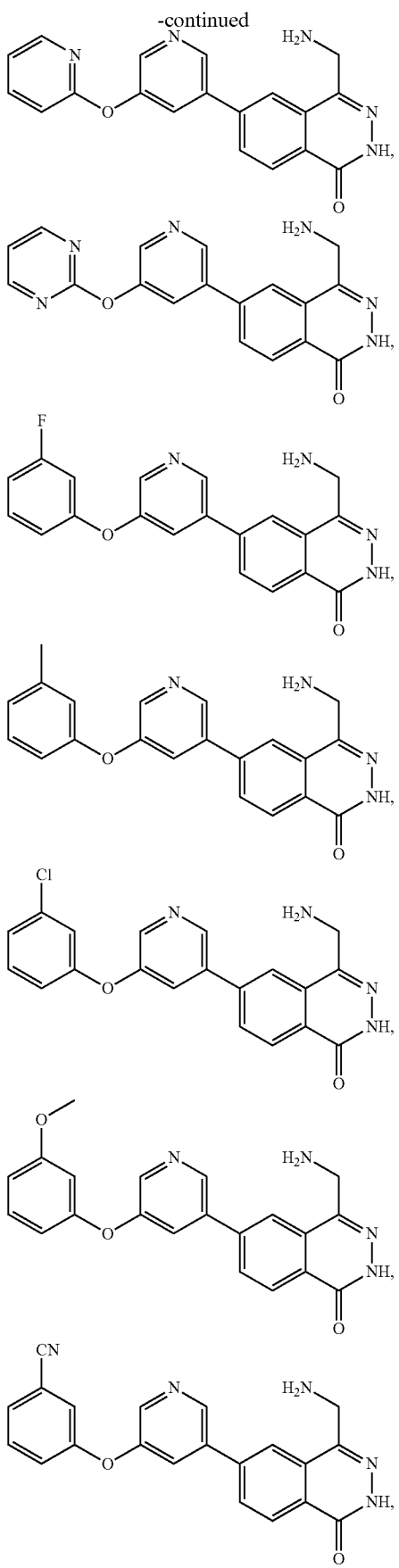
496
-continued
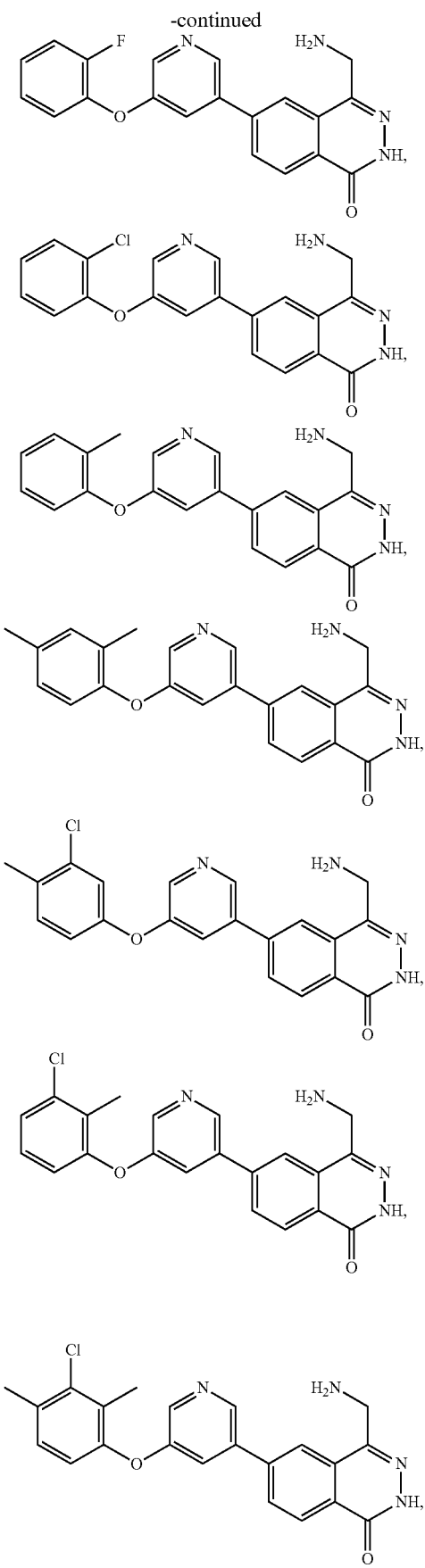

497
-continued
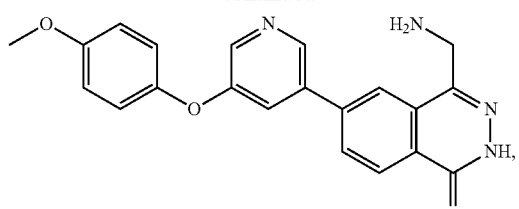
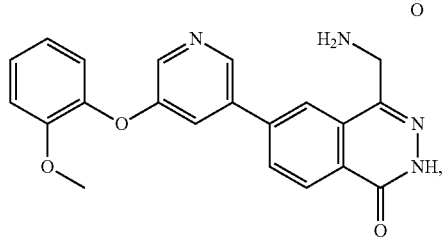
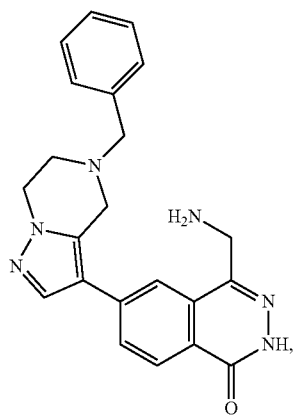
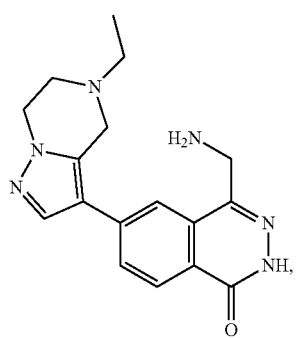
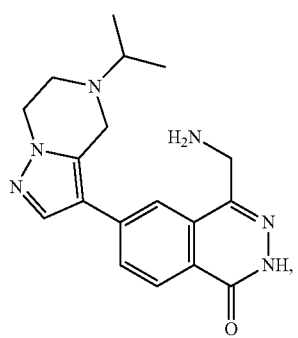
498
-continued
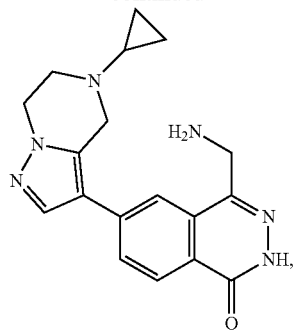
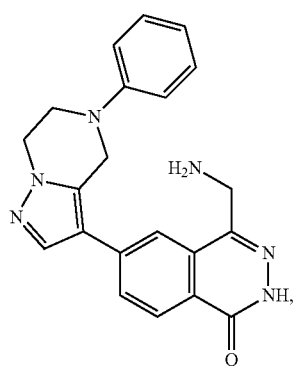
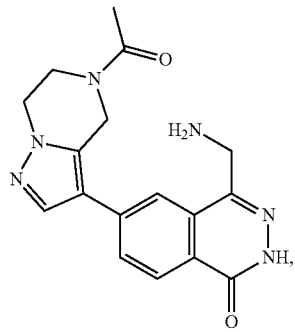
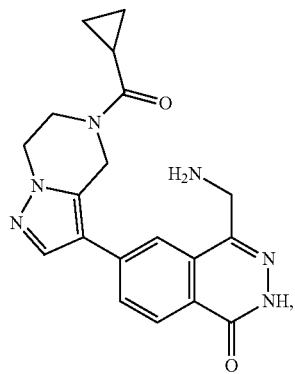

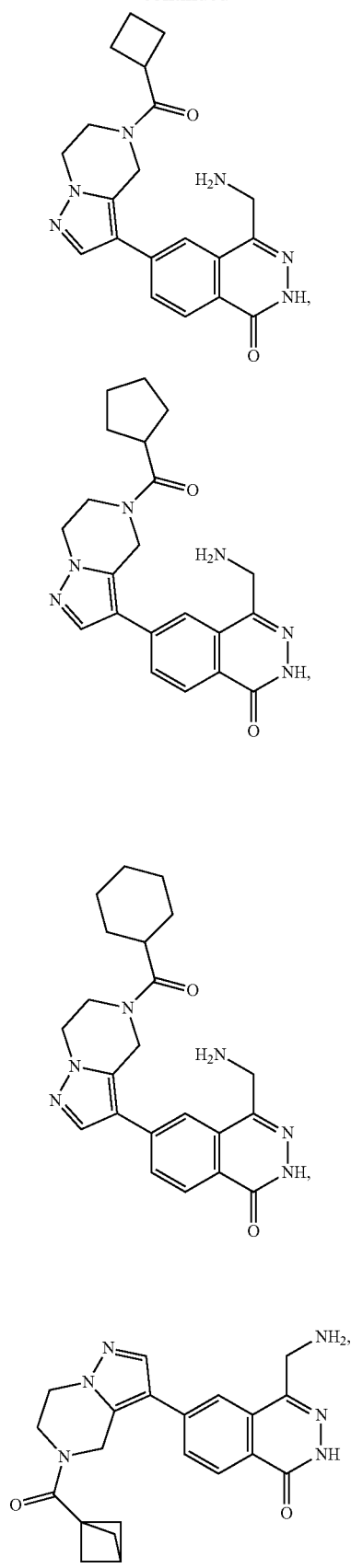
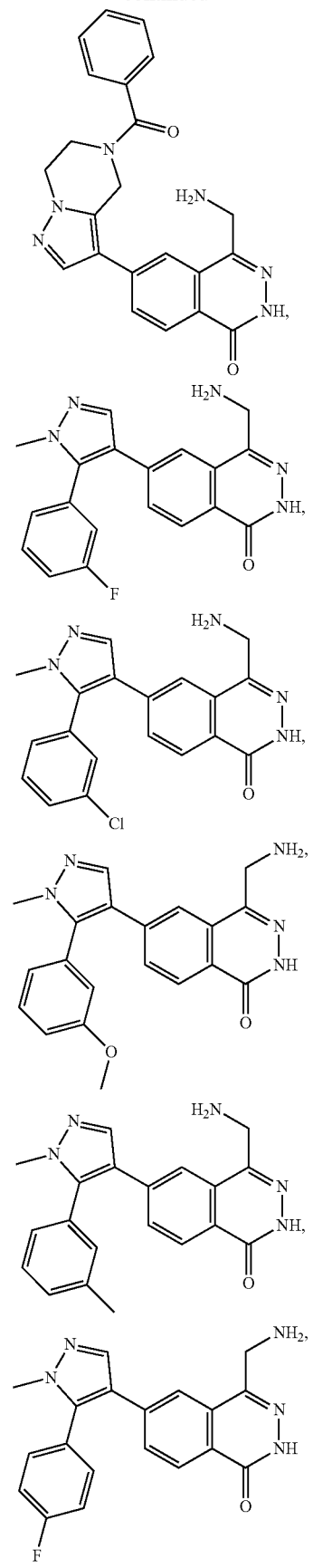

501
-continued
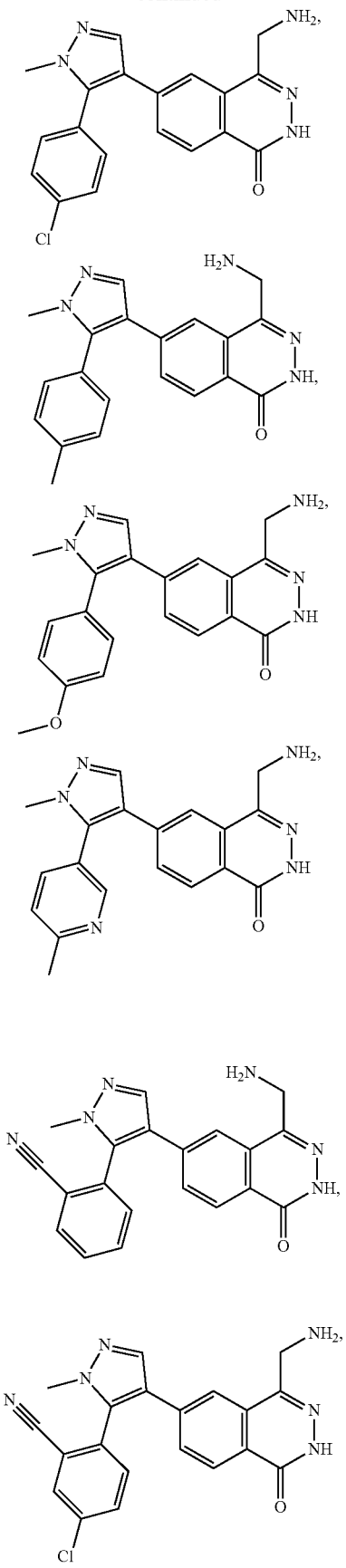
502
-continued
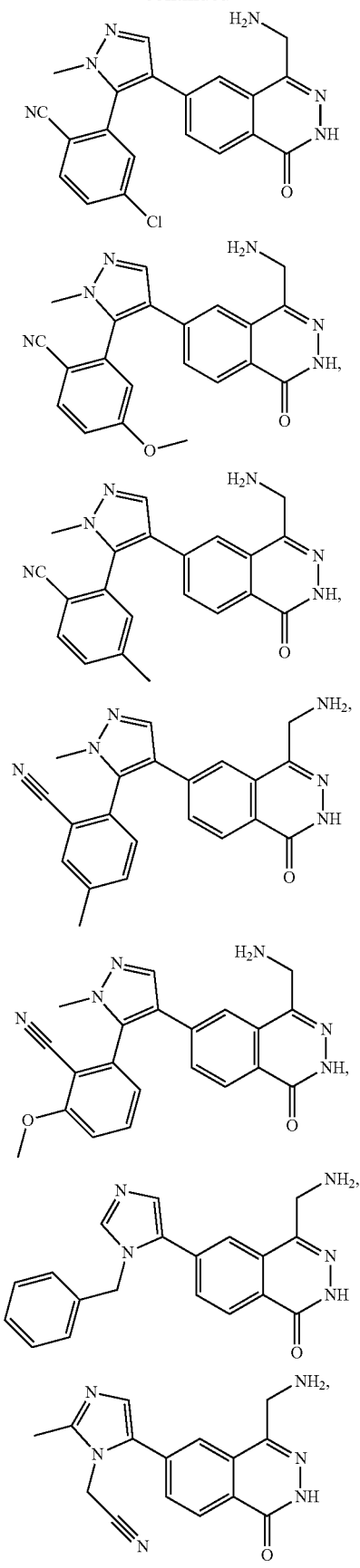

503
-continued
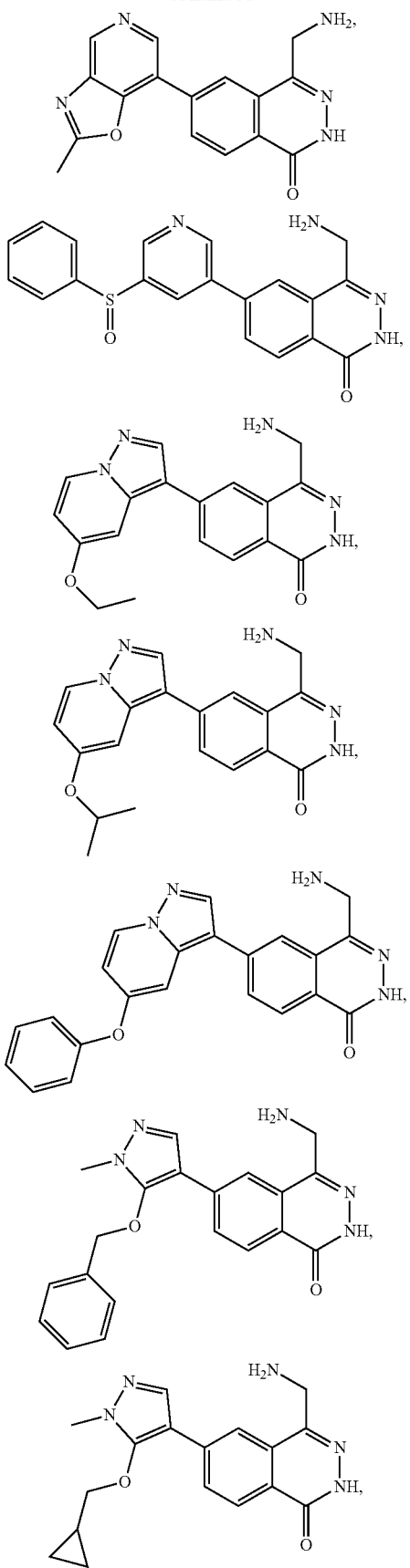
504
-continued
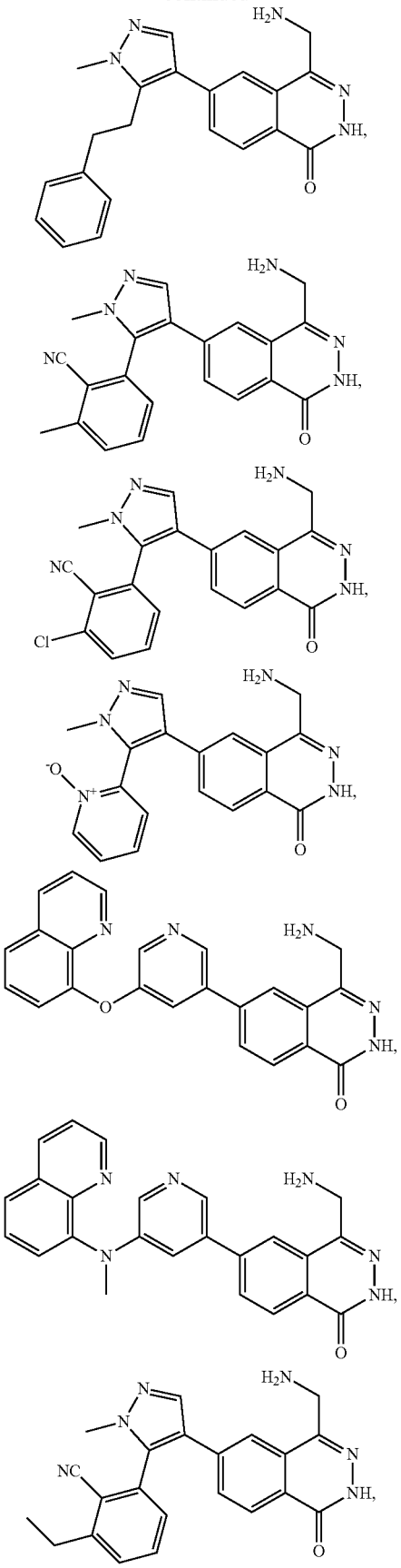

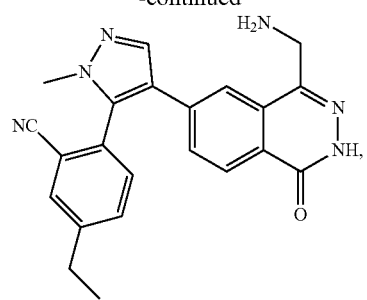
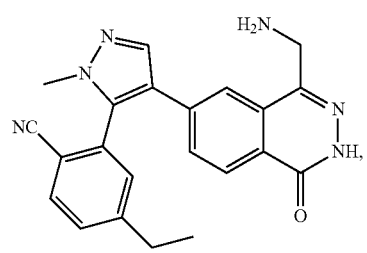
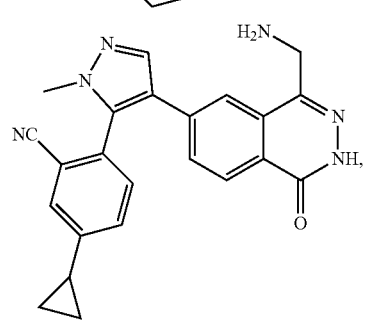
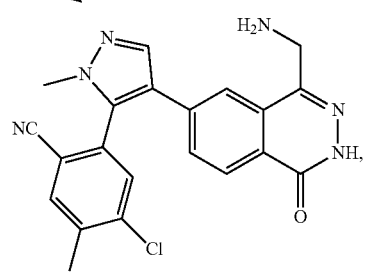
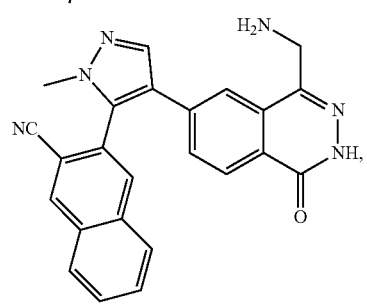
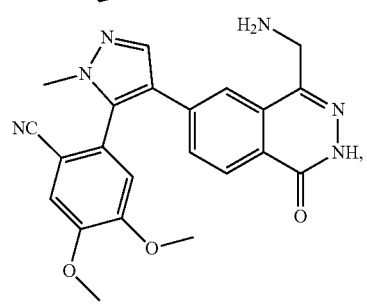
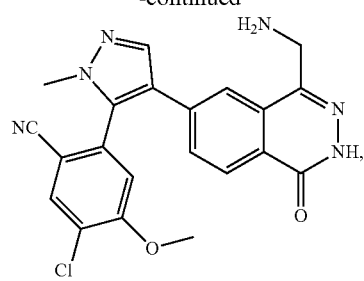
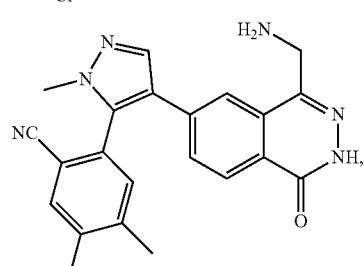
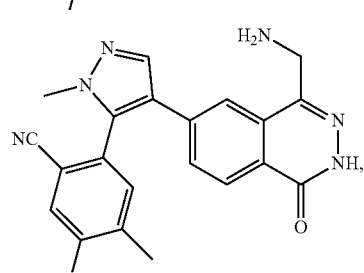
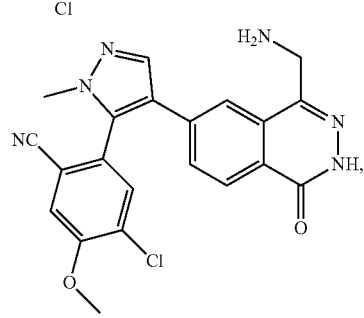
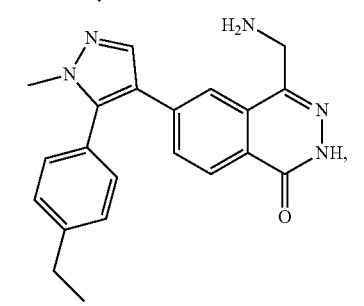
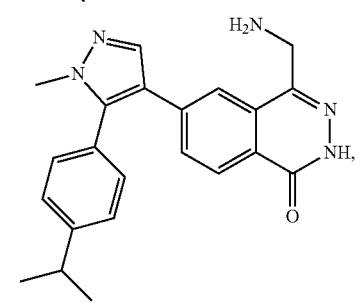

507
-continued
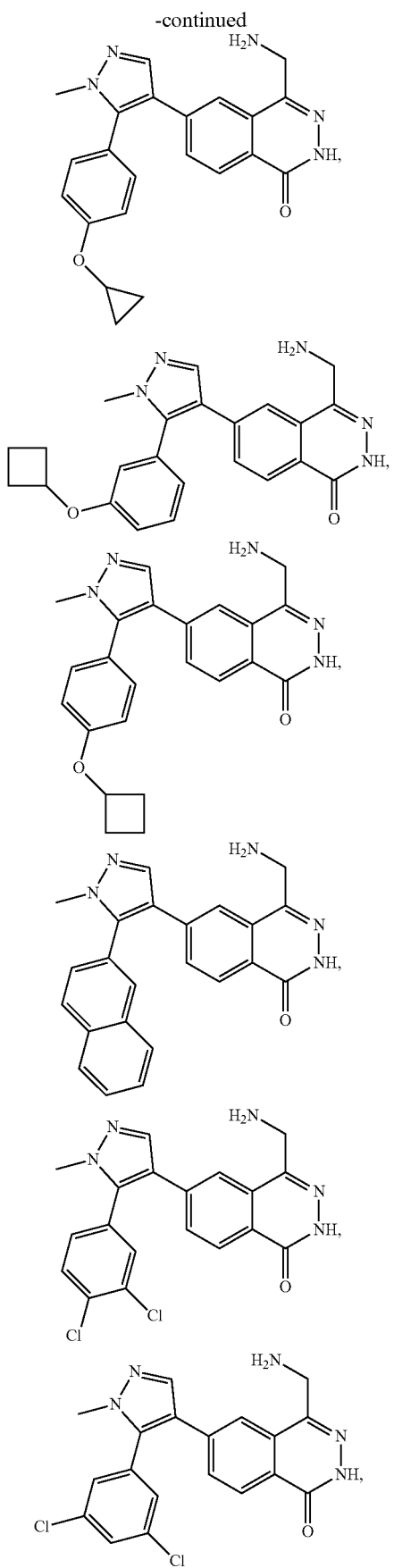
508
-continued
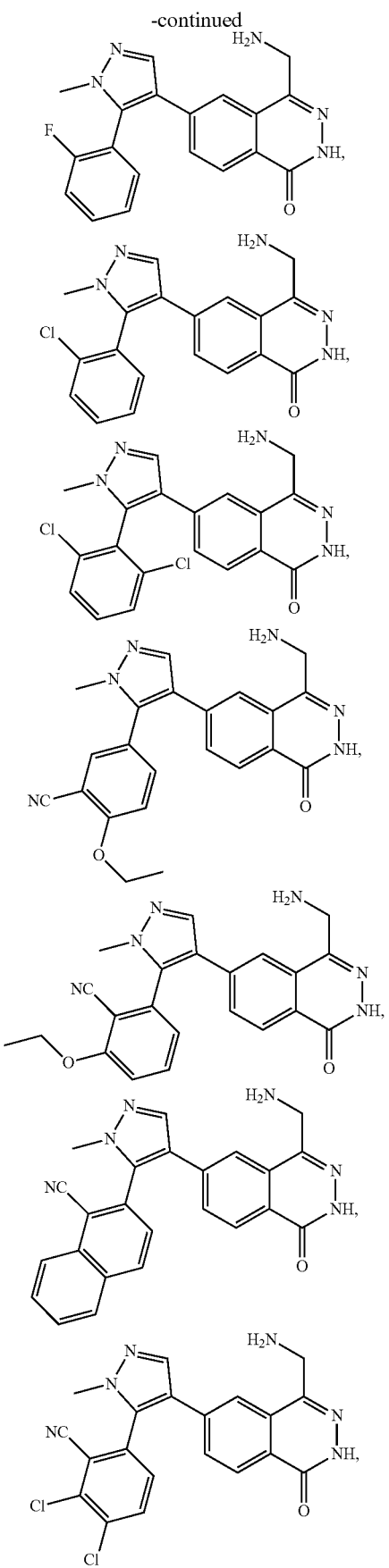

-continued
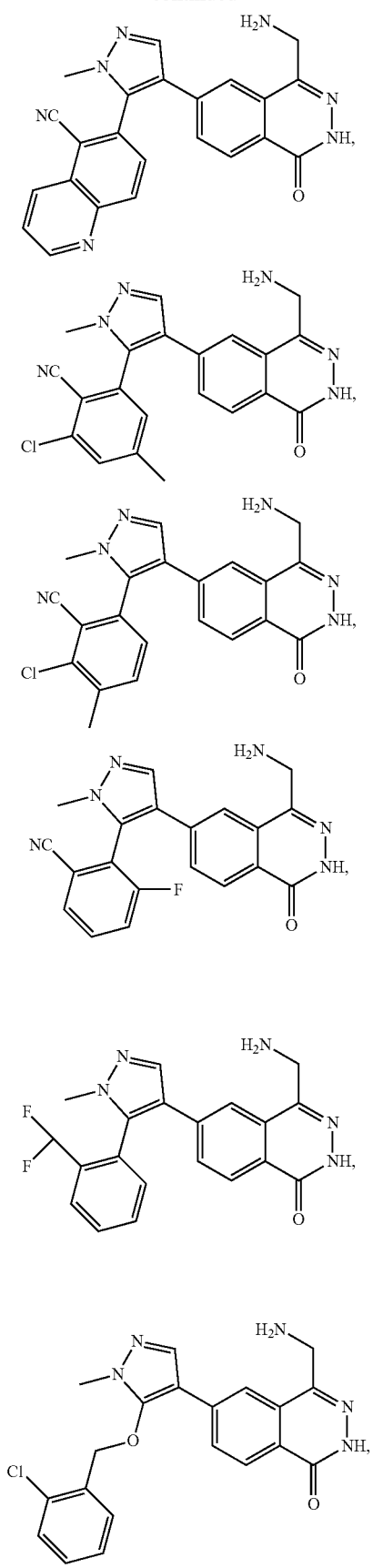
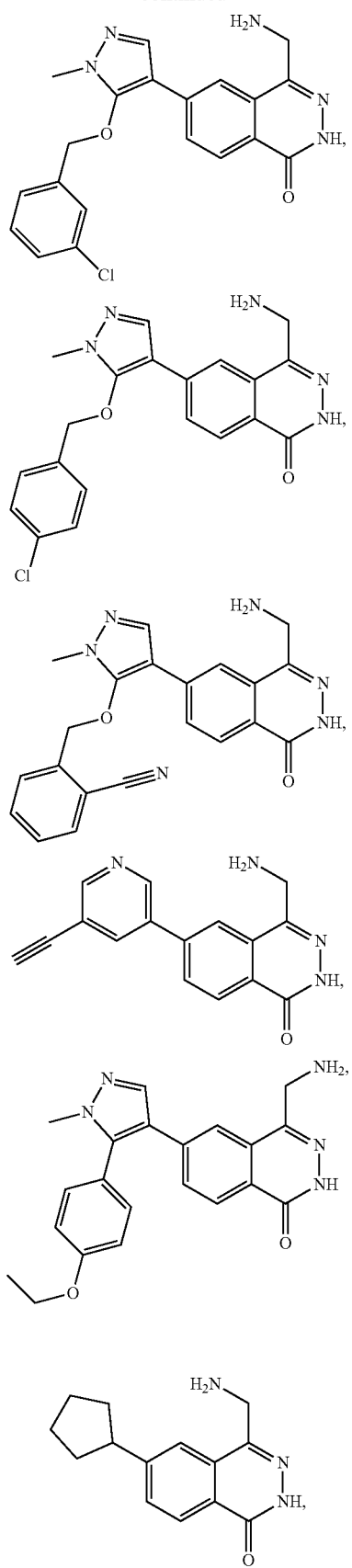

511
-continued
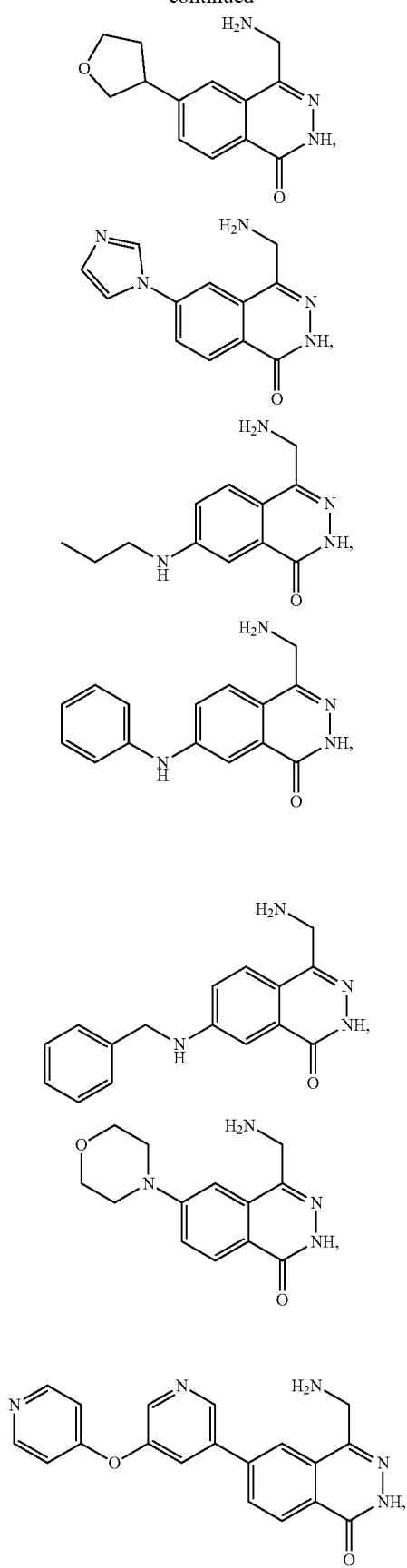
512
-continued
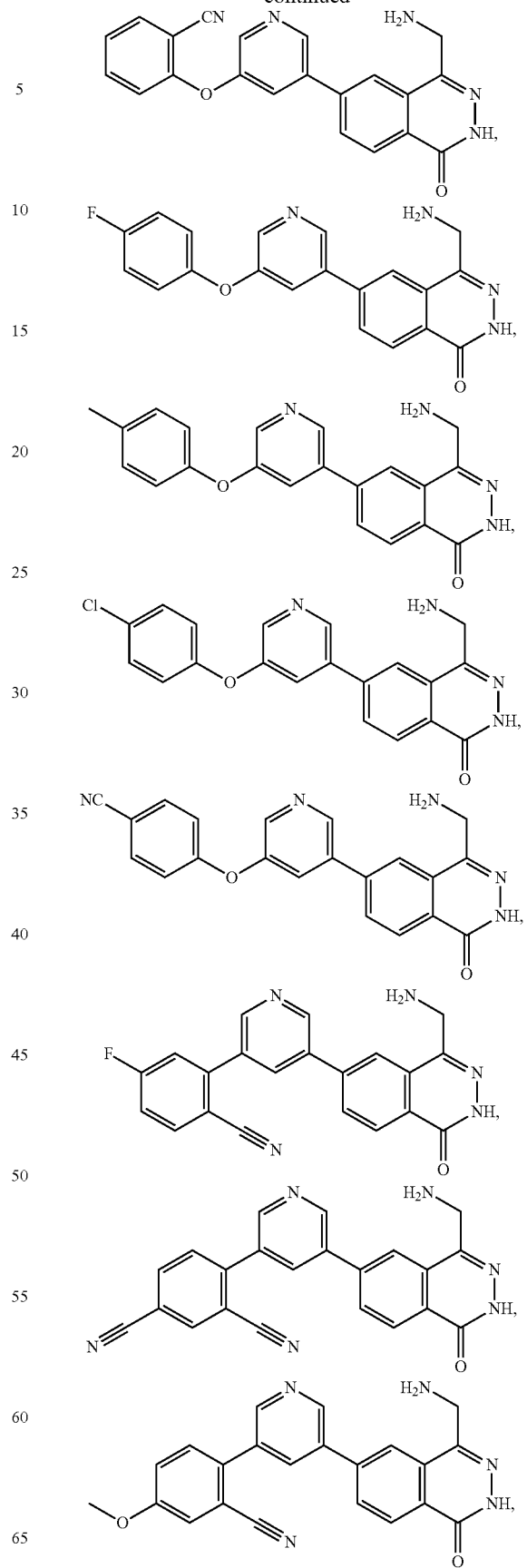

513
-continued
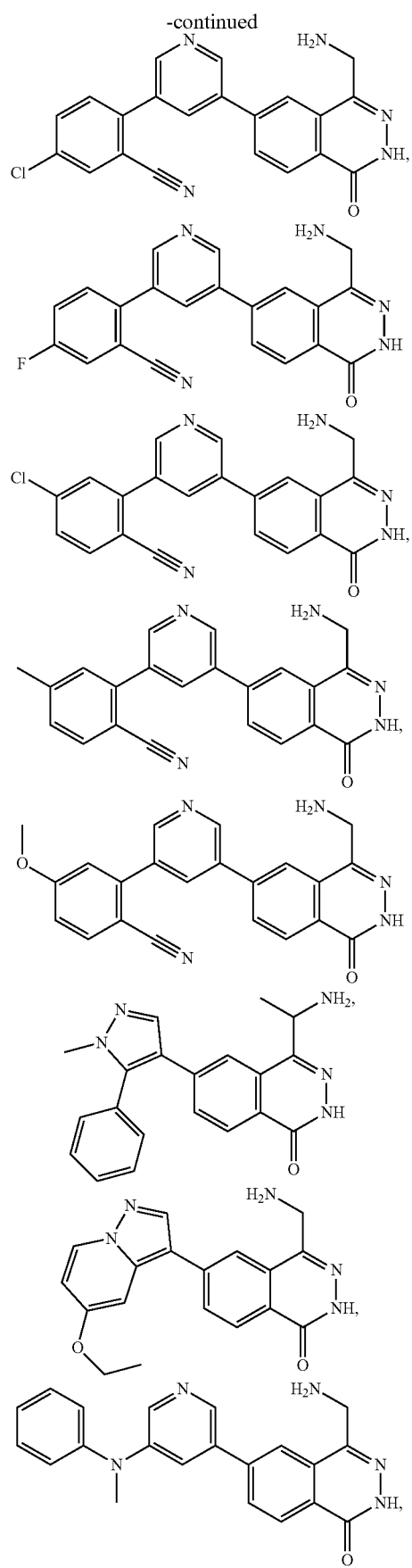
514
-continued
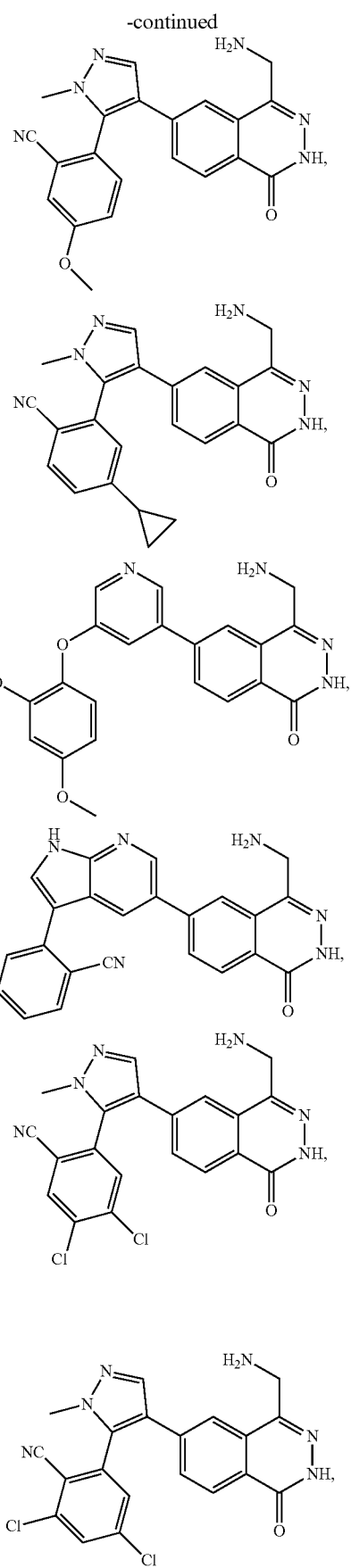

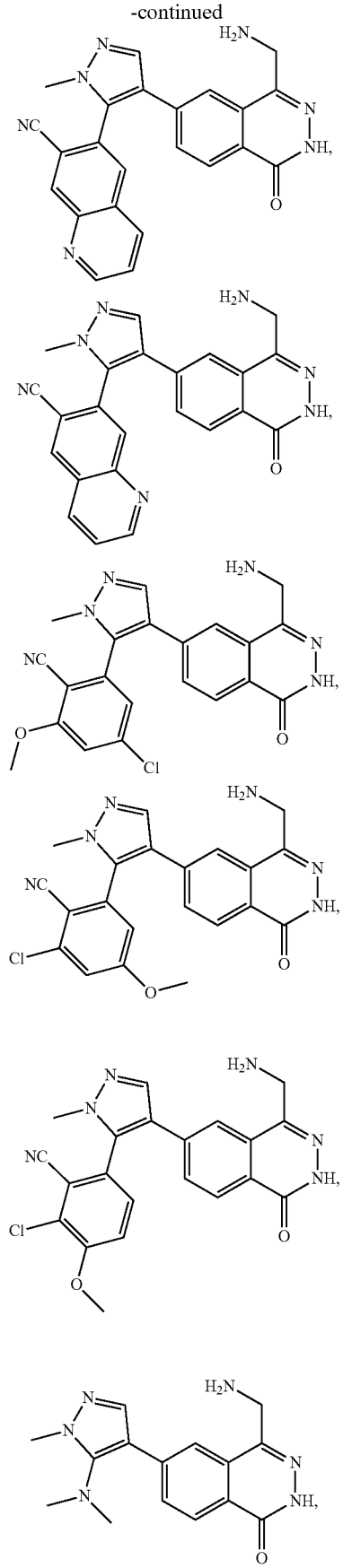
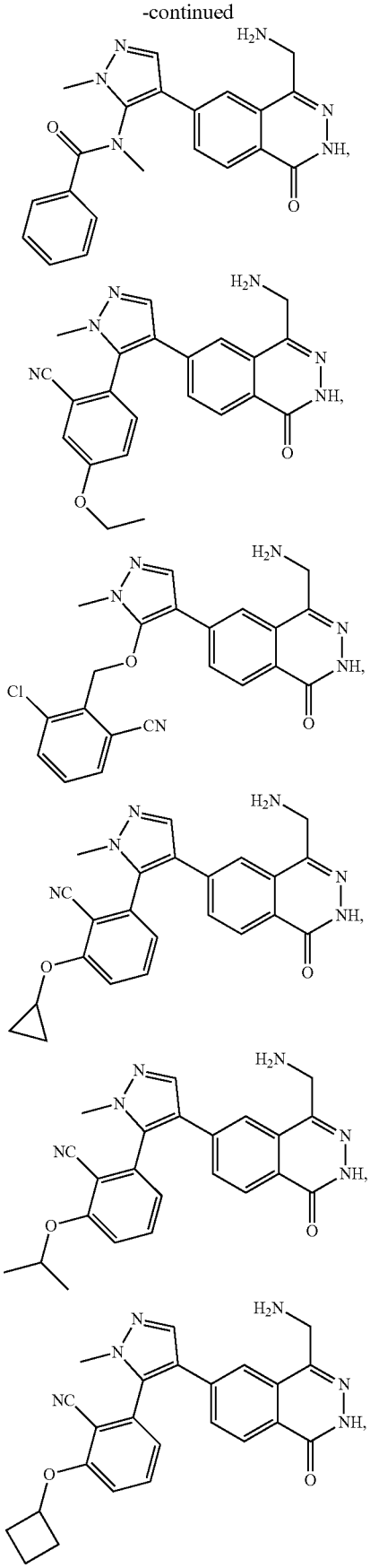

517
-continued
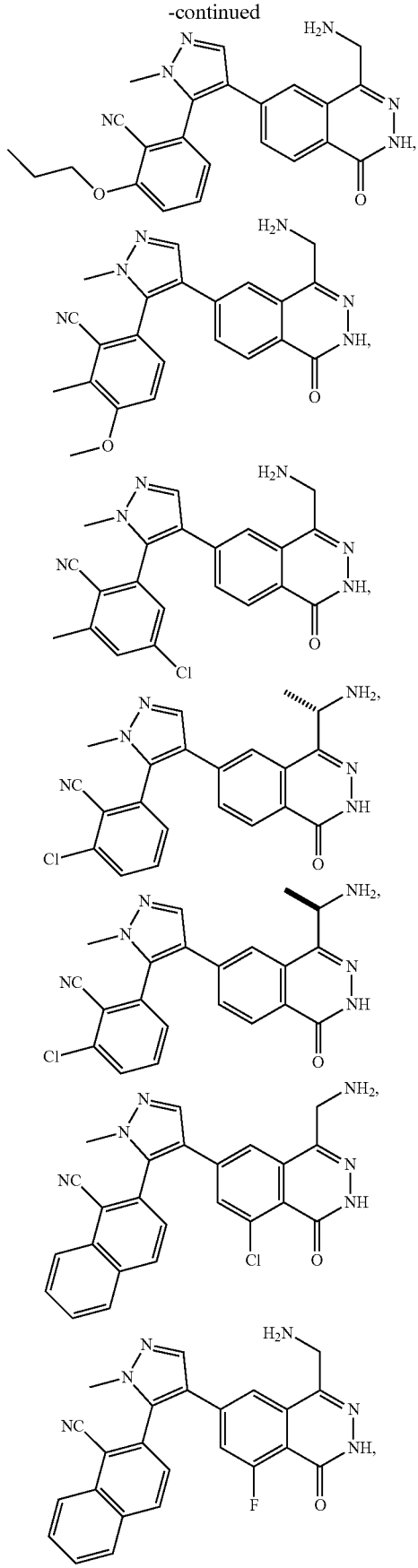
518
-continued
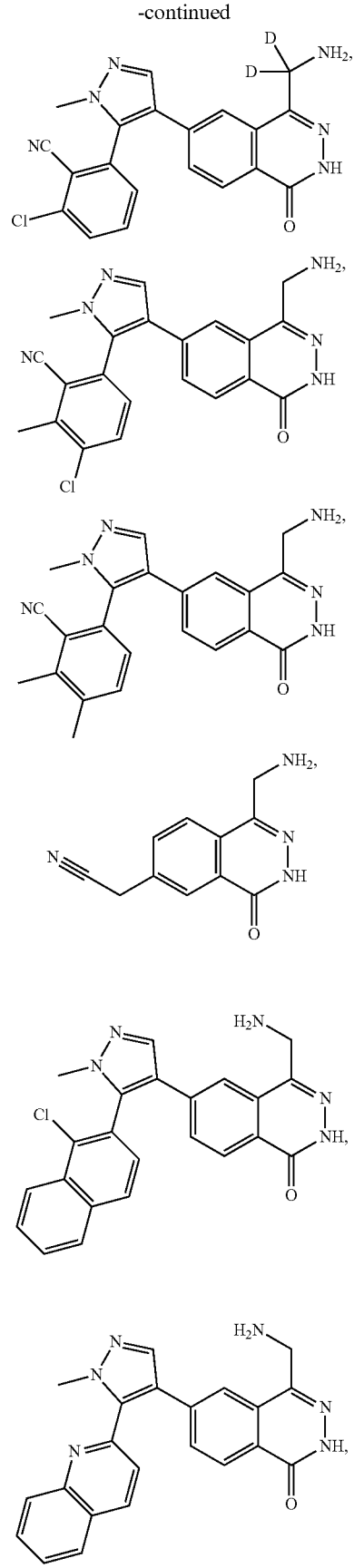

519
-continued
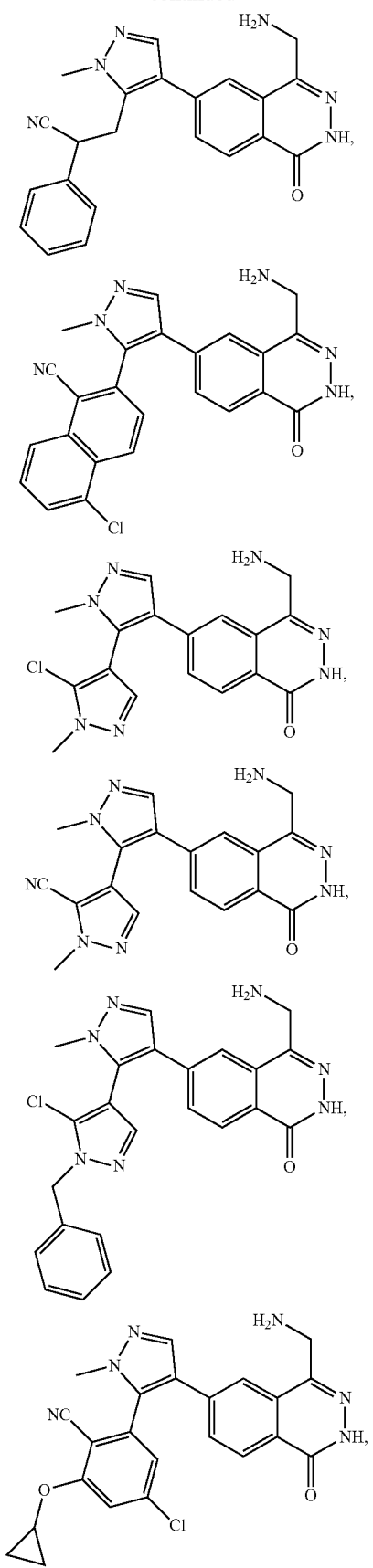
520
-continued
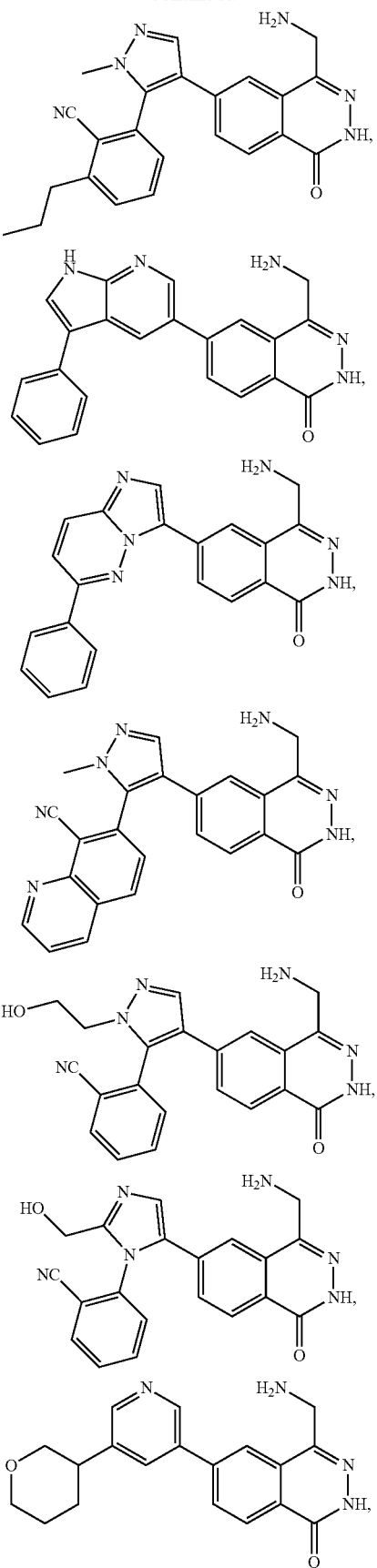

521
-continued
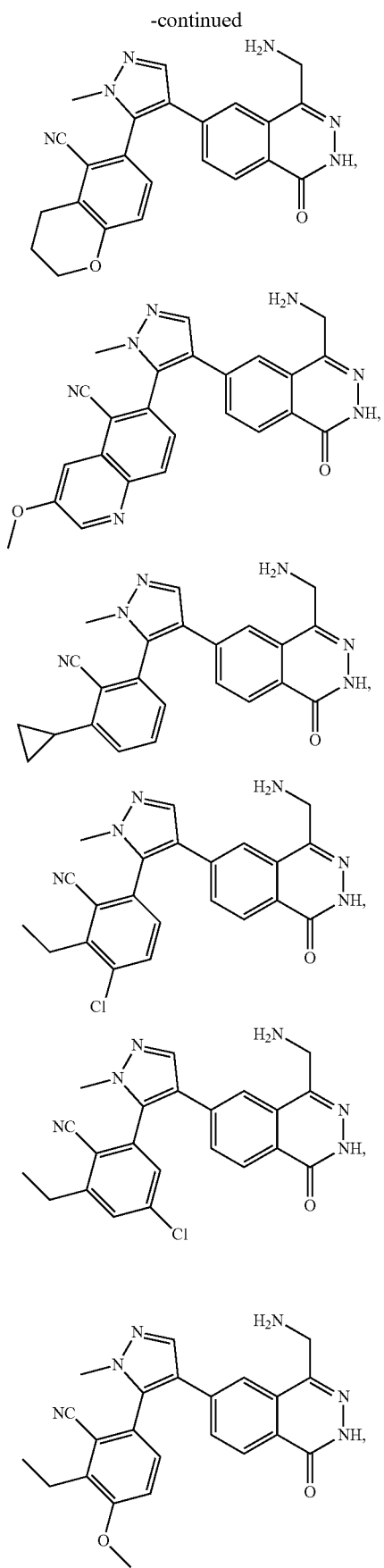
522
-continued
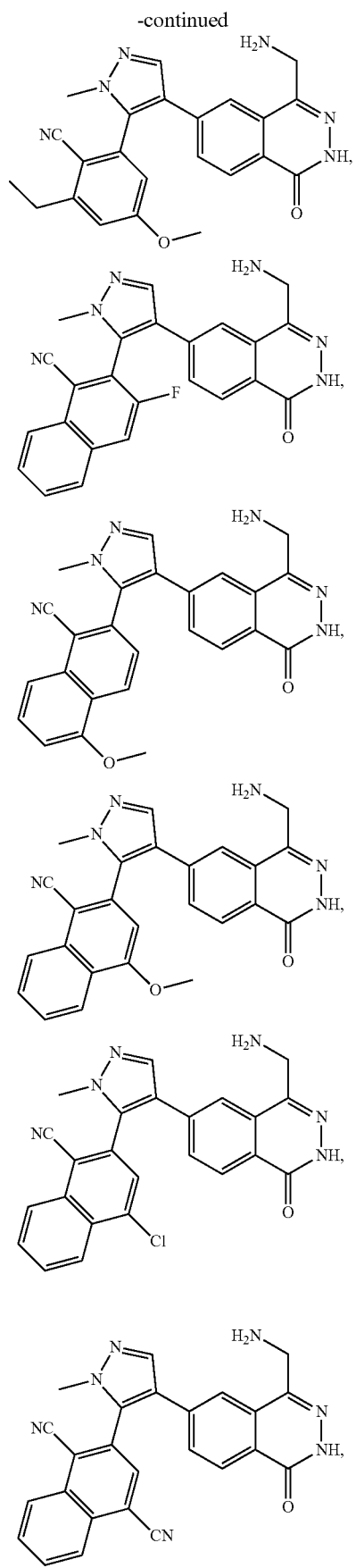

523
-continued
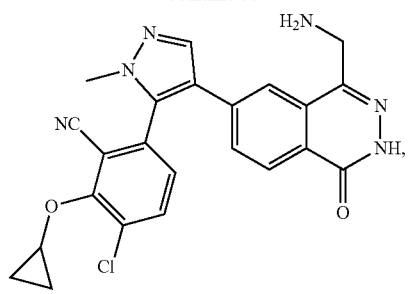
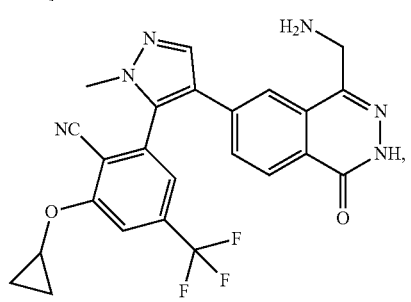
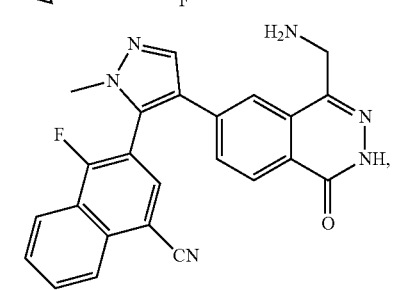
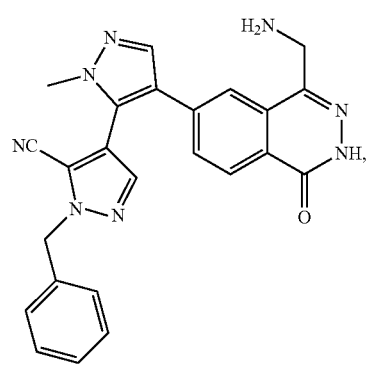
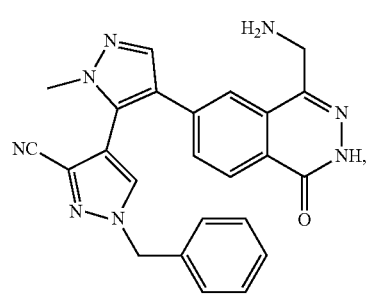
524
-continued
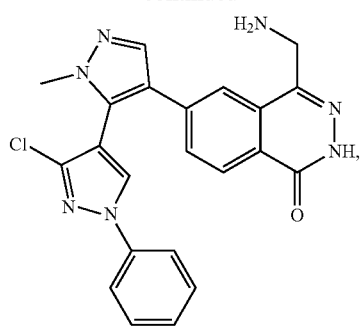
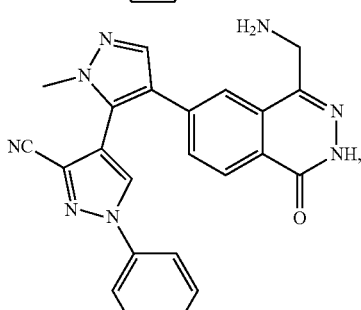
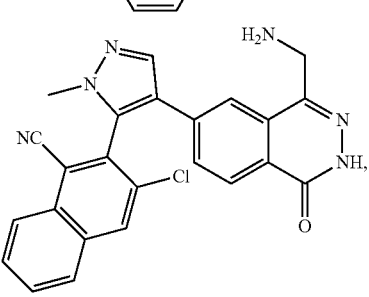
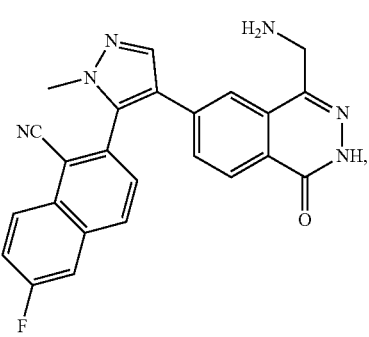
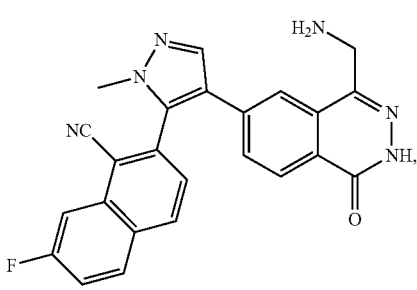

525
-continued
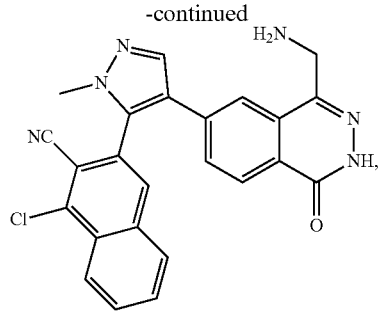
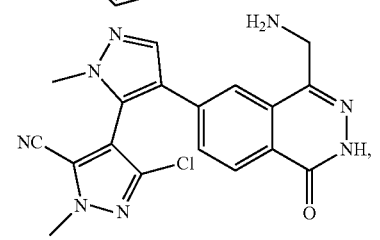
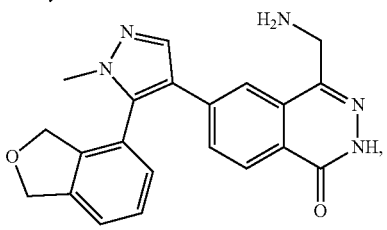
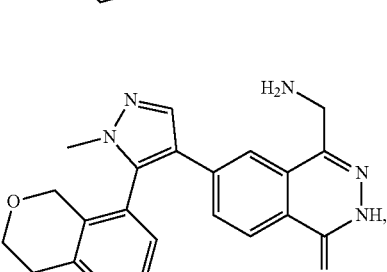
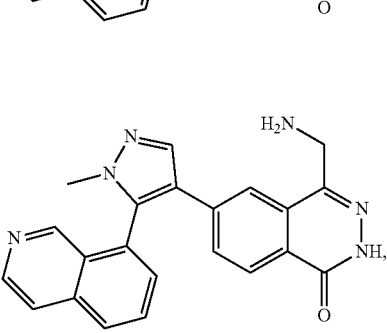
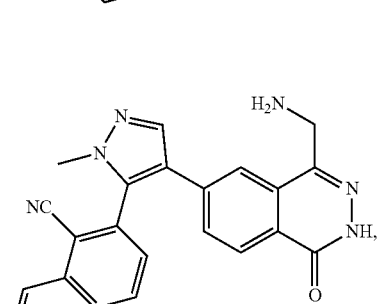
526
-continued
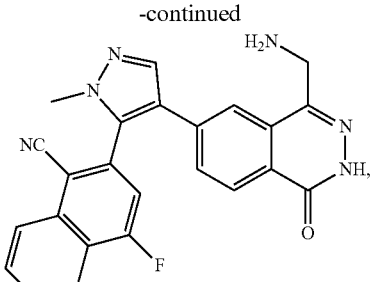
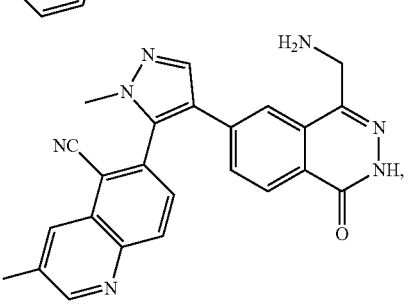
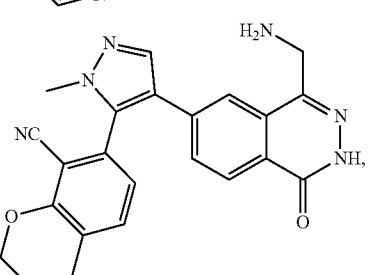
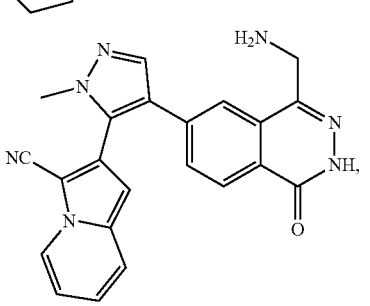
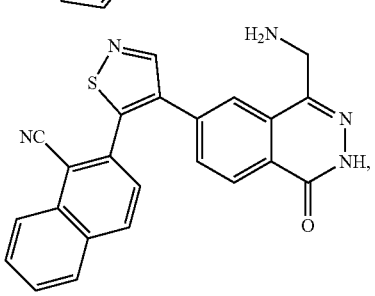
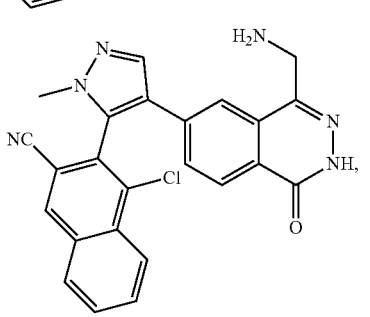

527
-continued
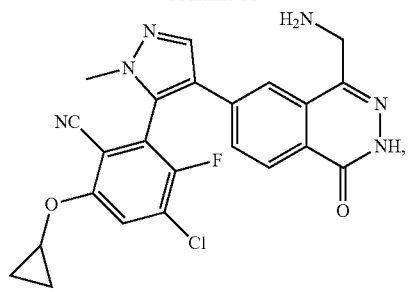
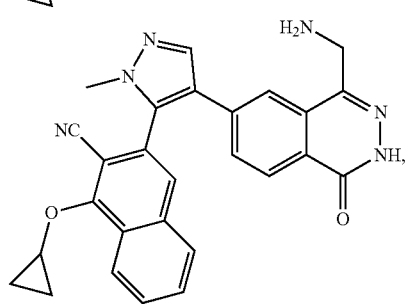
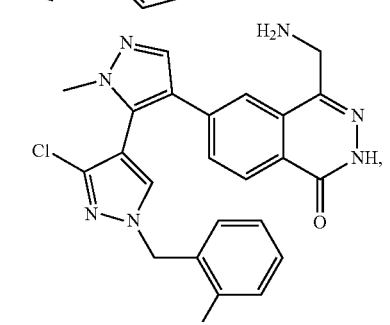
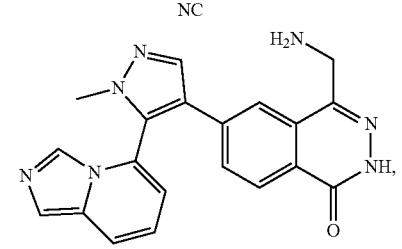
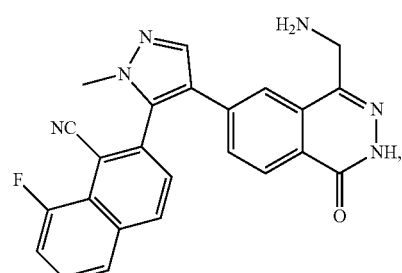
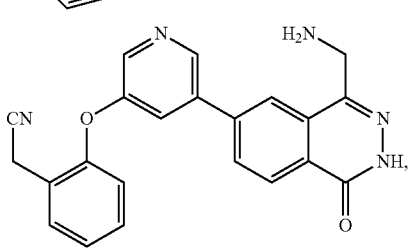
528
-continued
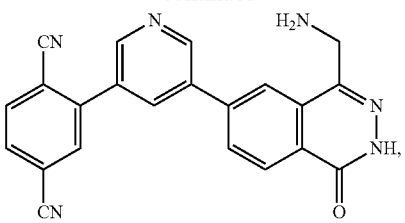
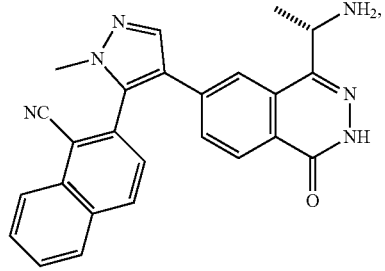
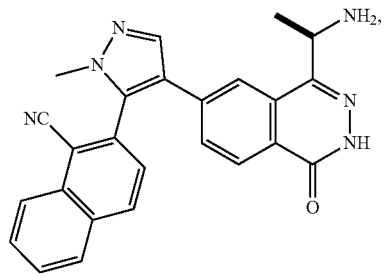
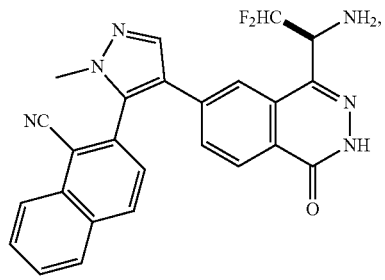
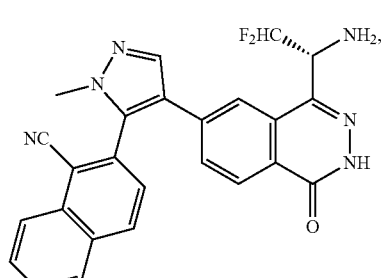
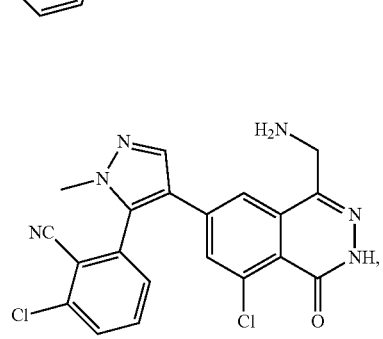

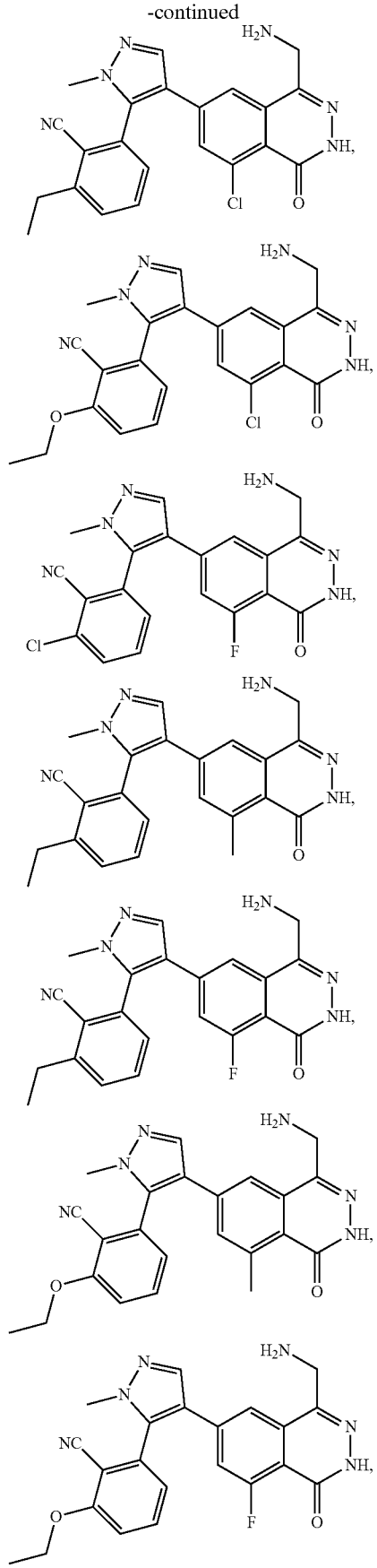
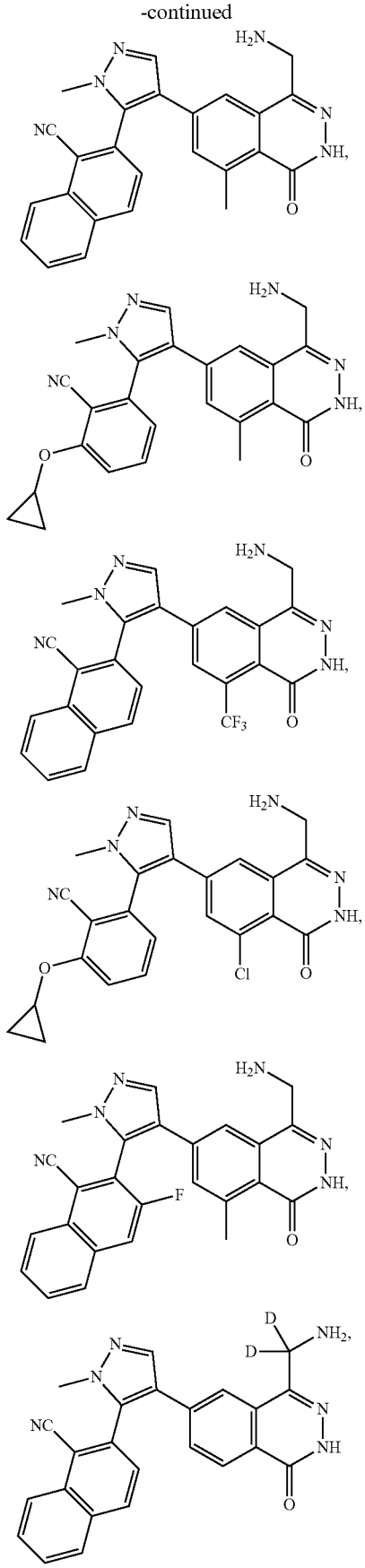

531
-continued
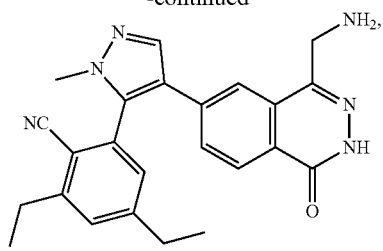
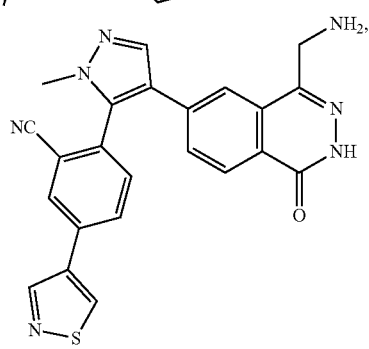
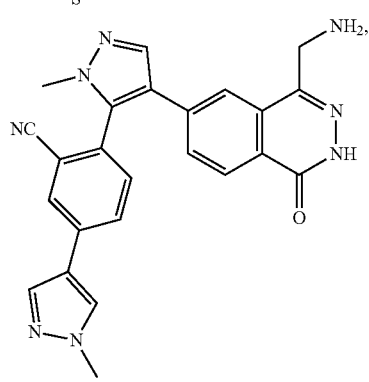
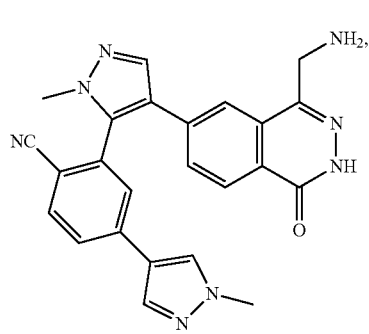
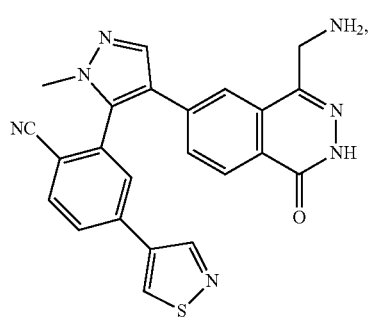
532
-continued
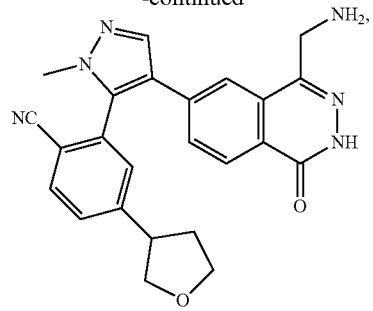
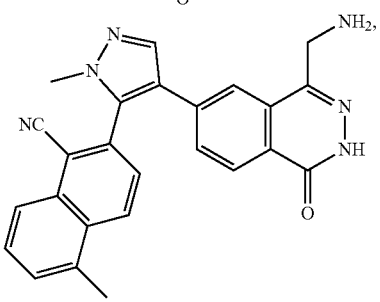
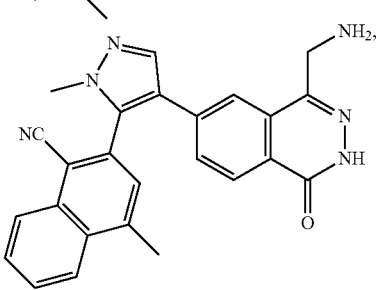
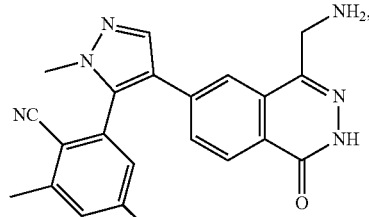
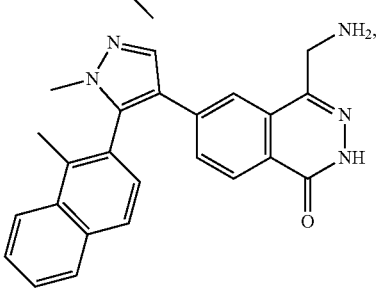
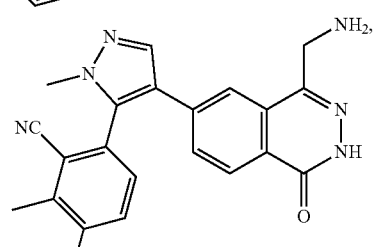

533
-continued
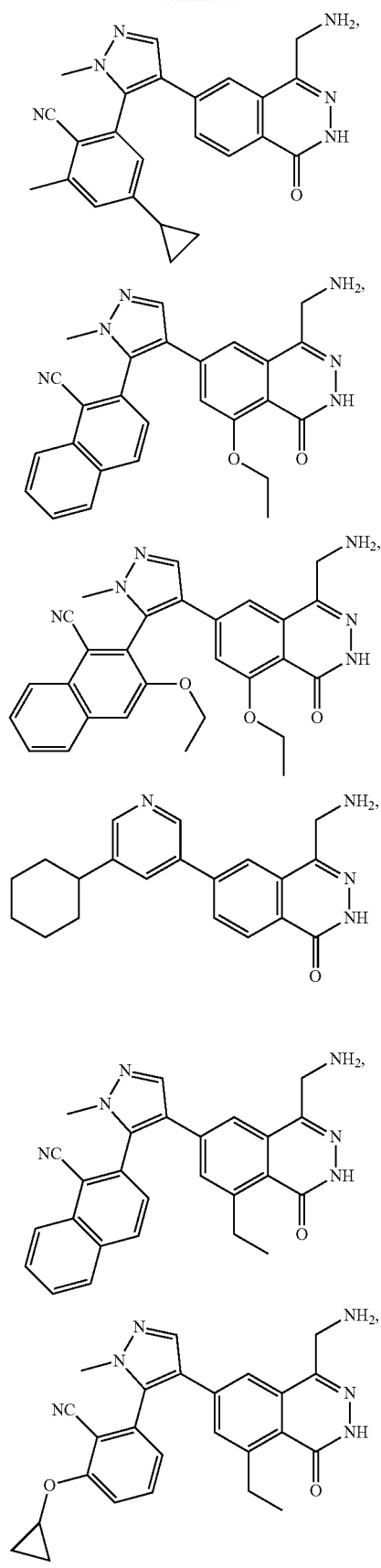
534
-continued
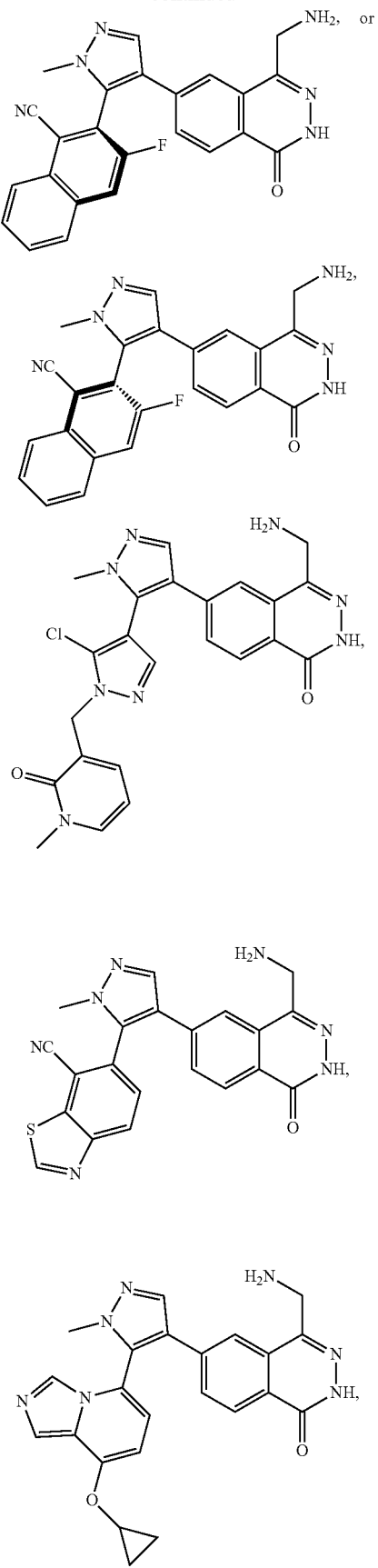

535
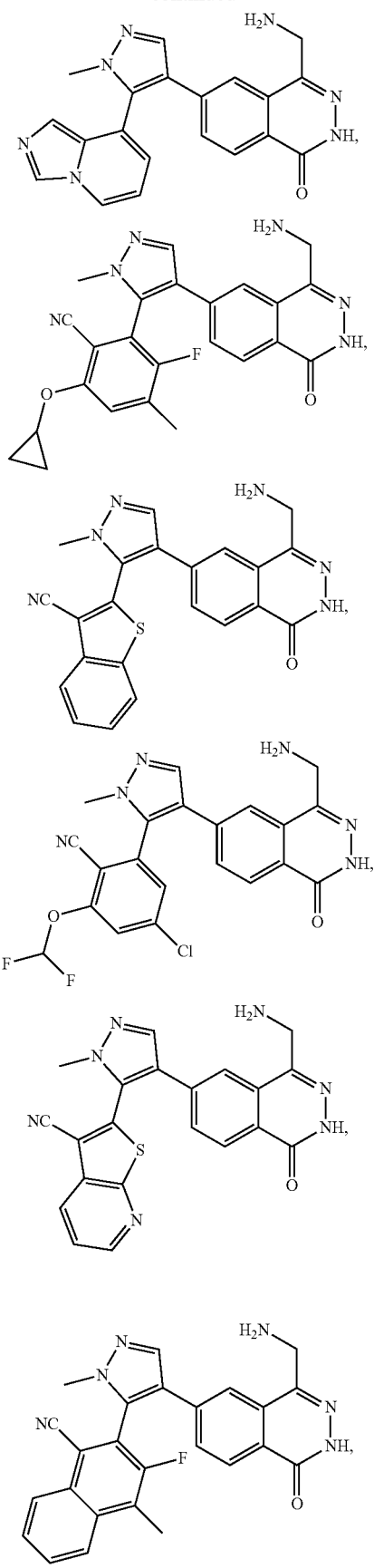
536
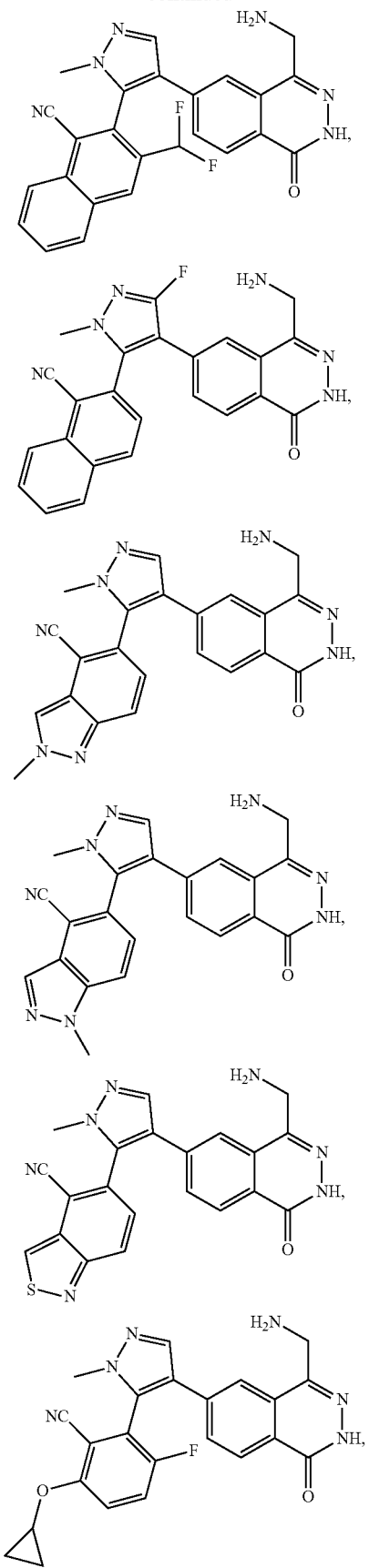

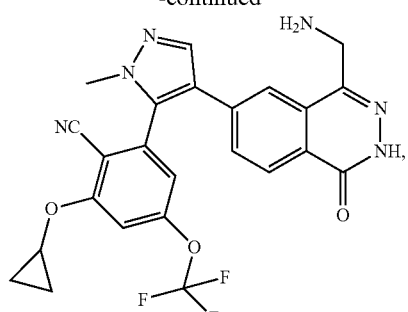
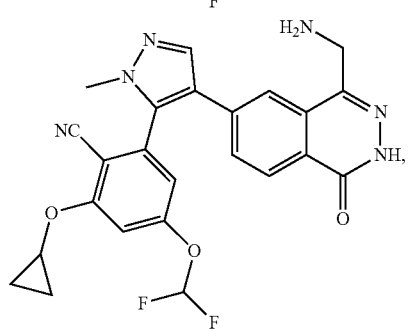
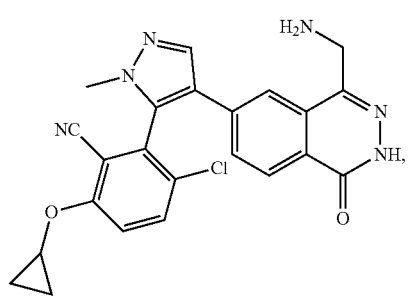
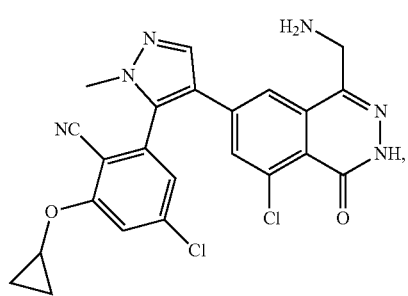
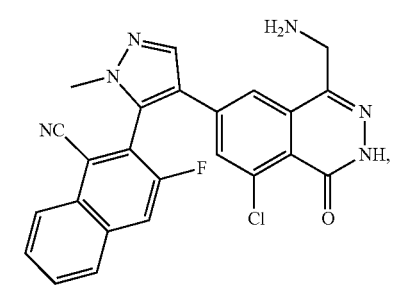
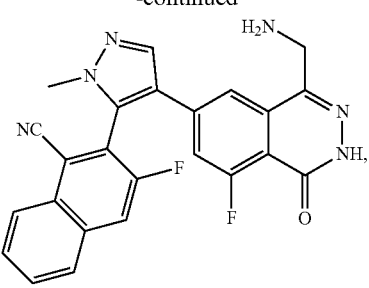
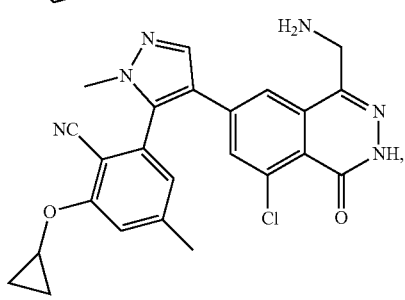
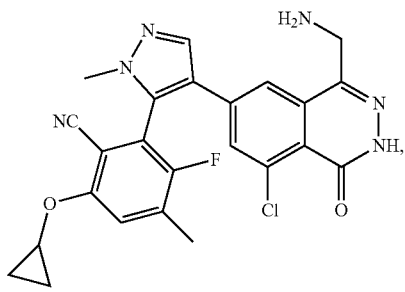
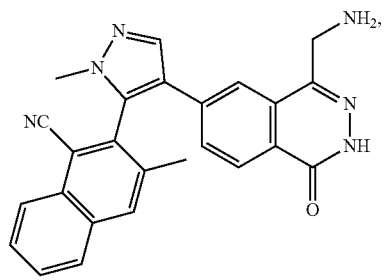
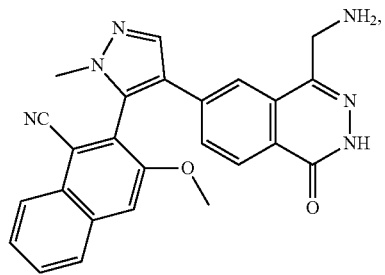
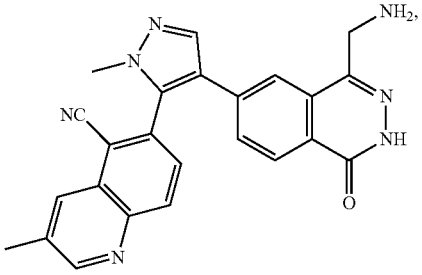

539
-continued
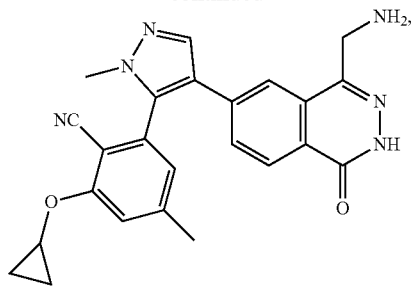
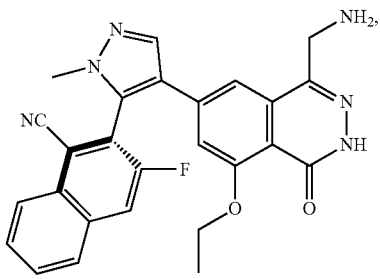
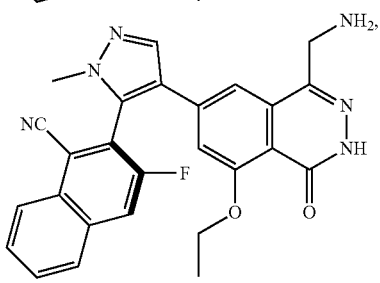
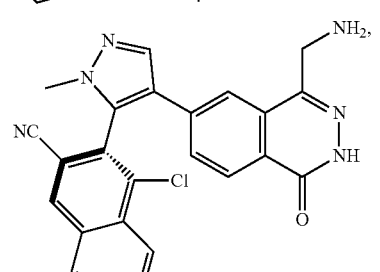
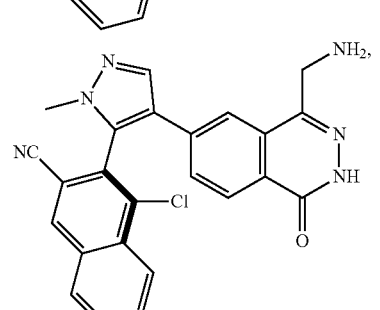
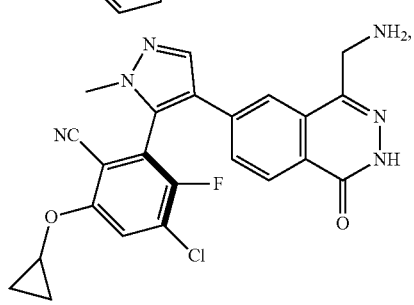
540
-continued
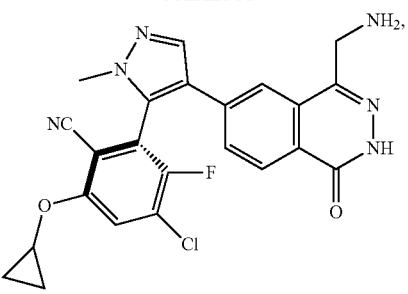
or a pharmaceutically acceptable salt thereof.
Clause 89. The compound of clause 1, wherein the compound is:
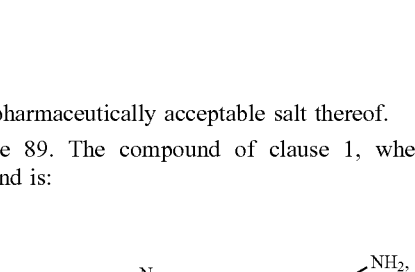
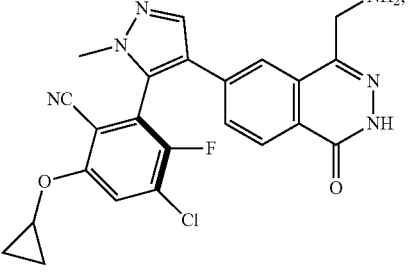
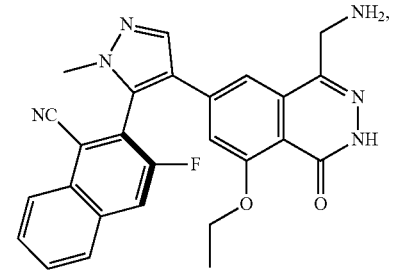
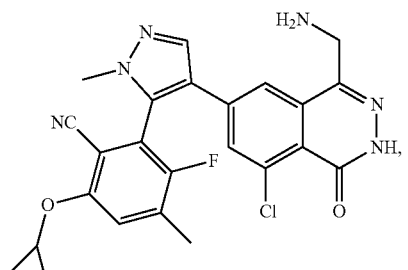
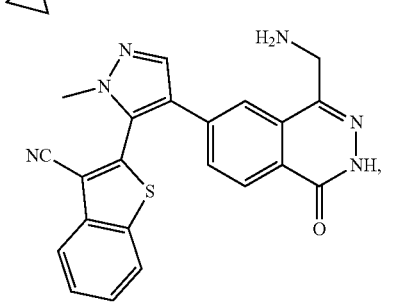

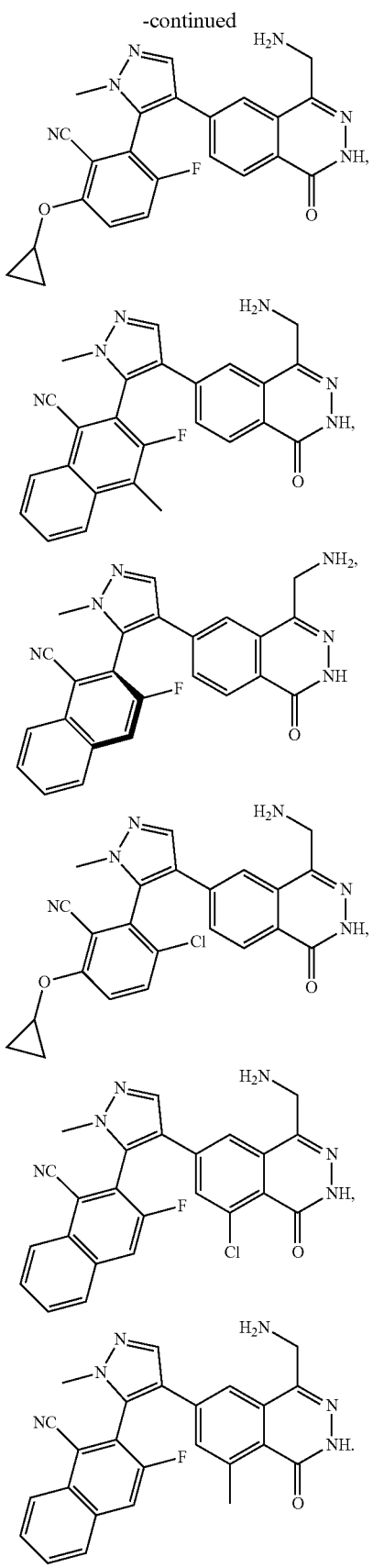

or a pharmaceutically acceptable salt thereof.

Clause 90. A pharmaceutical composition, comprising a therapeutically effective amount of a compound of Formula (I) according to any one of clauses 1-89 or a pharmaceutically acceptable salt or solvate thereof, and a pharmaceutically acceptable excipient.

Clause 91. A method for inhibiting PRMT5 activity in a cell, comprising contacting the cell in which inhibition of PRMT5 activity is desired with an effective amount of a compound of Formula (I) according to any one of clauses 1-89 or a pharmaceutically acceptable salt or solvate thereof, or a pharmaceutical composition according to clause 90.

Clause 92. A method for treating cancer comprising administering to a patient having cancer a therapeutically effective amount of a compound of Formula (I) according to any one of clauses 1-89 or a pharmaceutically acceptable salt or solvate thereof, or a pharmaceutically acceptable salt or solvate thereof, alone or combined with a pharmaceutically acceptable carrier, excipient or diluents.

Clause 93. The method of clause 92, wherein the therapeutically effective amount of the compound is between about 0.01 to 300 mg/kg per day.

Clause 94. The method of clause 92, wherein the therapeutically effective amount of the compound is between about 0.1 to 100 g/kg per day.

Clause 95. The method according to any one of clauses 91-94, wherein the cancer is selected from the group consisting of Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Biliary tract: gall bladder carcinoma, ampullary carcinoma, cholangiocarcinoma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma); Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma); Skin: malignant melanoma, basal cell carcinoma, squamous cell carcinoma, Kaposi's sarcoma, moles dysplastic nevi, lipoma, angioma, dermatofibroma, keloids, psoriasis; and Adrenal glands: neuroblastoma.

Clause 96. The method according to any one of clauses 91-95, wherein the cancer is a MTAP-associated cancer.

Clause 97. The method of clause 95, wherein the cancer is hepatocellular carcinoma, breast cancer, skin cancer, bladder cancer, liver cancer, pancreatic cancer, or head and neck cancer.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A method for inhibiting PRMT5 activity in a cell, comprising contacting the cell in which inhibition of PRMT5 activity is desired with an effective amount of a compound of Formula (I) or a pharmaceutically acceptable salt or solvate thereof, wherein Formula is

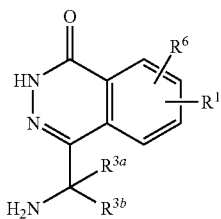

Formula (I)

or a pharmaceutically acceptable salt thereof; wherein:
$R^1$ is —Y-cycloalkyl, —Y-heterocyclyl, —Y-aryl, -Y-arylC1-C3alkyl or —Y-heteroaryl, wherein the cycloalkyl, the heterocyclyl, the aryl, and the heteroaryl portions are each optionally substituted with one or more $R^2$;
each Y is independently a bond or —NR$^4$—;
each $R^2$ is independently hydroxy, halogen, cyano, cyanomethyl, —(NR$^4$)$_2$, hydroxyalkyl, alkoxy, —SO$_2$C1-C3alkyl, —X-arylC1-C3alkyl, heteroalkyl, C2- C4 alkynyl, —X-haloalkyl, —X-C1-C5 alkyl, —Z-C1-C5 alkyl, heterocyclyl, —X-L-cycloalkyl, —Z— cycloalkyl, —X-aryl, —Z-aryl, or —X-heteroaryl, wherein the heterocyclyl, the cycloalkyl, the aryl and the heteroaryl are optionally substituted with one or more $R^5$;
each X is independently a bond, O, S, —NR$^4$— or —NR$^4$C(O)—;
each Z is independently a bond, —SO—, —SO$_2$—, —CH(OH)— or —C(O)—;
each L is independently a bond or C1-C3 alkylene;
$R^{3a}$ and $R^{3b}$ are each independently hydrogen or deuterium, or $R^{3a}$ and $R^{3b}$ together are oxo;
each $R^4$ is independently hydrogen or C1-C3 alkyl;
each $R^5$ is independently cyano, oxo, halogen, C1-C3 alkyl, hydroxyalkyl, alkoxy, —X-haloalkyl, —Z-cycloalkyl, —X-arylC1-C3alkyl, —X-arylC1-C3alkyl substituted with cyano, —X-L-cycloalkyl, —X-L-heteroaryl optionally substituted with one or more C1-C3alkyl or oxo, or —X-aryl; and
$R^6$ is hydrogen, halogen, C1-C3 alkyl, haloalkyl or alkoxy.

2. A method for treating cancer comprising administering to a patient having cancer a therapeutically effective amount of a compound of Formula (I) or a pharmaceutically acceptable salt or solvate thereof,
wherein the cancer is selected from the group consisting of bladder cancer, bone cancer, brain cancer, blood cancer, breast cancer, colorectal cancer, esophageal cancer, gastric cancer, head and neck cancer, kidney cancer, liver cancer, lung cancer, mesothelioma, ovarian cancer, pancreatic cancer, skin cancer, thyroid cancer and uterine cancer, and
wherein Formula (I) is

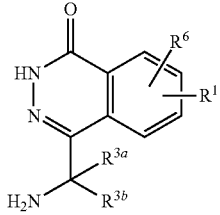

Formula (I)

wherein:
$R^1$ is —Y-cycloalkyl, —Y-heterocyclyl, —Y-aryl, —Y-arylC1-C3alkyl or —Y-heteroaryl, wherein the cycloalkyl, the heterocyclyl, the aryl, and the heteroaryl portions are each optionally substituted with one or more $R^2$;
each Y is independently a bond or —NR$^4$—;
each $R^2$ is independently hydroxy, halogen, cyano, cyanomethyl, —(NR$^4$)$_2$, hydroxyalkyl, alkoxy, —SO$_2$C1-C3alkyl, —X-arylC1-C3alkyl, heteroalkyl, C2- C4 alkynyl, —X-haloalkyl, —X-C1-C5 alkyl, —Z-C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$;
each X is independently a bond, O, S, —NR$^4$— or —NR$^4$C(O)—;
each Z is independently a bond, —SO—, —SO$_2$—, —CH(OH)— or —C(O)—;
each L is independently a bond or C1-C3 alkylene;
$R^{1a}$ and $R^{3b}$ are each independently hydrogen or deuterium, or $R^{3a}$ and $R^{3b}$ together are oxo;
each $R^4$ is independently hydrogen or C1-C3 alkyl;
each $R^5$ is independently cyano, oxo, halogen, C1-C3 alkyl, hydroxyalkyl, alkoxy, —X-haloalkyl, —Z-cycloalkyl, —X-arylC1-C3alkyl, —X-arylC1-C3alkyl substituted with cyano, —X-L-cycloalkyl, —X-L-heteroaryl optionally substituted with one or more C1-C3alkyl or oxo, or —X-aryl; and $R^6$ is hydrogen, halogen, C1-C3 alkyl, haloalkyl or alkoxy.

3. The method according to claim 2, wherein $R^1$ is —Y-heteroaryl optionally substituted with one or more $R^2$, and Y is a bond and the heteroaryl is pyrazolyl, imidazolyl, thiazolyl, isothiazolyl, oxazolyl, triazolyl, oxidazolyl, pyridyl, pyridiazinyl, pyrimidinyl, quinolinyl, isoquinolinyl, phthalazinyl, pyrazolopyridinyl, 1H-pyrrolopyridyl, pyrazolopyrimidinyl, imidazopyridyl, tetrahydropyrazolopyrazinyl, 2H-4$\lambda^4$-imidazopyrimidinyl, 2H-4$\lambda^4$-imidazopyridazinyl, oxazolopyridyl or 5,6-dihydro-8H-imidazooxazinyl, each of which is optionally substituted with one or more $R^2$.

4. The method according to claim 3, wherein the heteroaryl is tetrahydropyrazolopyrazinyl, optionally substituted with one or more $R^2$.

5. The method according to claim 2, wherein $R^1$ is —Y-heteroaryl optionally substituted with one or more $R^2$, and the heteroaryl is pyridyl, optionally substituted with one or two $R^2$.

6. The method according to claim 5, wherein the pyridyl is substituted with one $R^2$, and $R^2$ is hydroxy, halogen, cyano, —$(NR^4)_2$, hydroxyalkyl, alkoxy, —$SO_2$C1-C3alkyl, arylC1-C3alkyl, heteroalkyl, C2- C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R_5$.

7. The method according to claim 3, wherein $R^1$ is —Y-heteroaryl optionally substituted with one or more $R^2$, and the heteroaryl is pyrazolopyridinyl, optionally substituted with one or more $R^2$.

8. The method of claim 7, wherein the pyrazolylpyridinyl is substituted with one $R^2$, wherein the one $R^2$ is alkoxy or —X-aryl.

9. The method according to claim 2, wherein $R^1$ is —Y-aryl, wherein Y is —$NR^4$— and the aryl is phenyl optionally substituted with one or more $R^5$.

10. The method according to claim 2, wherein $R^1$ is —Y-arylC1-C3alkyl, wherein Y is —$NR^4$— and the arylC1-C3alkyl is benzyl.

11. The method according to claim 5, wherein the pyridyl is substituted with two $R^2$.

12. The method according to claim 3, wherein the heteroaryl is pyrimidinyl, optionally substituted with one or more $R^2$.

13. The method according to claim 12, wherein the pyrimidinyl is substituted with one $R^2$.

14. The method according to claim 3, wherein the heteroaryl is pyrazolyl, optionally substituted with one, two or three $R^2$ groups.

15. The method according to claim 14, wherein the pyrazolyl is substituted with one $R^2$.

16. The method according to claim 15, wherein $R^2$ is —X—C1-C5 alkyl, hydroxyalkyl, arylC1-C3alkyl, or —X-aryl optionally substituted with one or more $R^5$.

17. The method according to claim 14, wherein the pyrazolyl is substituted with two independently selected $R^2$.

18. The method according to claim 17, wherein the two $R^2$ groups are (1) independently -t —X—C1-C5 alkyl, (2) —X—C1-C5 alkyl and halogen, (3) —X—C1-C5 alkyl and alkoxy, (4) —X—C1-C5 alkyl and —$N(R^4)_2$, -(5) X—C1-C5 alkyl and —X-haloalkyl, (6) —X—C1-C5 alkyl and arylC1-C3alkyl, (7) —X—C1-C5 alkyl and —X-L-cyclolalkyl, -(8) —X—C1-C5 alkyl and -heterocyclyl, (9) —X—C1-C5 alkyl and —X-aryl optionally substituted with one or more $R^5$, (10) —X—C1-C5 alkyl and —X-heteroaryl optionally substituted with one or more $R^5$, (11) —X—C1-C5 alkyl and cyanomethyl, (12) —X—C1-C5 alkyl and cyano, (13) cyano and halogen, wherein the halogen is chlorine or fluorine, (14) cyano and —X-L-cycloalkyl, (15) independently halogen, (16) cyano and alkoxy, wherein each X is a bond, (17) cyano and —X-aryl, (18) cyano and —X-heteroaryl, (19) cyano and heterocyclyl (20) halogen and —X-arylC1-C3alkyl or —X-arylC1-C3alkyl substituted with cyano, and (21) halogen and —X-aryl.

19. The method according to claim 3, wherein the heteroaryl is imidazolyl, 1H-pyrrolopyridyl, tetrahydropyrazolopyrazinyl, 2H-4$\lambda^4$-imidazopyrimidinyl, 2H-4$\lambda^4$-imidazopyridazinyl, or oxazolopyridyl, each substituted with one $R^2$ group, wherein each $R^2$ is —X—C1-C5 alkyl, wherein X is a bond.

20. The method according to claim 3, wherein the heteroaryl is imidazopyridyl substituted with one $R^2$ group, wherein $R^2$ is cyano, alkoxy, halogen or —X—C1-C5 alkyl and X is a bond, or the heteroaryl is imidazopyridyl substituted with two $R^2$ groups, wherein one $R^2$ group is halogen and the second $R^2$ group is —X—C1-C5 alkyl, wherein X is a bond, or halogen.

21. A method according to claim 2, wherein the compound of Formula (I) has Formula (I-D):

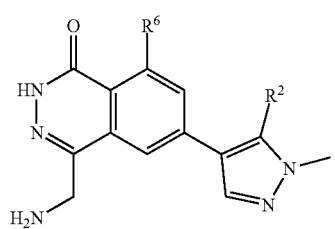

Formula (I-D)

wherein:

each Y is independently a bond or —$NR^4$—;

each $R^2$ is independently hydroxy, halogen, cyano, cyanomethyl, —$(NR^4)_2$, hydroxyalkyl, alkoxy, —$SO_2$C1-C3alkyl, —X-arylC1-C3alkyl, heteroalkyl, C2- C4 alkynyl, —X-haloalkyl, —X—C1-C5 alkyl, —Z—C1-C5 alkyl, heterocyclyl, —X-L-cycloalkyl, —Z-cycloalkyl, —X-aryl, —Z-aryl, or —X-heteroaryl, wherein the heterocyclyl, the cycloalkyl, the aryl and the heteroaryl are optionally substituted with one or more $R^5$;

each X is independently a bond, O, S, —$NR^4$— or —$NR^4C(O)$—;

each Z is independently a bond, —SO—, —$SO_2$—, —CH(OH)— or —C(O)—;

each L is independently a bond or C1-C3 alkylene;

each $R^4$ is independently hydrogen or C1-C3 alkyl;

each $R^5$ is independently cyano, oxo, halogen, C1-C3 alkyl, hydroxyalkyl, alkoxy, —X-haloalkyl, —Z-cycloalkyl, —X-arylC1-C3alkyl, —X-arylC1-C3alkyl substituted with cyano, —X—L-cycloalkyl, —X-L-heteroaryl optionally substituted with one or more C1-C3alkyl or oxo, or —X-aryl; and $R^6$ is hydrogen, halogen, C1-C3 alkyl, haloalkyl or alkoxy.

22. The method of claim 2, wherein the compound is:
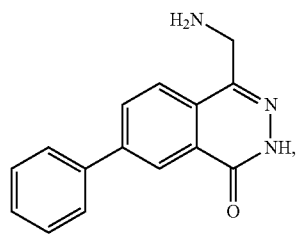
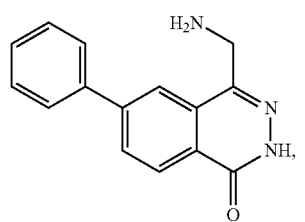
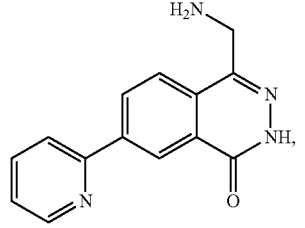
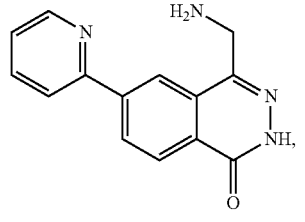
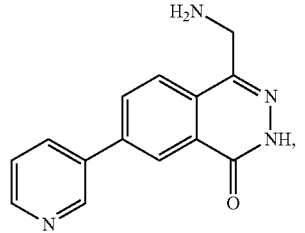
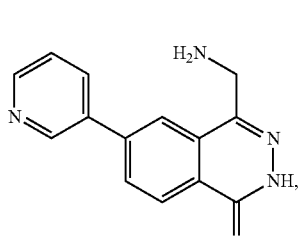
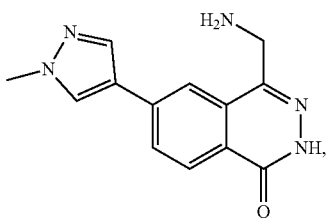
-continued
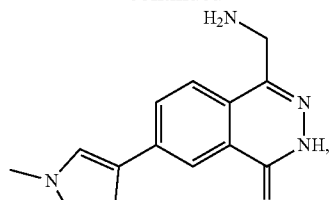
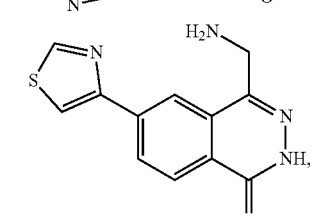
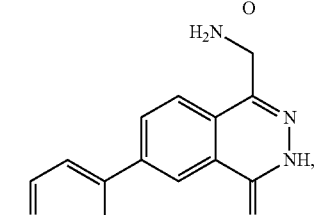
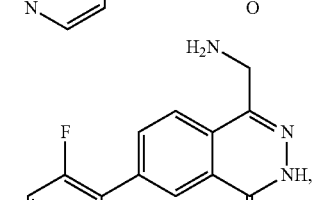
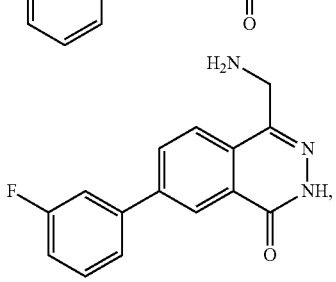
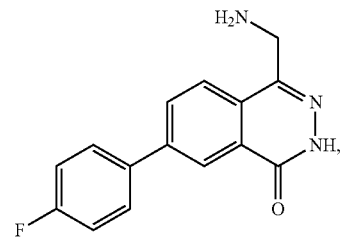
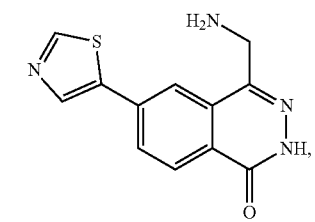

549
-continued
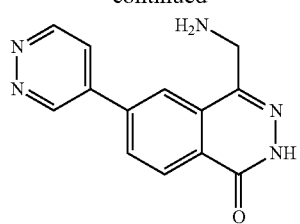
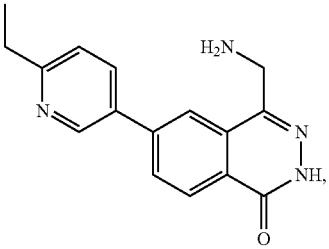
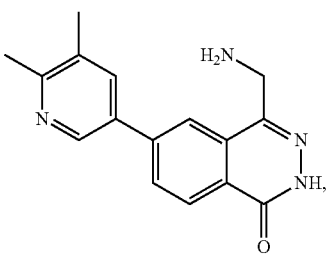
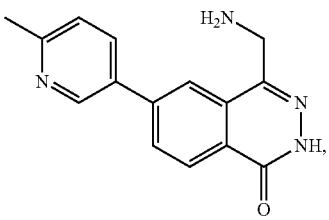
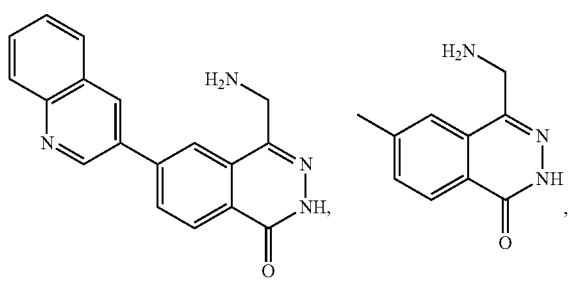
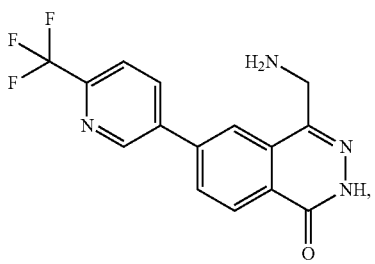
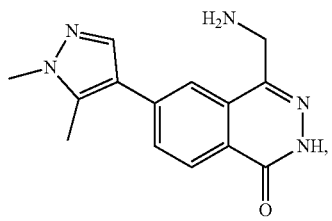
550
-continued
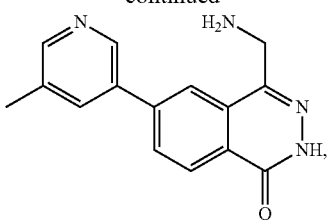
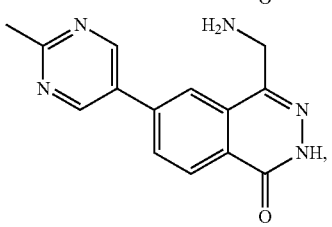
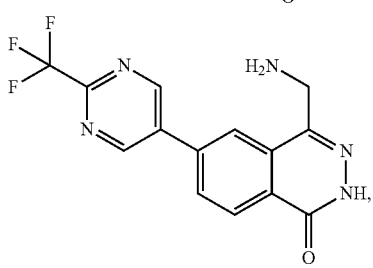
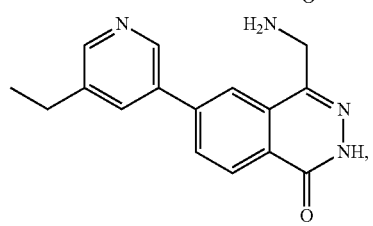
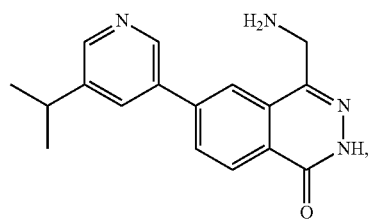
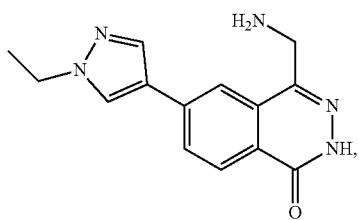
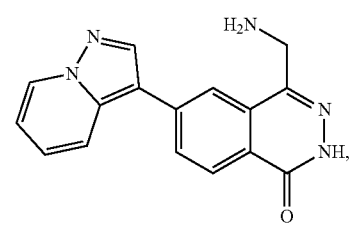

551
-continued
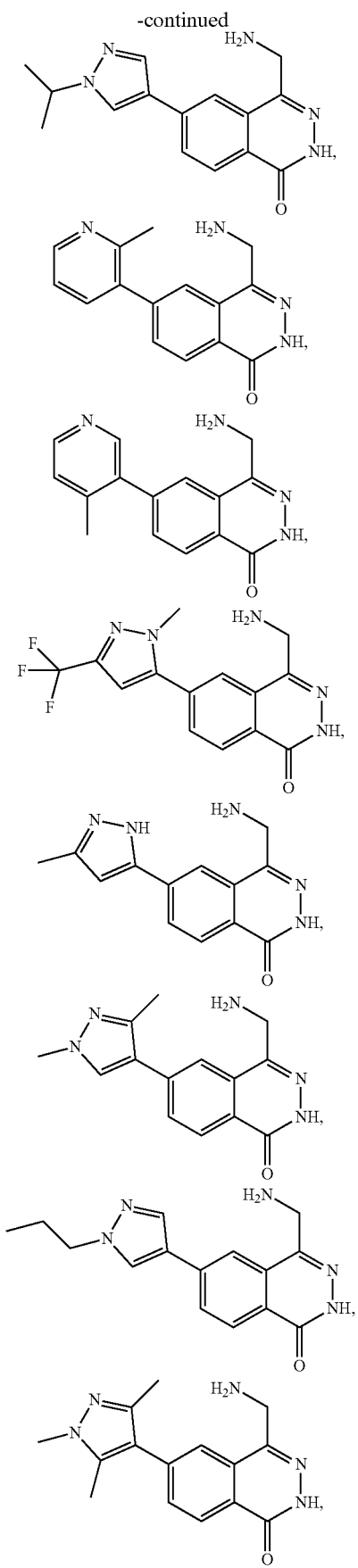
552
-continued
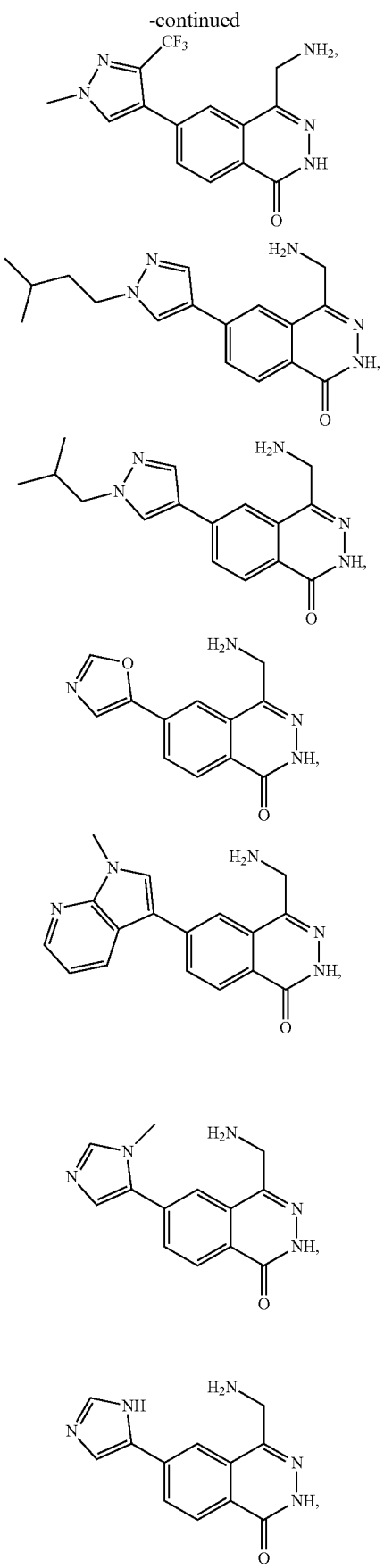

553
-continued
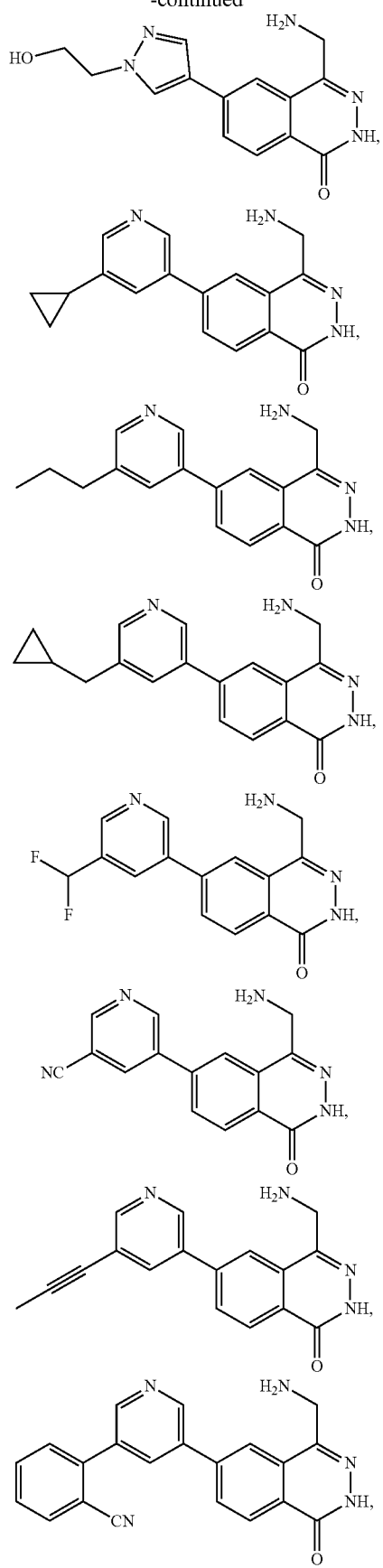
554
-continued
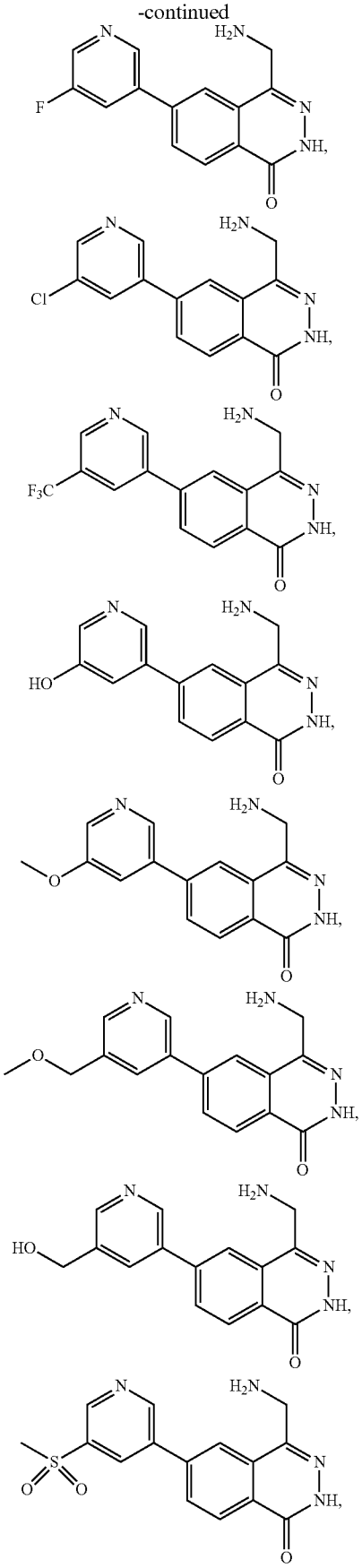

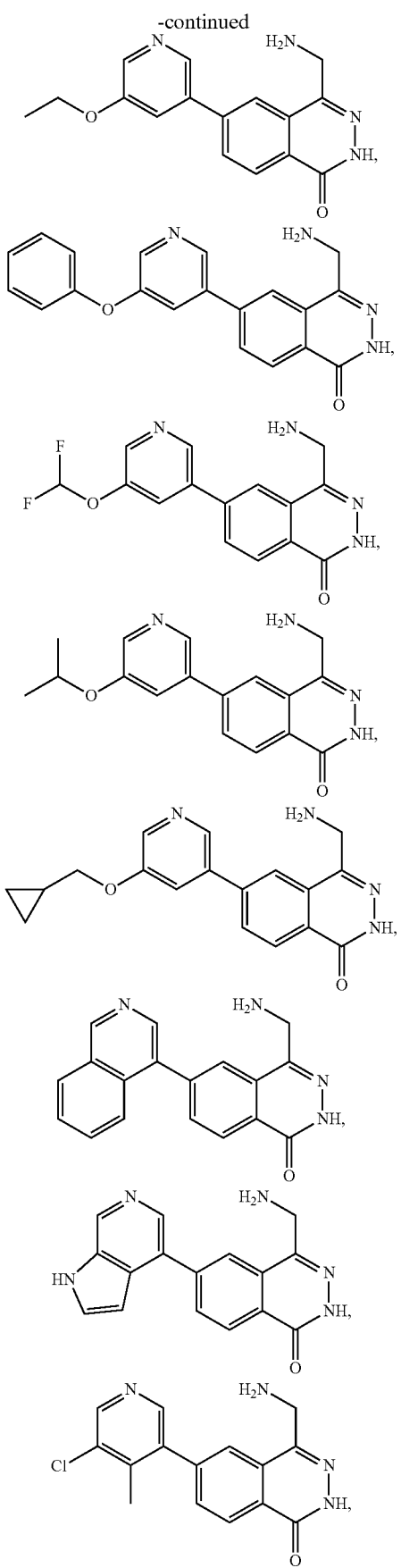
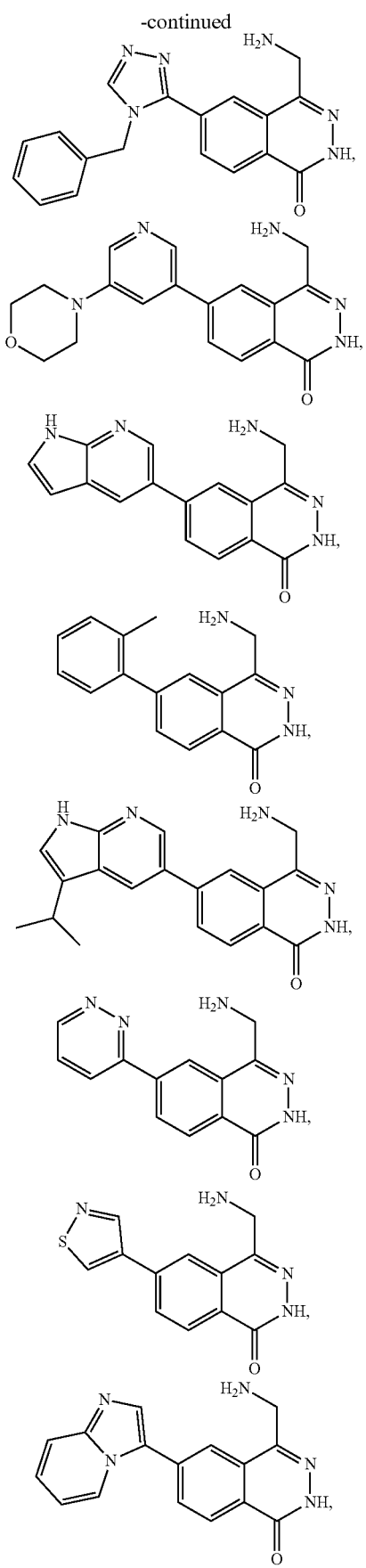

557
-continued
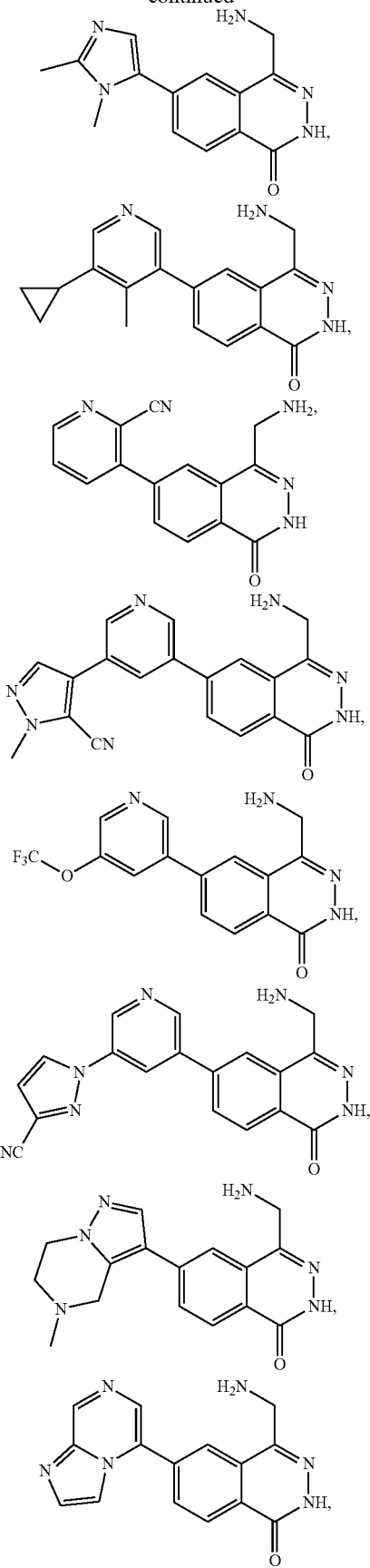
558
-continued
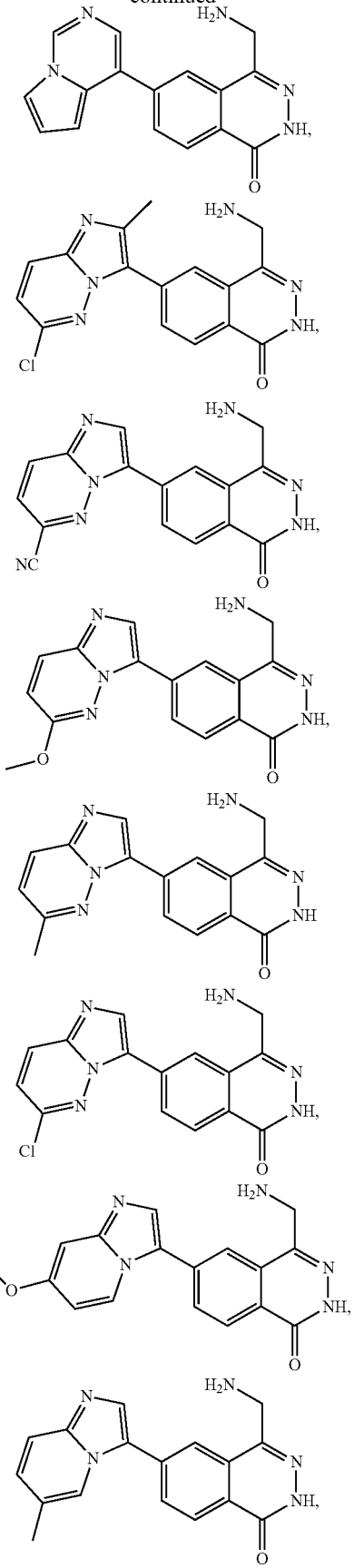

559
-continued
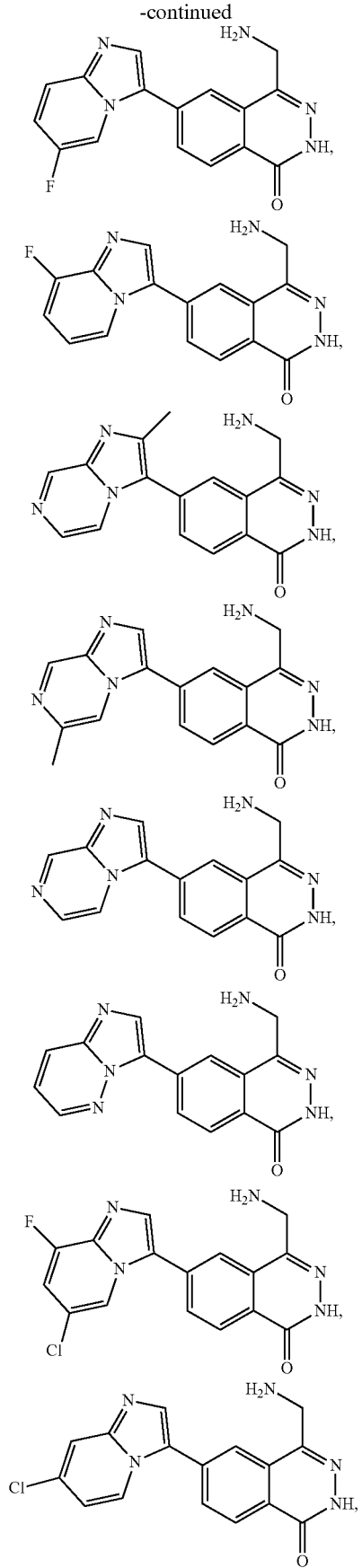
560
-continued
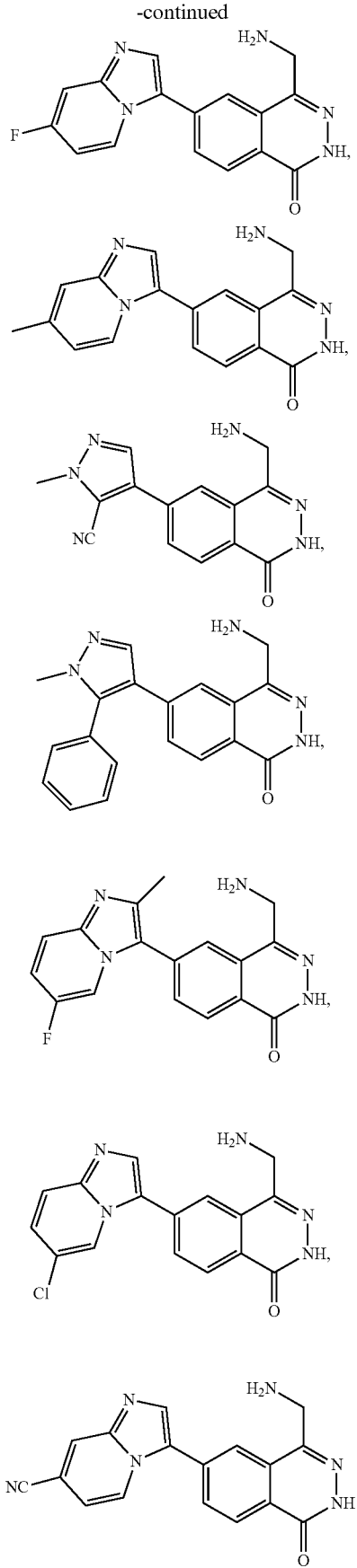

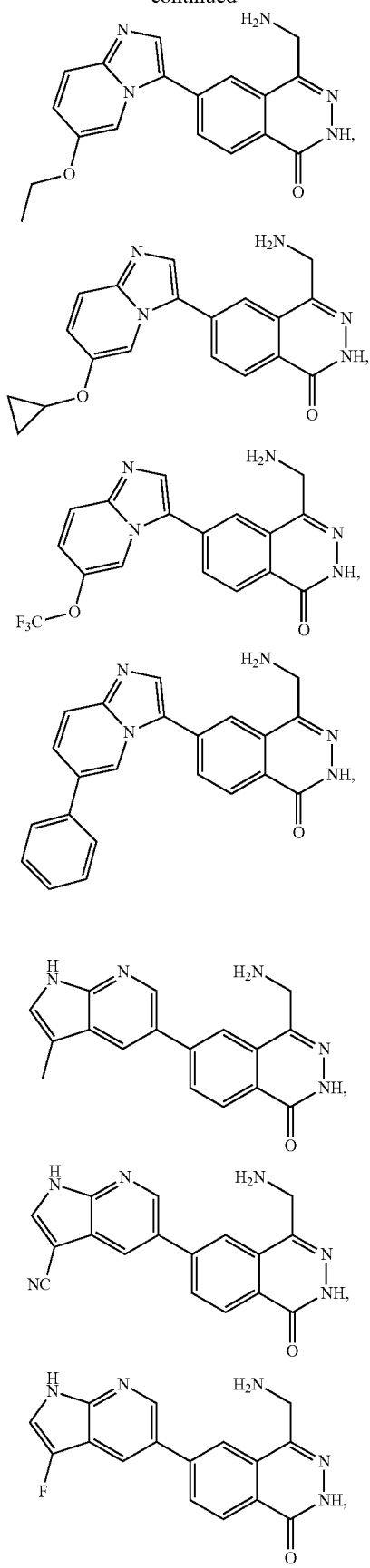
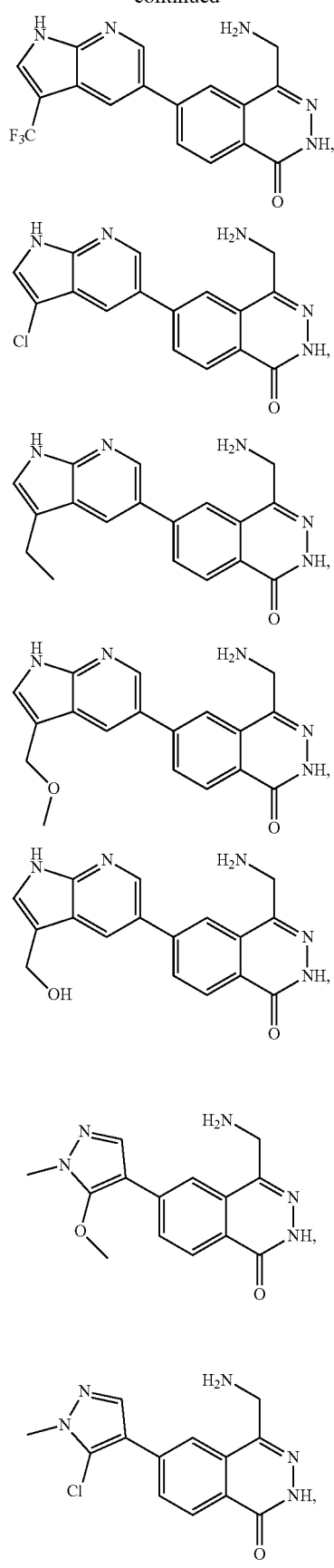

563
-continued
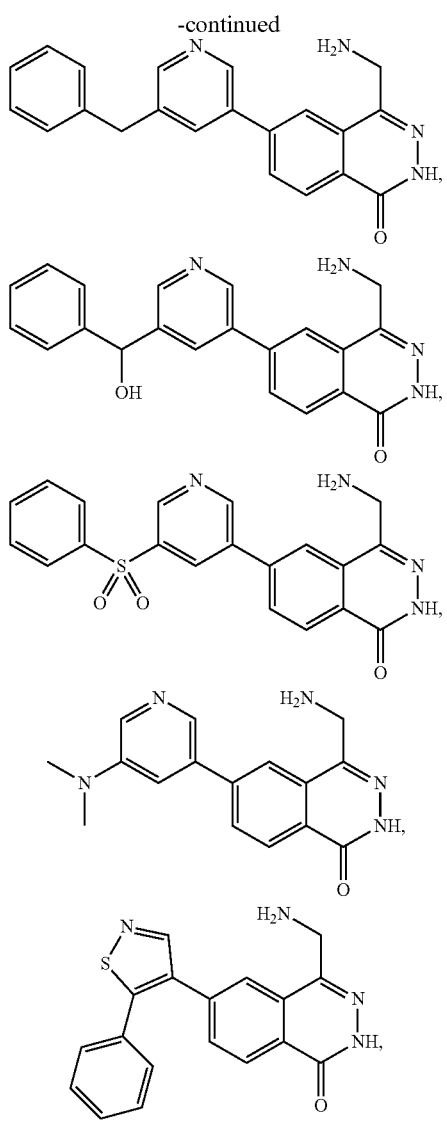
564
-continued
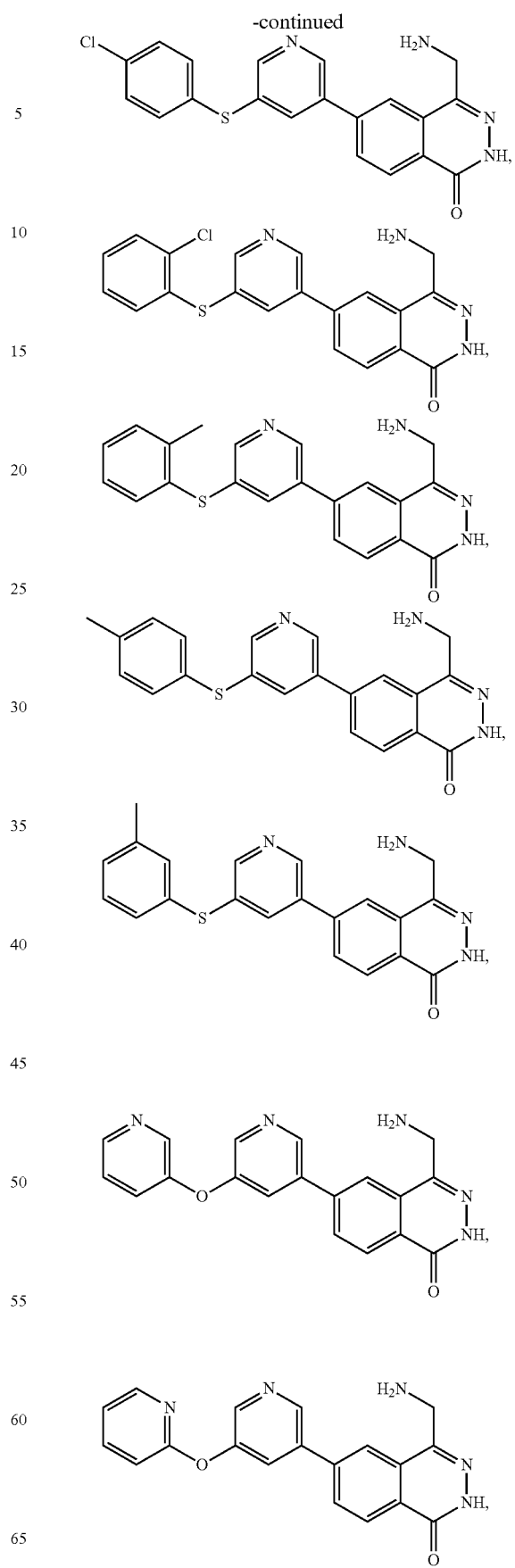

565
-continued
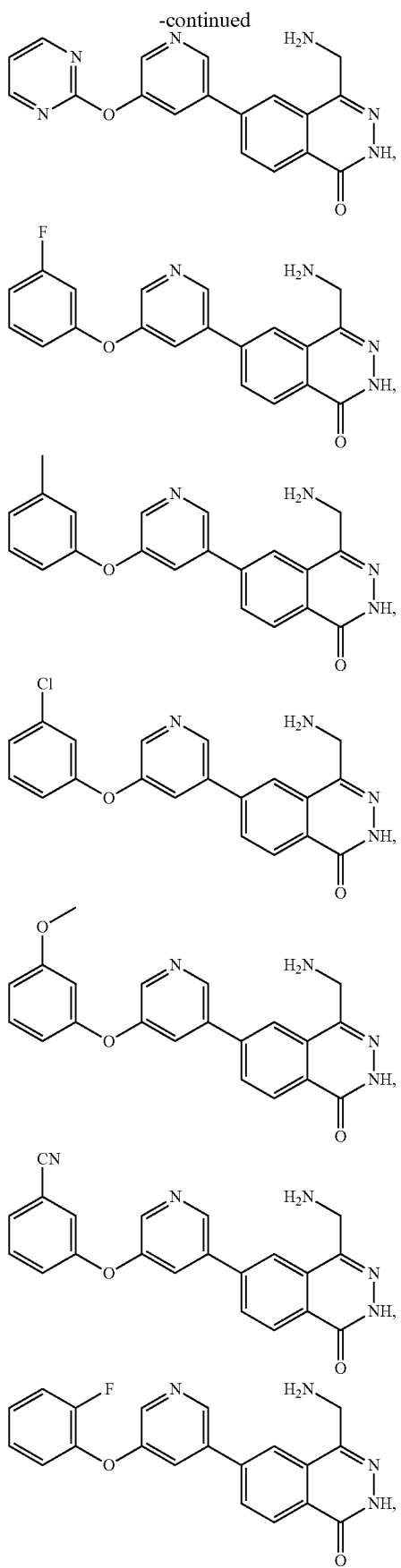
566
-continued
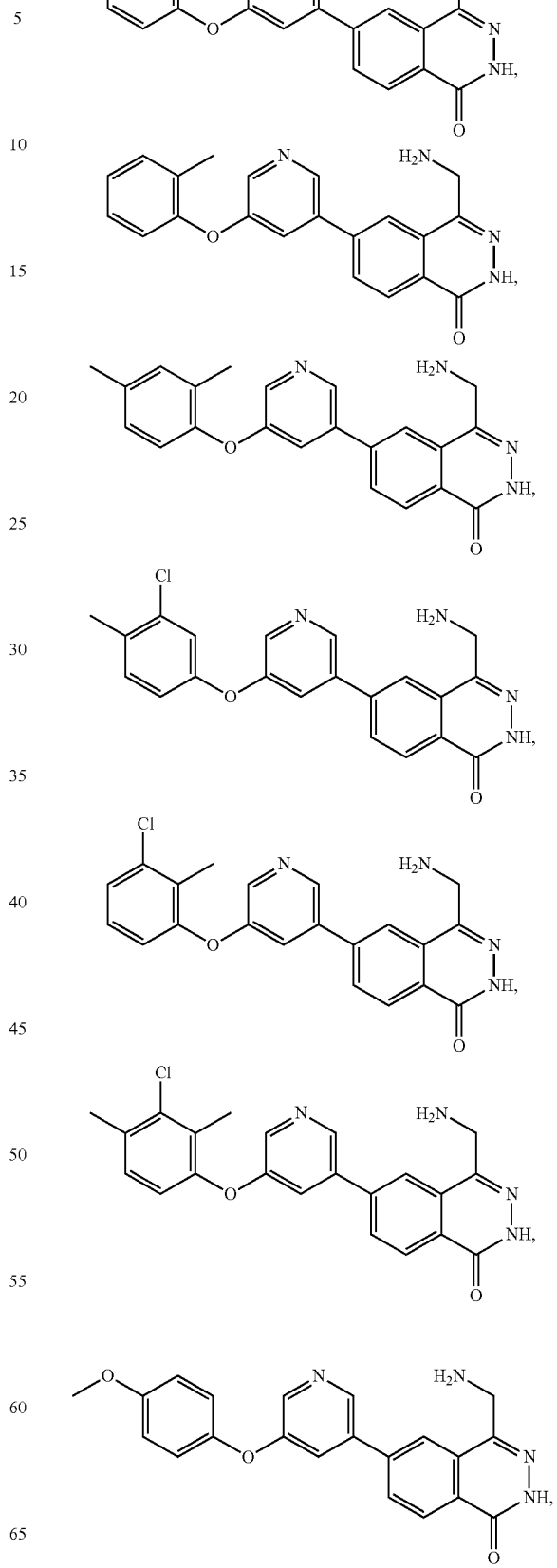

567
-continued
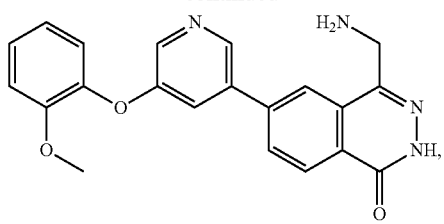
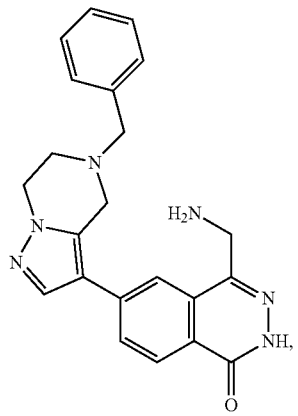
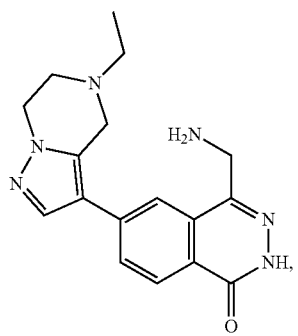
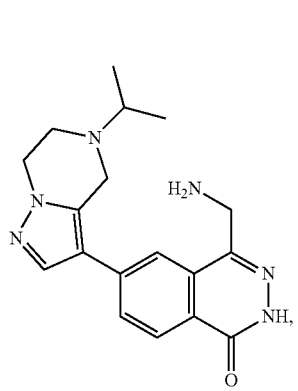
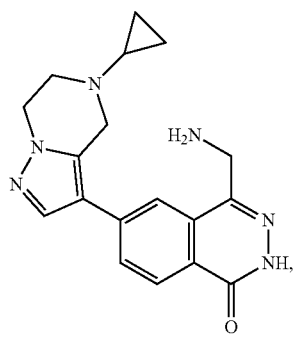
568
-continued
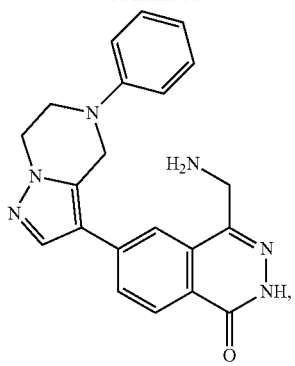
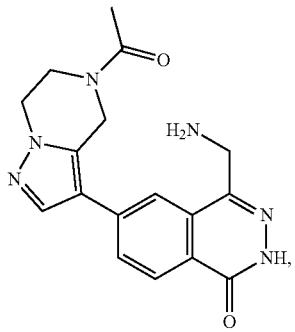
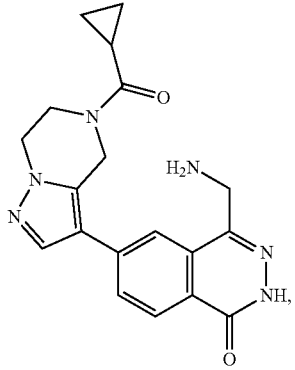
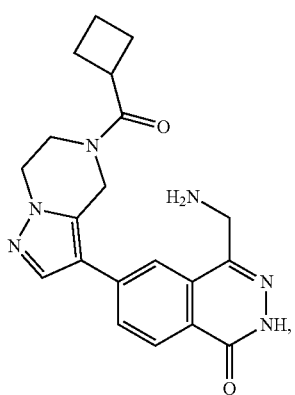

569
-continued
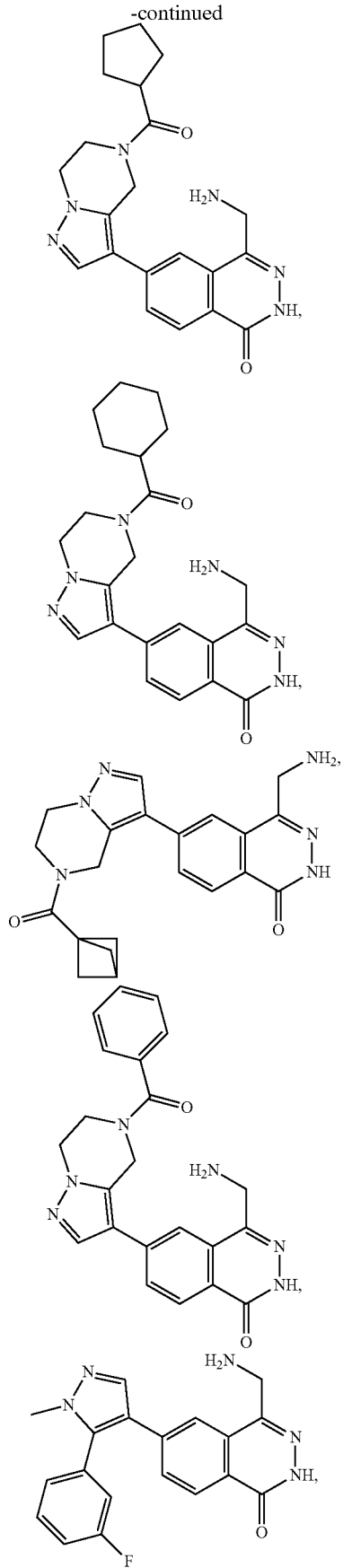
570
-continued
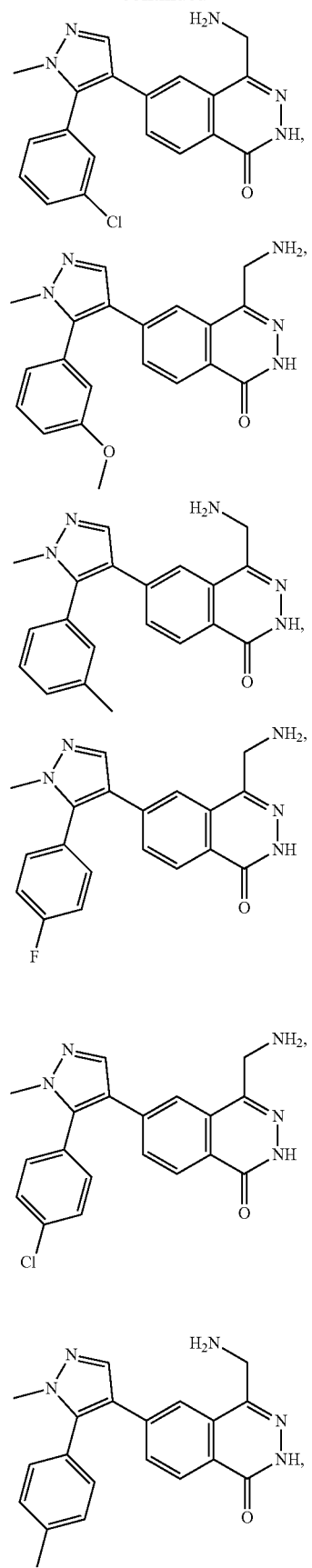

571
-continued
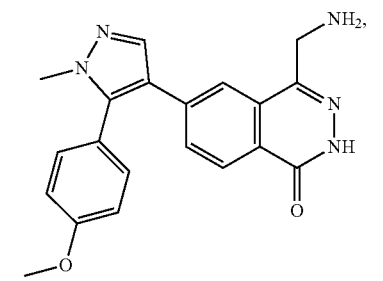
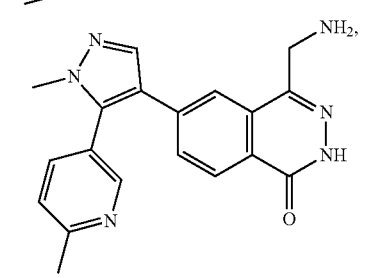
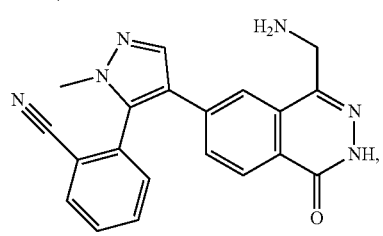
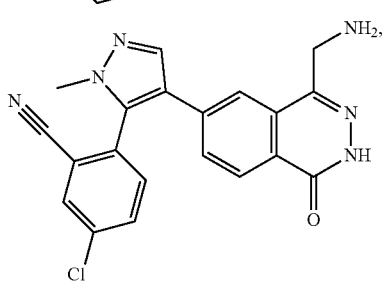
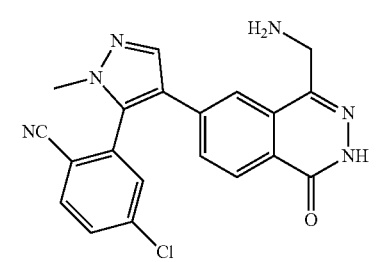
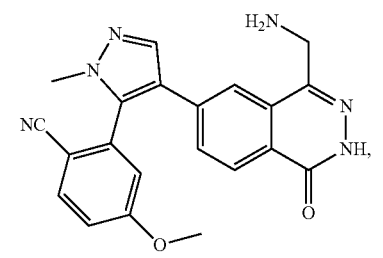
572
-continued
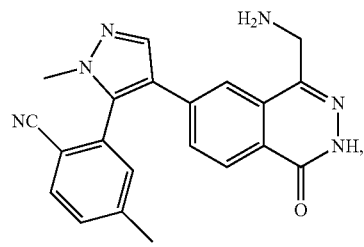
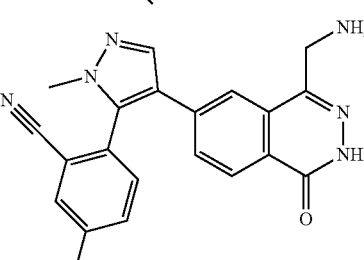
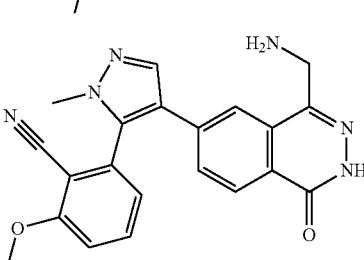
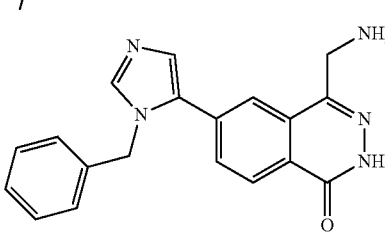
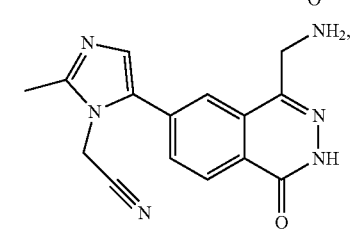
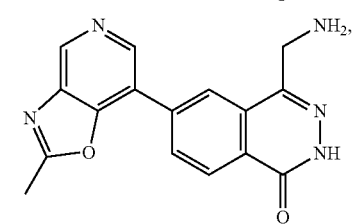
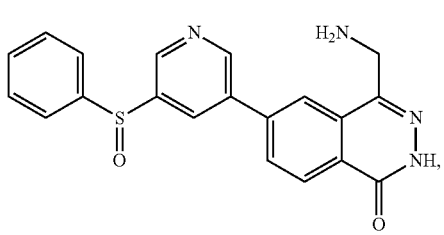

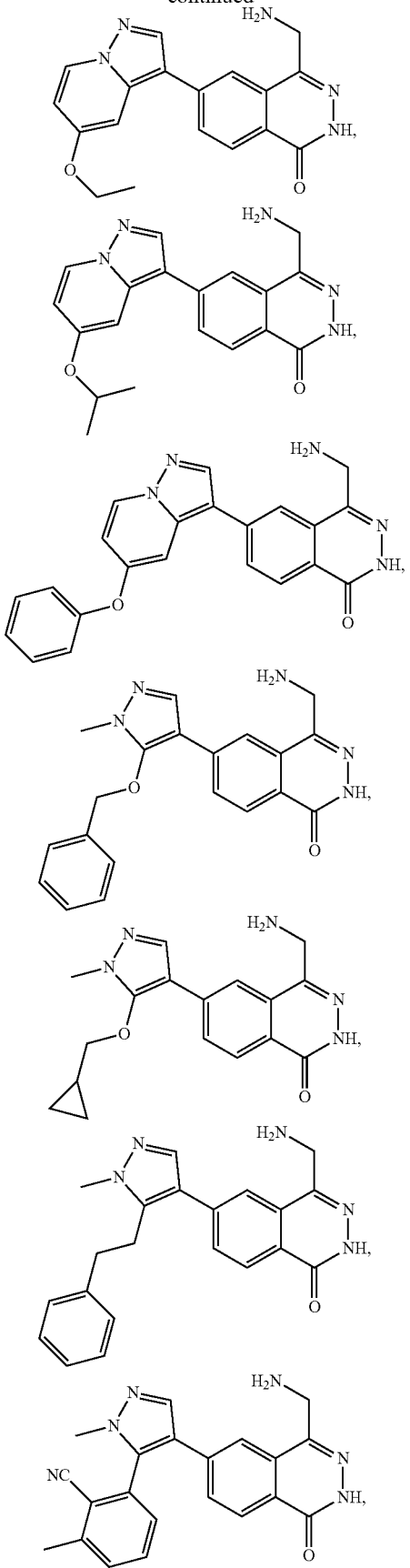
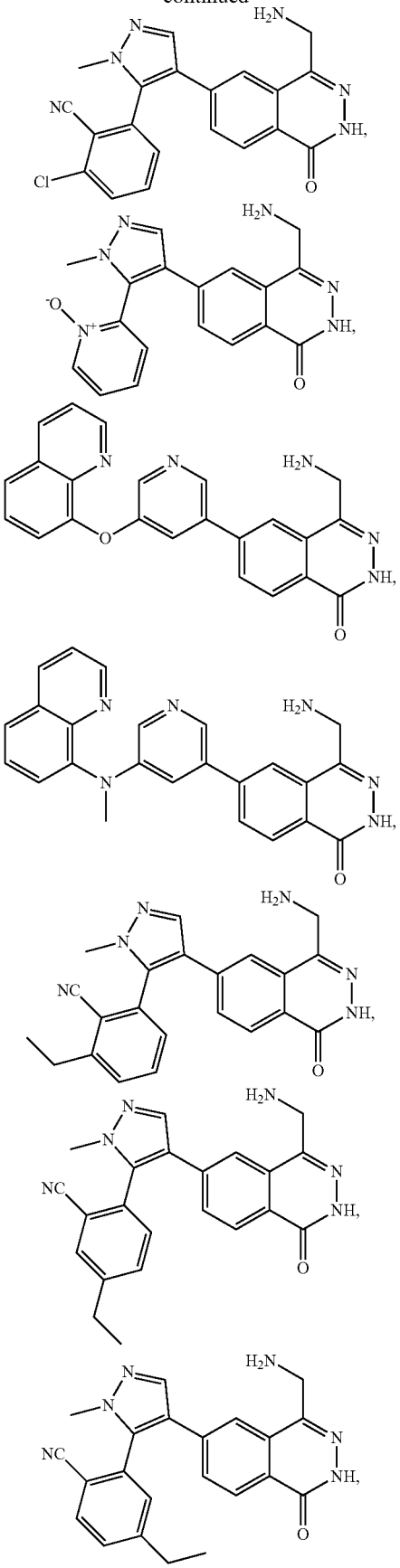

-continued
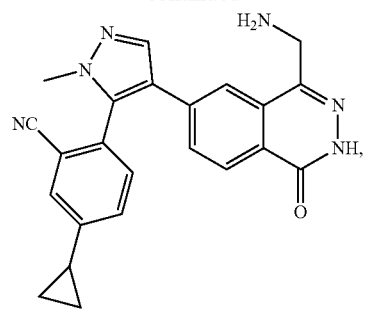
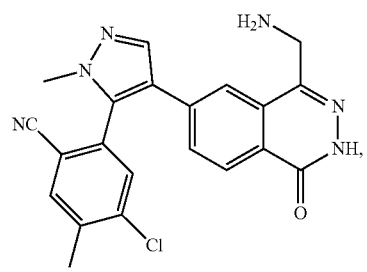
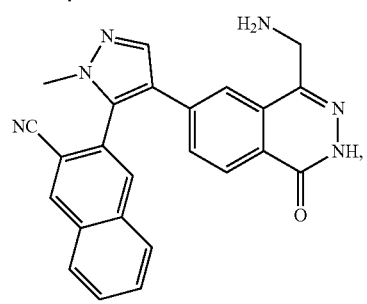
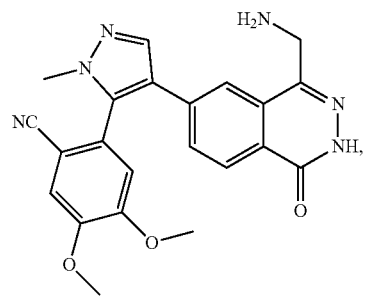
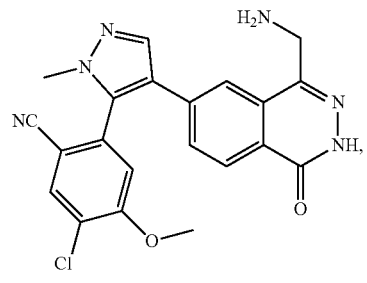
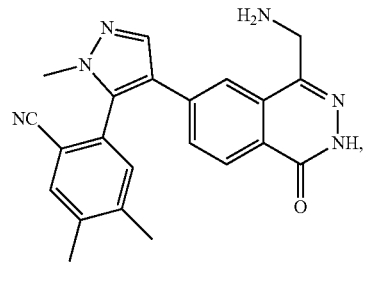
-continued
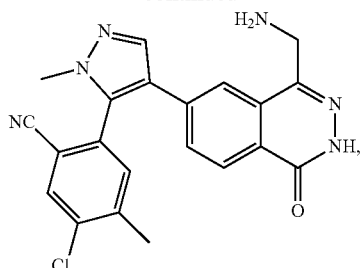
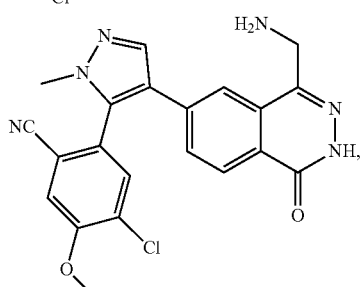
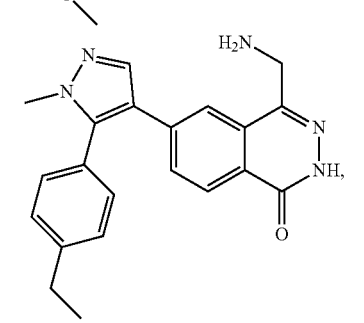
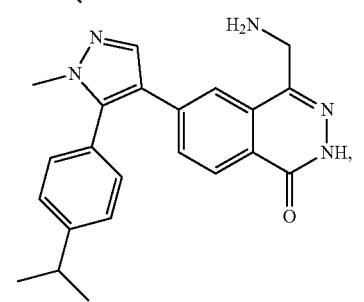
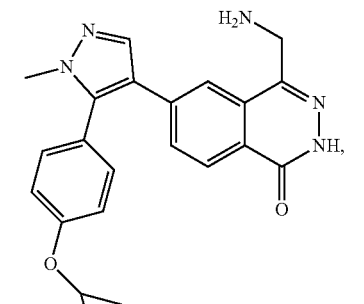
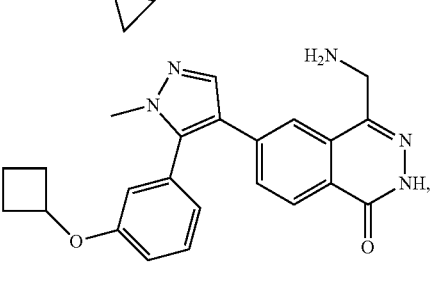

577
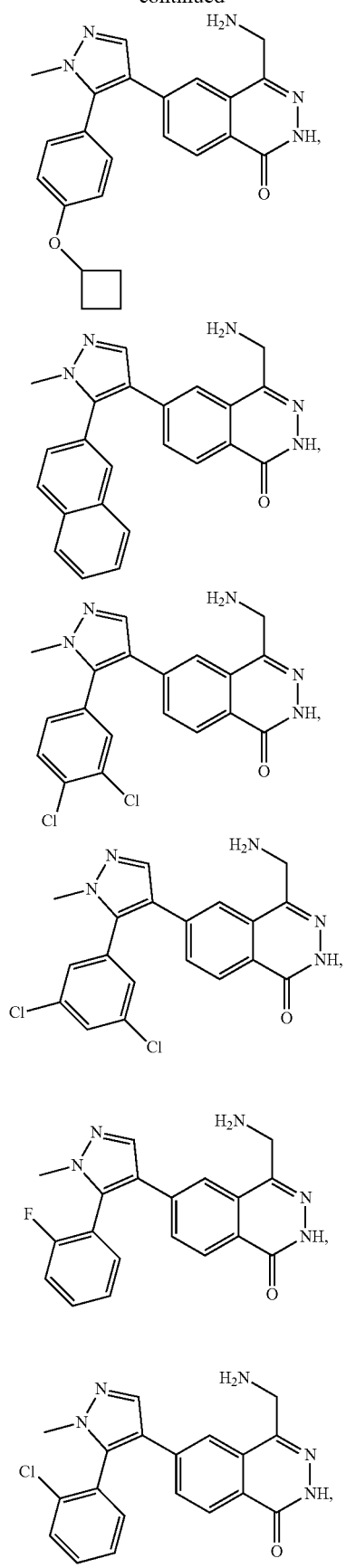
578
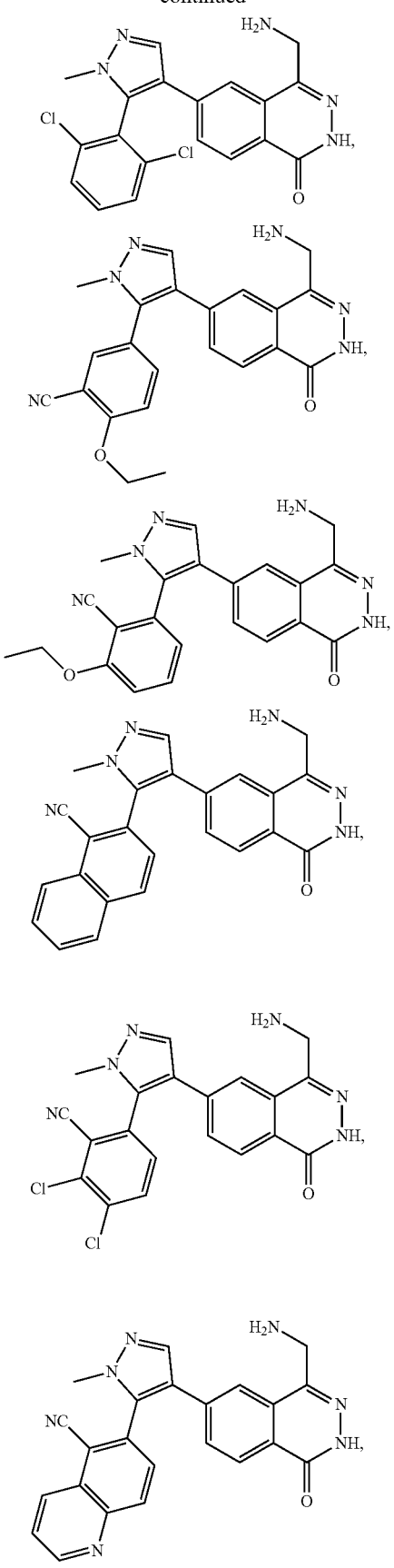

579
-continued
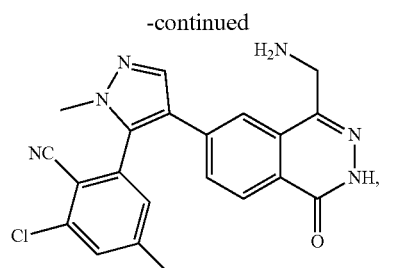
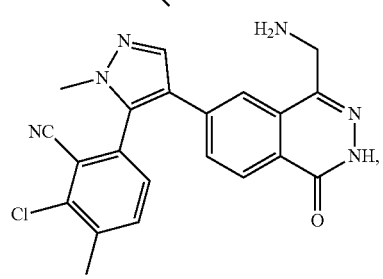
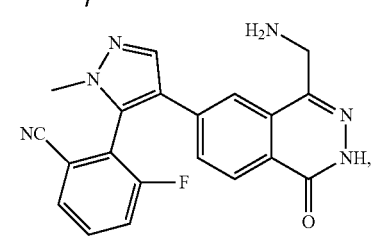
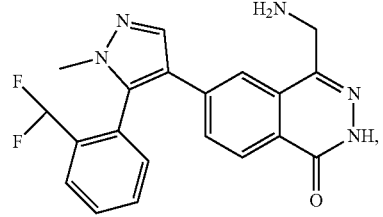
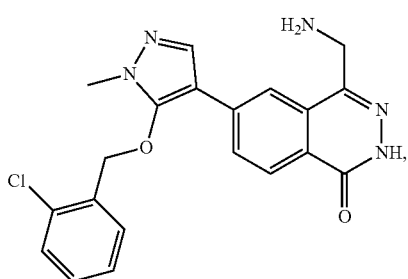
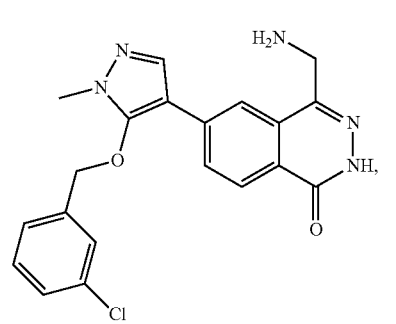
580
-continued
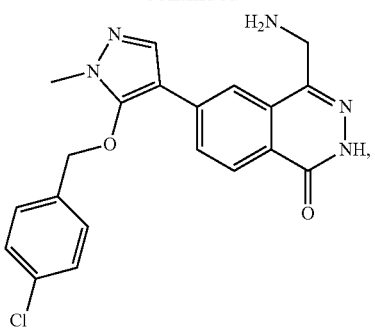
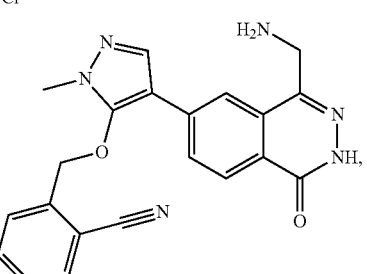
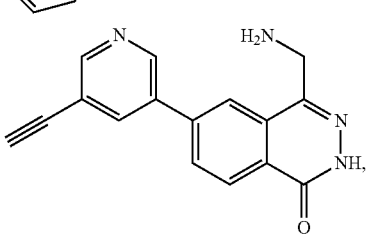
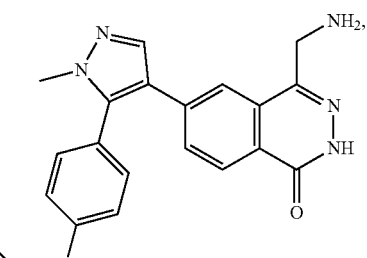
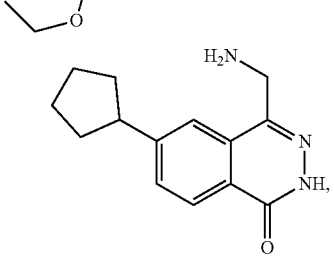
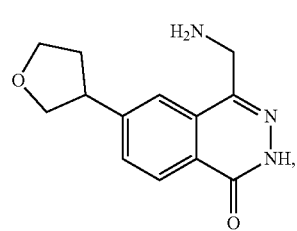

581
-continued
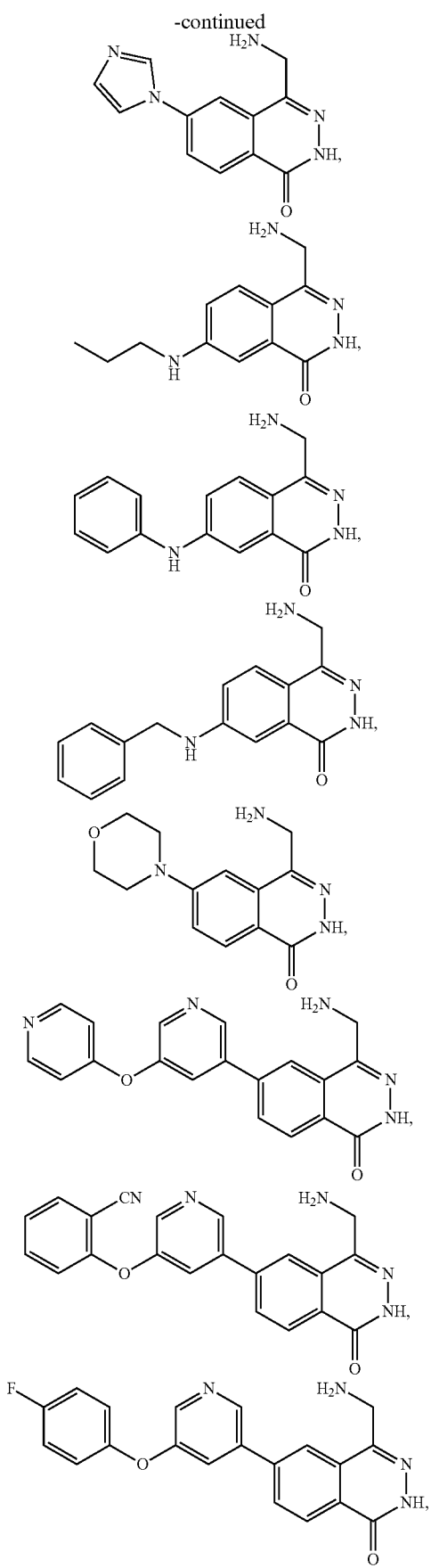
582
-continued
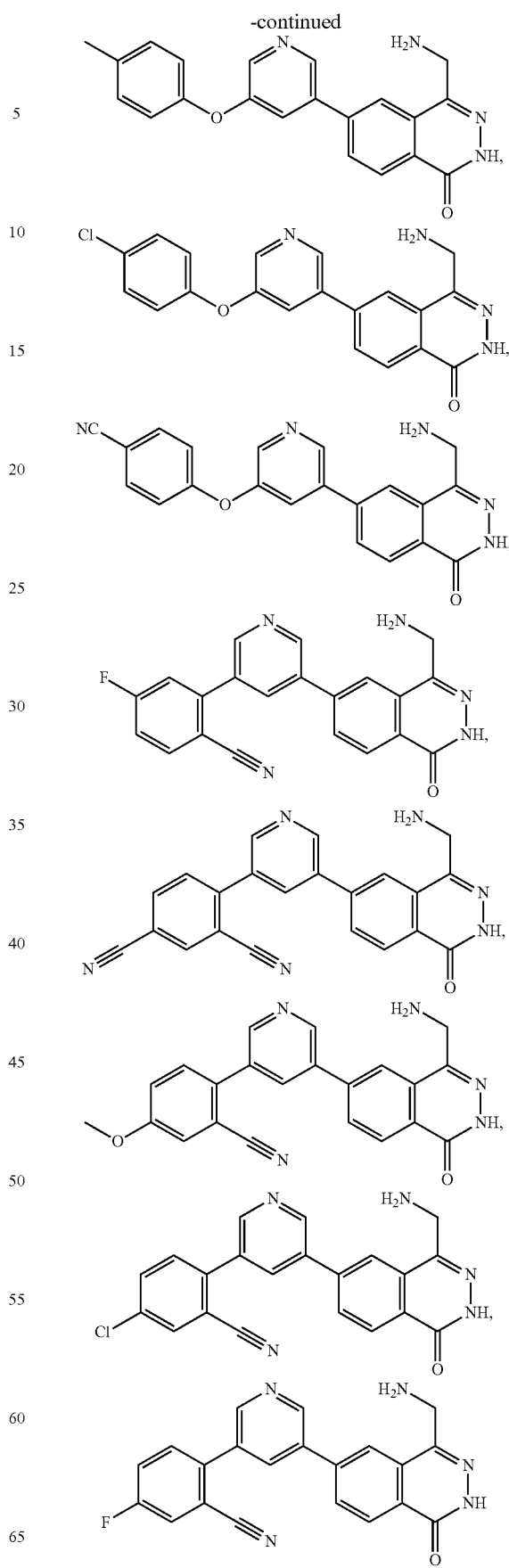

-continued
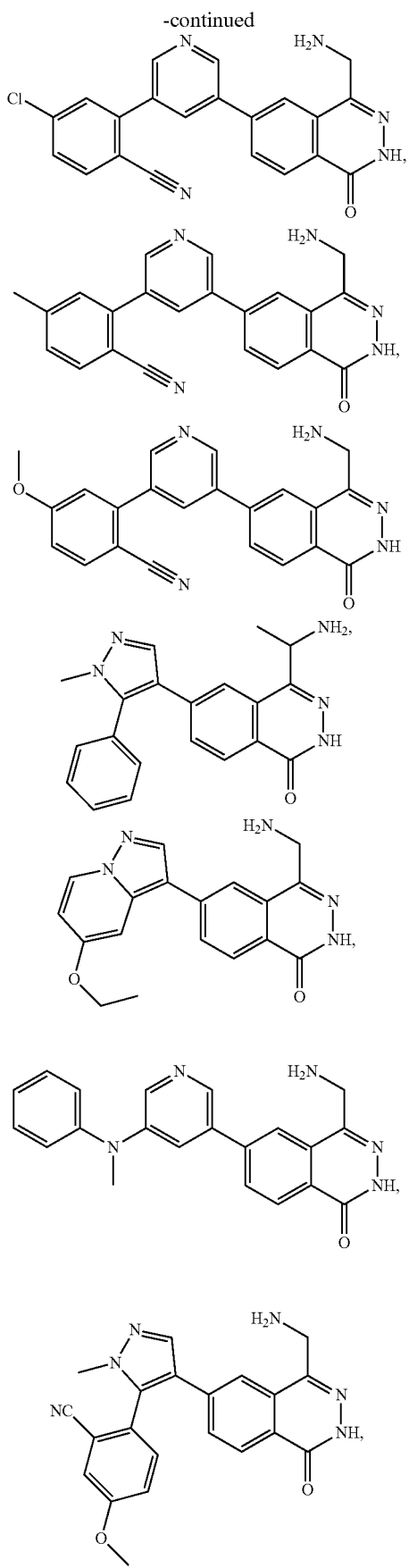
-continued
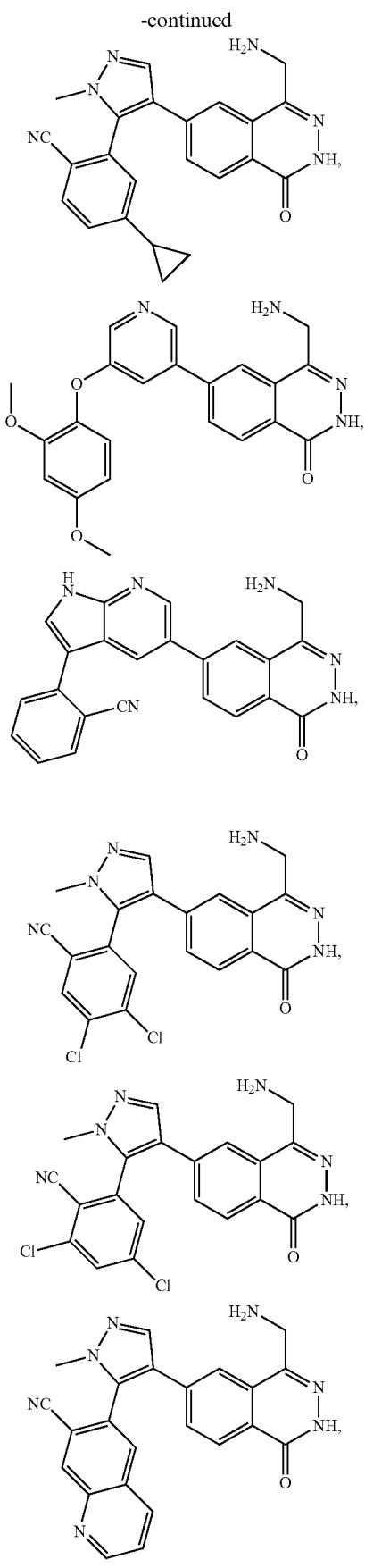

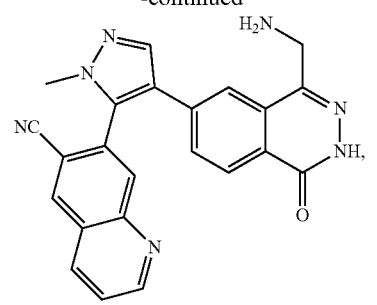
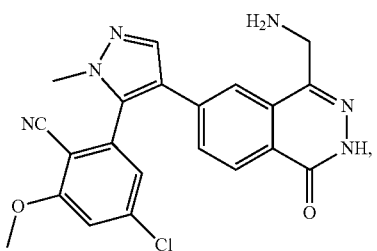
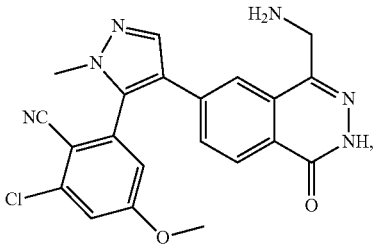
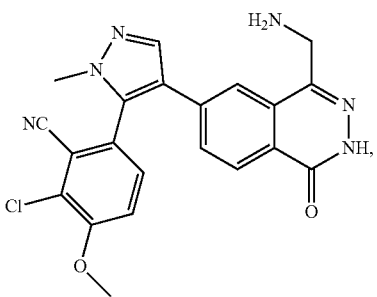
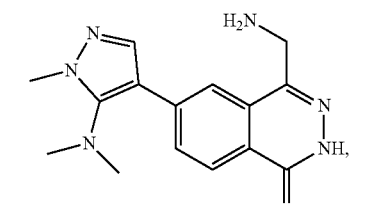
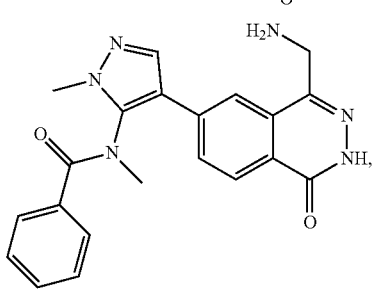
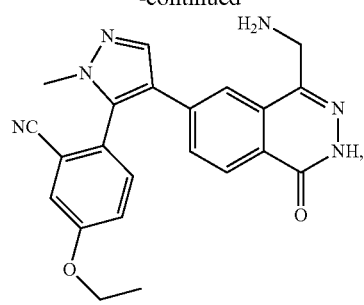
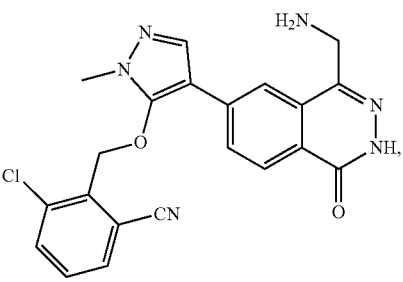
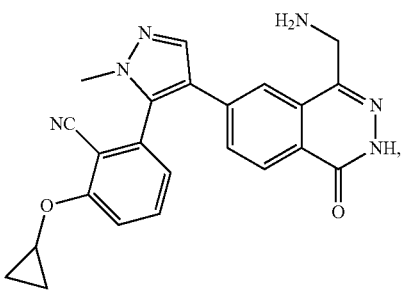
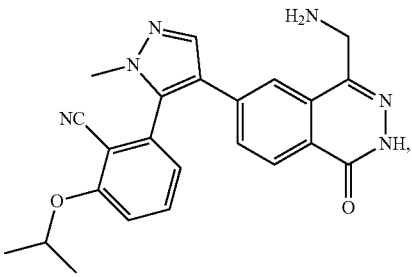
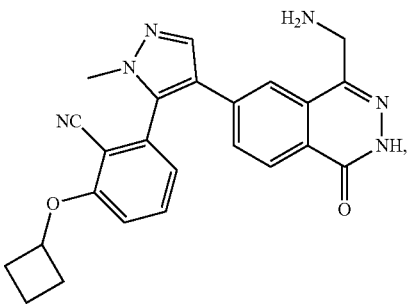
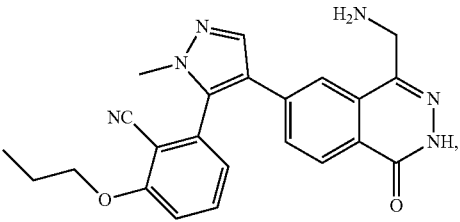

587
-continued
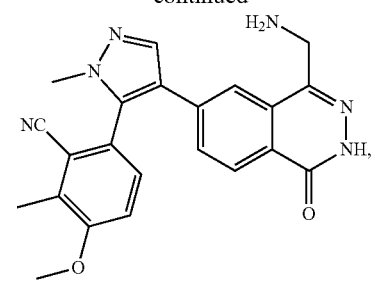
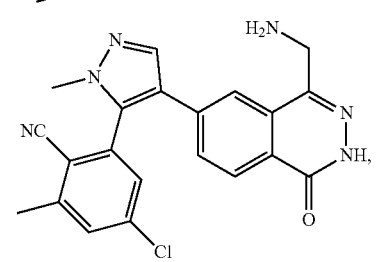
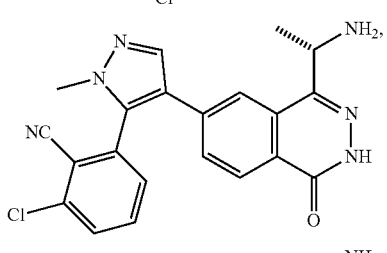
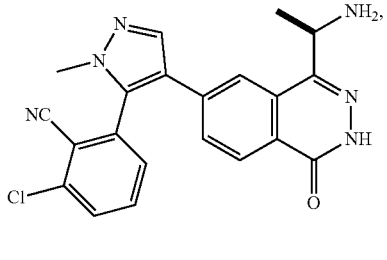
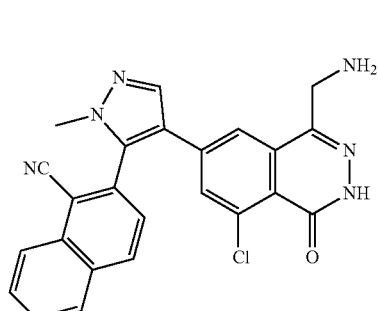
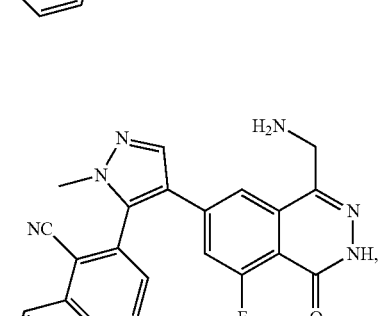
588
-continued
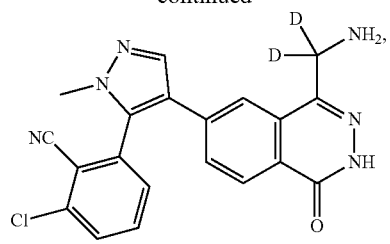
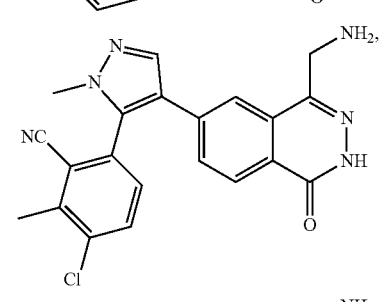
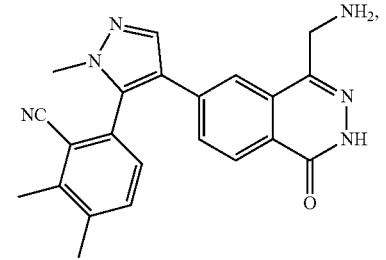
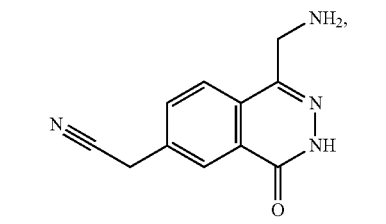
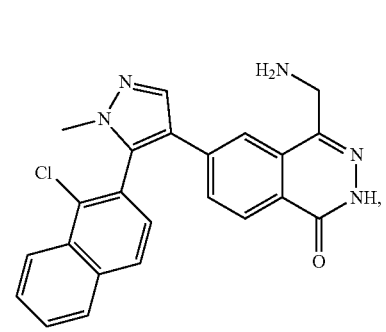
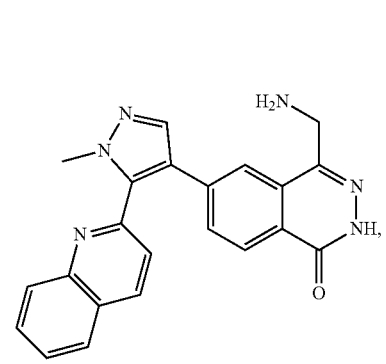

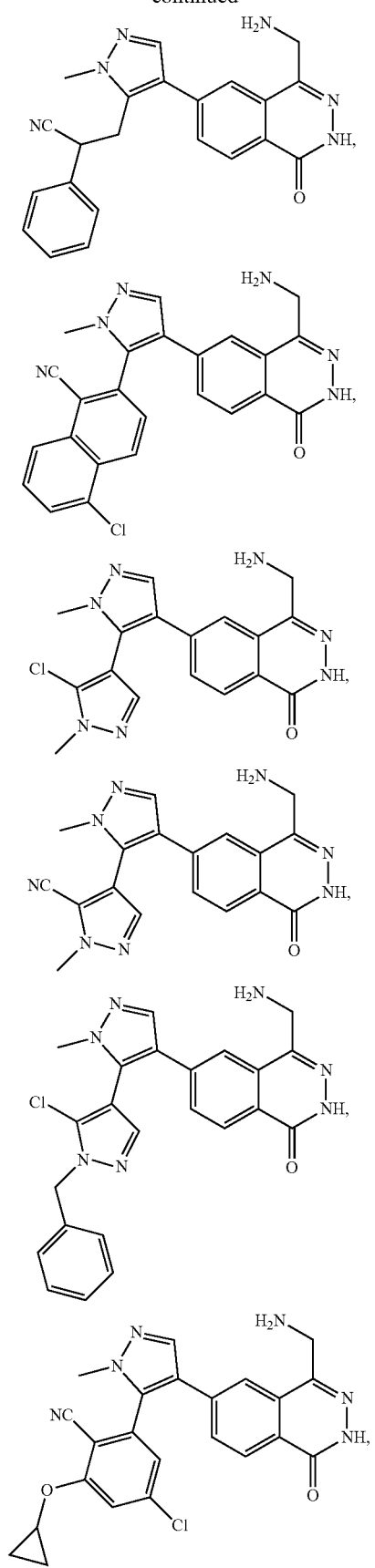
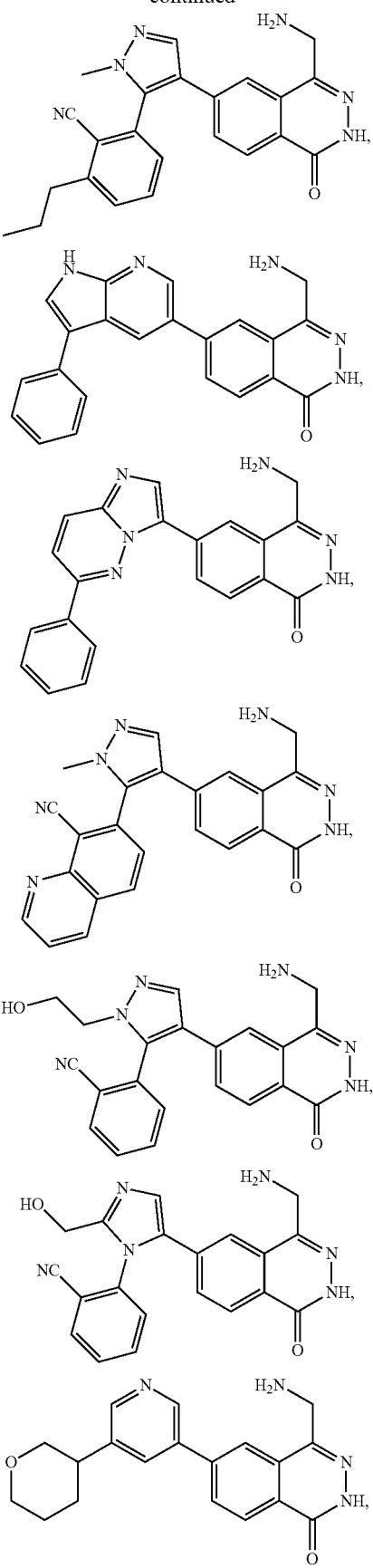

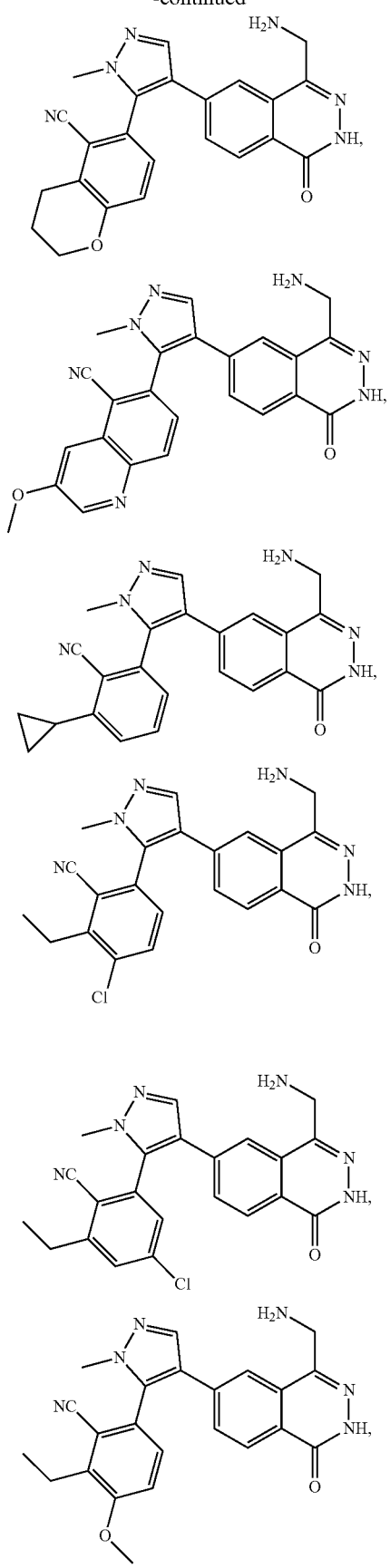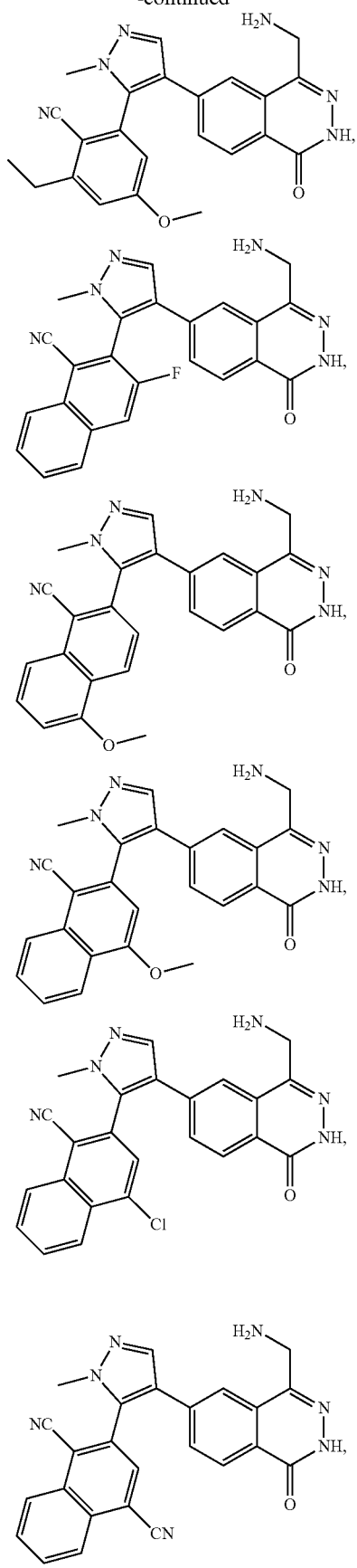

593
-continued
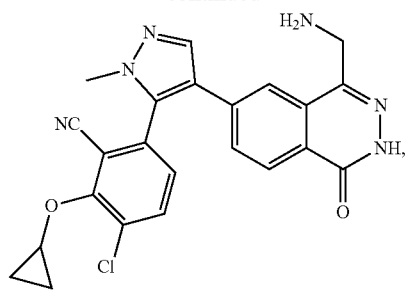
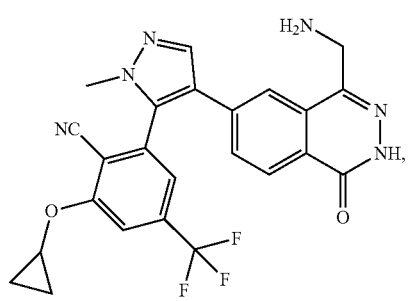
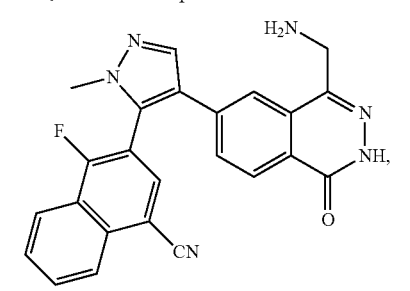
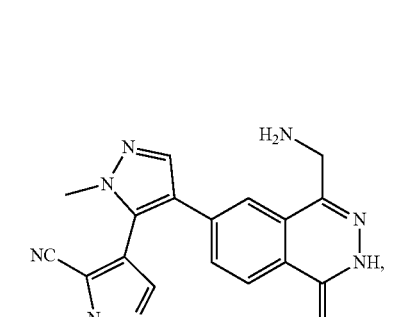
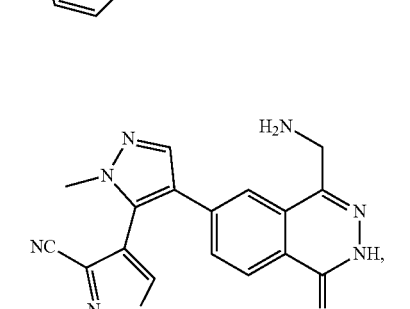
594
-continued
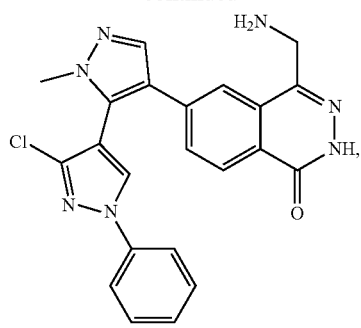
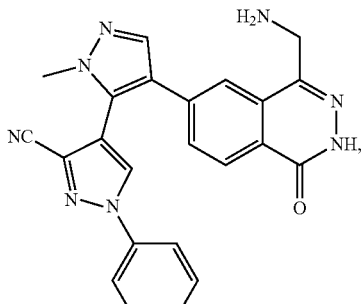
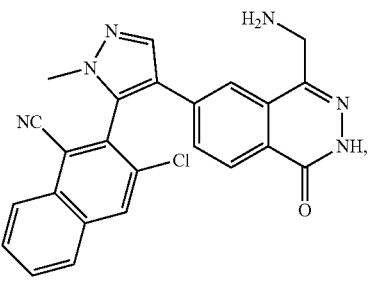
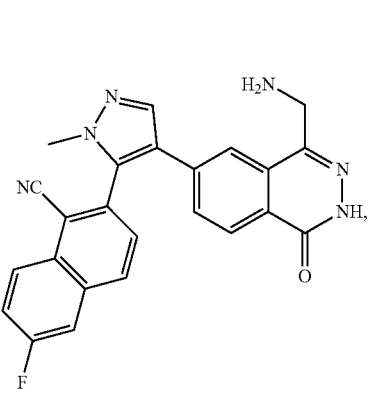
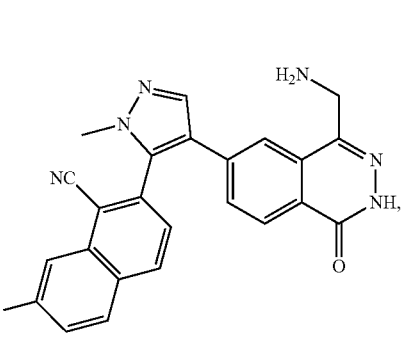

595
-continued
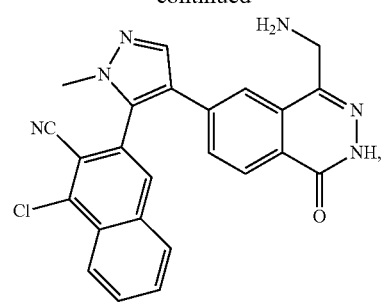
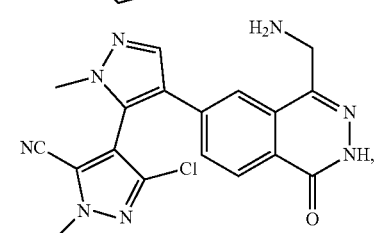
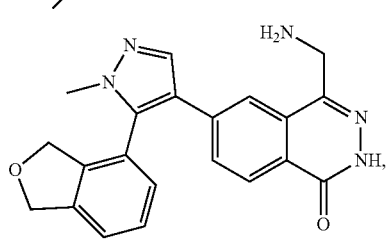
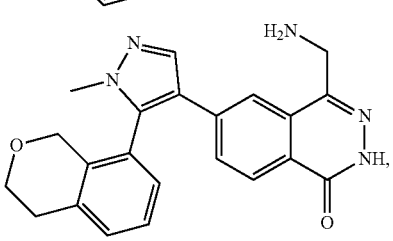
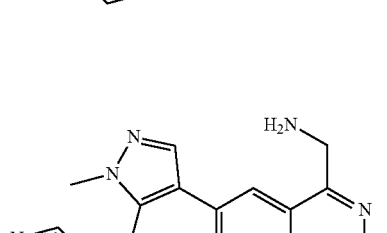
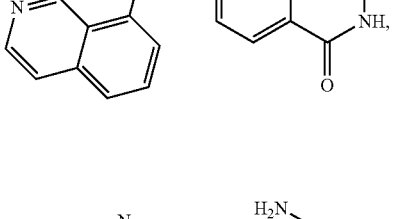
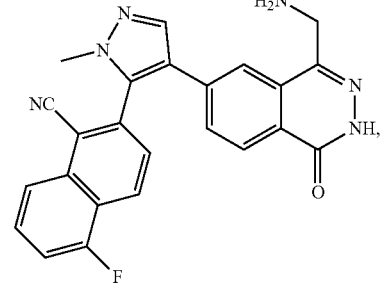
596
-continued
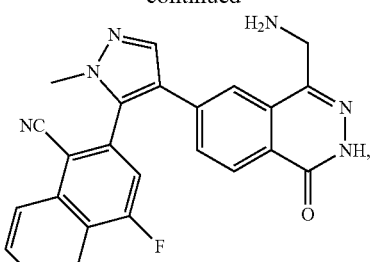
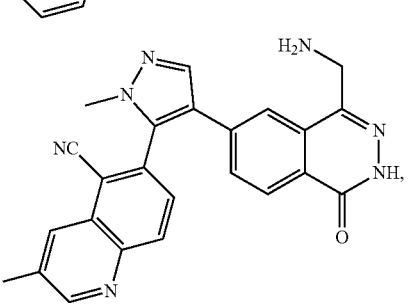
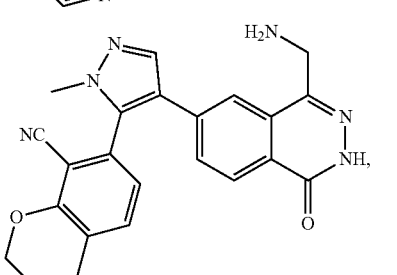
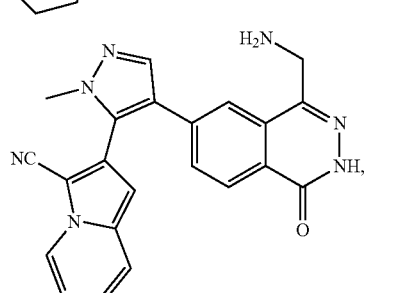
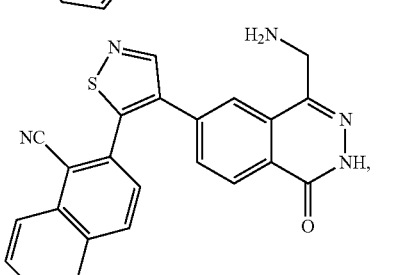
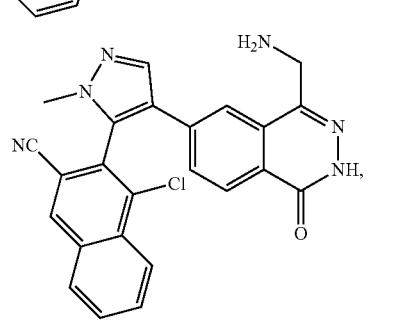

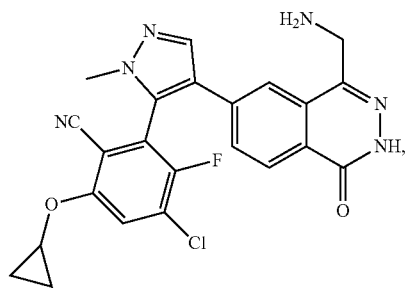
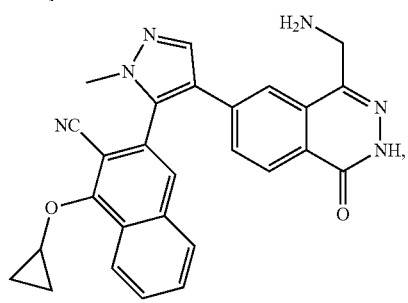
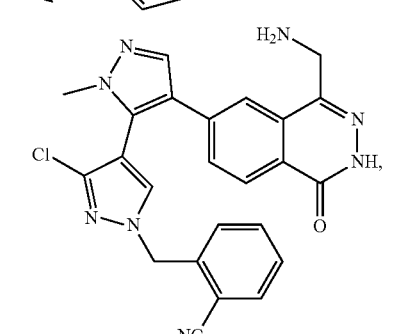
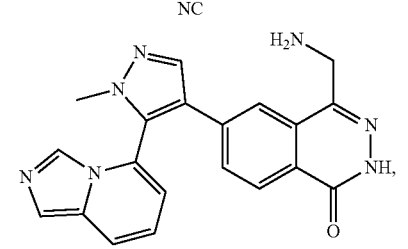
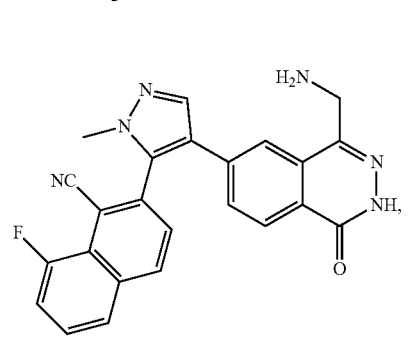
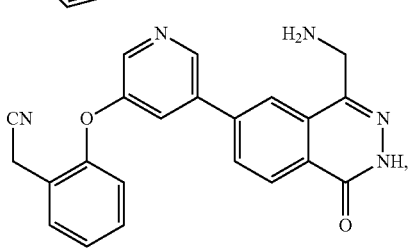
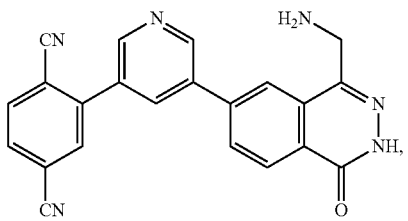
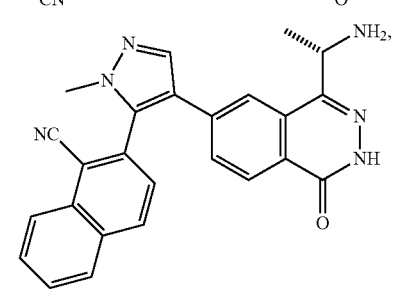
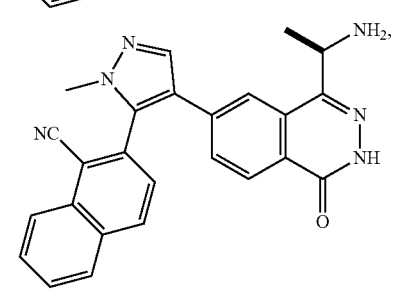
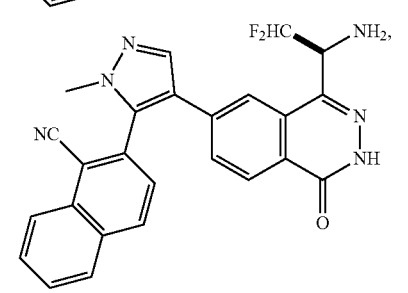
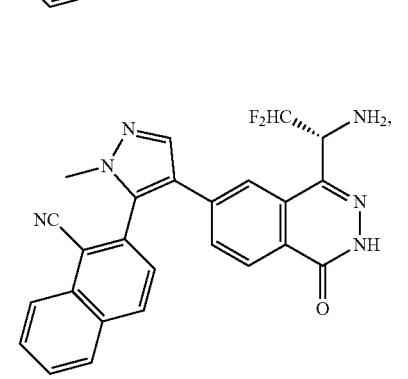
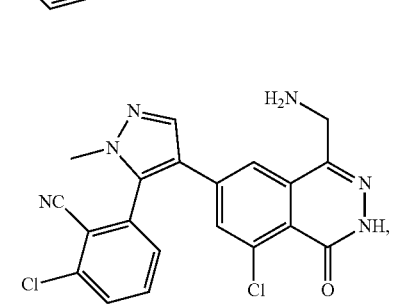

599
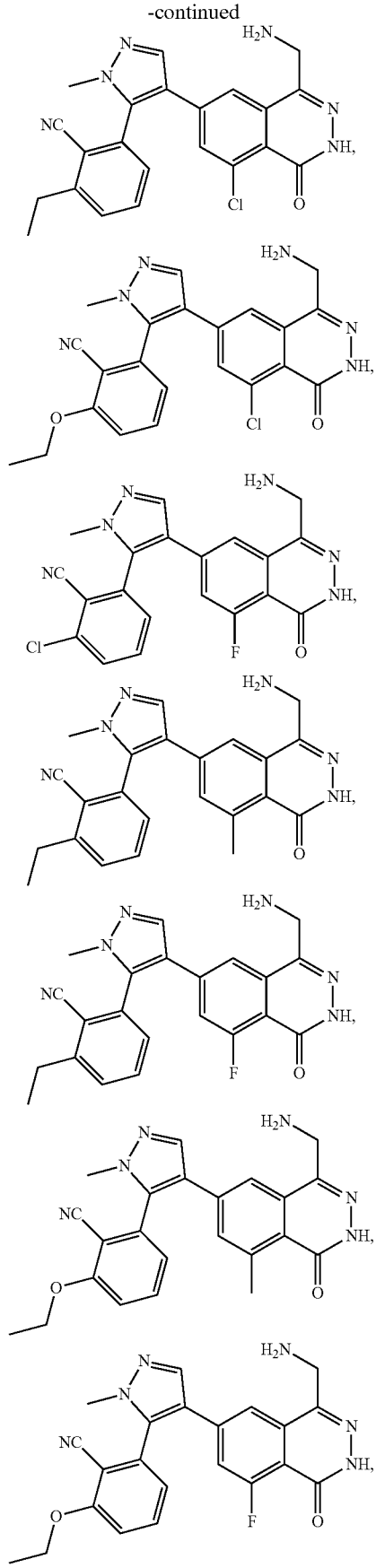
600
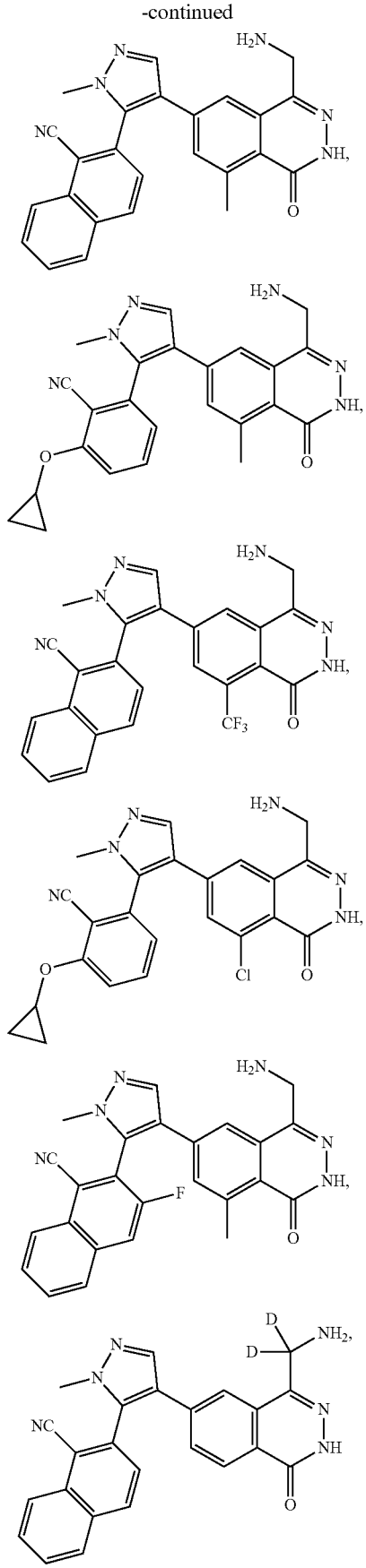

601
-continued
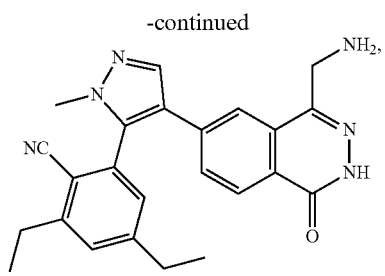
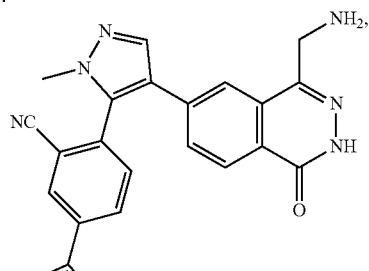
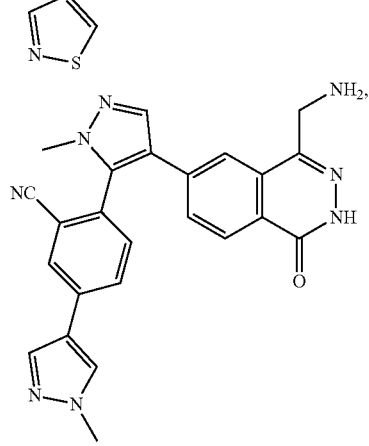
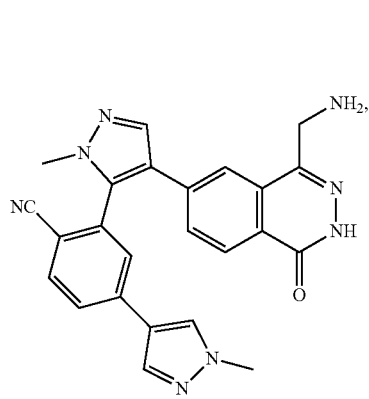
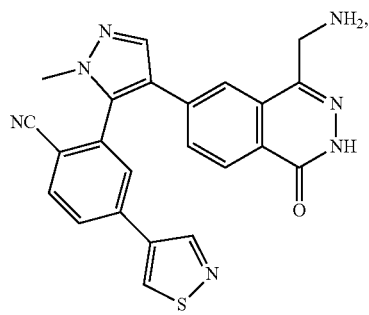
602
-continued
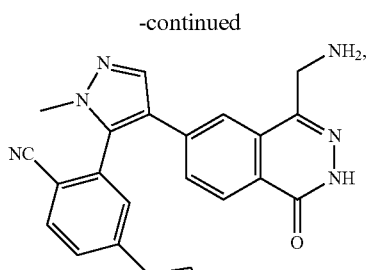
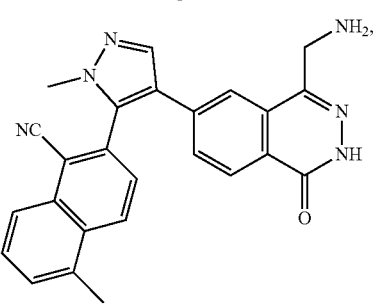
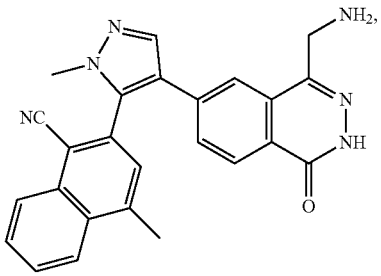
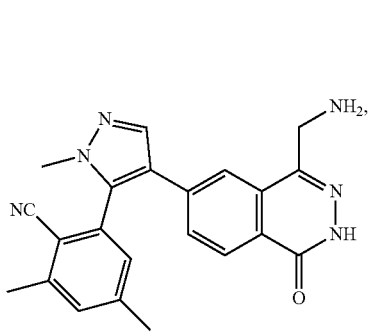
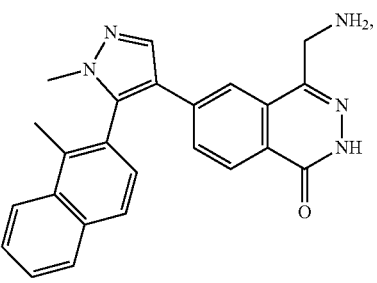

603
-continued
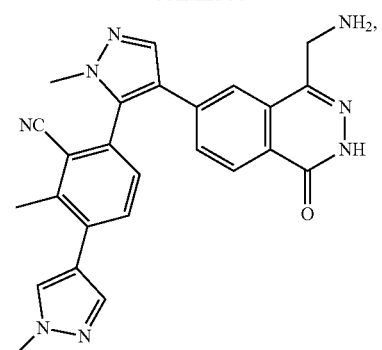
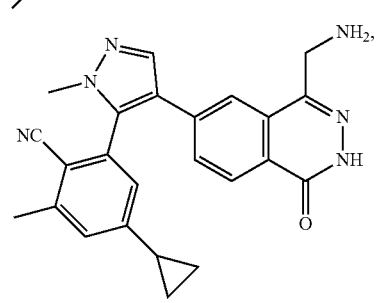
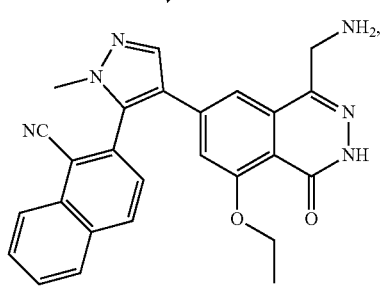
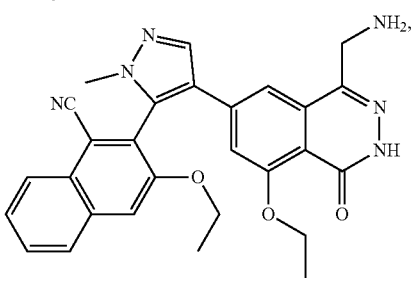
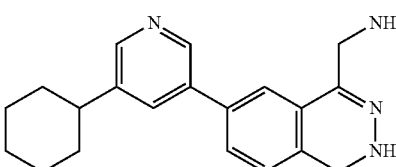
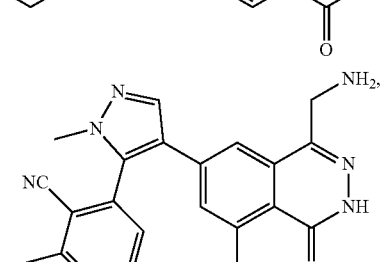
604
-continued
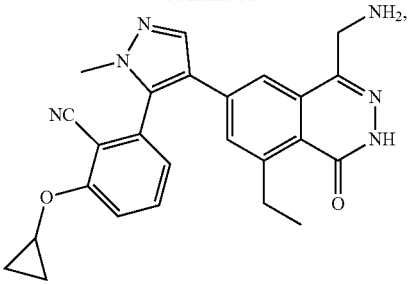
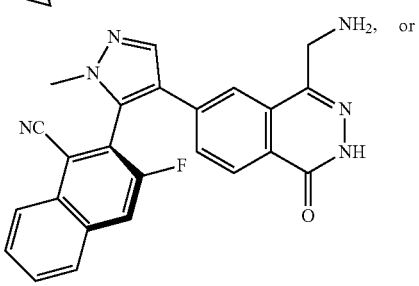 or
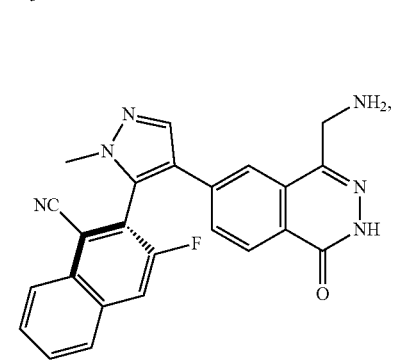
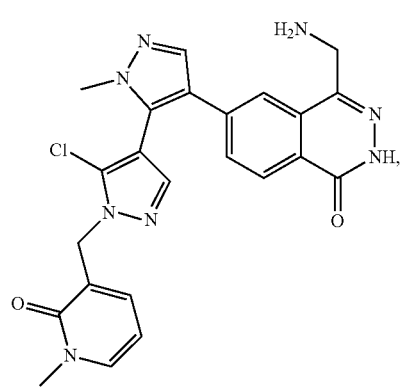
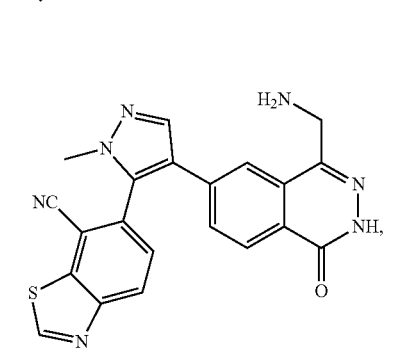

-continued
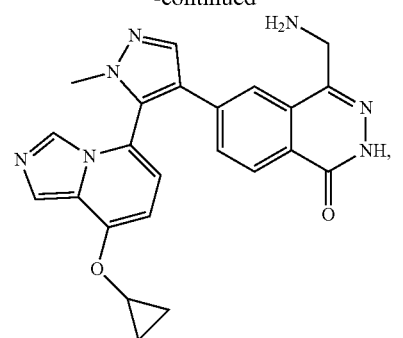
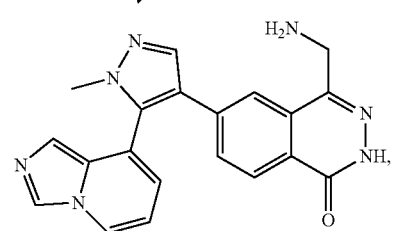
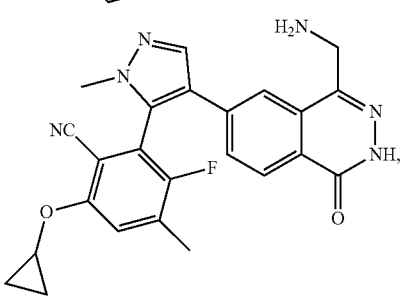
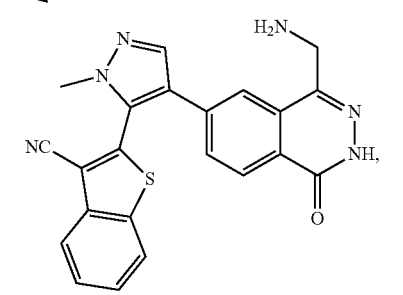
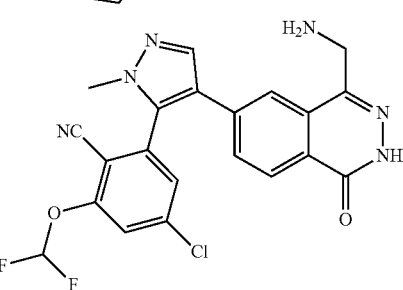
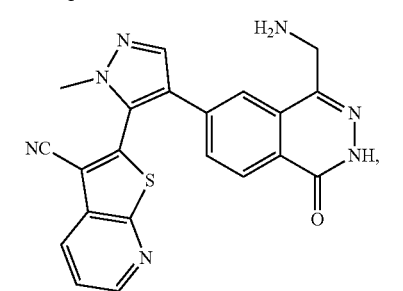
-continued
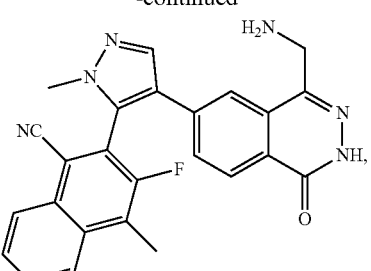
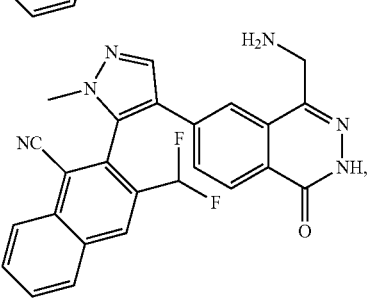
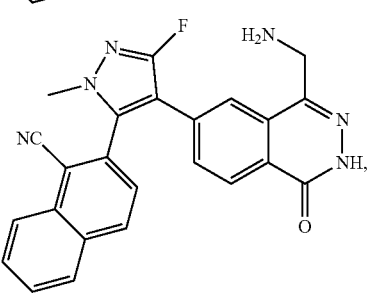
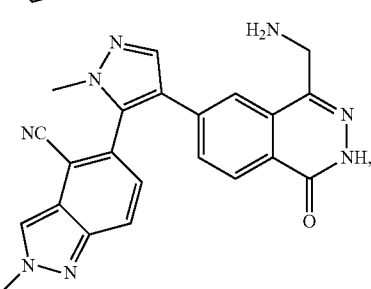
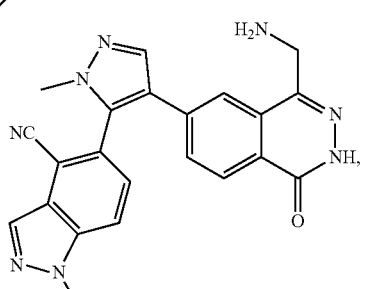
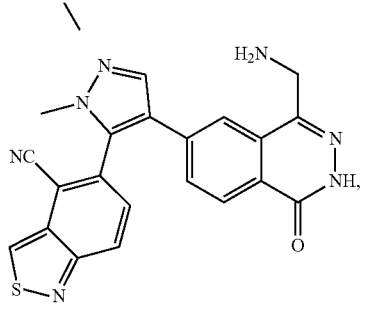

607
-continued
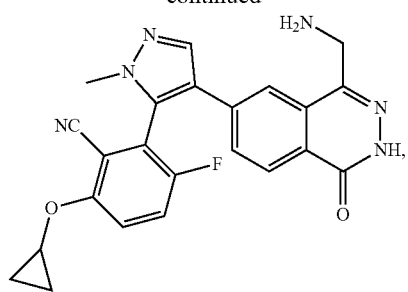
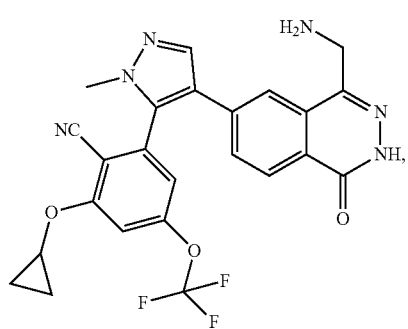
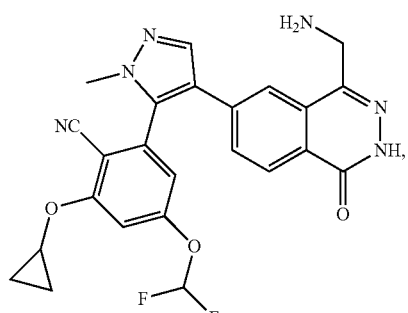
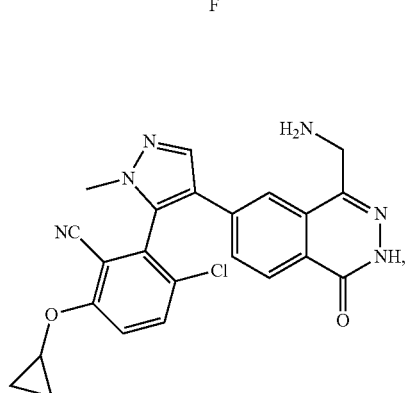
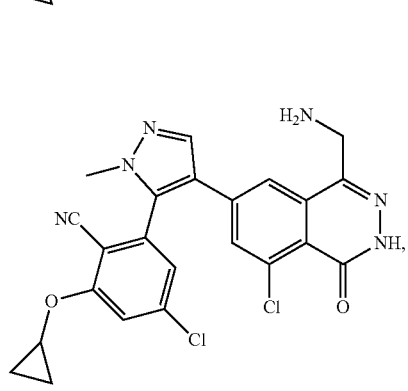
608
-continued
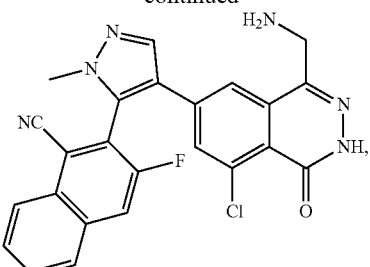
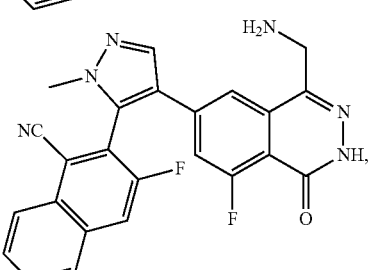
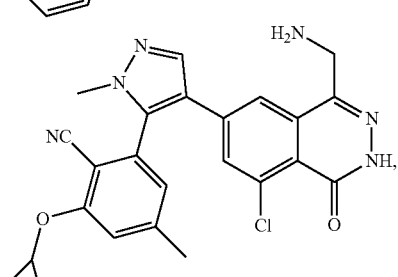
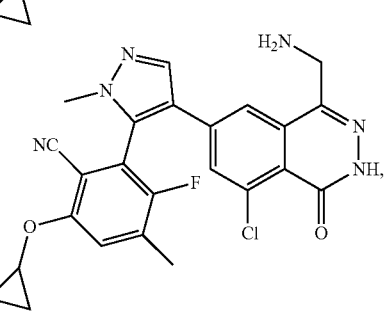
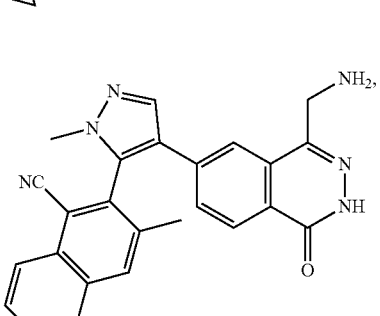
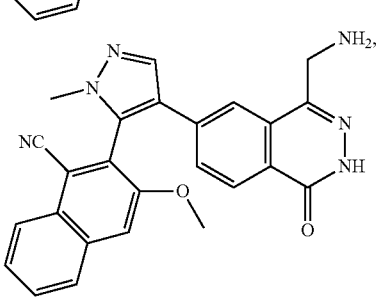

609
-continued
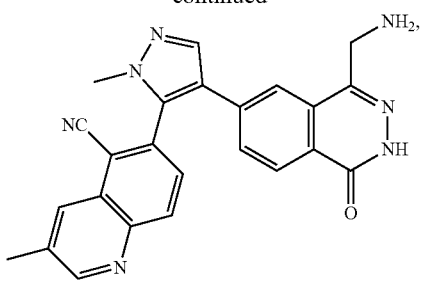
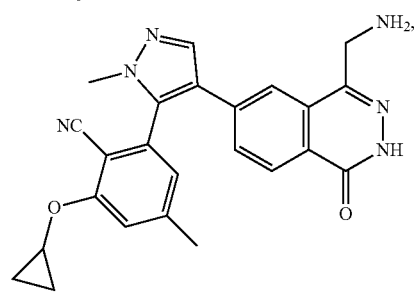
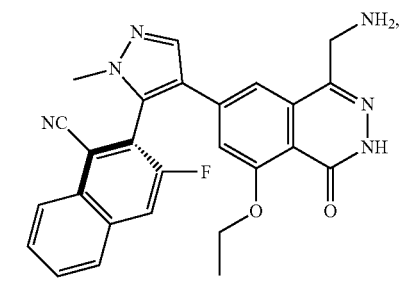
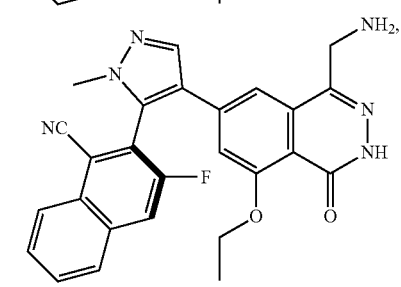
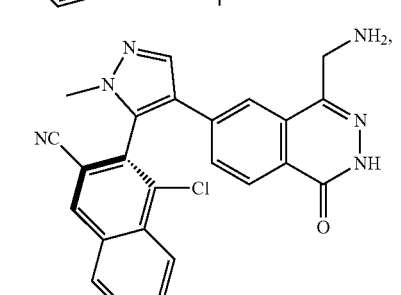
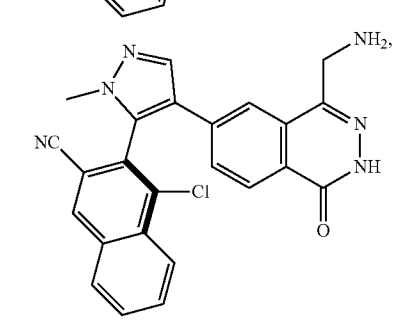
610
-continued
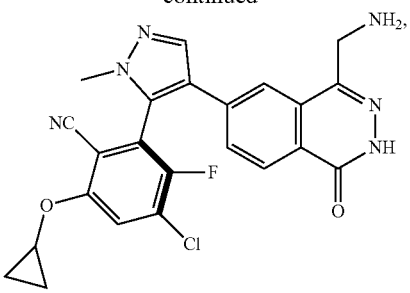
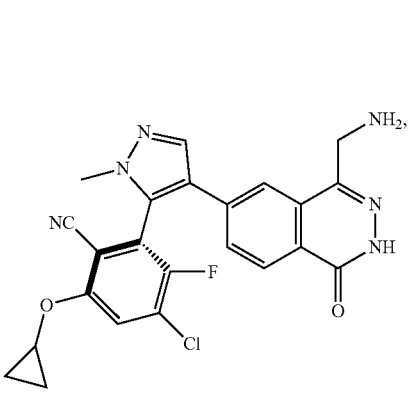
or a pharmaceutically acceptable salt thereof.
23. The method of claim 2, wherein the compound is:
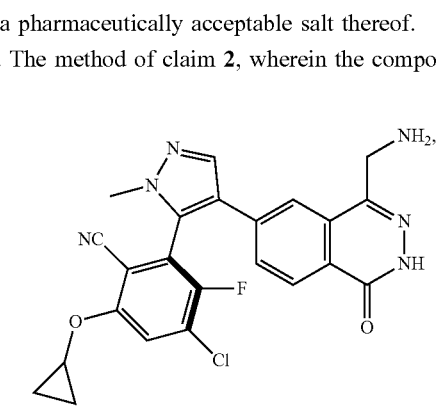
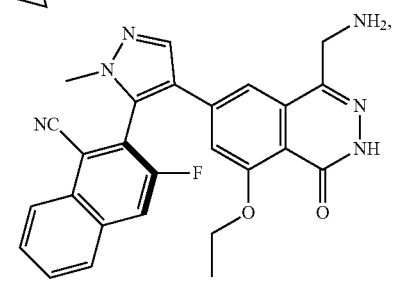
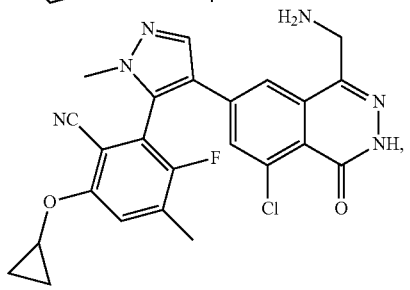

611

-continued

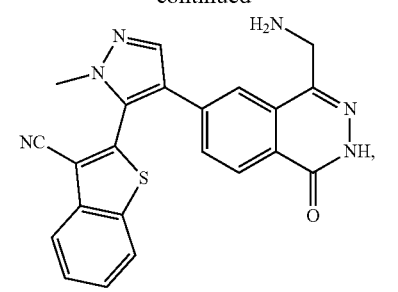

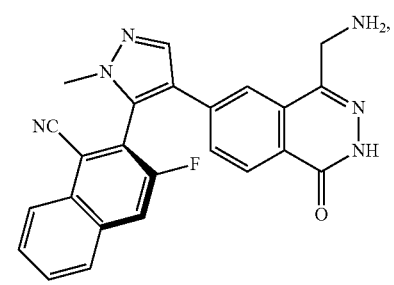

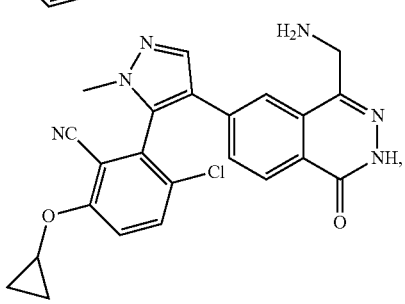

612

-continued

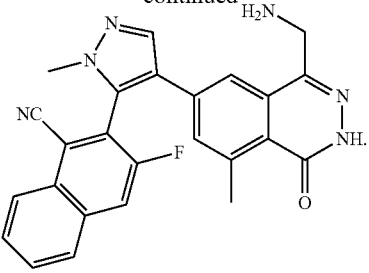

or a pharmaceutically acceptable salt thereof.

24. The method according to claim 2, wherein the cancer is selected from the group consisting of ovarian serous cystadenocarcinoma, squamous cell lung cancer, lung adenocarcinoma, mesothelioma; esophogeal squamous cell carcinoma, gastric adenocarcinoma, pancreatic ductal adenocarcinoma, kidney adenocarcinoma, bladder transitional cell carcinoma, hepatocellular carcinoma, cholangiocarcinoma, cholangiocarcinoma; osteosarcoma, multiple myeloma, astrocytoma, glioma, glioblastoma, uterine sarcoma, acute myeloid leukemia, acute lymphoblastic leukemia, non-Hodgkin's lymphoma, malignant melanoma, endometrial carcinoma and thyroid carcinoma.

25. The method according to claim 2, wherein the cancer is a MTAP-associated cancer.

26. The method of claim 24, wherein the compound is:

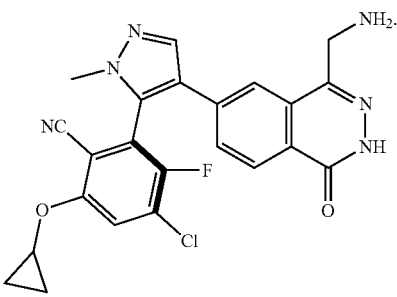

27. The method of claim 24, wherein the compound is

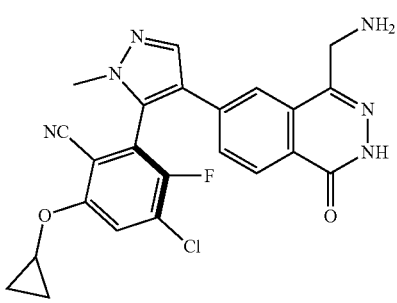

or a pharmaceutically acceptable salt thereof.

28. The method of claim 24, wherein the compound of Formula (I) is a pharmaceutically acceptable salt of

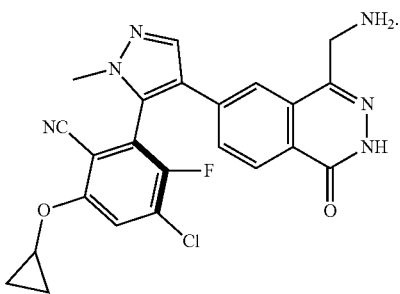

29. The method of claim 24, wherein the compound is 2-(4-(4-(aminomethyl)-1-oxo-1,2-dihydrophthalazin-6-yl)-1-methyl-1H-pyrazol-5-yl)-4-chloro-6-cyclopropoxy-3-fluorobenzonitrile.

30. A method for treating cancer comprising administering to a patient having cancer a therapeutically effective amount of a compound of Formula (I) or a pharmaceutically acceptable salt or solvate thereof,
wherein the cancer is a MTAP-associated cancer, and wherein Formula (I) is

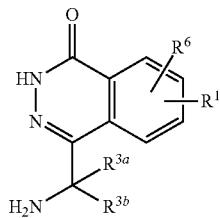

Formula (I)

wherein:

$R^1$ is —Y-cycloalkyl, —Y-heterocyclyl, —Y-aryl, —Y-arylC1-C3alkyl or —Y-heteroaryl, wherein the cycloalkyl, the heterocyclyl, the aryl, and the heteroaryl portions are each optionally substituted with one or more $R^2$;

each Y is independently a bond or —$NR^4$—;

each $R^2$ is independently hydroxy, halogen, cyano, cyanomethyl, —$(NR^4)_2$, hydroxyalkyl, alkoxy, —$SO_2$C1-C3alkyl, —X-arylC1-C3alkyl, heteroalkyl, C2- C4 alkynyl, —X-haloalkyl, —X—C1-C5 alkyl, —Z—C1-C5 alkyl, heterocyclyl, —X-L-cycloalkyl, —Z—cycloalkyl, —X-aryl, —Z-aryl, or —X-heteroaryl, wherein the heterocyclyl, the cycloalkyl, the aryl and the heteroaryl are optionally substituted with one or more $R^5$;

each X is independently a bond, O, S, —$NR^4$— or —$NR^4$C(O)—;

each Z is independently a bond, —SO—, —$SO_2$—, —CH(OH)— or —C(O)—;

each L is independently a bond or C1-C3 alkylene;

$R^{3a}$ and $R^{3b}$ are each independently hydrogen or deuterium, or $R^{3a}$ and $R^{3b}$ together are oxo;

each $R^4$ is independently hydrogen or C1-C3 alkyl;

each $R^5$ is independently cyano, oxo, halogen, C1-C3 alkyl, hydroxyalkyl, alkoxy, —X-haloalkyl, —Z-cycloalkyl, —X-arylC1-C3alkyl, —X-arylC1-C3alkyl substituted with cyano, —X-L-cycloalkyl, —X-L-heteroaryl optionally substituted with one or more C1-C3alkyl or oxo, or —X-aryl; and $R^6$ is hydrogen, halogen, C1-C3 alkyl, haloalkyl or alkoxy.

* * * * *